(12) United States Patent
Bakos et al.

(10) Patent No.: US 11,896,218 B2
(45) Date of Patent: Feb. 13, 2024

(54) METHOD OF USING A POWERED STAPLING DEVICE

(71) Applicant: Cilag GmbH International, Zug (CH)

(72) Inventors: Gregory J. Bakos, Mason, OH (US); Devanathan Raghavan, Mason, OH (US); Geoffrey C. Hueil, Mason, OH (US); Anil K. Nalagatla, Mason, OH (US); Frederick E. Shelton, IV, Hillsboro, OH (US); Jason L. Harris, Lebanon, OH (US); Adam D. Hensel, Cincinnati, OH (US); Seth D. Holdmeyer, Cincinnati, OH (US); Kevin M. Fiebig, Cincinnati, OH (US); Tylor C. Muhlenkamp, Cincinnati, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/211,145

(22) Filed: Mar. 24, 2021

(65) Prior Publication Data

US 2022/0304679 A1    Sep. 29, 2022

(51) Int. Cl.
*A61B 17/068* (2006.01)
*A61B 17/072* (2006.01)
(Continued)

(52) U.S. Cl.
CPC ........ *A61B 17/0686* (2013.01); *A61B 17/072* (2013.01); *A61B 17/07207* (2013.01);
(Continued)

(58) Field of Classification Search
CPC . B33Y 80/00; A61B 17/072; A61B 17/07207; A61B 2017/07271
(Continued)

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2012200594 A1 | 2/2012 |
|---|---|---|
| AU | 2012203035 A1 | 6/2012 |

(Continued)

OTHER PUBLICATIONS

Makerbot, 10 Advantages of 3D Printing, 2020 (retrieved via the wayback machine), Makerbot.com (Year: 2020).*

(Continued)

*Primary Examiner* — Andrew M Tecco
*Assistant Examiner* — Jacob A Smith
(74) *Attorney, Agent, or Firm* — Frost Brown Todd LLP

(57) ABSTRACT

A surgical stapling assembly is disclosed. The surgical stapling assembly can include a first jaw, a second jaw, an articulation joint, a closure drive comprising a first flexible rotary drive extending through the articulation joint, and a firing drive comprising a second flexible rotary drive extending through the articulation joint and rotatable independent of the first flexible rotary drive. The surgical stapling assembly can further include a 3D-printed component.

28 Claims, 270 Drawing Sheets

(51) Int. Cl.
*B33Y 80/00* (2015.01)
*A61B 17/00* (2006.01)

(52) U.S. Cl.
CPC ..... *B33Y 80/00* (2014.12); *A61B 2017/00389* (2013.01); *A61B 2017/00526* (2013.01); *A61B 2017/07257* (2013.01); *A61B 2017/07271* (2013.01); *A61B 2017/07278* (2013.01); *A61B 2017/07285* (2013.01)

(58) Field of Classification Search
USPC ...................................................... 227/180.1
See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 903,739 A | 11/1908 | Lesemann |
| 951,393 A | 3/1910 | Hahn |
| 1,075,556 A | 10/1913 | Fenoughty |
| 1,082,105 A | 12/1913 | Anderson |
| 1,188,721 A | 6/1916 | Bittner |
| 1,306,107 A | 6/1919 | Elliott |
| 1,314,601 A | 9/1919 | McCaskey |
| 1,466,128 A | 8/1923 | Hallenbeck |
| 1,677,337 A | 7/1928 | Grove |
| 1,794,907 A | 3/1931 | Kelly |
| 1,849,427 A | 3/1932 | Hook |
| 1,912,783 A | 6/1933 | Meyer |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | La Chapelle |
| 2,120,951 A | 6/1938 | Hodgman |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,108 A | 12/1940 | Ridgway |
| 2,224,882 A | 12/1940 | Peck |
| 2,256,295 A | 9/1941 | Schmid |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,420,552 A | 5/1947 | Morrill |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,825,178 A | 3/1958 | Hawkins |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse |
| 3,032,769 A | 5/1962 | Palmer |
| 3,035,256 A | 5/1962 | Egbert |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,252,643 A | 5/1966 | Strekopytov et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,315,863 A | 4/1967 | O'Dea |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,604,561 A | 9/1971 | Mallina et al. |
| 3,608,549 A | 9/1971 | Merrill |
| 3,616,278 A | 10/1971 | Jansen |
| 3,618,842 A | 11/1971 | Bryan |
| 3,635,394 A | 1/1972 | Natelson |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |
| 3,661,666 A | 5/1972 | Foster et al. |
| 3,662,939 A | 5/1972 | Bryan |
| 3,685,250 A | 8/1972 | Henry et al. |
| 3,688,966 A | 9/1972 | Perkins et al. |
| 3,692,224 A | 9/1972 | Astafiev et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,797,494 A | 3/1974 | Zaffaroni |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,822,818 A | 7/1974 | Strekopytov et al. |
| 3,825,007 A | 7/1974 | Rand |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |

(56) References Cited

U.S. PATENT DOCUMENTS

| | | |
|---|---|---|
| 3,894,174 A | 7/1975 | Cartun |
| 3,899,829 A | 8/1975 | Storm et al. |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,993,072 A | 11/1976 | Zaffaroni |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,047,654 A | 9/1977 | Alvarado |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,149,461 A | 4/1979 | Simeth |
| 4,154,122 A | 5/1979 | Severin |
| 4,160,857 A | 7/1979 | Nardella et al. |
| 4,169,476 A | 10/1979 | Hiltebrandt |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,250,817 A | 2/1981 | Michel |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,514,477 A | 4/1985 | Kobayashi |
| 4,520,817 A | 6/1985 | Green |
| 4,522,327 A | 6/1985 | Korthoff et al. |
| 4,523,707 A | 6/1985 | Blake, III et al. |
| 4,526,174 A | 7/1985 | Froehlich |

(56) References Cited

U.S. PATENT DOCUMENTS

| | | |
|---|---|---|
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,617,935 A | 10/1986 | Cartmell et al. |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,726,247 A | 2/1988 | Hormann |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,788,978 A | 12/1988 | Strekopytov et al. |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,495 A | 4/1989 | Hormann |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |

(56) References Cited

U.S. PATENT DOCUMENTS

| | | |
|---|---|---|
| 4,868,958 A | 9/1989 | Suzuki et al. |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,949,927 A | 8/1990 | Madocks et al. |
| 4,950,268 A | 8/1990 | Rink |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Arns et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,222 A | 4/1991 | Her |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,019,077 A | 5/1991 | De Bastiani et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,100,422 A | 3/1992 | Berguer et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,151 A | 10/1992 | Imran |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,163,842 A | 11/1992 | Nonomura |
| 5,164,652 A | 11/1992 | Johnson et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,188,126 A | 2/1993 | Fabian et al. |
| 5,190,517 A | 3/1993 | Zieve et al. |

(56) References Cited

U.S. PATENT DOCUMENTS

| | | |
|---|---|---|
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,236,629 A | 8/1993 | Mahabadi et al. |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,251,801 A | 10/1993 | Ruckdeschel et al. |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,269,794 A | 12/1993 | Rexroth |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,281,400 A | 1/1994 | Berry, Jr. |
| 5,282,806 A | 2/1994 | Haber et al. |
| 5,282,826 A | 2/1994 | Quadri |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,291,133 A | 3/1994 | Gokhale et al. |
| 5,292,053 A | 3/1994 | Bilotti et al. |
| 5,293,024 A | 3/1994 | Sugahara et al. |
| 5,297,714 A | 3/1994 | Kramer |
| 5,300,087 A | 4/1994 | Knoepfler |
| 5,302,148 A | 4/1994 | Heinz |
| 5,303,606 A | 4/1994 | Kokinda |
| 5,304,204 A | 4/1994 | Bregen |
| D347,474 S | 5/1994 | Olson |
| 5,307,976 A | 5/1994 | Olson et al. |
| 5,308,353 A | 5/1994 | Beurrier |
| 5,308,358 A | 5/1994 | Bond et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,318,589 A | 6/1994 | Lichtman |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,486 A | 7/1994 | Wilk |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,338,317 A | 8/1994 | Hasson et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,104 A | 9/1994 | Main et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,353,798 A | 10/1994 | Sieben |
| 5,354,215 A | 10/1994 | Viracola |
| 5,354,250 A | 10/1994 | Christensen |
| 5,354,303 A | 10/1994 | Spaeth et al. |
| 5,355,897 A | 10/1994 | Pietrafitta et al. |
| 5,356,006 A | 10/1994 | Alpern et al. |

(56) References Cited

U.S. PATENT DOCUMENTS

| | | |
|---|---|---|
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,368,599 A | 11/1994 | Hirsch et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,738 A | 1/1995 | Herbermann |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,072 A | 2/1995 | Imran |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,645 A | 7/1995 | Smith et al. |
| 5,431,654 A | 7/1995 | Nic |
| 5,431,666 A | 7/1995 | Sauer et al. |
| 5,431,668 A | 7/1995 | Burbank, III et al. |
| 5,433,721 A * | 7/1995 | Hooven ............... A61B 17/068 606/139 |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,824 A | 10/1995 | Fontayne et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |

(56) References Cited

U.S. PATENT DOCUMENTS

| | | | |
|---|---|---|---|
| 5,474,566 | A | 12/1995 | Alesi et al. |
| 5,474,570 | A | 12/1995 | Kockerling et al. |
| 5,474,738 | A | 12/1995 | Nichols et al. |
| 5,476,206 | A | 12/1995 | Green et al. |
| 5,476,479 | A | 12/1995 | Green et al. |
| 5,476,481 | A | 12/1995 | Schondorf |
| 5,478,003 | A | 12/1995 | Green et al. |
| 5,478,308 | A | 12/1995 | Cartmell et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,483,952 | A | 1/1996 | Aranyi |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,377 | A | 1/1996 | Smith et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,489,256 | A | 2/1996 | Adair |
| 5,489,290 | A | 2/1996 | Furnish |
| 5,490,819 | A | 2/1996 | Nicholas et al. |
| 5,492,671 | A | 2/1996 | Krafft |
| 5,496,312 | A | 3/1996 | Klicek |
| 5,496,317 | A | 3/1996 | Goble et al. |
| 5,497,933 | A | 3/1996 | DeFonzo et al. |
| 5,498,164 | A | 3/1996 | Ward et al. |
| 5,498,838 | A | 3/1996 | Furman |
| 5,501,654 | A | 3/1996 | Failla et al. |
| 5,503,320 | A | 4/1996 | Webster et al. |
| 5,503,635 | A | 4/1996 | Sauer et al. |
| 5,503,638 | A | 4/1996 | Cooper et al. |
| 5,505,363 | A | 4/1996 | Green et al. |
| 5,507,425 | A | 4/1996 | Ziglioli |
| 5,507,426 | A | 4/1996 | Young et al. |
| 5,507,773 | A | 4/1996 | Huitema et al. |
| 5,509,596 | A | 4/1996 | Green et al. |
| 5,509,916 | A | 4/1996 | Taylor |
| 5,509,918 | A | 4/1996 | Romano |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,694 | A | 10/1996 | Sauer et al. |
| 5,562,701 | A | 10/1996 | Huitema et al. |
| 5,562,702 | A | 10/1996 | Huitema et al. |
| 5,563,481 | A | 10/1996 | Krause |
| 5,564,615 | A | 10/1996 | Bishop et al. |
| 5,569,161 | A | 10/1996 | Ebling et al. |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,285 | A | 11/1996 | Chow et al. |
| 5,571,488 | A | 11/1996 | Beerstecher et al. |
| 5,573,169 | A | 11/1996 | Green et al. |
| 5,573,543 | A | 11/1996 | Akopov et al. |
| 5,574,431 | A | 11/1996 | McKeown et al. |
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,279 | A | 2/1997 | Slotman et al. |
| 5,599,344 | A | 2/1997 | Paterson |
| 5,599,350 | A | 2/1997 | Schulze et al. |
| 5,599,852 | A | 2/1997 | Scopelianos et al. |
| 5,601,224 | A | 2/1997 | Bishop et al. |
| 5,601,573 | A | 2/1997 | Fogelberg et al. |
| 5,601,604 | A | 2/1997 | Vincent |
| 5,602,449 | A | 2/1997 | Krause et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,303 | A | 3/1997 | Nakamura |
| 5,607,433 | A | 3/1997 | Polla et al. |

(56) References Cited

U.S. PATENT DOCUMENTS

| | | |
|---|---|---|
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,611,813 A | 3/1997 | Lichtman |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,631,973 A | 5/1997 | Green |
| 5,632,432 A * | 5/1997 | Schulze ............ A61B 17/07207 227/176.1 |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,637,110 A | 6/1997 | Pennybacker et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,656,917 A | 8/1997 | Theobald |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,664,404 A | 9/1997 | Ivanov et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,265 A | 12/1997 | Romano |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,704,792 A | 1/1998 | Sobhani |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |

(56) References Cited

U.S. PATENT DOCUMENTS

| | | |
|---|---|---|
| 5,728,121 A | 3/1998 | Bimbo et al. |
| 5,730,758 A | 3/1998 | Allgeyer |
| 5,732,712 A | 3/1998 | Adair |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,746,770 A | 5/1998 | Zeitels et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |
| 5,766,186 A | 6/1998 | Faraz et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,640 A | 6/1998 | Jacobus et al. |
| 5,769,748 A | 6/1998 | Eyerly et al. |
| 5,769,791 A | 6/1998 | Benaron et al. |
| 5,769,892 A | 6/1998 | Kingwell |
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,798,752 A | 8/1998 | Buxton et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,241 A | 9/1998 | Heimberger |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,240 A | 9/1998 | Robertson |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,664 A | 2/1999 | Speier et al. |
| 5,868,760 A | 2/1999 | McGuckin, Jr. |
| 5,868,790 A | 2/1999 | Vincent et al. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,881,943 A | 3/1999 | Heck et al. |
| 5,891,094 A | 4/1999 | Masterson et al. |

(56) References Cited

U.S. PATENT DOCUMENTS

| | | | |
|---|---|---|---|
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,855 A | 4/1999 | Jacobs |
| 5,893,863 A | 4/1999 | Yoon |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,149 A | 6/1999 | Welch et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,922,001 A | 7/1999 | Yoon |
| 5,922,003 A | 7/1999 | Anctil et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,980,569 A | 11/1999 | Scirica |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,275 A | 2/2000 | Horvitz et al. |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |
| 6,077,280 A | 6/2000 | Fossum |
| 6,077,286 A | 6/2000 | Cuschieri et al. |

(56) References Cited

U.S. PATENT DOCUMENTS

| | | |
|---|---|---|
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,090,123 A | 7/2000 | Culp et al. |
| 6,093,186 A | 7/2000 | Goble |
| 6,094,021 A | 7/2000 | Noro et al. |
| D429,252 S | 8/2000 | Haitani et al. |
| 6,099,537 A | 8/2000 | Sugai et al. |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| RE36,923 E | 10/2000 | Hiroi et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,186,957 B1 | 2/2001 | Milam |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,311 B1 | 3/2001 | Danek et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,235,036 B1 | 5/2001 | Gardner et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,246 B1 | 7/2001 | Pantages et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,269,997 B1 | 8/2001 | Balazs et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |

(56) References Cited

U.S. PATENT DOCUMENTS

| | | |
|---|---|---|
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,338,738 B1 | 1/2002 | Bellotti et al. |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,361,542 B1 | 3/2002 | Dimitriu et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,656 B2 | 9/2002 | Brissette et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,463,824 B1 | 10/2002 | Prell et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,063 B1 | 11/2002 | Frigard |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 | 12/2002 | Lang et al. |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,506,399 B2 | 1/2003 | Donovan |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |

(56) References Cited

U.S. PATENT DOCUMENTS

| | | |
|---|---|---|
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,844 B2 | 4/2003 | Lee et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,569,173 B1 | 5/2003 | Blatter et al. |
| 6,572,629 B2 | 6/2003 | Kalloo et al. |
| 6,575,969 B1 | 6/2003 | Rittman, III et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,626,901 B1 | 9/2003 | Treat et al. |
| 6,626,938 B1 | 9/2003 | Butaric et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B1 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |

(56) References Cited

U.S. PATENT DOCUMENTS

| | | |
|---|---|---|
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,825 B2 | 6/2004 | Shoenman et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,773,458 B1 | 8/2004 | Brauker et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,801,009 B2 | 10/2004 | Makaran et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,860,169 B2 | 3/2005 | Shinozaki |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B2 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,927,315 B1 | 8/2005 | Heinecke et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |

(56) References Cited

U.S. PATENT DOCUMENTS

| | | |
|---|---|---|
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 6,999,821 B2 | 2/2006 | Jenney et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,005,828 B2 | 2/2006 | Karikomi |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,412 B1 | 7/2006 | Reynolds et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,090,689 B2 | 8/2006 | Nagase et al. |
| 7,091,191 B2 | 8/2006 | Laredo et al. |

(56) References Cited

U.S. PATENT DOCUMENTS

| | | |
|---|---|---|
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,363 B2 | 9/2006 | Nishizawa et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,201 B2 | 9/2006 | Truckai et al. |
| 7,112,214 B2 | 9/2006 | Peterson et al. |
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,846 B2 | 1/2007 | Dycus et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,160,311 B2 | 1/2007 | Blatter et al. |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,169,146 B2 | 1/2007 | Truckai et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,197,965 B1 | 4/2007 | Anderson |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,205,959 B2 | 4/2007 | Henriksson |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |

(56) References Cited

U.S. PATENT DOCUMENTS

| | | |
|---|---|---|
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,273,488 B2 | 9/2007 | Nakamura et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,311,709 B2 | 12/2007 | Truckai et al. |
| 7,313,430 B2 | 12/2007 | Urquhart et al. |
| 7,314,473 B2 | 1/2008 | Jinno et al. |
| 7,317,955 B2 | 1/2008 | McGreevy |
| 7,320,704 B2 | 1/2008 | Lashinski et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,183 B2 | 2/2008 | Reddy et al. |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,398 B2 | 4/2008 | Kanazawa |
| 7,354,440 B2 | 4/2008 | Truckai et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,430,849 B1 | 10/2008 | Coutts et al. |
| 7,431,188 B1 | 10/2008 | Marczyk |
| 7,431,189 B2 | 10/2008 | Shelton, IV et al. |
| 7,431,230 B2 | 10/2008 | McPherson et al. |

(56) References Cited

U.S. PATENT DOCUMENTS

| | | | |
|---|---|---|---|
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| D580,942 S | 11/2008 | Oshiro et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,790 B1 | 5/2009 | Knodel et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,572,298 B2 | 8/2009 | Roller et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,605,826 B2 | 10/2009 | Sauer |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| 7,618,427 B2 | 11/2009 | Ortiz et al. |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |

(56) References Cited

U.S. PATENT DOCUMENTS

| | | |
|---|---|---|
| 7,625,662 B2 | 12/2009 | Vaisnys et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,016 B2 | 1/2010 | Nycz et al. |
| 7,644,484 B2 | 1/2010 | Vereschagin |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,670,337 B2 | 3/2010 | Young |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,706,853 B2 | 4/2010 | Hacker et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeller et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,735,704 B2 | 6/2010 | Bilotti |
| 7,736,254 B2 | 6/2010 | Schena |
| 7,736,306 B2 | 6/2010 | Brustad et al. |
| 7,736,356 B2 | 6/2010 | Cooper et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |

(56) References Cited

U.S. PATENT DOCUMENTS

| | | |
|---|---|---|
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,614 B1 | 8/2010 | McGonagle et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,782,382 B2 | 8/2010 | Fujimura |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,076 B2 | 10/2010 | Borovsky et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stotters et al. |
| 7,839,109 B2 | 11/2010 | Carmen, Jr. et al. |
| 7,840,253 B2 | 11/2010 | Tremblay et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scirica |
| 7,845,536 B2 | 12/2010 | Viola et al. |
| 7,845,537 B2 | 12/2010 | Shelton, IV et al. |
| 7,845,538 B2 | 12/2010 | Whitman |
| 7,845,912 B2 | 12/2010 | Sung et al. |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,554 B2 | 1/2011 | Hegeman et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,877,869 B2 | 2/2011 | Mehdizadeh et al. |
| 7,879,063 B2 | 2/2011 | Khosravi |
| 7,879,070 B2 | 2/2011 | Ortiz et al. |
| 7,879,367 B2 | 2/2011 | Heublein et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,887,755 B2 | 2/2011 | Mingerink et al. |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |

(56) References Cited

U.S. PATENT DOCUMENTS

| | | |
|---|---|---|
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,300 B2 | 5/2011 | Rethy et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,948,381 B2 | 5/2011 | Lindsay et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,952,464 B2 | 5/2011 | Nikitin et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |
| 7,976,563 B2 | 7/2011 | Summerer |
| 7,979,137 B2 | 7/2011 | Tracey et al. |
| 7,980,443 B2 | 7/2011 | Scheib et al. |
| 7,981,025 B2 | 7/2011 | Pool et al. |
| 7,981,102 B2 | 7/2011 | Patel et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,741 B2 | 9/2011 | Cole et al. |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,835 B2 | 10/2011 | Yasuda et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |

(56) References Cited

U.S. PATENT DOCUMENTS

| | | |
|---|---|---|
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,052,697 B2 | 11/2011 | Phillips |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,157,834 B2 | 4/2012 | Conlon |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |

(56) References Cited

U.S. PATENT DOCUMENTS

| | | |
|---|---|---|
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,230,235 B2 | 7/2012 | Goodman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,235,274 B2 | 8/2012 | Cappola |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,316,961 B2 | 11/2012 | Isobe et al. |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |

(56) References Cited

U.S. PATENT DOCUMENTS

| | | |
|---|---|---|
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,948 B2 | 1/2013 | Bahney |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DITizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,368,327 B2 | 2/2013 | Benning et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,374,723 B2 | 2/2013 | Zhao et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,377,059 B2 | 2/2013 | Deville et al. |
| 8,381,828 B2 | 2/2013 | Whitman et al. |
| 8,381,834 B2 | 2/2013 | Barhitte et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,972 B2 | 3/2013 | Kostrzewski |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,108 B2 | 3/2013 | Powell et al. |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| D680,646 S | 4/2013 | Hunt et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,211 B2 | 4/2013 | Baroud |
| 8,409,222 B2 | 4/2013 | Whitfield et al. |
| 8,409,223 B2 | 4/2013 | Sorrentino et al. |
| 8,409,234 B2 | 4/2013 | Stahler et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,419,755 B2 | 4/2013 | Deem et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,439,830 B2 | 5/2013 | McKinley et al. |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |

(56) References Cited

U.S. PATENT DOCUMENTS

| | | |
|---|---|---|
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| D686,244 S | 7/2013 | Moriya et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,486,047 B2 | 7/2013 | Stopek |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,852 B2 | 7/2013 | Viola |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,787 B2 | 9/2013 | Ludwin et al. |
| 8,523,881 B2 | 9/2013 | Cabiri et al. |
| 8,523,882 B2 | 9/2013 | Huitema et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,531,153 B2 | 9/2013 | Baarman et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,598 B2 | 11/2013 | Razzaque et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,591,400 B2 | 11/2013 | Sugiyama |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,431 B2 | 12/2013 | Timm et al. |
| 8,617,155 B2 | 12/2013 | Johnson et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |

(56) References Cited

U.S. PATENT DOCUMENTS

| | | |
|---|---|---|
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Bale et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |

(56) References Cited

U.S. PATENT DOCUMENTS

| | | |
|---|---|---|
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,098 B2 | 8/2014 | Long |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,466 B2 | 9/2014 | Cummings et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,004 B2 | 9/2014 | Holsten et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,845,622 B2 | 9/2014 | Paik et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,855,822 B2 | 10/2014 | Bartol et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Roßkamp et al. |
| 8,869,913 B2 | 10/2014 | Matthias et al. |
| 8,870,049 B2 | 10/2014 | Amid et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,871,829 B2 | 10/2014 | Gerold et al. |
| 8,875,971 B2 | 11/2014 | Hall et al. |
| 8,875,972 B2 | 11/2014 | Weisenburgh, II et al. |
| 8,876,698 B2 | 11/2014 | Sakamoto et al. |
| 8,876,857 B2 | 11/2014 | Burbank |
| 8,876,858 B2 | 11/2014 | Braun |
| 8,882,660 B2 | 11/2014 | Phee et al. |
| 8,882,792 B2 | 11/2014 | Dietz et al. |
| 8,884,560 B2 | 11/2014 | Ito |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,915,842 B2 | 12/2014 | Weisenburgh, II et al. |
| 8,915,940 B2 | 12/2014 | Steege et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,931,692 B2 | 1/2015 | Sancak |
| 8,936,614 B2 | 1/2015 | Allen, IV |
| 8,937,408 B2 | 1/2015 | Ganem et al. |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |

(56) References Cited

U.S. PATENT DOCUMENTS

| | | |
|---|---|---|
| 8,945,098 B2 | 2/2015 | Seibold et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,961,542 B2 | 2/2015 | Whitfield et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,004,799 B1 | 4/2015 | Tibbits |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,468 B2 | 5/2015 | Scarfogliero et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,028,529 B2 | 5/2015 | Fox et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,039,736 B2 | 5/2015 | Scirica et al. |
| 9,040,062 B2 | 5/2015 | Maeda et al. |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,070,068 B2 | 6/2015 | Coveley et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,586 B2 | 7/2015 | Hafner et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |

(56) References Cited

U.S. PATENT DOCUMENTS

| | | |
|---|---|---|
| 9,095,642 B2 | 8/2015 | Harder et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,359 B2 | 8/2015 | Smith et al. |
| 9,101,385 B2 | 8/2015 | Shelton, IV et al. |
| 9,101,475 B2 | 8/2015 | Wei et al. |
| 9,101,621 B2 | 8/2015 | Zeldis |
| 9,107,663 B2 | 8/2015 | Swensgard |
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,875 B2 | 8/2015 | Viola et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,154,189 B2 | 10/2015 | Von Novak et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,167,960 B2 | 10/2015 | Yamaguchi et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,832 B2 | 11/2015 | Diolaiti |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| D746,459 S | 12/2015 | Kaercher et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,211,125 B2 | 12/2015 | Boulnois et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Dugue et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,686 B2 | 1/2016 | Blair |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,226,799 B2 | 1/2016 | Lightcap et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,268 B2 | 2/2016 | Behnke, II et al. |
| 9,259,274 B2 | 2/2016 | Prisco |
| 9,259,275 B2 | 2/2016 | Burbank |

(56) References Cited

U.S. PATENT DOCUMENTS

| | | |
|---|---|---|
| 9,261,172 B2 | 2/2016 | Solomon et al. |
| 9,265,500 B2 | 2/2016 | Sorrentino et al. |
| 9,265,510 B2 | 2/2016 | Dietzel et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,283,334 B2 | 3/2016 | Mantell et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,339,342 B2 | 5/2016 | Prisco et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hall et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,223 B2 | 6/2016 | Scirica |
| 9,364,226 B2 | 6/2016 | Zemlok et al. |
| 9,364,228 B2 | 6/2016 | Straehnz et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,361 B2 | 6/2016 | Viola et al. |
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,385,640 B2 | 7/2016 | Sun et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,369 B1 | 7/2016 | Whitehurst et al. |
| 9,396,669 B2 | 7/2016 | Karkanias et al. |
| 9,398,905 B2 | 7/2016 | Martin |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |

(56) References Cited

U.S. PATENT DOCUMENTS

| | | |
|---|---|---|
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,402,682 B2 | 8/2016 | Worrell et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| 9,429,204 B2 | 8/2016 | Stefan et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Res et al. |
| 9,451,958 B2 | 9/2016 | Shelton, IV et al. |
| 9,452,020 B2 | 9/2016 | Griffiths et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,012 B2 | 10/2016 | Bonutti et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,513 B2 | 10/2016 | Ishida et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,477,649 B1 | 10/2016 | Davidson et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,515,366 B2 | 12/2016 | Herbsommer et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,005 B2 | 12/2016 | Williams et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,549,750 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,554,854 B2 | 1/2017 | Yates et al. |
| 9,559,624 B2 | 1/2017 | Philipp |
| 9,561,013 B2 | 2/2017 | Tsuchiya |
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,561,072 B2 | 2/2017 | Ko |
| 9,561,082 B2 | 2/2017 | Yen et al. |
| 9,566,061 B2 | 2/2017 | Aronhalt et al. |
| 9,566,062 B2 | 2/2017 | Boudreaux |
| 9,566,064 B2 | 2/2017 | Williams et al. |
| 9,566,065 B2 | 2/2017 | Knodel |
| 9,566,067 B2 | 2/2017 | Milliman et al. |
| 9,572,552 B1 | 2/2017 | Bodor et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |

(56) References Cited

U.S. PATENT DOCUMENTS

| | | |
|---|---|---|
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,651,032 B2 | 5/2017 | Weaver et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,661,991 B2 | 5/2017 | Glossop |
| 9,662,108 B2 | 5/2017 | Williams |
| 9,662,110 B2 | 5/2017 | Huang et al. |
| 9,662,111 B2 | 5/2017 | Holsten et al. |
| 9,662,116 B2 | 5/2017 | Smith et al. |
| 9,662,130 B2 | 5/2017 | Bartels et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,315 B2 | 7/2017 | Chen et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,700,334 B2 | 7/2017 | Hinman et al. |
| 9,700,381 B2 | 7/2017 | Girbau |
| 9,702,823 B2 | 7/2017 | Maher et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,466 B2 | 7/2017 | Kostrzewski |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |

(56) References Cited

U.S. PATENT DOCUMENTS

| | | |
|---|---|---|
| 9,730,757 B2 | 8/2017 | Brudniok |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,298 B2 | 8/2017 | Isbell, Jr. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,323 B2 | 8/2017 | Thapliyal et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,751,176 B2 | 9/2017 | McRoberts et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,759,265 B2 | 9/2017 | Bodtker |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,795,449 B2 | 10/2017 | Baldwin |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,429 B2 | 12/2017 | Weisenburgh, II et al. |
| 9,839,480 B2 | 12/2017 | Pribanic et al. |
| 9,839,481 B2 | 12/2017 | Blumenkranz et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,617 B2 | 1/2018 | Ma |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |

(56) References Cited

U.S. PATENT DOCUMENTS

| | | |
|---|---|---|
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,358 B2 | 2/2018 | Faller et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,117 B2 | 4/2018 | Hathaway et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,740 B2 | 5/2018 | Krause et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| 10,004,552 B1 | 6/2018 | Kleyman et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,046,904 B2 | 8/2018 | Evans et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |

(56) References Cited

U.S. PATENT DOCUMENTS

| | | |
|---|---|---|
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,642 B2 | 9/2018 | Marczyk et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,126 B2 | 10/2018 | Sauer |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter, III et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,123,845 B2 | 11/2018 | Yeung |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| 10,136,949 B2 | 11/2018 | Felder et al. |
| D835,659 S | 12/2018 | Anzures et al. |
| D836,124 S | 12/2018 | Fan |
| 10,143,474 B2 | 12/2018 | Bucciaglia et al. |
| 10,146,423 B1 | 12/2018 | Reed et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,161,816 B2 | 12/2018 | Jackson et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,911 B2 | 2/2019 | Miller et al. |
| 10,194,912 B2 | 2/2019 | Scheib et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |

(56) References Cited

U.S. PATENT DOCUMENTS

| | | |
|---|---|---|
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,645 B2 | 4/2019 | Kostrzewski |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,363 B2 | 4/2019 | Worrell et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,698 B2 | 5/2019 | Cappola et al. |
| 10,285,699 B2 | 5/2019 | Vendely et al. |
| 10,285,700 B2 | 5/2019 | Scheib |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,285,763 B2 | 5/2019 | Vale et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,578 B2 | 6/2019 | Leimbach et al. |
| 10,314,579 B2 | 6/2019 | Chowaniec et al. |
| 10,314,580 B2 | 6/2019 | Scheib et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |

(56) References Cited

U.S. PATENT DOCUMENTS

| | | |
|---|---|---|
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,866 B2 | 8/2019 | Wang et al. |
| 10,368,867 B2 | 8/2019 | Harris et al. |
| 10,368,892 B2 | 8/2019 | Stulen et al. |
| 10,374,544 B2 | 8/2019 | Yokoyama et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,631 B2 | 8/2019 | Collings et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D859,466 S | 9/2019 | Okada et al. |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,155 B2 | 9/2019 | Inoue |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,551 B2 | 9/2019 | Calderoni |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| D865,174 S | 10/2019 | Auld et al. |
| D865,175 S | 10/2019 | Widenhouse et al. |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,842 B2 | 10/2019 | Amariglio et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,482,292 B2 | 11/2019 | Clouser et al. |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |

(56) References Cited

U.S. PATENT DOCUMENTS

| | | |
|---|---|---|
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,000 B2 | 12/2019 | Swayze et al. |
| 10,500,004 B2 | 12/2019 | Hanuschik et al. |
| 10,500,309 B2 | 12/2019 | Shah et al. |
| 10,507,034 B2 | 12/2019 | Timm |
| 10,508,720 B2 | 12/2019 | Nicholas |
| 10,512,461 B2 | 12/2019 | Gupta et al. |
| 10,512,462 B2 | 12/2019 | Felder et al. |
| 10,512,464 B2 | 12/2019 | Park et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,524,870 B2 | 1/2020 | Saraliev et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderoni et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,412 B2 | 2/2020 | Bookbinder et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,493 B2 | 2/2020 | Blase et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,231 B2 | 3/2020 | Sgroi, Jr. et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,589,410 B2 | 3/2020 | Aho |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |
| 10,595,929 B2 | 3/2020 | Boudreaux et al. |
| 10,603,036 B2 | 3/2020 | Hunter et al. |
| 10,603,039 B2 | 3/2020 | Vendely et al. |
| 10,603,041 B2 | 3/2020 | Miller et al. |
| 10,603,117 B2 | 3/2020 | Schings et al. |
| 10,603,128 B2 | 3/2020 | Zergiebel et al. |
| D882,783 S | 4/2020 | Shelton, IV et al. |
| 10,610,224 B2 | 4/2020 | Shelton, IV et al. |
| 10,610,225 B2 | 4/2020 | Reed et al. |
| 10,610,236 B2 | 4/2020 | Baril |
| 10,610,313 B2 | 4/2020 | Bailey et al. |
| 10,610,346 B2 | 4/2020 | Schwartz |
| 10,617,411 B2 | 4/2020 | Williams |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,416 B2 | 4/2020 | Leimbach et al. |
| 10,617,417 B2 | 4/2020 | Baxter, III et al. |
| 10,617,418 B2 | 4/2020 | Barton et al. |
| 10,617,420 B2 | 4/2020 | Shelton, IV et al. |
| 10,617,438 B2 | 4/2020 | O'Keefe et al. |
| 10,624,616 B2 | 4/2020 | Mukherjee et al. |
| 10,624,630 B2 | 4/2020 | Deville et al. |
| 10,624,633 B2 | 4/2020 | Shelton, IV et al. |
| 10,624,634 B2 | 4/2020 | Shelton, IV et al. |
| 10,624,635 B2 | 4/2020 | Harris et al. |
| 10,624,709 B2 | 4/2020 | Remm |
| 10,624,861 B2 | 4/2020 | Widenhouse et al. |
| 10,625,062 B2 | 4/2020 | Matlock et al. |
| 10,631,857 B2 | 4/2020 | Kostrzewski |
| 10,631,858 B2 | 4/2020 | Burbank |
| 10,631,859 B2 | 4/2020 | Shelton, IV et al. |
| 10,631,860 B2 | 4/2020 | Bakos et al. |
| 10,636,104 B2 | 4/2020 | Mazar et al. |
| 10,639,018 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,089 B2 | 5/2020 | Manwaring et al. |
| 10,639,115 B2 | 5/2020 | Shelton, IV et al. |
| 10,642,633 B1 | 5/2020 | Chopra et al. |
| 10,645,905 B2 | 5/2020 | Gandola et al. |
| 10,646,220 B2 | 5/2020 | Shelton, IV et al. |
| 10,646,292 B2 | 5/2020 | Solomon et al. |
| 10,653,413 B2 | 5/2020 | Worthington et al. |
| 10,653,417 B2 | 5/2020 | Shelton, IV et al. |
| 10,653,435 B2 | 5/2020 | Shelton, IV et al. |
| 10,660,640 B2 | 5/2020 | Yates et al. |
| 10,667,408 B2 | 5/2020 | Sgroi, Jr. et al. |
| D888,953 S | 6/2020 | Baxter, III et al. |
| 10,667,808 B2 | 6/2020 | Baxter, III et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,818 B2 | 6/2020 | McLain et al. |
| 10,674,895 B2 | 6/2020 | Yeung et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,028 B2 | 6/2020 | Shelton, IV et al. |
| 10,675,035 B2 | 6/2020 | Zingman |
| 10,675,080 B2 | 6/2020 | Woloszko et al. |
| 10,675,102 B2 | 6/2020 | Forgione et al. |
| 10,677,035 B2 | 6/2020 | Balan et al. |
| 10,682,134 B2 | 6/2020 | Shelton, IV et al. |
| 10,682,136 B2 | 6/2020 | Harris et al. |
| 10,682,137 B2 | 6/2020 | Stokes et al. |
| 10,682,138 B2 | 6/2020 | Shelton, IV et al. |
| 10,682,141 B2 | 6/2020 | Moore et al. |
| 10,682,142 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |

(56) References Cited

U.S. PATENT DOCUMENTS

| | | |
|---|---|---|
| 10,687,812 B2 | 6/2020 | Shelton, IV et al. |
| 10,687,813 B2 | 6/2020 | Shelton, IV et al. |
| 10,687,817 B2 | 6/2020 | Shelton, IV et al. |
| 10,687,819 B2 | 6/2020 | Stokes et al. |
| 10,687,904 B2 | 6/2020 | Harris et al. |
| 10,695,053 B2 | 6/2020 | Hess et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,062 B2 | 6/2020 | Leimbach et al. |
| 10,695,063 B2 | 6/2020 | Morgan et al. |
| 10,695,074 B2 | 6/2020 | Carusillo |
| 10,695,081 B2 | 6/2020 | Shelton, IV et al. |
| 10,695,119 B2 | 6/2020 | Smith |
| 10,695,123 B2 | 6/2020 | Allen, IV |
| 10,695,187 B2 | 6/2020 | Moskowitz et al. |
| D890,784 S | 7/2020 | Shelton, IV et al. |
| 10,702,266 B2 | 7/2020 | Parihar et al. |
| 10,702,267 B2 | 7/2020 | Hess et al. |
| 10,702,270 B2 | 7/2020 | Shelton, IV et al. |
| 10,702,271 B2 | 7/2020 | Aranyi et al. |
| 10,705,660 B2 | 7/2020 | Xiao |
| 10,709,446 B2 | 7/2020 | Harris et al. |
| 10,709,468 B2 | 7/2020 | Shelton, IV et al. |
| 10,709,469 B2 | 7/2020 | Shelton, IV et al. |
| 10,709,496 B2 | 7/2020 | Moua et al. |
| 10,716,563 B2 | 7/2020 | Shelton, IV et al. |
| 10,716,565 B2 | 7/2020 | Shelton, IV et al. |
| 10,716,568 B2 | 7/2020 | Hall et al. |
| 10,716,614 B2 | 7/2020 | Yates et al. |
| 10,717,179 B2 | 7/2020 | Koenig et al. |
| 10,722,232 B2 | 7/2020 | Yates et al. |
| 10,722,233 B2 | 7/2020 | Wellman |
| 10,722,292 B2 | 7/2020 | Arya et al. |
| 10,722,293 B2 | 7/2020 | Arya et al. |
| 10,722,317 B2 | 7/2020 | Ward et al. |
| D893,717 S | 8/2020 | Messerly et al. |
| 10,729,432 B2 | 8/2020 | Shelton, IV et al. |
| 10,729,434 B2 | 8/2020 | Harris et al. |
| 10,729,435 B2 | 8/2020 | Richard |
| 10,729,436 B2 | 8/2020 | Shelton, IV et al. |
| 10,729,443 B2 | 8/2020 | Cabrera et al. |
| 10,729,458 B2 | 8/2020 | Stoddard et al. |
| 10,729,501 B2 | 8/2020 | Leimbach et al. |
| 10,729,509 B2 | 8/2020 | Shelton, IV et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,630 B2 | 8/2020 | Huang et al. |
| 10,736,633 B2 | 8/2020 | Vendely et al. |
| 10,736,634 B2 | 8/2020 | Shelton, IV et al. |
| 10,736,636 B2 | 8/2020 | Baxter, III et al. |
| 10,736,644 B2 | 8/2020 | Windolf et al. |
| 10,736,702 B2 | 8/2020 | Harris et al. |
| 10,737,398 B2 | 8/2020 | Remirez et al. |
| 10,743,849 B2 | 8/2020 | Shelton, IV et al. |
| 10,743,850 B2 | 8/2020 | Hibner et al. |
| 10,743,851 B2 | 8/2020 | Swayze et al. |
| 10,743,868 B2 | 8/2020 | Shelton, IV et al. |
| 10,743,870 B2 | 8/2020 | Hall et al. |
| 10,743,872 B2 | 8/2020 | Leimbach et al. |
| 10,743,873 B2 | 8/2020 | Overmyer et al. |
| 10,743,874 B2 | 8/2020 | Shelton, IV et al. |
| 10,743,875 B2 | 8/2020 | Shelton, IV et al. |
| 10,743,877 B2 | 8/2020 | Shelton, IV et al. |
| 10,743,930 B2 | 8/2020 | Nagtegaal |
| 10,751,048 B2 | 8/2020 | Whitman et al. |
| 10,751,053 B2 | 8/2020 | Harris et al. |
| 10,751,076 B2 | 8/2020 | Laurent et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,233 B2 | 9/2020 | Scheib et al. |
| 10,758,259 B2 | 9/2020 | Demmy et al. |
| 10,765,425 B2 | 9/2020 | Yates et al. |
| 10,765,427 B2 | 9/2020 | Shelton, IV et al. |
| 10,765,429 B2 | 9/2020 | Leimbach et al. |
| 10,765,430 B2 | 9/2020 | Wixey |
| 10,765,432 B2 | 9/2020 | Moore et al. |
| 10,765,442 B2 | 9/2020 | Strobl |
| 10,772,625 B2 | 9/2020 | Shelton, IV et al. |
| 10,772,628 B2 | 9/2020 | Chen et al. |
| 10,772,629 B2 | 9/2020 | Shelton, IV et al. |
| 10,772,630 B2 | 9/2020 | Wixey |
| 10,772,631 B2 | 9/2020 | Zergiebel et al. |
| 10,772,632 B2 | 9/2020 | Kostrzewski |
| 10,772,651 B2 | 9/2020 | Shelton, IV et al. |
| 10,779,818 B2 | 9/2020 | Zemlok et al. |
| 10,779,820 B2 | 9/2020 | Harris et al. |
| 10,779,821 B2 | 9/2020 | Harris et al. |
| 10,779,822 B2 | 9/2020 | Yates et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,826 B2 | 9/2020 | Shelton, IV et al. |
| 10,779,903 B2 | 9/2020 | Wise et al. |
| 10,780,539 B2 | 9/2020 | Shelton, IV et al. |
| 10,786,248 B2 | 9/2020 | Rousseau et al. |
| 10,786,253 B2 | 9/2020 | Shelton, IV et al. |
| 10,786,255 B2 | 9/2020 | Hodgkinson et al. |
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,910 B2 | 11/2020 | Gasparovich et al. |
| 10,820,939 B2 | 11/2020 | Sartor |
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| 10,842,523 B2 | 11/2020 | Shelton, IV et al. |
| D904,612 S | 12/2020 | Wynn et al. |
| D904,613 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,663 B2 | 12/2020 | Shelton, IV et al. |

(56) References Cited

U.S. PATENT DOCUMENTS

| | | |
|---|---|---|
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti, III et al. |
| 10,874,396 B2 | 12/2020 | Moore et al. |
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| D908,216 S | 1/2021 | Messerly et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, IV et al. |
| 10,888,322 B2 | 1/2021 | Morgan et al. |
| 10,888,323 B2 | 1/2021 | Chen et al. |
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Blasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,919,156 B2 | 2/2021 | Roberts et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,726 B2 | 3/2021 | Chowaniec |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,726 B2 | 3/2021 | Williams et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| 10,959,797 B2 | 3/2021 | Licht et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 10,973,515 B2 | 4/2021 | Harris et al. |
| 10,973,516 B2 | 4/2021 | Shelton, IV et al. |
| 10,973,517 B2 | 4/2021 | Wixey |
| 10,973,519 B2 | 4/2021 | Weir et al. |
| 10,973,520 B2 | 4/2021 | Shelton, IV et al. |
| 10,980,534 B2 | 4/2021 | Yates et al. |
| 10,980,535 B2 | 4/2021 | Yates et al. |
| 10,980,536 B2 | 4/2021 | Weaner et al. |
| 10,980,537 B2 | 4/2021 | Shelton, IV et al. |
| 10,980,538 B2 | 4/2021 | Nalagatla et al. |
| 10,980,539 B2 | 4/2021 | Harris et al. |
| 10,980,560 B2 | 4/2021 | Shelton, IV et al. |
| 10,983,646 B2 | 4/2021 | Yoon et al. |
| 10,987,102 B2 | 4/2021 | Gonzalez et al. |
| 10,987,178 B2 | 4/2021 | Shelton, IV et al. |
| 10,993,713 B2 | 5/2021 | Shelton, IV et al. |
| 10,993,715 B2 | 5/2021 | Shelton, IV et al. |
| 10,993,717 B2 | 5/2021 | Shelton, IV et al. |
| 11,000,274 B2 | 5/2021 | Shelton, IV et al. |
| 11,000,275 B2 | 5/2021 | Shelton, IV et al. |
| 11,000,277 B2 | 5/2021 | Giordano et al. |
| 11,000,278 B2 | 5/2021 | Shelton, IV et al. |
| 11,005,291 B2 | 5/2021 | Calderoni |
| 11,006,951 B2 | 5/2021 | Giordano et al. |
| 11,006,955 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,511 B2 | 5/2021 | Huang et al. |
| 11,013,552 B2 | 5/2021 | Widenhouse et al. |
| 11,013,563 B2 | 5/2021 | Shelton, IV et al. |
| 11,020,016 B2 | 6/2021 | Wallace et al. |
| 11,020,113 B2 | 6/2021 | Shelton, IV et al. |
| 11,020,115 B2 | 6/2021 | Scheib et al. |
| 11,026,678 B2 | 6/2021 | Overmyer et al. |
| 11,026,680 B2 | 6/2021 | Shelton, IV et al. |
| 11,026,684 B2 | 6/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,033,267 B2 | 6/2021 | Shelton, IV et al. |
| 11,039,834 B2 | 6/2021 | Harris et al. |
| 11,039,836 B2 | 6/2021 | Shelton, IV et al. |
| 11,039,837 B2 | 6/2021 | Shelton, IV et al. |
| 11,039,849 B2 | 6/2021 | Bucciaglia et al. |
| 11,045,189 B2 | 6/2021 | Yates et al. |
| 11,045,191 B2 | 6/2021 | Shelton, IV et al. |
| 11,045,192 B2 | 6/2021 | Harris et al. |
| 11,045,196 B2 | 6/2021 | Olson et al. |
| 11,045,197 B2 | 6/2021 | Shelton, IV et al. |
| 11,045,199 B2 | 6/2021 | Mozdzierz et al. |
| 11,051,807 B2 | 7/2021 | Shelton, IV et al. |
| 11,051,810 B2 | 7/2021 | Harris et al. |
| 11,051,811 B2 | 7/2021 | Shelton, IV et al. |
| 11,051,813 B2 | 7/2021 | Shelton, IV et al. |
| 11,051,836 B2 | 7/2021 | Shelton, IV et al. |
| 11,051,840 B2 | 7/2021 | Shelton, IV et al. |
| 11,051,873 B2 | 7/2021 | Wiener et al. |
| 11,058,418 B2 | 7/2021 | Shelton, IV et al. |
| 11,058,420 B2 | 7/2021 | Shelton, IV et al. |

(56) References Cited

U.S. PATENT DOCUMENTS

| | | |
|---|---|---|
| 11,058,422 B2 | 7/2021 | Harris et al. |
| 11,058,423 B2 | 7/2021 | Shelton, IV et al. |
| 11,058,425 B2 | 7/2021 | Widenhouse et al. |
| 11,058,426 B2 | 7/2021 | Nalagatla et al. |
| 11,058,498 B2 | 7/2021 | Shelton, IV et al. |
| 11,064,997 B2 | 7/2021 | Shelton, IV et al. |
| 11,064,998 B2 | 7/2021 | Shelton, IV |
| 11,065,048 B2 | 7/2021 | Messerly et al. |
| 11,069,012 B2 | 7/2021 | Shelton, IV et al. |
| 11,071,542 B2 | 7/2021 | Chen et al. |
| 11,071,543 B2 | 7/2021 | Shelton, IV et al. |
| 11,071,545 B2 | 7/2021 | Baber et al. |
| 11,071,554 B2 | 7/2021 | Parfett et al. |
| 11,071,560 B2 | 7/2021 | Deck et al. |
| 11,076,853 B2 | 8/2021 | Parfett et al. |
| 11,076,854 B2 | 8/2021 | Baber et al. |
| 11,076,921 B2 | 8/2021 | Shelton, IV et al. |
| 11,076,929 B2 | 8/2021 | Shelton, IV et al. |
| 11,083,452 B2 | 8/2021 | Schmid et al. |
| 11,083,453 B2 | 8/2021 | Shelton, IV et al. |
| 11,083,454 B2 | 8/2021 | Harris et al. |
| 11,083,456 B2 | 8/2021 | Shelton, IV et al. |
| 11,083,457 B2 | 8/2021 | Shelton, IV et al. |
| 11,083,458 B2 | 8/2021 | Harris et al. |
| 11,090,045 B2 | 8/2021 | Shelton, IV |
| 11,090,046 B2 | 8/2021 | Shelton, IV et al. |
| 11,090,047 B2 | 8/2021 | Shelton, IV et al. |
| 11,090,048 B2 | 8/2021 | Fanelli et al. |
| 11,090,075 B2 | 8/2021 | Hunter et al. |
| 11,096,688 B2 | 8/2021 | Shelton, IV et al. |
| 11,096,689 B2 | 8/2021 | Overmyer et al. |
| 11,096,750 B2 | 8/2021 | Mayer-Ullmann et al. |
| 11,100,631 B2 | 8/2021 | Yates et al. |
| 11,103,241 B2 | 8/2021 | Yates et al. |
| 11,103,248 B2 | 8/2021 | Shelton, IV et al. |
| 11,103,268 B2 | 8/2021 | Shelton, IV et al. |
| 11,103,269 B2 | 8/2021 | Shelton, IV et al. |
| 11,109,858 B2 | 9/2021 | Shelton, IV et al. |
| 11,109,859 B2 | 9/2021 | Overmyer et al. |
| 11,109,860 B2 | 9/2021 | Shelton, IV et al. |
| 11,109,866 B2 | 9/2021 | Shelton, IV et al. |
| 11,109,878 B2 | 9/2021 | Shelton, IV et al. |
| 11,109,925 B2 | 9/2021 | Cooper et al. |
| 11,116,485 B2 | 9/2021 | Scheib et al. |
| 11,116,502 B2 | 9/2021 | Shelton, IV et al. |
| 11,116,594 B2 | 9/2021 | Beardsley |
| 11,123,069 B2 | 9/2021 | Baxter, III et al. |
| 11,123,070 B2 | 9/2021 | Shelton, IV et al. |
| 11,129,611 B2 | 9/2021 | Shelton, IV et al. |
| 11,129,613 B2 | 9/2021 | Harris et al. |
| 11,129,615 B2 | 9/2021 | Scheib et al. |
| 11,129,616 B2 | 9/2021 | Shelton, IV et al. |
| 11,129,634 B2 | 9/2021 | Scheib et al. |
| 11,129,636 B2 | 9/2021 | Shelton, IV et al. |
| 11,129,666 B2 | 9/2021 | Messerly et al. |
| 11,129,680 B2 | 9/2021 | Shelton, IV et al. |
| 11,132,462 B2 | 9/2021 | Shelton, IV et al. |
| 11,133,106 B2 | 9/2021 | Shelton, IV et al. |
| 11,134,938 B2 | 10/2021 | Timm et al. |
| 11,134,940 B2 | 10/2021 | Shelton, IV et al. |
| 11,134,942 B2 | 10/2021 | Harris et al. |
| 11,134,943 B2 | 10/2021 | Giordano et al. |
| 11,134,944 B2 | 10/2021 | Wise et al. |
| 11,134,947 B2 | 10/2021 | Shelton, IV et al. |
| 11,135,352 B2 | 10/2021 | Shelton, IV et al. |
| 11,141,153 B2 | 10/2021 | Shelton, IV et al. |
| 11,141,154 B2 | 10/2021 | Shelton, IV et al. |
| 11,141,155 B2 | 10/2021 | Shelton, IV |
| 11,141,156 B2 | 10/2021 | Shelton, IV |
| 11,141,159 B2 | 10/2021 | Scheib et al. |
| 11,141,160 B2 | 10/2021 | Shelton, IV et al. |
| 11,147,547 B2 | 10/2021 | Shelton, IV et al. |
| 11,147,549 B2 | 10/2021 | Timm et al. |
| 11,147,551 B2 | 10/2021 | Shelton, IV |
| 11,147,553 B2 | 10/2021 | Shelton, IV |
| 11,147,554 B2 | 10/2021 | Aronhalt et al. |
| 11,154,296 B2 | 10/2021 | Aronhalt et al. |
| 11,154,297 B2 | 10/2021 | Swayze et al. |
| 11,154,298 B2 | 10/2021 | Timm et al. |
| 11,154,299 B2 | 10/2021 | Shelton, IV et al. |
| 11,154,300 B2 | 10/2021 | Nalagatla et al. |
| 11,154,301 B2 | 10/2021 | Beckman et al. |
| 11,160,551 B2 | 11/2021 | Shelton, IV et al. |
| 11,160,553 B2 | 11/2021 | Simms et al. |
| 11,160,601 B2 | 11/2021 | Worrell et al. |
| 11,166,716 B2 | 11/2021 | Shelton, IV et al. |
| 11,166,717 B2 | 11/2021 | Shelton, IV et al. |
| 11,166,720 B2 | 11/2021 | Giordano et al. |
| 11,166,772 B2 | 11/2021 | Shelton, IV et al. |
| 11,166,773 B2 | 11/2021 | Ragosta et al. |
| 11,172,580 B2 | 11/2021 | Gaertner, II |
| 11,172,927 B2 | 11/2021 | Shelton, IV |
| 11,172,929 B2 | 11/2021 | Shelton, IV |
| 11,179,150 B2 | 11/2021 | Yates et al. |
| 11,179,151 B2 | 11/2021 | Shelton, IV et al. |
| 11,179,152 B2 | 11/2021 | Morgan et al. |
| 11,179,153 B2 | 11/2021 | Shelton, IV |
| 11,179,155 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,191,543 B2 | 12/2021 | Overmyer et al. |
| 11,191,545 B2 | 12/2021 | Vendely et al. |
| 11,197,668 B2 | 12/2021 | Shelton, IV et al. |
| 11,197,670 B2 | 12/2021 | Shelton, IV et al. |
| 11,197,671 B2 | 12/2021 | Shelton, IV et al. |
| 11,197,672 B2 | 12/2021 | Dunki-Jacobs et al. |
| 11,202,570 B2 | 12/2021 | Shelton, IV et al. |
| 11,202,631 B2 | 12/2021 | Shelton, IV et al. |
| 11,202,633 B2 | 12/2021 | Harris et al. |
| 11,203,114 B2 | 12/2021 | Kikuchi |
| 11,207,064 B2 | 12/2021 | Shelton, IV et al. |
| 11,207,065 B2 | 12/2021 | Harris et al. |
| 11,207,067 B2 | 12/2021 | Shelton, IV et al. |
| 11,207,089 B2 | 12/2021 | Kostrzewski et al. |
| 11,207,090 B2 | 12/2021 | Shelton, IV et al. |
| 11,207,146 B2 | 12/2021 | Shelton, IV et al. |
| 11,213,293 B2 | 1/2022 | Worthington et al. |
| 11,213,294 B2 | 1/2022 | Shelton, IV et al. |
| 11,213,302 B2 | 1/2022 | Parfett et al. |
| 11,213,359 B2 | 1/2022 | Shelton, IV et al. |
| 11,219,453 B2 | 1/2022 | Shelton, IV et al. |
| 11,219,454 B2 | 1/2022 | Schings et al. |
| 11,219,455 B2 | 1/2022 | Shelton, IV et al. |
| 11,224,423 B2 | 1/2022 | Shelton, IV et al. |
| 11,224,426 B2 | 1/2022 | Shelton, IV et al. |
| 11,224,427 B2 | 1/2022 | Shelton, IV et al. |
| 11,224,428 B2 | 1/2022 | Scott et al. |
| 11,224,454 B2 | 1/2022 | Shelton, IV et al. |
| 11,224,497 B2 | 1/2022 | Shelton, IV et al. |
| 11,229,436 B2 | 1/2022 | Shelton, IV et al. |
| 11,229,437 B2 | 1/2022 | Shelton, IV et al. |
| 11,234,698 B2 | 2/2022 | Shelton, IV et al. |
| 11,234,700 B2 | 2/2022 | Ragosta et al. |
| 11,241,229 B2 | 2/2022 | Shelton, IV et al. |
| 11,241,230 B2 | 2/2022 | Shelton, IV et al. |
| 11,241,235 B2 | 2/2022 | Shelton, IV et al. |
| 11,246,590 B2 | 2/2022 | Swayze et al. |
| 11,246,616 B2 | 2/2022 | Shelton, IV et al. |
| 11,246,618 B2 | 2/2022 | Hall et al. |
| 11,246,678 B2 | 2/2022 | Shelton, IV et al. |
| 11,253,254 B2 | 2/2022 | Kimball et al. |
| 11,253,256 B2 | 2/2022 | Harris et al. |
| 11,259,799 B2 | 3/2022 | Overmyer et al. |
| 11,259,803 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,406 B2 | 3/2022 | Leimbach et al. |
| 11,266,409 B2 | 3/2022 | Huitema et al. |
| 11,266,410 B2 | 3/2022 | Shelton, IV et al. |
| 11,266,468 B2 | 3/2022 | Shelton, IV et al. |

(56) References Cited

U.S. PATENT DOCUMENTS

| | | |
|---|---|---|
| 11,272,927 B2 | 3/2022 | Swayze et al. |
| 11,272,928 B2 | 3/2022 | Shelton, IV |
| 11,272,931 B2 | 3/2022 | Boudreaux et al. |
| 11,272,938 B2 | 3/2022 | Shelton, IV et al. |
| 11,278,279 B2 | 3/2022 | Morgan et al. |
| 11,278,280 B2 | 3/2022 | Shelton, IV et al. |
| 11,278,284 B2 | 3/2022 | Shelton, IV et al. |
| 11,284,890 B2 | 3/2022 | Nalagatla et al. |
| 11,284,891 B2 | 3/2022 | Shelton, IV et al. |
| 11,284,898 B2 | 3/2022 | Baxter, III et al. |
| 11,284,953 B2 | 3/2022 | Shelton, IV et al. |
| 11,291,440 B2 | 4/2022 | Harris et al. |
| 11,291,441 B2 | 4/2022 | Giordano et al. |
| 11,291,443 B2 | 4/2022 | Viola et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,449 B2 | 4/2022 | Swensgard et al. |
| 11,291,451 B2 | 4/2022 | Shelton, IV |
| 11,291,465 B2 | 4/2022 | Parihar et al. |
| 11,291,510 B2 | 4/2022 | Shelton, IV et al. |
| 11,298,125 B2 | 4/2022 | Ming et al. |
| 11,298,127 B2 | 4/2022 | Shelton, IV |
| 11,298,128 B2 | 4/2022 | Messerly et al. |
| 11,298,129 B2 | 4/2022 | Bakos et al. |
| 11,298,130 B2 | 4/2022 | Bakos et al. |
| 11,298,132 B2 | 4/2022 | Shelton, IV et al. |
| 11,298,134 B2 | 4/2022 | Huitema et al. |
| 11,304,695 B2 | 4/2022 | Shelton, IV et al. |
| 11,304,696 B2 | 4/2022 | Shelton, IV et al. |
| 11,304,697 B2 | 4/2022 | Fanelli et al. |
| 11,304,699 B2 | 4/2022 | Shelton, IV et al. |
| 11,304,704 B2 | 4/2022 | Thomas et al. |
| 11,311,290 B2 | 4/2022 | Shelton, IV et al. |
| 11,311,292 B2 | 4/2022 | Shelton, IV et al. |
| 11,311,294 B2 | 4/2022 | Swayze et al. |
| 11,311,295 B2 | 4/2022 | Wingardner et al. |
| 11,311,342 B2 | 4/2022 | Parihar et al. |
| D950,728 S | 5/2022 | Bakos et al. |
| D952,144 S | 5/2022 | Boudreaux |
| 11,317,910 B2 | 5/2022 | Miller et al. |
| 11,317,912 B2 | 5/2022 | Jenkins et al. |
| 11,317,913 B2 | 5/2022 | Shelton, IV et al. |
| 11,317,915 B2 | 5/2022 | Boudreaux et al. |
| 11,317,917 B2 | 5/2022 | Shelton, IV et al. |
| 11,317,919 B2 | 5/2022 | Shelton, IV et al. |
| 11,317,978 B2 | 5/2022 | Cameron et al. |
| 11,324,501 B2 | 5/2022 | Shelton, IV et al. |
| 11,324,506 B2 | 5/2022 | Beckman et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,691 B2 | 5/2022 | Widenhouse et al. |
| 11,337,693 B2 | 5/2022 | Hess et al. |
| 11,337,698 B2 | 5/2022 | Baxter, III et al. |
| 11,344,299 B2 | 5/2022 | Yates et al. |
| 11,344,303 B2 | 5/2022 | Shelton, IV et al. |
| 11,350,843 B2 | 6/2022 | Shelton, IV et al. |
| 11,350,916 B2 | 6/2022 | Shelton, IV et al. |
| 11,350,928 B2 | 6/2022 | Shelton, IV et al. |
| 11,350,929 B2 | 6/2022 | Giordano et al. |
| 11,350,932 B2 | 6/2022 | Shelton, IV et al. |
| 11,350,934 B2 | 6/2022 | Bakos et al. |
| 11,350,935 B2 | 6/2022 | Shelton, IV et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,364,027 B2 | 6/2022 | Harris et al. |
| 11,364,046 B2 | 6/2022 | Shelton, IV et al. |
| 11,369,368 B2 | 6/2022 | Shelton, IV et al. |
| 11,369,376 B2 | 6/2022 | Simms et al. |
| 11,369,377 B2 | 6/2022 | Boudreaux et al. |
| 11,373,755 B2 | 6/2022 | Shelton, IV et al. |
| 11,376,001 B2 | 7/2022 | Shelton, IV et al. |
| 11,376,082 B2 | 7/2022 | Shelton, IV et al. |
| 11,376,098 B2 | 7/2022 | Shelton, IV et al. |
| 11,382,625 B2 | 7/2022 | Huitema et al. |
| 11,382,626 B2 | 7/2022 | Shelton, IV et al. |
| 11,382,627 B2 | 7/2022 | Huitema et al. |
| 11,382,628 B2 | 7/2022 | Baxter, III et al. |
| 11,382,638 B2 | 7/2022 | Harris et al. |
| 11,382,697 B2 | 7/2022 | Shelton, IV et al. |
| 11,389,160 B2 | 7/2022 | Shelton, IV et al. |
| 11,389,162 B2 | 7/2022 | Baber et al. |
| 11,389,164 B2 | 7/2022 | Yates et al. |
| 11,395,651 B2 | 7/2022 | Shelton, IV et al. |
| 11,395,652 B2 | 7/2022 | Parihar et al. |
| 11,399,828 B2 | 8/2022 | Swayze et al. |
| 11,399,829 B2 | 8/2022 | Leimbach et al. |
| 11,399,831 B2 | 8/2022 | Overmyer et al. |
| 11,399,837 B2 | 8/2022 | Shelton, IV et al. |
| 11,406,377 B2 | 8/2022 | Schmid et al. |
| 11,406,378 B2 | 8/2022 | Baxter, III et al. |
| 11,406,380 B2 | 8/2022 | Yates et al. |
| 11,406,381 B2 | 8/2022 | Parihar et al. |
| 11,406,382 B2 | 8/2022 | Shelton, IV et al. |
| 11,406,386 B2 | 8/2022 | Baber et al. |
| 11,406,390 B2 | 8/2022 | Shelton, IV et al. |
| 11,406,442 B2 | 8/2022 | Davison et al. |
| 11,410,259 B2 | 8/2022 | Harris et al. |
| 11,413,041 B2 | 8/2022 | Viola et al. |
| 11,413,042 B2 | 8/2022 | Shelton, IV et al. |
| 11,413,102 B2 | 8/2022 | Shelton, IV et al. |
| 11,419,606 B2 | 8/2022 | Overmyer et al. |
| 11,419,630 B2 | 8/2022 | Yates et al. |
| 11,424,027 B2 | 8/2022 | Shelton, IV |
| 11,426,160 B2 | 8/2022 | Shelton, IV et al. |
| 11,426,167 B2 | 8/2022 | Shelton, IV et al. |
| 11,426,251 B2 | 8/2022 | Kimball et al. |
| D964,564 S | 9/2022 | Boudreaux |
| 11,432,816 B2 | 9/2022 | Leimbach et al. |
| 11,432,836 B2 | 9/2022 | Dearden et al. |
| 11,432,885 B2 | 9/2022 | Shelton, IV et al. |
| 11,439,391 B2 | 9/2022 | Bruns et al. |
| 11,439,470 B2 | 9/2022 | Spivey et al. |
| 11,446,029 B2 | 9/2022 | Shelton, IV et al. |
| 11,446,034 B2 | 9/2022 | Shelton, IV et al. |
| 11,452,526 B2 | 9/2022 | Ross et al. |
| 11,452,528 B2 | 9/2022 | Leimbach et al. |
| D966,512 S | 10/2022 | Shelton, IV et al. |
| D967,421 S | 10/2022 | Shelton, IV et al. |
| 11,457,918 B2 | 10/2022 | Shelton, IV et al. |
| 11,464,511 B2 | 10/2022 | Timm et al. |
| 11,464,512 B2 | 10/2022 | Shelton, IV et al. |
| 11,464,513 B2 | 10/2022 | Shelton, IV et al. |
| 11,464,514 B2 | 10/2022 | Yates et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,157 B2 | 10/2022 | Baxter, III et al. |
| 11,478,241 B2 | 10/2022 | Shelton, IV et al. |
| 11,478,244 B2 | 10/2022 | DiNardo et al. |
| D971,232 S | 11/2022 | Siebel et al. |
| 11,484,307 B2 | 11/2022 | Hall et al. |
| 11,484,309 B2 | 11/2022 | Harris et al. |
| 11,484,311 B2 | 11/2022 | Shelton, IV et al. |
| 11,484,312 B2 | 11/2022 | Shelton, IV et al. |
| 11,490,889 B2 | 11/2022 | Overmyer et al. |
| 11,497,488 B2 | 11/2022 | Leimbach et al. |
| 11,497,489 B2 | 11/2022 | Baxter, III et al. |
| 11,497,492 B2 | 11/2022 | Shelton, IV |
| 11,497,499 B2 | 11/2022 | Shelton, IV et al. |
| 11,504,116 B2 | 11/2022 | Schmid et al. |
| 11,504,119 B2 | 11/2022 | Shelton, IV et al. |
| 11,504,122 B2 | 11/2022 | Shelton, IV et al. |
| 11,504,192 B2 | 11/2022 | Shelton, IV et al. |
| 11,510,671 B2 | 11/2022 | Shelton, IV et al. |
| 11,510,741 B2 | 11/2022 | Shelton, IV et al. |
| 11,517,304 B2 | 12/2022 | Yates et al. |
| 11,517,306 B2 | 12/2022 | Miller et al. |
| 11,517,309 B2 | 12/2022 | Bakos et al. |
| 11,517,311 B2 | 12/2022 | Lytle, IV et al. |
| 11,517,315 B2 | 12/2022 | Huitema et al. |
| 11,517,325 B2 | 12/2022 | Shelton, IV et al. |

(56) References Cited

U.S. PATENT DOCUMENTS

| | | |
|---|---|---|
| 11,517,390 B2 | 12/2022 | Baxter, III |
| 11,523,821 B2 | 12/2022 | Harris et al. |
| 11,523,822 B2 | 12/2022 | Shelton, IV et al. |
| 11,523,823 B2 | 12/2022 | Hunter et al. |
| 11,523,824 B2 | 12/2022 | Williams |
| 11,523,859 B2 | 12/2022 | Shelton, IV et al. |
| 11,529,137 B2 | 12/2022 | Shelton, IV et al. |
| 11,529,138 B2 | 12/2022 | Jaworek et al. |
| 11,529,139 B2 | 12/2022 | Shelton, IV et al. |
| 11,529,140 B2 | 12/2022 | Shelton, IV et al. |
| 11,529,142 B2 | 12/2022 | Leimbach et al. |
| 11,534,162 B2 | 12/2022 | Shelton, IV |
| 11,534,259 B2 | 12/2022 | Leimbach et al. |
| D974,560 S | 1/2023 | Shelton, IV et al. |
| D975,278 S | 1/2023 | Shelton, IV et al. |
| D975,850 S | 1/2023 | Shelton, IV et al. |
| D975,851 S | 1/2023 | Shelton, IV et al. |
| D976,401 S | 1/2023 | Shelton, IV et al. |
| 11,540,824 B2 | 1/2023 | Shelton, IV et al. |
| 11,540,829 B2 | 1/2023 | Shelton, IV et al. |
| 11,547,403 B2 | 1/2023 | Shelton, IV et al. |
| 11,547,404 B2 | 1/2023 | Shelton, IV et al. |
| 11,553,911 B2 | 1/2023 | Shelton, IV et al. |
| 11,553,916 B2 | 1/2023 | Vendely et al. |
| 11,553,919 B2 | 1/2023 | Shelton, IV et al. |
| 11,553,971 B2 | 1/2023 | Shelton, IV et al. |
| 11,559,302 B2 | 1/2023 | Timm et al. |
| 11,559,303 B2 | 1/2023 | Shelton, IV et al. |
| 11,559,304 B2 | 1/2023 | Boudreaux et al. |
| 11,559,307 B2 | 1/2023 | Shelton, IV et al. |
| 11,559,308 B2 | 1/2023 | Yates et al. |
| 11,559,496 B2 | 1/2023 | Widenhouse et al. |
| 11,564,679 B2 | 1/2023 | Parihar et al. |
| 11,564,682 B2 | 1/2023 | Timm et al. |
| 11,564,686 B2 | 1/2023 | Yates et al. |
| 11,564,688 B2 | 1/2023 | Swayze et al. |
| 11,564,703 B2 | 1/2023 | Shelton, IV et al. |
| 11,564,756 B2 | 1/2023 | Shelton, IV et al. |
| 11,571,207 B2 | 2/2023 | Shelton, IV et al. |
| 11,571,210 B2 | 2/2023 | Shelton, IV et al. |
| 11,571,212 B2 | 2/2023 | Yates et al. |
| 11,571,215 B2 | 2/2023 | Shelton, IV et al. |
| 11,571,231 B2 | 2/2023 | Hess et al. |
| 11,576,668 B2 | 2/2023 | Shelton, IV et al. |
| 11,576,672 B2 | 2/2023 | Shelton, IV et al. |
| 11,576,673 B2 | 2/2023 | Shelton, IV |
| 11,576,677 B2 | 2/2023 | Shelton, IV et al. |
| 11,583,274 B2 | 2/2023 | Widenhouse et al. |
| 11,583,277 B2 | 2/2023 | Shelton, IV et al. |
| 11,583,278 B2 | 2/2023 | Shelton, IV et al. |
| 11,583,279 B2 | 2/2023 | Smith et al. |
| 11,589,865 B2 | 2/2023 | Shelton, IV et al. |
| 11,589,888 B2 | 2/2023 | Shelton, IV et al. |
| 11,642,185 B2 | 5/2023 | Cappelleri et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0030219 A1 | 10/2001 | Green et al. |
| 2001/0034530 A1 | 10/2001 | Malackowski et al. |
| 2001/0045442 A1* | 11/2001 | Whitman ............ A61B 17/068 227/19 |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0023126 A1 | 2/2002 | Flavin |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0054158 A1 | 5/2002 | Asami |
| 2002/0065535 A1 | 5/2002 | Kneifel et al. |
| 2002/0066764 A1 | 6/2002 | Perry et al. |
| 2002/0082612 A1 | 6/2002 | Moll et al. |
| 2002/0087048 A1 | 7/2002 | Brock et al. |
| 2002/0087148 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0111621 A1 | 8/2002 | Wallace et al. |
| 2002/0111624 A1 | 8/2002 | Witt et al. |
| 2002/0116063 A1 | 8/2002 | Giannetti et al. |
| 2002/0117533 A1 | 8/2002 | Milliman et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0133236 A1 | 9/2002 | Rousseau |
| 2002/0134811 A1 | 9/2002 | Napier et al. |
| 2002/0135474 A1 | 9/2002 | Sylliassen |
| 2002/0138086 A1 | 9/2002 | Sixto et al. |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0161277 A1 | 10/2002 | Boone et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0018323 A1 | 1/2003 | Wallace et al. |
| 2003/0028236 A1 | 2/2003 | Gillick et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0047582 A1 | 3/2003 | Sonnenschein et al. |
| 2003/0050628 A1 | 3/2003 | Whitman et al. |
| 2003/0050654 A1 | 3/2003 | Whitman et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0105475 A1 | 6/2003 | Sancoff et al. |
| 2003/0114851 A1 | 6/2003 | Truckai et al. |
| 2003/0121586 A1 | 7/2003 | Mitra et al. |
| 2003/0135204 A1 | 7/2003 | Lee et al. |
| 2003/0135388 A1 | 7/2003 | Martucci et al. |
| 2003/0139741 A1 | 7/2003 | Goble et al. |
| 2003/0144660 A1 | 7/2003 | Mollenauer |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0158463 A1 | 8/2003 | Julian et al. |
| 2003/0163029 A1 | 8/2003 | Sonnenschein et al. |
| 2003/0163085 A1 | 8/2003 | Tanner et al. |
| 2003/0164172 A1 | 9/2003 | Chumas et al. |
| 2003/0181800 A1 | 9/2003 | Bonutti |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216619 A1 | 11/2003 | Scirica et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034287 A1 | 2/2004 | Hickle |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |

(56) References Cited

U.S. PATENT DOCUMENTS

| | | |
|---|---|---|
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093020 A1 | 5/2004 | Sinton |
| 2004/0093024 A1 | 5/2004 | Lousararian et al. |
| 2004/0094597 A1* | 5/2004 | Whitman ......... A61B 17/07207 227/180.1 |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0231870 A1 | 11/2004 | McCormick et al. |
| 2004/0232201 A1 | 11/2004 | Wenchell et al. |
| 2004/0236352 A1 | 11/2004 | Wang et al. |
| 2004/0239582 A1 | 12/2004 | Seymour |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254680 A1 | 12/2004 | Sunaoshi |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0023325 A1 | 2/2005 | Gresham et al. |
| 2005/0032511 A1 | 2/2005 | Malone et al. |
| 2005/0033352 A1 | 2/2005 | Zepf et al. |
| 2005/0044489 A1 | 2/2005 | Yamagami et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0067548 A1 | 3/2005 | Inoue |
| 2005/0070929 A1 | 3/2005 | Dalessandro et al. |
| 2005/0075561 A1 | 4/2005 | Golden |
| 2005/0079088 A1 | 4/2005 | Wirth et al. |
| 2005/0080342 A1 | 4/2005 | Gilreath et al. |
| 2005/0085693 A1 | 4/2005 | Belson et al. |
| 2005/0085838 A1 | 4/2005 | Thompson et al. |
| 2005/0090709 A1 | 4/2005 | Okada et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0119524 A1 | 6/2005 | Sekine et al. |
| 2005/0120836 A1 | 6/2005 | Anderson |
| 2005/0124855 A1 | 6/2005 | Jaffe et al. |
| 2005/0125028 A1 | 6/2005 | Looper et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0145672 A1 | 7/2005 | Schwemberger et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0191936 A1 | 9/2005 | Marine et al. |
| 2005/0197859 A1 | 9/2005 | Wilson et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0256546 A1 | 11/2005 | Vaisnys et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0267464 A1 | 12/2005 | Truckai et al. |
| 2005/0267529 A1 | 12/2005 | Crockett et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0008787 A1 | 1/2006 | Hayman et al. |
| 2006/0011698 A1 | 1/2006 | Okada et al. |
| 2006/0011699 A1* | 1/2006 | Olson ................. A61B 17/068 227/19 |
| 2006/0015009 A1 | 1/2006 | Jaffe et al. |
| 2006/0020167 A1 | 1/2006 | Sitzmann |
| 2006/0020258 A1 | 1/2006 | Strauss et al. |
| 2006/0020272 A1 | 1/2006 | Gildenberg |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |

(56) References Cited

U.S. PATENT DOCUMENTS

| | | |
|---|---|---|
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142656 A1 | 6/2006 | Malackowski et al. |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226196 A1 | 10/2006 | Hueil et al. |
| 2006/0226957 A1 | 10/2006 | Miller et al. |
| 2006/0235368 A1 | 10/2006 | Oz |
| 2006/0241666 A1 | 10/2006 | Briggs et al. |
| 2006/0241691 A1 | 10/2006 | Wilk |
| 2006/0244460 A1 | 11/2006 | Weaver |
| 2006/0247584 A1 | 11/2006 | Sheetz et al. |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289600 A1 | 12/2006 | Wales et al. |
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027459 A1 | 2/2007 | Horvath et al. |
| 2007/0027468 A1 | 2/2007 | Wales et al. |
| 2007/0027551 A1 | 2/2007 | Farnsworth et al. |
| 2007/0043338 A1 | 2/2007 | Moll et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0055305 A1 | 3/2007 | Schnyder et al. |
| 2007/0069851 A1 | 3/2007 | Sung et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0152829 A1 | 7/2007 | Lindsay et al. |
| 2007/0155010 A1 | 7/2007 | Farnsworth et al. |
| 2007/0162056 A1 | 7/2007 | Gerbi et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0179476 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0191915 A1 | 8/2007 | Strother et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0221701 A1 | 9/2007 | Ortiz et al. |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0260132 A1 | 11/2007 | Sterling |
| 2007/0260242 A1 | 11/2007 | Dycus et al. |
| 2007/0262592 A1 | 11/2007 | Hwang et al. |
| 2007/0270660 A1 | 11/2007 | Caylor et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0290027 A1 | 12/2007 | Maatta et al. |
| 2007/0296286 A1 | 12/2007 | Avenell |
| 2008/0000941 A1 | 1/2008 | Sonnenschein et al. |
| 2008/0003196 A1 | 1/2008 | Jonn et al. |
| 2008/0007237 A1 | 1/2008 | Nagashima et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0046000 A1 | 2/2008 | Lee et al. |
| 2008/0051833 A1 | 2/2008 | Gramuglia et al. |
| 2008/0064920 A1 | 3/2008 | Bakos et al. |
| 2008/0064921 A1 | 3/2008 | Larkin et al. |
| 2008/0065153 A1 | 3/2008 | Allard et al. |
| 2008/0069736 A1 | 3/2008 | Mingerink et al. |
| 2008/0071328 A1 | 3/2008 | Haubrich et al. |

(56) References Cited

U.S. PATENT DOCUMENTS

| | | |
|---|---|---|
| 2008/0077158 A1 | 3/2008 | Haider et al. |
| 2008/0078802 A1 | 4/2008 | Hess et al. |
| 2008/0081948 A1 | 4/2008 | Weisenburgh et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0083811 A1 | 4/2008 | Marczyk |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0094228 A1 | 4/2008 | Welch et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0126984 A1 | 5/2008 | Fleishman et al. |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0216704 A1 | 9/2008 | Eisenbeis et al. |
| 2008/0217376 A1 | 9/2008 | Clauson et al. |
| 2008/0234709 A1 | 9/2008 | Houser |
| 2008/0234866 A1 | 9/2008 | Kishi et al. |
| 2008/0242939 A1 | 10/2008 | Johnston |
| 2008/0243088 A1 | 10/2008 | Evans |
| 2008/0243143 A1 | 10/2008 | Kuhns et al. |
| 2008/0249536 A1 | 10/2008 | Stabler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255421 A1 | 10/2008 | Hegeman et al. |
| 2008/0255663 A1 | 10/2008 | Akpek et al. |
| 2008/0257935 A1* | 10/2008 | Viola ............... A61B 17/068 227/176.1 |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0296347 A1 | 12/2008 | Shelton, IV et al. |
| 2008/0297287 A1 | 12/2008 | Shachar et al. |
| 2008/0298784 A1 | 12/2008 | Kastner |
| 2008/0308504 A1 | 12/2008 | Hallan et al. |
| 2008/0308602 A1 | 12/2008 | Timm et al. |
| 2008/0308603 A1 | 12/2008 | Shelton et al. |
| 2008/0308607 A1 | 12/2008 | Timm et al. |
| 2008/0308807 A1 | 12/2008 | Yamazaki et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0007014 A1 | 1/2009 | Coomer et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0030437 A1 | 1/2009 | Houser et al. |
| 2009/0043253 A1 | 2/2009 | Podaima |
| 2009/0048583 A1 | 2/2009 | Williams et al. |
| 2009/0048589 A1 | 2/2009 | Takashino et al. |
| 2009/0053288 A1 | 2/2009 | Eskridge, Jr. et al. |
| 2009/0057369 A1 | 3/2009 | Smith et al. |
| 2009/0069806 A1 | 3/2009 | De La Mora Levy et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0095790 A1* | 4/2009 | Whitman ......... A61B 17/07207 227/175.1 |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0114701 A1 | 5/2009 | Zemlok et al. |
| 2009/0118762 A1 | 5/2009 | Crainch et al. |
| 2009/0119011 A1 | 5/2009 | Kondo et al. |
| 2009/0120994 A1 | 5/2009 | Murray et al. |
| 2009/0131819 A1 | 5/2009 | Ritchie et al. |
| 2009/0132400 A1 | 5/2009 | Conway |
| 2009/0135280 A1 | 5/2009 | Johnston et al. |
| 2009/0138003 A1 | 5/2009 | Deville et al. |
| 2009/0143797 A1 | 6/2009 | Smith et al. |
| 2009/0143855 A1 | 6/2009 | Weber et al. |
| 2009/0149871 A9 | 6/2009 | Kagan et al. |
| 2009/0167548 A1 | 7/2009 | Sugahara |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0204126 A1 | 8/2009 | Le |
| 2009/0204925 A1 | 8/2009 | Bhat et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0236401 A1 | 9/2009 | Cole et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |
| 2009/0262078 A1 | 10/2009 | Pizzi |
| 2009/0264940 A1 | 10/2009 | Beale et al. |
| 2009/0270895 A1 | 10/2009 | Churchill et al. |
| 2009/0273353 A1 | 11/2009 | Kroh et al. |
| 2009/0277288 A1 | 11/2009 | Doepker et al. |
| 2009/0278406 A1 | 11/2009 | Hoffman |
| 2009/0290016 A1 | 11/2009 | Suda |
| 2009/0292283 A1 | 11/2009 | Odom |

(56) References Cited

U.S. PATENT DOCUMENTS

| | | |
|---|---|---|
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0318936 A1 | 12/2009 | Harris et al. |
| 2009/0325859 A1 | 12/2009 | Ameer et al. |
| 2010/0002013 A1 | 1/2010 | Kagaya |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016853 A1 | 1/2010 | Burbank |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0036441 A1 | 2/2010 | Procter |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069833 A1 | 3/2010 | Wenderow et al. |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094312 A1 | 4/2010 | Ruiz Morales et al. |
| 2010/0094340 A1 | 4/2010 | Stopek et al. |
| 2010/0094400 A1 | 4/2010 | Bolduc et al. |
| 2010/0100123 A1 | 4/2010 | Bennett |
| 2010/0100124 A1 | 4/2010 | Calabrese et al. |
| 2010/0106167 A1 | 4/2010 | Boulnois et al. |
| 2010/0116519 A1 | 5/2010 | Garels |
| 2010/0122339 A1 | 5/2010 | Boccacci |
| 2010/0125786 A1 | 5/2010 | Ozawa et al. |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0168741 A1 | 7/2010 | Sanai et al. |
| 2010/0179022 A1 | 7/2010 | Shirokoshi |
| 2010/0180711 A1 | 7/2010 | Kilibarda et al. |
| 2010/0187285 A1 | 7/2010 | Harris et al. |
| 2010/0191255 A1 | 7/2010 | Crainich et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0194541 A1 | 8/2010 | Stevenson et al. |
| 2010/0198159 A1 | 8/2010 | Voss et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241115 A1 | 9/2010 | Benamou et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267525 A1 | 10/2010 | Tanner |
| 2010/0267662 A1 | 10/2010 | Fielder et al. |
| 2010/0274160 A1 | 10/2010 | Yachi et al. |
| 2010/0291184 A1 | 11/2010 | Clark et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0325568 A1 | 12/2010 | Pedersen et al. |
| 2010/0327041 A1 | 12/2010 | Milliman et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0028991 A1 | 2/2011 | Ikeda et al. |
| 2011/0029003 A1 | 2/2011 | Lavigne et al. |
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0095067 A1 | 4/2011 | Ohdaira |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118708 A1 | 5/2011 | Burbank et al. |
| 2011/0118754 A1 | 5/2011 | Dachs, II et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0198381 A1 | 8/2011 | McCardle et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0224543 A1 | 9/2011 | Johnson et al. |
| 2011/0225105 A1 | 9/2011 | Scholer et al. |
| 2011/0230713 A1 | 9/2011 | Kleemann et al. |
| 2011/0235168 A1 | 9/2011 | Sander |
| 2011/0238044 A1 | 9/2011 | Main et al. |
| 2011/0241597 A1 | 10/2011 | Zhu et al. |
| 2011/0251606 A1 | 10/2011 | Kerr |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278035 A1 | 11/2011 | Chen |
| 2011/0278343 A1 | 11/2011 | Knodel et al. |
| 2011/0279268 A1 | 11/2011 | Konishi et al. |
| 2011/0285507 A1 | 11/2011 | Nelson |
| 2011/0290856 A1 | 12/2011 | Shelton, IV et al. |
| 2011/0290858 A1 | 12/2011 | Whitman et al. |
| 2011/0292258 A1 | 12/2011 | Adler et al. |
| 2011/0293690 A1 | 12/2011 | Griffin et al. |
| 2011/0295295 A1 | 12/2011 | Shelton, IV et al. |
| 2011/0295299 A1 | 12/2011 | Braithwaite et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0008880 A1 | 1/2012 | Toth |
| 2012/0010615 A1 | 1/2012 | Cummings et al. |
| 2012/0016239 A1 | 1/2012 | Barthe et al. |
| 2012/0016413 A1 | 1/2012 | Timm et al. |

(56) References Cited

U.S. PATENT DOCUMENTS

| | | |
|---|---|---|
| 2012/0016467 A1 | 1/2012 | Chen et al. |
| 2012/0029272 A1 | 2/2012 | Shelton, IV et al. |
| 2012/0029550 A1 | 2/2012 | Forsell |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080491 A1 | 4/2012 | Shelton, IV et al. |
| 2012/0080498 A1* | 4/2012 | Shelton, IV ......... A61B 17/072 227/180.1 |
| 2012/0086276 A1 | 4/2012 | Sawyers |
| 2012/0095458 A1 | 4/2012 | Cybulski et al. |
| 2012/0101488 A1 | 4/2012 | Aldridge et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116263 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0132663 A1 | 5/2012 | Kasvikis et al. |
| 2012/0143175 A1 | 6/2012 | Hermann et al. |
| 2012/0171539 A1 | 7/2012 | Rejman et al. |
| 2012/0175398 A1 | 7/2012 | Sandborn et al. |
| 2012/0190964 A1 | 7/2012 | Hyde et al. |
| 2012/0197239 A1 | 8/2012 | Smith et al. |
| 2012/0197272 A1 | 8/2012 | Oray et al. |
| 2012/0203213 A1 | 8/2012 | Kimball et al. |
| 2012/0211542 A1 | 8/2012 | Racenet |
| 2012/0220990 A1 | 8/2012 | Mckenzie et al. |
| 2012/0233298 A1 | 9/2012 | Verbandt et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0241494 A1 | 9/2012 | Marczyk |
| 2012/0241503 A1 | 9/2012 | Baxter, III et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0256494 A1 | 10/2012 | Kesler et al. |
| 2012/0271327 A1 | 10/2012 | West et al. |
| 2012/0283707 A1 | 11/2012 | Giordano et al. |
| 2012/0286019 A1 | 11/2012 | Hueil et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296316 A1 | 11/2012 | Imuta |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0310254 A1 | 12/2012 | Manzo et al. |
| 2012/0312861 A1 | 12/2012 | Gurumurthy et al. |
| 2012/0316424 A1 | 12/2012 | Stopek |
| 2012/0330285 A1 | 12/2012 | Hartoumbekis et al. |
| 2012/0330329 A1 | 12/2012 | Harris et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0069088 A1 | 3/2013 | Speck et al. |
| 2013/0075447 A1 | 3/2013 | Weisenburgh, II et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0106352 A1 | 5/2013 | Nagamine |
| 2013/0112729 A1 | 5/2013 | Beardsley et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0146642 A1* | 6/2013 | Shelton, IV ..... A61B 17/07207 227/177.1 |
| 2013/0153639 A1 | 6/2013 | Hodgkinson et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0165908 A1 | 6/2013 | Purdy et al. |
| 2013/0169217 A1 | 7/2013 | Watanabe et al. |
| 2013/0172713 A1 | 7/2013 | Kirschenman |
| 2013/0172878 A1 | 7/2013 | Smith |
| 2013/0175315 A1 | 7/2013 | Milliman |
| 2013/0175317 A1 | 7/2013 | Yates et al. |
| 2013/0183769 A1 | 7/2013 | Tajima |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0231681 A1 | 9/2013 | Robinson et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267950 A1 | 10/2013 | Rosa et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0284792 A1 | 10/2013 | Ma |
| 2013/0289565 A1 | 10/2013 | Hassler, Jr. |
| 2013/0293353 A1 | 11/2013 | McPherson et al. |
| 2013/0303845 A1 | 11/2013 | Skula et al. |
| 2013/0304084 A1 | 11/2013 | Beira et al. |
| 2013/0306704 A1 | 11/2013 | Balbierz et al. |
| 2013/0327552 A1 | 12/2013 | Lovelass et al. |
| 2013/0331826 A1 | 12/2013 | Steege |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1* | 1/2014 | Shelton, IV ........... A61B 34/71 227/175.3 |
| 2014/0001234 A1 | 1/2014 | Shelton, IV et al. |
| 2014/0002322 A1 | 1/2014 | Kanome et al. |
| 2014/0005550 A1 | 1/2014 | Lu et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0008289 A1 | 1/2014 | Williams et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0041191 A1 | 2/2014 | Knodel |
| 2014/0048580 A1 | 2/2014 | Merchant et al. |
| 2014/0069240 A1 | 3/2014 | Dauvin et al. |
| 2014/0078715 A1 | 3/2014 | Pickard et al. |
| 2014/0081176 A1 | 3/2014 | Hassan |

(56) References Cited

U.S. PATENT DOCUMENTS

| | | |
|---|---|---|
| 2014/0088614 A1 | 3/2014 | Blumenkranz |
| 2014/0088639 A1 | 3/2014 | Bartels et al. |
| 2014/0094681 A1 | 4/2014 | Valentine et al. |
| 2014/0100558 A1 | 4/2014 | Schmitz et al. |
| 2014/0107697 A1 | 4/2014 | Patani et al. |
| 2014/0110453 A1 | 4/2014 | Wingardner et al. |
| 2014/0115229 A1 | 4/2014 | Kothamasu et al. |
| 2014/0131418 A1 | 5/2014 | Kostrzewski |
| 2014/0131419 A1 | 5/2014 | Bettuchi |
| 2014/0135832 A1 | 5/2014 | Park et al. |
| 2014/0148803 A1 | 5/2014 | Taylor |
| 2014/0151433 A1 | 6/2014 | Shelton, IV et al. |
| 2014/0155916 A1 | 6/2014 | Hodgkinson et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0183244 A1 | 7/2014 | Duque et al. |
| 2014/0188091 A1 | 7/2014 | Vidal et al. |
| 2014/0188101 A1 | 7/2014 | Bales, Jr. et al. |
| 2014/0188159 A1 | 7/2014 | Steege |
| 2014/0207124 A1 | 7/2014 | Aldridge et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0262408 A1 | 9/2014 | Woodard |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276720 A1 | 9/2014 | Parihar et al. |
| 2014/0276730 A1 | 9/2014 | Boudreaux et al. |
| 2014/0276776 A1 | 9/2014 | Parihar et al. |
| 2014/0284371 A1 | 9/2014 | Morgan et al. |
| 2014/0287703 A1 | 9/2014 | Herbsommer et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303646 A1* | 10/2014 | Morgan ............... A61B 17/105 606/130 |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0358163 A1 | 12/2014 | Farin et al. |
| 2014/0367445 A1 | 12/2014 | Ingmanson et al. |
| 2014/0371764 A1 | 12/2014 | Oyola et al. |
| 2014/0373003 A1 | 12/2014 | Grez et al. |
| 2014/0374130 A1 | 12/2014 | Nakamura et al. |
| 2014/0378950 A1 | 12/2014 | Chiu |
| 2015/0001272 A1 | 1/2015 | Sniffin et al. |
| 2015/0002089 A1 | 1/2015 | Rejman et al. |
| 2015/0022012 A1 | 1/2015 | Kim et al. |
| 2015/0025549 A1 | 1/2015 | Kilroy et al. |
| 2015/0025571 A1 | 1/2015 | Suzuki et al. |
| 2015/0034697 A1 | 2/2015 | Mastri et al. |
| 2015/0039010 A1 | 2/2015 | Beardsley et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060516 A1 | 3/2015 | Collings et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0067582 A1 | 3/2015 | Donnelly et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0080883 A1 | 3/2015 | Haverkost et al. |
| 2015/0082624 A1 | 3/2015 | Craig et al. |
| 2015/0083781 A1 | 3/2015 | Giordano et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0134077 A1 | 5/2015 | Shelton, IV et al. |
| 2015/0150620 A1 | 6/2015 | Miyamoto et al. |
| 2015/0173746 A1* | 6/2015 | Baxter, III ........ A61B 17/07207 227/176.1 |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209045 A1 | 7/2015 | Hodgkinson et al. |
| 2015/0216605 A1 | 8/2015 | Baldwin |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0230794 A1 | 8/2015 | Wellman et al. |
| 2015/0230861 A1 | 8/2015 | Woloszko et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272606 A1 | 10/2015 | Nobis |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297824 A1 | 10/2015 | Cabiri et al. |
| 2015/0303417 A1 | 10/2015 | Koeder et al. |
| 2015/0305743 A1 | 10/2015 | Casasanta et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366585 A1 | 12/2015 | Lemay et al. |
| 2015/0367497 A1 | 12/2015 | Ito et al. |
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0029998 A1 | 2/2016 | Brister et al. |
| 2016/0030042 A1 | 2/2016 | Heinrich et al. |
| 2016/0030043 A1 | 2/2016 | Fanelli et al. |
| 2016/0030076 A1 | 2/2016 | Faller et al. |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074035 A1 | 3/2016 | Whitman et al. |
| 2016/0074040 A1 | 3/2016 | Widenhouse et al. |
| 2016/0081678 A1 | 3/2016 | Kappel et al. |
| 2016/0082161 A1 | 3/2016 | Zilberman et al. |
| 2016/0089175 A1 | 3/2016 | Hibner et al. |

(56) References Cited

U.S. PATENT DOCUMENTS

| | | |
|---|---|---|
| 2016/0100838 A1 | 4/2016 | Beaupre et al. |
| 2016/0118201 A1 | 4/2016 | Nicholas et al. |
| 2016/0132026 A1 | 5/2016 | Wingardner et al. |
| 2016/0135835 A1 | 5/2016 | Onuma |
| 2016/0135895 A1 | 5/2016 | Faasse et al. |
| 2016/0139666 A1 | 5/2016 | Rubin et al. |
| 2016/0174969 A1 | 6/2016 | Kerr et al. |
| 2016/0174983 A1 | 6/2016 | Shelton, IV et al. |
| 2016/0175021 A1 | 6/2016 | Hassler, Jr. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192927 A1 | 7/2016 | Kostrzewski |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0220150 A1 | 8/2016 | Sharonov |
| 2016/0235494 A1 | 8/2016 | Shelton, IV et al. |
| 2016/0242783 A1 | 8/2016 | Shelton, IV et al. |
| 2016/0242855 A1 | 8/2016 | Fichtinger et al. |
| 2016/0249910 A1 | 9/2016 | Shelton, IV et al. |
| 2016/0249922 A1 | 9/2016 | Morgan et al. |
| 2016/0249929 A1 | 9/2016 | Cappola et al. |
| 2016/0256159 A1 | 9/2016 | Pinjala et al. |
| 2016/0256184 A1 | 9/2016 | Shelton, IV et al. |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0270781 A1 | 9/2016 | Scirica |
| 2016/0287265 A1 | 10/2016 | Macdonald et al. |
| 2016/0287279 A1 | 10/2016 | Bovay et al. |
| 2016/0302820 A1 | 10/2016 | Hibner et al. |
| 2016/0310143 A1 | 10/2016 | Bettuchi |
| 2016/0314716 A1 | 10/2016 | Grubbs |
| 2016/0314717 A1 | 10/2016 | Grubbs |
| 2016/0345972 A1 | 12/2016 | Beardsley et al. |
| 2016/0367122 A1 | 12/2016 | Ichimura et al. |
| 2016/0374669 A1 | 12/2016 | Overmyer et al. |
| 2016/0374716 A1 | 12/2016 | Kessler |
| 2017/0000549 A1 | 1/2017 | Gilbert et al. |
| 2017/0007234 A1 | 1/2017 | Chin et al. |
| 2017/0007244 A1 | 1/2017 | Shelton, IV et al. |
| 2017/0007245 A1 | 1/2017 | Shelton, IV et al. |
| 2017/0007347 A1 | 1/2017 | Jaworek et al. |
| 2017/0020616 A1 | 1/2017 | Vale et al. |
| 2017/0035419 A1 | 2/2017 | Decker et al. |
| 2017/0055819 A1 | 3/2017 | Hansen et al. |
| 2017/0055980 A1 | 3/2017 | Vendely et al. |
| 2017/0056008 A1 | 3/2017 | Shelton, IV et al. |
| 2017/0056016 A1 | 3/2017 | Barton et al. |
| 2017/0056018 A1 | 3/2017 | Zeiner et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086842 A1 | 3/2017 | Shelton, IV et al. |
| 2017/0086930 A1 | 3/2017 | Thompson et al. |
| 2017/0086932 A1 | 3/2017 | Auld et al. |
| 2017/0095922 A1 | 4/2017 | Licht et al. |
| 2017/0105727 A1 | 4/2017 | Scheib et al. |
| 2017/0105733 A1 | 4/2017 | Scheib et al. |
| 2017/0105786 A1 | 4/2017 | Scheib et al. |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0143336 A1 | 5/2017 | Shah et al. |
| 2017/0168187 A1 | 6/2017 | Calderon et al. |
| 2017/0172382 A1 | 6/2017 | Nir et al. |
| 2017/0172549 A1 | 6/2017 | Smaby et al. |
| 2017/0172662 A1 | 6/2017 | Panescu et al. |
| 2017/0181803 A1 | 6/2017 | Mayer-Ullmann et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196649 A1 | 7/2017 | Yates et al. |
| 2017/0202605 A1 | 7/2017 | Shelton, IV et al. |
| 2017/0202607 A1 | 7/2017 | Shelton, IV et al. |
| 2017/0202770 A1 | 7/2017 | Friedrich et al. |
| 2017/0224332 A1 | 8/2017 | Hunter et al. |
| 2017/0231628 A1 | 8/2017 | Shelton, IV et al. |
| 2017/0231629 A1 | 8/2017 | Stopek et al. |
| 2017/0238962 A1 | 8/2017 | Hansen et al. |
| 2017/0242455 A1 | 8/2017 | Dickens |
| 2017/0245949 A1 | 8/2017 | Randle |
| 2017/0249431 A1 | 8/2017 | Shelton, IV et al. |
| 2017/0252060 A1 | 9/2017 | Ellingson et al. |
| 2017/0255799 A1 | 9/2017 | Zhao et al. |
| 2017/0258471 A1 | 9/2017 | DiNardo et al. |
| 2017/0262110 A1 | 9/2017 | Polishchuk et al. |
| 2017/0265774 A1 | 9/2017 | Johnson et al. |
| 2017/0281186 A1 | 10/2017 | Shelton, IV et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0312042 A1 | 11/2017 | Giordano et al. |
| 2017/0319047 A1 | 11/2017 | Poulsen et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |
| 2017/0367695 A1 | 12/2017 | Shelton, IV et al. |
| 2018/0008265 A1 | 1/2018 | Hatanaka et al. |
| 2018/0042610 A1 | 2/2018 | Sgroi, Jr. |
| 2018/0042689 A1 | 2/2018 | Mozdzierz et al. |
| 2018/0049738 A1 | 2/2018 | Meloul et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0067004 A1 | 3/2018 | Sgroi, Jr. |
| 2018/0085117 A1 | 3/2018 | Shelton, IV et al. |
| 2018/0085120 A1 | 3/2018 | Viola |
| 2018/0092710 A1 | 4/2018 | Bosisio et al. |
| 2018/0114591 A1 | 4/2018 | Pribanic et al. |
| 2018/0116658 A1 | 5/2018 | Aronhalt, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125594 A1 | 5/2018 | Beardsley |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0133521 A1 | 5/2018 | Frushour et al. |
| 2018/0140299 A1 | 5/2018 | Weaner et al. |
| 2018/0146960 A1 | 5/2018 | Shelton, IV et al. |
| 2018/0153542 A1 | 6/2018 | Shelton, IV et al. |
| 2018/0153634 A1 | 6/2018 | Zemlok et al. |
| 2018/0161034 A1 | 6/2018 | Scheib et al. |
| 2018/0168572 A1 | 6/2018 | Burbank |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0168651 A1* | 6/2018 | Shelton, IV ...... A61B 17/07207 |
| 2018/0168754 A1 | 6/2018 | Overmyer |

(56) References Cited

U.S. PATENT DOCUMENTS

| | | |
|---|---|---|
| 2018/0168756 A1 | 6/2018 | Liao et al. |
| 2018/0206904 A1 | 7/2018 | Felder et al. |
| 2018/0228490 A1 | 8/2018 | Richard et al. |
| 2018/0231111 A1 | 8/2018 | Mika et al. |
| 2018/0231475 A1 | 8/2018 | Brown et al. |
| 2018/0235609 A1 | 8/2018 | Harris et al. |
| 2018/0235617 A1 | 8/2018 | Shelton, IV et al. |
| 2018/0235618 A1 | 8/2018 | Kostrzewski |
| 2018/0235626 A1 | 8/2018 | Shelton, IV et al. |
| 2018/0236181 A1 | 8/2018 | Marlin et al. |
| 2018/0242970 A1 | 8/2018 | Mozdzierz |
| 2018/0247711 A1 | 8/2018 | Terry |
| 2018/0250002 A1 | 9/2018 | Eschbach |
| 2018/0271553 A1 | 9/2018 | Worrell |
| 2018/0271604 A1 | 9/2018 | Grout et al. |
| 2018/0273597 A1 | 9/2018 | Stimson |
| 2018/0279994 A1 | 10/2018 | Schaer et al. |
| 2018/0280073 A1 | 10/2018 | Sanai et al. |
| 2018/0289371 A1 | 10/2018 | Wang et al. |
| 2018/0296216 A1 | 10/2018 | Shelton, IV et al. |
| 2018/0296290 A1 | 10/2018 | Namiki et al. |
| 2018/0317905 A1 | 11/2018 | Olson et al. |
| 2018/0317915 A1* | 11/2018 | McDonald, II ........ A61B 17/29 |
| 2018/0325514 A1 | 11/2018 | Harris et al. |
| 2018/0333169 A1 | 11/2018 | Leimbach et al. |
| 2018/0360446 A1 | 12/2018 | Shelton, IV et al. |
| 2018/0360456 A1 | 12/2018 | Shelton, IV et al. |
| 2018/0368066 A1 | 12/2018 | Howell et al. |
| 2018/0368839 A1 | 12/2018 | Shelton, IV et al. |
| 2018/0368841 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0372806 A1 | 12/2018 | Laughery et al. |
| 2018/0375165 A1 | 12/2018 | Shelton, IV et al. |
| 2019/0000457 A1 | 1/2019 | Shelton, IV et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000469 A1 | 1/2019 | Shelton, IV et al. |
| 2019/0000471 A1 | 1/2019 | Shelton, IV et al. |
| 2019/0000472 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000481 A1 | 1/2019 | Harris et al. |
| 2019/0000535 A1 | 1/2019 | Messerly et al. |
| 2019/0000536 A1 | 1/2019 | Yates et al. |
| 2019/0006047 A1 | 1/2019 | Gorek et al. |
| 2019/0008515 A1 | 1/2019 | Beardsley et al. |
| 2019/0015102 A1 | 1/2019 | Baber et al. |
| 2019/0015165 A1 | 1/2019 | Giordano et al. |
| 2019/0017311 A1 | 1/2019 | McGettrick et al. |
| 2019/0021733 A1 | 1/2019 | Burbank |
| 2019/0029682 A1 | 1/2019 | Huitema et al. |
| 2019/0029701 A1 | 1/2019 | Shelton, IV et al. |
| 2019/0038281 A1 | 2/2019 | Shelton, IV et al. |
| 2019/0038283 A1 | 2/2019 | Shelton, IV et al. |
| 2019/0038285 A1 | 2/2019 | Mozdzierz |
| 2019/0059986 A1 | 2/2019 | Shelton, IV et al. |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105039 A1 | 4/2019 | Morgan et al. |
| 2019/0105044 A1 | 4/2019 | Shelton, IV et al. |
| 2019/0110779 A1 | 4/2019 | Gardner et al. |
| 2019/0110791 A1 | 4/2019 | Shelton, IV et al. |
| 2019/0117224 A1 | 4/2019 | Setser et al. |
| 2019/0125320 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125342 A1 | 5/2019 | Beardsley et al. |
| 2019/0125344 A1 | 5/2019 | DiNardo et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125476 A1 | 5/2019 | Shelton, IV et al. |
| 2019/0133422 A1 | 5/2019 | Nakamura |
| 2019/0133577 A1 | 5/2019 | Weadock et al. |
| 2019/0138770 A1 | 5/2019 | Compaijen et al. |
| 2019/0142423 A1 | 5/2019 | Satti, III et al. |
| 2019/0150925 A1 | 5/2019 | Marczyk et al. |
| 2019/0151029 A1 | 5/2019 | Robinson |
| 2019/0175847 A1 | 6/2019 | Pocreva, III et al. |
| 2019/0183491 A1 | 6/2019 | Shelton, IV et al. |
| 2019/0183502 A1 | 6/2019 | Shelton, IV et al. |
| 2019/0183594 A1 | 6/2019 | Shelton, IV et al. |
| 2019/0192147 A1 | 6/2019 | Shelton, IV et al. |
| 2019/0192148 A1 | 6/2019 | Shelton, IV et al. |
| 2019/0192151 A1 | 6/2019 | Shelton, IV et al. |
| 2019/0192153 A1 | 6/2019 | Shelton, IV et al. |
| 2019/0192155 A1 | 6/2019 | Shelton, IV et al. |
| 2019/0192157 A1 | 6/2019 | Scott et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200989 A1 | 7/2019 | Burbank et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201034 A1 | 7/2019 | Shelton, IV et al. |
| 2019/0201045 A1 | 7/2019 | Yates et al. |
| 2019/0201079 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201136 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201158 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0239873 A1 | 8/2019 | Laurent et al. |
| 2019/0247048 A1 | 8/2019 | Gasparovich et al. |
| 2019/0261982 A1 | 8/2019 | Holsten |

(56) References Cited

U.S. PATENT DOCUMENTS

| | | |
|---|---|---|
| 2019/0261983 A1 | 8/2019 | Granger et al. |
| 2019/0261984 A1 | 8/2019 | Nelson et al. |
| 2019/0261987 A1 | 8/2019 | Viola et al. |
| 2019/0262153 A1 | 8/2019 | Tassoni et al. |
| 2019/0269400 A1 | 9/2019 | Mandakolathur Vasudevan et al. |
| 2019/0269402 A1 | 9/2019 | Murray et al. |
| 2019/0269428 A1 | 9/2019 | Allen et al. |
| 2019/0274685 A1 | 9/2019 | Olson et al. |
| 2019/0282233 A1 | 9/2019 | Burbank et al. |
| 2019/0290264 A1 | 9/2019 | Morgan et al. |
| 2019/0290266 A1 | 9/2019 | Scheib et al. |
| 2019/0290267 A1 | 9/2019 | Baxter, III et al. |
| 2019/0290297 A1 | 9/2019 | Haider et al. |
| 2019/0298353 A1 | 10/2019 | Shelton, IV et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0298381 A1 | 10/2019 | Kreidler et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307456 A1 | 10/2019 | Shelton, IV et al. |
| 2019/0314015 A1 | 10/2019 | Shelton, IV et al. |
| 2019/0321040 A1 | 10/2019 | Shelton, IV |
| 2019/0321062 A1 | 10/2019 | Williams |
| 2019/0328387 A1 | 10/2019 | Overmyer et al. |
| 2019/0343515 A1 | 11/2019 | Morgan et al. |
| 2019/0357909 A1 | 11/2019 | Huitema et al. |
| 2019/0388091 A1 | 12/2019 | Eschbach et al. |
| 2020/0000531 A1 | 1/2020 | Giordano et al. |
| 2020/0008802 A1 | 1/2020 | Aronhalt et al. |
| 2020/0008809 A1 | 1/2020 | Shelton, IV et al. |
| 2020/0008827 A1 | 1/2020 | Dearden et al. |
| 2020/0015817 A1 | 1/2020 | Harris et al. |
| 2020/0015915 A1 | 1/2020 | Swayze et al. |
| 2020/0030020 A1 | 1/2020 | Wang et al. |
| 2020/0037939 A1 | 2/2020 | Castagna et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0046355 A1 | 2/2020 | Harris et al. |
| 2020/0046356 A1 | 2/2020 | Baxter, III et al. |
| 2020/0054320 A1 | 2/2020 | Harris et al. |
| 2020/0054321 A1 | 2/2020 | Harris et al. |
| 2020/0054329 A1 | 2/2020 | Shelton, IV et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060523 A1 | 2/2020 | Matsuda et al. |
| 2020/0060713 A1 | 2/2020 | Leimbach et al. |
| 2020/0061385 A1 | 2/2020 | Schwarz et al. |
| 2020/0085431 A1 | 3/2020 | Swayze et al. |
| 2020/0085435 A1 | 3/2020 | Shelton, IV et al. |
| 2020/0085518 A1 | 3/2020 | Giordano et al. |
| 2020/0093484 A1 | 3/2020 | Shelton, IV et al. |
| 2020/0093506 A1 | 3/2020 | Leimbach et al. |
| 2020/0093550 A1 | 3/2020 | Spivey et al. |
| 2020/0100783 A1 | 4/2020 | Yates et al. |
| 2020/0107829 A1 | 4/2020 | Shelton, IV et al. |
| 2020/0114505 A1 | 4/2020 | Kikuchi |
| 2020/0138436 A1 | 5/2020 | Yates et al. |
| 2020/0138507 A1 | 5/2020 | Davison et al. |
| 2020/0138534 A1 | 5/2020 | Garcia Kilroy et al. |
| 2020/0146741 A1 | 5/2020 | Long et al. |
| 2020/0187943 A1 | 6/2020 | Shelton, IV et al. |
| 2020/0197027 A1 | 6/2020 | Hershberger et al. |
| 2020/0205810 A1 | 7/2020 | Posey et al. |
| 2020/0205811 A1 | 7/2020 | Posey et al. |
| 2020/0205823 A1 | 7/2020 | Vendely et al. |
| 2020/0214706 A1 | 7/2020 | Vendely et al. |
| 2020/0214731 A1 | 7/2020 | Shelton, IV et al. |
| 2020/0229814 A1 | 7/2020 | Amariglio et al. |
| 2020/0237371 A1 | 7/2020 | Huitema et al. |
| 2020/0261086 A1 | 8/2020 | Zeiner et al. |
| 2020/0268377 A1 | 8/2020 | Schmid et al. |
| 2020/0275927 A1 | 9/2020 | Shelton, IV et al. |
| 2020/0275930 A1 | 9/2020 | Harris et al. |
| 2020/0280219 A1 | 9/2020 | Laughery et al. |
| 2020/0289112 A1 | 9/2020 | Whitfield et al. |
| 2020/0297341 A1 | 9/2020 | Yates et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305870 A1 | 10/2020 | Shelton, IV |
| 2020/0305872 A1 | 10/2020 | Weidner et al. |
| 2020/0305874 A1 | 10/2020 | Huitema et al. |
| 2020/0315623 A1 | 10/2020 | Eisinger et al. |
| 2020/0323526 A1 | 10/2020 | Huang et al. |
| 2020/0330092 A1 | 10/2020 | Shelton, IV et al. |
| 2020/0330096 A1 | 10/2020 | Shelton, IV et al. |
| 2020/0330181 A1 | 10/2020 | Junger et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345363 A1 | 11/2020 | Shelton, IV et al. |
| 2020/0345435 A1 | 11/2020 | Traina |
| 2020/0352562 A1 | 11/2020 | Timm et al. |
| 2020/0367886 A1 | 11/2020 | Shelton, IV et al. |
| 2020/0375585 A1 | 12/2020 | Swayze et al. |
| 2020/0375597 A1 | 12/2020 | Shelton, IV et al. |
| 2020/0390444 A1 | 12/2020 | Harris et al. |
| 2020/0397430 A1 | 12/2020 | Patel et al. |
| 2020/0405292 A1 | 12/2020 | Shelton, IV et al. |
| 2020/0405293 A1 | 12/2020 | Shelton, IV et al. |
| 2020/0405296 A1 | 12/2020 | Shelton, IV et al. |
| 2020/0405302 A1 | 12/2020 | Shelton, IV et al. |
| 2020/0405304 A1 | 12/2020 | Mozdzierz et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405316 A1 | 12/2020 | Shelton, IV et al. |
| 2020/0405341 A1 | 12/2020 | Hess et al. |
| 2020/0405403 A1 | 12/2020 | Shelton, IV et al. |
| 2020/0405404 A1 | 12/2020 | Shelton, IV et al. |
| 2020/0405410 A1 | 12/2020 | Shelton, IV |
| 2020/0405439 A1 | 12/2020 | Shelton, IV et al. |
| 2020/0410177 A1 | 12/2020 | Shelton, IV |
| 2021/0000466 A1 | 1/2021 | Leimbach et al. |
| 2021/0000467 A1 | 1/2021 | Shelton, IV et al. |
| 2021/0007742 A1 | 1/2021 | Rector et al. |
| 2021/0015480 A1 | 1/2021 | Shelton, IV et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059670 A1 | 3/2021 | Overmyer et al. |
| 2021/0059672 A1 | 3/2021 | Giordano et al. |
| 2021/0059673 A1 | 3/2021 | Shelton, IV et al. |
| 2021/0068829 A1 | 3/2021 | Miller et al. |
| 2021/0068835 A1 | 3/2021 | Shelton, IV et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100982 A1 | 4/2021 | Laby et al. |
| 2021/0106333 A1 | 4/2021 | Shelton, IV et al. |

(56) References Cited

U.S. PATENT DOCUMENTS

| | | |
|---|---|---|
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0128153 A1 | 5/2021 | Sgroi |
| 2021/0137522 A1 | 5/2021 | Shelton, IV et al. |
| 2021/0153866 A1 | 5/2021 | Knapp et al. |
| 2021/0177401 A1 | 6/2021 | Abramek et al. |
| 2021/0177411 A1 | 6/2021 | Williams |
| 2021/0186492 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186499 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0204941 A1 | 7/2021 | Dewaele et al. |
| 2021/0204951 A1 | 7/2021 | Sgroi et al. |
| 2021/0212671 A1 | 7/2021 | Ramadan et al. |
| 2021/0212691 A1 | 7/2021 | Smith et al. |
| 2021/0212776 A1 | 7/2021 | Schmitt et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244411 A1 | 8/2021 | Smith et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275175 A1 | 9/2021 | Vadali et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0290322 A1 | 9/2021 | Traina |
| 2021/0298745 A1 | 9/2021 | Leimbach et al. |
| 2021/0298746 A1 | 9/2021 | Leimbach et al. |
| 2021/0307744 A1 | 10/2021 | Walcott et al. |
| 2021/0307748 A1 | 10/2021 | Harris et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0338260 A1 | 11/2021 | Le Rolland et al. |
| 2021/0353284 A1 | 11/2021 | Yang et al. |
| 2021/0369271 A1 | 12/2021 | Schings et al. |
| 2021/0369273 A1 | 12/2021 | Yates et al. |
| 2021/0378669 A1 | 12/2021 | Shelton, IV et al. |
| 2021/0393260 A1 | 12/2021 | Shelton, IV et al. |
| 2021/0393261 A1 | 12/2021 | Harris et al. |
| 2021/0393262 A1 | 12/2021 | Shelton, IV et al. |
| 2021/0393268 A1 | 12/2021 | Shelton, IV et al. |
| 2021/0393366 A1 | 12/2021 | Shelton, IV et al. |
| 2022/0000478 A1 | 1/2022 | Shelton, IV et al. |
| 2022/0000479 A1 | 1/2022 | Shelton, IV et al. |
| 2022/0015760 A1 | 1/2022 | Beardsley et al. |
| 2022/0031313 A1 | 2/2022 | Bakos et al. |
| 2022/0031314 A1 | 2/2022 | Bakos et al. |
| 2022/0031315 A1 | 2/2022 | Bakos et al. |
| 2022/0031319 A1 | 2/2022 | Witte et al. |
| 2022/0031320 A1 | 2/2022 | Hall et al. |
| 2022/0031322 A1 | 2/2022 | Parks |
| 2022/0031323 A1 | 2/2022 | Witte |
| 2022/0031324 A1 | 2/2022 | Hall et al. |
| 2022/0031345 A1 | 2/2022 | Witte |
| 2022/0031346 A1 | 2/2022 | Parks |
| 2022/0031350 A1 | 2/2022 | Witte |
| 2022/0031351 A1 | 2/2022 | Moubarak et al. |
| 2022/0049593 A1 | 2/2022 | Groover et al. |
| 2022/0054125 A1 | 2/2022 | Ji et al. |
| 2022/0054130 A1 | 2/2022 | Overmyer et al. |
| 2022/0061836 A1 | 3/2022 | Parihar et al. |
| 2022/0061843 A1 | 3/2022 | Vendely et al. |
| 2022/0061845 A1 | 3/2022 | Shelton, IV et al. |
| 2022/0061862 A1 | 3/2022 | Shelton, IV et al. |
| 2022/0071630 A1 | 3/2022 | Swayze et al. |
| 2022/0071631 A1 | 3/2022 | Harris et al. |
| 2022/0071632 A1 | 3/2022 | Patel et al. |
| 2022/0071635 A1 | 3/2022 | Shelton, IV et al. |
| 2022/0079580 A1 | 3/2022 | Vendely et al. |
| 2022/0079586 A1 | 3/2022 | Shelton, IV et al. |
| 2022/0079588 A1 | 3/2022 | Harris et al. |
| 2022/0079589 A1 | 3/2022 | Harris et al. |
| 2022/0079590 A1 | 3/2022 | Harris et al. |
| 2022/0079595 A1 | 3/2022 | Huitema et al. |
| 2022/0079596 A1 | 3/2022 | Huitema et al. |
| 2022/0087676 A1 | 3/2022 | Shelton, IV et al. |
| 2022/0104816 A1 | 4/2022 | Fernandes et al. |
| 2022/0104820 A1 | 4/2022 | Shelton, IV et al. |
| 2022/0117602 A1 | 4/2022 | Wise et al. |
| 2022/0133299 A1 | 5/2022 | Baxter, III |
| 2022/0133300 A1 | 5/2022 | Leimbach et al. |
| 2022/0133301 A1 | 5/2022 | Leimbach |
| 2022/0133302 A1 | 5/2022 | Zerkle et al. |
| 2022/0133303 A1 | 5/2022 | Huang |
| 2022/0133304 A1 | 5/2022 | Leimbach et al. |
| 2022/0133310 A1 | 5/2022 | Ross |
| 2022/0133311 A1 | 5/2022 | Huang |
| 2022/0133312 A1 | 5/2022 | Huang |
| 2022/0142643 A1 | 5/2022 | Shelton, IV et al. |
| 2022/0151611 A1 | 5/2022 | Shelton, IV et al. |
| 2022/0151613 A1 | 5/2022 | Vendely et al. |
| 2022/0151614 A1 | 5/2022 | Vendely et al. |
| 2022/0151615 A1 | 5/2022 | Shelton, IV et al. |
| 2022/0151616 A1 | 5/2022 | Shelton, IV et al. |
| 2022/0160358 A1 | 5/2022 | Wixey |
| 2022/0167968 A1 | 6/2022 | Worthington et al. |
| 2022/0167970 A1 | 6/2022 | Aronhalt et al. |
| 2022/0167971 A1 | 6/2022 | Shelton, IV et al. |
| 2022/0167972 A1 | 6/2022 | Shelton, IV et al. |
| 2022/0167973 A1 | 6/2022 | Shelton, IV et al. |
| 2022/0167974 A1 | 6/2022 | Shelton, IV et al. |
| 2022/0167975 A1 | 6/2022 | Shelton, IV et al. |
| 2022/0167977 A1 | 6/2022 | Shelton, IV et al. |
| 2022/0167979 A1 | 6/2022 | Yates et al. |
| 2022/0167980 A1 | 6/2022 | Shelton, IV et al. |
| 2022/0167981 A1 | 6/2022 | Shelton, IV et al. |
| 2022/0167982 A1 | 6/2022 | Shelton, IV et al. |
| 2022/0167983 A1 | 6/2022 | Shelton, IV et al. |
| 2022/0167984 A1 | 6/2022 | Shelton, IV et al. |
| 2022/0167995 A1 | 6/2022 | Parfett et al. |
| 2022/0168038 A1 | 6/2022 | Shelton, IV et al. |
| 2022/0175370 A1 | 6/2022 | Shelton, IV et al. |
| 2022/0175371 A1 | 6/2022 | Hess et al. |
| 2022/0175372 A1 | 6/2022 | Shelton, IV et al. |
| 2022/0175375 A1 | 6/2022 | Harris et al. |
| 2022/0175378 A1 | 6/2022 | Leimbach et al. |
| 2022/0175381 A1 | 6/2022 | Scheib et al. |
| 2022/0183685 A1 | 6/2022 | Shelton, IV et al. |
| 2022/0211367 A1 | 7/2022 | Schmid et al. |
| 2022/0218332 A1 | 7/2022 | Shelton, IV et al. |
| 2022/0218333 A1 | 7/2022 | Parihar et al. |

(56) References Cited

U.S. PATENT DOCUMENTS

| | | |
|---|---|---|
| 2022/0218334 A1 | 7/2022 | Parihar et al. |
| 2022/0218336 A1 | 7/2022 | Timm et al. |
| 2022/0218337 A1 | 7/2022 | Timm et al. |
| 2022/0218338 A1 | 7/2022 | Shelton, IV et al. |
| 2022/0218340 A1 | 7/2022 | Harris et al. |
| 2022/0218344 A1 | 7/2022 | Leimbach et al. |
| 2022/0218345 A1 | 7/2022 | Shelton, IV et al. |
| 2022/0218346 A1 | 7/2022 | Shelton, IV et al. |
| 2022/0218347 A1 | 7/2022 | Shelton, IV et al. |
| 2022/0218348 A1 | 7/2022 | Swensgard et al. |
| 2022/0218349 A1 | 7/2022 | Shelton, IV et al. |
| 2022/0218350 A1 | 7/2022 | Shelton, IV et al. |
| 2022/0218351 A1 | 7/2022 | Shelton, IV et al. |
| 2022/0218376 A1 | 7/2022 | Shelton, IV et al. |
| 2022/0218378 A1 | 7/2022 | Shelton, IV et al. |
| 2022/0218381 A1 | 7/2022 | Leimbach et al. |
| 2022/0218382 A1 | 7/2022 | Leimbach et al. |
| 2022/0225980 A1 | 7/2022 | Shelton, IV et al. |
| 2022/0225982 A1 | 7/2022 | Yates et al. |
| 2022/0225986 A1 | 7/2022 | Shelton, IV et al. |
| 2022/0225993 A1 | 7/2022 | Huitema et al. |
| 2022/0225994 A1 | 7/2022 | Setser et al. |
| 2022/0226012 A1 | 7/2022 | Shelton, IV et al. |
| 2022/0226013 A1 | 7/2022 | Hall et al. |
| 2022/0233184 A1 | 7/2022 | Parihar et al. |
| 2022/0233185 A1 | 7/2022 | Parihar et al. |
| 2022/0233186 A1 | 7/2022 | Timm et al. |
| 2022/0233187 A1 | 7/2022 | Timm et al. |
| 2022/0233188 A1 | 7/2022 | Timm et al. |
| 2022/0233194 A1 | 7/2022 | Baxter, III et al. |
| 2022/0233195 A1 | 7/2022 | Shelton, IV et al. |
| 2022/0233257 A1 | 7/2022 | Shelton, IV et al. |
| 2022/0240928 A1 | 8/2022 | Timm et al. |
| 2022/0240929 A1 | 8/2022 | Timm et al. |
| 2022/0240930 A1 | 8/2022 | Yates et al. |
| 2022/0240936 A1 | 8/2022 | Huitema et al. |
| 2022/0240937 A1 | 8/2022 | Shelton, IV et al. |
| 2022/0249095 A1 | 8/2022 | Shelton, IV et al. |
| 2022/0265272 A1 | 8/2022 | Li et al. |
| 2022/0273291 A1 | 9/2022 | Shelton, IV et al. |
| 2022/0273292 A1 | 9/2022 | Shelton, IV et al. |
| 2022/0273293 A1 | 9/2022 | Shelton, IV et al. |
| 2022/0273294 A1 | 9/2022 | Creamer et al. |
| 2022/0273299 A1 | 9/2022 | Shelton, IV et al. |
| 2022/0273300 A1 | 9/2022 | Shelton, IV et al. |
| 2022/0273301 A1 | 9/2022 | Creamer et al. |
| 2022/0273302 A1 | 9/2022 | Shelton, IV et al. |
| 2022/0273303 A1 | 9/2022 | Creamer et al. |
| 2022/0273304 A1 | 9/2022 | Shelton, IV et al. |
| 2022/0273305 A1 | 9/2022 | Shelton, IV et al. |
| 2022/0273306 A1 | 9/2022 | Shelton, IV et al. |
| 2022/0273307 A1 | 9/2022 | Shelton, IV et al. |
| 2022/0273308 A1 | 9/2022 | Shelton, IV et al. |
| 2022/0278438 A1 | 9/2022 | Shelton, IV et al. |
| 2022/0287711 A1 | 9/2022 | Ming et al. |
| 2022/0296230 A1 | 9/2022 | Adams et al. |
| 2022/0296231 A1 | 9/2022 | Adams et al. |
| 2022/0296232 A1 | 9/2022 | Adams et al. |
| 2022/0296233 A1 | 9/2022 | Morgan et al. |
| 2022/0296234 A1 | 9/2022 | Shelton, IV et al. |
| 2022/0296235 A1 | 9/2022 | Morgan et al. |
| 2022/0296236 A1 | 9/2022 | Bakos et al. |
| 2022/0296237 A1 | 9/2022 | Bakos et al. |
| 2022/0304680 A1 | 9/2022 | Shelton, IV et al. |
| 2022/0304681 A1 | 9/2022 | Shelton, IV et al. |
| 2022/0304682 A1 | 9/2022 | Shelton, IV et al. |
| 2022/0304683 A1 | 9/2022 | Shelton, IV et al. |
| 2022/0304684 A1 | 9/2022 | Bakos et al. |
| 2022/0304685 A1 | 9/2022 | Bakos et al. |
| 2022/0304686 A1 | 9/2022 | Shelton, IV et al. |
| 2022/0304687 A1 | 9/2022 | Shelton, IV et al. |
| 2022/0304688 A1 | 9/2022 | Shelton, IV et al. |
| 2022/0304689 A1 | 9/2022 | Shelton, IV |
| 2022/0304690 A1 | 9/2022 | Baxter, III et al. |
| 2022/0304714 A1 | 9/2022 | Shelton, IV et al. |
| 2022/0304715 A1 | 9/2022 | Shelton, IV |
| 2022/0313253 A1 | 10/2022 | Shelton, IV et al. |
| 2022/0313263 A1 | 10/2022 | Huitema et al. |
| 2022/0313619 A1 | 10/2022 | Schmid et al. |
| 2022/0323067 A1 | 10/2022 | Overmyer et al. |
| 2022/0323070 A1 | 10/2022 | Ross et al. |
| 2022/0330940 A1 | 10/2022 | Shelton, IV et al. |
| 2022/0338870 A1 | 10/2022 | Swayze et al. |
| 2022/0346774 A1 | 11/2022 | Hess et al. |
| 2022/0346775 A1 | 11/2022 | Hess et al. |
| 2022/0354493 A1 | 11/2022 | Shelton, IV et al. |
| 2022/0354495 A1 | 11/2022 | Baxter, III et al. |
| 2022/0361879 A1 | 11/2022 | Baxter, III et al. |
| 2022/0370069 A1 | 11/2022 | Simms et al. |
| 2022/0378418 A1 | 12/2022 | Huang et al. |
| 2022/0378420 A1 | 12/2022 | Leimbach et al. |
| 2022/0378424 A1 | 12/2022 | Huang et al. |
| 2022/0378425 A1 | 12/2022 | Huang et al. |
| 2022/0378426 A1 | 12/2022 | Huang et al. |
| 2022/0378427 A1 | 12/2022 | Huang et al. |
| 2022/0378428 A1 | 12/2022 | Shelton, IV et al. |
| 2022/0378435 A1 | 12/2022 | Dholakia et al. |
| 2022/0387030 A1 | 12/2022 | Shelton, IV et al. |
| 2022/0387031 A1 | 12/2022 | Yates et al. |
| 2022/0387032 A1 | 12/2022 | Huitema et al. |
| 2022/0387033 A1 | 12/2022 | Huitema et al. |
| 2022/0387034 A1 | 12/2022 | Huitema et al. |
| 2022/0387035 A1 | 12/2022 | Huitema et al. |
| 2022/0387036 A1 | 12/2022 | Huitema et al. |
| 2022/0387037 A1 | 12/2022 | Huitema et al. |
| 2022/0387038 A1 | 12/2022 | Huitema et al. |
| 2022/0387125 A1 | 12/2022 | Leimbach et al. |

FOREIGN PATENT DOCUMENTS

| | | |
|---|---|---|
| AU | 2012268848 A1 | 1/2013 |
| AU | 2011218702 B2 | 6/2013 |
| AU | 2012200178 B2 | 7/2013 |
| BR | 112013007744 A2 | 6/2016 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2785249 Y | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101188900 A | 5/2008 |
| CN | 101203085 A | 6/2008 |
| CN | 101273908 A | 10/2008 |
| CN | 101378791 A | 3/2009 |
| CN | 101507635 A | 8/2009 |
| CN | 101522120 A | 9/2009 |
| CN | 101669833 A | 3/2010 |
| CN | 101716090 A | 6/2010 |
| CN | 101721236 A | 6/2010 |
| CN | 101756727 A | 6/2010 |
| CN | 101828940 A | 9/2010 |
| CN | 101856250 A | 10/2010 |
| CN | 101873834 A | 10/2010 |
| CN | 201719298 U | 1/2011 |
| CN | 102038532 A | 5/2011 |

(56) References Cited

FOREIGN PATENT DOCUMENTS

| | | |
|---|---|---|
| CN | 201879759 U | 6/2011 |
| CN | 201949071 U | 8/2011 |
| CN | 102217961 A | 10/2011 |
| CN | 102217963 A | 10/2011 |
| CN | 102243850 A | 11/2011 |
| CN | 102247182 A | 11/2011 |
| CN | 102247183 A | 11/2011 |
| CN | 101779977 B | 12/2011 |
| CN | 102309352 A | 1/2012 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 102743201 A | 10/2012 |
| CN | 202489990 U | 10/2012 |
| CN | 102228387 B | 11/2012 |
| CN | 102835977 A | 12/2012 |
| CN | 202568350 U | 12/2012 |
| CN | 103037781 A | 4/2013 |
| CN | 103083053 A | 5/2013 |
| CN | 103391037 A | 11/2013 |
| CN | 203328751 U | 12/2013 |
| CN | 103505264 A | 1/2014 |
| CN | 103584893 A | 2/2014 |
| CN | 103635150 A | 3/2014 |
| CN | 103690212 A | 4/2014 |
| CN | 103764046 A | 4/2014 |
| CN | 203564285 U | 4/2014 |
| CN | 203564287 U | 4/2014 |
| CN | 203564287 U | 4/2014 |
| CN | 203597997 U | 5/2014 |
| CN | 103829981 A | 6/2014 |
| CN | 103829983 A | 6/2014 |
| CN | 103860221 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 104027145 A | 9/2014 |
| CN | 203815517 U | 9/2014 |
| CN | 102783741 B | 10/2014 |
| CN | 102973300 B | 10/2014 |
| CN | 204092074 U | 1/2015 |
| CN | 104337556 A | 2/2015 |
| CN | 204158440 U | 2/2015 |
| CN | 204158441 U | 2/2015 |
| CN | 102469995 B | 3/2015 |
| CN | 104422849 A | 3/2015 |
| CN | 104586463 A | 5/2015 |
| CN | 204520822 U | 8/2015 |
| CN | 204636451 U | 9/2015 |
| CN | 103860225 B | 3/2016 |
| CN | 103750872 B | 5/2016 |
| CN | 105919642 A | 9/2016 |
| CN | 103648410 B | 10/2016 |
| CN | 105997173 A | 10/2016 |
| CN | 106344091 A | 1/2017 |
| CN | 104921730 B | 9/2017 |
| CN | 104349800 B | 11/2017 |
| CN | 107635483 A | 1/2018 |
| CN | 208625784 U | 3/2019 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004041871 A1 | 3/2006 |
| DE | 102004063606 A1 | 7/2006 |
| DE | 202007003114 U1 | 6/2007 |
| DE | 102010013150 A1 | 9/2011 |
| DE | 102012213322 A1 | 1/2014 |
| DE | 102013101158 A1 | 8/2014 |
| EM | 002220467-0008 | 4/2013 |
| EP | 0000756 A1 | 2/1979 |
| EP | 0122046 A1 | 10/1984 |
| EP | 0129442 B1 | 11/1987 |
| EP | 0251444 A1 | 1/1988 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0516544 B1 | 3/1996 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1064882 A1 | 1/2001 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1382304 A1 | 1/2004 |
| EP | 1407719 A2 | 4/2004 |
| EP | 0996378 B1 | 6/2004 |
| EP | 1558161 A1 | 8/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 2044888 A2 | 4/2009 |
| EP | 1719461 B1 | 6/2009 |
| EP | 2116196 A2 | 11/2009 |
| EP | 2153793 A2 | 2/2010 |
| EP | 2153793 A2 | 2/2010 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2529671 A2 | 12/2012 |

(56) References Cited

FOREIGN PATENT DOCUMENTS

| | | |
|---|---|---|
| EP | 2586378 A2 | 5/2013 |
| EP | 2606812 A1 | 6/2013 |
| EP | 2644118 A2 | 10/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2772195 A2 | 9/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2878274 A1 | 6/2015 |
| EP | 2898839 A1 | 7/2015 |
| EP | 2932918 A1 | 10/2015 |
| EP | 2992836 A2 | 3/2016 |
| EP | 3015080 A2 | 5/2016 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3061404 A1 | 8/2016 |
| EP | 3075327 B1 | 10/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135208 A2 | 3/2017 |
| EP | 3135225 A2 | 3/2017 |
| EP | 2789299 B1 | 5/2017 |
| EP | 3225190 A2 | 10/2017 |
| EP | 3228259 A1 | 10/2017 |
| EP | 3235445 A1 | 10/2017 |
| EP | 3326548 A1 | 5/2018 |
| EP | 3338660 A1 | 6/2018 |
| EP | 3338697 A1 | 6/2018 |
| EP | 3338702 A1 | 6/2018 |
| EP | 3363378 A1 | 8/2018 |
| EP | 3409216 A1 | 12/2018 |
| EP | 3420925 A1 | 1/2019 |
| EP | 3476301 A1 | 5/2019 |
| EP | 3476334 A1 | 5/2019 |
| EP | 3275378 B1 | 7/2019 |
| EP | 3505095 A1 | 7/2019 |
| EP | 3545861 A2 | 10/2019 |
| EP | 3714805 A1 | 9/2020 |
| EP | 3756572 A2 | 10/2020 |
| EP | 3791810 A1 | 3/2021 |
| EP | 3791810 A1 | 3/2021 |
| EP | 3838172 A1 | 6/2021 |
| ES | 1070456 U | 9/2009 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S6333137 A | 2/1988 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |
| JP | H0385009 U | 8/1991 |
| JP | H0489041 A | 3/1992 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H0636757 A | 2/1994 |
| JP | H06237937 A | 8/1994 |
| JP | H06304176 A | 11/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H0950795 A | 2/1997 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |

(56) References Cited

FOREIGN PATENT DOCUMENTS

| | | |
|---|---|---|
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008154804 A | 7/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | 2011200665 A | 10/2011 |
| JP | D1432094 | 12/2011 |
| JP | 1433631 S | 2/2012 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541982 A | 11/2013 |
| JP | 2013541983 A | 11/2013 |
| JP | 2013541997 A | 11/2013 |
| JP | 2014018667 A | 2/2014 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015516838 A | 6/2015 |
| JP | 2015521524 A | 7/2015 |
| JP | 2015521525 A | 7/2015 |
| JP | 2016007800 A | 1/2016 |
| JP | 2016508792 A | 3/2016 |
| JP | 2016512057 A | 4/2016 |
| JP | 2016530949 A | 10/2016 |
| JP | 2017513563 A | 6/2017 |
| JP | 1601498 S | 4/2018 |
| JP | 2019513530 A | 5/2019 |
| JP | 2020501797 A | 1/2020 |
| JP | D1677030 S | 1/2021 |
| JP | D1696539 S | 10/2021 |
| KR | 20100110134 A | 10/2010 |
| KR | 20110003229 A | 1/2011 |
| KR | 300631507 | 3/2012 |
| KR | 300747646 | 6/2014 |
| KR | 20180053811 A | 5/2018 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1042742 A1 | 9/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0036690 A2 | 6/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |

(56) References Cited

FOREIGN PATENT DOCUMENTS

| | | | |
|---|---|---|---|
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO 2009/091497 | A2 | 7/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO 2016/182933 | A1 | 11/2016 |
| WO | WO-2017138905 | A1 | 8/2017 |
| WO | WO-2018011664 | A1 | 1/2018 |
| WO | WO 2018/049198 | A1 | 3/2018 |
| WO | WO-2019036490 | A1 | 2/2019 |
| WO | WO-2019130087 | A1 | 7/2019 |
| WO | WO-2019130089 | A1 | 7/2019 |
| WO | WO 2019/165403 | A1 | 8/2019 |
| WO | WO-2019208902 | A1 | 10/2019 |
| WO | WO 2020/214397 | A1 | 10/2020 |
| WO | WO 2021/189234 | A1 | 9/2021 |
| WO | WO-2021189234 | A1 | 9/2021 |

OTHER PUBLICATIONS

Yang et al.; "4D printing reconfigurable, deployable and mechanically tunable metamaterials," Material Horizons, vol. 6, pp. 1244-1250 (2019).
Design U.S. Appl. No. 29/736,648, filed Jun. 2, 2020.
Design U.S. Appl. No. 29/736,649, filed Jun. 2, 2020.
Design U.S. Appl. No. 29/736,651, filed Jun. 2, 2020.
Design U.S. Appl. No. 29/736,652, filed Jun. 2, 2020.
Design U.S. Appl. No. 29/736,653, filed Jun. 2, 2020.
Design U.S. Appl. No. 29/736,654, filed Jun. 2, 2020.
Design U.S. Appl. No. 29/736,655, filed Jun. 2, 2020.
U.S. Appl. No. 16/720,766, filed Dec. 19, 2019.
ASTM procedure D2240-00, "Standard Test Method for Rubber Property—Durometer Hardness," (Published Aug. 2000).
ASTM procedure D2240-05, "Standard Test Method for Rubber Property—Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

(56) References Cited

OTHER PUBLICATIONS

Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7(2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (1 column, heading "Materials for Soft Orthoses", 7th bullet point); (Year: 2007).
Lee, Youbok, "Antenna Circuit Design for RFID Applications," 2003, pp. 1-5 Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsvstems.pdf>.
Schroeter, John, "*Demystifying UHF Gen 2 RFID, HF RFID*," Online Article, Jun. 2, 2008, pp. 1-3, <https://www.edn.com/design/industrial-control/4019123/Demvstifying-UHF-Gen-2-RFID-HF-RFID>.
Adeeb, et al., "*An Inductive Link-Based Wireless Power Transfer System for Biomedical Applications*," Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.ccm/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.

(56) References Cited

OTHER PUBLICATIONS stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.
U.S. Appl. No. 62/798,651, filed Jan. 30, 2019.
U.S. Appl. No. 62/840,602, filed Apr. 30, 2019.
U.S. Appl. No. 17/211,161.
U.S. Appl. No. 17/211,168.
U.S. Appl. No. 17/211,172.
U.S. Appl. No. 17/211,175.
U.S. Appl. No. 17/211,182.
U.S. Appl. No. 17/211,189.
U.S. Appl. No. 17/211,192.
U.S. Appl. No. 17/211,197.
U.S. Appl. No. 17/211,207.
U.S. Appl. No. 17/211,210.
U.S. Appl. No. 17/211,222.
U.S. Appl. No. 17/211,230.
U.S. Appl. No. 17/211,242.
International Search Report and Written Opinion dated Jun. 24, 2022 for Application No. PCT/IB2022/052518, 16 pgs.
International Search Report and Written Opinion dated Jul. 8, 2022 for Application No. PCT/IB2022/052521, 13 pgs.
International Search Report and Written Opinion dated Jul. 15, 2022 for Application No. PCT/IB2022/052528, 16 pgs.
International Search Report and Written Opinion dated Oct. 6, 2022 for Application No. PCT/IB2022/052552, 20 pgs.
International Search Report and Written Opinion dated Sep. 14, 2022 for Application No. PCT/IB2022/052550, 16 pgs.
International Search Report and Written Opinion dated Jul. 6, 2022 for Application No. PCT/IB2022/052548, 16 pgs.
International Search Report and Written Opinion dated Jul. 20, 2022 for Application No. PCT/IB2022/052537, 21 pgs.
International Search Report and Written Opinion dated Jun. 29, 2022 for Application No. PCT/IB2022/052527, 17 pgs.
International Search Report and Written Opinion dated Jul. 5, 2022 for Application No. PCT/IB2022/052526, 15 pgs.
International Search Report and Written Opinion dated Jul. 13, 2022 for Application No. PCT/IB2022/052531, 16 pgs.
International Search Report and Written Opinion dated Aug. 30, 2022 for Application No. PCT/IB2022/052535, 22 pgs.
International Search Report and Written Opinion dated Jul. 15, 2022 for Application No. PCT/IB2022/052540, 15 pgs.
International Search Report and Written Opinion dated Jun. 28, 2022 for Application No. PCT/IB2022/052520, 14 pgs.

* cited by examiner

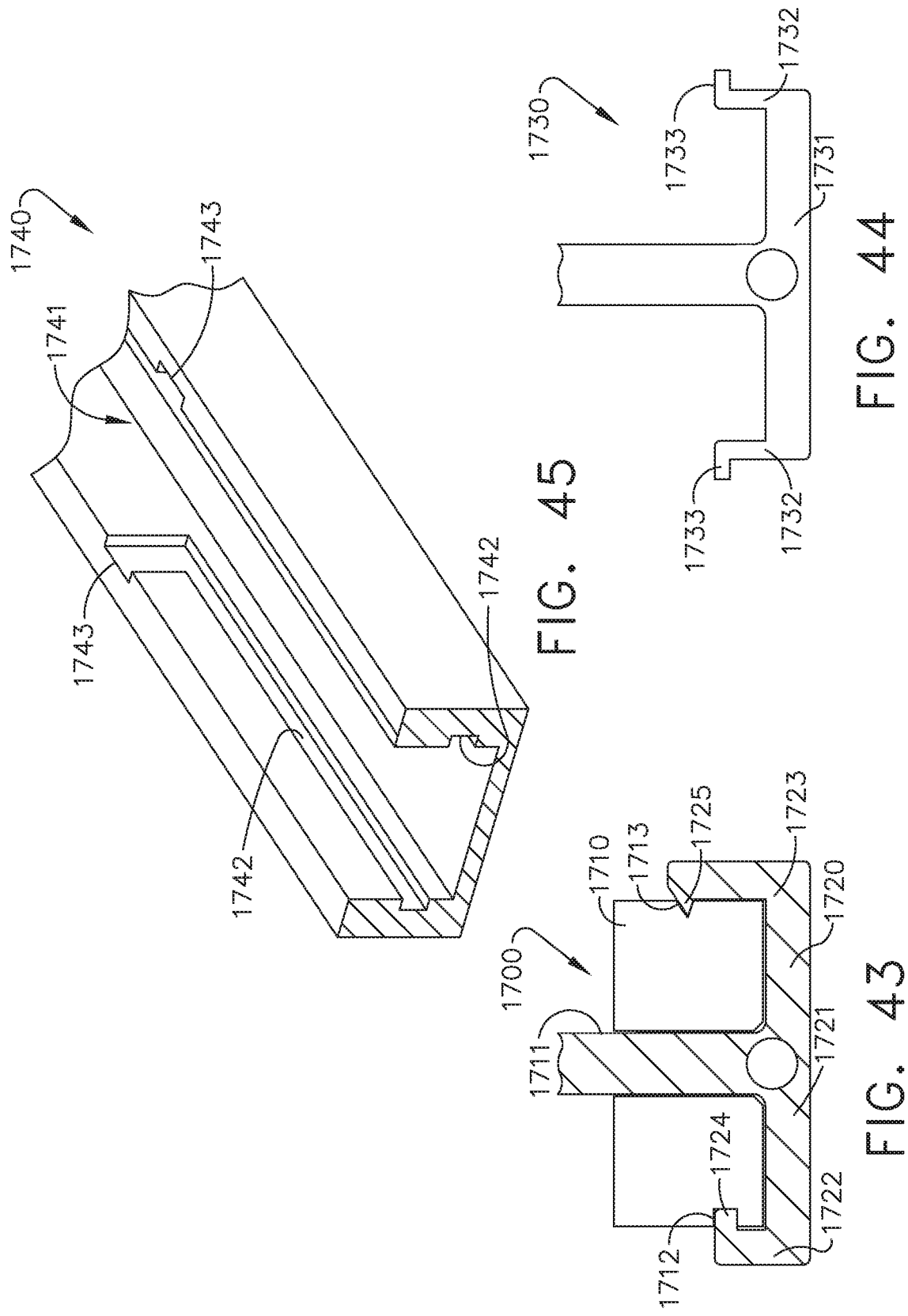

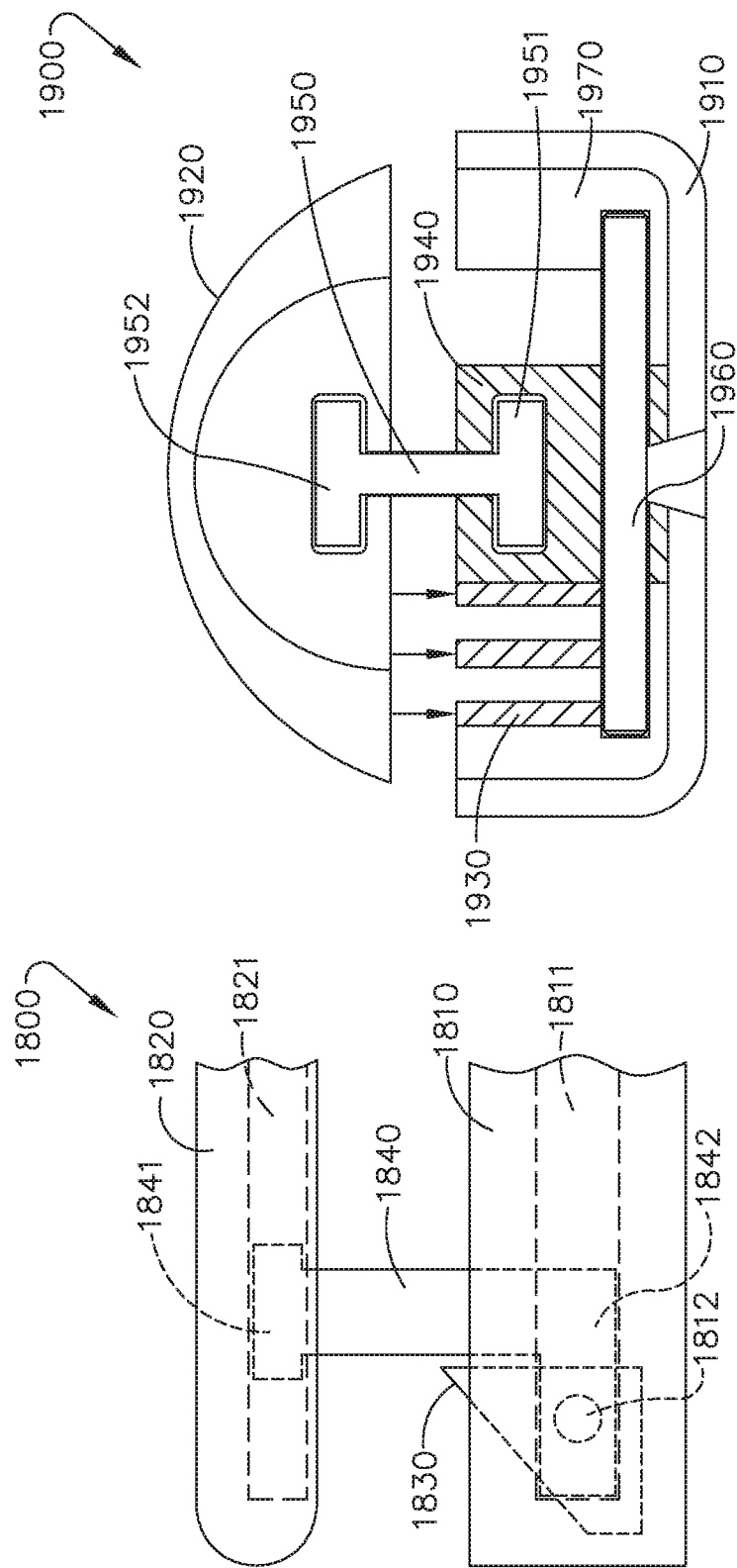

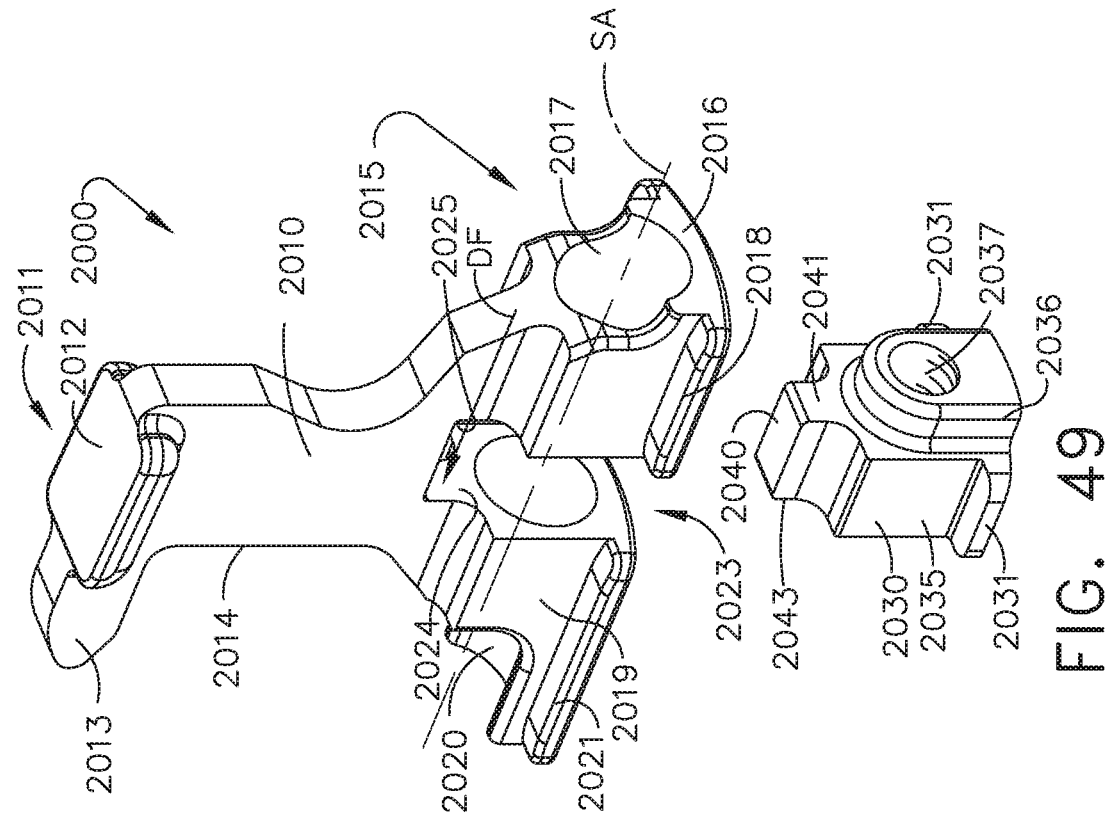
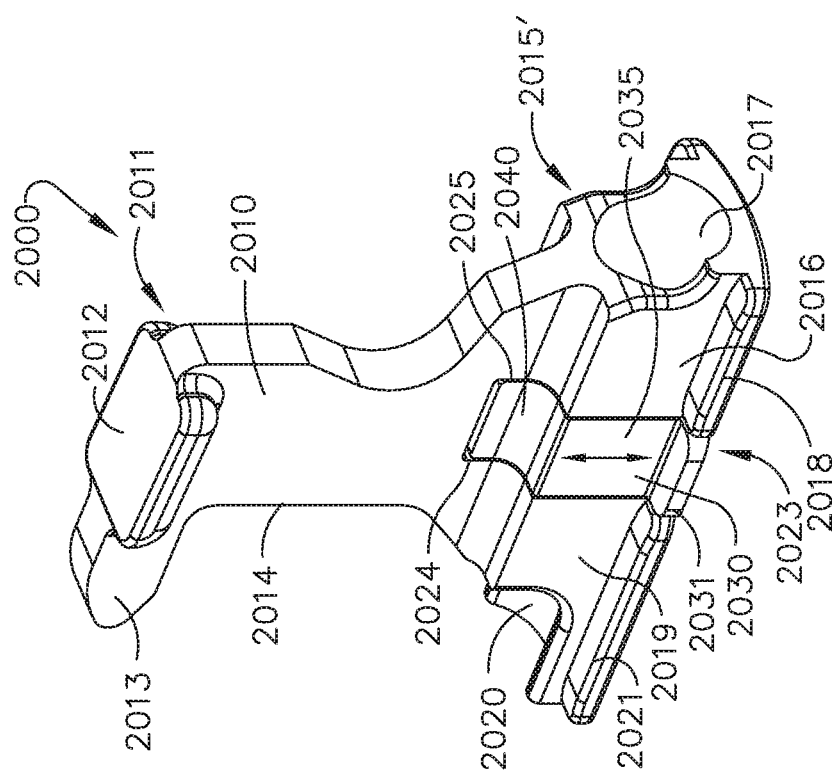

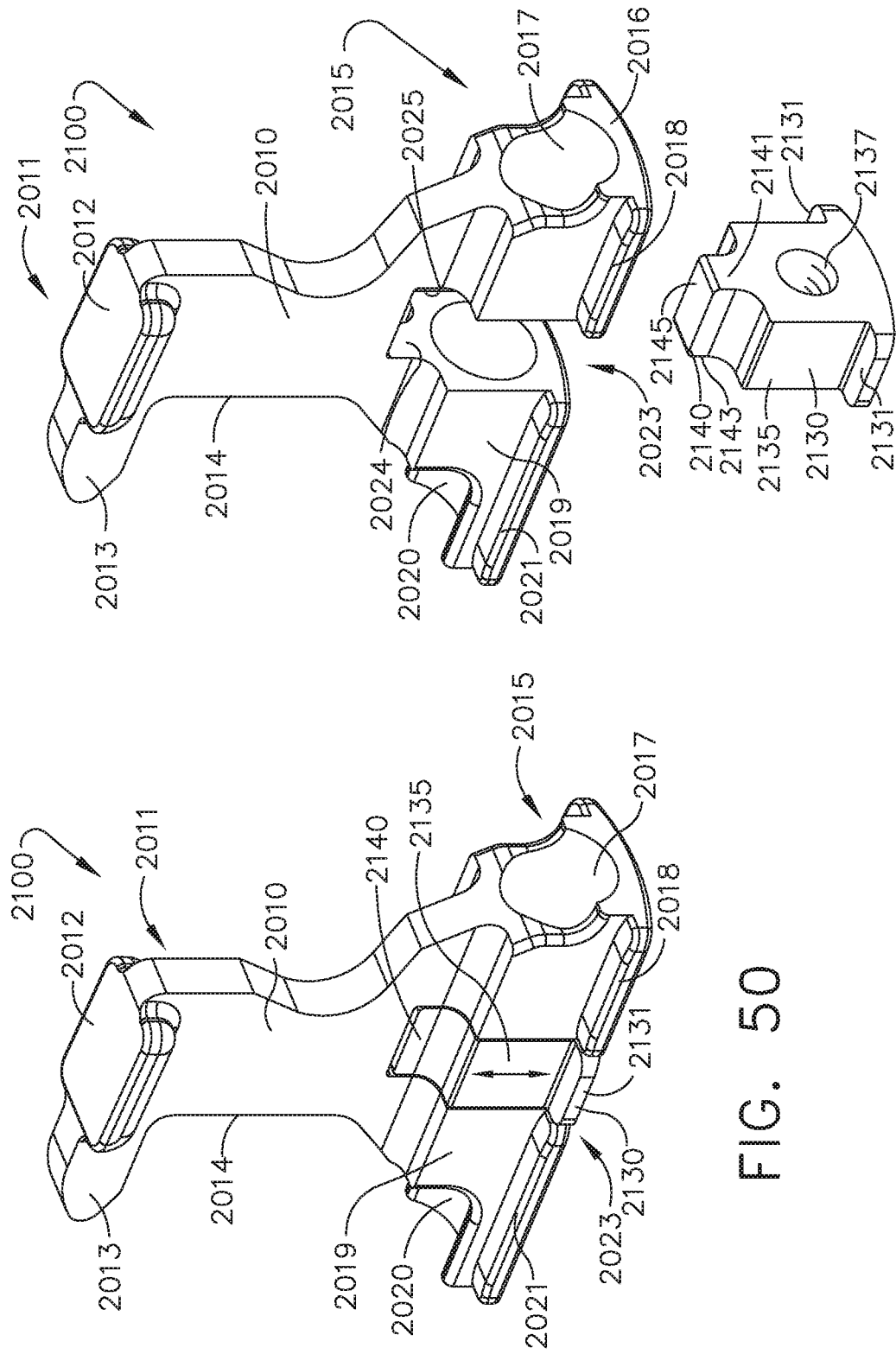

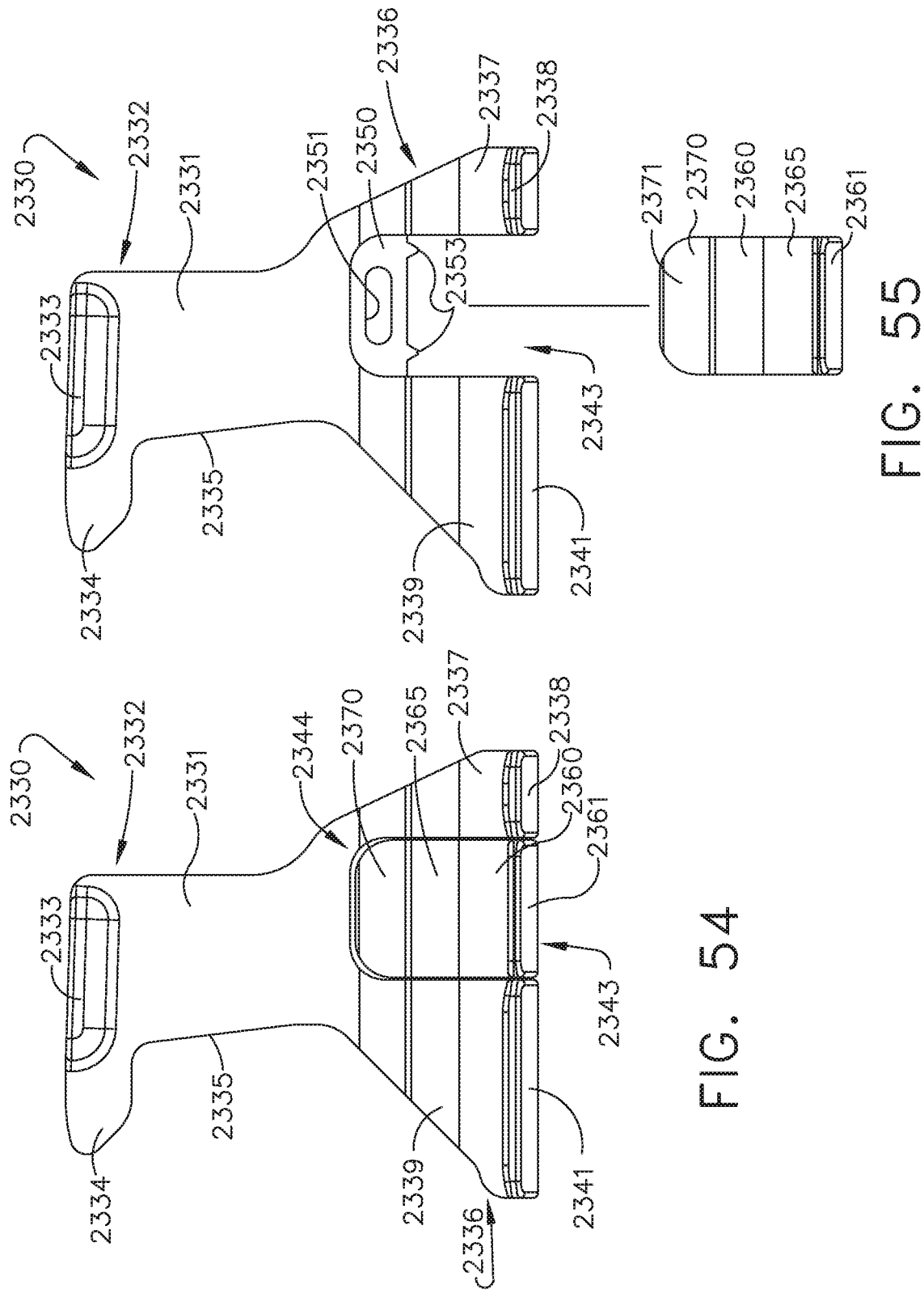

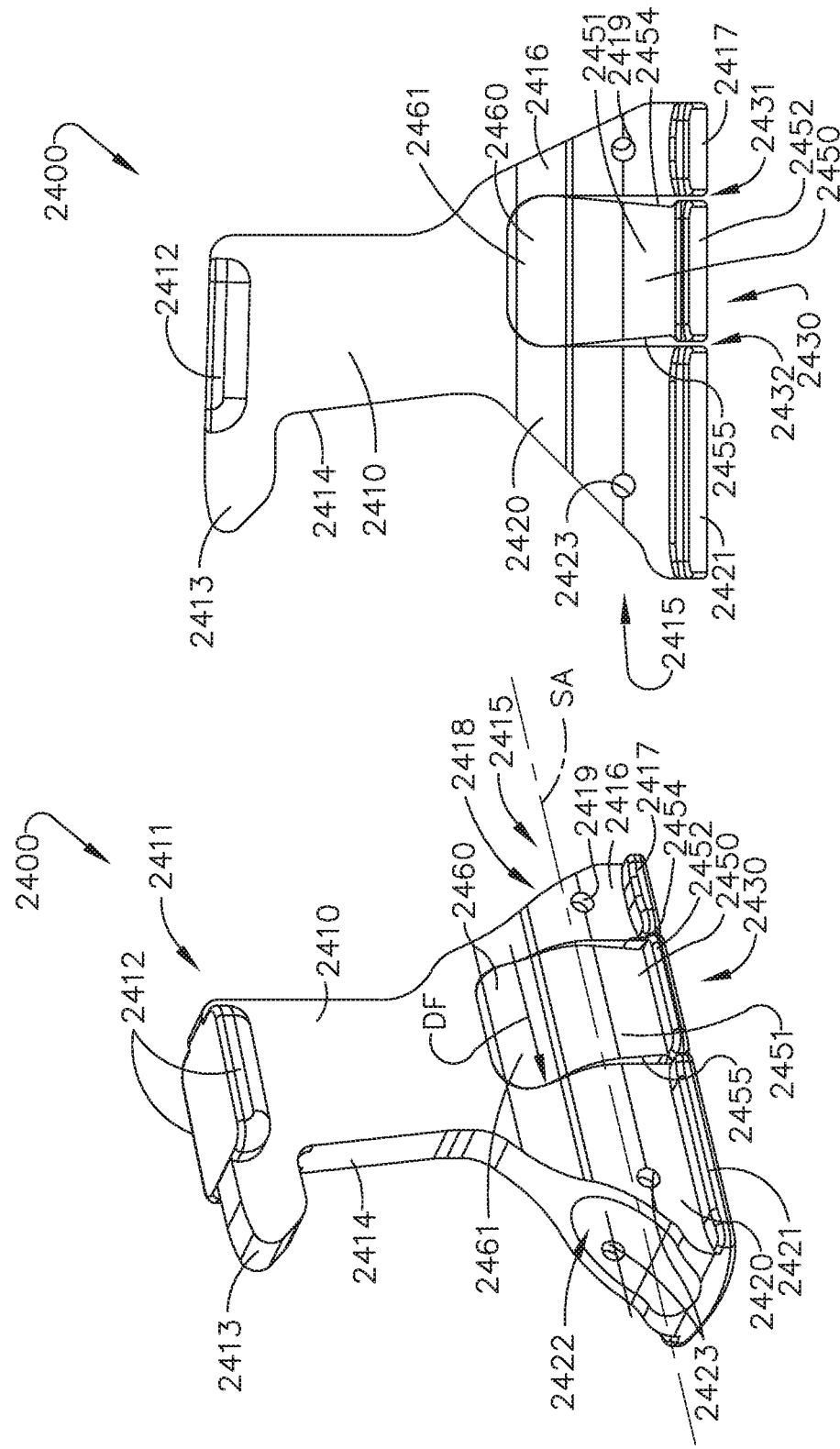

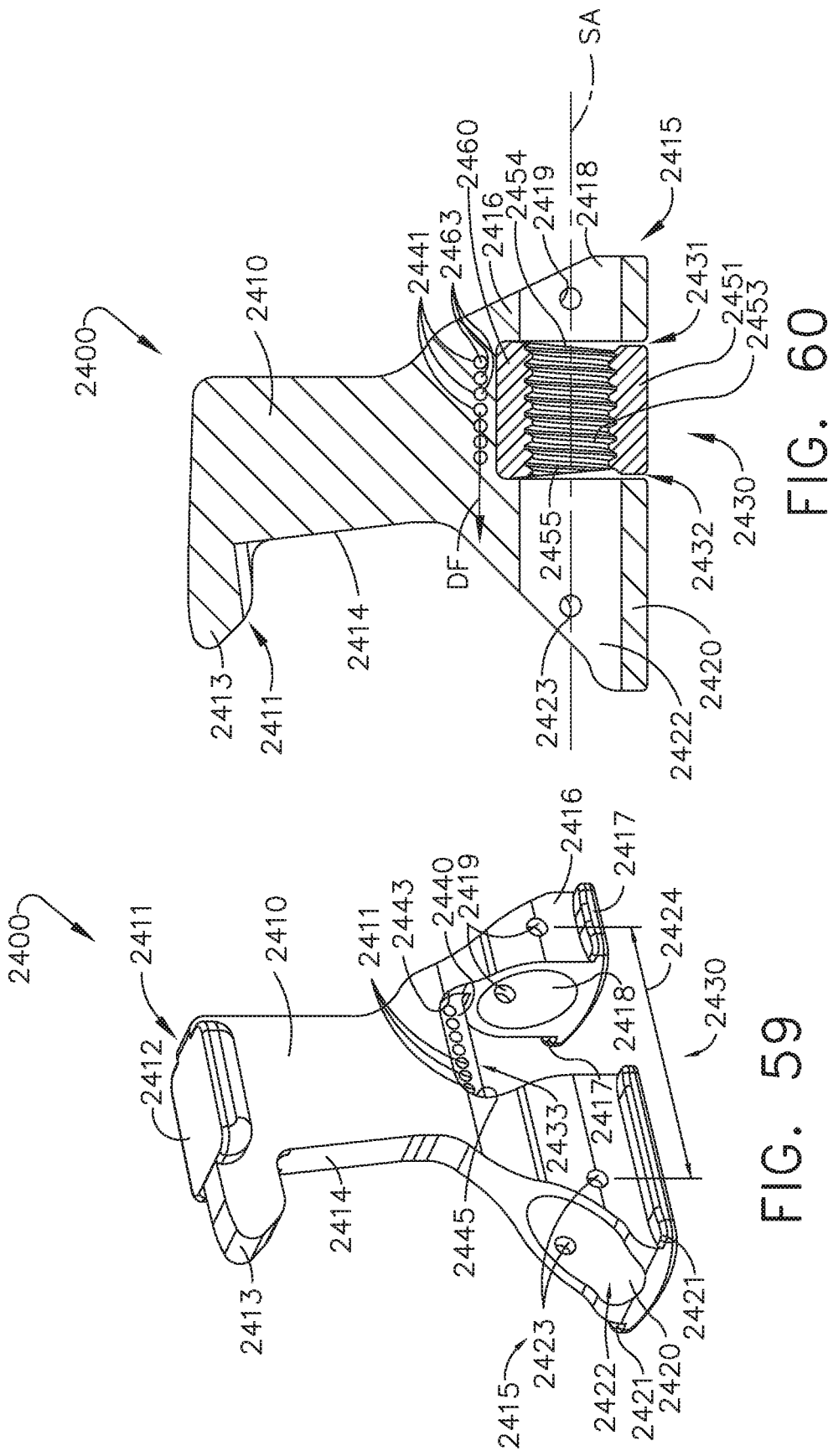

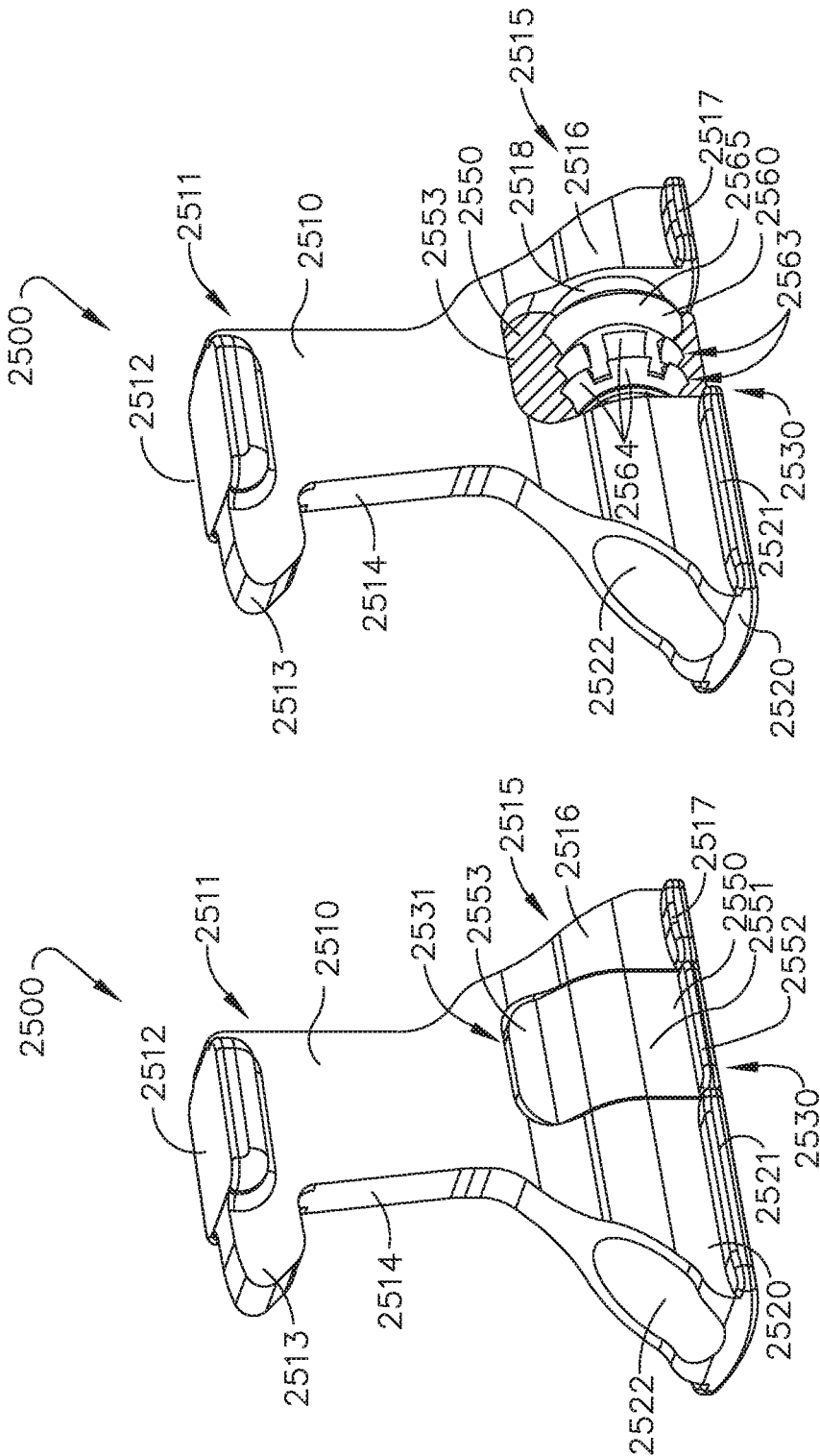

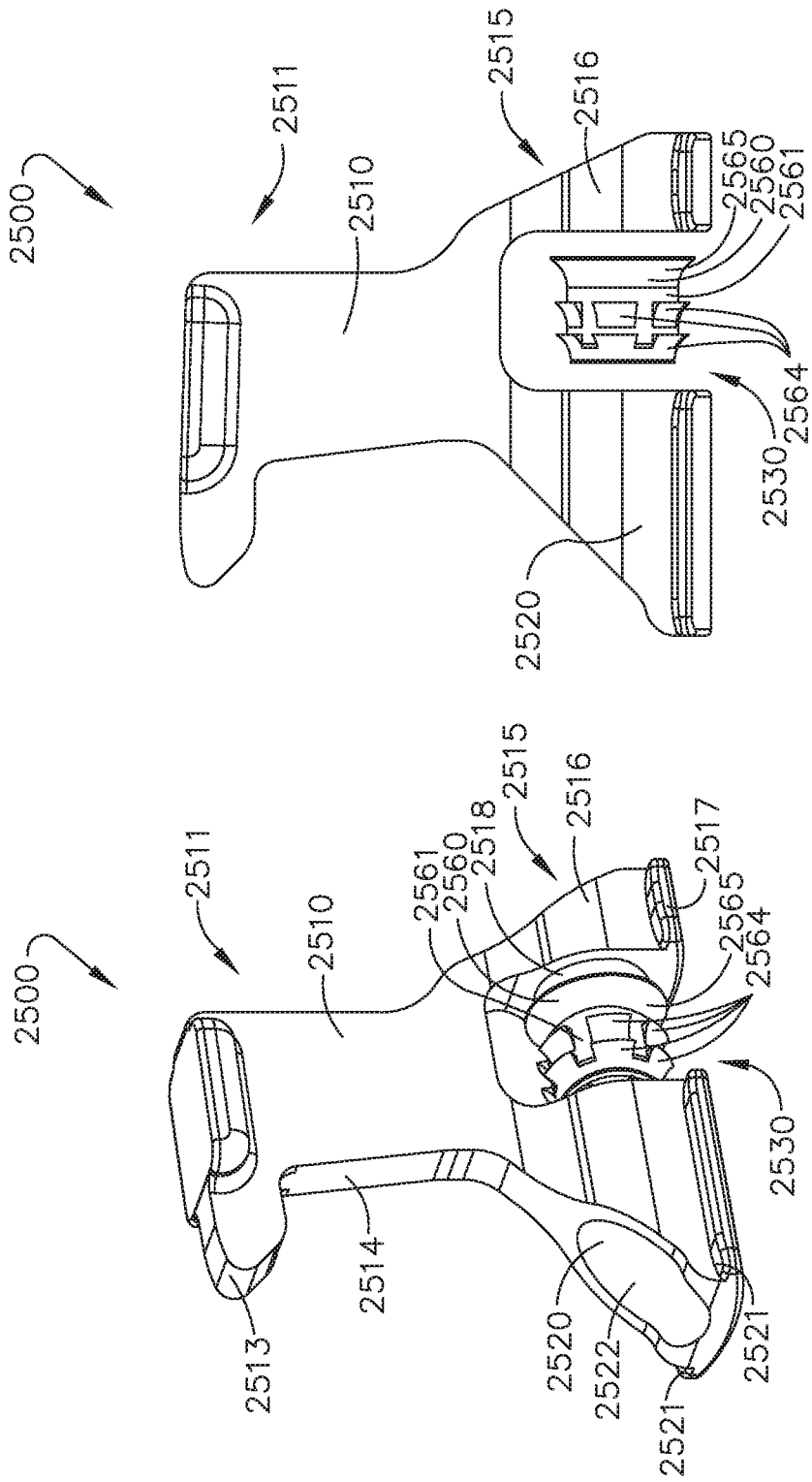

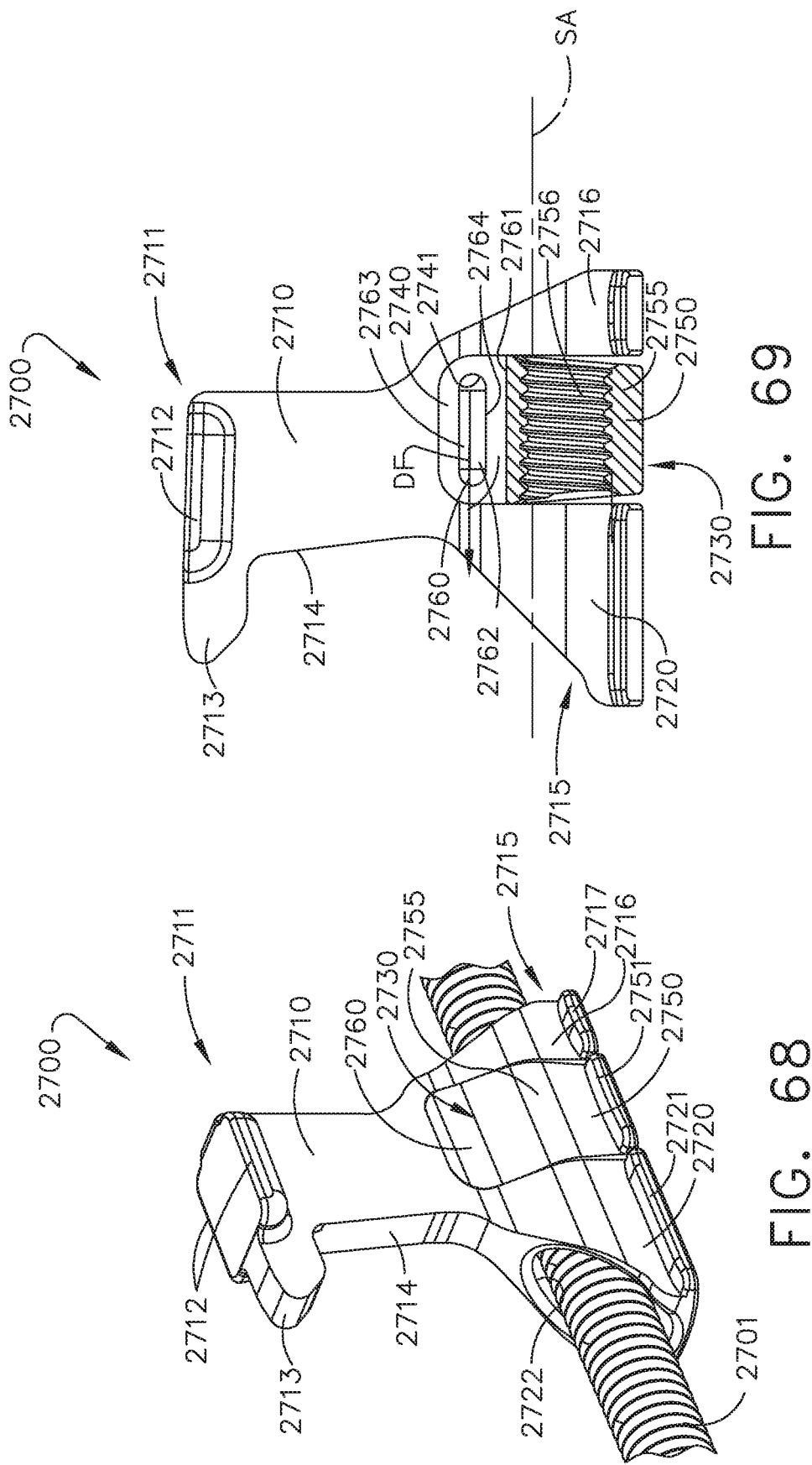

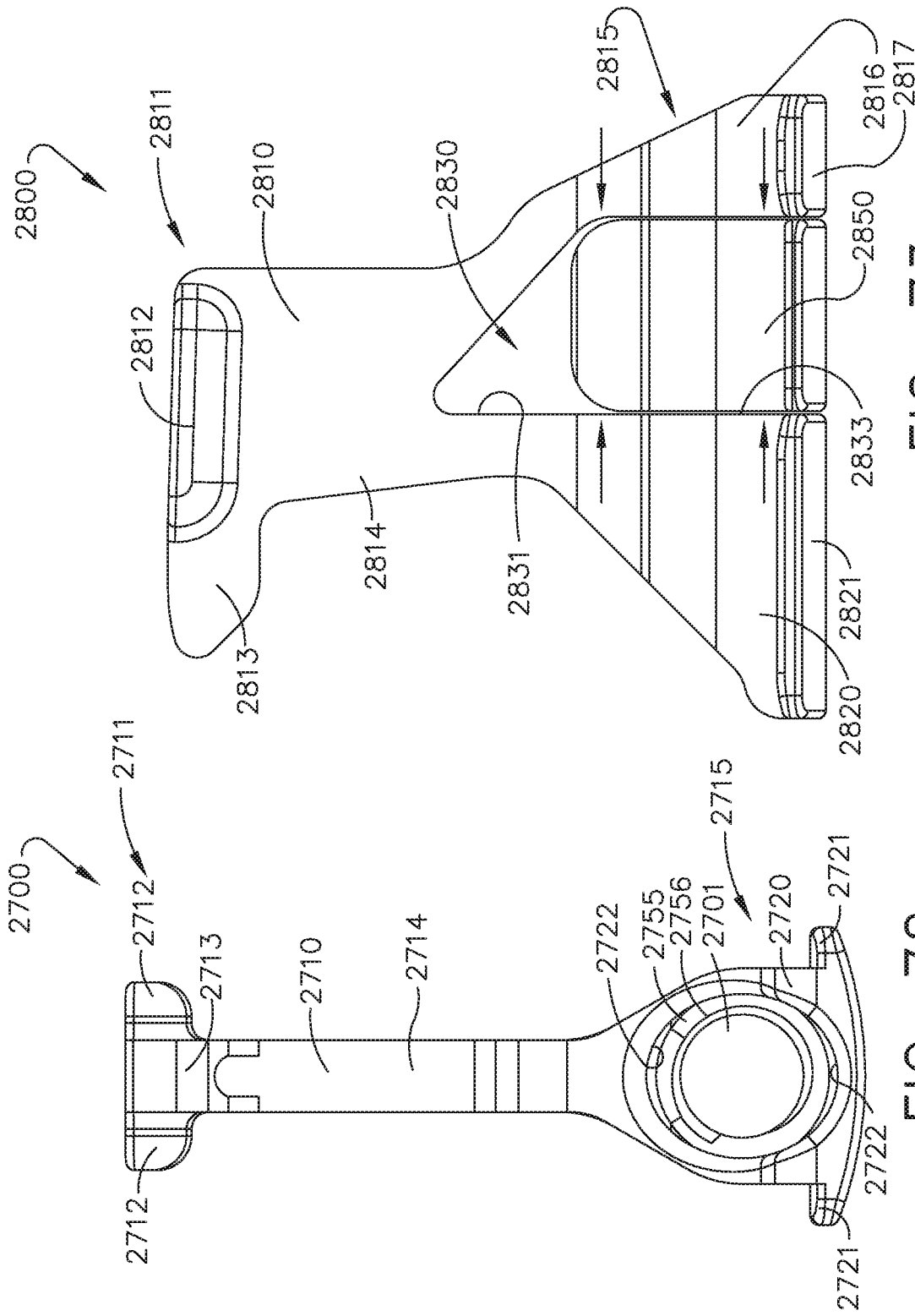

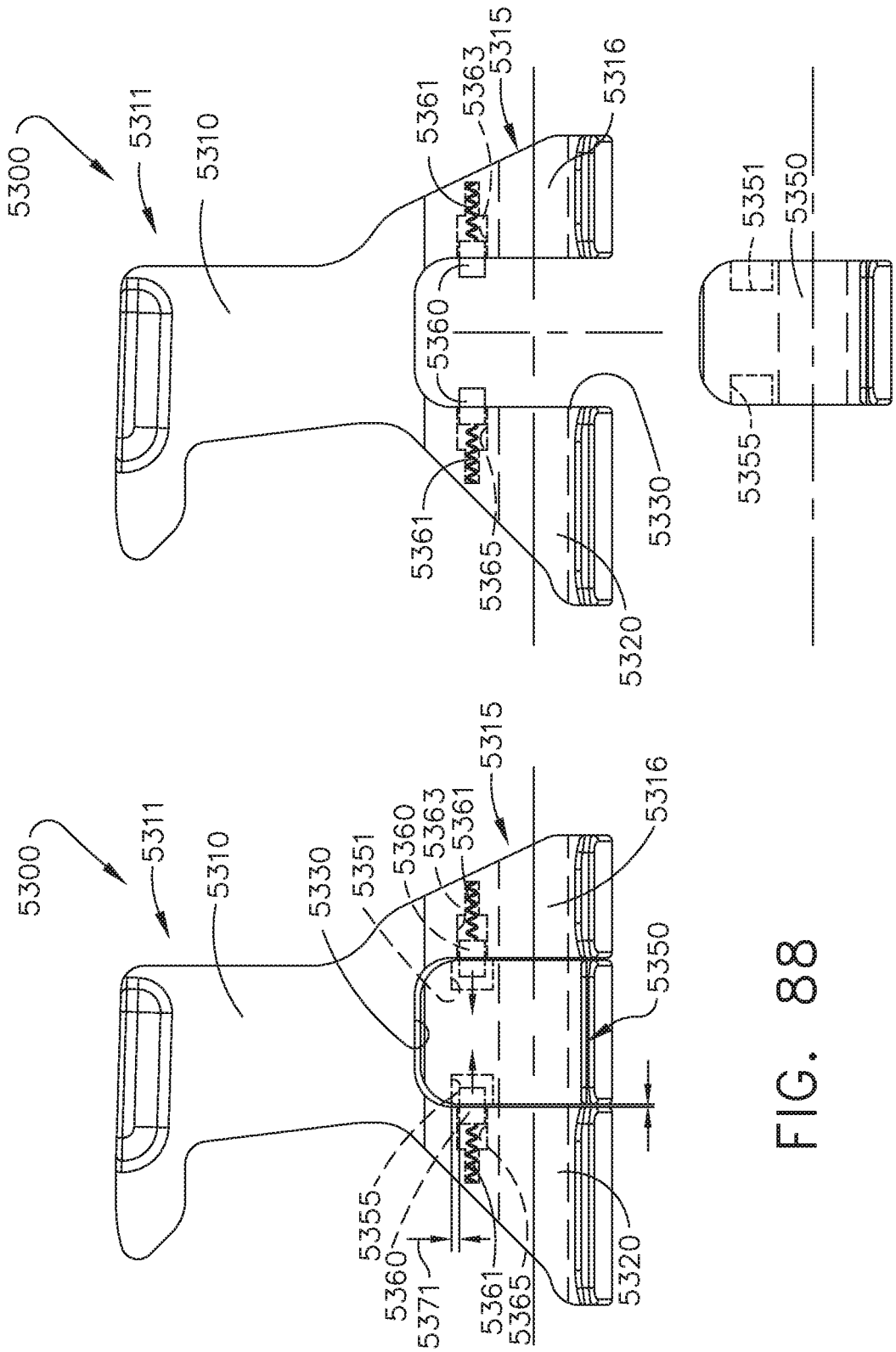

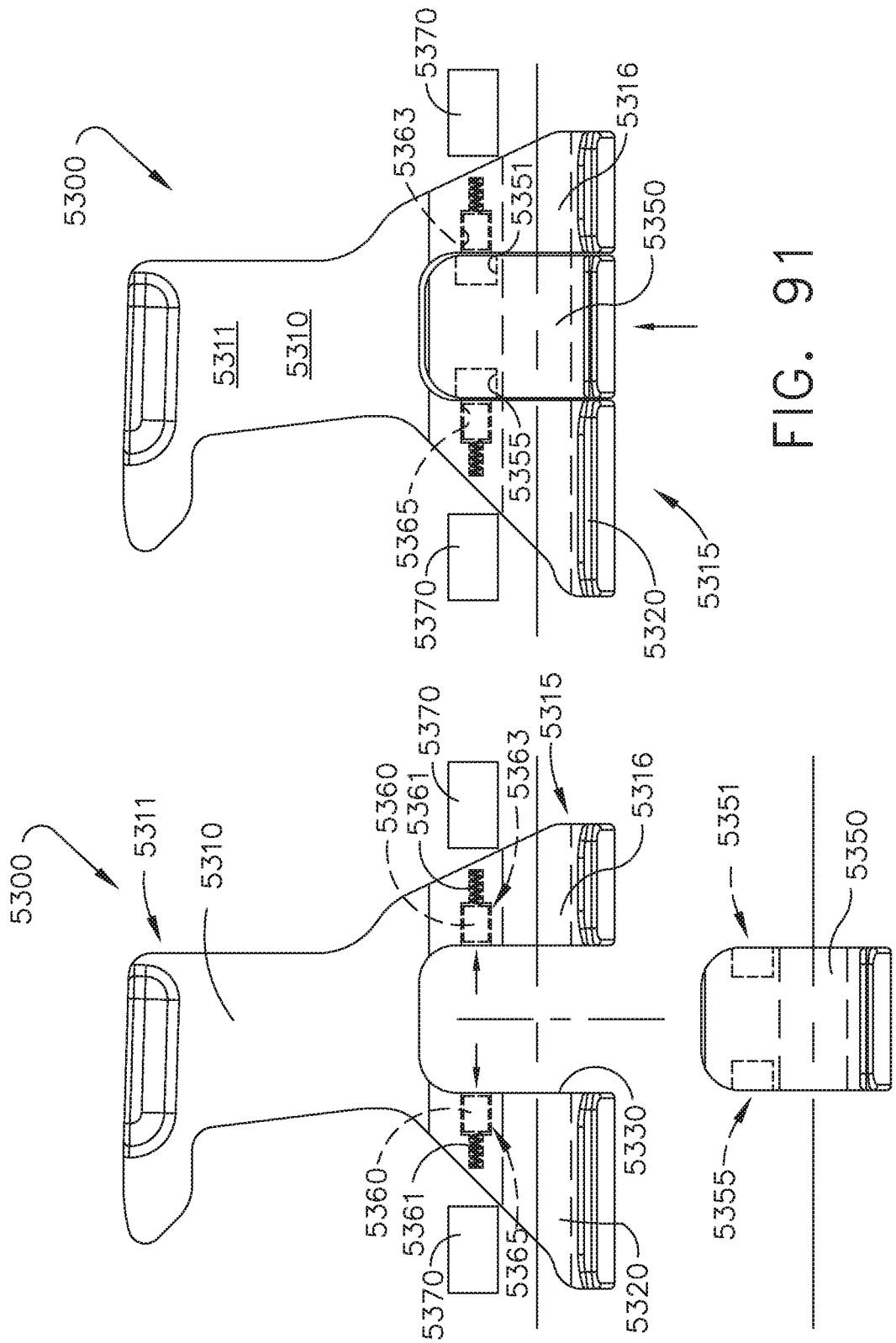

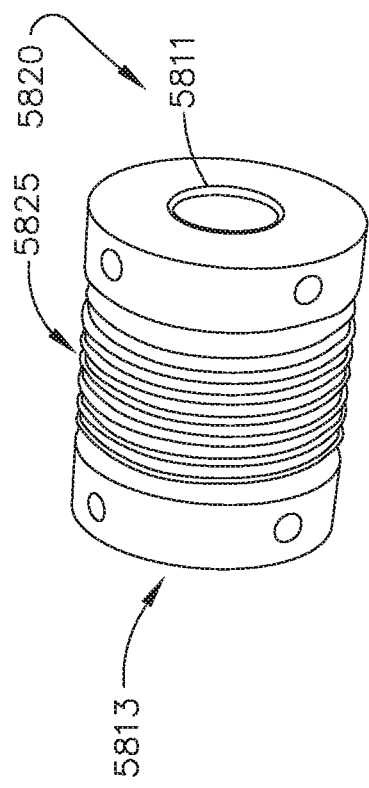
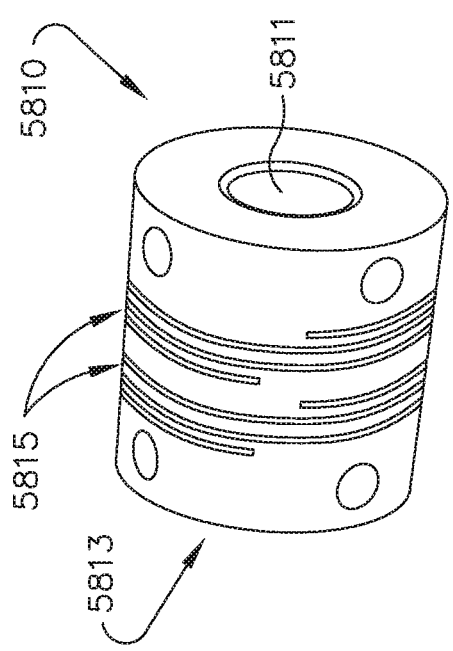
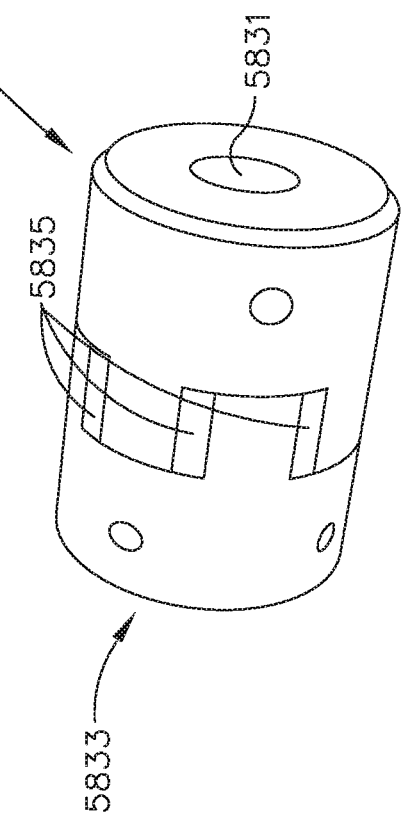

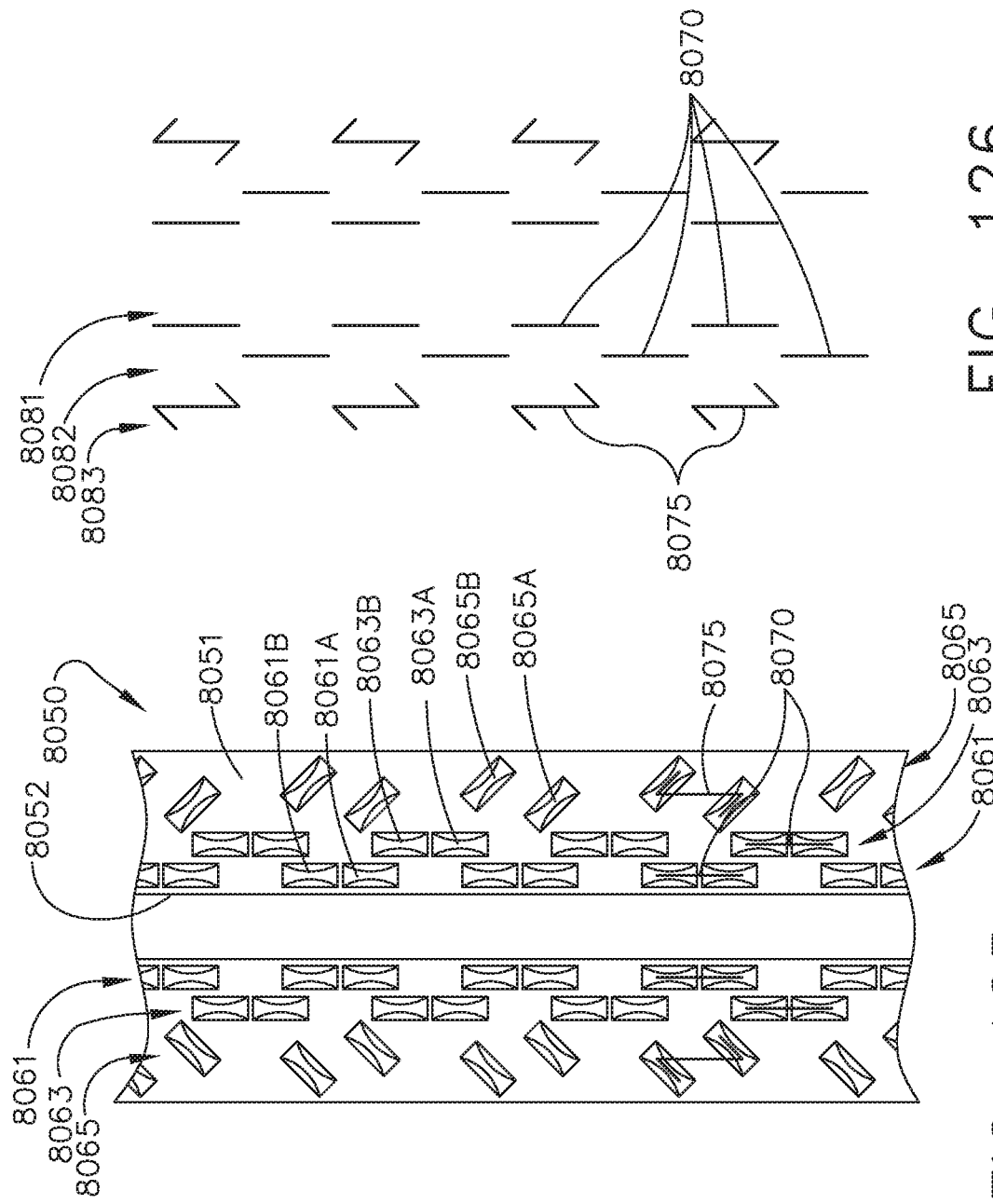

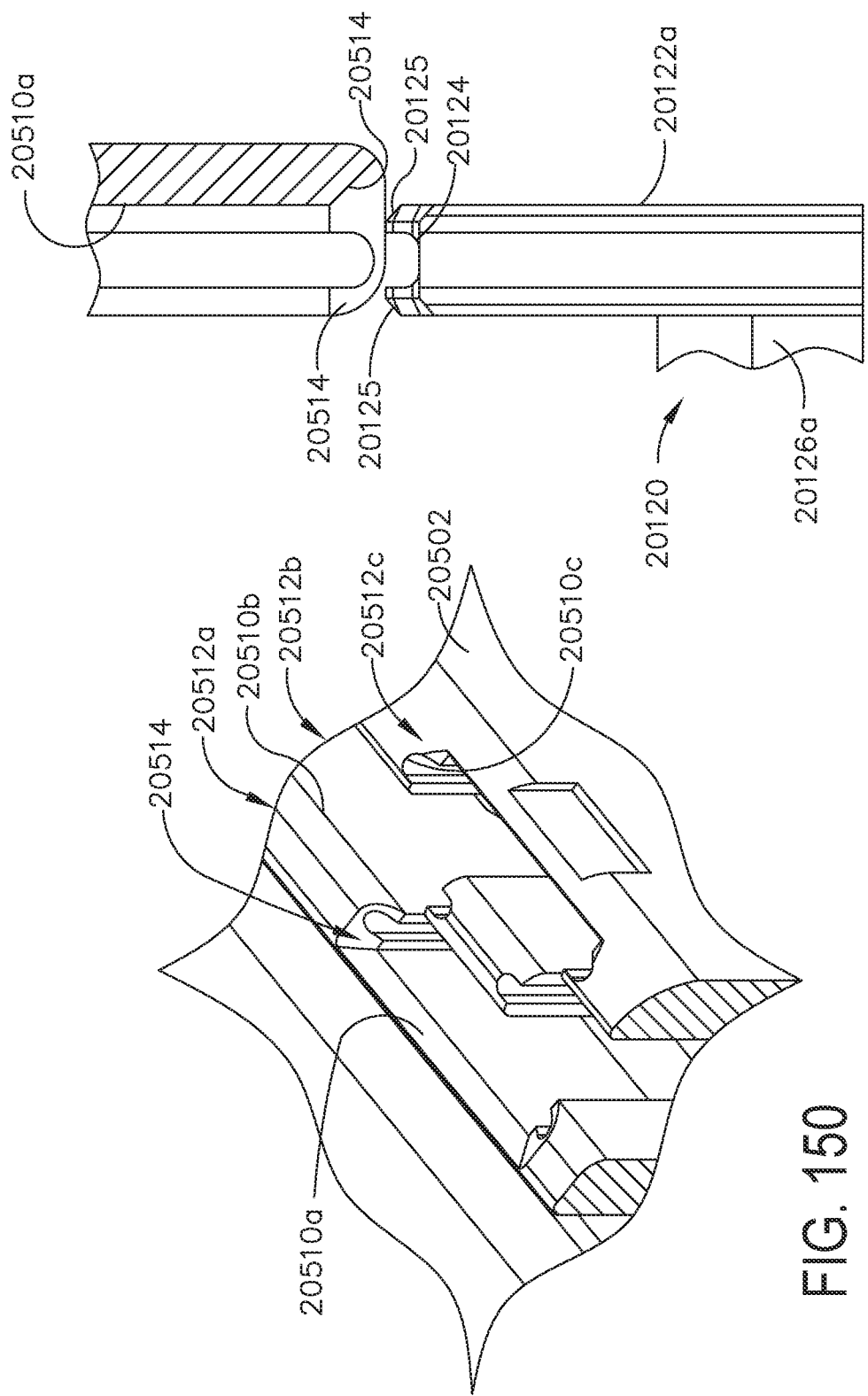

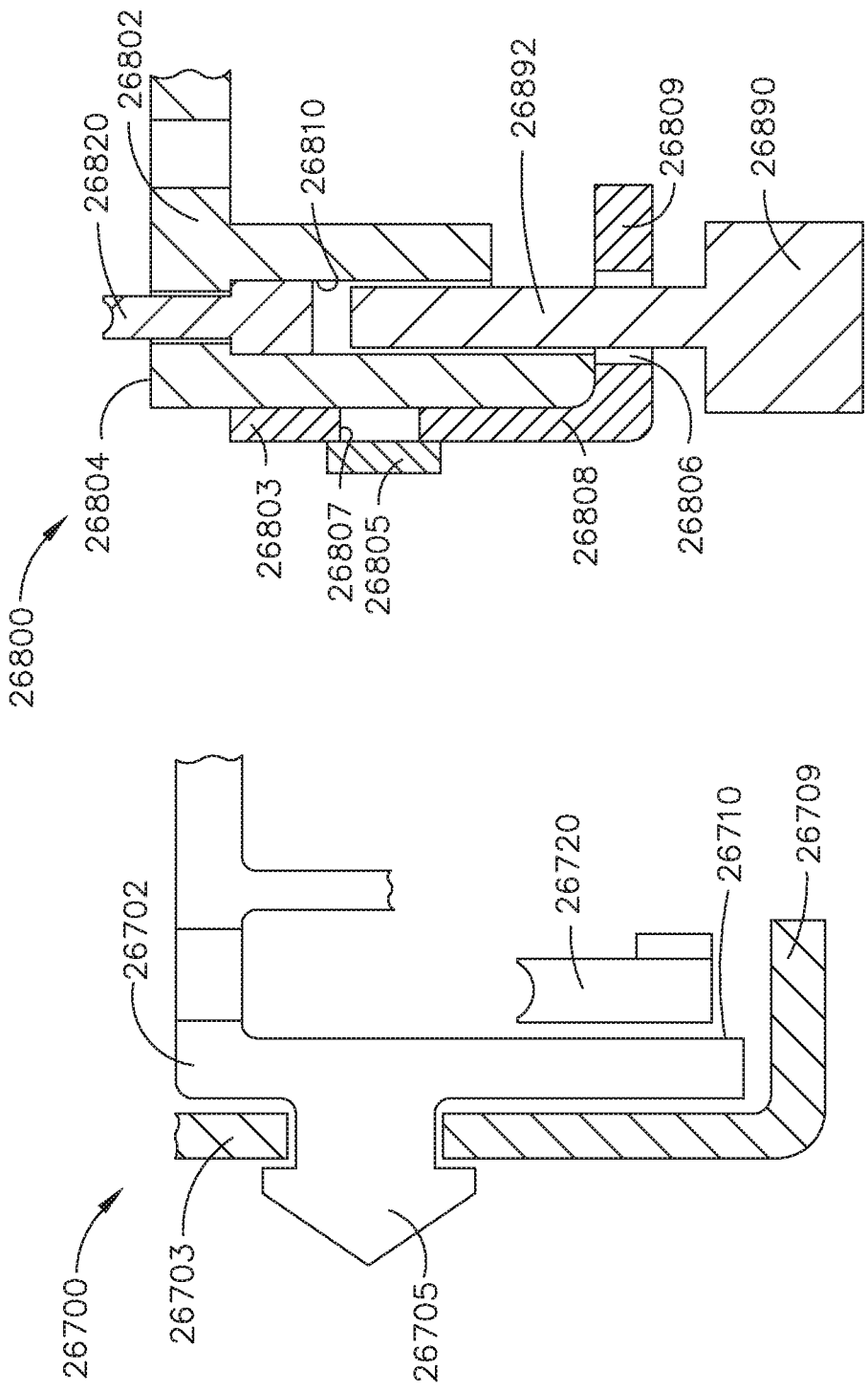

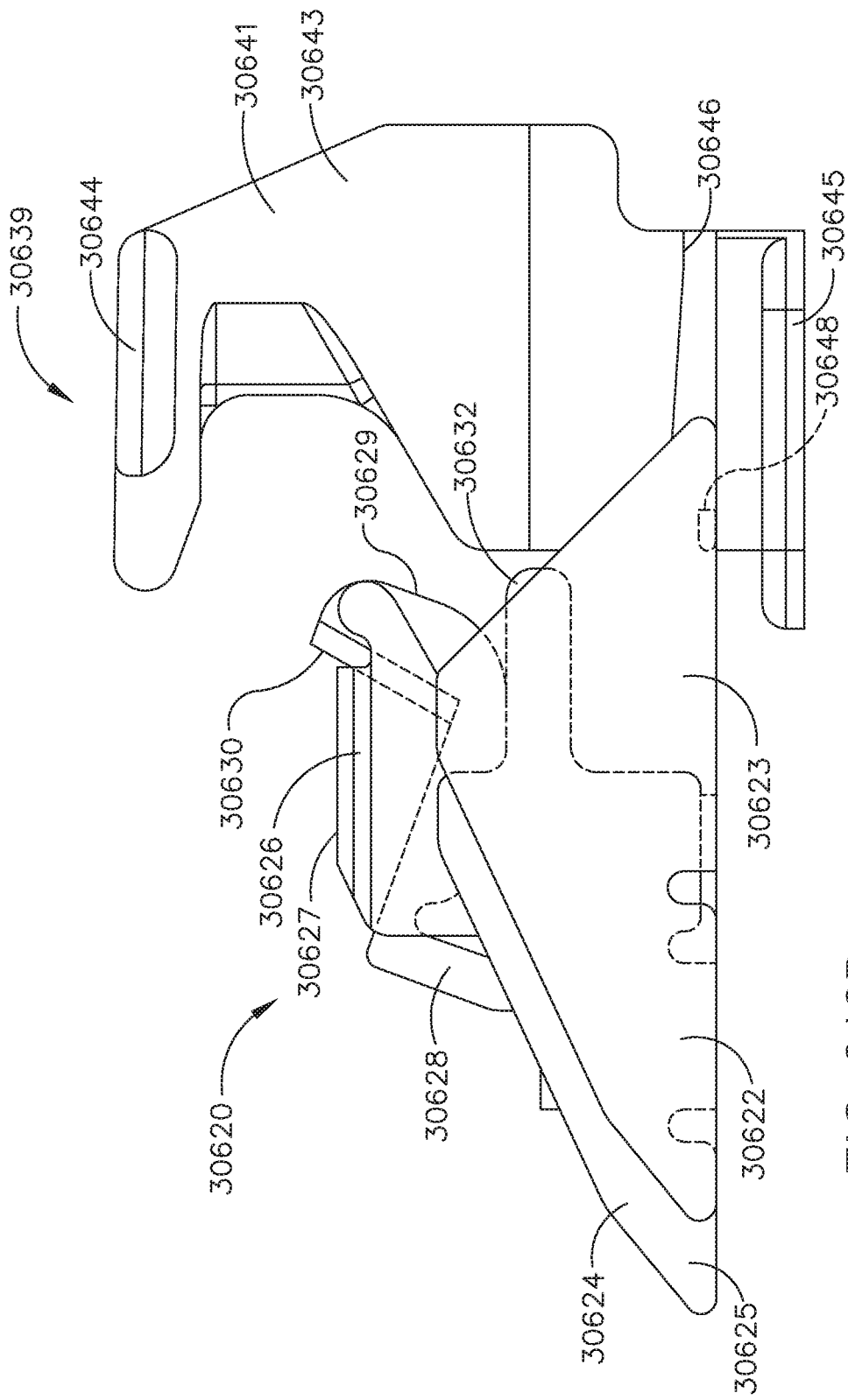

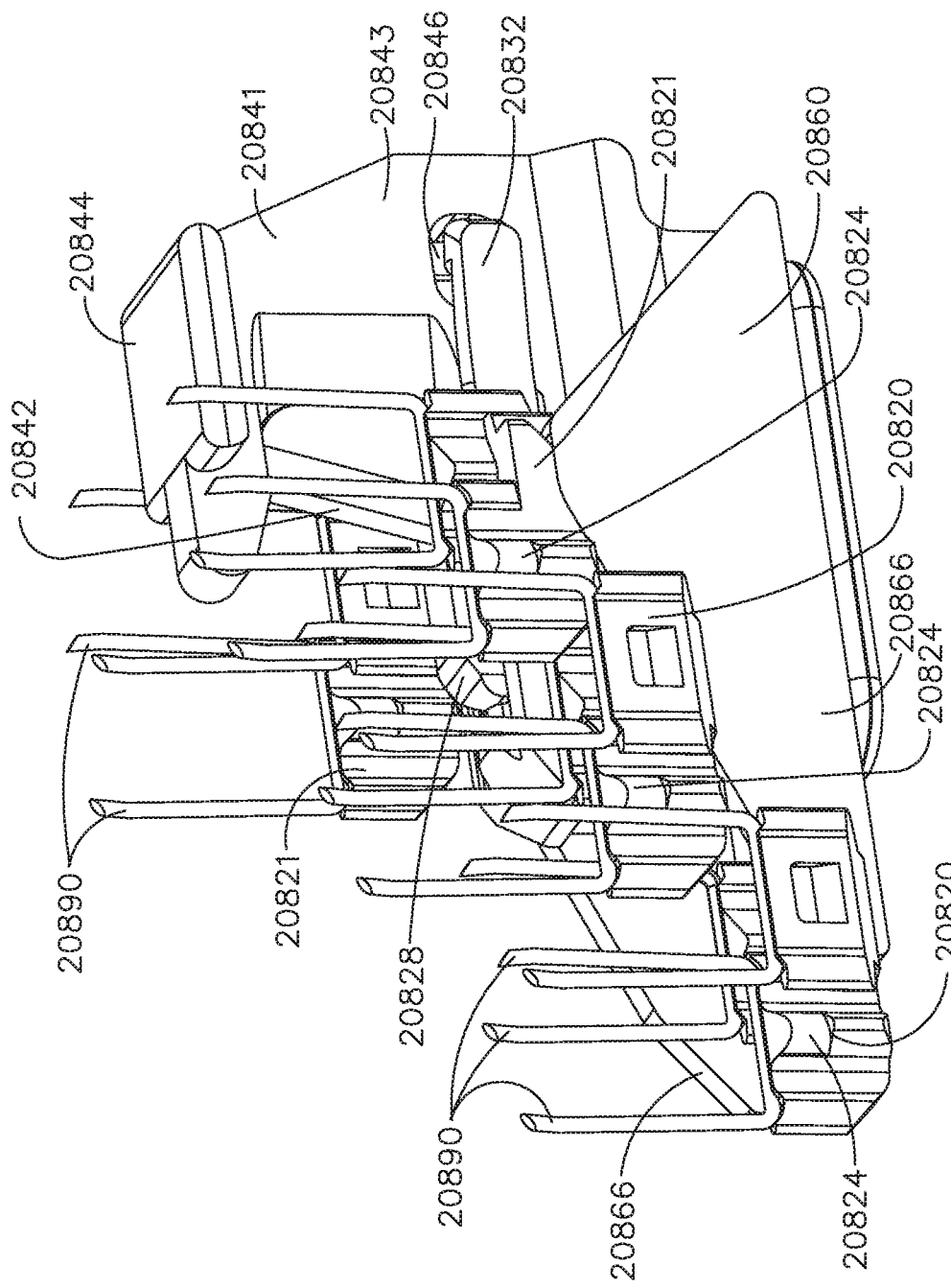

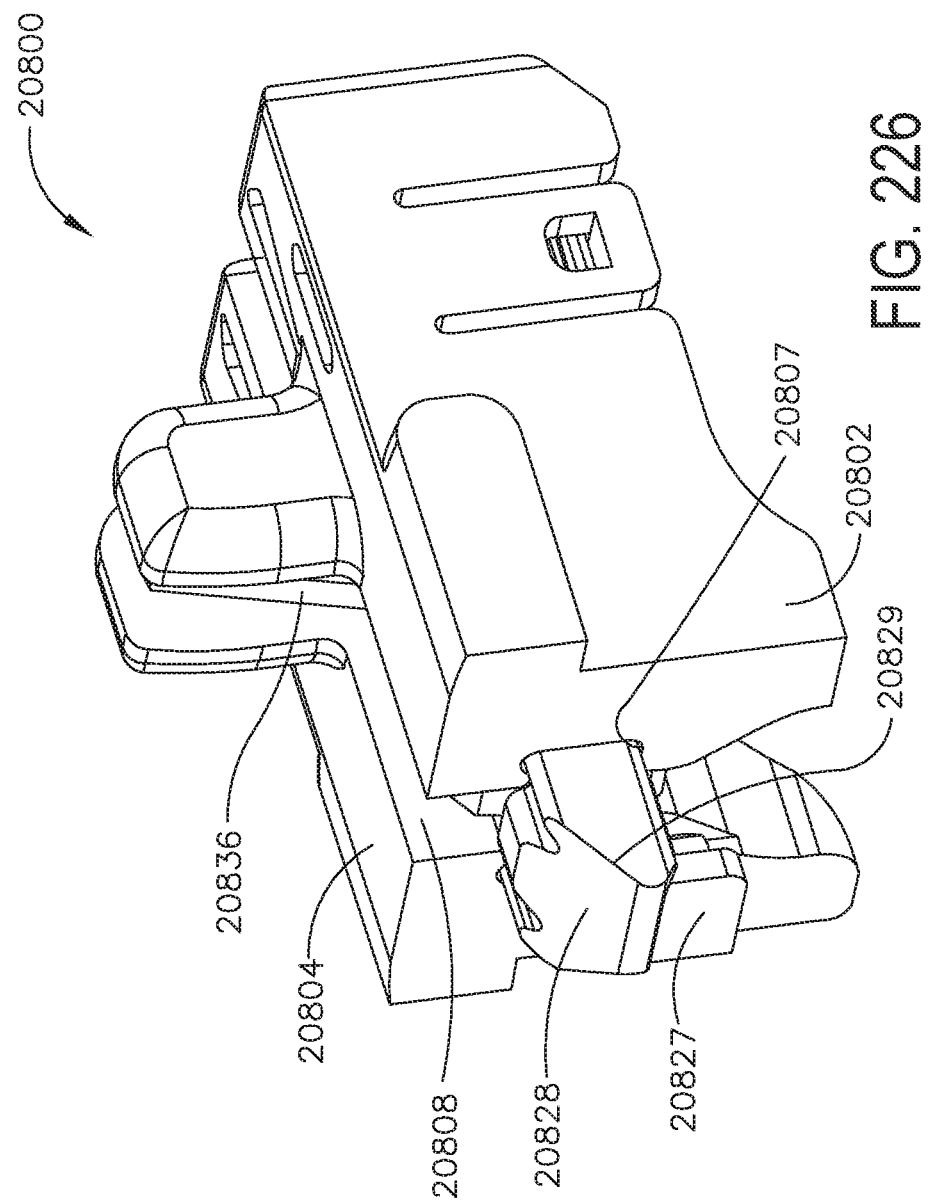

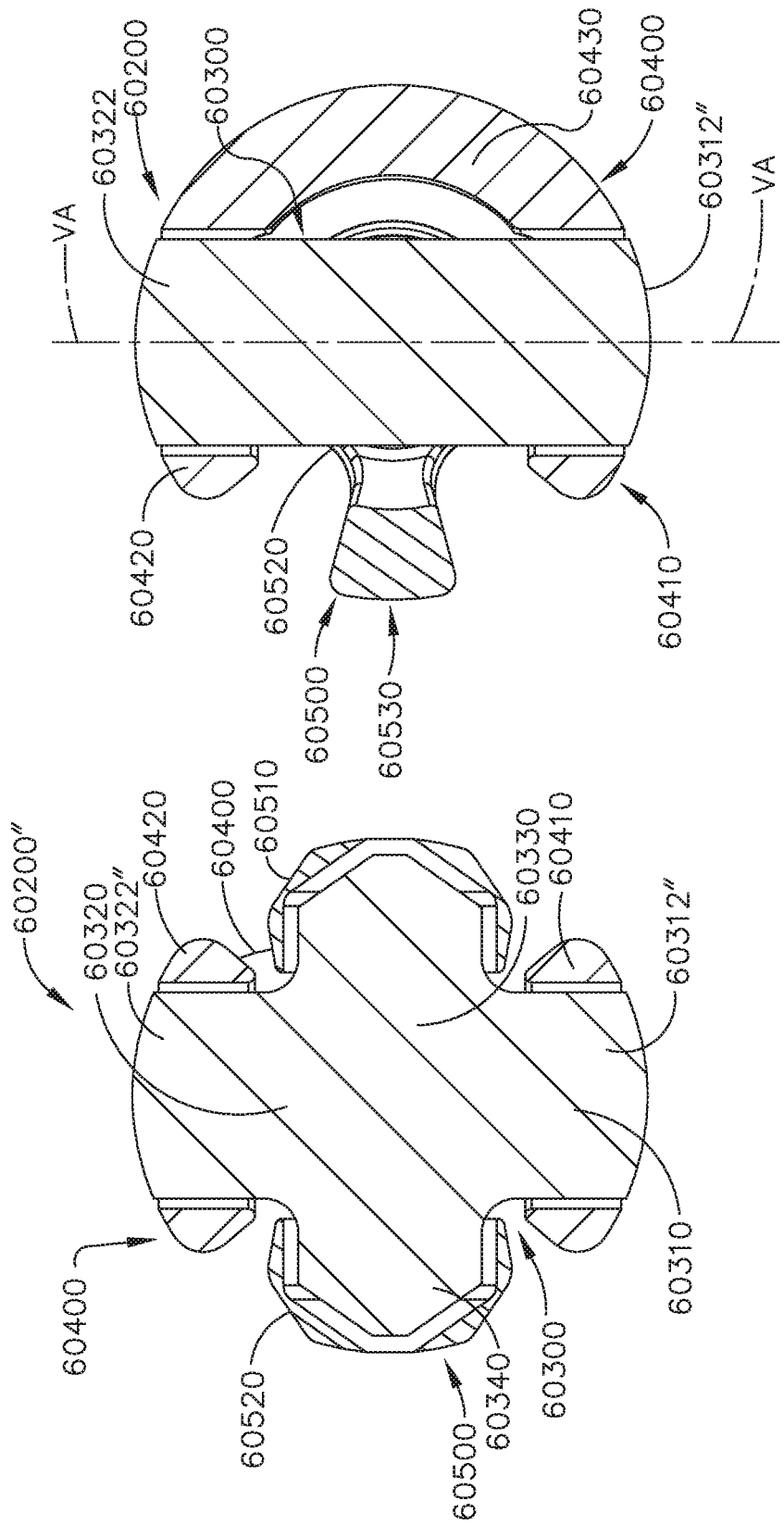

FIG. 290

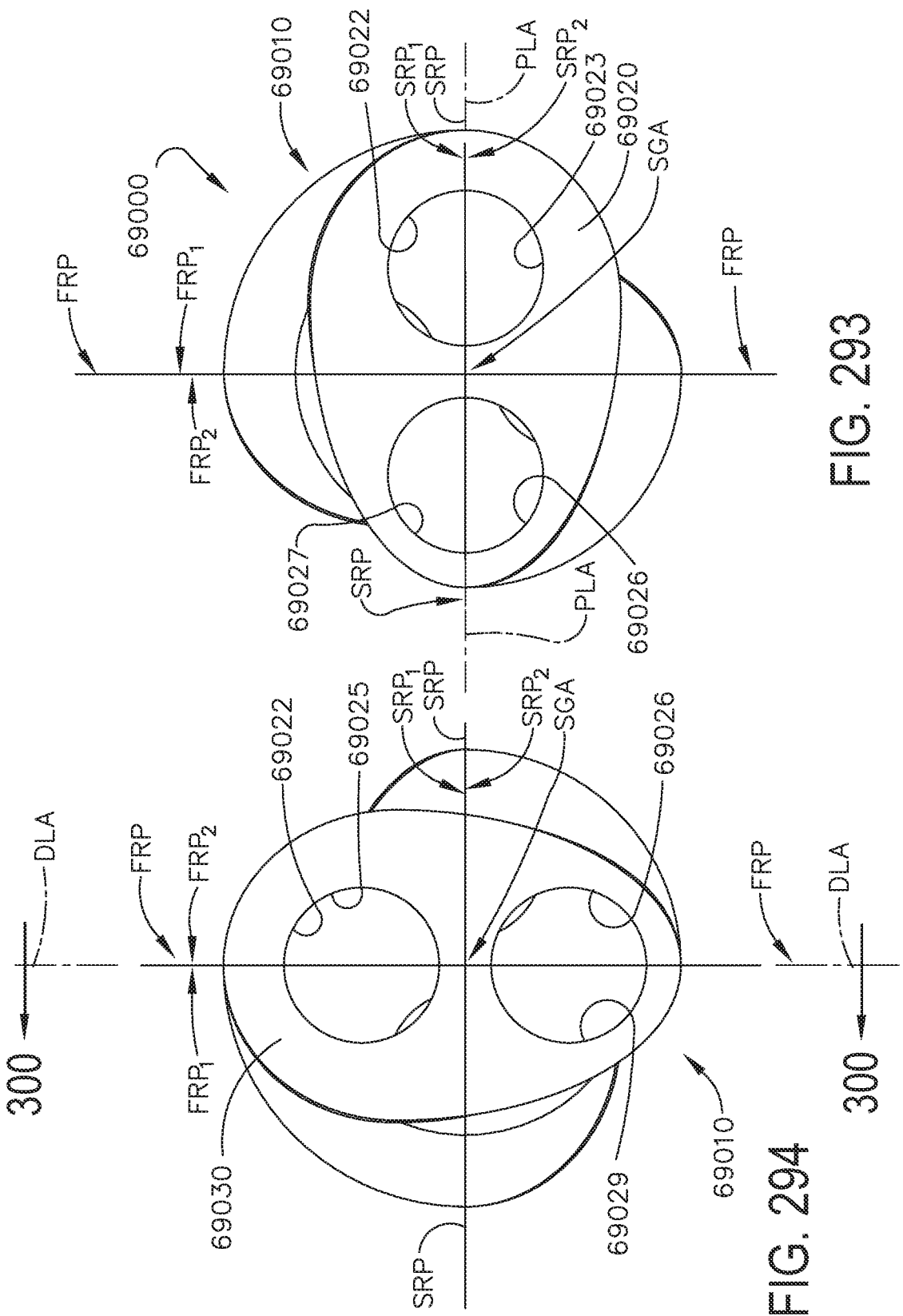

METHOD OF USING A POWERED STAPLING DEVICE

BACKGROUND

The present invention relates to surgical instruments and, in various arrangements, to surgical stapling and cutting instruments, end effectors, and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 43 is a cross-sectional elevation view of portions of a stapling assembly including a sled and a cartridge support, in accordance with at least one aspect of the present disclosure.

FIG. 44 is an elevation view of a sled configured to fit within guide slots of a staple cartridge or cartridge support of a stapling assembly, in accordance with at least one aspect of the present disclosure.

FIG. 45 is a cross-sectional perspective view of a portion of a cartridge support configured to receive a sled therein, in accordance with at least one aspect of the present disclosure.

FIG. 46 is a schematic of portions of a stapling assembly including an anvil, a firing member, a cartridge jaw, and a sled pinned to the firing member, in accordance with at least one aspect of the present disclosure.

FIG. 47 is a cross-sectional view of a stapling assembly comprising a cartridge channel and an anvil, in accordance with at least one aspect of the present disclosure.

FIG. 48 is a perspective view of a firing member assembly comprising a primary body portion and a drive nut, in accordance with at least one aspect of the present disclosure.

FIG. 49 is an exploded perspective view of the firing member assembly of FIG. 48, in accordance with at least one aspect of the present disclosure.

FIG. 50 is a perspective view of a firing member assembly comprising the primary body portion of the firing member assembly of FIG. 48 and a drive nut, in accordance with at least one aspect of the present disclosure.

FIG. 51 is an exploded perspective view of the firing member assembly of FIG. 50, in accordance with at least one aspect of the present disclosure.

FIG. 54 is an elevation view of the firing member assembly of FIG. 53, in accordance with at least one aspect of the present disclosure.

FIG. 55 is an exploded elevation view of the firing member assembly of FIG. 53, in accordance with at least one aspect of the present disclosure.

FIG. 57 is a perspective view of a firing member assembly comprising a primary body portion and a drive nut, in accordance with at least one aspect of the present disclosure.

FIG. 58 is an elevation view of the firing member assembly of FIG. 57, in accordance with at least one aspect of the present disclosure.

FIG. 59 is a perspective view of the primary body portion of the firing member assembly of FIG. 57, in accordance with at least one aspect of the present disclosure.

FIG. 60 is a cross-sectional elevation view of the firing member assembly of FIG. 57, in accordance with at least one aspect of the present disclosure.

FIG. 62 is a perspective view of a firing member assembly comprising a primary body portion and a drive nut assembly comprising an internal drive nut and an external drive portion, in accordance with at least one aspect of the present disclosure.

FIG. 63 is a perspective view of the firing member assembly of FIG. 62, wherein a portion of the external drive portion of the drive nut is cutaway for illustrative purposes to expose the internal drive nut, in accordance with at least one aspect of the present disclosure.

FIG. 64 is a perspective view of the primary body portion and internal drive nut of the firing member assembly of FIG. 62, in accordance with at least one aspect of the present disclosure.

FIG. 65 is an elevation view of the primary body portion and the internal drive nut of the firing member assembly of FIG. 62, in accordance with at least one aspect of the present disclosure.

FIG. 68 is a perspective view of a firing member assembly threadably coupled with a firing drive screw, wherein the firing member assembly comprises a primary body portion and a drive nut, in accordance with at least one aspect of the present disclosure.

FIG. 69 is a partial cross-sectional elevation view of the firing member assembly of FIG. 68, wherein the drive nut is cross-sectioned through a vertical plane, in accordance with at least one aspect of the present disclosure.

FIG. 72 is an elevation view of the firing member assembly of FIG. 68, in accordance with at least one aspect of the present disclosure.

FIG. 73 is an elevation view of a firing member assembly comprising a primary body portion and a drive nut, in accordance with at least one aspect of the present disclosure.

FIG. 88 is an elevation view of a firing member assembly comprising a primary body portion and a drive nut floatably mounted within the primary body portion, in accordance with at least one aspect of the present disclosure.

FIG. 89 is an elevation view of the firing member assembly of FIG. 88 pre-assembly, in accordance with at least one aspect of the present disclosure.

FIG. 90 is an elevation view of the firing member assembly of FIG. 88 mid-assembly, in accordance with at least one aspect of the present disclosure.

FIG. 91 is an elevation view of the firing member assembly of FIG. 88 partially assembled, in accordance with at least one aspect of the present disclosure.

FIG. 98 is a perspective view of a shaft coupling for use with a drive system of a surgical stapling assembly, in accordance with at least one aspect of the present disclosure.

FIG. 99 is a perspective view of a shaft coupling for use with a drive system of a surgical stapling assembly, in accordance with at least one aspect of the present disclosure.

FIG. 100 is a perspective view of a shaft coupling for use with a drive system of a surgical stapling assembly, in accordance with at least one aspect of the present disclosure.

FIG. 106 is a cross-sectional elevation view of a drive assembly mounted to a channel flange with a locking member, wherein FIG. 106 illustrates the drive assembly in a pre-assembled configuration, in accordance with at least one aspect of the present disclosure.

FIG. 107 is a cross-sectional elevation view of the drive assembly and the channel flange of FIG. 106, wherein FIG. 107 illustrates the drive assembly in an assembled configuration, in accordance with at least one aspect of the present disclosure.

FIG. 119 is a perspective view of the firing member of FIG. 118, in accordance with at least one aspect of the present disclosure.

FIG. 120 is a cross-sectional elevation view of the firing drive assembly of FIG. 118, wherein the bailout is illustrated in an unactuated configuration, in accordance with at least one aspect of the present disclosure.

FIG. 121 is a cross-sectional elevation view of the firing drive assembly of FIG. 118 taken through a housing component of the bailout, wherein the bailout is illustrated in the unactuated configuration, in accordance with at least one aspect of the present disclosure.

FIG. 122 is a cross-sectional elevation view of the firing drive assembly of FIG. 118, wherein the bailout is illustrated in an actuated configuration, in accordance with at least one aspect of the present disclosure.

FIG. 123 is a cross-sectional elevation view of the firing drive assembly of FIG. 118 taken through a housing component of the bailout, wherein the bailout is illustrated in the actuated configuration, in accordance with at least one aspect of the present disclosure.

FIG. 124 is a perspective view of a surgical stapling assembly, in accordance with at least one aspect of the present disclosure.

FIG. 125 is a plan view of an anvil surface of an anvil of the surgical stapling assembly of FIG. 124, in accordance with at least one aspect of the present disclosure.

FIG. 126 is a plan view of formed staple lines of the surgical stapling assembly of FIG. 124, in accordance with at least one aspect of the present disclosure.

FIG. 127 is an end elevation view and a side elevation view of a planar formed staple, in accordance with at least one aspect of the present disclosure.

FIG. 128 is an end elevation view and a side elevation view of a non-planar formed staple, in accordance with at least one aspect of the present disclosure.

FIG. 129 is a cross-sectional elevation view of an anvil comprising a plurality of staple forming pocket rows, in accordance with at least one aspect of the present disclosure.

FIG. 130 is an elevation view of a sled for use with a staple cartridge, in accordance with at least one aspect of the present disclosure.

Figure 131:
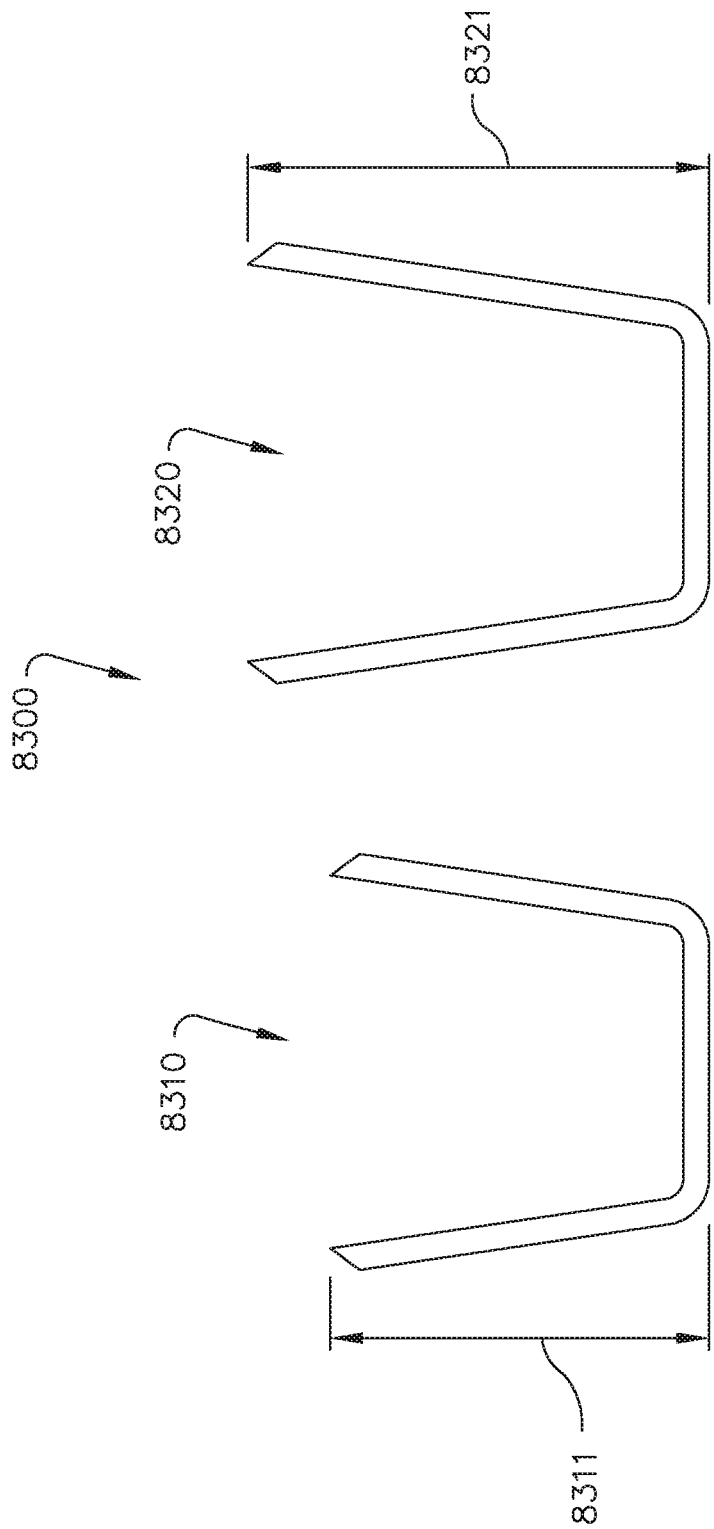

FIG. 131 is an elevation view of a first staple and a second staple for use with a surgical stapling assembly, in accordance with at least one aspect of the present disclosure.

Figure 132:
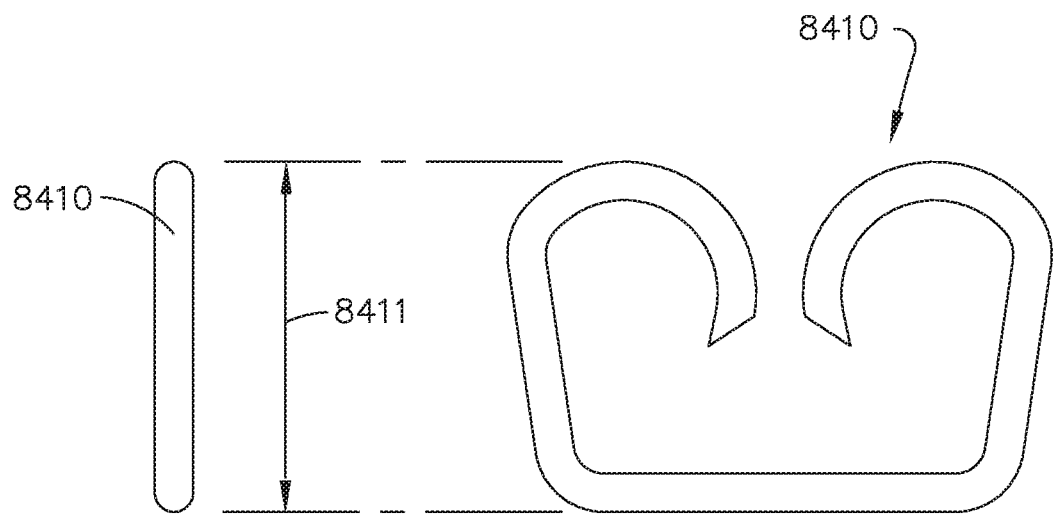

FIG. 132 is an end elevation view and a side elevation view of a planar formed staple, in accordance with at least one aspect of the present disclosure.

Figure 133:
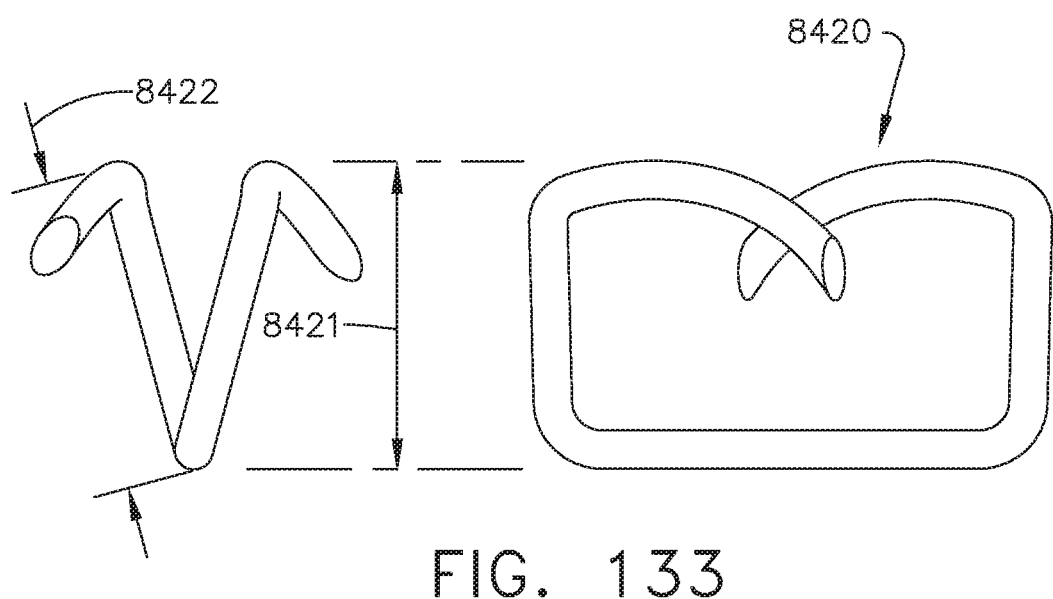

FIG. 133 is an end elevation view and a side elevation view of a non-planar formed staple, in accordance with at least one aspect of the present disclosure.

Figure 134:
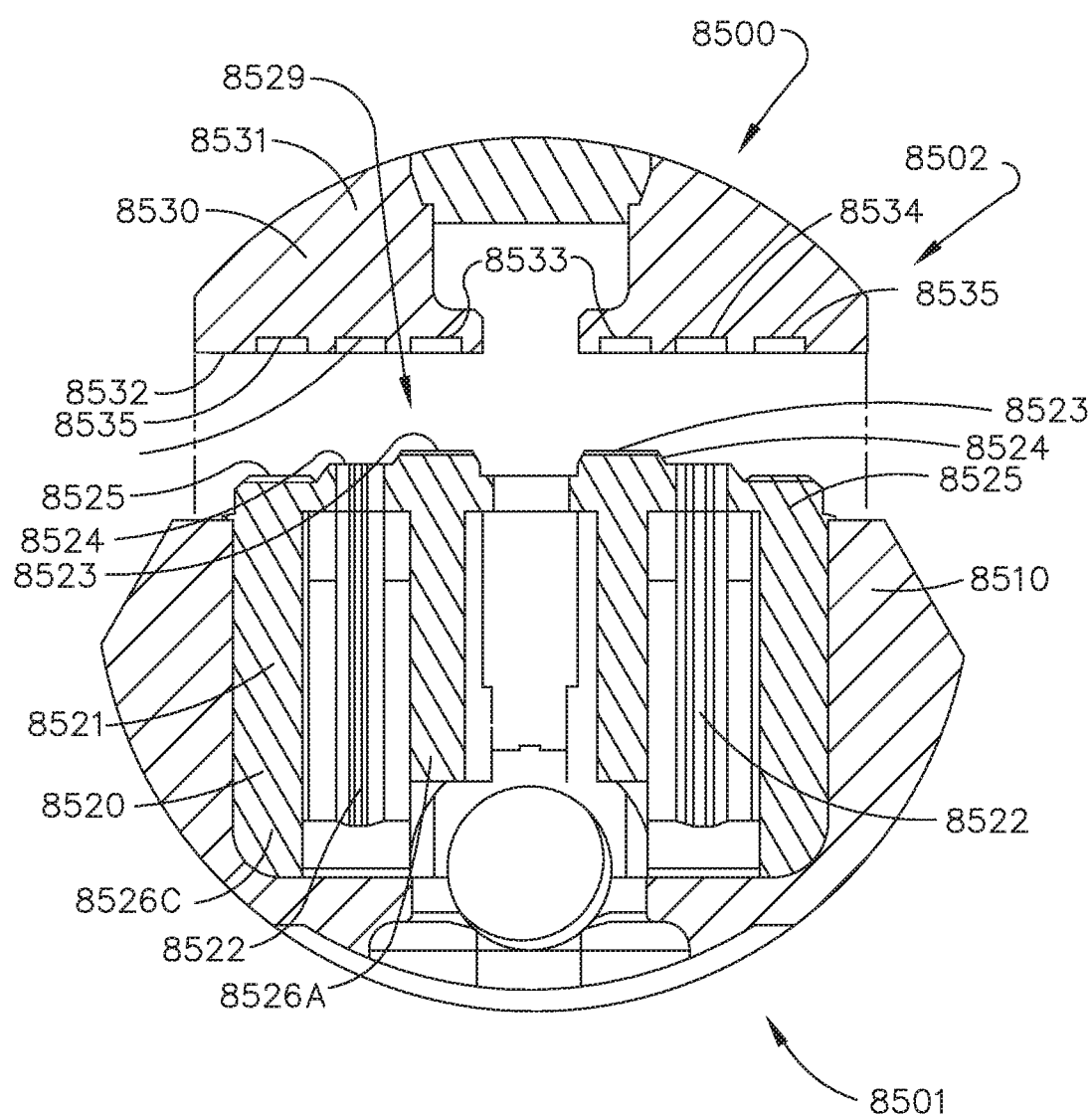

FIG. 134 is a cross-sectional elevation view of a surgical stapling assembly, in accordance with at least one aspect of the present disclosure.

Figure 135:
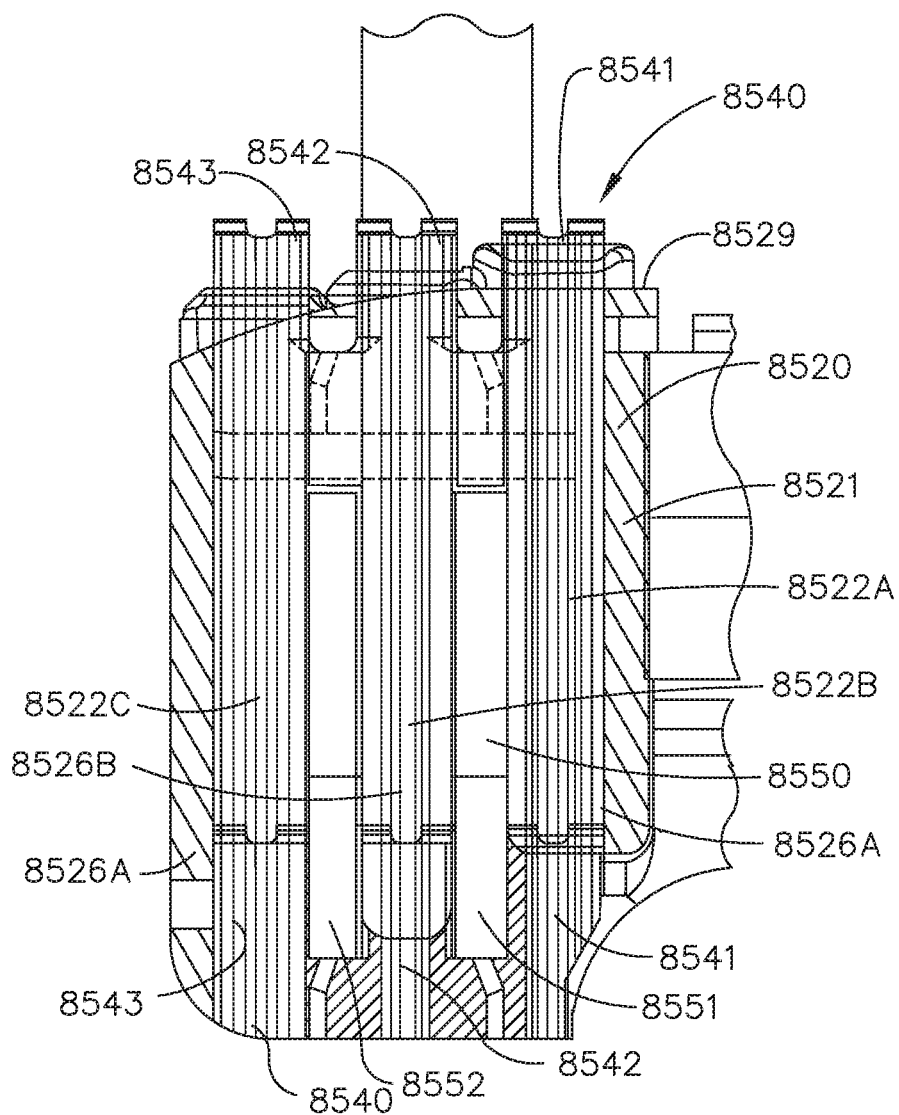

FIG. 135 is a partial cross-sectional elevation view of the surgical stapling assembly of FIG. 134, in accordance with at least one aspect of the present disclosure.

Figure 136:
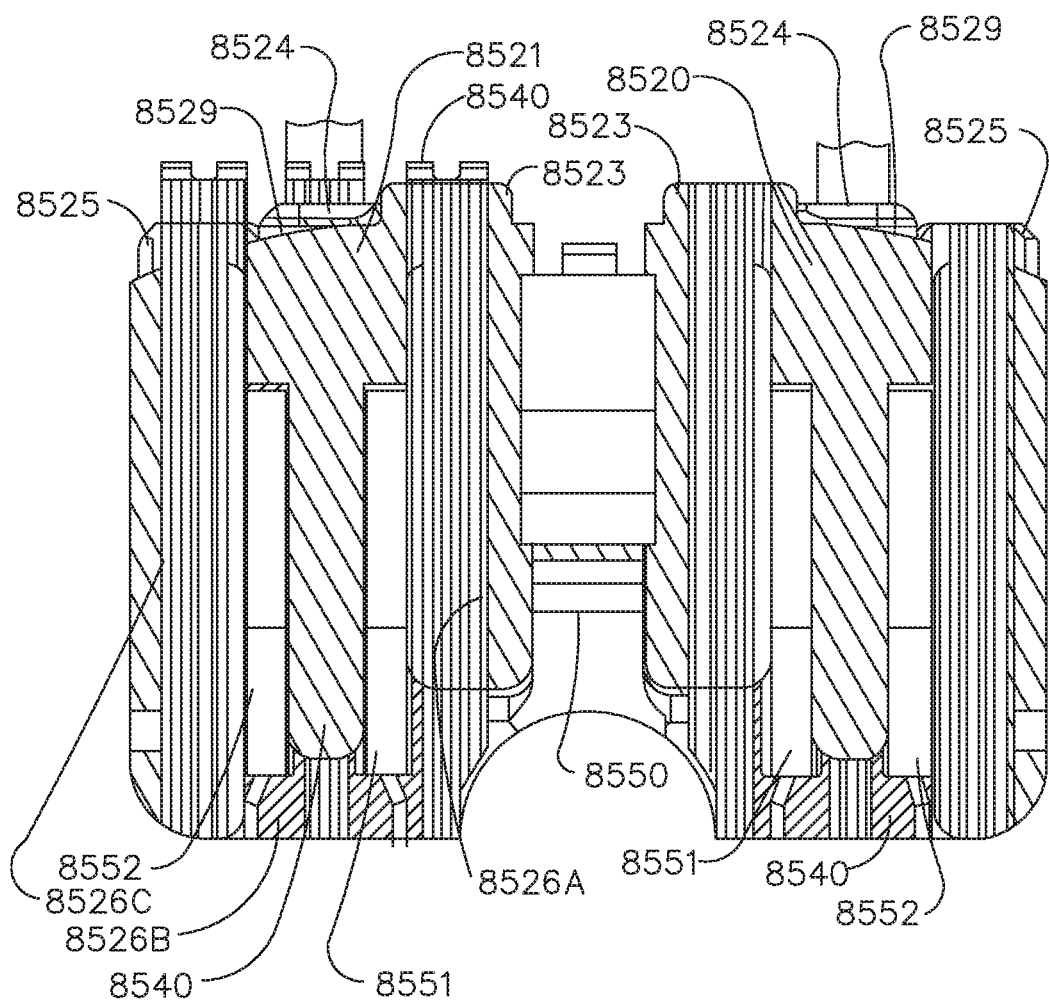

FIG. 136 is a cross-sectional elevation view of a staple cartridge and staple drivers of the surgical stapling assembly of FIG. 134, in accordance with at least one aspect of the present disclosure.

Figure 137:
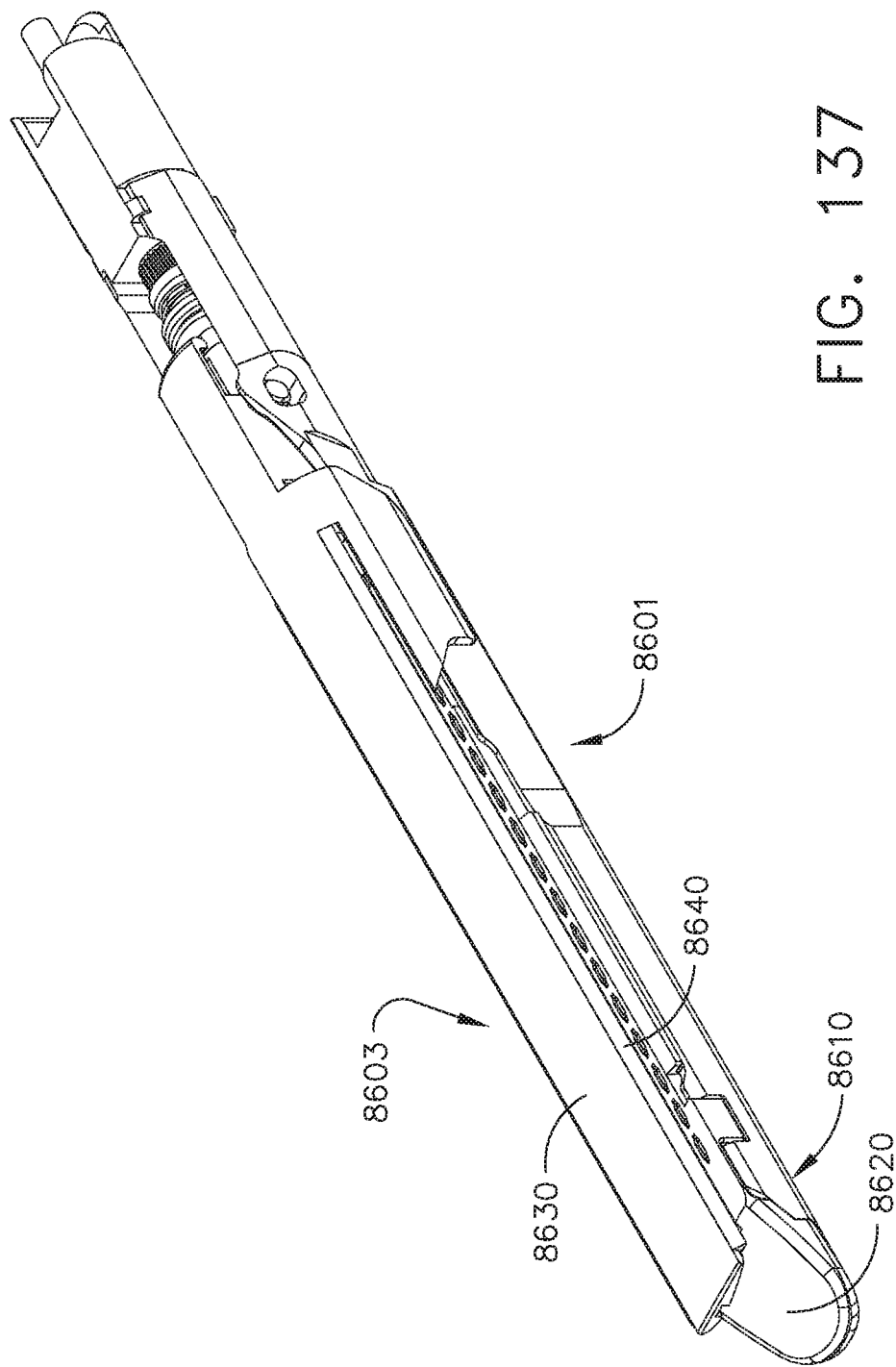

FIG. 137 is a perspective view of a surgical stapling assembly comprising a replaceable staple cartridge and a replaceable anvil plate, in accordance with at least one aspect of the present disclosure.

Figure 138:
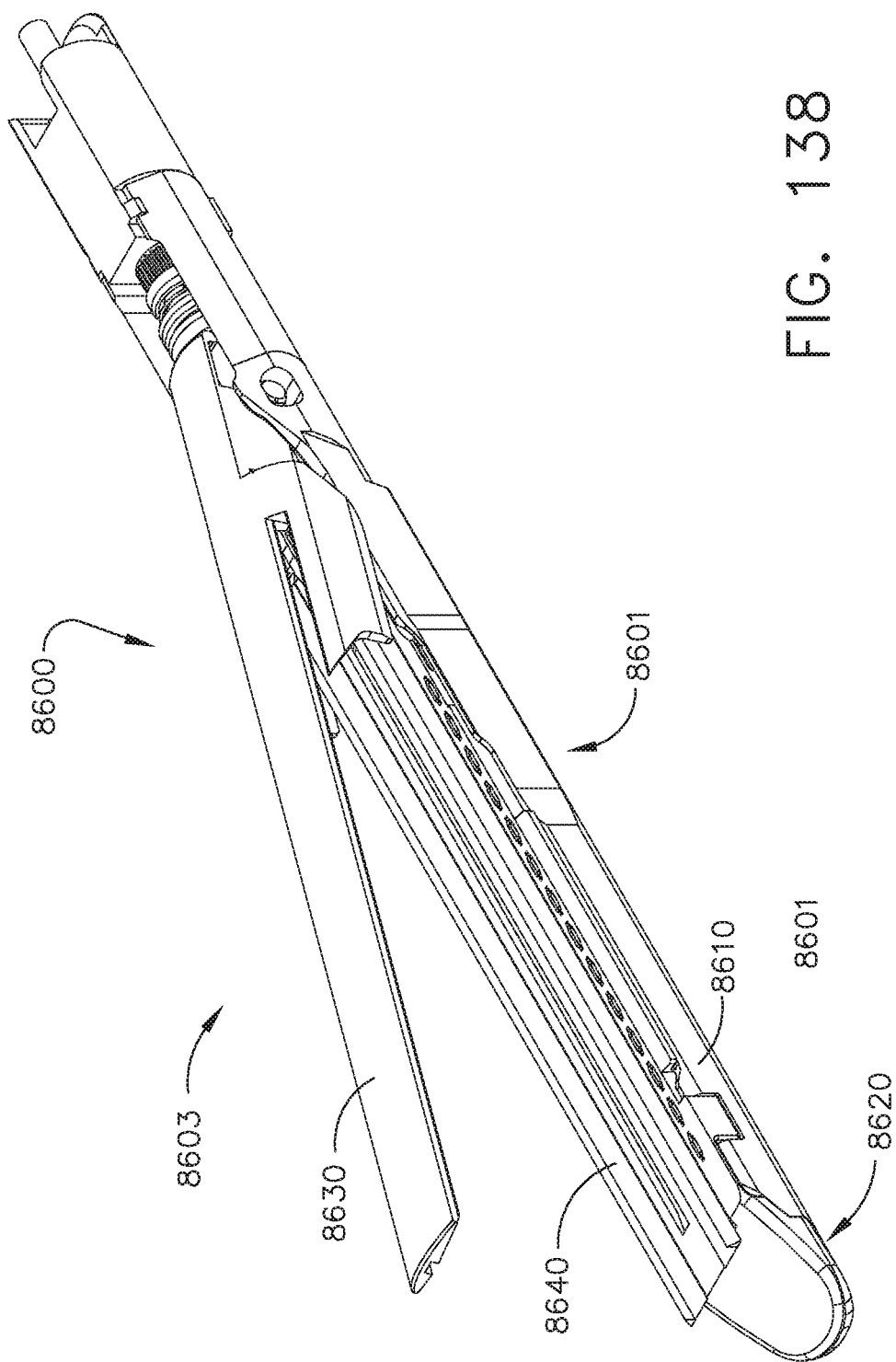

FIG. 138 is a perspective view of the surgical stapling assembly of FIG. 137 illustrated in an unclamped configuration, wherein the anvil plate is not attached to an anvil jaw of the surgical stapling assembly, in accordance with at least one aspect of the present disclosure.

Figure 139:
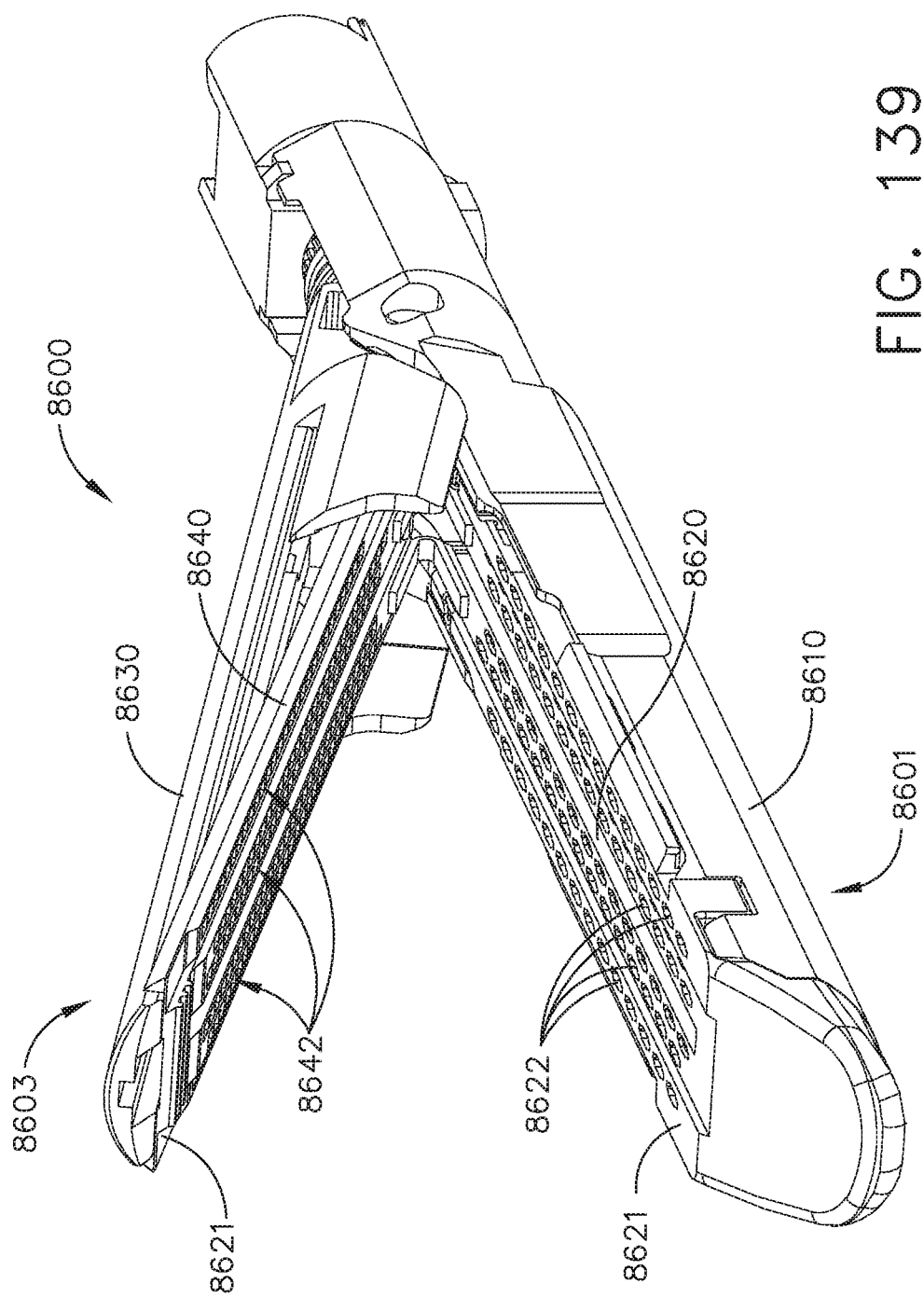

FIG. 139 is a perspective view of the surgical stapling assembly of FIG. 137, wherein the anvil plate is partially attached to the anvil jaw, in accordance with at least one aspect of the present disclosure.

Figure 140:
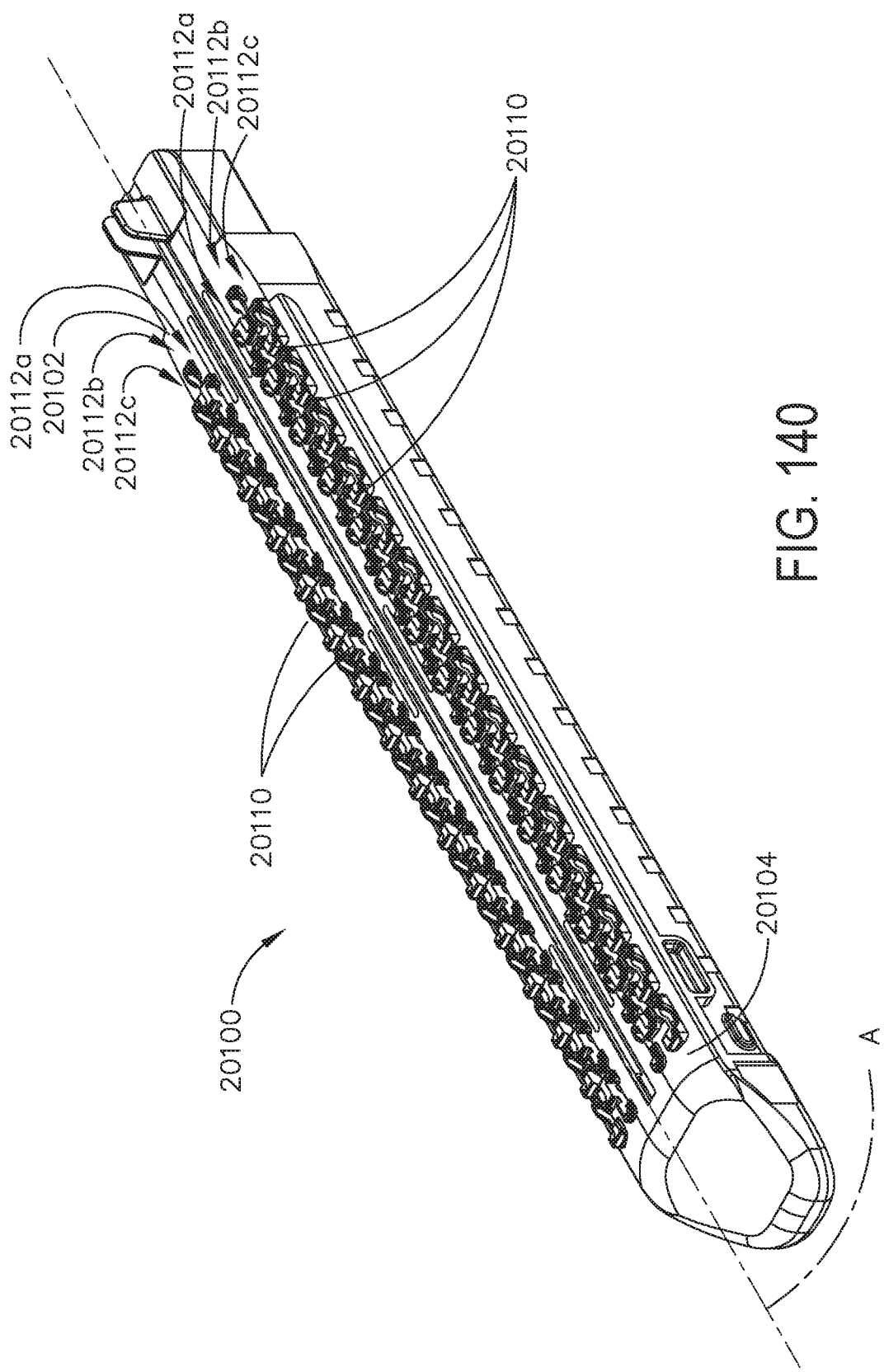

FIG. 140 is a perspective view of a staple cartridge, according to various aspects of the present disclosure.

Figure 141:
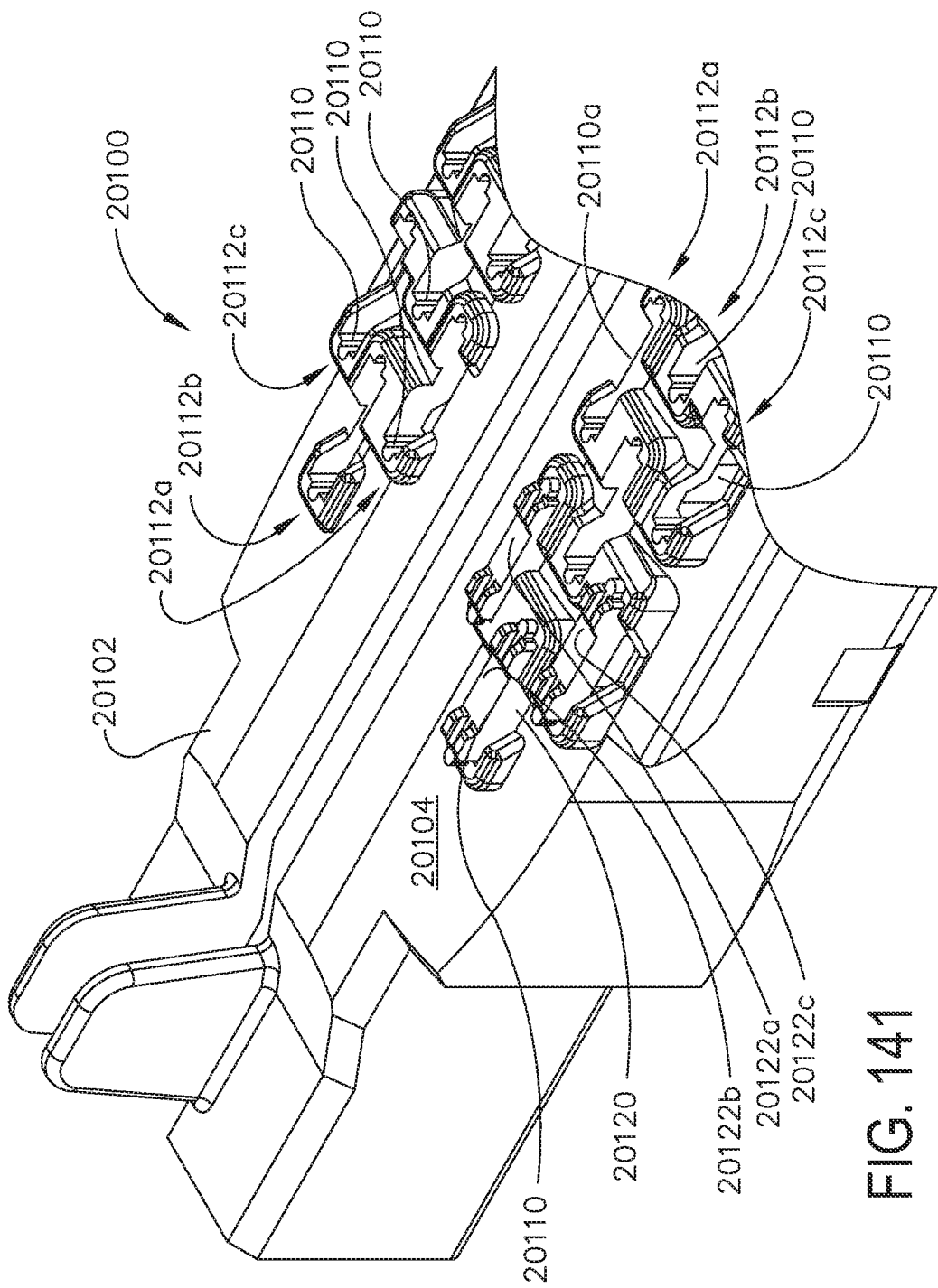

FIG. 141 is a perspective view of a portion of the staple cartridge of FIG. 140, depicting a triple driver in a fired configuration in the staple cartridge, according to various aspects of the present disclosure.

Figure 142:
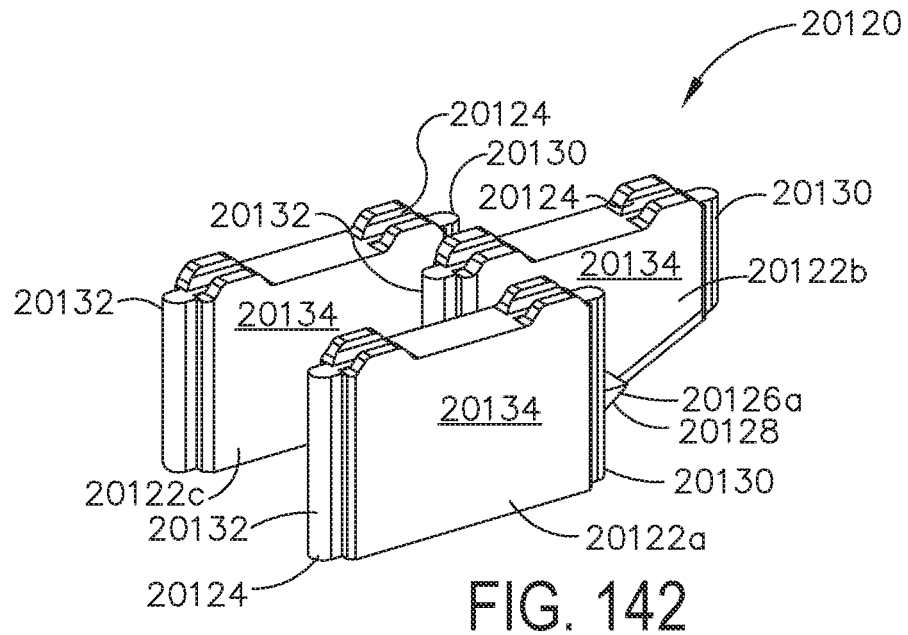

FIG. 142 is a perspective view of the triple driver of FIG. 141, according to various aspects of the present disclosure.

Figure 143:
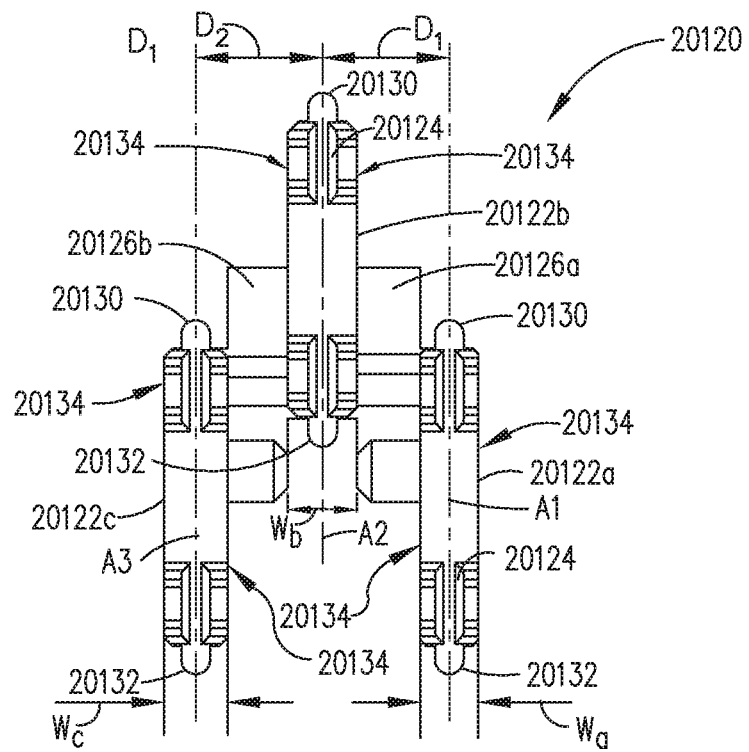

FIG. 143 is a plan view of the triple driver of FIG. 142, according to various aspects of the present disclosure.

Figure 144:
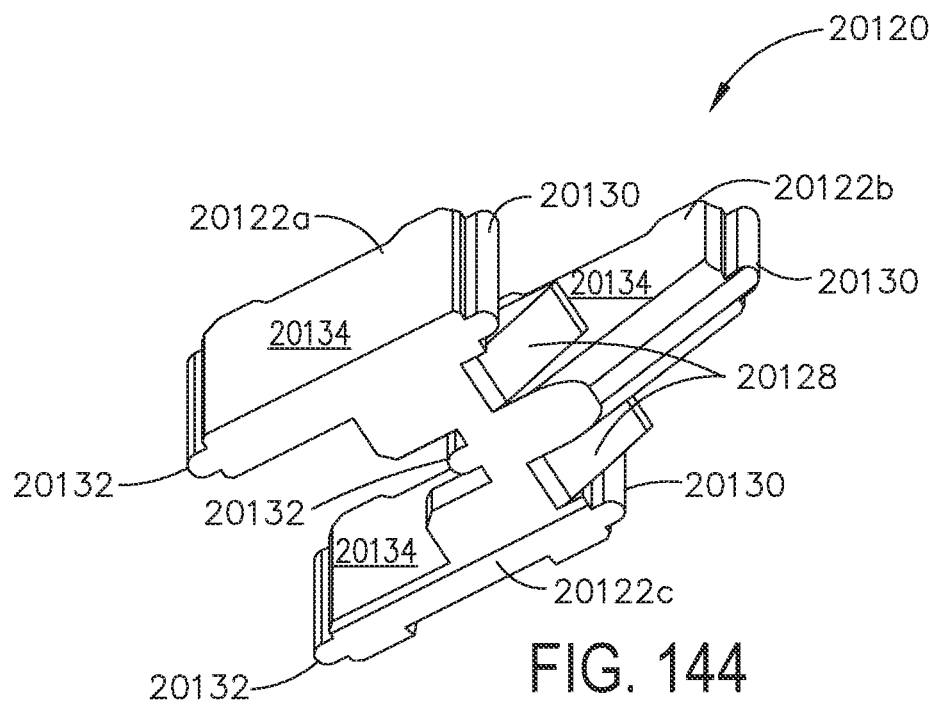

FIG. 144 is a bottom perspective view of the triple driver of FIG. 142, according to various aspects of the present disclosure.

Figure 145:
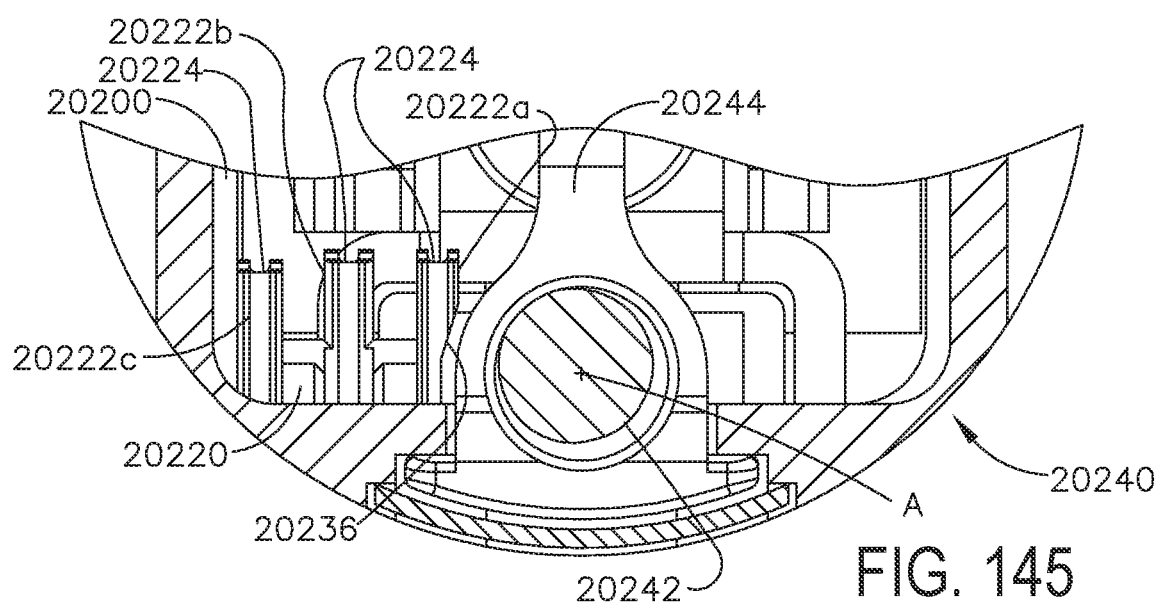

FIG. 145 is an elevation cross-section view of a portion of an end effector, depicting a staple cartridge therein with portions of the staple cartridge hidden for illustrative purposes, according to various aspects of the present disclosure.

Figure 146:
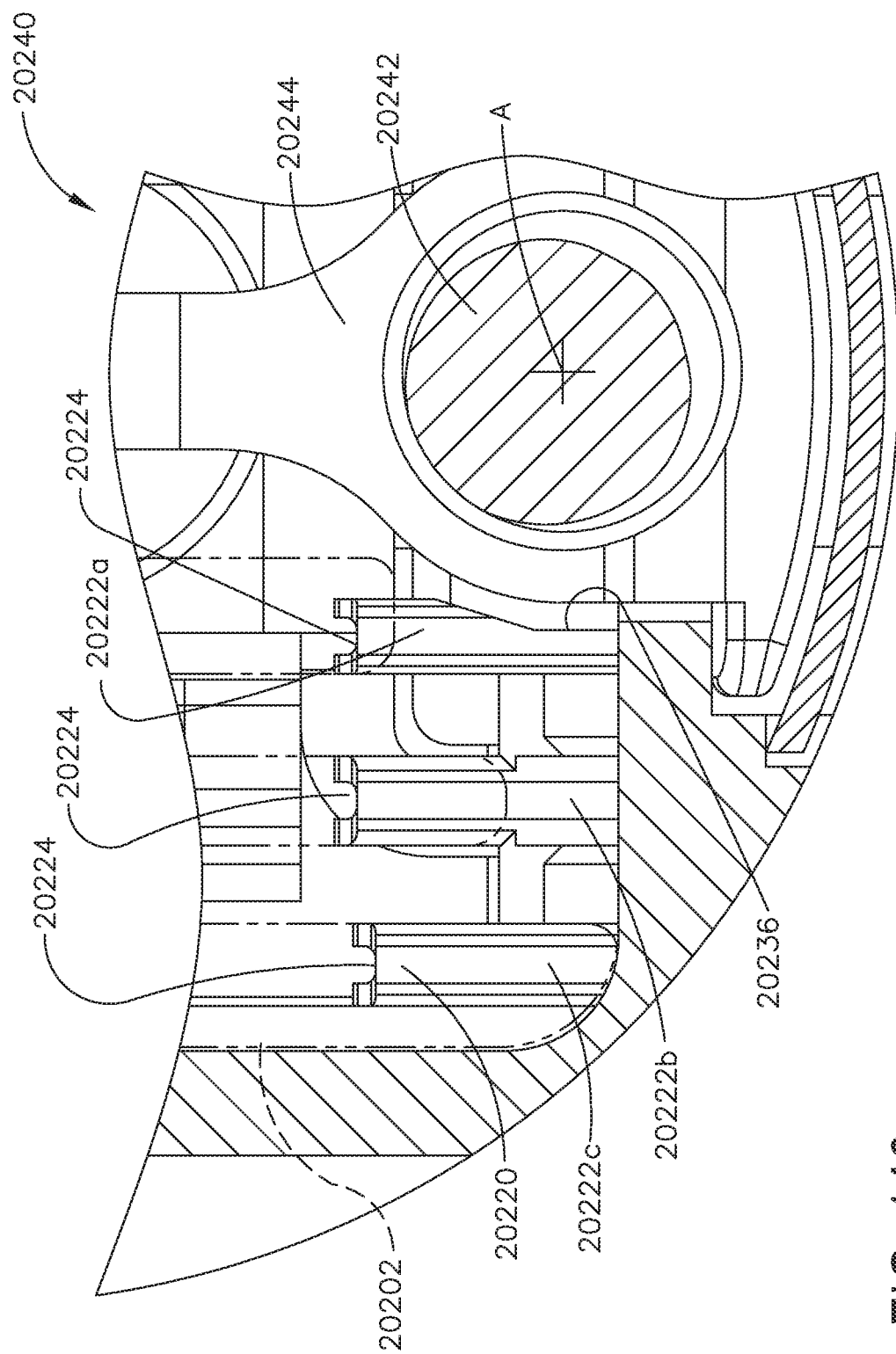

FIG. 146 is a detail view of the end effector of FIG. 145, according to various aspects of the present disclosure.

Figure 147:
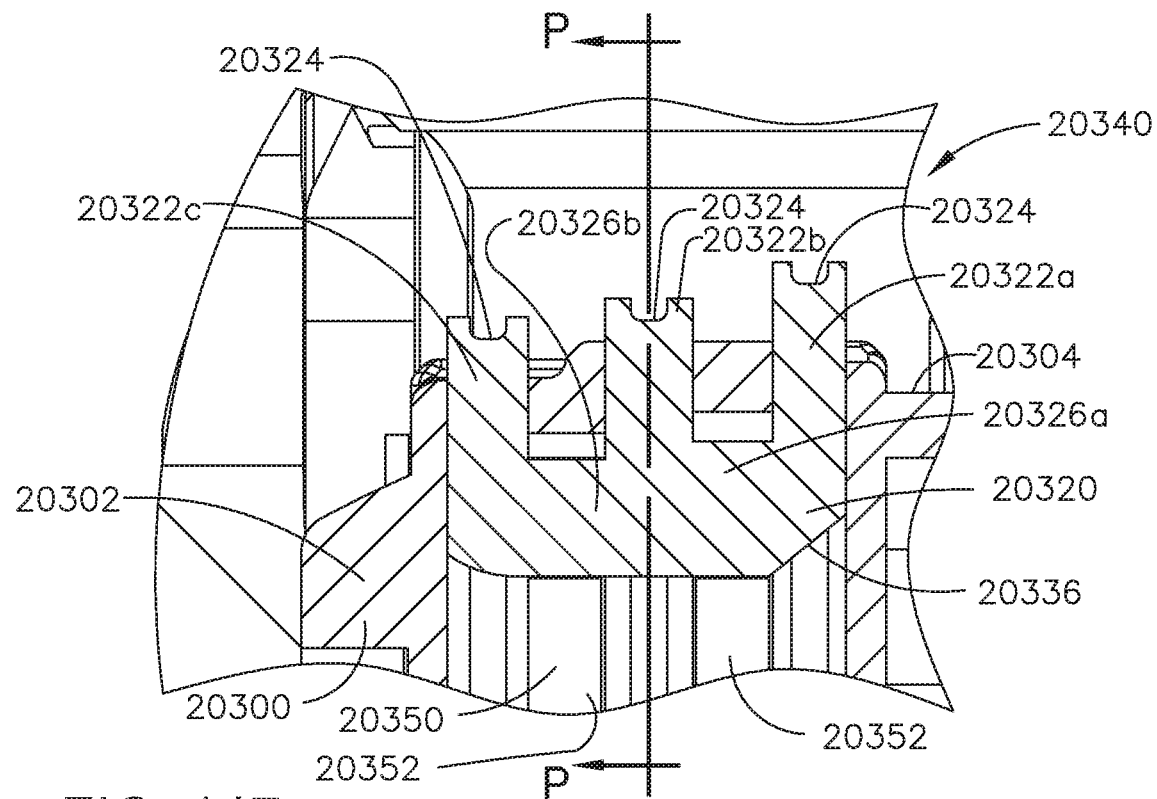

FIG. 147 is an elevation cross-section view of a portion of an end effector including a staple cartridge therein, according to various aspects of the present disclosure.

Figure 148:
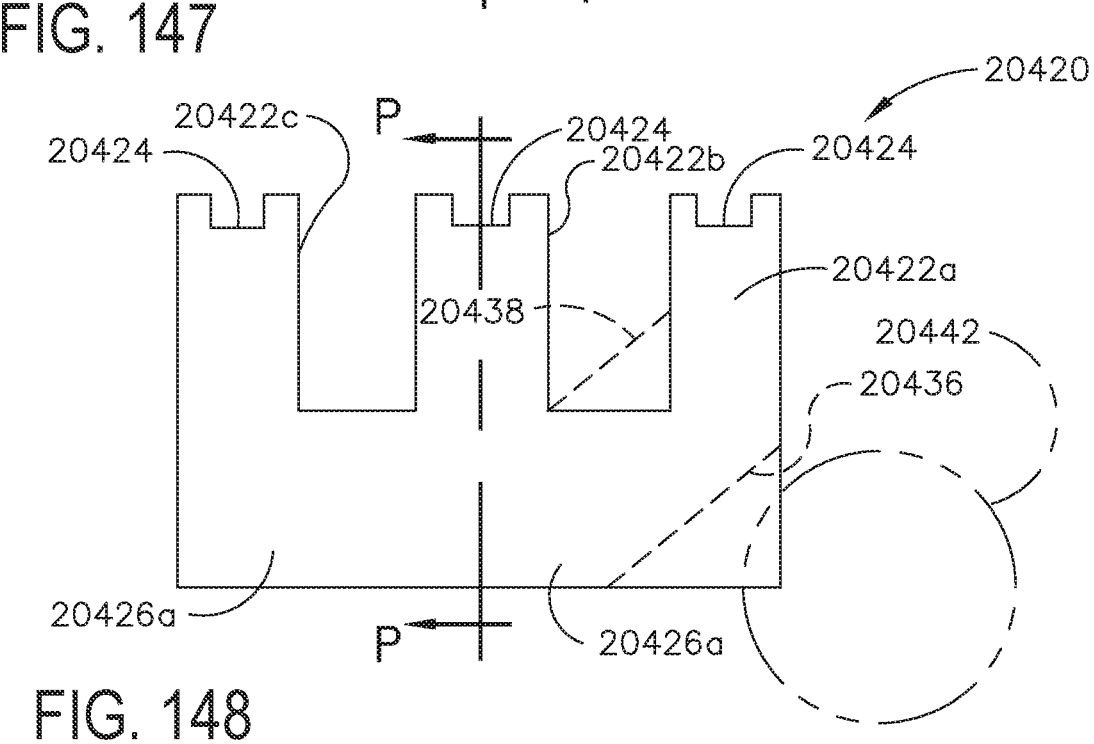

FIG. 148 is a schematic of a triple driver, depicting a modified geometry with dashed lines and showing relative positioning of a rotary drive screw with phantom lines, according to various aspects of the present disclosure.

Figure 149:
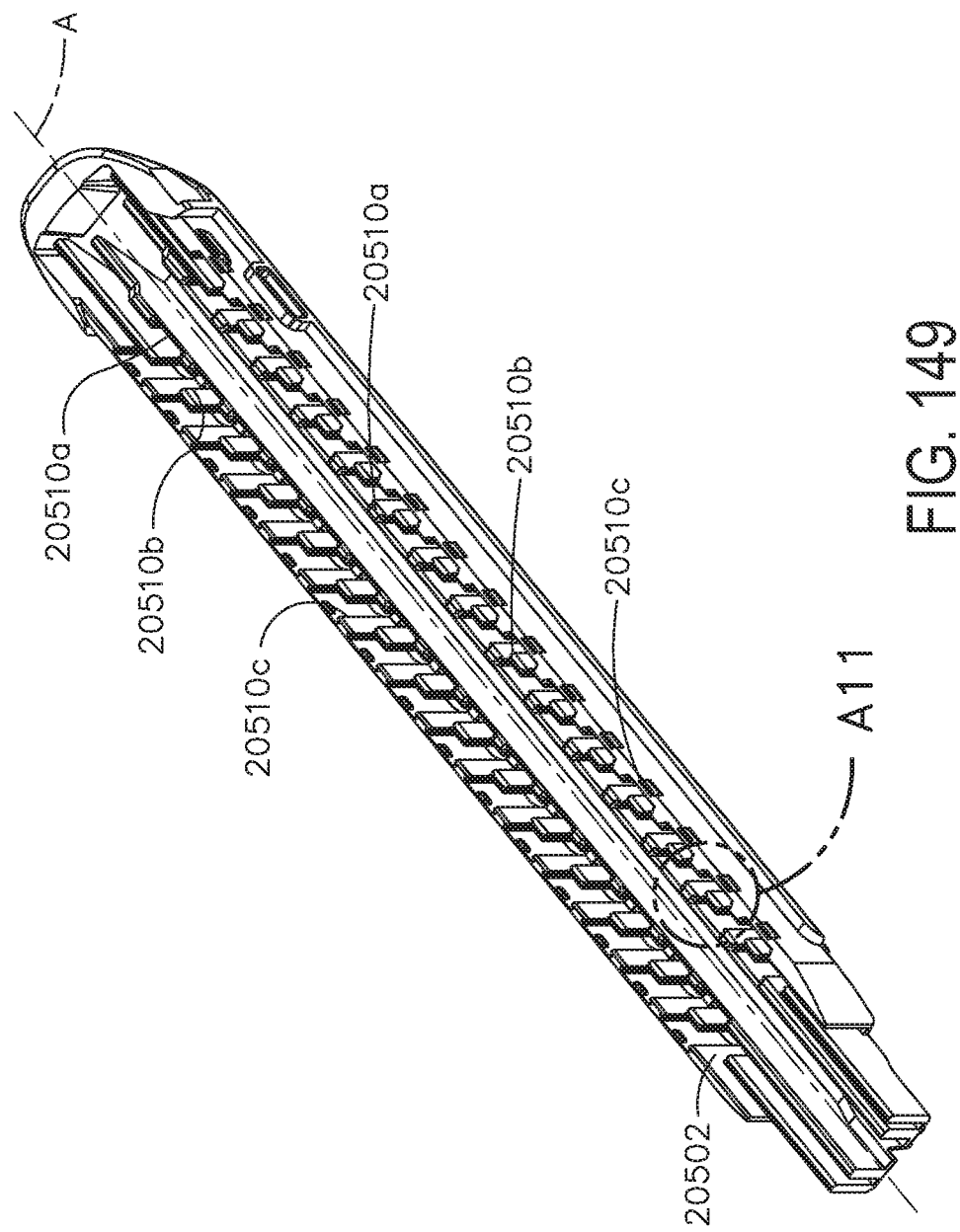

FIG. 149 is a bottom perspective view of a cartridge body with portions hidden for illustrative purposes, according to various aspects of the present disclosure.

FIG. 150 is a detail view of a portion of the cartridge body of FIG. 149, depicting a chamfer defined into the cartridge body around an inner staple cavity, according to various aspects of the present disclosure.

FIG. 151 is an elevation cross-section view of an inner support column of a driver and a portion of the cartridge body of FIG. 149, depicting the inner support column in an unfired configuration relative to an inner staple cavity, according to various aspects of the present disclosure.

Figure 152:
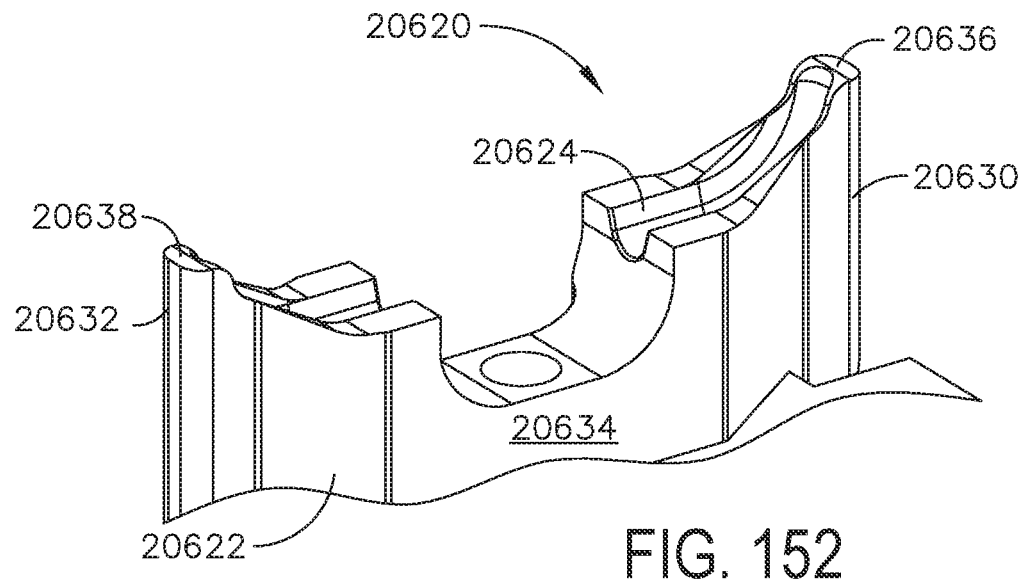

FIG. 152 is a perspective view of a portion of a support column of a driver, according to various aspects of the present disclosure.

Figure 153:
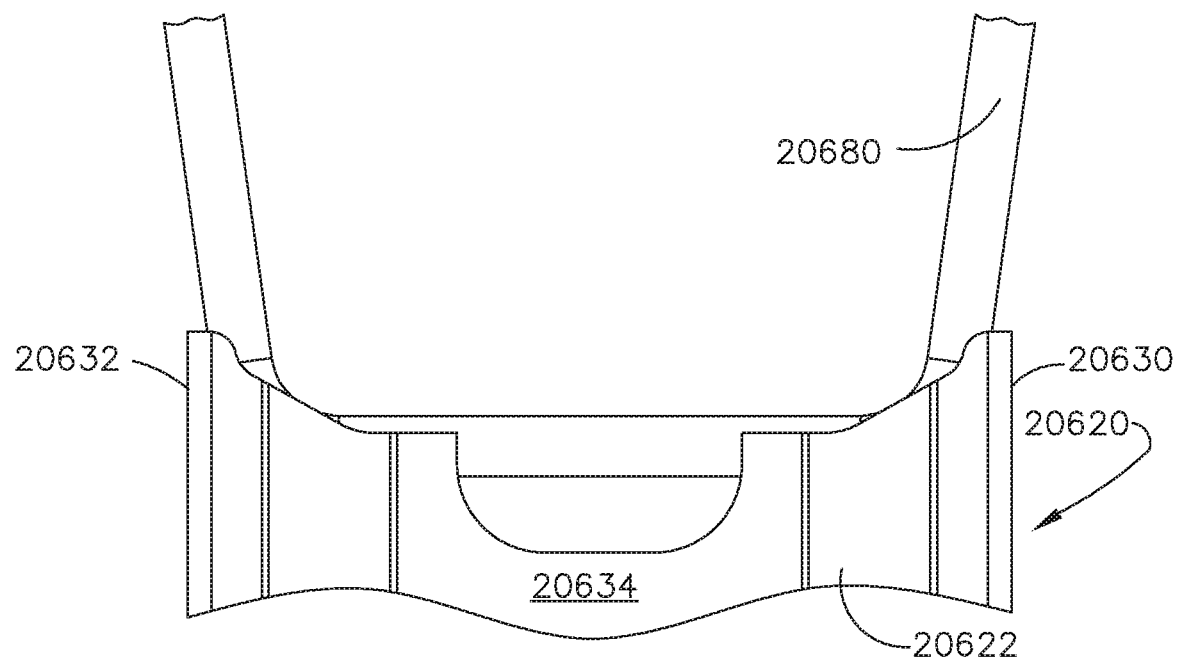

FIG. 153 is an elevational view of the portion of the support column of FIG. 152, depicting a portion of a staple supported on the support column, according to various aspects of the present disclosure.

Figure 154:
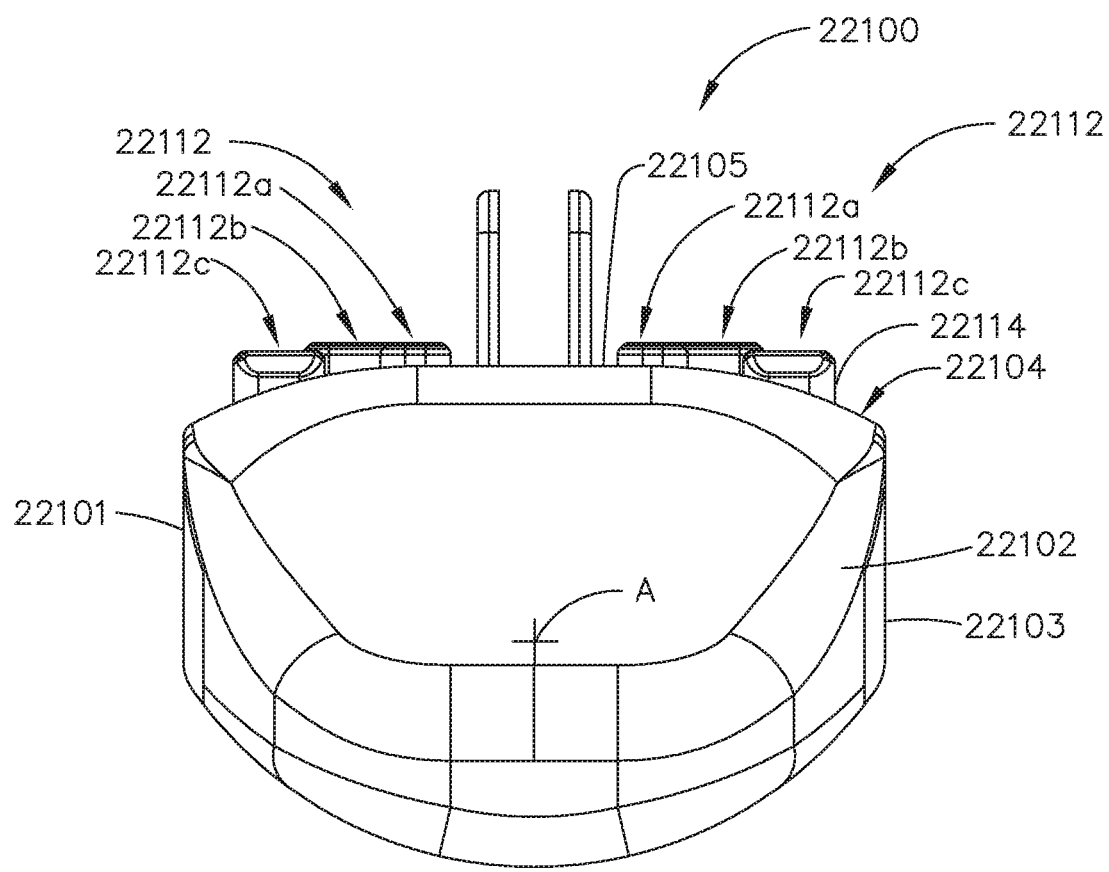

FIG. 154 is an elevation view of a staple cartridge, according to various aspects of the present disclosure.

Figure 155:
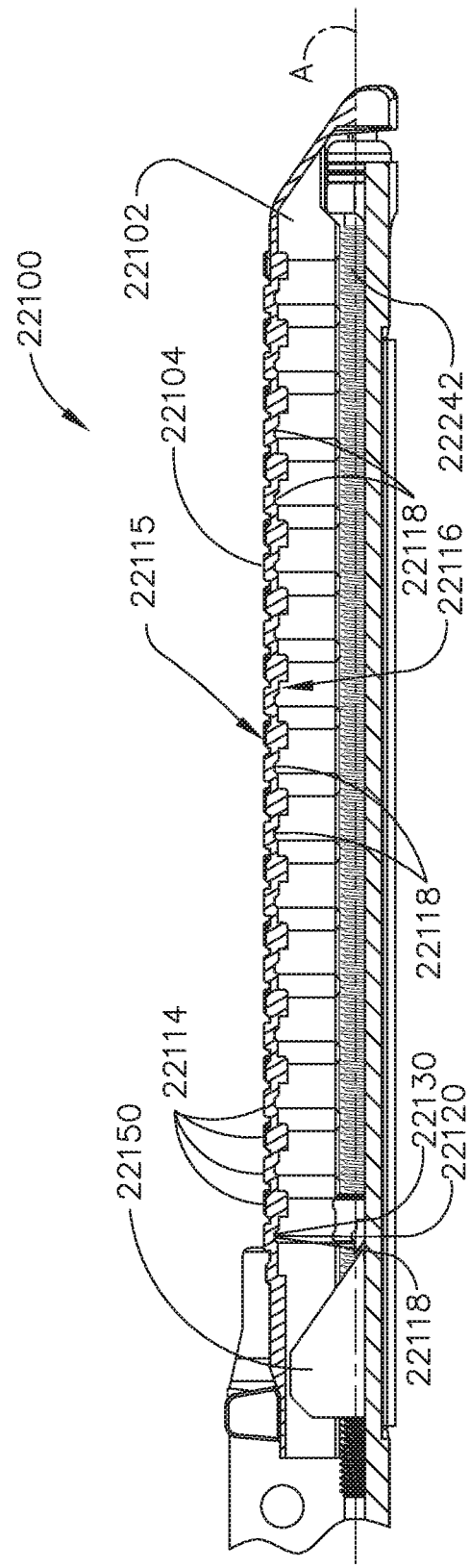

FIG. 155 is an elevation cross-section view of the staple cartridge of FIG. 154 taken along a plane A shown in FIG. 154, according to various aspects of the present disclosure.

Figure 156:
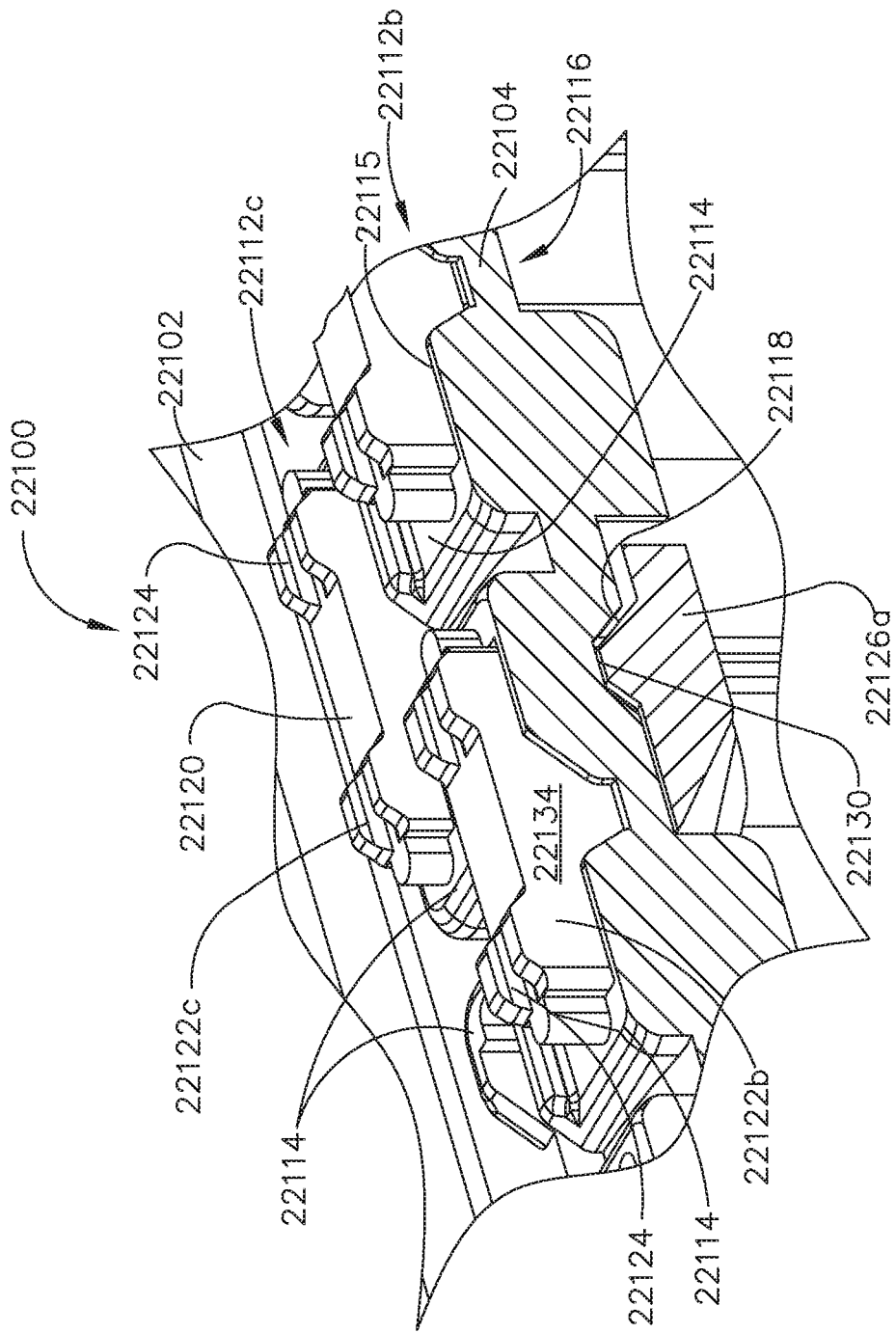

FIG. 156 is a perspective cross-section view of a portion of the staple cartridge of FIG. 154 taken along the plane A shown in FIG. 154, depicting a driver in a fully fired position therein, according to various aspects of the present disclosure.

Figure 157:
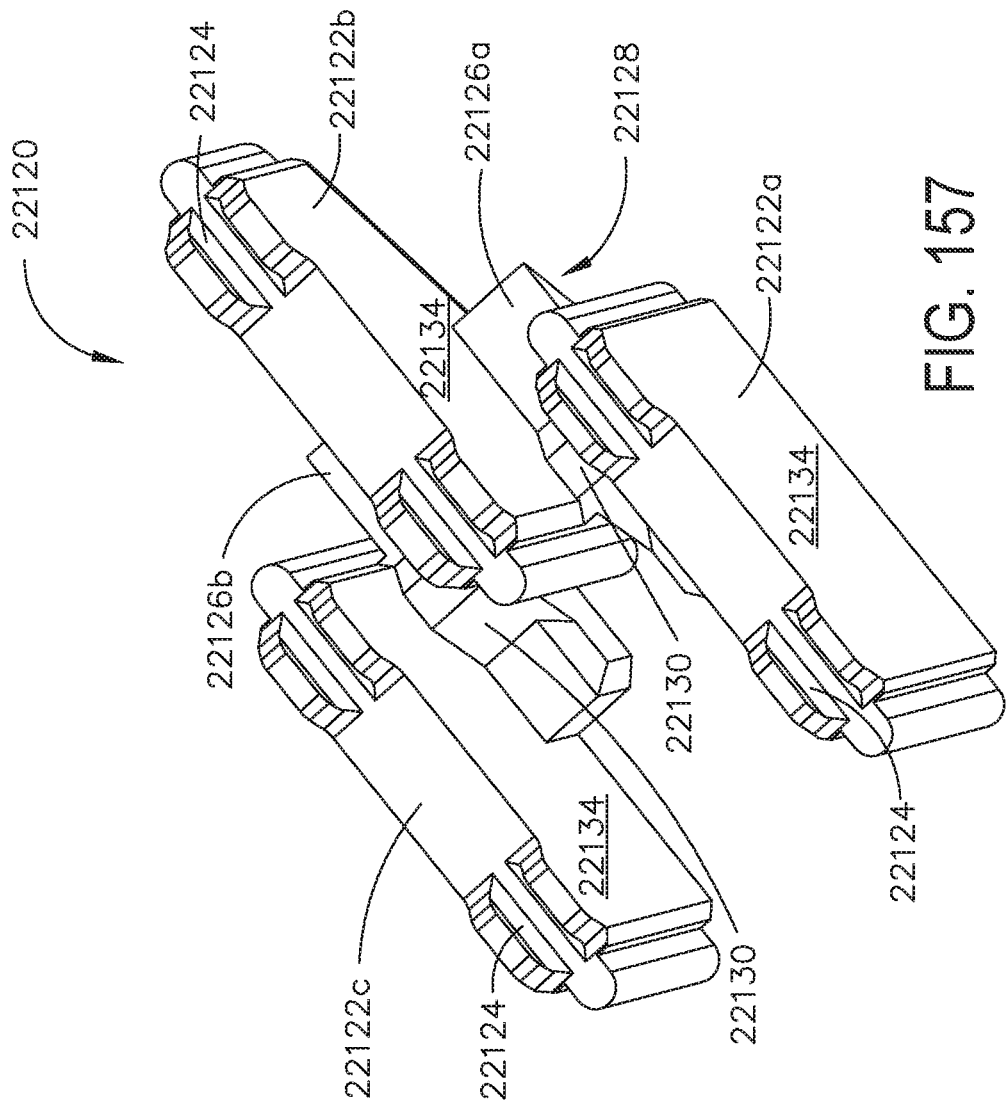

FIG. 157 is a perspective view of the driver of FIG. 156, according to various aspects of the present disclosure.

Figure 158:
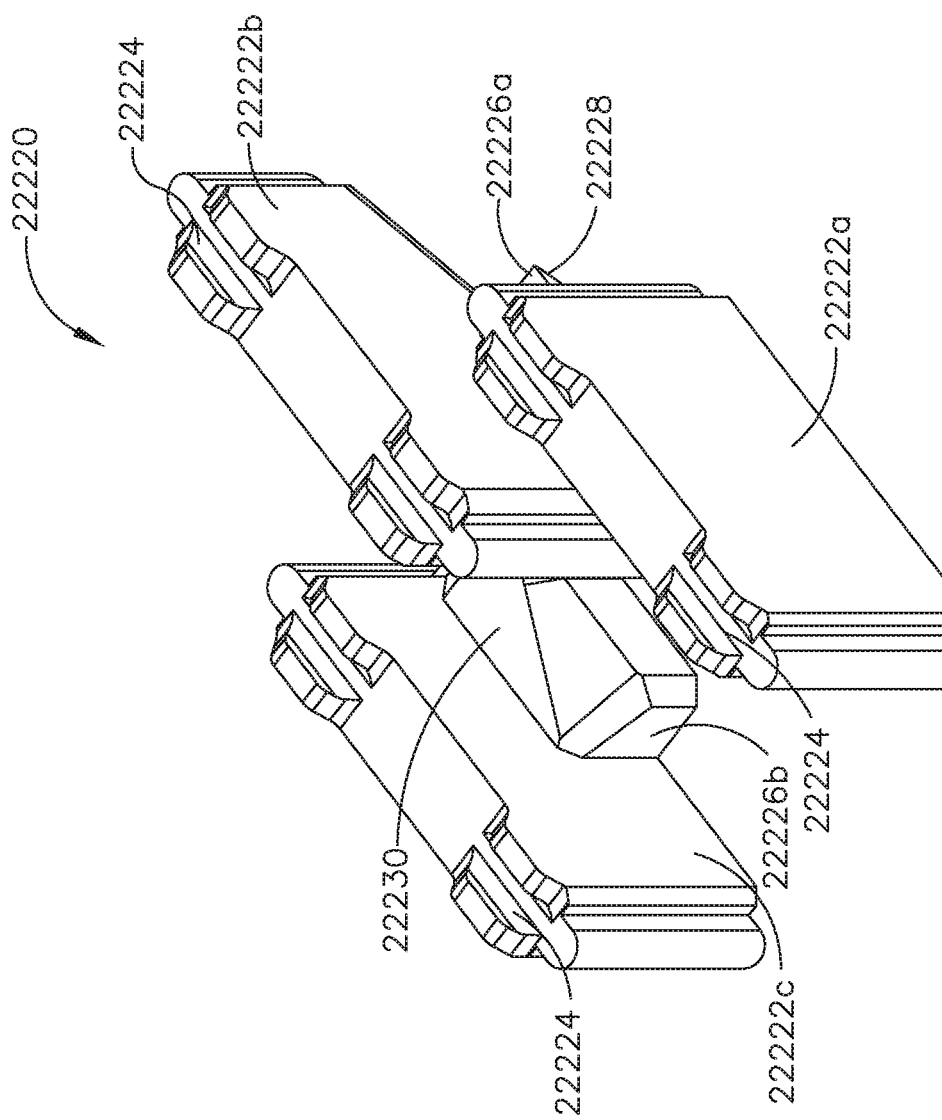

FIG. 158 is a perspective view of a driver, according to various aspects of the present disclosure.

Figure 159:
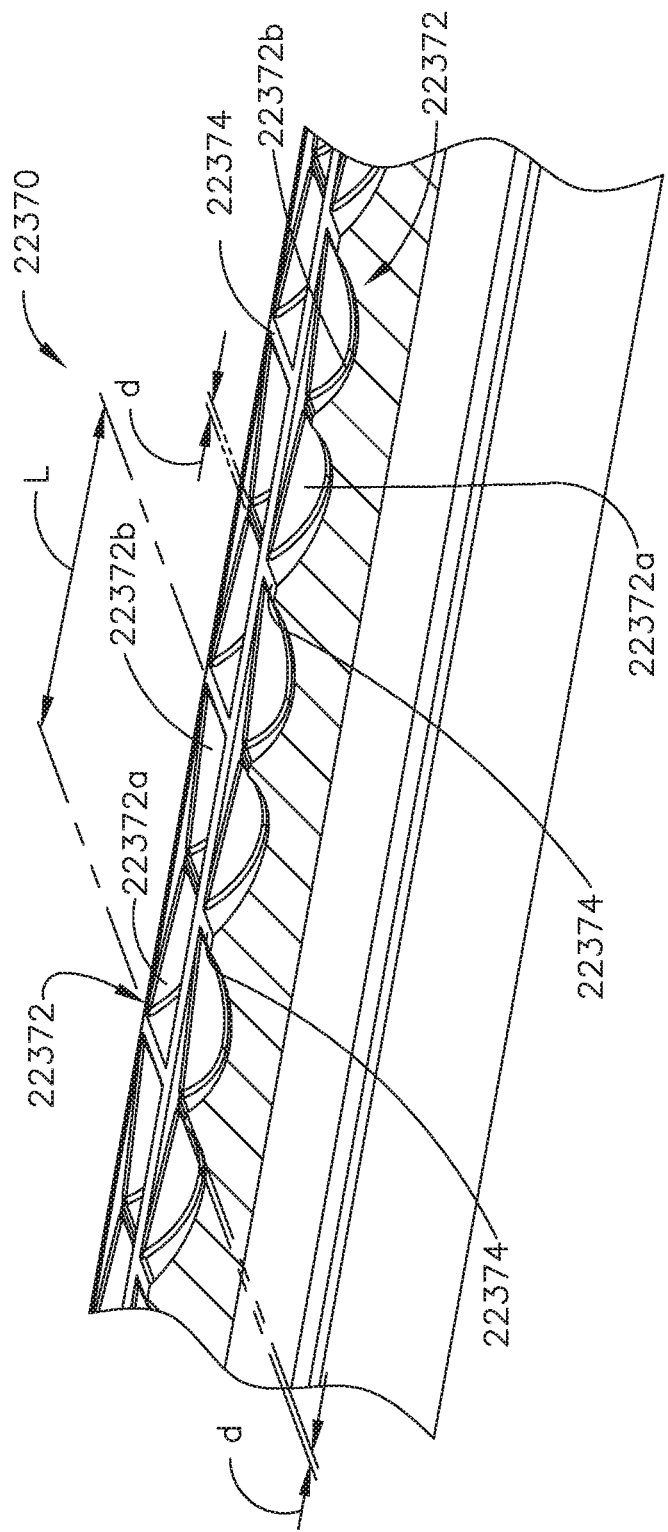

FIG. 159 is a perspective cross-section view of a portion of an anvil, according to various aspects of the present disclosure.

Figure 160:
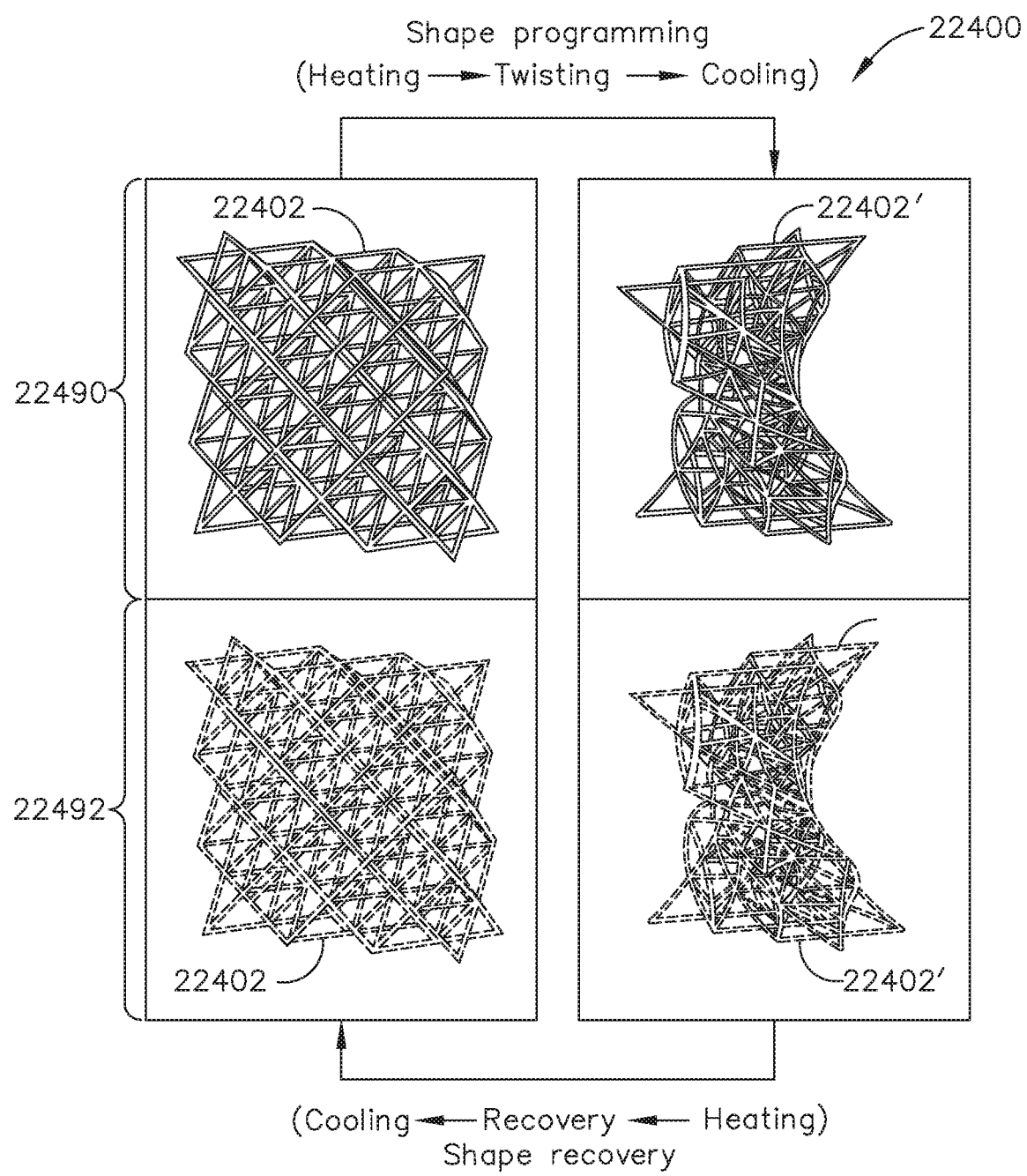

FIG. 160 is a schematic depicting a deformation process for a 4D printed matrix for a staple cartridge, according to various aspects of the present disclosure.

Figure 161:
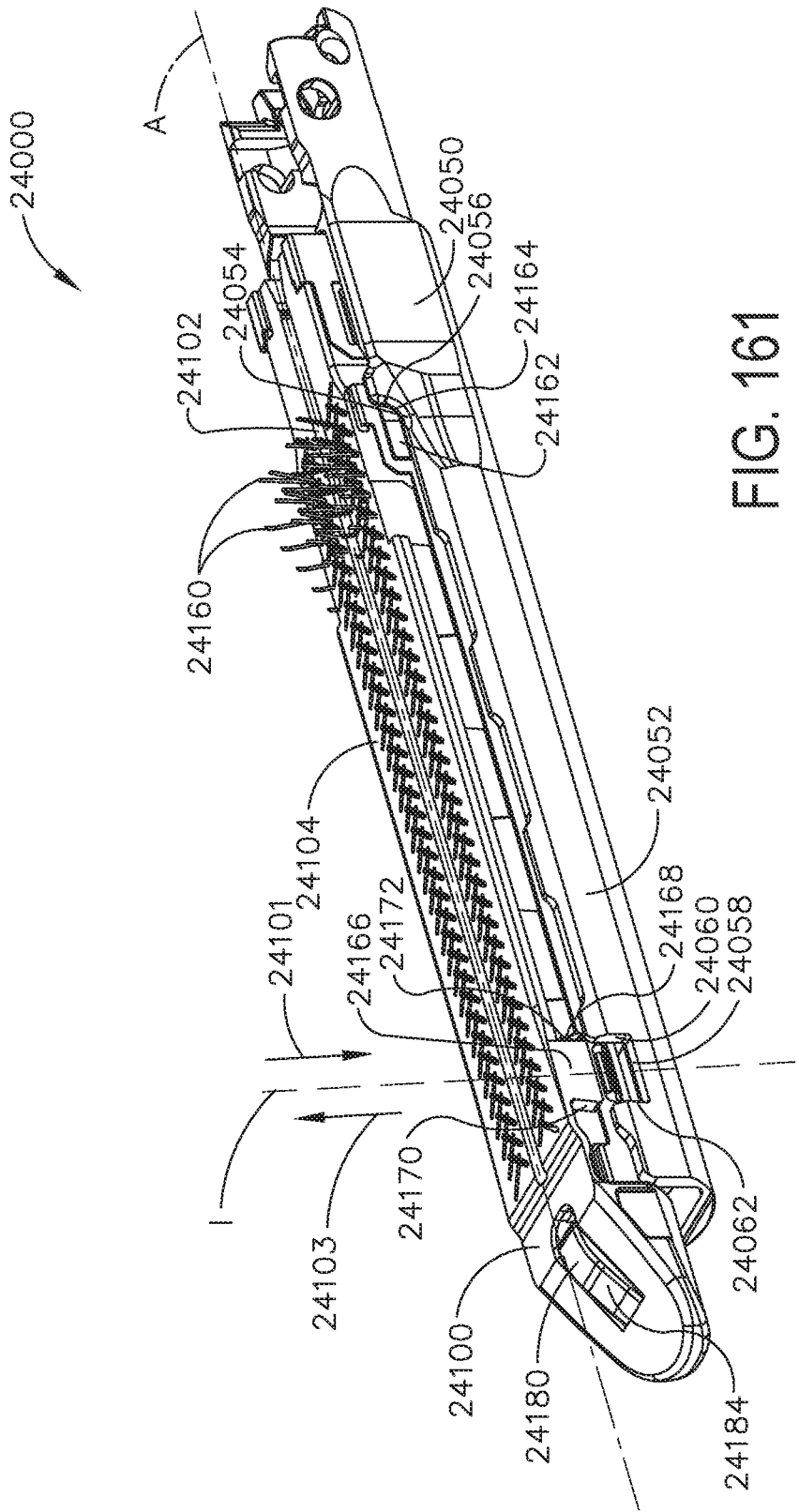

FIG. 161 is a perspective view of a staple cartridge and a channel, depicting alignment and leveraging features for installing the staple cartridge into the channel, further depicting the staple cartridge in an aligned and partially installed configuration relative to the channel, according to various aspects of the present disclosure.

Figure 162:
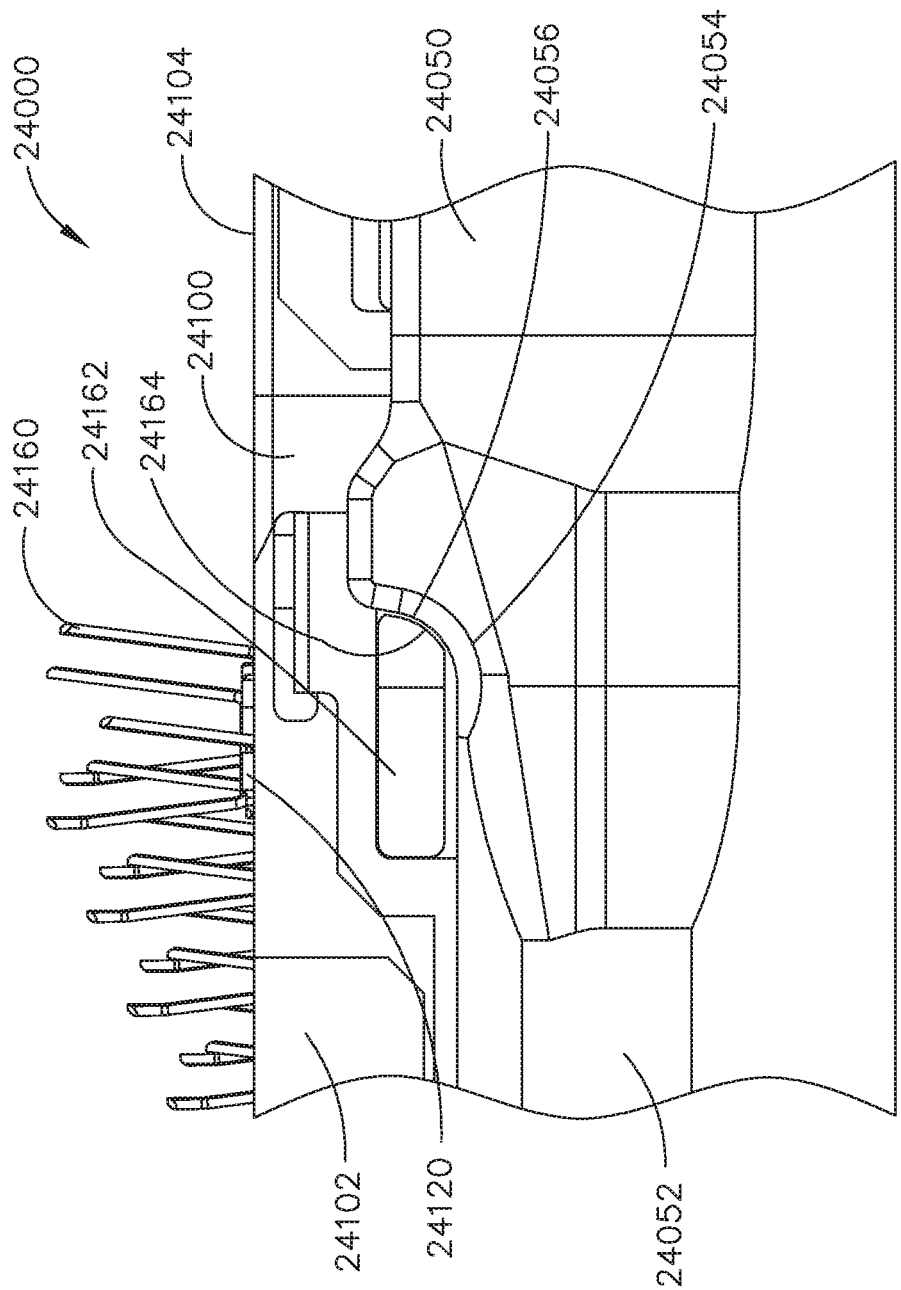

FIG. 162 is an elevation view of a proximal portion of the staple cartridge and the channel of FIG. 161 depicting the staple cartridge in the aligned and partially installed configuration, according to various aspects of the present disclosure.

Figure 163:
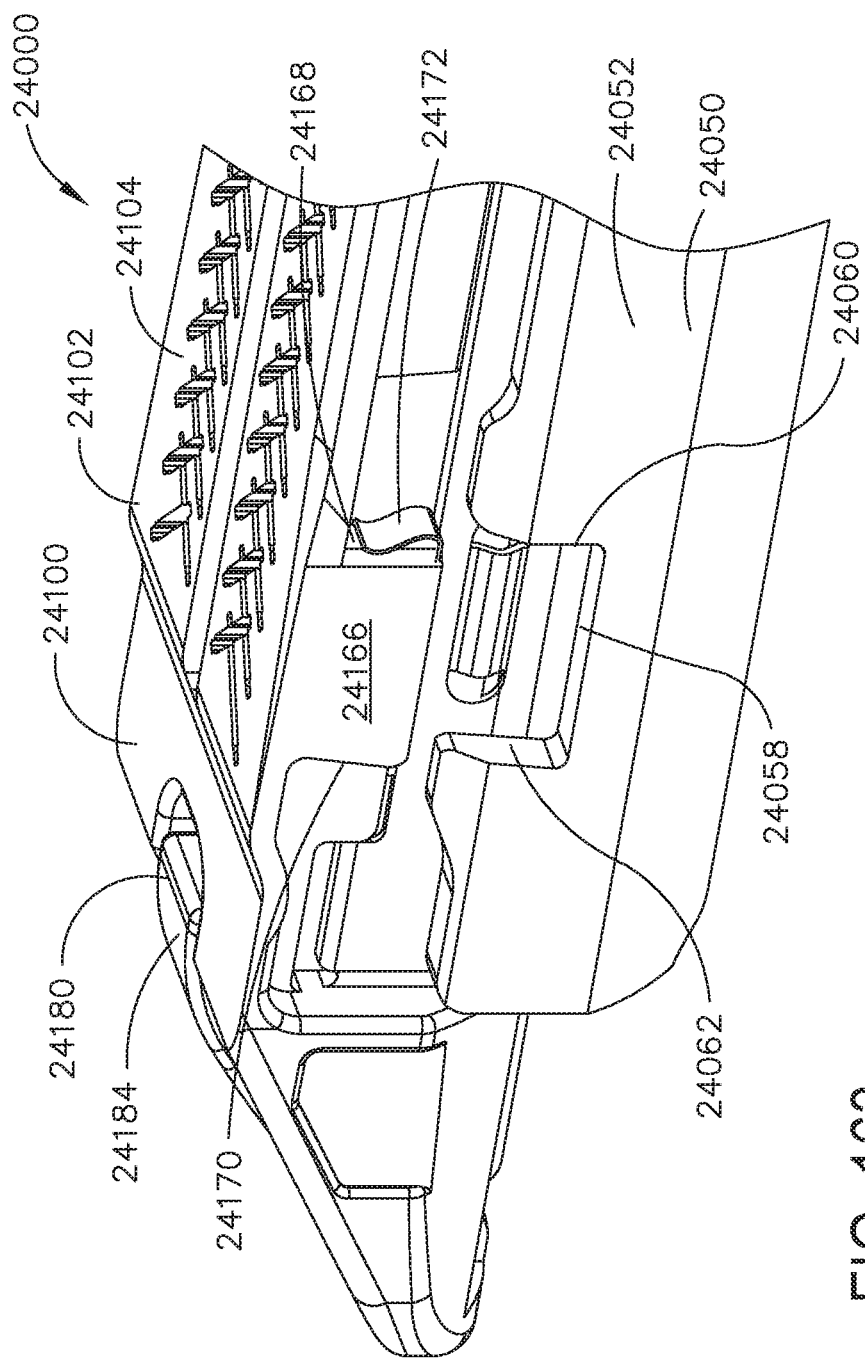

FIG. 163 is a perspective view of a distal portion of the staple cartridge and the channel of FIG. 161, depicting the staple cartridge in the aligned and partially installed configuration, according to various aspects of the present disclosure.

Figure 164:
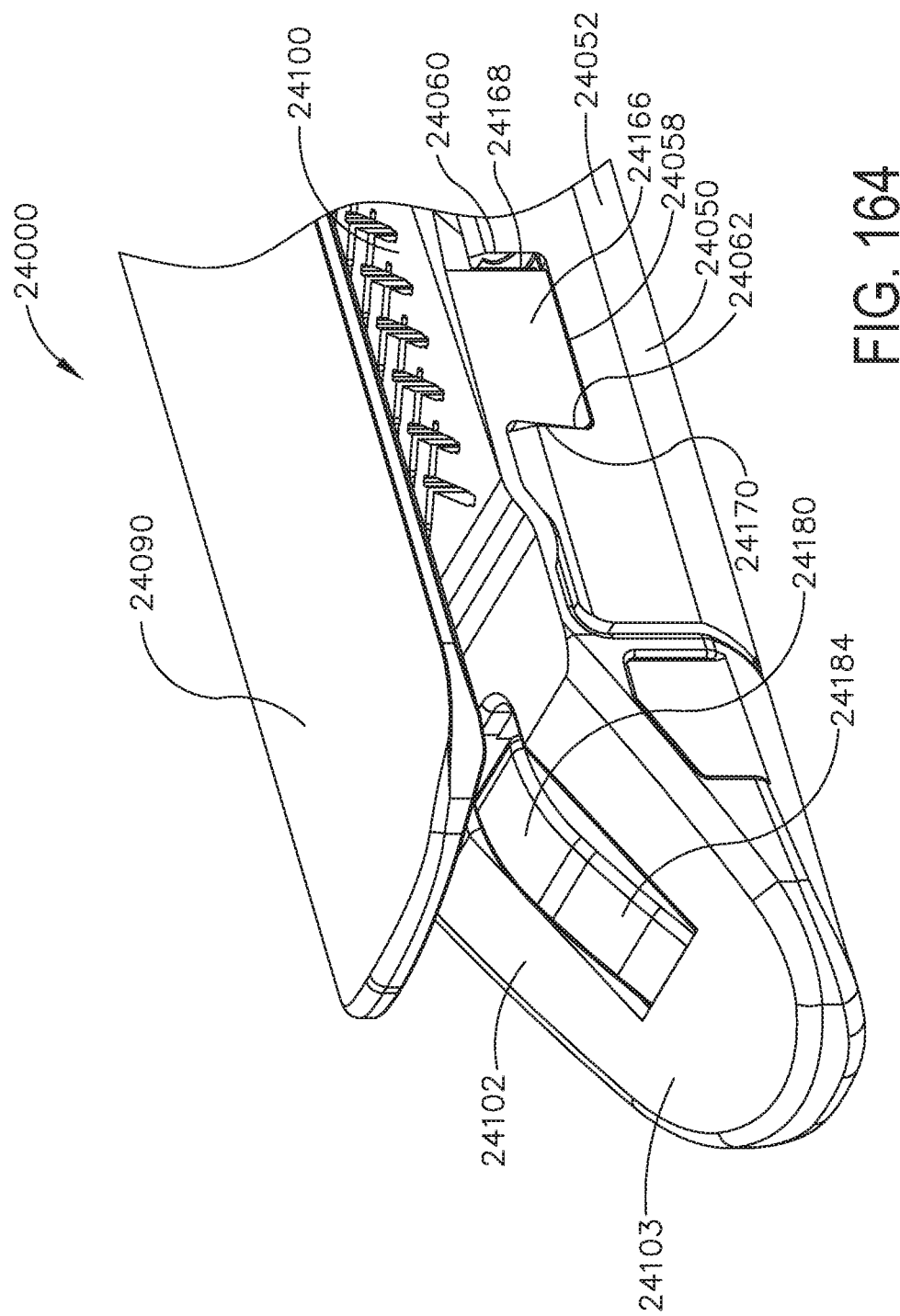

FIG. 164 is a perspective view of a distal portion of the staple cartridge and the channel of FIG. 161, depicting the staple cartridge installed and fully seated in the channel, further depicting an anvil in a clamped configuration relative to the staple cartridge, according to various aspects of the present disclosure.

Figure 165:
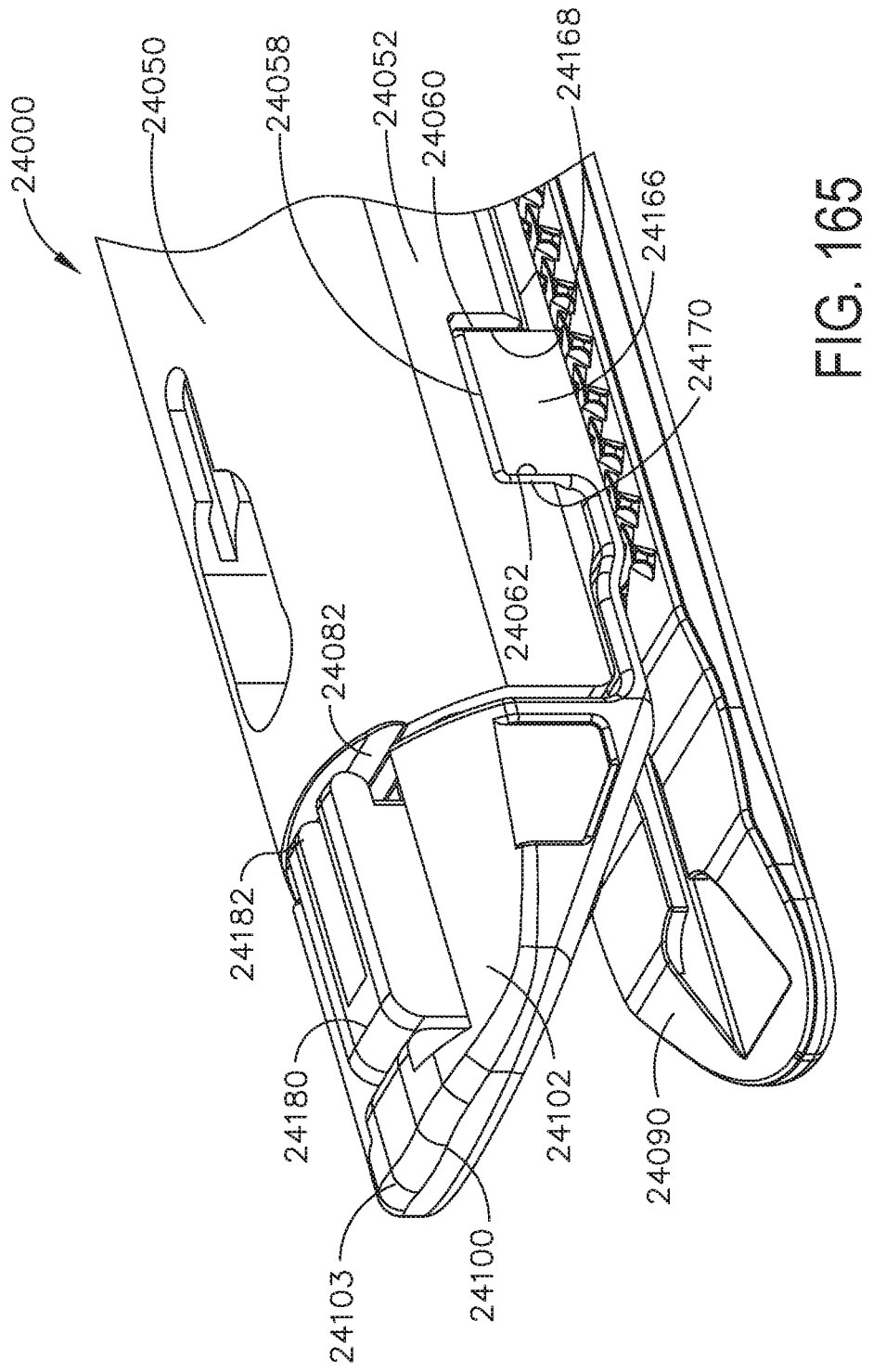

FIG. 165 is a perspective view of the distal portion of the staple cartridge, the channel, and the anvil of FIG. 164, depicting the staple cartridge installed and fully seated in the channel, and further depicting a latch on the underside of the staple cartridge in a latched position relative to the channel, according to various aspects of the present disclosure.

Figure 166:
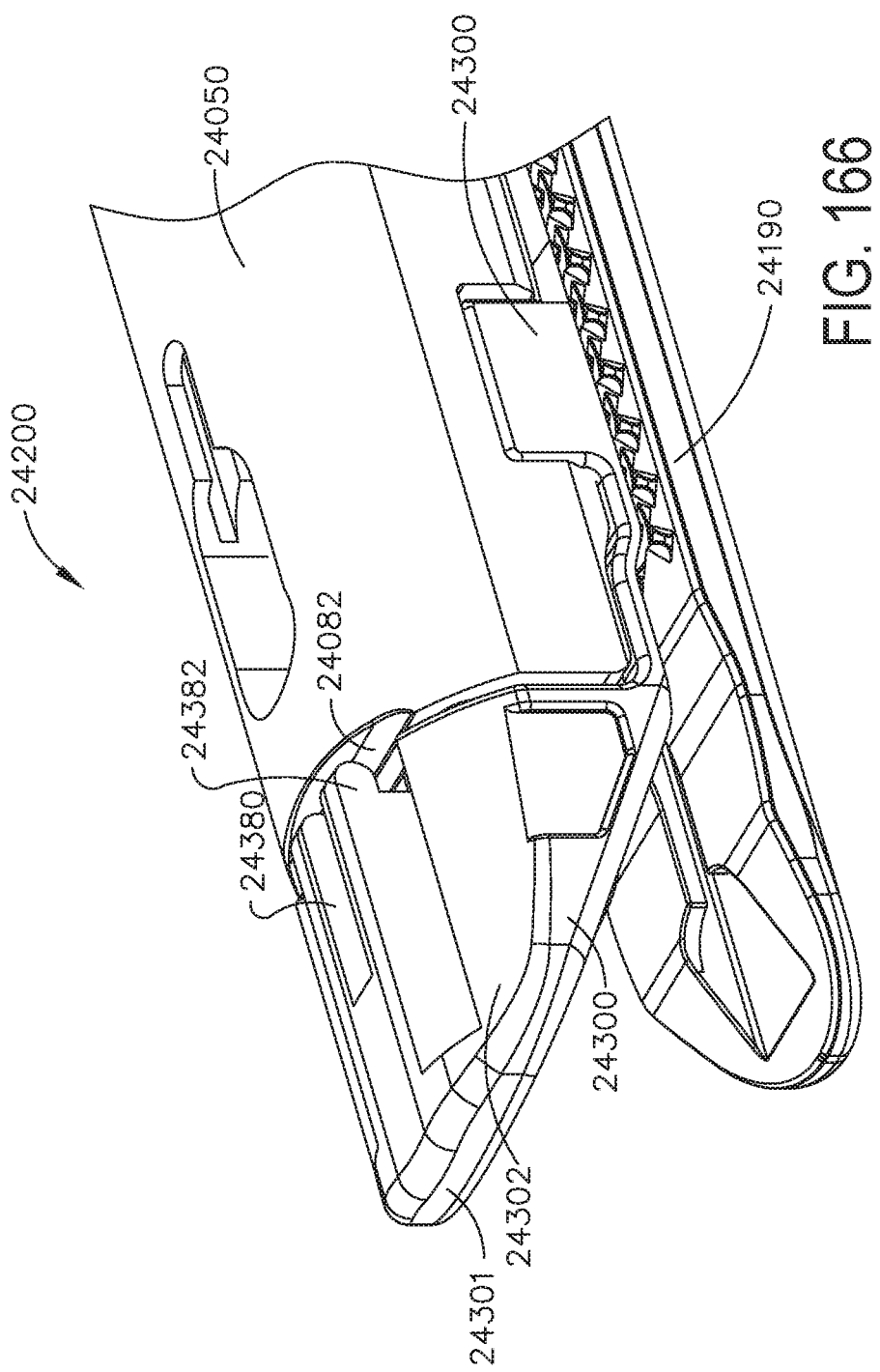

FIG. 166 is a perspective view of a distal portion of a staple cartridge, a channel, and an anvil, depicting the staple cartridge installed in the channel and the anvil in a clamped configuration relative to the staple cartridge, further depicting a flexible latch on the underside of the staple cartridge in a latched position relative to the channel, according to various aspects of the present disclosure.

Figure 167:
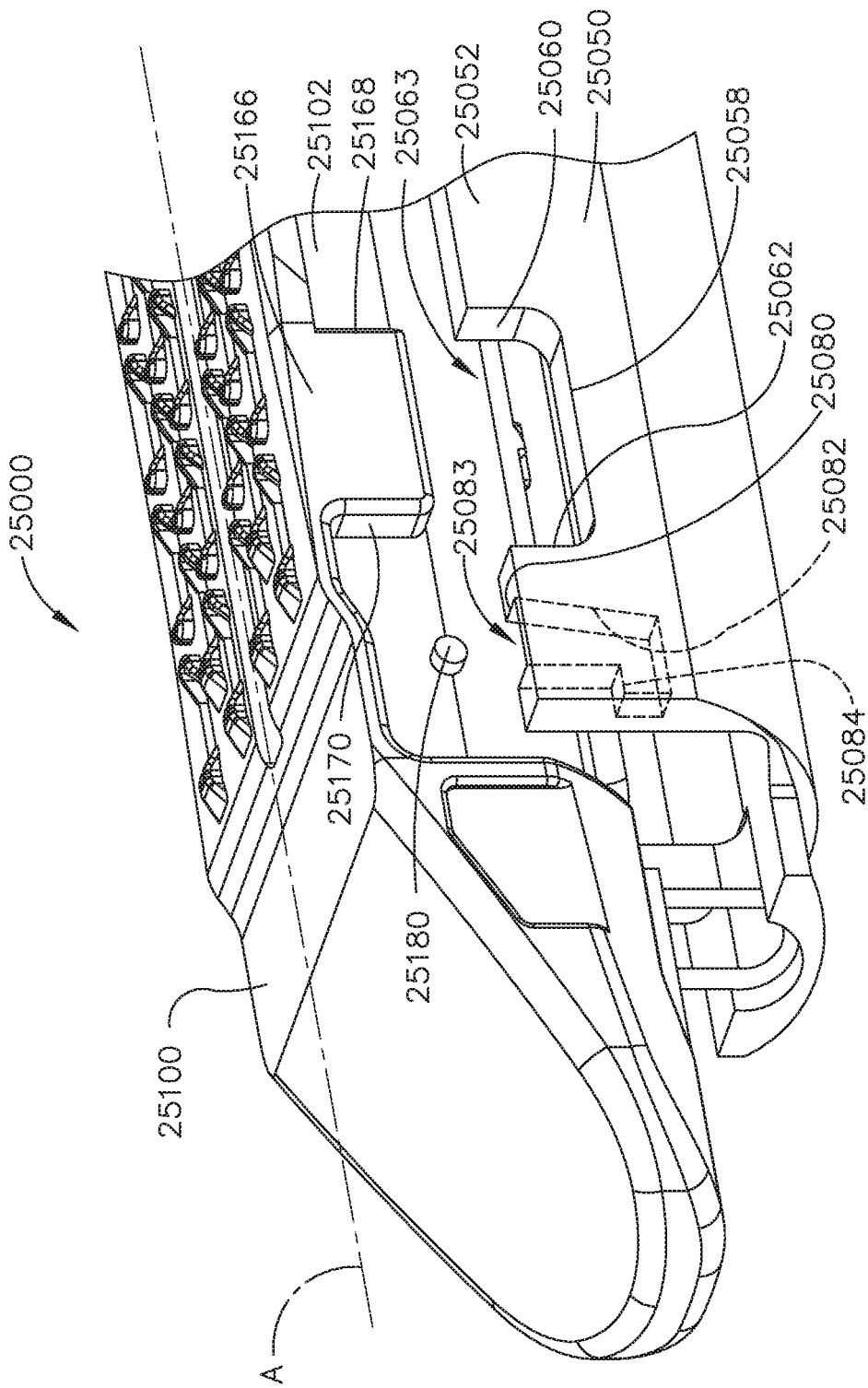

FIG. 167 is a perspective view of a channel and a staple cartridge, depicting alignment and leveraging features for installing the staple cartridge into the channel, further depicting the staple cartridge in an aligned and partially installed configuration relative to the channel, according to various aspects of the present disclosure.

Figure 168:
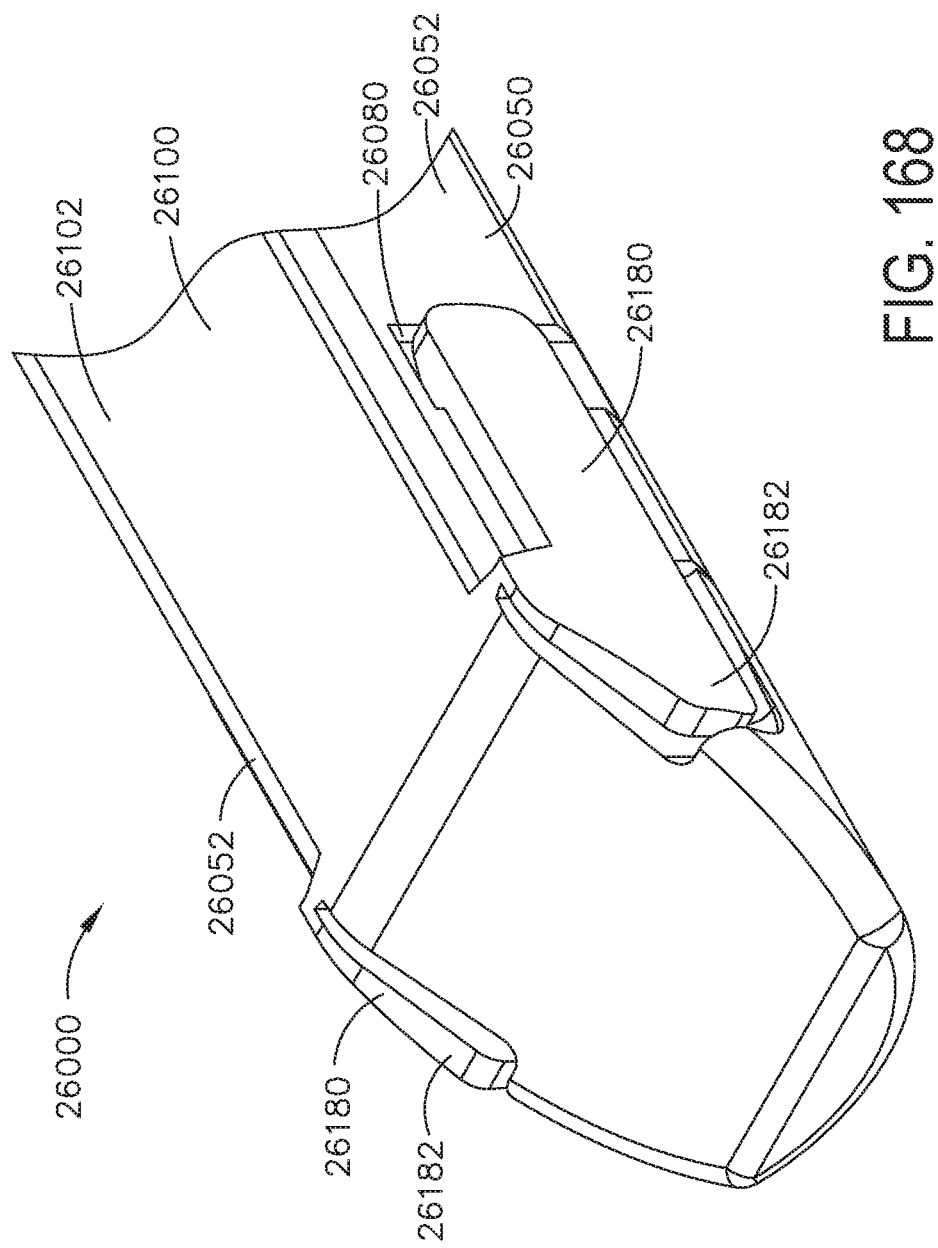

FIG. 168 is a perspective view of a portion of a staple cartridge and a channel, depicting lateral latching arms of the staple cartridge engaged with lateral passages in sidewalls of the channel, according to various aspects of the present disclosure.

Figure 169:
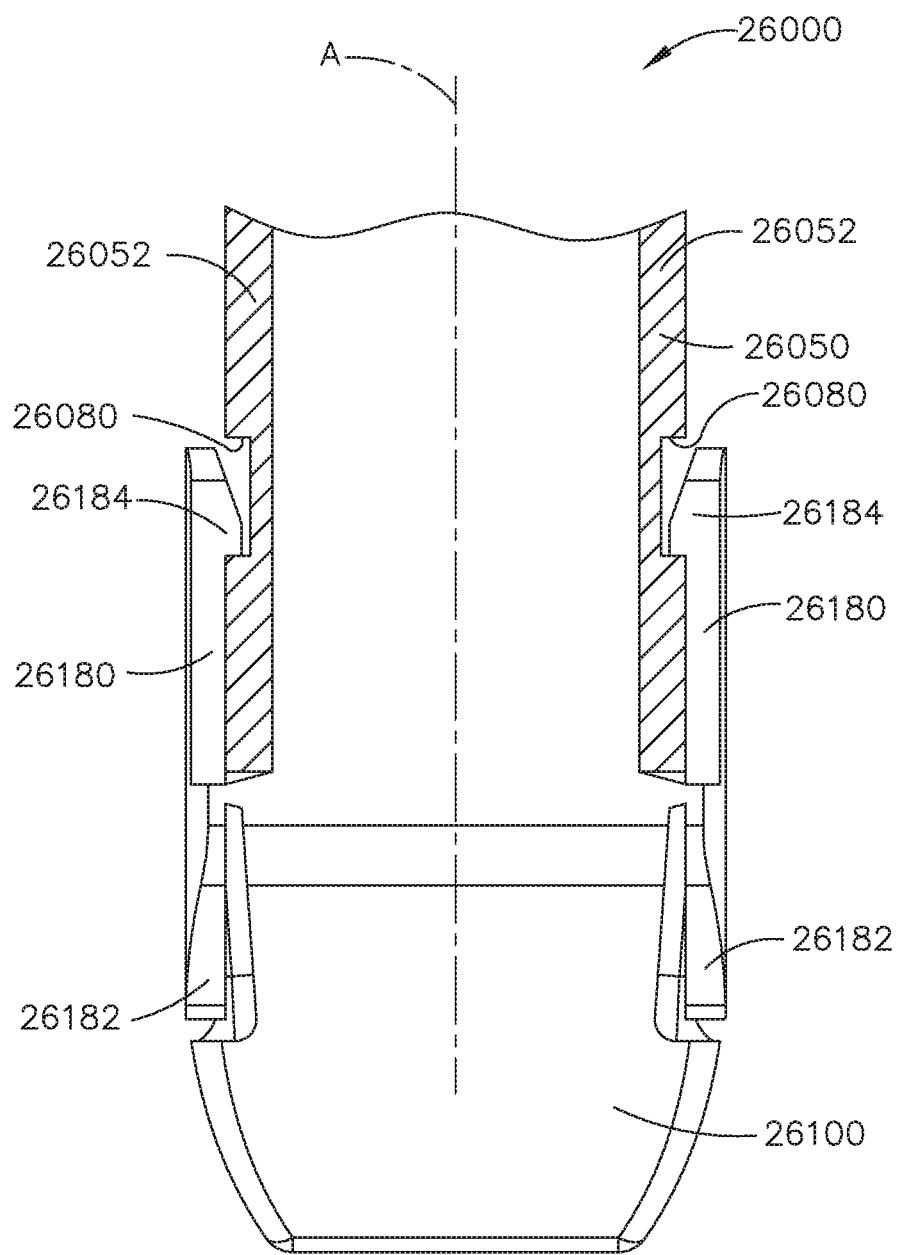

FIG. 169 is a plan partial cross-section view of the portion of the staple cartridge and the channel of FIG. 168, depicting the lateral latching arms of the staple cartridge engaged with lateral passages in sidewalls of the channel, according to various aspects of the present disclosure.

Figure 170:
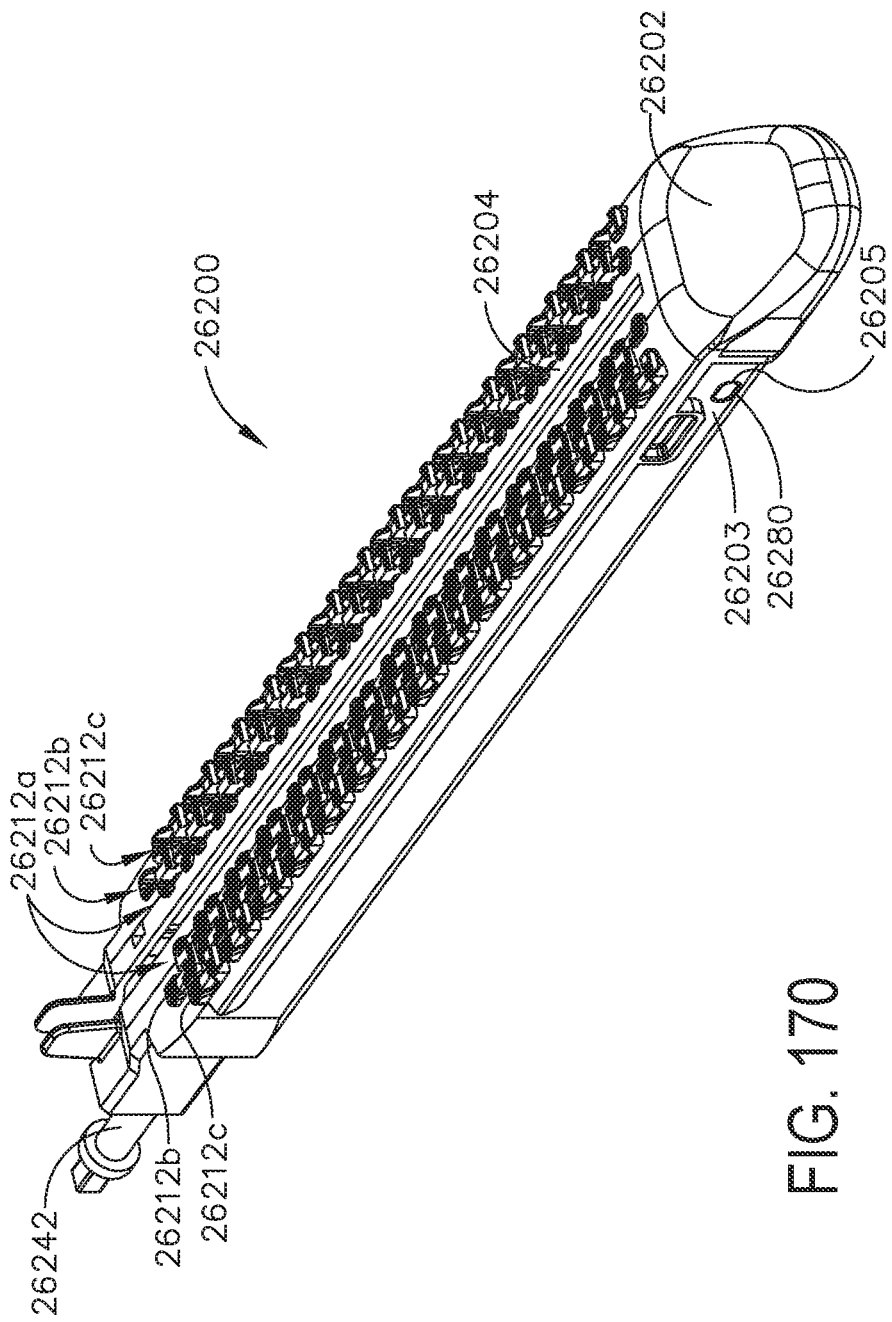

FIG. 170 is a perspective view of a staple cartridge and a rotary drive screw, according to various aspects of the present disclosure.

Figure 171:
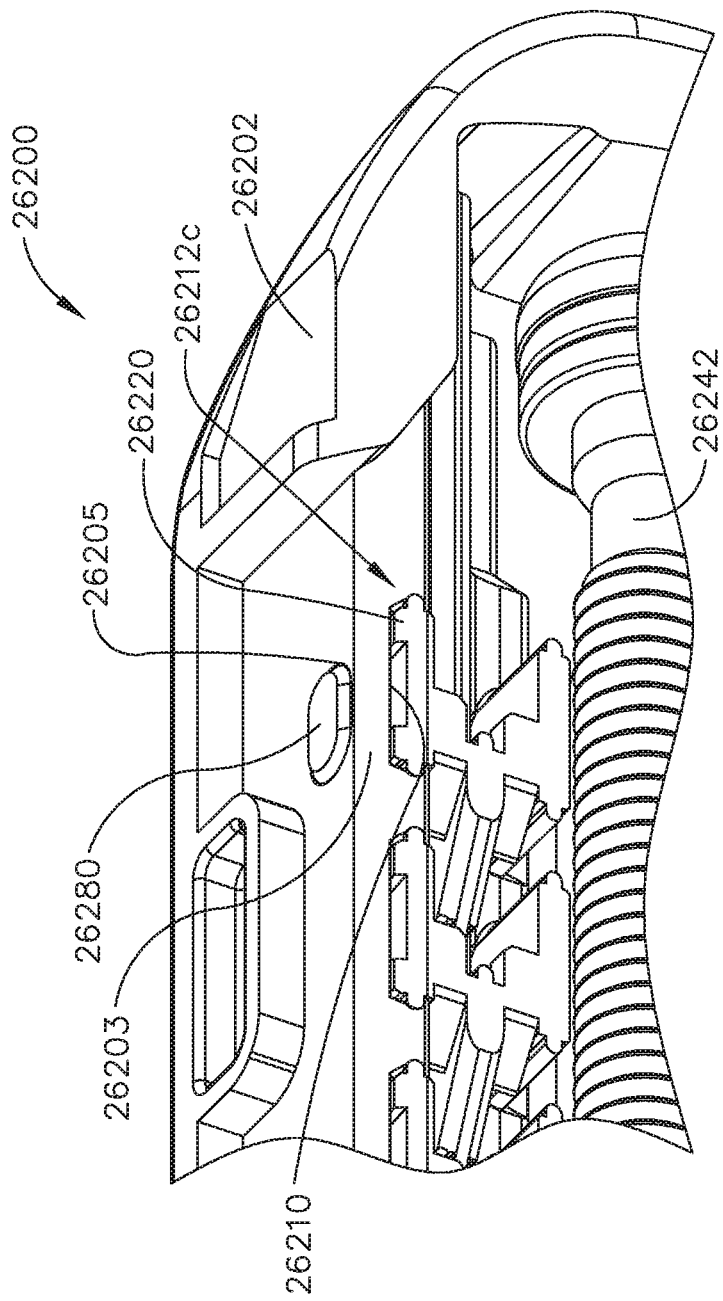

FIG. 171 is a perspective view of a distal portion of the staple cartridge and the rotary drive screw of FIG. 170, depicting a cartridge body and drivers with the drivers in their unfired positions in the cartridge body, according to various aspects of the present disclosure.

Figure 172:
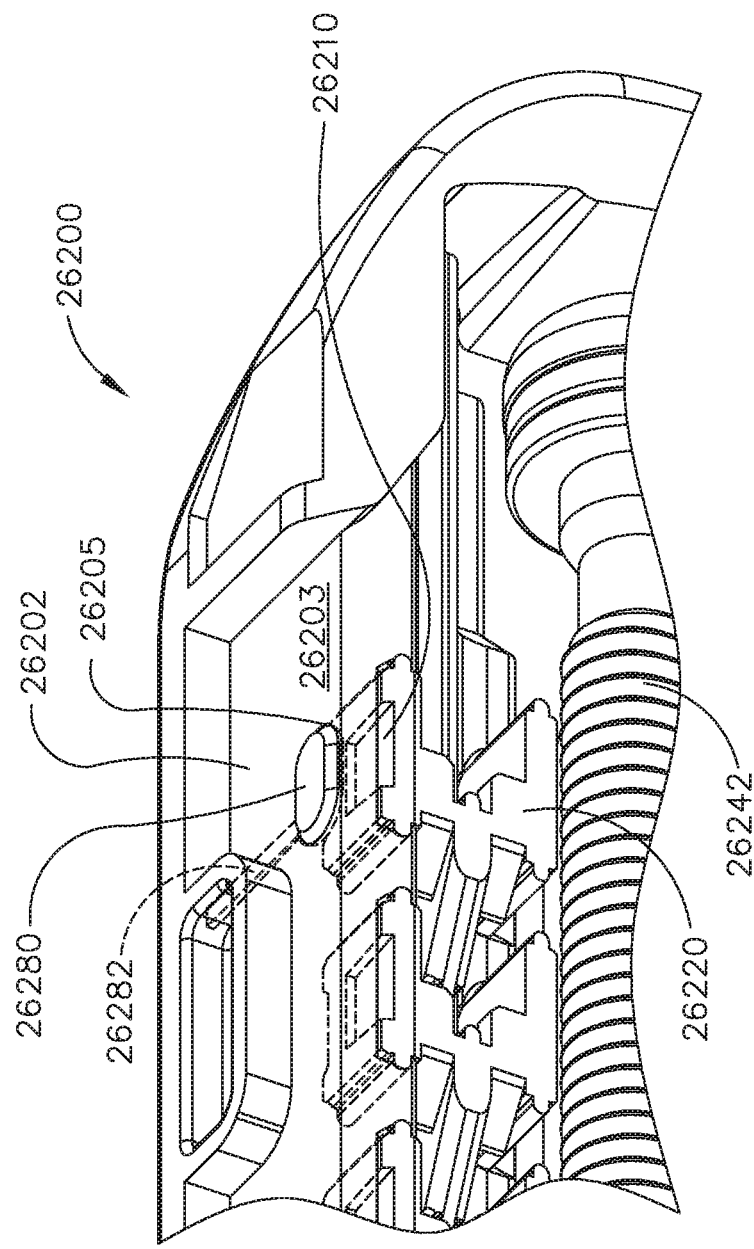

FIG. 172 is a perspective view of the distal portion of the staple cartridge and the rotary drive screw of FIG. 171 with the drivers in their unfired positions and depicting hidden internal features with dashed lines for illustrative purposes, according to various aspects of the present disclosure.

Figure 173:
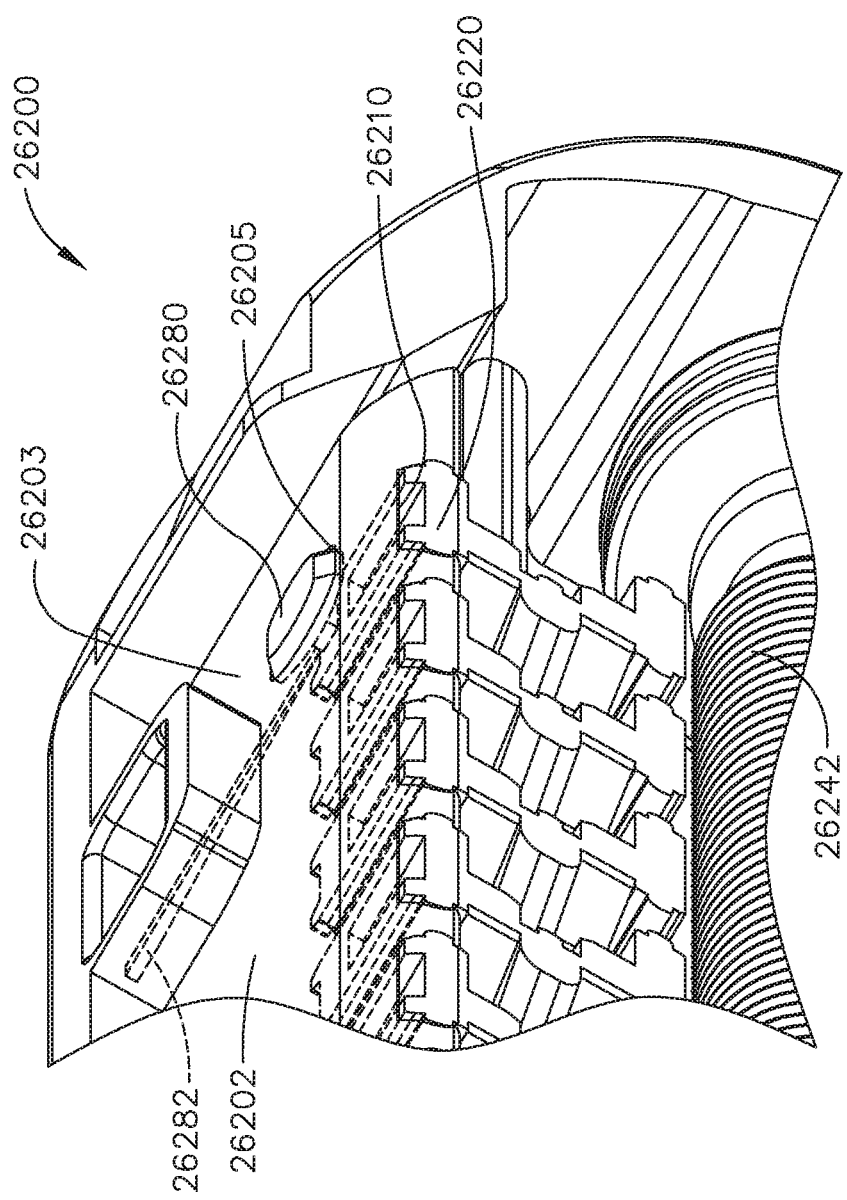

FIG. 173 is another perspective view of a distal portion of the staple cartridge and the rotary drive screw of FIG. 171 with the drivers in their unfired positions and depicting hidden internal features with dashed lines for illustrative purposes, according to various aspects of the present disclosure.

Figure 174:
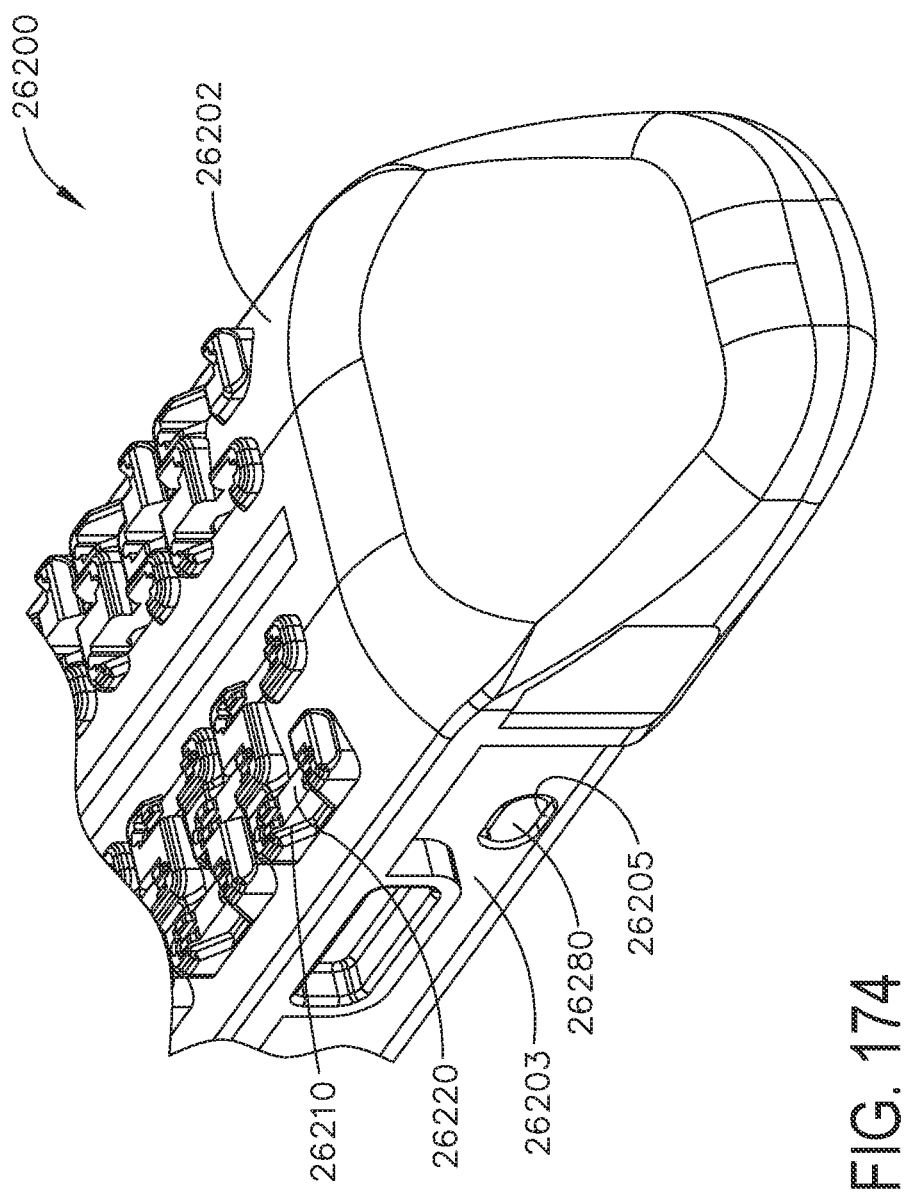

FIG. 174 is a perspective view of a distal portion of the staple cartridge of FIG. 170 with the drivers moved to their fired positions in the cartridge body, according to various aspects of the present disclosure.

Figure 175:
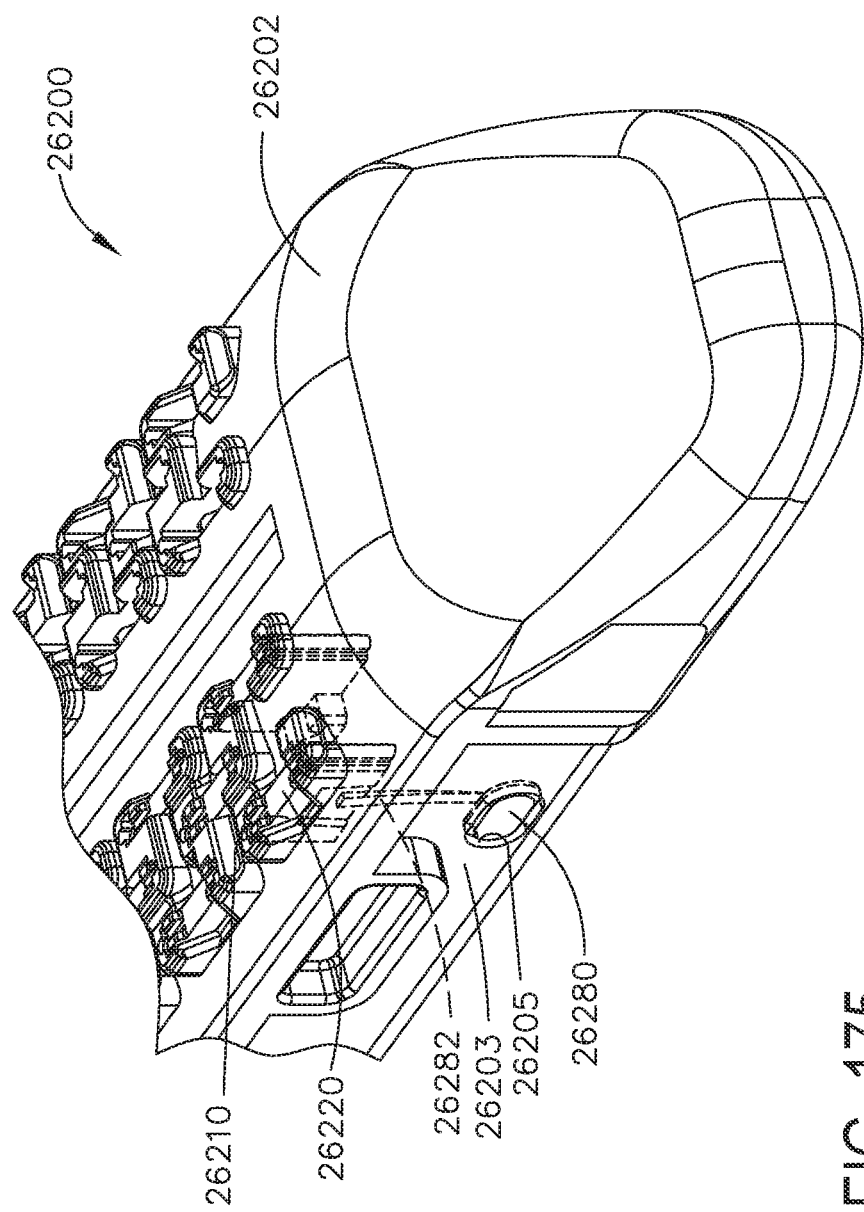

FIG. 175 is a perspective view of the distal portion of the staple cartridge of FIG. 174 with the drivers in their fired positions and depicting hidden internal features with dashed lines for illustrative purposes, according to various aspects of the present disclosure.

Figure 176:
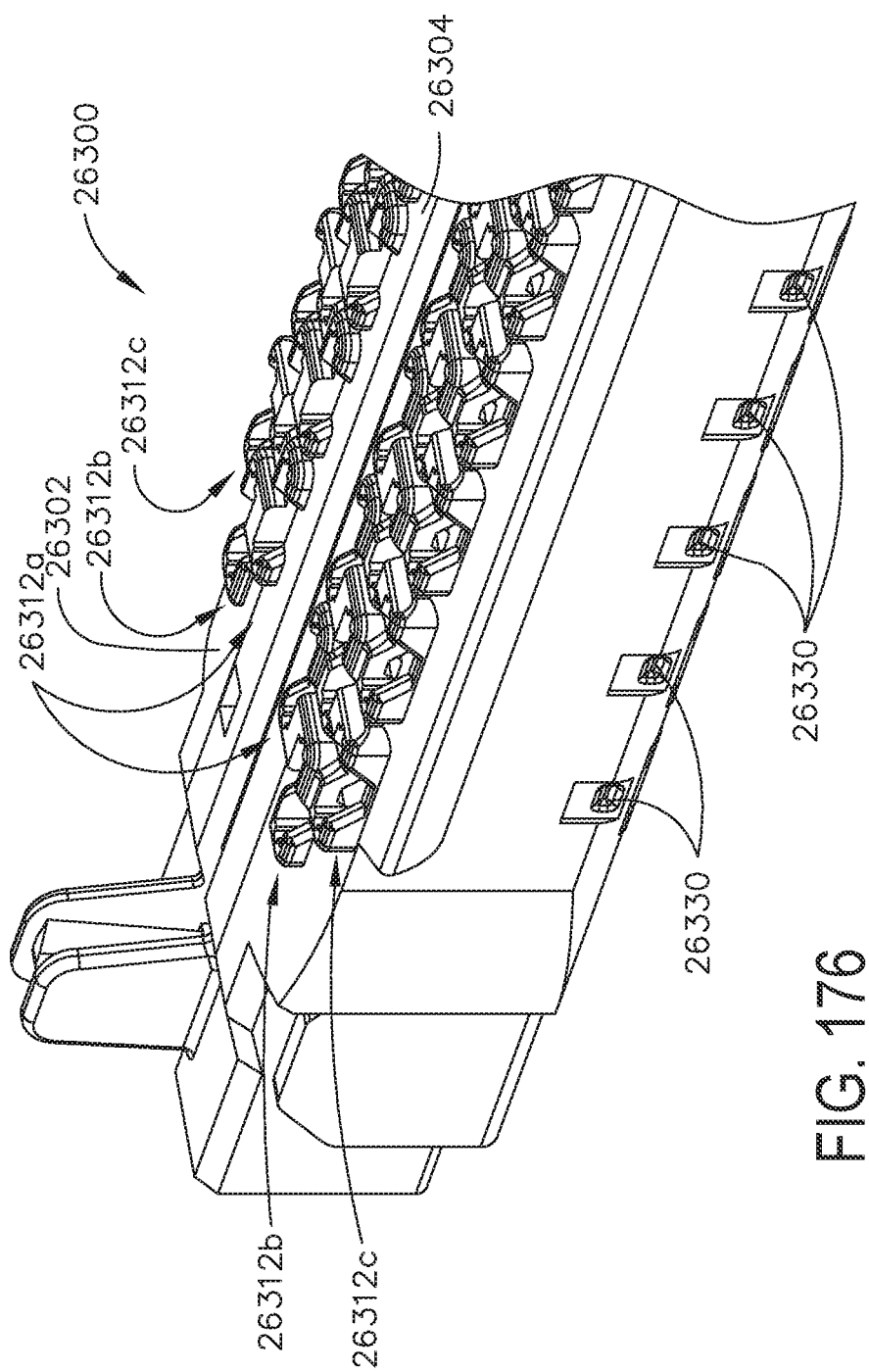

FIG. 176 is a perspective view of a proximal portion of a staple cartridge having a row of indentations, according to various aspects of the present disclosure.

Figure 177:
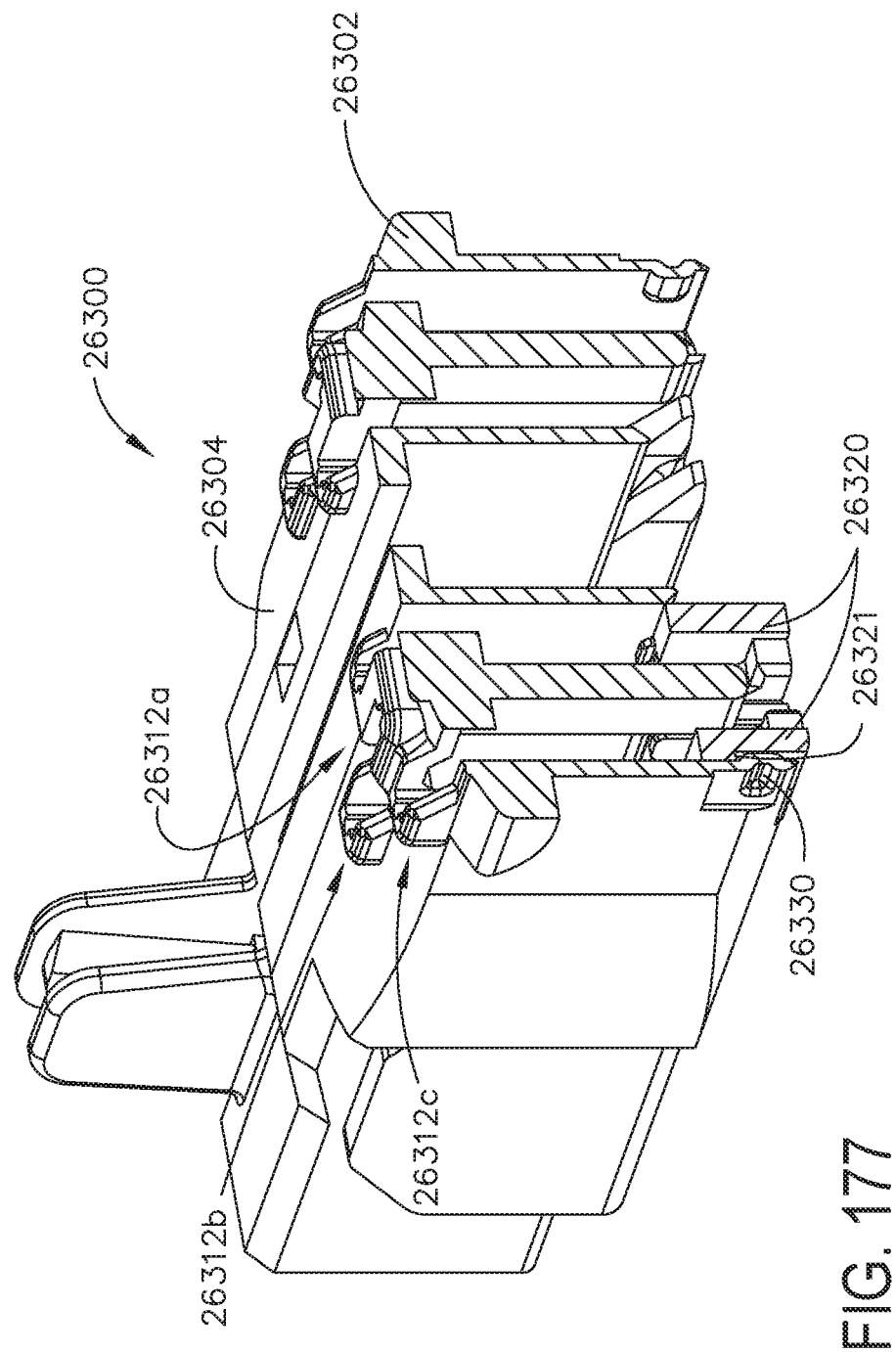

FIG. 177 is a perspective cross-section view of the staple cartridge of FIG. 176, depicting an indentation in the cartridge body engaged with a lip on a sidewall of a driver, according to various aspects of the present disclosure.

Figure 178:
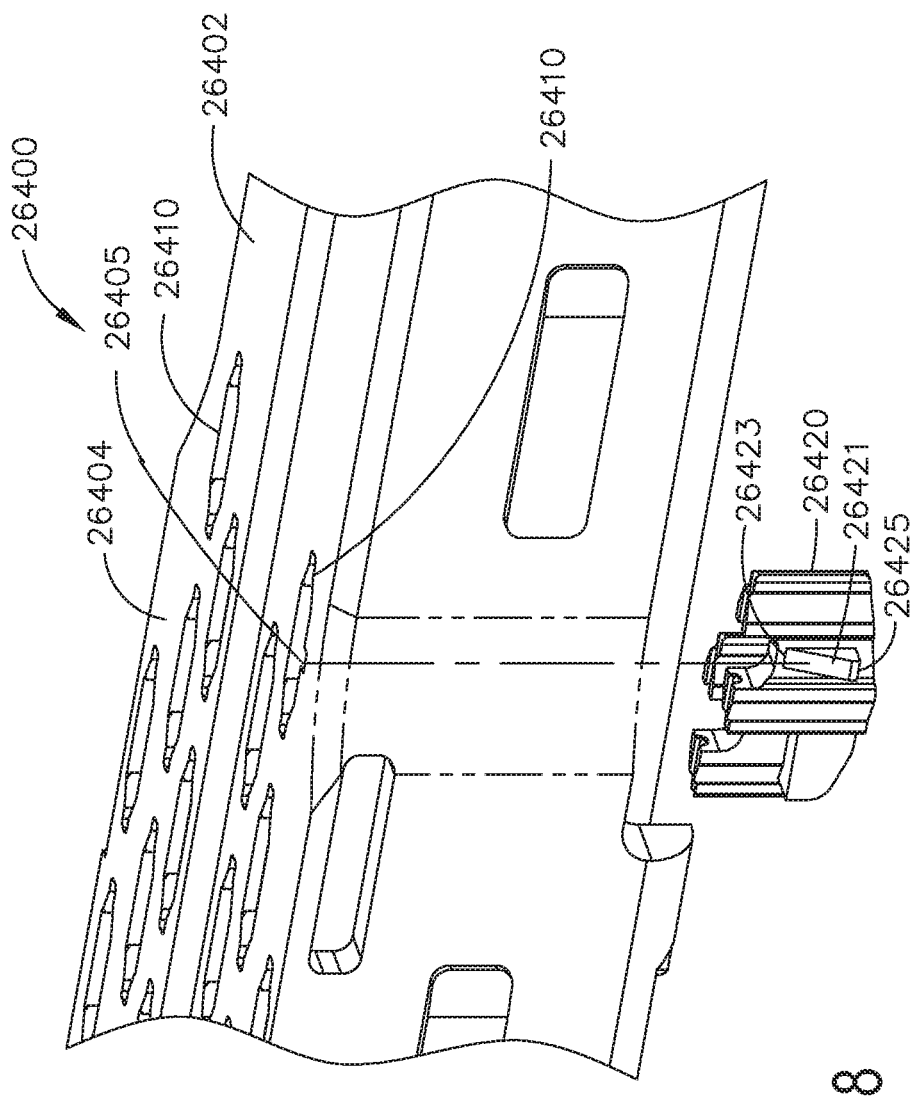

FIG. 178 is a perspective exploded view of a portion of a cartridge body and a driver having interference features for engaging the cartridge body, according to various aspects of the present disclosure.

Figure 179:
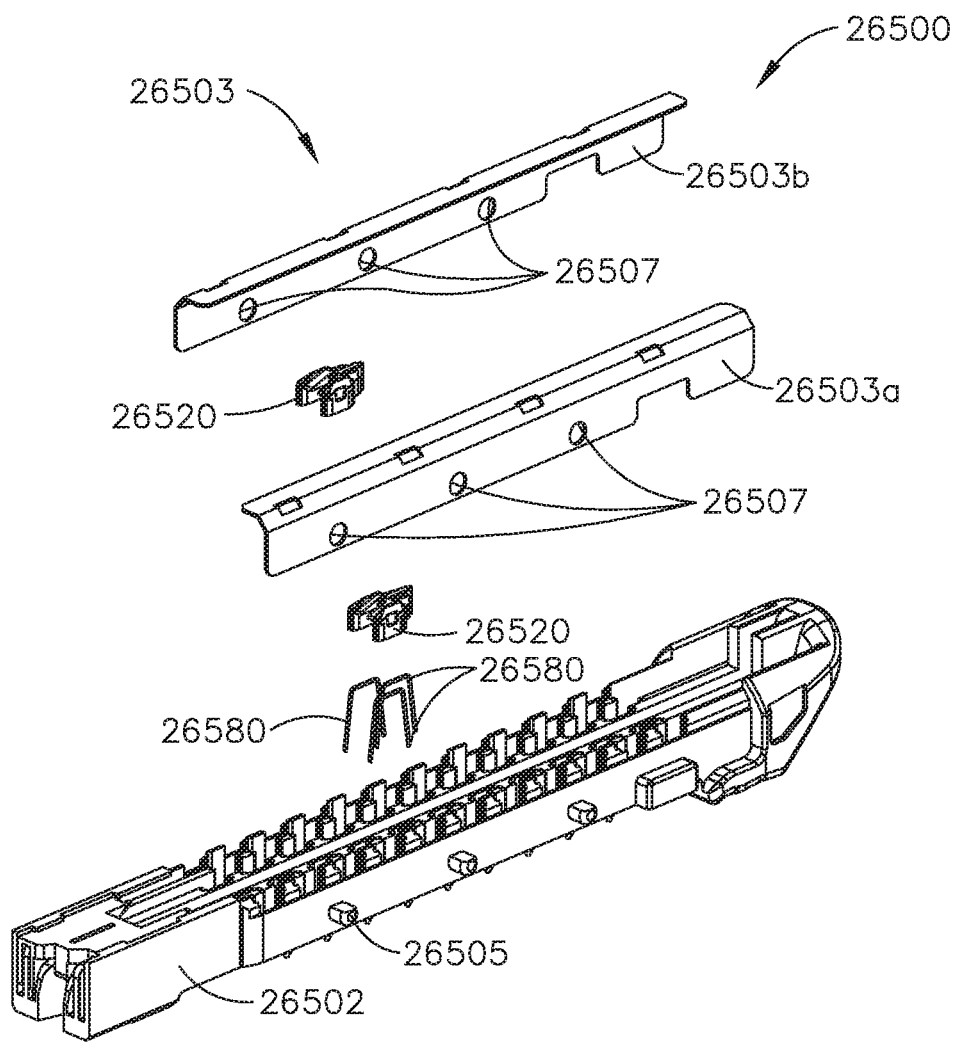

FIG. 179 is a perspective exploded view of a staple cartridge, according to various aspects of the present disclosure.

Figure 180:
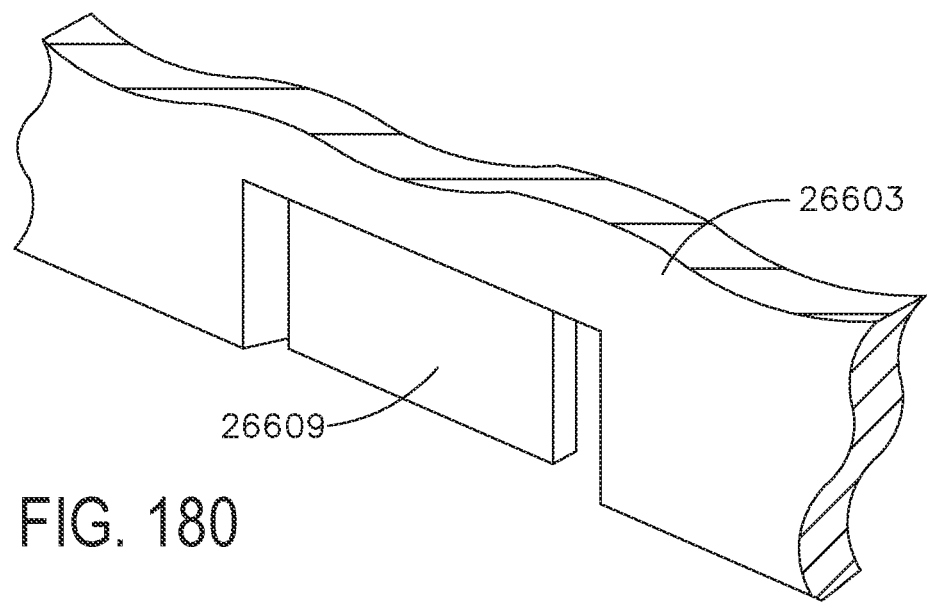

FIG. 180 is perspective view of a portion of a cartridge frame and arm thereof in an unformed configuration, according to various aspects of the present disclosure.

Figure 181:
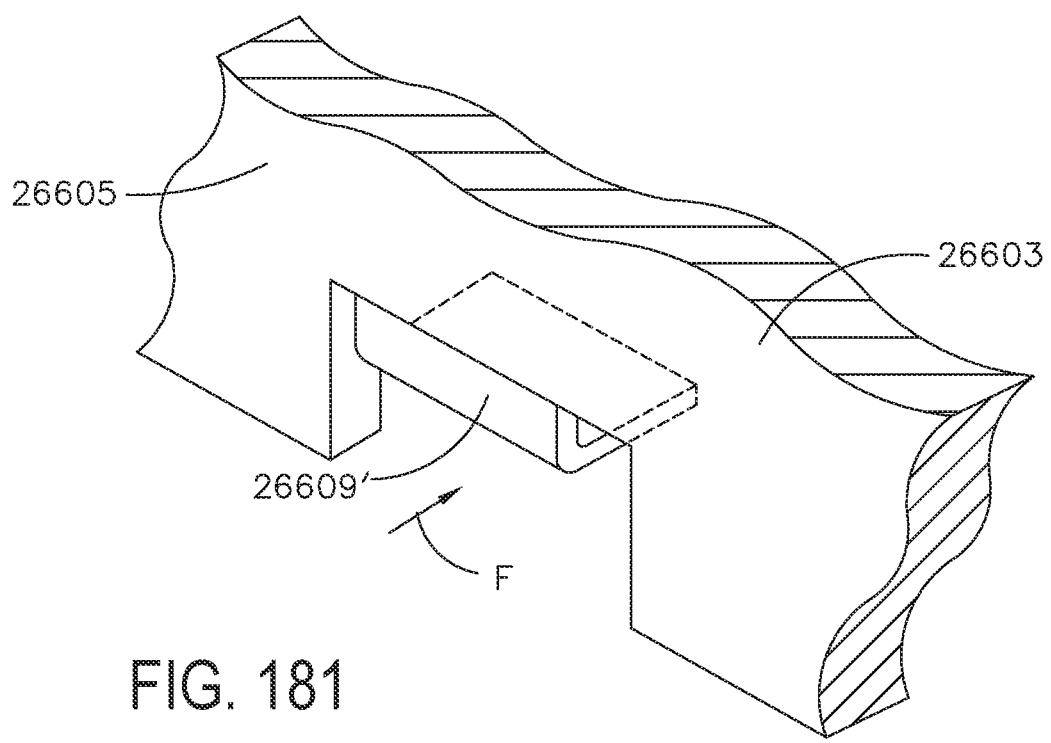

FIG. 181 is a perspective view of the portion of the cartridge frame and the arm of FIG. 180, depicting the arm in a formed configuration, according to various aspects of the present disclosure.

FIG. 182 is an elevation cross-section view of a cartridge body and a cartridge frame depicting a heat staked retention feature therebetween, according to various aspects of the present disclosure.

FIG. 183 is an elevation cross-section view of a cartridge body and a cartridge frame during a heat staking process, according to various aspects of the present disclosure.

Figure 184:
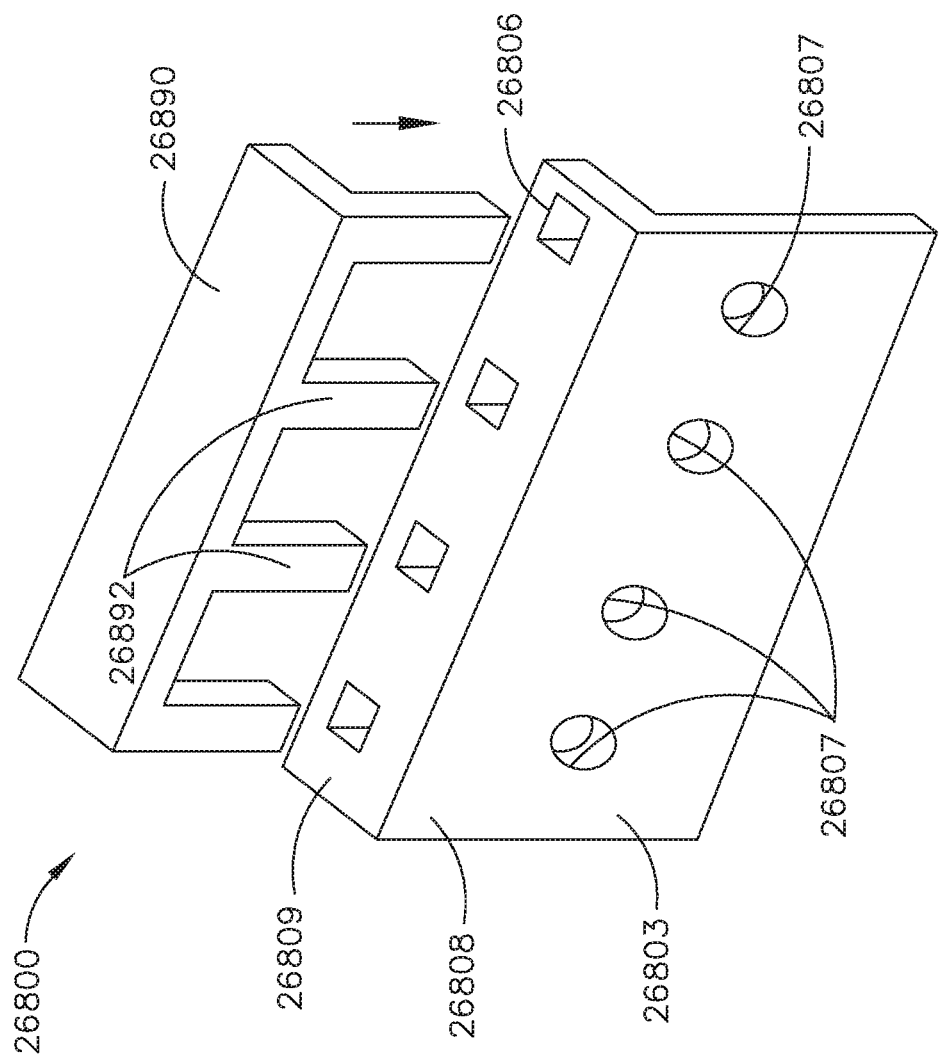

FIG. 184 is a perspective view of a cartridge frame and an insert support for use during the heat staking process of FIG. 183, according to various aspects of the present disclosure.

Figure 185:
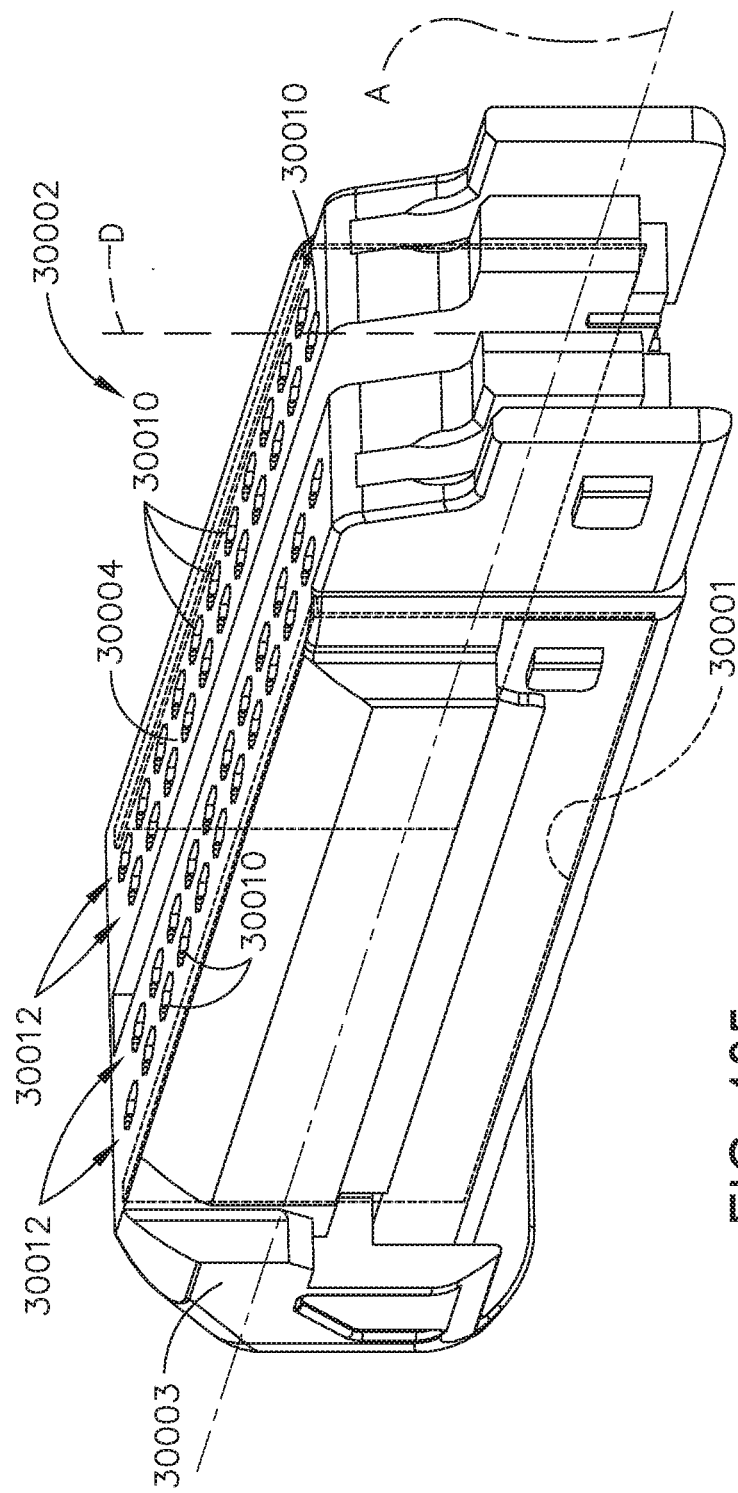

FIG. 185 is a perspective view of a composite cartridge body including a metal pan and plastic composite material, depicting the hidden metal pan with dashed lines for illustrative purposes, according to various aspects of the present disclosure.

Figure 186:
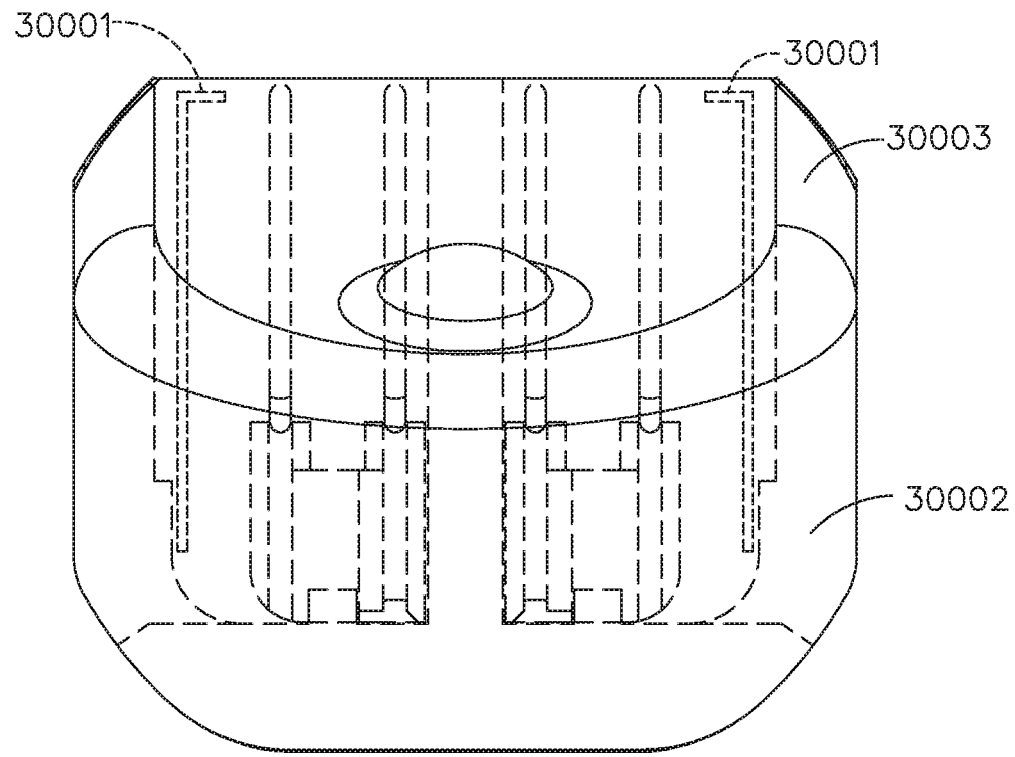

FIG. 186 is an elevation view of the composite cartridge body of FIG. 185 depicting the hidden metal pan with dashed lines for illustrative purposes, according to various aspects of the present disclosure.

Figure 187:
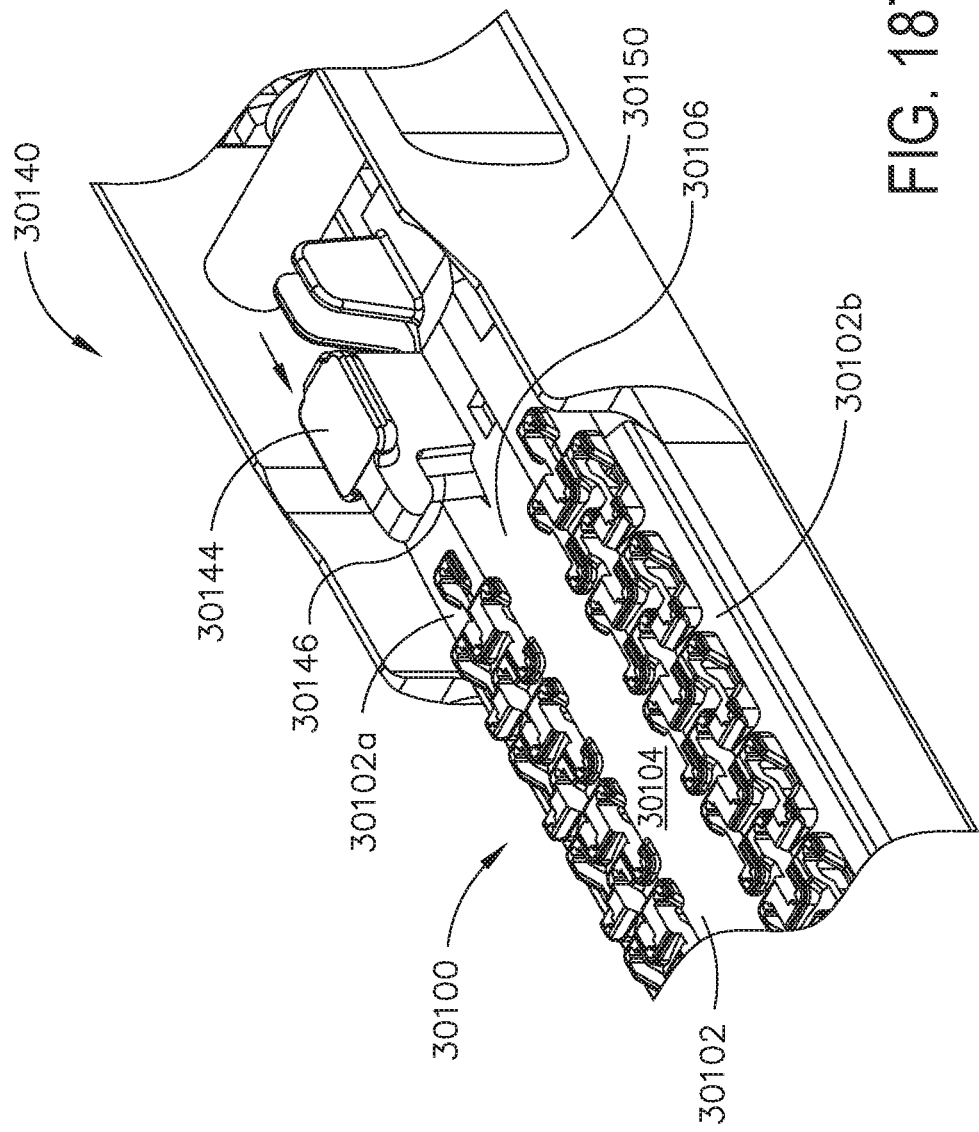

FIG. 187 is a perspective view of a portion of a surgical end effector including a staple cartridge positioned therein, according to various aspects of the present disclosure.

Figure 188:
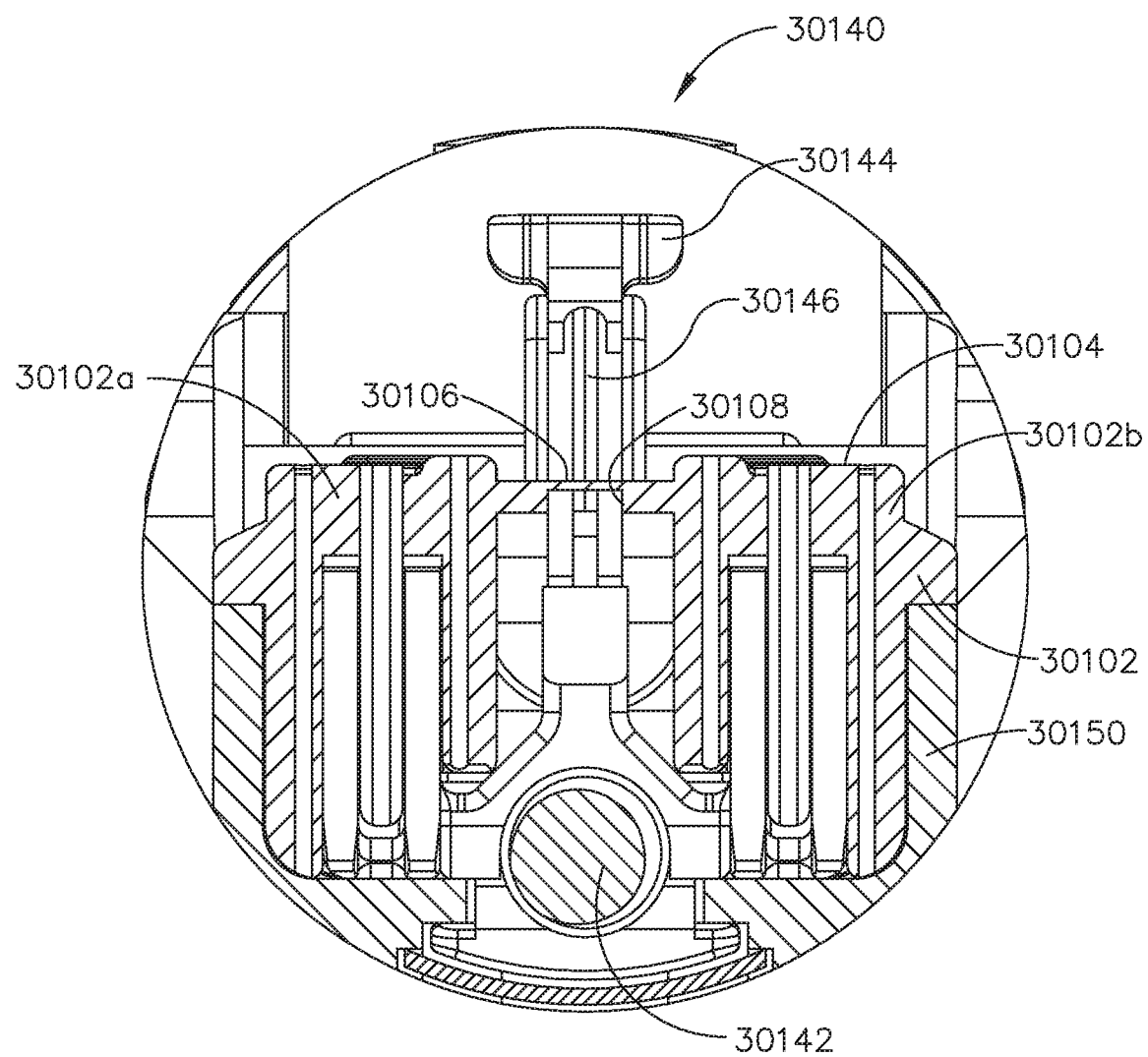

FIG. 188 is an elevation cross-section view of the portion of the surgical end effector and staple cartridge of FIG. 187, according to various aspects of the present disclosure.

Figure 189:
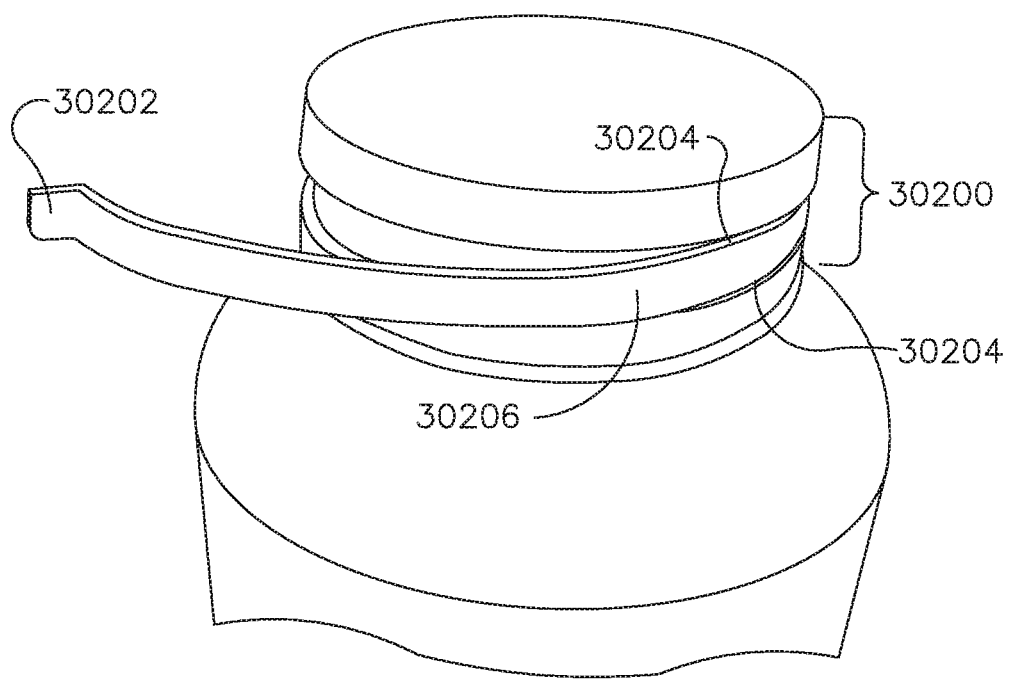

FIG. 189 is a perspective view of a tamper-evident tear-away lid, according to various aspects of the present disclosure.

Figure 190:
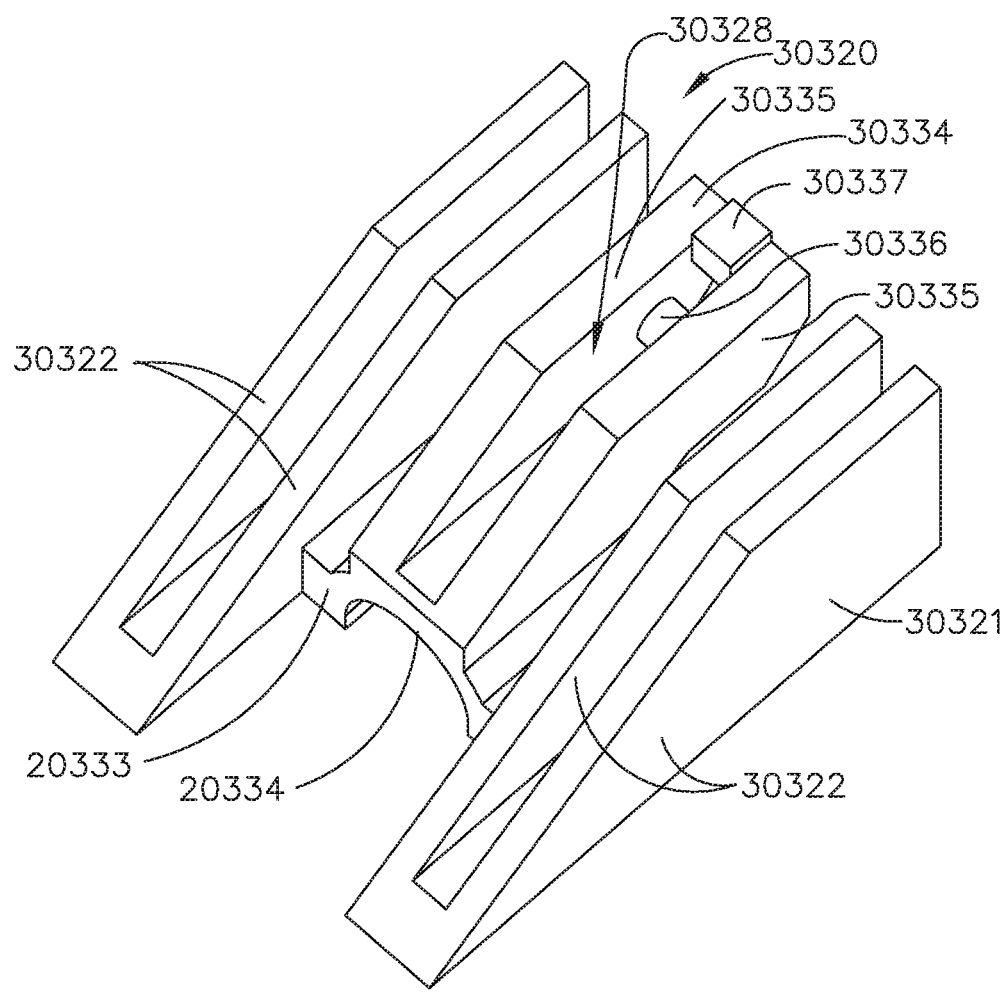

FIG. 190 is a perspective view of a body of a sled assembly, according to various aspects of the present disclosure.

Figure 191:
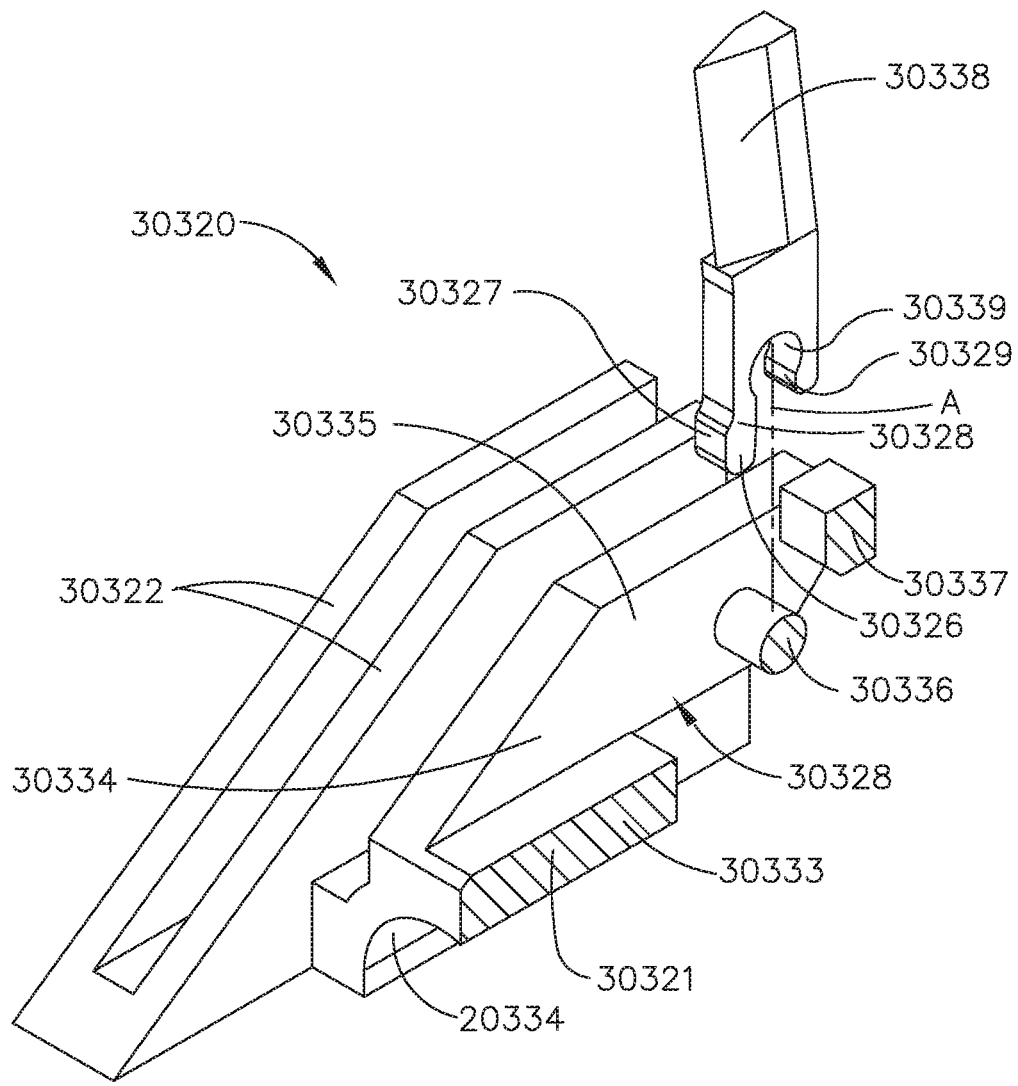

FIG. 191 is a perspective, exploded cross-section view of the sled assembly of FIG. 190 including the body and a knife, according to various aspects of the present disclosure.

Figure 192:
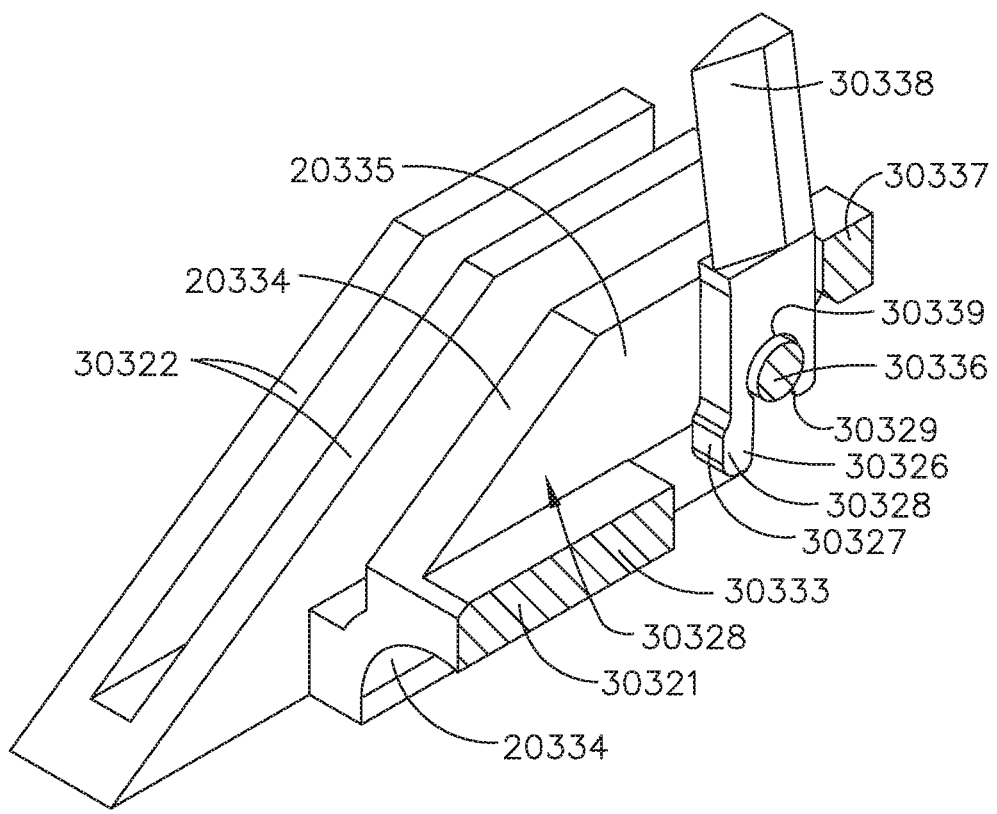

FIG. 192 is a perspective cross-section view of the sled assembly of FIG. 190, according to various aspects of the present disclosure.

Figure 193:
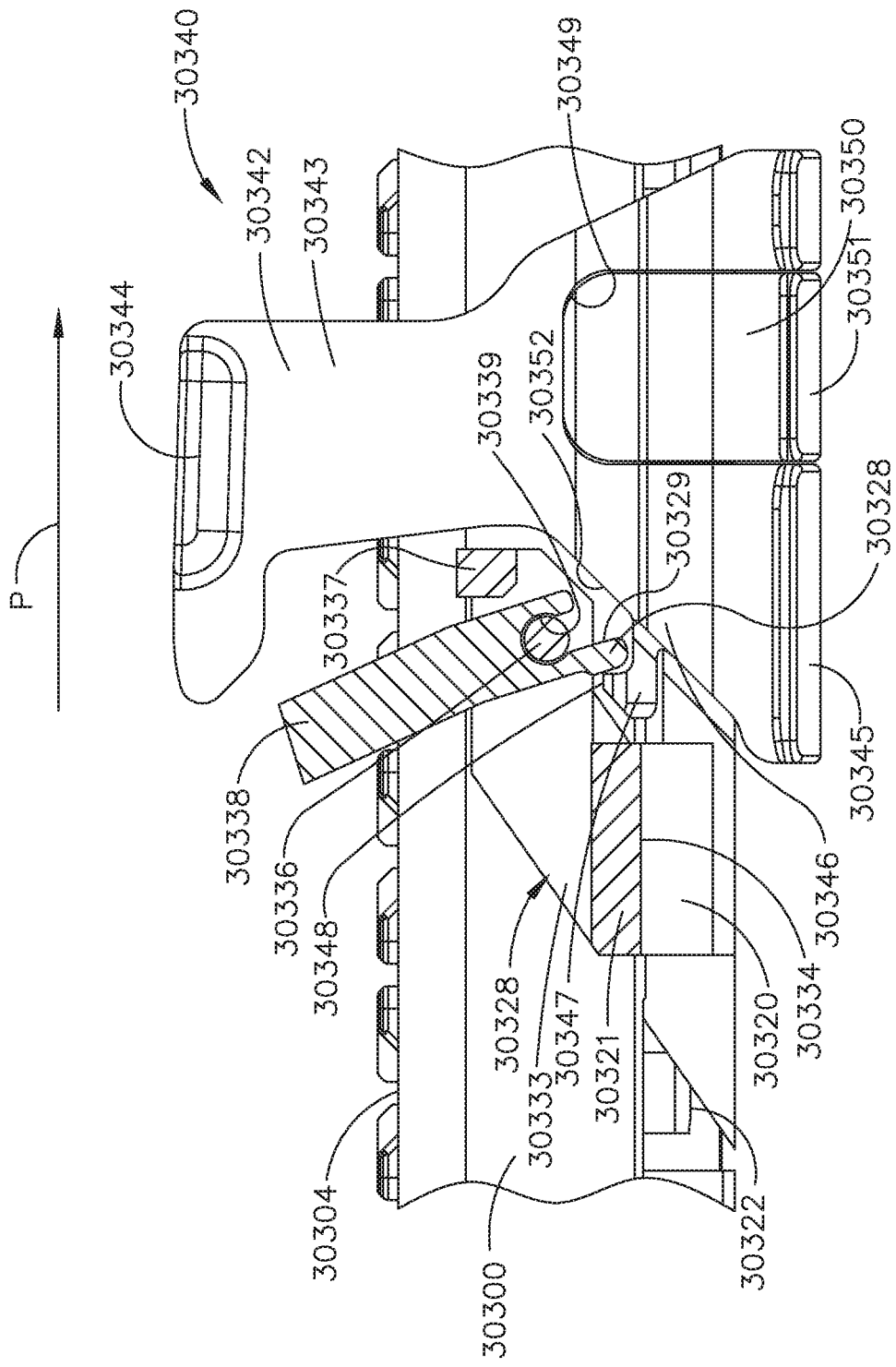

FIG. 193 is an elevation partial cross-section view of an end effector with portions removed for illustrative purposes, depicting a firing member, a cartridge body, and the sled assembly of FIG. 190, according to various aspects of the present disclosure.

Figure 194:
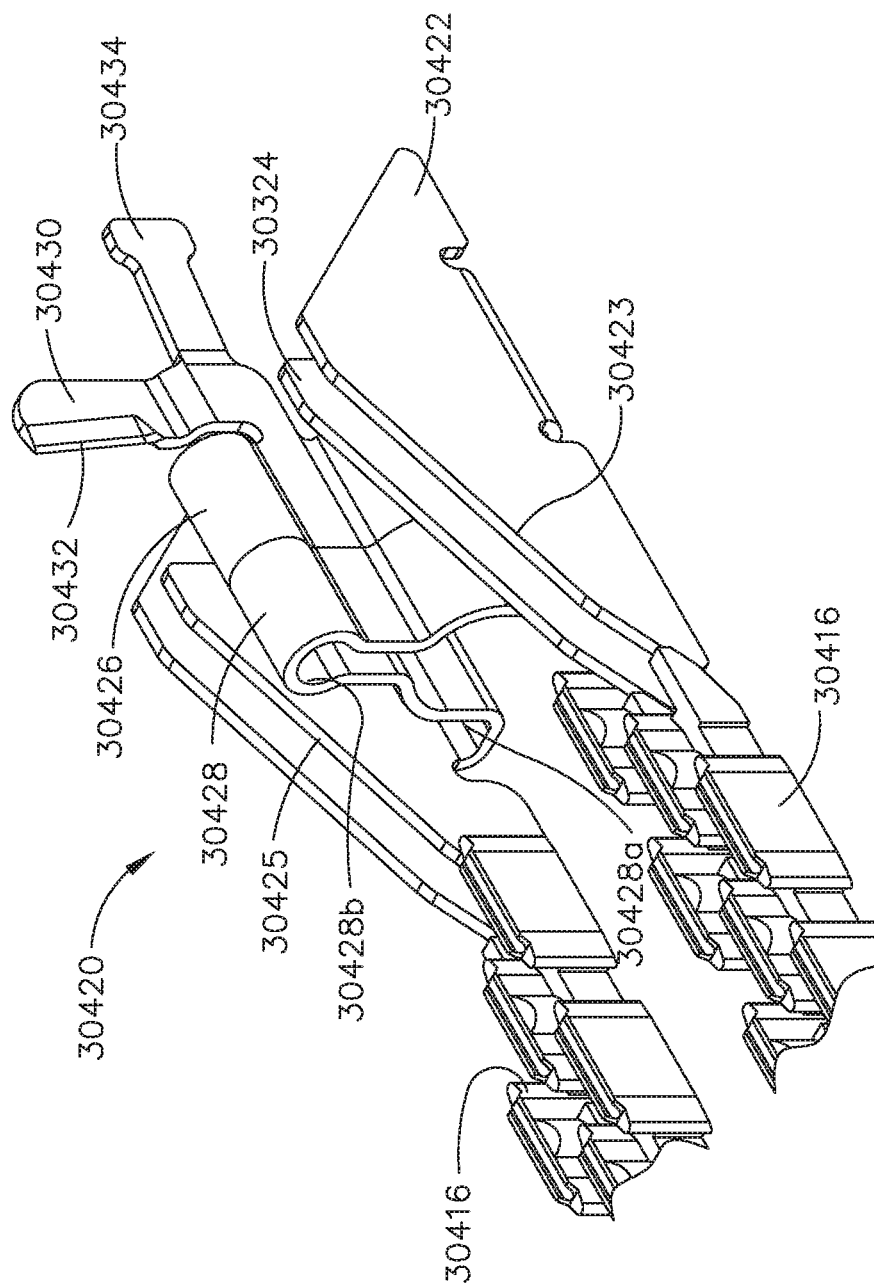

FIG. 194 is a perspective view of a sled assembly aligned with rows of drivers, according to various aspects of the present disclosure.

Figure 195:
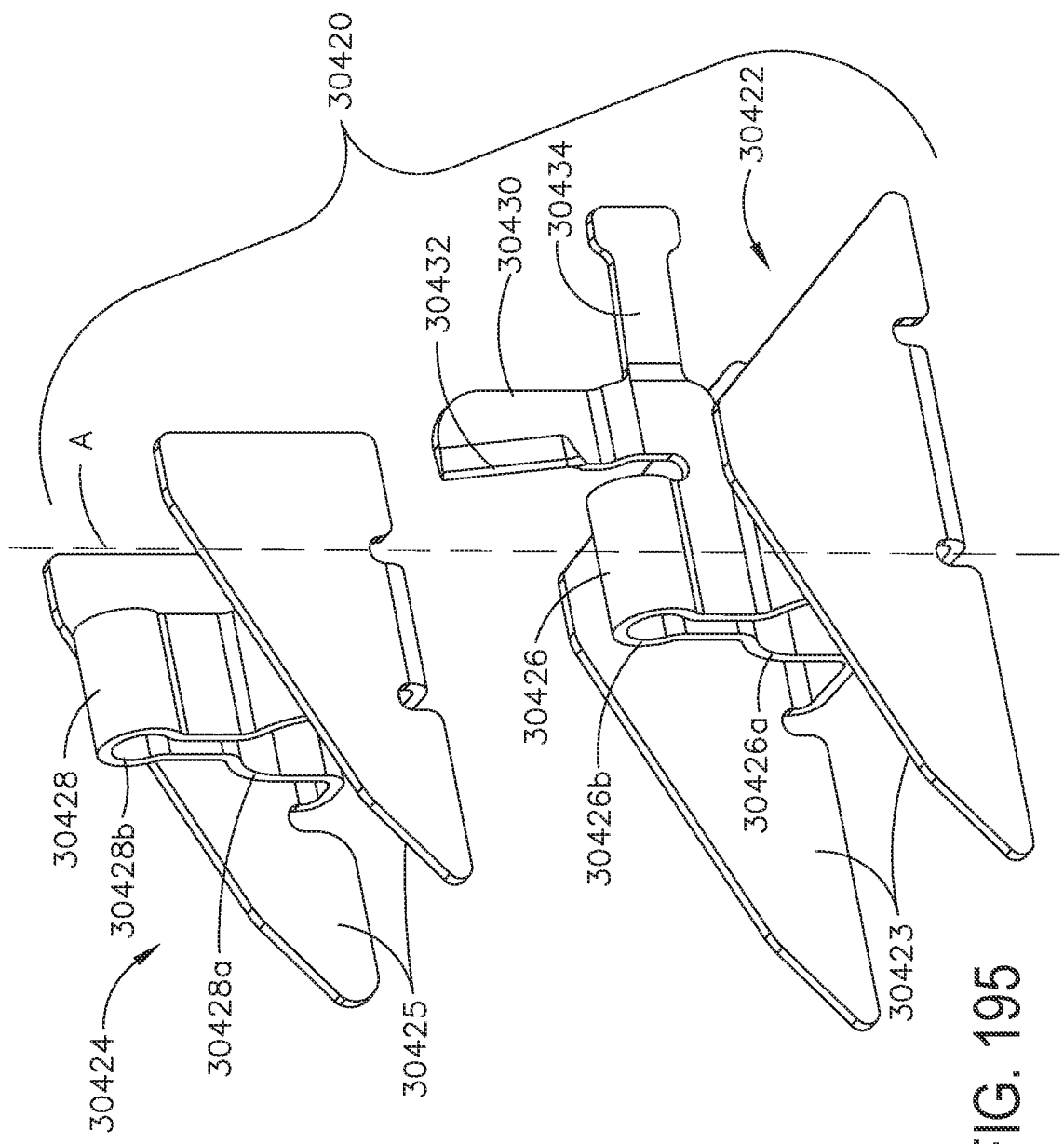

FIG. 195 is a perspective exploded view of the sled assembly of FIG. 194, according to various aspects of the present disclosure.

Figure 196:
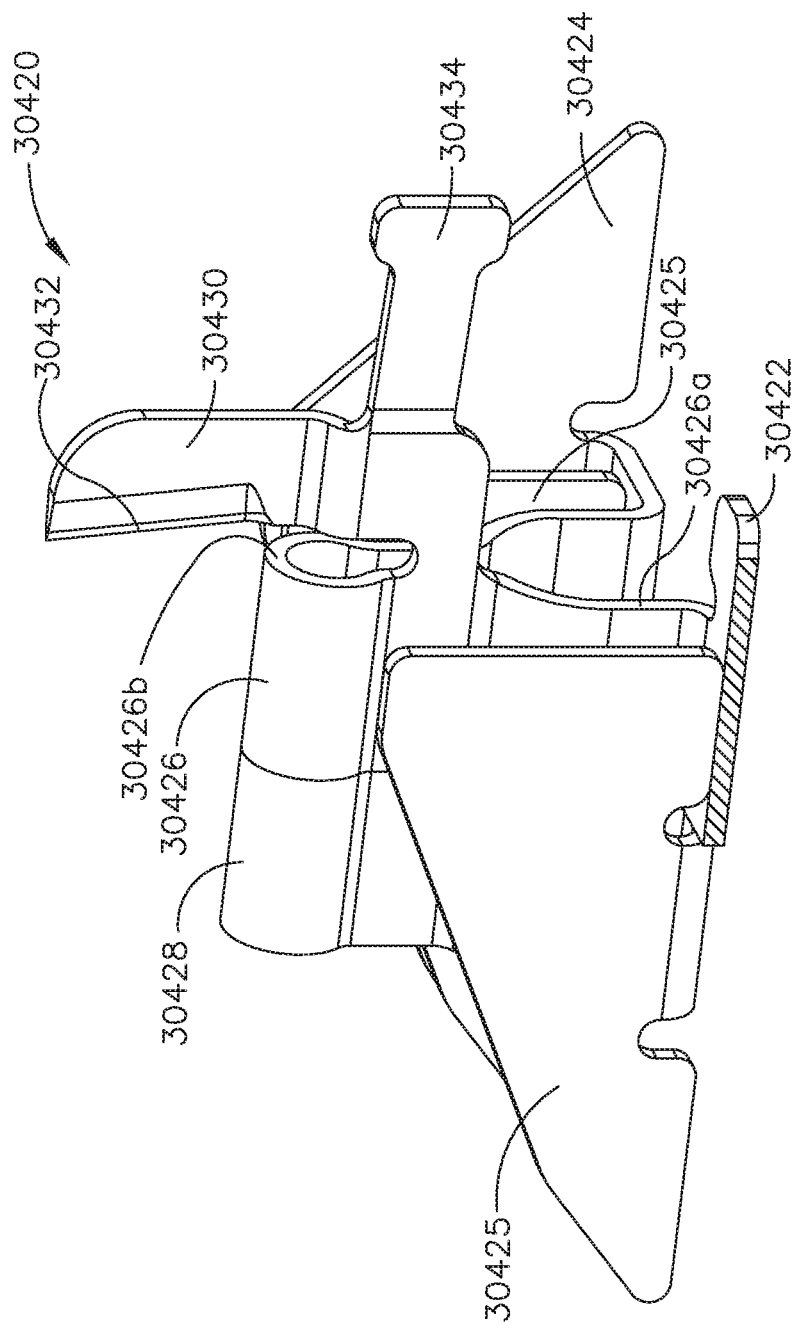

FIG. 196 is a perspective partial cross-section view of the sled assembly of FIG. 194, according to various aspects of the present disclosure.

Figure 197:
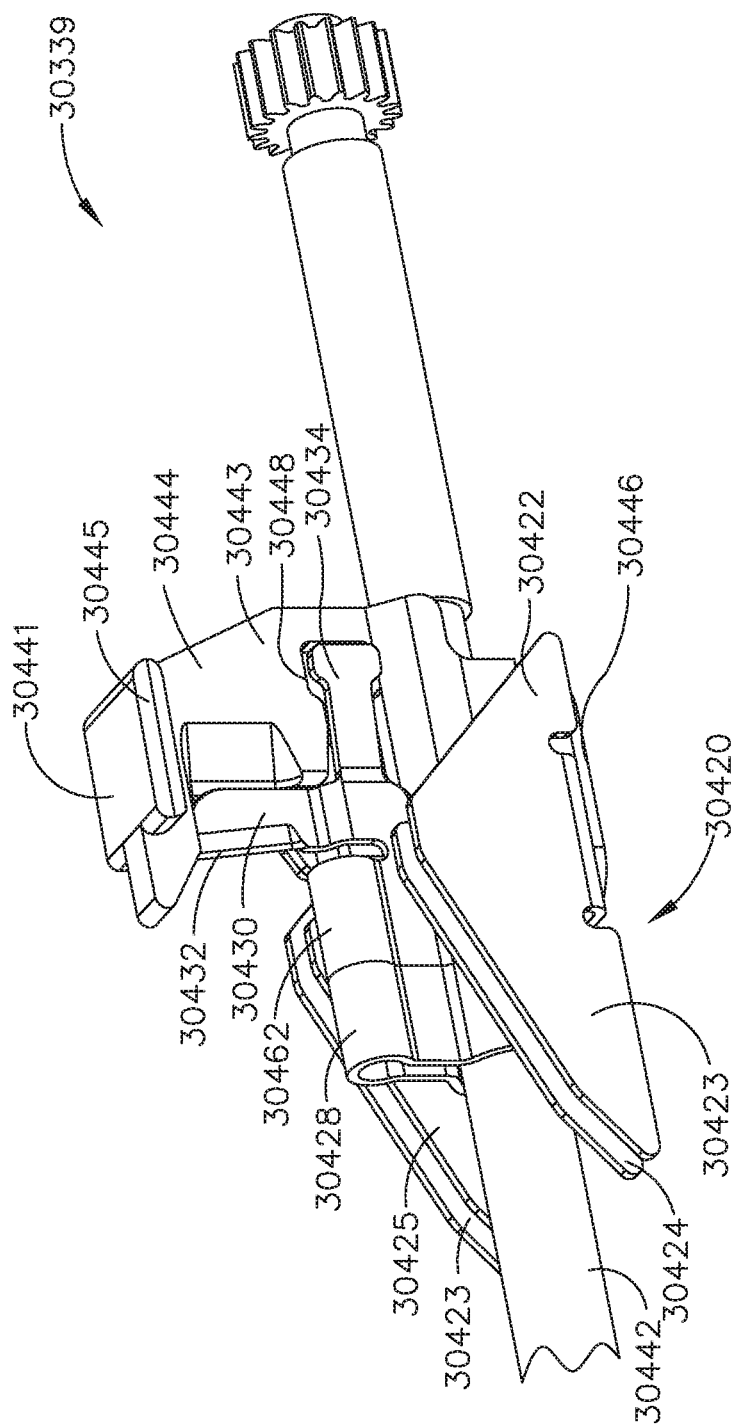

FIG. 197 is a perspective view of the sled assembly of FIG. 194 engaged with a firing system including a rotary drive screw and a firing member threadably coupled to the rotary drive screw, according to various aspects of the present disclosure.

Figure 198:
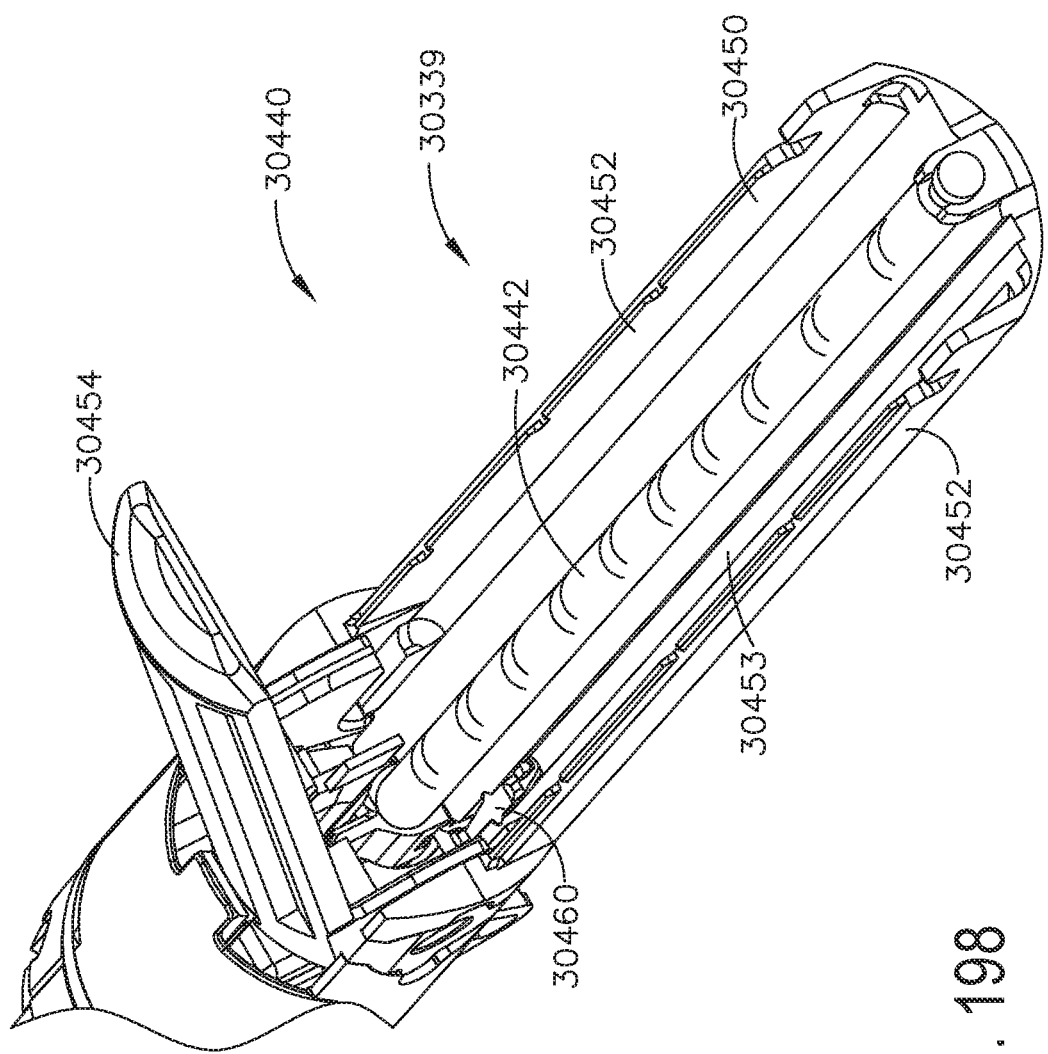

FIG. 198 is a perspective view of an end effector including a lockout in a locked configuration, according to various aspects of the present disclosure.

Figure 199:
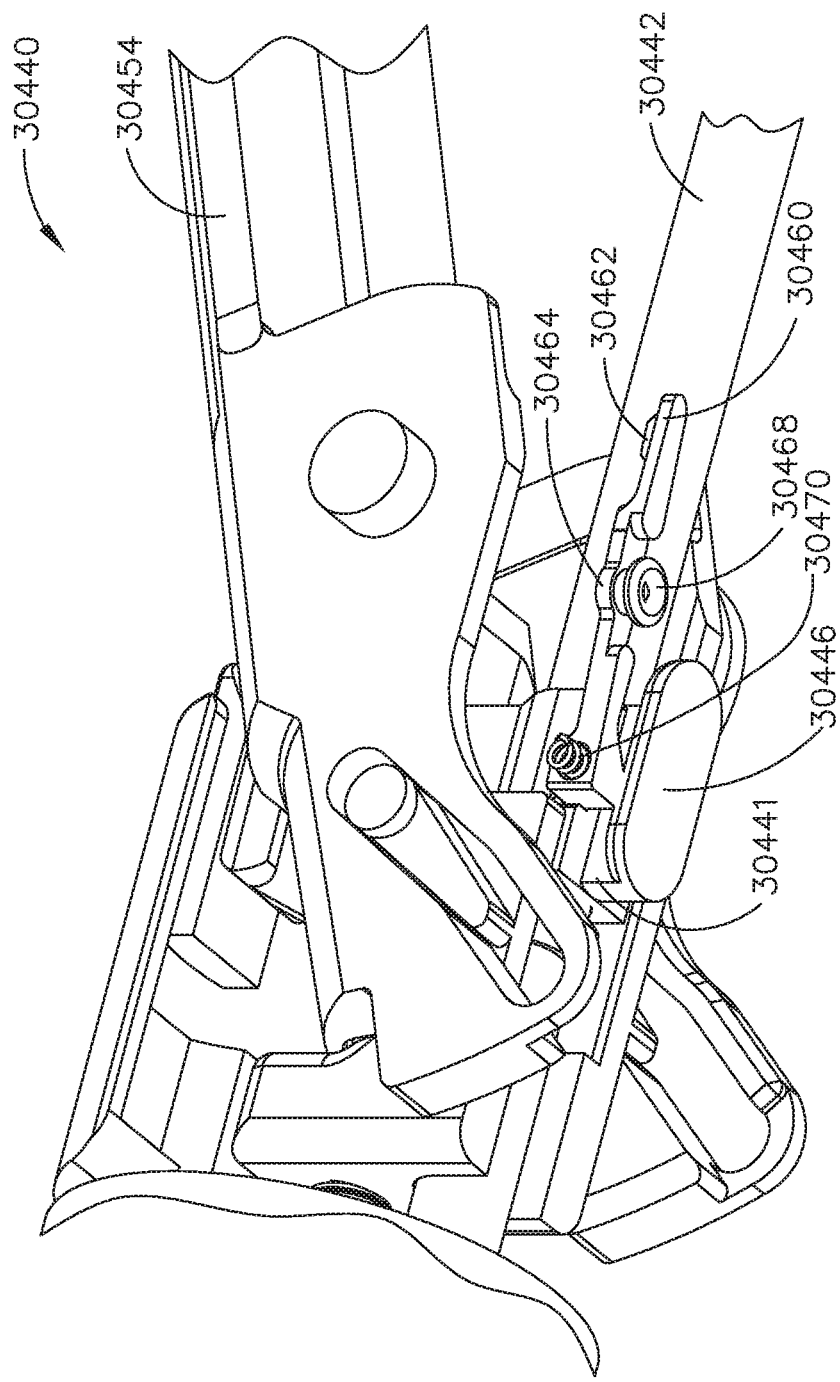

FIG. 199 is a perspective view of a portion of the end effector of FIG. 198 with parts removed for illustrative purposes, depicting the lockout in the locked configuration, according to various aspects of the present disclosure.

Figure 200:
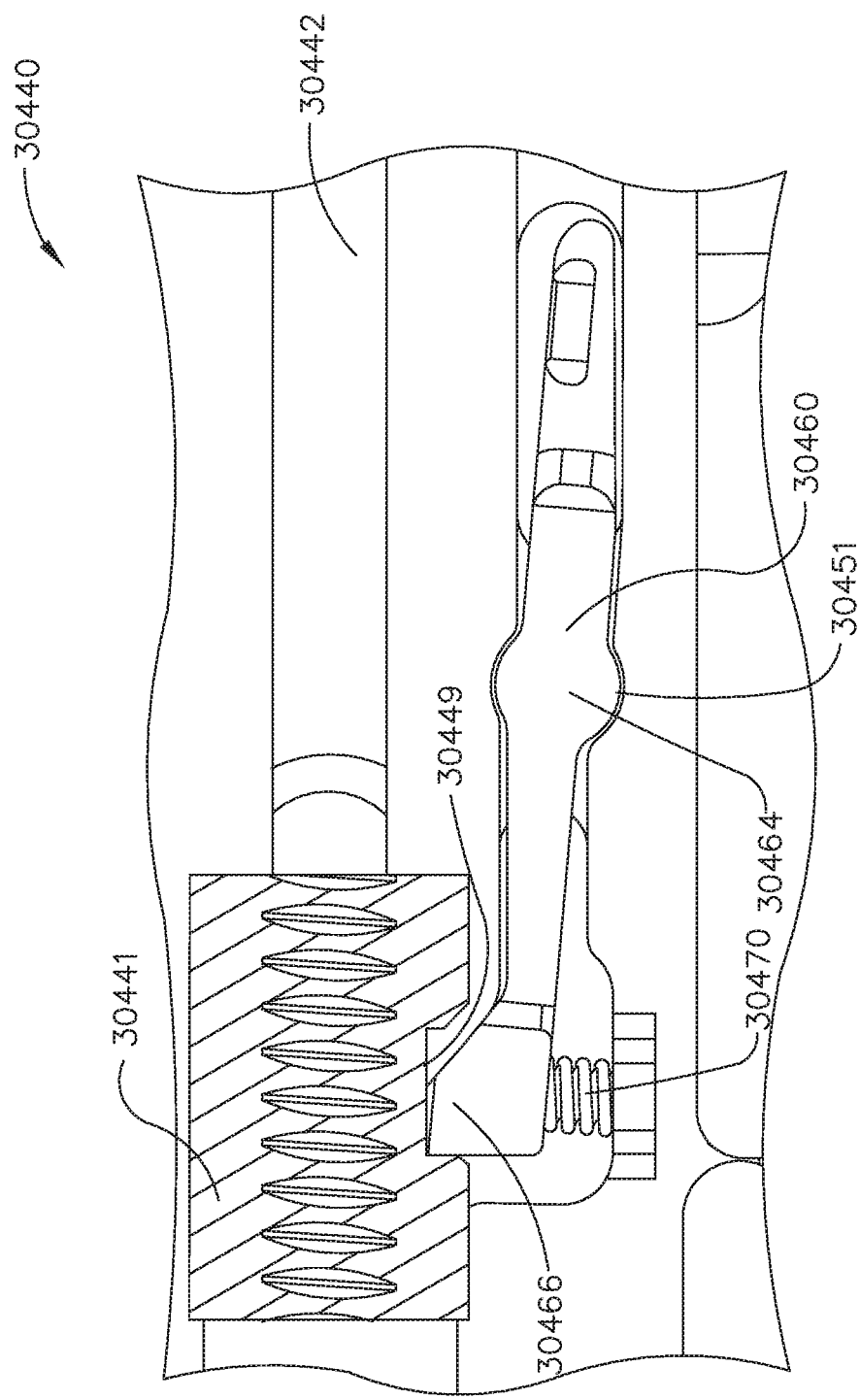

FIG. 200 is an elevation cross-section view of a portion of the end effector of FIG. 198, depicting the lockout in the locked configuration, according to various aspects of the present disclosure.

Figure 201:
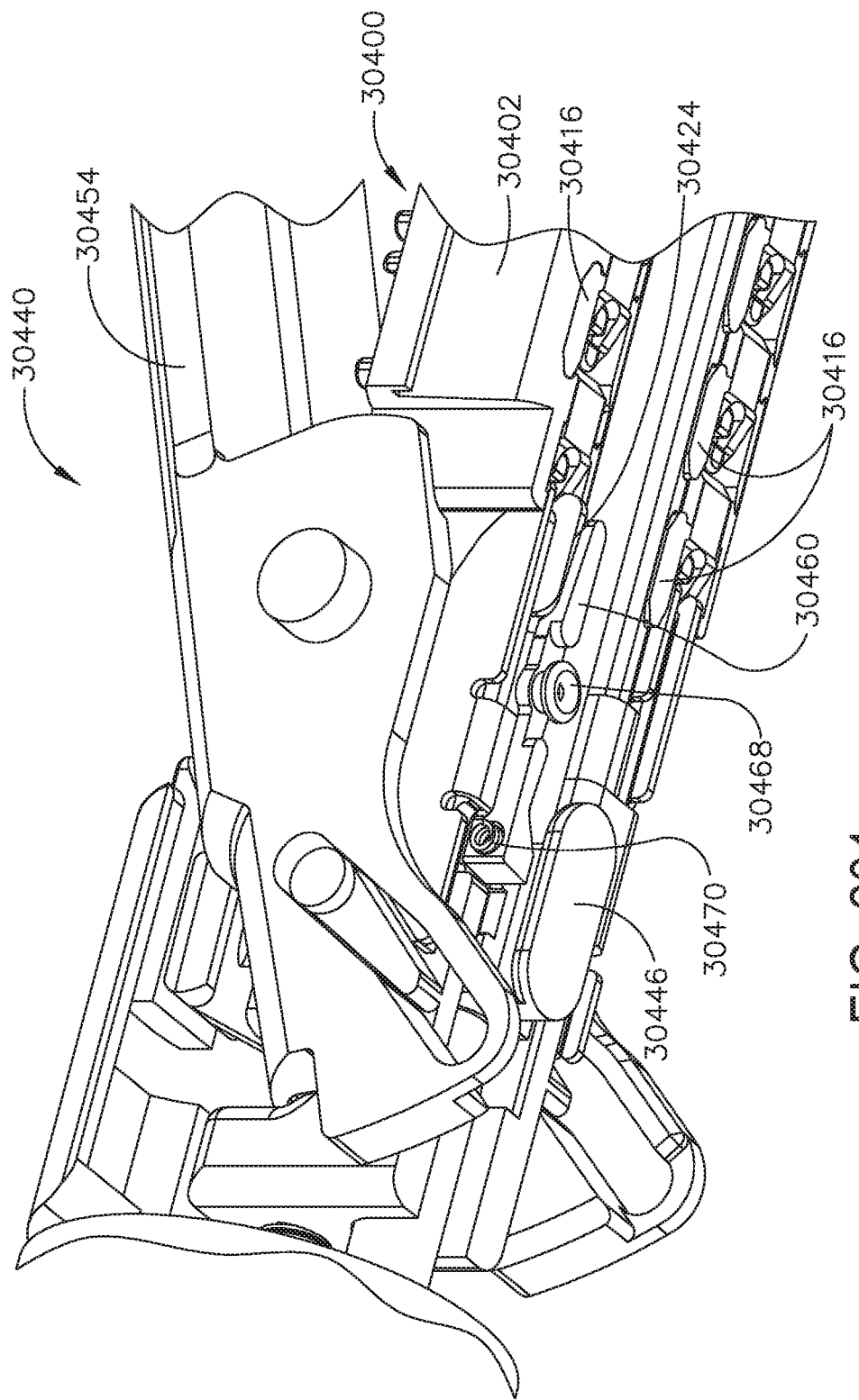

FIG. 201 is a perspective view of a portion of the end effector of FIG. 198 with parts removed for illustrative purposes, depicting a staple cartridge including the sled assembly of FIG. 194 installed in the end effector, further depicting the lockout in the unlocked configuration, according to various aspects of the present disclosure.

Figure 202:
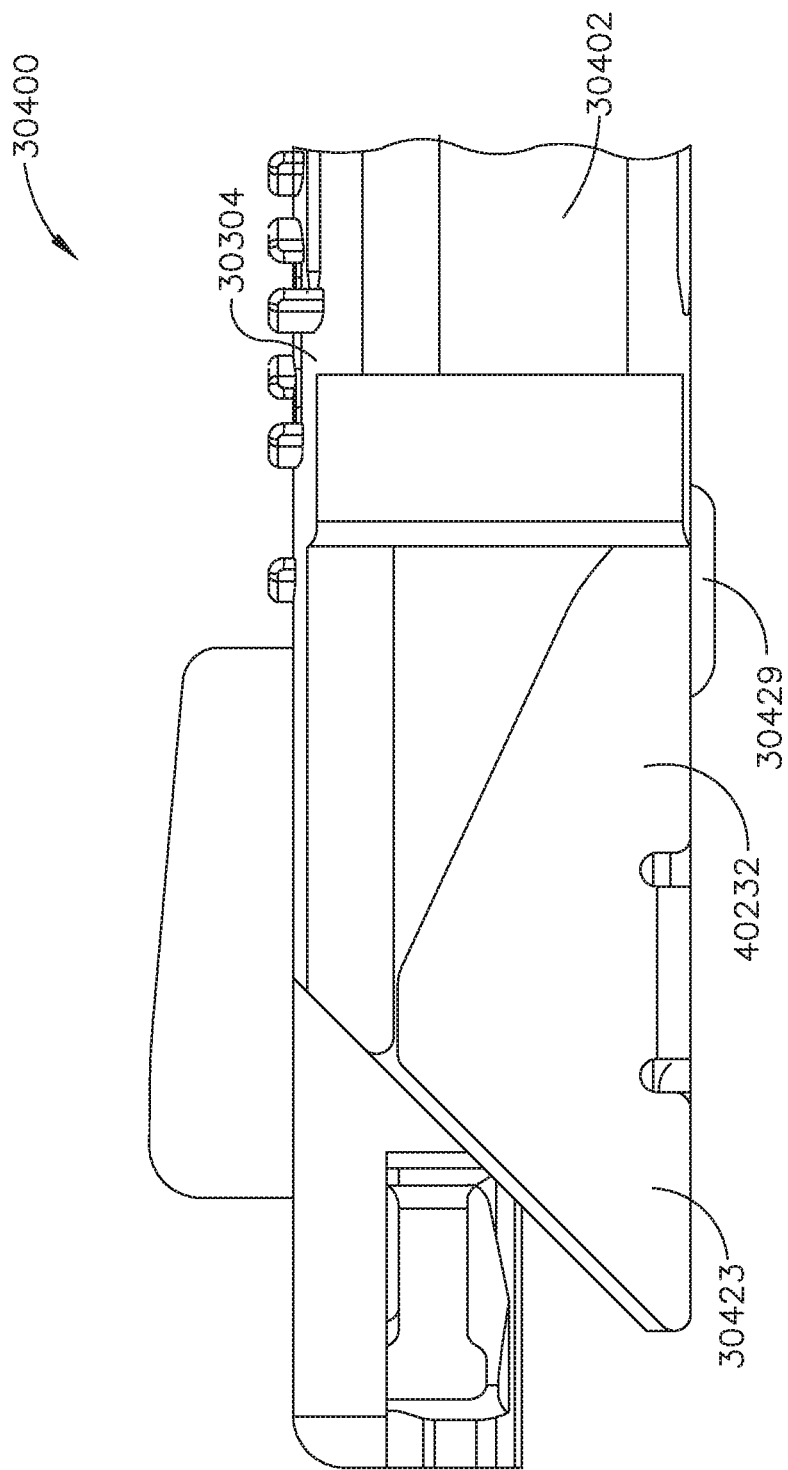

FIG. 202 is an elevation view of a portion of the staple cartridge and the sled assembly of FIG. 201, depicting the sled assembly in an unfired position, according to various aspects of the present disclosure.

Figure 203:
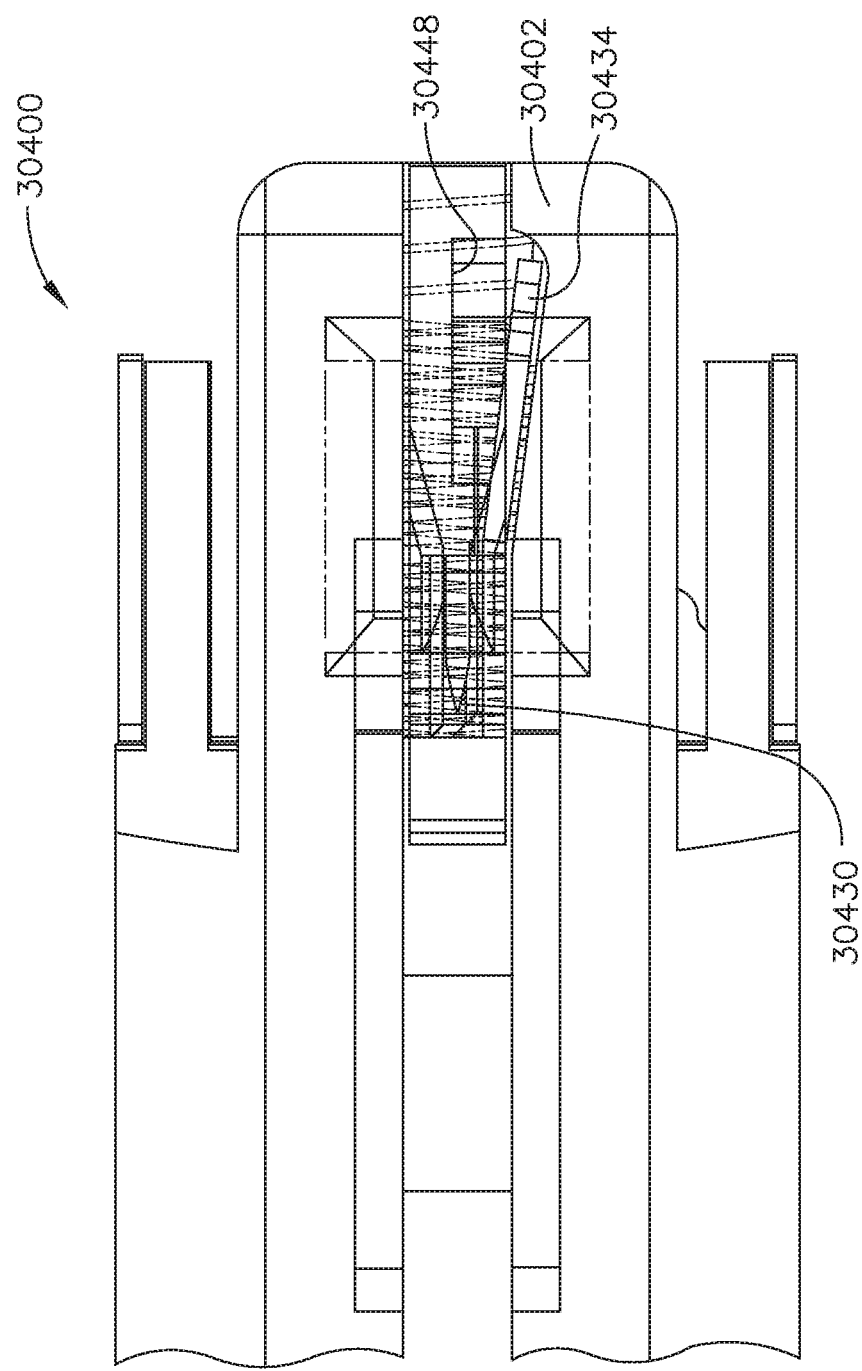

FIG. 203 is a plan view of a portion of the underside of the staple cartridge and the sled assembly of FIG. 201, depicting a portion of the firing assembly with phantom lines for illustrative purposes, according to various aspects of the present disclosure.

Figure 204:
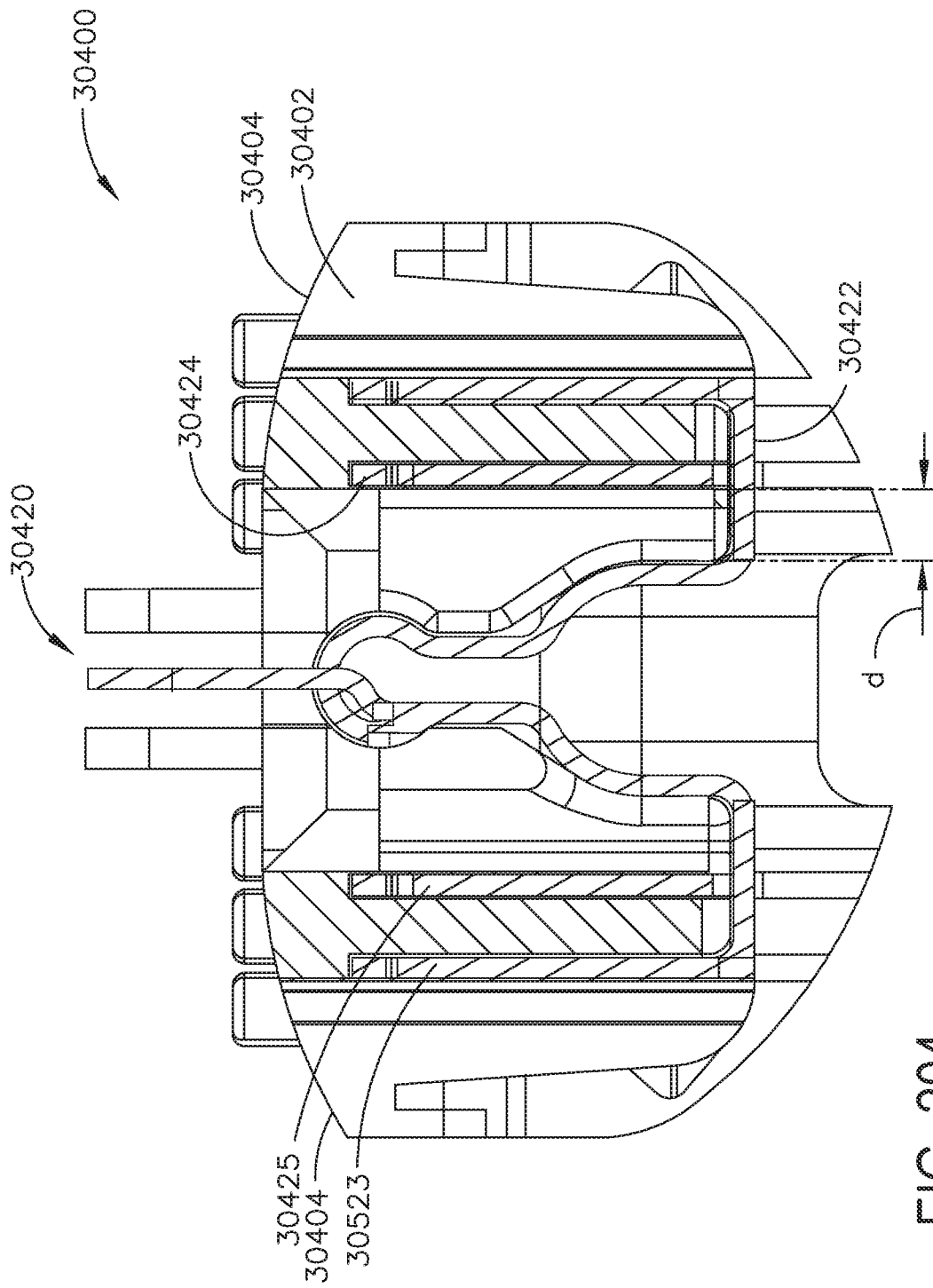

FIG. 204 is an elevation cross-section view of the staple cartridge of FIG. 201, according to various aspects of the present disclosure.

Figure 205:
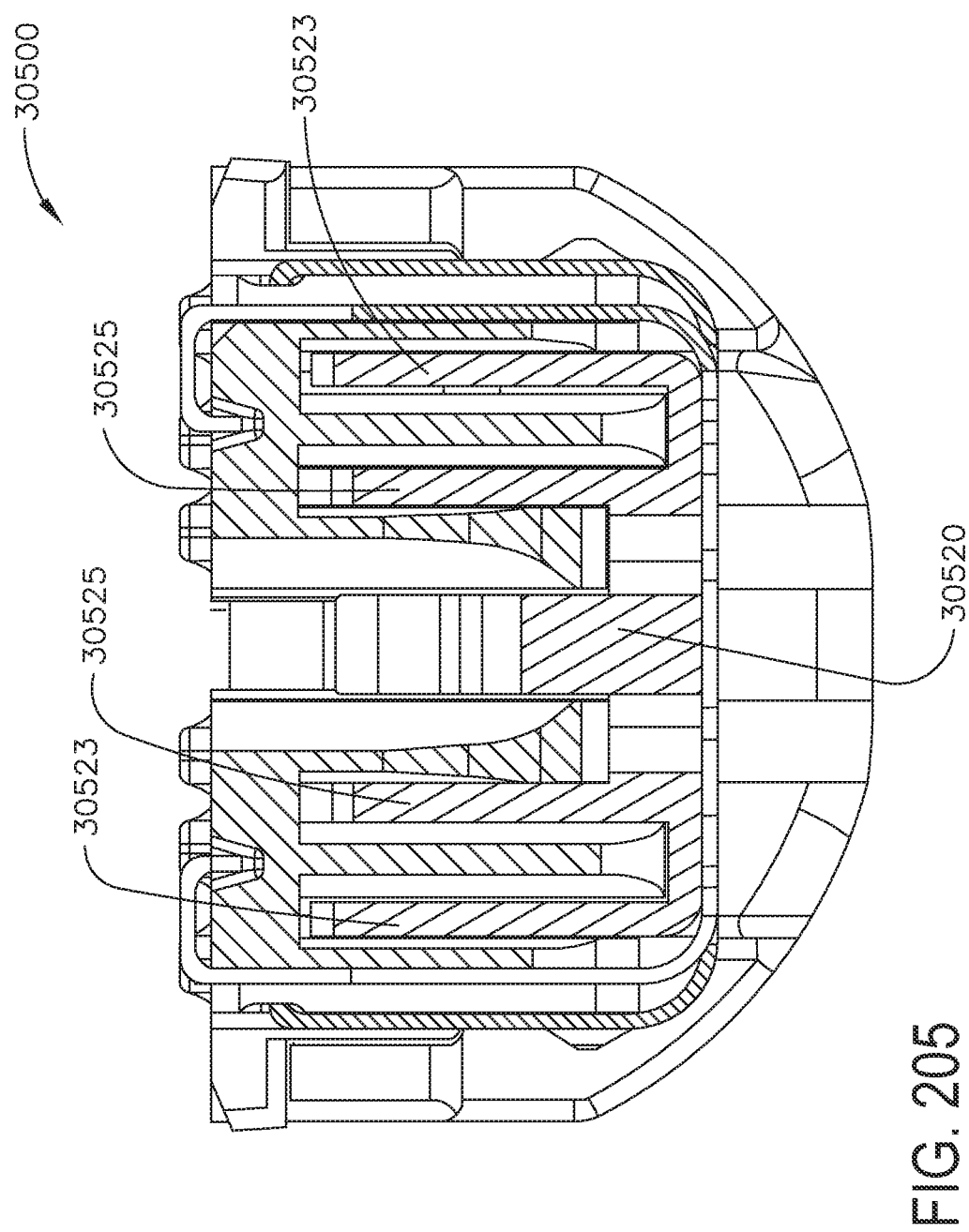

FIG. 205 is an elevation cross-section view of a staple cartridge, according to various aspects of the present disclosure.

Figure 206:
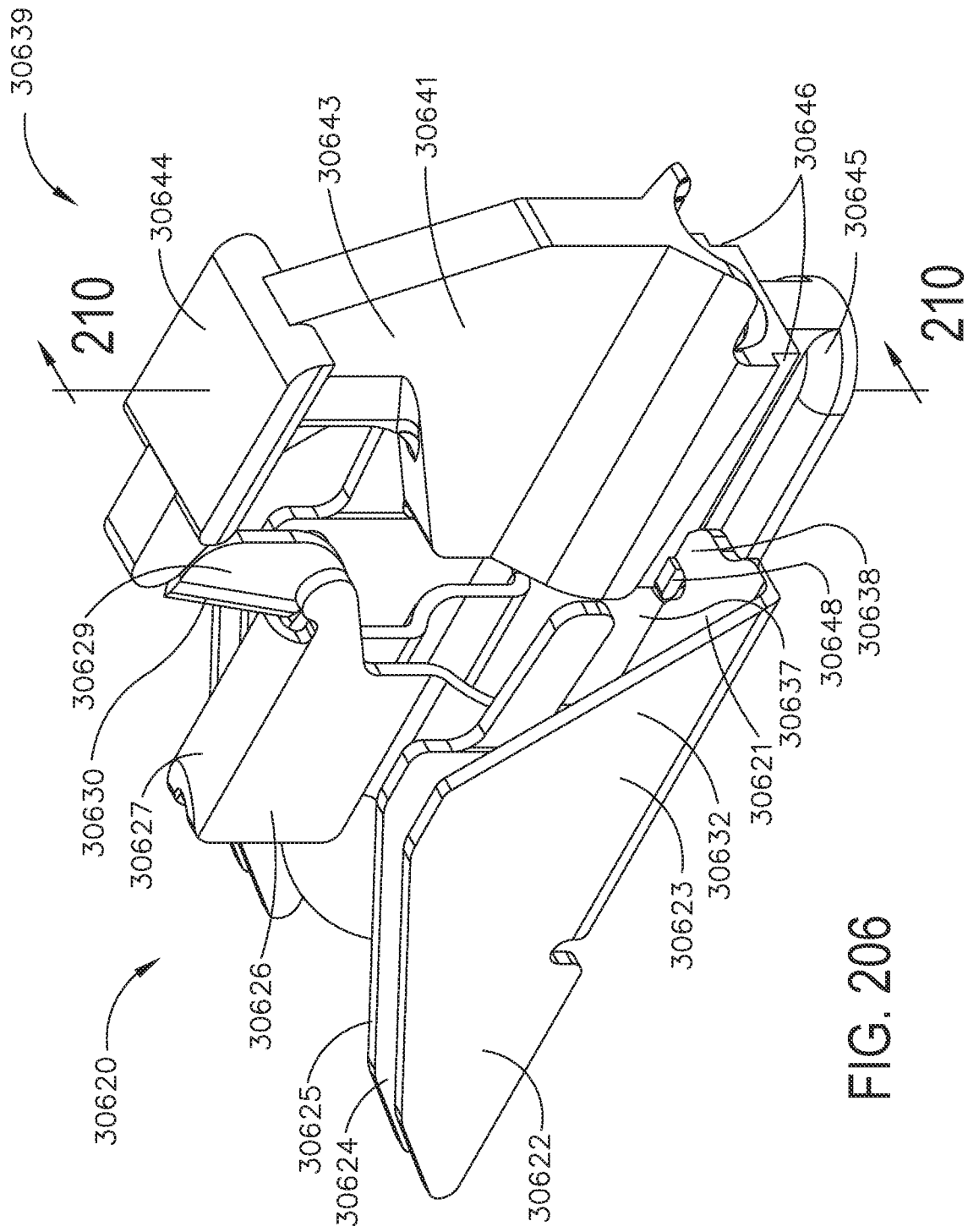

FIG. 206 is a perspective view of a firing member and a sled assembly, depicting the firing member in an unfired configuration, according to various aspects of the present disclosure.

Figure 207:
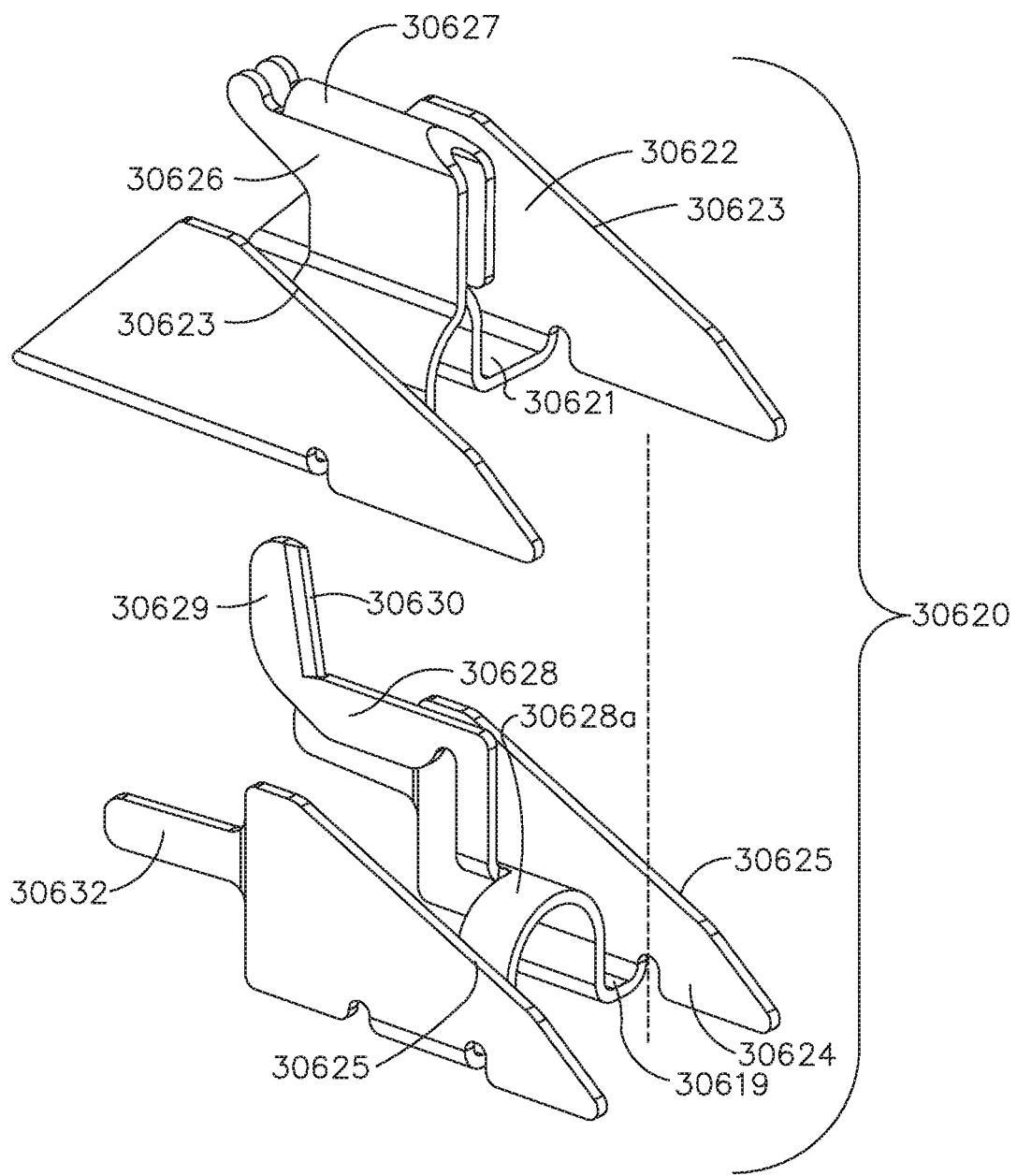

FIG. 207 is an exploded view of the sled assembly of FIG. 206, according to various aspects of the present disclosure.

Figure 208:
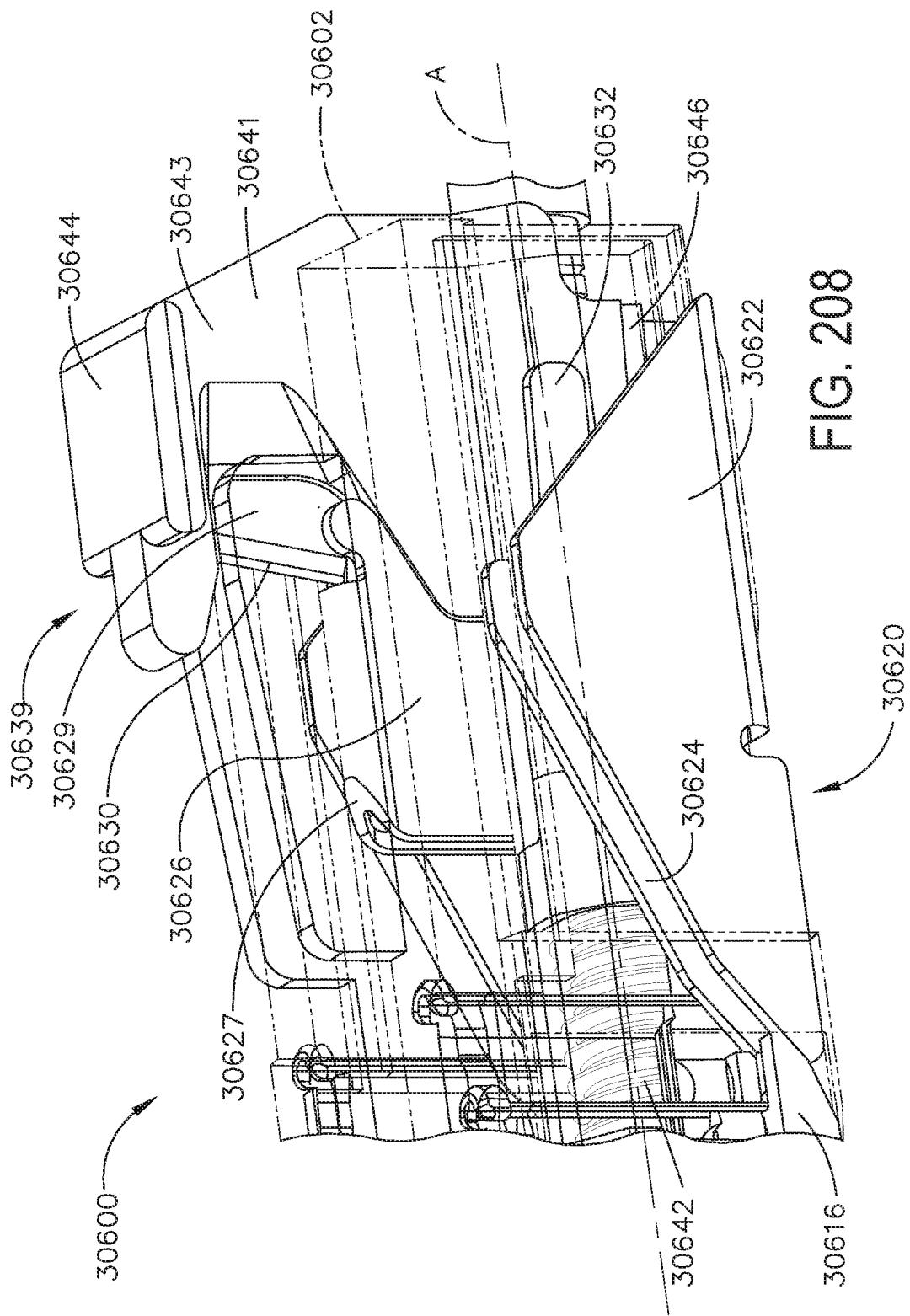

FIG. 208 is a perspective view of the firing member and the sled assembly of FIG. 206 relative to a cartridge body which is shown in phantom lines for illustrative purposes, depicting the firing assembly in a first advanced configuration in which the firing member is moved into driving engagement with the sled assembly, which is moved into driving engagement with drivers in the cartridge body, according to various aspects of the present disclosure.

Figure 209:
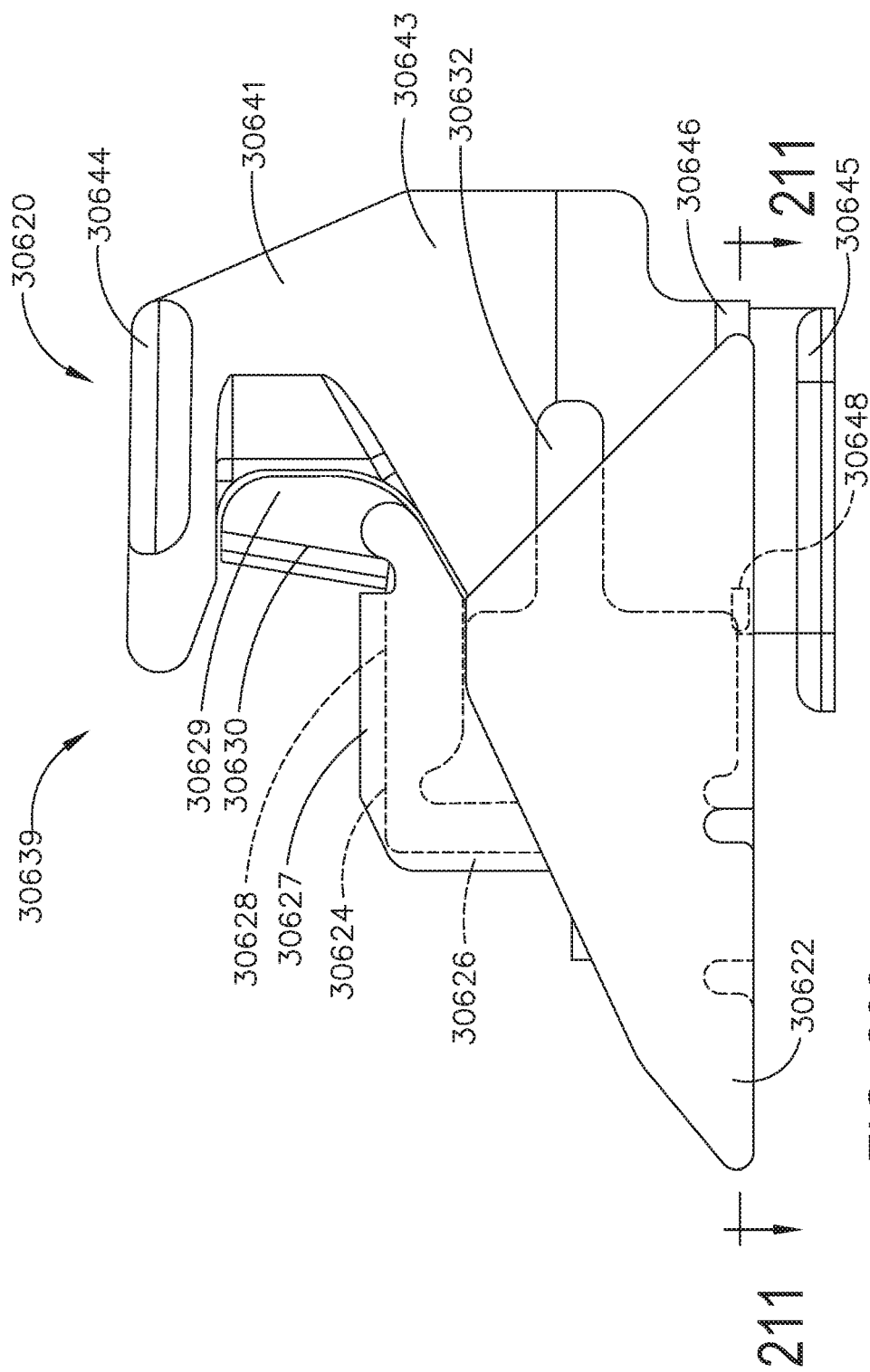

FIG. 209 is an elevation view of the firing member and the sled assembly of FIG. 206 with certain hidden features shown with dashed lines for illustrative purposes, depicting the firing member in the first advanced configuration, according to various aspects of the present disclosure.

Figure 210:
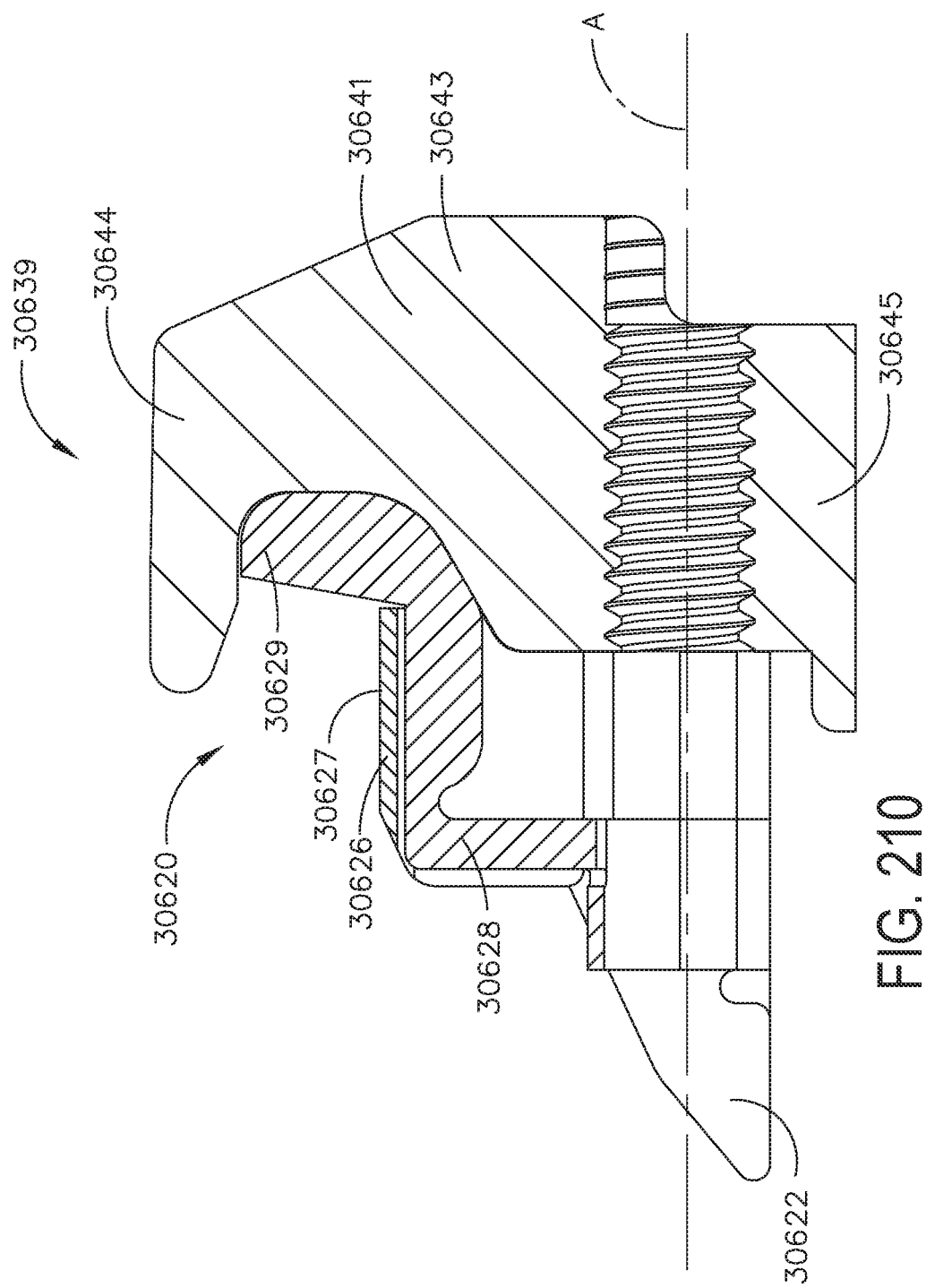

FIG. 210 is an elevation cross-section view of the firing member and the sled assembly of FIG. 206 taken along the line 210-210 indicated in FIG. 206, depicting the firing member in the first advanced configuration, according to various aspects of the present disclosure.

Figure 211:
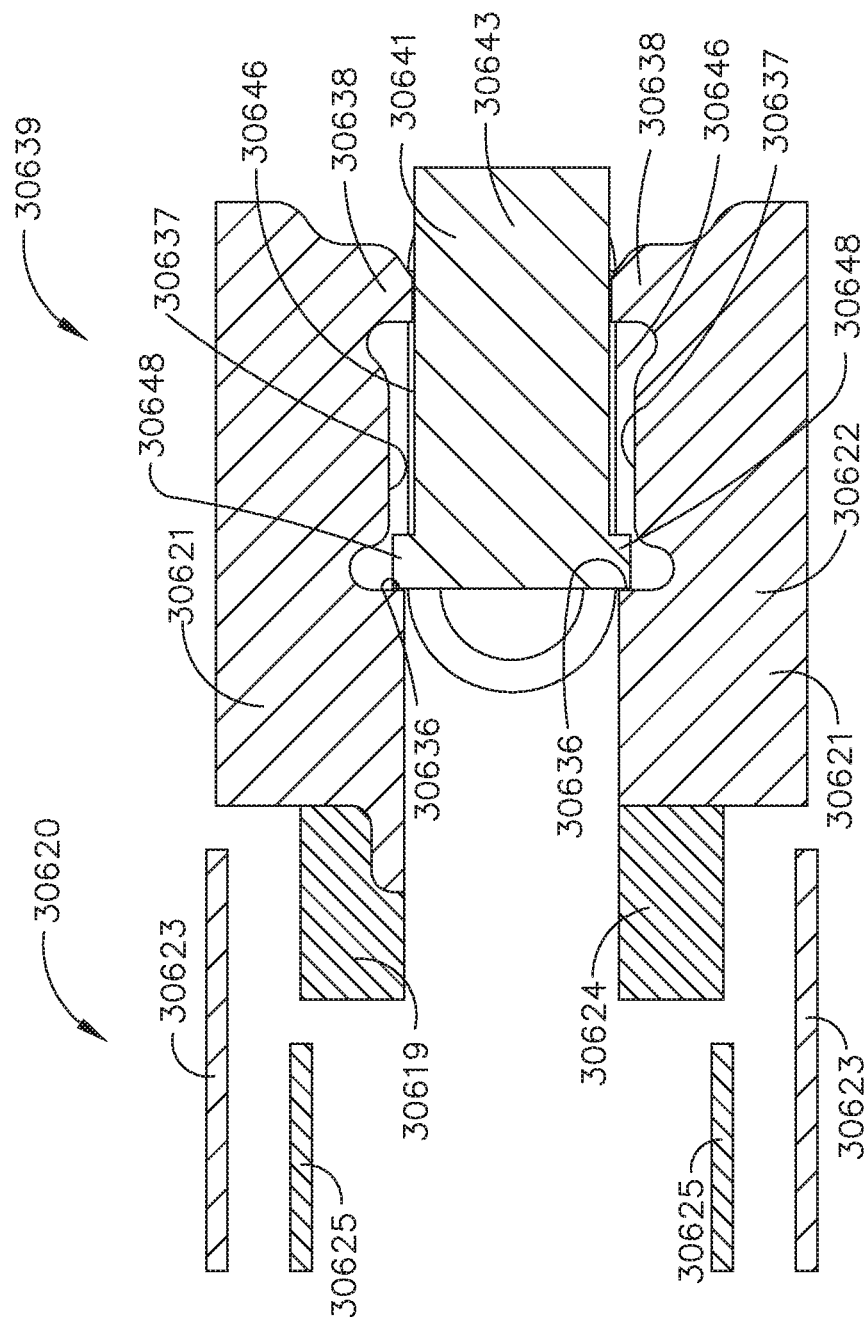

FIG. 211 is an elevation cross-section view of the firing member and the sled assembly of FIG. 206 taken along the line 211-211 indicated in FIG. 209, depicting the firing member in the first advanced configuration, according to various aspects of the present disclosure.

Figure 212A:
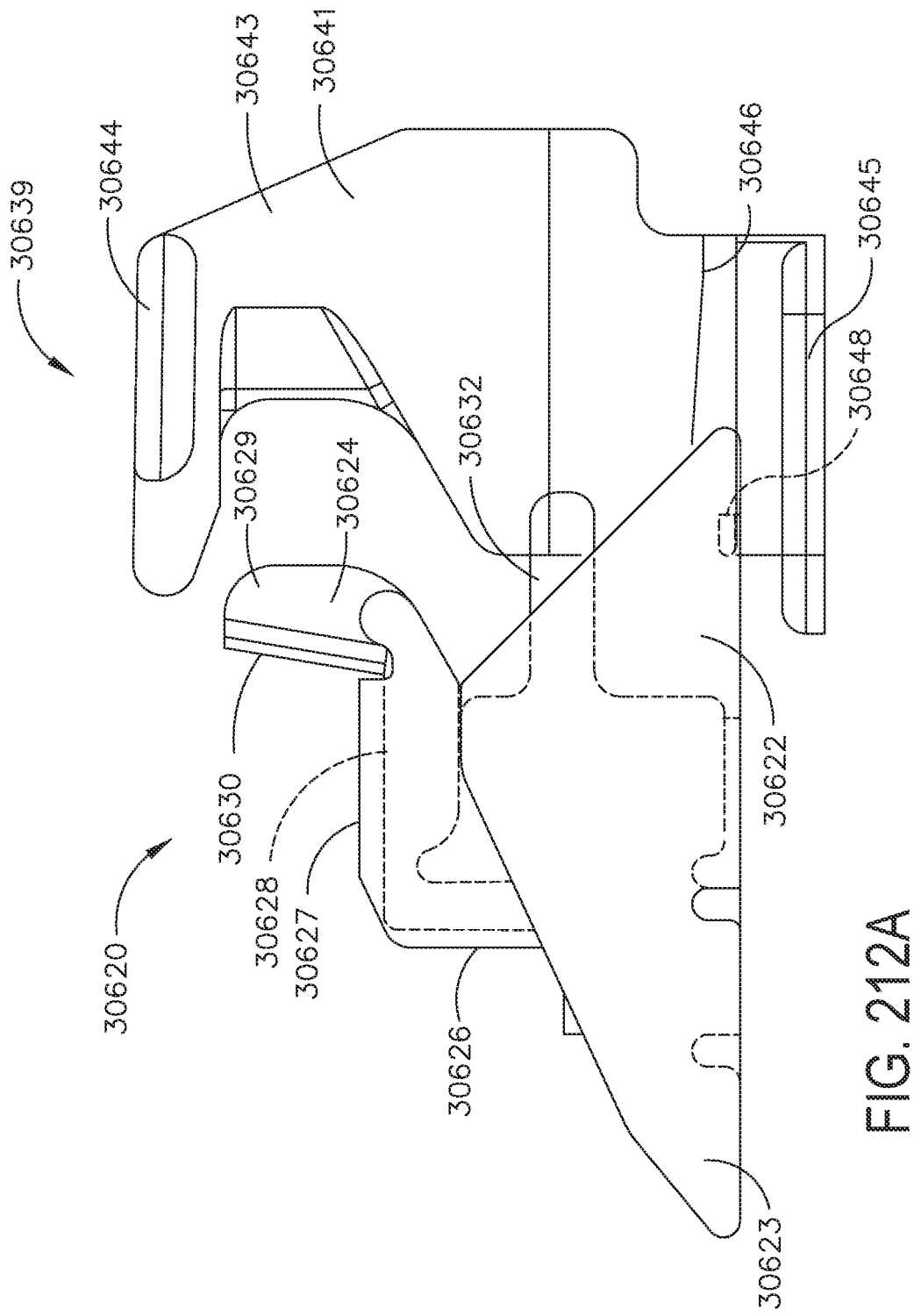

FIG. 212A is an elevation view of the firing member and the sled assembly of FIG. 206 with certain hidden features shown with dashed lines for illustrative purposes, depicting the firing member in a first retracted configuration, according to various aspects of the present disclosure.

FIG. 212B is an elevation view of the firing member and the sled assembly of FIG. 206 with certain hidden features shown with dashed lines for illustrative purposes, depicting the firing member in a second retracted configuration, according to various aspects of the present disclosure.

Figure 212C:
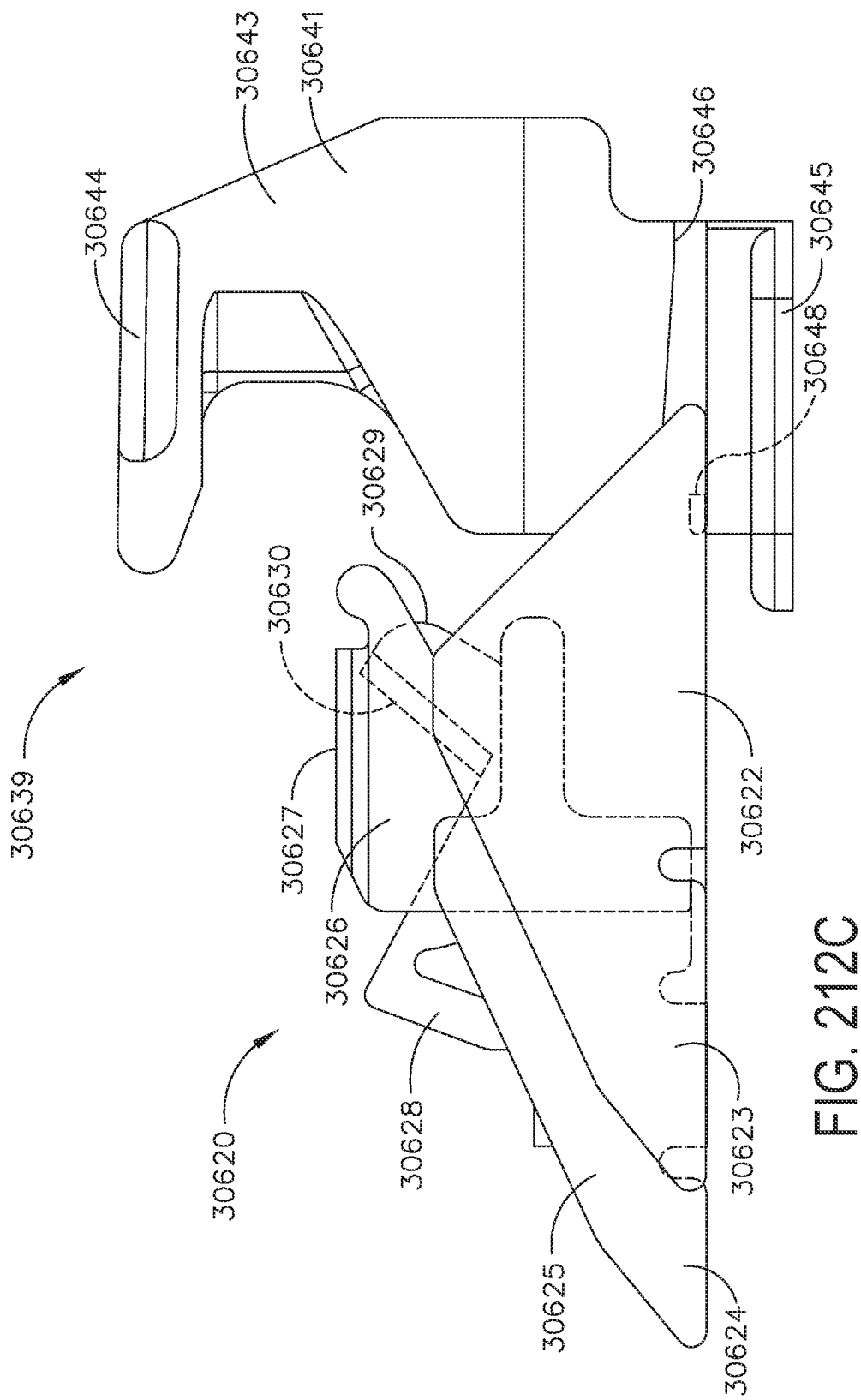

FIG. 212C is an elevation view of the firing member and the sled assembly of FIG. 206 with certain hidden features shown with dashed lines for illustrative purposes, depicting the firing member in a third retracted configuration, according to various aspects of the present disclosure.

Figure 212D:
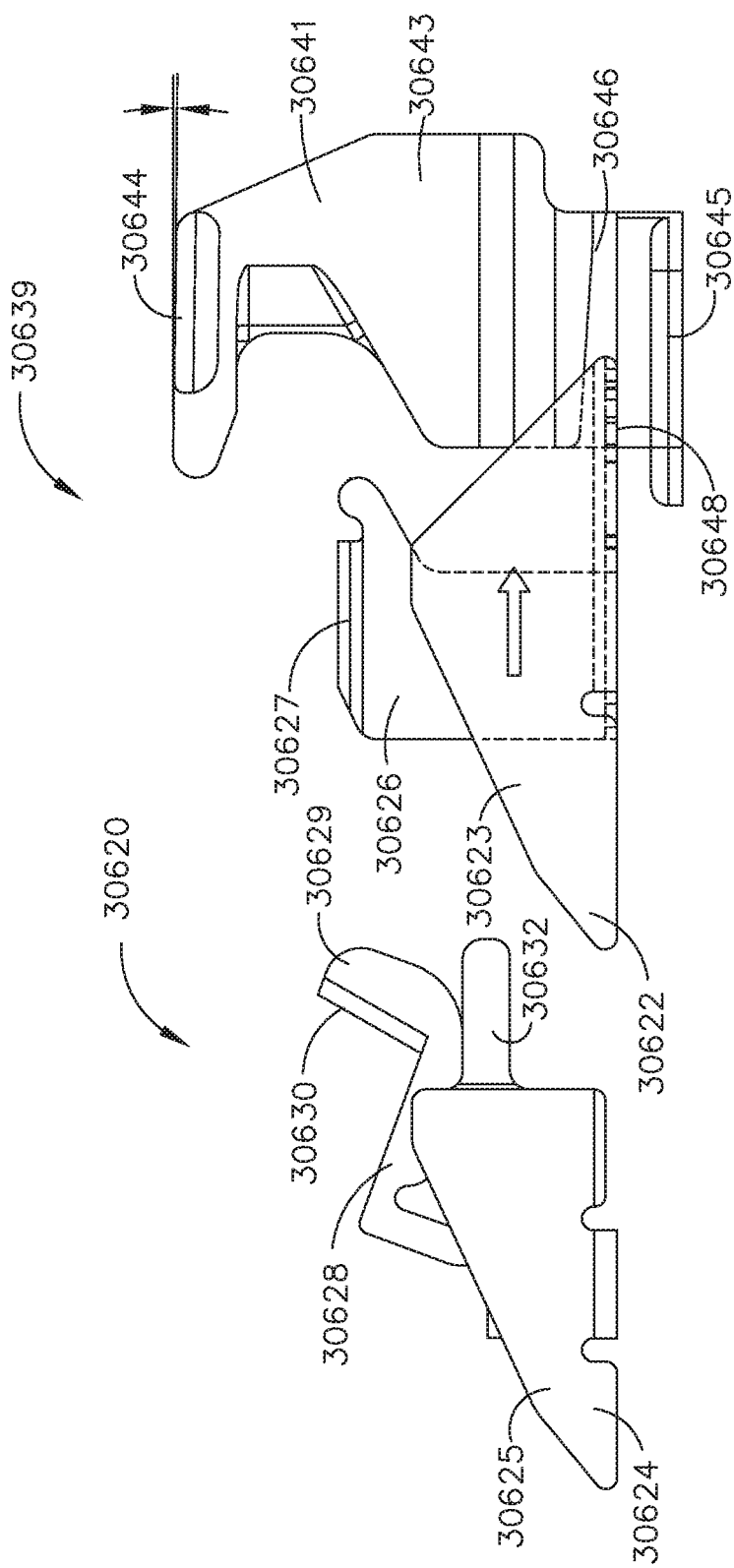

FIG. 212D is an elevation view of the firing member and the sled assembly of FIG. 206 with certain hidden features shown with dashed lines for illustrative purposes, depicting the firing member in a fourth retracted configuration, according to various aspects of the present disclosure.

Figure 213:
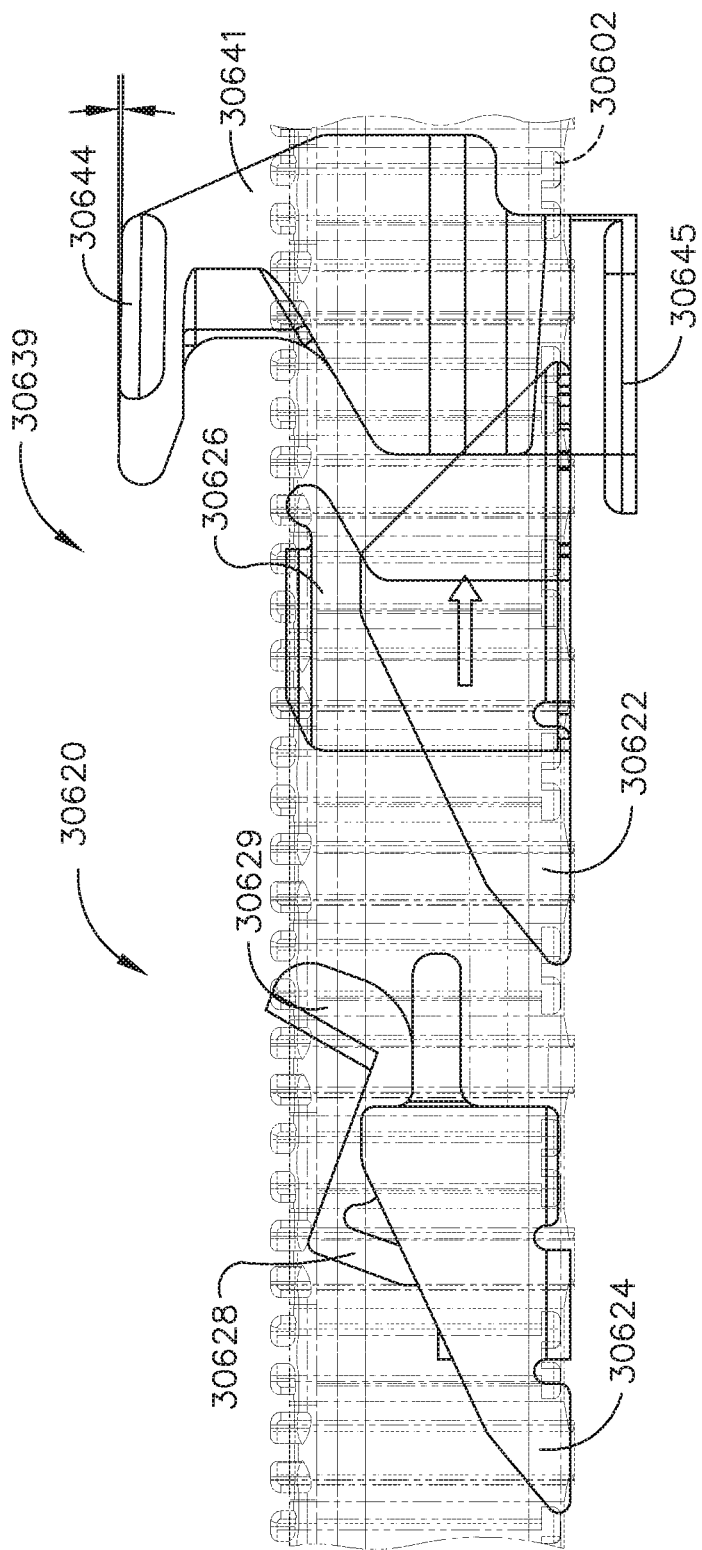

FIG. 213 is an elevation view of the firing member and the sled assembly of FIG. 206 relative to the cartridge body of FIG. 208, depicting the firing member in the fourth retracted configuration of FIG. 212D, wherein the cartridge body is shown in phantom lines for illustrative purposes, according to various aspects of the present disclosure.

Figure 214:
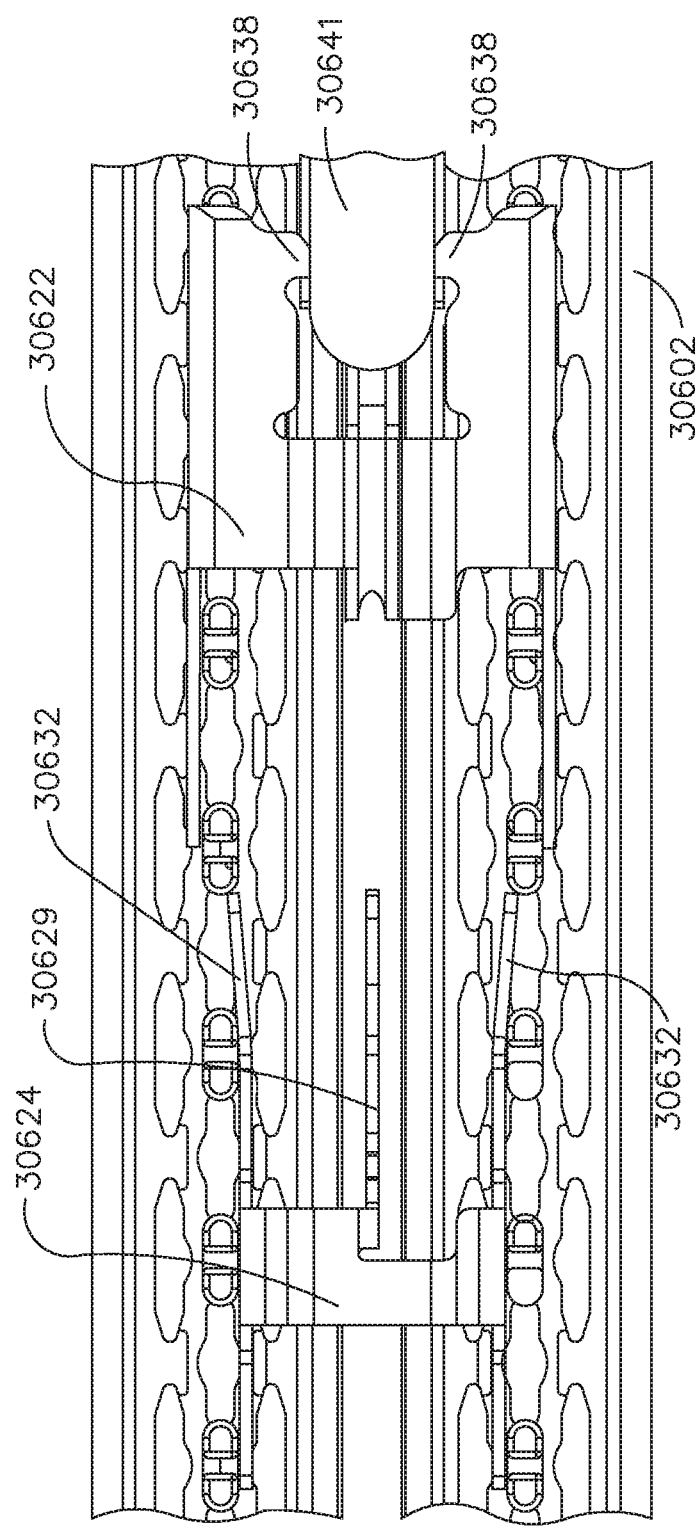

FIG. 214 is a plan view of the firing member and the sled assembly of FIG. 206 and the cartridge body of FIG. 208, depicting the firing assembly in the fourth retracted configuration of FIG. 212D, according to various aspects of the present disclosure.

Figure 215:
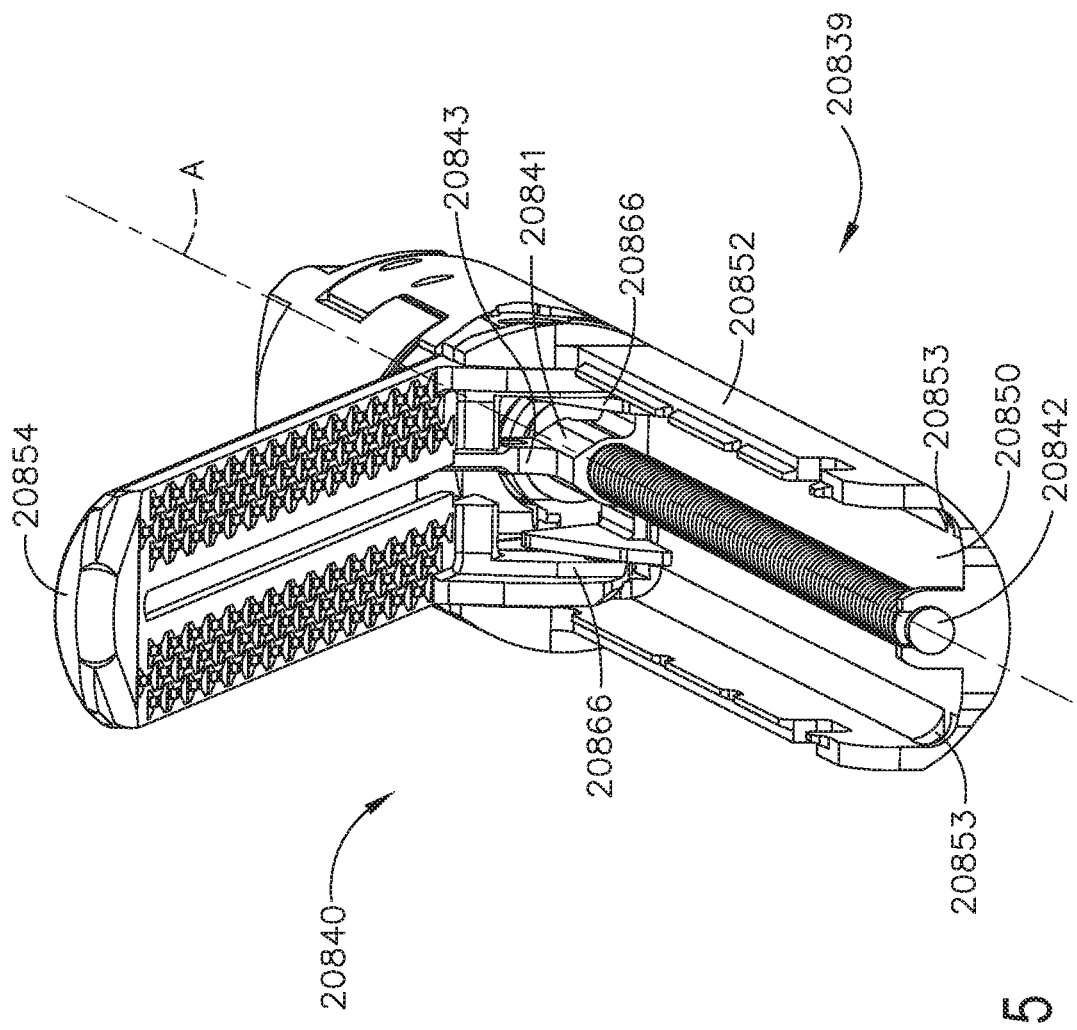

FIG. 215 is a perspective view of a surgical end effector having a firing assembly including a rotary drive screw and a reusable firing member with an integral two-rail sled, according to various aspects of the present disclosure.

Figure 216A:
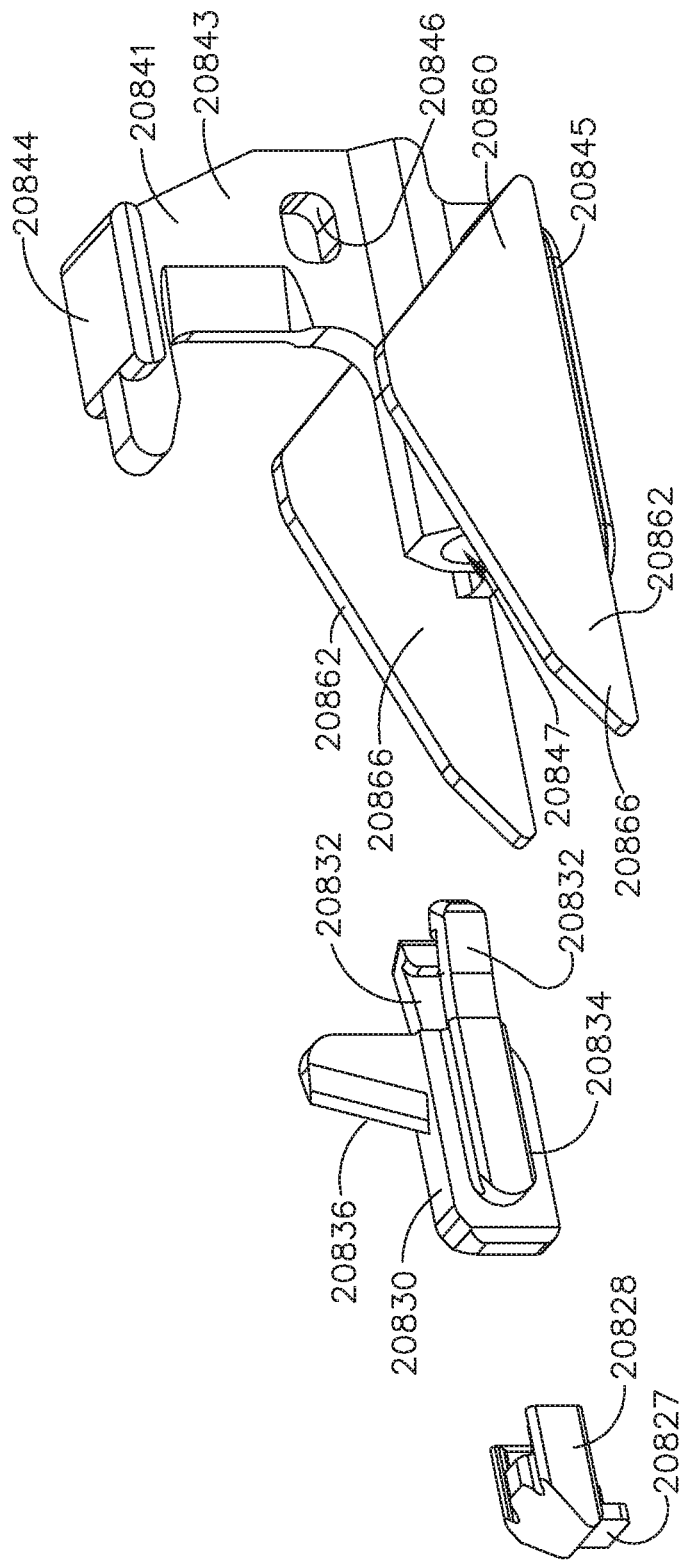

FIG. 216A is an exploded perspective view of the reusable firing member of FIG. 215 and a single-use knife and a firing indicator for use with the reusable firing member, according to various aspects of the present disclosure.

FIG. 216B is a perspective view of the single-use knife and firing indicator of FIG. 216A assembled to the reusable firing member of FIG. 215, and further depicting triple drivers and staples thereon being deployed by the integral two-rail sled of the reusable firing member, according to various aspects of the present disclosure.

Figure 217:
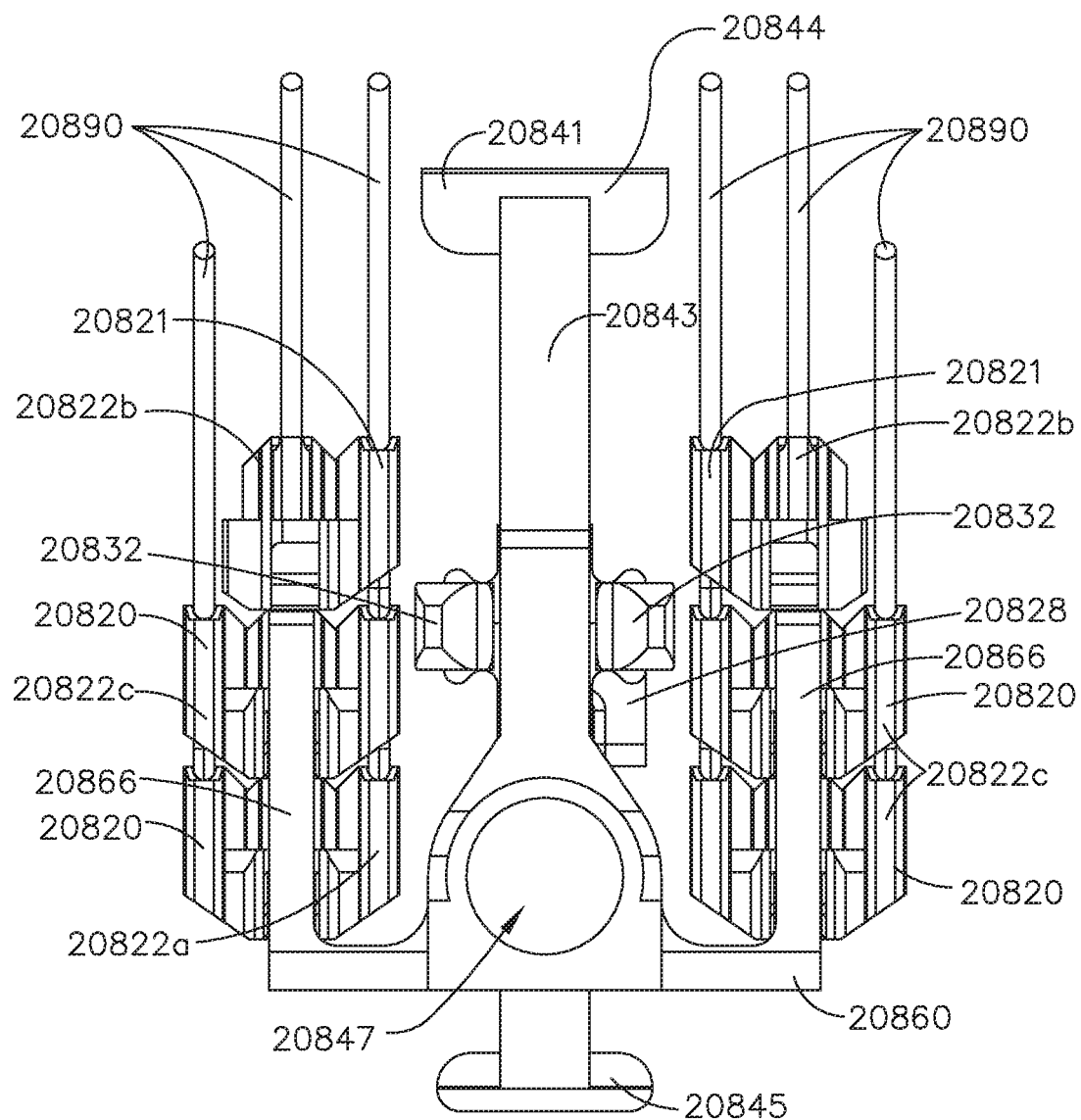

FIG. 217 is an elevation view of the triple drivers, staples, and the reusable firing member of FIG. 216B, according to various aspects of the present disclosure.

Figure 218:
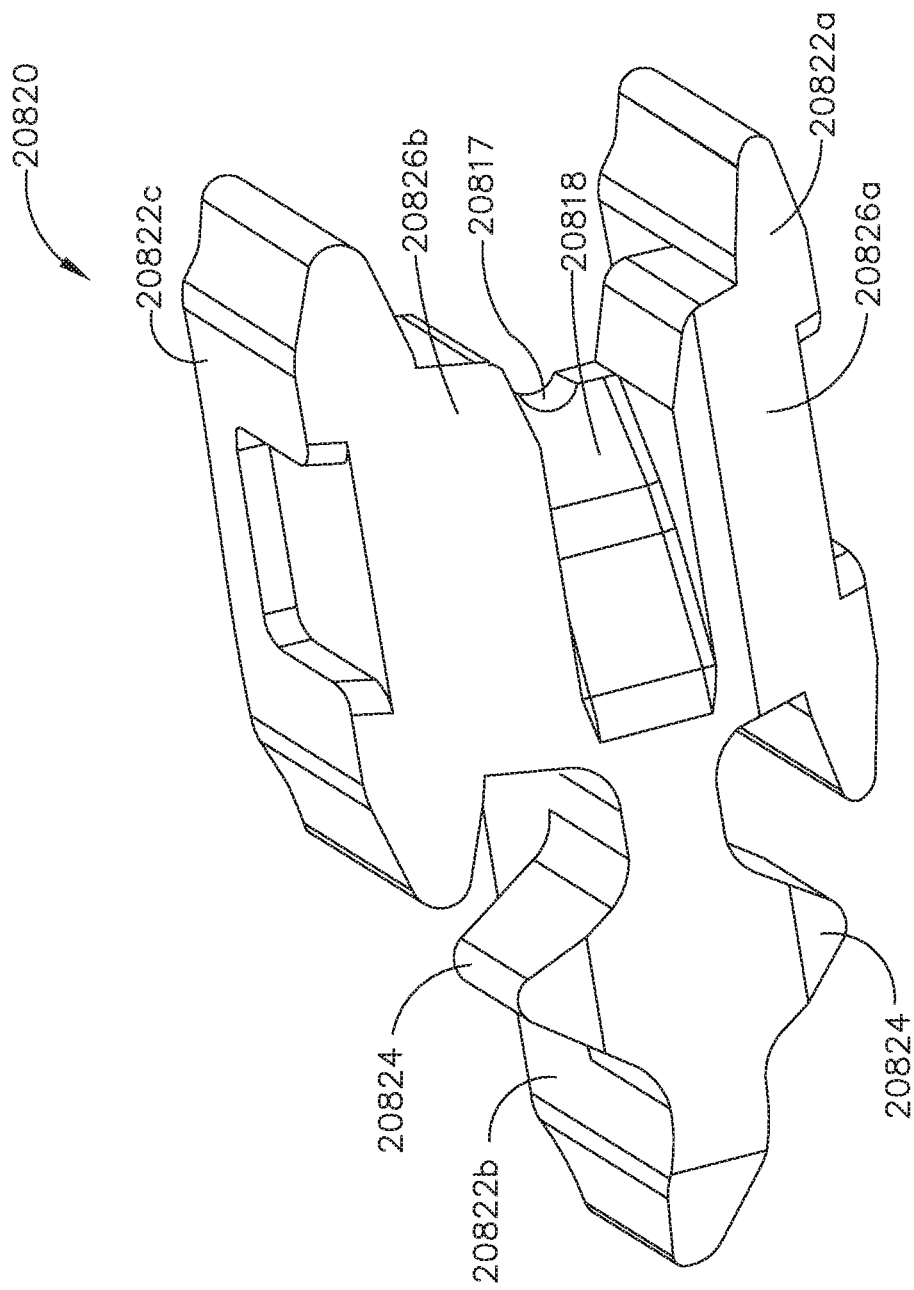

FIG. 218 is a perspective view of one of the triple drivers of FIG. 216B, according to various aspects of the present disclosure.

Figure 219:
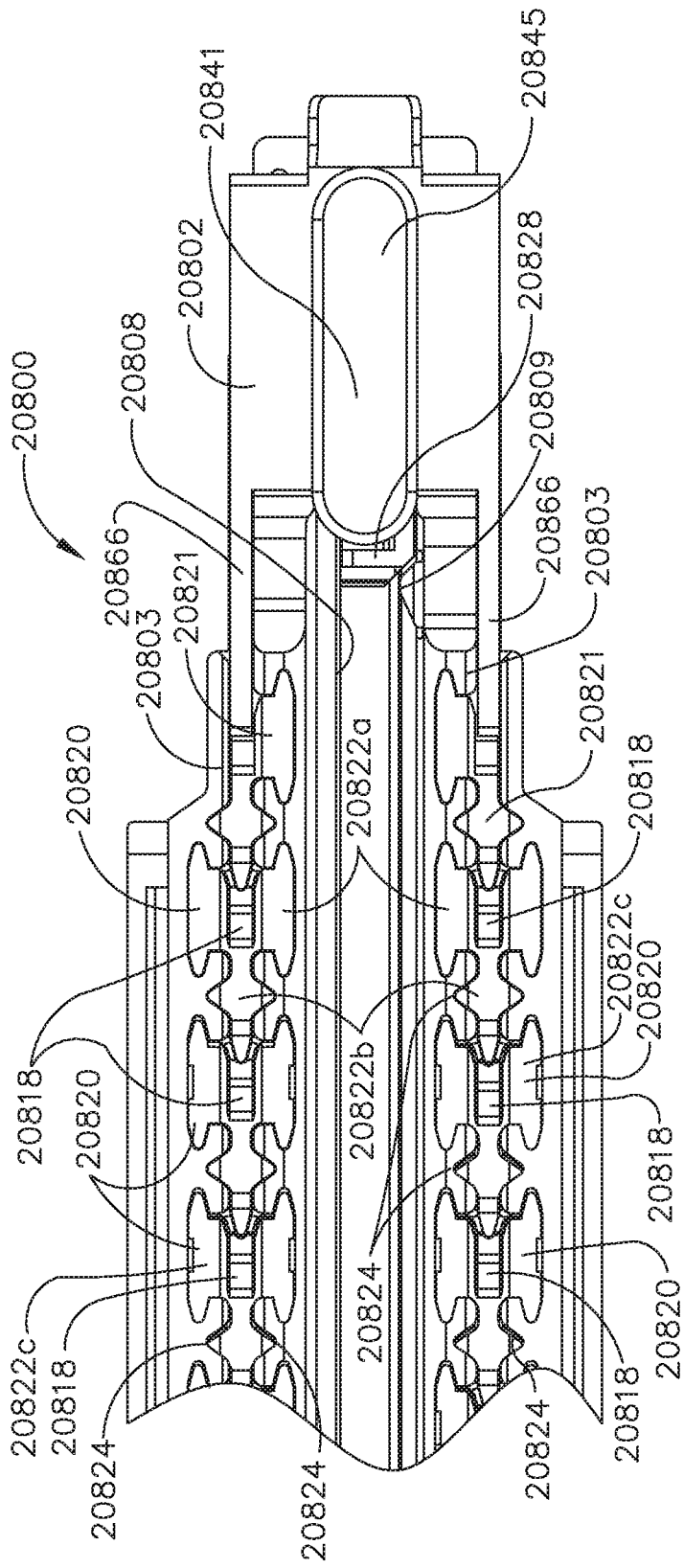

FIG. 219 is a plan view of a portion of a cartridge body housing the triple drivers of FIG. 216B, and further depicting the firing member of FIG. 216A, according to various aspects of the present disclosure.

Figure 220:
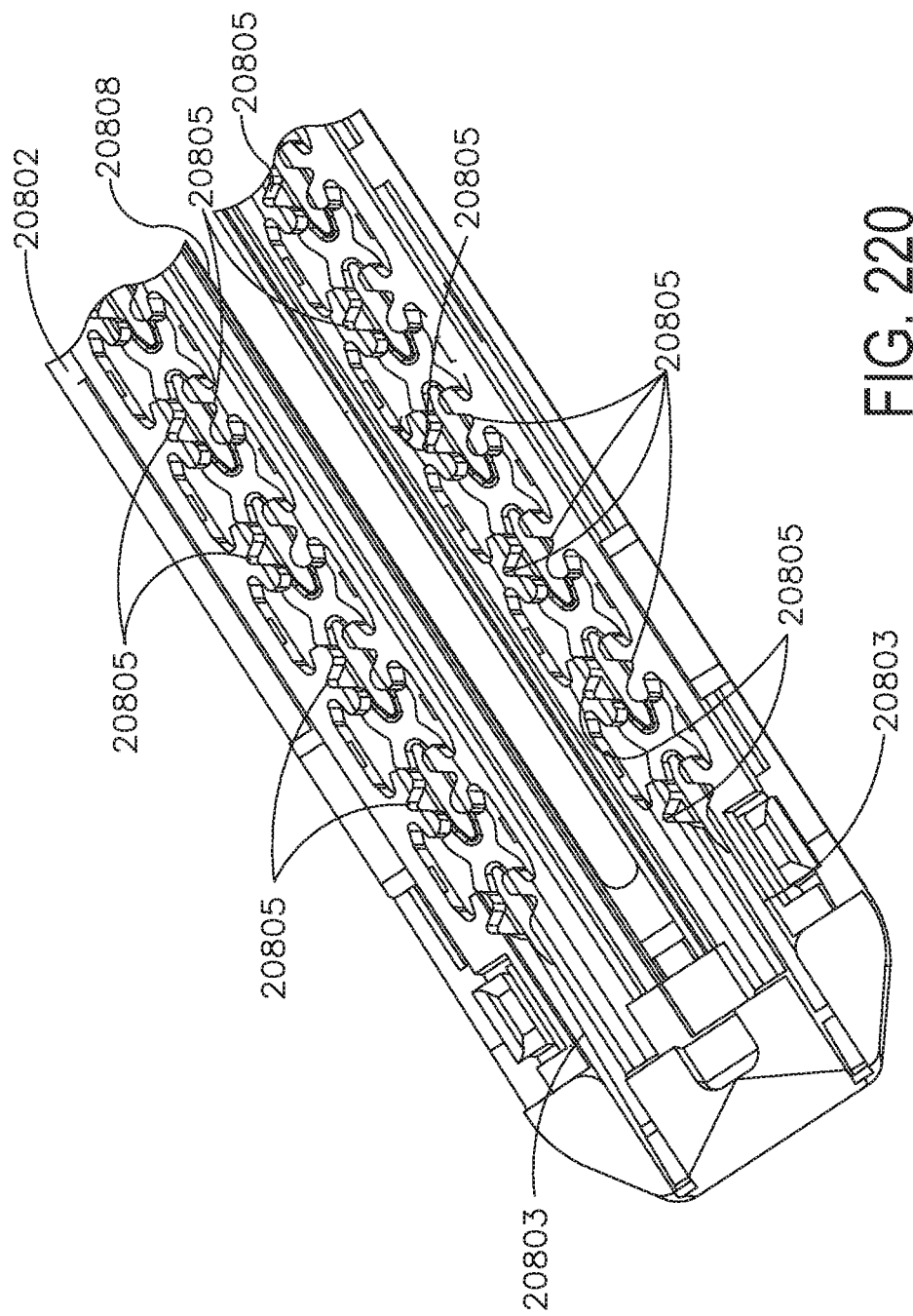

FIG. 220 is perspective view of the underside of a portion of the cartridge body of FIG. 219, according to various aspects of the present disclosure.

Figure 221:
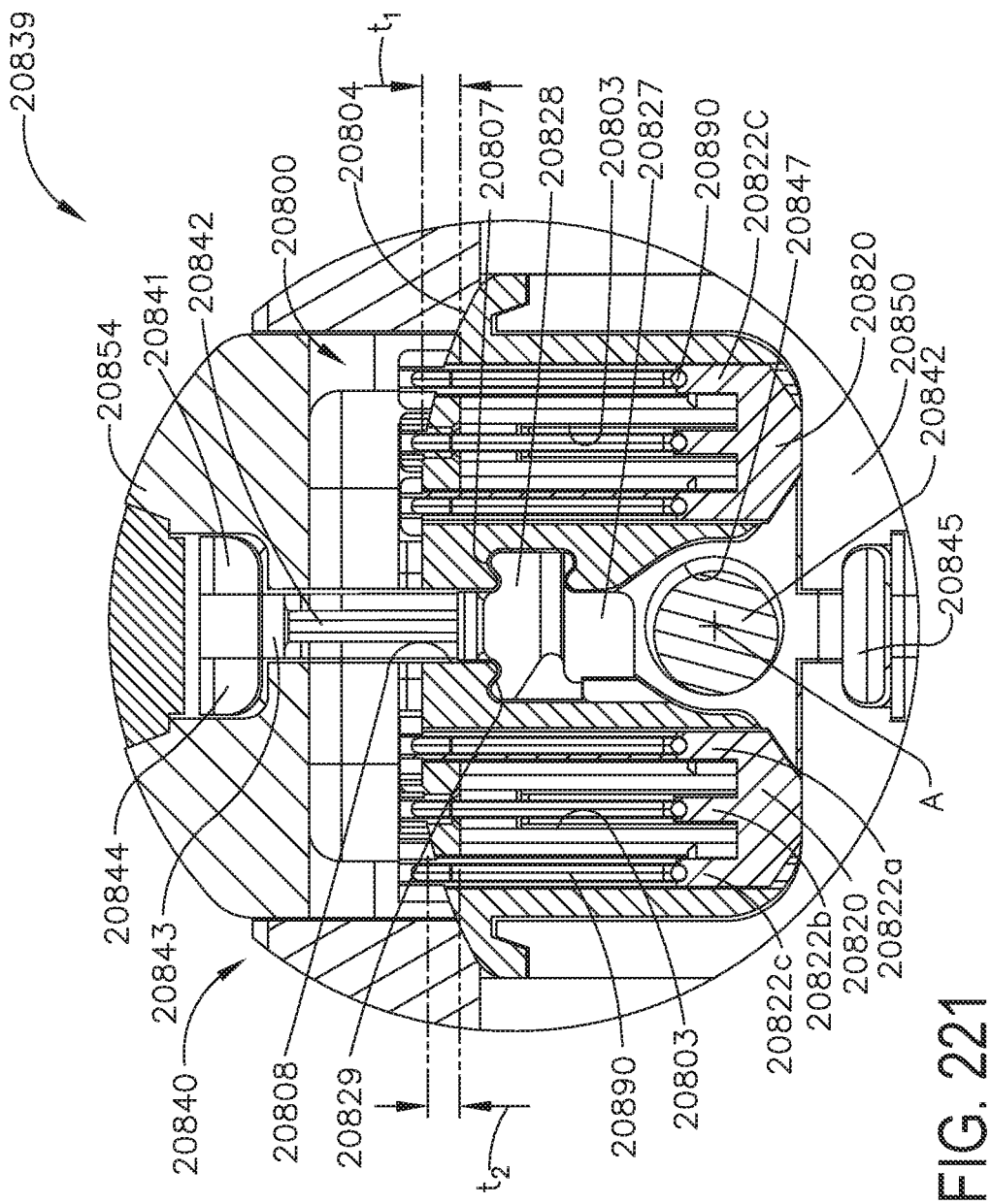

FIG. 221 is an elevation cross-section view of an end effector including the cartridge body, the firing member, and the triple drivers of FIG. 219, according to various aspects of the present disclosure.

Figure 222:
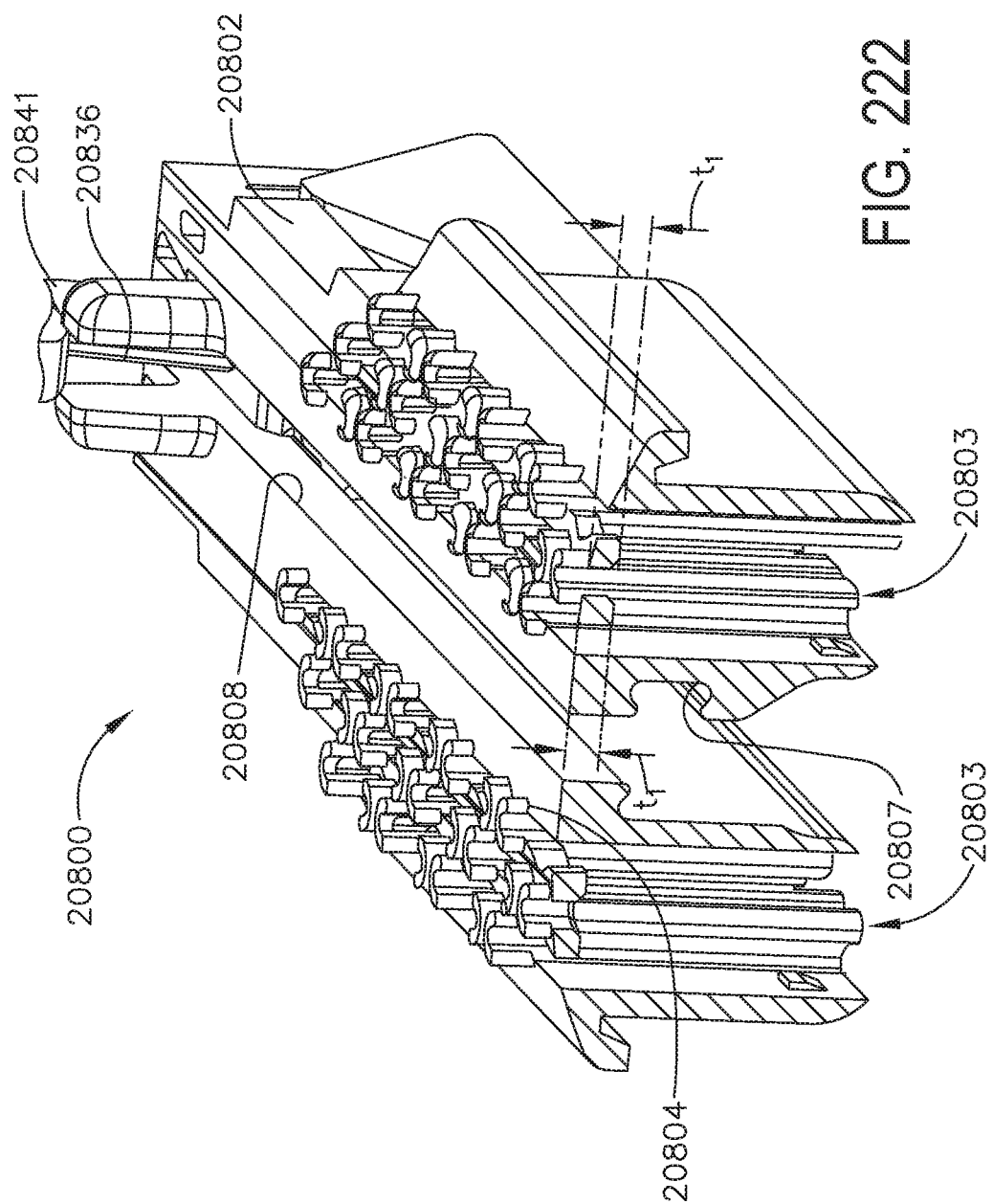

FIG. 222 is a perspective cross-section view of the cartridge body of FIG. 219, according to various aspects of the present disclosure.

Figure 223:
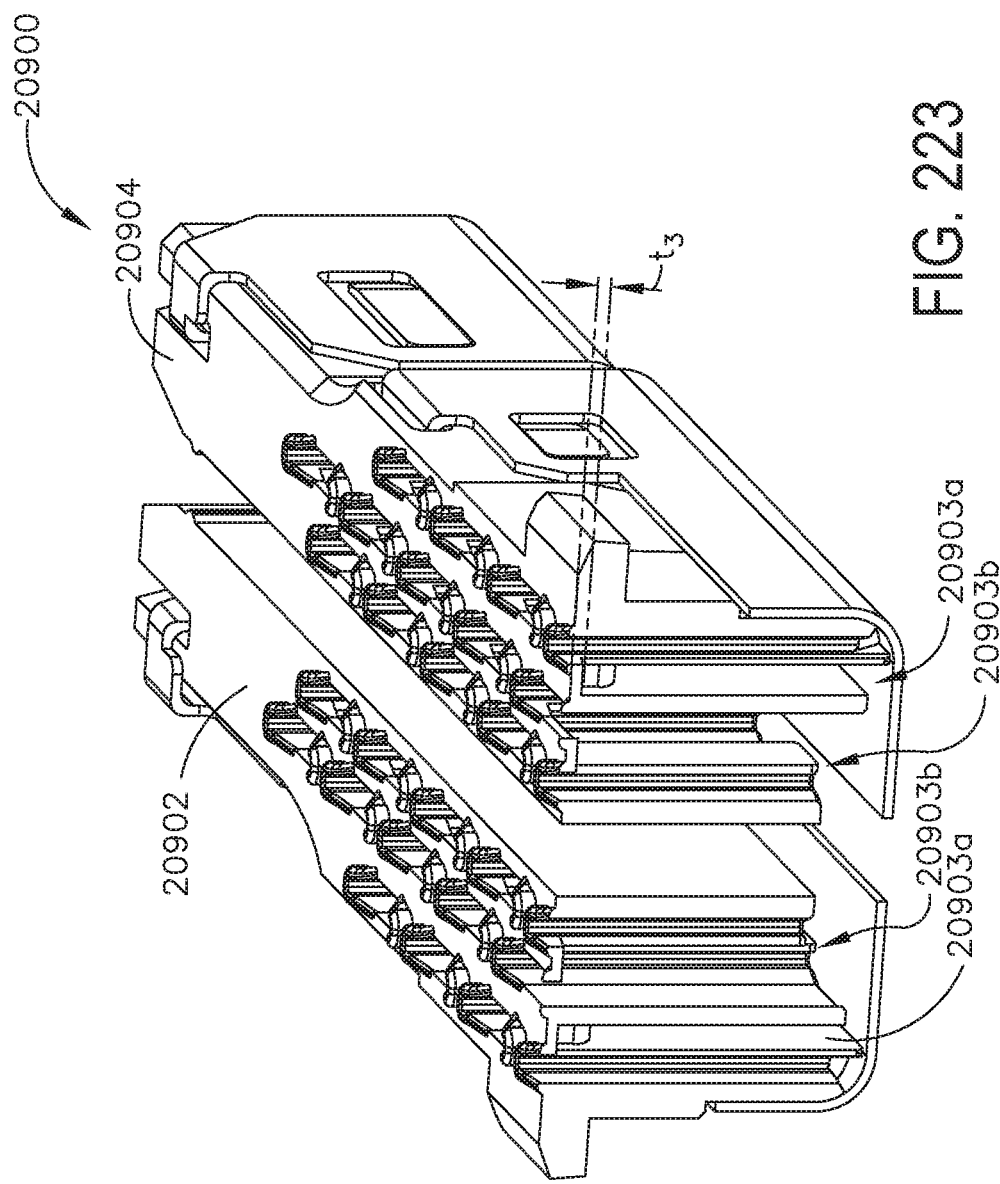

FIG. 223 is a perspective view of a cartridge body, according to various aspects of the present disclosure.

Figure 224:
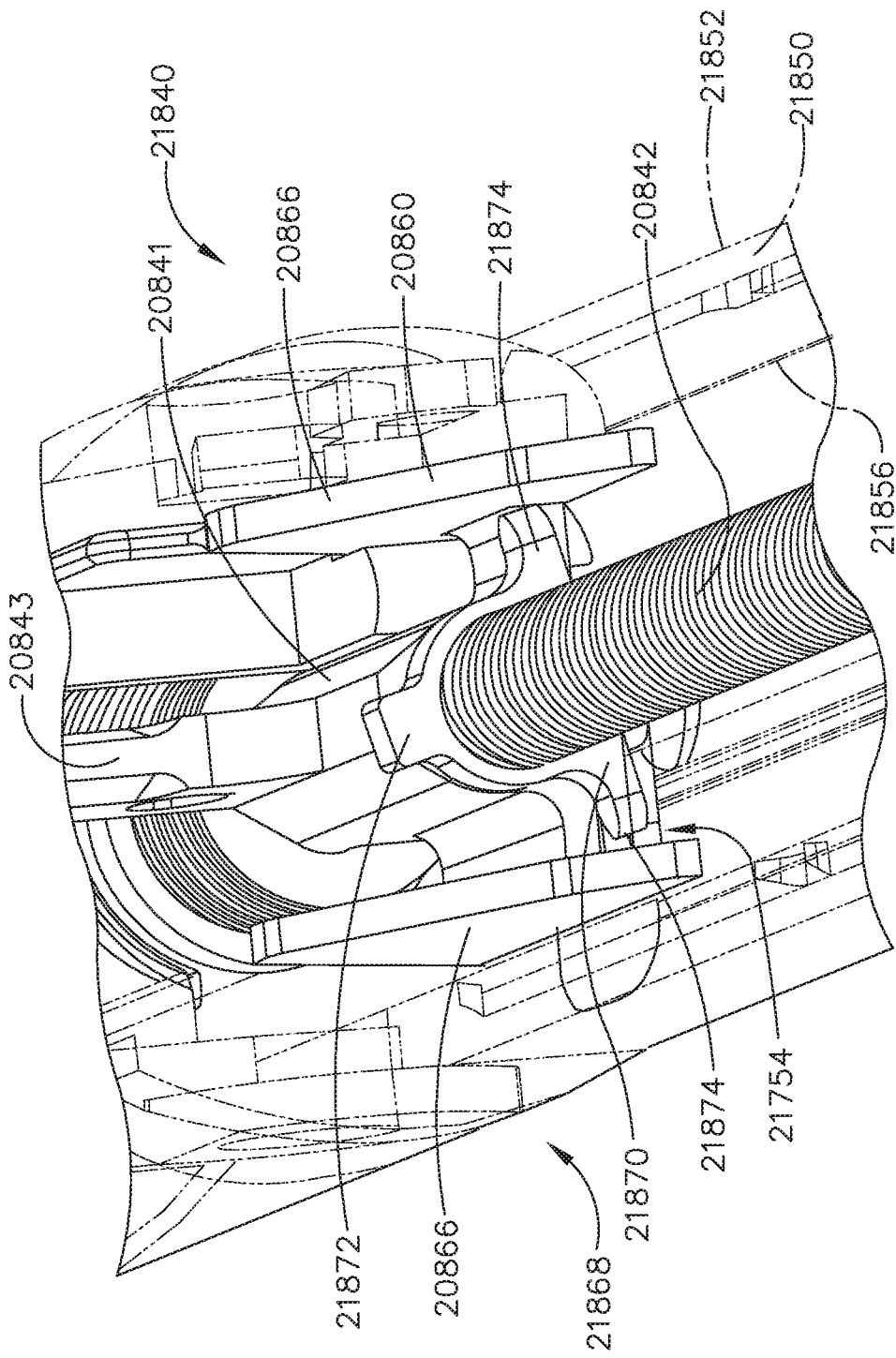

FIG. 224 is a perspective view of a portion of an end effector including the drive assembly of FIG. 215, depicting a lockout arrangement including a lock nut mounted to the rotary drive screw, wherein the lockout nut is in a locked position, according to various aspects of the present disclosure.

Figure 225A:
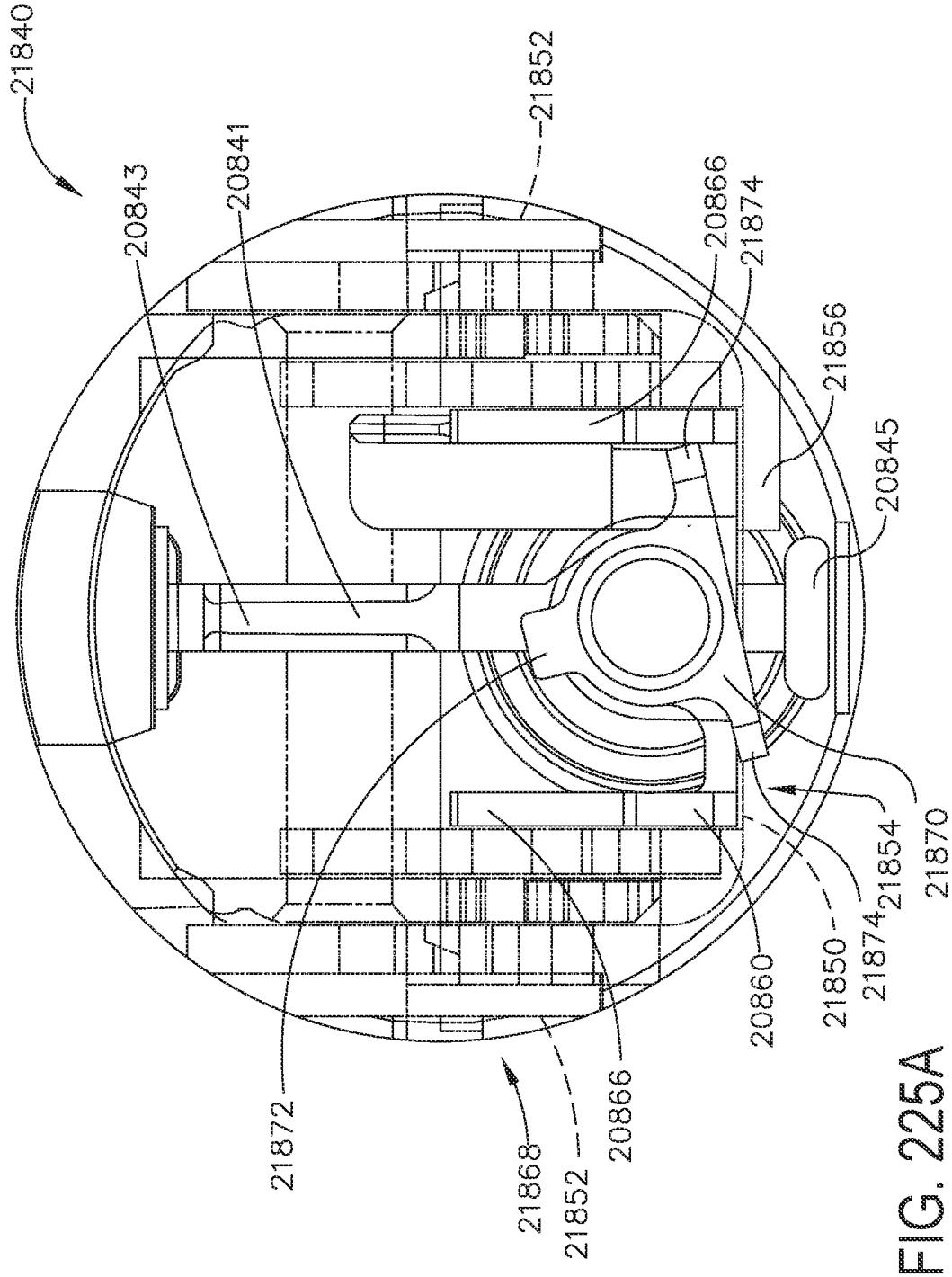

FIG. 225A is an elevation view of the end effector of FIG. 224 with certain parts removed and other parts hidden and shown with phantom lines, depicting the lock nut in the locked position, according to various aspects of the present disclosure.

Figure 225B:
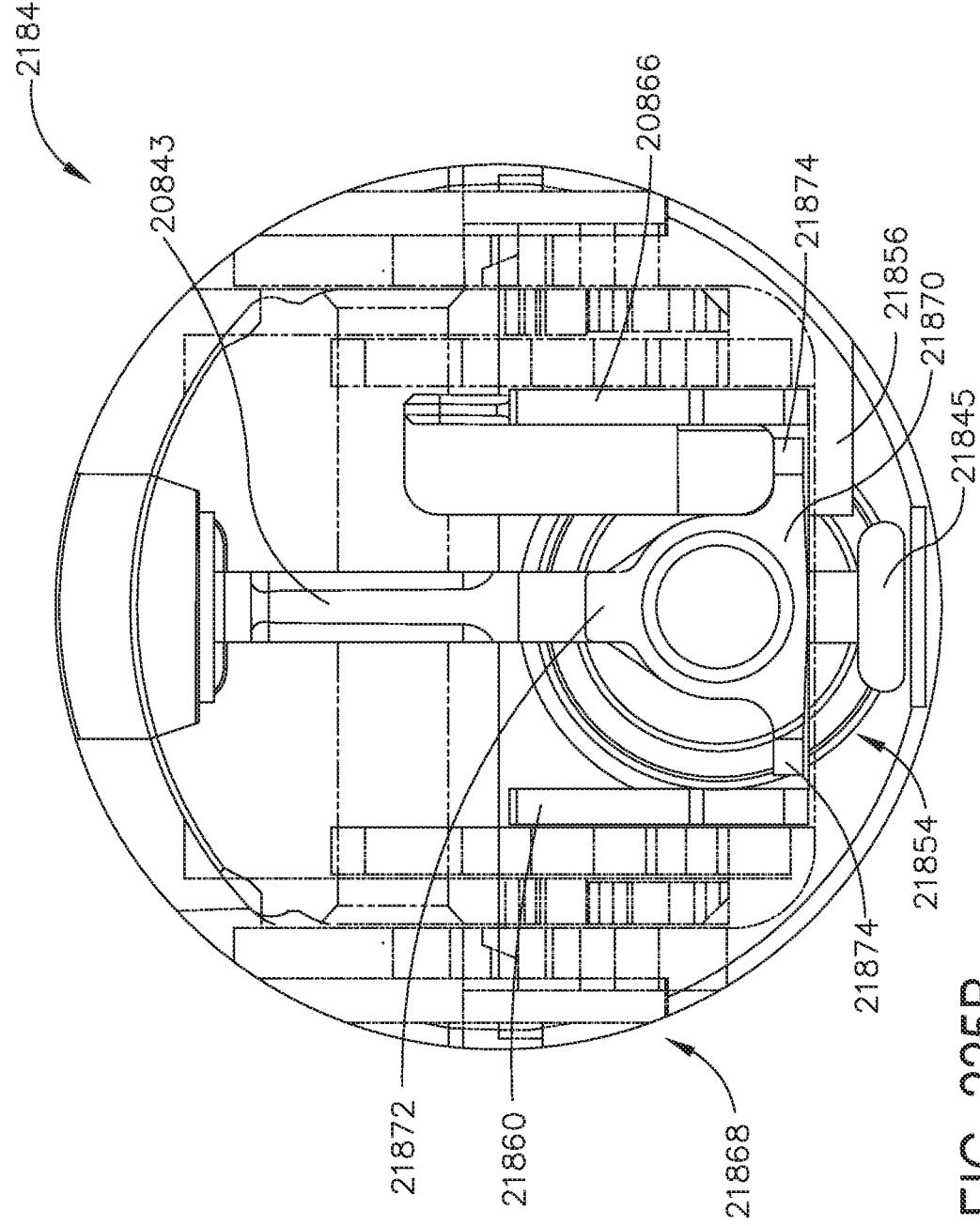

FIG. 225B is an elevation cross-section view of the end effector of FIG. 224 with certain parts removed and other parts hidden and shown with phantom lines, depicting the lock nut in an unlocked position, according to various aspects of the present disclosure.

FIG. 226 is a perspective view of a portion of the cartridge body of FIG. 219 and further depicting a lockout key in a proximal position in the cartridge body, according to various aspects of the present disclosure.

Figure 227:
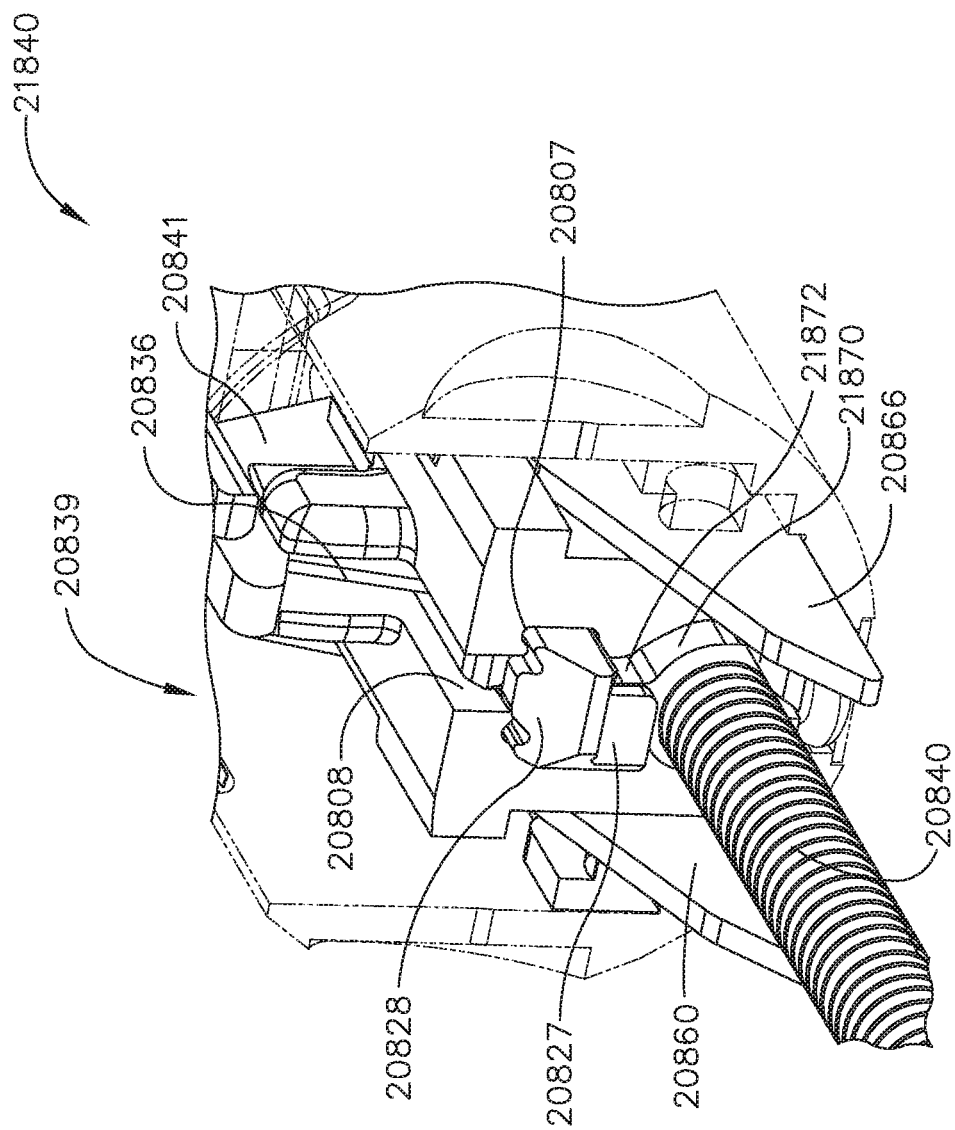

FIG. 227 is a perspective view of a portion of the end effector of FIG. 224 with the cartridge body of FIG. 226 installed in the end effector and the lockout key in a proximal position in which the lockout key is positioned to overcome the lockout arrangement by moving the lock nut to the unlocked position of FIG. 225B, according to various aspects of the present disclosure.

Figure 228:
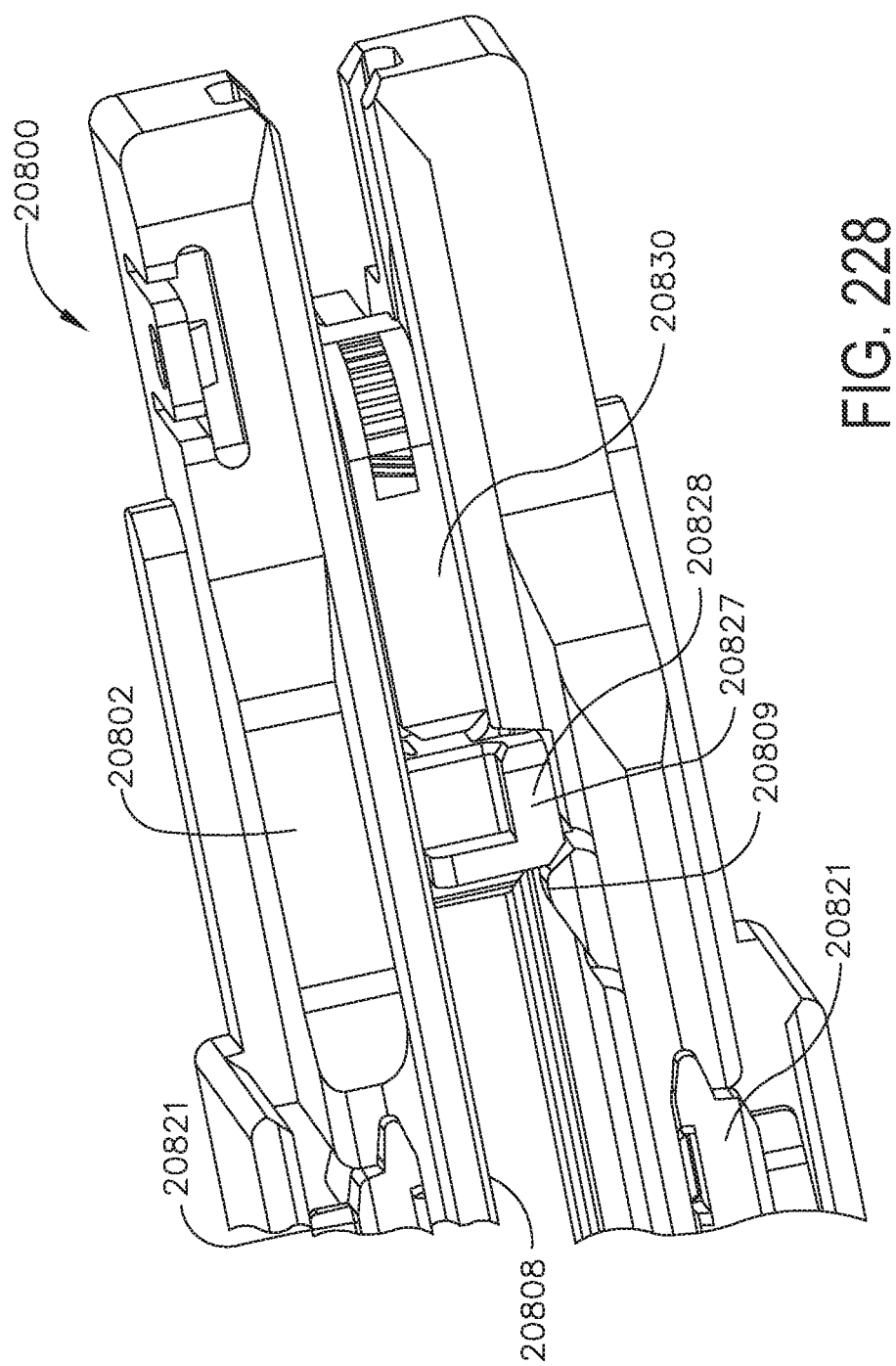

FIG. 228 is a perspective view of a portion of the underside of the cartridge body of FIG. 226, depicting the lockout key in the unfired position, according to various aspects of the present disclosure.

Figure 229:
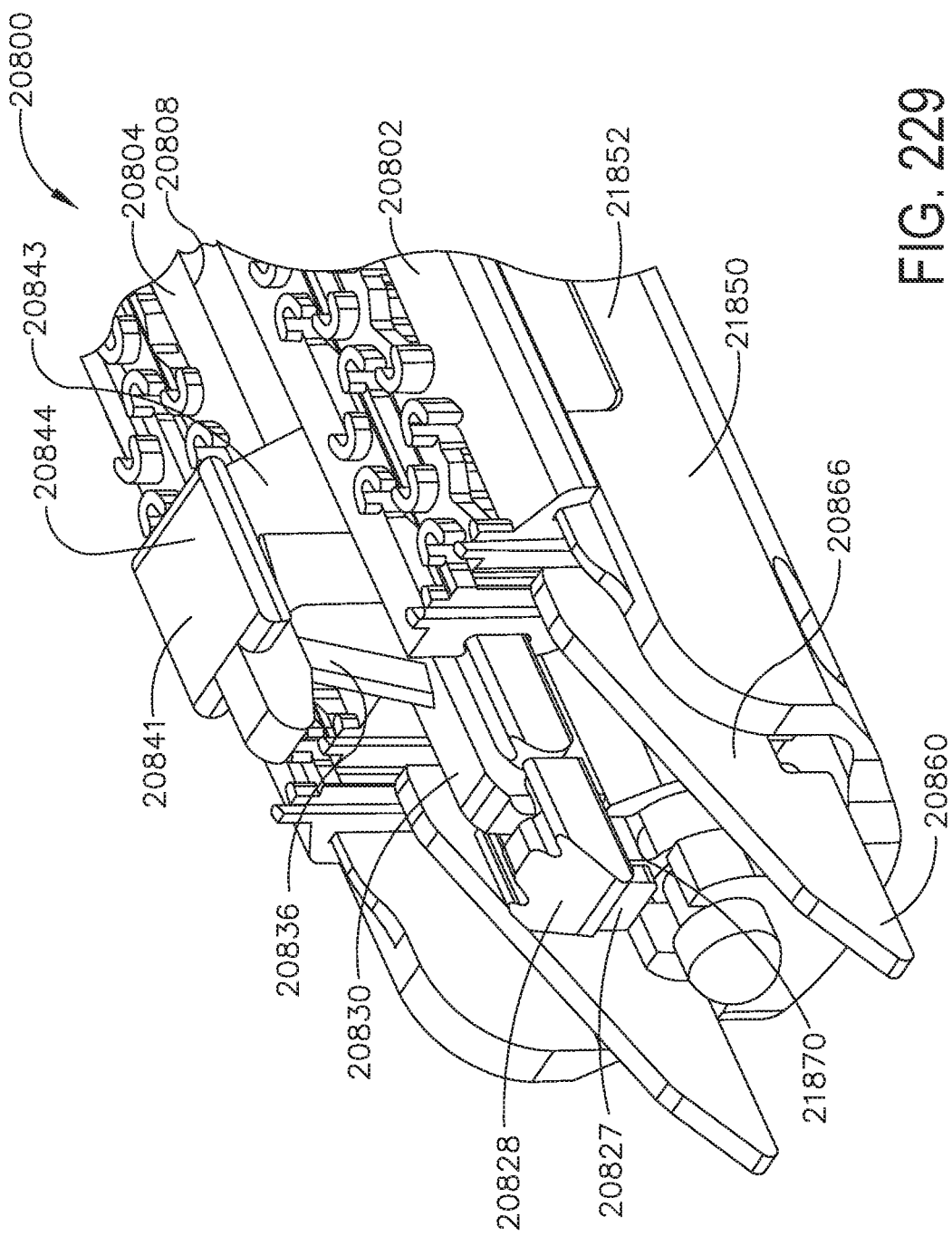

FIG. 229 is a perspective partial cutaway view of a portion of the end effector of FIG. 224 with the cartridge body of FIG. 226 installed in the end effector and partially cutaway for illustrative purposes to expose the lockout key advanced to a distal position, according to various aspects of the present disclosure.

Figure 230:
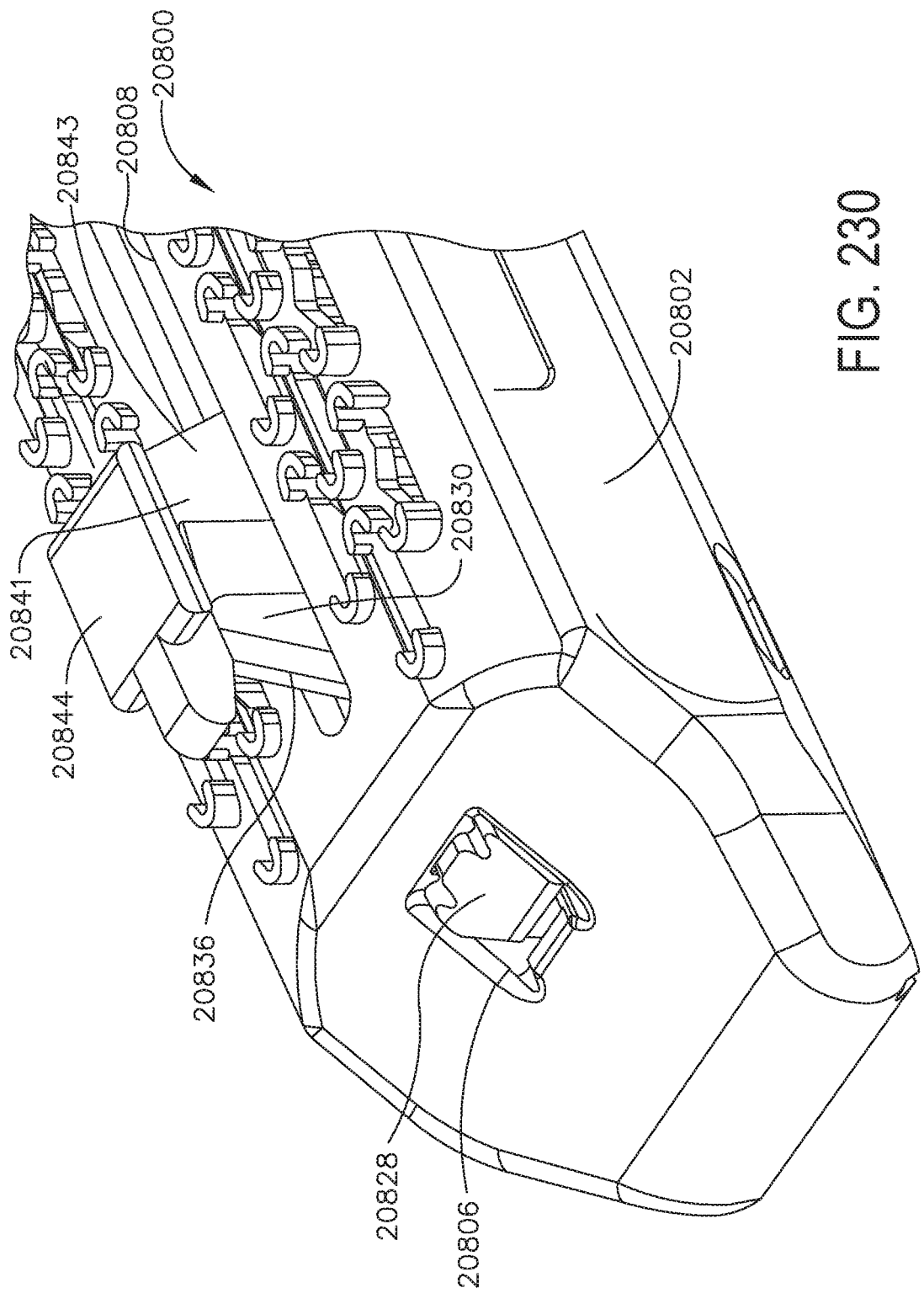

FIG. 230 is a perspective view of the portion of the end effector and the cartridge body of FIG. 229 with the lockout key in the distal position, according to various aspects of the present disclosure.

Figure 231:
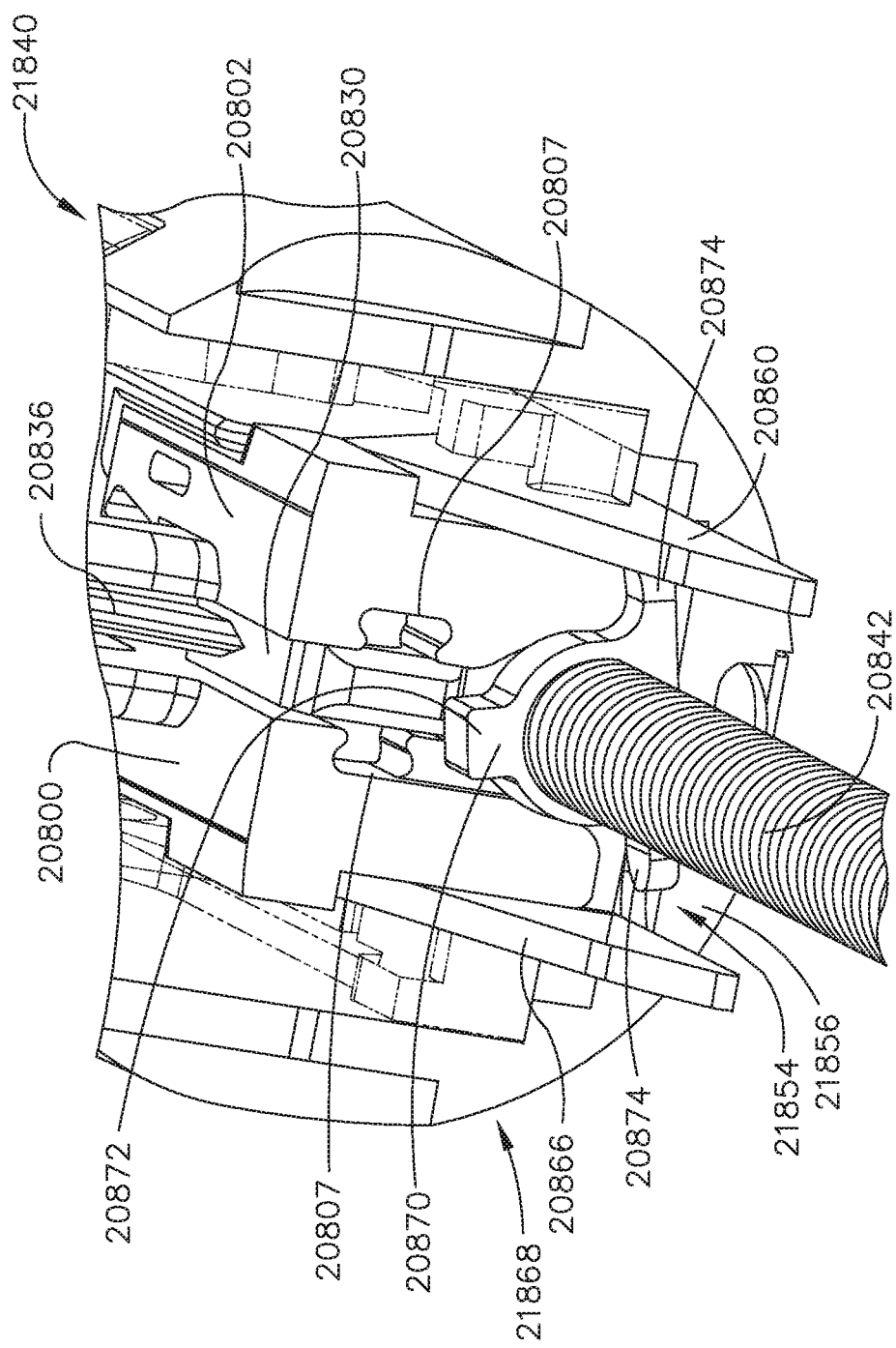

FIG. 231 is a perspective partial cutaway view of a portion of the end effector of FIG. 224 with the cartridge body of FIG. 226 installed in the end effector and partially cutaway for illustrative purposes to expose the lock nut in the locked position, according to various aspects of the present disclosure.

Figure 232:
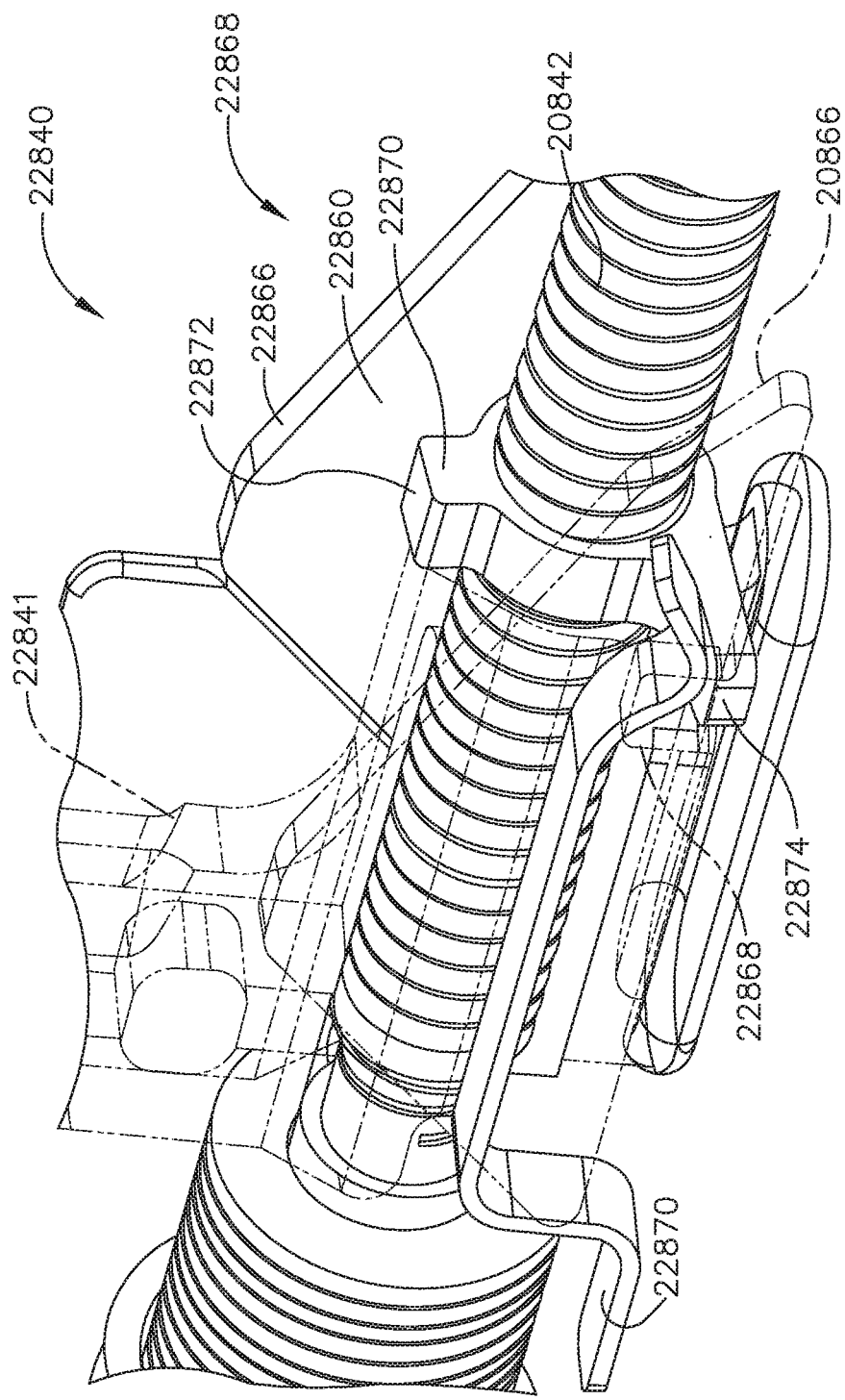

FIG. 232 is a perspective view of a portion of an end effector with certain portions removed and other portions transparent and shown with phantom lines for illustrative purposes, depicting a lockout arrangement in a locked configuration, according to various aspects of the present disclosure.

Figure 233:
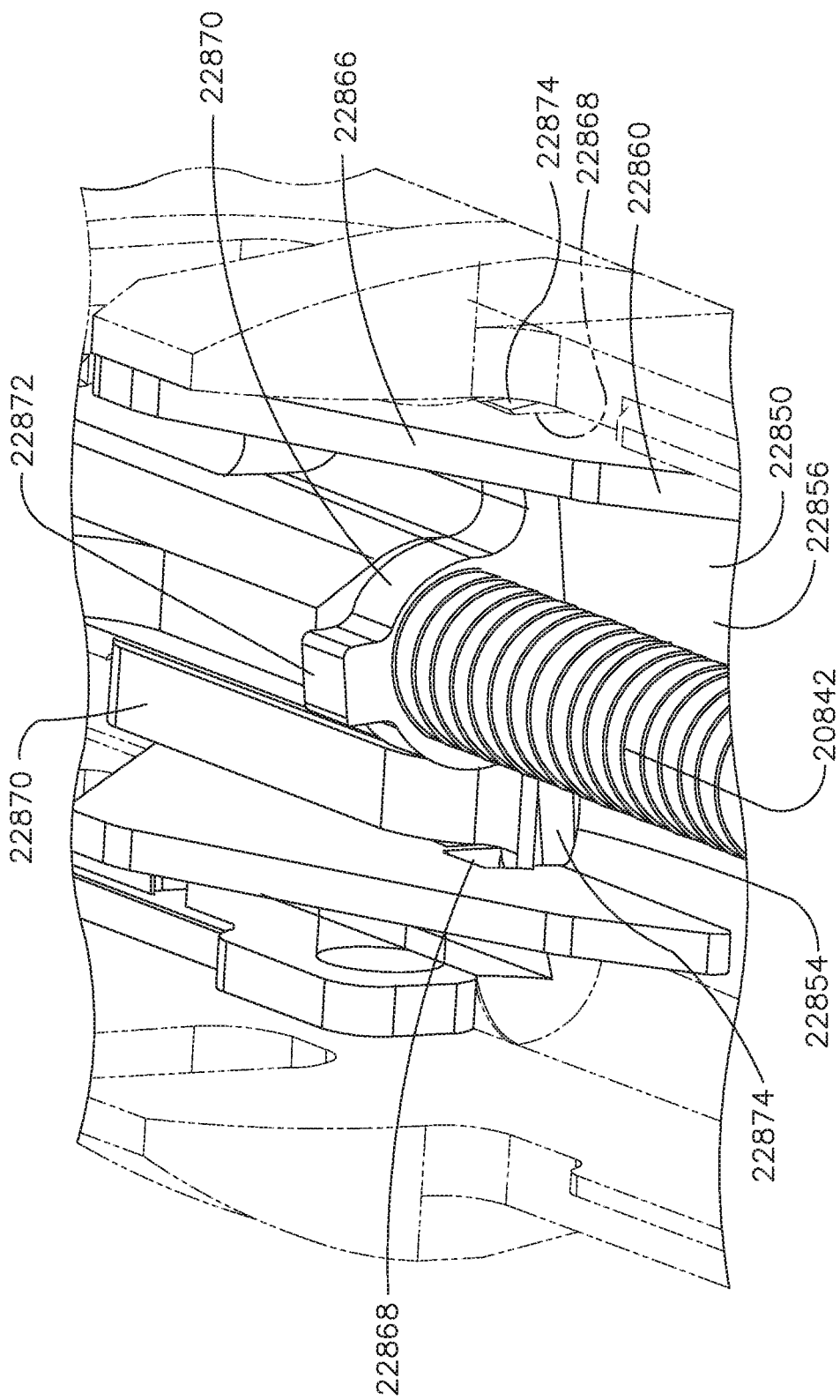

FIG. 233 is a perspective view of a portion of the end effector of FIG. 232 with certain portions removed and other portions transparent for illustrative purposes, depicting the lockout arrangement in the locked configuration, according to various aspects of the present disclosure.

Figure 234:
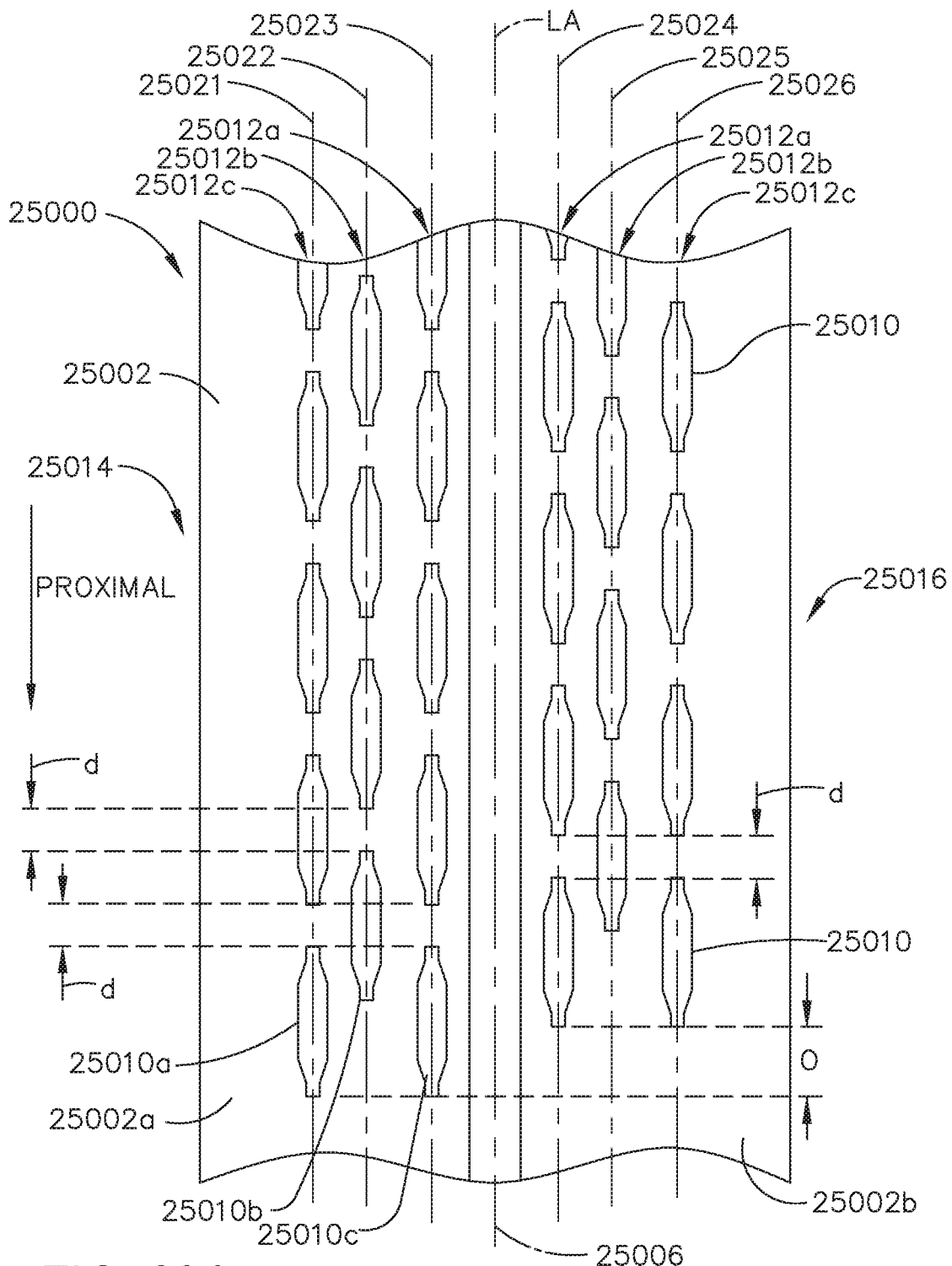

FIG. 234 is a plan view of a staple cartridge depicting patterns of staple cavities, according to various aspects of the present disclosure.

Figure 235:
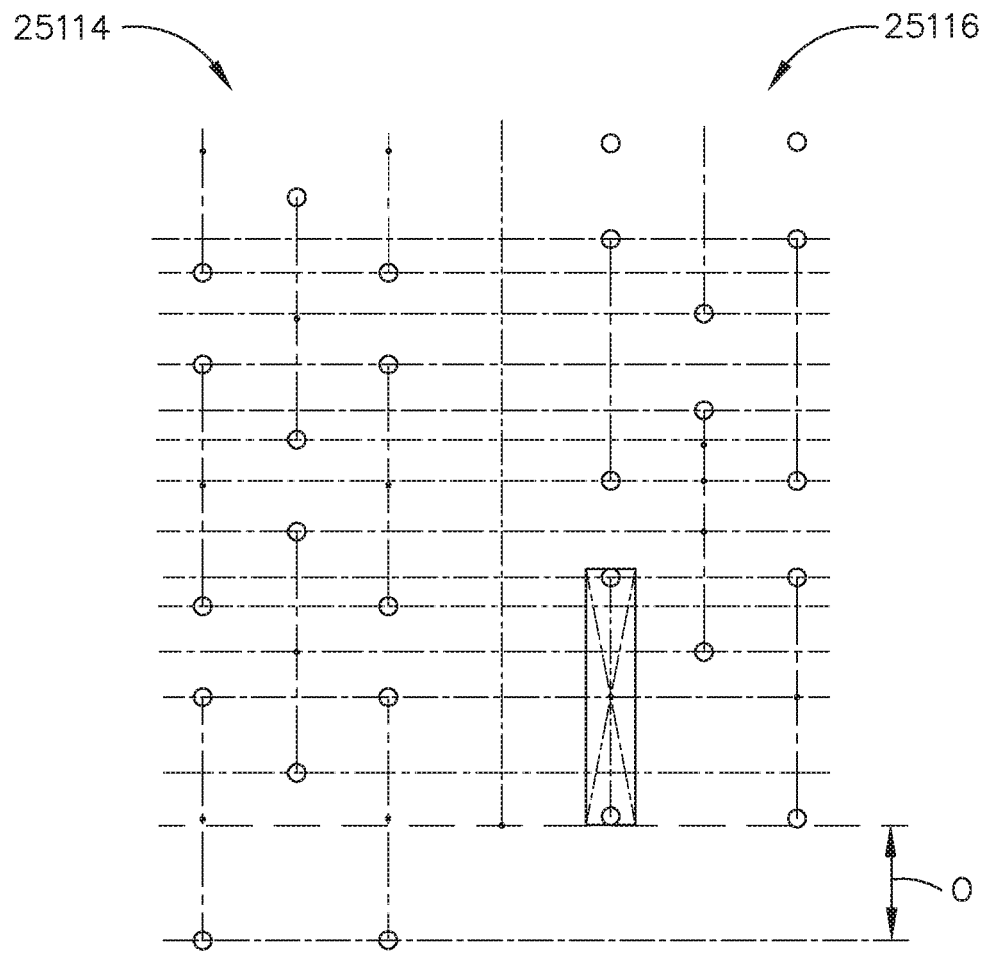

FIG. 235 is a schematic depicting staple cavity patterns for a staple cartridge, according to various aspects of the present disclosure.

Figure 236:
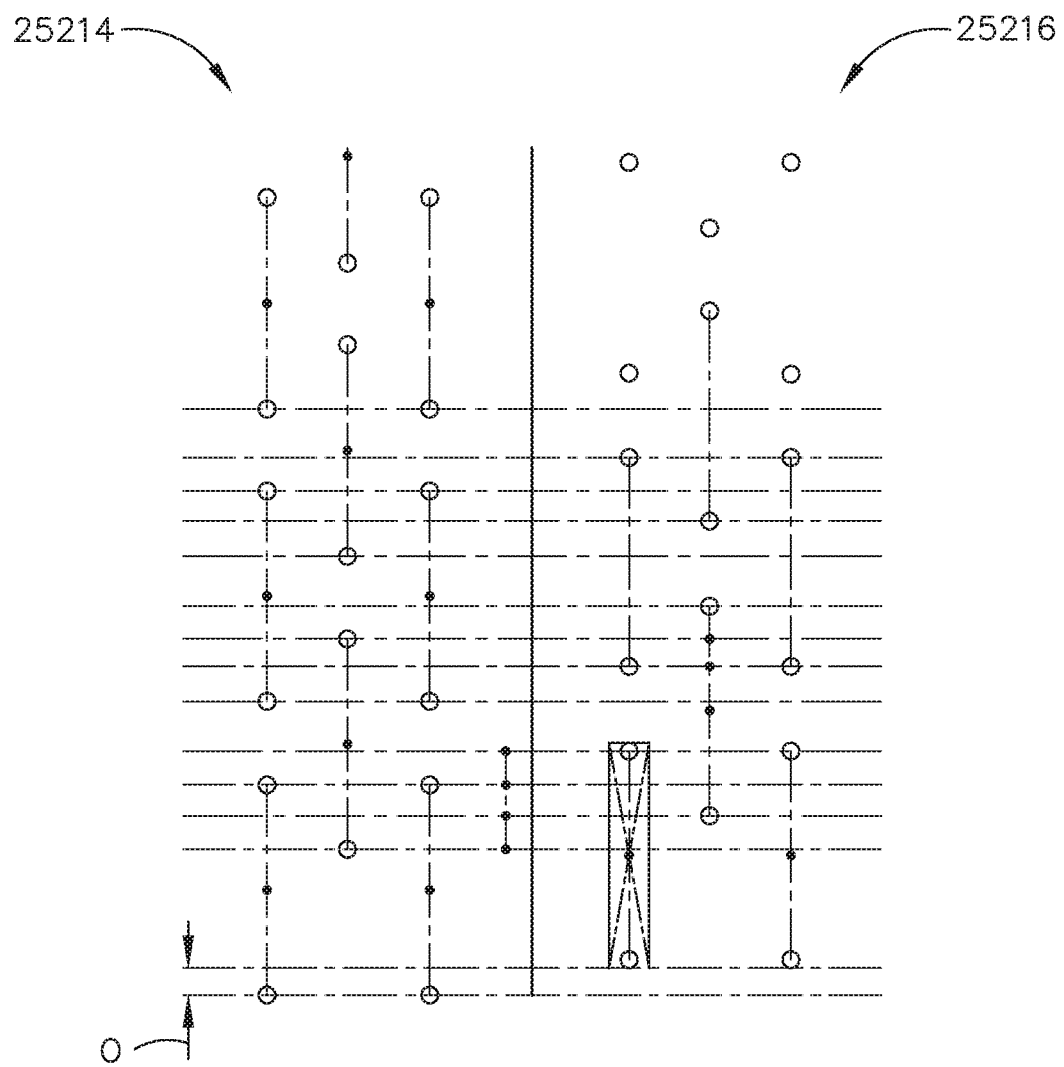

FIG. 236 is a schematic depicting staple cavity patterns for a staple cartridge, according to various aspects of the present disclosure.

Figure 237:
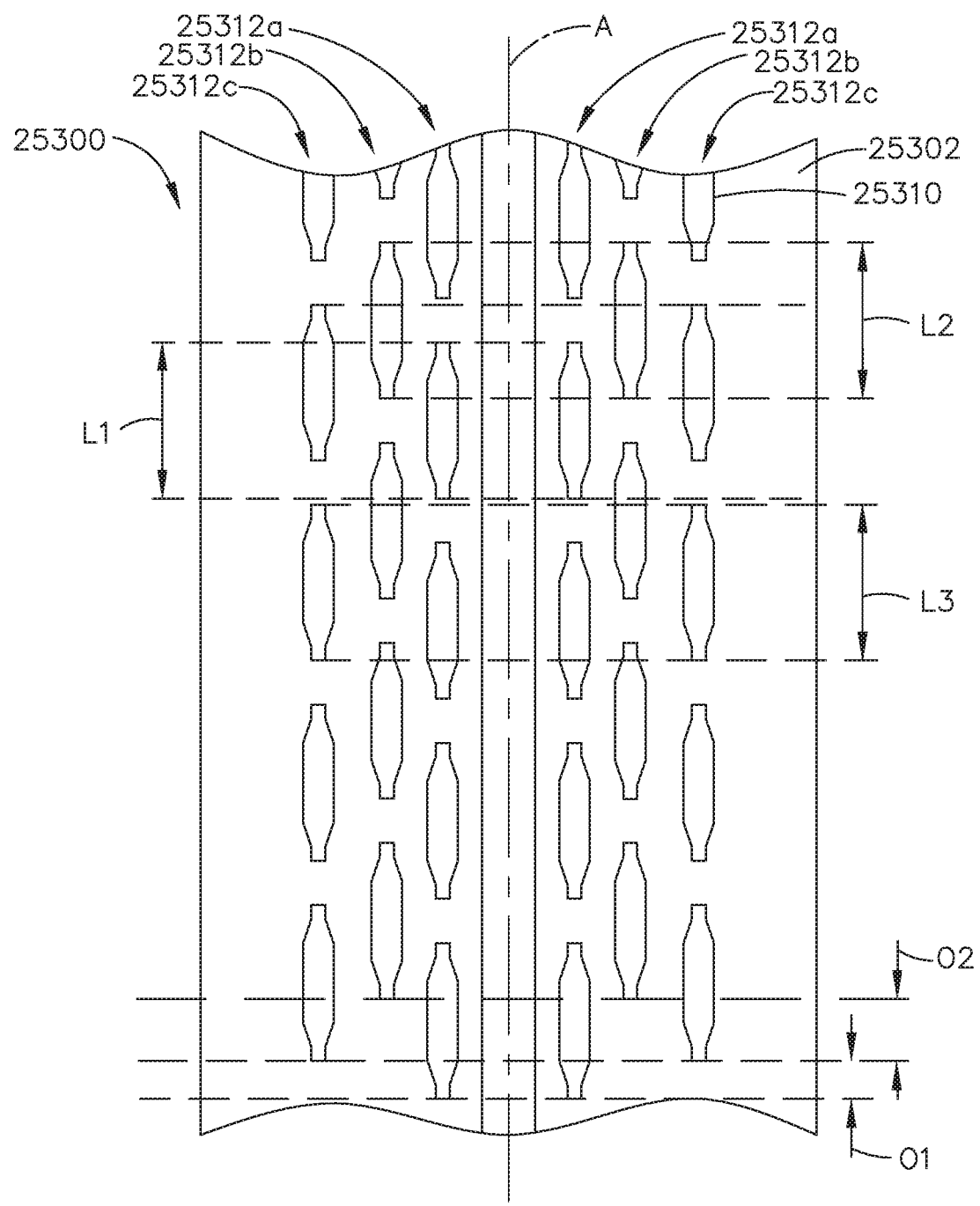

FIG. 237 is a plan view of a staple cartridge depicting patterns of staple cavities, according to various aspects of the present disclosure.

Figure 238:
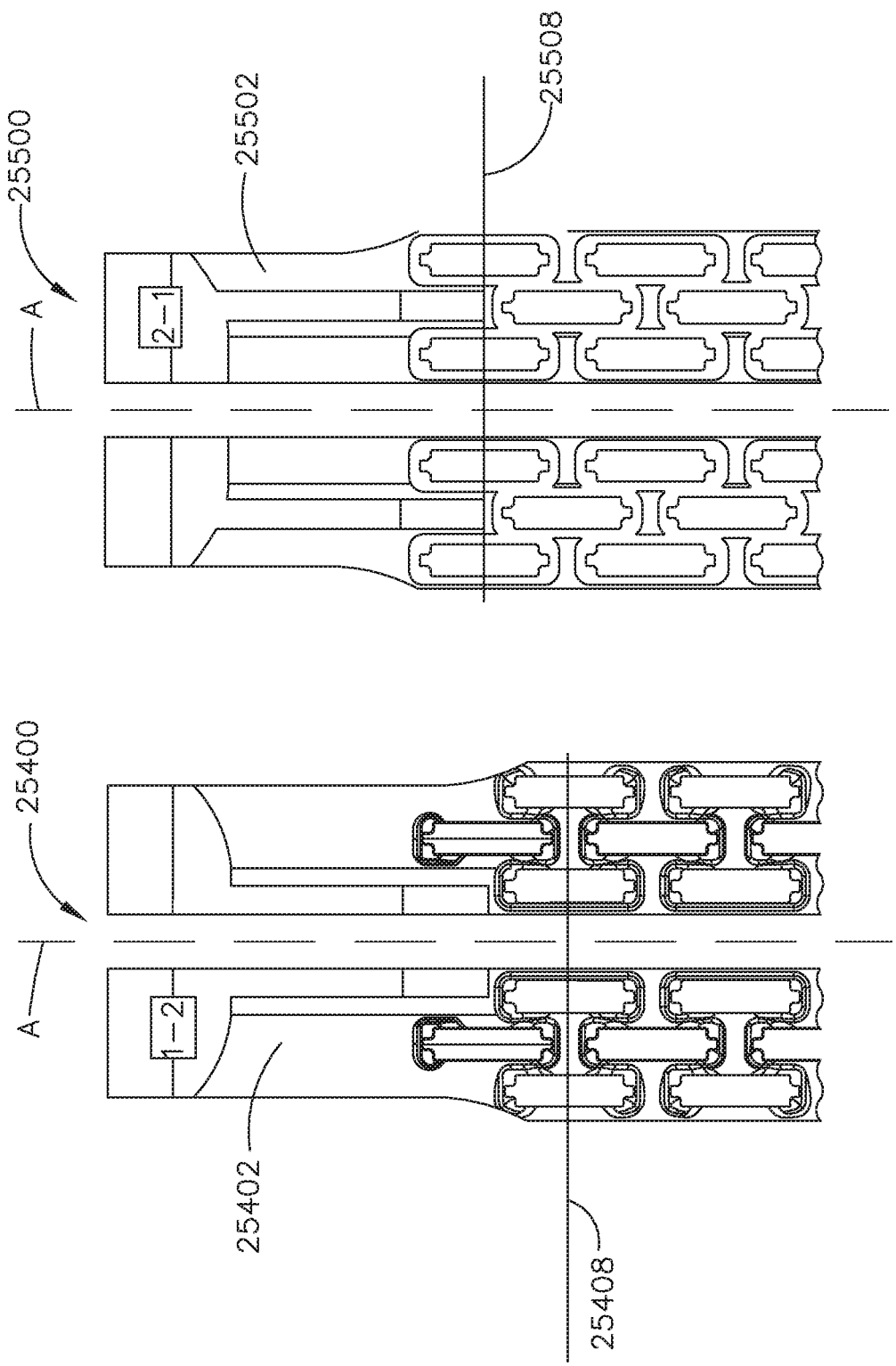

FIG. 238 is a plan view of staple cartridges schematically depicting a tissue stop, according to various aspects of the present disclosure.

Figure 239:
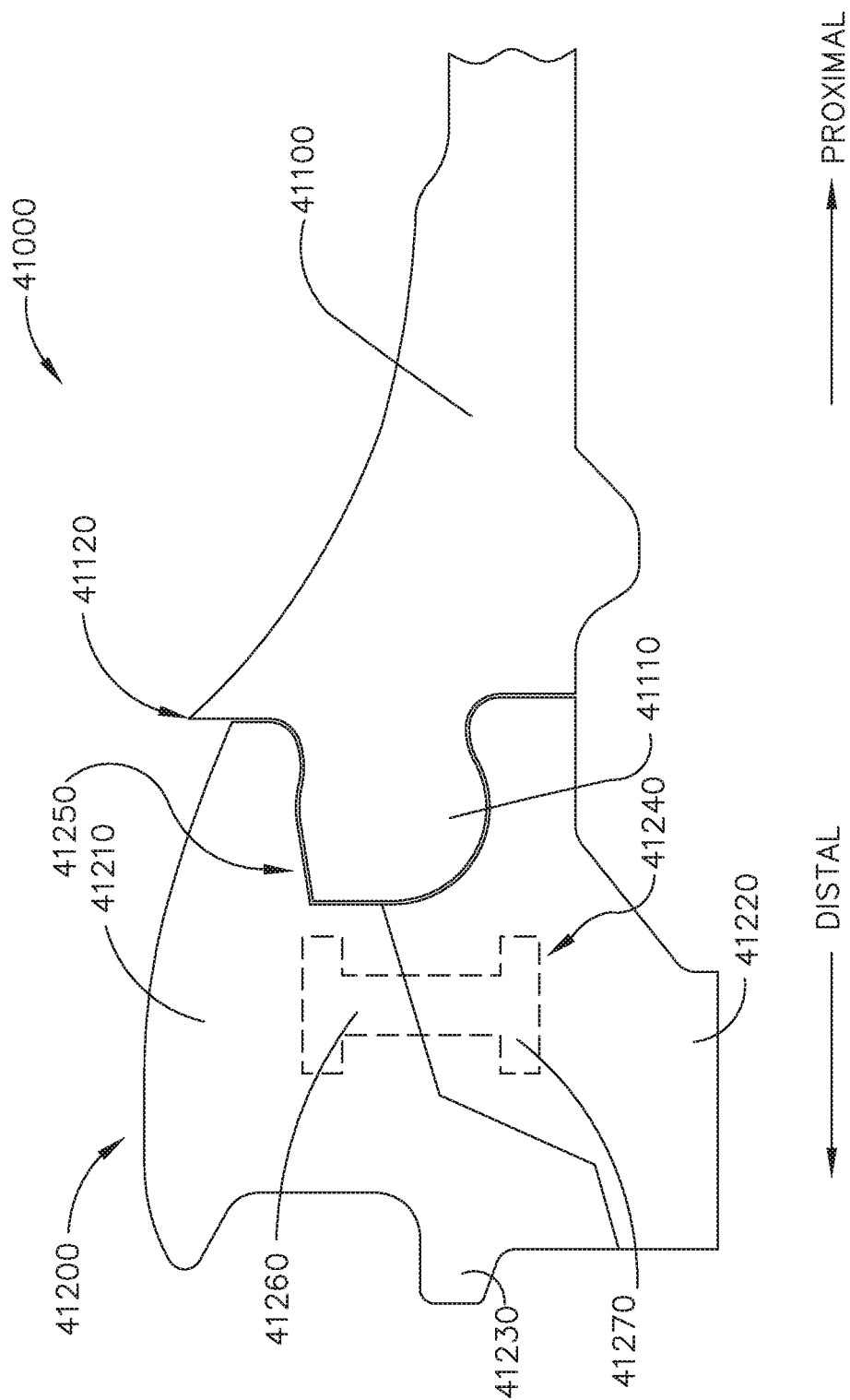

FIG. 239 is a side elevation view of a firing member, according to various aspects of the present disclosure.

Figure 240:
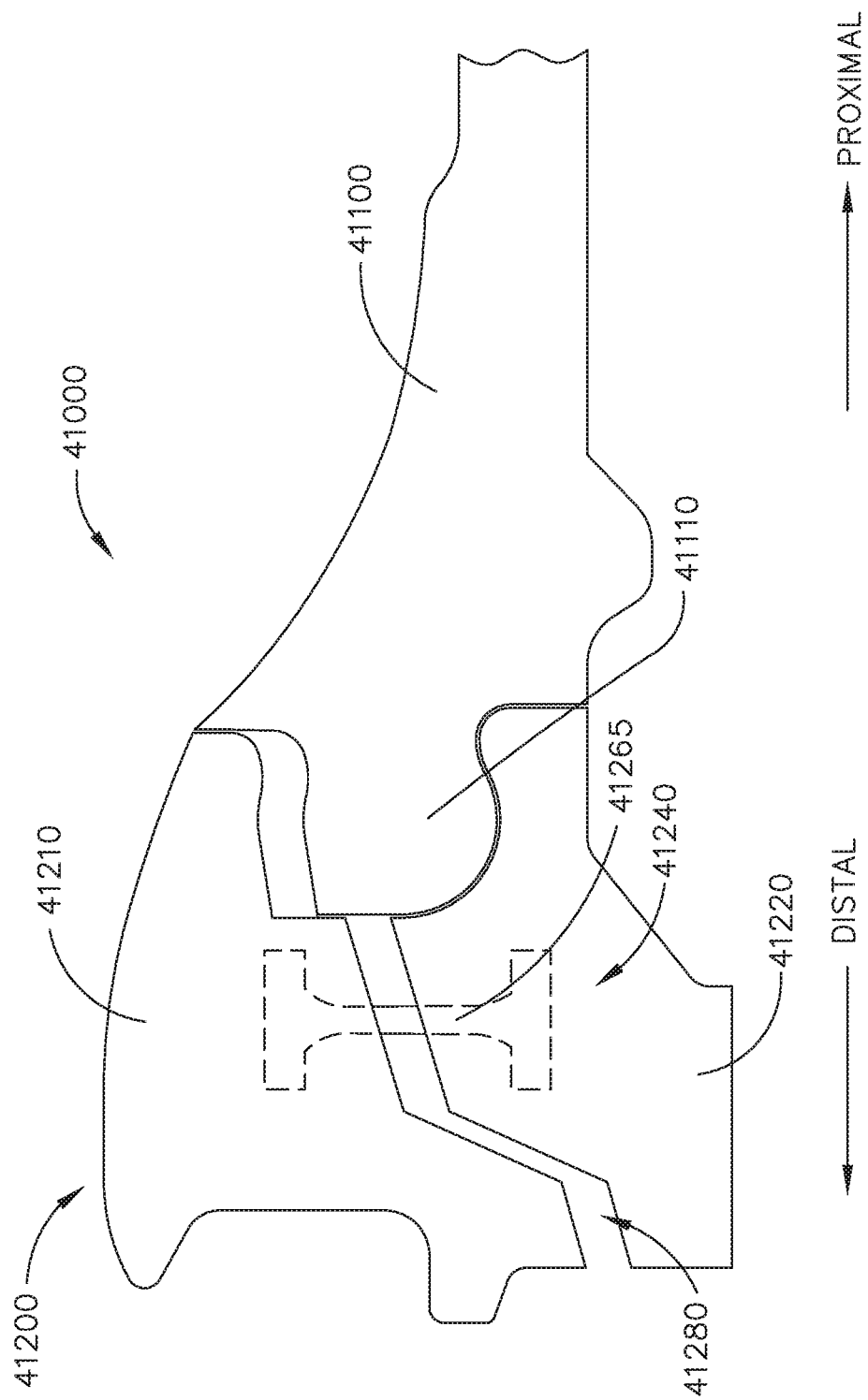

FIG. 240 is a side elevation view of the firing member of FIG. 239 in an expanded configuration, according to various aspects of the present disclosure.

Figure 241:
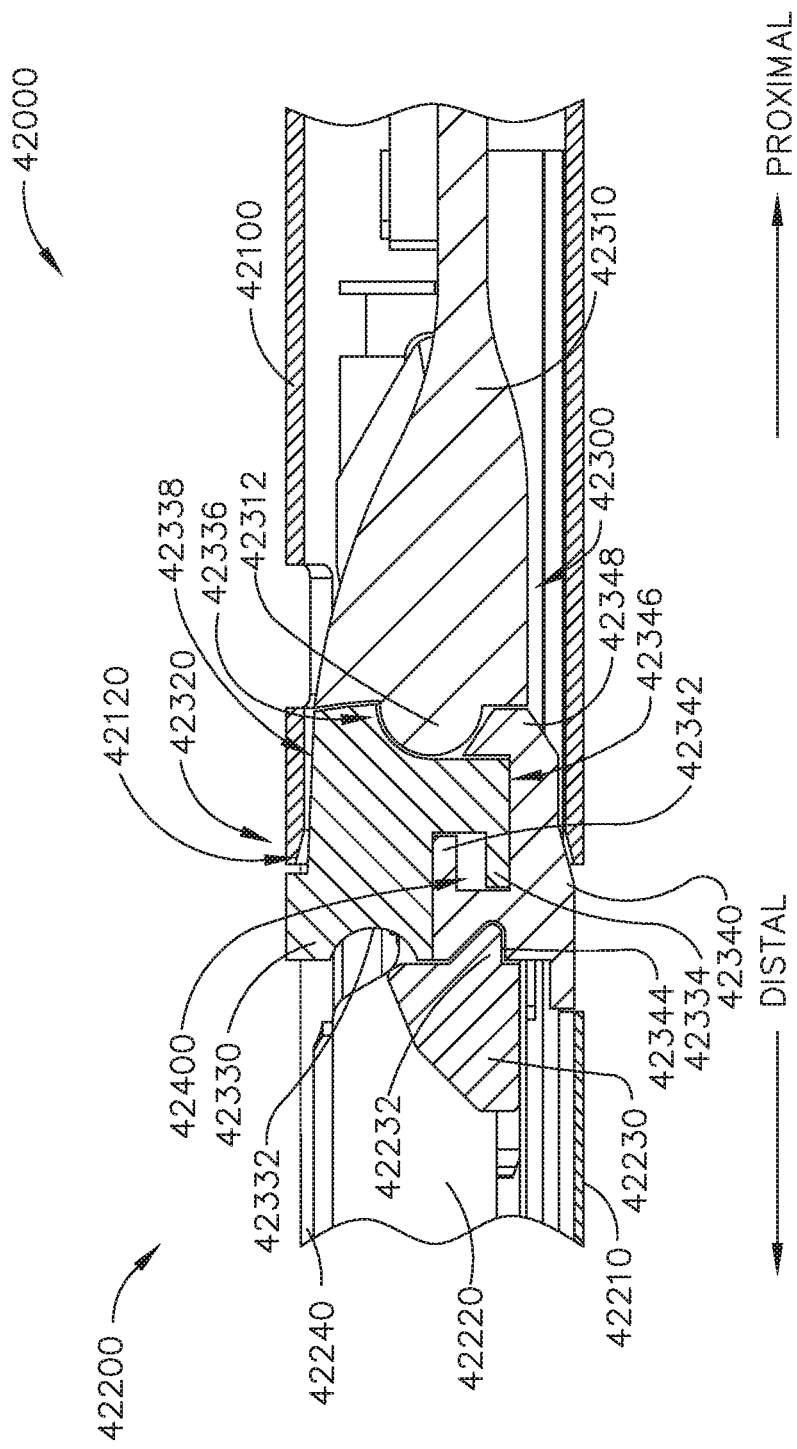

FIG. 241 is an elevation cross-section view of a portion of a surgical instrument including an expandable knife portion, according to various aspects of the present disclosure.

Figure 242:
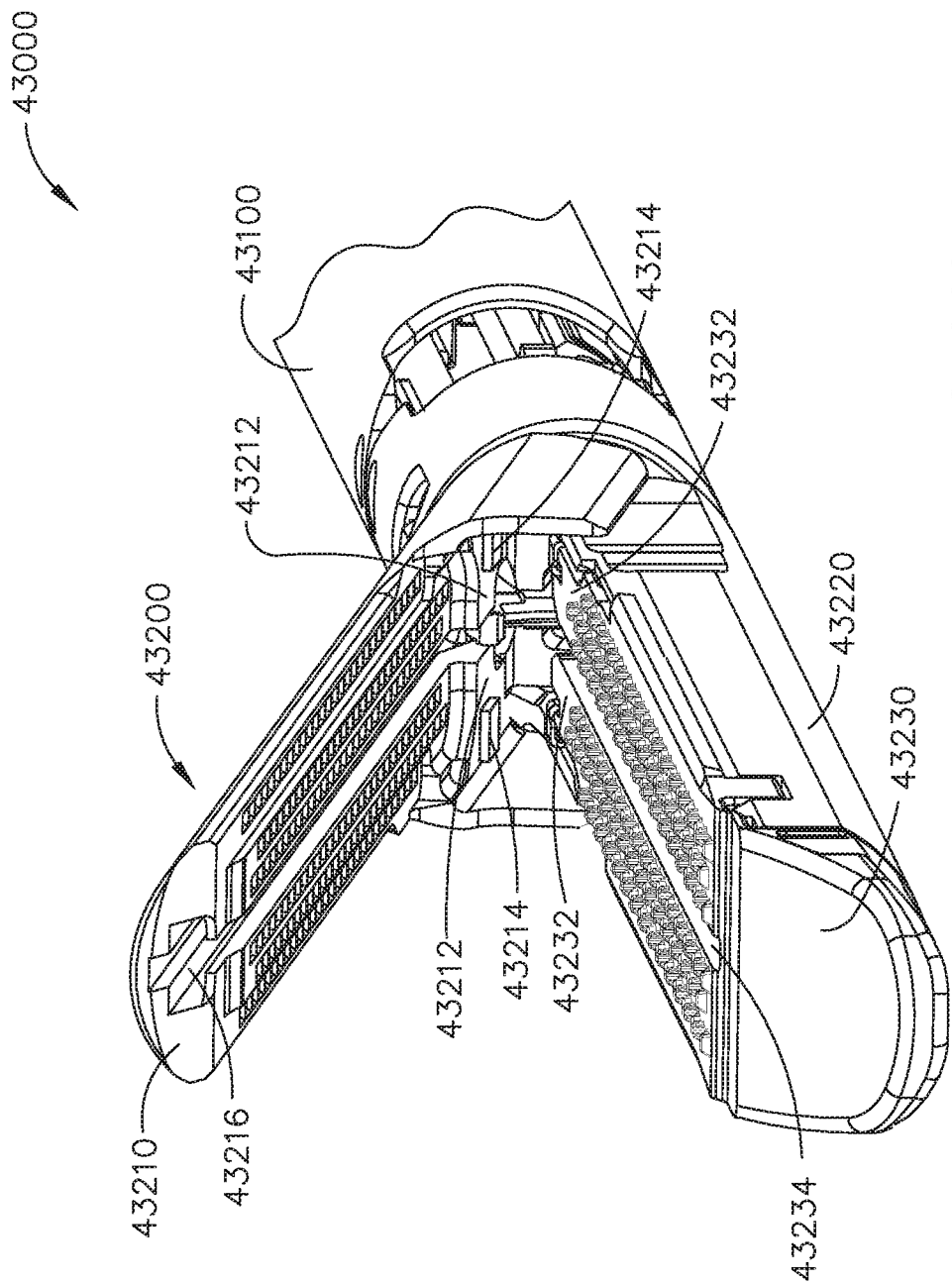

FIG. 242 is a perspective view of a surgical instrument including an anvil having a low durometer material, depicting the surgical instrument in an open configuration, according to various aspects of the present disclosure.

Figure 243:
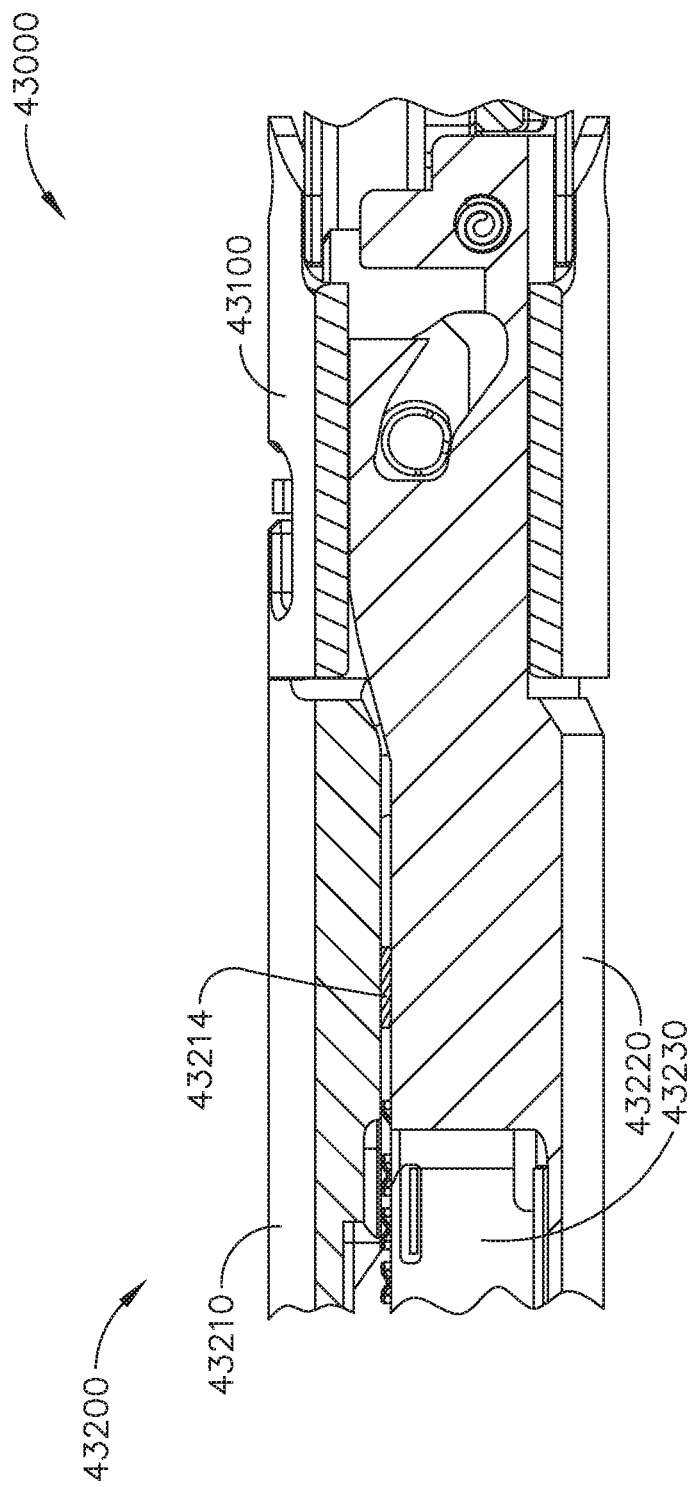

FIG. 243 is an elevation cross-section view of the surgical instrument of FIG. 242, depicting the surgical instrument in a closed configuration, according to various aspects of the present disclosure.

Figure 244:
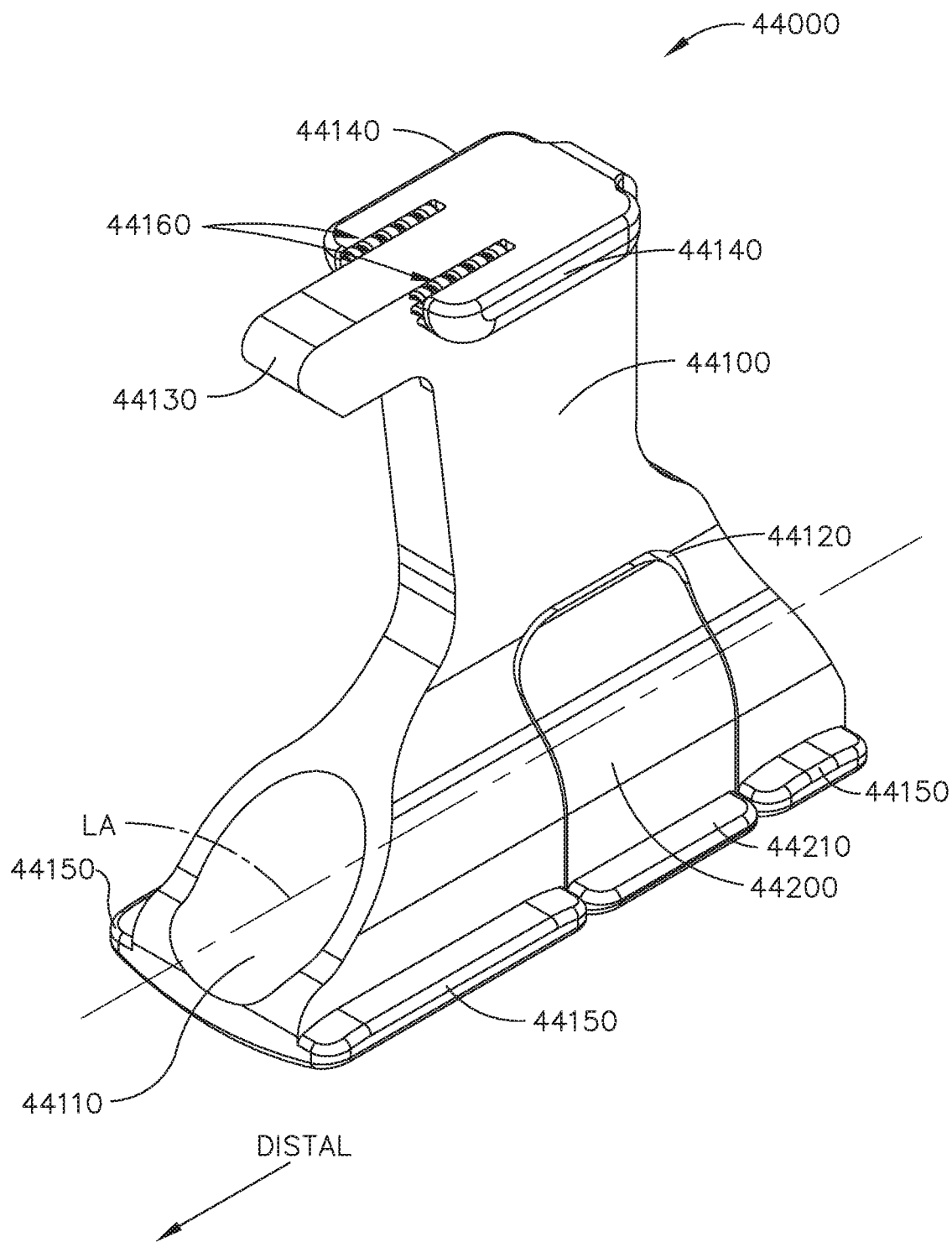

FIG. 244 is a perspective view of a firing member for use with a surgical instrument, according to various aspects of the present disclosure.

Figure 245:
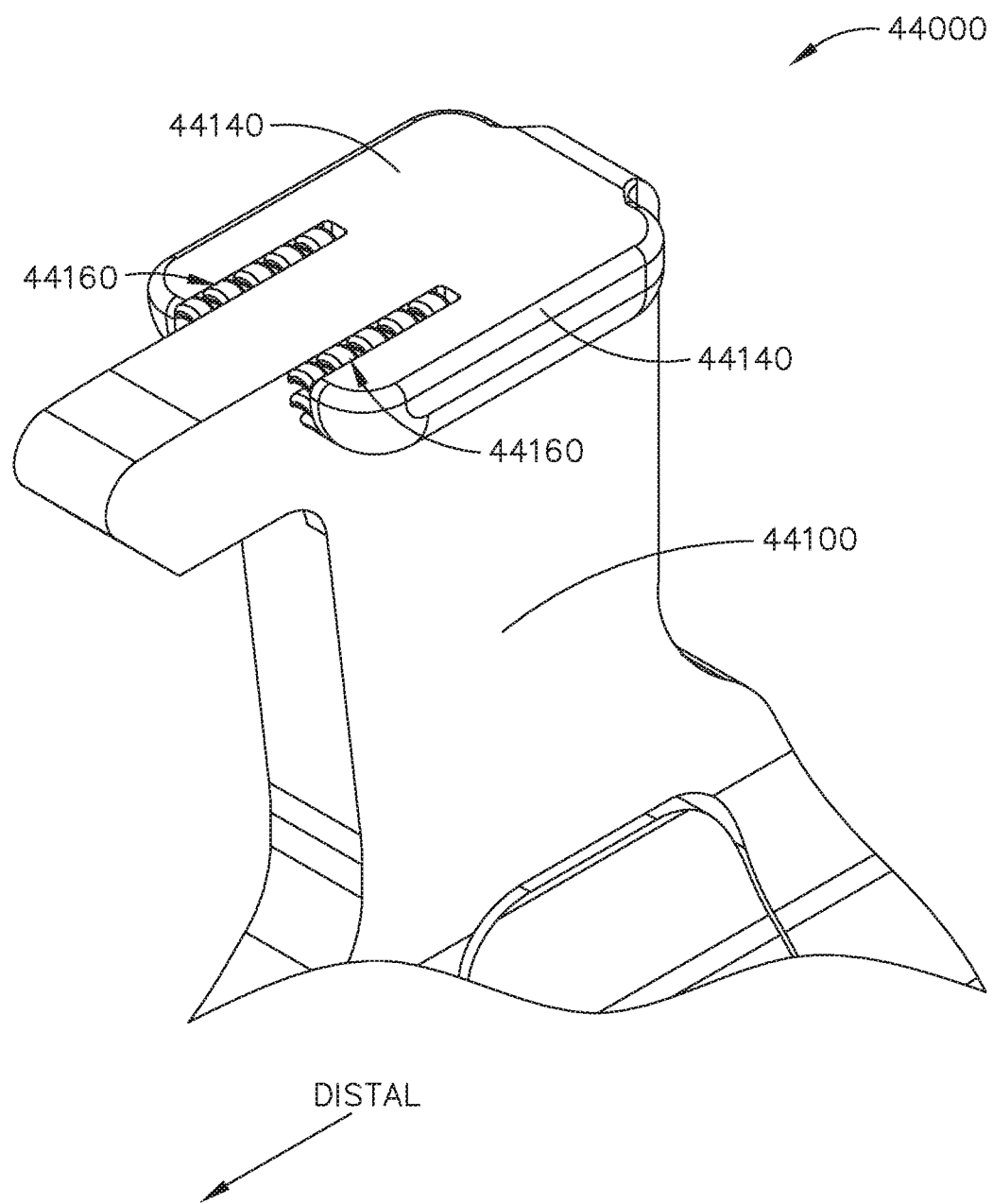

FIG. 245 is an enlarged view of a portion of the firing member of FIG. 244, according to various aspects of the present disclosure.

Figure 246:
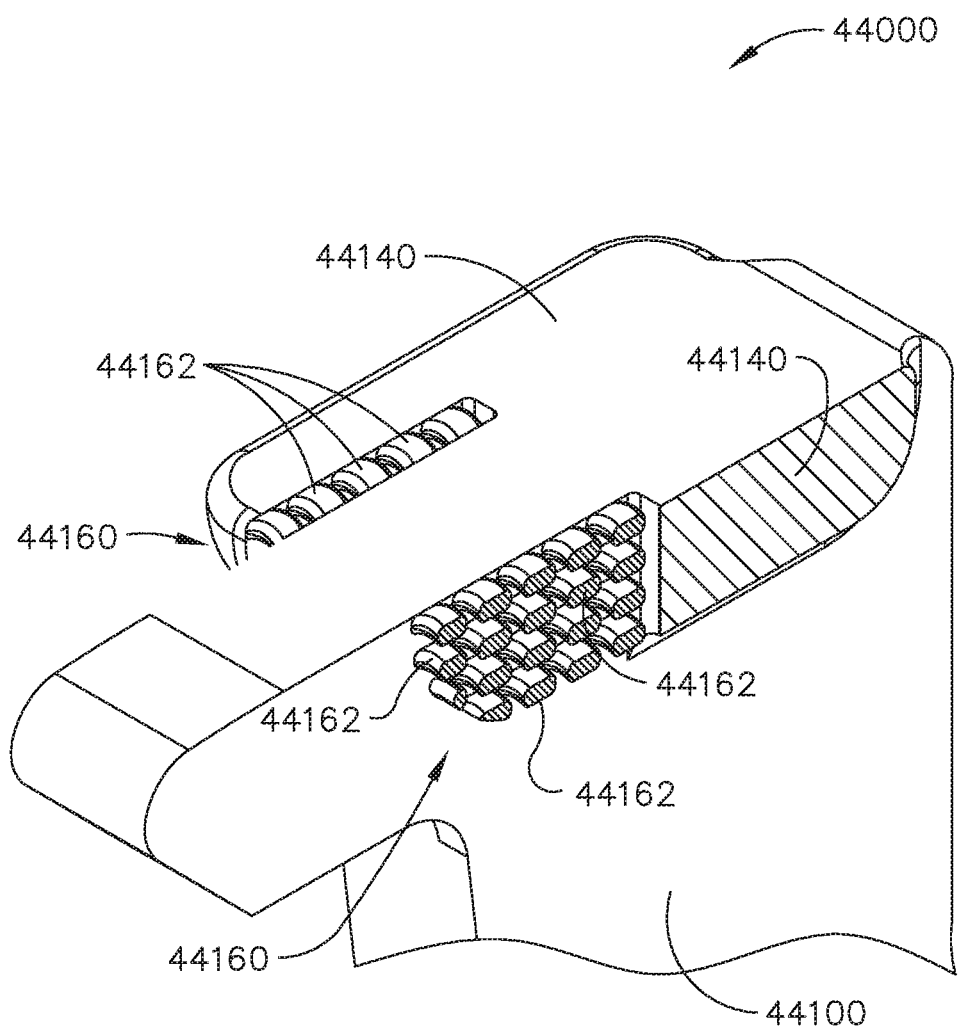

FIG. 246 is a perspective partial cross-section view of a portion of the firing member of FIG. 244, according to various aspects of the present disclosure.

Figure 247:
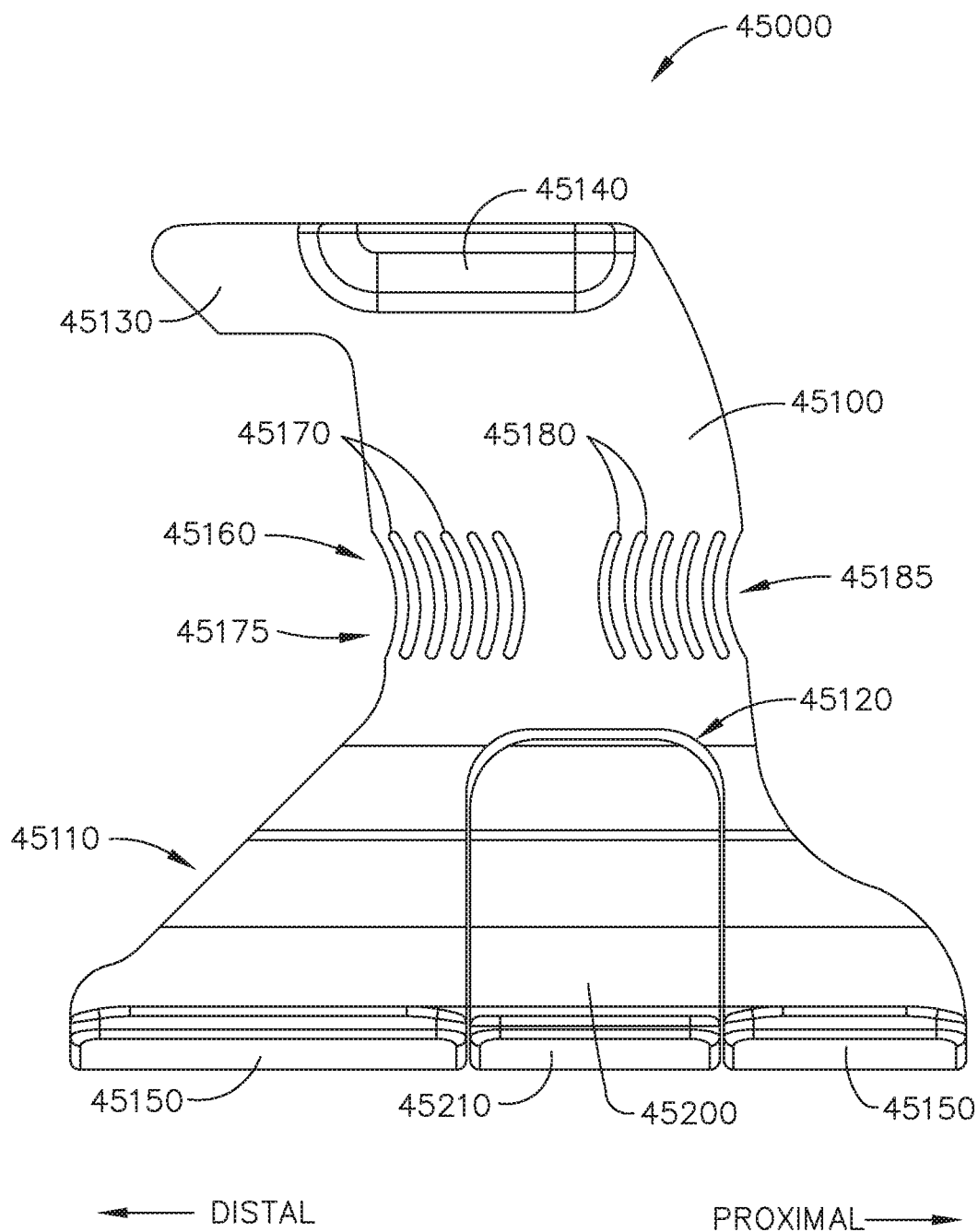

FIG. 247 is a side elevation view of a firing member for use with a surgical instrument, depicting the firing member in a first configuration, according to various aspects of the present disclosure.

Figure 248:
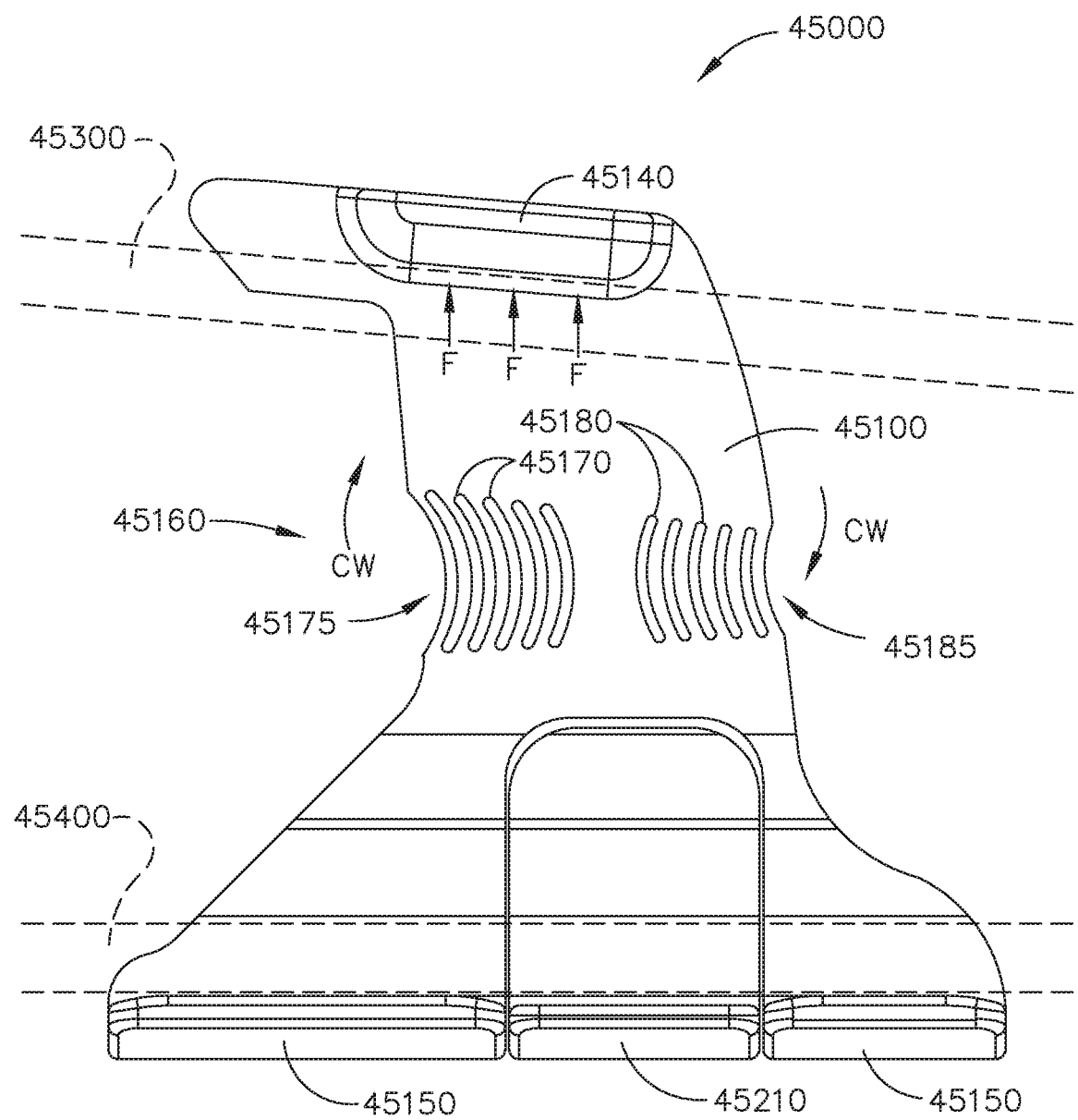

FIG. 248 is side elevation view of the firing member of FIG. 247 in a second configuration in which the firing member is deformed from the first configuration to a loaded configuration and depicting portions of a channel and an anvil with dashed lines for environmental structure, according to various aspects of the present disclosure.

Figure 249:
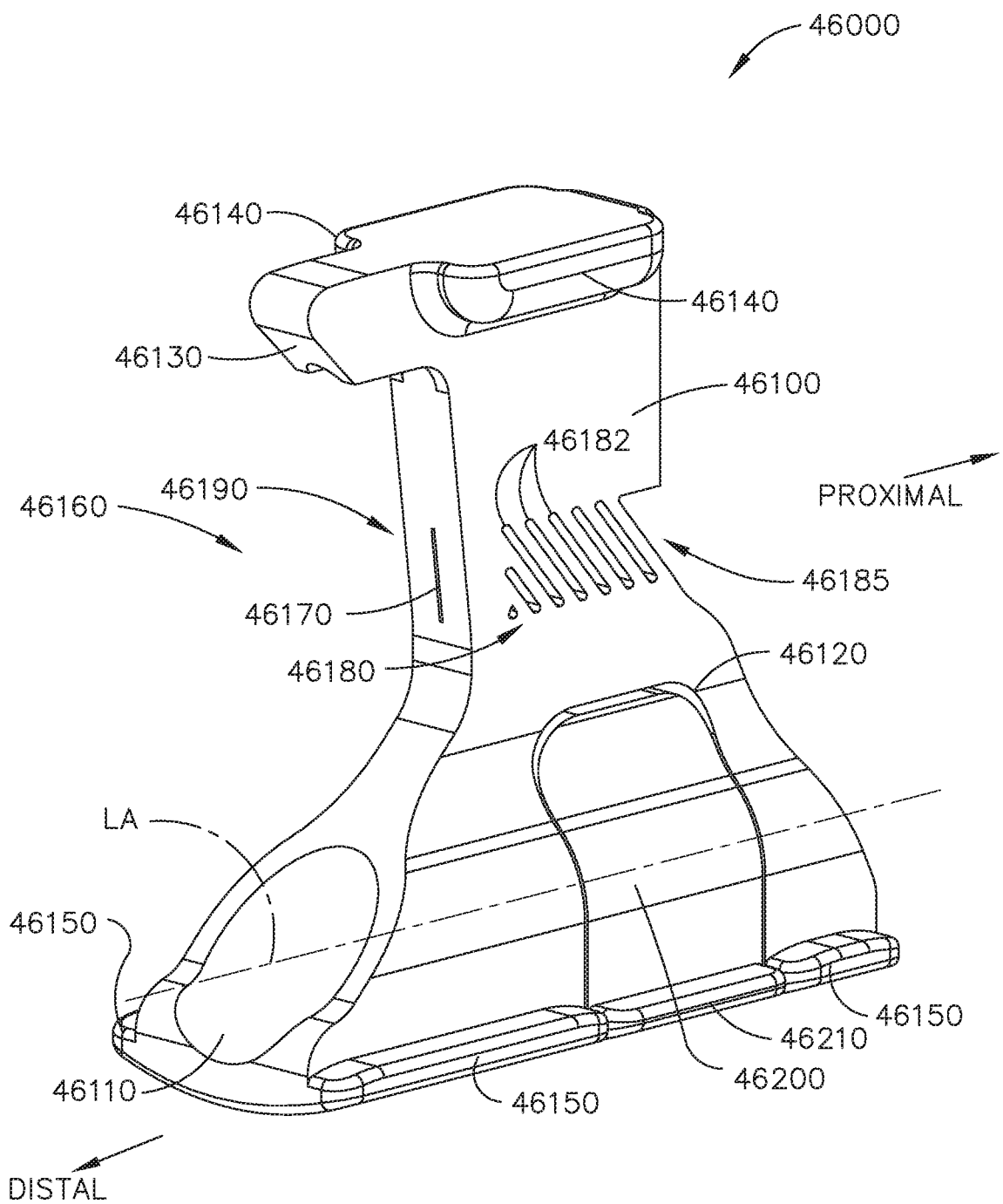

FIG. 249 is a perspective view of a firing member for use with a surgical instrument, according to various aspects of the present disclosure.

Figure 250:
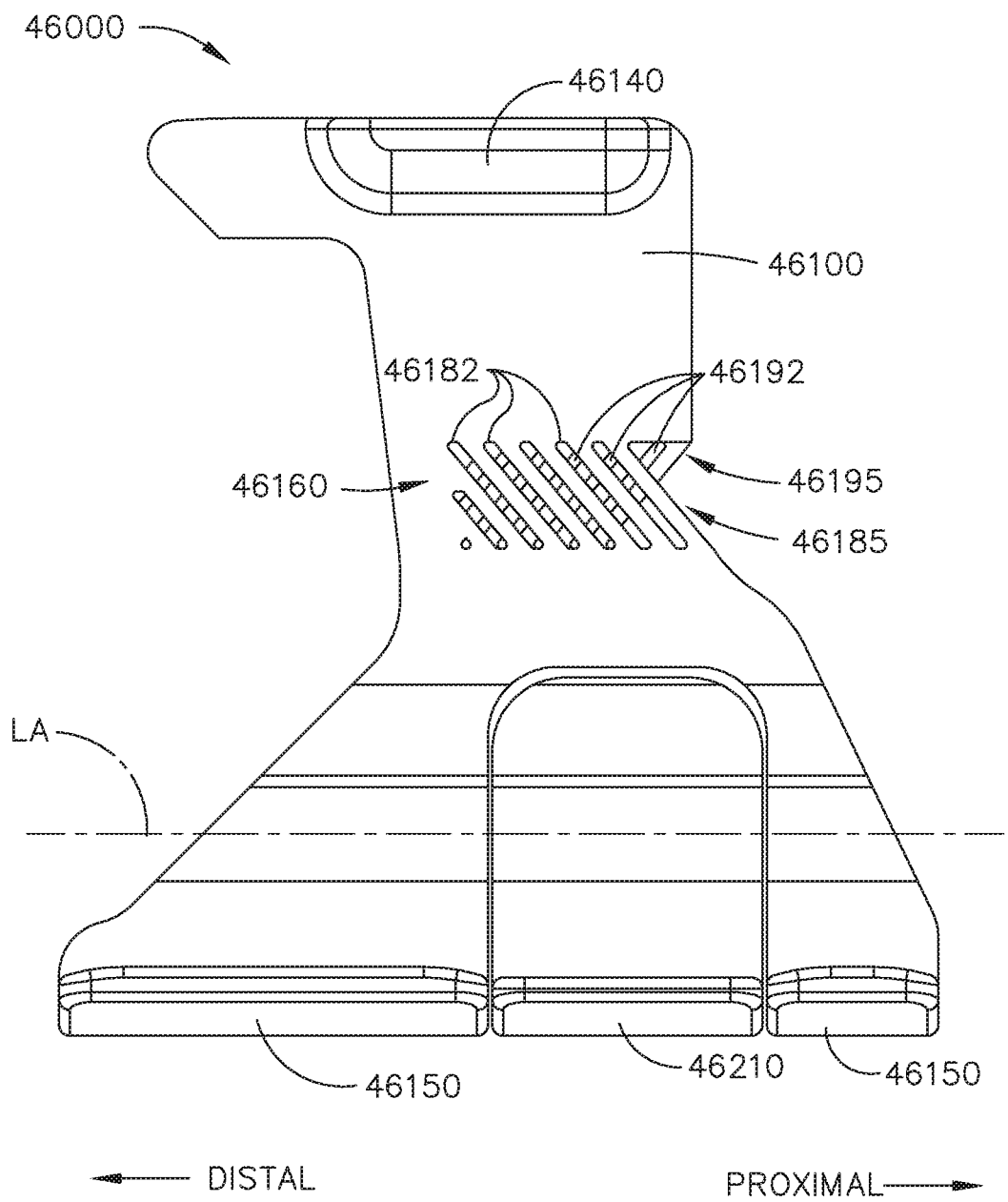

FIG. 250 is side elevation view of the firing member of FIG. 249, according to various aspects of the present disclosure.

Figure 251:
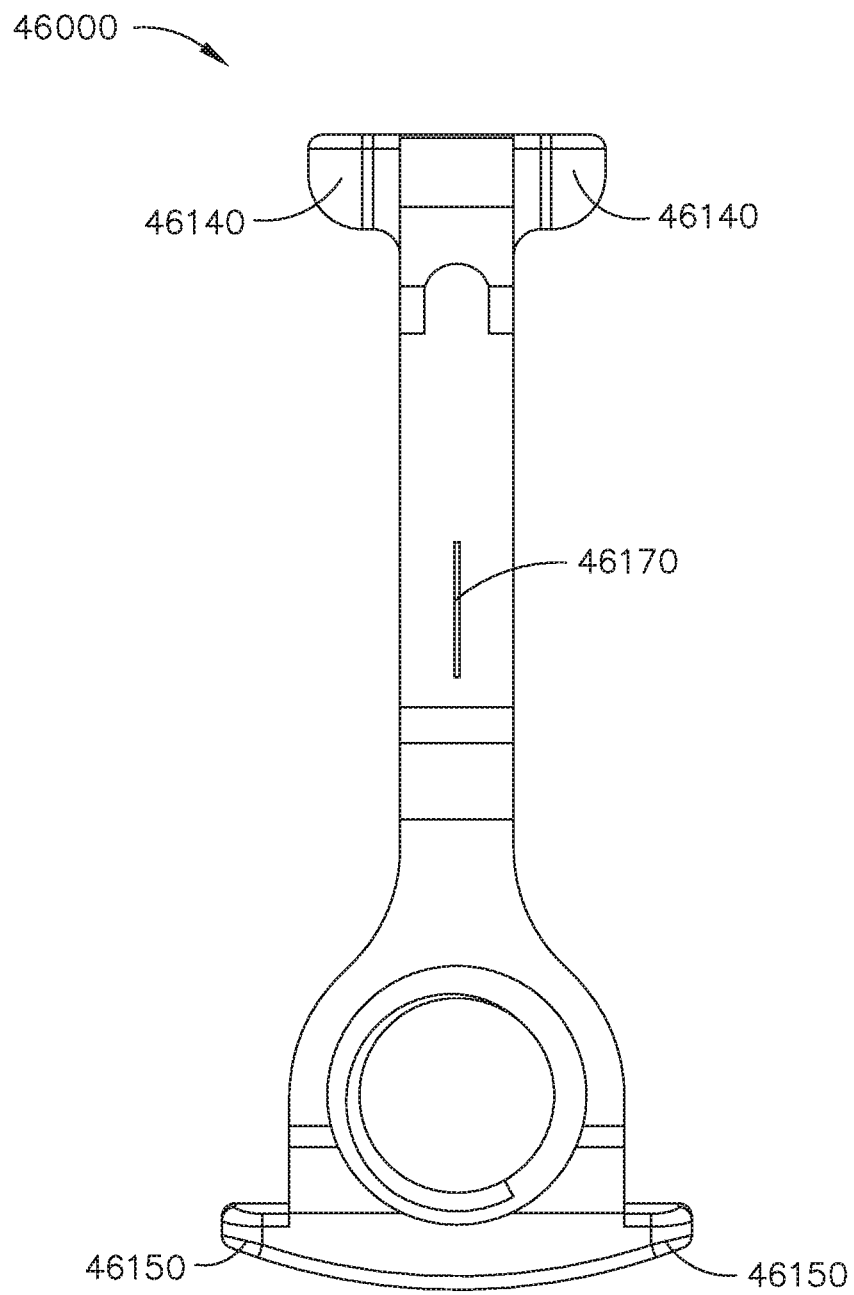

FIG. 251 is a front elevation view of the firing member of FIG. 249, according to various aspects of the present disclosure.

Figure 252:
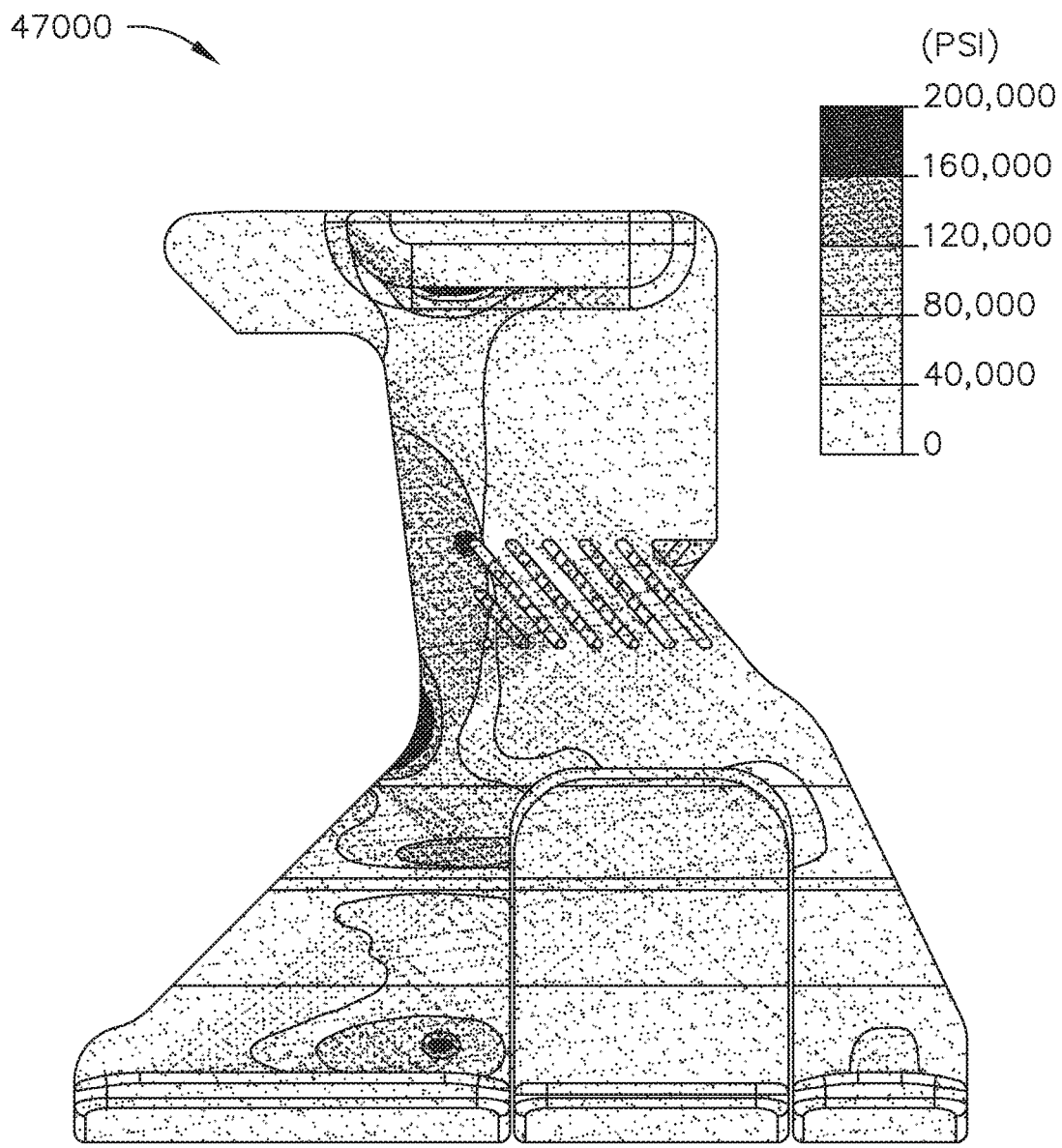

FIG. 252 is graphical representation of exemplary forces imparted on the firing member of FIG. 249 during a firing stroke, according to various aspects of the present disclosure.

Figure 253:
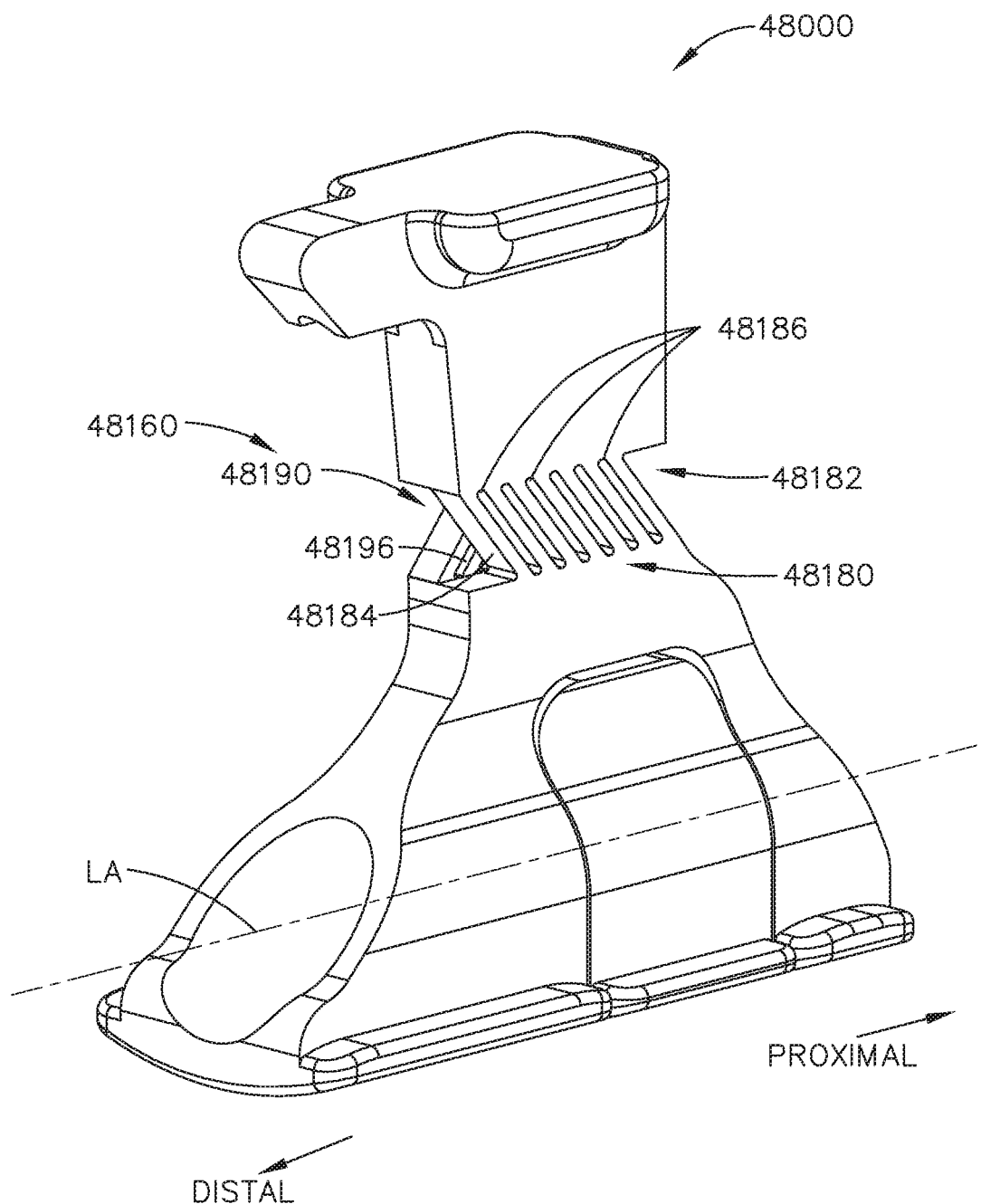

FIG. 253 is a perspective view of a firing member for use with a surgical instrument, according to various aspects of the present disclosure.

Figure 254:
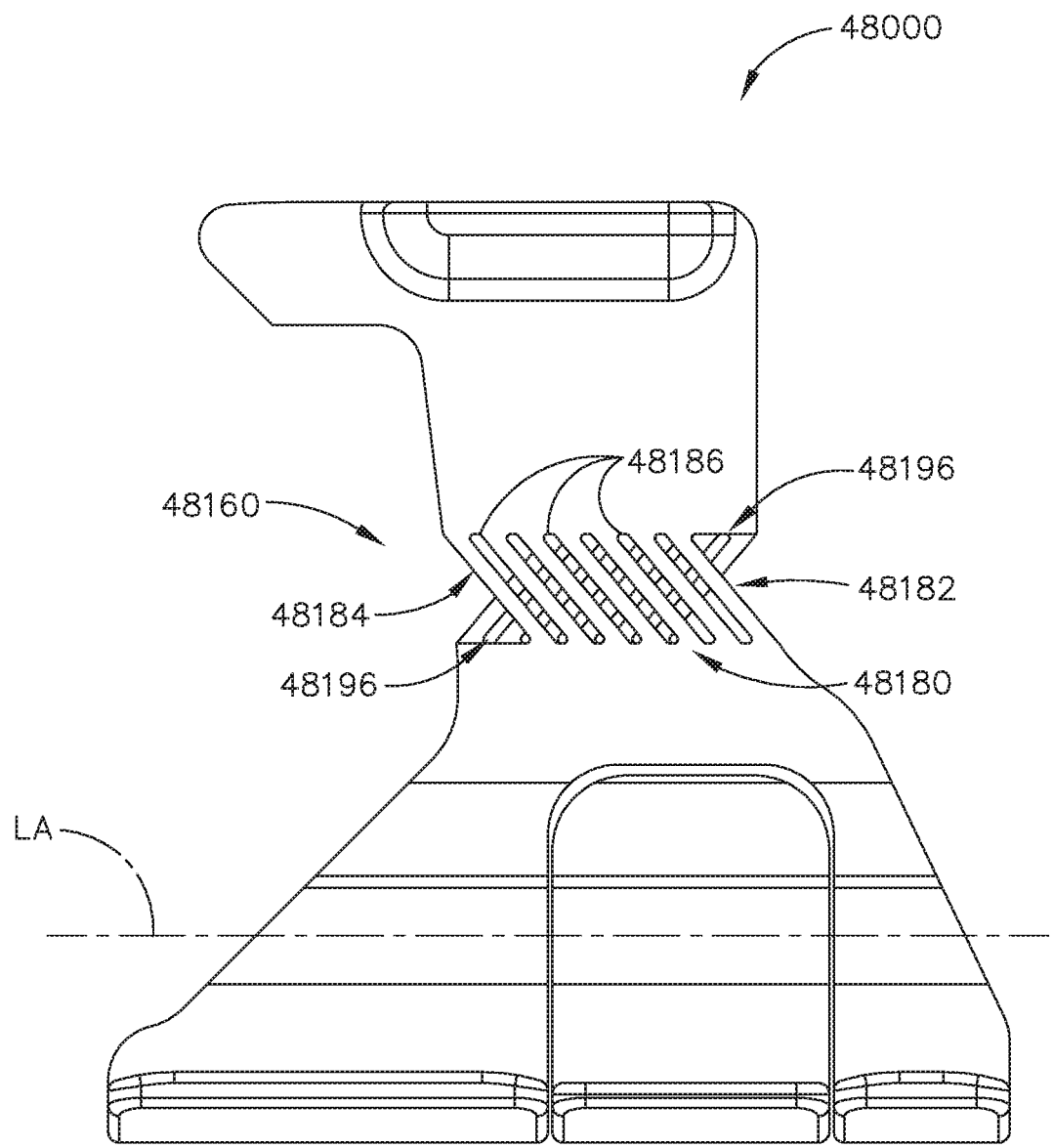

FIG. 254 is a side elevation view of the firing member of FIG. 253, according to various aspects of the present disclosure.

Figure 255:
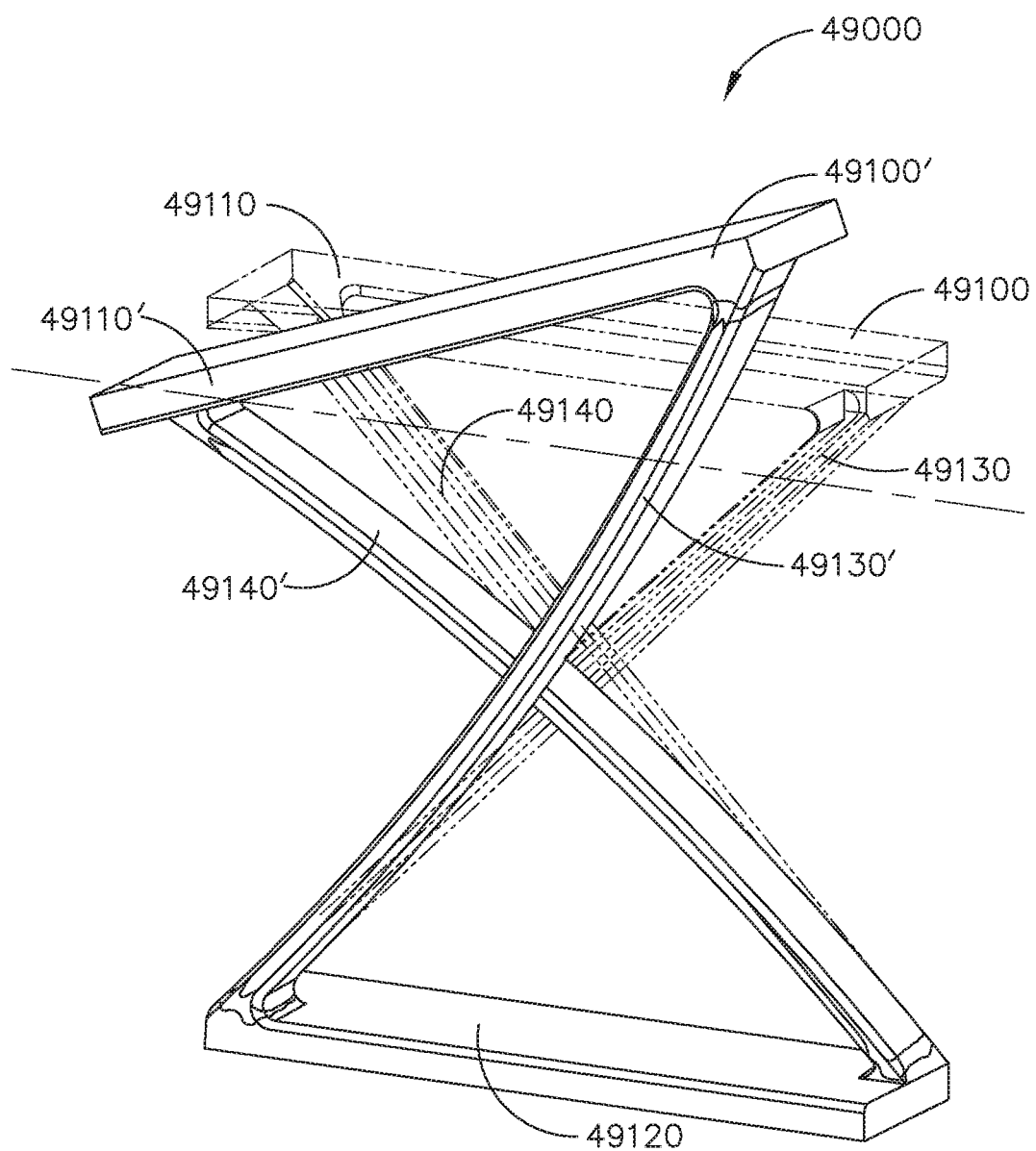

FIG. 255 is a perspective view of a model structure before force loading shown in phantom lines and during force loading shown with solid lines, according to various aspects of the present disclosure.

Figure 256:
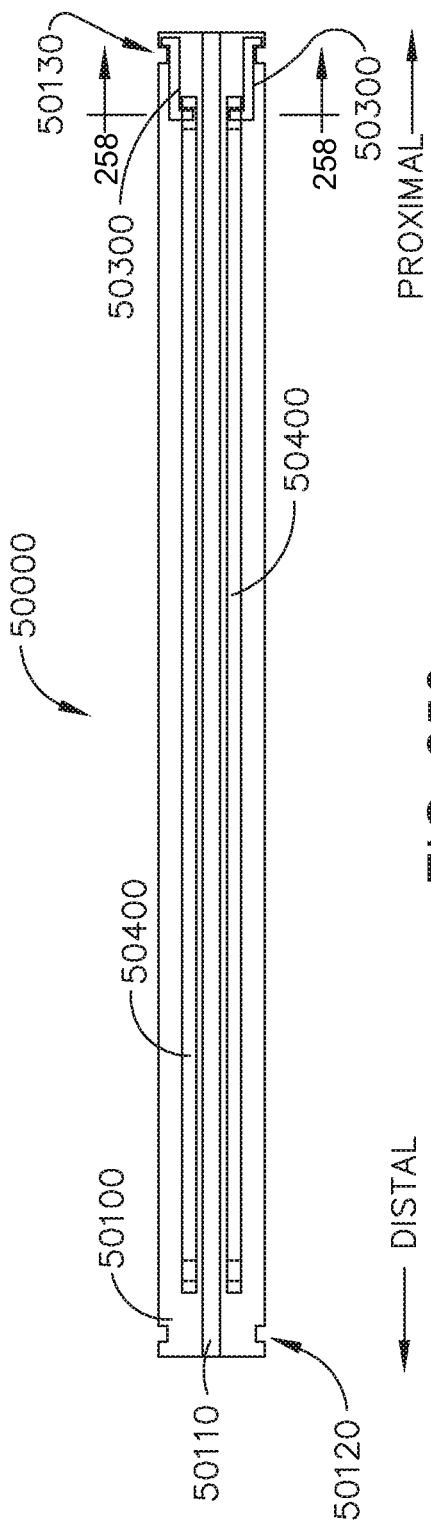

FIG. 256 is an elevation view of a channel retainer having substrate portions, according to various aspects of the present disclosure.

Figure 257:
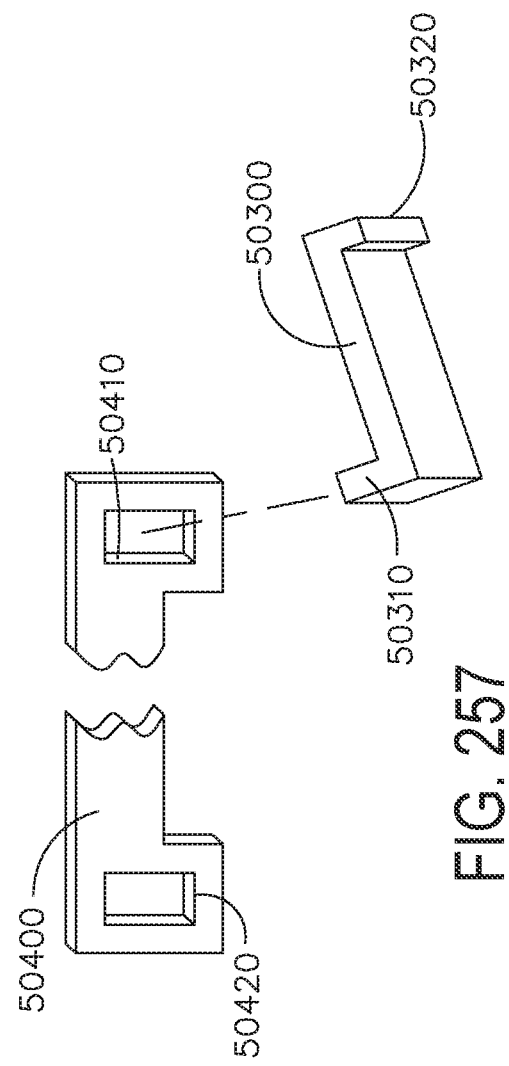

FIG. 257 is a perspective exploded view of a portion of the substrate elements of FIG. 256, according to various aspects of the present disclosure.

Figure 258:
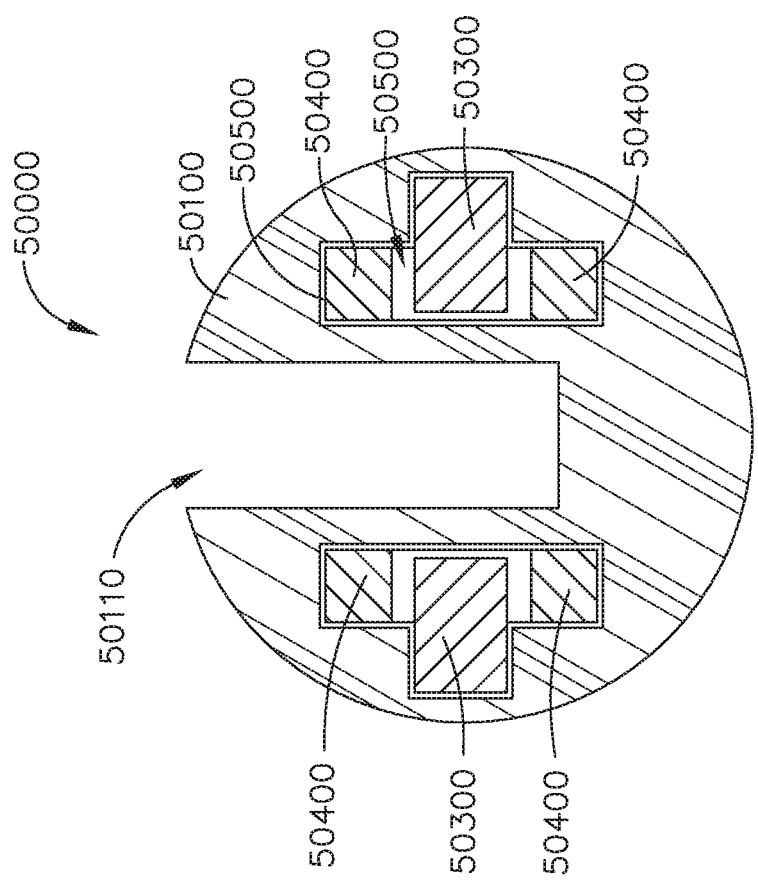

FIG. 258 is an elevation cross-section view of the channel retainer of FIG. 256 taken along the line 258-258 indicated in FIG. 256, according to various aspects of the present disclosure.

Figure 259:
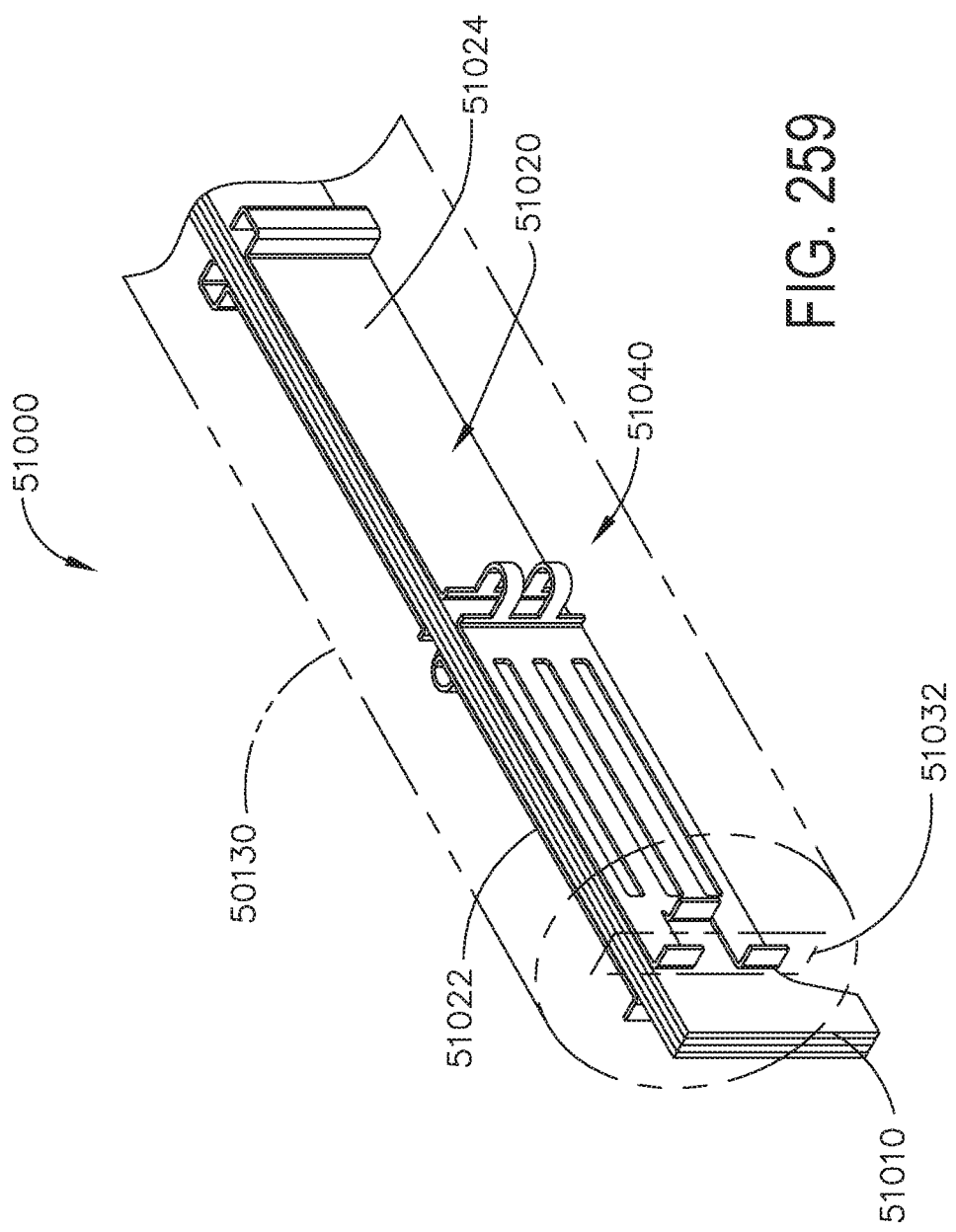

FIG. 259 is a perspective view of a portion of a surgical instrument comprising an over-molded sleeve depicted with phantom lines, and further depicting a firing bar support within the over-molded sleeve, according to various aspects of the present disclosure.

Figure 260:
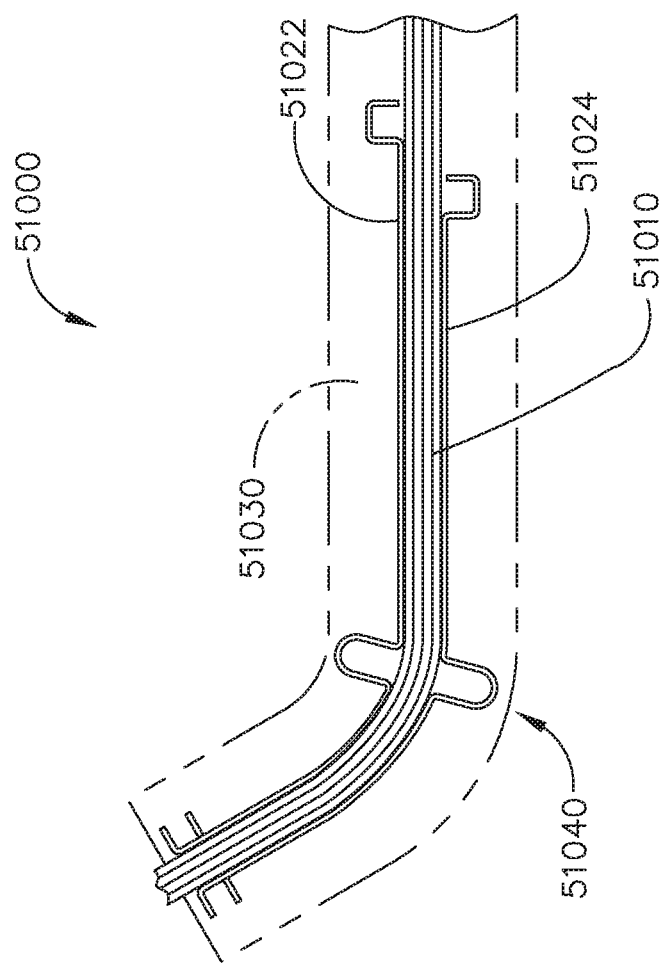

FIG. 260 is a plan view of the portion of the surgical instrument of FIG. 259 depicted with phantom lines for the over-molded sleeve, and further depicting the instrument in an articulated configuration, according to various aspects of the present disclosure.

Figure 261:
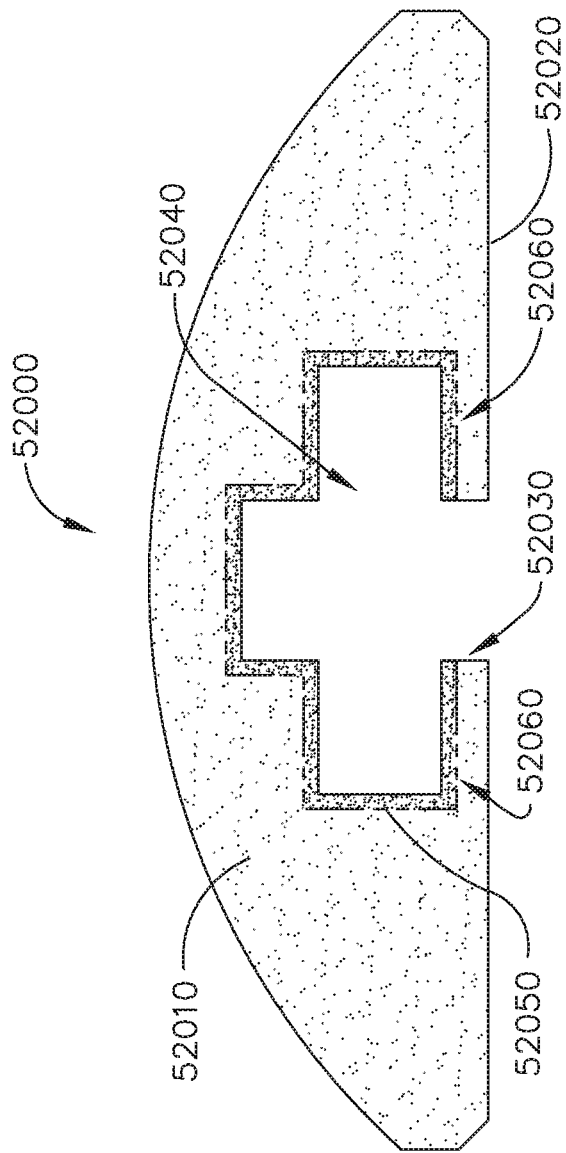

FIG. 261 is an elevation cross-section view of an anvil for use with a surgical instrument, according to various aspects of the present disclosure.

Figure 262:
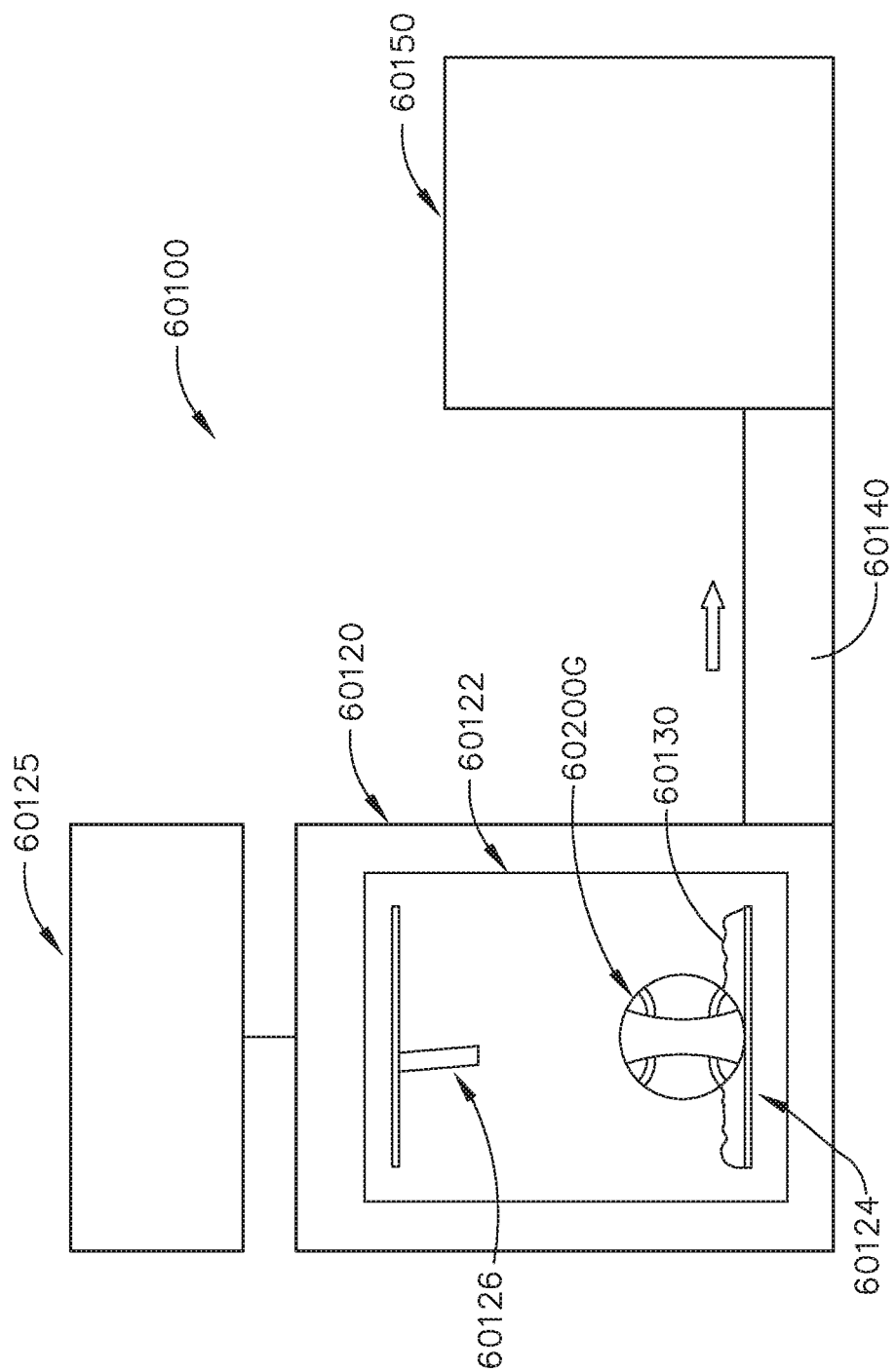

FIG. 262 is a diagrammatical depiction of an example of an additive manufacturing system, in accordance with at least one aspect of the present disclosure.

Figure 263:
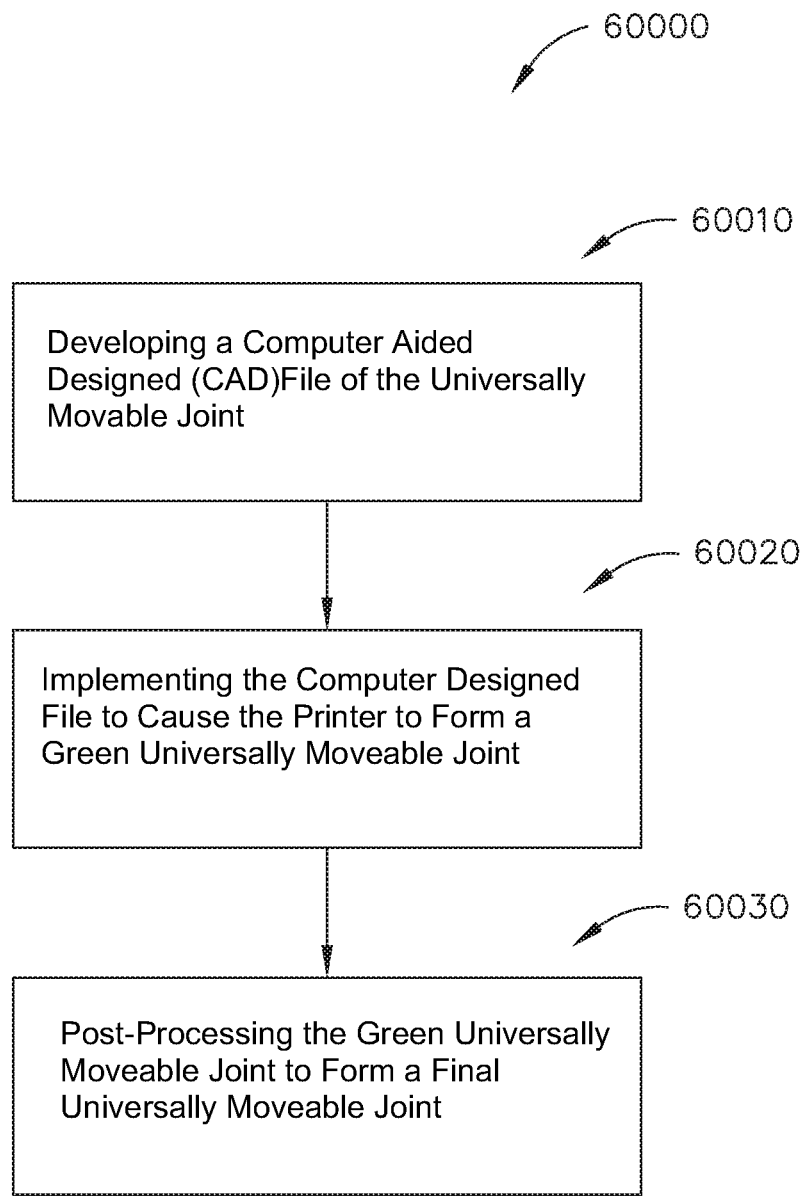

FIG. 263 is a chart depicting one form of a manufacturing process that may be implemented by the additive manufacturing system of FIG. 262, in accordance with at least one aspect of the present disclosure.

Figure 264:
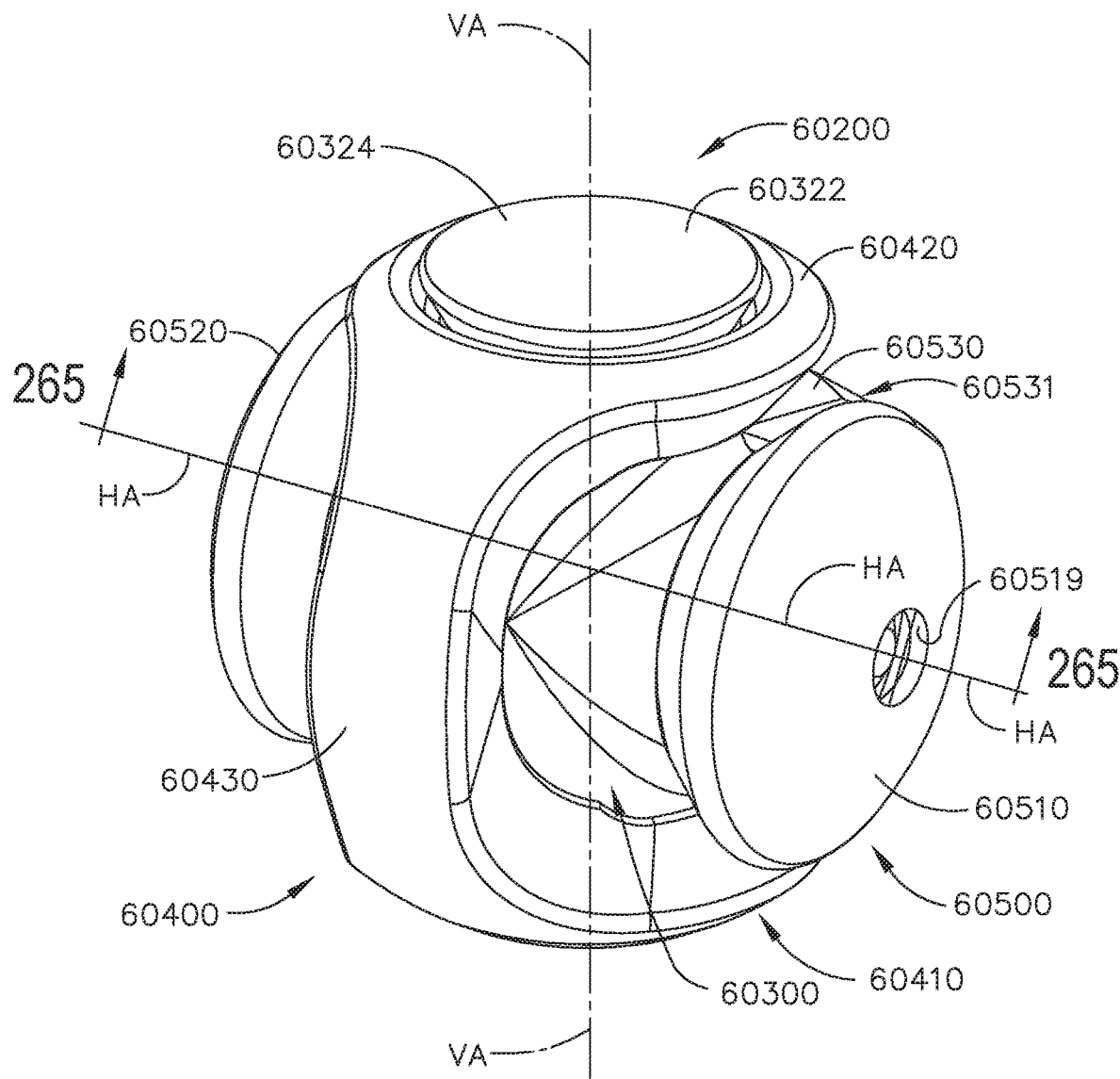

FIG. 264 is a perspective view of one form of a universally movable joint that may be formed using the manufacturing process of FIG. 263 and the additive manufacturing system of FIG. 262, in accordance with at least one aspect of the present disclosure.

Figure 265:
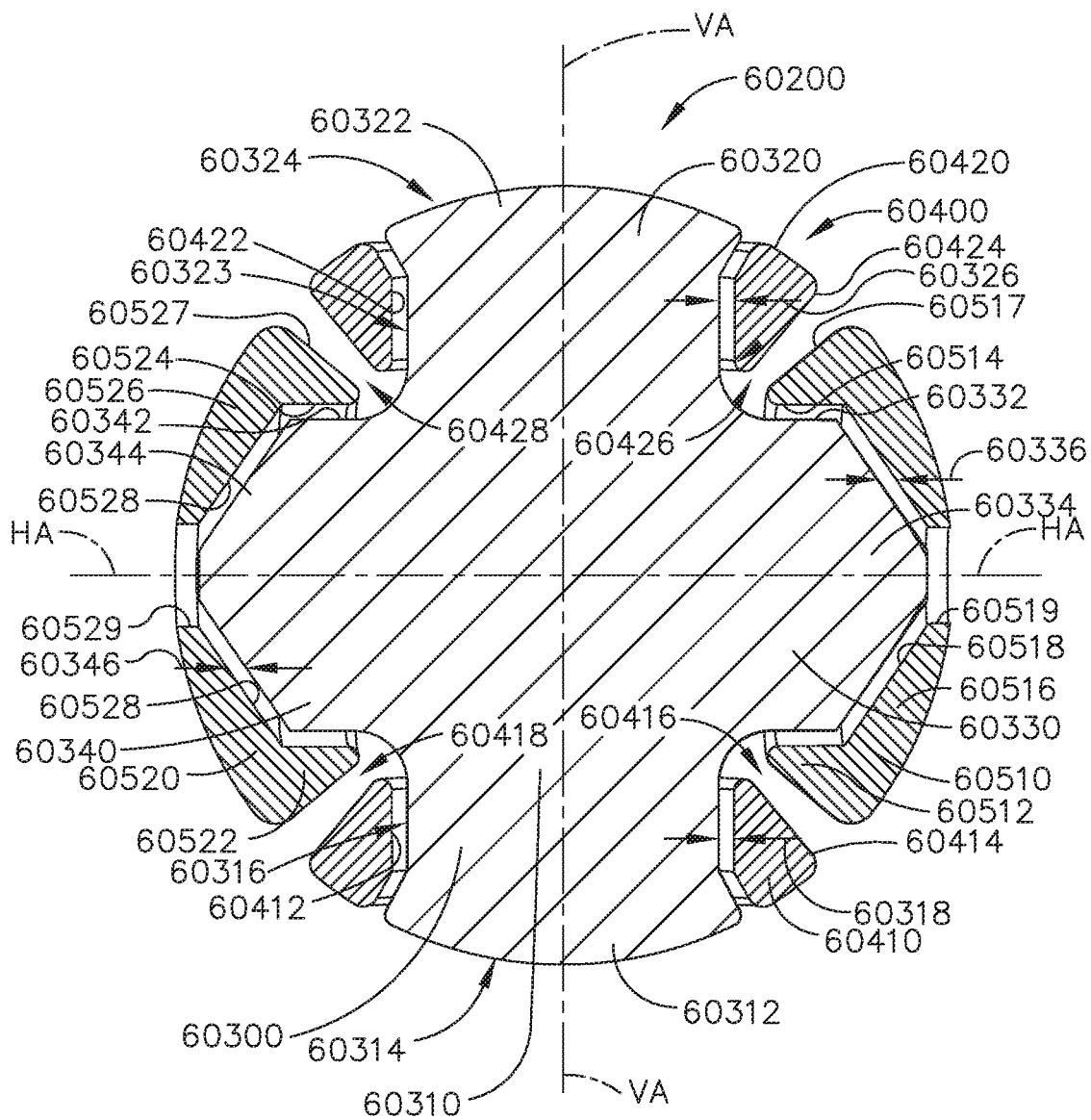

FIG. 265 is a cross-sectional view of the universally movable joint of FIG. 264 taken along the line 265-265, in accordance with at least one aspect of the present disclosure.

Figure 266:
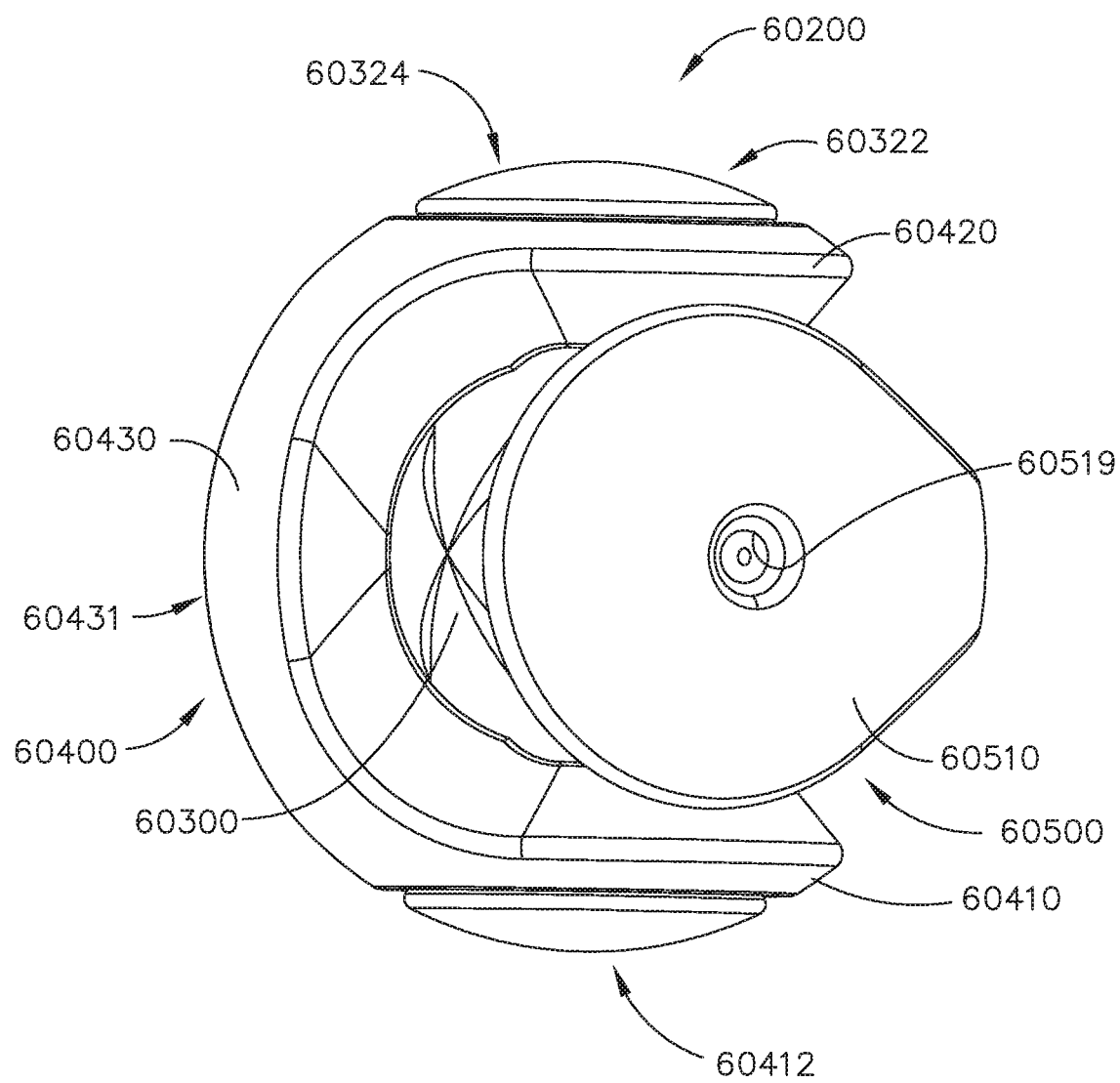

FIG. 266 is another perspective view of the universally movable joint of FIG. 264, in accordance with at least one aspect of the present disclosure.

Figure 267:
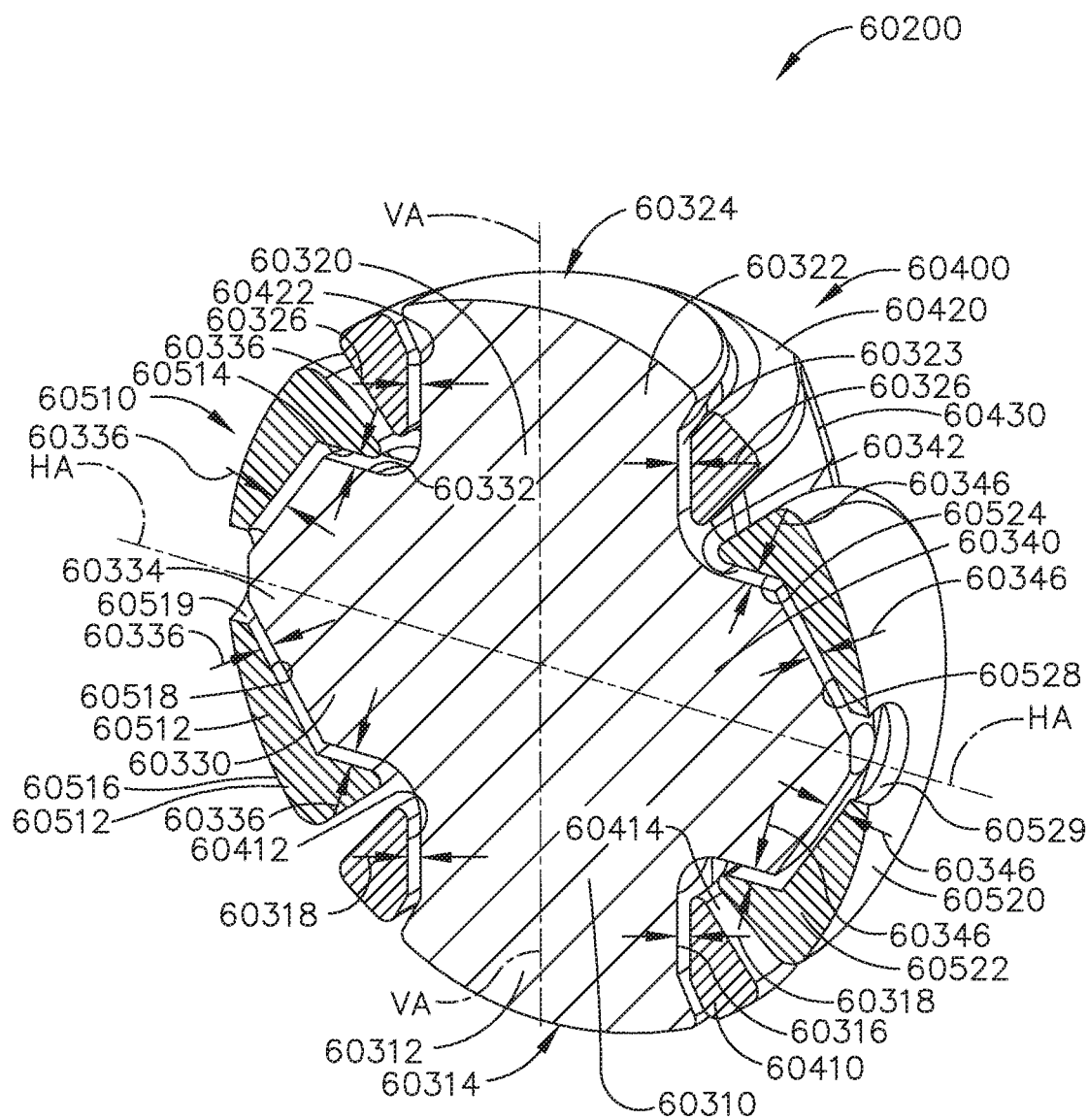

FIG. 267 is a cross-sectional perspective view of the universally movable joint of FIG. 264, in accordance with at least one aspect of the present disclosure.

Figure 268:
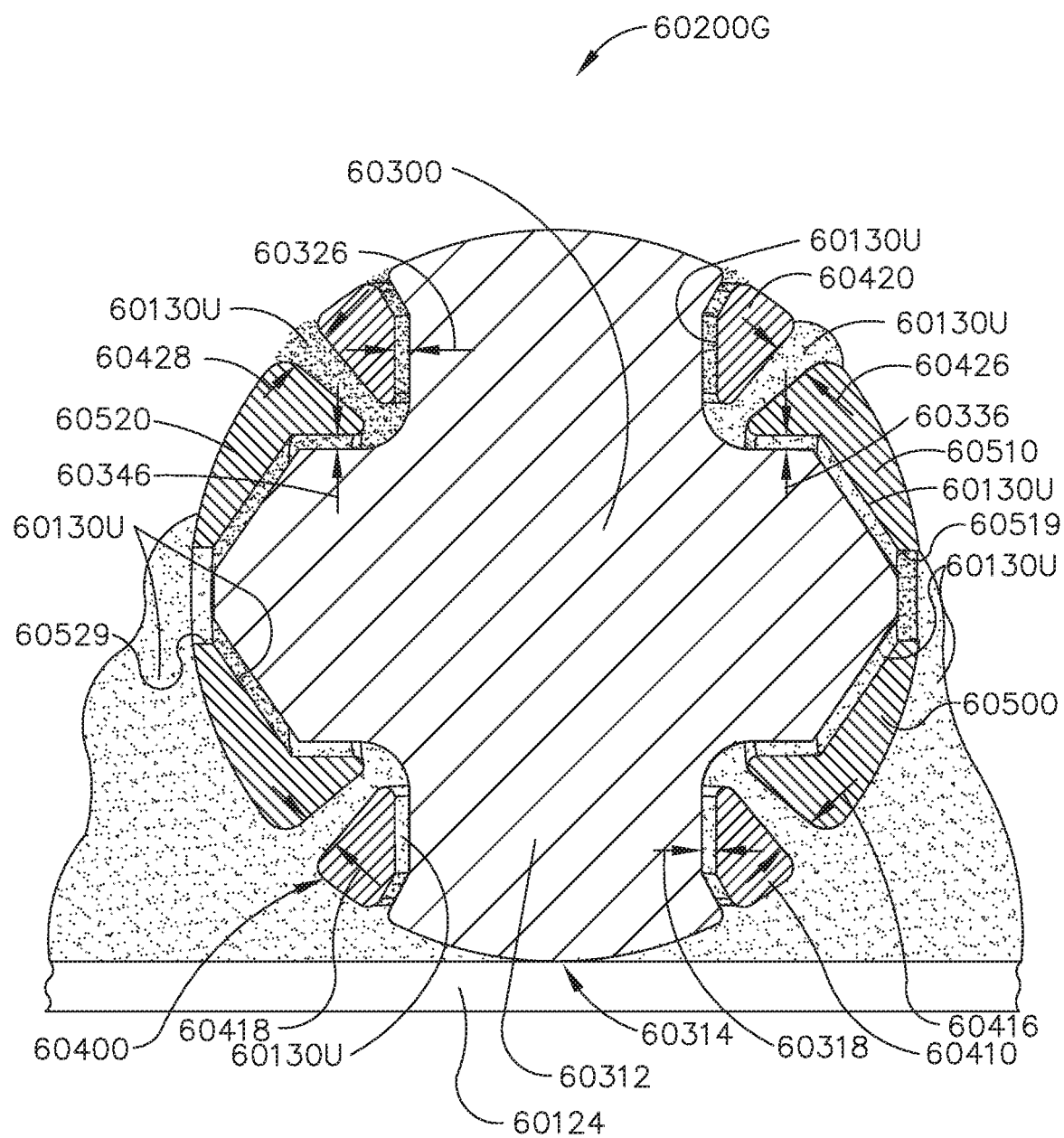

FIG. 268 is another cross-sectional view of the universally movable joint of FIG. 264 supported on a build plate of the additive manufacturing system of FIG. 262, in accordance with at least one aspect of the present disclosure.

Figure 268A:
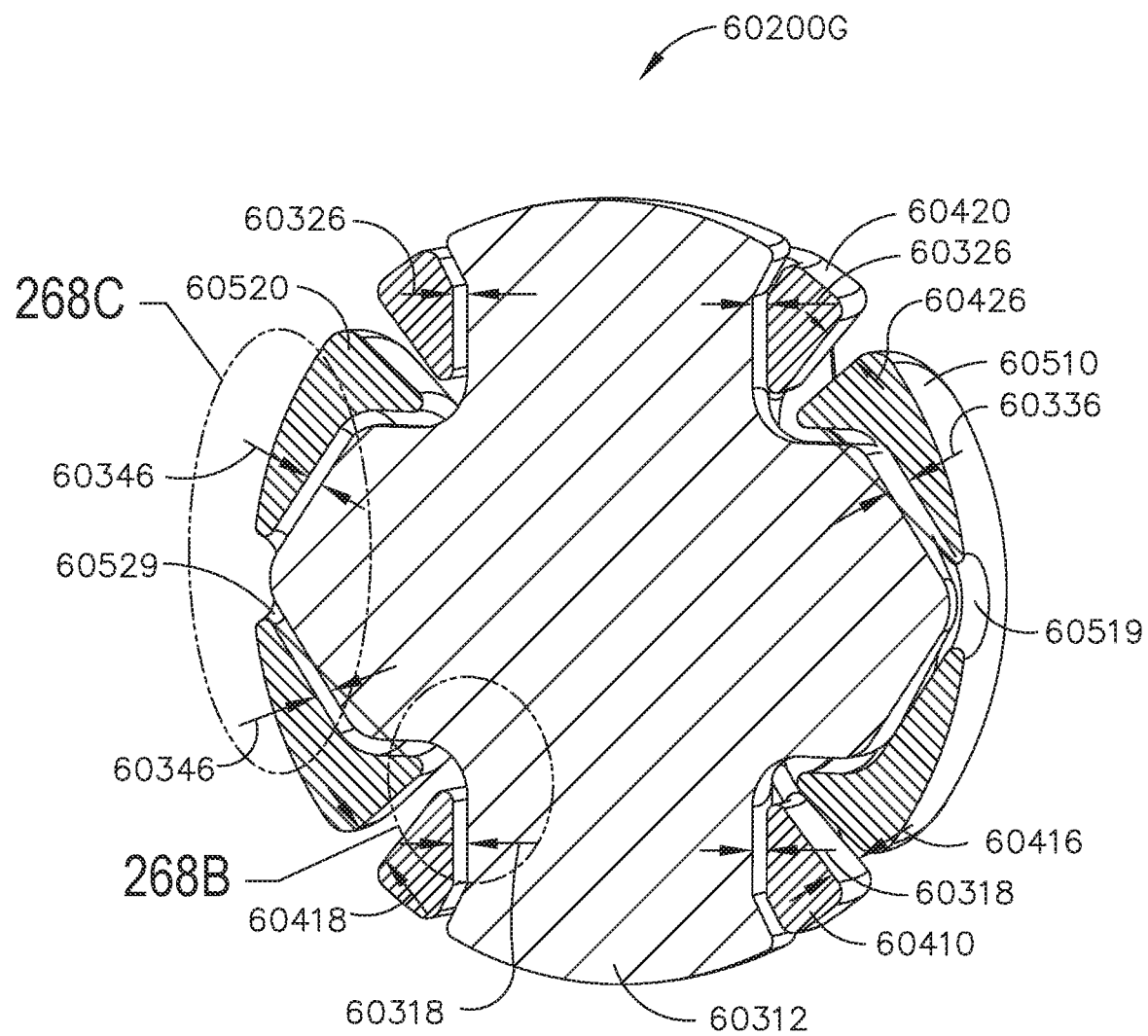

FIG. 268A is another cross-sectional perspective view of the universally movable joint of FIG. 264 in green form, in accordance with at least one aspect of the present disclosure.

Figure 268B:
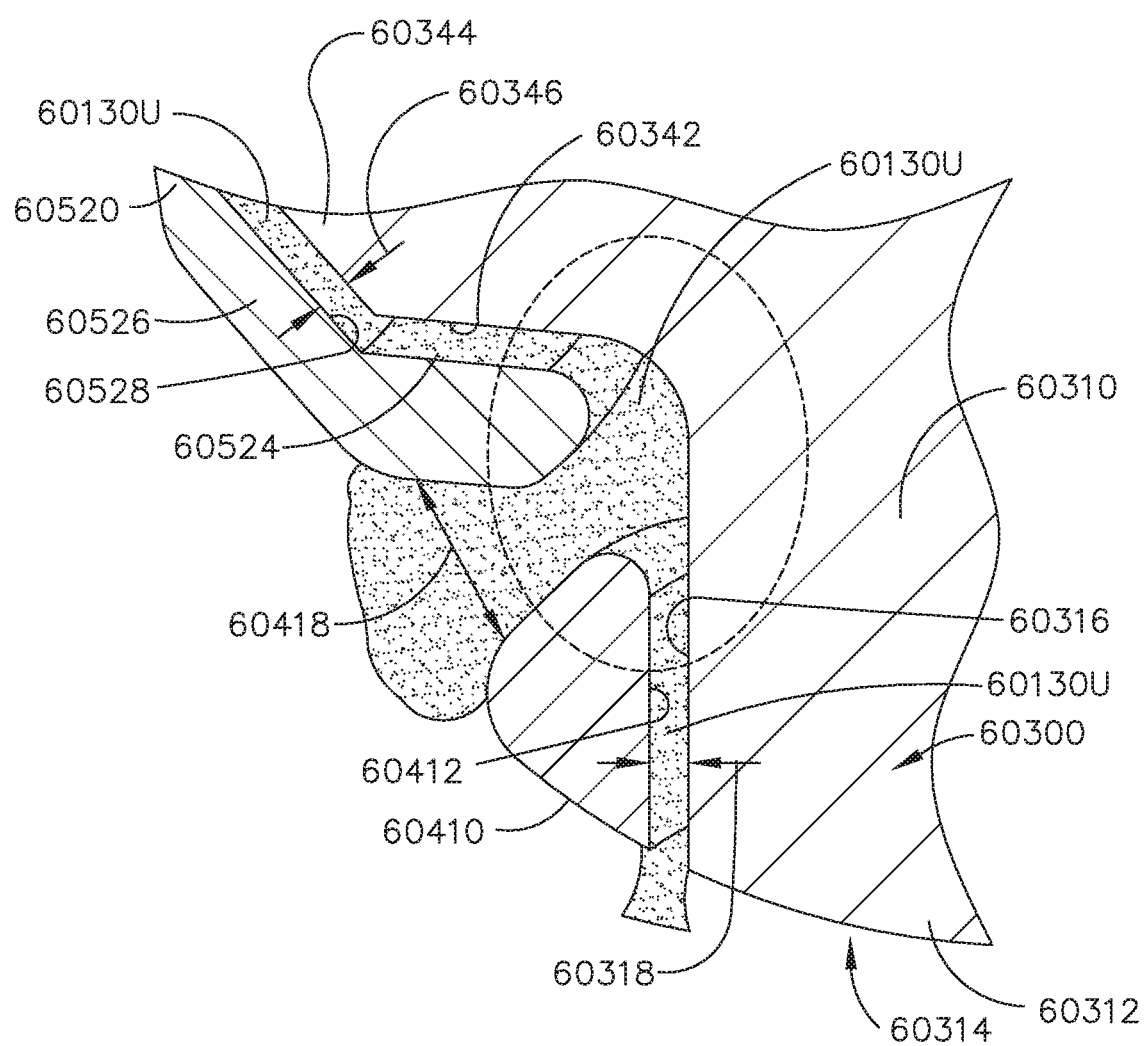

FIG. 268B is an enlarged view of a portion of a second cap and a bottom joint ring and a fillet space therebetween filled with an amount of build material in a first state during the formation of the green universally movable joint of FIG. 268, in accordance with at least one aspect of the present disclosure.

Figure 268C:
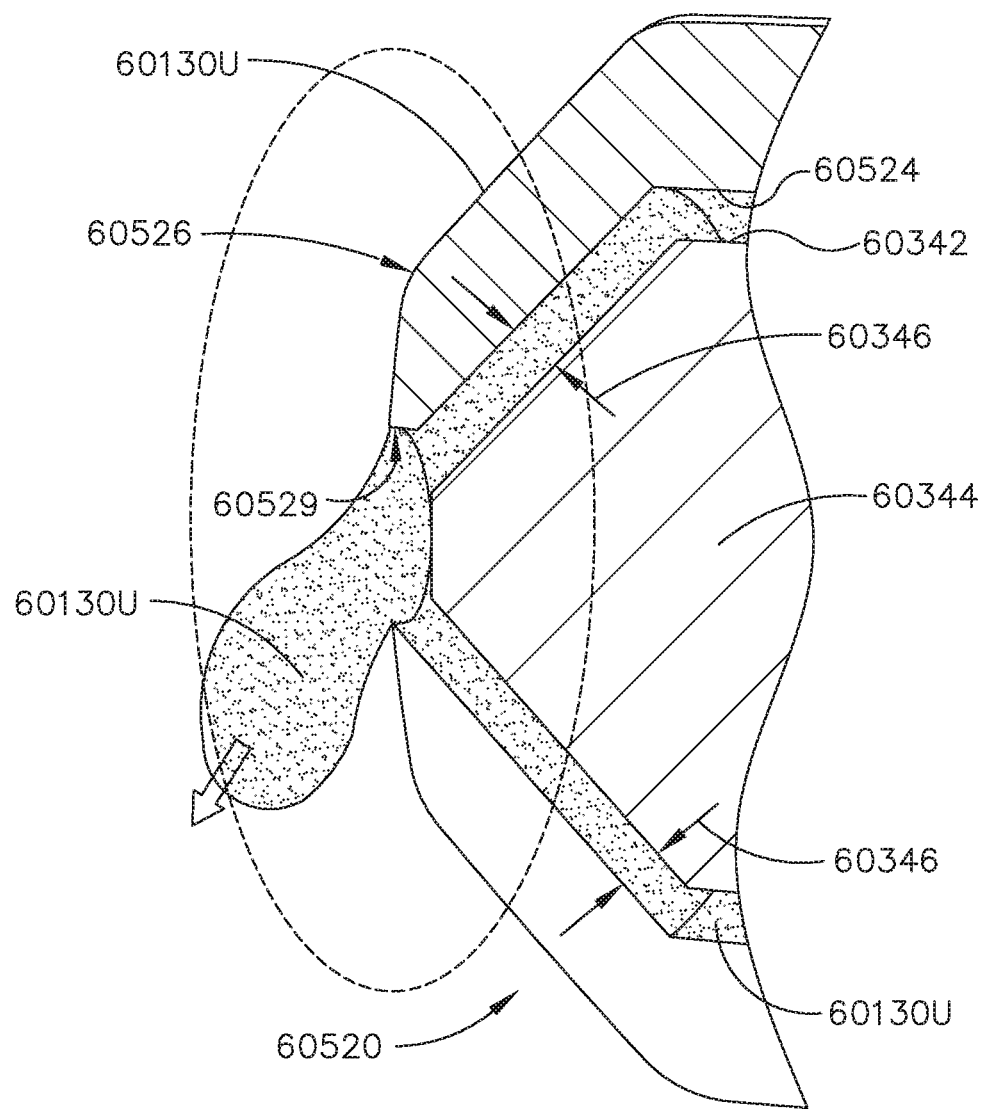

FIG. 268C is an enlarged view of a portion of a second cap and a portion of a joint spine of the green universally movable joint of FIG. 268 illustrating amounts of a build material in a first state located in a second horizontal joint space between the second cap and the joint spine, in accordance with at least one aspect of the present disclosure.

Figure 269:
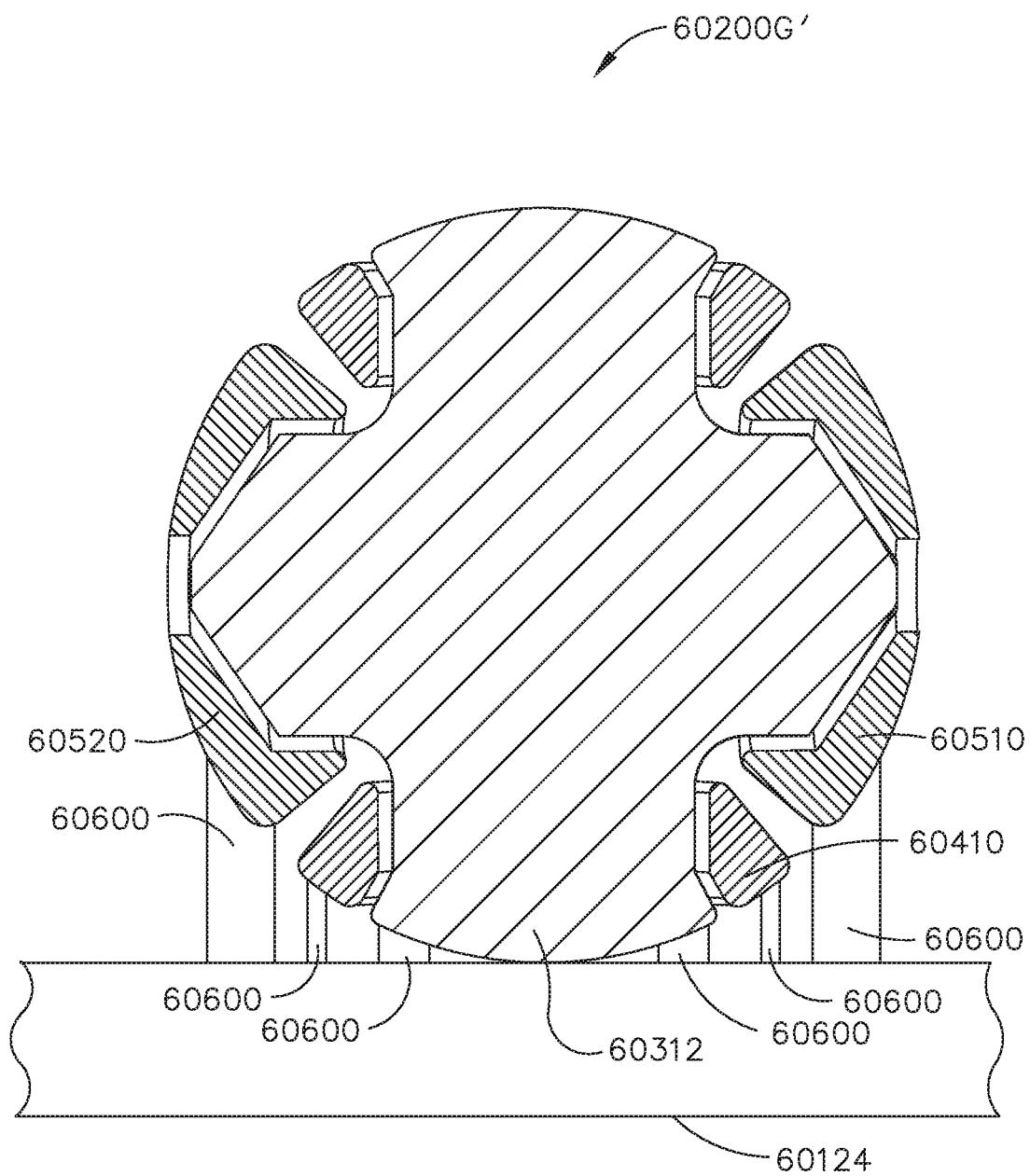

FIG. 269 is a cross-sectional view of another universally movable joint in green form supported on a build plate of the additive manufacturing system of FIG. 262 by multiple support members, in accordance with at least one aspect of the present disclosure.

Figure 270:
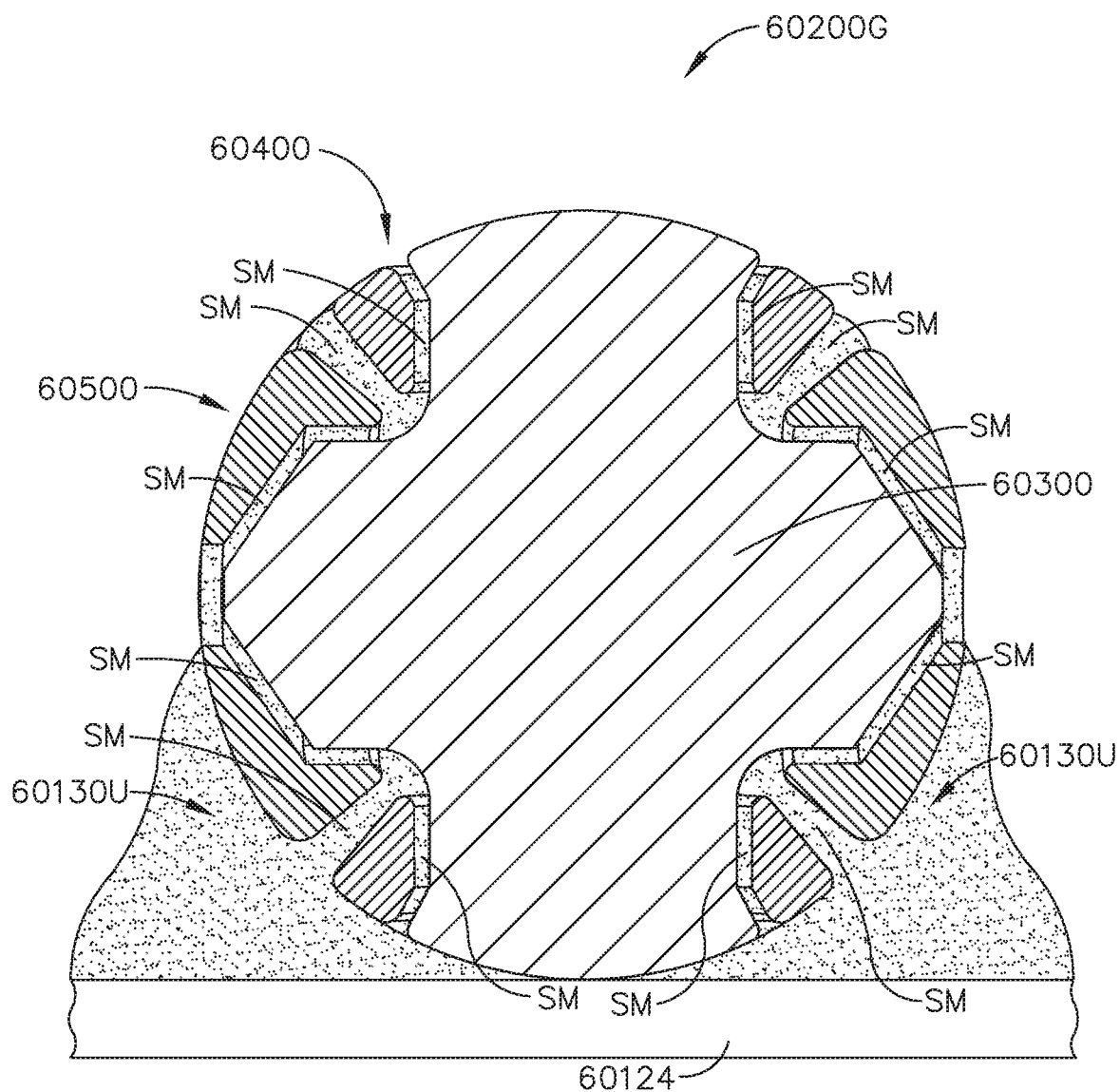

FIG. 270 is a cross-sectional view of another universally movable joint in green formed supported on a build plate of the additive manufacturing system of FIG. 262, wherein a build material and a separate support material are employed during the manufacturing process, in accordance with at least one aspect of the present disclosure.

Figure 271:
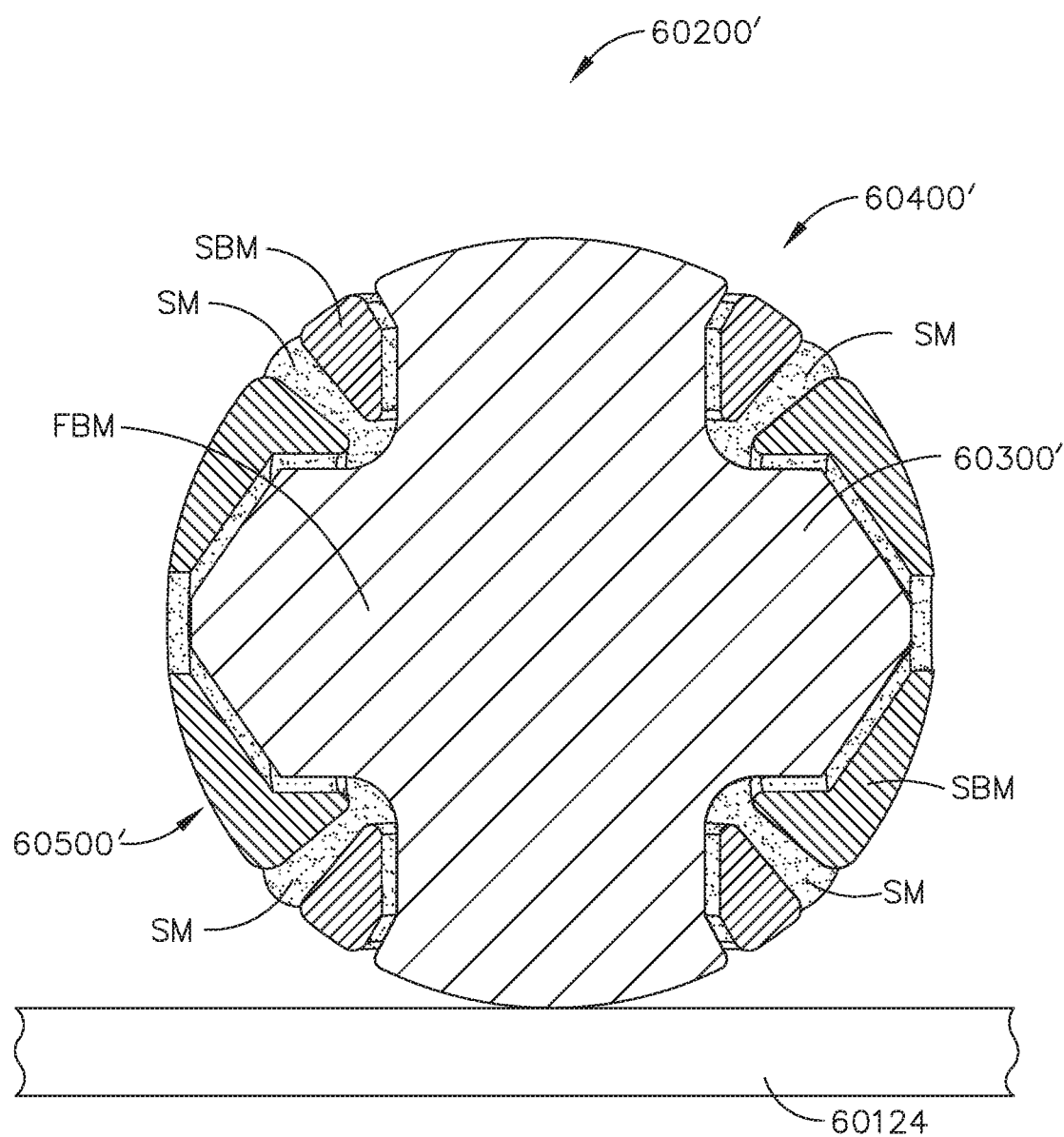

FIG. 271 is a cross-sectional view of another universally movable joint in green formed supported on a build plate of the additive manufacturing system of FIG. 262, wherein a joint spine is formed from a first build material and a vertical U-joint member and a horizontal U-joint member are formed from a second build material and a separate support material is employed during the manufacturing process, in accordance with at least one aspect of the present disclosure.

Figure 272:
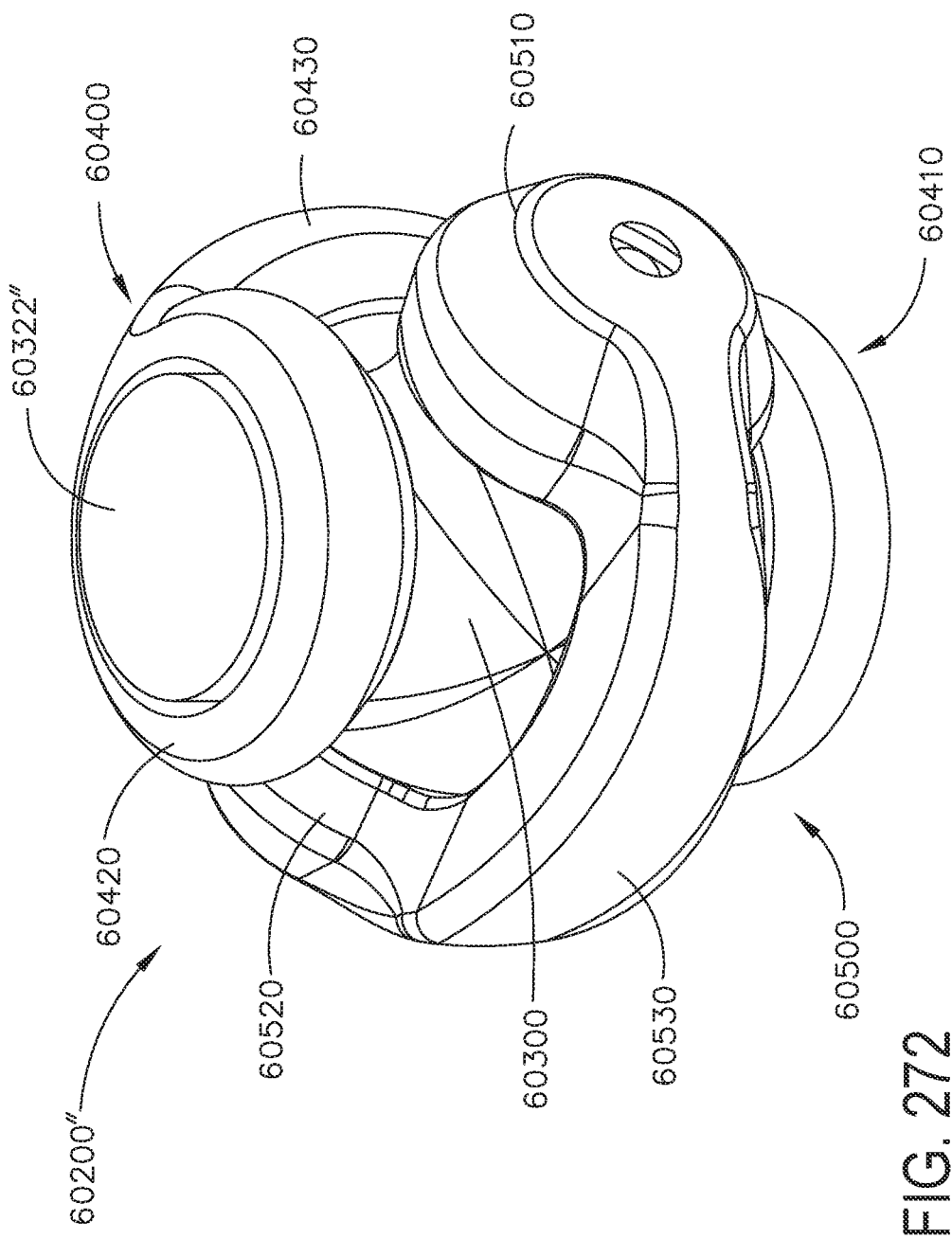

FIG. 272 is a perspective view of another universally movable joint embodiment, in accordance with at least one aspect of the present disclosure.

FIG. 273 is a cross-sectional view of the universally movable joint of FIG. 272, in accordance with at least one aspect of the present disclosure.

FIG. 274 is another cross-sectional view of the universally movable joint of FIG. 272, in accordance with at least one aspect of the present disclosure.

Figure 275:
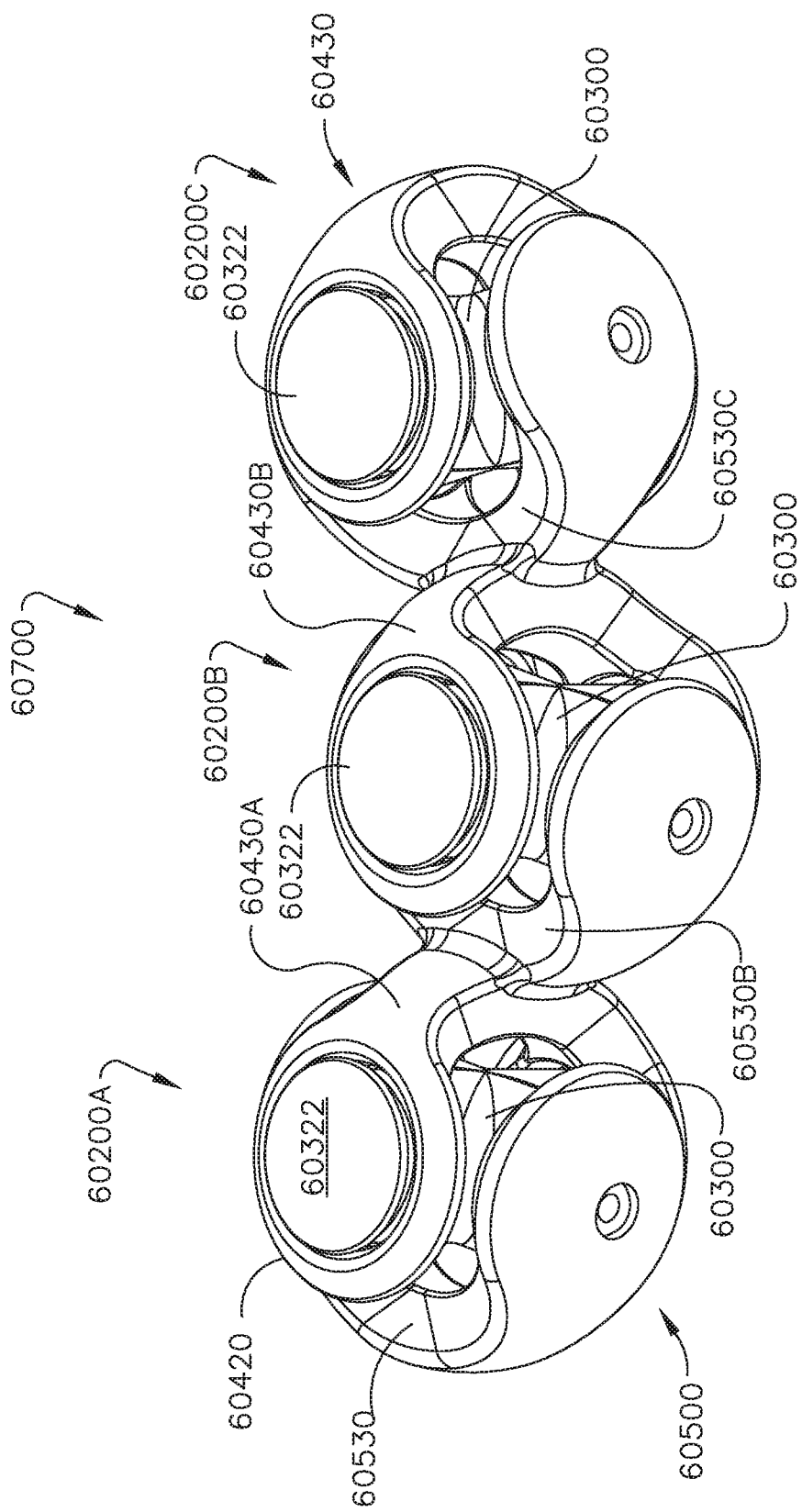

FIG. 275 is a perspective view of a universally movable drive shaft segment that comprises multiple universally movable joints that may be formed using the additive manufacturing system of FIG. 262 and/or the manufacturing process of FIG. 263, in accordance with at least one aspect of the present disclosure.

Figure 276:
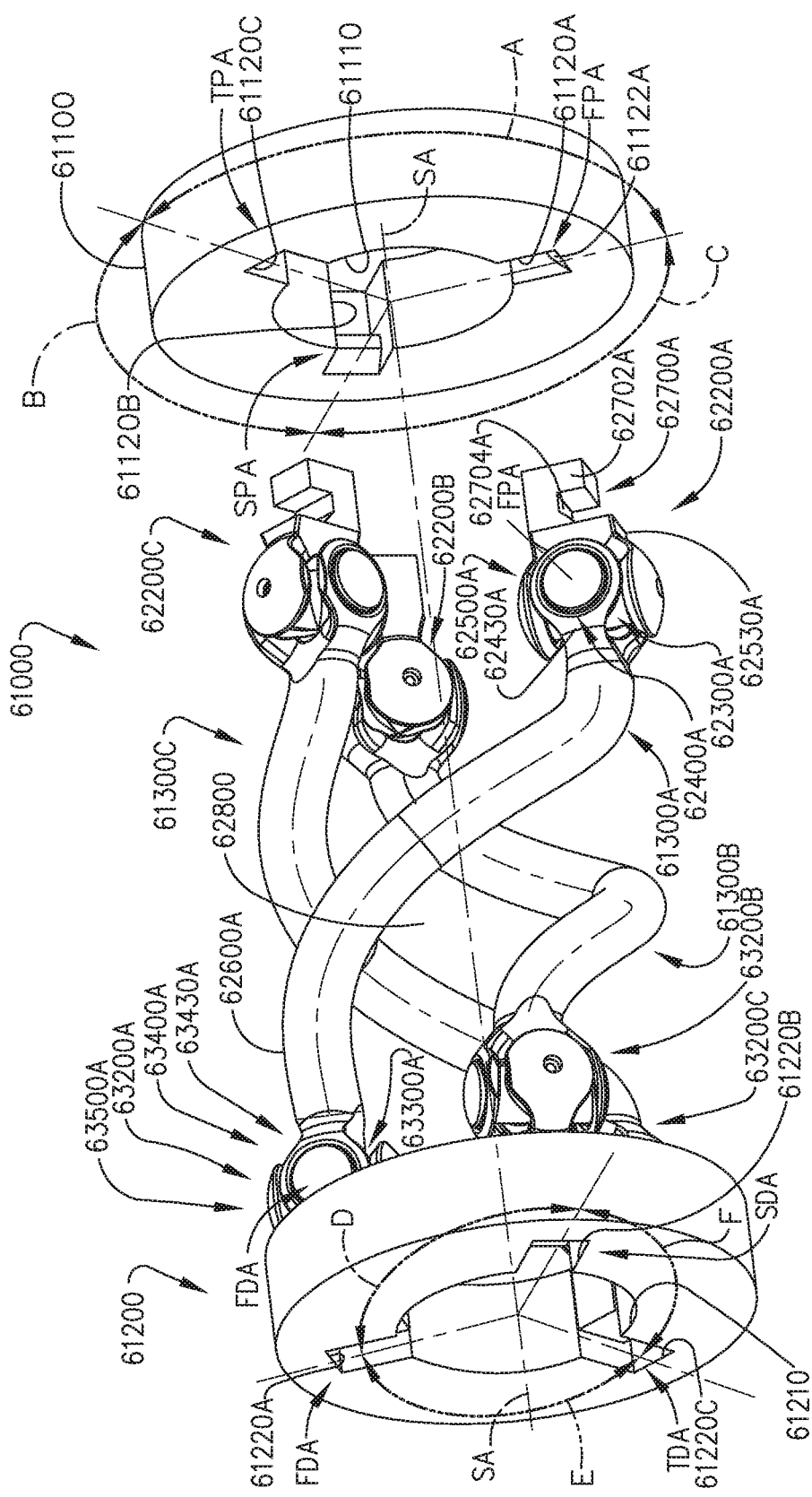

FIG. 276 is an exploded perspective assembly view of an articulation joint assembly embodiment that may be formed using the additive manufacturing system of FIG. 262 and/or the manufacturing process of FIG. 263, in accordance with at least one aspect of the present disclosure.

Figure 277:
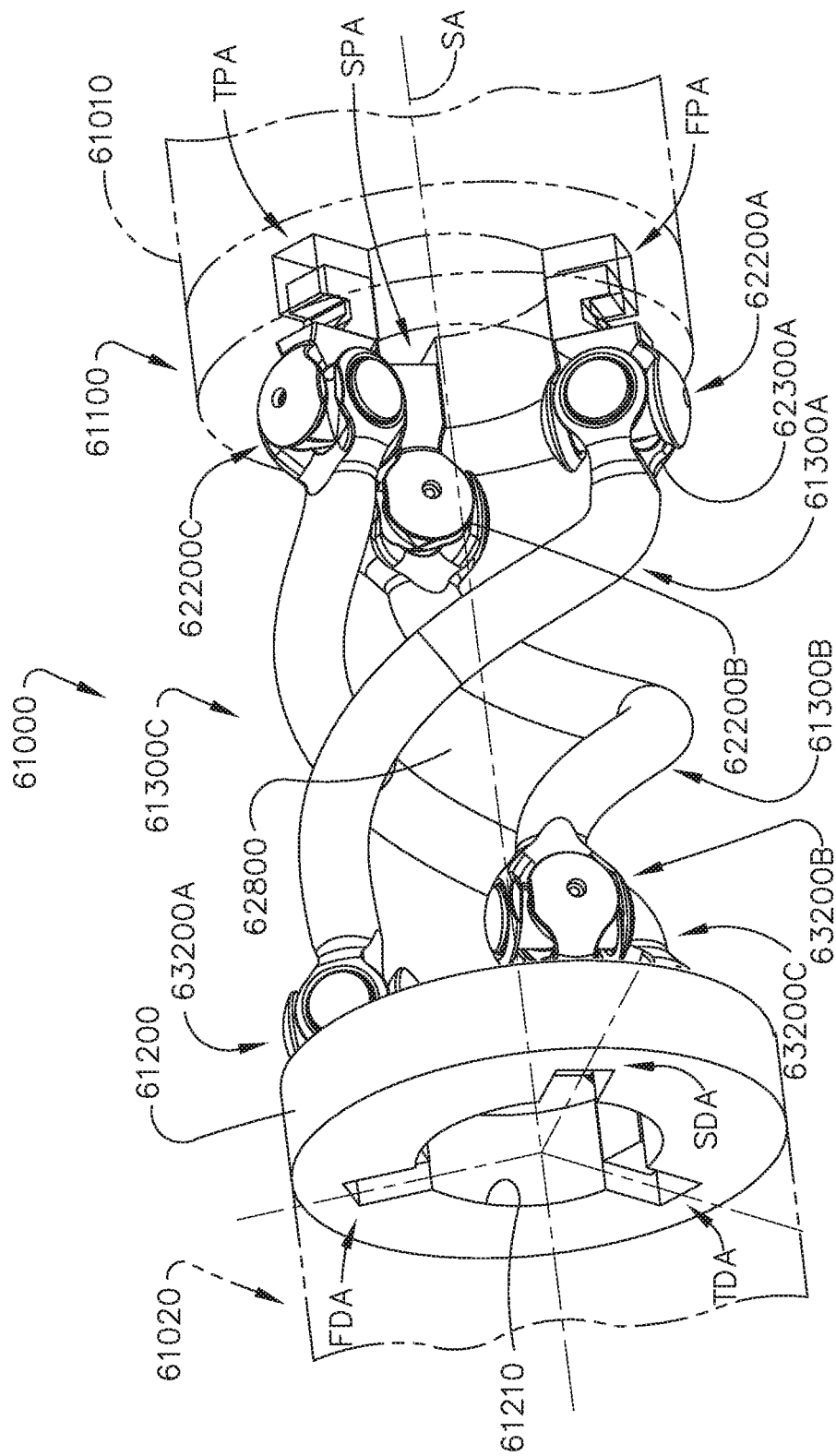

FIG. 277 is a perspective view of the articulation joint assembly of FIG. 276 showing a portion of a shaft assembly and a portion of an end effector in phantom lines, in accordance with at least one aspect of the present disclosure.

Figure 278:
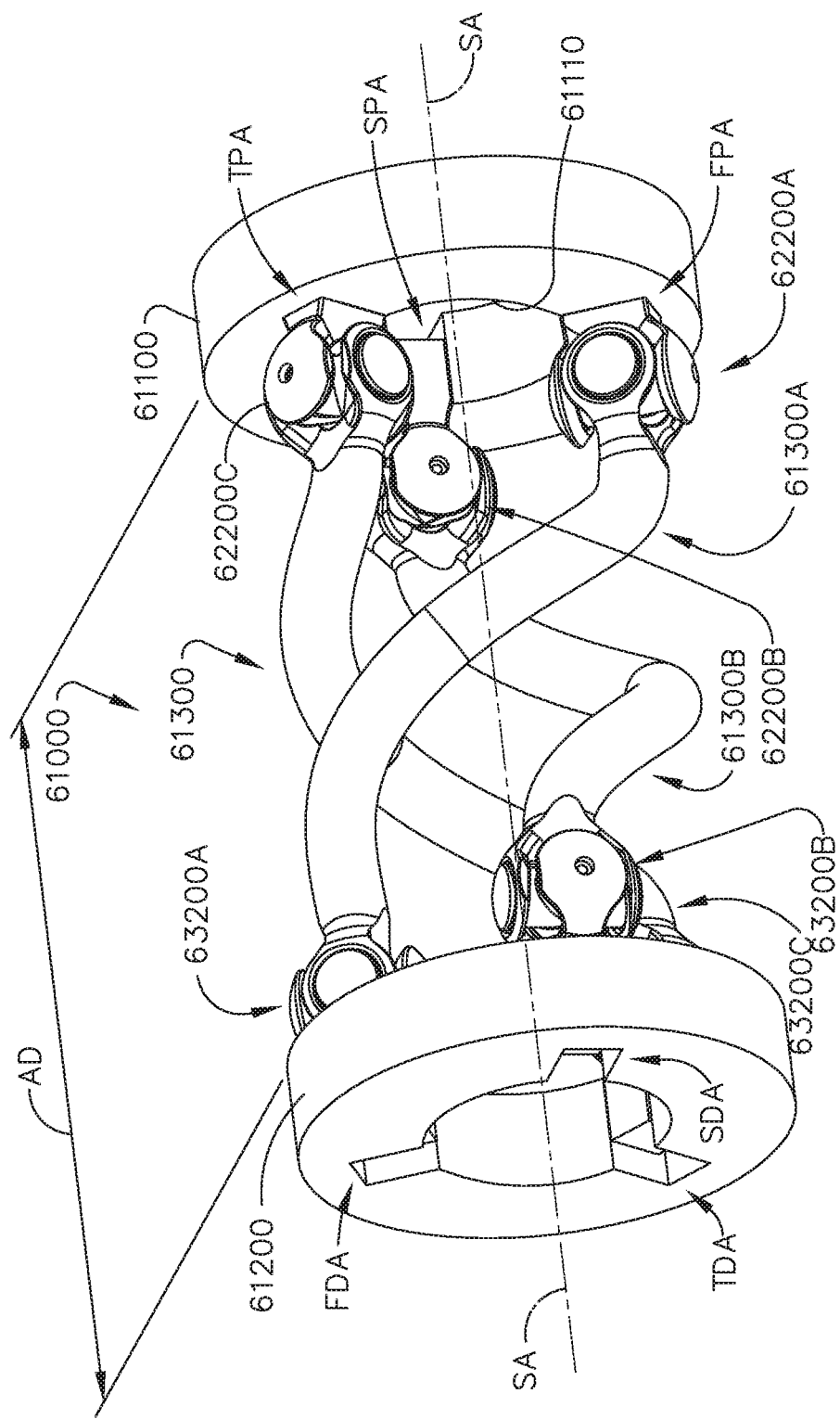

FIG. 278 is another perspective view of the articulation joint assembly of FIG. 276, in accordance with at least one aspect of the present disclosure.

Figure 279:
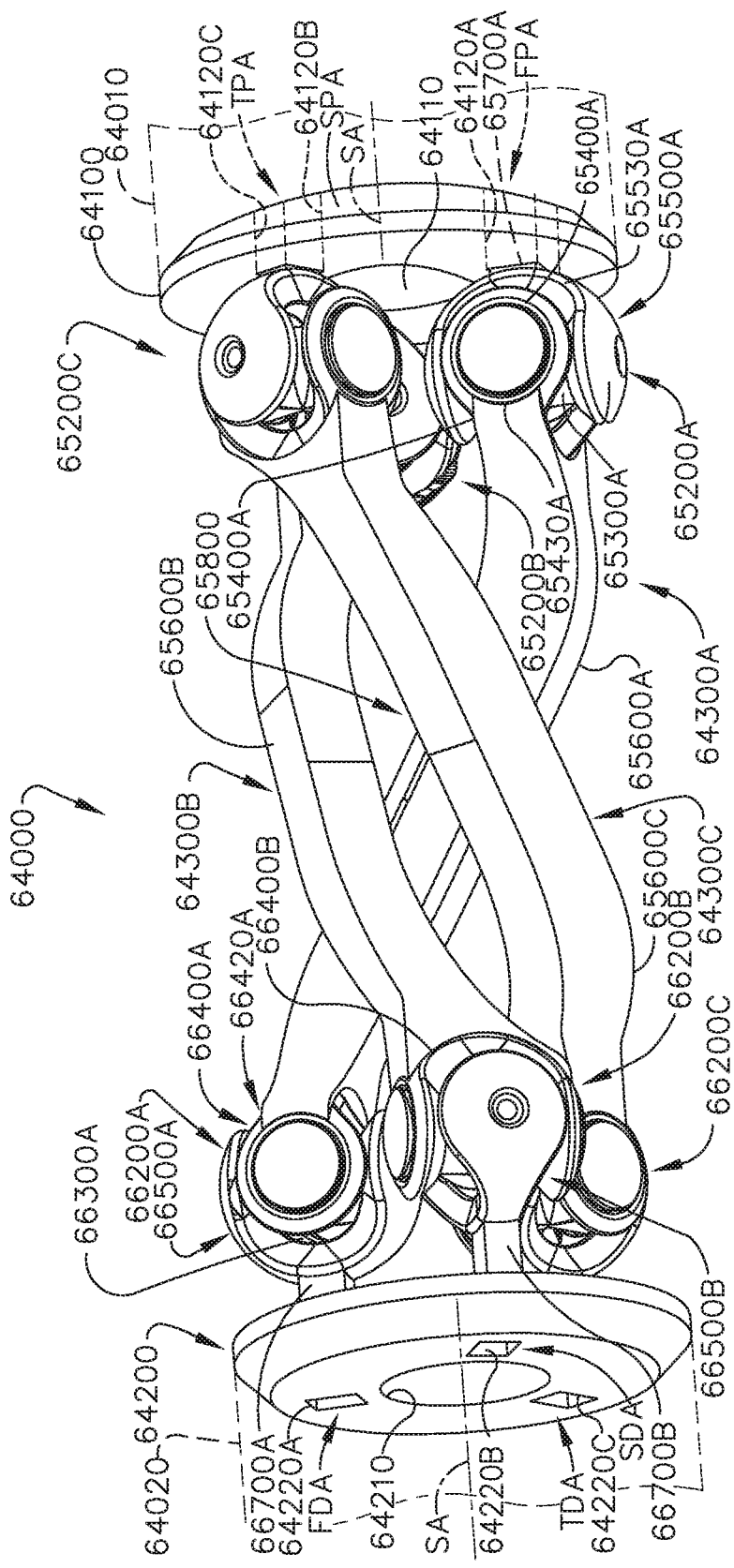

FIG. 279 is a perspective assembly view of another articulation joint assembly embodiment that may be formed using the additive manufacturing system of FIG. 262 and/or the manufacturing process of FIG. 263, in accordance with at least one aspect of the present disclosure.

Figure 280:
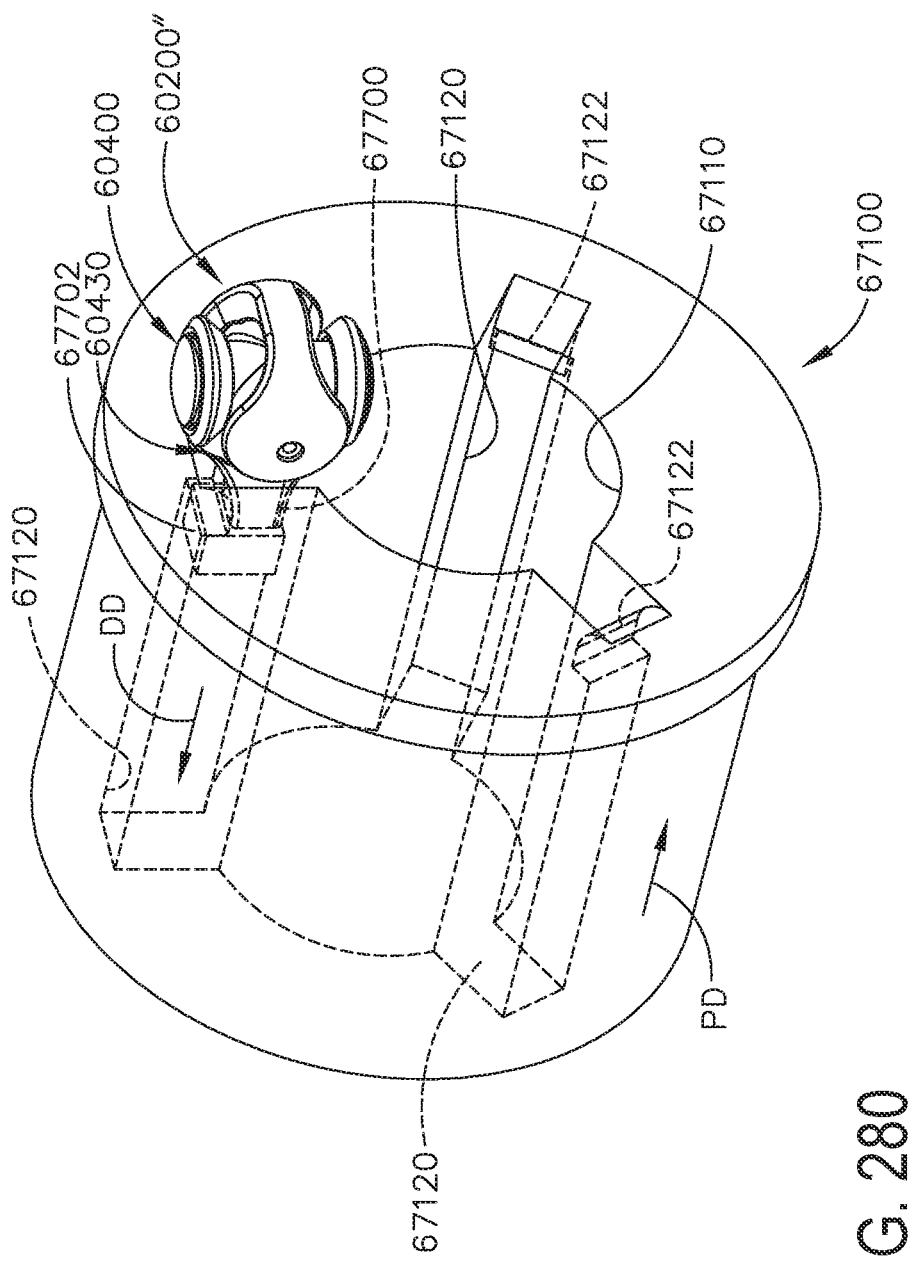

FIG. 280 is a perspective view of a mounting member embodiment and a universally movable joint embodiment, in accordance with at least one aspect of the present disclosure.

Figure 281:
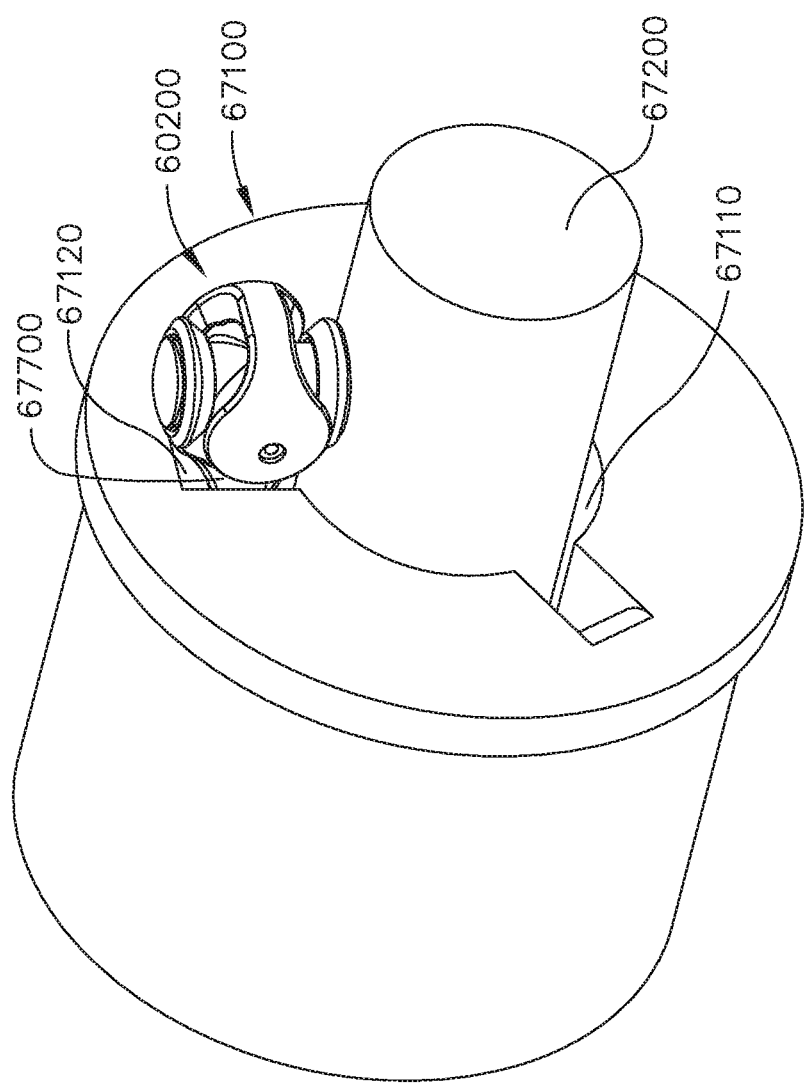

FIG. 281 is another perspective view of the mounting member and universally movable joint of FIG. 280 with a portion of a shaft, a conduit or a shaft guide extending through a center passage in the mounting member, in accordance with at least one aspect of the present disclosure.

Figure 282:
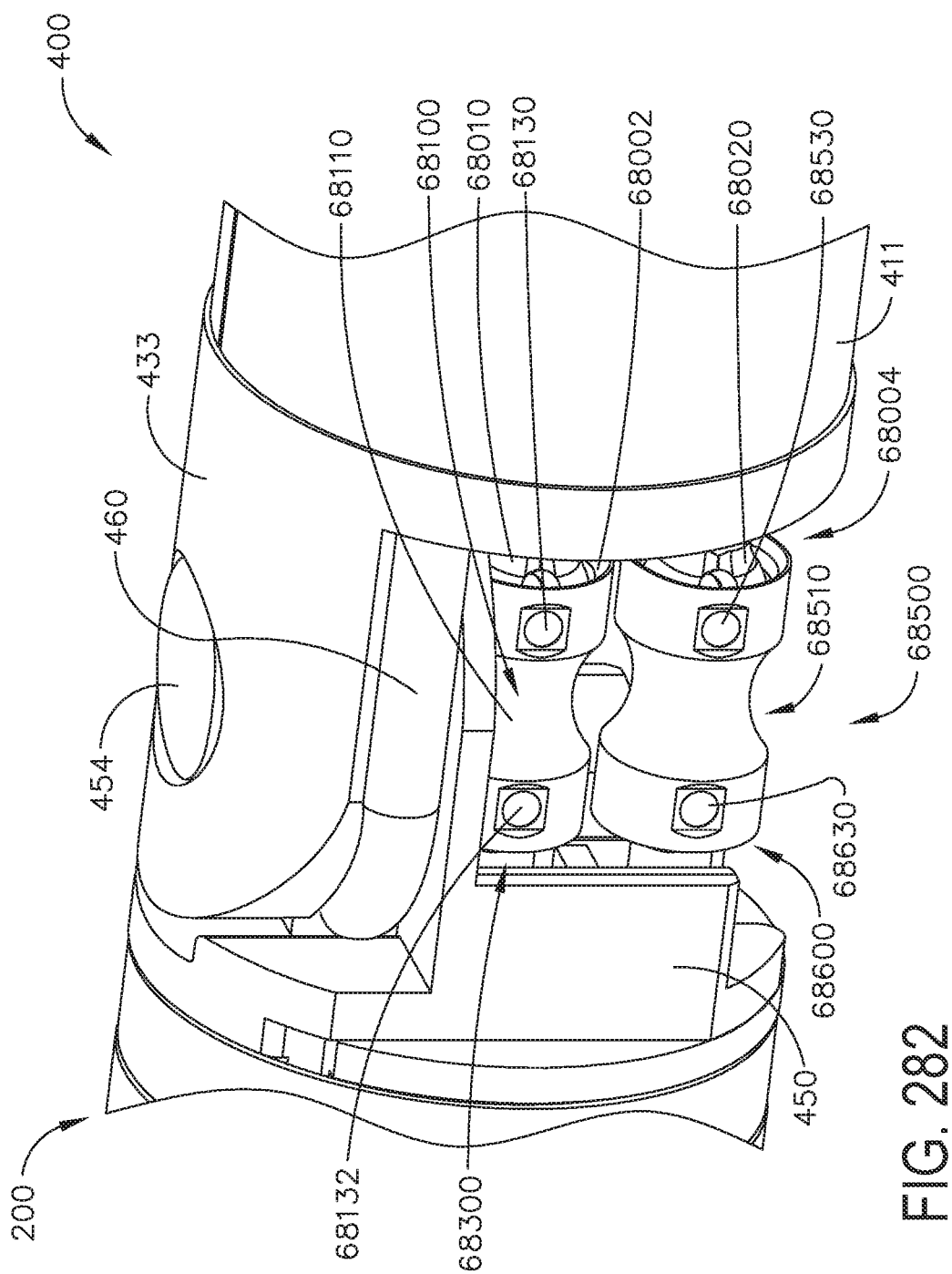

FIG. 282 is a perspective view of a portion of an articulation joint embodiment coupling an end effector to a shaft assembly, in accordance with at least one aspect of the present disclosure.

Figure 283:
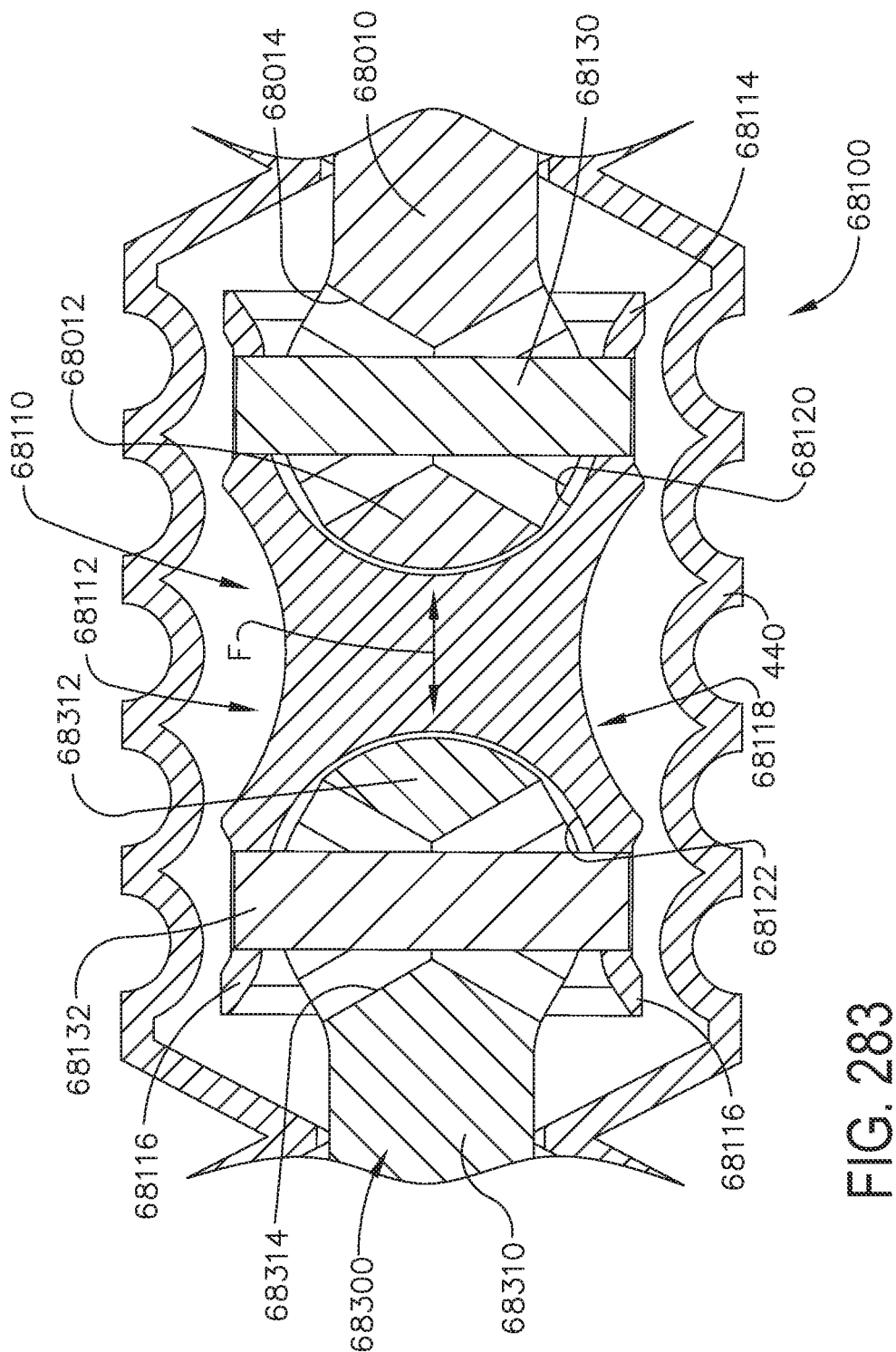

FIG. 283 is a cross-sectional view of an intermediate closure drive shaft portion of the articulation joint of FIG. 282, in accordance with at least one aspect of the present disclosure.

Figure 284:
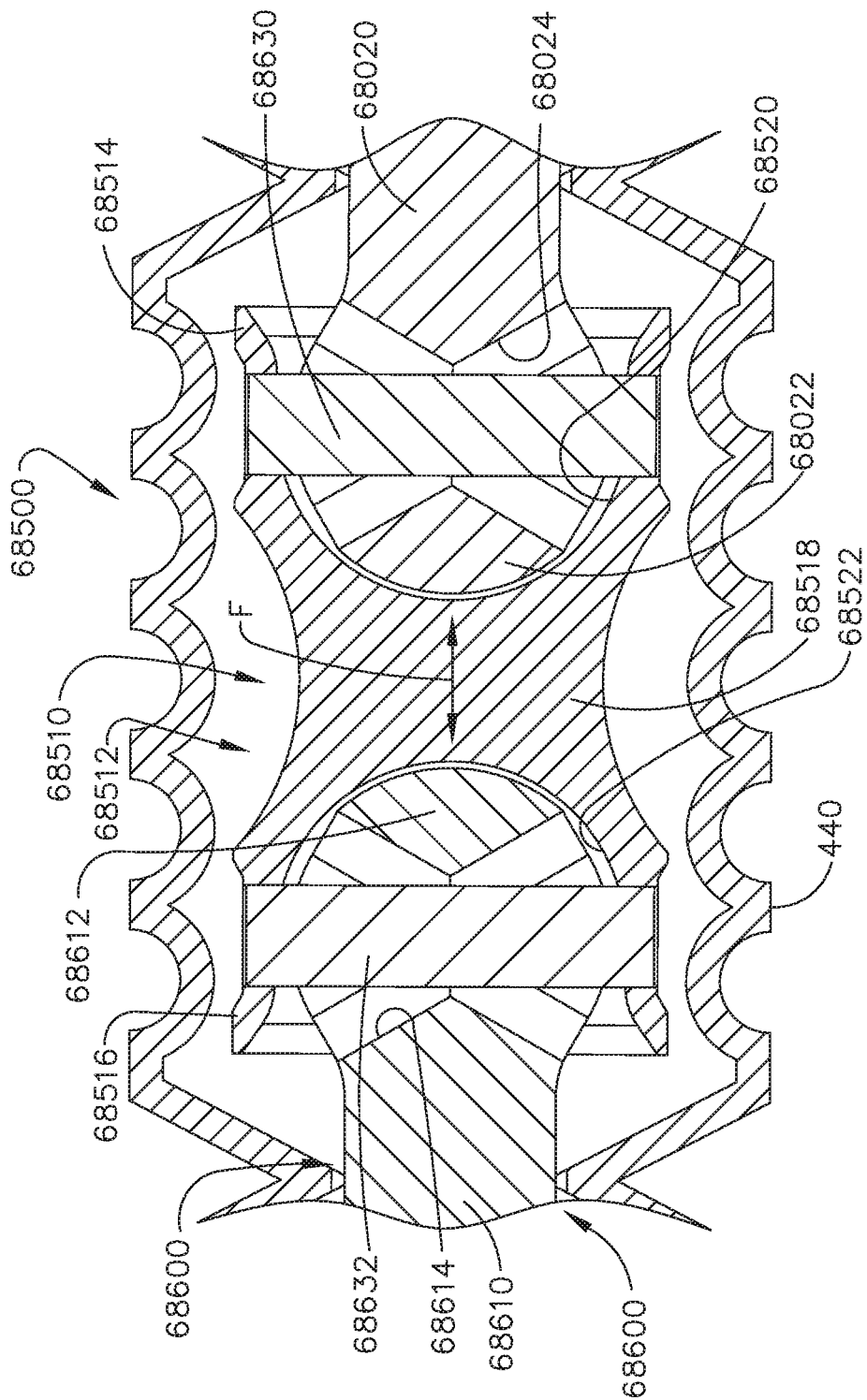

FIG. 284 is a cross-sectional view of an intermediate firing drive shaft portion of the articulation joint of FIG. 282, in accordance with at least one aspect of the present disclosure.

Figure 285:
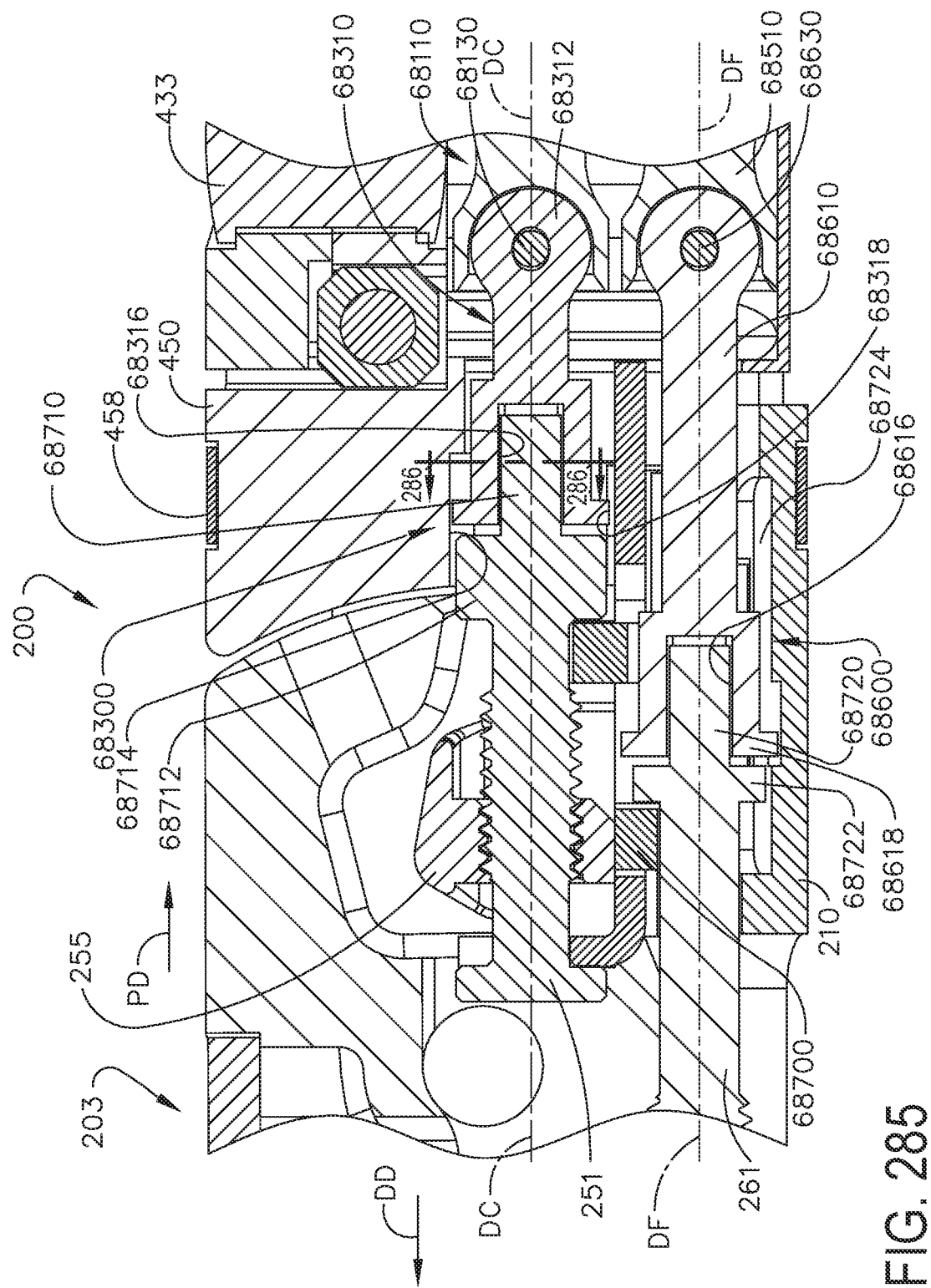

FIG. 285 is a cross-sectional view of a portion of the end effector of FIG. 282 showing a coupling between a distal closure drive shaft and a closure screw and a coupling between a distal firing drive shaft and a firing screw, in accordance with at least one aspect of the present disclosure.

Figure 286:
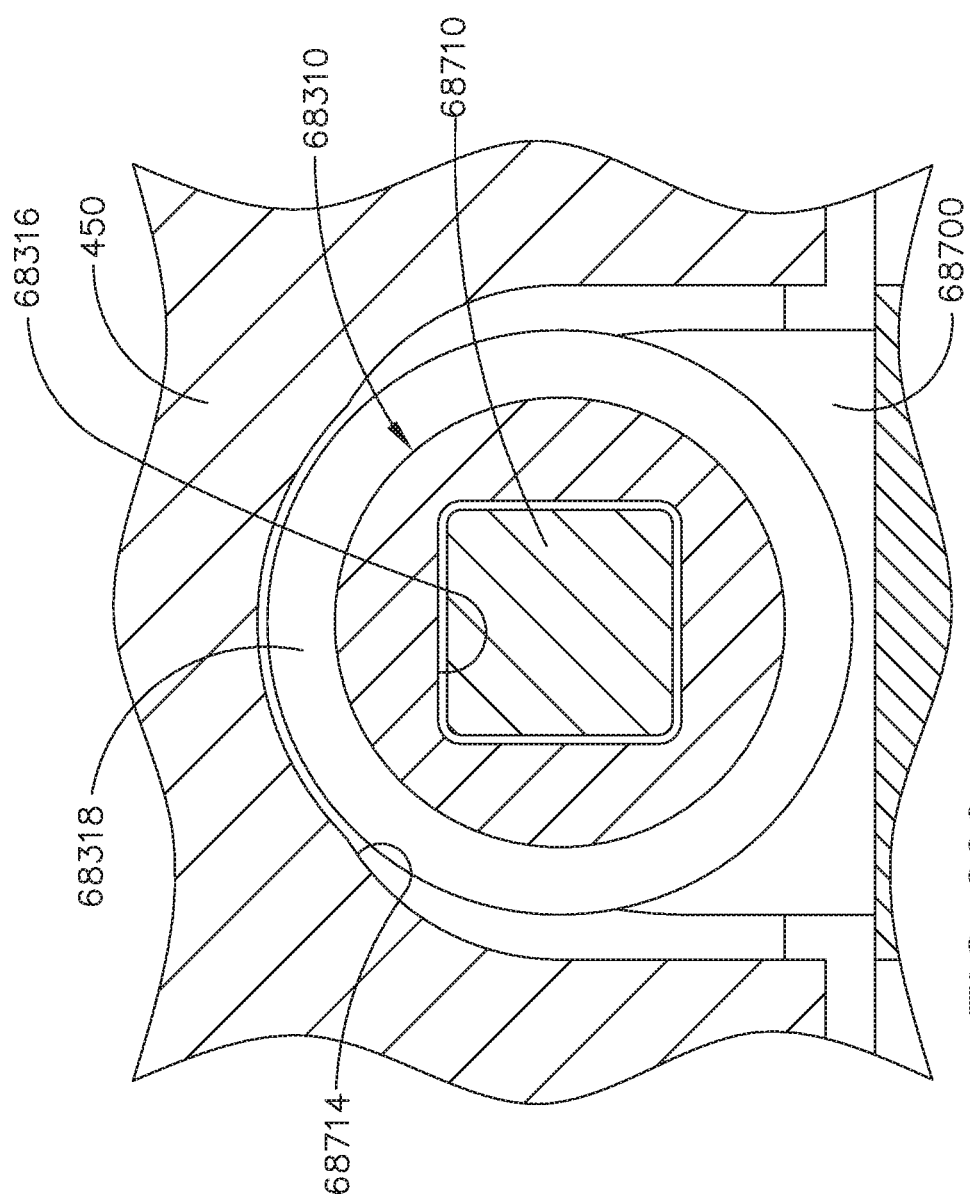

FIG. 286 is a cross-sectional end view of a closure coupler of FIG. 285 taken along section line 286-286 in FIG. 285, in accordance with at least one aspect of the present disclosure.

Figure 287:
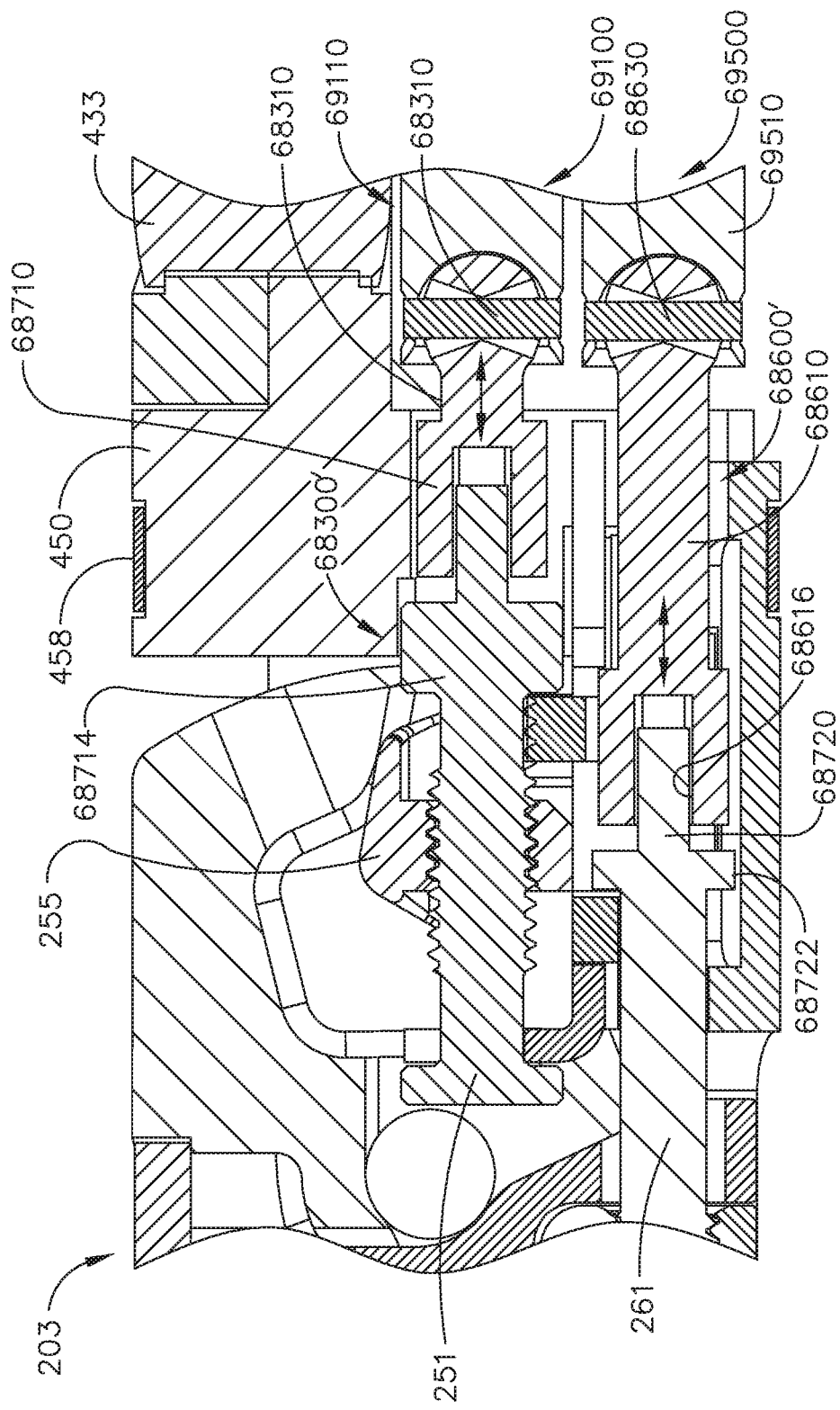

FIG. 287 is a cross-sectional view of a portion of another end effector showing a coupling between a distal closure drive shaft and a closure screw and a coupling between a distal firing drive shaft and a firing screw, in accordance with at least one aspect of the present disclosure.

Figure 288:
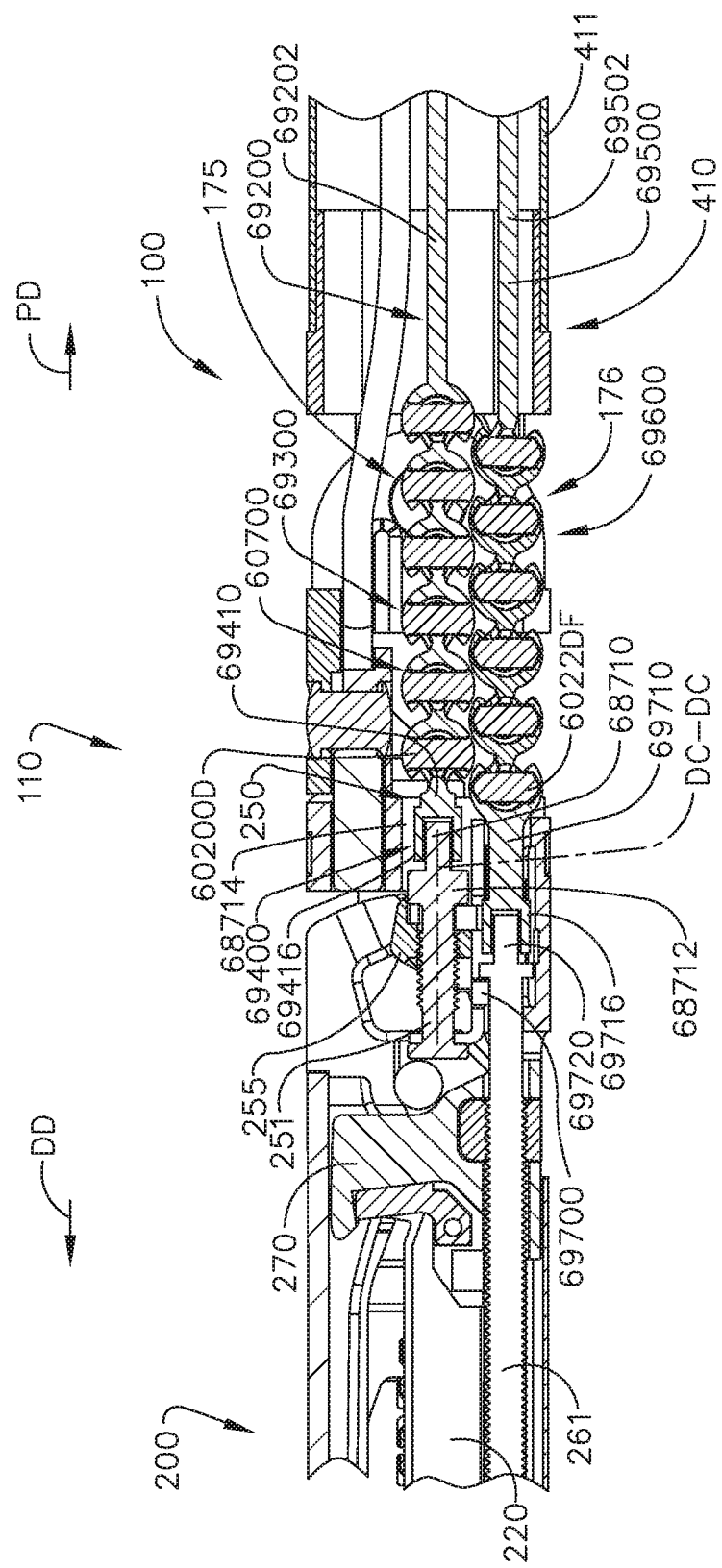

FIG. 288 is a cross-sectional view of an articulation region of another surgical instrument, in accordance with at least one aspect of the present disclosure.

Figure 289:
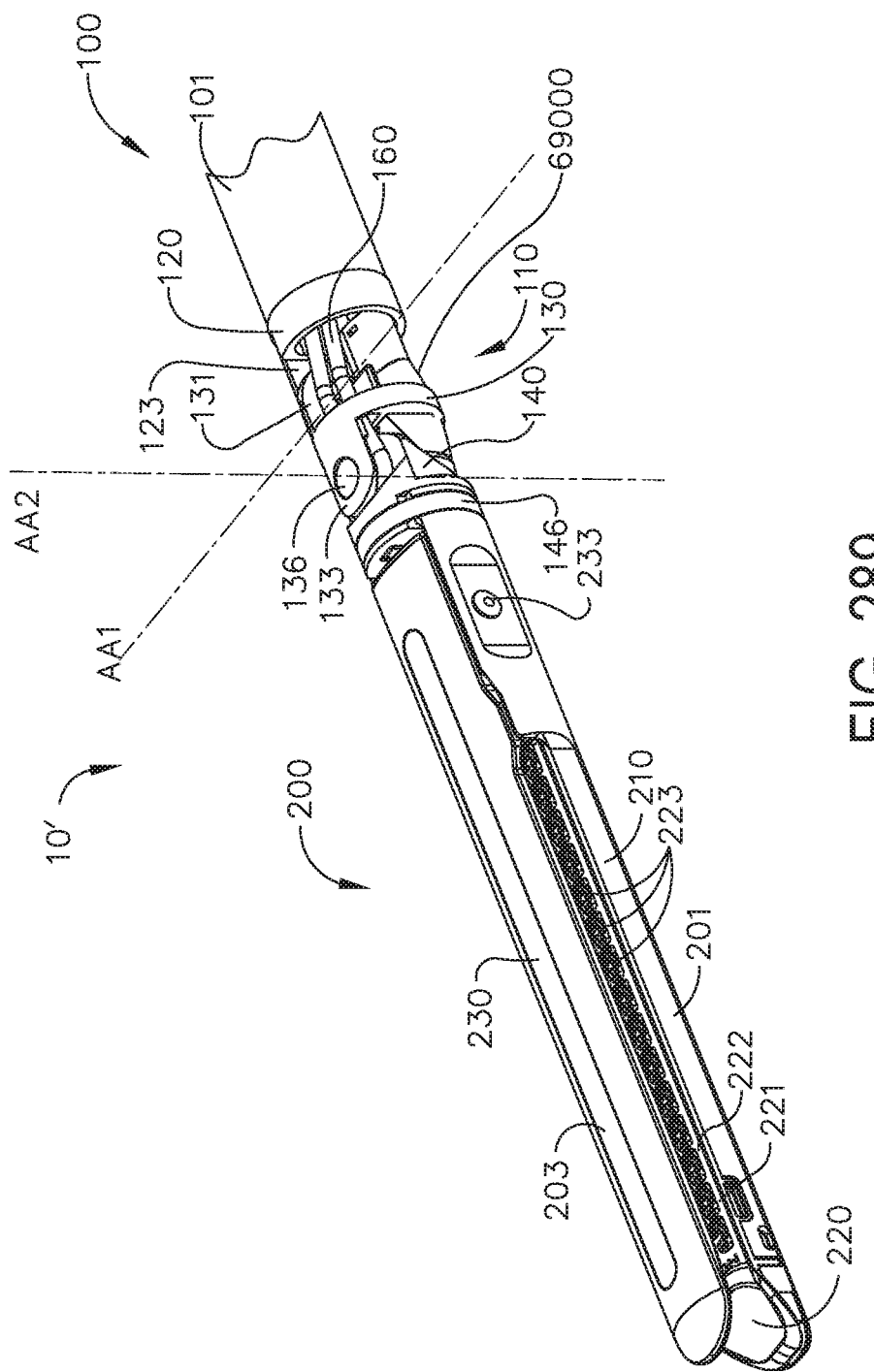

FIG. 289 is a perspective view of a portion of another surgical instrument, in accordance with at least one aspect of the present disclosure.

Figure 290:
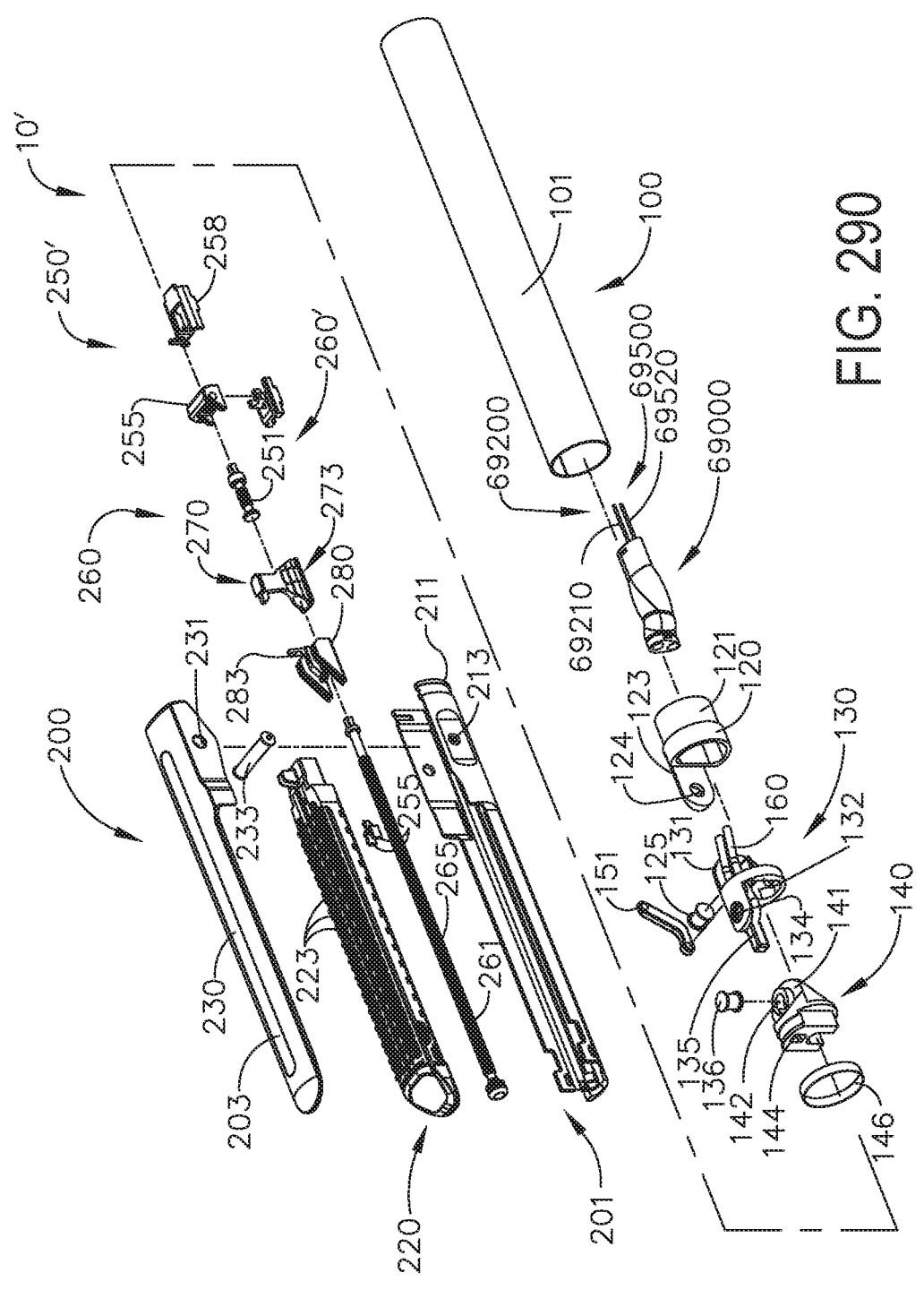

FIG. 290 is an exploded assembly view of a portion of the surgical instrument of FIG. 289, in accordance with at least one aspect of the present disclosure.

Figure 291:
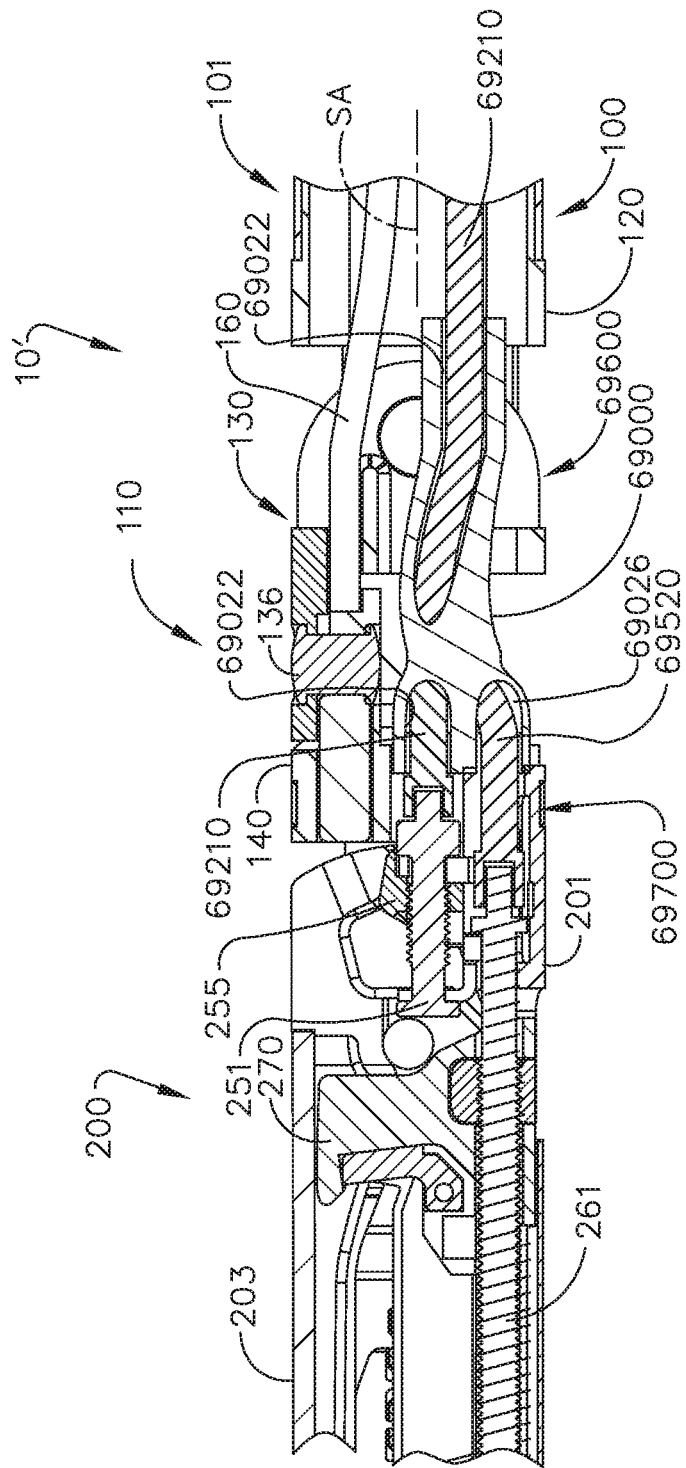

FIG. 291 is a cross-sectional view of a portion of the surgical instrument of FIG. 289, in accordance with at least one aspect of the present disclosure.

Figure 292:
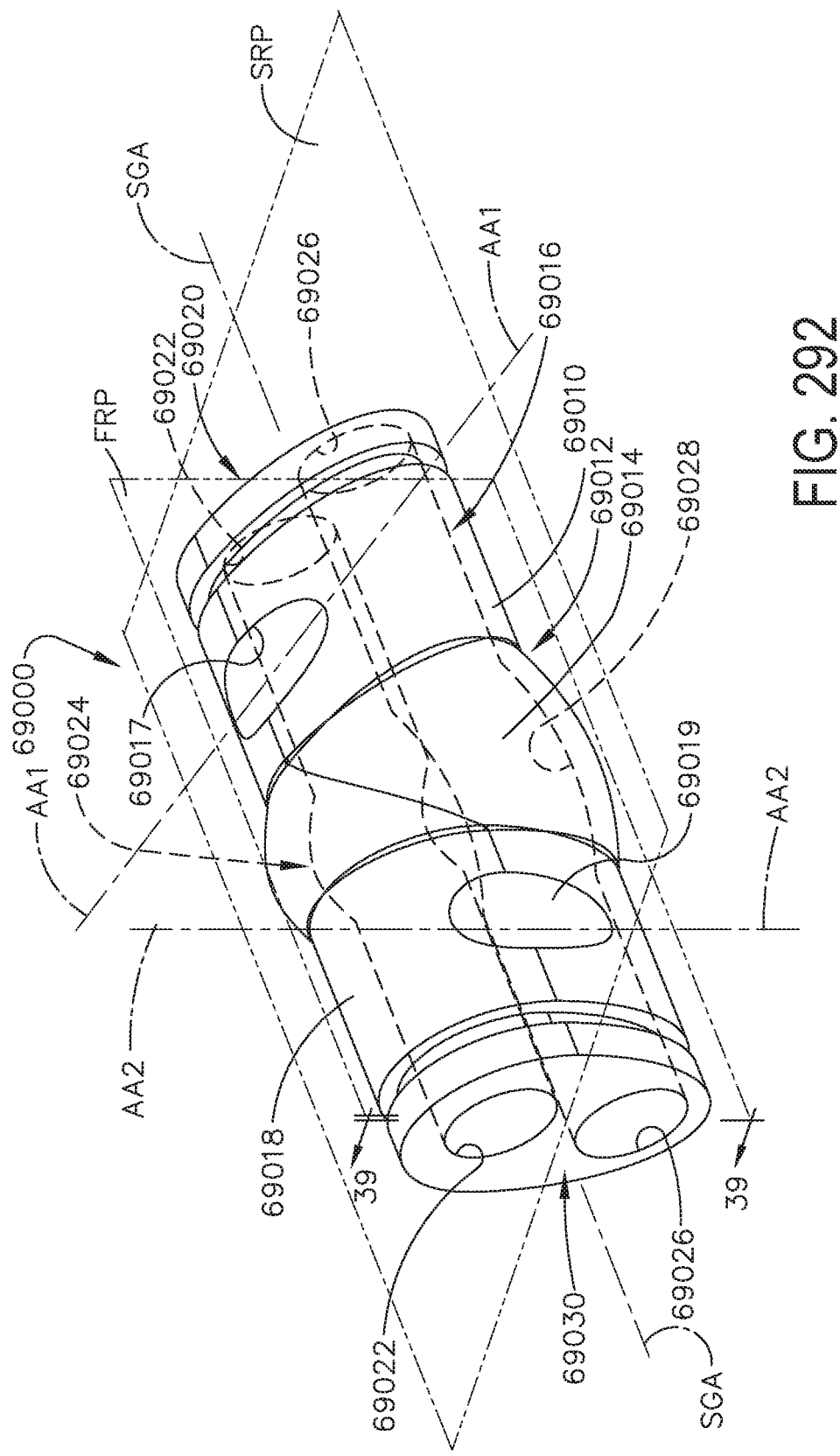

FIG. 292 is a perspective view of a shaft guide embodiment, in accordance with at least one aspect of the present disclosure.

FIG. 293 is a proximal end view of the shaft guide embodiment of FIG. 292, in accordance with at least one aspect of the present disclosure.

FIG. 294 is a distal end view of the shaft guide embodiment of FIG. 292, in accordance with at least one aspect of the present disclosure.

Figure 295:
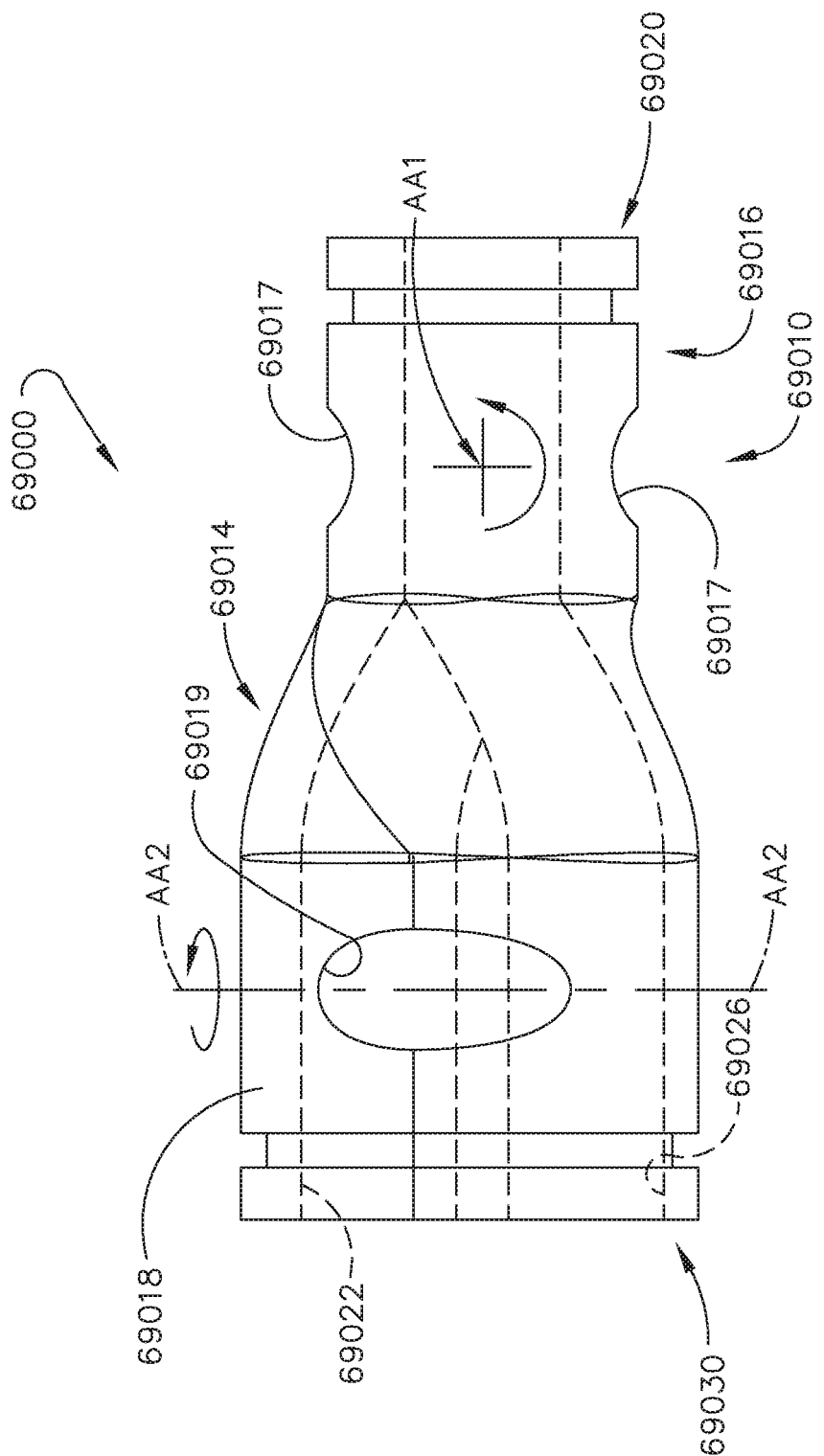

FIG. 295 is a side view of the shaft guide embodiment of FIG. 292, in accordance with at least one aspect of the present disclosure.

Figure 296:
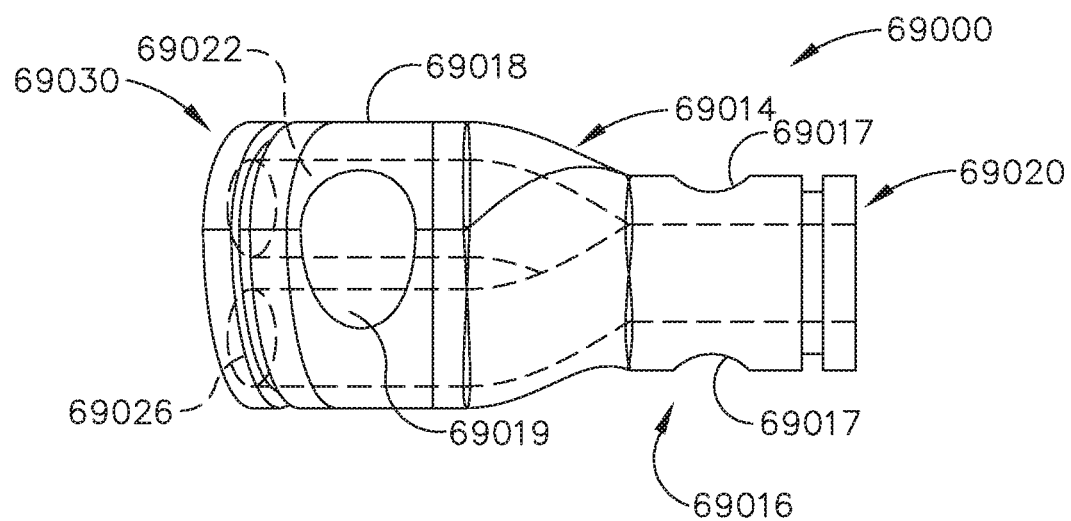

FIG. 296 is another side view of the shaft guide embodiment of FIG. 292, in accordance with at least one aspect of the present disclosure.

Figure 297:
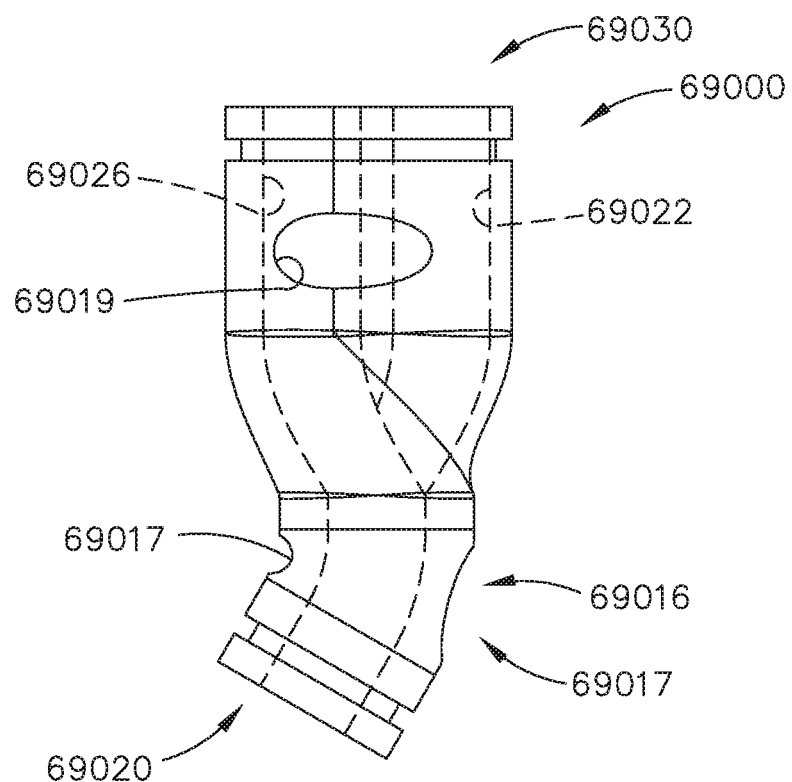

FIG. 297 is another view of the shaft guide embodiment of FIG. 292 in a flexed position, in accordance with at least one aspect of the present disclosure.

Figure 298:
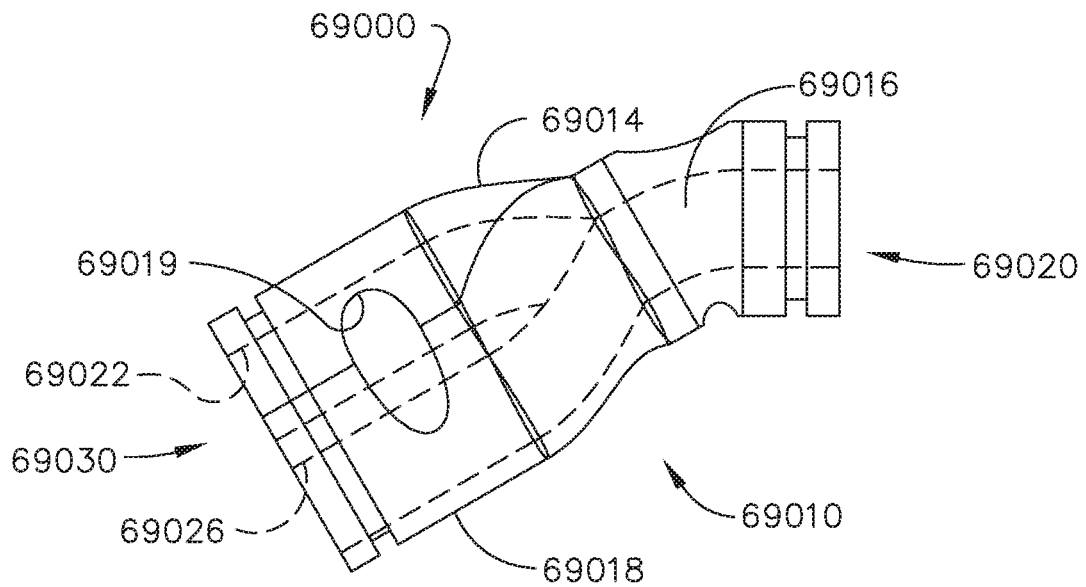

FIG. 298 is another view of the shaft guide embodiment of FIG. 292 in another flexed position, in accordance with at least one aspect of the present disclosure.

Figure 299:
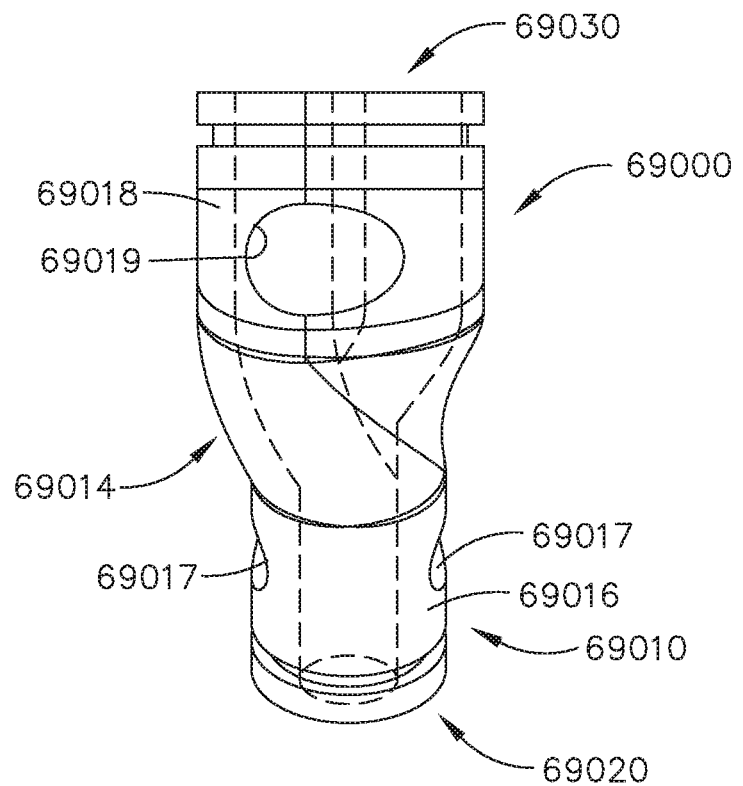

FIG. 299 is another view of the shaft guide embodiment of FIG. 292, in accordance with at least one aspect of the present disclosure.

Figure 300:
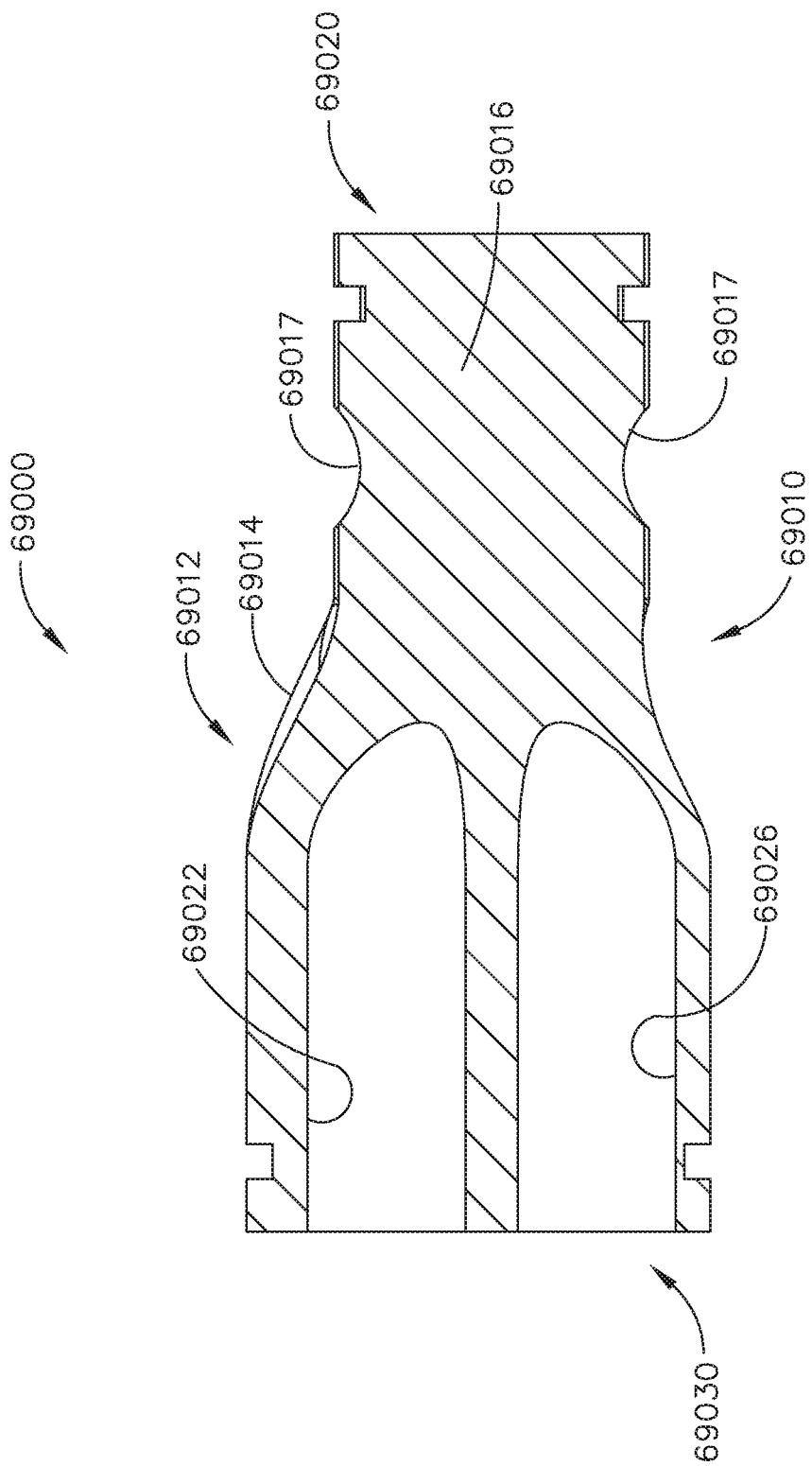

FIG. 300 is a cross-sectional view of the shaft guide embodiment of FIG. 294 taken along section line 300-300 in FIG. 294, in accordance with at least one aspect of the present disclosure.

Figure 301:
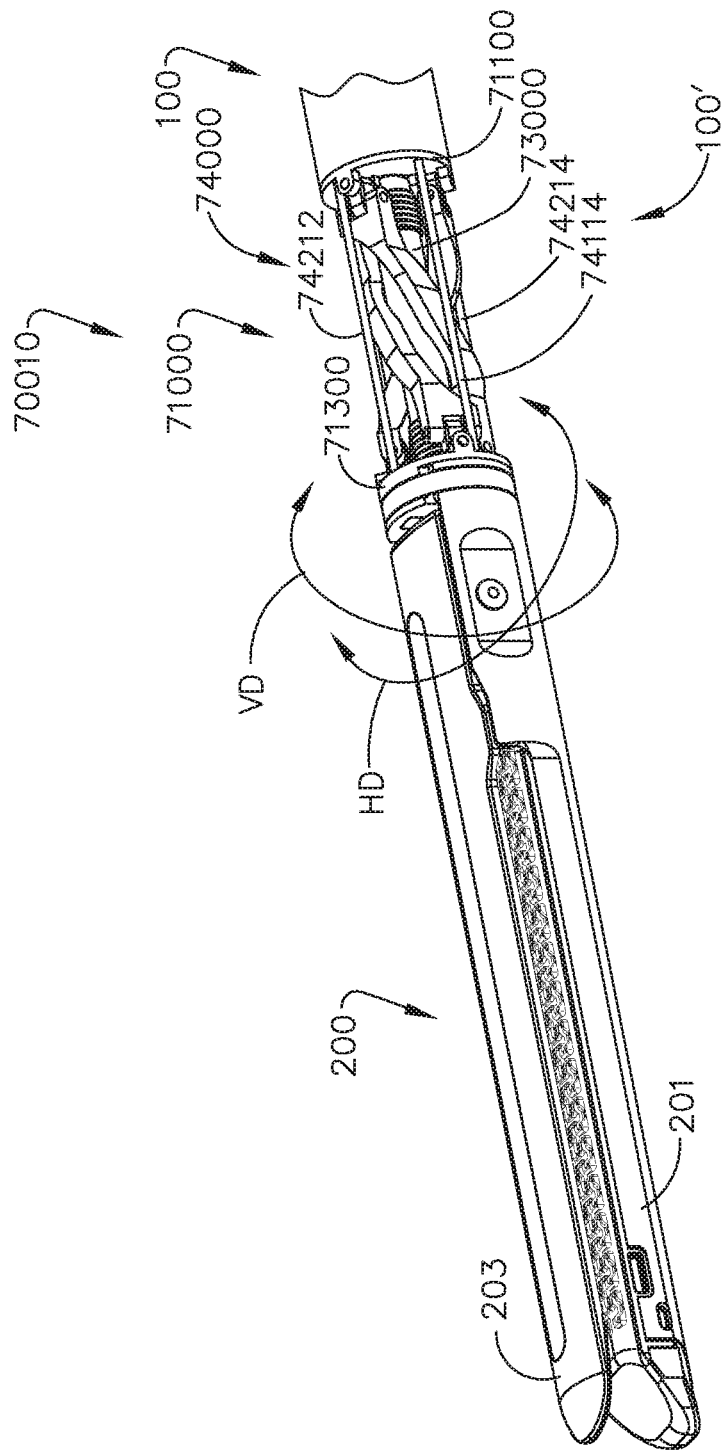

FIG. 301 is a perspective view of a portion of another surgical instrument, in accordance with at least one aspect of the present disclosure.

Figure 302:
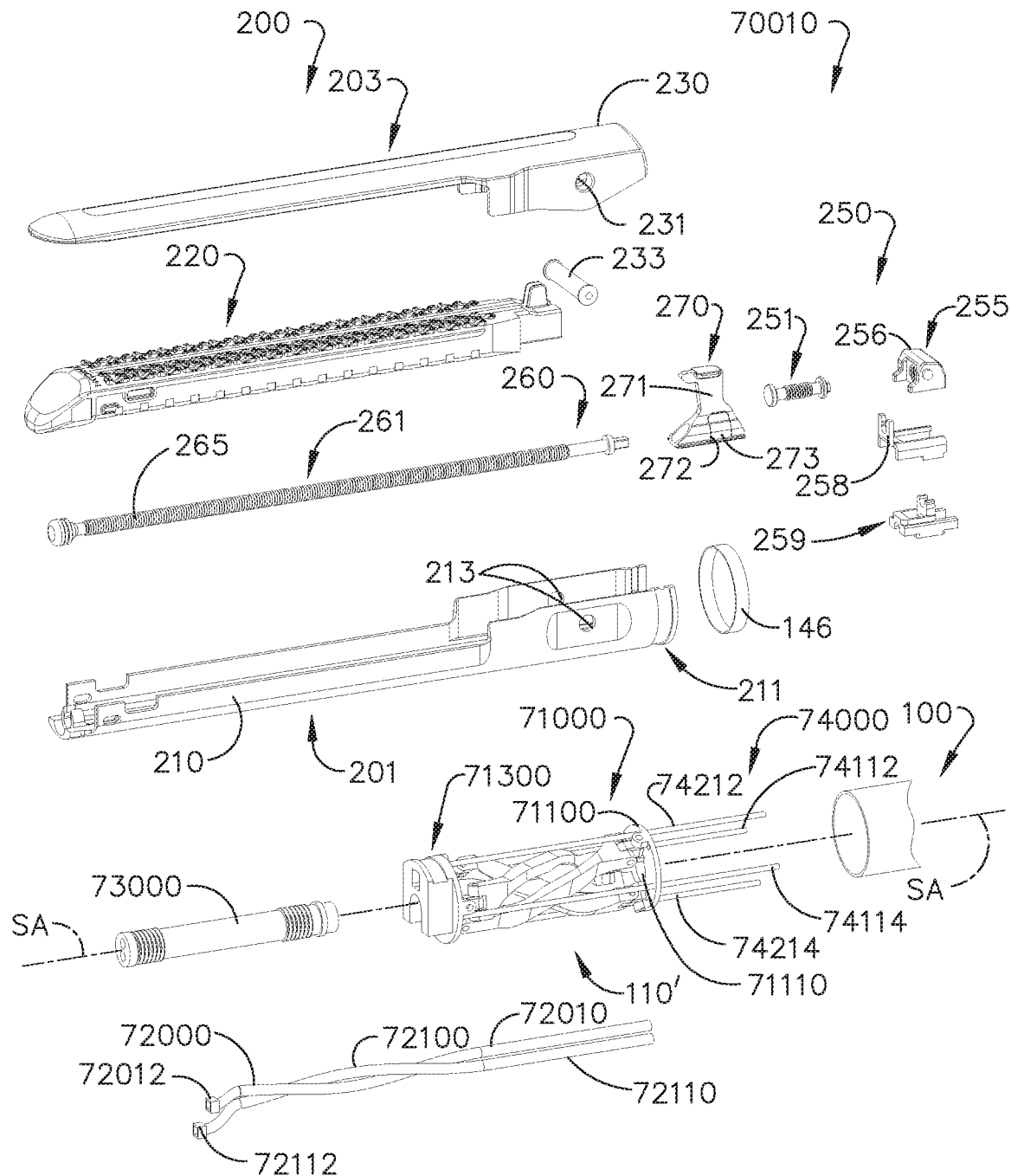

FIG. 302 is an exploded assembly view of a portion of the surgical instrument of FIG. 301, in accordance with at least one aspect of the present disclosure.

Figure 303:
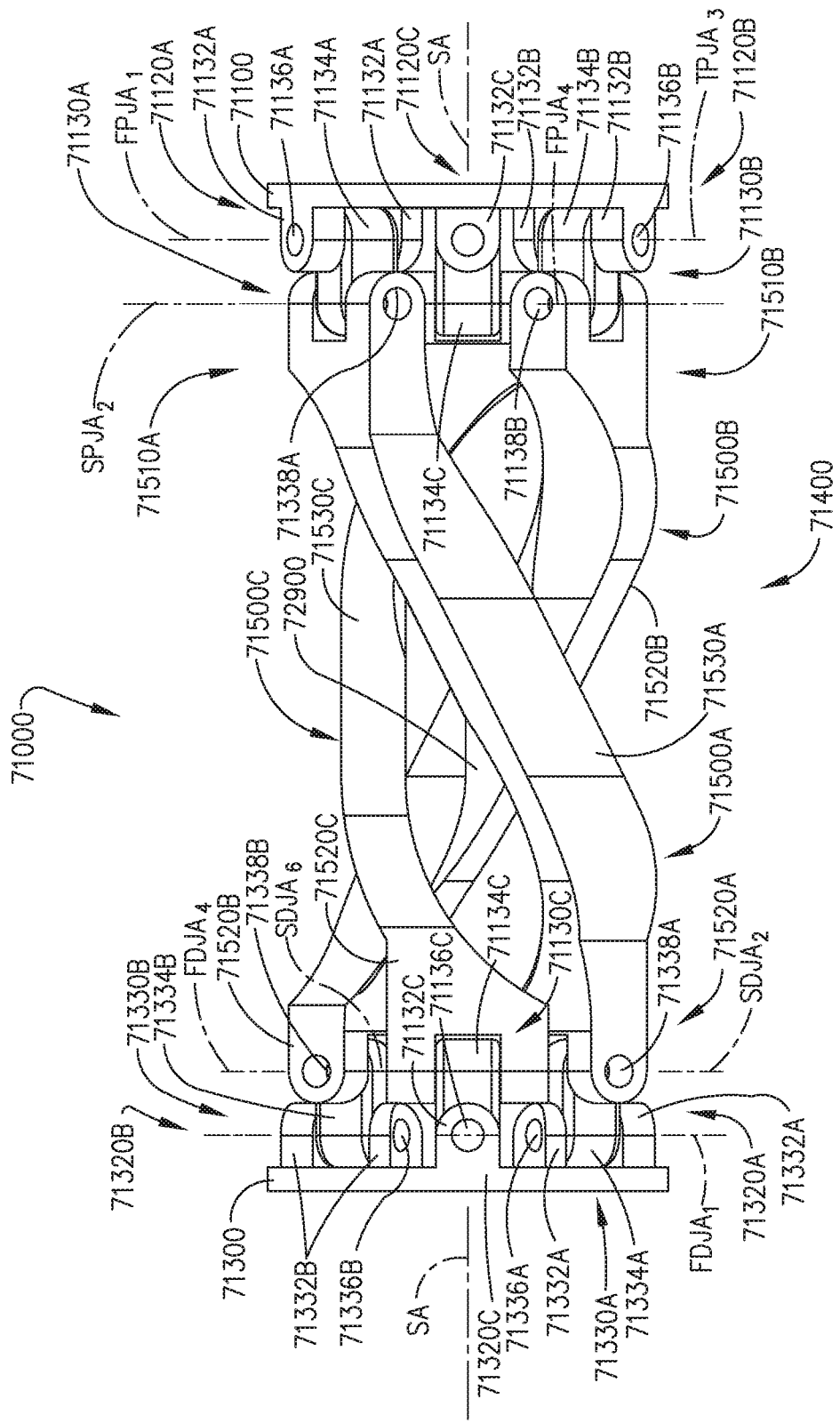

FIG. 303 is a side view of an articulation joint assembly of the surgical instrument of FIG. 301, in accordance with at least one aspect of the present disclosure.

Figure 304:
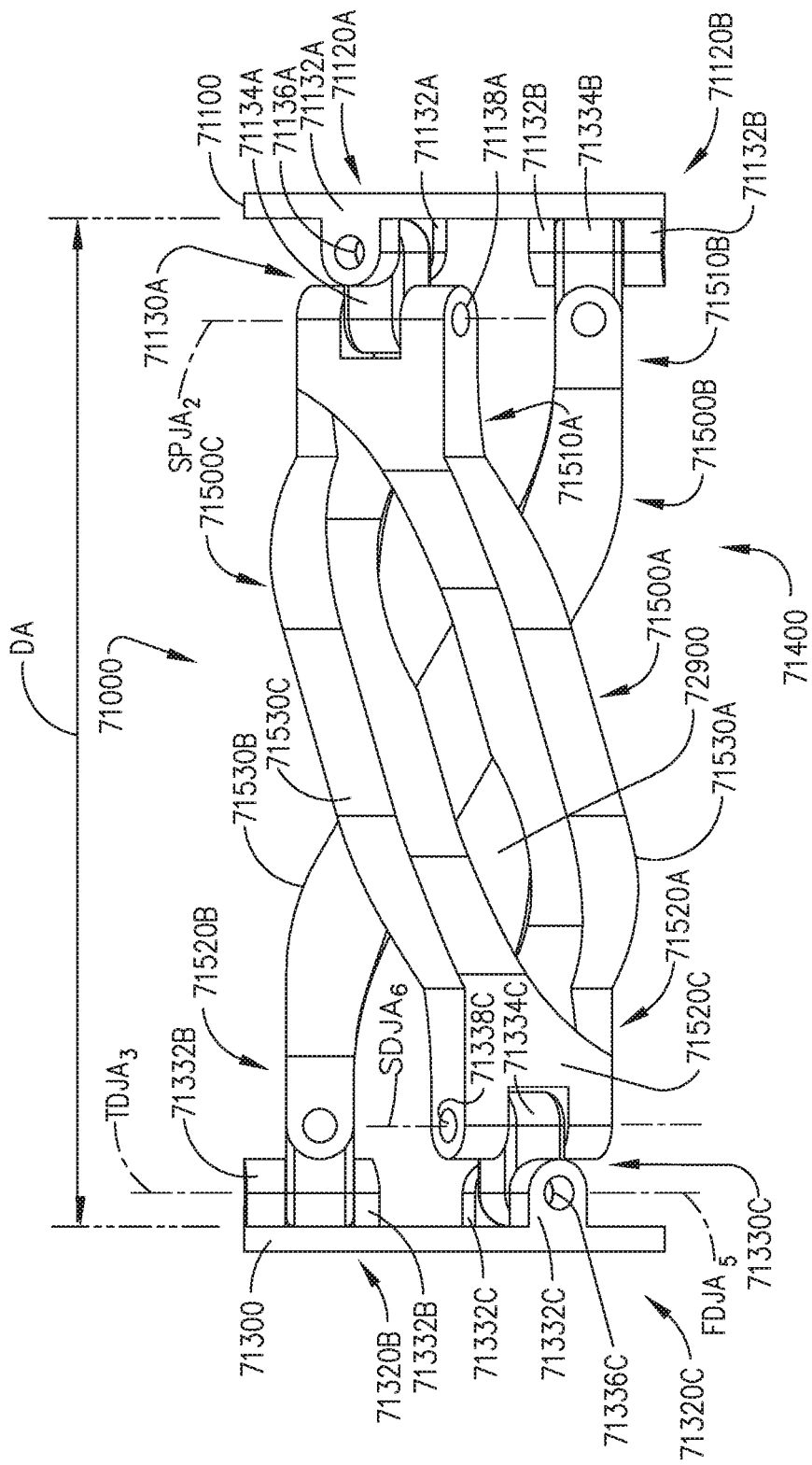

FIG. 304 is another side view of the articulation joint assembly of the surgical instrument of FIG. 301, in accordance with at least one aspect of the present disclosure.

Figure 305:
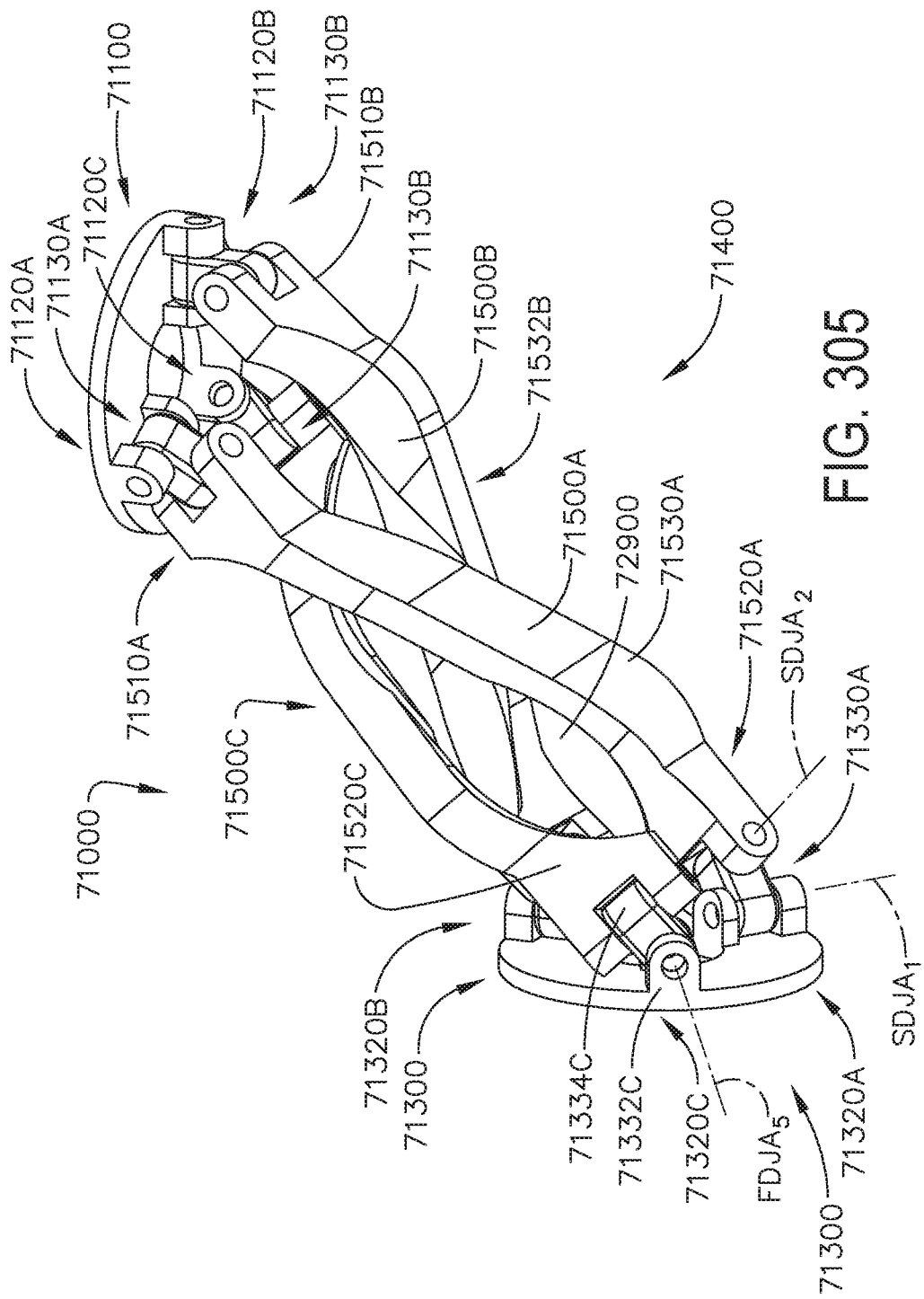

FIG. 305 is another view of the articulation joint assembly of the surgical instrument of FIG. 301 in articulated configuration, in accordance with at least one aspect of the present disclosure.

Figure 306:
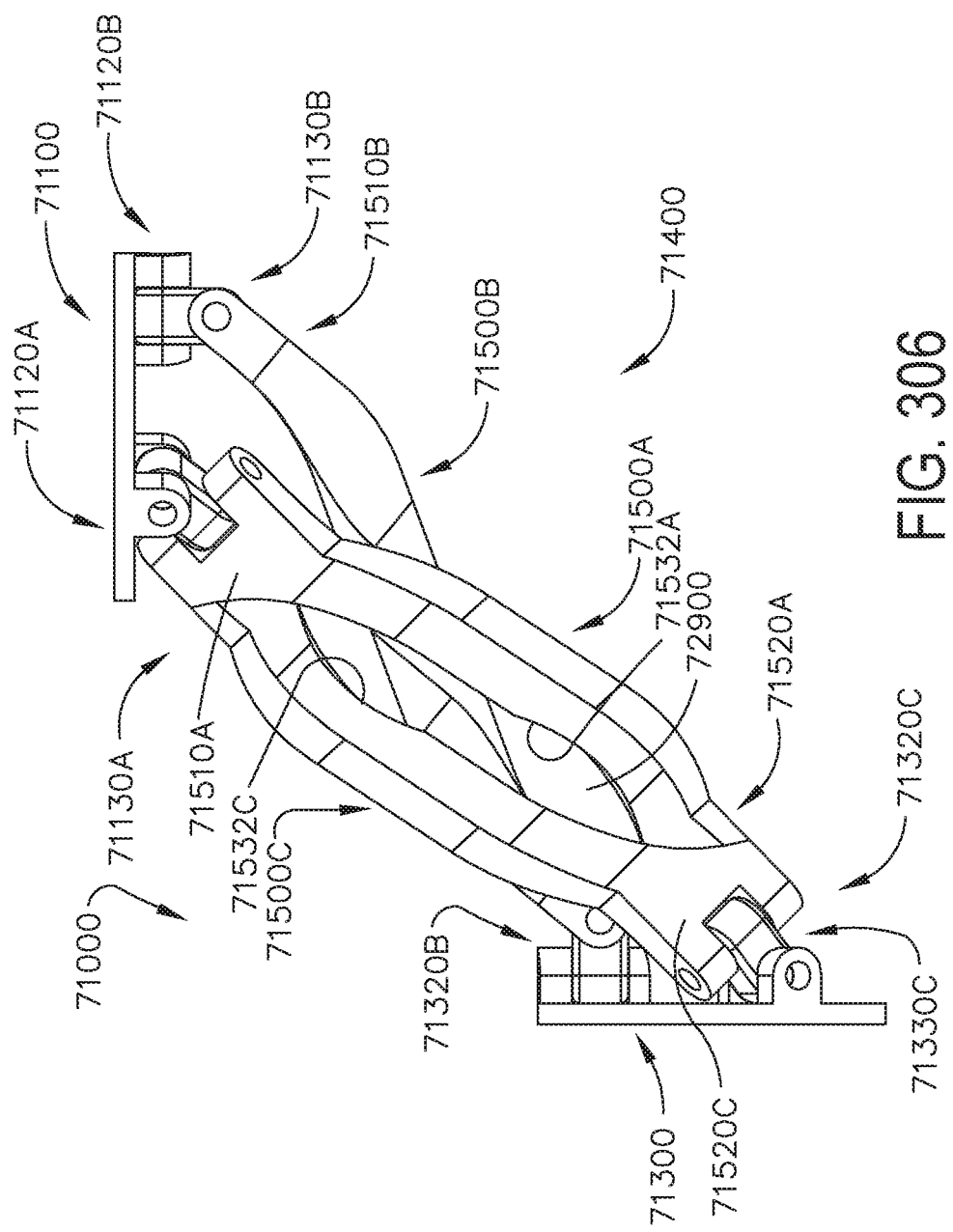

FIG. 306 is another view of the articulation joint assembly of the surgical instrument of FIG. 301 in another articulated configuration, in accordance with at least one aspect of the present disclosure.

Figure 307:
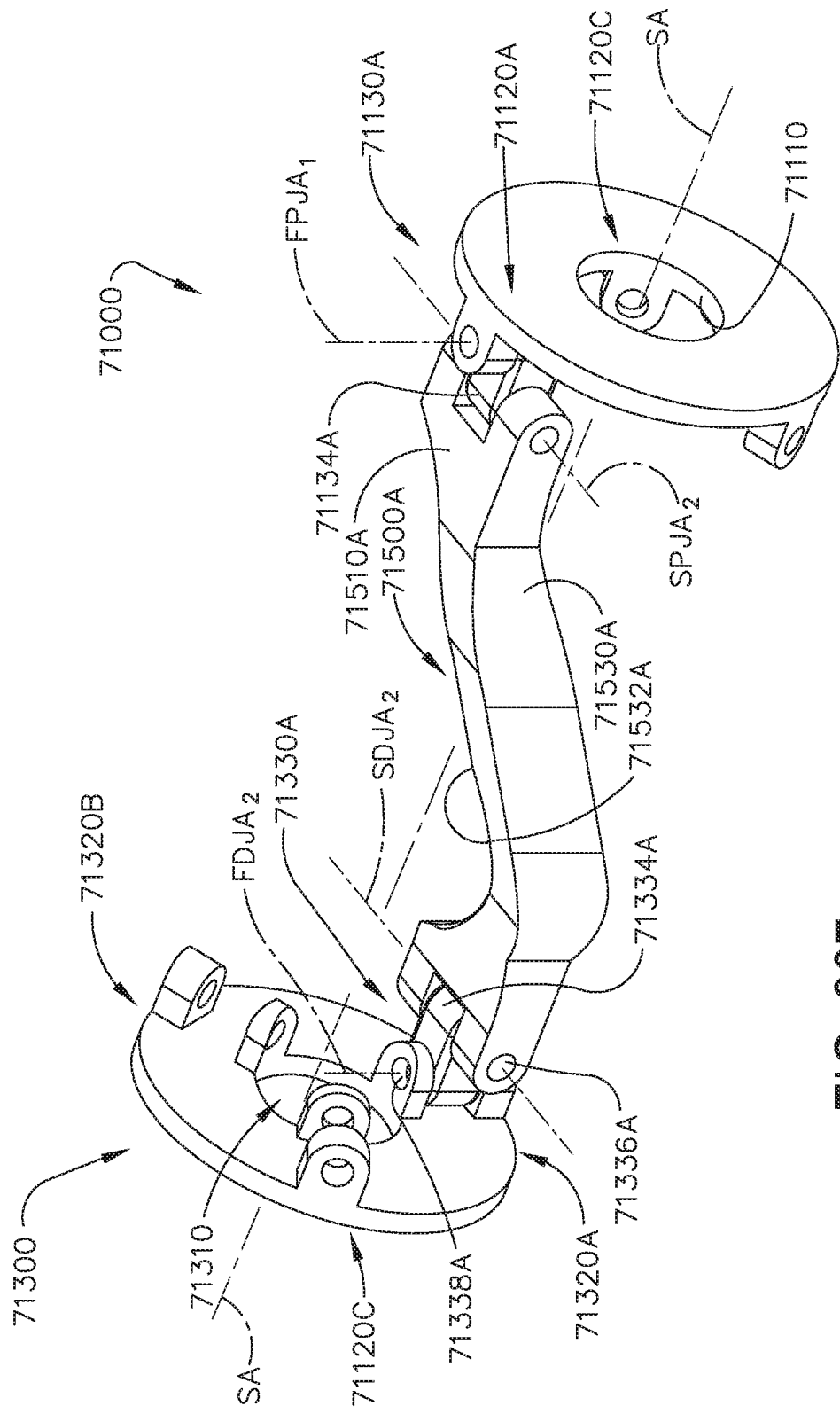

FIG. 307 is a perspective view of the articulation joint assembly of FIG. 306 with two articulation link members removed for clarity, in accordance with at least one aspect of the present disclosure.

Figure 308:
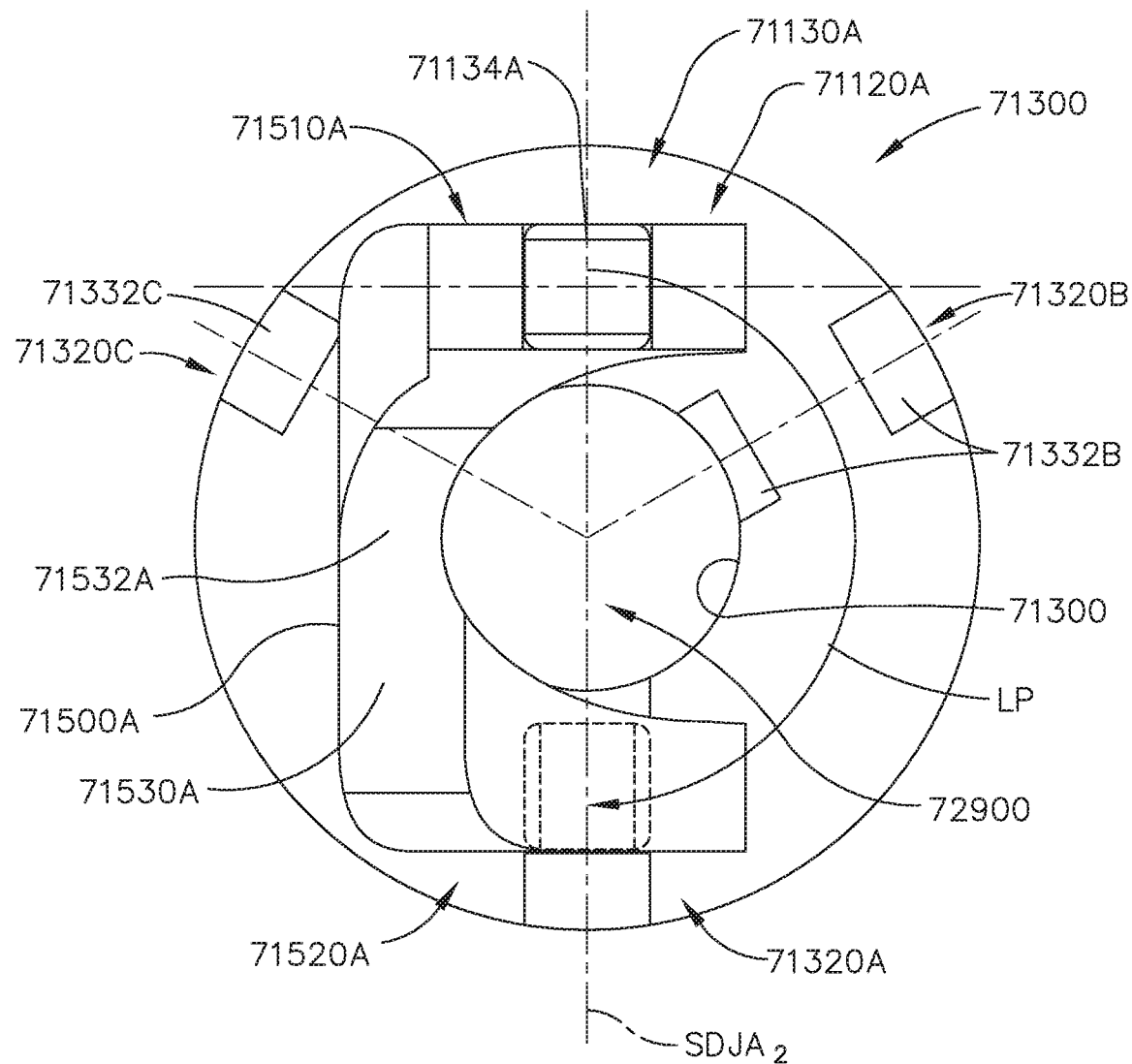

FIG. 308 is an end view of a portion of the articulation joint assembly of FIG. 307, in accordance with at least one aspect of the present disclosure.

Figure 309:
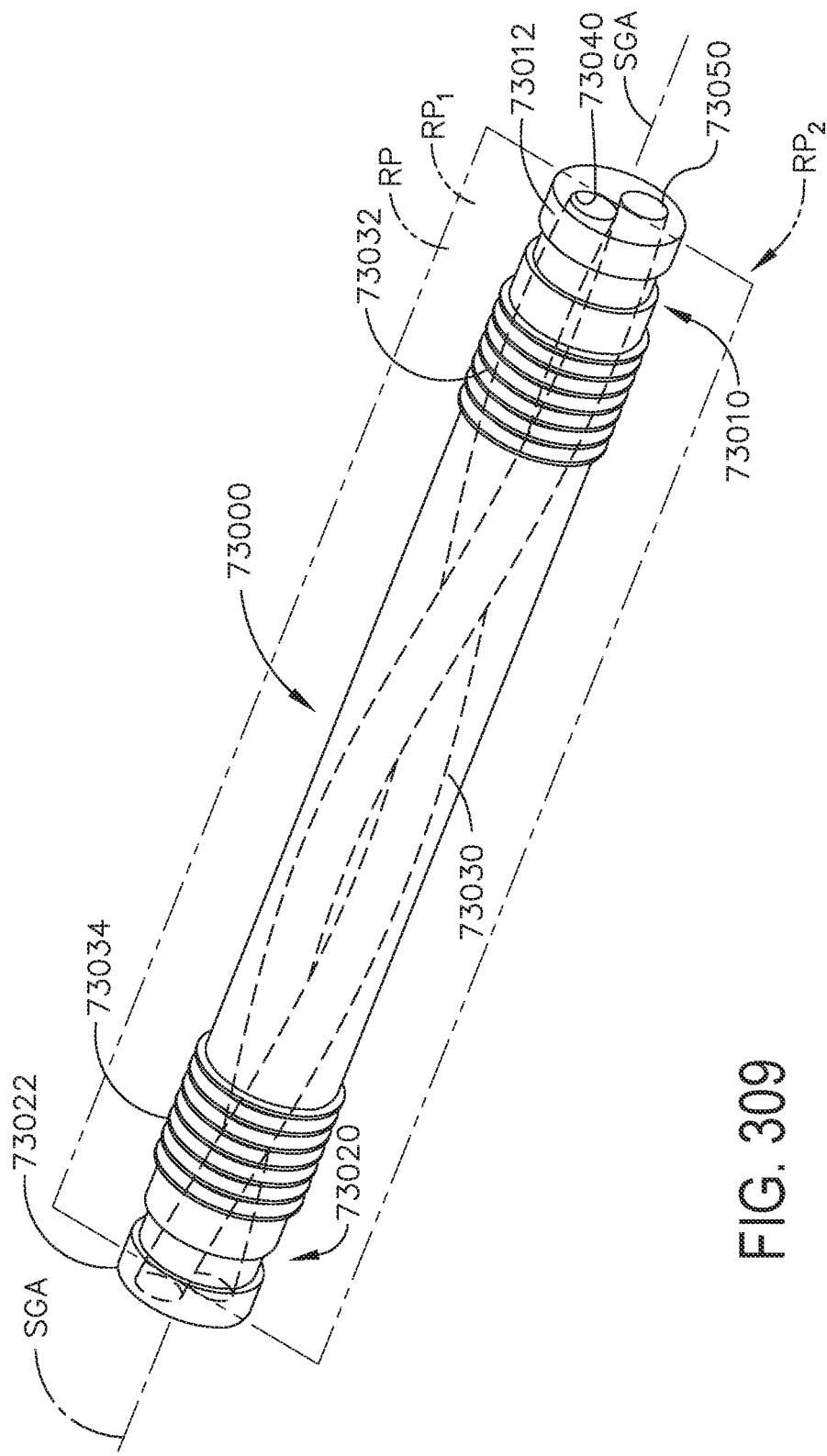

FIG. 309 is a perspective view of a shaft guide of the articulation joint assembly of the surgical instrument of FIG. 301, in accordance with at least one aspect of the present disclosure.

Figure 310:
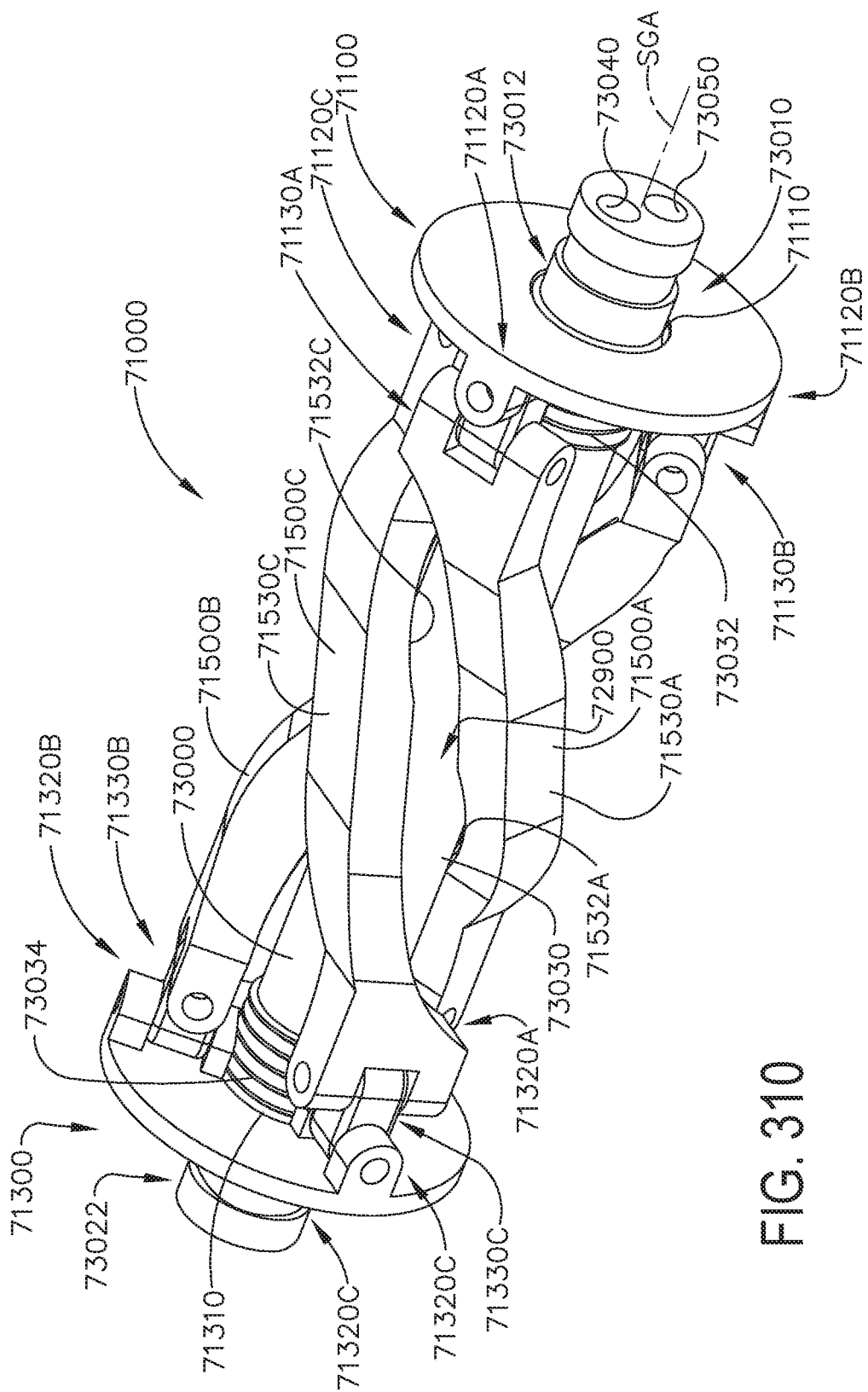

FIG. 310 is a perspective view of the articulation joint assembly of the surgical instrument of FIG. 301, in accordance with at least one aspect of the present disclosure.

Figure 311:
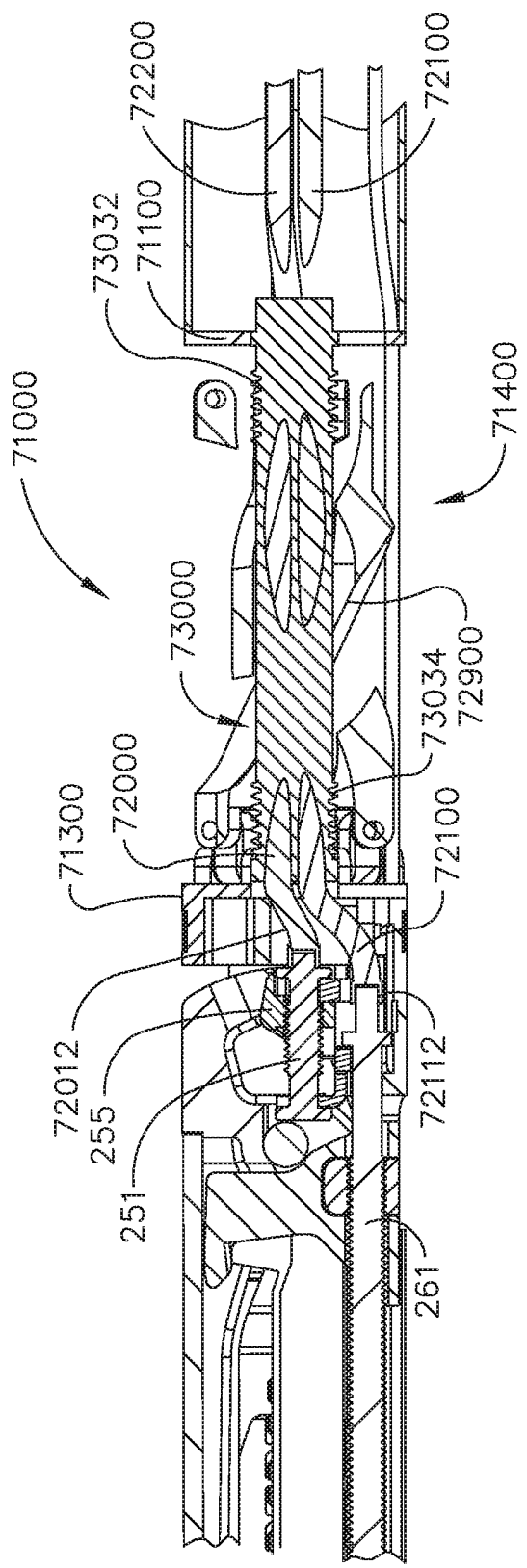

FIG. 311 is a cross-sectional view of the articulation joint assembly of the surgical instrument of FIG. 301, in accordance with at least one aspect of the present disclosure.

Figure 312:
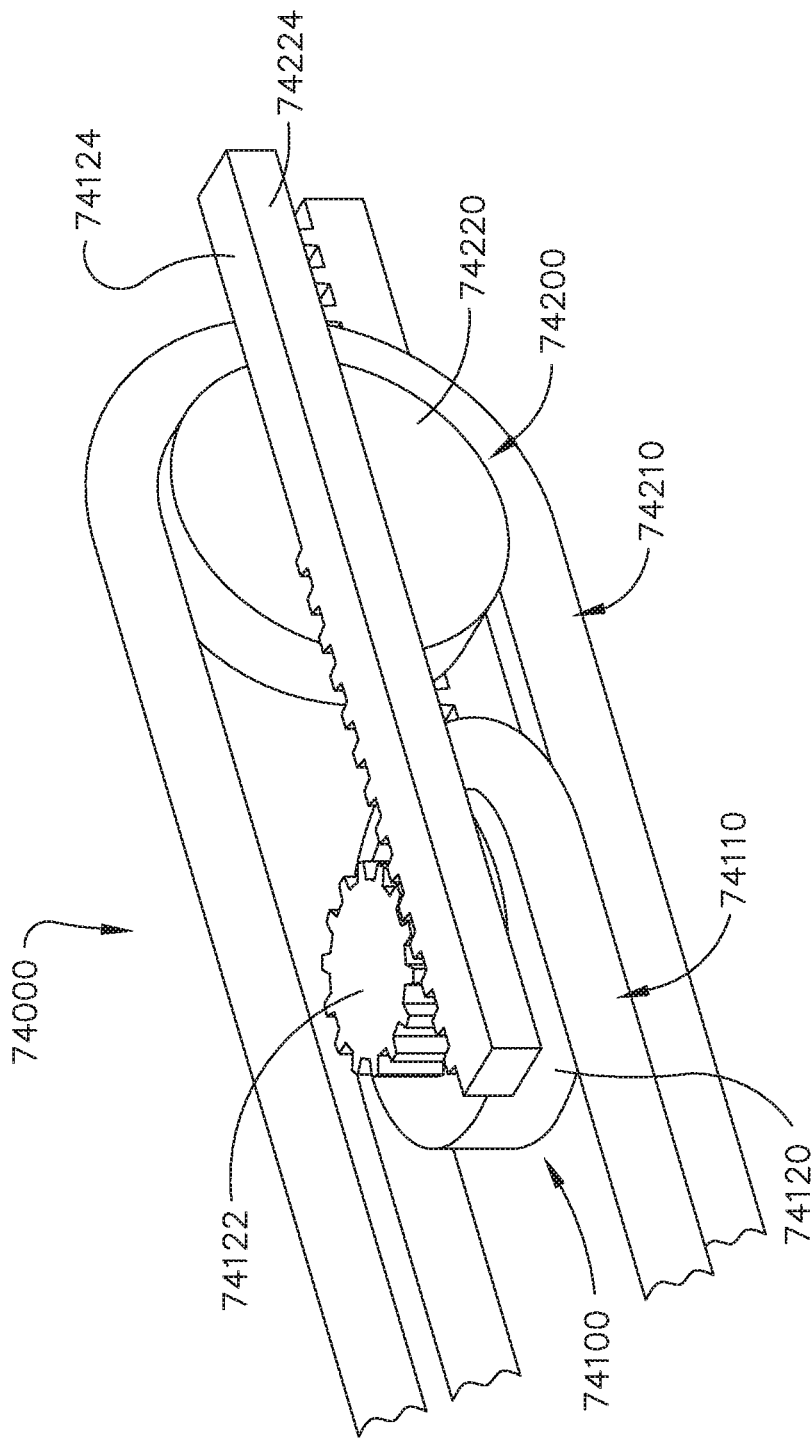

FIG. 312 is a partial perspective view of an articulation system, in accordance with at least one aspect of the present disclosure.

Figure 313:
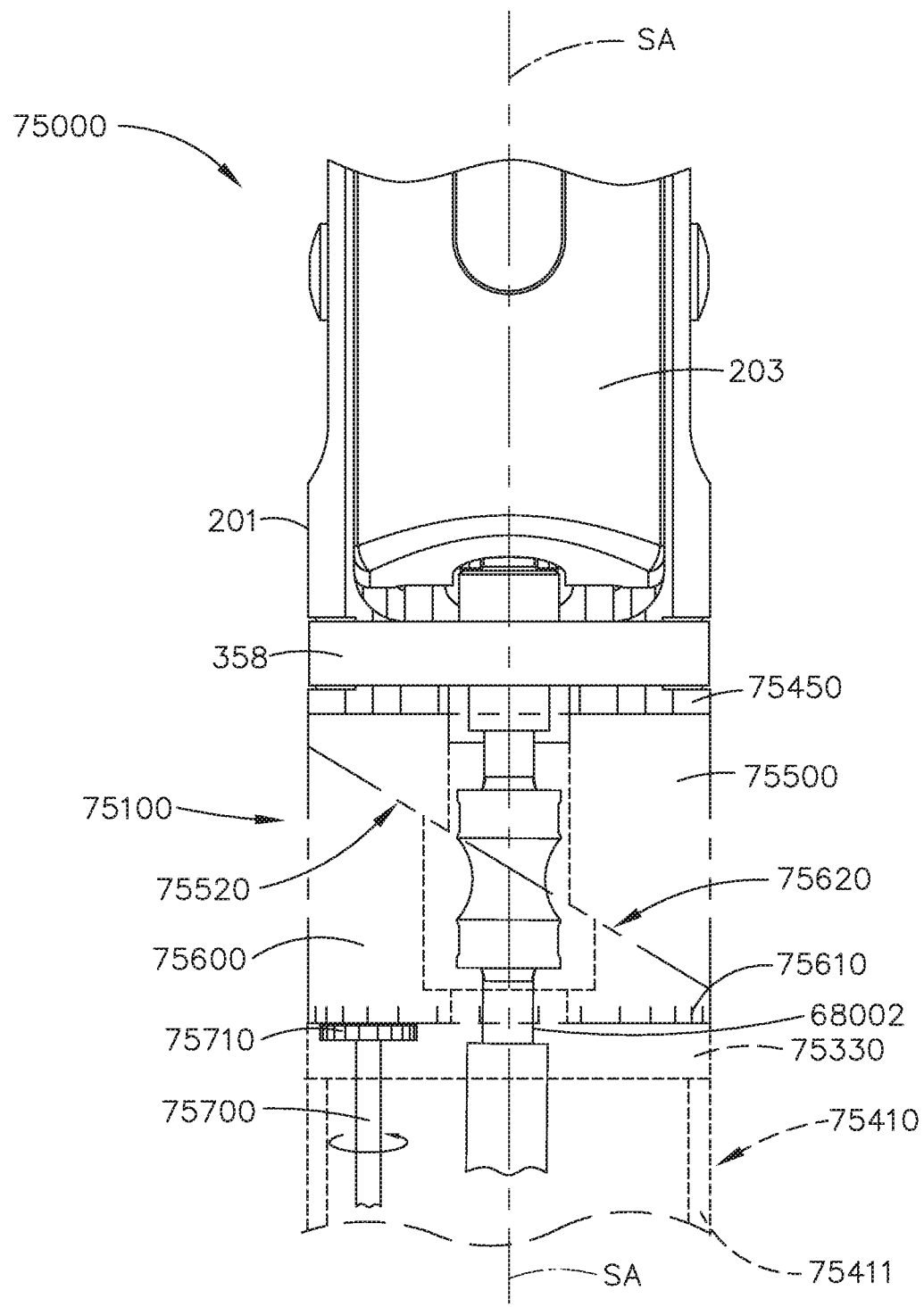

FIG. 313 is a top view of a portion of another end effector in an unarticulated position, in accordance with at least one aspect of the present disclosure.

Figure 314:
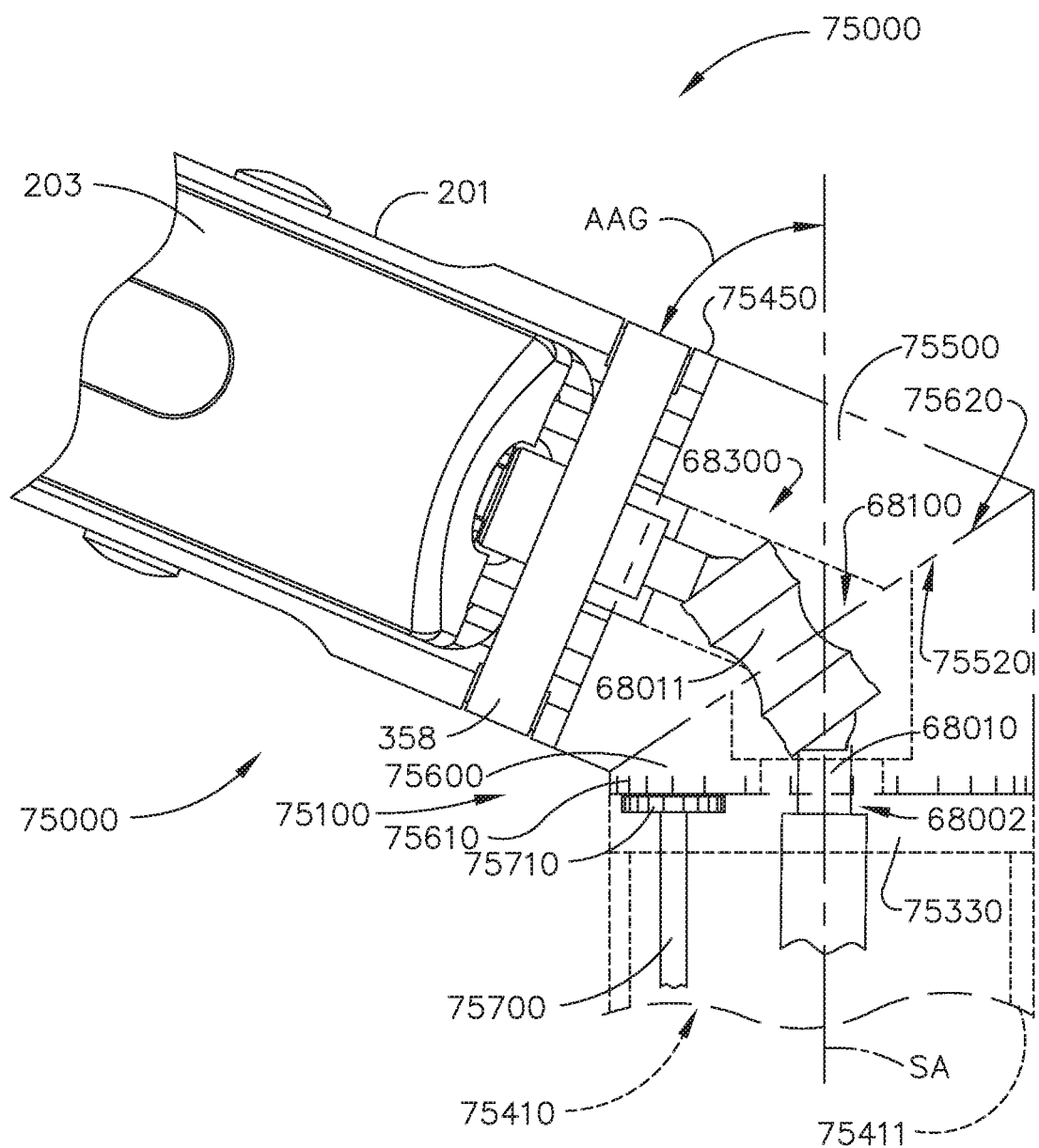

FIG. 314 is another top view of the end effector of FIG. 313 in a fully articulated position, in accordance with at least one aspect of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. patent applications that were filed on Mar. 24, 2021 and which are each herein incorporated by reference in their respective entireties:

U.S. Patent Application entitled SURGICAL STAPLING ASSEMBLY COMPRISING NONPLANAR STAPLES AND PLANAR STAPLES, U.S. patent appliction Ser. No. 17/211,161, published as U.S. Pub. No. 2022/034684 on Sep. 29, 2022;

U.S. Patent Application entitled SURGICAL STAPLE CARTRIDGE COMPRISING LONGITUDINAL SUPPORT BEAM, U.S. patent appliction Ser. No. 17/211,168, published as U.S. Pub. No. 2022/0340685 on Sep. 29, 2022;

U.S. Patent Application entitled ROTARY-DRIVEN SURGICAL STAPLING ASSEMBLY COMPRISING ECCENTRICALLY DRIVEN FIRING MEMBER, U.S. patent appliction Ser. No. 17/211,172, published as U.S. Pub. No. 2022/0304686 on Sep. 29, 2022;

U.S. Patent Application entitled ROTARY-DRIVEN SURGICAL STAPLING ASSEMBLY COMPRISING A FLOATABLE COMPONENT, U.S. patent appliction Ser. No. 17/211,175, published as U.S. Pub. No. 2022/0304687 on Sep. 29, 2022;

U.S. Patent Application entitled DRIVERS FOR FASTENER CARTRIDGE ASSEMBLIES HAVING ROTARY DRIVE SCREWS, U.S. patent appliction Ser. No. 17/211,182, published as U.S. Pub. No. 2022/0304680 on Sep. 29, 2022;

U.S. Patent Application entitled MATING FEATURES BETWEEN DRIVERS AND UNDERSIDE OF A CARTRIDGE DECK, U.S. patent appliction Ser. No. 17/211,189, published as U.S. Pub. No. 2022/034681 on Sep. 29, 2022;

U.S. Patent Application entitled LEVERAGING SURFACES FOR CARTRIDGE INSTALLATION, U.S. patent appliction Ser. No. 17/211,192, published as U.S. Pub. No. 2022/0304690 on Sep. 29, 2022;

U.S. Patent Application entitled FASTENER CARTRIDGE WITH NON-REPEATING FASTENER ROWS, U.S. patent appliction Ser. No. 17/211,197, published as U.S. Pub. No. 2022/0304682 on Sep. 29, 2022;

U.S. Patent Application entitled FIRING MEMBERS HAVING FLEXIBLE PORTIONS FOR ADAPTING TO A LOAD DURING A SURGICAL FIRING STROKE, U.S. patent appliction Ser. No. 17/211,207, published as U.S. Pub. No. 2022/0304688 on Sep. 29, 2022;

U.S. Patent Application entitled STAPLING ASSEMBLY COMPONENTS HAVING METAL SUBSTRATES AND PLASTIC BODIES, U.S. patent appliction Ser. No. 17/211,210, published as U.S. Pub. No. 2022/0304689 on Sep. 29, 2022;

U.S. Patent Application entitled MULTI-AXIS PIVOT JOINTS FOR SURGICAL INSTRUMENTS AND METHODS OF MANUFACTURING SAME, U.S. patent appliction Ser. No. 17/211,222, published as U.S. Pub. No. 2022/0304714 on Sep. 29, 2022;

U.S. Patent Application entitled JOINT ARRANGEMENTS FOR MULTI-PLANAR ALIGNMENT AND SUPPORT OF OPERATIONAL DRIVE SHAFTS IN ARTICULATABLE SURGICAL INSTRUMENTS, U.S. patent appliction Ser. No. 17/211,230, published as U.S. Pub. No. 2022/0304715 on Sep. 29, 2022; and U.S. Patent Application entitled SURGICAL INSTRUMENT ARTICULATION JOINT ARRANGEMENTS COMPRISING MULTIPLE MOVING LINKAGE FEATURES, U.S. patent appliction Ser. No. 17/211,242, published as U.S. Pub. No. 2022/0304683 on Sep. 29, 2022.

Applicant of the present application owns the following U.S. Patent Applications and U.S. Patents that were filed on Dec. 19, 2017 and which are each herein incorporated by reference in their respective entireties:

U.S. Pat. No. 10,835,330, entitled METHOD FOR DETERMINING THE POSITION OF A ROTATABLE JAW OF A SURGICAL INSTRUMENT ATTACHMENT ASSEMBLY;

U.S. Pat. No. 10,716,565, entitled SURGICAL INSTRUMENTS WITH DUAL ARTICULATION DRIVERS;

U.S. patent application Ser. No. 15/847,325, entitled SURGICAL TOOLS CONFIGURED FOR INTERCHANGEABLE USE WITH DIFFERENT CONTROLLER INTERFACES, now U.S. Patent Application Publication No. 2019/0183491, issued as U.S. Pat. No. 11,020,112 on Jun. 1, 2021;

U.S. Pat. No. 10,729,509, entitled SURGICAL INSTRUMENT COMPRISING CLOSURE AND FIRING LOCKING MECHANISM;

U.S. patent application Ser. No. 15/847,315, entitled ROBOTIC ATTACHMENT COMPRISING EXTERIOR DRIVE ACTUATOR, now U.S. Patent Application Publication No. 2019/0183594, issued as U.S. Pat. No. 11,045,270 on Jun. 29, 2021; and U.S. Design Pat. No. D910,847, entitled SURGICAL INSTRUMENT ASSEMBLY.

Applicant of the present application owns the following U.S. Patent Applications and U.S. Patents that were filed on Jun. 28, 2017 and which are each herein incorporated by reference in their respective entireties:

U.S. patent application Ser. No. 15/635,693, entitled SURGICAL INSTRUMENT COMPRISING AN OFFSET ARTICULATION JOINT, now U.S. Patent Application Publication No. 2019/0000466, issued as U.S. Pat. No. 11,058,424 on Jul. 13, 2021;

U.S. patent application Ser. No. 15/635,729, entitled SURGICAL INSTRUMENT COMPRISING AN ARTICULATION SYSTEM RATIO, now U.S. Patent Application Publication No. 2019/0000467, issued as U.S. Pat. No. 11,000,279 on May 11, 2021;

U.S. patent application Ser. No. 15/635,785, entitled SURGICAL INSTRUMENT COMPRISING AN ARTICULATION SYSTEM RATIO, now U.S. Patent Application Publication No. 2019/0000469, issued as U.S. Pat. No. 11,083,455 on Aug. 10, 2021;

U.S. patent application Ser. No. 15/635,808, entitled SURGICAL INSTRUMENT COMPRISING FIRING MEMBER SUPPORTS, now U.S. Patent Application Publication No. 2019/0000471, issued as U.S. Pat. No. 11,259,805 on Mar. 1, 2022;

U.S. patent application Ser. No. 15/635,837, entitled SURGICAL INSTRUMENT COMPRISING AN ARTICULATION SYSTEM LOCKABLE TO A FRAME, now U.S. Patent Application Publication No. 2019/0000472, issued as U.S. Pat. No. 11,246,592 on Feb. 15, 2022;

U.S. Pat. No. 10,779,824, entitled SURGICAL INSTRUMENT COMPRISING AN ARTICULATION SYSTEM LOCKABLE BY A CLOSURE SYSTEM;

U.S. patent application Ser. No. 15/636,029, entitled SURGICAL INSTRUMENT COMPRISING A SHAFT INCLUDING A HOUSING ARRANGEMENT, now U.S. Patent Application Publication No. 2019/0000477;

U.S. patent application Ser. No. 15/635,958, entitled SURGICAL INSTRUMENT COMPRISING SELECTIVELY ACTUATABLE ROTATABLE COUPLERS, now U.S. Patent Application Publication No. 2019/0000474, issued as U.S. Pat. No. 11,389,161 on Jul. 19, 2022;

U.S. patent application Ser. No. 15/635,981, entitled SURGICAL STAPLING INSTRUMENTS COMPRISING SHORTENED STAPLE CARTRIDGE NOSES, now U.S. Patent Application Publication No. 2019/0000475;

U.S. patent application Ser. No. 15/636,009, entitled SURGICAL INSTRUMENT COMPRISING A SHAFT INCLUDING A CLOSURE TUBE PROFILE, now U.S. Patent Application Publication No. 2019/0000476, issued as U.S. Pat. No. 11,484,310 on Nov. 1, 2022;

U.S. Pat. No. 10,765,427, entitled METHOD FOR ARTICULATING A SURGICAL INSTRUMENT;

U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS, now U.S. Patent Application Publication No. 2019/0000457, issued as U.S. Pat. No. 11,020,114 on Jun. 1, 2021;

U.S. Pat. No. 10,588,633, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS, now U.S. Patent Application Publication No. 2019/0000459, now abandoned;

U.S. Pat. No. 10,786,253, entitled SURGICAL END EFFECTORS WITH IMPROVED JAW APERTURE ARRANGEMENTS;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT AXIS, now U.S. Patent Application Publication No. 2019/0000461, now abandoned;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW, now U.S. Patent Application Publication No. 2019/0000462, issued as U.S. Pat. No. 11,478,242 on Oct. 25, 2022;

U.S. Pat. No. 10,758,232, entitled SURGICAL INSTRUMENT WITH POSITIVE JAW OPENING FEATURES;

U.S. Pat. No. 10,639,037, entitled SURGICAL INSTRUMENT WITH AXIALLY MOVABLE CLOSURE MEMBER;

U.S. Pat. No. 10,695,057, entitled SURGICAL INSTRUMENT LOCKOUT ARRANGEMENT;

U.S. Design Pat. No. D851,762, entitled ANVIL;

U.S. Design Pat. No. D854,151, entitled SURGICAL INSTRUMENT SHAFT; and

U.S. Design Pat. No. D869,655, entitled SURGICAL FASTENER CARTRIDGE.

Applicant of the present application owns the following U.S. Patent Applications and U.S. Patents that were filed on Jun. 27, 2017 and which are each herein incorporated by reference in their respective entireties:

U.S. patent application Ser. No. 15/634,024, entitled SURGICAL ANVIL MANUFACTURING METHODS, now U.S. Patent Application Publication No. 2018/0368839, issued as U.S. Pat. No. 11,266,405 on Mar. 8, 2022;

U.S. Pat. No. 10,772,629, entitled SURGICAL ANVIL ARRANGEMENTS;

U.S. patent application Ser. No. 15/634,046, entitled SURGICAL ANVIL ARRANGEMENTS, now U.S. Patent Application Publication No. 2018/0368841, issued as U.S. Pat. No. 10,993,716 on May 4, 2021;

U.S. Pat. No. 10,856,869, entitled SURGICAL ANVIL ARRANGEMENTS;

U.S. patent application Ser. No. 15/634,068, entitled SURGICAL FIRING MEMBER ARRANGEMENTS, now U.S. Patent Application Publication No. 2018/0368843, issued as U.S. Pat. No. 11,324,503 on May 10, 2022;

U.S. patent application Ser. No. 15/634,076, entitled STAPLE FORMING POCKET ARRANGEMENTS, now U.S. Patent Application Publication No. 2018/0368844, now abandoned;

U.S. patent application Ser. No. 15/634,090, entitled STAPLE FORMING POCKET ARRANGEMENTS, now U.S. Patent Application Publication No. 2018/0368845, issued as U.S. Pat. No. 11,090,049 on Aug. 17, 2021;

U.S. patent application Ser. No. 15/634,099, entitled SURGICAL END EFFECTORS AND ANVILS, now U.S. Patent Application Publication No. 2018/0368846, issued as U.S. Pat. No. 11,141,154 on Oct. 21, 2021; and U.S. Pat. No. 10,631,859, entitled ARTICULATION SYSTEMS FOR SURGICAL INSTRUMENTS.

Applicant of the present application owns the following U.S. Patent Applications that were filed on Jun. 2, 2020 and which are each herein incorporated by reference in their respective entireties:

U.S. Design patent application Ser. No. 29/736,648, issued as U.S. Pat. No. D967,421 on Oct. 18, 2022, entitled STAPLE CARTRIDGE;

U.S. Design patent application Ser. No. 29/736,649, issued as U.S. Pat. No. D966,512 on Oct. 11, 2022, entitled STAPLE CARTRIDGE;

U.S. Design patent application Ser. No. 29/736,651, issued as U.S. Pat. No. D975,278 on Jan. 10, 2023, entitled STAPLE CARTRIDGE;

U.S. Design patent application Ser. No. 29/736,652, issued as U.S. Pat. No. D975,850 on Jan. 17, 2023, entitled STAPLE CARTRIDGE;

U.S. Design patent application Ser. No. 29/736,653, entitled STAPLE CARTRIDGE, issued as U.S. Pat. No. D974,560 on Jan. 3, 2023;

U.S. Design patent application Ser. No. 29/736,654, issued as U.S. Pat. No. D975,851 on Jan. 17, 2023, entitled STAPLE CARTRIDGE; and U.S. Design patent application Ser. No. 29/736,655, issued as U.S. Pat. No. D976,401 on Jan. 24, 2023, entitled STAPLE CARTRIDGE.

Applicant of the present application owns the following U.S. Design Patent Applications and U.S. Patents that were filed on Nov. 14, 2016, and which are each herein incorporated by reference in their respective entireties:

U.S. patent application Ser. No. 15/350,621, now U.S. Patent Application Publication No. 2018/0132849, now abandoned, entitled STAPLE FORMING POCKET CONFIGURATIONS FOR CIRCULAR STAPLER ANVIL;

U.S. patent application Ser. No. 15/350,624, now U.S. Patent Application Publication No. 2018/0132854, issued as U.S. Pat. No. 10,603,041 on Mar. 31, 2020, entitled CIRCULAR SURGICAL STAPLER WITH ANGULARLY ASYMMETRIC DECK FEATURES;

U.S. Design Pat. No. D833,608, titled STAPLING HEAD FEATURE FOR SURGICAL STAPLER; and U.S. Design Pat. No. D830,550, titled SURGICAL STAPLER.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical device. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical device are used in many orientations and positions, and these terms are not intended to be limiting and/or absolute. In the following description, terms such as "first," "second," "top," "bottom," "up," "down," and the like are words of convenience and are not to be construed as limiting terms.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various surgical devices disclosed herein can be inserted into a body in any way, such as through a natural orifice, through an incision or puncture hole formed in tissue, etc. The working portions or end effector portions of the surgical devices can be inserted directly into a patient's body or can be inserted through an access device that has a working channel through which the end effector and elongate shaft of a surgical device can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue to be stapled. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples are contemplated.

The staples are supported by staple drivers in the cartridge body. The drivers are movable between a first, or unfired, position and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent a proximal end of the cartridge body and a distal position adjacent a distal end of the cartridge body. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected into the tissue ahead of the knife transecting the tissue.

FIGS. 1-8 depict a surgical stapling instrument 10 configured to clamp, staple, and cut tissue of a patient. The surgical stapling instrument 10 comprises a handle 20, a shaft assembly 100 attached to the handle 20, and an end effector 200. To cut and staple tissue of a patient, the end effector 200 comprises a cartridge jaw 201 and an anvil jaw 203. The anvil jaw 203 is pivotable relative to the cartridge jaw 203 to clamp tissue between the anvil jaw 203 and the cartridge jaw 203. Once tissue is clamped between the jaws 201, 203, the surgical stapling instrument 10 may be actuated to advance a firing member through the jaws 201, 203 to staple and cut tissue with the end effector 200 as discussed in greater detail below.

Discussed in greater detail below, the end effector 200 is articulatable by way of an articulation region 110 of the shaft assembly 100. Such articulation provides a user of the surgical stapling instrument 10 with the ability to position and/or maneuver the end effector 200 near the target tissue more accurately.

The handle 20 comprises a housing 21 configured to house various mechanical and electrical components and a handle portion 22 extending from the housing 21. The handle portion 22 is configured to fit in the palm of a user and/or be gripped and/or held by a user using the surgical stapling instrument 10. The handle 20 further comprises various actuators and/or triggers configured to be actuated by a user to operate one or more functions of the surgical stapling instrument 10. The handle 20 comprises a closure trigger 24, a firing trigger 25, and at least one articulation actuator 26. When actuated by a user, the closure trigger 24 is configured to clamp tissue with the end effector 200 by moving the anvil jaw 203 toward the cartridge jaw 201. When actuated by a user, the firing trigger 25 is configured to cut and staple tissue with the end effector 200 by advancing a firing member to eject staples and cut tissue with a knife. When actuated by a user, the articulation actuator 26 is configured to articulate the end effector 200 relative to the shaft assembly 100 by way of the articulation region 110. The triggers and actuators of the surgical stapling instrument 10 can either trigger one or more motors within the handle 20 to actuate various function of the surgical stapling instrument 10 and/or manually drive various drive shafts and components to actuate various function of the surgical stapling instrument 10.

The handle 20 further comprises a nozzle assembly 30 configured to support the shaft assembly 100 therein. The nozzle assembly 30 comprises an actuation wheel 31 configured to be rotated by a user to rotate the shaft assembly 100 and end effector 200 about a longitudinal axis LA relative to the handle 20. Such a mechanism permits the user of the surgical stapling instrument 10 to rotate only the shaft assembly 100 and/or end effector 200 without having to rotate the entire handle 20.

The handle 20 further comprises a battery 23 configured to provide power to various electronic components, sensors, and/or motors of the surgical stapling instrument 10. Embodiments are envisioned where the surgical stapling instrument 10 is directly connected to a power source. Embodiments are also envisioned where the surgical stapling instrument 10 is entirely manual or, non-powered, for example. Embodiments are further envisioned where articulation of the end effector, clamping and unclamping of the jaws, firing of the end effector staple and cut tissue, and shaft and/or end effector rotation are all powered systems.

In at least one instance, the shaft assembly 100 and the end effector 200 may be modular and removable from the handle 20. In at least one instance, the end effector 200 may be modular in that the end effector 200 can be removed from the shaft assembly 100 and replaced with a different end effector. In at least one instance, the shaft assembly 100 and/or the end effector 200 is employable in a surgical robotic environment. Such an embodiment would provide powered inputs from a surgical robotic interface to actuate each function of the end effector 200. Examples of such surgical robots and surgical tools are further described in U.S. Patent Application Publication No. 2020/0138534, titled ROBOTIC SURGICAL SYSTEM, which published on May 7, 2020, which is incorporated by reference herein in its entirety.

In at least one instance, the shaft assembly 100 and the end effector 200 are configured to be used with a surgical robot. In such an instance, the shaft assembly 100 and the end effector 200 are configured to be coupled to a surgical robot comprising a plurality of output drives. The plurality of output drives of the surgical robot are configured to mate with the drive systems of the shaft assembly 100 and end effector 200. In such an instance, the surgical robot can actuate the various different functions of the end effector 200 such as, for example, articulating the end effector about multiple different articulation joints, rotating the shaft assembly 100 and/or end effector 200 about its longitudinal axis, clamping the end effector 200 to clamp tissue between the jaws of the end effector 200, and/or firing the end effector 200 to cut and/or staple tissue.

The shaft assembly 100 is configured to house various drive system components and/or electronic components of the surgical stapling instrument 10 so that the end effector 200 and shaft assembly 100 may be inserted through a trocar for laparoscopic surgery. The various drive system components are configured to be actuated by the various triggers and actuators of the handle 20. Such components can include drive shafts for articulation, drive shafts for clamping and unclamping the end effector 200, and/or drive shafts for firing the end effector 200. Such drive shafts may be rotated by a drive system in the handle 20 or a surgical robotic interface in the instance where the shaft assembly 100 is connected to the same. In various aspects, a stapling end effector can include two independently rotatable drive members-one for grasping tissue and one for firing staples, for example. The stapling end effector can further include an articulation joint, and the rotary motions can be transmitted through the articulation joint. In various aspects, the stapling end effector can include one or more 3D printed assemblies, which can be incorporated into an articulation, grasping, or firing systems.

Such drive shafts may be actuated by a drive system in the handle 20 or a surgical robotic interface in the instance where the shaft assembly 100 is connected to the same. Such drive shafts may comprise linear actuation, rotary actuation, or a combination thereof. A combination of rotary actuation and linear actuation may employ a series of rack gears and/or drive screws, for example.

In at least one instance, the shaft assembly 100 is also configured to house electrical leads for various sensors and/or motors, for example, positioned within the shaft assembly 100 and/or end effector 200, for example.

The shaft assembly 100 comprises an outer shaft 101 extending from the nozzle assembly 30 to the articulation region 110 comprising dual articulation joints, discussed in greater detail below. The articulation region 110 allows the end effector 200 to be articulated relative to the outer shaft 101 in two distinct planes about two separate axes AA1, AA2.

Figure 1:
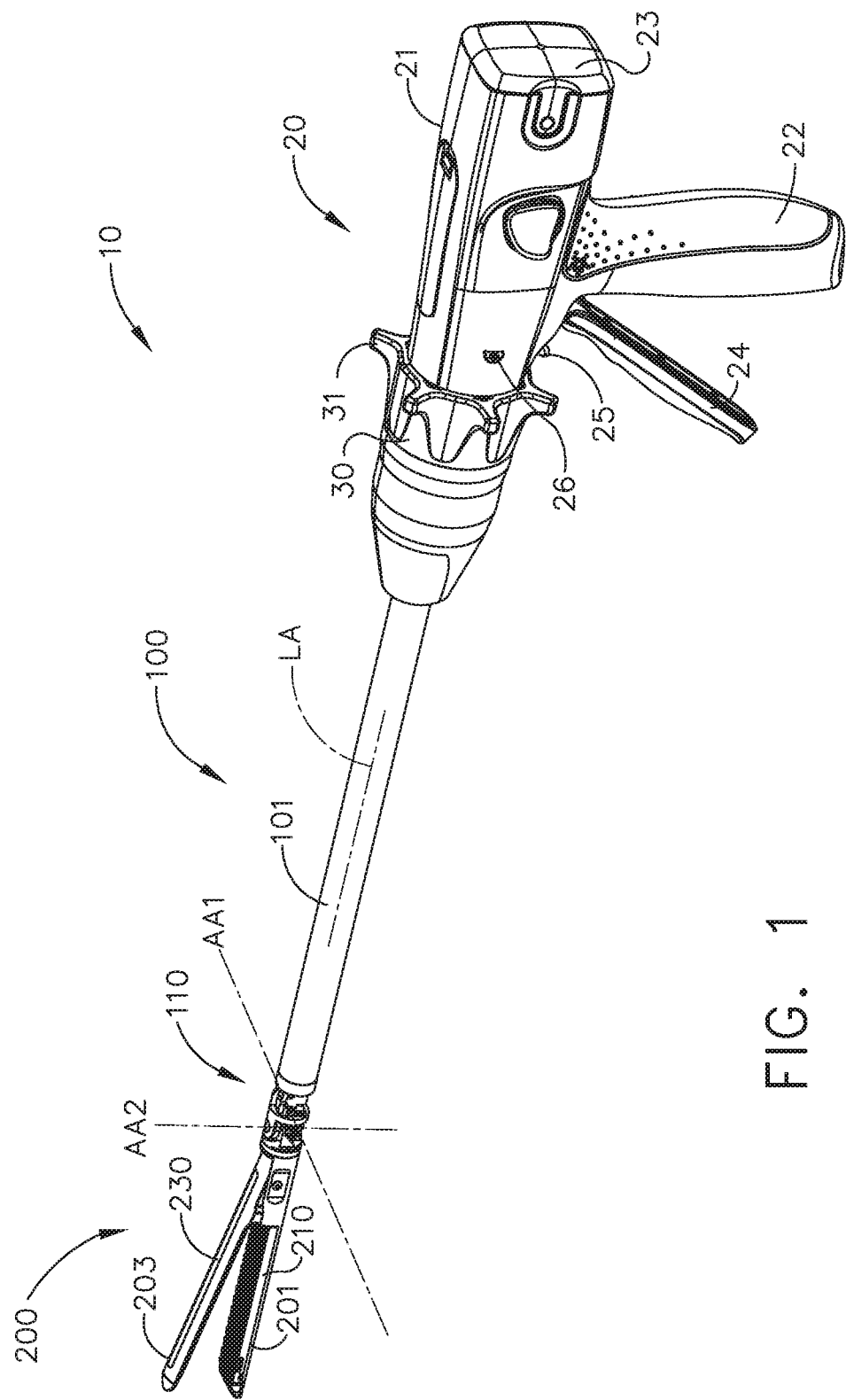
FIG. 1 is a perspective view of a surgical stapling instrument comprising a handle, a shaft assembly, and an end effector, in accordance with at least one aspect of the present disclosure.
Figure 2:
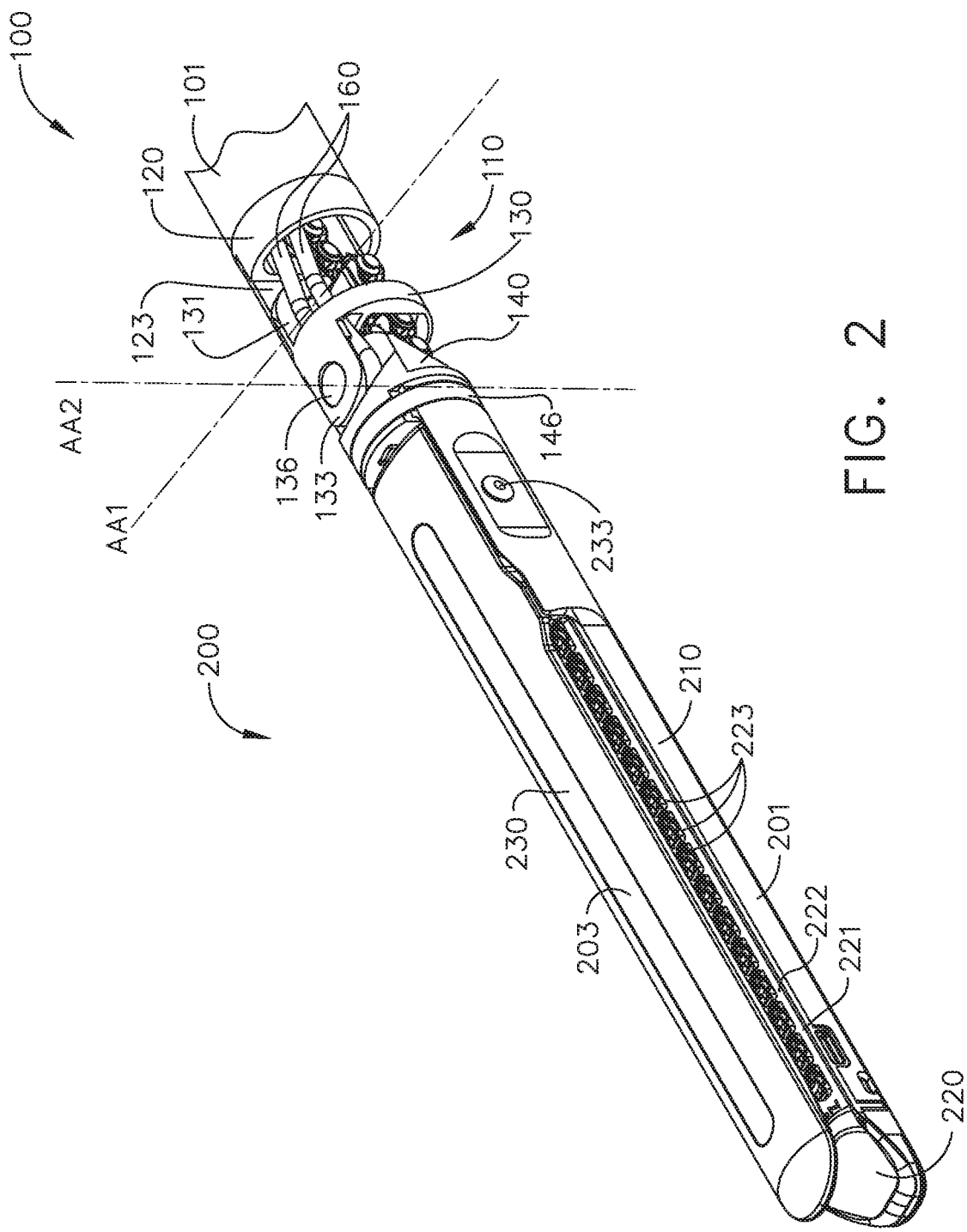
FIG. 2 is a perspective view of the end effector and a portion of the shaft assembly of the surgical stapling instrument of FIG. 1, wherein the end effector is illustrated in a straight, or non-articulated, configuration, in accordance with at least one aspect of the present disclosure.
Figure 3:
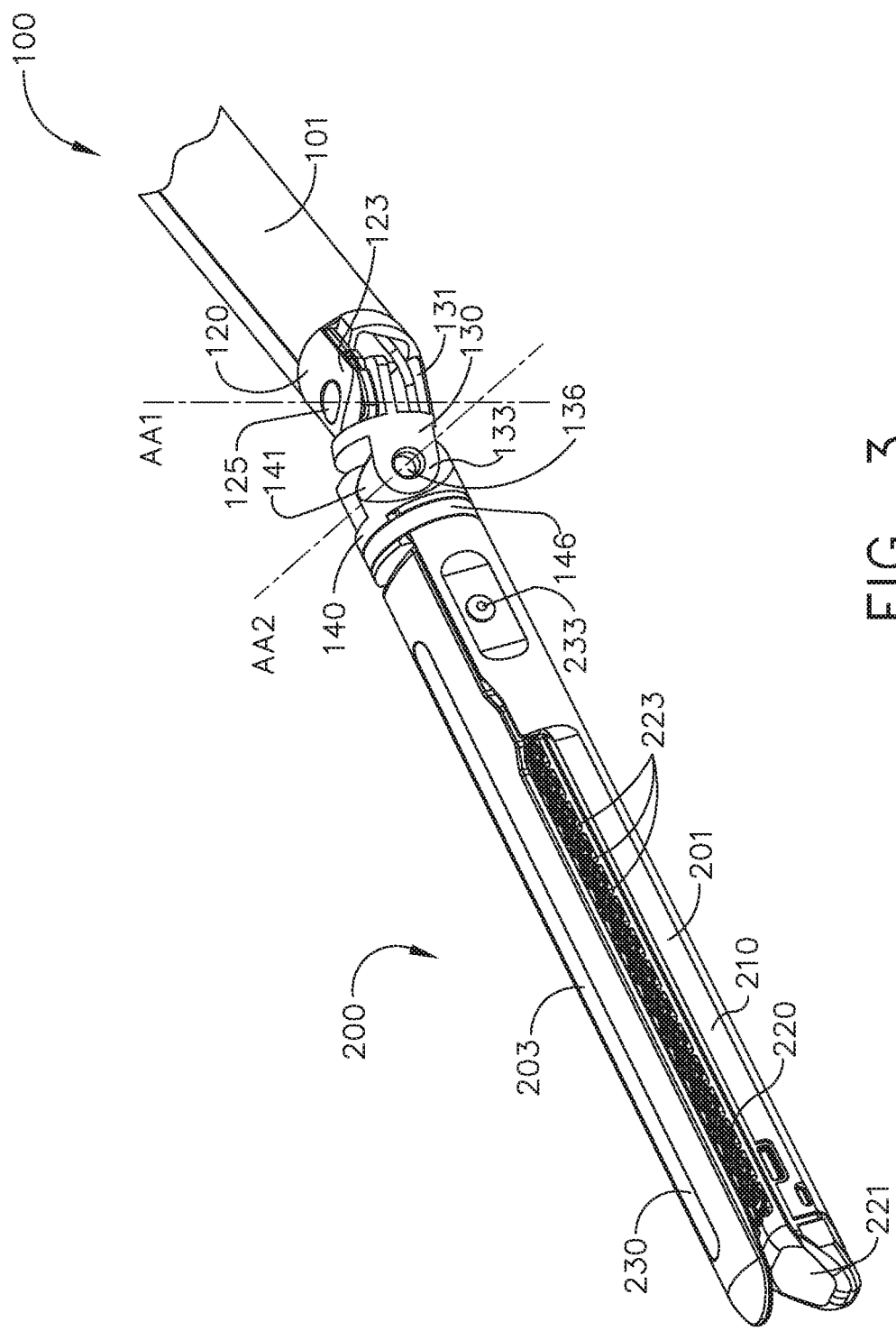
FIG. 3 is a perspective view of the end effector and a portion of the shaft assembly of the surgical stapling instrument of FIG. 1, wherein the end effector is illustrated in an articulated configuration, in accordance with at least one aspect of the present disclosure.
Figure 4:
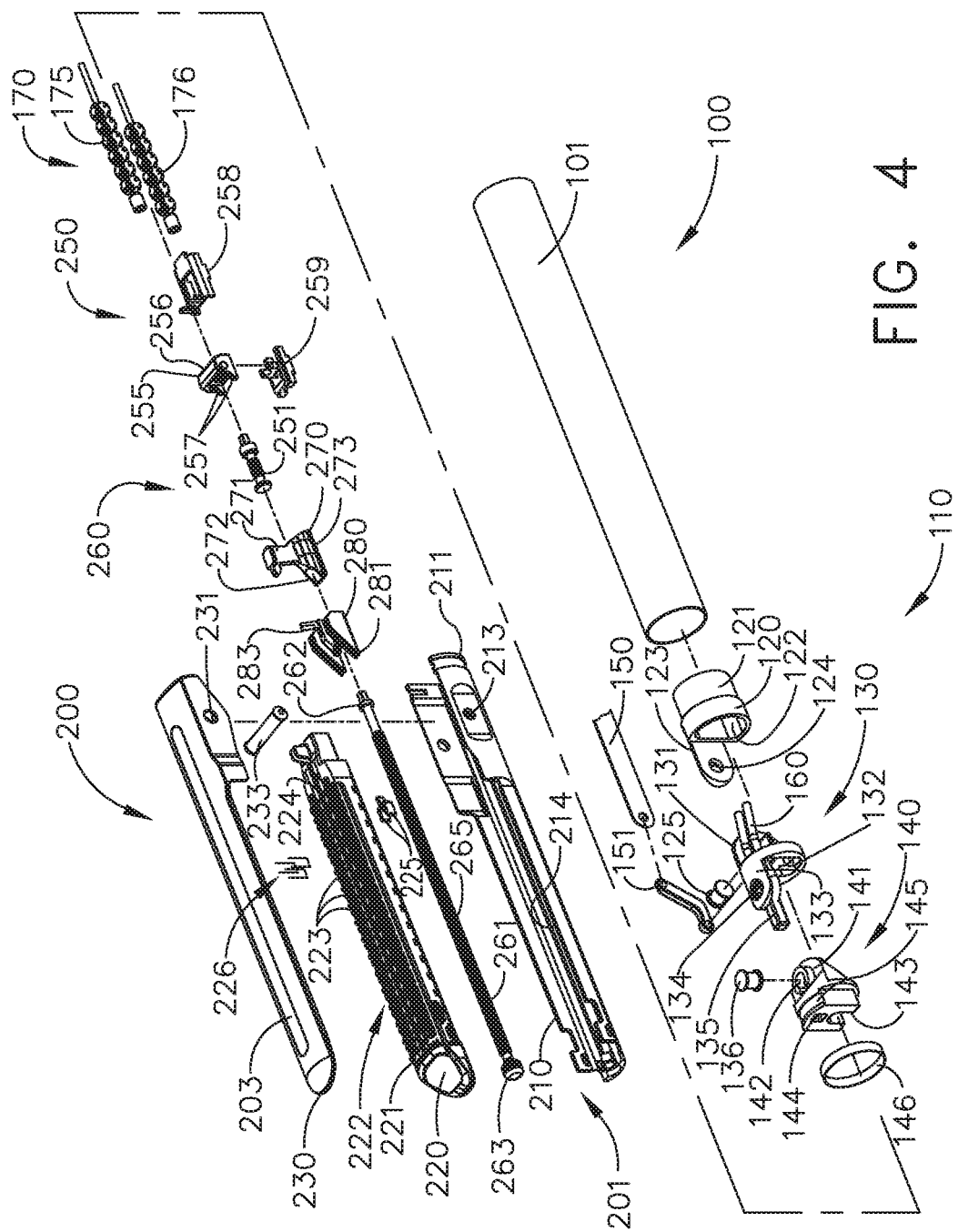
FIG. 4 is an exploded perspective view of the end effector and a portion of the shaft assembly of the surgical stapling instrument of FIG. 1, in accordance with at least one aspect of the present disclosure.
Figure 5:
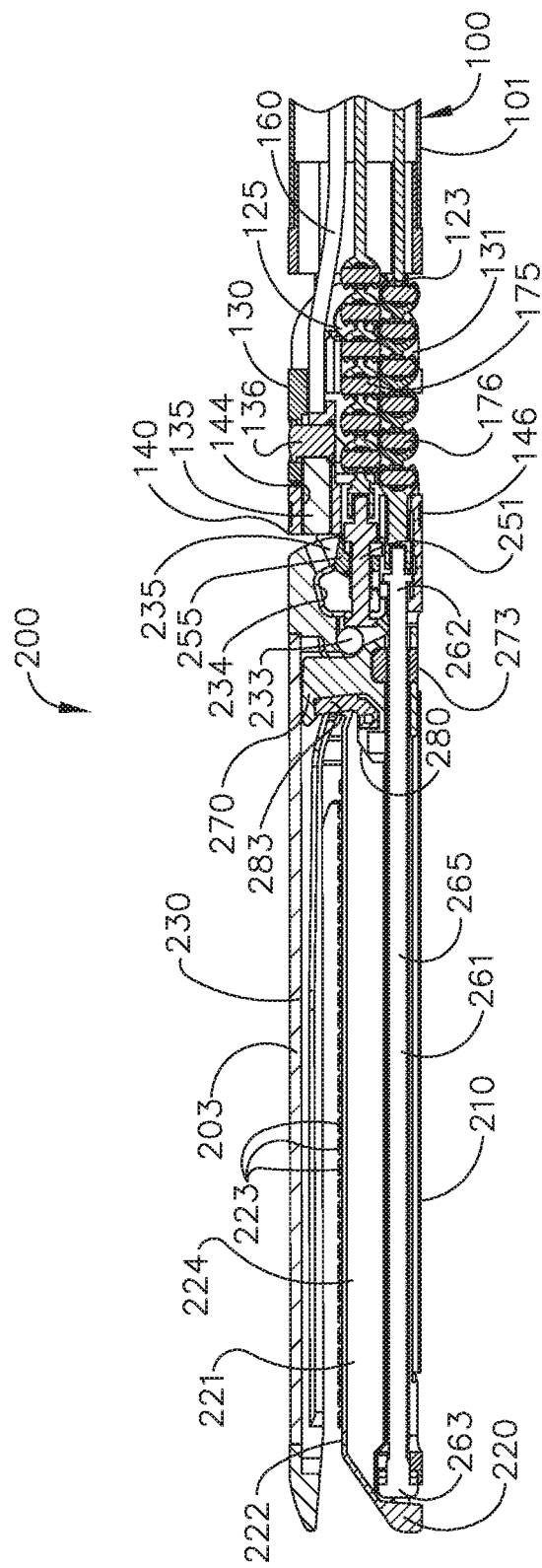
FIG. 5 is a cross-sectional elevation view of the end effector and a portion of the shaft assembly of the surgical stapling instrument of FIG. 1, wherein the end effector is illustrated in an unfired, clamped configuration, in accordance with at least one aspect of the present disclosure.
Figure 6:
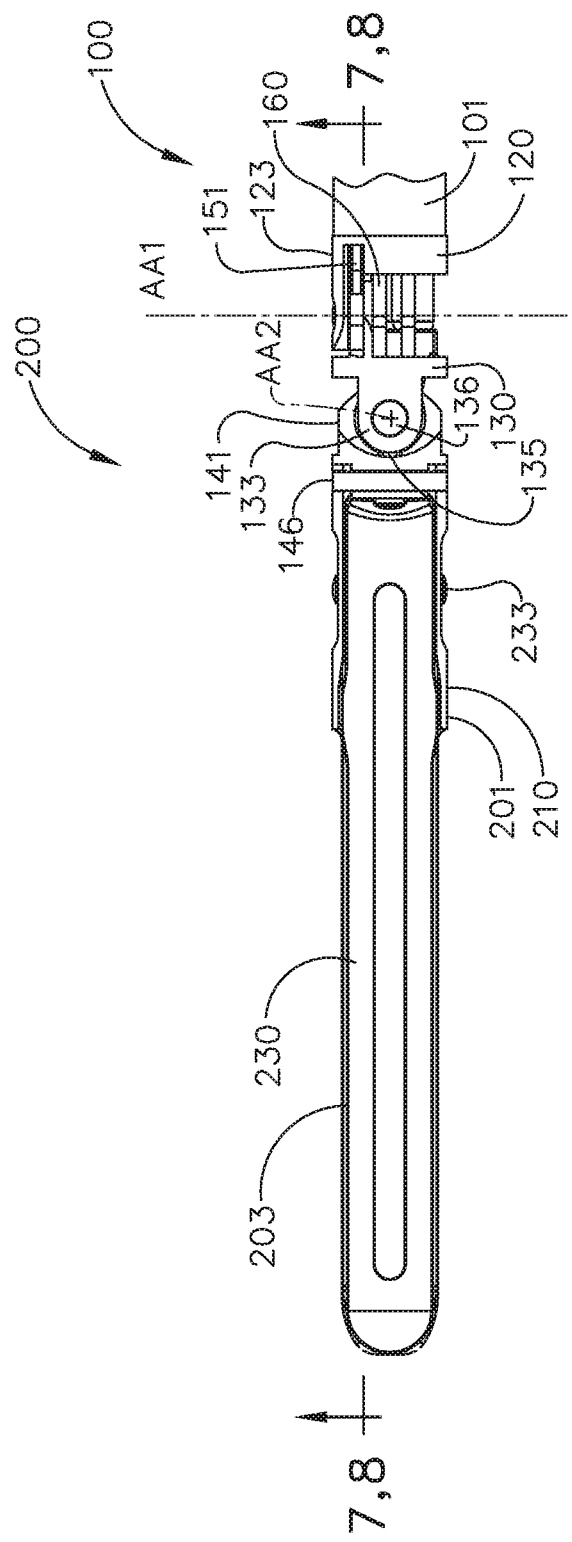
FIG. 6 is a plan view of the end effector and a portion of the shaft assembly of the surgical stapling instrument of FIG. 1, in accordance with at least one aspect of the present disclosure.
Figure 7:
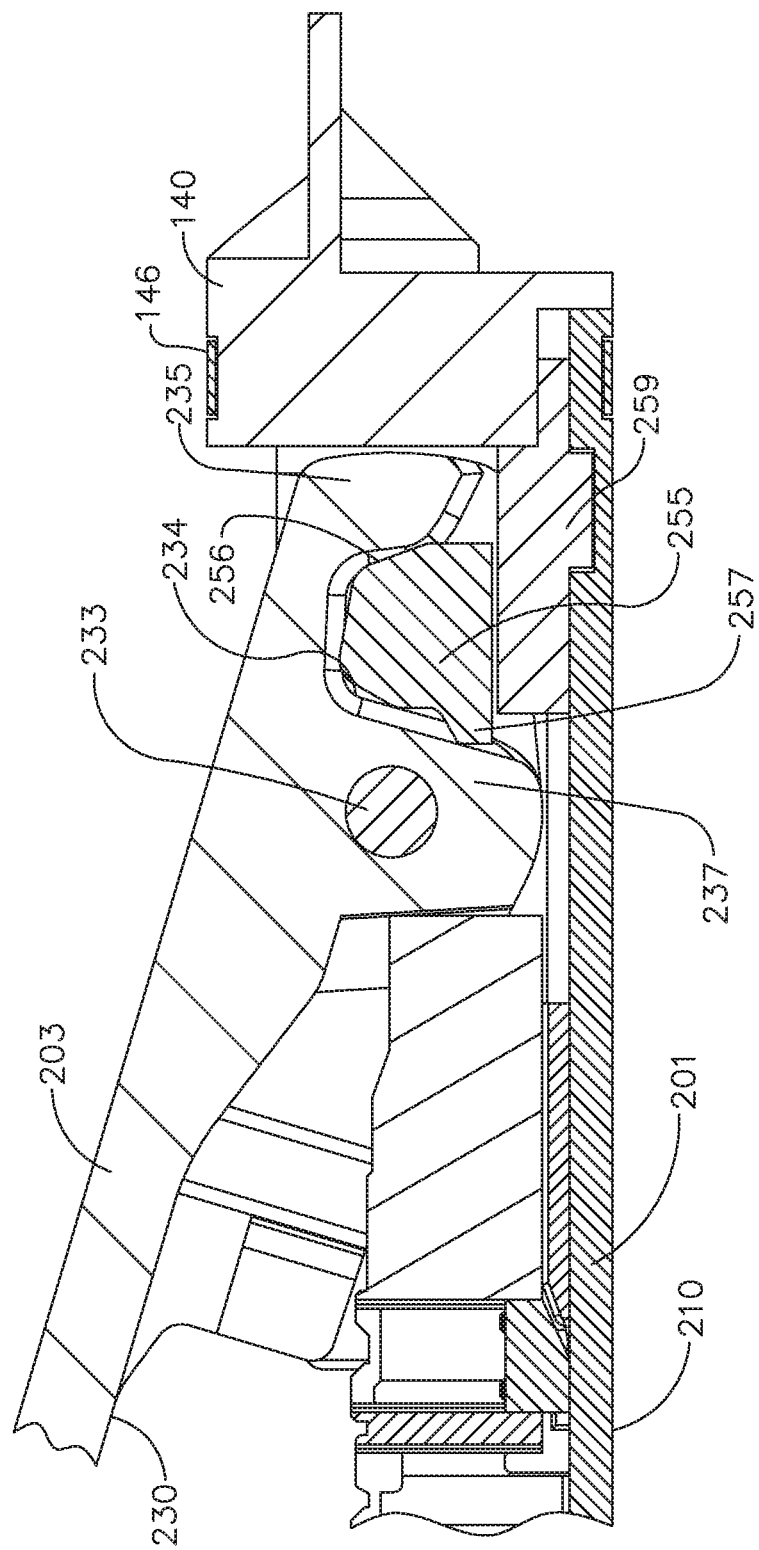
FIG. 7 is a cross-sectional elevation view of the end effector and a portion of the shaft assembly of FIG. 1 taken along section line 7-7 in FIG. 6, wherein the end effector is illustrated in an open configuration, in accordance with at least one aspect of the present disclosure.

Referring now primarily to FIG. 4, articulation of the end effector 200 will now be described. The articulation region 110 comprises two distinct articulation joints and two articulation actuators 150, 160. This allows the end effector 200 to be articulated in two different planes about two different axes AA1, AA2 independently of each other. The articulation region 110 comprises a proximal joint shaft component 120, an intermediate joint shaft component 130, and a distal joint shaft component 140. The proximal joint shaft component 120 is attached to a distal end of the shaft assembly 100, the intermediate joint shaft component 130 is pivotally connected to the proximal joint shaft component 120 and the distal joint shaft component 140, and the distal joint shaft component 140 is fixedly attached to the end effector 200 by way of a retention ring 146. Discussed in greater detail below, this arrangement provides articulation of the end effector 200 relative to the shaft assembly 100 about axis AA1 and axis AA2 independently of each other.

The proximal joint shaft component 120 comprises a proximal annular portion 121 fixedly fitted within the outer shaft 101. The proximal joint shaft component 120 also includes a hollow passage 122 to allow various drive system components to pass therethrough, and further includes an articulation tab 123 comprising a pin hole 124 configured to receive articulation pin 125. The articulation pin 125 pivotally connects the proximal joint shaft component 120 to a proximal articulation tab 131 of the intermediate joint shaft component 130. To articulate the end effector 200 about axis AA1, the articulation actuator 150 is actuated linearly either in a distal direction or a proximal direction. Such an actuator may comprise a bar or rod made of any suitable material such as metal and/or plastic, for example. The articulation actuator 150 is pivotally mounted to an articulation crosslink 151. The articulation crosslink 151 is pivotally mounted to the intermediate joint shaft component 130 off-axis relative to the articulation pin 125 so that when the articulation actuator 150 is actuated, a torque is applied to the intermediate joint shaft component 130 off-axis relative to the articulation pin 125 by the articulation crosslink 151 to cause the intermediate joint shaft component 130 and, thus, the end effector 200, to pivot about axis AA1 relative to the proximal joint shaft component 120.

The intermediate joint shaft component 130 is pivotally connected to the proximal joint shaft component 120 by way of the articulation pin 125 which defines axis AA1. Specifically, the intermediate joint shaft component 130 comprises a proximal articulation tab 131 that is pivotally connected to the proximal joint shaft component 120 by way of the articulation pin 125. The intermediate joint shaft component 130 further comprises a hollow passage 132 configured to allow various drive system components to pass therethrough and a distal articulation tab 133. The distal articulation tab 133 comprises a pin hole 134 configured to receive another articulation pin 136, which defines axis AA2, and a distally-protruding key 135.

To articulate the end effector 200 about axis AA2, the articulation cable 160 is actuated to apply an articulation torque to a proximal tab 141 of the distal joint shaft component 140 by way of the key 135. The articulation cable 160 is fixed to the key 135 such that, as the cable 160 is rotated, the key 135 is pivoted relative to the intermediate joint shaft component 130. The key 135 is fitted within a key hole 144 of the distal joint shaft component 140. Notably, the key 135 is not fixed to the intermediate joint shaft component 130 and the key 135 can be rotated relative to the intermediate joint shaft component 130. The articulation cable 160 also contacts the proximal tab 141 around the pin hole 142. This provides an additional torque moment from the articulation cable 160 to the distal joint shaft component 140. The articulation pin 136 is received within the pin hole 142 to pivotally couple the intermediate joint shaft component 130 and the distal joint shaft component 140.

In at least one instance, the articulation cable 160 is only able to be pulled in a proximal direction. In such an instance, only one side of the articulation cable 160 would be pulled proximally to articulate the end effector 200 in the desired direction. In at least one instance, the articulation cable 160 is pushed and pulled antagonistically. In other words, the cable 160 can comprise a rigid construction such that one side of the articulation cable 160 is pushed distally while the other side of the articulation cable 160 is pulled proximally. Such an arrangement can allow the articulation forces to be divided between the pushed half of the cable 160 and the pulled half of the cable 160. In at least one instance, the push-pull arrangement allows greater articulation forces to be transmitted to the corresponding articulation joint. Such forces may be necessary in an arrangement with two articulation joints. For example, if the proximal articulation joint is fully articulated, more force may be required of the articulation actuator meant to articulate the distal articulation joint owing to the stretching and/or lengthened distance that the articulation actuator for the distal articulation joint must travel.

The distal joint shaft component 140 further comprises a cutout 143 to allow various drive components to pass therethrough. The retention ring 146 secures a channel 210 of the cartridge jaw 201 to the distal joint shaft component 140 thereby fixing the end effector assembly 200 to a distal end of the articulation region 110.

As discussed above, the anvil jaw 201 is movable relative to the cartridge jaw 203 to clamp and unclamp tissue with the end effector 200. Operation of this function of the end effector 200 will now be described. The cartridge jaw 201 comprises the channel 210 and a staple cartridge 220 configured to be received within a cavity 214 of the channel 210. The channel 210 further comprises an annular groove 211 configured to receive the retention ring 146 and a pair of pivot holes 213 configured to receive a jaw-coupling pin 233. The jaw coupling pin 233 permits the anvil jaw 203 to be pivoted relative to the cartridge jaw 201.

The anvil jaw 203 comprises an anvil body 230 and a pair of pivot holes 231. The pivot holes 231 in the proximal portion of the anvil jaw 203 are configured to receive the jaw-coupling pin 233 thereby pivotally coupling the anvil jaw 203 to the cartridge jaw 201. To open and close the anvil jaw 203 relative to the cartridge jaw 201, a closure drive 250 is provided.

The closure drive 250 is actuated by a flexible drive segment 175 comprised of universally-movable joints arranged or formed end-to-end. In various instances, the flexible drive segment 175 can includes serial 3D-printed universal joints, which are printed all together as a single continuous system. Discussed in greater detail below, the flexible drive segment 175 is driven by an input shaft traversing through the shaft assembly 100. The flexible drive segment 175 transmits rotary actuation motions through the dual articulation joints. The closure drive 250 comprises a closure screw 251 and a closure wedge 255 threadably coupled to the closure screw 251. The closure wedge 255 is configured to positively cam the anvil jaw 203 open and closed. The closure screw 251 is supported by a first support body 258 and a second support body 259 secured within the channel 210.

To move the anvil jaw 203 between a clamped position (FIG. 8) and an unclamped position (FIG. 7), a closure drive shaft is actuated to actuate the flexible drive segment 175. The flexible drive segment 175 is configured to rotate the closure screw 251, which displaces the closure wedge 255. For example, the closure wedge 255 is threadably coupled to the closure screw 251 and rotational travel of the closure wedge 255 with the staple cartridge 220 is restrained. The closure screw 251 drives the closure wedge 255 proximally or distally depending on which direction the closure screw 251 is rotated.

To clamp the end effector 200 from an unclamped position (FIG. 7), the closure wedge 255 is moved proximally. As the closure wedge 255 is moved proximally, a proximal cam surface 256 of the closure wedge 255 contacts a corresponding cam surface 234 defined in a proximal end 235 of the anvil body 230. As the cam surface 256 contacts the cam surface 234, a force is applied to the proximal end 235 of the anvil body 230 causing the anvil body 230 to rotate into the clamped position (FIG. 8) about the pin 233.

To open or unclamp the end effector 200 from a clamped position (FIG. 8), the closure wedge 255 is moved distally by rotating the closure screw 251 in a direction opposite to the direction that causes the closure wedge 255 to move proximally. As the closure wedge 255 is moved distally, a pair of nubs 257 extending from a distal end of the closure wedge 255 contact the cam surface 234 near a downwardly extending tab 237 of the anvil body 230. As the nubs 257 contact the cam surface 234 near the tab 237, a force is applied to the anvil body 230 to rotate the anvil body 230 into the open position (FIG. 7) about the pin 233.

Figure 8:
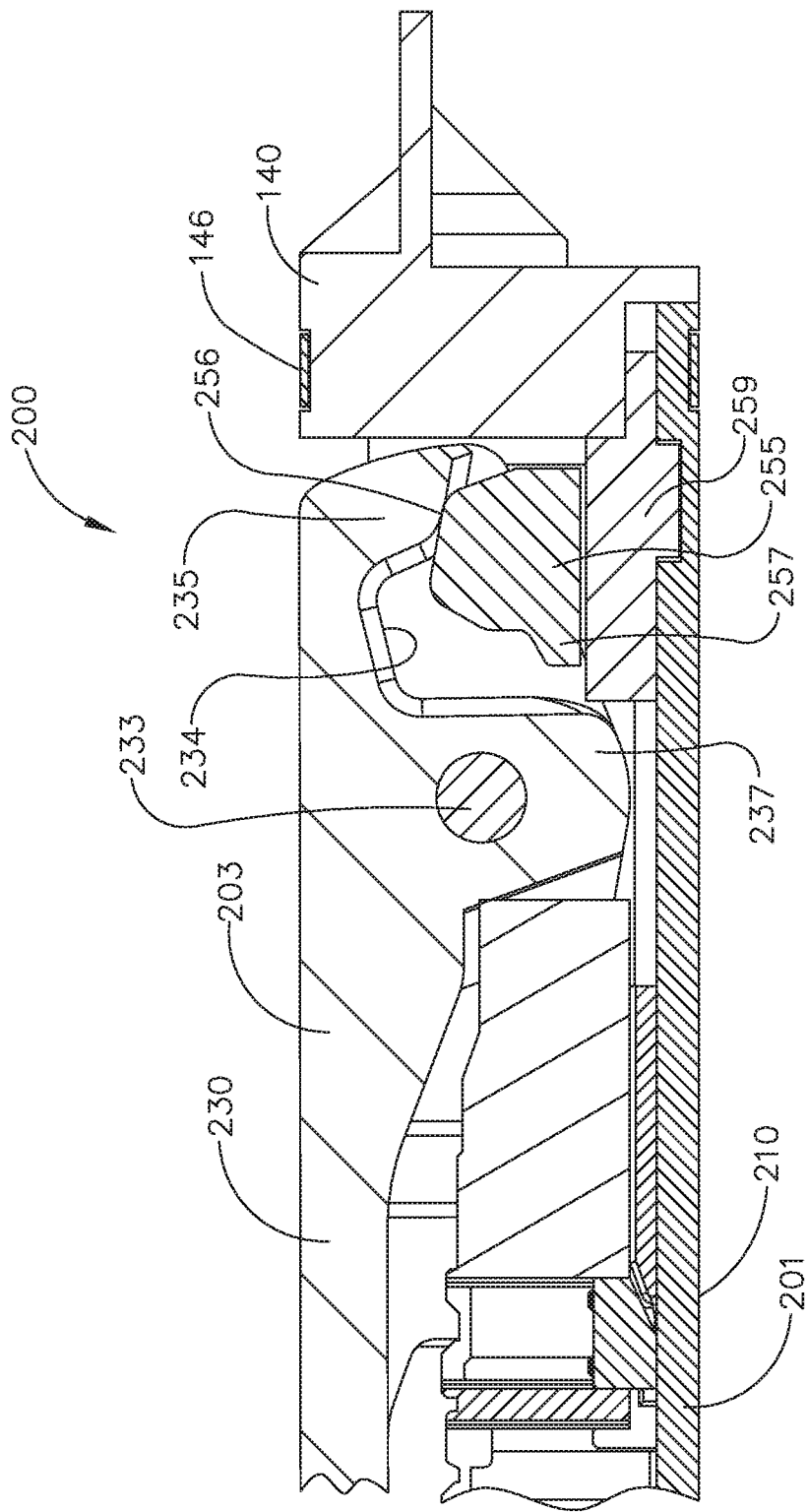
FIG. 8 is a cross-sectional elevation view of the end effector and a portion of the shaft assembly of FIG. 1 taken along section line 8-8 in FIG. 6, wherein the end effector is illustrated in a clamped configuration, in accordance with at least one aspect of the present disclosure.

In at least one instance, the profile of the cam surface 234 corresponds to the profile of the cam surface 256. For example, the cam surface 234 and the cam surface 256 may match such that a maximum cam force is applied to the anvil body 230 to cause the desired rotation of the anvil body 230. As can be seen in FIG. 8, for example, the cam surface 234 defined by the proximal end 235 of the anvil body 230 comprises a ramped section similar to that of the upper ramped section of the cam surface 256.

As discussed above, the surgical stapling instrument 10 may be actuated to advance a firing member through the jaws 201, 203 to staple and cut tissue with the end effector 200. The function of deploying staples 226 from the staple cartridge 220 and cutting tissue with knife 283 will now be described. The staple cartridge 220 comprises a cartridge body 221, a plurality of staple drivers 225, and a plurality of staples 226 removably stored within the cartridge body 221. The cartridge body 221 comprises a deck surface 222, a plurality of staple cavities 223 arranged in longitudinal rows defined in the cartridge body 221, and a longitudinal slot 224 bifurcating the cartridge body 221. The knife 283 is configured to be driven through the longitudinal slot 224 to cut tissue clamped between the anvil body 230 and the deck surface 221.

The deck surface 221 comprises a laterally-contoured tissue-supporting surface. In various aspects, the contour of the deck surface 221 can form a peak along a central portion of the cartridge body 221. Such a peak can overlay a longitudinally-extending firing screw 261 that extends through the central portion of the cartridge body 221, which is further described herein. The increased height along the peak can be associated with a smaller tissue gap along a firing path of the knife 283 in various instances. In certain aspects of the present disclosure, driver heights, formed staple heights, staple pocket extension heights, and/or staple overdrive distances can also vary laterally along the deck surface 221. Laterally-variable staple formation (e.g. a combination of 2D staples and 3D staples) is also contemplated and further described herein.

The staple drivers 225 are configured to be lifted by a sled 280 as the sled 280 is pushed distally through the staple cartridge 220 to eject the staples 226 supported by the staple drivers 225 in the staple cavities 223. The sled 280 comprises ramps 281 to contact the staple drivers 225. The sled 280 also includes the knife 283. The sled 280 is configured to be pushed by a firing member 270.

To deploy the staples 226 and cut tissue with the knife 283, the end effector 200 comprises a firing drive 260. The firing drive 260 is actuated by a flexible drive shaft 176. Discussed in greater detail below, the flexible drive shaft 176 is driven by an input shaft traversing through the shaft assembly 100. The flexible drive shaft 176 transmits rotary actuation motions through the dual articulation joints. The firing drive 260 comprises a firing screw 261 configured to be rotated by the flexible drive shaft 176. The firing screw 261 comprises journals supported within bearings in the support member 259 and the channel 210. In various instances, the firing screw 261 can float relative to the channel 210, as further described herein. The firing screw 261 comprises a proximal end 262 supported within the support member 259 and the channel 210, a distal end 263 supported within the channel 210, and threads 265 extending along a portion of the length of the firing screw 261.

The firing member 270 is threadably coupled to the firing screw 261 such that as the firing screw 261 is rotated, the firing member 270 is advanced distally or retracted proximally along the firing screw 261. Specifically, the firing member 270 comprises a body portion 271 comprising a hollow passage 272 defined therein. The firing screw 261 is configured to be received within the hollow passage 272 and is configured to be threadably coupled with a threaded component 273 of the firing member 270. Thus, as the firing screw 261 is rotated, the threaded component 273 applies a linear force to the body portion 271 to advance the firing member 270 distally or retract the firing member 270 proximally. As the firing member 270 is advanced distally, the firing member 270 pushes the sled 280. Distal movement of the sled 280 causes the ejection of the staples 223 by engaging the plurality of staple drivers 225, as further described herein. The driver 225 is a triple driver, which is configured to simultaneously fire multiple staples 223. The driver 225 can comprise lateral asymmetries, as further described herein, to maximum the width of the sled rails and accommodate the firing screw 261 down the center of the cartridge 220 in various instances.

At a point during firing of the end effector 200, a user may retract the firing member 270 to allow unclamping of the jaws 201, 203. In at least one instance, the full retraction of the firing member 270 is required to open the jaws 201, 203 where upper and lower camming members are provided on the body portion 271 which can only be disengaged from the jaws 201, 203 once the firing member 270 is fully retracted.

In various instances, the firing member 270 can be a hybrid construction of plastic and metal portions as further described herein. In various instances, the threaded component 273 can be a metal component, for example, which is incorporated into the firing member body 271 with insert molding or over molding.

The firing member 270 can also be referred to an I-beam in certain instances. The firing member 270 can include a complex 3D-printed geometry comprising a lattice pattern of spaces therein. In various instances, 3D printing can allow the firing member or a portion thereof to act as a spring and allows a portion to more readily flex, which can improve the force distribution and/or tolerances during a firing stroke, for example.

Figure 9:
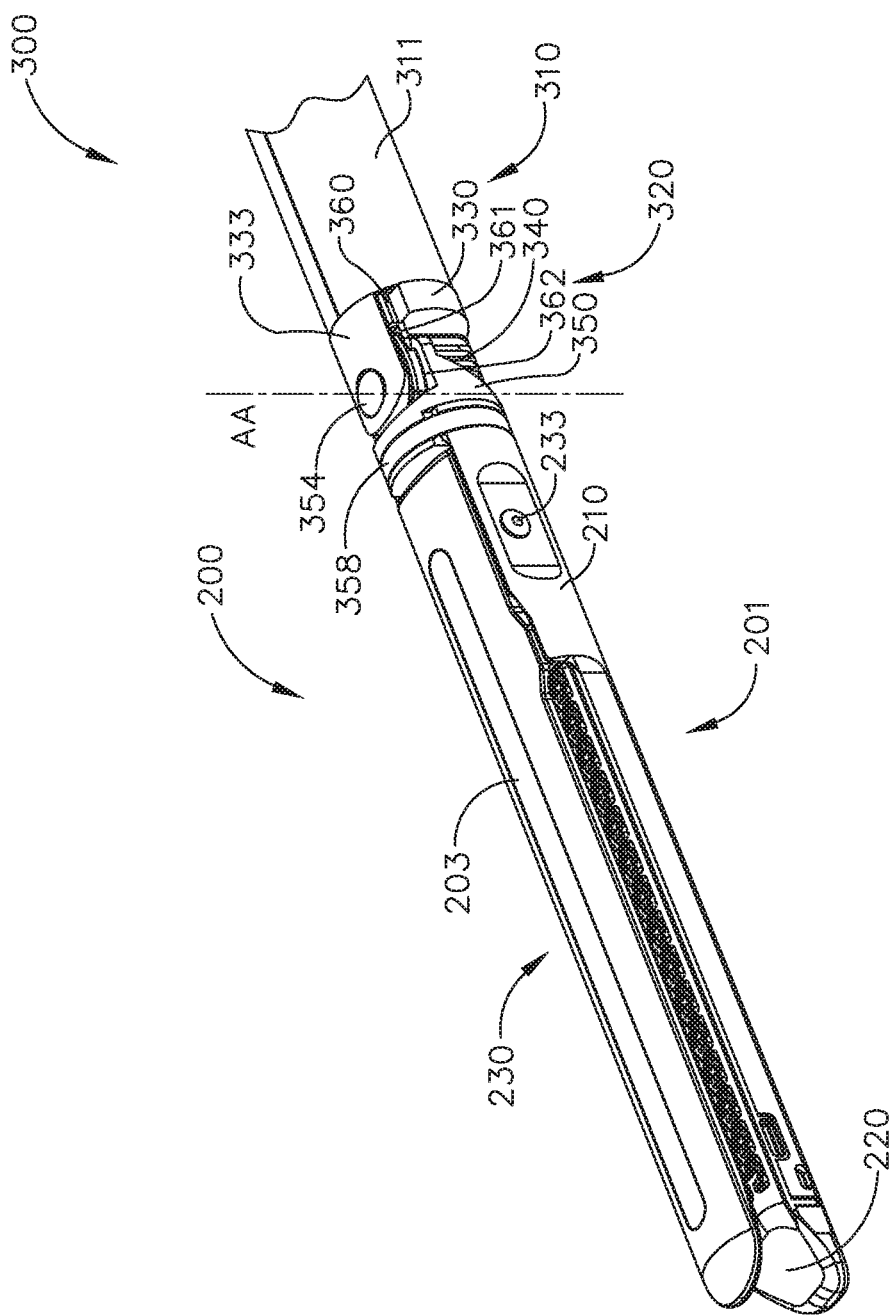
FIG. 9 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 10:
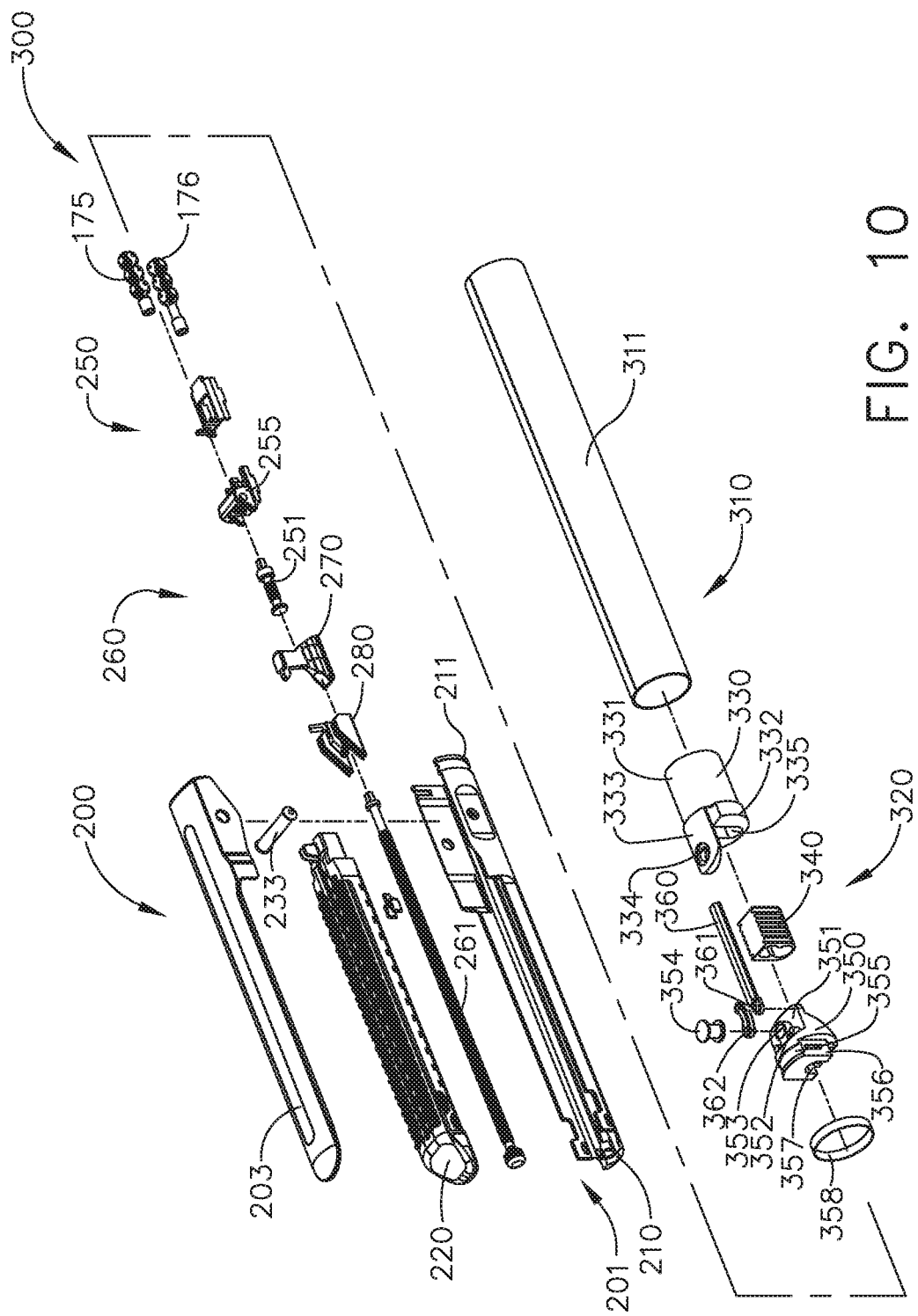
FIG. 10 is an exploded perspective view of the surgical stapling assembly of FIG. 9, in accordance with at least one aspect of the present disclosure.
Figure 11:
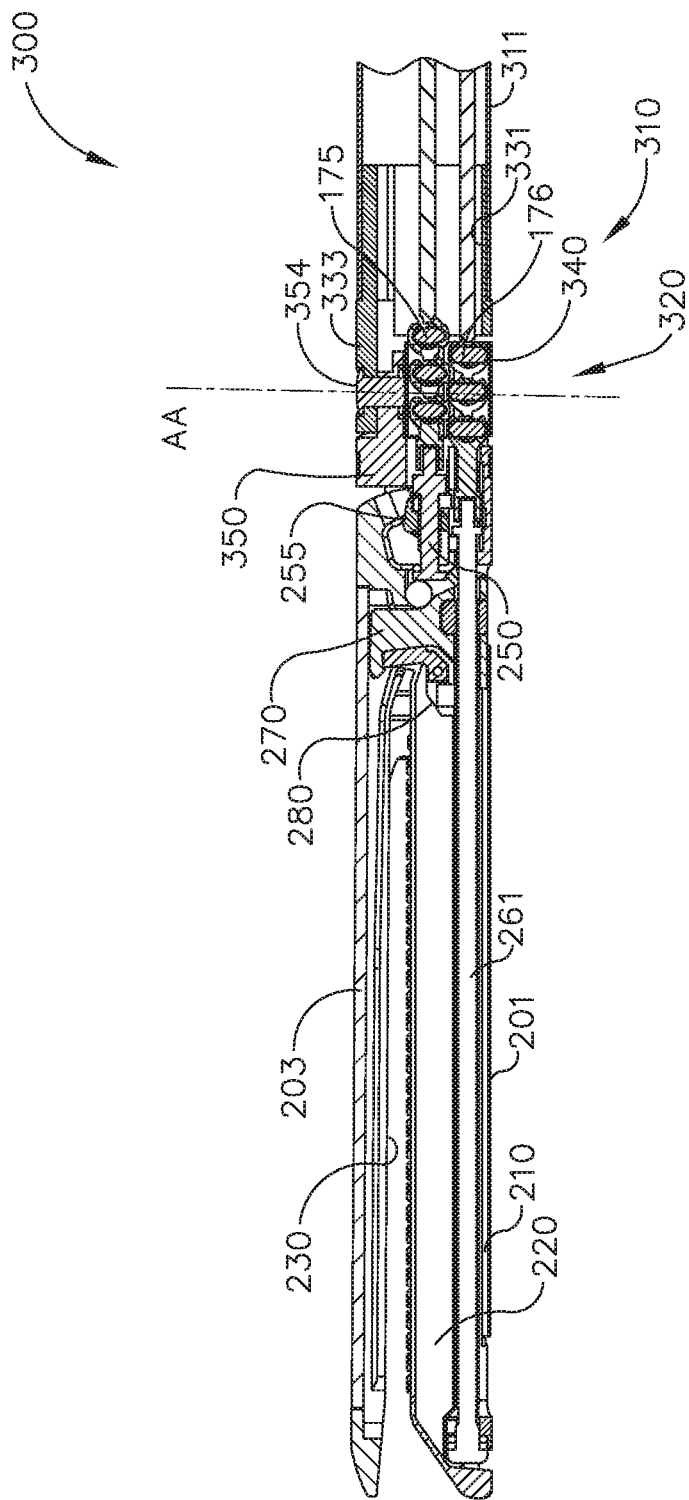
FIG. 11 is a cross-sectional elevation view of the surgical stapling assembly of FIG. 9, wherein the end effector is illustrated in an unfired, clamped configuration, in accordance with at least one aspect of the present disclosure.

FIGS. 9-11 depict a surgical stapling assembly 300 comprising a shaft assembly 310 and the end effector 200 of FIGS. 1-8 attached to the shaft assembly 310. The shaft assembly 310 may be similar in many respects to various other shaft assemblies discussed herein; however, the shaft assembly 310 comprises a single articulation joint and an articulation bar configured to articulate the end effector 200 about the single articulation joint. The surgical stapling assembly 300 is configured to cut and staple tissue. The surgical stapling assembly 300 may be attached to a surgical instrument handle and/or surgical robotic interface. The surgical instrument handle and/or surgical robotic interface can be configured to actuate various functions of the surgical stapling assembly 300. The shaft assembly 310 comprises an articulation joint 320. Discussed in greater detail below, the end effector 200 is configured to be articulated relative to an outer shaft 311 of the shaft assembly 310 about axis AA.

The shaft assembly 310 comprises the outer shaft 311, a first shaft joint component 330, and a second shaft joint component 350 pivotally coupled to the first shaft joint component 330 by way of an articulation pin 354. The first shaft joint component 330 comprises a proximal tube portion 331 configured to fit within the inner diameter of the outer shaft 311. Such a fit may comprise a press fit, for example. However, any suitable attachment means can be used. The first shaft joint component 330 also includes a distal portion 332. The distal portion 332 comprises an articulation tab 333 comprising a pin hole 334 defined therein and a hollow passage 335 through which various drive components of the surgical stapling assembly 300 can pass. Such drive components can include articulation actuators, closure actuators, and/or firing actuators for example.

The first shaft joint component 330 is pivotally connected to the second shaft joint component 350 by way of the articulation pin 354. The articulation pin 354 is also received within a pin hole 353 of a proximally-extending articulation tab 351 of the second shaft joint component 350. The pin hole 353 is axially aligned with the pin hole 334. The articulation pin 354 allows the second shaft joint component 350 to be articulated relative to the first shaft joint component 330 about the articulation axis AA. The second shaft joint component 350 further comprises a pin protrusion 352 extending from the proximal-extending articulation tab 351. Discussed in greater detail below, the pin protrusion 352 is configured to be pivotally coupled to an articulation drive system. The second shaft joint component 350 further comprises a distal portion 355 comprising an annular groove 356 configured to receive a retention ring 358. The distal portion 355 also includes a hollow passage 357 through which various drive components of the surgical stapling assembly 300 can pass. The retention ring 358 is configured to hold the first jaw 201 to the second shaft joint component 350 by fitting within the annular groove 211 of the cartridge channel 210 and the annular groove 356 of the second shaft joint component 350.

To articulate the end effector 200 about the articulation axis AA, an articulation bar 360 is provided. The articulation bar 360 may be actuated by any suitable means such as, for example, by a robotic or motorized input and/or a manual handle trigger. The articulation bar 360 may be actuated in a proximal direction and a distal direction, for example. Embodiments are envisioned where the articulation system comprises rotary driven actuation in addition to or, in lieu of, linear actuation. The articulation bar 360 extends through the outer shaft 311. The articulation bar 360 comprises a distal end 361 pivotally coupled to an articulation link 362. The articulation link 362 is pivotally coupled to the pin protrusion 352 extending from the proximally-extending articulation tab 351 off center with respect to the articulation axis AA. Such off-center coupling of the articulation link 362 allows the articulation bar 360 to apply a force to the second joint shaft component 350 to rotate the second shaft joint component 350 and, thus, the end effector 200, relative to the first joint shaft component 330. The articulation bar 360 can be advanced distally to rotate the end effector 200 in a first direction about the articulation axis AA and retracted proximally to rotate the end effector 200 in a second direction opposite the first direction about the articulation axis AA.

The shaft assembly 310 further comprises an articulation component support structure 340 positioned within the articulation joint 320. Such a support structure can provide support to various drive components configured to pass through the articulation joint 320 to the end effector 200 as the end effector 200 is articulated. The support structure 340 may also serve to isolate the drive components from tissue remnants during use.

Figure 12:
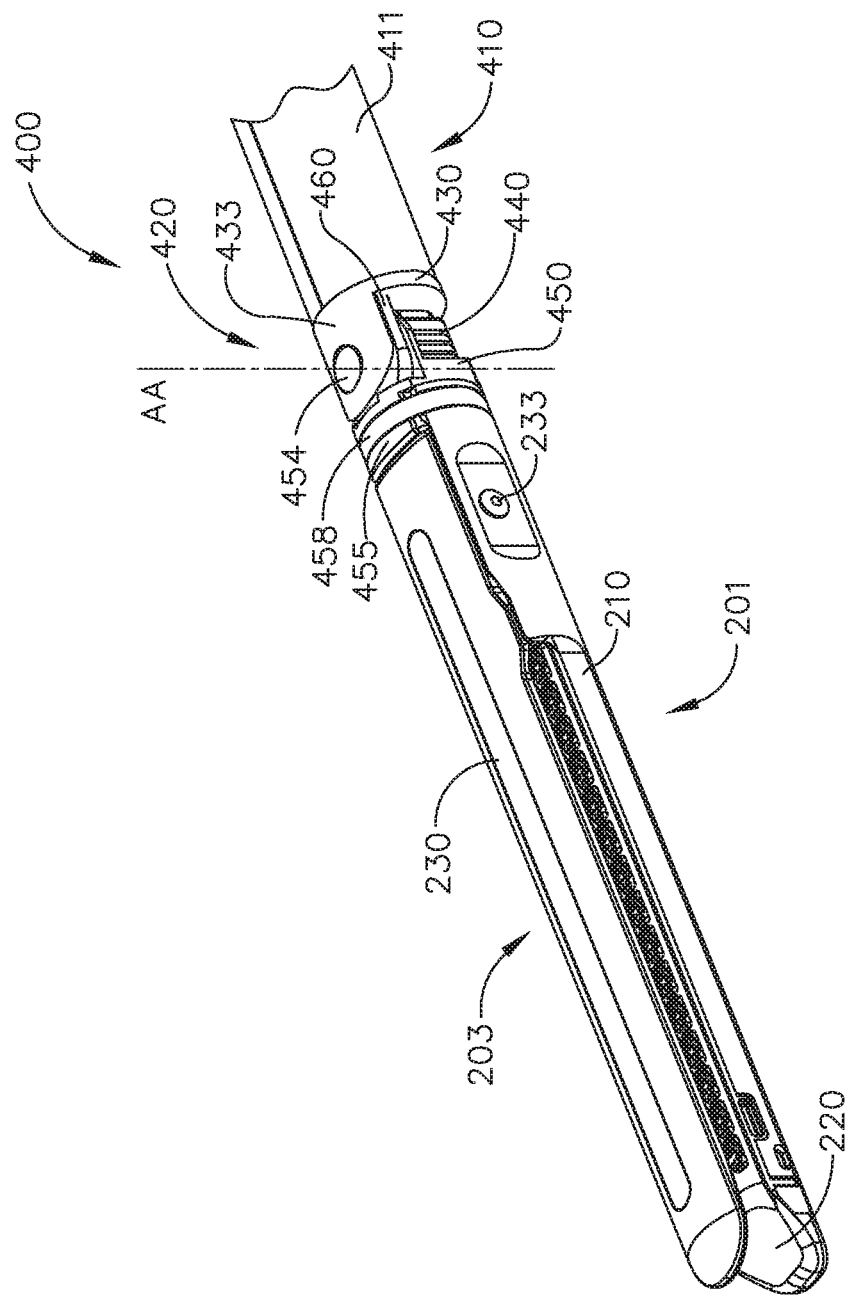
FIG. 12 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 13:
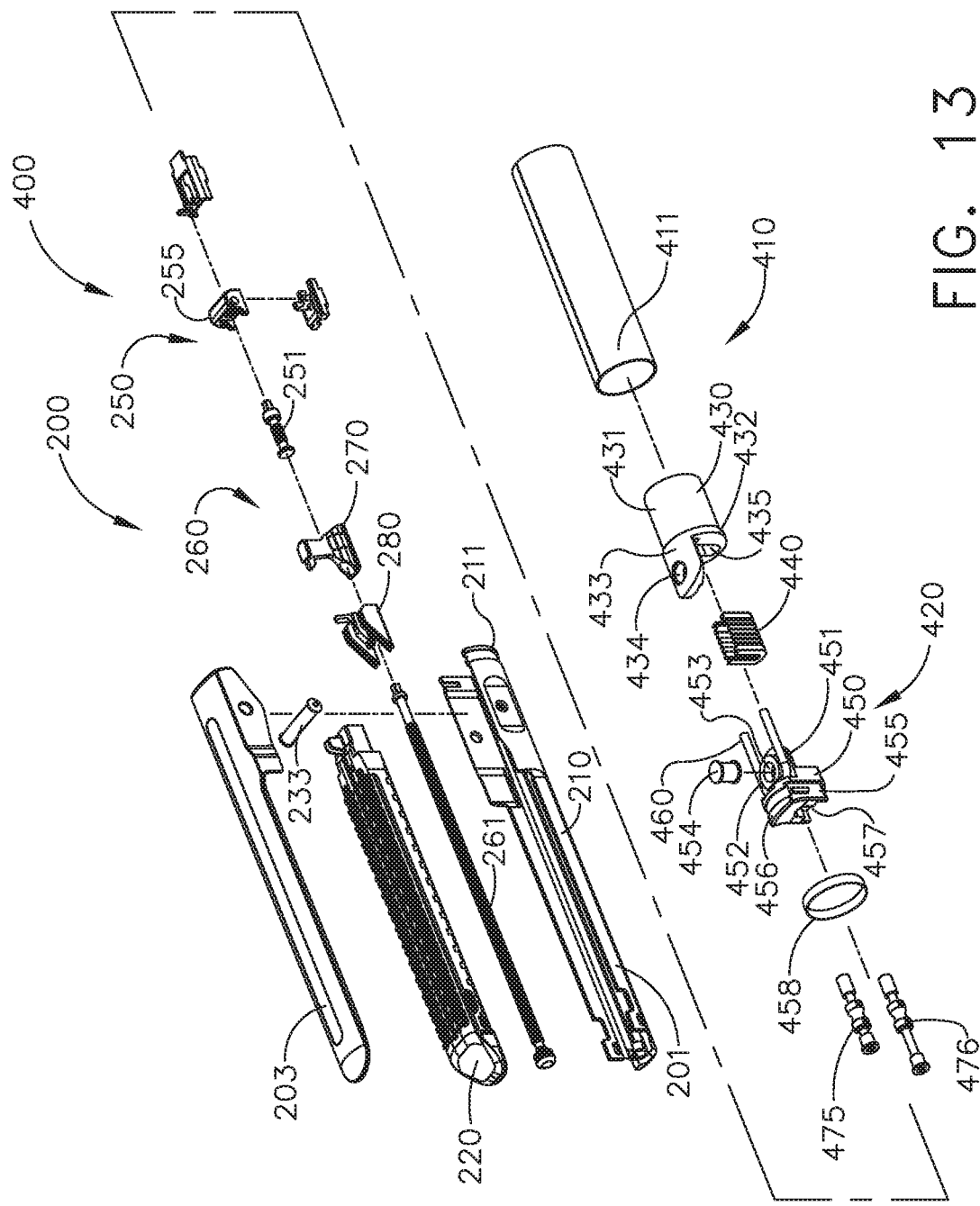
FIG. 13 is an exploded perspective view of the surgical stapling assembly of FIG. 12, in accordance with at least one aspect of the present disclosure.
Figure 14:
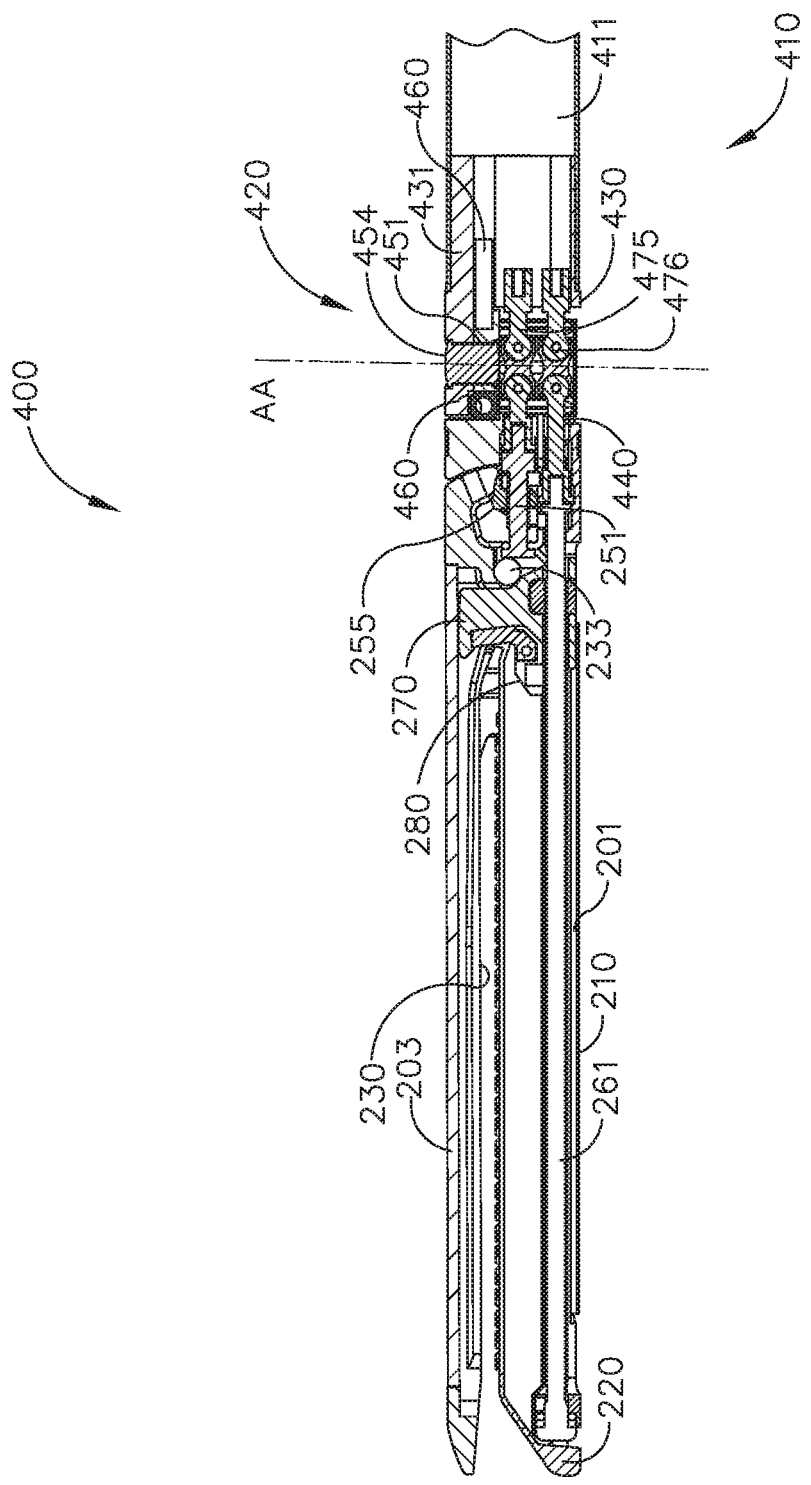
FIG. 14 is a cross-sectional elevation view of the surgical stapling assembly of FIG. 12, wherein the end effector is illustrated in an unfired, clamped configuration, in accordance with at least one aspect of the present disclosure.

FIGS. 12-14 depict a surgical stapling assembly 400 comprising a shaft assembly 410 and the end effector 200 of FIGS. 1-8 attached to the shaft assembly 410. The shaft assembly 410 may be similar in many respects to various other shaft assemblies discussed herein; however, the shaft assembly 410 comprises a single articulation joint and an articulation cable configured to articulate the end effector 200 about the single articulation joint. The surgical stapling assembly 400 is configured to cut and staple tissue. The surgical stapling assembly 400 may be attached to a surgical instrument handle and/or surgical robotic interface. The surgical instrument handle and/or surgical robotic interface can be configured to actuate various functions of the surgical stapling assembly 400. The shaft assembly 410 comprises an articulation joint 420. Discussed in greater detail below, the end effector 200 is configured to be articulated relative to an outer shaft 411 of the shaft assembly 310 about an axis AA.

The shaft assembly 410 comprises the outer shaft 411, a first shaft joint component 430, and a second shaft joint component 450 pivotally coupled to the first shaft joint component 430 by way of an articulation pin 454. The first shaft joint component 430 comprises a proximal tube portion 431 configured to fit within the inner diameter of the outer shaft 411. Such a fit may comprise a press fit, for example. However, any suitable attachment means can be used. The first shaft joint component 430 also includes a distal portion 432, which comprises an articulation tab 433 comprising a pin hole 434 defined therein. The distal portion 432 further defines a hollow passage 435 through which various drive components of the surgical stapling assembly 400 can pass. Such drive components can include articulation actuators, closure actuators, and/or firing actuators, for example.

The first shaft joint component 430 is pivotally connected to the second shaft joint component 450 by way of the articulation pin 454. The articulation pin 454 is also received within a pin hole 453 of a proximally-extending articulation tab 451 of the second shaft joint component 450. The articulation pin 454 allows the second shaft joint component 450 to be articulated relative to the first shaft joint component 430 about the articulation axis AA. The second shaft joint component 450 further comprises a drive ring structure 452. The drive ring structure 452 extends from the proximally-extending articulation tab 451 and further defines a portion of the pin hole 453. Discussed in greater detail below, the drive ring structure 452 is configured to be engaged by an articulation drive system. The second shaft joint component 450 further comprises a distal portion 455 comprising an annular groove 456 configured to receive a retention ring 458. A hollow passage 457 through the distal portion 455 is configured to receive various drive components of the surgical stapling assembly 400 therethrough. The retention ring 458 is configured to hold the first jaw 201 to the second shaft joint component 450 by fitting within the annular groove 211 of the cartridge channel 210 and the annular groove 456 of the second shaft joint component 450.

To articulate the end effector 200 about the articulation axis AA, an articulation cable 460 is provided. The articulation cable 460 may be actuated by any suitable means such as, for example, by a robotic input and/or a manual trigger on a handle of a handheld surgical instrument. The articulation cable 460 may comprise an antagonistic actuation profile. In other words, as a first side of the articulation cable 460 is pulled proximally a second side of the articulation cable 460 is allowed to advance distally like a pulley system. Similarly, as the second side is pulled proximally, the first side is allowed to advance distally. The articulation cable 460 extends through the outer shaft 411. The articulation cable 460 is positioned around the drive ring structure 452 and frictionally retained thereon to permit rotation of the second shaft joint component 450 as the articulation cable 460 is actuated. As the articulation cable 460 is actuated, the articulation cable 460 is configured to apply a rotational torque to the drive ring structure 452 of the second joint shaft component 450 and, thus, the end effector 200. Such torque is configured to cause the second joint shaft component 450 to rotate, or pivot, relative to the first joint shaft component 430 thereby articulating the end effector 200 relative to the outer shaft 411. A first side of the articulation cable 460 can pulled to rotate the end effector 200 in a first direction about the articulation axis AA and a second side of the articulation cable 460 can be pulled to rotate the end effector 200 in a second direction opposite the first direction about the articulation axis AA.

The shaft assembly 410 further comprises an articulation component support structure 440 positioned within the articulation joint 420. Such a support structure 440 can provide support to various drive components configured to pass through the articulation joint 420 to the end effector 200 as the end effector 200 is articulated. The support structure 440 may also serve to isolate the drive components from tissue remnants during use.

The surgical stapling assembly 400 further comprises a closure drive shaft segment 475 and a firing drive shaft segment 476 each configured to transmit rotary motion through the articulation joint 420 to the end effector 200. The drive shaft segments 475, 476 are configured to passively expand and contract longitudinally as the end effector 200 is articulated. For example, articulation can cause expansion and contraction of the drive shaft segments 475, 476 to account for the respective longitudinal stretching of or contracting of the length of the drive shafts owing to articulation of the end effector 200 relative to the shaft assembly 410. During expansion and contraction of the drive shaft segments 475, 476, the drive shaft segments 475, 476 maintain rotary driving engagement with corresponding input shafts extending through the outer shaft 411 and output shafts in the end effector 200. In at least one instance, the output shafts comprise the closure screw 251, which is configured to effect grasping, closing, or tissue manipulation with the jaws 201, 203, and the firing screw 261, which is configured to effect clamping of the jaws 201, 203 and firing of the firing member 270.

Figure 15:
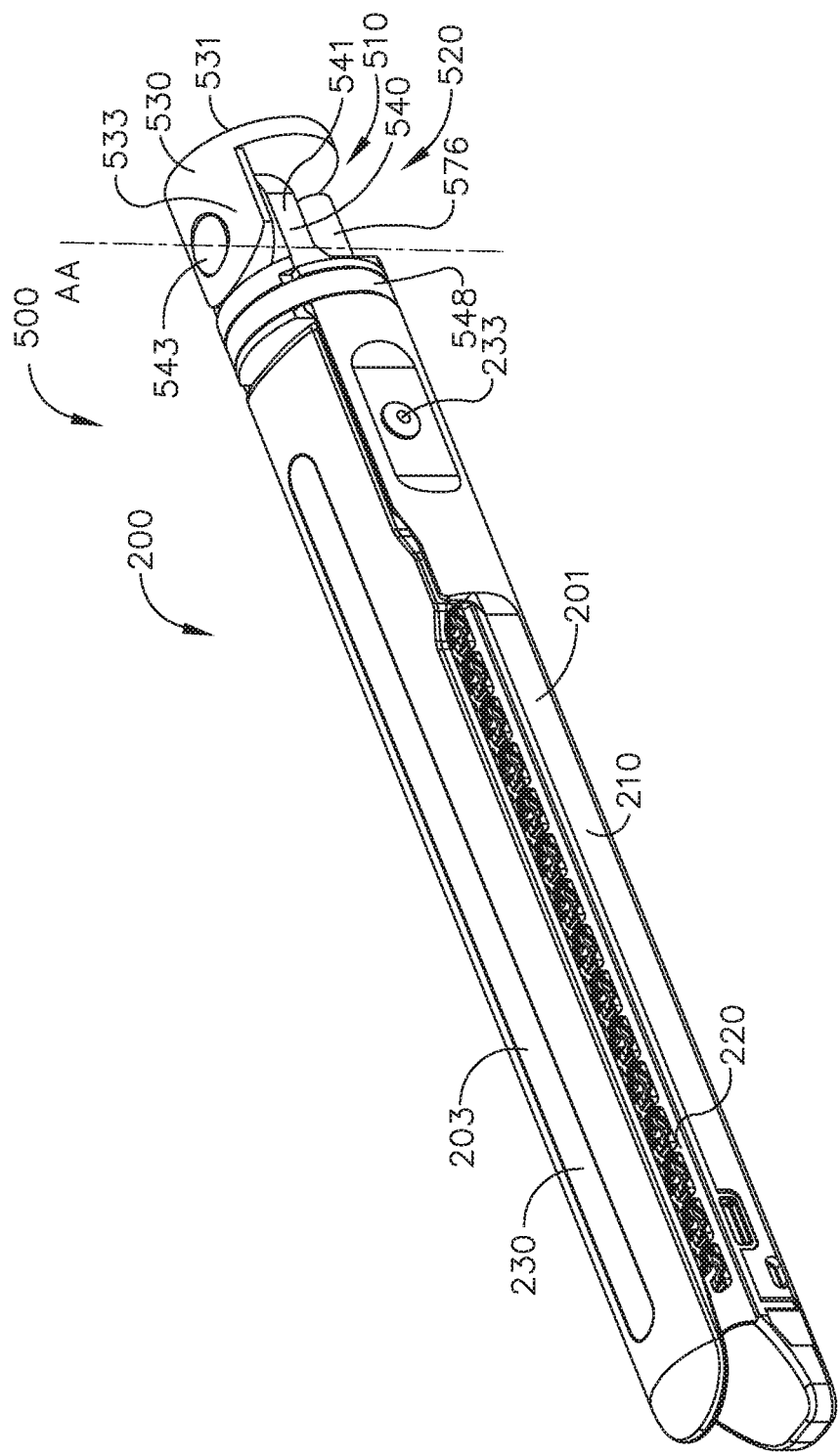
FIG. 15 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 16:
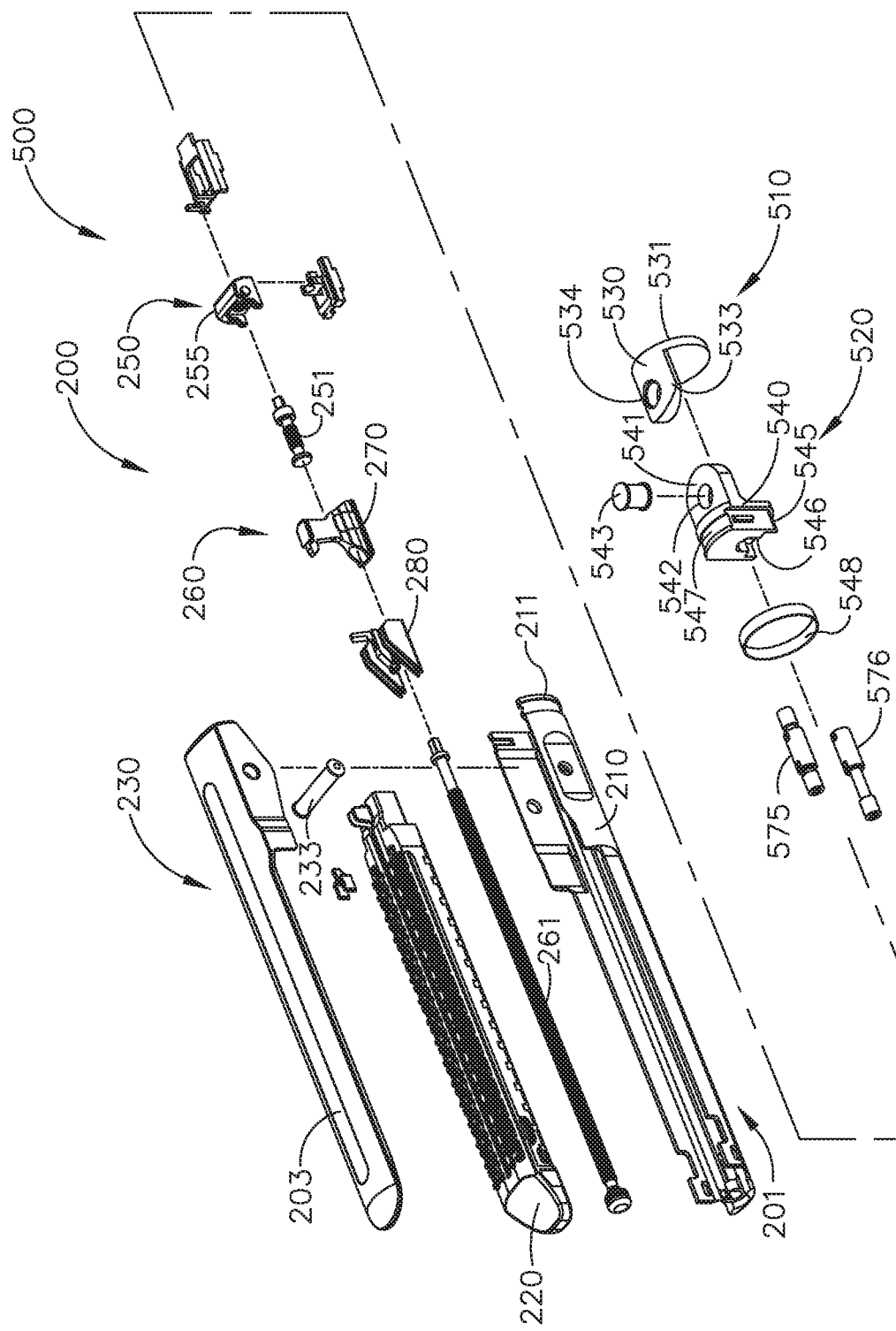
FIG. 16 is an exploded perspective view of the surgical stapling assembly of FIG. 15, in accordance with at least one aspect of the present disclosure.
Figure 17:
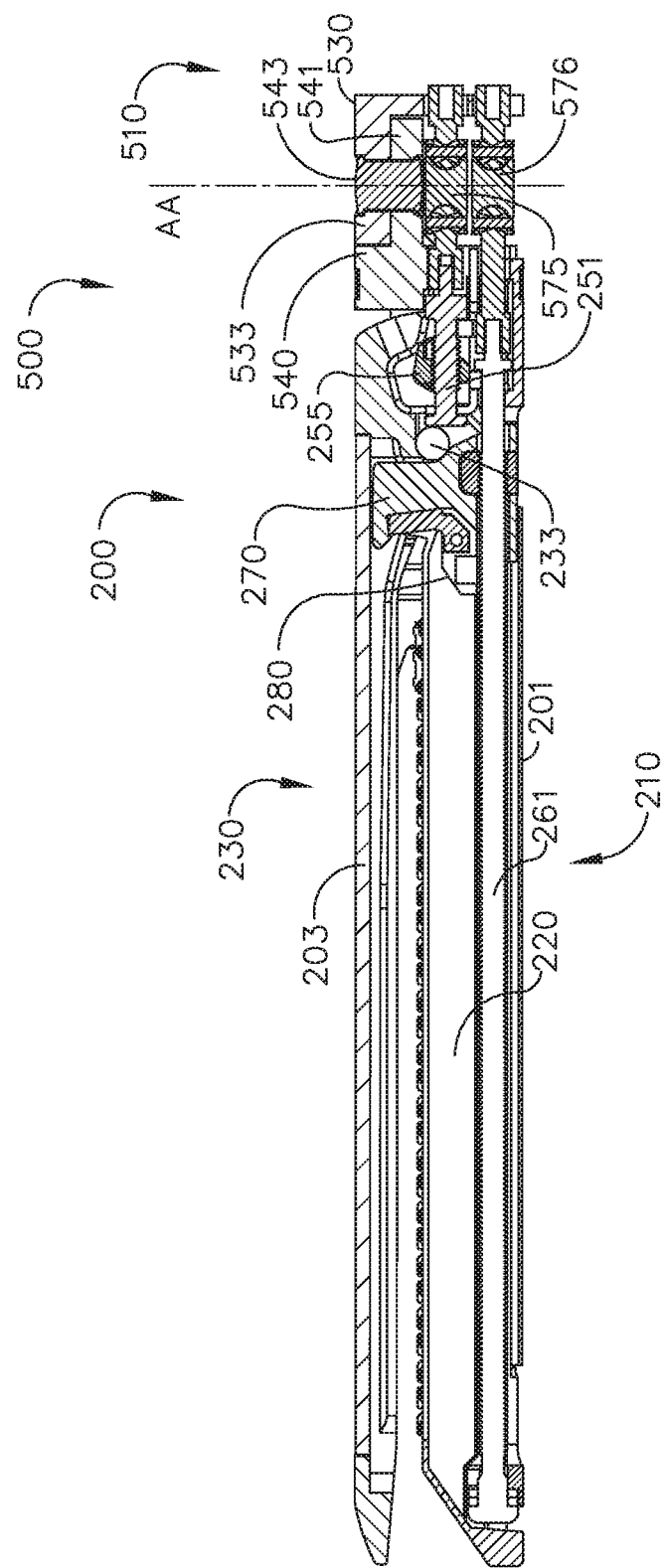
FIG. 17 is a cross-sectional elevation view of the surgical stapling assembly of FIG. 15, wherein the end effector is illustrated in an unfired, clamped configuration, in accordance with at least one aspect of the present disclosure.

FIGS. 15-17 depict a surgical stapling assembly 500 comprising a shaft assembly 510 and the end effector 200 of FIGS. 1-8 attached to the shaft assembly 510. The shaft assembly 510 may be similar in many respects to various other shaft assemblies discussed herein; however, the shaft assembly 510 comprises a single articulation joint and drive shaft segments configured to passively expand and contract. The surgical stapling assembly 500 is configured to cut and staple tissue. The surgical stapling assembly 500 may be attached to a surgical instrument handle and/or surgical robotic interface. The surgical instrument handle and/or surgical robotic interface can be configured to actuate various functions of the surgical stapling assembly 500. The shaft assembly 510 comprises an articulation joint 520. Discussed in greater detail below, the end effector 200 is configured to be articulated about an axis AA.

The shaft assembly 510 comprises a first shaft joint component 530 and a second shaft joint component 540 pivotally coupled to the first shaft joint component 530 by way of an articulation pin 543. The first shaft joint component 530 is configured to be attached to a shaft of a surgical instrument assembly and/or a surgical robotic interface. The first shaft joint component 530 comprises a proximal portion 531 and an articulation tab 533 comprising a pin hole 534 defined therein. In at least one instance, the first shaft joint component 530 comprises a hollow passage through which various drive components of the surgical stapling assembly 400 can pass. Such drive components can include articulation actuators, closure actuators, and/or firing actuators for example.

The first shaft joint component 530 is pivotally connected to the second shaft joint component 540 by way of the articulation pin 543. The articulation pin 543 is also received within a pin hole 542 of a proximally-extending articulation tab 541 of the second shaft joint component 540. The articulation pin 543 allows the second shaft joint component 540 to be articulated relative to the first shaft joint component 530 about the articulation axis AA. The second shaft joint component 540 further comprises a distal portion 545 comprising an annular groove 547 configured to receive a retention ring 548 and a hollow passage 546 through which various drive components of the surgical stapling assembly 500 can pass. The retention ring 548 is configured to hold the first jaw 201 to the second shaft joint component 540 by fitting within the annular groove 211 of the cartridge channel 210 and the annular groove 547 of the second shaft joint component 540.

Any suitable articulation drive system can be used to articulate the end effector 200 about axis AA. In at least one instance, the end effector 200 is passively articulated. In such an instance, the end effector 200 may be pressed against tissue, for example, to apply a force to the end effector 200 and cause the end effector 200 to articulate about an articulation axis. In at least one instance, the end effector 200 further comprises a spring configured to apply a neutral biasing force to the second shaft joint segment 540, for example, to cause the end effector 200 to be biased toward an unarticulated configuration.

The surgical stapling assembly 500 further comprises a closure drive shaft segment 575 and a firing drive shaft segment 576 each configured to transmit rotary motion through the articulation joint 520 to the end effector 200. The drive shaft segments 575, 576 are configured to passively expand and contract longitudinally as the end effector 200 is articulated. Articulation causes the drive shaft segments 575, 576 to expand and contract to account for the longitudinal stretching of or contracting of the length of the drive shafts owing to articulation of the end effector 200. During expansion and contraction of the drive shaft segments 575, 576, the drive shaft segments 575, 576 maintain rotary driving engagement with corresponding input shafts and output shafts in the end effector 200. In at least one instance, the output shafts comprise the closure screw 251 and the firing screw 261, which are further described herein.

Figure 18:
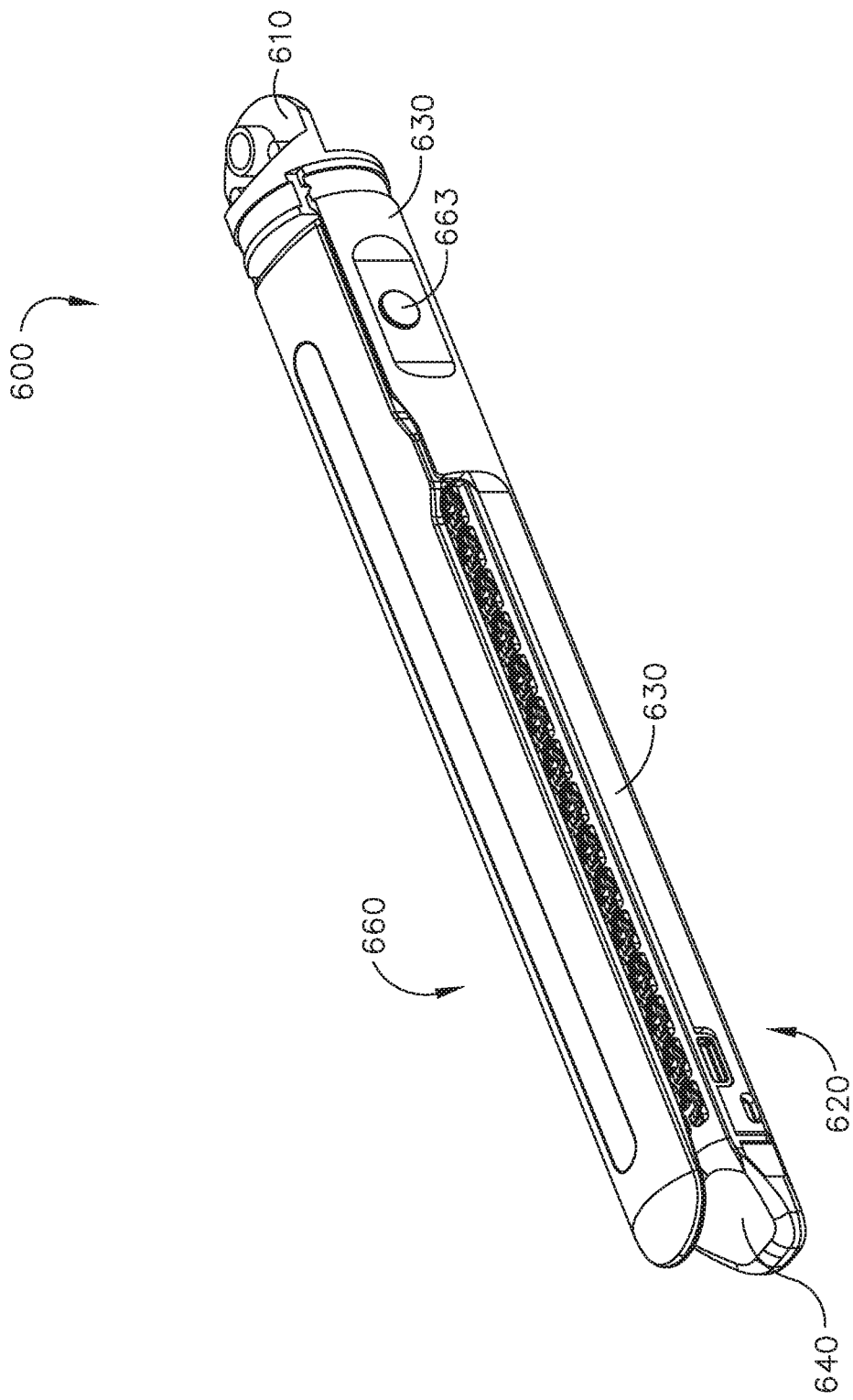
FIG. 18 is a perspective view of a surgical end effector assembly comprising the end effector of FIG. 1 and a flexible firing drive system, in accordance with at least one aspect of the present disclosure.
Figure 19:
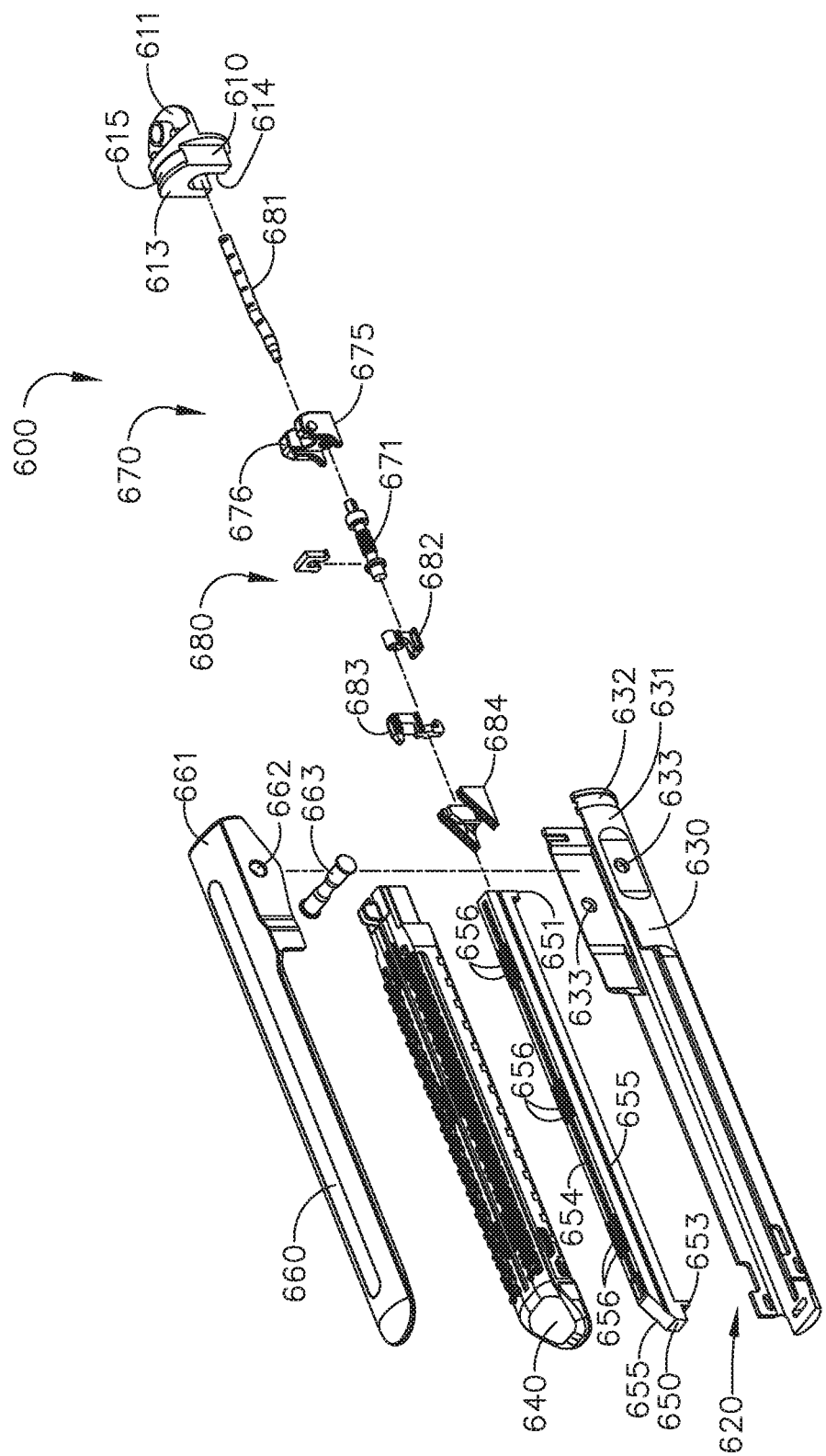
FIG. 19 is an exploded perspective view of the surgical stapling assembly of FIG. 18, in accordance with at least one aspect of the present disclosure.
Figure 20:
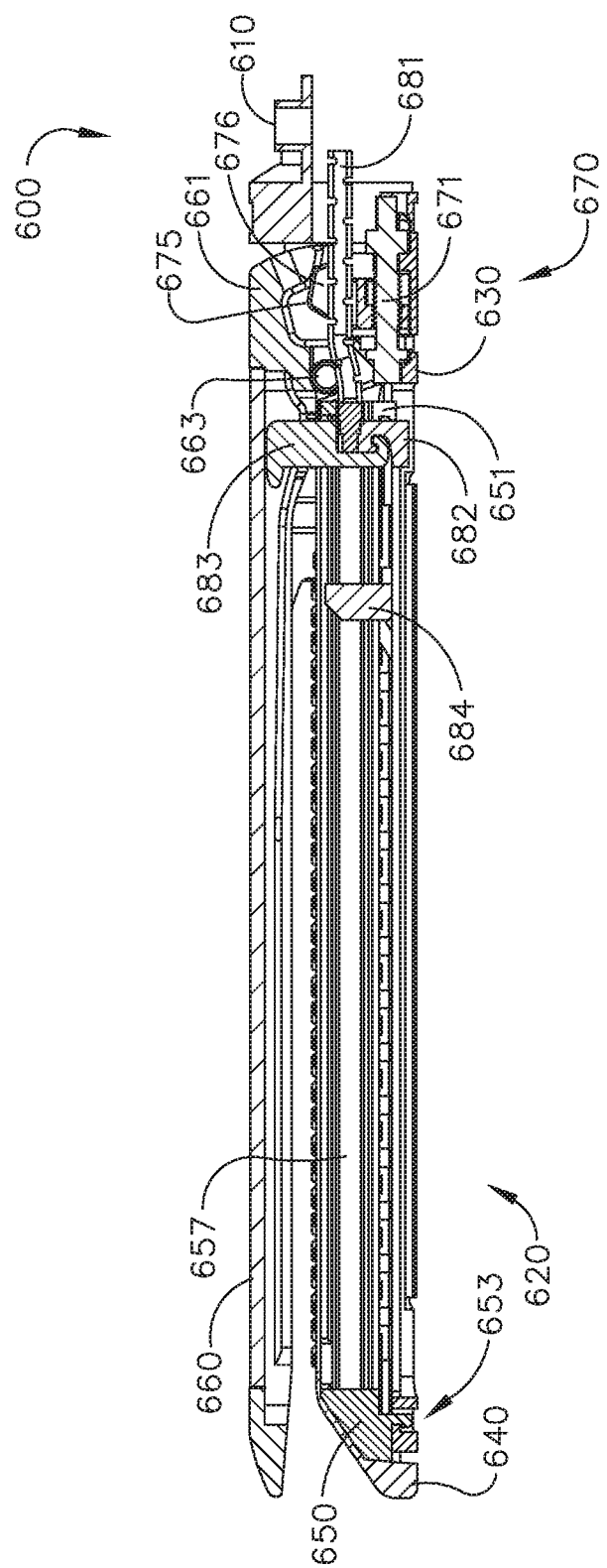
FIG. 20 is a cross-sectional elevation view of the surgical end effector assembly of FIG. 18, wherein the surgical end effector assembly is illustrated in an unfired, clamped configuration, in accordance with at least one aspect of the present disclosure.

FIGS. 18-20 depict a surgical stapling end effector assembly 600 comprising a shaft portion 610 and an end effector 600. The end effector assembly 600 is similar in many respects to various other end effector assemblies disclosed herein; however, the end effector assembly 600 comprises a multi-component firing member driven by a flexible firing shaft. The end effector assembly 600 is configured to cut and staple tissue. The end effector assembly 600 may be attached to a surgical instrument handle and/or surgical robotic interface by way of a proximal tab 611 of the shaft portion 610. The surgical instrument handle and/or surgical robotic interface can be configured to actuate various functions of the end effector assembly 600. The end effector assembly 600 comprises a cartridge channel jaw 620 and an anvil jaw 660 pivotally mounted to the cartridge channel jaw 620 to clamp tissue between the cartridge channel jaw 620 and the anvil jaw 660.

The cartridge channel jaw 620 comprises a channel 630 comprising a proximal end 631, a staple cartridge 640 configured to store a plurality of staples therein and configured to be received within the channel 630, and a support brace 650 fitted within the staple cartridge 640. The staple cartridge 640 and the support brace 650 are configured to be assembled together prior to installing the staple cartridge 640 into the channel 630. Discussed in greater detail below, the support brace 650 is configured to further support a firing member assembly as the firing member assembly is advanced through the end effector assembly 600.

The anvil jaw 660 is configured to form staples ejected from the staple cartridge 640. The anvil jaw 660 comprises a proximal end 661 comprising a pair of pin holes 662 defined therein configured to receive a coupling pin 663. The anvil jaw 660 is pivotable about the coupling pin 663 between an unclamped position and a fully clamped position. The coupling pin 663 is also received within a pair of pin holes 633 defined in the proximal end 631 of the channel 630. The coupling pin 663 serves to pivotally mount the anvil jaw 660 to the channel 630. In at least one instance, the channel 630 is mounted to the shaft portion 610 by way of a retention ring, or band, that fits around an annular groove 632 of the channel 630 and annular groove 615 of the shaft portion 610. The retention ring, or band, is configured to hold the channel 630 to the shaft portion 610.

The end effector assembly 600 comprises a closure drive 670 configured to grasp tissue between the anvil jaw 660 and the cartridge channel jaw 620 by pivoting the anvil jaw 660 relative to the channel 630. The end effector assembly 600 also includes a firing drive 680 configured to clamp, staple, and cut tissue by deploying a plurality of staples from the staple cartridge 640. The closure drive 670 comprises a closure screw 671 positioned within the channel 630 and a closure wedge 675 threadably coupled to the closure screw 671. As the closure screw 671 is rotated, the closure wedge 675 is advanced distally or retracted proximally to open or close the anvil jaw 660, respectively. The closure drive 670 may be actuated by any suitable means. For example, a rotary drive shaft may extend through the shaft portion 610 from an actuation interface, for example, to rotate the closure screw 671. Other examples of suitable rotary drive shafts are further described herein.

The firing drive 680 comprises a flexible drive shaft 681 that is configured to be moved linearly through the end effector assembly 600. The flexible drive shaft 681 may be actuated by a robotic input and/or a manually-actuated drive shaft of a handle assembly, for example. The flexible drive shaft 681 is configured to extend through a hollow passage 614 of a distal end 613 of the shaft portion 610 and is flexible so that the end effector assembly 600 may be articulated relative to a shaft from which the end effector 600 extends. The flexible drive shaft 681 extends through a clearance slot 676 defined in the closure wedge 675 and is fixedly attached to a lower firing member 682. The lower firing member 682 is configured to be reused with different staple cartridges.

The staple cartridge 640 comprises a disposable upper firing member 683 configured to hookingly engage or, latch, onto the lower firing member 682 such that the lower firing member 582 can push or, drive, the upper firing member 683 through the staple cartridge 640 and support brace 650. In other words, the firing actuation involves a two-part firing member—a disposable upper firing member 683 incorporated into the cartridge 640 and a reusable lower firing member 682 incorporated into the firing drive 680, which can be coupled together when the cartridge 640 is seated in the elongate channel 630. The two-part firing member is further described herein.

The upper firing member 683 comprises an upper flange configured to engage and position the anvil jaw 660, a knife edge configured to cut tissue, and a latch portion configured to hookingly engage the lower firing member 682. The staple cartridge 640 further comprises a sled 684 configured to engage staple drivers positioned within the staple cartridge 640 to eject staples from the staple cartridge 640. Because a knife and cutting edge are incorporated into the disposable upper firing member 683 of the staple cartridge 640, a new and/or fresh cutting edge can be supplied with each staple cartridge loaded into the end effector assembly 600.

The lower firing member 682 and the upper firing member 683 are configured to move through the support brace 650 such that the vertical loads associated with the firing sequence are configured to be distributed through the support brace 650, the staple cartridge 640, the channel 630, and the anvil jaw 660. The support brace 650 may be comprised of a metal material, for example, to be inserted within the staple cartridge 640. The support brace 650 comprises key rails 655 configured to fit within corresponding key slots defined in a longitudinal slot of the staple cartridge 640. The support brace 650 further comprises a longitudinal slot 653 configured to receive the knife of the upper firing member 683, a cylindrical passage 657 configured to receive a portion of the upper firing member 683, a portion of the lower firing member 682, and the flexible drive shaft 681. The support brace 650 further comprises vertical key extensions 656 configured to be received within corresponding key holes in the cartridge deck. Such extensions may be visible through the cartridge deck when the support brace 650 is installed within the staple cartridge 640. In at least one instance, the support brace 650 is configured to be inserted into the staple cartridge 640 from the bottom of the staple cartridge 640 facing the channel 630.

The support brace 650 further comprises a proximal tab 651 and a distal tab 653, which are both configured to be engaged with the channel 630. The tabs 651, 653 are configured to distribute at least some of the forces transmitted through the assembly 600 by the firing drive 680 and corresponding components. The distal tab 651 may serve to block the upper and lower firing members 683, 682 from being pushed through a distal end of the support brace 650 by sharing and/or redistributing the load applied to the support brace 650 by the firing drive 680 with the channel 630.

When the staple cartridge 640 is replaced so that the end effector assembly 600 can be reused, the staple cartridge 640 is removed from the channel jaw 630. Removing the staple cartridge 640 from the channel jaw 630 removes the upper firing member 683, the sled 684, the support brace 650, and the staple cartridge 640. A fresh knife can be provided with a replacement staple cartridge.

Figure 21:
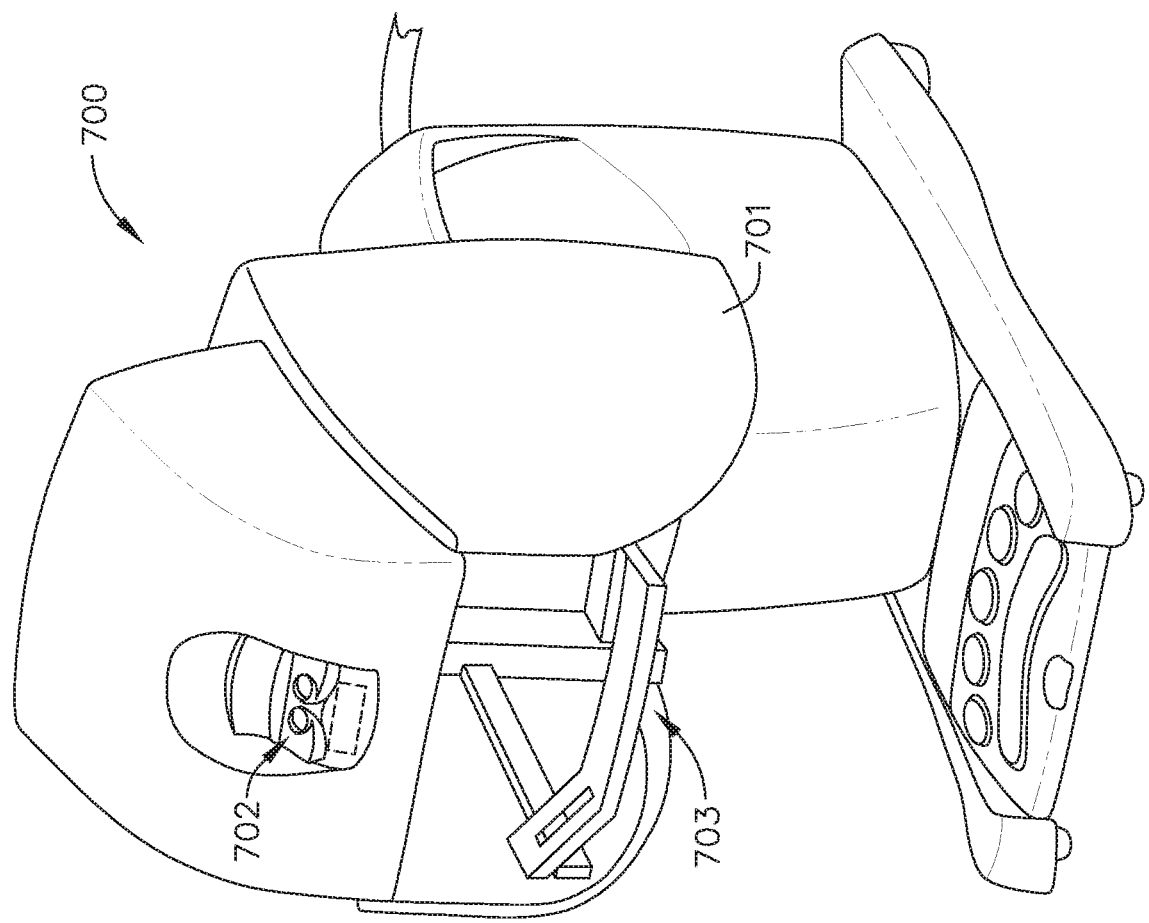
FIG. 21 is a perspective view of robotic controller, in accordance with at least one aspect of the present disclosure.
Figure 22:
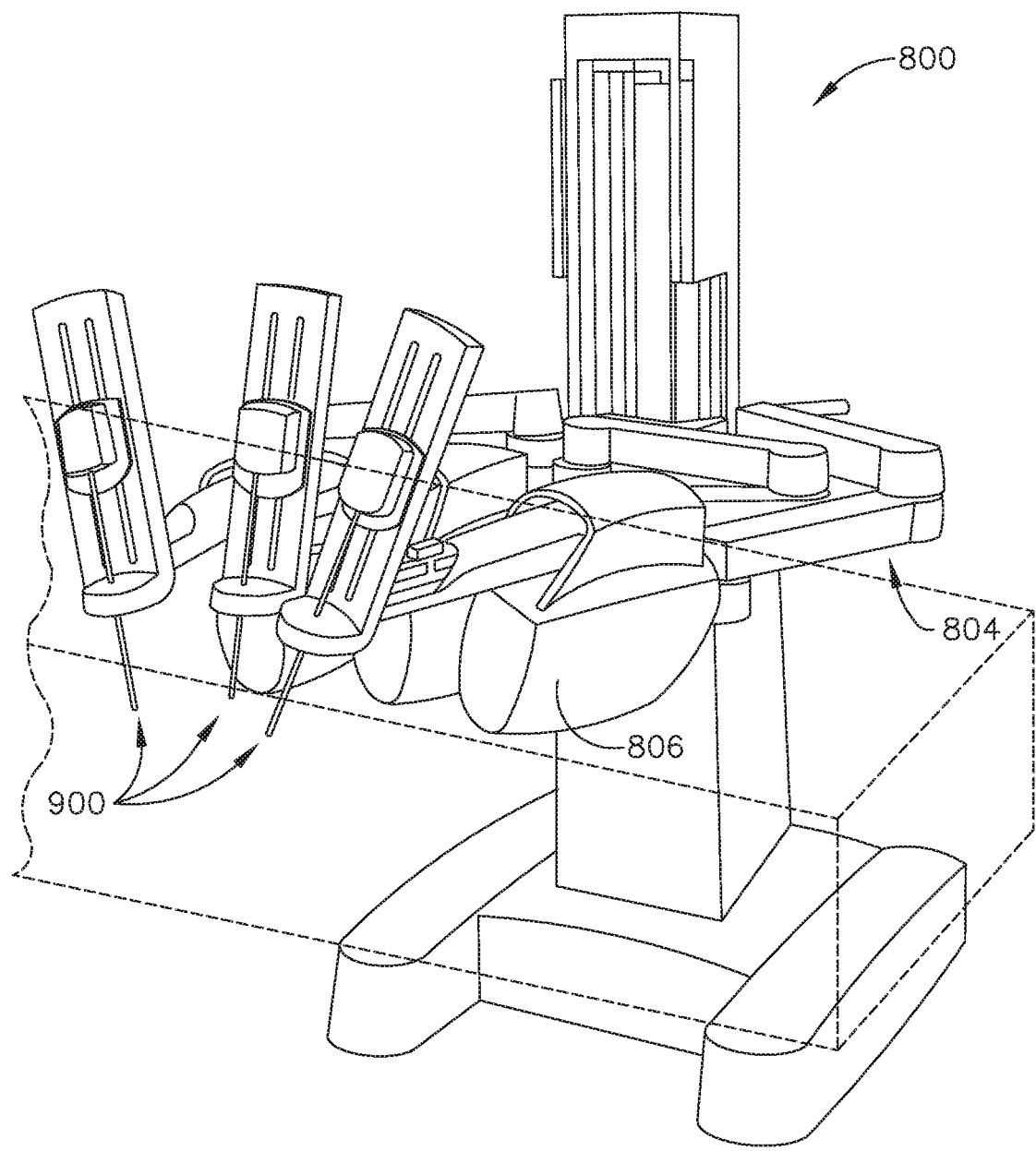
FIG. 22 is a perspective view of a robotic arm cart for a robotic surgical system, depicting manipulators on the robotic arm cart operably supporting surgical tools, in accordance with at least one aspect of the present disclosure.
Figure 23:
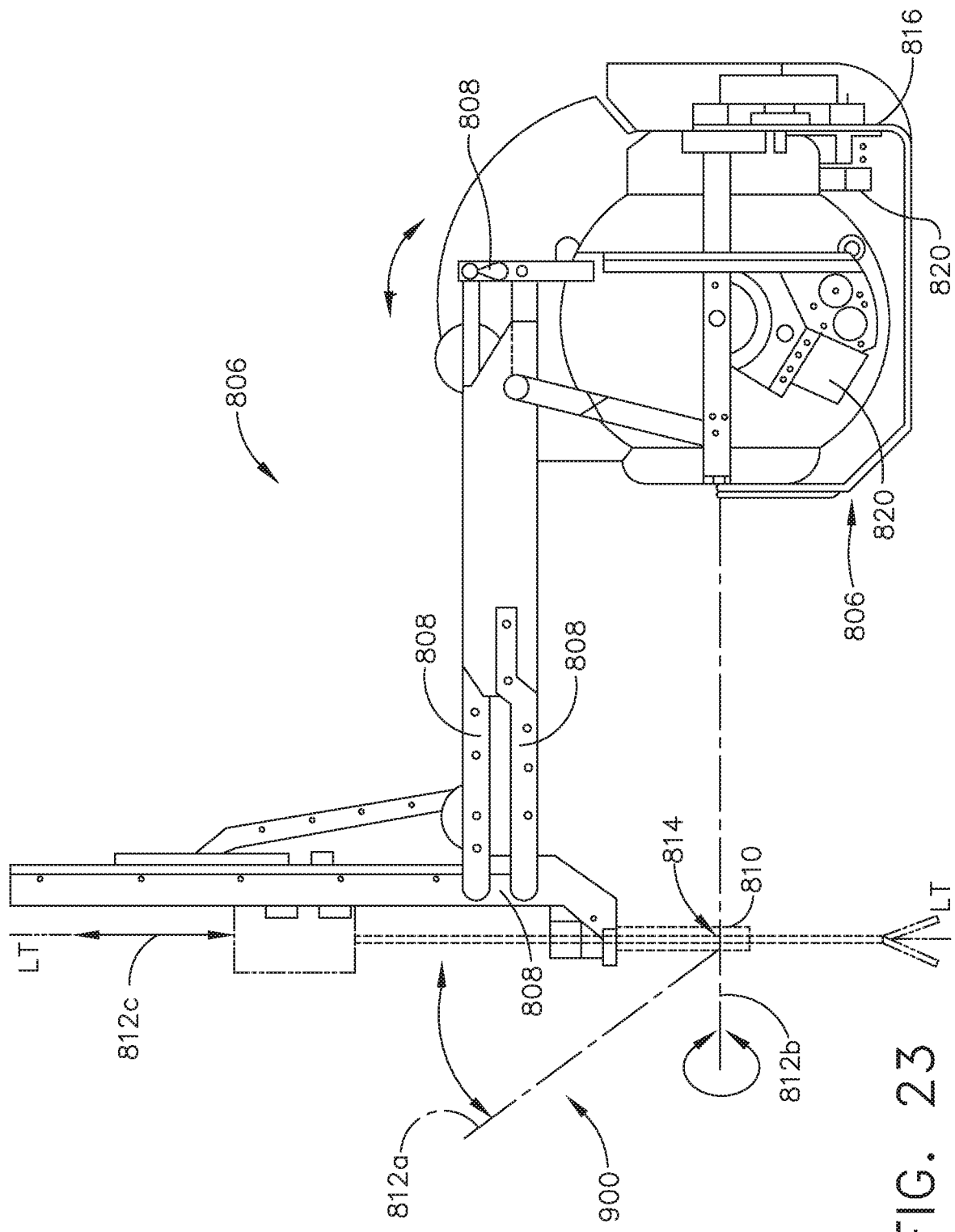
FIG. 23 is a side view of a manipulator of the surgical arm cart of FIG. 22 and a surgical grasping tool, in accordance with at least one aspect of the present disclosure.

Various embodiments disclosed herein may be employed in connection with a robotic system 700. An exemplary robotic system is depicted in FIGS. 21-23, for example. FIG. 21 depicts a master controller 701 that may be used in connection with a surgical robot, such as the robotic arm slave cart 800 depicted in FIG. 22, for example. Master controller 701 and robotic arm slave cart 800, as well as their respective components and control systems are collectively referred to herein as a robotic system 700. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. As is known, the master controller 701 generally includes controllers (generally represented as 703 in FIG. 21) which are grasped by the surgeon and manipulated in space while the surgeon views the procedure via a stereo display 702. The controllers 701 generally comprise manual input devices which preferably move with multiple degrees of freedom, and which often further have an actuatable handle, trigger, or actuator for actuating tools (for example, for closing grasping jaws, applying an electrical potential to an electrode, or the like).

As can be seen in FIG. 22, in one form, the robotic arm cart 800 may be configured to actuate one or more surgical tools, generally designated as 900. Various robotic surgery systems and methods employing master controller and robotic arm cart arrangements are disclosed in U.S. Pat. No. 6,132,368, entitled MULTI-COMPONENT TELEPRESENCE SYSTEM AND METHOD, the entire disclosure of which is hereby incorporated by reference herein.

In various forms, the robotic arm cart 800 includes a base 702 from which, in the illustrated embodiment, surgical tools 900 may be supported. In various forms, the surgical tool(s) 900 may be supported by a series of manually articulatable linkages, generally referred to as set-up joints 804, and a robotic manipulator 806. In various embodiments, the linkage and joint arrangement may facilitate rotation of a surgical tool around a point in space, as more fully described in U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 812a, sometimes called the pitch axis. The links supporting the parallelogram linkage are pivotally mounted to set-up joints 804 (FIG. 22) so that the surgical tool further rotates about an axis 812b, sometimes called the yaw axis. The pitch and yaw axes 812a, 812b intersect at the remote center 814, which is aligned along an elongate shaft of the surgical tool 900. The surgical tool 900 may have further degrees of driven freedom as supported by the manipulator 806, including sliding motion of the surgical tool 900 along the longitudinal axis "LT-LT". As the surgical tool 900 slides along the tool axis LT-LT relative to manipulator 806 (arrow 812c), the remote center 814 remains fixed relative to the base 816 of the manipulator 806. Hence, the entire manipulator is generally moved to re-position the remote center 814. Linkage 808 of manipulator 806 may be driven by a series of motors 820. These motors actively move linkage 808 in response to commands from a processor of a control system. The motors 820 may also be employed to manipulate the surgical tool 900. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein.

While the data communication between a robotic component and the processor of the robotic surgical system is primarily described herein with reference to communication between the surgical tool and the master controller 701, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 21-23 and described in the aforementioned references.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

Various surgical instruments employ a variety of different drive shaft arrangements that serve to transmit drive motions from a corresponding source of drive motions that is supported in a handle of the surgical instrument or other portion of an automated or robotically controlled system. These drive shaft arrangements must be able to accommodate significant articulated orientations of the end effector while effectively transmitting such drive motions across the articulation joint of the surgical instrument. In addition, due to the above-mentioned size constraints dictated by the sizes of trocars through which the instrument shafts must be inserted, these drive shaft components must occupy as little space as possible within the shaft. To accommodate such requirements, many drive shaft arrangements comprise several movable elements that are coupled together in series. The small sizes (e.g., 4 mm diameter) and numbers of components lead to difficult and lengthy assembly procedures that add to the cost and complexity of the device.

As further described herein, a powered stapling device can include two independently rotatable drive members: a first rotary drive member configured to effect closing of the jaws of the end effector and a second rotary drive member configured to effect firing of a staple cartridge installed in the end effector. The first and second rotary drive members are flexible and configured to extend through at least one articulation joint. In such instances, the first and second rotary drive members can transmit rotary actuation motions through the articulation joint(s) when in a non-flexed configuration and when in a flexed configuration. Exemplary rotary drive members are further described herein.

The powered stapling assembly further comprises a first jaw, a second jaw, a closure drive comprising the first rotary drive member extending through the articulation joint, and a firing drive comprising the second rotary drive member extending through the articulation joint. The second rotary drive member can be rotatable independent of the first rotary drive member. The closure drive can be activated by a closure trigger, for example, whereupon an actuation of the closure drive effects a rotation of the first rotary drive member, which transmits a rotary motion through the articulation joint to a closure screw. The closure drive further comprises a closure wedge threadably coupled to the closure screw, wherein the closure wedge is configured to engage the first jaw to move the first jaw from an open position to a closed position upon rotation of the first rotary drive member.

The firing drive can be activated by a firing trigger, for example, which is separate from the closure trigger. The rotation of the second rotary drive member is separate from the rotation of the first rotary drive member, and a closure motion is separate and distinct from a firing motion. Activation of the firing drive effects a rotation of the second rotary drive member, which transmits a rotary motion through the articulation joint to a firing screw. The firing drive further comprises a firing member threadably coupled to the firing screw, wherein the firing member is configured to camming engage the first jaw and the second jaw and to move a cutting member and/or a staple-firing sled upon rotation of the second rotary drive member.

In various instances, at least one component in the powered stapling device can be a 3D-printed component. 3D-printed components can be incorporated into an articulation system, a closure/grasping system, and/or a firing system, as further described herein. 3D printing technology can be utilized to improve component capabilities in certain instances. For example, 3D printing can allow the printed component to exhibit metamaterial properties, such that the 3D-printed components exhibits greater structural strength and stiffness while allowing precision in the forming of small detailed features and optimizing other properties of the component such as selective flexibility and/or lubrication, for example. Exemplary 3D-printed components for the powered stapling device are further described herein and include the flexible rotatable drive member(s), e.g. serial 3D-printed universal joints, the firing member or I-beam, and/or the staple cartridge and/or sub-components thereof. In one instance, the staple cartridge can be a composite plastic-metal 3D-printed component. 3D printing of various components and considerations therefor are further described herein.

A method of stapling with such surgical stapling assemblies is also contemplated. The method can include obtaining the surgical stapling assembly and activating, by the closure trigger, the closure drive, wherein the closure wedge is configured to engage the first jaw to move the first jaw from an open position to a closed position upon a rotation of the first rotary drive member. The method can further includes activating, by the firing trigger, the firing drive, wherein the firing member is configured to camming engage the first jaw and the second jaw and to advance a cutting member and a staple-firing sled during a firing motion upon a rotation of the second rotary drive member. Various applications of 3D-printed components in such assemblies are further described herein.

FIGS. 24-33 depict an end effector assembly 1000 for stapling tissue. The end effector assembly 1000 is similar to the end effector assembly 600; however, the end effector assembly 1000 and the accompanying description comprise further details than the end effector assembly 600. The end effector assembly 1000 comprises a shaft portion 1010 and end effector comprising a first jaw 1011 and a second jaw 1013 movable relative to the first jaw 1011. The end effector assembly 1000 is configured to cut and staple tissue captured between the jaws 1011, 1013. The end effector assembly 1000 may be attached to a surgical instrument handle and/or surgical robotic interface by way of the shaft portion 1010. The surgical instrument handle and/or surgical robotic interface can be configured to actuate various functions of the end effector assembly 1000. The first jaw 1011 comprises a cartridge channel 1020 and the second jaw 1013 comprises an anvil 1080 pivotally mounted to the cartridge channel 1020 by way of pin 1084 to clamp tissue between the jaws 1011, 1013.

The end effector assembly 1000 further comprises a replaceable staple cartridge 1050 configured to be installed within the cartridge channel 1020 and a support beam 1100 positioned within the staple cartridge 1050. Discussed in greater detail below, the support beam 1100 is configured to provide additional internal support to the end effector assembly 1100 within the staple cartridge 1050. The staple cartridge 1050 comprises a cartridge body 1055 comprising a proximal end 1051, a distal end 1053, and a cartridge deck 1056. The cartridge body 1055 further comprises a plurality of staple cavities 1057 arranged in longitudinal rows defined in the deck 1056, and a longitudinal slot 1059 defined in the deck 1056 and configured to receive a portion of a firing member assembly discussed in greater detail below.

The replaceable staple cartridge 1050 is configured to removably store a plurality of staples within the staple cavities 1057. The staples are configured to be ejected from the staple cartridge and against an anvil surface 1083 of the anvil 1080 to form the staples and staple tissue captured between the deck 1056 and the anvil surface 1083. To eject the staples, a sled 1070 is pushed from a proximal end 1051 of the staple cartridge 1050 toward a distal end 1053 of the staple cartridge 1050 by the firing member assembly. As the sled 1070 translates longitudinally within the staple cartridge 1050, the sled 1070 is configured to contact and lift a plurality of staple drivers supporting the staples within the staple cartridge 1050 and form the staples against the anvil surface 1083.

Figure 25:
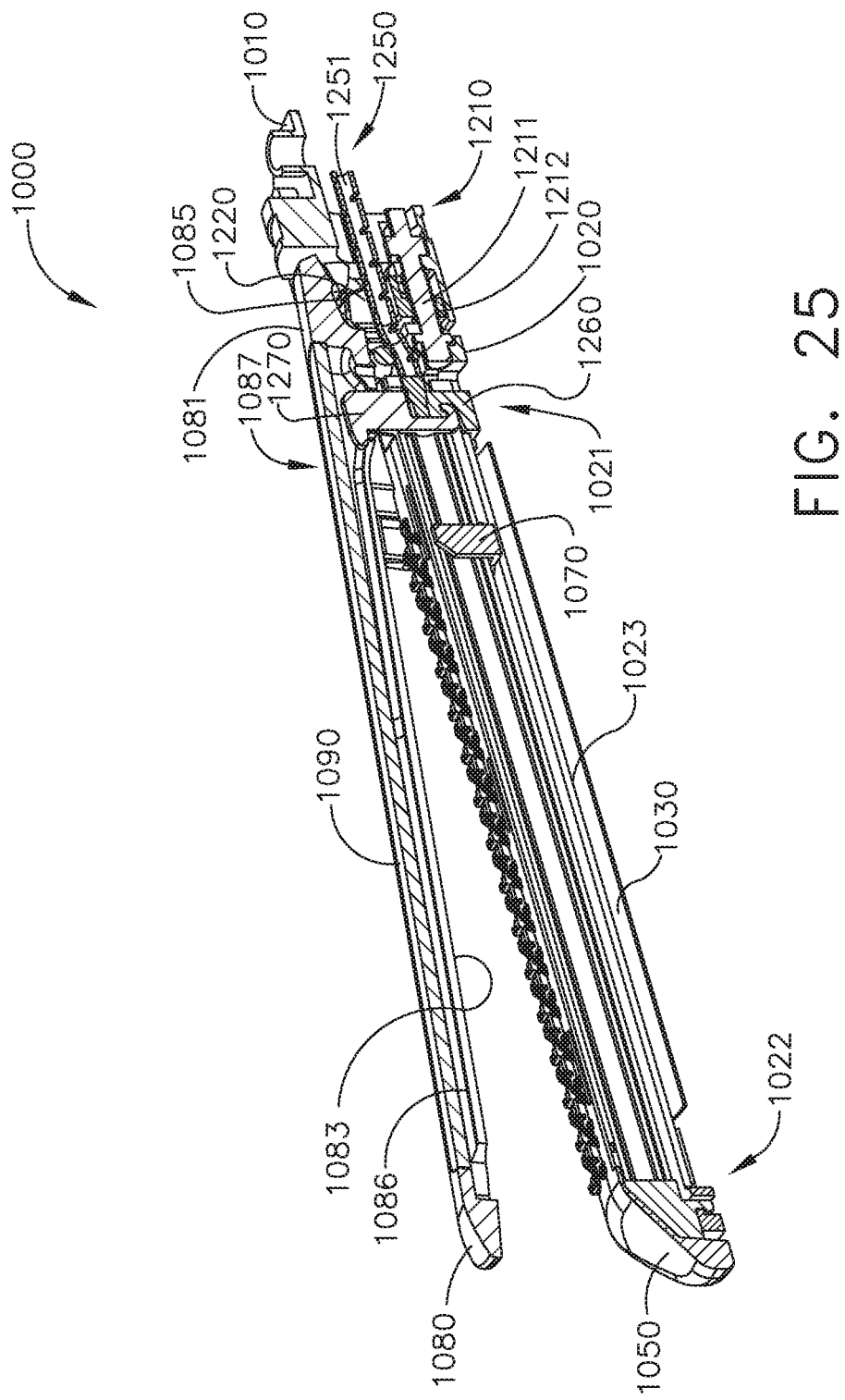
FIG. 25 is a cross-sectional perspective view of the end effector assembly of FIG. 24, in accordance with at least one aspect of the present disclosure.
Figure 26:
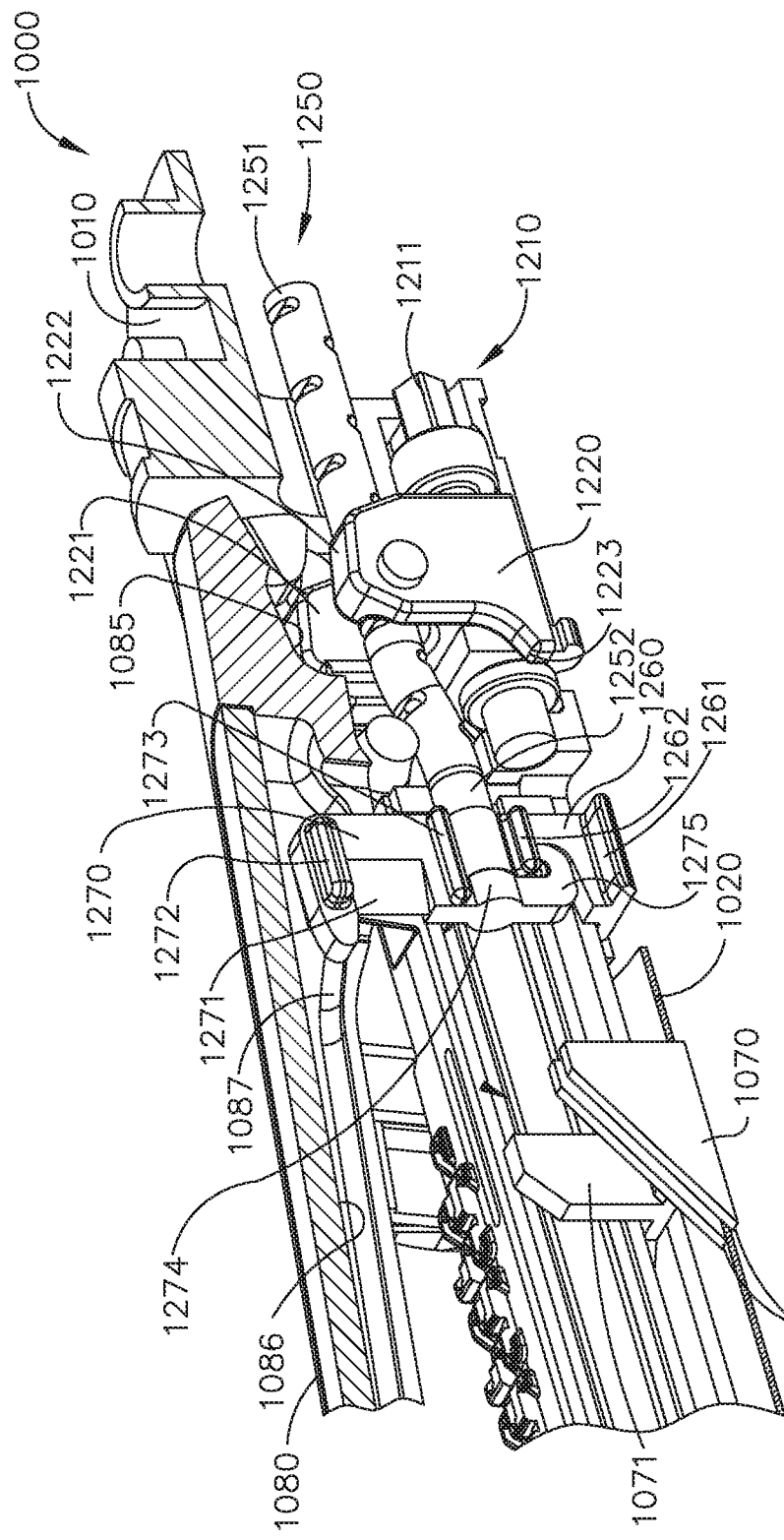
FIG. 26 is a partial cross-sectional perspective view of the end effector assembly of FIG. 24, wherein the end effector assembly comprises a firing drive configured to deploy staples from the staple cartridge and a closure drive configured to open and close the anvil relative to the channel, in accordance with at least one aspect of the present disclosure.
Figure 27:
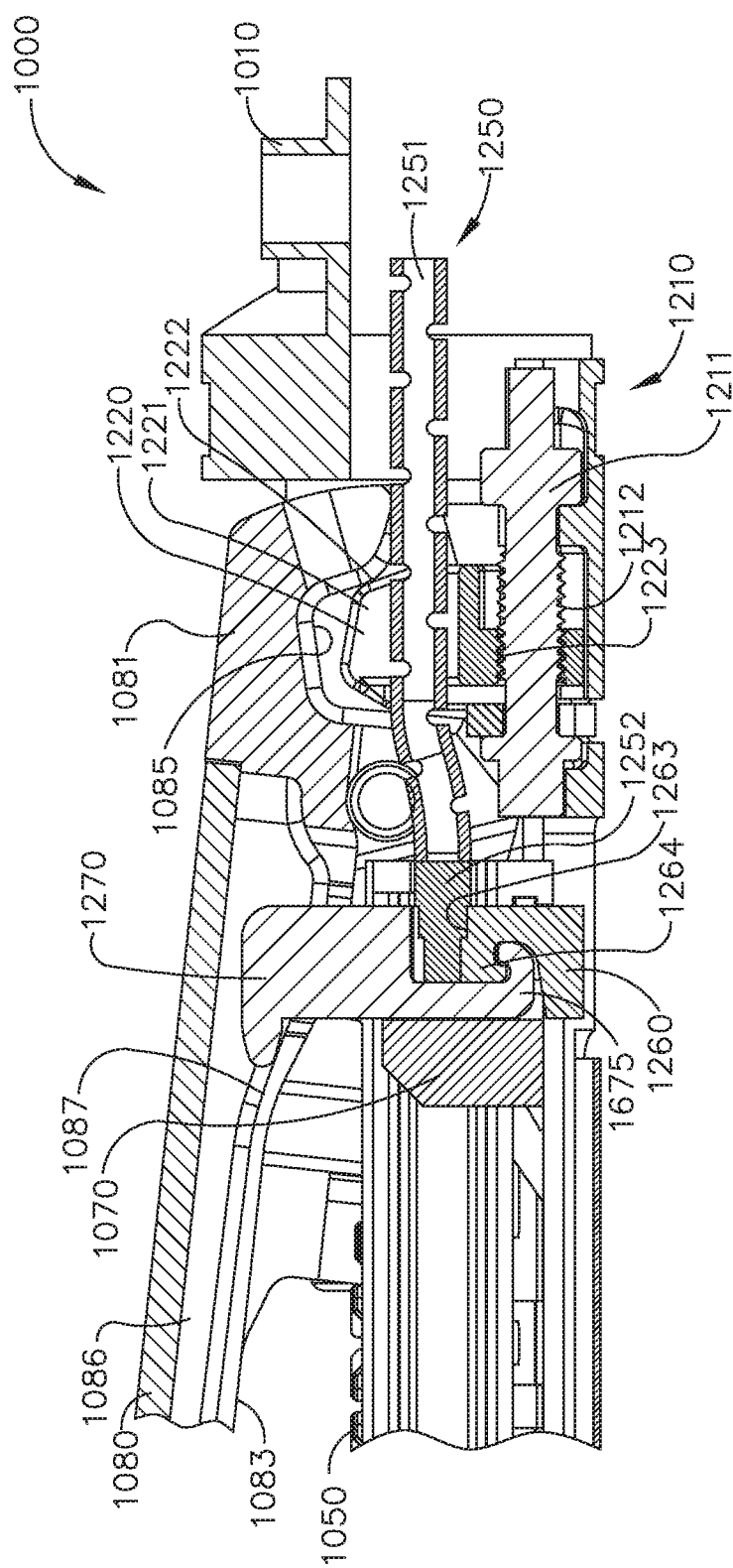
FIG. 27 is a cross-sectional elevation view of the end effector assembly of FIG. 24, in accordance with at least one aspect of the present disclosure.

To open and close the anvil 1080 relative to the cartridge channel 1020 and staple cartridge 1050, a closure drive 1210 is provided. Referring to FIGS. 25-27, the closure drive 1210 comprises a rotary closure drive 1211 configured to be actuated by a rotary output shaft of a surgical instrument handle and/or robotic interface, for example. The rotary closure drive 1211 is supported within a proximal end 1021 of the channel 1020 and comprises threads 1212. The closure drive 1210 further comprises a closure wedge 1220 comprising threads 1223 threadably coupled to threads 1212 of the rotary closure drive 1211. Thus, as the rotary closure drive 1211 is rotated, the closure wedge 1220 is configured to translate longitudinally within anvil cavity 1085 defined in a proximal end 1081 of the anvil 1080. The rotary closure drive 1211 can be referred to as a closure screw in various instances.

The closure wedge 1220 comprises an opening cam surface 1222 and closure cam nubs 1223. To close the anvil 1080, the closure wedge 1220 is moved proximally by the rotary closure drive 1221 so that the opening cam surface 1222 defined thereon engages the proximal end 1081 of the anvil 1080 thereby pivoting the anvil 1080 about the pin 1084 toward a closed position. To open the anvil 1080, the closure wedge 1220 is moved distally by the rotary closure drive 1221 so that the closure cam numbs 1223 engage the proximal end 1081 of the anvil 1080 thereby pivoting the anvil 1080 about the pin 1084 toward an open position. The closure wedge 1220 further comprises a u-shaped slot 1221 configured to allow a linearly-actuated firing drive to pass therethrough, discussed in greater detail below.

To fire the end effector assembly 1000, a firing drive 1250 is provided. The firing drive 1250 comprises a flexible firing shaft 1251 configured to be actuated by a linear output shaft of a surgical instrument handle and or robotic interface. The flexible firing shaft 1251 passes through the u-shaped slot 1221 of the closure wedge 1220 toward a firing assembly comprising a lower firing member 1260 and an upper firing member 1270. The firing shaft 1251 comprises a distal end 1252 fixed within a drive slot 1263 defined in a guide portion 1265 of the lower firing member 1260. In at least one instance, the firing shaft 1251 is rotatably supported (e.g. journaled) within the drive slot 1263 such that the firing shaft 1251 may push and pull the lower firing member 1260 while being able to rotate within the drive slot 1263. Such a configuration can permit rotation of the flexible firing shaft 1251 relative to the lower firing member 1260 while maintaining linearly-actuatable engagement. The anvil 1080 further comprises an upper anvil cap 1090 configured to be attached to the anvil 1080. The anvil cap 1090 can be welded to the anvil 1080, for example, and can serve to strengthen the anvil 1080. The channel 1020 can also comprise a channel cap 1030.

The lower firing member 1260 comprises a lower camming flange 1261 extending laterally from the lower firing member 1260, an upper camming flange 1262 extending laterally from the lower firing member 1260, and the guide portion 1265 configured to be received within the support beam 1100, discussed in greater detail below. The lower camming flange 1261 is configured to engage the channel 1020 during a firing stroke to maintain a defined clamped tissue gap between the staple cartridge 1050 and the anvil 1080. The upper camming flange 1262 is configured to engage the support beam 1100 during a firing stroke. Discussed in greater detail below, providing multiple camming flanges within the firing assembly can aid in distributing clamping forces within the end effector assembly 1000. When discussing the camming flanges, it should be understood that, as can be seen in the drawings, the flanges extend laterally outwardly from both sides of the primary body portions of the firing members.

An upper firing member 1270 is also provided. The upper firing member 1270 is configured to be advanced through the firing stroke by the lower firing member 1260. The guide portion 1265 is configured to push a guide portion 1274 of the upper firing member 1270. The upper firing member 1270 comprises an upper camming flange 1272 extending laterally from the upper firing member 1270, a lower camming flange 1273 extending laterally from the upper firing member 1270, and the guide portion 1274 configured to be received within the support beam 1100, discussed in greater detail below. The upper camming flange 1272 is configured to engage the anvil 1080 during a firing stroke. Specifically, the upper camming flange 1272 is configured to apply clamping forces to the anvil 1080 within a slot 1086. At the beginning of a firing stroke, the upper camming flange 1272 is configured to engage a proximal ramp portion 1087 of the slot 1086 to begin applying clamping forces within the end effector assembly 1000.

The lower camming flange 1273 of the upper firing member 1270 is configured to engage the support beam 1100 during a firing stroke. Such a lower camming flange 1273 can provide an additional camming flange within the firing member assembly to help distribute clamping forces within the end effector assembly 1000. The upper firing member 1270 further comprises a cutting edge, or knife, 1271 configured to cut tissue clamped between the staple cartridge 1050 and the anvil 1280. The upper firing member 1270 further comprises a drive surface 1276 defined on the front of the upper firing member 1270. The drive surface 1276 is configured to push a drive flange 1071 of the sled 1070. As the sled 1070 is advanced through the end effector assembly 1000 by the upper firing member 1270, sled rails 1072 of the sled 1070 are configured to engage staple drivers, lift the staple drivers, and eject the staples to staple tissue.

In at least one instance, the upper firing member 1270 is disposable and the lower firing member 1260 is reusable. In such an instance, the upper firing member 1270 is replaced and comes with the staple cartridge 1050 positioned in a ready to install, or ready to fire position. In other words, every time a new staple cartridge is to be installed, the user receives a new upper firing member. Such a configuration can provide a fresh knife with each fresh staple cartridge.

The lower firing member 1260 comprises a receiving hook slot 1264 and the upper firing member 1270 comprises a hook portion 1275 configured to be received within the receiving hook slot 1264. The staple cartridge 1050 including the sled 1070 and the upper firing member 1270 may be installed at an angle similar to that of the anvil 1080 positioned in its open position. Such an angle allows a user to latch, or hook, the upper firing member 1270 into the lower firing member 1260 as the user installs the staple cartridge 1050 into the channel 1020. In at least one instance, the lower firing member 1260 is configured to push and pull the upper firing member 1270 within the end effector assembly 1000 by pushing the guide portion 1274 with the guide portion 1265 and pulling the hook portion 1275 with the hook portion 1264. In certain instances, alignment and/or leveraging features intermediate the staple cartridge 1050 and the channel 1020 are configured to interact to ensure proper alignment and insertion of the staple cartridge 1050.

Because a fresh and disposable knife can be provided each time a staple cartridge is installed, the staple cartridge 1050 further comprises knife guard tabs 1060 extending upwardly from the deck 1056. The knife guard tabs 1060 may protect a user from getting cut by the knife edge 1271 when handling the staple cartridge 1050. The knife guard tabs 1060 may also prevent tissue from being inadvertently cut when tissue is being clamped by the end effector assembly 1000 and prior to the cutting motion. If tissue leaks toward the knife guard tabs 1060 prior to firing, the knife guard tabs 1060 will protect unstapled tissue before firing.

As discussed above, various types of firing and clamping forces are present within the end effector assembly 1000. The support beam 1100 is configured to help distribute the clamping forces within the end effector assembly to various components to reduce the possibility of any single component failing by increasing the distribution of forces within the end effector assembly. In end effectors without a support beam, clamping forces may be primarily applied to a channel and an anvil. The end effector assembly 1000 permits a greater distribution of clamping forces within the end effector assembly 1000.

Referring primarily to FIGS. 28-33, the internal support beam 1100 is positioned within an internal longitudinal channel 1060 of the staple cartridge 1050. The internal support beam 1100 may comprise of a stronger material than the cartridge body 1055. In at least one instance, the support beam 1100 comprises of a metal material and the cartridge body 1055 comprises of a polymer. In such an instance, the support beam 1100 can help distribute clamping forces within the end effector assembly 1100 by making the support beam 1100 of a material which is stronger than the material of the cartridge body 1055.

The support beam 1100 comprises an upper surface 1110 comprising a plurality of protrusions 1111 protruding therefrom and configured to be received within corresponding slots 1058 defined the deck 1056 of the staple cartridge 1050. The protrusions 1111 may provide additional lateral and longitudinal support within the staple cartridge 1050. In other words, the protrusions 1111 can prevent the support beam 1100 from sliding laterally or longitudinally relative to the cartridge body 1055. The protrusions 1111 can also help align the support beam 1100 to the cartridge body 1055 when assembling the support beam 1100 and the cartridge body 1055. In at least one instance, the support beam 1100 is installed in the staple cartridge 1050 prior to packaging. In such an instance, the replaceable staple cartridge 1050 already comprises the support beam 1100. Thus, when the staple cartridge 1050 is replaced, a new support beam is provided.

The support beam 1100 may be slid vertically into the internal longitudinal channel 1060 of the cartridge body 1055 from the bottom of the staple cartridge 1050 opposite the deck 1056. The cartridge body 1055 further comprises lateral rails, or ledges, 1062 defined on channel walls 1061 of the internal longitudinal channel 1060. The rails 1062 are configured to fit within corresponding slots 1109 defined in the sides of the support beam 1100. The rails 1062 are configured to hold the support beam 1100 within the cartridge body 1055 and prevent the support beam 1100 from falling out of the bottom of the cartridge body 1055. The internal longitudinal channel 1060 further comprises an upper surface 1063 defined underneath a thickness of the deck 1056. The upper surface 1110 of the support beam 1100 is configured to abut the upper surface 1063.

In at least one instance, the cartridge body 1055 is overmolded onto the support beam 1100. Such a configuration can provide various internal features otherwise difficult to provide where the parts need to be separately manufactured and assembled after they are manufactured. In at least one instance, the cartridge body 1055 is overmolded and/or insert molded onto the support beam 1100 and the upper firing member 1270. In such instances, the staples, staple drivers, and sled can be assembled into the staple cartridge 1050 and support beam 1100 after the overmolding process is complete. In at least one instance, the support beam 1100 is insert molded into the staple cartridge 1050.

The support beam 1100 further comprises a longitudinal cavity 1120 comprising a lower cam slot 1121, an upper cam slot 1123, and a cylindrical slot 1122. The lower cam slot 1121 is configured to receive the upper camming flange 1262 of the lower firing member 1260. The upper cam slot 1123 is configured to receive the lower camming flange 1273 of the upper firing member 1270. The cylindrical slot 1122 is configured to receive the guide portion 1274, the guide portion 1265, and the flexible firing shaft 1251 as the upper and lower firing members 1270, 1260 are advanced through the end effector assembly 1000. The longitudinal cavity 1120 is also configured to receive the drive flange 1071 of the sled 1070 as the sled 1070 is pushed by the upper firing member 1270. In at least one instance, the flexible firing shaft 1251 is configured to be closely received within the cylindrical slot 1122 such that the cross sectional profile of each substantially matches. In such an instance, the cylindrical slot 1122 can serve to help prevent buckling of the flexible firing shaft 1251 as the flexible firing shaft 1251 is advanced through the cylindrical slot 1122. As compressive forces are experienced by the flexible firing shaft 1251, the cylindrical slot 1122 can support the length of the flexible firing shaft 1251 positioned therein and help to prevent buckling of the flexible firing shaft 1251.

As discussed above, the support beam 1100 is configured to help distribute clamping forces applied to the end effector assembly 1100 by the flanges 1272, 1273, 1262, and 1261. The guide portions 1274, 1265 may also apply vertical clamping forces by way of the flanges 1272, 1273, 1262, and 1261 and can also help distribute the clamping forces through the support beam 1100. As the upper firing member 1270 and the lower firing member 1260 are advanced through the end effector assembly 1000, the flanges 1272, 1273, 1262, and 1261 can apply vertical clamping forces to the anvil 1080, the channel 1020, and the support beam 1100. These forces may be primarily distributed between the anvil 1080, the channel 1020, and the support beam 1100; the components stronger than the staple cartridge 1050 that may primarily consist of metal. Distributing the clamping loads through these components can reduce the vertical crushing forces applied to the cartridge body 1055, itself. Such an arrangement can also reduce the likelihood of any of the flanges 1272, 1273, 1262, and 1261 shearing from their respective firing member body because they can share the vertical clamping forces along the vertical length of the end effector assembly 1000. The support beam 1100 can also provide additional support between the channel 1020 and the anvil 1080 rather than relying on just the channel 1020 and the anvil 1080 to handle all of the clamping forces applied by only a channel flange and an anvil flange.

In at least one instance, the upper and lower firing members 1270, 1260 are referred to as dual I-beams. This configuration can allow for a central longitudinal cavity such as the cylindrical slot 1122 defined in the support beam 1100 positioned between the upper flange 1262 of the lower firing member 1260 and the lower flange 1273 of the upper firing member 1270.

The guide portions 1265, 1274 may also help strengthen the firing members 1260, 1270 by providing a rounded portion engaged with the support beam 1100. The rounded portions can also provide a source of strength to the firing members 1260, 1270 because they can handle significant vertical forces. To fail, they would likely require shear-type failure rather than a bending-type failure making the rounded portions stronger than lateral flanges in certain instances. Having firing members with both lateral flanges and rounded portions can increase the overall strength of the firing assembly as it pertains to vertical clamping forces experienced within the end effector assembly 1000. All of the vertical clamping forces can serve to maintain a predefined tissue gap between the staple cartridge 1050 and the anvil 1080.

Longitudinal loads are also experienced within an end effector assembly 1000. For example, a firing member assembly can experience longitudinal loads applied by tissue on the knife 1271. A firing member assembly can also experience longitudinal loads generated by the clamping forces applied to the channel 1020 and the anvil 1080. Longitudinal loads can also be experienced when the firing member assembly abuts components in its proximal-most position. Longitudinal loads can also be experienced when the firing member assembly and/or sled abuts the distal end of the end effector assembly 1000. In such an instance, the sled and/or firing member assembly components may be pushed distally into the nose of the staple cartridge, anvil, and/or support beam. The end effector assembly 1000 also comprises features to help distribute these longitudinal loads within the end effector assembly 1000.

The support beam 1100 comprises a proximal hook 1102 (FIG. 29) and a distal hook 1104 (FIG. 30) extending downwardly from the support beam 1100. The proximal hook 1102 is configured to be received within a corresponding channel aperture 1023 defined in the proximal end 1021 of the channel 1020. The proximal hook 1102 can be latched into the aperture 1023 as the staple cartridge 1050 and support beam 1100 are installed into the channel 1020. The hook 1102 may be installed with an audible click, for example, to inform a user of successful installation. The hook 1102 may also be visible from underneath the channel 1020 so that a user can see if the hook 1102 has been properly engaged with the channel 1020. The distal hook 1104 is configured to be received within a corresponding channel aperture 1024 defined in the distal end 1022 of the channel 1020. The distal hook 1104 may be snapped into the aperture 1024 by way of the sloped surface 1104' after the proximal hook 1102 is successfully installed into the proximal end 1021 of the channel 1022. The hooks 1102, 1104 may serve to distribute longitudinal loads experienced within the end effector assembly 1000. The distal hook 1104 can cause the firing members 1260, 1270 to apply forces primarily to the channel 1020 instead of the distal end, or nose, 1053 of the staple cartridge 1050 at the end of the firing stroke. Such a configuration may protect the integrity of the nose 1053 of the staple cartridge 1050 which is typically made of a more brittle material than the channel 1020. The channel 1020 can serve to support the distally applied forces by the firing members 1260, 1270 in lieu of the cartridge nose 1053. The distal end 1103 of the support beam 1100 also comprises a fitted profile configured to fit within the nose 1053 of the staple cartridge 1053.

As discussed above, the upper firing member 1270 can be disposable and removed with the staple cartridge 1050 so that a new upper firing member can be installed within a new staple cartridge. In such an instance, the upper firing member 70 can be moved into its proximal-most position after a firing stroke is completed. When the upper firing member 1270 is pulled into its proximal-most position, the anvil 1080 may be pivoted open by the closure drive 1210. As the anvil 1080 is pivoted open, the engagement surface 1087 may tilt the upper firing member proximally relative to the lower firing member 1260 and unlatch the hook 1275. At such point, the staple cartridge 1050 and upper firing member 1270 can be pried and/or unsnapped out of the channel 1020 so that a new staple cartridge, support beam, and upper firing member may be installed in the channel 1020 and the end effector assembly 1000 can be used again.

Figure 34:
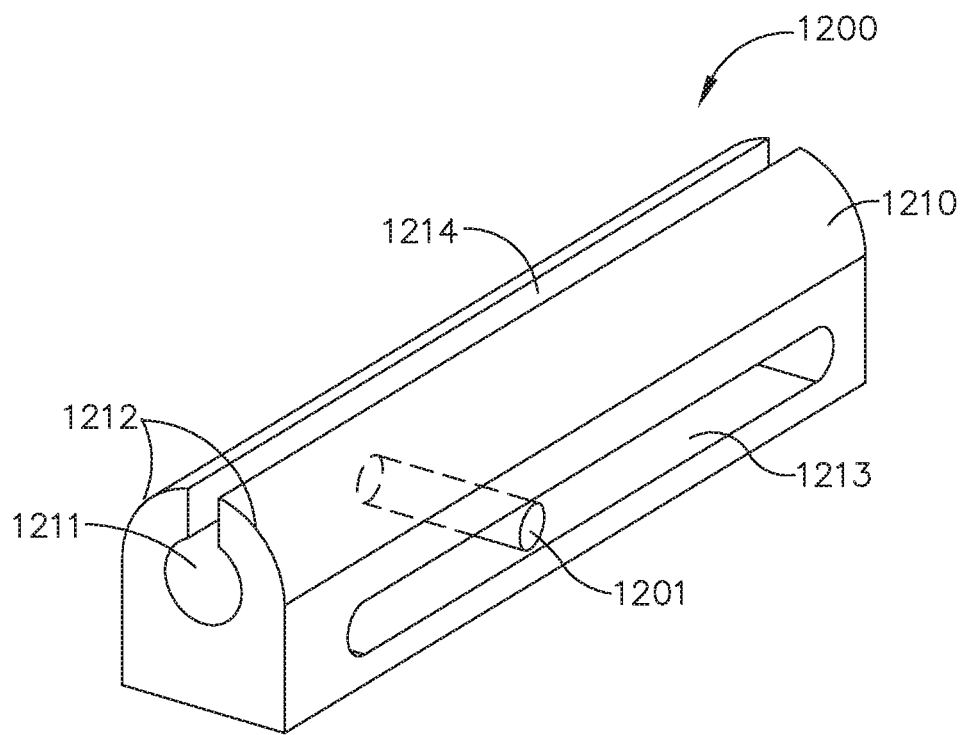
FIG. 34 is a perspective view of a support beam for use with a stapling assembly, in accordance with at least one aspect of the present disclosure.
Figure 35:
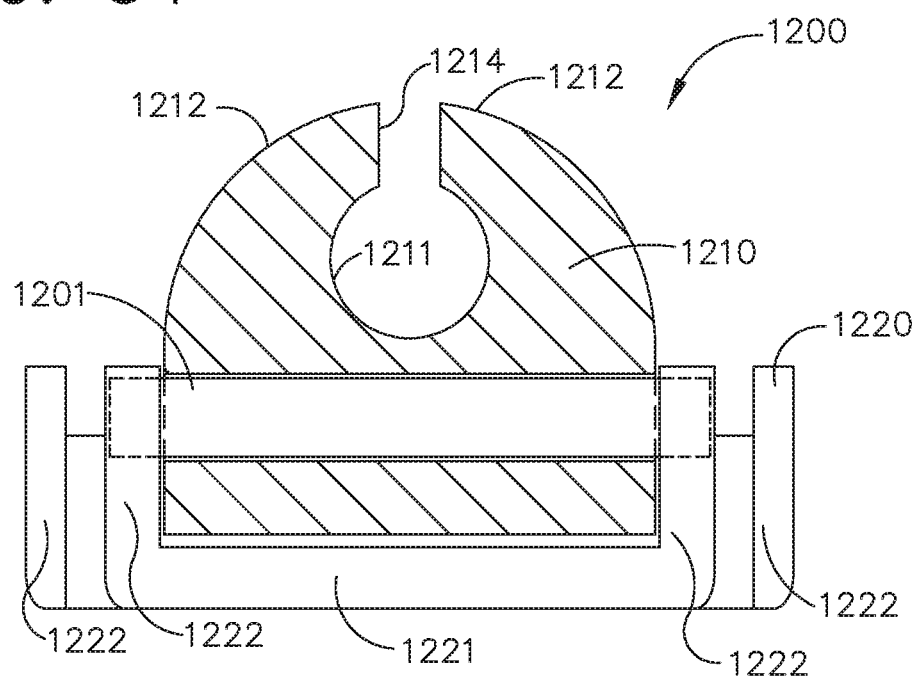
FIG. 35 is an cross-sectional elevation view of the support beam of FIG. 34 and a sled pinned to the support beam, in accordance with at least one aspect of the present disclosure.

FIGS. 34 and 35 depict portions of a stapling assembly 1200 comprising a support beam 1210, a firing member, such as a sled, 1220, and a coupling member 1201 coupling the firing member 1220 to the support beam 1210. The stapling assembly 1200 can be used within any suitable staple cartridge such as those disclosed herein. The support beam 1210 comprises a central drive cavity 1211 configured to receive at least a portion of a firing beam and/or firing member assembly, such as the upper and lower firing members discussed above, an upper slot 1214 configured to receive at least a portion of a firing member assembly, and a pair of horizontal slots 1213 configured to receive the coupling member 1201. The upper slot 1214 may be aligned with a longitudinal slot defined in a deck of a staple cartridge. The coupling member 1201 may comprise of a pin, for example.

The firing member 1220 is configured to eject staples from a staple cartridge as the firing member is advanced through a staple cartridge and the support beam 1210. The support beam 1210 further comprises at least partially curved walls, or flanges, 1212 partially encompassing the central drive cavity 1211. The firing member 1220 comprises drive ramps 1222 configured to push staples and/or staple drivers out of a staple cartridge.

In at least one instance a firing member assembly is configured to push on only the firing member 1220 to advance the firing member 1220 through a staple cartridge and the support beam 1210. Such a configuration can permit the majority of firing force to be applied directly to the firing member 1220. In at least one instance, a firing member assembly is configured push on both the coupling member 1201 and the firing member 1220 to advance the firing member 1220 through a staple cartridge and the support beam 1210. Such a configuration can permit sharing of the applied firing forces and can distribute the applied firing forces throughout the coupling member 1201 and the firing member 1220.

In at least one instance, a firing member assembly is configured to push on only the coupling member 1201 to advance the firing member 1220 through a staple cartridge and the support beam 1210. Such a configuration can permit a more focused firing force application on a component made of metal rather than a component made of a polymer in certain instances. For example, the firing member 1220 may consist of a polymer while the coupling member 1201 may comprise of a metal. In at least one instance, the firing member 1220 and the coupling member 1201 comprise the same material.

Applying the firing forces to a coupling member such as the coupling member 1201, for example, can spread out the application of the firing forces laterally with respect to the longitudinal travel path of the firing member 1220. This lateral distribution can help distribute firing forces throughout the support beam 1210. The firing member 1220 is configured to surround a bottom of the support beam 1210. Such a configuration can permit the use of differently sized sleds within a cartridge channel.

Figure 36:
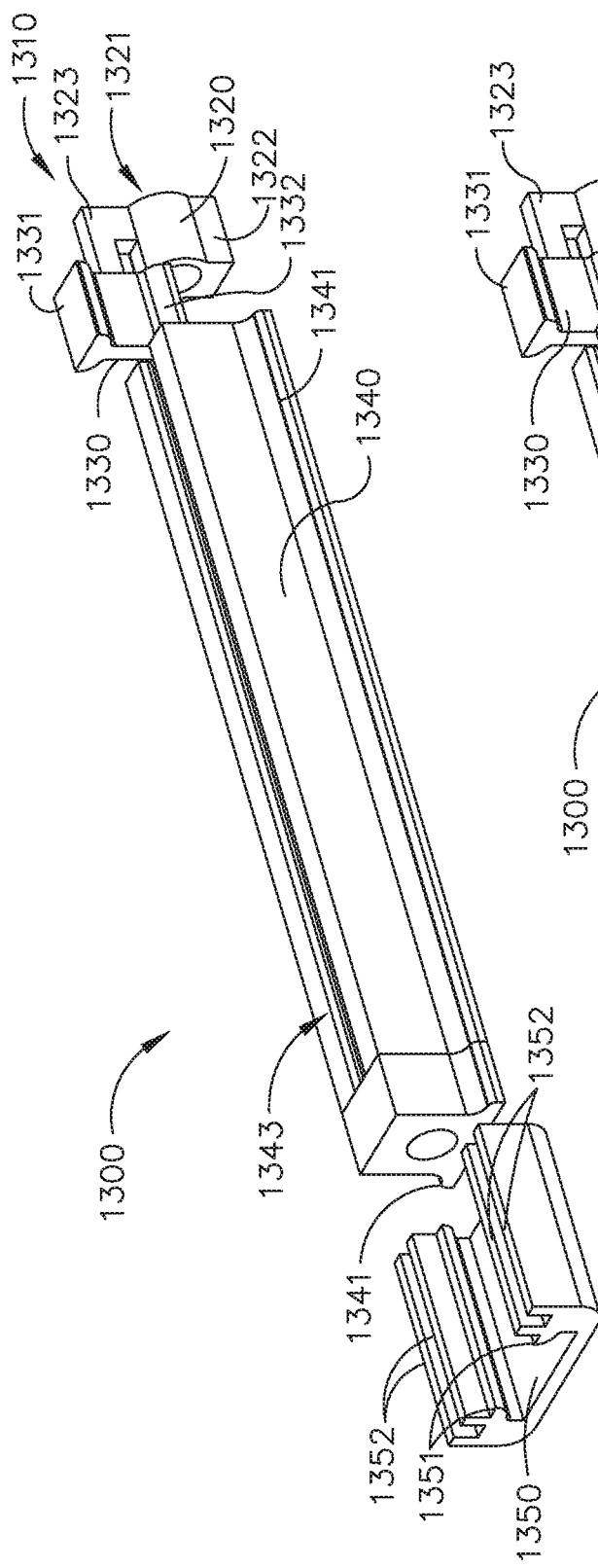
FIG. 36 is an exploded perspective view of portions of a stapling assembly including a support beam, a firing member assembly, and a sled, in accordance with at least one aspect of the present disclosure.
Figure 37:
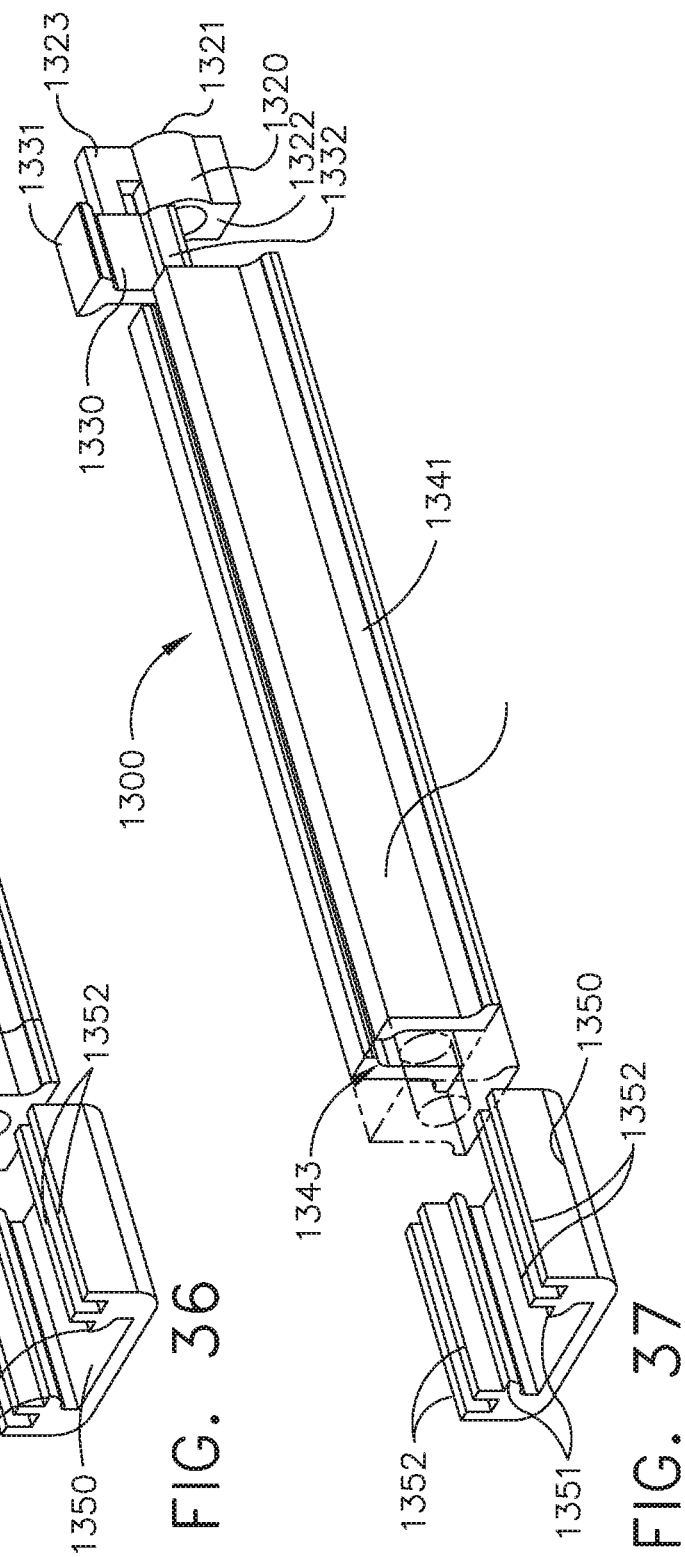
FIG. 37 is an exploded perspective view of the portions of the stapling assembly of FIG. 33, wherein a distal end of the support beam is shown in hidden lines to show the profile of a longitudinal channel of the support beam, in accordance with at least one aspect of the present disclosure.

FIGS. 36 and 37 depict a stapling assembly 1300 configured to be used with any suitable staple cartridge disclosed herein. The stapling assembly 1300 comprises a firing assembly 1310 configured to be actuated by a firing shaft, a support beam 1340 configured to be positioned with a staple cartridge, and a sled, or firing member, 1350 configured to eject staples from the staple cartridge. The firing assembly 1310 comprises a lower firing member 1320 and an upper firing member 1330 configured to be actuated by the lower firing member 1320. The lower firing member 1320 comprises a drive portion 1323 configured to drive the upper firing member 1330, a shaft connection cavity 1321 configured to receive a firing shaft therein, and a bottom 1322. The upper firing member 1330 comprises an upper flange 1331 configured to engage an anvil, for example, and a lower flange 1332 configured to engage a portion of the support beam 1340.

The support beam 1340 comprises a longitudinal channel 1343 configured to receive the firing member assembly 1310 therein and flared ledges 1341 configured to support the firing member 1350. The lower flange 1332 is configured to apply camming forces to the support beam 1340 within the longitudinal channel 1343. Collectively, the upper flange 1331 and the lower flange 1332 are configured to maintain a predefined tissue gap between a staple cartridge and an anvil.

The sled 1350 comprises guide arms 1351 configured to be supported by the flared ledges 1341 of the support beam 1340 and drive ramps 1352 configured to eject staples from a staple cartridge. The sled 1350 can be slid onto one end of the support beam 1340 for assembly. The sled 1350 hangs from the flared ledges 1341. Such a configuration can permit use of differently sized sleds for different cartridges and the same support beam 1340. The firing member assembly 1310 is configured to push the sled 1350 through a firing stroke. The flared ledges 1341 can further serve to transfer vertical camming forces applied by the firing member assembly 1310 to the staple cartridge. In at least one instance, the vertical camming forces applied by the firing member assembly 1310 are isolated from the staple cartridge. In such an instance, the support beam 1340 is configured to experience most, if not all, of the vertical clamping forces in addition to the anvil and/or channel, for example. Such a configuration can focus vertical clamping forces onto stronger components such as those components made of metal.

Figure 38:
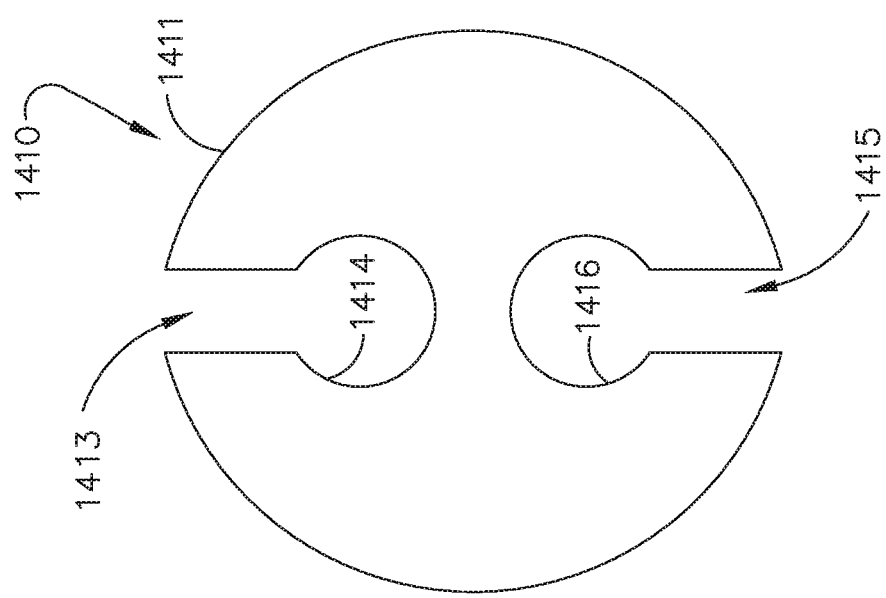
FIG. 38 is an elevation view of a support beam for use with a stapling assembly, in accordance with at least one aspect of the present disclosure.

Alternative support beam geometries are also contemplated. For example, FIG. 38 depicts a support beam 1410 configured to be positioned within a staple cartridge such as those staple cartridges disclosed herein. The support beam 1410 is configured to help distribute vertical clamping forces throughout an end effector assembly. The support beam 1410 comprises a substantially round, oval, or radial outer perimeter 1411 and thus cross-sectional profile. The support beam 1410 further comprises an upper channel 1413 and a lower channel 1415. The channels 1413, 1415 are configured to receive one or more components of a firing member assembly such those disclosed herein. The channel 1413 comprises a cylindrical cavity portion 1414 and can receive a guide portion of an upper firing member, for example. The channel 1415 comprises a cylindrical cavity portion 1416 and can receive a guide portion of a lower firing member, for example. The substantially radial cross-sectional profile of the support beam can serve to strengthen the support beam 1410. In such a configuration, it is less likely that the support beam 1410 will fail due to bending loads applied by vertical clamping forces. Rounded camming flanges can also be used with the support beam 1410. Rounded camming flanges can provide a strengthened flange system within an end effector assembly, as further described herein.

Figure 39:
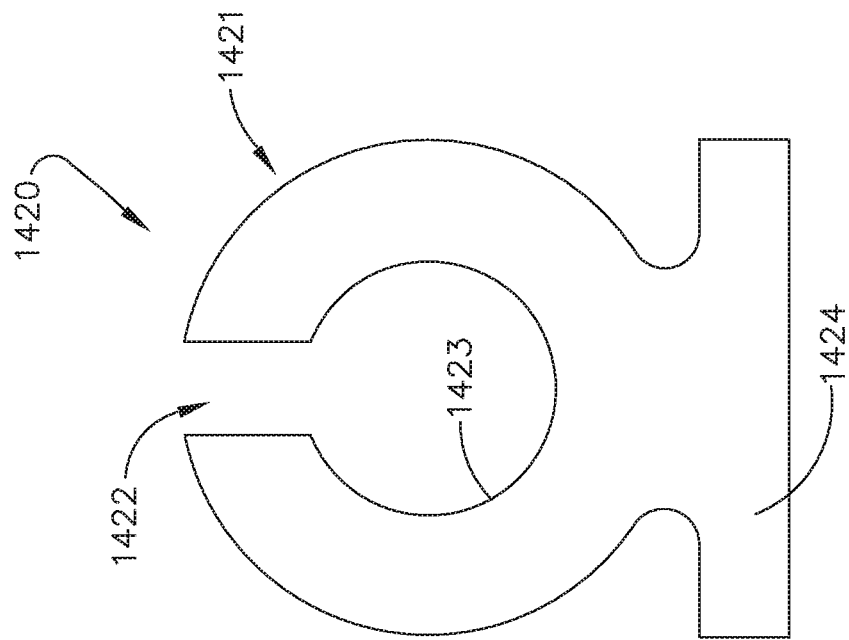
FIG. 39 is an elevation view of a support beam for use with a stapling assembly, in accordance with at least one aspect of the present disclosure.

FIG. 39 depicts a support beam 1420 configured to be positioned within a staple cartridge such as those staple cartridges disclosed herein. The support beam 1420 is configured to help distribute vertical clamping forces throughout an end effector assembly. The support beam 1420 comprises a substantially round, or radial, outer perimeter 1421 and thus cross-sectional profile. The support beam 1410 further comprises a lower flange 1424 extending from the substantially round, or radial, outer perimeter 1421. In at least one instance, the lower flange 1424 is configured to engage the bottom of a staple cartridge, for example, and can comprise one of the flanges in a multi-flange system. In such an instance, a firing member of a firing member assembly may comprise a flange-receiving cavity rather than a laterally extending flange.

The support beam 1420 further comprises an upper channel 1422. The channel 1422 is configured to receive one or more components of a firing member assembly such those disclosed herein. The channel 1422 comprises a cylindrical cavity portion 1423 and can receive a guide portion of an upper firing member, for example.

Figure 40:
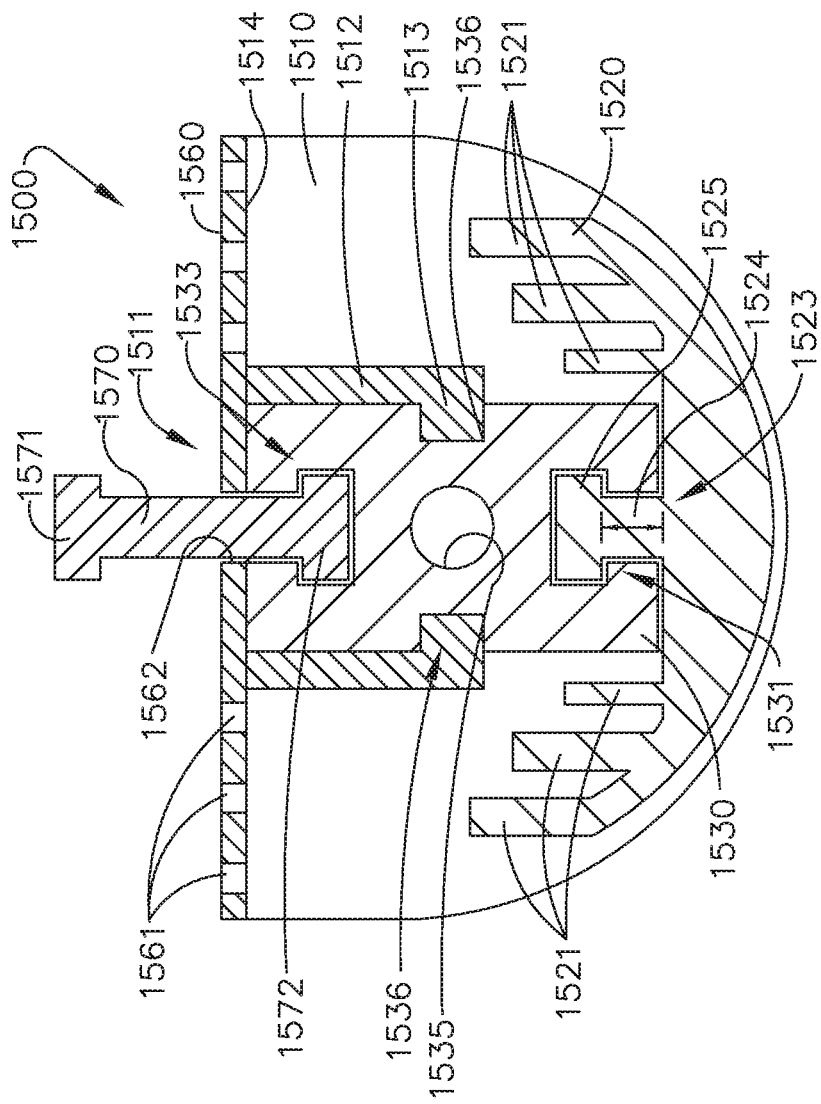
FIG. 40 is a cross-sectional elevation view of a stapling assembly comprising a staple cartridge, a sled, a cartridge support, and an I-beam, in accordance with at least one aspect of the present disclosure.
Figure 41:
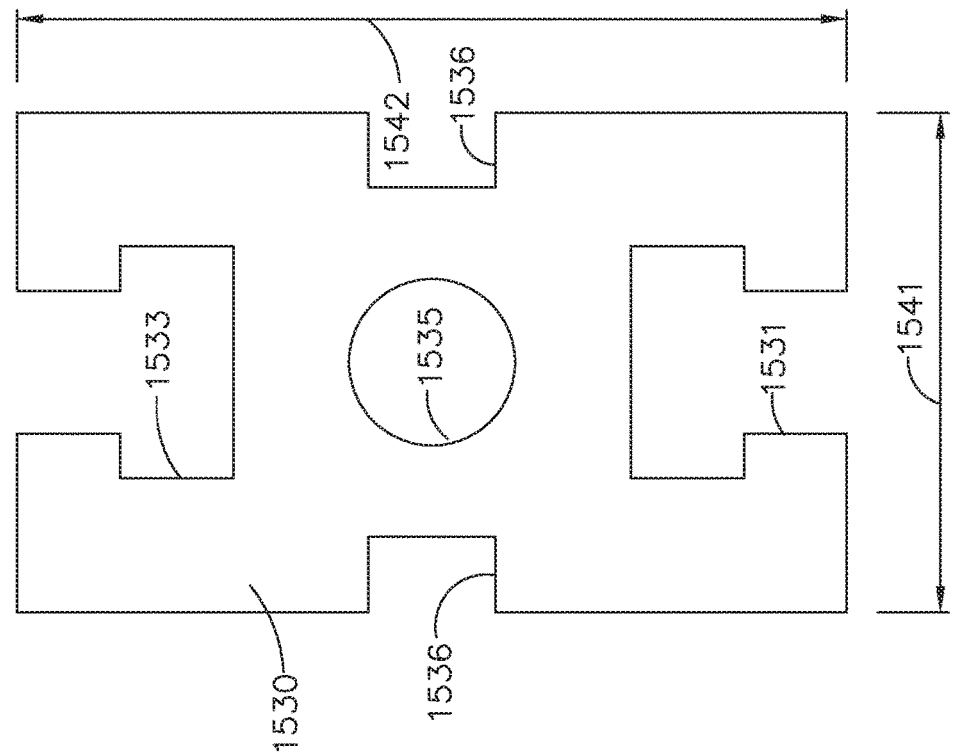
FIG. 41 is an elevation view of the cartridge support of FIG. 40, in accordance with at least one aspect of the present disclosure.

FIGS. 40 and 41 depict a stapling assembly 1500 configured to cut and staple tissue of a patient. The stapling assembly 1500 comprises a staple cartridge 1510 configured to removably store a plurality of staples therein, a sled 1520 comprising drive ramps 1521 configured to eject the staples stored within the staple cartridge 1510, and an I-beam 1570 configured to push the sled 1520 through the staple cartridge 1510. The stapling assembly 1500 further comprises a cartridge support 1530 positioned within a longitudinal channel 1511 of the staple cartridge 1510 defined by inner walls 1512 and ledges 1513. The cartridge support 1530 comprises an upper cam channel 1533 configured to receive a lower camming flange 1572 of the I-beam 1570 and a lower cam channel 1531 configured to receive a camming flange 1523 of the sled 1520.

The camming flange 1523 comprises a support portion 1524 extending upwardly into the cam channel 1531 and a flange 1525. The flange 1525 extends from the support portion 1524 to form a T-shape; however, other geometries are also contemplated. As the sled 1520 is advanced through the staple cartridge 1510 and the cartridge support 1530, the flange 1525 moves through the cam channel 1531. The cartridge support 1530 is configured to support the vertical clamping forces applied within the stapling assembly 1500 by the I-beam 1570 and the sled 1520.

The stapling assembly 1500 further comprises a deck plate 1560 positioned on a deck surface 1514 of the staple cartridge 1510. The deck plate 1560 may help distribute clamping forces within the stapling assembly 1500. The deck plate 1560 may be comprised of a metal material, for example. The deck plate 1560 comprises a plurality of apertures 1561 configured to be aligned with staple cavities defined in the staple cartridge 1510. The deck plate 1560 further comprises a longitudinal slot 1562 aligned with the longitudinal channel 1511. The cartridge support 1530 further comprises a central cylindrical support cavity 1535 configured to receive at least a portion of a firing member assembly. For example, the central cylindrical support cavity 1535 is configured to receive a linear actuator, guide portions of firing member components, and/or a guide portion of a sled, for example.

Referring primarily to FIG. 41, the cartridge support 1530 comprises longitudinal slots 1536 configured to receive ledges 1513 of the staple cartridge 1510. The width 1541 and the height 1542 can be adjusted to accommodate different size cartridges, staples, and/or staple drivers, for example. The width 1541 and height 1542 of the cartridge support 1530 can also be adjusted for different tissue gap distances between the staple cartridge 1510 and an anvil. In at least one instance, the width 1541 and height 1542 can be adjusted to tune the clamping load distribution for different scenarios. For example, a stapling instrument with lower clamping forces may be served better by a cartridge support with a thinner width than the cartridge support 1530.

Figure 42:
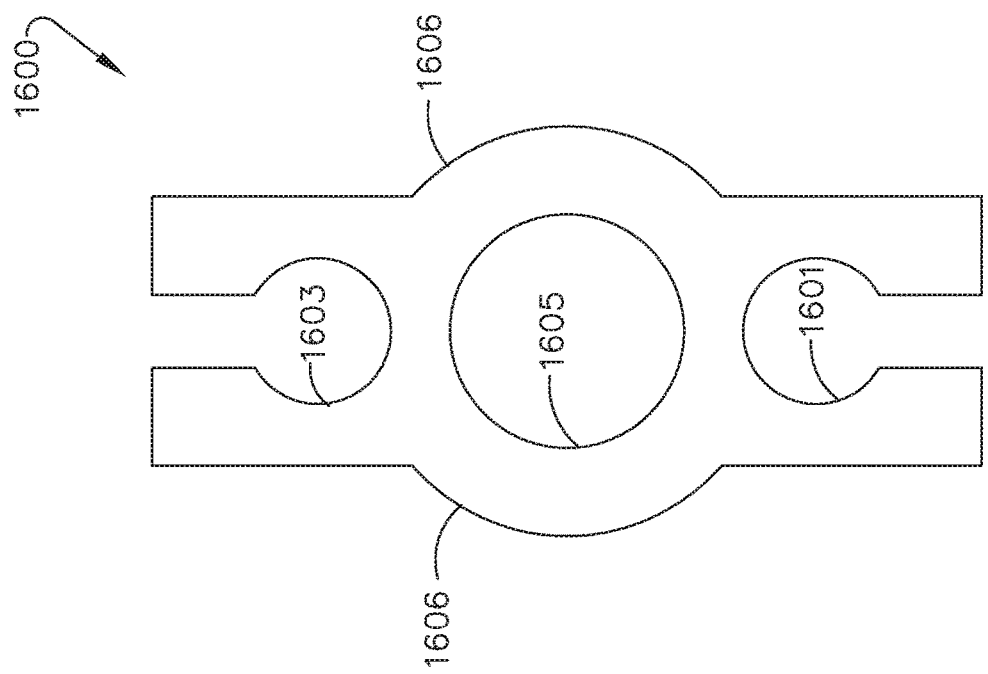
FIG. 42 is an elevation view of a cartridge support for use with a surgical stapling assembly, in accordance with at least one aspect of the present disclosure.

FIG. 42 depicts a cartridge support 1600 configured to be positioned within a staple cartridge such as those staple cartridges disclosed herein. The cartridge support 1600 comprises a cylindrical central portion 1606 defining a central longitudinal guide cavity 1605, an upper cam channel 1603, and lower cam channel 1601 each configured to receive a camming flange. The central longitudinal guide cavity 1605 can be configured to receive guide portions of one or more components a firing assembly such as a sled, upper firing member, or lower firing member. The central longitudinal guide cavity 1605 can also be configured to receive a firing shaft therein. The cam channels 1601, 1603 comprise a radial cross section. Such an arrangement can reduce the likelihood of failure of the respective flanges received therein due to bending loads.

FIG. 43 depicts a stapling assembly 1700 comprising a cartridge support 1710 and a sled 1720. The cartridge support 1710 comprises a longitudinal slot 1711 configured to receive at least a portion of the sled 1720 therethrough during a firing stroke. The sled 1720 comprises a bottom portion 1721 configured to be threadably coupled to a firing drive screw, for example, and a first arm 1722 extending from the bottom portion 1721 upwardly around a first side of the cartridge support 1710. The sled 1720 further comprises a second arm 1723 extending from the bottom portion 1721 upwardly around a second side of the cartridge support 1710. The arms 1722, 1723 each comprise a guide tooth 1724, 1725, respectively, received within corresponding slots 1712, 1713, respectively, of the cartridge support 1710. The engagement features for securing the sled 1720 in the cartridge support 1710 are asymmetric relative to a vertical centerline plane. More specifically, the arms 1722, 1723 comprise different geometries, e.g. different heights, and the guide teeth 1724, 1724 also comprise different geometries, e.g. different lengths and/or shapes. The slots 1712, 1713 comprise a profile similar to the tooth they are configured to receive. Such a configuration can provide a means for ensuring that the sled 1720 is installed in the correct direction. Such a configuration can also allow for fine tuning of loads applied to the sled 1720 through the differently sized arms 1722, 1723.

FIG. 44 depicts a sled 1730 configured to be used with any suitable staple cartridge and/or staple cartridge support discussed herein. Unlike the sled 1720, the sled 1730 comprises arms 1732 comprising the same height and profile. The arms 1732 extend from bottom portion 1731 and comprise teeth 1733 extending outwardly with respect to the sled 1731. Such a sled can be configured to be guided by a cartridge support and/or staple cartridge within internal guide slots defined in the cartridge support and/or staple cartridge owing to the outwardly extending teeth 1733.

FIG. 45 depicts a cartridge support 1740 comprising a central cavity 1741 configured to receive the sled 1730 (FIG. 45), for example, therein. The central cavity 1741 comprises laterally opposed slots 1742 comprising vertical installation portions 1743 configured to receive teeth 1733, for example. A firing member assembly can be configured to push the sled 1730 through the cartridge support 1740 during a firing stroke.

FIG. 46 depicts a stapling assembly 1800 comprising a cartridge jaw 1810, an anvil 1820, a firing member 1840, and a sled 1830 configured to be pushed through the cartridge jaw 1810 by the firing member 1840. The sled 1830 is pinned to the firing member 1840 by way of a pin 1812. As the firing member 1840 is advanced by a firing shaft, for example, the sled 1830 is pushed by way of the pin 1812. The firing member 1840 comprises a bottom flange 1842 configured to be received within a slot 1811 of the cartridge jaw 1810 and an upper flange 1841 configured to be received within a slot 1821 defined in the anvil 1820.

FIG. 47 depicts a surgical stapling assembly 1900 comprising a cartridge channel 1910 and an anvil 1920. The surgical stapling assembly 1900 further comprises a support beam 1940 and a staple cartridge 1970. The surgical stapling assembly 1900 further comprises a firing member 1950 comprising an upper flange 1952 configured to engage the anvil 1920 and a lower flange 1951 configured to engage the support beam 1940. The surgical stapling assembly further comprises a sled 1930 pinned to the staple cartridge 1970 and the support beam 1940 by way of pin 1960.

In various instances, firing member assemblies configured to be driven by firing drive screws positioned within an end effector can bind during the firing stroke. The binding can exist at the threaded coupling engagement between the firing member assembly and the firing drive screw. Such binding can be attributed to the location of the transfer of drive forces from the drive screw to the firing member assembly in certain instances. In various instances, the location of the transfer of drive force occurs immediately adjacent the threads of the firing drive screw and the receiving threads of the firing member assembly. Because the firing drive screw is generally positioned within a cartridge channel jaw, the location of the transfer force is positioned a distance away from the center of mass and/or drive center of the firing member assembly. This application of force can cause a torque load applied to the firing member assembly which may cause the threaded engagement between the firing drive screw and the firing member assembly to bind.

Various firing member assemblies are disclosed herein which may move the location of the transfer force closer to the center of mass and/or drive center of the firing member assembly to reduce incidences of binding. More specifically, these configurations can reduce the likelihood of thread binding between the firing member assembly and the firing drive screw. Such configurations may also provide a more efficient transfer of force from the firing drive screw, to the firing member assembly, to the sled and/or cutting member. A more direct force application to the sled and/or cutting member by the firing member assembly can reduce the over drive force necessary of the firing drive screw. Such a direct force applied near the center of the firing member assembly can also reduce the required drive force to maintain a predefined tissue gap using the upper and lower camming flanges of the firing member assembly. This can be attributed to centering the force application to the firing member assembly at a vertical center, or near the center, of the camming flanges.

FIGS. 48 and 49 depict a firing member assembly 2000 configured to be used within a surgical stapling assembly such as those disclosed herein. The firing member assembly 2000 is configured to be actuated by a firing drive screw to cut and staple tissue. Specifically, the firing member assembly 2000 is configured to push a sled to deploy staples from a staple cartridge. In at least one instance, the sled comprises a cutting member configured to cut tissue as the firing member assembly 2000 is actuated through an end effector. In another instance, the cutting member is part of the firing member assembly. The firing member assembly 2000 is further configured to maintain a predefined tissue gap by providing camming flanges, which engage an upper jaw and lower jaw of an end effector.

The firing member assembly 2000 comprises a primary body portion, or distal head, 2010 and a drive nut 2030 configured to fit within a drive cavity, or receptacle, 2023 of the primary body portion 2010. The primary body portion 2010 comprises an upper portion 2011 comprising a jaw-engaging flange 2012. The upper portion 2011 further comprises a distal nose 2013, which can be used to clamp a jaw from an unclamped position. The primary body portion 2010 comprises a drive surface 2014 configured to push a sled and/or a cutting member, for example. The primary body portion 2010 further comprises a lower portion 2015 comprising a proximal portion 2016 and a distal portion 2019 defining the drive cavity 2023. The proximal portion 2016 comprises a proximal lower flange 2018 extending laterally therefrom and a drive screw duct 2017. The distal portion 2019 comprises a distal lower flange 2021 and a drive screw duct 2020. The drive screw ducts 2017, 2020 are aligned with each other are configured to receive a firing drive screw therethrough; however, the drive screw ducts 2017, 2020 are not threadably coupled with the drive screw. Rather, the drive screw ducts 2017, 2020 can comprise support channels, for example, configured to support the firing drive screw (e.g. firing screw 261 in FIGS. 4 and 5) threadably coupled with the firing member assembly 2000.

The drive nut 2030 is configured to be threadably coupled with a firing drive screw and is configured to apply actuation forces to the primary body portion 2010. The drive nut 2030 is configured to fit within the drive cavity 2023. The drive nut 2030 comprises a lower threaded portion 2035 comprising a camming flange 2031 configured to engage a jaw of an end effector, a threaded channel 2037 configured to be threadably coupled with a firing drive screw, and a proximal protrusion 2036 configured to fit within the drive cavity 2023. The drive nut 2030 further comprises an upper drive portion 2040 extending upwardly from the threaded portion 2035. The drive portion 2040 comprises a proximal drive surface 2041 and a distal drive surface 2043. The proximal drive surface 2041 is configured to push on a proximal drive surface 2025 of the drive cavity 2023 when the firing member assembly 2000 is moved proximally and the distal drive surface 2043 is configured to push on a distal drive surface 2024 of the drive cavity 2023 when the firing member assembly 2000 is moved distally.

As can be seen in FIG. 49, the drive nut 2030 is configured to apply a drive force DF to the primary body portion 2010 off center with respect to a longitudinal screw axis SA. The longitudinal screw axis SA is defined by a longitudinal centerline though a drive screw configured to actuate the firing member assembly 2000. The longitudinal screw axis SA may also be synonymous with a longitudinal centerline defined through the ducts 2017, 2020.

In at least one instance, the drive nut 2030 comprises a substantially similar cross-sectional profile to the primary body portion 2010. The drive portion 2040 is configured to apply an axial drive force to the primary body portion 2010 away from and/or off-axis with respect to the firing drive screw and threads 2037.

FIGS. 50 and 51 depict a firing member assembly 2100 comprising the primary body portion 2010 of the firing member assembly 2000 and a drive nut 2130. The firing member assembly 2100 is similar to the firing member assembly 2000 except for the drive nut 2100. The drive nut 2100 is configured to fit within the drive cavity 2023 of the primary body portion 2010. Unlike the drive nut 2030, the drive nut 2130 does not include a proximal protrusion. The drive nut 2130 comprises a lower threaded portion 2135 comprising a camming flange 2131 configured to engage a jaw of an end effector and a threaded channel 2137 configured to be threadably coupled with a firing drive screw. The drive nut 2130 further comprises an upper drive portion 2140 extending upwardly from the threaded portion 2135. The drive portion 2140 comprises a proximal drive surface 2141 and a distal drive surface 2143. The proximal drive surface 2141 is configured to push on the proximal drive surface 2025 of the drive cavity 2023 when the firing member assembly is moved proximally and the distal drive surface 2043 is configured to push on the distal drive surface 2024 of the drive cavity 2023 when the firing member assembly is moved distally. The drive portion 2140 also comprises an upper surface 2145. The upper surface 2145 does not abut the primary body portion 2010 within the drive cavity 2023. Embodiments are envisioned where the upper surface 2145 abuts the primary body portion 2010 within the drive cavity 2023. In at least one instance, the flange 2131 is configured to prevent the drive nut 2130 from rotating with the firing drive screw during actuation.

Figure 52:
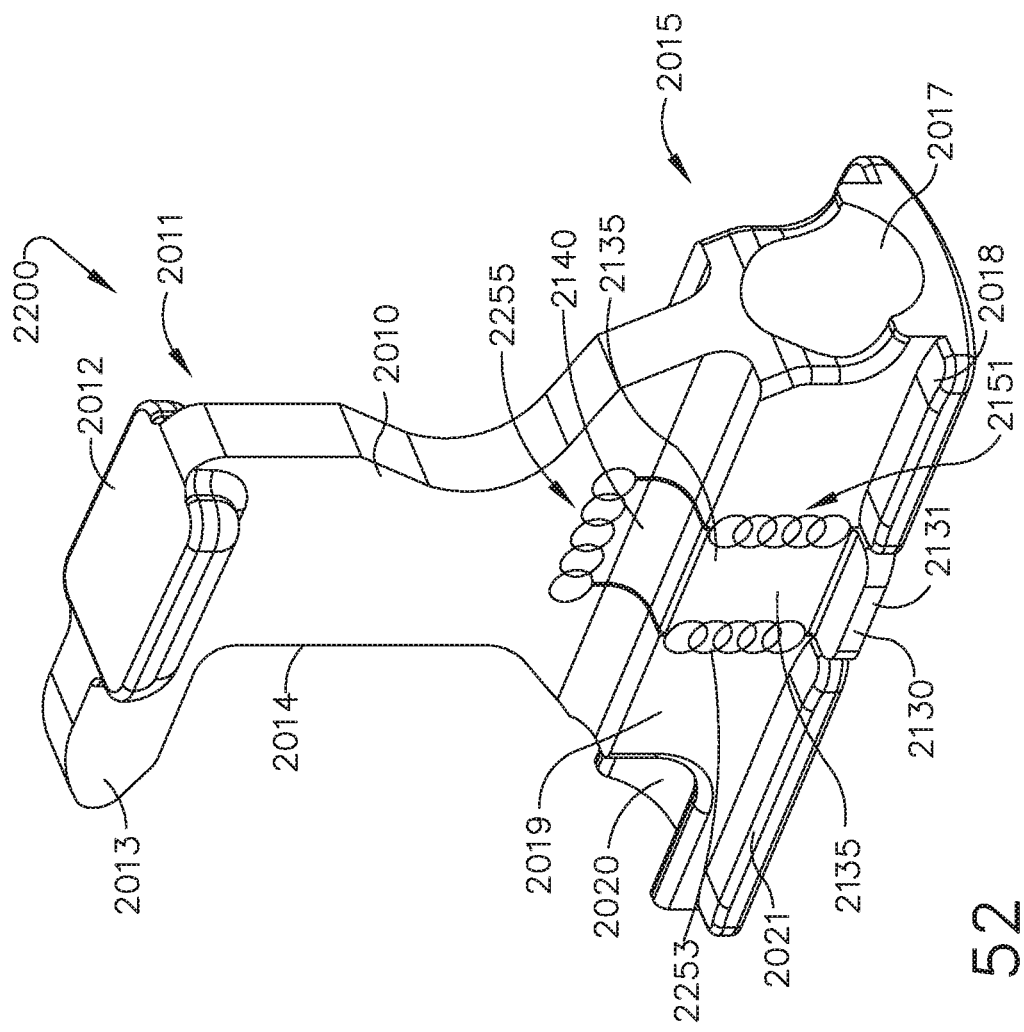
FIG. 52 is a perspective view of the firing member assembly of FIG. 50, wherein the drive nut is welded to the primary body portion, in accordance with at least one aspect of the present disclosure.

FIG. 52 depicts a firing member assembly 2200 comprising the primary body portion 2010 of the firing member assembly 2000 and the drive nut 2130. The firing member assembly 2100 is similar to the firing member assembly 2100 except for welds 2251, 2253, 2255. Unlike the firing member assembly 2100, the welds 2251, 2253, 2255 provide positive attachment mechanisms within the drive cavity 2023 to attach the drive nut 2130 to the primary body portion 2010. Stated differently, the drive nut 2130 is welded to the primary body portion 2010. Welding can take place after the drive nut 2130 is positioned within the drive cavity 2023 and threaded to a firing drive screw. The threaded portion 2135 of the drive nut 2130 is welded to the proximal portion 2016 of the primary body portion 2010 and the distal portion 2019 of the primary body portion 2010. The upper surface 2045 of the drive portion 2140 is also welded to the primary body portion 2010. These welds can provide strength to the firing member assembly 2200.

Figure 53:
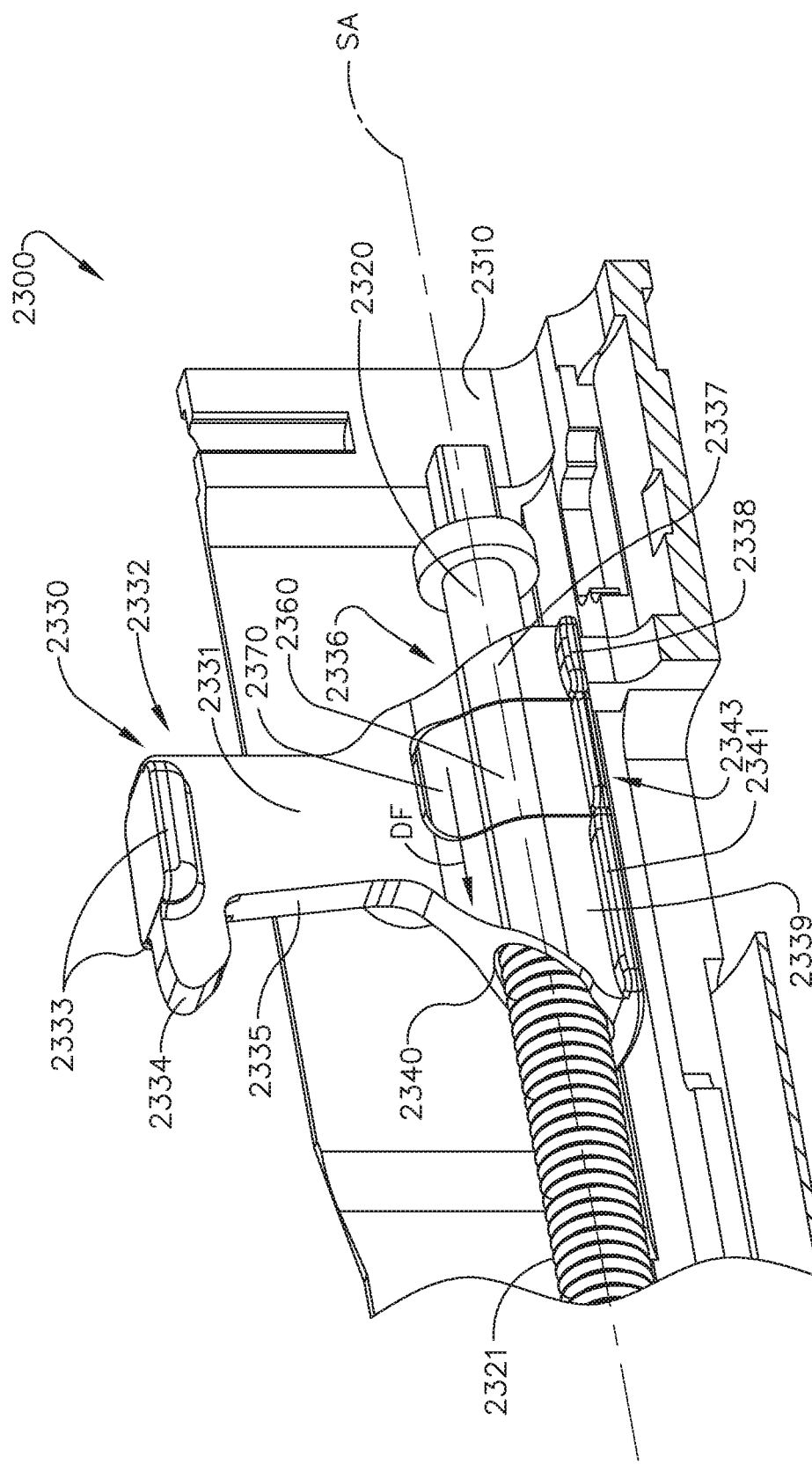
FIG. 53 is a partial cross-sectional, exploded perspective view of a stapling assembly comprising a channel jaw, a drive screw, and a firing member assembly, in accordance with at least one aspect of the present disclosure.

FIGS. 53-56 depict a stapling assembly 2300 comprising a channel jaw 2310, a firing drive screw, or rotary drive member, 2320 comprising threads 2321, and a firing member assembly 2330. The firing member assembly 2330 is similar to the firing member assemblies discussed above; however, the firing member assembly 2330 comprises a different drive nut and attachment means for attaching the drive nut to the primary body portion. As can be seen in FIG. 53, the firing member assembly 2330 is threadably coupled to the threads 2321 of the firing drive screw 2320. The firing drive screw 2320 is configured to be supported within the channel jaw 2310. The firing member assembly 2330 is configured to be actuated proximally and distally through a firing stroke relative to the channel jaw 2310.

The firing member assembly 2330 comprises a primary body portion 2331 and a drive nut 2360 configured to fit within a drive cavity, or receptacle, 2343 of the primary body portion 2331. The primary body portion 2331 comprises an upper portion 2332 comprising an anvil-engaging flange 2333. The upper portion 2332 further comprises a distal nose 2334 which can be used to clamp an anvil jaw from an unclamped position. The primary body portion 2331 comprises a drive surface 2335 configured to push a sled and/or a cutting member, for example. The primary body portion 2331 further comprises a lower portion 2336 comprising a proximal portion 2337 and a distal portion 2339 defining the drive cavity 2343. The proximal portion 2337 comprises a proximal lower flange 2338 extending laterally therefrom and a drive screw duct. The distal portion 2339 comprises a distal lower flange 2341 and a drive screw duct 2340. The flanges 2338, 2341 are configured to engage the channel jaw 2310 to affirmatively hold a consistent tissue gap between an anvil jaw and the channel jaw 2310. The drive screw duct of the proximal portion 2337 and the drive screw duct 2340 are aligned with each other and are configured to non-threadably receive the firing drive screw 2320 therethrough.

The drive nut 2360 comprises a threaded portion 2365 configured to be threadably coupled with the firing drive screw 2320 by way of threads 2366, and a drive portion 2070. The drive nut 2360 further comprises a lower camming flange 2361 also configured to cammingly engage the channel jaw 2310 during a firing stroke. The drive portion 2370 comprises laterally opposing tabs 2371 extending upwardly from the threaded portion 2365. The drive tabs 2371 are configured to cradle, or straddle, a corresponding drive tab 2350 extending downwardly from the primary body portion 2331 and into the drive cavity 2343. The drive portion 2370 further comprises an internal cross member, or brace, 2372 connecting the tabs 2371 to each other and securing, or attaching, the drive portion 2370 to the drive tab 2350 and, thus, the primary body portion 2331. The cross member 2372 is configured to be received within a drive slot 2351 defined in the drive tab 2350. As the drive nut 2360 is actuated, forces can be applied to the primary body portion 2331 from the cross member 2372 to the drive tab 2350 within the slot 2351. Such a configuration can provide a drive force to the primary body portion 2331 off center with respect to the drive screw 2320 and nearer the center of the firing member assembly 2330. Stated another way, the drive nut 2360 can apply a drive force eccentrically with respect to a longitudinal axis of the drive screw 2320 to the primary body portion 2331. This can be seen in FIG. 53, for example. The drive nut 2360 can apply drive force DF to the primary body portion 2310 off center with respect to longitudinal screw axis SA.

The drive tab 2350 further comprises a pair of drive teeth 2353 extending downwardly therefrom within an internal channel 2367 defined in the drive nut 2360. The drive teeth 2353 are configured to mate with the threads 2321 of the drive screw 2320 directly. The teeth 2353 may bolster the threaded engagement of the firing drive screw 2320 and the firing member assembly 2330 as a whole.

In at least one instance, the drive nut 2360 is insert molded over the drive screw 2320. This permits complex shapes of a drive nut and allows for finely tuned engagement features between the drive nut 2360 and the primary body portion 2331. Such an engagement feature comprises the cross member 2372, for example. Once molded over the drive screw 2320 and through the slot 2351, the drive nut 2360 is permanently fixed to the primary body portion 2331 notwithstanding destroying the drive nut 2360 to remove the drive nut 2360 from the primary body portion 2331.

In at least one instance, the drive nut 2360 is snapped to the drive tab 2350. For example, the drive nut 2360 may comprise a degree of flexibility and a manufactured split, or break, in the material corresponding to the internal channel 2367 permitting the drive nut 2360 to be spread around the drive tab 2350 and snapped thereto. In at least one instance, the drive nut 2360 is separated between a drive tab 2350 and one side of the cross member 2372 such that the drive tabs 2359 may be pried apart to position the cross member 2372 into the slot 2351.

In at least one instance, the cross member 2372 is configured to shear off of the drive nut 2360 if a firing force between the drive screw 2320 and the drive nut 2360 exceeds a predetermined threshold. Such a configuration can provide a safety feature so as to not over drive a firing member assembly through a firing stroke when a firing member assembly experiences a higher than normal load.

FIGS. 57-61 depict a firing member assembly 2400. The firing member assembly 2400 is similar to the firing member assemblies discussed above; however, the firing member assembly 2400 comprises a different drive nut and attachment means for attaching the drive nut to the primary body portion. The firing member assembly 2400 also comprises registration features for use with a molding tool. The firing member assembly 2400 is configured to be threadably coupled to a firing drive screw and is configured to be actuated proximally and distally through a firing stroke by way of the firing drive screw.

The firing member assembly 2400 comprises a primary body portion, or distal head, 2410 and a drive nut 2450 configured to fit within a drive cavity, or receptacle, 2430 of the primary body portion 2410. The primary body portion 2410 comprises an upper portion 2411 comprising a jaw-engaging flange 2412. The upper portion 2411 further comprises a distal nose 2413 which can be used to clamp an anvil jaw from an unclamped position. The primary body portion 2410 further comprises a drive surface 2414 configured to push a sled and/or a cutting member, for example. The primary body portion 2410 further comprises a lower portion 2415 comprising a proximal portion 2416 and a distal portion 2420 defining the drive cavity 2430. The proximal portion 2416 comprises a proximal lower flange 2417 extending laterally therefrom and a drive screw duct 2418. The distal portion 2420 comprises a distal lower flange 2421 and a drive screw duct 2422. The flanges 2417, 2421 are configured to engage a jaw of an end effector to affirmatively hold a consistent tissue gap between the jaw and another jaw of the end effector. The drive screw ducts 2418, 2422 are aligned with each other are configured to non-threadably receive the firing drive screw therethrough. Discussed in greater detail below, the proximal portion 2416 and the distal portion 2420 each comprise registration apertures 2423 configured for use during an overmolding and/or insert molding process.

The drive nut 2450 comprises a threaded portion, or driven portion, 2451 configured to be threadably coupled with a firing drive screw by way of threads 2453 and comprises a drive portion, or driving portion, 2460. The drive nut 2450 further comprises a lower camming flange 2452 also configured to cammingly engage an end effector jaw during a firing stroke. The drive nut 2450 comprises a substantially trapezoidal shape. Discussed in greater detail below, the firing member assembly 2400 comprises a proximal clearance void, or longitudinal space, 2431 defined between the proximal portion 2416 and a proximal drive surface 2454 of the threaded portion 2451 and a distal clearance void, or longitudinal space, 2455 defined between the distal portion 2420 and a distal drive surface 2455 of the threaded portion 2451.

The drive portion 2460 comprises laterally opposing tabs 2461 extending upwardly from the threaded portion 2451. It should be appreciated that the primary body portion 2410 and the drive nut 2450 is symmetrical relative to vertical plane defined by the primary body portion 2410 but for the threads 2453. The drive tabs 2461 are configured to cradle, or straddle, a corresponding drive tab 2440 extending downwardly from the primary body portion 2410 and into an upper portion 2433 of the drive cavity 2430. The drive portion 2060 further comprises a plurality of internal cross members, or ribs, 2463 extending between the tabs 2461. The ribs 2463 secure, or attach, the drive portion 2460 to the drive tab 2440 and, thus, the primary body portion 2410. The ribs 2463 are configured to be received within a plurality of corresponding apertures 2441 defined in the drive tab 2440. As the drive nut 2450 is actuated, force can be applied to the primary body portion 2410 from the ribs 2463 to the drive tab 2440 within the slots 2441. Such a configuration can provide a drive force to the primary body portion 2331 off center with respect to the drive screw positioned within the threaded channel 2453 and nearer the center of the firing member assembly 2400. As can be seen in FIGS. 57 and 60, the drive nut 2450 can apply a drive force DF to the primary body portion 2410 off center with respect to a longitudinal screw axis SA.

The tabs 2461 of the drive nut 2450 are further configured to apply force to the primary body portion 2410 within the upper portion 2433 of the drive cavity 2430 to proximal drive surface 2443 and distal drive surface 2445. These additional drive surfaces can further center the application of drive force to the primary body portion 2410 nearer the center of the firing member assembly 2400.

As discussed above, the firing member assembly 2400 comprises clearance voids 2431, 2432 positioned between the threaded portion 2451 of the drive nut 2450 and the proximal and distal portions 2416, 2420 of the primary body portion 2410. The clearance voids are configured to further center the application of drive force within the firing member assembly 2400 from the drive nut 2450 to the primary body portion 2410. The clearance voids 2431, 2432 prevent the threaded portion 2451 from contacting the proximal and distal portions 2416, 2420 of the primary body portion 2410 thereby preventing the application of drive force immediately adjacent the drive screw configured to drive the firing member assembly 2400.

The clearance voids 2431, 2432 can also be configured to control overall deflection of the drive nut 2450. In various instances, a firing drive screw can deflect relative to the end effector in which it is positioned. This can be attributed to clamping forces applied to the jaws of an end effector during a firing stroke, among other things. Notably, as the drive screw deflects, the drive nut 2450 will be urged to deflect, or rotate, relative to the primary body portion 2410, along with the drive screw owing to the threaded engagement between the drive nut 2450 and the firing drive screw. The trapezoidal shape and clearance voids 2431, 2432 provide a degree of flexibility, or forgiveness, for the drive nut 2450 to deflect and rotate with the firing drive screw. Permitting this forgiveness within the firing member assembly 2400 can help prevent binding of the threaded engagement between the drive nut 2450 and the firing screw. A rigid firing assembly and drive nut combination, for example, may afford little to no flexibility further increasing the likelihood of thread binding, for example. In certain cases, other components of the firing member assembly such as camming flanges and/or the driving cross members discussed above may elastically deform owing to bending and/or shearing forces within an end effector assembly. In at least one instance, the drive cavity 2430 comprises a trapezoidal shape in addition to or in lieu of the drive nut 2450.

In at least one instance, the drive nut 2450 is insert molded over a drive screw. This permits complex shapes of a drive nut and allows for finely tuned engagement features between the drive nut 2450 and the primary body portion 2410. Such an engagement feature comprises the ribs 2463, for example. In at least one instance, the drive nut 2450 is overmolded onto the primary body portion 2410.

As discussed above, the proximal portion 2416 and the distal portion 2420 each comprise registration apertures 2419, 2423 configured for use during an overmolding and/or insert molding process. The registration apertures 2419, 2423 are configured to hold the primary body portion 2410 within a molding tool and are aligned at the equator, or center, of the ducts 2418, 2020. This positioning can help align the mold used for the drive nut 2450 with the ducts 2418, 2020 for manufacturing so that the drive nut 2450 and, specifically, the threaded portion 2451 is aligned with the ducts 2418, 2020. This alignment ensures that a firing drive screw is aligned within the ducts 2018, 2020 and the threaded portion 2451 upon assembly. In at least one instance, a firing drive screw and the primary body portion 2410 are both presented prior to molding the drive nut 2450. In such an instance, the drive nut 2450 can be molded around the pre-placed primary body portion 2410 and firing drive screw. In at least one instance, only the primary body portion 2410 is presented prior to molding the drive nut 2450.

FIGS. 62-66 depict a firing member assembly 2500. The firing member assembly 2500 is similar to the firing member assemblies discussed above; however, the firing member assembly 2500 comprises a drive nut assembly comprising an external drive portion 2550 and an internal drive nut 2560 positioned within the external drive portion 2550. The firing member assembly 2500 is configured to be threadably coupled to a firing drive screw and is configured to be actuated proximally and distally through a firing stroke by way of the firing drive screw within an end effector assembly.

The firing member assembly 2500 comprises a primary body portion 2510 and a drive nut assembly configured to fit within a drive cavity, or receptacle, 2530 of the primary body portion 25510. The primary body portion 2510 comprises an upper portion 2511 comprising an anvil-engaging flange 2512. The upper portion 2511 further comprises a distal nose 2513 which can be used to clamp an anvil jaw from an unclamped position. The primary body portion 2510 further comprises a drive surface 2514 configured to push a sled and/or a cutting member, for example. The primary body portion 2510 further comprises a lower portion 2515 comprising a proximal portion 2516 and a distal portion 2520 defining the drive cavity 2530. The proximal portion 2516 comprises a proximal lower flange 2517 extending laterally therefrom and a drive screw duct 2518. The distal portion 2520 comprises a distal lower flange 2521 and a drive screw duct 2522. The flanges 2517, 2521 are configured to engage a jaw of an end effector to affirmatively hold a consistent tissue gap between the jaw and another jaw of the end effector. The drive screw ducts 2518, 2522 are aligned with each other are configured to non-threadably receive the firing drive screw therethrough.

As discussed above, the drive nut assembly comprises the external drive portion 2550 and the internal drive nut 2560 positioned within the external drive portion 2550. In at least one instance, the internal drive nut 2560 comprises a stock drive nut comprised of a metallic material, for example. In at least one instance, the external drive portion 2550 comprises of a polymer, for example, and is overmolded and/or insert molded within the firing member assembly 2500. In such an instance, the drive nut assembly comprises a hybrid multi-material drive nut assembly and may have metamaterial properties in certain instances. In at least one instance, the external drive portion 2560 is insert molded to the internal drive nut 2550 and then the drive nut assembly is positioned within the drive cavity 2530 for assembly to a firing drive screw and the primary body portion 2510. Regardless, the drive nut assembly comprises a multi-piece arrangement.

The external drive portion 2550 comprises a lower portion 2551 comprising a flange 2552. The lower portion 2551 is configured to surround and secure the internal drive nut 2560 within the drive nut assembly. The external drive portion 2550 further comprises a drive tab 2553 positioned within an upper portion of the drive cavity 2530. The drive cavity 2530 further comprises a clearance slot 2531 positioned between the drive tab 2553 and the primary body portion 2510. Such a clearance slot 2531 can permit the drive nut assembly to float with the firing drive screw relative to the primary body portion 2510. In such an instance, the primary body portion 2510 can be constrained by various elements of an end effector assembly such as, for example, an anvil jaw and a channel jaw.

As discussed above, the external drive portion 2550 is configured to secure the internal drive nut 2560 therein and in line with a screw axis SA. The screw axis SA is defined as the center of the ducts 2518, 2522 and a primary cylindrical portion 2561 of the internal drive nut 2560. Threads 2562 are defined in the primary cylindrical portion 2561 of the internal drive nut 2560. The threads 2562 are configured to be threadably engaged, or coupled, with threads of a firing drive screw. The internal drive nut 2560 further comprises rows 2563 of gripping features 2564 configured to prevent rotation of the internal drive nut 2560 relative to the external drive portion 2550 during drive screw rotation. The external drive portion 2550 can envelop the internal drive nut 2560 during the molding process. The internal drive nut 2560 further comprises a flared proximal end 2565. The flared proximal end 2565 can aid assembly of the firing member assembly 2500 with a firing drive screw. For example, a firing drive screw can be inserted in through the duct 2518 and guided into the threads 2562 of the internal drive nut 2560 by the flared proximal end 2565.

In at least one instance, the gripping features 2564 can aid in the manufacturing process of the drive nut assembly. For example, the gripping features 2564 may fit into corresponding slots of a mold configured to hold the drive nut 2560 during molding of the external drive portion 2550.

Figure 67:
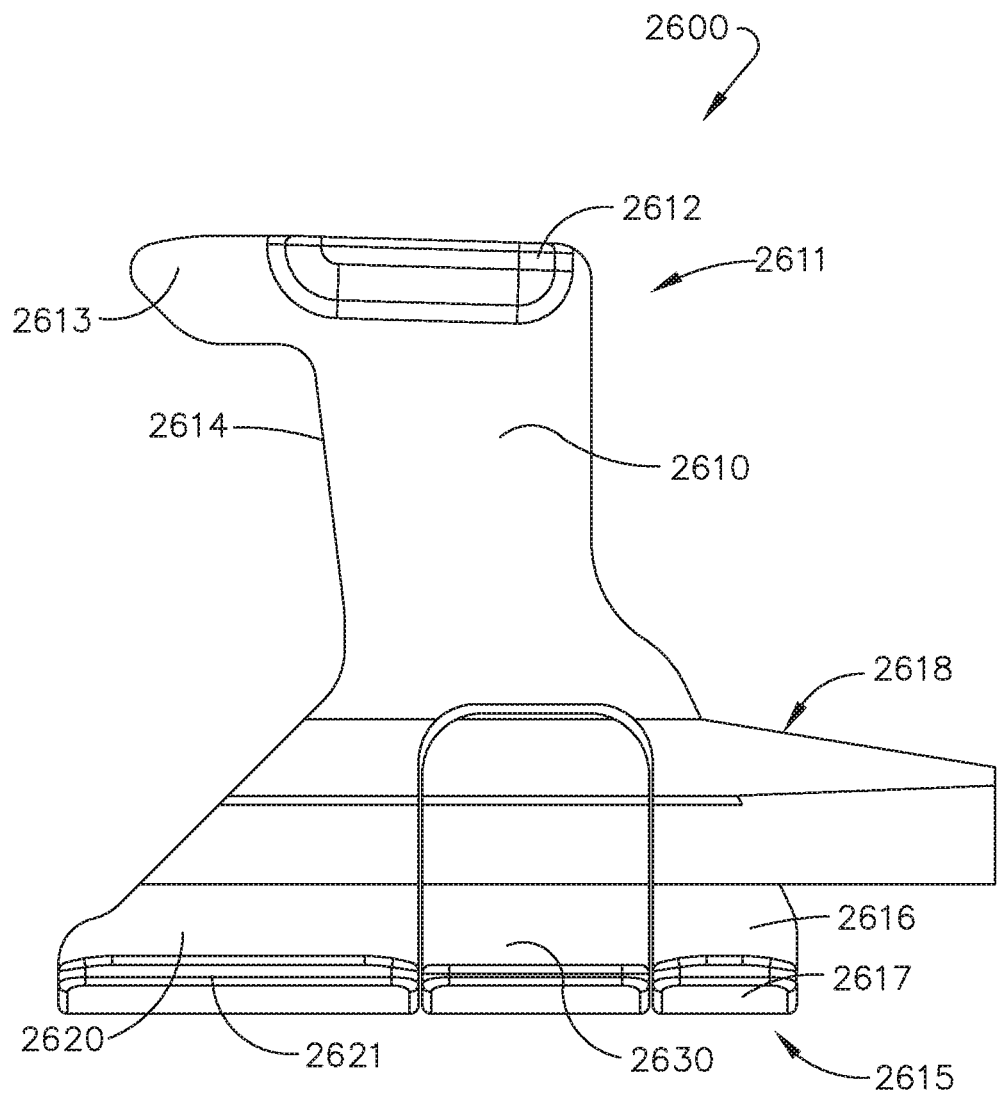
FIG. 67 is an elevation view of a firing member assembly comprising a primary body portion and a drive nut, wherein the primary body portion comprises a proximal tail extension, in accordance with at least one aspect of the present disclosure.

FIG. 67 depicts a firing member assembly 2600. The firing assembly 2600 is similar to the firing member assemblies discussed above; however, the firing member assembly 2600 comprises a proximal tail extension configured to further support the firing member assembly 2600 through a firing stroke. The firing member assembly 2600 is configured to be threadably coupled to a firing drive screw and is configured to be actuated proximally and distally through the firing stroke by way of the firing drive screw within an end effector assembly.

The firing member assembly 2600 comprises a primary body portion 2610 and a drive nut 2630. The primary body portion 2610 comprises an upper portion 2611 and a lower portion 2615. The upper portion 2611 comprises an anvil-camming flange 2612. The upper portion 2611 further comprises a distal nose 2613 configured to close a jaw of an end effector from an open position to a closed position. The primary body portion 2610 further comprises a drive surface 2614 configured to push a sled and/or a cutting member, for example. The lower portion 2615 comprises a proximal portion 2616 comprising a proximal lower flange 2617 and a proximal tail extension 2618. The lower portion 2615 further comprises a distal portion 2620 comprising a distal lower flange 2621. The flanges 2617, 2621, 2612 can be configured to maintain a predefined tissue gap between a staple cartridge and an anvil throughout a firing stroke of the firing member assembly 2600.

The proximal tail extension 2618 is an extension of a screw duct, such as those described above, of the proximal portion 2616. Such a proximal tail extension can further support the firing member assembly 2500 through a firing stroke. Such a proximal tail extension may also resist deflection, or rotation, of the primary body portion 2610 which may cause a threaded engagement between the drive nut 2630 and the firing drive screw to bind.

FIGS. 68-72 depicts a firing member assembly 2700 threadably coupled with a firing drive screw 2701. The firing assembly 2700 is similar to the firing member assemblies discussed above; however, the firing member assembly 2700 comprises a primary body portion 2710 and a drive nut 2750 snappable to the primary body portion 2710. The firing member assembly 2700 is configured to be actuated proximally and distally through a firing stroke by way of the firing drive screw 2701 within an end effector assembly.

The primary body portion 2710 comprises an upper portion 2711 and a lower portion 2715 defining a drive cavity 2730. The drive nut 2750 is configured to be positioned within the drive cavity 2730. The upper portion 2711 comprises a jaw-camming flange 2712. The upper portion 2711 further comprises a distal nose 2713 configured to close a jaw of an end effector from an open position to a closed position. The primary body portion 2710 further comprises a drive surface 2714 configured to push a sled, for example. The lower portion 2715 comprises a proximal portion 2716 comprising a proximal lower flange 2717. The lower portion 2715 further comprises a distal portion 27720 comprising a distal lower flange 2721 and a drive screw duct 2722 defined therein configured to non-threadably receive the firing drive screw 2701. The flanges 2617, 2721, 2712 can be configured to maintain a predefined tissue gap between a staple cartridge and an anvil throughout a firing stroke of the firing member assembly 2700.

In at least one instance, a profile or perimeter of the drive screw duct 2722 and/or a proximal portion of the drive screw duct can be oval shaped and/or oblong or, non-circular, for example. Such a configuration can reduce the likelihood of a deflected drive screw rubbing or interfering inside the screw ducts, which can cause stack-up losses in the event of such drive screw deflection. Stack-up losses can refer to the various problematic engagements of the drive screw and other components within the system that would result in various interferences in a scenario where the drive screw is deflected substantially. For example, if a drive screw is deflected substantially, the deflected drive screw, as discussed above, may rub against a drive screw duct, the deflected drive screw may cause the threads of a drive nut to bind, and/or the deflected drive screw may bind near its connection with a firing output shaft, for example. Providing features to minimize such stack-up losses can prevent premature failure of components and/or reduce the firing forces necessary to drive a firing member assembly, for example.

In at least one instance, the drive screw duct 2722 and/or a proximal portion of the drive screw duct comprises filleted or chamfered edges. Such a configuration can further reduce the likelihood of the ducts contacting and binding with the firing drive screw.

In at least one instance, a screw duct of a primary body portion can provide lateral and/or vertical support to the drive screw such that, should the drive screw be loaded enough to induce bending of the drive screw, the drive screw duct can prevent the drive screw from bending at least near the threaded drive nut. Such a configuration can help prevent binding between the threads of the drive screw and the threaded drive nut.

In at least one instance, a sled of a staple cartridge can comprise a distally extending cradle support feature extending from a distal end of the sled. The cradle support feature may also support the firing drive screw and help prevent bending of the firing drive screw at least near the cradle support feature. In at least one instance, the sled prevents bending of the drive screw in only one direction. In at least one instance, the sled comprises a proximal cradle support feature in addition to or in lieu of the distal cradle support feature.

The drive nut 2750 comprises a jaw-engaging flange 2751, a threaded portion 2755 configured to be threadably coupled with the firing drive screw 2701 by way of threads 2756, and laterally-opposing drive tabs 2760 extending upwardly from the threaded portion 2755. The drive nut 2750 comprises a substantially trapezoidal shape such as those drive nuts comprising a trapezoidal shape discussed herein.

Figure 71:
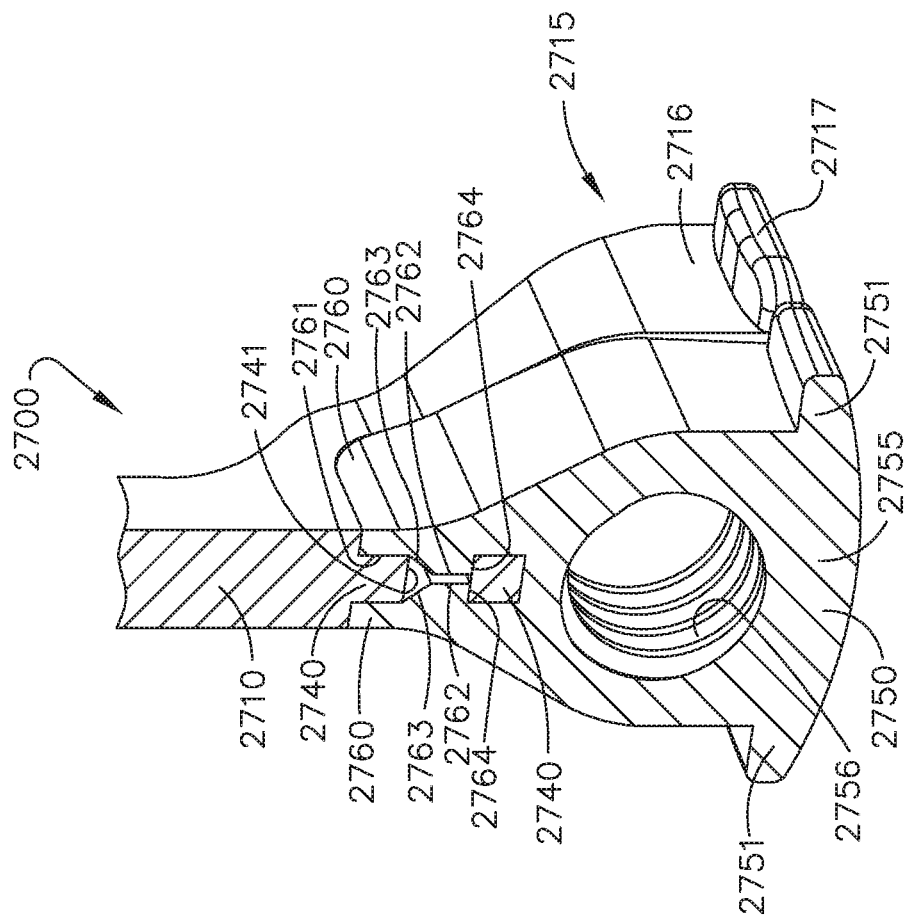
FIG. 71 is a perspective, cross-sectional view of the firing member assembly of FIG. 68, in accordance with at least one aspect of the present disclosure.
Figure 70:
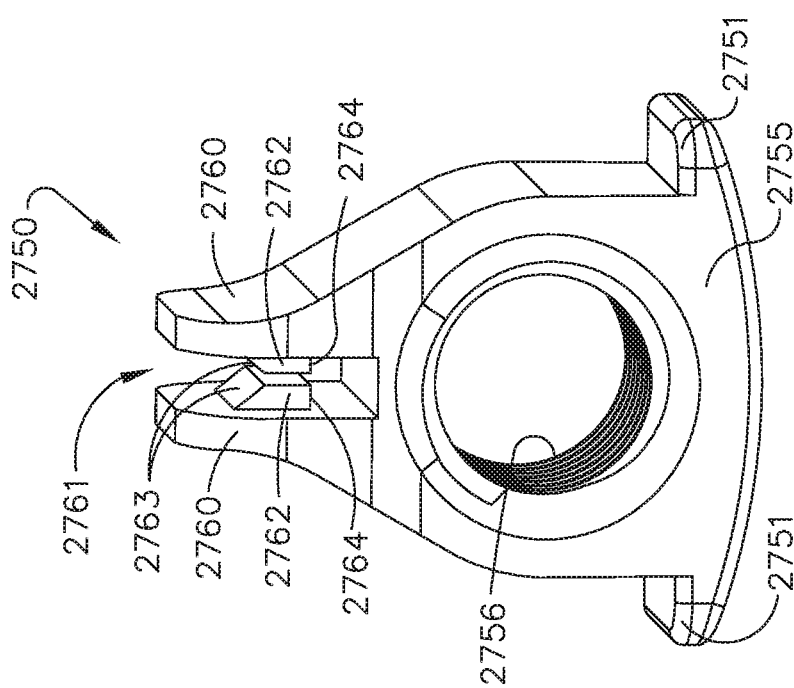
FIG. 70 is a perspective view of the drive nut of the firing member assembly of FIG. 68, in accordance with at least one aspect of the present disclosure.
Figure 74:
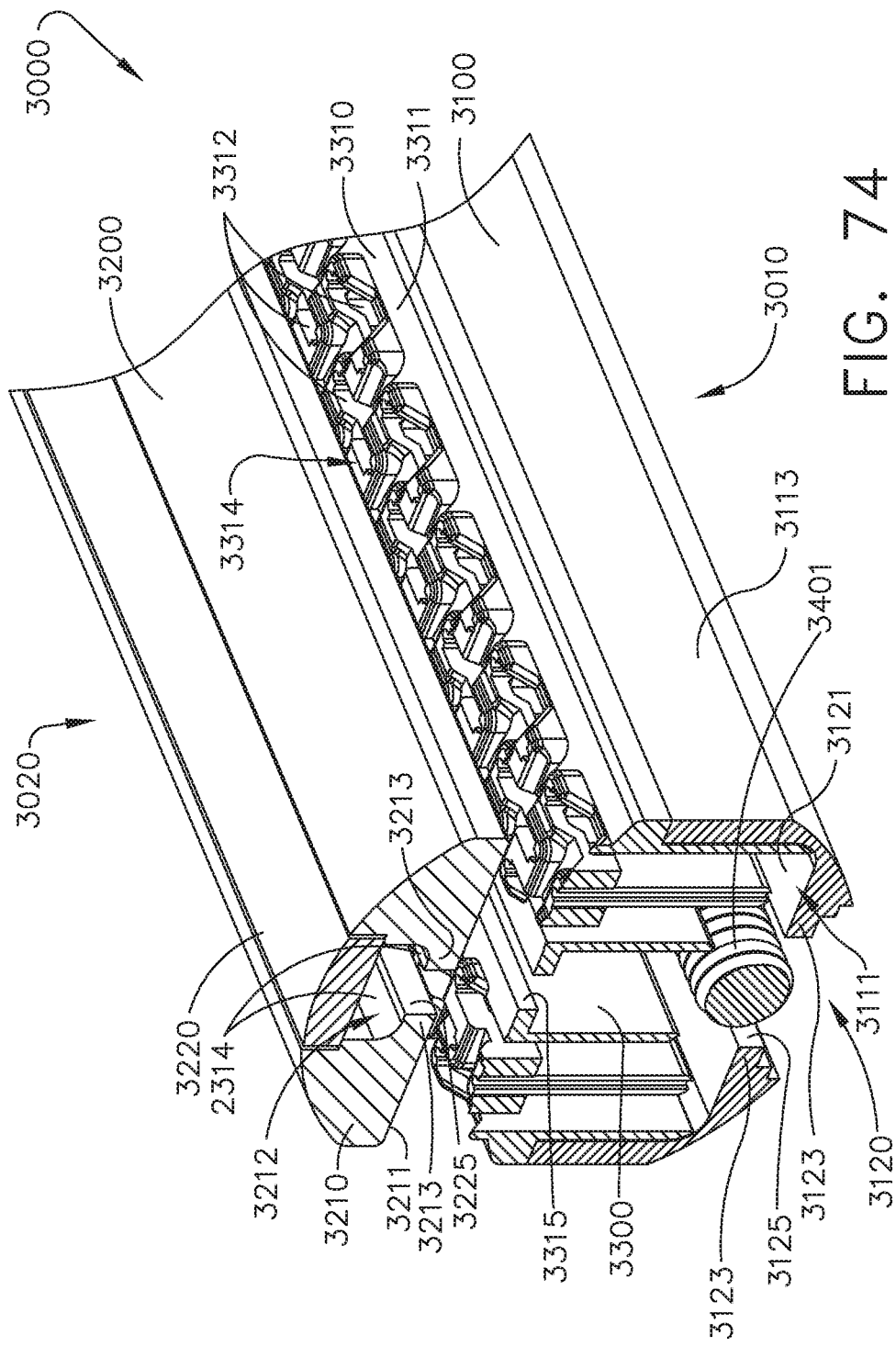
FIG. 74 is a cross-sectional perspective view of an end effector assembly comprising a cartridge channel, a staple cartridge, an anvil, and a firing assembly, in accordance with at least one aspect of the present disclosure.
Figure 75:
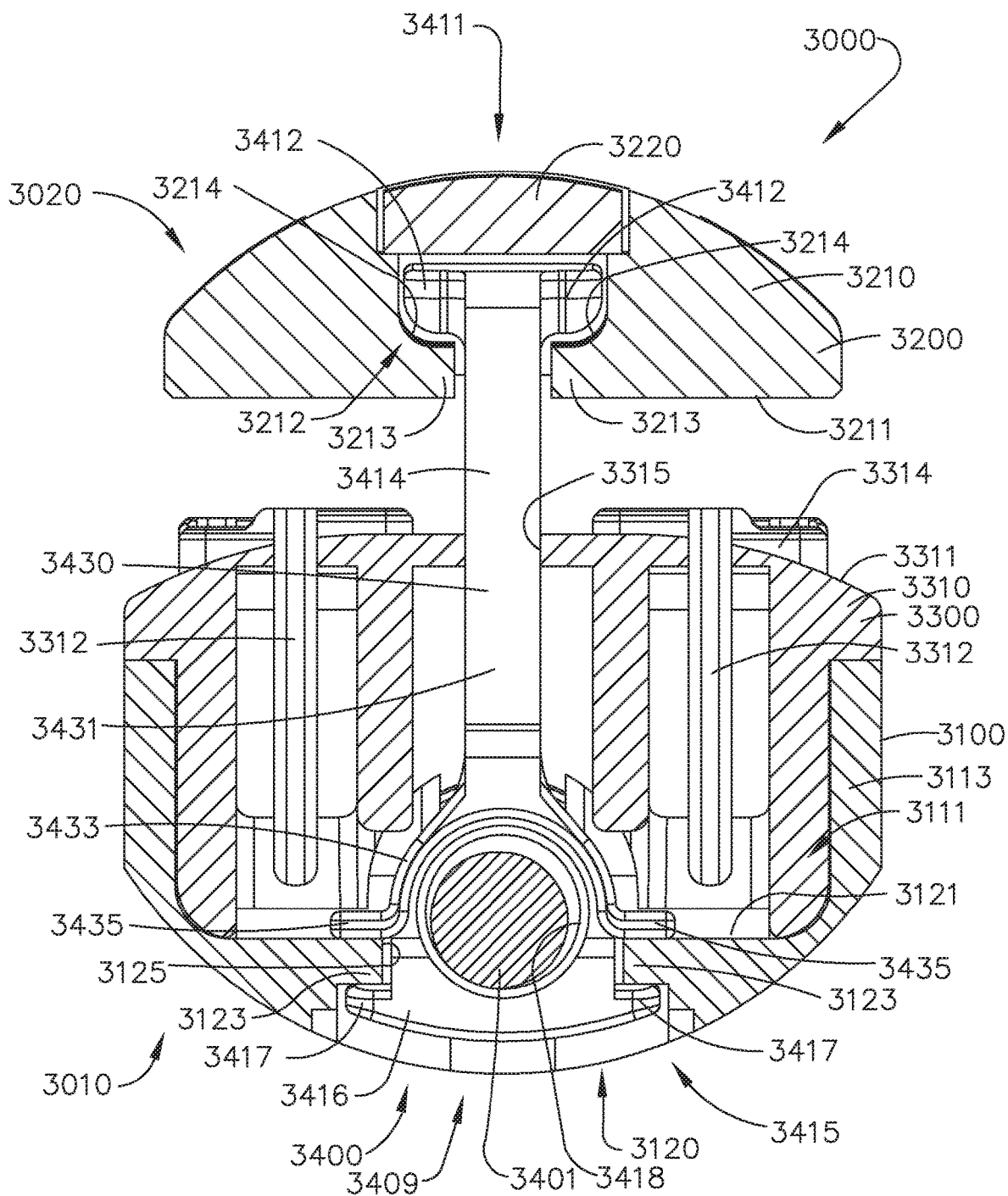
FIG. 75 is a cross-sectional elevation view of the end effector assembly of FIG. 74 viewed from a proximal end of the end effector assembly, in accordance with at least one aspect of the present disclosure.
Figure 76:
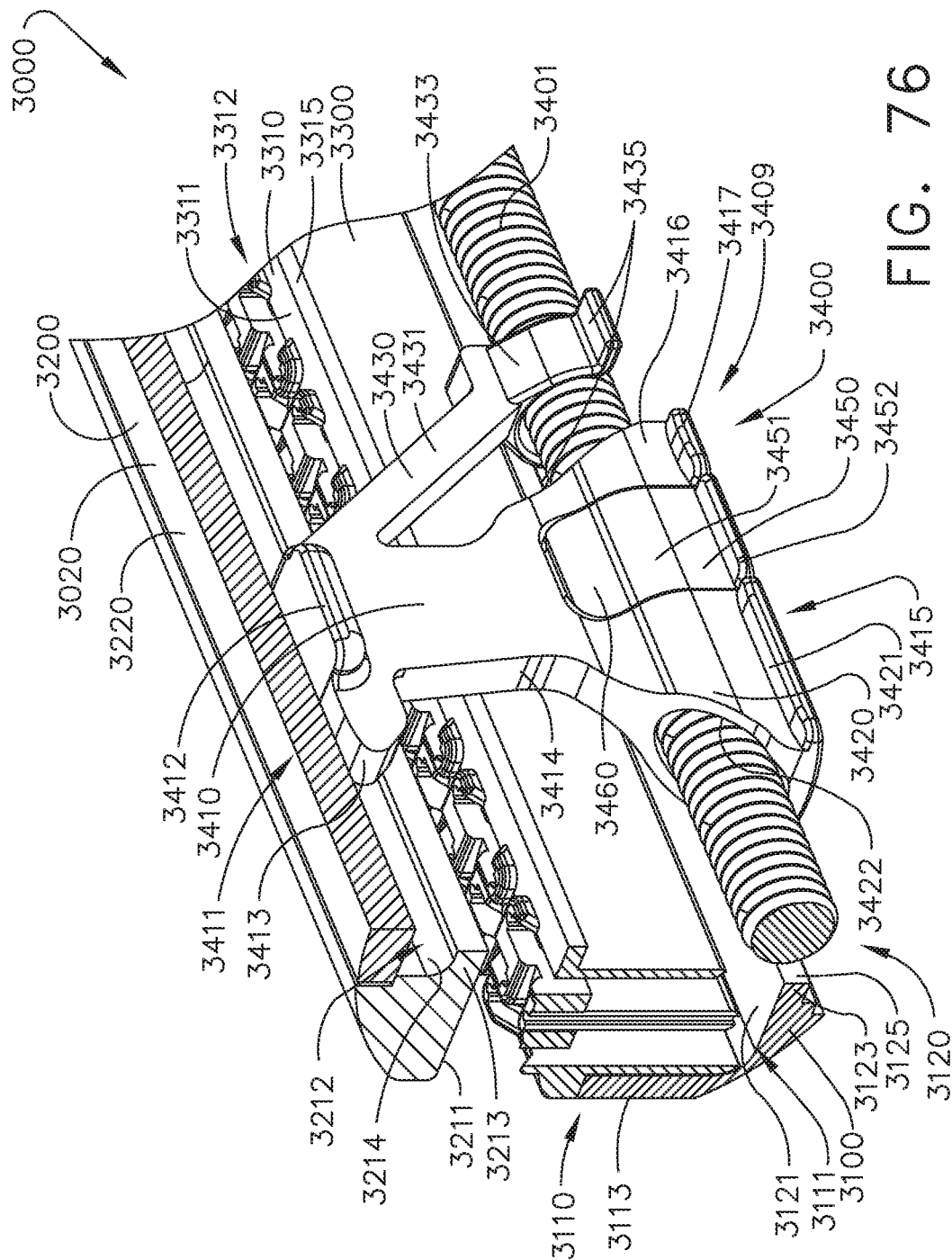
FIG. 76 is a partial cross-sectional perspective view of the end effector assembly of FIG. 74, wherein the firing member assembly comprises a firing drive screw and a firing member assembly, in accordance with at least one aspect of the present disclosure.
Figure 77:
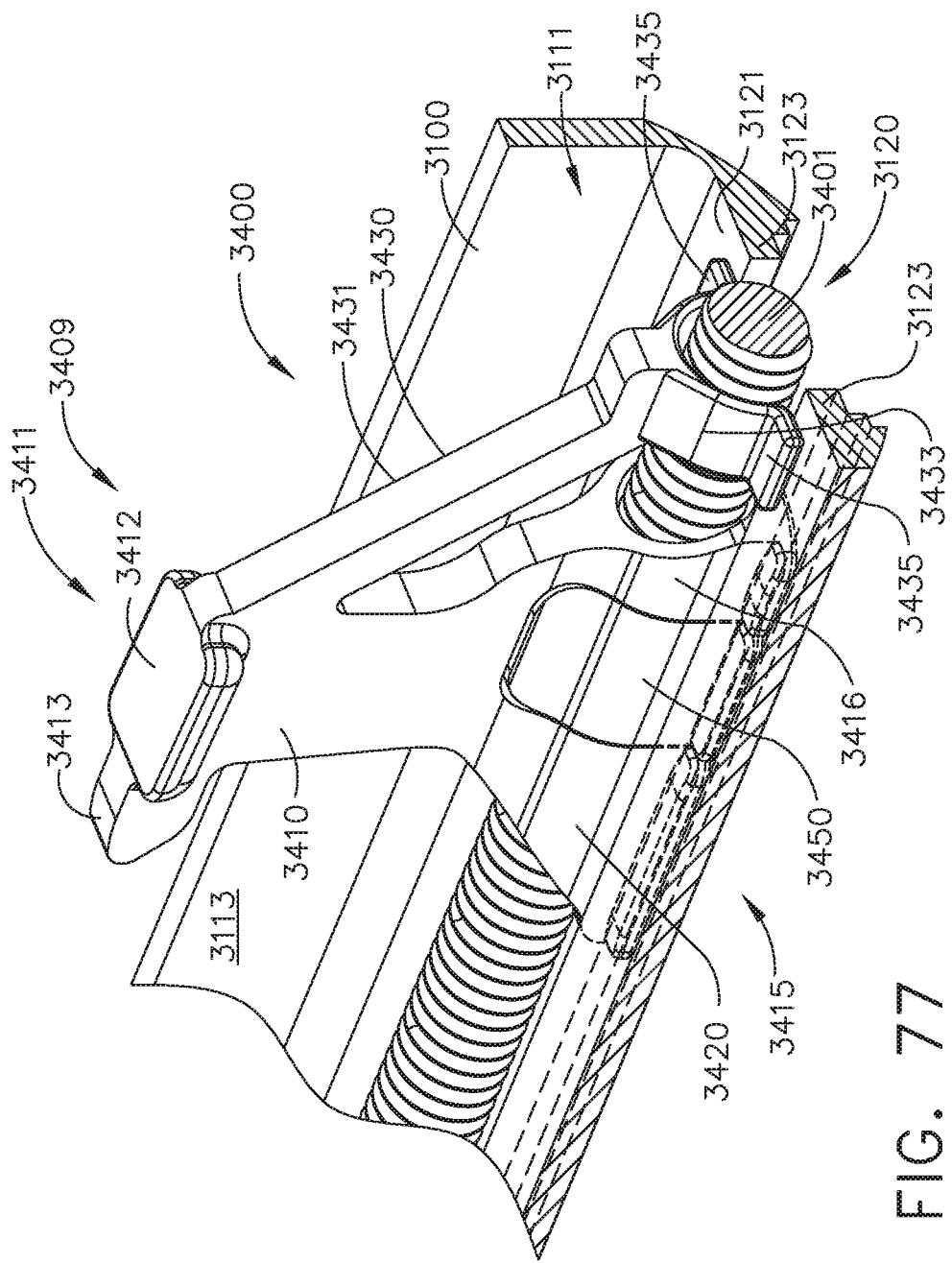
FIG. 77 is a partial cross-sectional perspective view of the channel and the firing assembly of FIG. 74, wherein certain hidden features are shown with dashed lines for illustrative purposes, in accordance with at least one aspect of the present disclosure.

The drive tabs 2760 are configured to cradle, or straddle, a corresponding drive tab 2740 extending downwardly from the primary body portion 2710. The drive tabs 2760 define a slot 2761 therebetween and each comprise a snap nub 2762 protruding inwardly therefrom. The snap nubs 2762 each comprise a sloped upper surface 2763 and a latch surface 2764. As can be seen in FIG. 71, the drive tabs 2760 are configured to snap to the drive tab 2740 of the primary body portion 2710. Specifically, the drive tab 2740 comprises a horizontally extending slot 2741 defined therein and the snap nubs 2762 are configured to widen the drive tabs 2760 during installation of the drive nut 2750 with the primary body portion 2710 enough such that the latch surfaces 2764 clear the drive tab 2740 and can bias inwardly into the slot 2741. In at least one instance, the snap nubs 2762 are not configured to transfer any longitudinal drive forces from the firing drive screw 2701 to the primary body portion 2710. Instead, the drive tabs 2760 are configured to fit within the drive cavity 2730 such that the drive tabs 2760 directly push and pull the primary body portion 2710 relative to the firing drive screw similar to various firing member assemblies discussed herein. Such a configuration can alleviate the reliance on the internal cross members of the drive nut 2750 to transfer firing force from the firing drive screw 2701 to the primary body portion 2710. This can be advantageous in that the drive nut 2750 can remain attached to the primary body portion 2710 through the drive nubs 2762 through higher than normal loads. Like various drive tabs discussed herein, the drive tabs 2760 of the drive nut 2750 are further configured to apply force to the primary body portion 2710 nearer the center of the primary body portion 2710. As can be seen in FIG. 69, the drive nut 2750 is configured to apply a drive force DF to the primary body portion 2710 off axis with respect to a longitudinal screw axis SA.

In at least one instance, the drive nut 2750 is injection molded prior to being snapped onto the primary body portion 2710. In at least one instance, the drive nut 2750 is insert molded onto the primary body portion 2710 and the firing drive screw 2701. In such an instance, the drive nut 2750 may be snapped off and replaced should the drive nut 2750 wear out over time, for example.

FIG. 73 depicts a firing member assembly 2800 comprising a primary body portion 2810 and a drive nut 2850 configured to be threadably coupled to a firing drive screw. The firing member assembly 2800 is similar to various firing member assemblies discussed above; however, the firing member assembly 2800 further comprises a drive cavity 2830 configured to permit the primary body portion 2810 to flex during a firing drive stroke as discussed in greater detail below.

The primary body portion 2810 comprises an upper portion 2811 comprising a flange 2812 extending laterally therefrom and a distal nose 2813 configured to close a jaw from an open position during a closure stroke. The primary body portion 2810 further comprises a drive surface 2814 configured to push a sled and/or a cutting member through a staple firing stroke, for example. Other embodiments are envisioned where various other surfaces on the front of the primary body portion 2810 are configured to drive various components such as a sled and/or a cutting member, for example. The primary body portion 2810 further comprises a lower portion 2815 comprising a proximal portion 2816 comprising a proximal lower flange 2817 and a distal portion 2820 comprising a distal lower flange 2821. Collectively, the flanges 2812, 2817, 2821 are configured to affirmatively space opposing jaws during a firing stroke and maintain a consistent tissue gap between the opposing jaws.

The drive nut 2850 is positioned within the drive cavity 2830 and is configured to be threadably coupled to a firing drive screw. The drive nut 2850 is configured to apply axial drive forces to the primary body portion 2810 as the firing drive screw is actuated to move the firing member assembly 2810 proximally and distally within an end effector. The drive cavity 2830 comprises a lower portion 2833 where the drive nut 2850 is primarily positioned and is configured to float within and comprises an upper triangular portion 2831. The upper triangular portion 2831 is configured to permit the primary body portion 2810 to flex during a firing stroke. For example, under clamping loads, the triangular portion 2831 is configured to permit the proximal portion 2816 to flex longitudinally away from the distal portion 2820. Such flexion can provide forgiveness within the firing member assembly 2800 so as to prevent binding, for example. In addition to flexion of the primary body portion 2810, the drive nut 2850 is configured to float within the drive cavity 2850. Collectively, such an arrangement can reduce binding engagement between the threaded connections and/or binding engagement between the flanges and jaws.

Various drive nuts disclosed herein comprise a laterally extending flange aligned with the proximal and distal lower flanges of the lower portions of the primary body portions. Such a flange can prevent the drive nut from rotating with a firing drive screw. Such a flange can comprise a rounded bottom so as to reduce binding engagement with a corresponding jaw. For example, the proximal and distal lower flanges can be configured to handle the majority of the clamping loads while the drive nut flange is provided for support to the drive nut but not necessarily to handle high clamping loads. Rounding the flange can reduce the overall contact with the corresponding jaw thus reducing the likelihood of the flange from binding against the corresponding jaw. In such an instance, the flange, or lateral fin, of the drive nut is configured to be loose within the corresponding jaw, such as a channel jaw, for example. This loose engagement between the flange and the corresponding jaw can provide the anti-rotation feature without requiring the flange to handle high clamping loads. In at least one instance, the lateral fin is overall thinner and comprises a top edge which is positioned below top edges of corresponding proximal and distal lower flanges of a primary body portion.

In at least one instance, the primary body portions are machined from a metallic material and the drive nuts are injection molded, insert molded, or overmolded from a polymer and/or a plastic material. Such a configuration can reduce manufacturing costs and machining complexity as various molding processes can allow for more complex geometries and shapes. Various molding processes can also allow for various order of component assembly and manufacturing. As discussed above, insert molding allows the multi-material firing member assembly to comprise various materials as well as complex integrated geometries between the different materials. Moreover, insert molding, for example, permits the firing drive screw to be positioned within the firing member assembly prior to molding of the drive nut.

FIGS. 74-78 depict an end effector assembly 3000 configured to cut and staple the tissue of a patient. The end effector assembly 3000 comprises a first jaw 3010 and a second jaw 3020 movable relative to the first jaw 3010. Embodiments are envisioned where the first jaw 3010 is movable relative to the second jaw 3020. The first jaw 3010 comprises a cartridge channel 3100 and a replaceable staple cartridge 3300 configured to be removably positioned within the cartridge channel 3100. The second jaw 3020 comprises an anvil 3200 configured to deform staples removably stored in the staple cartridge 3300 during a staple firing stroke. The second jaw 3020 is movable, or pivotable, relative to the first jaw 3010 to clamp tissue between the anvil 3200 and the staple cartridge 3300. Once tissue is clamped between the anvil 3200 and the staple cartridge 3300, the end effector assembly 3000 is fired to eject staples and cut tissue with a firing assembly 3400 of the end effector assembly 3000.

Discussed in greater detail below, the firing assembly 3400 comprises a firing drive screw 3401 supported within the cartridge channel 3100. The firing assembly 3400 further comprises a firing member assembly 3409 threadably coupled to the firing drive screw 3401 which is configured to push a sled to deploy staples from the staple cartridge 3300 during a firing stroke, push a cutting member to cut tissue during the firing stroke, and maintain a consistent tissue gap between the staple cartridge 3300 and the anvil 3200 during the firing stroke.

The cartridge channel 3100 comprises a longitudinal channel cavity 3111 within which the staple cartridge 3300 is removably positioned. The cartridge channel 3100 also comprises side walls 3113 configured to support the staple cartridge 3300. In at least one instance, the staple cartridge comprises ledges configured to rest on top of the side walls 3113. The cartridge channel 3100 further comprises a base portion 3120. The base portion 3120 comprises an internal bottom surface 3121 and camming ledges 3123. A longitudinal slot 3125 is defined between the camming ledges 3123 and is configured to receive at least a portion of the firing assembly 3400 therethrough.

The anvil 3200 comprises a body portion 3210 and an anvil cap 3220 configured to be attached to the body portion 3210 within a longitudinal channel 3212. The body portion 3210 comprises an anvil surface 3211. The anvil surface 3211 comprises a plurality of staple forming pockets aligned with staple cavities 3312 defined in a deck 3311 of staple cartridge body 3310. The body portion 3210 also comprises camming ledges 3213 extending laterally inwardly into the longitudinal channel 3212 and defining a longitudinal slot 3225 therebetween. Discussed in greater detail below, the camming ledges 3123, 3213 are configured to be cooperatively engaged by corresponding flanges of the firing member assembly 3409 to affirmatively space the jaws 3010, 3020 relative to each other. In at least one instance, a predefined tissue gap is defined between the cartridge deck 3311 and the anvil surface 3211 during a firing stroke by way of the engagement of the flanges of the firing member assembly 3409 with the camming ledges 3213, 3123.

The staple cartridge 3300 further comprises deck protrusions, or pocket extenders, 3314 configured to extend the effective height of each staple cavity 3312. The deck protrusions 3314 can be configured to help grip tissue clamped between the jaws 3010, 3020. The staple cartridge 3300 further comprises a longitudinal slot 3315 configured to receive at least a portion of the firing member assembly 3409 therethrough. As discussed above, a sled and/or cutting member is configured to be advanced through the jaws 3010, 3020 to cut tissue and fire staples during a staple firing stroke with the firing assembly 4400.

The firing assembly 3400 comprises the firing drive screw 3401 and the firing member assembly 3409 threadably coupled to the firing drive screw 3401. The firing member assembly 3409 comprises a primary body portion 3410, a drive nut 3450 configured to be threadably coupled to the firing drive screw 3401, and a rear support brace 3430. The primary body portion 3410 comprises an upper portion 3411 comprising an anvil-engaging flange 3412 and a distal nose portion 3413. The anvil-engaging flange 3412 is configured to move within the longitudinal channel 3212 and, more specifically, configured to apply clamping pressure to the upper surface 3214 of the camming ledges 3213. In at least one instance, the anvil cap 3220 is configured to provide an upper boundary to the anvil-camming flange 3412. Nonetheless, the anvil-camming flange 3412 is configured to move within the longitudinal channel 3212 during a firing stroke to apply camming forces thereto to ensure a consistent tissue gap distance between the cartridge deck 3311 and the anvil surface 3211.

The primary body portion 3410 further comprises a lower portion 3415 comprising a proximal portion 3416 comprising a channel-camming flange 3417 and a screw duct 3418 configured to non-threadably receive the firing drive screw 3401 therethrough. The lower portion 3415 further comprises a distal portion 3420 comprising a channel-camming flange 3421 and a screw duct 3422 configured to non-threadably receive the firing drive screw 3401. The drive nut 3450 is configured to fit between the proximal portion 3416 and the distal portion 3420. The drive nut 3450 comprises a threaded portion 3451 configured to be threadably coupled to the firing drive screw 3401 and comprising a channel-camming flange 3452. In at least one instance, the channel-camming flange 3452 comprises a thickness that is less than the thickness of the channel-camming flanges 3417, 3421. The drive nut 3450 also comprises a drive tab 3460 extending upwardly toward the primary body portion 3410. The drive nut 3450 is configured to apply axial drive forces proximally and distally to the primary body portion 3410 to move the firing member assembly 3409 through jaws 3010, 3020. The channel-camming flanges 3417, 3452, 3421 are configured to apply camming forces to the camming ledges 3123. Collectively, the camming flange 3412 and the flanges 3417, 3452, 3421 are configured to maintain a consistent tissue gap distance between the cartridge deck 3311 and the anvil surface 3211.

Firing member assemblies can be subject to loads which would cause off center moment loading. For example, the anvil ledges engaged with upper camming flanges 3412 can apply an off-center moment load to the firing member 3400 in certain instances, such as when thick and/or tough tissue is clamped between the jaws. It can be advantageous to provide a means for counter-acting such off center moment loading. The firing member assembly 3409 comprises a rear support brace 3430 extending at an angle proximally from the upper portion 3411 of the primary body portion 3410. The rear support brace 3430 comprises a strut member 3431 and an arcuate brace portion 3433 extending from the strut member 3431. The arcuate brace portion 3433 comprises laterally extending flanges 3435 configured to support the rear support brace 3430 and counteract moment loading of the primary body portion 3410. The flanges 3435 are configured to ride against the internal bottom surface 3121. Notably, the flanges 3435 ride above the camming ledges 3123 such that the flanges 3432 of the rear support brace 3430 and the channel-camming flanges 3421 contact opposite sides of the base portion 3120 of the channel 3100.

In at least one instance, should the primary body portion 3410 be loaded and cause rotation in an opposite direction, the flanges 3435 may provide flexibility to lift off of the internal bottom surface 3121 and resist torqueing of the anvil-camming flanges 3412 out of substantially parallel alignment with the longitudinal channel 3214. The rear support brace 3430 can be configured to provide a degree of flexibility so as to permit some flexion of the primary body portion 3410 during loading while preventing a magnitude of flexion that would cause binding if the threaded engagement between the drive nut 3450 and the firing drive screw 3401. In certain instances, the rear support brace 3430 can act as a spring feature for balancing the load.

Embodiments are envisioned where the flanges 3435 are positioned under the ledges 3123. Embodiments are also envisioned where two sets of flanges are provided. One set of flanges can be positioned above the ledges 3123 and one set of flanges can be positioned below the ledges 3123.

In various instances, the rear support brace 3430 acts a spring member for the firing member assembly 3409 to balance various loads experienced by the firing member assembly 3409. Moreover, a clearance is provided between the arcuate brace portion 3433 and the firing drive screw 3401. Such a configuration can prevent I-beam roll, for example, and balance an I-beam, or firing member assembly, throughout a staple firing stroke. Embodiments are envisioned where the arcuate brace portion 3433 is also threaded and threadably coupled to the firing drive screw 3401.

Figure 78:
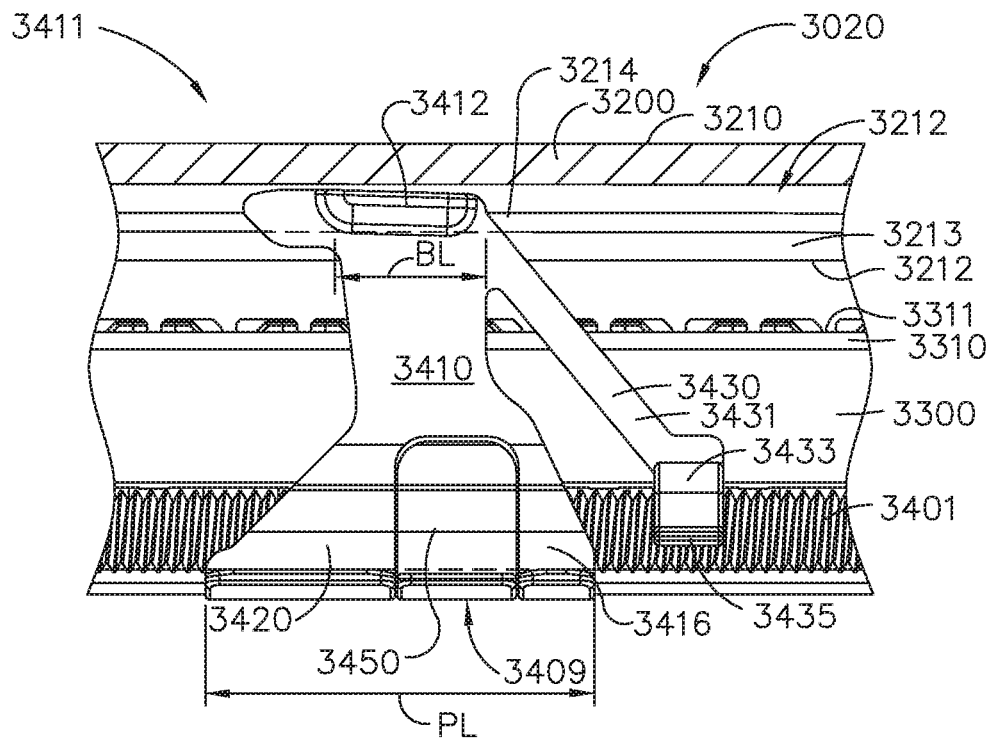
FIG. 78 is a partial cross-sectional elevation view of the end effector assembly of FIG. 74, in accordance with at least one aspect of the present disclosure.

In various instances, the geometries of various firing member components can be optimized. Referring to FIG. 78, for example, the length of a central portion of the primary body portion 3410 is referred to as the body length BL and the length of the lower flanges 3417, 3421, collectively, are referred to as the pin length PL. Generally, the pin length PL is about twice the length of the body length BL. This may also apply to the upper flange 3412. However, in certain instances, the upper flange 3412, for example, may comprise a shorter pin length than twice the body length BL at least because the rear support brace 3430 can help prevent the upper flange 3412 from rotating and/or deflecting under load. In various instances, the longer the pin length, the more likely the corresponding flange is will bind within its slot. In such instances, the clearance slot within which the flange is positioned should be smaller so as to reduce binding between the flange and the clearance slot.

Figure 79:
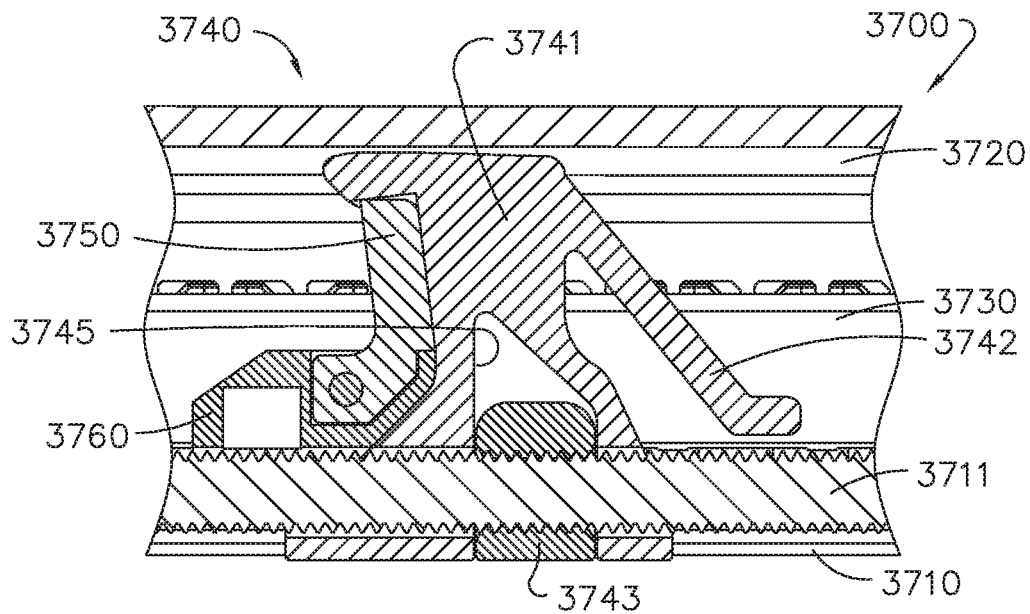
FIG. 79 is a cross-sectional elevation view of a surgical stapling assembly comprising a channel, a staple cartridge, an anvil, and a firing assembly comprising a drive screw, a firing member assembly, and a sled, in accordance with at least one aspect of the present disclosure.
Figure 80:
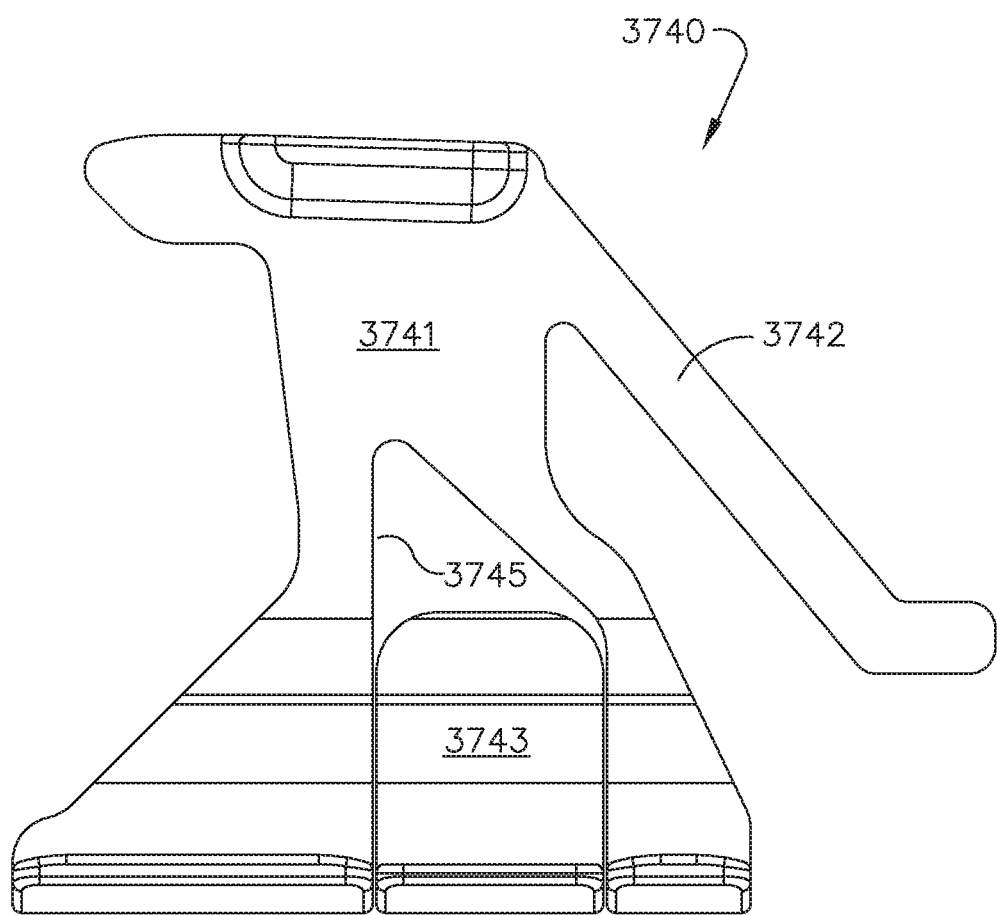
FIG. 80 is an elevation view of the firing member assembly of FIG. 79, in accordance with at least one aspect of the present disclosure.

FIGS. 79 and 80 depict a surgical stapling assembly 3700 similar to those discussed above. However, the surgical stapling assembly 3700 combines a triangular drive cavity cutout in addition to various other features discussed herein. The surgical stapling assembly 3700 comprises a channel jaw 3710, a staple cartridge 3730 configured to be received within the channel jaw 3710, and a firing drive screw 3711 supported within the channel jaw 3710. The surgical stapling assembly 3700 further comprises an anvil jaw 3720 configured to deform staples ejected from the staple cartridge 3730. The surgical stapling assembly further comprises a firing member assembly 3740 configured to be actuated by the firing drive screw 3711 through the jaws 3710, 3720. The firing member assembly 3740 comprises a primary body portion 3741, a rear support brace 3745, and a drive nut 3743 threadably coupled to the firing drive screw 3711. The primary body portion 3741 comprises a triangular drive cavity cutout 3745 configured to provide an additional spring feature within the firing member assembly 3740 configured to balance various loads experienced by the firing member assembly 3740. The surgical stapling assembly 3700 further comprises a knife 3750 configured to cut tissue during a firing stroke and a sled 3760 configured to deploy staples from the staple cartridge 3730. The knife 3750 and the sled 3760 can each experience and transfer loads to the firing member assembly 3740.

The knife 3750 is a component of the sled 3760 and is mounted to the sled 3760 at a pivot. During a distal firing motion, the knife 3750 can assume the upright configuration shown in FIG. 79, in which the knife 3750 protrudes out of the cartridge body and the cutting edge thereof is configured to cut tissue. During a proximal firing motion, the knife 3750 can assume a shielded configuration, in which at least a portion of the cutting edge of the knife 3750 is shielded by the fastener cartridge. The knife 3750 can pivot between the upright configuration and the shielded configuration in response to the firing direction and/or various mechanical lockouts and/or biasing mechanisms in the staple cartridge.

Figure 81:
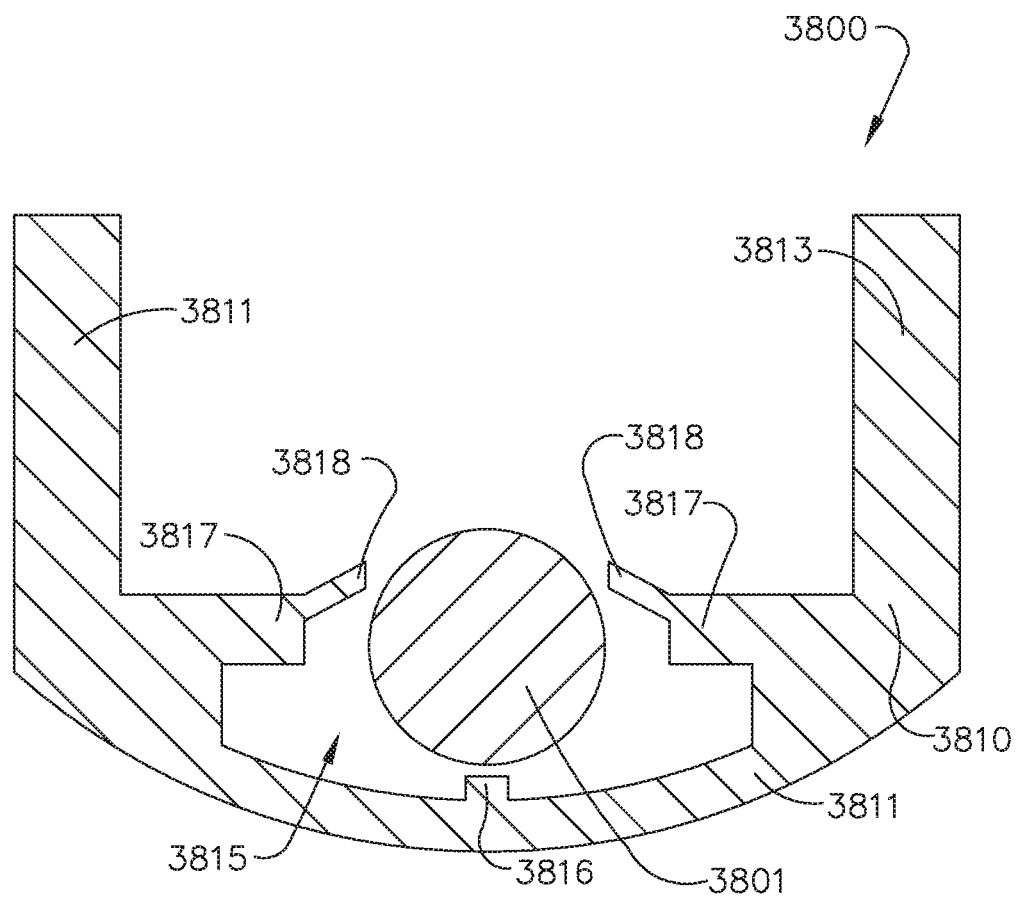
FIG. 81 is a cross-sectional elevation view of a jaw assembly for use with a surgical stapling assembly, wherein the jaw assembly comprises a channel and a firing drive screw, in accordance with at least one aspect of the present disclosure.

FIG. 81 depicts a jaw assembly 3800 configured to support a firing drive screw 3801 therein. Under high loads, a firing drive screw may tend to buckle. The jaw assembly 3800 is configured to prevent buckling of the firing drive screw 3801. The jaw assembly comprises a channel jaw 3810 comprising a bottom 3811 and channel walls 3813 extending from the bottom 3811. The bottom 3811 comprises a drive cavity 3815 configured to receive the firing drive screw 3801 and one or more flanges such as the camming flanges discussed herein. The bottom 3811 further comprises a lower support 3816 and lateral supports 3818 extending from camming ledges 3817. The lower support 3816 and lateral supports 3818 are configured to restrain the firing drive screw 3801 from buckling under high loads. In at least one instance, the supports 3816, 3818 are positioned only near the middle of the firing stroke and channel jaw, for example. Such an arrangement may suffice owing to the fact that, under high loads, the firing drive screw 3801 may tend to buckle near the center of its effective length. In at least one instance, the supports 3816, 3818 may be longitudinal ribs that extend along the majority of the length of the firing drive screw 3801 and channel jaw 3810. The supports 3818 can comprise of metal arms and act as hard stops for the firing drive screw 3801.

In at least one instance, the supports 3818 comprise plastic arms. In such an instance, the supports 3818 can be pried out of the way of a firing member assembly by the firing member assembly as the firing member assembly passes by the supports 3818 during a firing stroke. Such a configuration can be advantageous at least because once the firing member assembly reaches the location of the supports 3818 during the firing stroke, the firing member assembly can then, itself, support the firing drive screw 3801 and prevent buckling thereof.

In various instances, balancing an I-beam, or firing member assembly, can be advantageous so as to optimize loading of the firing member assembly between the anvil camming flanges and channel camming flanges, for example. Various forces are applied to the firing member assembly. These forces are applied by the firing drive screw and/or the drive nut, the anvil camming flanges, the channel camming flanges, the tissue, and/or the sled configured to deploy staples. It may be advantageous to balance these forces such that the driving force provided by the drive screw is driving the firing member assembly at an optimal location. A less than optimal driving force application may result in unnecessary roll, rotation, and/or rocking, of the firing member assembly relative to the firing screw and/or relative to a longitudinal axis defined by the firing screw. Torsional loads may cause such roll, rotation, and/or rocking, for example. Applying the drive force at a location to optimally counteract the predictable torsional loads applied to the firing member assembly can help prevent the roll, rotation, and/or rocking of the firing member assembly.

In various instances, the channel/anvil camming flanges, or pins, comprise width and length that is configured to be tuned relative to their corresponding slots through which they are received. In at least one instance, the greater the length of the flange along the longitudinal axis, the less clearance is required within its corresponding camming slot. In other words, the corresponding camming slot may comprise a geometry to more tightly receive the flange. On the other hand, the lesser the length of the flange along the longitudinal axis, the greater the clearance required within its corresponding camming slot. In other words, the corresponding camming slot may comprise a geometry to more loosely receive the flange. In at least one instance, an ideal length of one or more of the flanges may comprise about twice the width of the primary body portion of the firing member assembly. Notably, the thickness of the of primary body portion is synonymous with the portion of the primary body portion configured to travel through the longitudinal staple cartridge slot.

In various instances, drive nuts disclosed herein are configured to float up and down relative to the primary body portion of the firing member assembly, up and down and side to side relative to the primary body portion of the firing member assembly, and/or side to side relative to the primary body portion of the firing member assembly. The floating of the drive nut can reduce the likelihood of the drive screw binding with various other components. As discussed above, a drive nut may be rigidly welded to a primary body portion in certain instances.

In various instances, the various components of the surgical stapling assemblies disclosed herein can be assembled in a particular order so as to prevent inadvertent disassembly. For example, various components can be introduced during assembly after the firing member assembly is introduced, which would otherwise tend to fall out or be disassembled inadvertently without a holding force in the assembly provided by flanges of the firing member assembly, for example. Components and sub-assemblies in addition to or other than the firing member assembly may also provide assembly holding forces, for example. For example, a drive screw can be pre-loaded, as discussed herein, and can provide an internal assembly holding force during assembly. The drive screw may be installed into the surgical stapling assembly prior to various other components. In certain instances, the above-discussed assembly holding forces could actually encourage inadvertent disassembly of one or more components. In such instances, such components would be installed after certain components so as to ensure that, when such components are installed, the entire assembly at that point in time can maintain an assembled state so as to reduce the likelihood of inadvertent disassembly.

In at least one instance, a plastic and/or metal injection molded (MIM) drive nut of a firing member assembly can first be assembled to the primary body portion of the firing member assembly. Once the drive nut is positioned, then a drive screw can be threaded into the drive nut through corresponding ducts of the primary body portion. Assembling in such a manner allows the drive screw to couple the drive nut and primary body portion of the firing member assembly so as to prevent inadvertent disassembly of the drive nut and the primary body portion.

Further to the above, the drive screw ends can then be coupled to their corresponding supports with their corresponding attachment means. For example, any bearings and/or springs used, for example, can all be assembled at this time. This would prevent the firing member assembly from running off of the proximal end or distal end of the drive screw. Additionally, should the firing member assembly be overdriven, for example, the thrust bearings would already be presented and the firing member assembly would predictably deflect a channel for example, through the thrust bearing and/or channel support flange, for example, rather than abnormally loading only the thrust bearing and or distal head portion of the drive screw, for example. If the firing member assembly is advanced into a thrust bearing and/or distal head portion of the drive screw, the firing member assembly may exert an unexpected load onto the thrust bearing and/or distal head portion of the drive screw and possibly cause premature failure of the thrust bearing and/or distal head portion, for example. This can be attribute to not being assembled to their corresponding channel support flanges, for example, with which the ends of the drive screw are designed to interact and cooperatively load. Without the channel flanges and the channel, for example, a distal head portion of a drive screw can be sheared off if prematurely loaded prior to the installation of the drive screw into the channel support flanges, for example.

In at least one instance, a firing member assembly is advanced beyond its distal-most position during actual operation of a surgical stapling assembly on the drive screw so that the flanges of the firing member assembly can be inserted within their corresponding slots in the anvil, channel, and/or staple cartridge, for example. Once the flanges are aligned with their corresponding slots, the drive screw can be rotated to move the firing member assembly proximally thereby moving the flanges into their corresponding slots. As such point, the drive screw can then be seated within its support flanges, for example. In at least one instance, using such a sequential assembly method can prevent the flanges from coming loose out of their respective slots during assembly, for example.

In at least one instance, the various supports positioned within the proximal end of an end effector assembly are configured to support a proximal end of a firing drive screw and are configured to support a closure drive screw interlock with a cartridge channel, for example. In such an instance, an anvil can be introduced to the end effector assembly and pinned to the cartridge channel with a pivot pin after the various supports are positioned in the cartridge channel. The pivot pin, itself, can prevent vertical decoupling loads from decoupling various components of the end effector assembly. In such an instance, lateral channel walls along with lateral tissue stops, lateral walls of the anvil configured to straddle the lateral channel walls upon clamping tissue, can prevent lateral decoupling loads from decoupling various components of the end effector assembly. In various instances, the end effector assembly is configured such that each component and sub-assembly is assemble-able and disassemble-able in one unique sequential manner. This would ensure that the system can be assembled in only one way which provides support and prevents inadvertent disassembly during assembly.

In various instances, one or more components of surgical stapling assemblies discussed herein can be 3D printed. More specifically, such components can be made using a graphite-based selective laser sintering process, which can be an additive manufacturing process allowing for complex geometries of parts while eliminating the need for expensive tooling. Specifically, thrust bearings and/or drive nuts of firing member assemblies can be manufactured using this process. In various instances, a drive nut can be 3D printed out of graphite and steel, for example. In at least one instance, between about 1% and about 5% of the component comprises graphite and the rest of the component comprises a steel material. In such an instance, the exposed graphite of the drive nut, for example, could provide a degree of lubrication within the threaded connection, for example.

Figure 82:
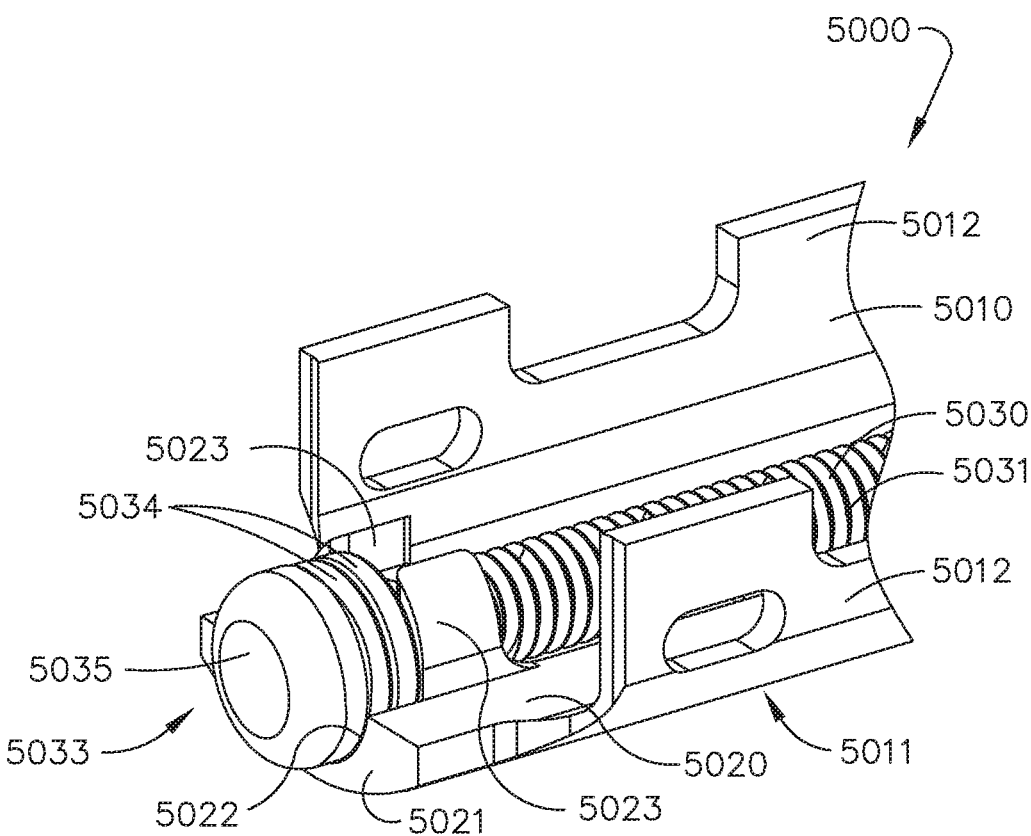
FIG. 82 is a perspective view of a surgical stapling assembly comprising a staple cartridge, a cartridge channel, and a firing drive assembly, wherein the staple cartridge is hidden in FIG. 82, in accordance with at least one aspect of the present disclosure.
Figure 83:
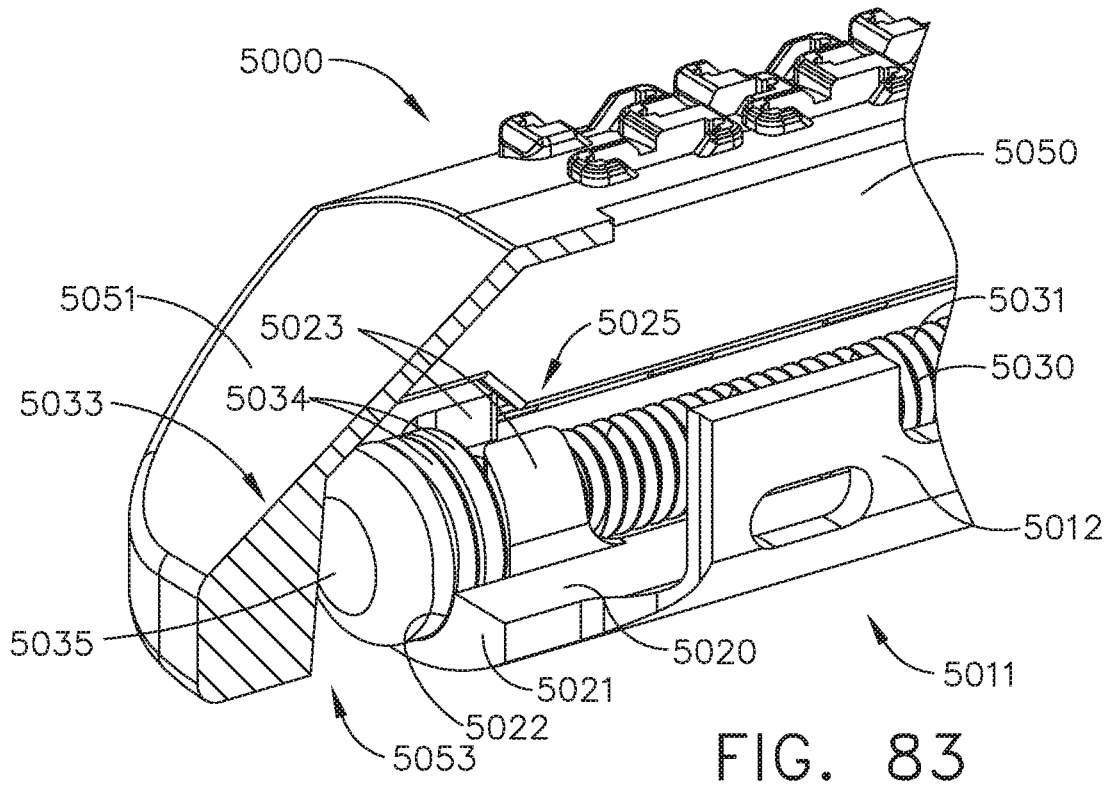
FIG. 83 is a partial cross-sectional perspective view of the surgical stapling assembly of FIG. 82, in accordance with at least one aspect of the present disclosure.
Figure 84:
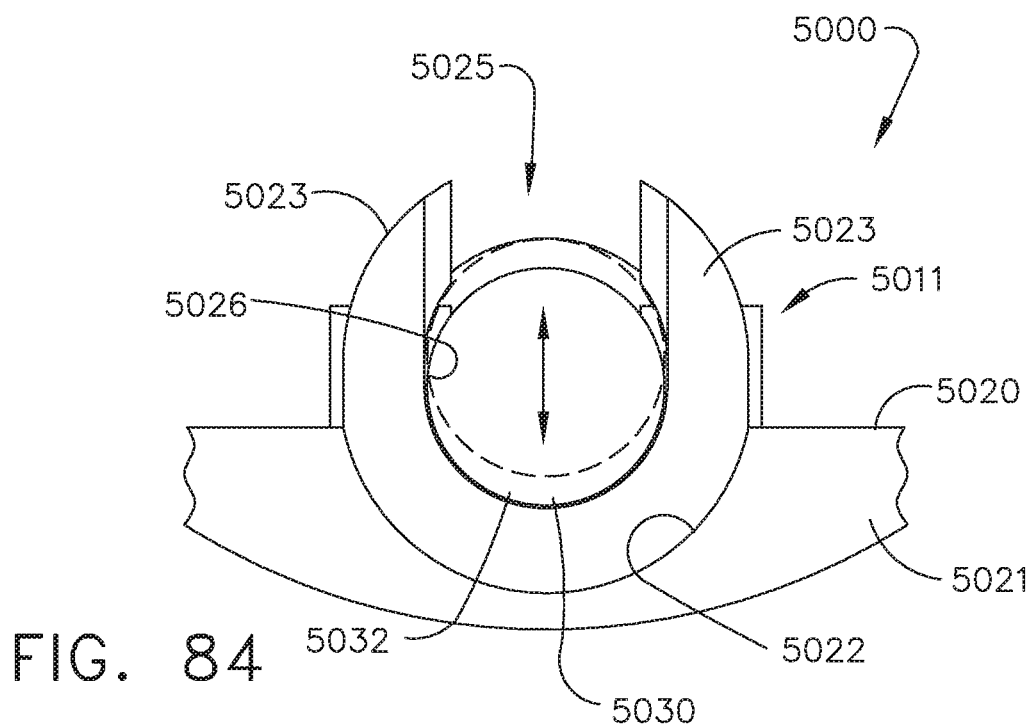
FIG. 84 is an elevation view of a portion of the cartridge channel and the firing member assembly of FIG. 82, wherein a distal support head and pair of bushings are hidden in FIG. 84, in accordance with at least one aspect of the present disclosure.

In various instances, firing member assemblies are configured to be driven by firing drive screws positioned within an end effector. The firing member assemblies and/or the firing drive screws can experience various loads during a firing stroke. For example, a firing member assembly can experience loads applied thereto by tissue as the firing member assembly is advanced through a firing stroke. The firing member assembly can be subject to various loads applied thereto by the firing drive screw itself. The firing member assembly can also experience loads generated by the engagement of camming flanges of the firing member assembly with a cartridge channel jaw and/or an anvil jaw. The firing drive screw can also be subject to various loads during various stages of use of an end effector assembly within which the screw is positioned. For example, the firing drive screw may be subject to bending loads owing to camming and/or clamping forces applied within the end effector assembly when the jaws are closed to clamp tissue and/or when tissue is further clamped by flanges of a firing member assembly during a staple firing stroke. Discussed herein are various arrangements configured to manage the various loads experienced by firing member assemblies and firing drive screws. Such arrangements can reduce binding of a firing drive screw with various components, for example. Such arrangements can also be employed with a closure drive system. For example, in various instances, an end effector assembly can comprise a separate closure drive screw configured to open and close a jaw relative to another jaw. In such instances, the closure drive screw can also be subject to various loads which may cause bending and/or binding with various drive components, for example FIGS. 82-84 depict a surgical stapling assembly 5000 comprising a cartridge channel 5010, a staple cartridge 5050 seated within the cartridge channel 5010, and a rotary drive assembly 5030 supported within the channel 5010. The cartridge channel 5010 comprises a distal portion 5011, a bottom 5020, and sidewalls 5012 extending vertically from the bottom 5020. The bottom 5020 comprises a distal end 5021, an annular cradle slot 5022 defined in the distal end 5021 of the bottom, and a pair of arcuate flanges 5023 extending upwardly from the bottom 5020. The arcuate flanges 5023 are configured to floatably support the rotary drive assembly 5030. Various features of the distal end 5021 comprise a distal mount, for example, of the drive screw 5031.

The rotary drive assembly 5030 comprises a threaded screw portion 5031 and a distal end 5033 supported by the distal portion 5011 of the cartridge channel 5010. The distal end 5033 of the rotary drive assembly 5030 comprises two thrust bearings, or bushings, 5034 for example, configured to contact the arcuate flanges 5023. The distal end 5033 further comprises a distal support head 5035 configured to support the thrust bearings 5034 against the arcuate flanges 5023. The distal support head 5035 may be formed using an orbital forming process on a distal end of a firing drive screw, for example. This forming process can take place, for example, after one or more bushings and/or bearings are positioned on the distal end of the firing drive screw.

The arcuate flanges 5023 define a float cavity 5025 therebetween in the distal portion 5011 of the cartridge channel 5010. A portion 5032 of the rotary drive assembly 5030 is configured to be supported within the float cavity 5025 such that the distal end 5033 of the rotary drive assembly 5030 is permitted to float within the float cavity 5025 upon deflection of the cartridge channel 5010, for example. In such an instance where the distal portion 5011 of the cartridge channel 5011 is deflected downwardly, the distal end 5033 of the rotary drive assembly 5030 can remain relatively unloaded by floating within the float cavity 5025. As can be seen in FIG. 84, the float cavity 5025 comprises a vertical slot portion 5026 configured to permit a predefined float distance, or vertical limit of floatation, of the drive assembly 5030 and/or portion 5032 of the rotary drive assembly 5030. The portion 5032 may be limited in its ability to float vertically within the float cavity 5025 by the flanges 5023, for example.

Embodiments are envisioned where there is no vertical limiting feature defined by the bottom 5020 of the cartridge channel 5010. In at least one instance, the annular cradle slot 5022 is configured to support the bushings 5034 and/or the distal support head 5035. In at least one instance, the annular cradle slot 5022 defines a lower vertical limiting feature, or stop, configured to prevent the distal end 5033 of the rotary drive assembly 5030 from floating below a certain threshold defined by contact between the bushings 5034 and/or 5035 with the annular cradle slot 5022, for example. In at least one instance, the vertical slot portion 5026 and the flanges 5023 define an upper vertical limiting feature, or stop, configured to prevent the distal end 5033 of the rotary drive assembly 5030 from floating above a certain threshold defined by contact between the distal end 5033 and the flanges 5023.

As can be seen in FIG. 83, the staple cartridge 5050 comprises a distal nose 5051 defining a nose cavity 5053 therein. The nose cavity 5053 may provide space for the distal end 5033 of the rotary drive assembly to float within.

In at least one instance, a proximal end of the rotary drive assembly 5030 is fixed in place. In at least one instance, the proximal end of the rotary drive assembly 5030 is also configured to float relative to the cartridge channel 5010.

In at least one instance, a spring is provided at a proximal mounting location and/or distal mounting location of a firing drive screw within a cartridge channel, for example. The spring is configured to bias the firing drive screw into a neutral configuration. In at least one instance, the spring is configured to counteract bending loads applied to the firing drive screw. In at least one instance, one or more magnets are provided within a mounting location and a screw magnet of opposite polarity is provided on the firing drive screw at the mounting location. Such a configuration can bias the firing drive screw toward a neutral configuration as well as counteract bending loads applied to the firing drive screw. Such a spring may comprise a vertically deformable bushing, for example. In at least one instance, a coil spring is employed within the mounting location.

In various instances, the flexible floatation mounts described herein are configured to permit a limited vertical range of floatation of the rotary drive assembly relative to the cartridge channel. For example, a vertical floatation range of 0.0002-0.0003 inches can be permitted by the distal mounts described herein. In other instances, a vertical floatation range of 0.001 inches can be permitted and, in certain instances, of up to 0.0015 inches can be permitted by the flexible floatation mounts. The size of the vertical floatation range can be configured to avoid lateral loads being applied to the rotary drive assembly, which is well-suited for tension loads but may result in bending under lateral loads. Instead, the rotary drive assembly can float within the limited vertical range of floatation to ensure the rotary drive assembly is not laterally loaded. Even when thick and/or tough tissue is clamped between the jaws and the anvil is bowed in the clamped configuration, the vertical range of floatation can allow shifting of the rotary drive assembly and avoid lateral loads on the rotary drive assembly.

In at least one instance, flanges of a firing member assembly are configured to define the limited vertical range of floatation of a firing drive screw through the threaded connection between the firing member assembly and the firing drive screw. For example, an anvil-engaging flange may contact an upper portion of an anvil slot and/or a channel-engaging flange may contact an upper portion of a channel slot to provide an upper stop for the firing drive screw. Further to the above, the anvil-engaging flange may contact a lower portion of the anvil slot and/or the channel-engaging flange may contact a lower portion of the channel slot to provide a lower stop for the firing drive screw. In at least one instance, a drive nut cutout, drive cavity, and/or receptacle configured to receive a drive nut is configured to further define the vertical range of flotation of a firing drive screw.

Figure 85:
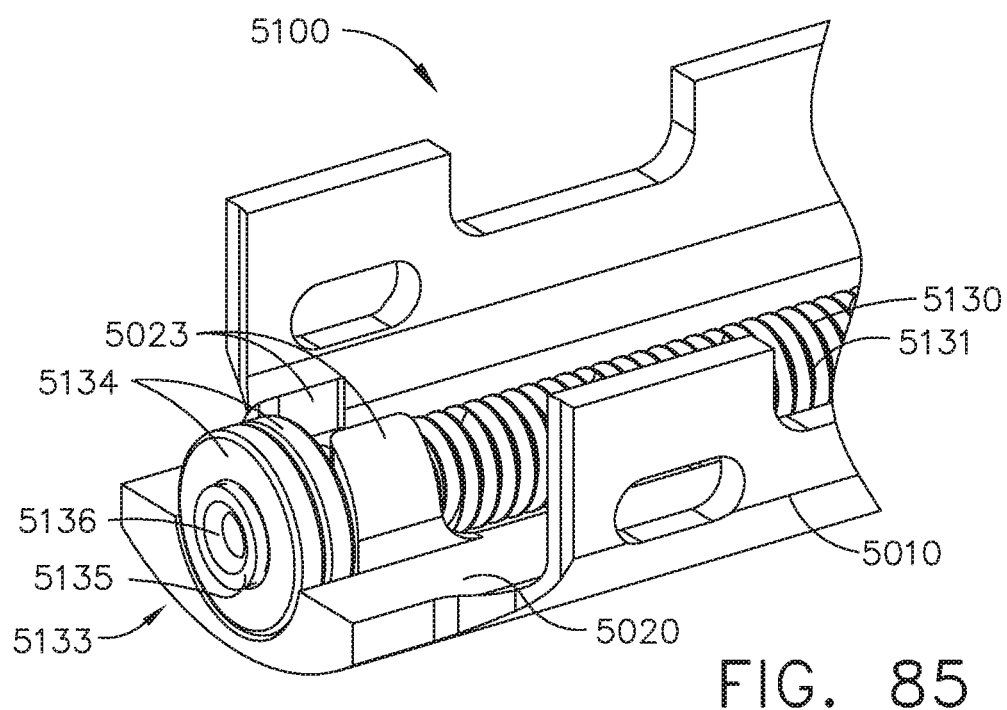
FIG. 85 is a perspective view of a surgical stapling assembly comprising a cartridge channel and a firing member assembly supported by support flanges of the cartridge channel, in accordance with at least one aspect of the present disclosure.

FIG. 85 depicts a surgical stapling assembly 5100 comprising the cartridge channel 5010 of the surgical stapling assembly 5000. The surgical stapling assembly 5100 comprises a rotary drive assembly 5130 comprising a threaded portion 5131 and a distal end 5133. The distal end 5133 comprises one or more bearings 5134 configured to support the distal end 5133 against the flanges 5023. The distal end 5133 further comprises a distal support head 5135 comprising a swaged screw end 5136. The swaged screw end 5136 may be externally swaged and/or internally swaged. The swaged screw end 5136 is configured to provide a distal bearing surface for the one or more bearings 5134. The rotary drive assembly 5130 is configured to float within the cartridge channel 5010 similar to the rotary drive assembly 5030.

Any suitable bushings and/or bearings can be employed with any of the various rotary drive assemblies and/or firing drive screws disclosed herein. In at least one instance, a compression bushing can be used at a proximal or distal end of a firing drive screw within a cartridge channel. Such a compression bushing can provide a compressive pre-load to a firing drive screw, for example, once installed in a cartridge channel. Such a compressive pre-load can prevent the firing drive screw from disengaging from any support elements supporting the firing drive screw in the cartridge channel. For example, a compression bushing can be used at one more ends of the firing drive screw to prevent the proximal end and/or distal end of the firing drive screw from disengaging from a corresponding support such as, for example, arcuate flanges extending from the cartridge channel.

A compressive pre-load can be induced by a spring, a longitudinal screw, and/or a rivet, for example, on a compression bushing. In such an instance, the compression bushing will tend to expand radially under a compressive pre-load. Such radial expansion can fill an annular cradle support and/or float cavity such as those discussed herein. This tendency for the compression bushing to fill such slots and/or cavities, for example, can help prevent the firing drive screw from longitudinally, laterally, and/or vertically de-seating from the support elements such as the arcuate flanges discussed herein.

In at least one instance, a bushing and/or bearing configure to support a rotary drive assembly disclosed herein comprises a flange extending radially outward therefrom. The flange is configure to be positioned on the side of the channel support flange opposite the distal support head of the firing drive screw. The radial flange can then be biased away from the channel support flange and, thus, the distal support head by a spring. In such an instance, the spring would push against the channel support flange and the radial flange of the bushing, for example. In such an instance, the radial flange and the spring can be configured to pull the distal support head into the channel support flange. In at least one instance, this pulling force applied to the distal support head can be configured to seat the distal support head such that the firing drive screw cannot be lifted directly out of the channel support flange without first pulling the firing drive screw distally and overcoming the force applied by the spring. Overcoming the force would then disengage the distal support head from the channel support flange only then allowing the firing drive screw to be lifted out of the channel support flange.

Further to the above, the spring can be compressed by a distal tightening screw configured to pull the distal support head proximally toward the channel support flange relative to the bushing comprising the radial flange, for example. Other embodiments are contemplated where a bearing is positioned distal to the channel support flange and then a nut is threaded onto the drive screw. The nut can then be turned to compress the bearing against the channel support flange.

Figure 86:
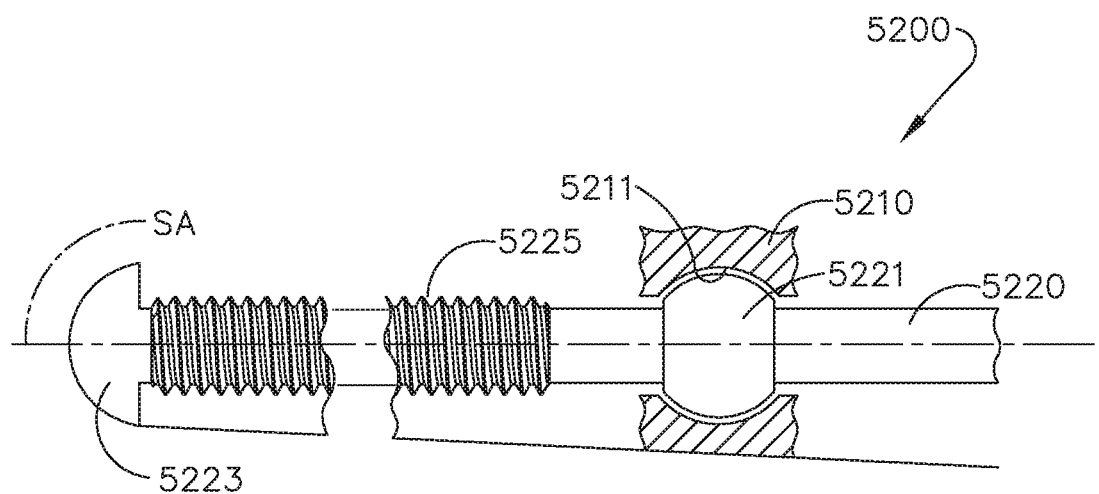
FIG. 86 is an elevation view of a portion of a surgical stapling assembly comprising a firing drive screw and a channel support, wherein a proximal end of the firing drive screw is pivotally mounted at the cartridge support, in accordance with at least one aspect of the present disclosure.
Figure 87:
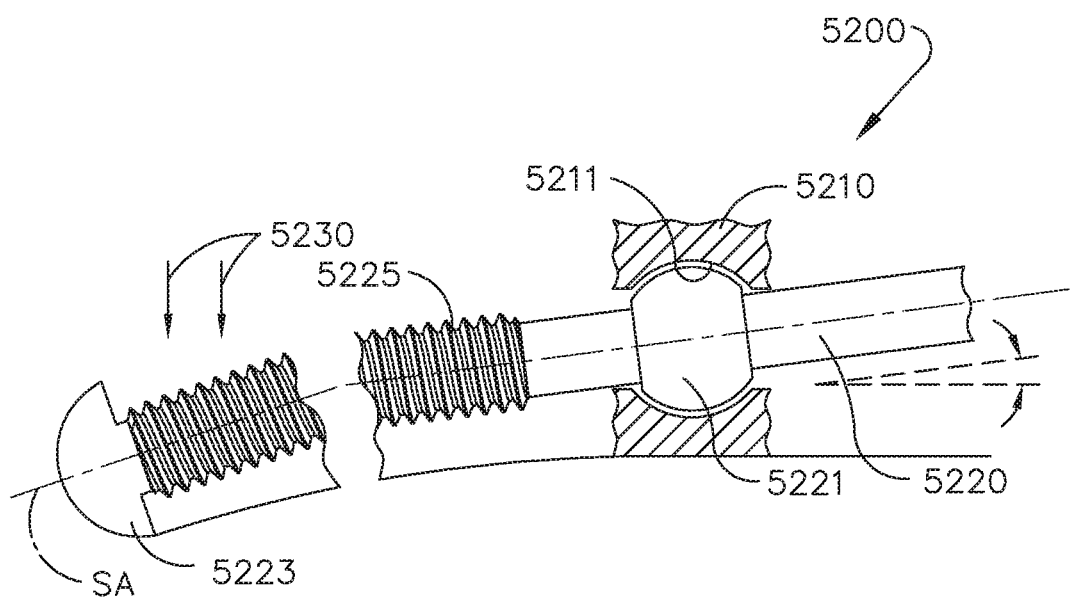
FIG. 87 is an elevation view of the portion of the surgical stapling assembly of FIG. 86, wherein the firing drive screw is illustrated in a loaded configuration, in accordance with at least one aspect of the present disclosure.

FIGS. 86 and 87 depict a surgical stapling assembly 5200 comprising a support channel 5210 and a firing drive screw 5220 configured to actuate a firing member assembly such as the firing member assemblies disclosed herein. The firing drive screw 5220 defines a screw axis SA. As discussed above, firing drive screws used within surgical end effector assemblies can be subject to bending loads. As can be seen in FIG. 87, arrows 5230 indicate a bending load being applied to a distal end 5223 of the firing drive screw 5220. The firing drive screw 5220 comprises a proximal ball joint 25221 mounted within a ball joint socket, or mount, 5211 of a channel support 5211. Such a configuration permits the firing drive screw 5220 to pivot relative to the channel support 5211 upon experiencing a bending load. In at least one instance, the ball joint 5221 and socket 5211 permit the firing drive screw 5220 to pivot without significantly bending the firing drive screw 5220. Bending can cause binding of the threaded portion 5225 and a firing member assembly, for example. The ball and socket joint can be finely tuned to permit a predefined amount of pivot so as to not permit the firing drive screw 5220 to pivot outside of the permitted predefined amount and possibly cause other issues within an end effector assembly. In at least one instance, the proximal mounting location of the firing drive screw 5220 comprises a radial and/or spherical shape to permit a slight rotation of the firing drive screw 5220 relative to the screw axis SA. Such a configuration can also prevent binding and/or gouging of the firing drive screw 5220 within the proximal mounting location.

In at least one instance, a proximal and/or distal end of a drive screw is support within a channel and/or anvil, for example, by way of more than one support flange extending from the channel and/or anvil. For example, the more than one support flange can comprise a plurality of flanges in series with each other. One or more corresponding thrust bearings of the drive screw can be configured to be supported against the more than one support flange. Such a configuration can help support the drive screw should the drive screw want to move proximally and distally, for example. In at least one instance, a separate thrust bearing is provided on the drive screw for each support flange extending from the channel and/or anvil, for example. In at least one instance, each thrust bearing is configured to engage only its corresponding support flange. In other instances, one thrust bearing is provided between two flanges where the one thrust bearing is configured to engage both flanges in a proximal direction and a distal direction. In such an instance, one or more additional thrust bearings can be provided proximal to both support flanges and/or distal to both support flanges. Such arrangements may provide multiple thrust surfaces as opposed to a single thrust surface for a drive screw.

In at least one instance, a thrust surface of a support flange, for example, comprises a recessed inner donut hole, for example. In such an instance, a thrust bearing of a drive screw can be configured to be received within the recessed inner donut hole. In at least one instance, a deformable thrust bearing is compressed into the recessed hole. In at least one instance, the deformable thrust bearing comprises a diameter which is greater than an outer diameter of the recessed hole. Such a configuration can provide additional support to the drive screw. In at least one instance, the deformable thrust bearing comprises a soft, low-density polyethylene washer. In at least one instance, the thrust bearing is compressed using an orbital forming process. In at least one instance, the thrust bearing can comprise a threaded washer, for example.

In various instances, springs and/or magnets can be integrated in various components of an end effector assembly to allow various components of the end effector assembly to float and/or move relative to each other under load. For example, springs and/or magnets can be integrated in proximal and/or distal mount locations where a firing drive screw is supported by a cartridge channel, for example. Another example includes integrating springs and/or magnets in a firing member assembly to permit a drive nut thereof to float relative to a primary body portion, for example.

FIGS. 88-91 depict a firing member assembly 5300 configured to push a sled and/or cutting member through a staple firing stroke within an end effector assembly. The firing member assembly 5300 comprises a primary body portion 5010 and a threaded drive nut 5350 configured to be threadably coupled to a firing drive screw. The drive nut 5350 is configured to apply axial drive forces to the primary body portion 5010 to push and pull the primary body portion 5010 through an end effector assembly. The primary body portion 5010 comprises an upper portion 5311 configured to engage a first jaw of the end effector assembly and a lower portion 5315 configured to engage a second jaw of the end effector assembly. The lower portion 5315 comprises a proximal portion 5316 and a distal portion 5320 each configured to non-threadably receive the firing drive screw therethrough. A drive nut cavity 5330 is defined between the proximal portion 5316 and the distal portion 5320 which is configured to receive the drive nut 5350 therein. The firing member assembly 5300 further comprises magnetic elements 5360 configured to couple the drive nut 5350 to the primary body portion 5310.

The magnetic elements 5360 can comprise cylindrical rods, or pins, and/or rectangular rods, or pins, for example. Nonetheless, one of the magnetic elements 5360 is attached to and spring loaded by a spring 5361 within a proximal channel 5363 defined in the proximal portion 5316. Another one of the magnetic elements 5360 is attached to and spring loaded by a spring 5361 within a distal channel 5365 defined in the distal portion 5320. To mount the drive nut 5350 to the body portion 5310, the magnetic elements 5360 are retracted in their respective channels 5363, 5365 by externally presented magnets 5370 (FIG. 90) which are configured to overcome the spring force applied to the magnetic elements by the springs 5361. Only then can the drive nut 5350 be inserted into the drive nut cavity 5330. Once the drive nut 5350 is in position, the externally presented magnets 5370 may be moved away from the magnetic elements 5360 to allow the springs 5361 to bias the magnetic elements 5360 inwardly toward the drive nut 5350.

Specifically, the magnetic elements 5360 are configured to reside within a corresponding proximal channel 5351 defined in the drive nut 5350 and a corresponding distal channel 5355 defined in the drive nut 5350. The channels 5351, 5355 comprise a width and/or diameter which is greater than the width and/or diameter of the magnetic elements 5360. This difference in size allows the drive nut 5350 to float relative to the primary body portion 5310. The amount of floatation of the drive nut 5350 relative to the primary body portion 5310 may be defined and limited, at least in part, by the difference 5371 in size of the magnetic elements 5360 and the channels 5351, 5355. In at least one instance, one of the width and/or height is substantially the same as the width and/or height of the magnetic elements 5360. Such a configuration will permit floatation of the drive nut in only one plane. For example, if the vertical height of the magnetic elements 5360 and the drive nut channels 5351, 5355 are substantially the same and the width of the drive nut channels 5351, 5355 are greater than the width of the magnetic elements 5360, the drive nut 5350 is permitted to float only horizontally, or laterally, with respect to the primary body portion 5310. On the other hand, where the widths are substantially the same and the vertical heights differ, the drive nut 5350 is permitted to float only vertically with respect to the primary body portion 5310. Any floatation may be ultimately limited by the size of drive screw ducts of the proximal portion 5316 and the distal portion 5320, as discussed in greater detail above.

In at least one instance, the channels, or pockets, 5363, 5365 may be machined into a metal primary body portion. In at least one instance, the channels, or pockets, 5351, 5355 may be part of an injection mold when manufacturing the drive nut 5350. In at least one instance, the magnetic elements 5360 can comprise steel pins, for example. In at least one instance, the arrangement discussed above can reduce the need for exact alignment of an internal threaded channel defined in the drive nut to be coupled with the firing drive screw with corresponding drive screw ducts of the primary body portion. In such an instance, if the internal threaded channel is molded slightly off center with respect to the corresponding drive screw ducts of the primary body portion, the magnetic element arrangement discussed above can permit the drive nut 5350 to float into alignment with the primary body portion 5310. The flotation of the drive nut 5350 may also help prevent binding of the drive nut 5350 and a firing drive screw, for example. In at least one instance, a third degree of motion can be controlled and defined by the proximal portion 5316 and distal portion 5320 which can define the amount flotation, if any, which is permitted along a longitudinal axis relative to the primary body portion 5310.

In various instances, a firing drive screw can be configured so as to provide a compliant drive screw which can accommodate various loads experienced by the firing drive screw and reduce the likelihood of drive screw binding, for example. Such a compliant drive screw can automatically adapt and/or conform under different loaded conditions, for example. Such compliance may result in changing the shape of the drive screw itself, as discussed in greater detail below.

Figure 93:
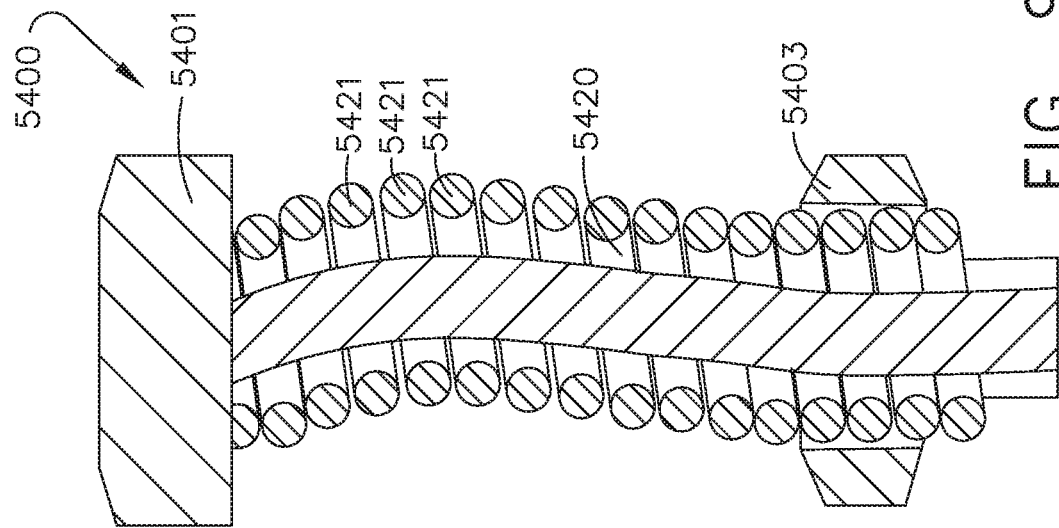
FIG. 93 is a cross-sectional schematic of the flexible firing drive screw of FIG. 92, in accordance with at least one aspect of the present disclosure.
Figure 92:
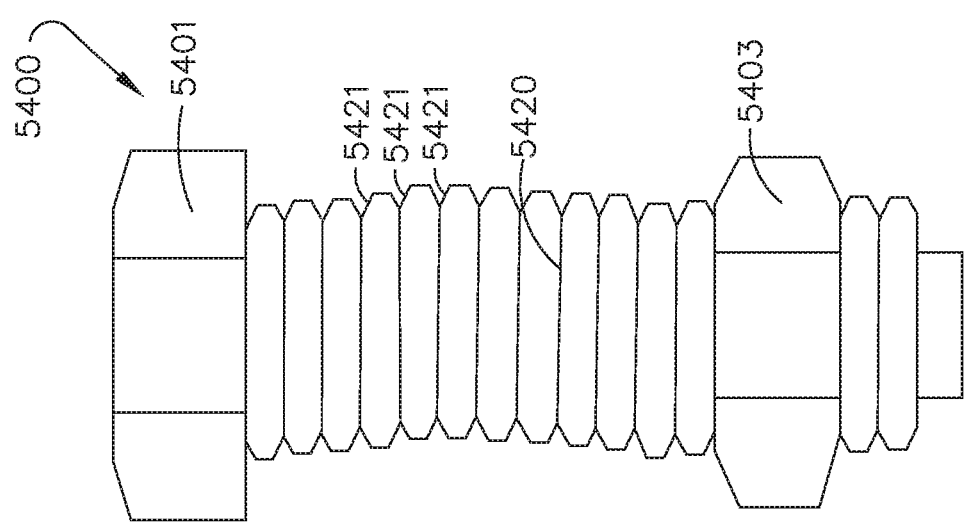
FIG. 92 is an elevation view of a flexible firing drive screw comprising a flexible core member and an outer helical member, in accordance with at least one aspect of the present disclosure.

FIGS. 92 and 93 depict a firing drive screw 5400 configured to automatically adapt under load. The firing drive screw 5400 comprises a cable or primary core member 5410 comprising a proximal end 5401 and a distal end 5403. The distal end 5403 may comprise a flange portion extending directly therefrom and/or a press fit thrust bearing, for example. The firing drive screw 5400 also comprises a spring or helical member 5420 defining individual threaded sections 5421 configured to provide a threaded interface for a threaded firing member assembly, for example. The primary core member 5410 comprises a flexible material such that the primary core member 5410 can flex and adapt its shape under load. Along with the primary core member 5410, the helical member 5420 also comprises a flexible material such that the helical member 5420 can flex along with the primary core member 5410 under load. This flexibility of the core member 5410 and the helical member 5420 allows the individual threaded sections 5421 to shift relative to each other. Each individual threaded section 5421 can shift relative to one another. However, the threaded sections 5421 can be configured to shift semi-independently. Such a configuration can permit slight shifting of each member 5421; however, all of the threaded sections 5421 are part of the single helical member 5420 so shifting of one threaded section 5421 can cause some shifting of one or more adjacent helical members and so on. This can also be referred to as splaying of the threaded sections 5421 when the firing drive screw 5420 is under load. The firing drive screw 5420 can reduce the likelihood of drive screw binding under load. In various instances, the primary core member 5410 and the helical member can comprise different materials. Although the schematic cross-sectional view of FIG. 93 depicts a space or gap between the inside diameter of the helical member 5420 and the outside diameter of the primary core member 5410, in other instances the inside diameter of the helical member 5420 is in contact and/or abutting the outside diameter of the primary core member 5410.

Figure 94:
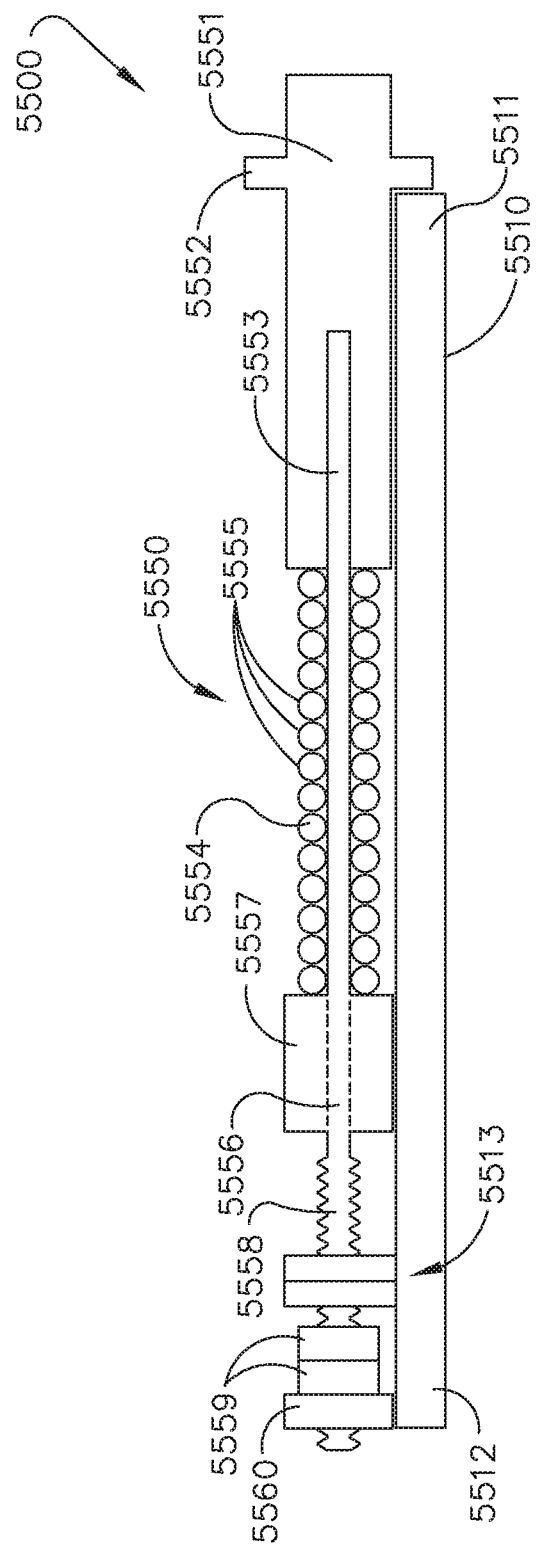
FIG. 94 is a schematic representation of a firing assembly comprising a flexible firing drive screw, in accordance with at least one aspect of the present disclosure.

FIG. 94 is a schematic representation of a firing assembly 5500 comprising a flexible firing drive screw 5550. The firing drive screw 5550 may comprise many similarities to the firing drive screw 5400, for example, among other disclosed herein. The firing assembly 5500 comprises a firing drive screw 5550 mounted to a channel frame 5510. A proximal drive member, or solid bushing, 5551 of the firing drive screw 5550 comprises a flange 5552 configured to be supported by a proximal end 5511 of the channel frame 5510. A distal portion 5556 of the firing drive screw 5550 is configured to be support by a distal support flange 5513 extending from the channel frame 5512. The firing drive screw 5550 further comprises a flexible core member 5556 and a helical member 5554 surrounding the flexible core member 5556 and defining threaded sections, or regions, 5555. The helical member 5554 is attached to the proximal drive member 5551 and a sleeve/plug 5557 is fixedly attached to the distal portion 5556 of the firing drive screw 5550. For example, proximal drive member 5551 can be swaged onto the flexible core member 5556 of the firing drive screw 5556. The distal portion 5556 comprises a threaded section 5558, bushings 5559, and a distal nut 5560 threadably coupled to the threaded section 5558. A pair of bushings 5559 are positioned proximal to the distal nut 5560 in the socket and can sandwiched between the distal nut 560 and the distal support flange 551 (see, e.g. bearings 5034 in FIG. 82).

In at least one instance, the inner diameter of the helical member 5554 is configured to surround and contact an outer diameter of the flexible core member 5553. The helical member 5554 may comprise a type of coil spring, for example. The flexible core member 5553 may comprise a flexible cable, for example. In at least one instance, the helical member 5554 is manufactured with an inner diameter that is less than the outer diameter of the flexible core member 5553. In such an instance, the helical member 5554 can be counter-rotated to increase its inner diameter for assembly onto the flexible core member 5553. Once the helical member 5554 is positioned on the flexible core member 5553, the helical member 5554 can be released. Once the helical member 5554 is released, it will bias back to its neutral, non-loaded configuration and synch, or pinch, itself tightly to the flexible core member 5553. In at least one instance, the helical member 5554 is welded to the flexible core member 5553 at various locations along the length of the flexible core member 5553.

In at least one instance, the nut 5560 is configured to be tightened and/or loosened to provide the desired configuration of the helical member 5554. Tightening and/or loosening the nut 5560 can also allow for adjustment of tension of the flexible core member 5553. Adjusting the tension of the flexible core member 5553 can directly correlate to the amount of deflection permitted of the flexible core member 5553 along its length under load. A tighter cable may permit less flexion than a looser cable, for example. This can be tuned during manufacturing to a desired tension, for example. Embodiments are envisioned where it is tuned differently for different size cartridges and/or surgical stapling systems requiring different firing forces, for example.

In various instances, a firing drive screw is provided that is configured to minimize plastic deformation thereof under various loads. Such a firing drive screw can comprise variations in cross-sectional geometry along its longitudinal length. Such variations can result in a portion of a firing drive screw which is more flexible than an adjacent portion of the firing drive screw. The more flexible portion of the firing drive screw may be subject to greater bending loads than the less flexible portion, for example. Variations of the firing drive screw can be located at a proximal portion, an intermediate portion, a distal portion, or any combination thereof. Locations of variations can depend on application and areas of the firing drive screw subject to the highest loads, for example.

Figure 95:
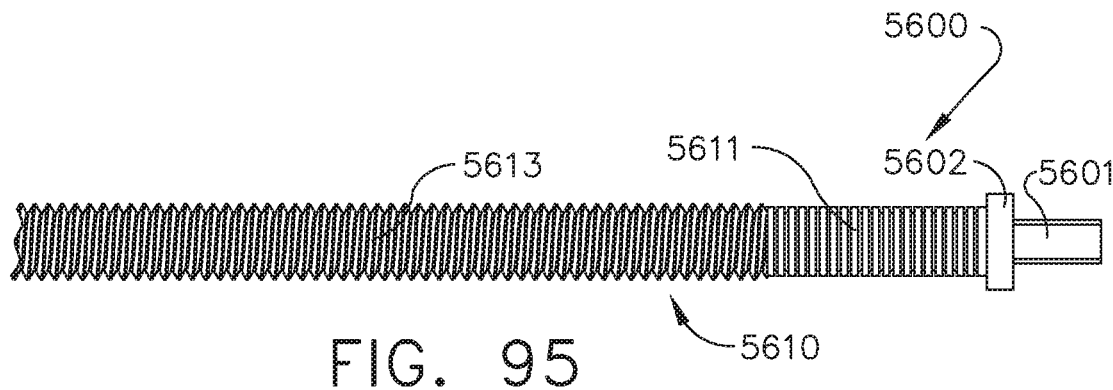
FIG. 95 is an elevation view of a portion of a firing drive screw for use with a surgical stapling assembly, in accordance with at least one aspect of the present disclosure.

FIG. 95 depicts a firing drive screw 5600 configured to be used with a surgical stapling assembly such the surgical stapling assemblies discussed herein. The firing drive screw 5600 comprises a proximal driven end 5601 configured to be attached to a rotary drive shaft. The firing drive screw 5600 also comprises a proximal flange 5602 configured to be supported within a frame component of an end effector assembly, for example. The firing drive screw 5600 comprises a screw shaft 5610 comprising a primary threaded portion 5613 and a proximal necked down portion 5611. The proximal necked down portion 5611 comprises a smaller cross-sectional diameter than the primary threaded portion 5613. Such a variation in the cross-sectional diameter can permit slight bending of the necked down portion 5611 to reduce the over bending effect on the primary threaded portion 5613. Reducing the bending effect on the primary threaded portion 5613, where a firing member assembly is configured to be threadably driven proximally and distally relative thereto, can reduce the likelihood of drive screw binding in the section of the firing drive screw 5600 engaged with the firing member assembly. In at least one instance, a firing member assembly is also configured to threadably travel through the necked down portion 5611; however, in at least one instance, high drive forces may not be required through the length of the stroke that consists of the necked down portion 5611.

Figure 96:
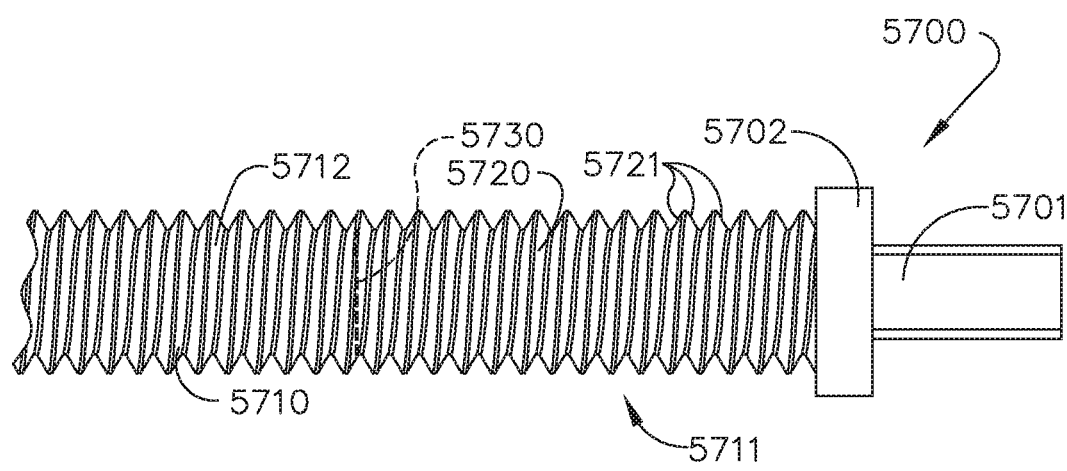
FIG. 96 is an elevation view of a portion of a firing drive screw for use with a surgical stapling assembly, wherein the firing drive screw comprises an overmolded section of threads, in accordance with at least one aspect of the present disclosure.
Figure 97:
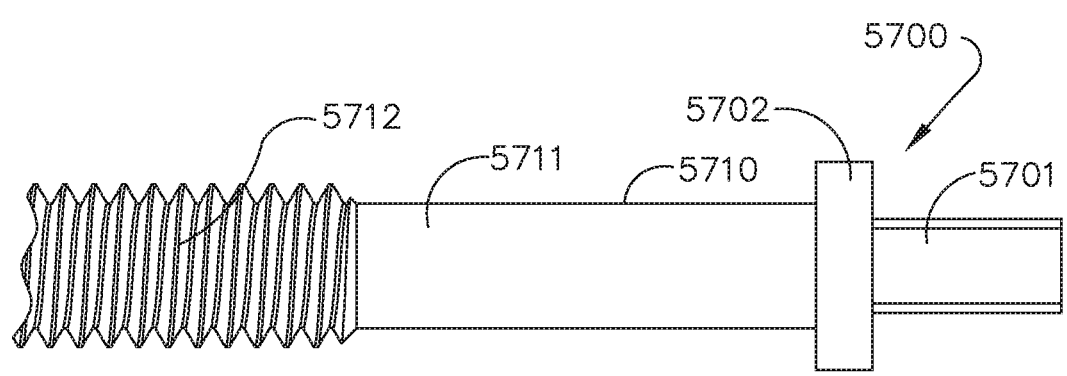
FIG. 97 is an elevation view of a portion of the firing drive screw of FIG. 96, wherein the overmolded section of threads are removed for clarity, in accordance with at least one aspect of the present disclosure.

FIGS. 96 and 97 depict a firing drive screw 5700 comprising a proximal driven end 5701 and a mounting flange 5702. The firing drive screw 5700 further comprises a proximal section 5720 of threads 5721 which is overmolded and/or insert molded, for example, onto a proximal portion 5711 of a primary shaft 5710 of the firing drive screw 5700. The firing drive screw 5700 comprises a primary threaded portion 5712, which comprises a cross-sectional diameter which is greater than the diameter of the proximal portion 5711. As discussed above, the variation in cross-sectional diameter can permit flexion of the primary shaft 5710 and localize the flexion to the proximal portion 5711 specifically so as to reduce the likelihood of drive screw binding with a drive nut of a firing member assembly. The threads 5721 can consist of a polymer material while the primary shaft 5710 consists of a metallic material, for example. The threads 5721 can help maintain a consistent thread pattern along a travel stroke of a firing member assembly threadably coupled to the firing drive screw 5700.

In at least one instance, various portions along the length of a firing drive screw comprise overmolded plastic threaded sections, for example. In at least one instance, various overmolded portions can accommodate manufacturing tolerance differences between a drive nut of a firing assembly and a firing drive screw thread profile and, in certain instances, can provide a more lubricious threaded engagement surface, for example. In at least one instance, a central section, midway through a firing stroke, section of a firing drive screw comprises a varied cross-sectional profile.

FIGS. 98-100 depict various types of shaft couplings 5810, 5820, 5830 that can be used with a firing drive screw such as those firing drive screws disclosed herein. The shaft couplings 5810, 5820, 5830 can be positioned at any location along the length of a firing drive screw to provide a location intended to localize bending of the firing drive screw. The shaft couplings 5810, 5820, 5830 are configured to convert rotary shaft motion from one shaft to another shaft. The shaft couplings 5810 can introduce little to no backlash in the firing drive screw with which it is employed. The shaft couplings 5810, 5820, 5830 can permit a degree of angular misalignment of shafts owing to bending forces applied to a firing drive screw within an end effector, parallel misalignment of shafts, and/or axial movement of shafts, for example.

The shaft coupling 5810 may be a beam coupling, for example. The coupling 5810 comprises a proximal hub 5811 configured to be attached to a distal end of a portion of a firing drive screw, a distal hub 5813 configured to be attached to a proximal end of another portion of a firing drive screw, and helical cutouts 5815 configured to flex during scenarios of shaft misalignment.

The shaft coupling 5820 may be a bellow coupling, for example. The coupling 5820 comprises a proximal hub 5821 configured to be attached to a distal end of a portion of a firing drive screw, a distal hub 5823 configured to be attached to a proximal end of another portion of a firing drive screw, and a flexible corrugation portion 5825 configured to flex during scenarios of shaft misalignment.

The shaft coupling 5830 may be a curved jaw coupling, for example. The coupling 5830 comprises a proximal hub 5831 configured to be attached to a distal end of a portion of a firing drive screw, a distal hub 5833 configured to be attached to a proximal end of another portion of a firing drive screw, and a spider gear comprising teeth 5835. The spider gear can comprise of a softer material configured to flex between the hubs 5831, 5833 while retaining drive engagement between the spider gear, the proximal hub 5831, and the distal hub 5833.

In an end effector assembly, such couplings 5810, 5820, and 5830 can permit bending of a firing drive screw at the coupling itself and reduce bending within the threaded shafts themselves. As discussed herein, bending of a threaded shaft can cause binding of a firing drive screw and a firing member assembly which are threadably coupled to each other.

Figure 101:
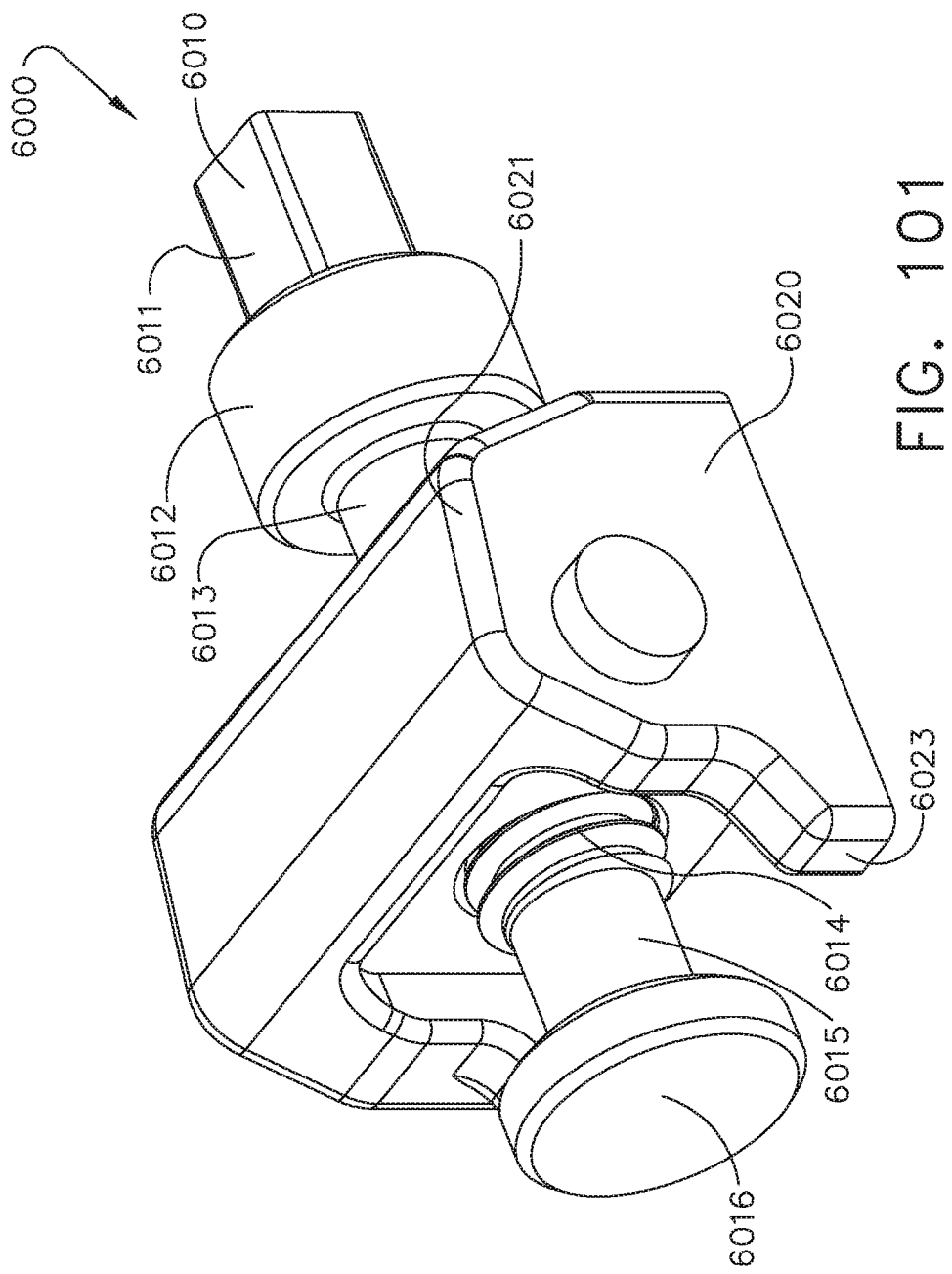
FIG. 101 is a perspective view of a closure drive assembly comprising a closure drive screw and a closure wedge configured to open and close a jaw of an end effector assembly, in accordance with at least one aspect of the present disclosure.
Figure 102:
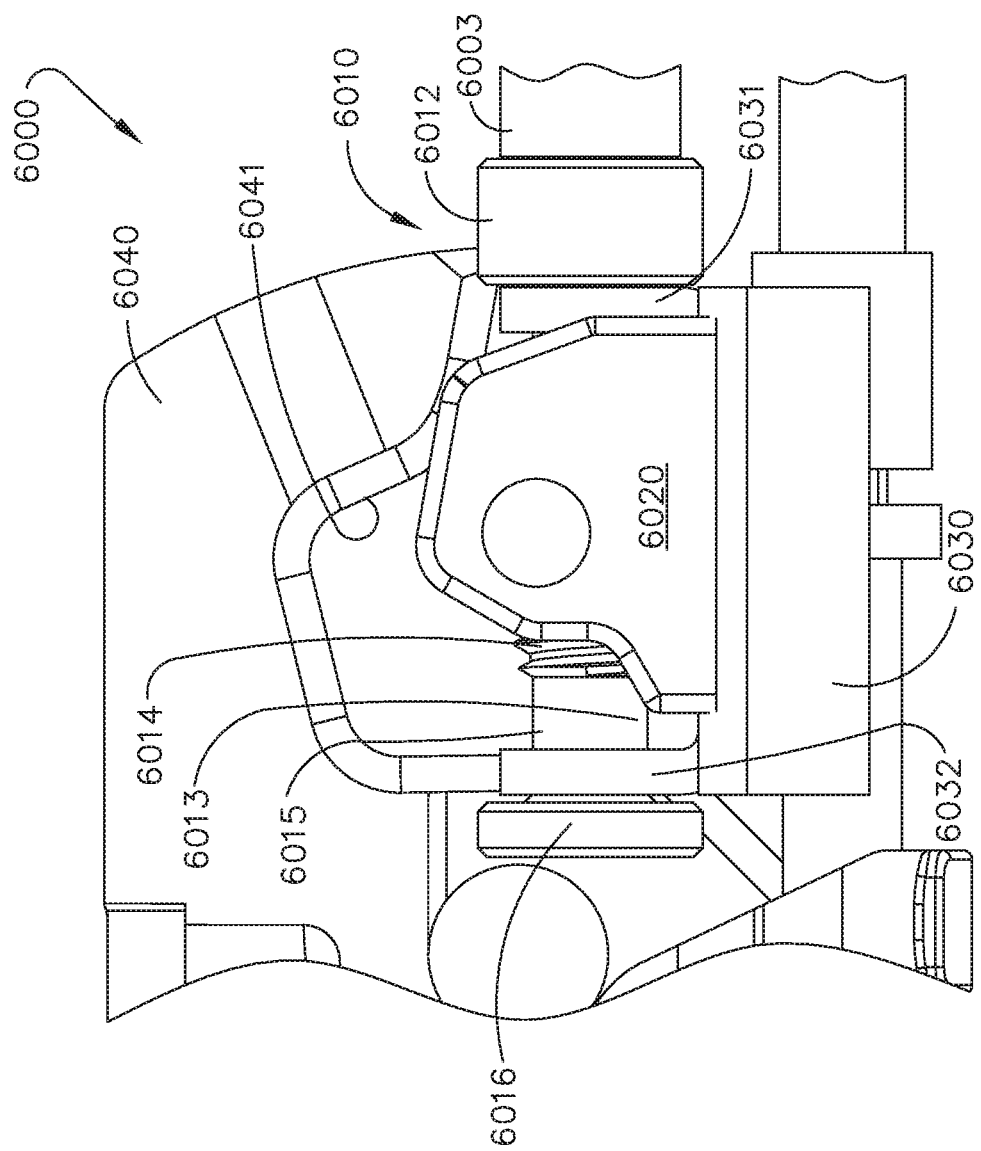
FIG. 102 is an elevation view of the closure drive assembly of FIG. 101 and an anvil, in accordance with at least one aspect of the present disclosure.
Figure 103:
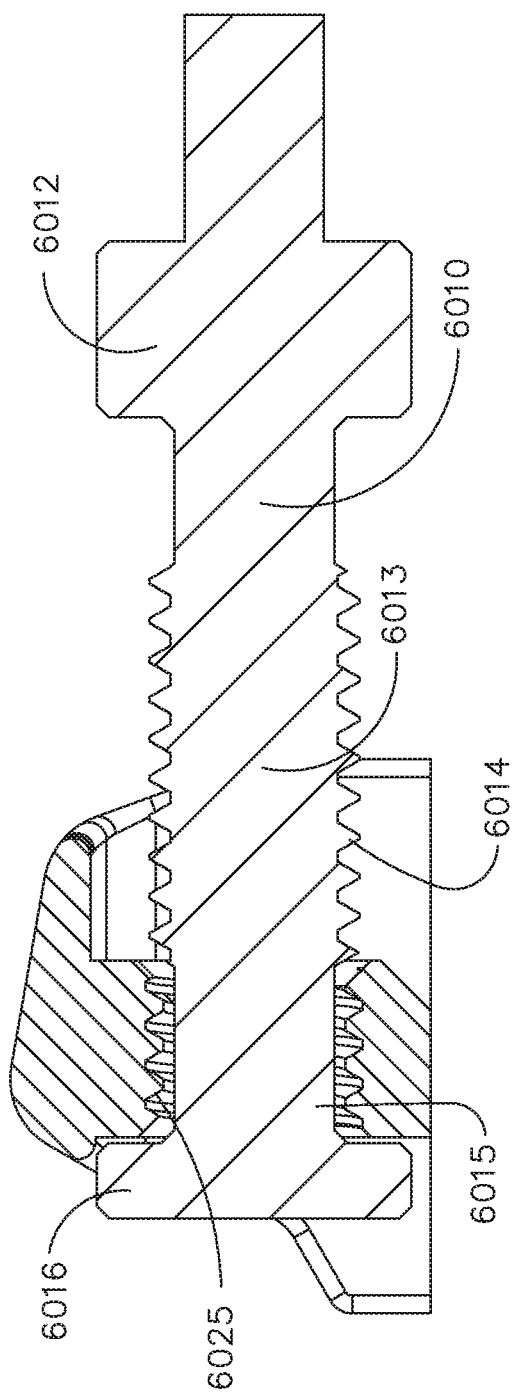
FIG. 103 is a cross-sectional elevation view of the closure drive assembly of FIG. 101, in accordance with at least one aspect of the present disclosure.

FIGS. 101-103 depict a closure drive assembly 6000 comprising a closure drive 6010 and a closure nut, or wedge, 6020 threadably coupled to the closure drive 6010. The closure nut 6010 is configured to open and close a jaw 6040 of the closure drive assembly 6000 relative to an opposing jaw with cam nubs 6023 and cam surface 6021, respectively. The closure drive assembly 6000 comprises a support element 6030 configured to support the closure drive 6010 thereon. The support element 6030 can be fixed to a channel retainer, for example. The support element 6030 comprises shaft seating flanges 6031, 6032 configured to support a closure drive screw 6013 of the closure drive 6010 therein. The closure drive 6010 further comprises a proximal driven portion 6010 configured to be driven by a rotary closure drive shaft, a thrust bearing 6012 configured to abut the flange 6031, and a distal thrust bearing portion 6016 configured to abut the flange 6032.

The closure drive screw 6013 comprises a threaded section 6014 and a distal non-threaded section 6015. The closure nut 6020 further comprises an internal threaded section 6025 configured to be threadably engaged with the threaded section 6014 such that the closure nut can be advanced proximally and distally along the threaded section to open and close the jaw 6003. In at least one instance, the closure nut 6020 is configured to be 3D printed onto the pre-manufactured closure drive 6010. The closure nut 6020 may comprise of a metal material and/or a polymer material, for example. The closure nut 6020 is configured to be printed around the distal non-threaded section 6015. Such an arrangement can allow the internal threaded section 6025 of the closure nut 6020 to be printed with an effective diameter which is slightly smaller than if the closure nut were printed directly around the threaded section 6015. Printed on the closure drive screw 6013, the closure nut 6020 can be effectively trapped between the bearing 6012 and bearing portion 6016 preventing inadvertent disassembly after manufacturing. In at least one instance, the bearing 6012 and the bearing portion 6016 are printed on the drive screw 6013 prior to printing of the closure nut 6020.

In at least one instance, one or more portions of the closure drive 6010 are also 3D printed. In such an instance, the closure drive 6010 can be 3D printed to be a size that is slightly larger than the desired size. For example, the closure drive 6010 can be scaled 0.5% larger than the desired size. In such an instance, various details of the closure drive 6010 requiring precise dimensions can be machined after the closure drive 6010 is printed. Such a manufacturing process can decrease machining waste and reduce the amount of time required to manufacture one or more parts, in certain instances. For example, a closure drive comprising a shaft with a non-threaded section and a threaded section where the non-threaded section comprises a diameter less than or equal to a minor diameter of the threaded section requires at least the removal of a ring of material with a width of the thread depth at the non-threaded section. 3D printing such a closure drive can allow the non-threaded section to be printed much closer to the minor diameter of the threads, albeit slightly larger for the reasons discussed above.

Figure 104:
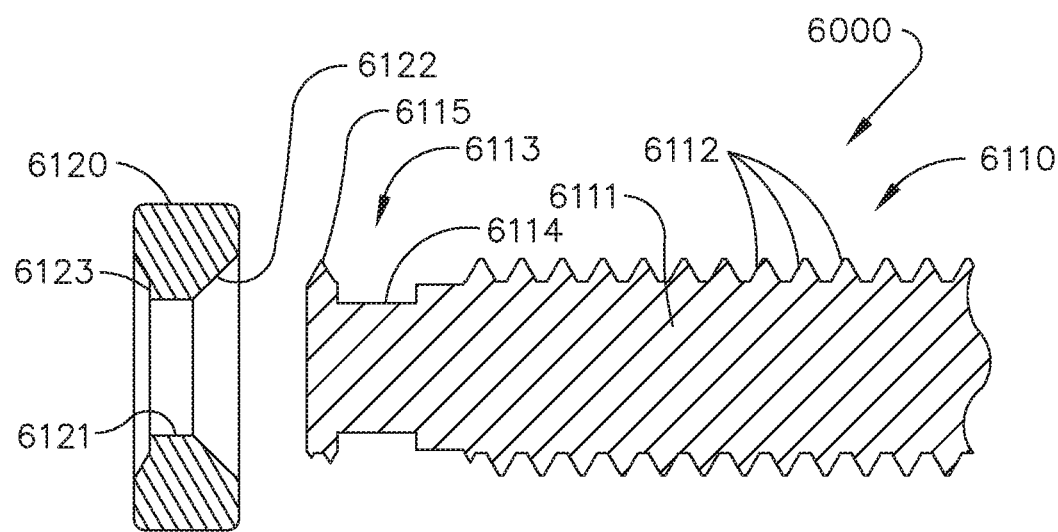
FIG. 104 is a cross-sectional elevation view of a closure drive comprising a drive screw and a restraining collar, wherein the restraining collar is not installed onto the drive screw, in accordance with at least one aspect of the present disclosure.
Figure 105:
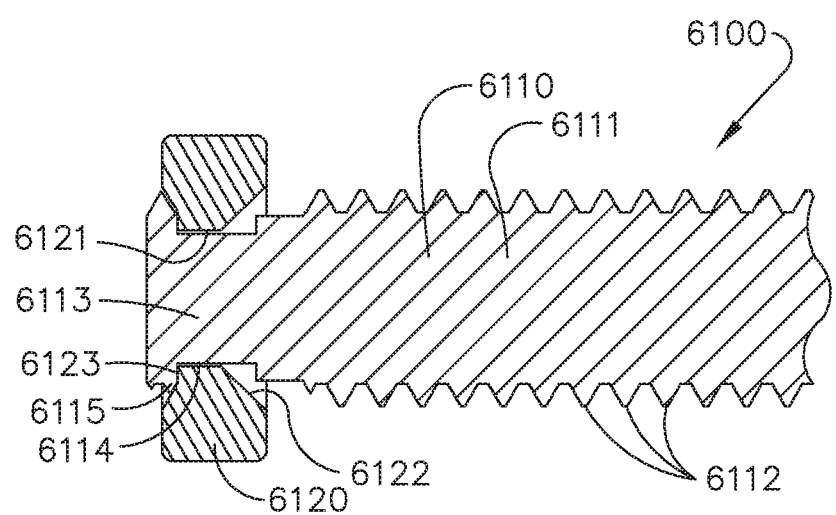
FIG. 105 is a cross-sectional elevation view of the closure drive of FIG. 104, wherein the restraining collar is installed onto the drive screw, in accordance with at least one aspect of the present disclosure.

FIGS. 104 and 105 depict a closure drive 6100 comprising a drive screw 6110 and a restraining collar 6120 configured to be secured to the drive screw 6110. The restraining collar 6120 can be similar to the distal thrust bearing portion 6016 of the closure drive 6010. The restraining collar 6120 can be configured to support the closure drive 6110 against a support flange, for example. The restraining collar 6120 may be referred to as a washer, a nut, and/or a flange, for example. The drive screw 6110 comprises a primary threaded portion 6111 comprising threads 6112. The primary threaded portion 6111 can be configured to drive a closure nut, for example, proximally and distally thereon to open and close a jaw of an end effector.

The drive screw 6110 further comprises a distal end 6113 comprising an annular slot 6114 and a thread 6115. The annular slot 6114 is configured to support the restraining collar 6120 therein. The thread 6115 is configured to permit the installation of the restraining collar 6120 as well as prevent the removal of the restraining collar 6120 from the drive screw 6110. The restraining collar 6120 comprises a proximal ramp surface 6122 defined therein. The proximal ramp surface 6122 is configured to permit the restraining collar 6120 to be screw onto the thread 6115 of the drive screw 6110 such that the restraining collar 6120 can clear the thread 6115 and fit an internal support surface 6121 to the annular slot 6114. Once installed onto the drive screw 6110, the thread 6115 resides distal to a distal, vertical, wall 6123 defined in the restraining collar 6120. The distal wall 6123 is configured to prevent the restraining collar 6120 from being pulled off of the distal end 6113 of the drive screw 6110.

In at least one instance, the drive screw 6110 is machined and/or 3D printed from a metallic material. In at least one instance, the restraining collar 6120 is molded and/or 3D printed from a polymer. In at least one instance, the restraining collar 6120 is constructed from a material which permits a degree of flexibility so as to allow the restraining collar 6120 to flex around and clear the thread 6115. A great degree of force may be required to install the restraining collar 6120 onto the drive screw 6110. In at least one instance, a greater degree of force may be required to remove the restraining collar 6120 from the drive screw 6110 at least owing the distal wall 6123.

In at least one instance, such a restraining collar can be used with a firing drive screw configured to threadably drive a firing member assembly. In various instances, such a restraining collar is used at a proximal end of a drive screw, a distal end of a drive screw, or both ends of a drive screw.

In at least one instance, a restraining collar is installed onto a drive screw with a lock washer. In such an instance, the thread and/or threads that the restraining collar is configured to be installed over can be configured so as to further tighten the locking engagement of the lock washer and the restraining collar when the drive screw is under load, for example. For example, each end of the restraining collar can comprise threads comprising opposite thread directions. For example, a proximal end of the restraining collar can comprise left handed threads and a distal end of the restraining collar can comprise right handed threads or vice-versa. Once installed, the restraining collar can be introduced to the opposite thread pattern such that, as the restraining collar is encouraged off of the distal end of the drive screw, the opposite thread pattern can serve to further tighten the locking engagement of the lock washer and restraining collar.

In at least one instance, a firing drive screw and/or closure drive screw can be 3D printed. In such instances, various features can be printed directly with the drive screw. For example, support flanges, bearings, restraining collars, etc., can be printed directly onto the drive screw. In at least one instance, one or more of these various features can comprise a different material than the drive screw itself. In such instances, the features comprising a material different than the drive screw can be printed directly onto the metal, for example, drive screw. In at least one instance, the various features comprise the same material as the drive screw. In such instances, the various metal, for example, features can be printed onto a metal drive screw using a process called directed energy deposition, for example. In at least one instance, various features can comprise a different material that, after printed, for example, onto the drive screw, can be welded to the drive screw.

In various instances, the use of different material features on the drive screw such as flanges, for example, can provide a lower coefficient of friction between the flange and a support structure as compared to a support structure and flange both comprising a metal material, for example. Manufacturing the features after the primary portion of the drive screw is machined, for example, can also reduce the manufacturing time and cost of the entire closure drive.

Figure 106:
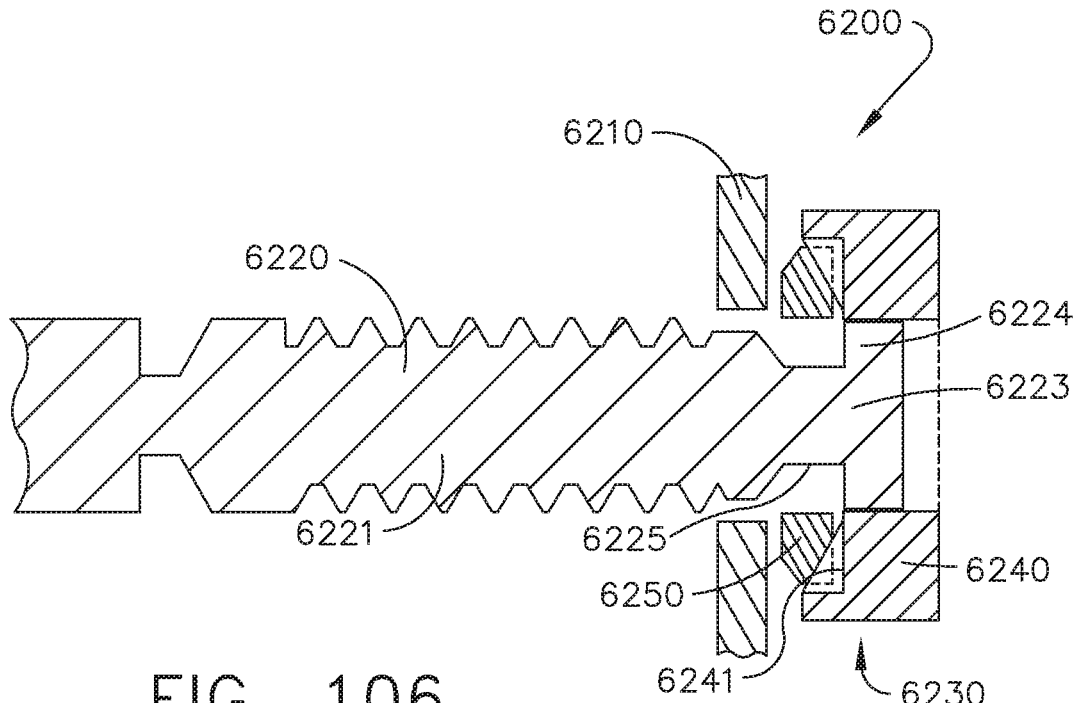
Figure 107:
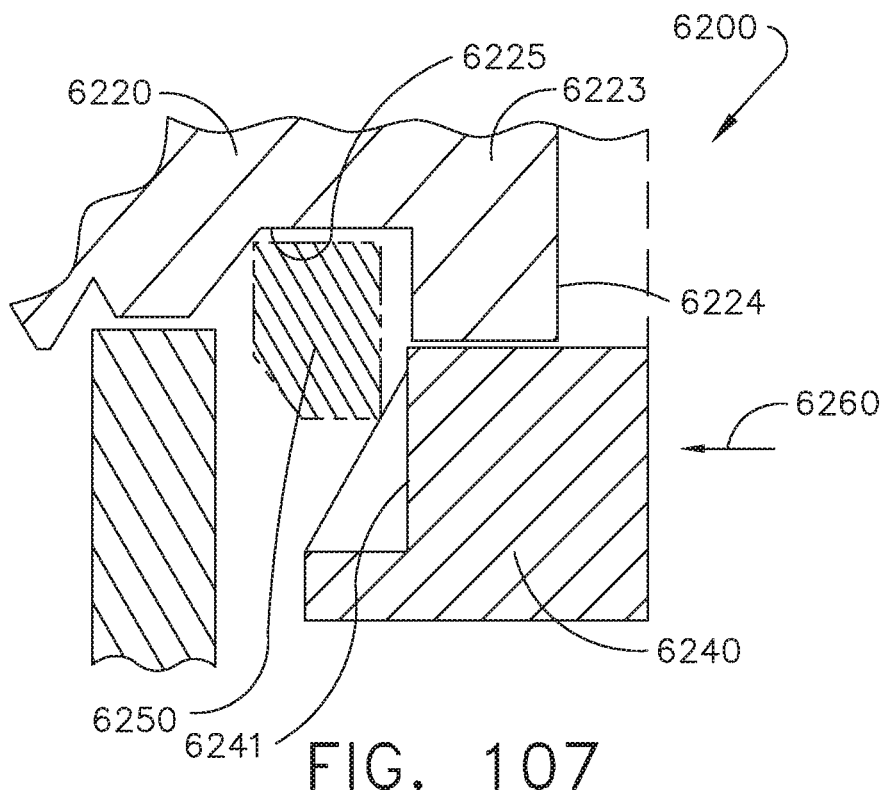

FIGS. 106 and 107 depict a drive assembly 6200 mounted to a channel flange 6210. The drive assembly 6200 comprises a drive screw shaft 6220 comprising a threaded portion configured to be threadably coupled to a firing member of a surgical stapling assembly. The drive screw shaft 6220 further comprises a distal end 6223 comprising a flanged end 6224 and an annular slot 6225. To secure the drive screw shaft 6220 to the channel flange 6210, a locking assembly 6230 is provided. The locking assembly 6230 comprises a distal nut 6240 and a locking member 6250. The locking member 6250 is configured to be locked into the annular slot 6225 to provide an abutment surface for the distal end 6223 of the drive screw shaft 6220 to be secured against. The distal nut 6240 can be threaded onto the distal end 6223 after the locking member 6250 is positioned on the drive screw shaft 6220 against the channel flange 6210. As the distal nut 6240 is tightened, or moved proximally toward the channel flange 6210, the locking member 6250 can comprise a flexible material so as to be urged into the annular slot 6225 by a ramped surface 6241 of the distal nut 6240. In at least one instance, the locking member 6250 is configured to mushroom and/or balloon in shape as pressure is applied thereto by the distal nut 6240. In at least one instance, the distal nut 6240 comprises a metal material. In at least one instance, the locking member 6250 comprises a deformable restraint for the drive screw shaft 6200. As a load is applied to the drive screw shaft in direction 6260, for example, the drive screw shaft 6220 is prevented from pulling proximally relative to the channel flange 6210 because of the expansion of the locking member 6250. The flanged end 6224 can transfer the load to the locking member 6250 which transfers the load to the channel flange 6210.

In at least one instance, a drive screw shaft such as those discussed herein can be manufactured using a subtractive manufacturing process such as, for example, a Swiss screw manufacturing process, for example. Such a manufacturing process can reduce material waste and manufacturing time of the drive screw, for example. Such a manufacturing process can also allow for high precision machining of such a relatively small drive screw where diameters along the length of such a drive screw shaft may vary and comprise relatively small differences in size.

In various instances, a locking member, such as the locking member 6250, for example, comprises a rubber material and/or a low-density polyethylene and/or polypropylene, for example. The material of the locking member can be selected based on its ability to shear under load such that, under a pre-determined threshold load, the locking member may shear to prevent other part failure within the system. Such a locking member can also automatically center a drive screw shaft as the locking member is installed by being uniformly restricted therearound.

In various instances, end effector assemblies such as those disclosed herein can comprise stackable supports configured to support one more drives of the end effector assembly. For example, one or more stackable supports are configured to support a closure drive and a firing drive which are non-concentric. The one or more stackable supports are configured to support one or more drives against a common frame element such as, for example, a channel jaw.

Figure 108:
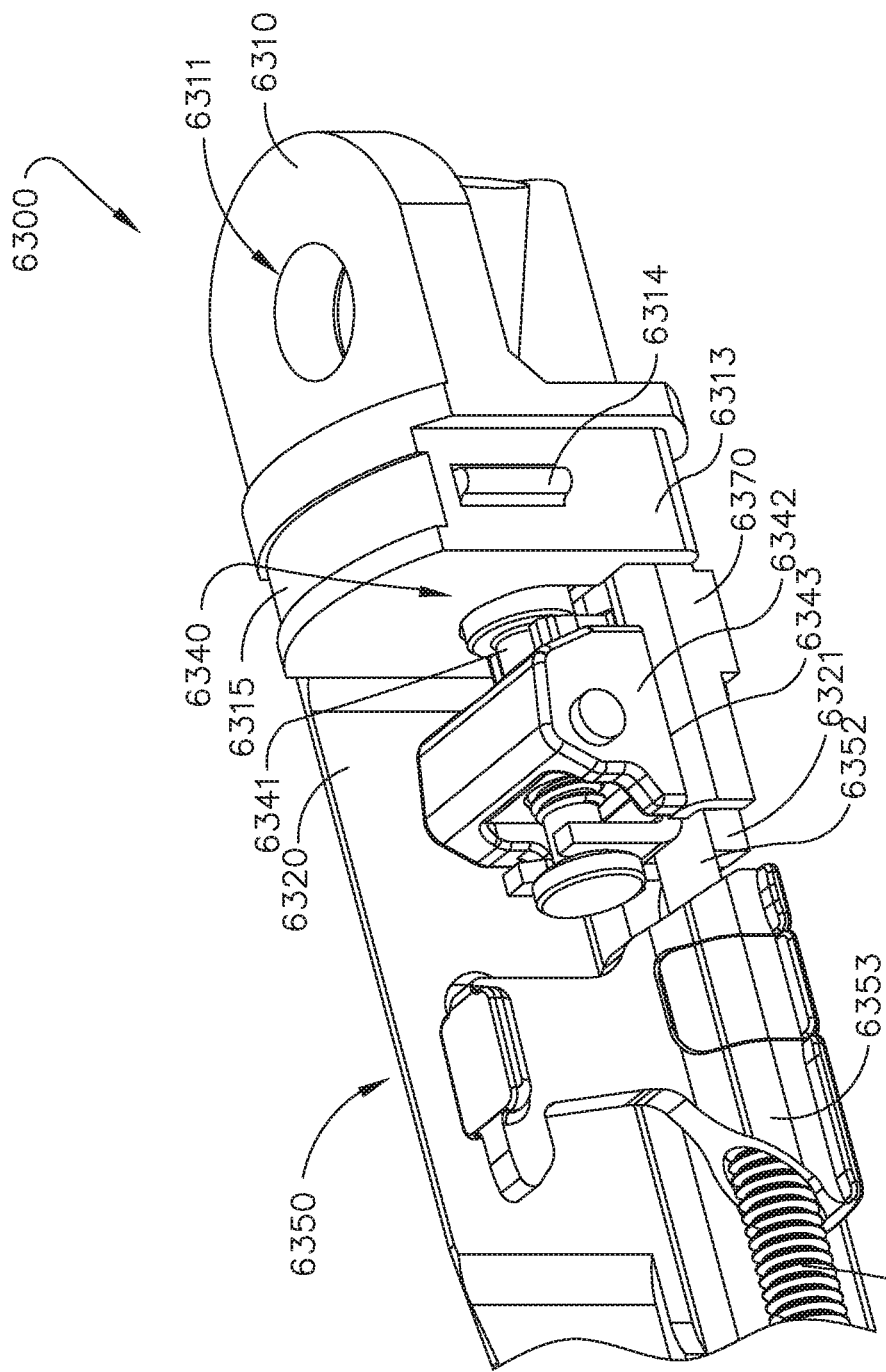
FIG. 108 is a perspective view of a surgical stapling assembly comprising a channel jaw, a closure drive, a firing drive, and support components positioned within the channel jaw and with portions of the surgical stapling assembly hidden for illustrative purposes, in accordance with at least one aspect of the present disclosure.
Figure 109:
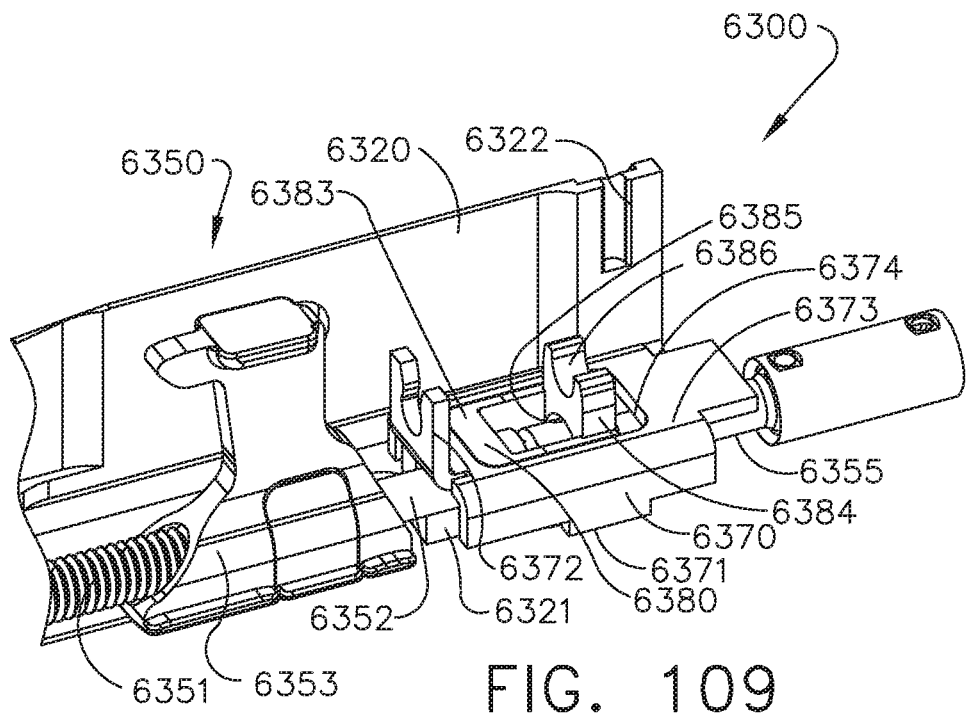
FIG. 109 is a perspective view of the surgical stapling assembly of FIG. 108, wherein various components are hidden for clarity, in accordance with at least one aspect of the present disclosure.
Figure 110:
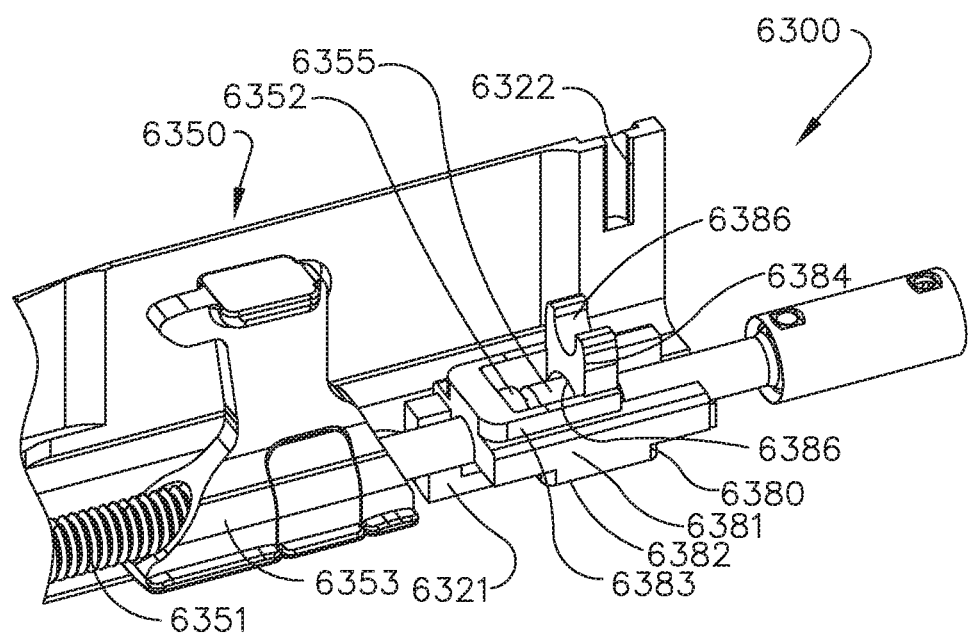
FIG. 110 is a perspective view of the surgical stapling assembly of FIG. 108, wherein various components are hidden for clarity, in accordance with at least one aspect of the present disclosure.

FIGS. 108-110 depict a surgical stapling assembly 6300. The surgical stapling assembly 6300 comprises a joint component 6310 and a channel jaw 6320. The channel jaw 6320 is attached the joint component 6310 by a securement band, or ring, configured to be received within an annular slot 6315 of the joint component 6310. The channel jaw 6320 comprises a bottom 6321 and vertical slots 6322 on each side of the channel jaw 6320 configured to receive tabs 6314 on each side of the joint component 6310. The joint component 6310 defines an articulation pin slot 6311 therein. The channel jaw 6310 may be articulated about an axis defined by the articulation pin slot 6311. The joint component 6310 is configured to receive one or more drive shafts therethrough to drive a closure drive 6340 and a firing drive 6350 of the surgical stapling assembly 6300.

The closure drive 6340 comprises a drive screw 6341 and a closure wedge 6342 threadably coupled to the drive screw 6341. The closure wedge 6342 is configured to be actuated proximally and distally with the drive screw 6341 to open and close a jaw opposing the channel jaw 6320 such as, for example, an anvil jaw. The firing drive 6350 comprises a drive screw 6351 comprising a proximal end 6352 and a firing member assembly 6353 configured to be threadably coupled to the drive screw 6351. The firing drive 6350 is configured to eject staples from a staple cartridge and cut tissue of a patient during a staple firing stroke as the firing member assembly 6350 is actuated along the drive screw 6351.

The closure drive 6340 and the firing drive 6350 are supported within the channel jaw 6320 by a lower support element, or mount, 6380 and an upper support element, or mount, 6370. The support elements 6370, 6380 may be stackable and support one or more elements of the closure drive 6340 and firing drive 6350. The lower support element 6380 comprises a lower portion 6381 and an upper portion 6383. The lower portion 6381 comprises a key 6382 configured to be received within a corresponding slot defined in the channel jaw 6320. Such a key and slot configuration can prevent the lower support element 6380 from moving relative to the channel jaw 6320. The upper portion 6383 comprises a shaft support 6384 comprising a lower arcuate support portion 6385 and an upper arcuate support portion 6386. The lower arcuate support portion 6385 is configured to receive an input shaft 6355 of the firing drive 6350 which is configured to couple and drive the proximal end 6352 of the drive screw 6351. The upper arcuate support portion 6386 is configured to receive and support the drive screw 6341 of the closure drive 6340.

The upper support element 6370 can be received on top of the lower support element 6380 in a track-like manner. For example, a corresponding cavity defined in the upper support element 6370 can be configured to receive the upper portion 6383 of the lower support element 6370 such that the upper support element 6370 fits and surrounds the upper portion 6383 upon installation. The upper support element 6370 further comprises a key 6371 configured to be received within a corresponding slot defined in the channel jaw 6320. The upper support element 6370 further comprises a top surface 6373 and a distal support tab 6372 configured to receive and support a portion of the drive screw 6341 therein. The top surface 6373 is configured to support a bottom surface 6343 of the closure wedge 6342 thereon. In at least one instance, a closure wedge track is defined on the top surface 6373, and the closure wedge 6342 can mate with and ride along the closure wedge track during proximal and distal travel. The upper support element 6370 further comprises a window 6374 configured to receive the upper portion 6383. Both the upper support element 6370 and the lower support element 6380 can be supported by the bottom 6321 of the channel jaw 6320.

In at least one instance, the upper and/or lower support elements 6370, 6380 can be supported within corresponding tracks defined in the channel jaw 6320 such that the upper and lower support elements 6370, 6380 are permitted a degree of longitudinal travel while still being supported by the channel jaw 6320. This can help during clamping, unclamping, and/or articulation of an end effector assembly where various drive shaft components are required to lengthen or shorten owing to the clamping, unclamping, and/or articulation motions and associated forces of the end effector assembly.

In at least one instance, the upper and/or lower support elements 6370, 6380 are manufactured from a single material into a single component. Such a configuration can be achieved using a metal machining process, for example. In at least one instance, the upper and/or lower support elements 6370, 6380 are manufactured separately. In such an instance, one of the upper and lower support elements 6370, 6380 comprises a machined component and the other of the upper and lower support elements 6370, 6380 comprises a sheet stamped component, for example. In at least one instance, both of the upper and lower support elements 6370, 6380 are stamped.

Various types of closure wedges and/or nuts are disclosed herein. The closure wedges can comprise a camming surface configured to close a jaw and one or more camming surfaces configured to open the jaw. In various instance, angles of the corresponding cam surfaces can comprise steeper angles relative to the engaging surface of the jaw which they cammingly engage. The camming surfaces can be tuned such that the drive force required from a corresponding closure drive screw is minimal while maintaining more than sufficient closure drive cam forces.

Figure 111:
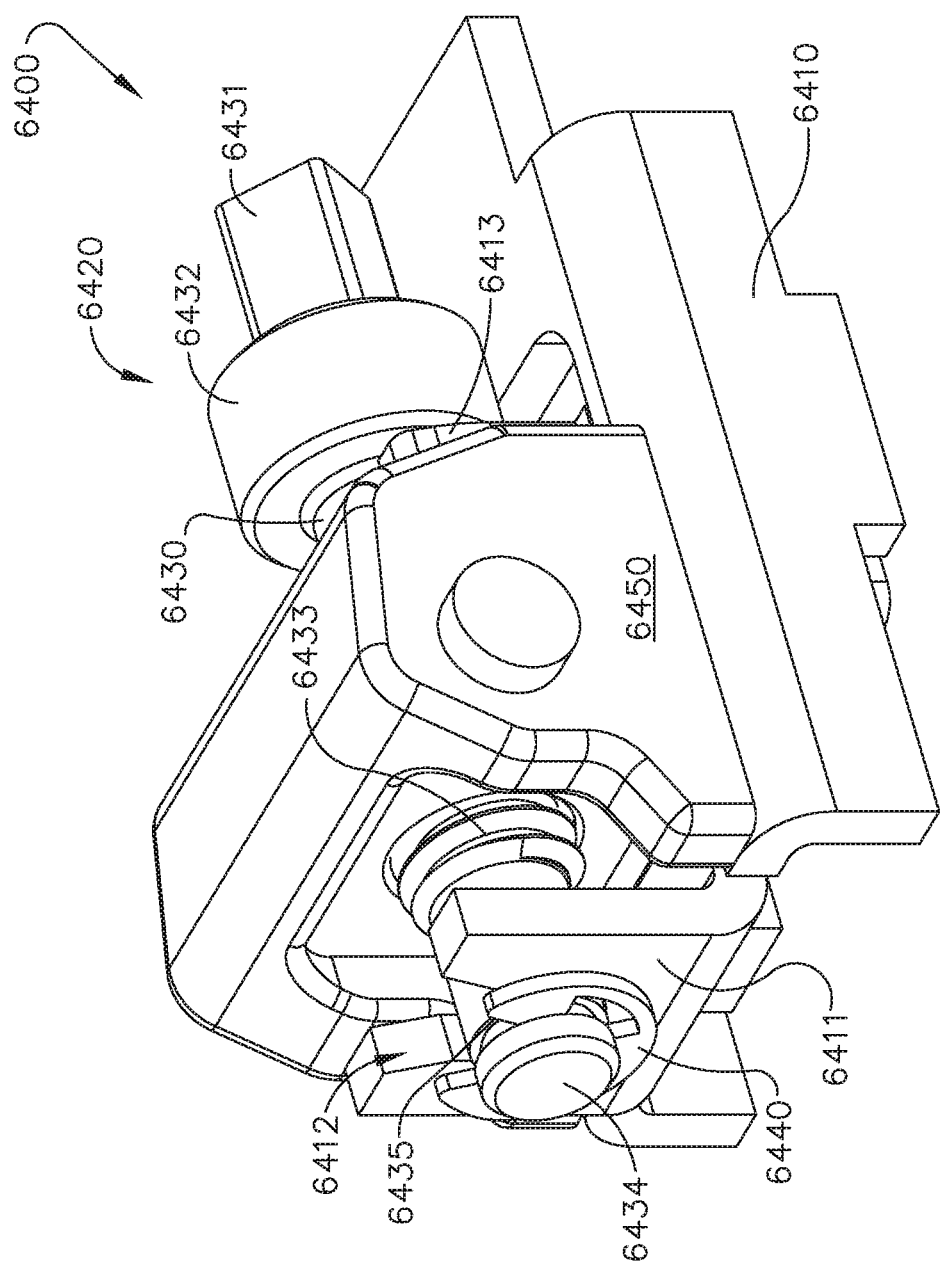
FIG. 111 is a perspective view of a closure drive assembly comprising a closure drive and a support element, in accordance with at least one aspect of the present disclosure.
Figure 112:
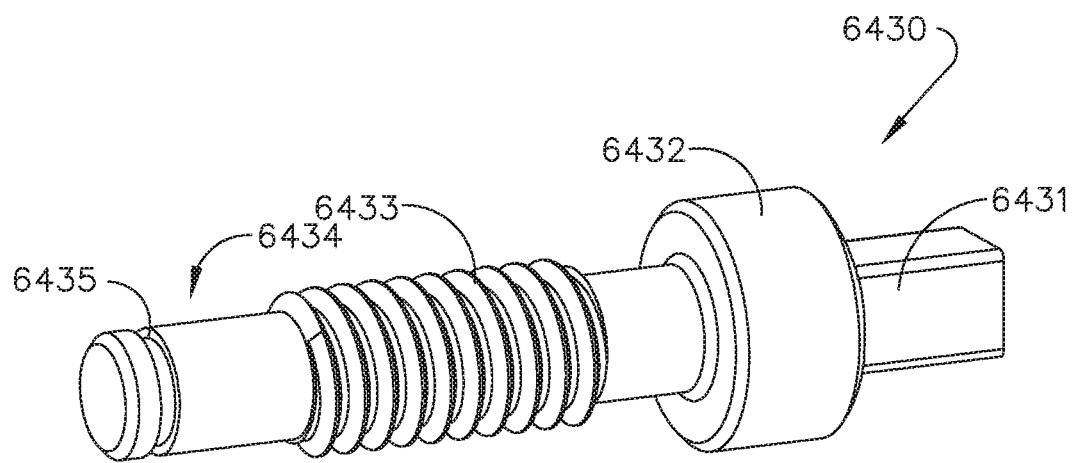
FIG. 112 is a perspective view of a drive screw shaft of the closure drive assembly of FIG. 111, in accordance with at least one aspect of the present disclosure.
Figure 113:
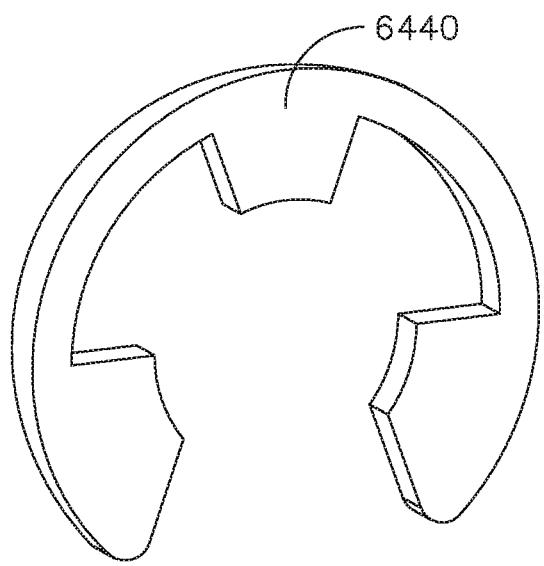
FIG. 113 is a perspective view of a retention clip of the closure drive assembly of FIG. 111, in accordance with at least one aspect of the present disclosure.

FIGS. 111-113 depict a closure drive assembly 6400 configured to open and close a jaw of an end effector assembly. The closure drive assembly 6400 comprises a jaw support element 6410 and a closure drive 6420 supported by support flanges 6411, 6413 of the jaw support element 6410. The closure drive 6420 comprises a drive screw shaft 6430 comprising a proximal end 6431 configured to be rotated by a rotary drive shaft, a proximal bearing portion 6432 configured to prevent the drive screw shaft 6430 from moving distally relative to the flange 6413, and a threaded portion 6433 configured to be threadably coupled to a closure wedge 6450. The drive screw shaft 6430 further comprises a distal end 6434 supported within flange support slot 6412 of the flange 6411 and secured to the flange 6411 by way of a clip 6440. The clip 6440 is configured to be received within a clip slot 6435 defined in the distal end 6435 of the drive screw shaft 6430. The clip 6440 is configured to prevent the drive screw shaft 6430 from moving proximally relative to the flange 6411. The clip 6440 may comprise an e-clip, for example. However, any suitable clip, retention clip, and/or retention ring, may be used. In at least one instance, the closure wedge 6450 may be threaded onto the drive screw shaft 6430 from the distal end 6434.

FIGS. 114-117 depict a closure drive 6500 comprising a drive screw shaft 6510 and a closure drive nut, or wedge, 6540 configured to open and close a jaw of an end effector assembly. The drive screw shaft 6510 comprises a proximal end 6511 and a distal end 6515. The proximal end 6511 comprises a driven portion 6512 configured to be rotated by a rotary drive shaft, a proximal bearing portion 6513, and a threaded portion 6514 configured to be threadably coupled to the closure wedge 6540. The distal end 6515 comprises an attachment section 6516 comprising a diameter less than the diameter of the drive screw shaft 6510 immediately proximal to the attachment section 6516. The attachment section 6516 is configured to receive a locking member, or radial washer 6520, thereon.

Figure 116:
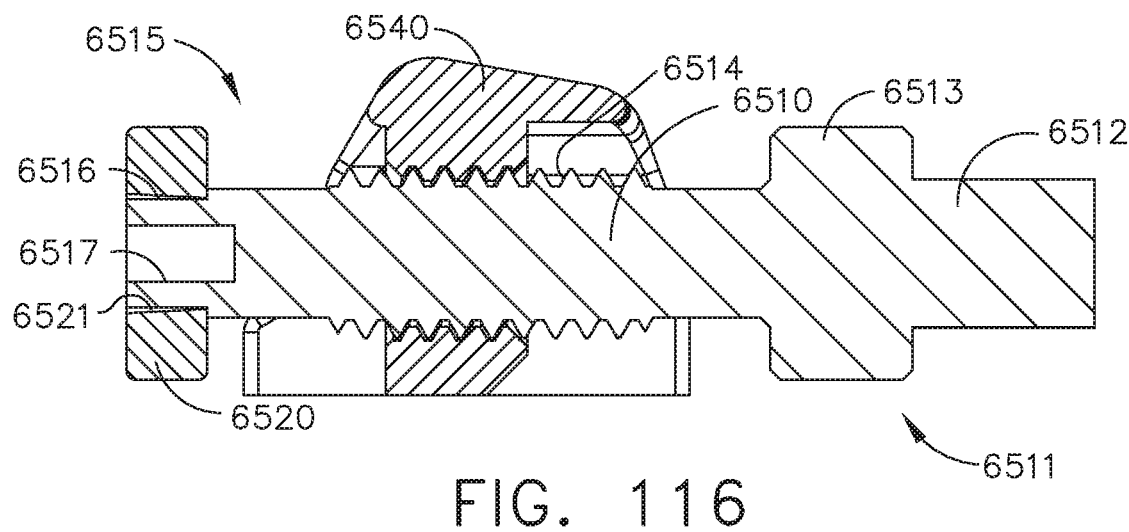
FIG. 116 is a cross-sectional elevation view of the closure drive of FIG. 114, wherein a distal end of the drive screw shaft is illustrated in a pre-formed configuration, in accordance with at least one aspect of the present disclosure.
Figure 117:
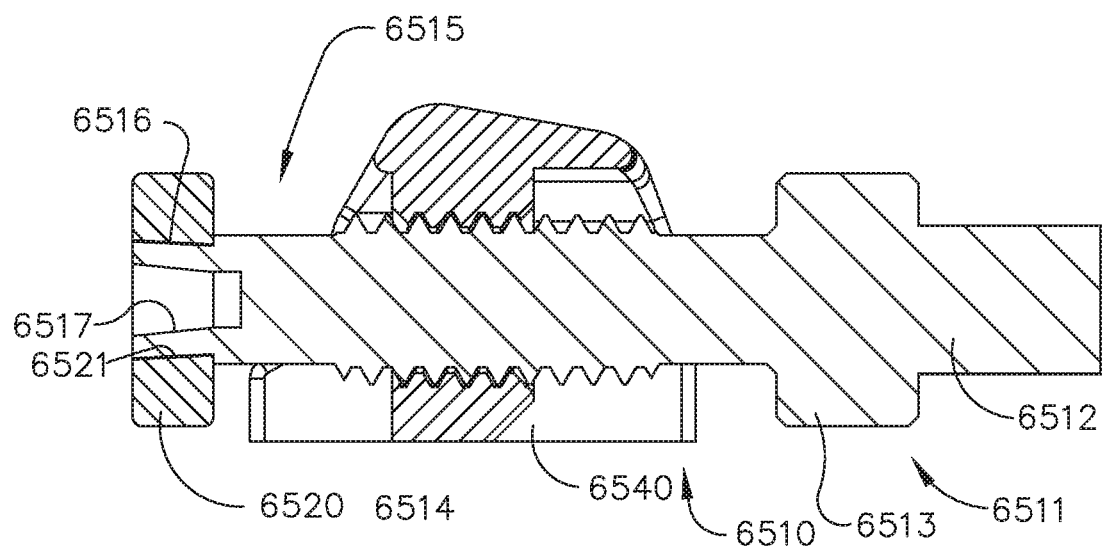
FIG. 117 is a cross-sectional elevation view of the closure drive of FIG. 114, wherein the distal end of the drive screw shaft is illustrated in a formed configuration, in accordance with at least one aspect of the present disclosure.
Figure 118:
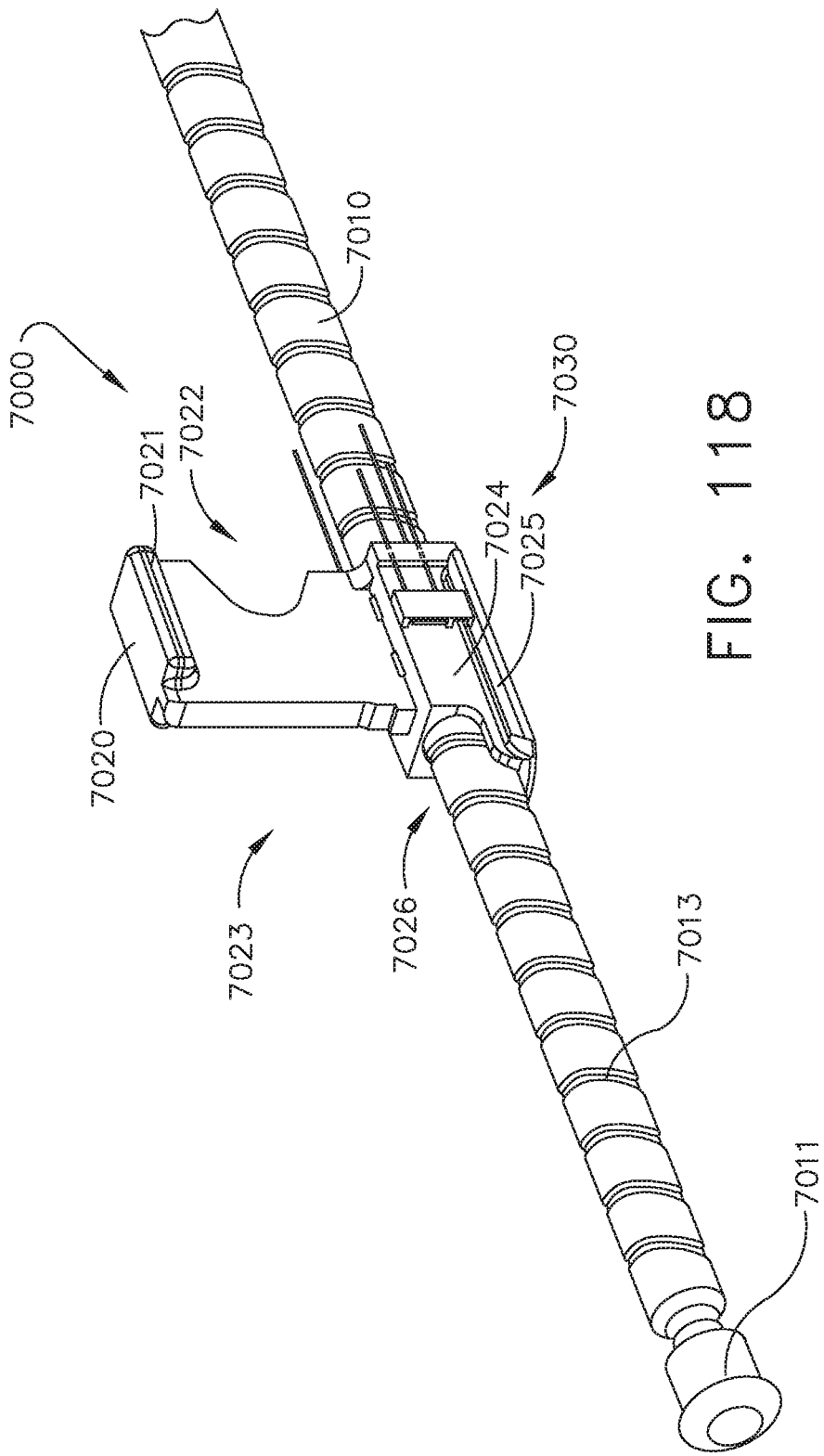
FIG. 118 is a perspective view of a firing drive assembly comprising a rotary firing shaft, a firing member threadably coupled to the rotary firing shaft, and a bailout configured to disengage the threaded engagement between the rotary firing shaft and the firing member, in accordance with at least one aspect of the present disclosure.
Figure 119:
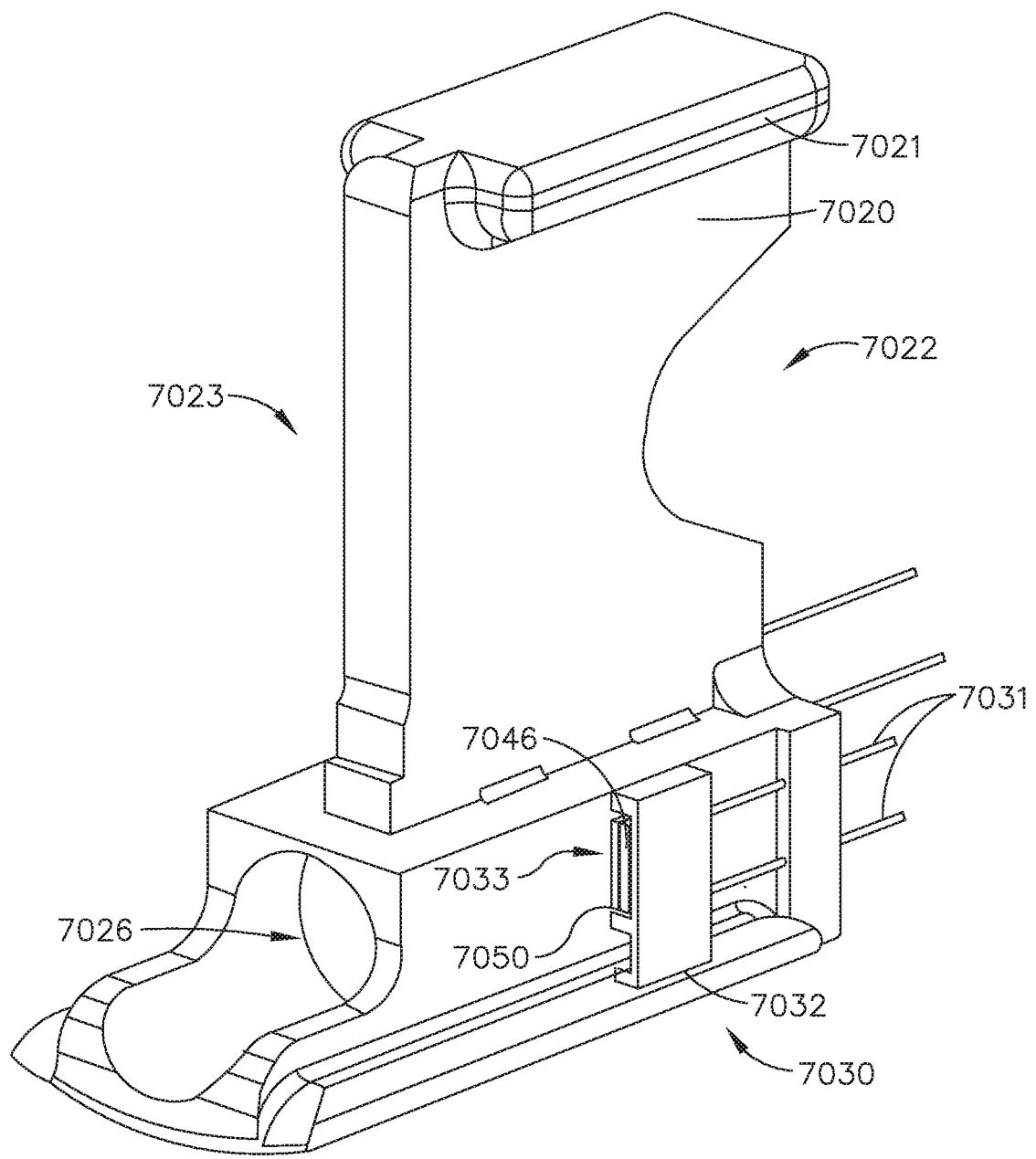
Figure 120:
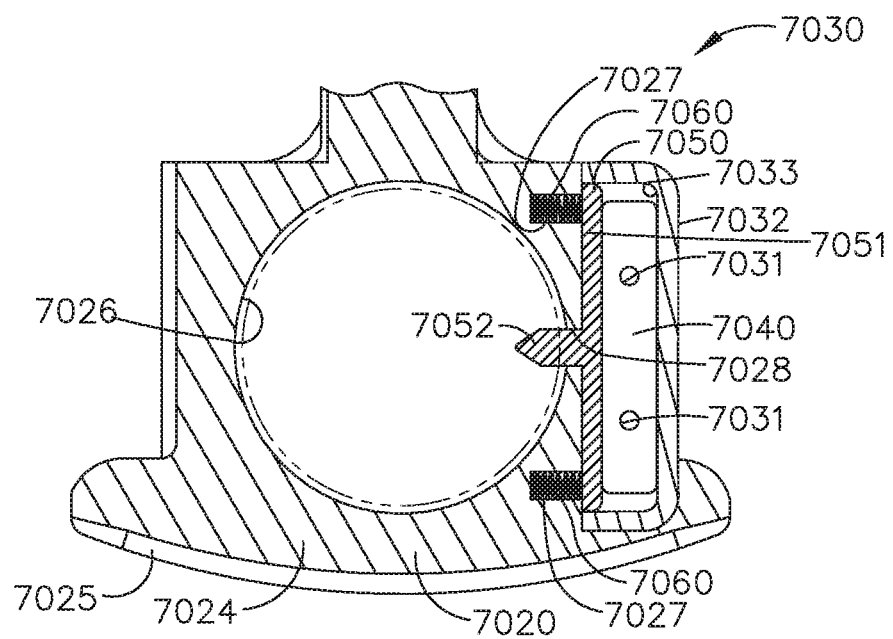
Figure 121:
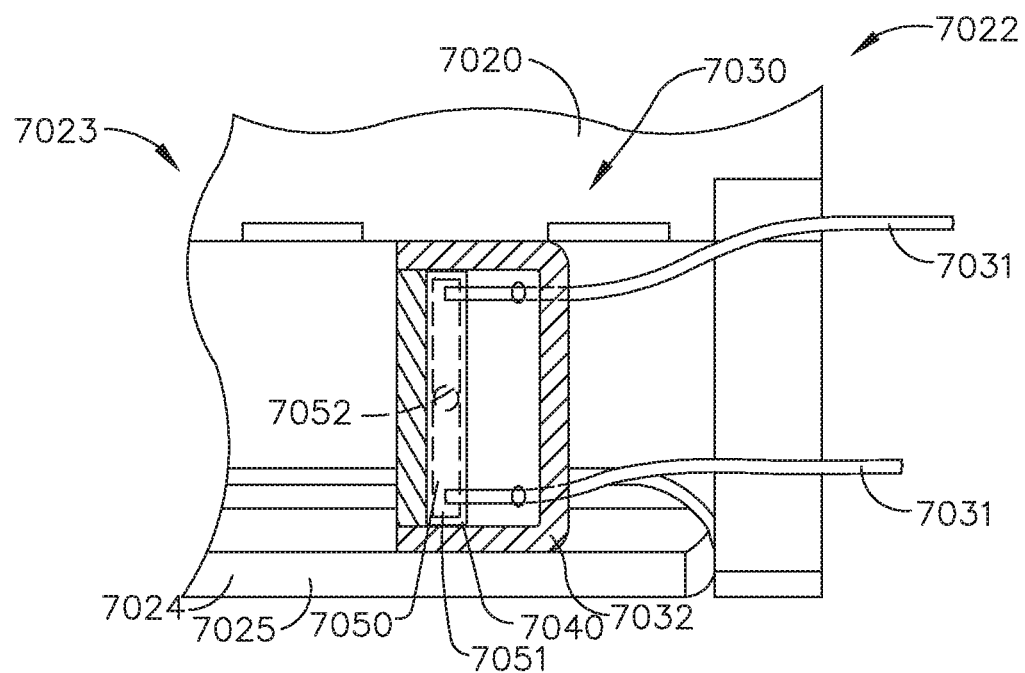
Figure 122:
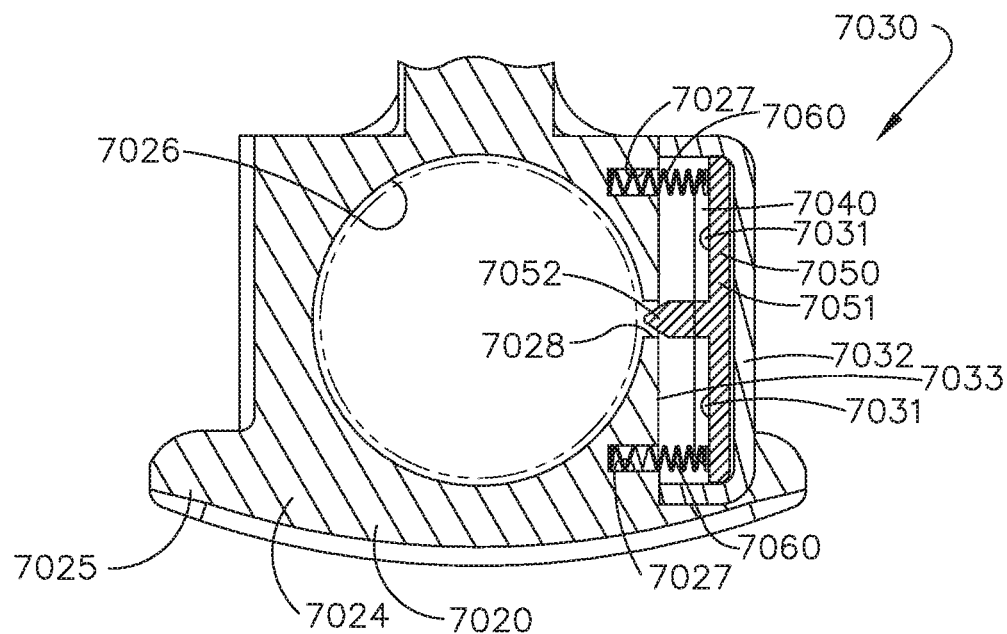
Figure 123:
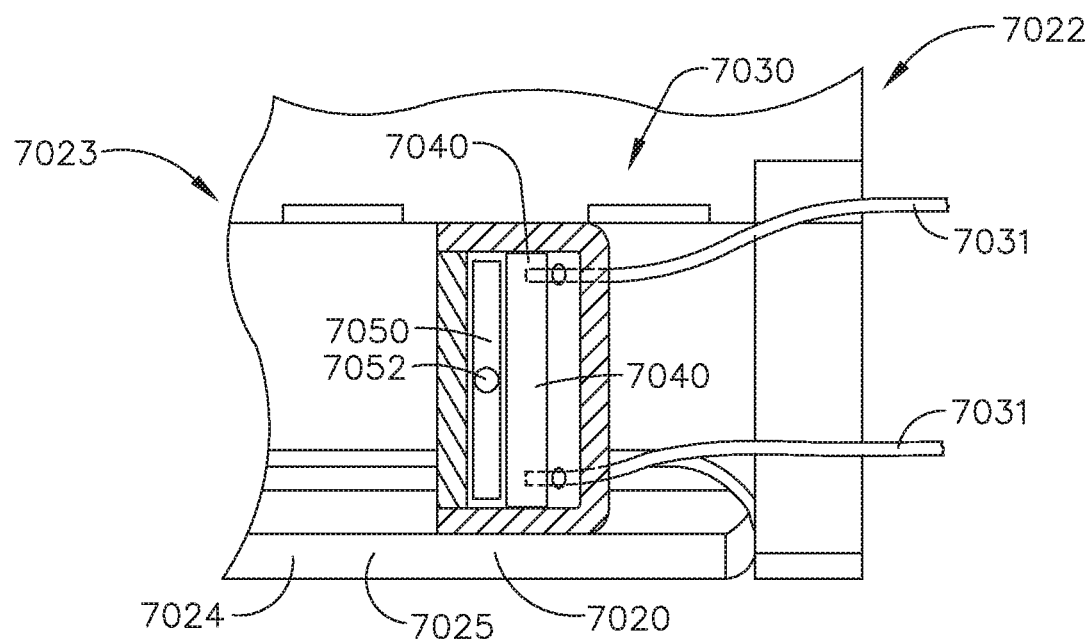
Figure 124:
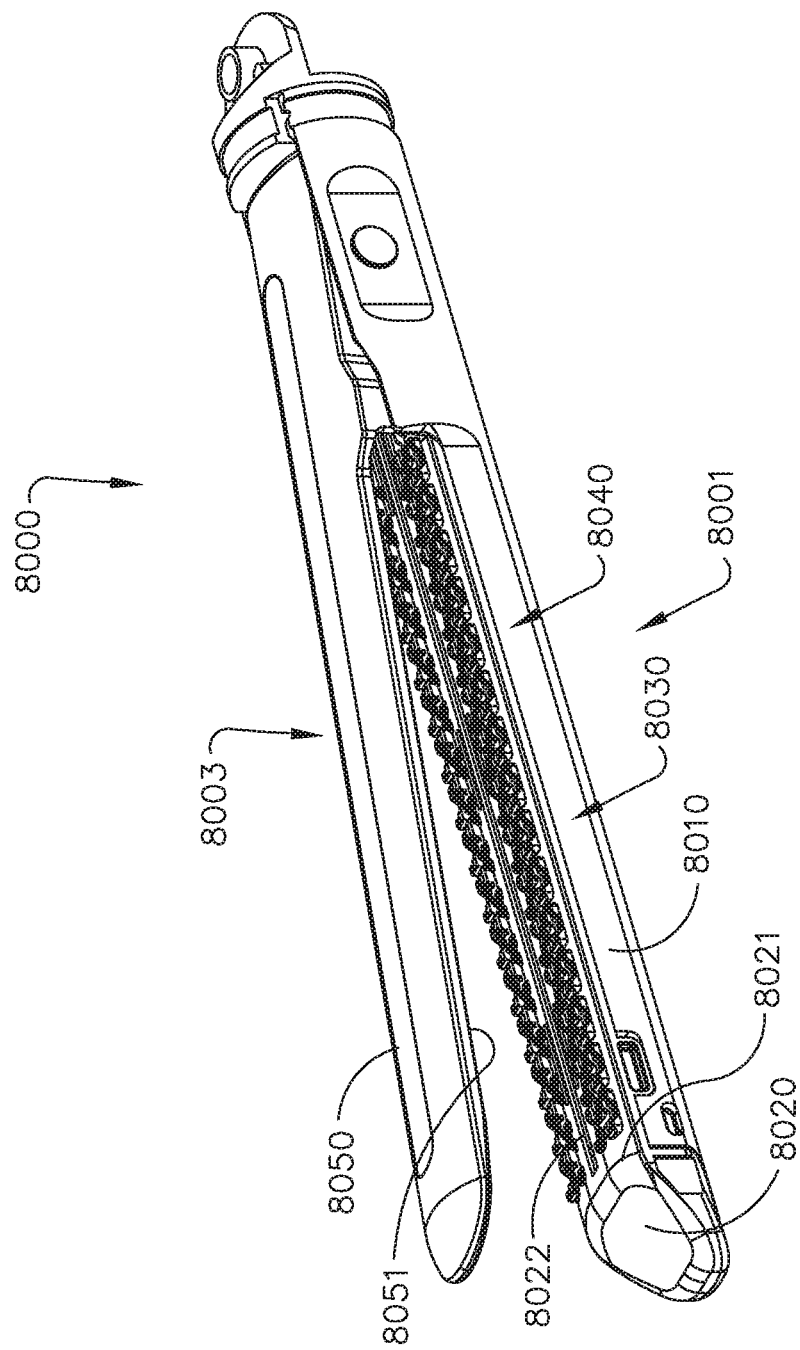

Turning now to FIGS. 116 and 117, installation of the locking member 6520 will now be described. The distal end 6515 may be swaged, for example, to radially expand the attachment section 6516. This radial expansion can provide a frictional holding engagement between the locking member 6520 and the attachment section 6516. A central slot 6517 is provided. The slot 6517 can be used to insert a swaging tool therein to expand the attachment section 6516 to lock the locking member 6520 in place. In at least one instance, the locking member 6520 is deformable and swaging of the attachment section 6516, for example, is configured to deform the locking member 6520 into an installed configuration.

In at least one instance, the locking member 6520 is pinned to the attachment section 6516 in addition to or in lieu of the swaging process discussed above. In at least one instance, the locking member 6520 further comprises an annular groove and the attachment section 6516 further comprises a corresponding annular slot defined on the outside thereof configured to receive the annular groove of the locking member 6520. In at least one instance, a hole is machined in the drive screw and a dowel pin is configured to be inserted into the hole to retain a closure wedge on the drive screw.

In at least one instance, a high density polyethylene washer is positioned proximal to the locking member 6520. The high density polyethylene washer may also comprise a deformable support flange such that the washer is deformed when the locking member 6520 is assembled to the drive screw shaft 6510, for example.

In at least one instance, a deformable washer used herein comprises a grooved and/or knurled face. Such a grooved and/or knurled face can be used to compensate for tolerance stack-ups of various components within a drive system. For example, such a grooved and/or knurled face can wear slightly after a first stage of actuation after assembly so as to compensate for tolerance stack-ups.

FIGS. 118-123 depict a firing drive assembly 7000 comprising a rotary drive shaft 7010, a firing member 7020 threadably coupled to the rotary drive shaft 7010, and a bailout assembly 7030 configured to threadably couple the firing member 7020 to the rotary drive shaft 7010 and permit the bailing out of and/or disengagement of the threaded engagement between the rotary drive shaft 7010 and firing member 7020. The rotary drive shaft 7010 comprises a distal end 7011 and a threaded, or grooved, section 7013. The firing member 7020 comprises an upper flange, a proximal edge 7022, and a distal edge 7023. The firing member 7020 further comprises a lower portion 7024 comprising a drive shaft duct 7026 configured to receive the rotary drive shaft 7010 therethrough. The lower portion 7024 further comprises a lower flange 7025.

The bailout assembly 7030 comprises bailout actuators, or cables, 7031 and a housing 7032 defining a housing cavity 7033. The bailout assembly 7030 further comprises a biasing plate 7040 and an actuator plate 7050. The actuator plate 7050 comprises a primary plate portion 7051 and a point, or pin, 7052 extending inwardly therefrom to be received and driven by the threaded section 7013 of the rotary drive shaft 7013. The pin 7052 is configured to be received within a pin slot 7028 defined in the lower portion 7024 to drivingly engage the threaded, or grooved, section 7013. The actuator plate 7050 is spring loaded against the lower portion 7024 with springs 7060 positioned within spring slots 7027 defined in the lower portion 7024. The springs 7060 are configured to bias the actuator plate 7050 out of threaded engagement with the rotary drive shaft 7010.

To hold the actuator plate 7050 in threaded engagement with the rotary drive shaft 7010, the biasing plate 7040 is positioned, or wedged, between the housing 7032 and the primary plate portion 7051 within the housing cavity 7033. This wedging engagement overcomes the spring force applied to the actuator plate 7050 by the springs 7060 and keeps the pin 7052 engaged with the threaded section 7013 of the rotary drive shaft 7010. In various instances, the firing drive assembly 7000 may become stuck or jammed within an end effector assembly due to a variety of circumstances. The bailout assembly 7030 allows for the firing member 7020 to be disengaged from the rotary drive shaft 7010 and pulled proximally independently of the rotary drive shaft 7010 to overcome a stuck or jammed scenario.

To bailout the firing drive assembly 7000, the pin 7052 is moved from an inward-most position (FIG. 120, FIG. 121) to an outward-most position (FIG. 122, FIG. 123) disengaging the pin 7052 and, thus, the firing member 7020, from the rotary drive shaft 7010. To achieve this motion, the biasing plate 7040 is pulled proximally by the actuators 7031 to move the biasing plate 7040 out of the way of the actuator plate 7050 so as to allow the springs 7060 to push the primary plate portion 7051 and, thus, the pin 7052 out of threaded engagement with the threaded section 7013 of the rotary drive shaft 7010. At such point, the actuators 7031 can continue to be pulled proximally to apply a pulling force to the firing member 7020 through the biasing plate 7040. The housing cavity 7033 comprises a proximal limit wall configured to transfer the pulling force from the biasing plate 7040 to the firing member 7050. Once the firing member 7020 is pulled into its proximal most position the end effector assembly may be opened and removed from a surgical site, for example.

In at least one instance, the firing drive assembly 7000 and end effector assembly employing the firing drive assembly 7000 may not be usable again due to the nature of the bailout assembly 7030. For example, the bailout assembly 7030 may not be able to be reset back into threaded engagement with the rotary drive shaft 7010. In at least one instance, the bailout assembly 7030 may be capable of being reset and reused. In at least one instance, another pin 7052 and corresponding structure is provided on the other side of the firing member 7020. The same, or separate, cables may be provided to actuate the other pin in such an instance.

In at least one instance, the actuators, or cables, may be controlled using a geared pulley system. In at least one instance, the cables may be motor driven. In at least one instance, the cables are manually actuatable. In at least one instance, the cables may be manually actuatable and motor driven. For example, during a power failure, the manual actuation method could be used where the motor driven system is temporarily down. In at least one instance, the cables are permitted to lengthen as the firing member is actuated so as to not prematurely actuate the bailout assembly. The cables may be passively moved or actively moved to accommodate movement of the firing member.

In various instances, surgical stapling arrangements are provided which are configured to form staples, such as traditional wire staples, differently within a single staple cartridge. More specifically, a staple cartridge may store staples with identical unformed heights, size, and shape, for example. In such an instance, different features are provided so as to form the same unformed staples into different final formed configurations. In at least one instance, the varied forming of staples varies progressively along the lateral width of the staple cartridge. More specifically, an inner row of staples may be formed into a planar, or 2D, formed configuration while an intermediate row of staples and/or an outer row of staples may be formed into a non-planar, or 3D, formed configuration. Such an arrangement can provide varied stapled tissue compression along the lateral width of the staple cartridge.

Further to the above, such surgical stapling arrangements can comprise tissue gripping features, or staple cavity extensions, defined on a deck of the staple cartridge. Such tissue gripping features can vary in shape and/or size, for example, laterally across the staple cartridge. The deck of the staple cartridge may comprise a curved surface where an apex of such a curved deck is defined at a longitudinal slot of the staple cartridge. The deck of the staple cartridge may also comprise one or more flat surfaces either providing a single flat surface in which all of the staple rows are defined or a stepped deck arrangement where various stepped portions of the deck comprise one or more corresponding staple rows defined therein.

The tissue gripping features may also be interconnected along the lateral width of the staple cartridge. For example, on each side of a longitudinal slot of the staple cartridge, the staple cartridge may comprise three rows of staple cavities and, thus, three rows of staples removably stored therein. The tissue gripping features, or deck protrusions, may be positioned around each cavity of each row; however, the tissue gripping features can be interconnected between one or more of the staple cavity rows while still varying in shape and/or size, for example. Such tissue gripping features can provide varied tissue compression along the lateral width of a staple cartridge. The varying size tissue gripping features can be advantageous when forming certain rows of staples into a non-planar, 3D configuration, and certain rows of staples into a planar, 2D configuration. Such features can be tuned specifically for the corresponding staple configuration of the staples to be formed through tissue gripped by the features. For example, gripping features configured to grip tissue to be stapled between an anvil and a row of staple cavities comprising staples configured to be formed into a non-planar configuration can comprise a first profile and gripping features configured to grip tissue to be stapled between an anvil and a row of staple cavities comprising staples configured to be formed into a planar configuration can comprise a second profile, wherein the first profile is different than second profile. In certain instances, the gripping features aligned with the rows of 3D staples can include cutouts in the areas where curved, formed legs would interfere. For example, the rows aligned with 2D staples can include full gripping features surrounding the staple cavity, and the rows aligned with the 3D staples can include gripping features with cutouts therearound to accommodate the staple legs during the 3D formation thereof.

In various instances, staples formed into a planar configuration and staples formed into a non-planar configuration may result in different formed compression heights. This can be attributed to a distance required to be traveled by legs of each staple to their corresponding staple forming pocket defined in an anvil. For example, legs of staples formed into a non-planar configuration may have to travel on a diagonal to a corresponding staple forming pocket. Without altering any other features of the stapling assembly, this distance may be farther than the distance required to be traveled by legs of staples formed into a planar configuration to a corresponding staple forming pocket.

In various instances, the distance which each leg must travel to be formed into its corresponding configuration, non-planar or planar, may be tuned by altering one or more features of a surgical stapling assembly. In at least one instance, the depths of staple forming pockets defined in the anvil are adjusted corresponding to the formed configuration of the staple to be formed thereby. In at least one instance, the unformed length of the staples are configured to be adjusted corresponding to the formed configuration of the staple to be formed thereby. In at least one instance, a corresponding driver height is adjusted corresponding to the formed configuration of the staple to be formed thereby. In at least one instance, one or more of these adjustments are combined together to accommodate 2D formed staples and 3D formed staples.

FIGS. 124-128 depict a surgical stapling assembly 8000. The surgical stapling assembly 8000 comprises a cartridge jaw 8001 comprising a cartridge channel 8010 and a staple cartridge 8020. The surgical stapling assembly 8000 also comprises an anvil jaw 8003 comprising an anvil 8050. The staple cartridge 8020 comprises a plurality of staple cavities 8030 and a longitudinal slot 8022 defined in a cartridge deck 8021. The staple cartridge 8020 also comprises and a plurality of tissue-gripping features, or cavity extensions, 8040 defined on the deck 8021. The staple cavities 8030 are aligned in longitudinal rows offset with respect to each other. In this instance, the staple cartridge 8020 comprises three rows of staple cavities on each side of the longitudinal slot; however, any suitable number of rows of staple cavities can be employed. The staple cavities 8030 are configured to removably store staples which are configured to be ejected toward staple forming pockets defined in an anvil surface 8051 of the anvil 8050.

Referring to FIGS. 125 and 126, the anvil 8050 comprises an anvil slot 8052 defined in the anvil surface 8051. The anvil 8050 further comprises a pair of inner staple forming pocket rows 8061, a pair of intermediate staple forming pocket rows 8063, and a pair of outer staple forming pocket rows 8065. The rows 8061, 8063, 8065 are aligned with corresponding rows of the staple cavities 8030. The inner staple row 8081 comprises staples 8070 which are configured to be formed by the staple forming pocket rows 8061, the intermediate staple row 8082 comprises staples 8070 which are configured to be formed by the staple forming pocket rows 8063, and the outer staple row 8083 comprises staples 8075 which are configured to be formed by the staple forming pocket rows 8065. The staple tip entry location of the pockets in the stapling forming pocket row 8065 is aligned, or substantially aligned, with the tips of the staples in the outer staple row 8065; however, the staple tip exit location of those pockets can be laterally offset from the staples positioned in the outer staple row 8065. The staples 8070, 8075 comprise traditional wire staples. The staples 8070, 8075 comprise the same unformed height. The staples 8070 are formed into a planar configuration while the staples 8075 are formed into a non-planar configuration.

Each pair of forming pockets of the row 8061 comprises a proximal forming pocket 8061A and a distal forming pocket 8061B. Each pair of forming pockets of the row 8063 comprises a proximal forming pocket 8063A and a distal forming pocket 8063B. Each pair of forming pockets of the row 8065 comprises a proximal forming pocket 8065A and a distal forming pocket 8065B. The forming pockets 8061A, 8061B comprise centerline axes, or longitudinal pocket axes, which are aligned with each other along the row 8061. Similarly, the forming pockets 8063A, 8063B comprise centerline axes, or longitudinal pocket axes, which are aligned with each other along the row 8063. The forming pockets 8065A, 8065B comprise centerline axes, or transverse pocket axes, which are transverse with respect to the centerline axes of the pockets 8061A, 8061B and the centerline axes of the pockets 8063A, 8063B. The centerline axes of the pockets 8065A, 8065B may be substantially parallel to each other. Further to the above, a proximal leg of one of the staples 8070 is configured to enter the proximal forming pocket 8065A and a distal leg of the staple is configured to enter the distal forming pocket 8065B. The forming pockets 8065A, 8065B are configured to direct the legs of the staple 8075 laterally away from a crown of the staple or, laterally away from each other (see FIG. 126). This variance in 2D formed staples and 3D formed staples laterally along the width of the stapling assembly 8000 with respect to a longitudinal axis defined thereby can provide varied tissue compression on the stapled tissue. For example, the outer 3D staples may provide less tissue compression as compared to the inner 2D formed staples near the cut line of the tissue.

As can be seen in FIG. 125, a gap is defined longitudinally between each pair of forming pockets 8061A, 8061B, a gap is defined longitudinally between each pair of forming pockets 8063A, 8063B, and a gap is defined between each pair of forming pockets 8065A, 8065B. The gap defined between the forming pockets 8061A, 8061B may be substantially the same and/or similar to the gap defined between the forming pockets 8063A, 8063B. The gap defined between the forming pockets 8065A, 8065B is larger than the gap defined between the forming pockets 8061A, 8061B and the gap defined between the forming pockets 8063A, 8063B. The gap defined between the forming pockets 8065A, 8065B may be defined as the space intermediate the forming pockets 8065A, 8065B.

Figure 127:
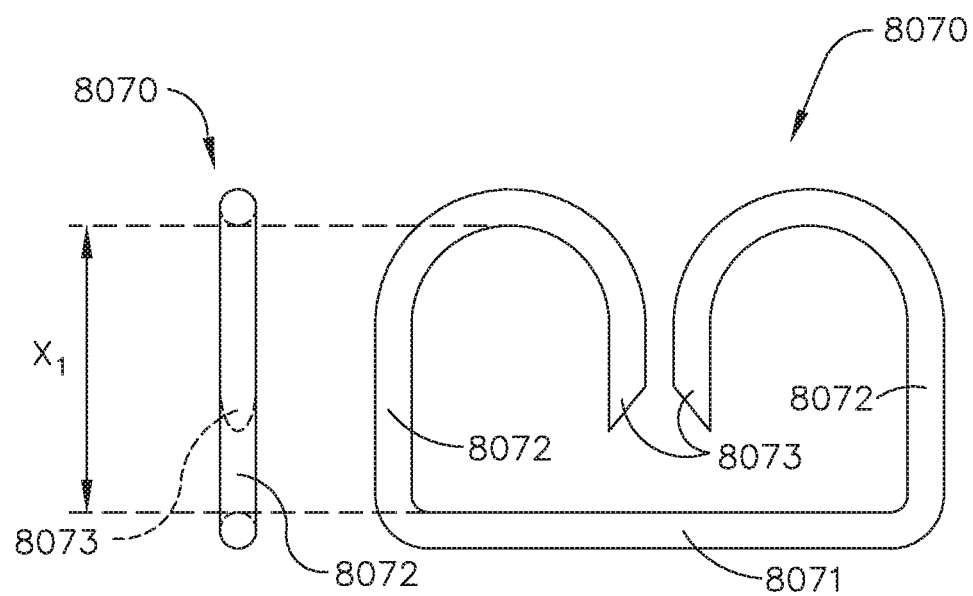
Figure 128:
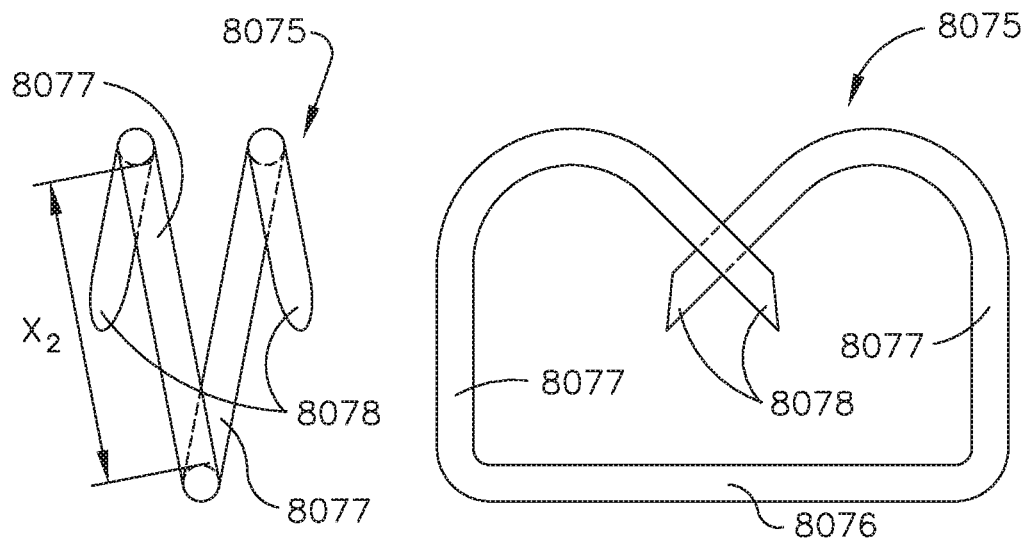

As can be seen in FIGS. 127 and 128, the staples 8070 are formed into a planar configuration and the staples 8075 are formed into a non-planar configuration. The staple 8070 comprises a crown 8071 and legs 8072 extending from the crown 8071. The legs 8072 further comprise staple tip portions 8073 configured to pierce tissue and enter corresponding forming pockets. The staples 8070 define a formed compression height "$X_1$" which is the effective height of tissue compression captured by the staple 8070. The staple 8075 comprises a crown 8076 and legs 8077 extending from the crown 8076. The legs 8077 further comprise staple tip portions 8078 configured to pierce tissue and enter corresponding forming pockets. The staples 8075 define a formed compression height "$X_2$" which is the effective height of tissue compression captured by the staple 8075. Because of the non-planar formed configuration of the staple 8075, the formed compression height $X_2$ is taller than the formed compression height $X_1$. In at least one instance, this is desirable and can provide a progressive reduction in compression as the staple lines move laterally away from the cut line. For example, a tighter formed compression height near the cut line may provide adequate tissue sealing pressure and a looser formed compression height away from the cut line progressively reduces pressure on the tissue as the staple lines move laterally outwardly with respect to the cut line.

In at least one instance, the legs 8077 are formed at different angles away from the crown 8076 with respect to each other. For example, a proximal leg can be formed away from the crown at a first angle and the distal leg can be formed away from the crown in the opposite direction at a second angle. The first angle is different than the second angle. This would allow for a narrow footprint of the corresponding staple forming pockets. Moreover, when stamping these pocket shapes into the anvil, the different angles and/or narrower footprint can ensure that the wall between adjacent rows of forming pockets is sufficiently maintained, which can prevent bleeding or washout of features in one row into those in an adjacent row during the stamping process.

3D staples can be intermixed within and/or across longitudinal rows, which can maximum use of the anvil surface and further nest the pockets and allow a narrower footprint.

In certain instances, intermixing of 3D staple pockets can improve tissue pressure dispersion along the anvil. In at least one instance, the 3D staple pockets can be positioned along an outermost row of pockets to further ease and/or taper the tissue pressure along the edges of the staple line farthest from the cut line.

In various instances, the gripping features 8040 and the curved deck 8021 can provide laterally varying tissue gaps. More specifically, the gap for tissue to be captured between each corresponding row of staple cavities and staple forming pockets is varied between each row. The outer-most row comprises the tallest gripping features as compared to the inner row and intermediate row. This may provide additional tissue compression in a row where the 3D staples are configured to be formed. This may provide greater stability during staple forming owing to the additional cavity extension length of the outer staple cavities. The taller gripping features can maintain a similar compression profile between the gripping features and the corresponding forming pockets; however, the portion of the deck surface 8021 that the outer row of staple cavities are defined in is further away from the anvil than the portion of the deck surface 8021 that the inner row of staple cavities and the intermediate row of staple cavities are defined in due to the lateral curvature of the deck. Collectively, the taller gripping features and the lower deck surface can provide a more stable platform for 3D formed staples in certain instances.

In various instances, flat form, or stamped, staples can be used in addition to or in lieu of wire staples. In various instances, two of the three rows of staples on each side of a cartridge are configured to be formed into a non-planar configuration while the other one of the three rows on that side of the cartridge is configured to be formed into a planar configuration. In at least one instance, the same longitudinal row of staples comprises both planar formed staples as well as non-planar formed staples. In at least one instance, the unformed height of staples within the same row is varied. In at least one instance, the unformed height of staples within different rows is varied. In at least one instance, planar staples and non-planar staples are varied along axes transverse to a longitudinal slot of a staple cartridge to spread staple pressure. In at least one instance, staple legs of non-planar formed staples are formed laterally on one side of the crown rather than opposite directions relative to the crown away from each other. In such an instance, the row gap between each row can be substantially similar at least because the legs, although forming away from the crown upon ejection, can be formed back toward the crown to tighten the staple lines. Such a configuration can help maintain a consistent lateral row gap between each row of staple forming pockets.

Figure 129:
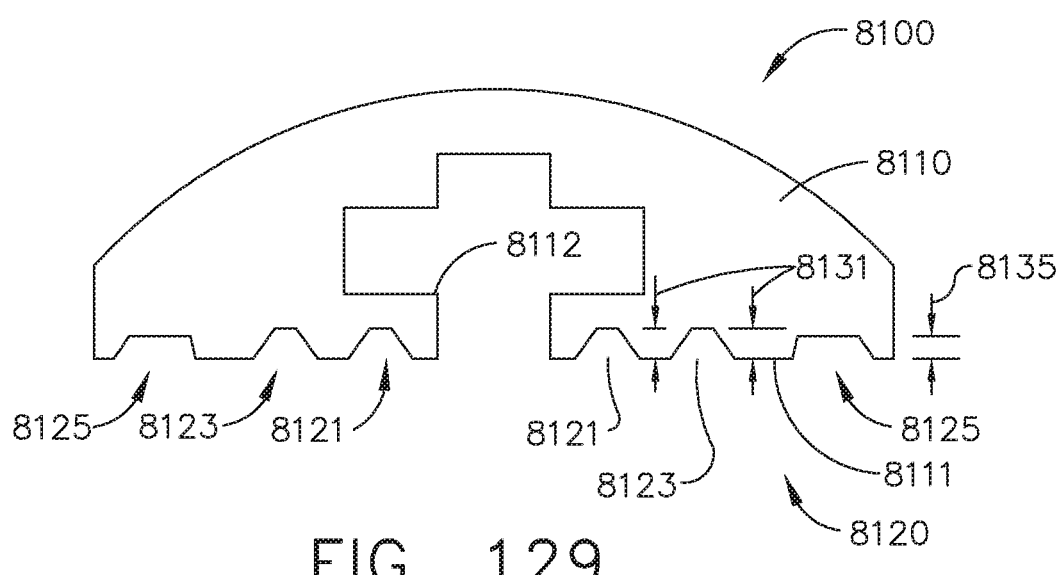

As discussed above, one or more adjustments can be made to vary the final formed height and/or compression height of the staples as there form can vary laterally, row-to-row, for example. FIG. 129 depicts an anvil 8100 configured to deform staples ejected from a staple cartridge. The anvil 8100 comprises an anvil body 8110 comprising an anvil surface 8111 and a firing member slot 8112 defined in the anvil body 8110. The anvil surface 8111 comprises a plurality of staple forming pocket rows comprising inner rows 8121, intermediate rows 8123, and outer rows 8125. The inner and intermediate rows 8121, 8123 are configured to form staples into a planar configuration and the outer rows 8125 are configured to form staples into a non-planar configuration. As can be seen in FIG. 129, the inner and intermediate rows 8121, 8123 define a pocket depth 8131 and the outer rows define a pocket depth 8135 which is shallower than the pocket depth 8131. This shallower pocket depth can accommodate for loss in compression or final formed height owing to the diagonal forming path of the non-planar staples. In at least one instance, the pocket depths are tuned so that the final compression height is the same between non-planar staples and planar staples. In another instance, the pocket depths are tuned so that the final compression heights between non-planar staples and planar staples are different.

Figure 130:
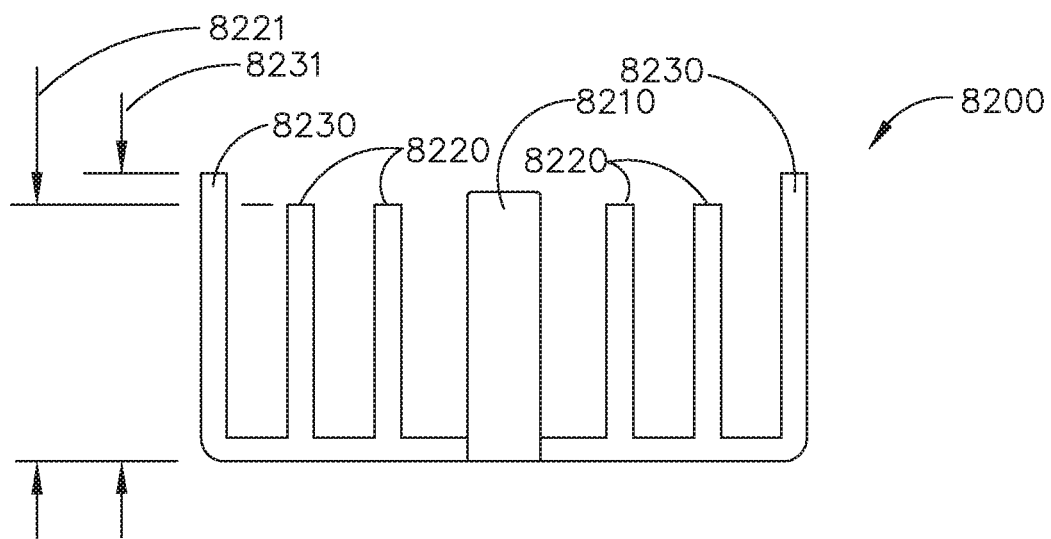

FIG. 130 depicts a sled 8200 comprising inner ramps 8220 and outer ramps 8230. The inner ramps are configured to lift staples a height 8221 and the outer ramps 8230 are configured to lift staples a height 8231. The ramps 8220 are configured to lift staples to be formed into a planar configuration and the ramps 8230 are configured to lift staples to be formed into a non-planar configuration. The height 8231 may accommodate for loss in compression or final formed height owing to the diagonal forming path of the non-planar staples.

FIG. 131 depicts staples 8300 to be used with a surgical stapling assembly. The staples 8300 comprise a first staple 8310 comprising a first unformed height 8311 and a second staple 8320 comprising a second unformed height 8321. The first unformed height 8311 is less than the second unformed height 8321. The different unformed heights can accommodate for loss in compression or final formed height owing to the diagonal forming path of the non-planar staples. The second staple 8320 can be configured to be formed into a non-planar configuration while the first staple 8310 can be configured to be formed into a planar configuration.

FIGS. 132 and 133 depict staples 8410, 8420. The staple 8410 formed into a planar configuration defines a final compression height 8411 and the staple 8420 formed into a non-planar configuration defines final compression height 8421. The final compression height 8421 is less than the compression height 8411; however, the staple 8420 defines a distance 8422 defined between the apex of each formed leg and the crown. The distance 8422 may be substantially equal to the final compression height 8411. The distance 8422 may be the effective compression height of the staple 8420.

In various instances, surgical stapling assemblies are provided which are configured to overdrive staples from a staple cartridge. The amount of staple overdrive may vary from row to row. In various instances, staple drivers can comprising varying amounts of support from a corresponding staple cartridge support wall. More specifically, inner staple drivers can be supported less by a staple cartridge support wall than outer staple drivers owing to the geometry of the cartridge body and firing assembly and/or drive screw therein. In various instances, a tissue gap can be varied from row to row while maintaining a similar, or the same, driving distance between the rows.

FIGS. 134-136 depict a surgical stapling assembly 8500. The surgical stapling assembly 8500 comprises a lower jaw 8501 and an upper jaw 8502. The lower jaw 8501 comprises a cartridge channel 8510 and a staple cartridge 8520 configured to be received within the cartridge channel 8510. The upper jaw 8502 comprises an anvil 8530 comprising an anvil body 8531. The anvil body 8531 comprises an anvil surface 8532 and a plurality of forming pockets defined in the anvil surface 8532. The anvil surface 8532 comprises inner forming pockets 8533, intermediate forming pockets 8534, and outer forming pockets 8535. The staple cartridge comprises a plurality of staple cavities 8522 comprising inner staple cavities 8522A aligned with inner forming pockets 8533, intermediate staple cavities 8522B aligned with intermediate forming pockets 8534, and outer cavities 8522C aligned with outer forming pockets 8534. The staple cavities 8522 are configured to store a corresponding driver and staple therein to be ejected to the forming pockets aligned therewith.

The staple cartridge 8520 comprises a curved cartridge deck 8529 comprising a plurality of staple cavities 8522 defined therein and a plurality of tissue gripping features, or cavity extensions, 8523, 8524, 8525 extending from the cartridge deck 8529. The staple cartridge 8520 also comprises a sled 8550 comprising ramps 8551, 8552. The staple cartridge 8520 comprises a plurality of drivers 8540 sequentially aligned to eject rows of staples from the staple cavities when lifted by ramps 8551, 8552. Each driver 8540 comprises an inner row support, or inner support column, 8541 configured to support and drive a staple to be stored and ejected from an inner staple cavity 8522A, an intermediate row support, or intermediate support column, 8542 configured to support and drive a staple to be stored and ejected from an intermediate staple cavity 8522B, and an outer row support, or outer support column, 8543 configured to support and drive a staple to be stored and ejected from an outer staple cavity 8522C.

As can be seen in FIG. 135, the staple cartridge 8520 comprises inner support walls 8526A configured to support inner row support 8541 as the driver 8540 is lifted by sled 8550, intermediate support walls, or columns, 8526B configured to support intermediate row support 8542 as the driver 8540 is lifted by sled 8550, and outer support walls 8526c configured to support outer row support 8543 as the driver 8540 is lifted by sled 8550. As can be seen in FIG. 135, the level of support contact between each support 8541, 8542, 8543 and its corresponding support wall 8526A, 8526B, 8526C varies from row to row. In an unfired position, the outer support 8541 has the most support contact, the intermediate support 8542 has less support contact than the outer support 8541, and the inner support 8541 has the least amount of support contact. As can also be seen in FIG. 135, the supports 8541, 8542, 8543 are overdriven to the same limit resulting in the same driving forming distance of each staple supported by the supports 8541, 8542, 8543; however, the amount of overdrive relative to their corresponding gripping feature 8523, 8524, 8525 varies from row to row. The outer row is overdriven past its gripping features the most, and the inner row is overdrive past its gripping features the least.

As discussed herein, staple cartridges can be replaced within a surgical stapling assembly. In various instances, anvil plates are provided which can also be replaced. In such instances, the anvil plate may come with a corresponding staple cartridge such that a fresh staple cartridge and anvil plate are packaged together and are replaced within the surgical stapling assembly together. In such instances, various features of the anvil plates and corresponding staple cartridge can be tuned specifically for each other. For example, different anvil plates can comprise staple forming pockets with different patterns, staple forming pockets with different forming depths, and/or varied staple forming pocket types from row to row, for example, among other things.

A universal fitment profile can be used for a variety of anvil plates such that the stapling assembly may receive several different anvil plates. Replacing an anvil plate can also provide fresh staple forming pockets. The anvil plate and staple cartridge can be paired based on staple leg length, types of staples stored in the staple cartridge, and/or desired formed height of the staples. In such instances, an anvil jaw configured to receive the anvil plate can be manufactured with or without staple forming pockets defined directly thereon. This may reduce manufacturing costs because the anvil jaw can be reused in different scenarios rather than introducing an entirely different surgical stapling instrument with different types of forming pockets.

FIGS. 137-139 depict a surgical stapling assembly 8600 comprising a first jaw 8601 and a second jaw 8603 movable relative to the first jaw 8601 to clamp tissue therebetween. The surgical stapling assembly 8600 is configured to cut and staple tissue captured between the jaws 8601, 8603. The first jaw 8601 comprises a replaceable staple cartridge 8620 configured to removably store a plurality of staples in a plurality of staple cavities 8622 therein defined in a deck surface 8621 of the staple cartridge 8620. The first jaw 8601 further comprises a cartridge channel 8610 configured to receive the replaceable staple cartridge 8620 therein. As discussed above, various different types of staple cartridges can be installed within the cartridge channel 8610. Various differences between replaceable staple cartridges can include different unformed staple leg height and/or orientation, different cartridge length, and/or different staple diameter, for example.

The second jaw 8603 comprises a replaceable anvil plate 8640 comprising an anvil surface 8641 and a plurality of forming pockets 8642 defined in the anvil surface 8641. The second jaw 8603 further comprises an upper anvil jaw portion 8630 configured to receive the replaceable anvil plate 8640 therein. In at least one instance, the replaceable anvil plate 8640 is slid into a distal end of the anvil jaw portion 8630. In at least one instance, the replaceable anvil plate 8640 is configured to be snapped into the anvil jaw portion 8630. In at least one instance, the anvil jaw portion 8630 comprises deformable arms made of a metallic material, for example, hanging from the perimeter of the anvil jaw portion 8630. The deformable arms can be configured to deform upon clamping of the jaws 8601, 8603 together after positioning the anvil plate 8640. Upon attaining a fully clamped position, the deformable arms are deformed and, in their deformed configuration, are configured to grasp and retain the anvil plate 8640 to the anvil jaw portion 8630. In at least one instance, a clampable member is configured to be clamped by the jaws 8601, 8603 to affix the anvil plate 8640 to the anvil jaw portion 8630. In such an instance, the clampable member can be responsible for deforming the deformable arms. After the anvil plate 8640 is secured to the anvil jaw portion 8630, the clampable member may be removed and discarded before the surgical stapling assembly 8600 is used. In at least one instance, the deformable members are part of the anvil plate 8630 and are configured to be secured to the anvil jaw portion 8630.

In at least one instance, an anvil cap is configured to be positioned on a distal end of the anvil jaw portion 8630. The anvil cap is configured to secure the anvil plate 8640 to the anvil jaw portion 8630. In at least one instance, the anvil plate 8640 is slid into the anvil jaw portion 8630 and, without the anvil cap, can only be removed by pulling the anvil plate 8640 distally from the distal end of the anvil jaw portion 8630. Such an anvil cap can secure the anvil plate 8640 at the distal end of the anvil jaw portion 8630. In at least one instance, the distal end of the anvil jaw portion 8630 comprises threads and the anvil cap comprises corresponding threads configured to be threaded onto the threads on the distal end of the anvil jaw portion 8630 to secure the anvil cap to the anvil jaw portion 8630. In at least one instance, the anvil cap comprises a polymer material. In at least one instance, the anvil cap is snapped onto the distal end of the anvil jaw portion 8630 and unsnapped from the distal of anvil jaw portion 8630 to replace the anvil plate 8640. In various instances, a user can install and uninstall the anvil cap. In other instances, a specific tool is required to install and/or uninstall the anvil cap from the anvil jaw portion 8630. In at least one instance, the specific tool is provided with the replaceable anvil plate 8640 and/or replaceable staple cartridge 8620. As discussed above, a replaceable anvil plate and a replaceable staple cartridge can come as a single replaceable unit to be installed within a surgical stapling assembly. In various instances, a user can mix and match anvil plates and replaceable staple cartridges to tune the type of staple line, tissue compression, and/or gripping pressure, for example, desired for a particular use. This can be based on the targeted tissue and/or type of operation, for example. For example, the one or more rows of forming pockets 8642 in certain anvil plates 8640 can include forming pockets having transverse pocket axes and configured to form 3D or non-planar staples, as further described herein, while other rows of forming pockets 8642 include forming pockets having aligned pocket axes and configured to form 2D or planar staples. Additionally or alternatively, the anvil plate can include a stepped and/or contoured surface to optimize the tissue gap for certain applications.

In various instances, a surgical end effector and or stapling assembly for a surgical device can include a rotary drive screw or rotary drive member, as further described herein. A rotary drive screw can extend through a channel and/or portion of a staple cartridge to a distal location in the end effector. The rotary drive screw can facilitate clamping and/or firing of the staple cartridge, as further described herein. The rotary drive screw can extend along a longitudinal axis and can be aligned with a centerline of the staple cartridge extending from a proximal end to a distal end thereof.

A rotary drive screw through an end effector can take up a substantial portion of the limited real estate along the longitudinal center portion of the end effector and staple cartridge thereof. In various instances, the rotary drive screw may interfere with certain existing firing components, such as the drivers and/or the sled, for example. The small footprint of the staple cartridge and the significant firing forces applied to various components in an end effector and staple cartridge can pose various challenges to structural variations and/or the relocation of certain components.

For example, the firing component(s) in a staple cartridge having a rotary drive screw therethrough need to be modified to avoid interference and provide a sufficient clearance around the rotary drive screw while withstanding the firing forces and balancing torques during the firing stroke in order to minimize damage to the components and/or misfiring of the staples. In various instances, the rows of staples can be condensed (i.e. a denser staple arrangement) and/or shifted laterally outboard away from the rotary drive screw to increase lateral space around the centerline of the staple cartridge. Relocation and/or increased density of the staple rows may require various adaptions to the firing components such as the drivers and/or the sled, for example.

In various instances, the drivers and/or the sled can be modified to correspond to the relocated and/or condensed staple rows while minimizing jams and/or incidences of misfiring. Modifications to the staple drivers may include structural and geometric variations to the staple support columns and/or bridges therebetween, for example. In certain instances, an upper portion of the driver (e.g. the widths of the staple supporting columns) can be asymmetric relative to a centerline of the driver. Additionally or alternatively, a lower portion of the driver (e.g. the bridges and/or base of the staple supporting columns) can be asymmetric relative to a centerline of the driver.

For example, in one aspect of the present disclosure, a staple cartridge can include a body extending along a longitudinal axis, rows of staples, and a triple driver configured to fire three staples simultaneously. The rows of staples can include an inner row on a first side of the longitudinal axis, wherein the inner row comprises an inner staple. The rows of staples can also include an intermediate row on the first side of the longitudinal axis, wherein the intermediate row comprises an intermediate staple. Furthermore, the rows of staples can include an outer row on the first side of the longitudinal axis, wherein the outer row comprises an outer staple. The intermediate row can be equilaterally spaced from the inner row and the outer row. The triple driver can include an inner support column defining a first width, wherein the inner support column is configured to support the inner staple. The triple driver can also include an intermediate support column defining a second width, wherein the intermediate support column is configured to support the intermediate staple. Further, the triple driver can include an outer support column defining a third width, wherein the outer support column is configured to support the outer staple. The first width can be less than the second width and less than the third width. In certain instances, the first width, the second width, and the third width can all be different.

In various aspects of the present disclosure, varied widths of the staple support columns of a multi-staple driver can be configured to provide a wider space for the sled rails while optimizing real estate for a rotary drive screw along a central longitudinal portion of the staple cartridge. Various improvements to the staple cartridge, including to the drivers and the cartridge body, for example, and advantages thereof are further described herein.

Figure 24:
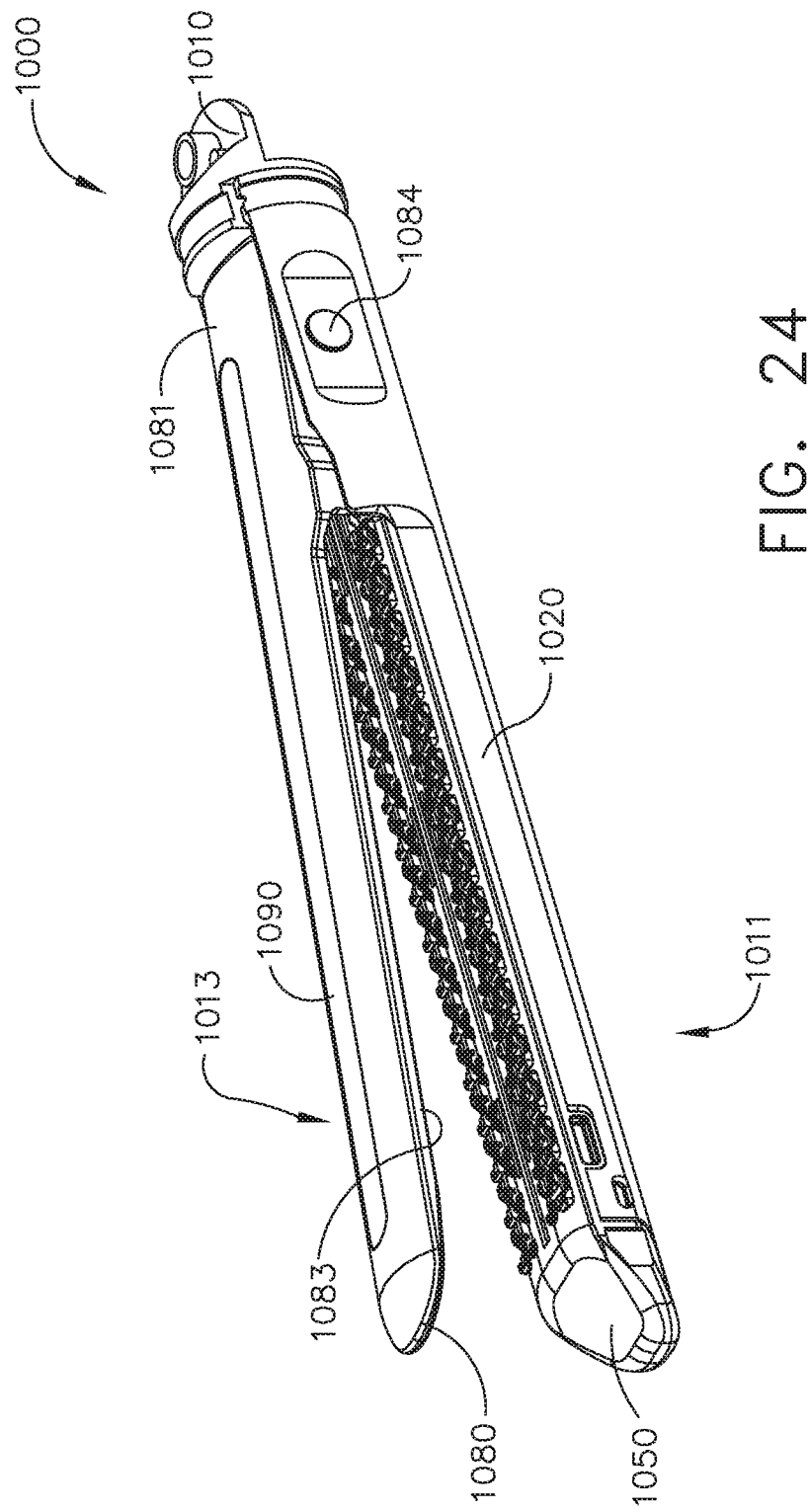
FIG. 24 is a perspective view of an end effector assembly comprising an anvil, a channel, and a staple cartridge, in accordance with at least one aspect of the present disclosure.

Referring now to FIGS. 24 and 25, a staple cartridge 20100 includes a body 20102 extending along a longitudinal axis A. Staples are removably positioned in the body 20102. The staples can be ejected from the body 20102 and fired into tissue, for example, during a firing stroke. The staples are arranged in longitudinal rows on either side of the longitudinal axis A. The cartridge body 20102 also includes a deck 20104, which can be referred to as a tissue-supporting surface, for example. The deck 20104 is a laterally-curved tissue-supporting surface and defines a curved surface or contour from a first lateral side of the body 20102 to a second lateral side of the body 20102. A peak in the laterally-curved tissue-supporting deck 20104 is defined at an intermediate portion of the body 20102. The peak can be positioned between the longitudinal rows of staples and overlie the longitudinal axis A, for example. In various instances, a rotary drive screw, like the firing screw 261 (FIGS. 4 and 5), for example, extends through a portion of the staple cartridge 20100, as further described herein.

The staples are positioned in cavities 20110 defined in the cartridge body 20102. The staples are arranged in longitudinal rows on either side of the longitudinal axis A. For example, the cavities 20110 are arranged in cavity rows 20112. The cavity rows include an inner row 20112a, an intermediate row 20112b, and an outer row 20112c on each side of the longitudinal axis A. The intermediate row 20112b is equilaterally spaced between the inner row 20112a and the outer row 20112c. For example, the inner cavity row 20112a can be laterally spaced inward from the intermediate cavity row 20112b by a distance, and the outer cavity row 20112c can be laterally spaced outward from the intermediate cavity row 20112*b* by the same distance. The rotary drive screw can be aligned with the longitudinal axis A, and can extend through the cartridge body 20102 adjacent to the inner cavity rows 20112*a*. The rotary drive screw can be between and parallel to the inner cavity rows 20112*a*, for example.

The inner rows 20112*a* hold inner staples, the intermediate rows 20112*b* hold intermediate staples, and the outer rows 20112*c* hold outer staples. In various instances, the inner staples, the intermediate staples, and the outer staples can be identical. In other instances, the inner staples, the intermediate staples, and/or the outer staples can be each be different with respect to staple type (e.g. wire or stamped), material, and/or size (e.g. different heights), for example. The reader will appreciate that various staples, staple cavities, staple drivers, and staple cartridges are described herein. However, in certain instances, alternative fasteners can be utilized and such fasteners can be incorporated into fastener cavities, driven by fastener drivers, and/or fired from fastener cartridges which be similar to the staple cavities, staple drivers and/or staple cartridges described herein in many aspects.

The staple cartridge 20100 may have a different arrangement of staples. For example, the staple cartridge 20100 may have less than three rows of staples on each side of the longitudinal axis A and, in one aspect, may only have two rows of staples on each side of the longitudinal axis A. In still other instances, the staple cartridge 20100 can include four or more rows of staples on one or more sides of the longitudinal axis A. In various instances, the rows of staples may be asymmetrical relative to the longitudinal axis A. For example, the first side of the staple cartridge 20100 can have a different number of rows of staples than the second side of the staple cartridge 20100.

Each staple cavity 20110 includes a proximal end, a distal end, and lateral guide surfaces intermediate the proximal end and the distal end. The staple cavities 20110 are structured and dimensioned to guide drivers 20120 through the staple cavities 20110 toward the deck 20104. More specifically, the geometry of the staple cavities 20110 can complement the geometry of the drivers 20120. For example, the lateral guide surfaces in each staple cavity 20110 are configured to guide sidewalls 20134 of the driver 20120 (e.g. sidewalls of the staple-supporting columns) as the driver 20120 moves through the staple cavity 20110. Additionally or alternatively, the proximal end and/or the distal end of each staple cavity 20110 can include an upright groove configured to slidably receive an end and/or tongue thereof of the driver 20120. Alternative tongue and groove arrangements are also contemplated, which can be configured to guide the drivers 20120 through the staple cavities 20110 during firing of the staples from the staple cartridge 20100.

The drivers 20120 are configured to support and drive multiple staples from the cartridge body 20102 during a firing stroke. The drivers 20120 can movably support staples spanning two or more longitudinal rows of staple cavities 20112. For example, the drivers 20120 can movably support an inner staple, an intermediate staple, and an outer staple on the same side of the staple cartridge 20100.

Figure 28:
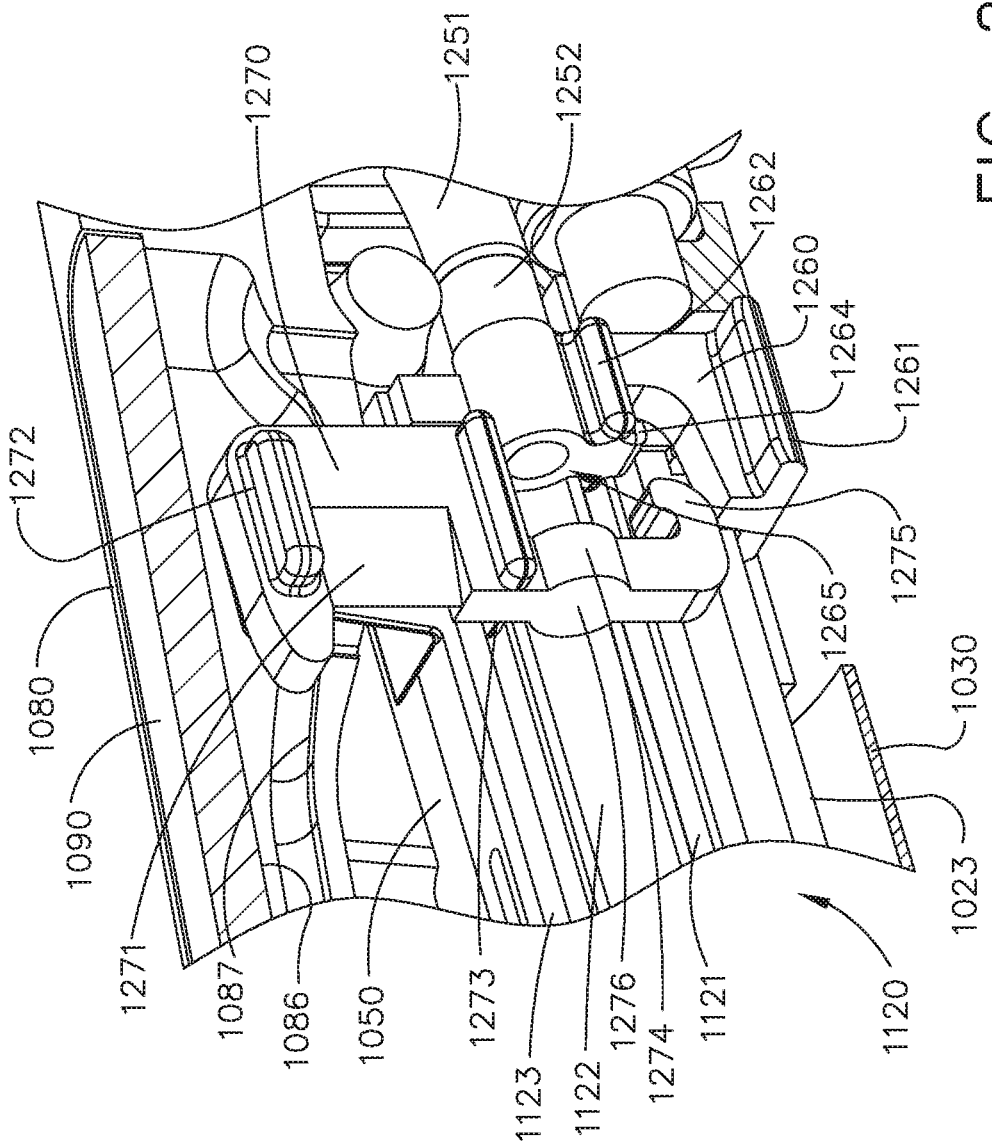
FIG. 28 is a partial cross-sectional perspective view of the end effector assembly of FIG. 24, wherein the end effector assembly comprises a firing assembly comprising an upper firing member and a lower firing member, and wherein the upper firing member is illustrated disengaged from the lower firing member, in accordance with at least one aspect of the present disclosure.

Referring primarily now to FIGS. 26-28, the driver 20120 is shown. Multiple drivers like the driver 20120 are incorporated into the staple cartridge 20100, for example. The driver 20120 is a triple driver, which is configured to drive three staples simultaneously. The driver 20120 includes three support columns—an inner support column 20122*a* configured to support an inner staple in an inner row of staples, an intermediate support column 20122*b* laterally outboard of the inner support column 20122*a* configured to support an intermediate staple in an intermediate row of staples, and an outer support column 20122*c* laterally outboard of the intermediate support column 20122*b* and configured to support an outer staple in an outer row of staples. The support columns 20122*a*, 20122*b*, 20122*c* of each drive 20120 can be longitudinally staggered in various instances.

The driver 20120 also includes bridges 20126 extending between adjacent support columns 20122. For example, a first bridge 20126*a* extends between the inner support column 20122*a* and the intermediate support column 20122*b*, and a second bridge 20126*b* extends between the intermediate support column 20122*b* and the outer support column 20122*c*. The bridges 20126*a*, 20126*b* each include a ramped underside 20128 configured to be drivingly engaged by a sled during a firing stroke. Stated differently, each driver 20120 is configured to be engaged and lifted by two parallel sled rails along the ramped undersides 20128 of the driver 20120. For example, a sled can be configured to move along a firing path during a firing stroke. The sled can comprise a central portion aligned with the longitudinal axis A, a first rail on a first side of the longitudinal axis A that is configured to driving engage the ramped underside 20128 of the first bridge 20126*a*, and a second rail on a second side of the longitudinal axis A that is configured to drivingly engage the ramped underside 20128 of the second bridge 20126*b*. Sleds and firing motions thereof are further described herein.

Each support column 20122 includes a proximal end 20130, a distal end 20132, and a pair of opposing sidewalls 20134 extending longitudinally between the proximal end 20130 and the distal end 20132. The sidewalls 20134 are configured to slidably engage the lateral guide surfaces in the respective staple cavity 20110 during a firing motion. Each support column 20122 includes a staple-supporting cradle 20124. A base of the staple can be held in the staple-supporting cradle 20124.

The staple-supporting cradles 20124 are each aligned with one of an inner axis A1, an intermediate axis A2, or an outer axis A3, which correspond to the axes defining the longitudinal rows of staples and staple cavities 20110 on one side of the staple cartridge 20100. A first lateral distance D1 is defined between the inner axis A1 and the intermediate axis A2, and a second lateral distance D2 is defined between the outer axis A3 and the intermediate axis A2. The axes are equilaterally spaced; the first lateral distance D1 and the second lateral distance D2 are the same. Though the lateral distances D1, D2 between the axes and adjacent rows of staple cavities 20110 are the same, the driver 20120 is asymmetrical relative to a centerline of the driver 20120. For example, the centerline of the driver 20120 corresponds to the intermediate axis A2 and the inner and outer staples are positioned equidistant from intermediate axis A2; however, the driver 20120 is not symmetrical about the intermediate axis A2.

Referring primarily to FIG. 143, the inner support column 20122*a* defines a first width Wa between its sidewalls 20134, the intermediate support column 20122*b* defines a second width Wb between its sidewalls 20134, and the outer support column 20122*c* defines a third width Wc between its sidewalls 20134. The first width Wa is different than the second width Wb and the third width Wc. For example, the first width Wa can be reduced or narrowed to less than the second width Wb and less than the third width Wc to accommodate the rotary drive screw through a center portion of the staple cartridge 20100. In certain instances, one or more narrower support columns 20122 can effectively narrow and reduce the footprint of the driver 20120 while maximizing the width the bridge 20126 and, thus, maximizing the width of the sled rails, which engage the ramped undersides 20128 of the bridges 20126 and deliver the firing force to the driver 20120, for example. In various instances, increasing the width of the bridge 20126 and the sled rails may improve the stiffness of the sled rails and minimize deformations and/or damage to the sled during a firing stroke.

The widths Wa, Wb, and Wc are all different. For example, the width Wb of the intermediate support column 20122b is greater than the width Wa of the inner support column 20122a and the width Wc of the outer support column 20122c. The width Wc is less than the width Wb of the intermediate support column 20122b and greater than the width Wa of the inner support column 20122a. The differing widths Wa, Wb, and Wc are configured to optimize the width of the driver 20120 to accommodate a rotary drive screw along the longitudinal axis A, while effectively transferring the firing force and minimizing torque and mis-firings, for example.

As provided herein, in certain instances, the width of the staple support columns on the drivers can be varied to accommodate a rotary drive screw positioned in the staple cartridge. Additionally or alternatively, in certain aspects of the present disclosure, the lower portions of a driver can also vary laterally and the lower portion (e.g. the lower portion of the support columns and/or the bridges) may be asymmetric relative to a centerline through the intermediate support column. For example, a lower portion of the drivers can be improved to increase the available real estate in a longitudinal center portion of the staple cartridge. An asymmetric geometry for the lower portion of the drivers can be selected to improve the strength and stiffness of the triple driver while minimizing the height of the driver. In various instances, though the support column thickness and/or bridge geometry can vary laterally, the support columns can be equally spaced from a centroid of the substantially triangular triple driver. For example, the intermediate support column can be longitudinally aligned with the centroid, and the inner and outer support columns can be longitudinally offset from the centroid. In various instances, the ramped surfaces can be equilaterally spaced from the centroid of the triple driver.

Figure 29:
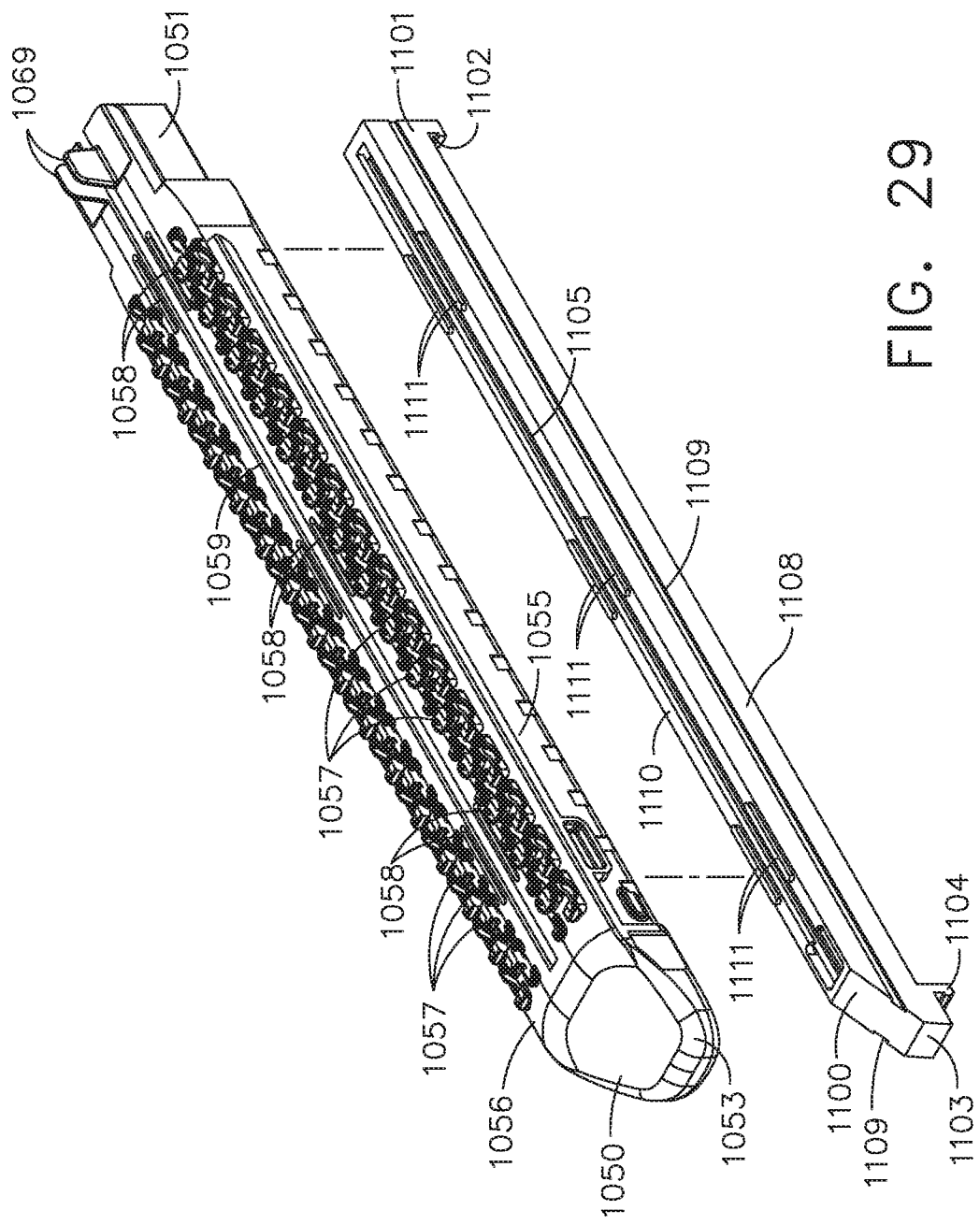
FIG. 29 is an exploded perspective view of the staple cartridge and a support beam of the end effector assembly of FIG. 24, in accordance with at least one aspect of the present disclosure.
Figure 30:
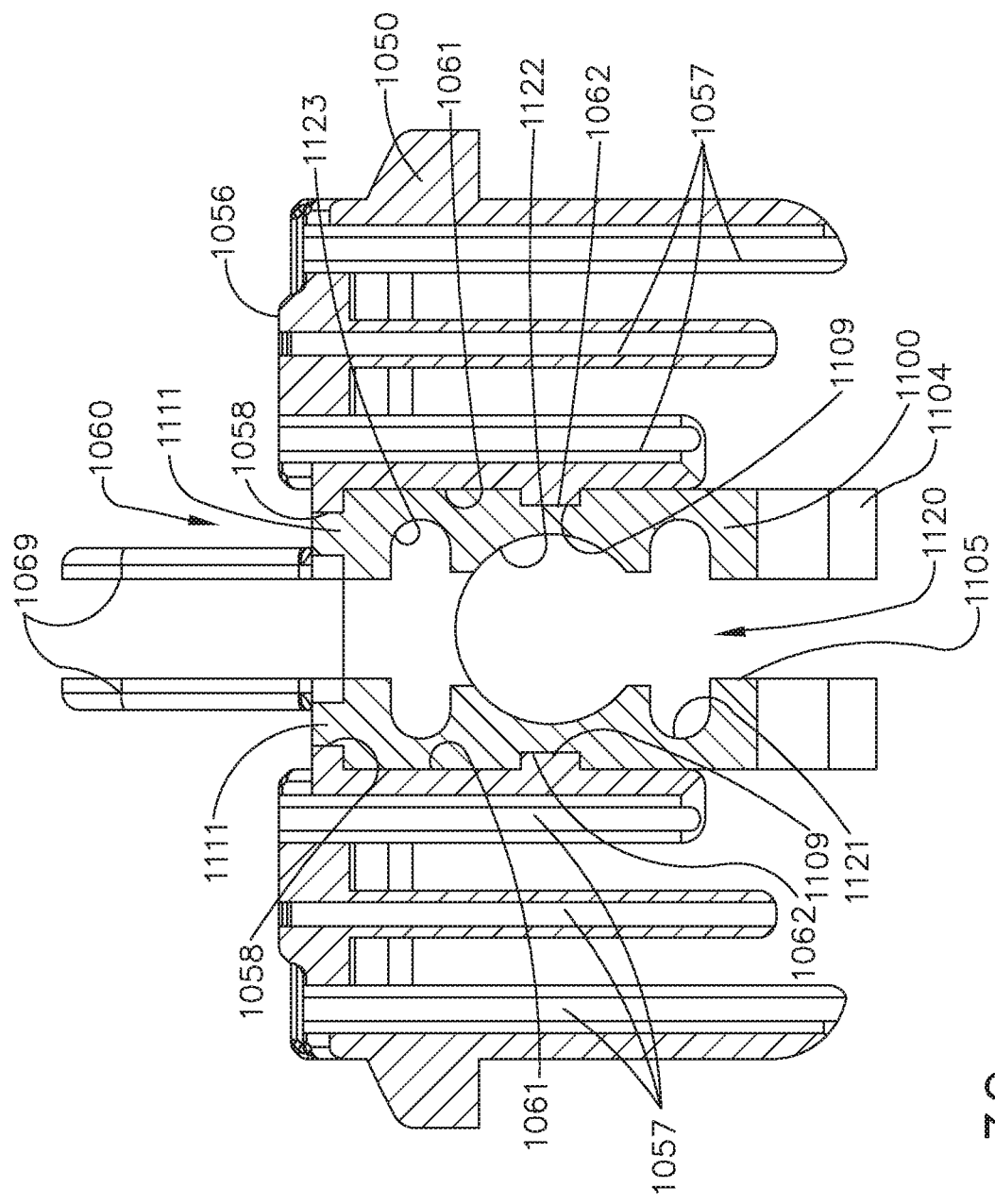
FIG. 30 is a cross-sectional perspective view of the staple cartridge and the support beam of the end effector assembly of FIG. 24, in accordance with at least one aspect of the present disclosure.
Figure 31:
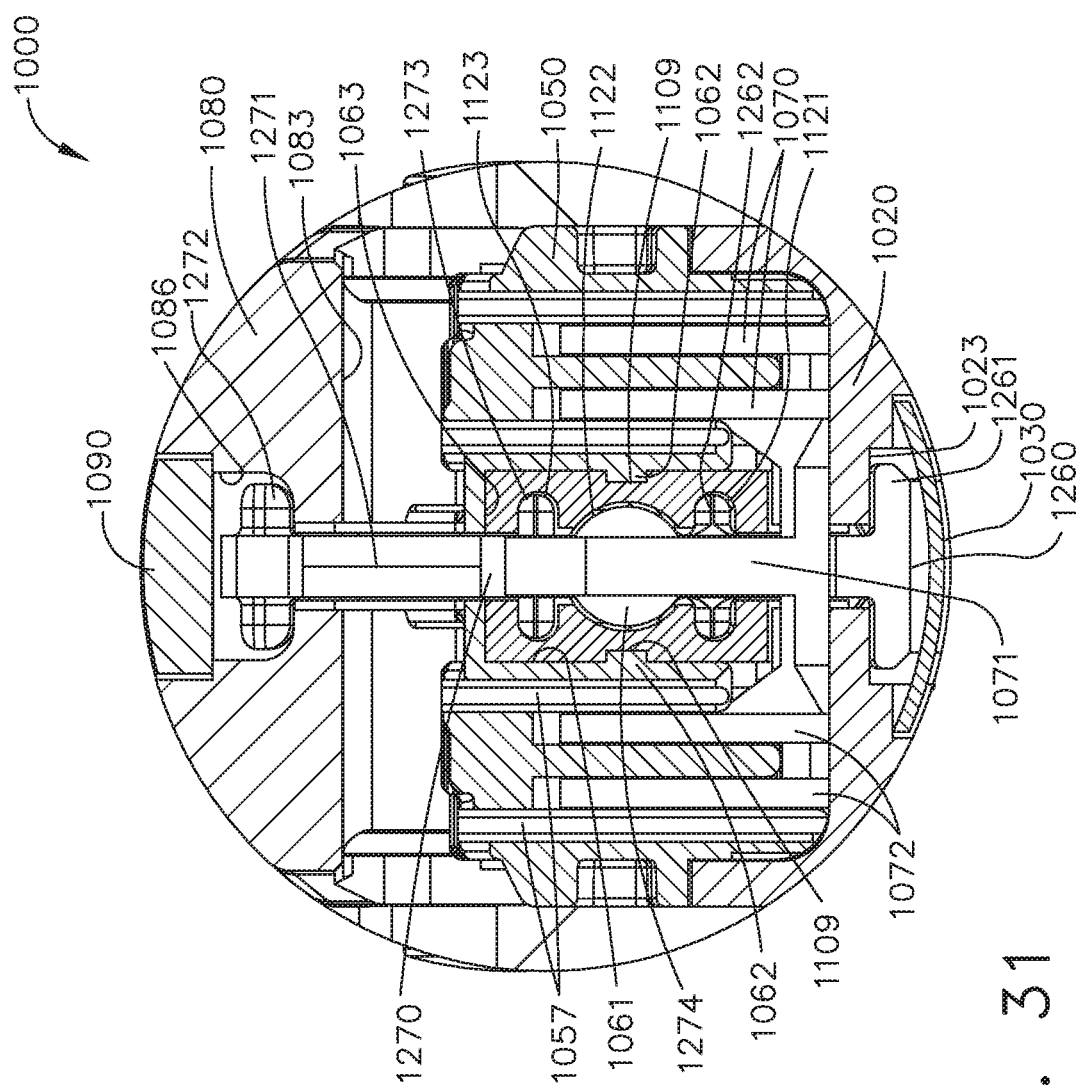
FIG. 31 is a cross-sectional elevation view of the end effector assembly of FIG. 24, in accordance with at least one aspect of the present disclosure.
Figure 32:
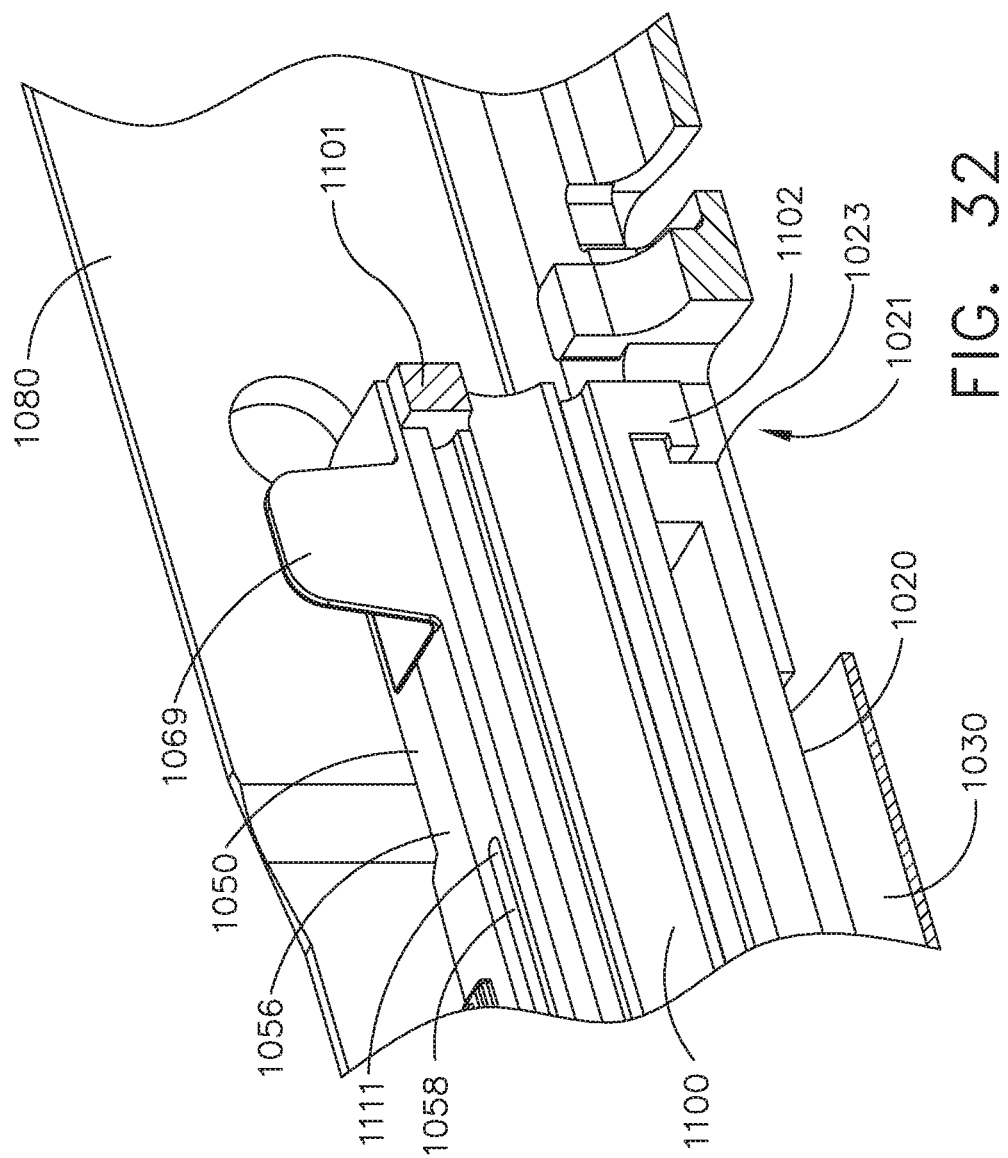
FIG. 32 is a cross-sectional perspective view of a proximal end of the end effector assembly of FIG. 24 with various components not shown for clarity, in accordance with at least one aspect of the present disclosure.

Referring to FIGS. 29 and 30, an end effector 20240 including a staple cartridge 20200 and a triple driver 20220 is shown. The staple cartridge 20200 is similar in many aspects to the staple cartridge 20100 (FIG. 140), and the triple driver 20220 is similar in many aspects to the triple driver 20120 (FIG. 142). For example, the staple cartridge 20200 includes a cartridge body 20202 including three rows of staple cavities on each side of the rotary drive screw 20242, and the triple driver 20220 include three parallel staple-supporting cradles 20224 configured to support staples, wherein the triple driver 20220 is configured to fire staples from an inner row, an intermediate row, and an outer row.

The end effector 20240 includes a rotary drive screw 20242 and a firing member 20244, which are similar to the firing screw 261 (FIGS. 4 and 5) and the firing member 270 (FIGS. 4 and 5), respectively. The firing member 20244 is configured to move through the staple cartridge 20200 during a firing stroke to advance the sled and lift the driver 20220.

The driver 20220 includes an inner support column 20222a, an intermediate support column 20222b, and an outer support column 20222c. The columns 20222 comprise different widths, as further described herein. In various aspects of the present disclosure, one or more of the columns 20222 can also include a different height than the other columns. In various instances, the different heights are configured to form staples to varying heights, which can correspond to the contour of a laterally-curved tissue-support surface or deck of the cartridge body, for example.

The lower portion of the driver 20220 includes a chamfered inner edge 20236. The chamfered inner edge 20236 is a cutaway or scalloped edge dimensioned to accommodate the drive screw 20242 and a lower portion of the firing member 20244. For example, the drive screw 20242 extends along the longitudinal axis A and is positioned between the drivers 20220 on opposite sides of the longitudinal axis A. In such instances, the drive screw 20242 can extend through the staple cartridge 20200 while minimizing the dimensions of staple cartridge 20200 and end effector 20240. The chamfered inner edge 20236 comprises a cutaway into a base portion of the inner support column 20222a, which provides a clearance for the firing components positioned along the longitudinal center portion of the end effector 20240. Moreover, the chamfered inner edge 20236 is configured to provide a space closer to a vertical centerline of the of the end effector, i.e. equidistance between the upper cam and the lower cam, which can improve and/or help to balance the forces during the firing stroke.

Additionally or alternatively, the bridges of a driver can vary laterally and/or be asymmetric relative to a centerline through the intermediate support column of the driver. Referring now to FIG. 147, an end effector 20340 including a staple cartridge 20300 and a triple driver 20320 is shown. The staple cartridge 20300 is similar in many aspects to the staple cartridge 20100 (see FIG. 140), and the triple driver 20320 is similar in many aspects to the triple driver 20120 (see FIG. 142). For example, the staple cartridge 20300 includes a cartridge body 20302 and deck 20304; three rows of staple cavities are positioned on each side of the rotary drive screw, and the triple driver 20320 includes three parallel staple-supporting cradles 20324 configured to support staples, wherein the triple driver 20320 is configured to fire staples from an inner row, an intermediate row, and an outer row. The driver 20320 is depicted in a fired configuration in FIG. 147, in which an upper portion of staple support columns extend through the deck 20304 (i.e. staple overdrive).

The end effector 20340 can include a rotary drive screw and a firing member, as further described herein, the firing member moves through the staple cartridge 20300 during a firing stroke to advance a sled 20350 having rails 20352 to lift the driver 20320. The driver 20320 includes an inner support column 20322a, an intermediate support column 20322b, and an outer support column 20322c. The columns 20322 comprise different widths, as further described herein. In various aspects of the present disclosure, one or more of the columns 20322 can also include a different height than the other columns, as further described herein.

The lower portion of the driver 20320 includes a chamfered inner edge 20336, which is similar in many aspects to the chamfered edge 20236 (FIG. 145). The lower portion of the driver 20320 also includes the bridges 20326 between adjacent staple support columns 20322. A first bridge 20326a connects the inner support column 20322a to the intermediate support column 20322b, and a second bridge 20326b connects the intermediate support column 20322b to the outer support column 20322c. The geometry of the first bridge 20326a is different than the geometry of the second bridge 20326b. Stated differently, the bridges 20326a are asymmetric relative to a vertical plane P (FIG. 147) through the driver 20320 and aligned with an axis of an intermediate staple base/crown supported thereon.

The first bridge 20326a is taller than the second bridge 20326b. In various instances, as further described herein, a central longitudinal portion of the staple cartridge 20300 can be taller and define a greater height at a peak of the laterally-curved tissue support surface than along the sides of the staple cartridge 20300. As a result, the staple cartridge 20300 can accommodate additional material and/or increased height/volume of the driver 20320 between the inner support column 20322a and the intermediate support column 20322b than between the outer support column 20322c and the intermediate support column 20322b. The increased height of the first bridge 20326a from the base surface compared to the second bridge 20326b can compensate for rigidity losses resulting from the chamfered inner edge 20336, for example. Additionally or alternatively, the greater height of the first bridge 20326a compared to the second bridge 20326b can improve the stiffness and strength of the triple driver 20320, while minimizing the dimensions and maintaining a compact form factor for the staple cartridge 20300 and the end effector 20340.

In certain instances, an upper portion of the first bridge 20326a can be configured to guide the driver 20320 through the staple cavities during an initial portion of the firing motion through the staple cavities. For example, when the inner support column 20322a is in an unfired position, the inner support column 20322a may be at least partially unsupported or unguided by lateral guide surfaces because of cutouts in a central portion of the cartridge body assembly 20300 to accommodate the rotary drive screw. In the absence of certain lateral support surfaces around the inner support column 20322a, the driver 20320 may be prone to torque and/or misfiring. However, the increased height of the first bridge 20326a can be configured to engage an upright support surface in the cartridge body during an initial portion of the firing motion to improve the guidance and support of the driver 20320.

Referring now to FIG. 148, an alternative driver geometry for a driver 20420 is shown. The driver 20420 is a triple driver and is similar in many aspects to the triple driver 20120 (FIG. 142). For example, the triple driver 20420 includes three parallel staple-supporting cradles 20424 configured to support staples, and the triple driver 20420 is configured to fire staples from an inner row, an intermediate row, and an outer row. The driver 20420 can be incorporated in various staple cartridges disclosed herein. For example, the driver 20420 can be utilized with a staple cartridge adapted to receive a rotary drive screw extending along a longitudinal axis and with a variable height deck.

The driver 20420 includes an inner support column 20422a, an intermediate support column 20422b, and an outer support column 20422c. The columns 20422 comprise different widths, as further described herein. In various aspects of the present disclosure, one or more of the support columns 20422 can also include a different height than the other support columns, as further described herein.

The lower portion of the driver 20420 includes a chamfered inner edge 20436, which is similar in many aspects to the chamfered edge 20236 (FIG. 145). The lower portion of the driver 20420 also includes bridges between adjacent staple support columns 20422. A first bridge 20426a connects the inner support column 20422a to the intermediate support column 20422b, and a second bridge 20426b connects the intermediate support column 20422b to the outer support column 20422c. Variations to the geometry of a lower portion of the driver 20420 are indicated with dashed lines in the schematic illustration of FIG. 148. For example, to provide adequate space and clearance along a central longitudinal portion of the staple cartridge for a rotary drive screw 20442, which is similar to the firing screw 261 (FIGS. 4 and 5) in many aspects, the driver 20420 includes the chamfered inner edge 20436 and the upper gusset 20438 between the first bridge 20426a and the inner support column 20422a. In such instances, the driver 20420 can provide a space and clearance for the rotary drive screw 20442 while maintaining sufficient structural integrity and stiffness to appropriately transfer the firing loads.

In various instances, a tallest height of the variable height deck and the staple cartridge can be adjacent to the rotary drive screw 20442. In such instances, a tighter tissue gap can be defined along the firing bar and cutting edge. The portion of the variable height deck overlaying the inner support column 20422a and/or first bridge 20426a can define the greatest height and, thus, in certain aspects, can fit the heightened first bridge 20426a and/or the gusset 20438 intermediate the first bridge 20426a and the inner support column 20422a.

In certain instances, one or more gusset plates can extend between an upper edge of the first bridge 20426a and the inner support column 20424. In certain instances, the gusset 20438 can comprise a longitudinal gusset rib along at least a portion of the length of the inner support column 20422a and the first bridge 20426a. The driver 20420 is asymmetric relative to a vertical plane P (FIG. 148) through the intermediate support column 20422b and aligned with the longitudinal axis of a staple base supported therein. For example, the first bridge 20426a can define a different geometry and different cross-sectional profile than the second bridge 20426b owing to the gusset 20438 and/or to the chamfered inner edge 20436.

In certain instances, to accommodate a rotary drive screw along a central portion of the staple cartridge, a portion of the cartridge body can be cutaway. The cartridge body can include additional guides and support features configured to guide the driver through the staple cavity and toward the deck of the cartridge body. The guides can be configured to engage and support the driver even when a portion the driver is not fully seated within the staple cavity.

Figure 33:
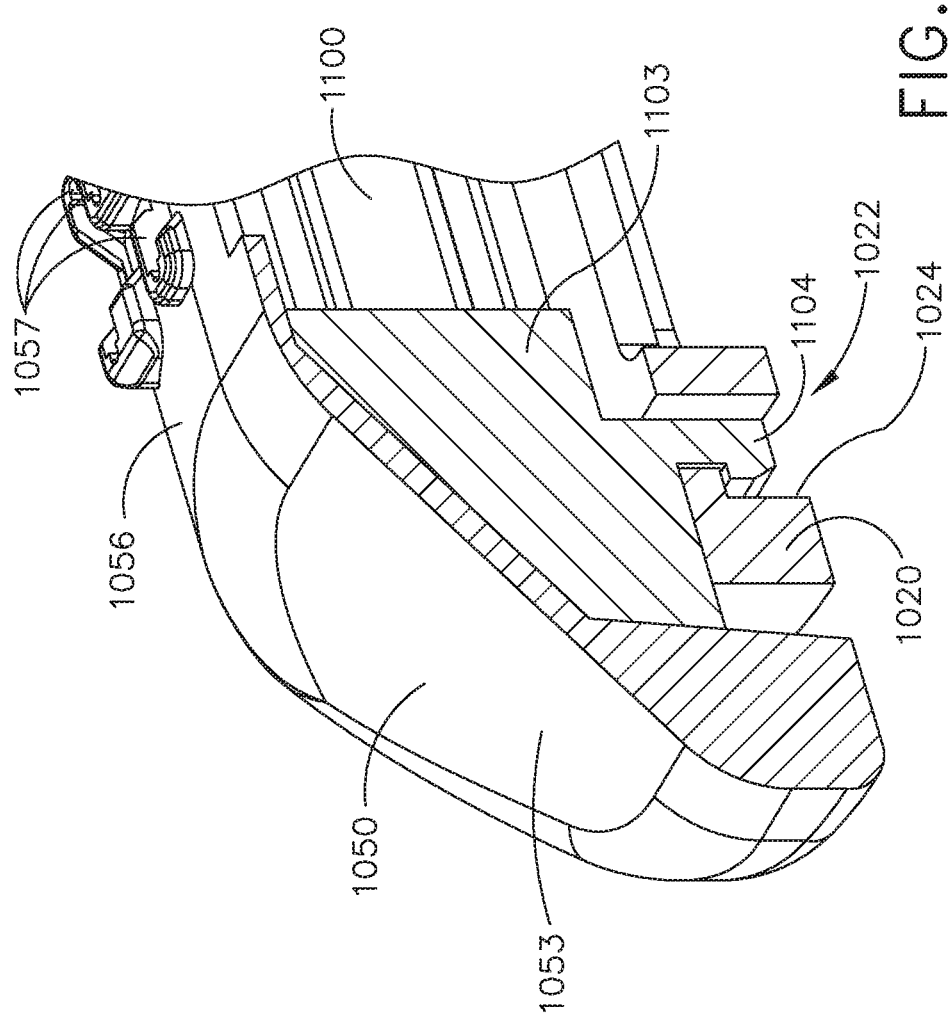
FIG. 33 is a cross-sectional perspective view of a distal end of the end effector assembly of FIG. 24, in accordance with at least one aspect of the present disclosure.

Referring to FIGS. 33 and 34, a cartridge body 20502 is shown. In various instances, the cartridge body 20502 can be similar in many aspects to the cartridge body 20102 (FIG. 140) and can be incorporated into the staple cartridge 20100 and use the drivers 20120 (FIG. 142). Staples can be positioned in cavities 20510a, 20510b, 20510c defined in the cartridge body 20502. The staples are arranged in longitudinal rows on either side of a longitudinal axis A along a centerline of the cartridge body 20502. For example, the cavities 20510a, 20510b, 20510c are arranged in cavity rows. The cavity rows include an inner row 20512a, an intermediate row 20512b, and an outer row 20512c on each side of the longitudinal axis. A rotary drive screw (e.g. firing screw 261 in FIGS. 4 and 5) can be aligned with the longitudinal axis A, and can extend through the cartridge body 20502 adjacent to the inner cavity rows 20512a. The rotary drive screw can be between and parallel to the inner cavity rows 20512a, for example.

Referring primarily to FIG. 150, the cartridge body 20502 includes guide surfaces 20514 extending around the inner cavities 20510a in the inner row 20512a. In various instances, the guide surfaces 20514 are configured to guide the driver (e.g. the inner support column 20122a of the triple driver 20120) into and through the inner cavity 20510a even when the inner support column 20122a is not fully seated in the inner cavity 20510a before firing. In various instances, the guide surfaces 20514 are circumferential chamfers on the underside cartridge surface extending around the inner cavities 20510*a*. Such circumferential chamfers are configured to prevent inadvertent snags and hang-ups as the inner support column of the driver is advanced into the inner cavity 20510*a*. In other instances, the guide surfaces 20514 can comprise a fillet, for example. The guide surfaces 20514 can extend around the entire perimeter of the inner cavities 20510*a*. In other instances, the guide surfaces 20514 can be positioned around a portion of the perimeter, e.g. a first lateral side, a proximal end, and/or a distal end.

Referring also to FIG. 151, a portion of the inner cavity 20510*a* and the driver 20120 is shown. The lower edge of the inner cavity 20510*a* includes the guide surfaces 20514 extending around the inner cavity 20510*a*. The top edge of the inner support column 20122*a* also includes a guide surface 20125, which is configured to guide the inner support column 20122*a* into alignment with the inner cavity 20510*a* even when the inner support column 20122*a* is not fully seated in the inner cavity 20510*a* prior to the firing stroke and initial lift of the driver 20120 by a sled. In such instances, the guide surfaces 20514, 20125 on the lower edge of the inner cavity 20510*a* and the top edge of the inner support column 20122*a*, respectively, are configured to interact to ensure the inner support column 20122*a* moves smoothly into the inner cavity 20510*a* during a firing stroke. As further described herein, the inner support column 20122*a* may not be fully seated in the inner cavity 20510*a* prior to the firing stroke owing to the space required by the rotary drive screw along a central longitudinal portion of the cartridge body 20502.

Referring now to FIGS. 36 and 37, a portion of a driver 20620 is shown. In various aspects of the present disclosure, the driver 20620 can be a triple driver and similar in many aspects to the driver 20120 (FIG. 142). The driver 20620 can be incorporated into the staple cartridge 20100 (FIG. 140) in various aspects of the present disclosure. The driver 20620 includes a support column 20622 configured to support a staple 20680 (FIG. 153). The support column 20622 includes a proximal end 20630, a distal end 20632, and a pair of opposing sidewalls 20634 extending longitudinally between the proximal end 20630 and the distal end 20632. The sidewalls 20634 are configured to slidably engage the lateral guide surfaces in the respective staple cavity. The support column 20622 also includes a staple-supporting cradle 20624, and a base of the staple 20860 can be held in the staple-supporting cradle 20624.

The driver 20630 further includes proximal and distal upright features 20636, 20638 or extensions, which extend away from the base of the driver 20630 and away from the staple-supporting cradle 20624. The proximal upright feature 20636 is a proximal-most feature of the support column 20622 and extends from the proximal end 20630 of the support column 20622. The distal upright feature 20638 is a distal-most feature of the support column 20622 and extends from the distal end 20636 of the support column 20622. In the driver's unfired position, the proximal and distal upright features 20636, 20638 can be below the deck of the staple cartridge and extend toward the deck. The proximal and distal upright features 20636, 20638 can be configured to support the staple 20680 and guide the staple legs during formation, for example.

The proximal and distal upright features 20636, 20638 are the tallest portions of the support column 20622. In certain instances, when the driver is moved to the fired position, the proximal and distal upright features 20636, 20638 can extend above the deck and facilitate gripping and/or holding of tissue adjacent to the staples 20860. For example, the proximal and distal upright features 20636, 20638 can grip tissue at the proximal end and the distal end of the staple cavity. Moreover, the proximal and distal upright features 20636, 20638 can act as guide surfaces for the driver 20630 and can guide the support column 20632 into the fastener cavity in certain instances. For example, when the support column 20622 is not fully seated in the staple cavity prior to firing, as further described herein, the proximal and distal upright features 20636, 20638 are configured to guide the support column 20622 into alignment with the staple cavity during the firing motion.

In certain instances, the proximal and distal upright features 20636, 20638 may be incorporated into an inner support column (i.e. the support column adjacent to a firing path and/or rotary drive screw). In such instances, the proximal and distal upright features 20636, 20638 can engage the staple cavity during the firing stroke and are configured to guide the inner support column even if the inner support column is not fully seated in the staple cavity prior to firing, as further described herein. In other instances, the intermediate support column and/or the outer support column can also include at least one of a proximal upright feature 20636 and/or a distal upright feature 20638.

In certain aspects of the present disclosure, the proximal and distal upright features 20636, 20638 are configured to be received into recesses along an underside of the tissue-supporting deck when the driver 20620 is in the fully advanced position. As further described herein, the underside of the tissue-supporting deck can include an array of recesses that fit within the pocket extenders on the anvil-facing side of the deck. Pocket extenders can surround or at least partially surround the openings in the tissue-supporting deck to grip tissue and/or guide the staple legs during the firing stroke. The nesting of features on the driver with underside recesses in the tissue-supporting deck is further described herein. Nesting of the proximal and distal upright features in the pocket extenders or ridges of the cartridge deck can maintain the desired tissue gap and deck thickness in various instances.

In certain instances, a replaceable staple cartridge can be used with each firing stroke and then replaced with another replaceable staple cartridge for a subsequent firing stroke. The replaceable staple cartridge can include a cartridge body, drivers, staples, and a sled, as further described herein. Reusable, multi-fire cutting edges can be incorporated into the end effector and advanced relative to the replaceable staple cartridge in certain instances. For example, an end effector can include a firing member, such as an I-beam or an E-beam, for example, having a distal-facing upright cutting edge along a leading edge thereof. Exemplary firing members having a reusable cutting edge for use during multiple firing strokes are further described herein. In certain instances, reusable knives and the cutting edge(s) thereof can be a hardened part, which may be expensive to manufacture. In certain instances, the placement of a reusable knife in a surgical device may limit the number of times the surgical device can be reused. Moreover, to resist dulling of the knife with multiple firings, a reusable knife may not be as sharp as a single-use knife in certain instances.

In other instances, a firing member, end effector, and/or surgical device may not include a multi-fire tissue-transecting knife. Instead of being incorporated into the surgical device itself, for example, a knife can be incorporated into a replaceable staple cartridge, for example. In such instances, a fresh cutting edge can be used with each firing stroke.

Various replaceable staple cartridge assemblies having a tissue-transecting knife are described herein. In one instance, the firing member can include an integral sled component and the knife can be releasably attached or mounted to the firing member upon insertion of the staple cartridge into the surgical device or end effector thereof having the firing member.

Referring now to FIG. 215, an end effector 20840 having a firing member 20841 with an integral sled 20860 and attachment features (e.g. a recess 20846) for connecting to a single-use knife 20830 is shown. The end effector 20840 is similar in many aspects to the end effector 200 (see FIGS. 4 and 5) and is configured to cut and staple the tissue of a patient. For example, the end effector 20840 includes a cartridge jaw 20850 having opposing sidewalls 20852, and the end effector 20840 also includes an anvil jaw 20854. The cartridge jaw 20850 is configured to receive a staple cartridge, such as a replaceable staple cartridge 20800 shown in FIG. 219, for example. The end effector 20840 also includes a firing drive system 20839 that includes a rotary drive screw 20842 (FIG. 221) and the firing member 20841, which are similar to the firing screw 261 (FIGS. 4 and 5) and the firing member 270 (FIGS. 4 and 5), respectively. The firing member 20841 is driven through the end effector 20840 upon a rotation of the rotary drive screw 20842 during a firing stroke to fire staples from the staple cartridge 20800. The rotary drive screw 20842 extends along a longitudinal axis A through the fastener cartridge 20800.

Referring primarily to FIG. 216A, the firing member 20841 includes an upright body portion 20843, upper cam members 20844 extending laterally from both sides of the upright body portion 20843, and lower cam members 20845 extending laterally from both sides of the upright body portion 20843. When the end effector 20840 is in a clamped configuration (FIG. 221), the upper cam members 20844 are configured to cammingly engage an anvil jaw 20854 of the end effector 20840 during a firing stroke, and the lower cam members 20845 are configured to cammingly engage the cartridge jaw 20850 of the end effector 20840 during the firing stroke. The upper and lower cam members 20844, 20845 are configured to clamp the jaws of the end effector 20840 and define a tissue gap during a firing stroke, as further described herein with respect to various firing members (e.g. I-beams and E-beams). A threaded opening 20847 through the upright body portion 20843 is configured to receive the rotary drive screw 20842 therethrough. In other instances, a threaded nut can be threadably coupled to the rotary drive screw 20842 and mounted to the firing member 20841. Various threaded nuts and alternative firing members are further described herein.

Referring still to FIG. 216A, the firing member 20841 further includes an integrated sled 20860. The sled 20860 has two rails 20866. One of the rails 20866 is configured to engage a row of staple drivers on each side of the surgical end effector 20800. Stated differently, the sled 20860 includes a single rail 20866 for each side of the surgical end effector 20800, i.e. for each side of the staple cartridge 20800 (FIG. 219). A single rail on each side can save lateral space in the surgical end effector 20840, which can provide additional space to accommodate the rotary drive screw 20842 along the central portion of the surgical end effector 20840. In such instances, the sled 20860 can be a reusable component that is provided with the firing member 20841 and the surgical device, for example.

Referring primarily to FIG. 219, the firing member 20841 is driven through the staple cartridge 20800, which includes a cartridge body 20802 and drivers 20820, 20821 movably positioned therein. The drivers 20820 are triple drivers, and the drivers 20821 are double drivers. In various instances, the proximal-most drivers in the staple cartridge 20800 are the double drivers 20821 and, in other instances, one or more of the proximal-most drivers can be single drivers. The double drivers 20821 include a lateral flange that includes a ramped surface for driving engagement by the sled rail 20866 that is also aligned with ramped recesses 20818 (FIG. 218) on the triple drivers 20820. Stated differently, the double drives 20821 and the triple drivers 20820 are both driven by a single sled rail 20866 on each side of the fastener cartridge 20800.

Parallel longitudinal slots 20803 (FIG. 219) through the cartridge body 20802 are dimensioned to receive the rails 20866 during the firing stroke. Stated differently, as the upright body portion 20843 of the firing member 20841 moves through a central longitudinal slot 20808 in the cartridge body 20802, the rails 20866 move along parallel slots 20803 along an underside of the cartridge body 20802. The parallel longitudinal slots 20803 are also parallel to the longitudinal slot 20808 through which the upright body portion 20843 of the firing member 20841 protrudes.

In other instances, the integral sled of a firing member 20841 can more than one rail on each side. For example, integrated sleds having four rails and six rails are also contemplated.

The firing member 20841 is adapted to releasably connect to the knife 20830. The knife 20830 includes opposing spring arms 20832, which extend proximally toward the upright body portion 20843 of the firing member 20841 and resiliently engage the upright body portion 20843. The spring arms 20832 snap around the upright body portion 20843 and extend into a cavity 20846 defined into the upright body portion 20843. The knife 20830 also includes a longitudinal body 20834, which is configured to rest and/or nest on a complementary surface on the firing member 20841 over the threaded opening 20847 for the rotary drive screw 20842, for example. The knife 20830 further includes an upright cutting edge 20836, which is configured to extend above a tissue-supporting deck 20804 (FIG. 221) to transect tissue during a firing stroke.

In various instances, the fastener cartridge 20800 and the cartridge jaw 20850 can include alignment and/or leveraging features for facilitating installation of the fastener cartridge 20800 into the cartridge jaw 20850. Various alignment and leveraging features are further described herein. These features can also align the knife 20830 with the firing member 20841 and, more specifically, align the spring arms 20832 with the cavity 20846, to ensure the knife 20830 is connected to the firing member 20841 upon insertion of the staple cartridge 20800 into the cartridge jaw 20850.

In the unfired staple cartridge 20800, the knife 20830 is aligned with the indicator sled 20828, which is configured to be pushed distally by the knife 20830 during the firing stroke. As further described herein, the indicator sled 20828 provides a visible indication to a clinician and/or user when a firing stroke has been completed by moving into a window 20806 (FIG. 230) in the nose of the cartridge body 20802, as further described herein. Moreover, the indicator sled 20808 is configured to selectively overcome a missing and/or spent cartridge lockout in certain instances, as further described herein.

The indicator sled 20828 and the knife 20830 are components of the staple cartridge 20800. When the staple cartridge 20800 is installed in the surgical end effector 20840, the knife 20830 is brought into alignment with the firing member 20841 such that the spring arms 20832 resiliently engage the opening 20846. The insertion angle of the staple cartridge 20800 is configured to ensure the proper alignment of the spring arms 20832 and the opening 20846. In such instances, a fresh knife can be provided with each staple cartridge 20800 and for each firing stroke.

Referring primarily to FIGS. 100B and 101, the integral sled 20862 is configured to drivingly engage the triple drivers 20820 during a firing stroke. The firing member 20841 and the sled 20862 move along a longitudinal path in the staple cartridge 20800 during a firing stroke to lift the drivers 20820 along transverse axes.

The triple drivers 20820 are lifted by a single sled rail 20862 on each side of the staple cartridge 20800. Each triple driver 20820 includes a recessed ramp 20818 (FIG. 218), which is positioned and dimensioned to receive the sled rail 20862. Stated differently, the sled 20860 has a single rail 20862 on each side of the central portion, and the single rail 20872 is configured to lift and drive the triple drivers 20820. In effect, a single rail 20862 is configured to fire all the staples on one side of the staple cartridge 20800 and is configured to fire staples across three rows (e.g. inner row, intermediate row, outer row) via the triple drivers 20820. Referring primarily to FIG. 218, the triple driver 20820 includes the recessed ramp 20818 (FIG. 218), which is dimensioned to receive the sled rail 20862. The recessed ramp 20818 extends along a central portion of the triple driver 20820 (e.g. underlying an intermediate/middle support column), as further described herein.

The triple driver 20820 can be similar to the triple driver 20120 (FIG. 142) in many aspects. For example, the triple driver 20820 is configured to support three staples 20890 (FIGS. 100B and 101), and to lift the three staples 20890 simultaneously. The triple driver 20820 also includes three support columns—an inner support column 20822a configured to support an inner staple 20890 in an inner row of staples, an intermediate support column 20822b laterally outboard of the inner support column 20822a configured to support an intermediate staple 20890 in an intermediate row of staples, and an outer support column 20822b laterally outboard of the intermediate support column 20822b and configured to support an outer staple 20890 in an outer row of staples.

The triple driver 20820 also includes bridges 20826 extending between adjacent support columns 20822. For example, a first bridge 20826a extends between the inner support column 20822a and the intermediate support column 20822b, and a second bridge 20826b extends between the intermediate support column 20822b and the outer support column 20822c. The recessed ramp 20818, which is aligned with the drive rail 20866, is positioned between the first bridge 20826a and the second bridge 20826b and proximal to the intermediate support column 20822b.

More specifically, the recessed ramp 20818 is longitudinally aligned with the intermediate support column 20822b. Consequently, the intermediate support columns 20822b of the drivers 28020 are positioned in the parallel longitudinal slots 20803 through the cartridge body 20802 and are unsupported, or at least unsupported along a lower portion thereof, by the cartridge body 20802 when in the unfired positions in the cartridge body 20802. In such instances, the staple 20890 in the intermediate row of staples on each side of the cartridge body is supported by the intermediate support column 20822b and guided largely by a tissue-supporting deck 20804 of the cartridge body 20802. In certain instances, pocket extenders and/or ridges along the tissue-supporting deck 20804 can further guide the staples 20890 during the firing stroke.

The triple driver 20820 can be symmetrical about a longitudinal axis along the recessed ramp 20818. In various instances, the triple driver 20820 can include wings 20824, which extend laterally outward on both sides of the intermediate support column 20822b. The wings 20824 are configured to prevent driver roll and to strengthen the intermediate support column 20822b, in certain instances. For example, the wings 20824 can help balance the intermediate support column 20822b during the firing stroke when the intermediate support column 20822b is unsupported, or largely unsupported, by the cartridge body 20802.

Referring primarily to FIG. 219, the wings 20824 extend into complementary grooves 20805 in the cartridge body 20802. During a firing stroke, the wings 20824 move in the grooves 20805 upward toward the tissue-supporting deck 20804. Referring primarily to FIG. 220, the grooves 20805 are positioned on either side of the intermediate staple cavities and extend from the underside of the cartridge body 20802 to the tissue-supporting deck 20804. In certain instances, the tissue-supporting deck 20804 can catch, block, and/or stop further upward motion of the wings 20824 to retain the drivers 20820 in the cartridge body 20800 upon completion of the firing stroke.

Referring still to FIG. 219, a distal portion of the intermediate support column 20822b is further configured to nest in a portion of the adjacent triple driver 20820. More specifically, the triple driver 20820 include a proximal groove 20817 (FIG. 218), which is dimensioned to receive a distal tip of the adjacent (e.g. directly behind/proximal) triple driver 20820. The nesting arrangement of triple drivers 20820 arranged end-to-end with nesting features therebetween is configured to further facilitate alignment and cooperative support of the triple drivers 20820 in the cartridge body 20802.

In short, the staple cartridge 20800 can include triple drivers 20820 which are configured to be lifted by a single sled rail 20866 that pushes on a center portion and ramped recess 20818 of the triple driver 20820 during a firing stroke. The triple drivers 20820 can further includes wings 20824 on both sides, which prevent roll of the triple driver 20820 during the firing stroke. The wings 20824 can move in corresponding slots in the cartridge body 20802. In certain instances, the sled 20860 can be integrally-formed with the firing member 20841 (e.g. an I-beam or E-beam). In such instances, the sled 20860 can be a reusable component along with the firing member 20842; however, a fresh knife 20830 can be provided with each staple cartridge 20800. In other instances, the sled can be a discrete component in the staple cartridge and, in certain instances, the firing member 20841 can include an integral cutting edge.

In various instances, triple drivers and a firing member with an integral two-rail sled, as described herein, can allow the triple driver to be narrower and, thus, allow more space in the cartridge body for a rotary drive screw. For example, the rotary drive screw can be positioned farther upward in the end effector closer to the upper cam of the firing member, rather than along the lowest portion of the end effector. Narrower drivers can provide a tighter staple line, for example, which may also improve homeostasis in certain instances. Additionally, the inner rows of staples can be moved laterally outward to accommodate the rotary drive screw, which may reduce the likelihood and/or incidences of staple tear out. Moreover, the cartridge body can provide a robust design without narrower support columns, towers, and/or thin sidewalls between the staple cavities and/or the longitudinal slot for the firing member. The sled rails can also be wider in certain instances and, thus, may be less prone to bending under substantial firing loads. In certain instances, the staple overdrive can be minimized when bending and flexing of the sled rails is limited.

Referring primarily to FIG. 222, the staple cartridge 20800 includes robust support walls for withstanding a clamping load, and the tissue-supporting deck 20804 defines a thickness t1 along an inner edge of the intermediate staple cavity and a thickness t2 along an outer edge of the intermediate staple cavity. Conversely, referring now to a staple cartridge 20900 having a cartridge body 20902 and a tissue-supporting deck 20904, the support walls of the cartridge body 20902 can be narrower than the walls in the cartridge body 20802. Moreover, the tissue-supporting deck 20904 has a thickness t3, which is less than the thickness t1 and thickness t2 of the tissue-supporting deck 20804. The cartridge body 20902 is adapted to receive a four-rail sled, for example.

Effecting a firing stroke when a staple cartridge is missing from the surgical end effector can result in a knife transecting the clamped tissue without any means for sealing the transection. For example, without staples, such as staples, for example, a stapling device cannot staple and seal the cut tissue. Similarly, if an empty or spent staple cartridge is loaded in the end effector, i.e. a staple cartridge without staples or without a full set of staples, the tissue also would not be fully sealed along the transection. A missing cartridge lockout can prevent a firing stroke when a staple cartridge is missing from the end effector and a spent cartridge lockout can prevent a firing stroke when a spent staple cartridge is loaded in the end effector. In certain instances, a lockout can prevent a firing stroke when the staple cartridge is missing and spent. In instances in which a rotary firing screw extends through the end effector, the lockout can be configured to limit and/or prevent rotation of the rotary firing screw and, thus, to prevent the firing stroke.

In one aspect, a lock nut can be positioned on the rotary drive screw and a lockout key can be incorporated into a movable feature in the staple cartridge. In the locked configuration, the lock nut rotates out of firing alignment and into a lockout notch in the end effector. Upon installing an unfired staple cartridge in the end effector, the lockout key engages the lock nut to rotate it into firing alignment and out of the lockout notch. The lock nut moves distally along the rotary drive screw during the firing stroke and the lockout key is also pushed distally during the firing stroke. The lockout key can remain in a distal position upon completion of the firing stroke and/or retraction of the firing member; however, the lock nut can return to a proximal position in the end effector. Because the staple cartridge has been fired (e.g. spent), the lock nut again rotates out of firing alignment and into the lockout notch to prevent a subsequent firing stroke until a replacement unfired staple cartridge is installed in the end effector. In other instances, a lock on the rotary drive screw may not be threadably engaged with the rotary drive screw and a spring can bias the lock into a lockout notch to selectively prevent a firing stroke.

Such a lockout arrangement can be configured to prevent a firing stroke when a staple cartridge is missing and/or when the staple cartridge in the end effector has been spent/fired. Moreover, these arrangements can take up a minimal amount of space in the end effector. Moreover, the components can be simple and robust. In the instances of a lock nut threadably coupled to the rotary drive screw, only a single additional component in the end effector is needed for the lockout configuration. In various instances, the lockout key can provide a visual indication to a clinician that the staple cartridge has already been fired.

Referring now to FIGS. 108-115, a lockout arrangement 21868 and various components thereof are shown. The lockout arrangement 21868 is incorporated into a surgical end effector 21840, which is similar to the surgical end effector 20840 (see FIG. 215) in many aspects. Moreover, the end effector 21840 is adapted to receive the staple cartridge 20800 (see FIG. 219). The end effector 21840 includes a cartridge jaw 21850, which is similar to the cartridge jaw 20850 (see FIG. 215); however, the cartridge jaw 21850 further includes a lockout notch 21854 defined in a bottom side 21856.

More specifically, the cartridge jaw 21850 includes a bottom side 21856 and sidewalls 21852 forming a channel that is dimensioned and structured to receive the staple cartridge 20800 therein. The lockout notch 21854 comprises a lateral recess or opening in a proximal portion of the bottom side 21856. The lockout notch 21854 is aligned with a lockout nut 21874 threadably coupled to the rotary drive screw 20842 when the rotary drive screw 20842 and lockout nut 21874 thereon are in an unfired or proximal position.

The lock nut 21870 includes a central threaded aperture through a body portion, opposing flanges 21874, and a lug 21872. The flanges 21874 and the lug 21872 extend radially outward from the body portion. In an unlocked position (FIGS. 109B and 111), the flanges 21874 extend laterally outward to an inside surface of the bottom side 21856 of the cartridge channel 21850 and are positioned to ride along and/or adjacent to the inside surface. Moreover, in an unlocked positioned, the lug 21872 is aligned with the upright body portion 20843 of the firing member 20841. In the locked position (see FIGS. 108, 109A, 115), the flanges 21874 are rotated out of alignment with the inside surface of the bottom side 21856 such that one of the flanges 21874 rotates into the lockout notch 21854. Moreover, in the locked position, the lug 21872 is rotated out of firing alignment with the upright body portion 20843 of the firing member 20841.

The lock nut 21870 is threadably coupled to the rotary drive screw 20842. A rotation of the rotary drive screw 20842 can rotate the lock nut 21870 therewith unless the rotation of the lock nut 21870 is prevented or blocked. Initially, when the end effector 21840 is without a staple cartridge therein (FIGS. 108 and 109A), the rotation of the rotary drive screw 20842 is configured to rotate the lock nut 21870 such that one of the flanges 21874 is rotated into the lockout notch 21854 aligned therewith. When an unspent staple cartridge 20800 is installed in the surgical end effector 21840, the lockout nut 21854 is rotated to the unlocked position. The unlocked position of the lockout nut 21854 is shown in FIG. 225B; however, the staple cartridge is hidden for illustrative purposes.

Referring primarily to FIGS. 111 and 112, the lockout key 20828 includes a foot 20827, which extends into a space in the cartridge body 20802 above the rotary drive screw 20842. When an unfired staple cartridge 20800 is installed in the end effector 21840, the foot 20827 of the lockout key 20828 rotates the lockout nut 21870 into the unlocked position. More specifically, the foot 20827 includes beveled surfaces configured to engage and abut the lug 21872 to bias and rotate the lug 21872 into alignment with the upright body portion 20843. Referring primarily to FIG. 228, the cartridge body 20802 includes a detent 20809, which extends toward the longitudinal slot 20808 in the cartridge body 20802. The detent 20809 is configured to hold the lockout key 20828 in place upon insertion of the staple cartridge 20800 into the end effector 21840.

The lockout key 20828 also defines a contoured profile 20829 that corresponds to a contoured profile track 20807 in the cartridge body 20802. The contoured profile track 20807 is configured to resist rotation of the lockout key 20828 as the lockout key 20828 is pushed distally. In various instances, the foot 20827 forms a nook into which the lug 21872 is received. The foot 20827 rotates the lug 20872 into the unlocked position. Subsequently, during a firing stroke, the lug 21872 can remain engaged with the nook in the lockout key 20828 and can push the lockout key 20828 distally through the contoured profile track 20807. The firing force can be sufficient to overcome the detent 20809 holding the foot 20827 in a proximal position the cartridge body 20802.

Additionally or alternatively, the knife 20830 can push the lockout key 20828 distally through the cartridge body 20802. The knife 20830 also comprises a contoured profile, which is configured to travel through the contoured profile track 20807 without rotating out of firing alignment during the firing stroke.

Figure 114:
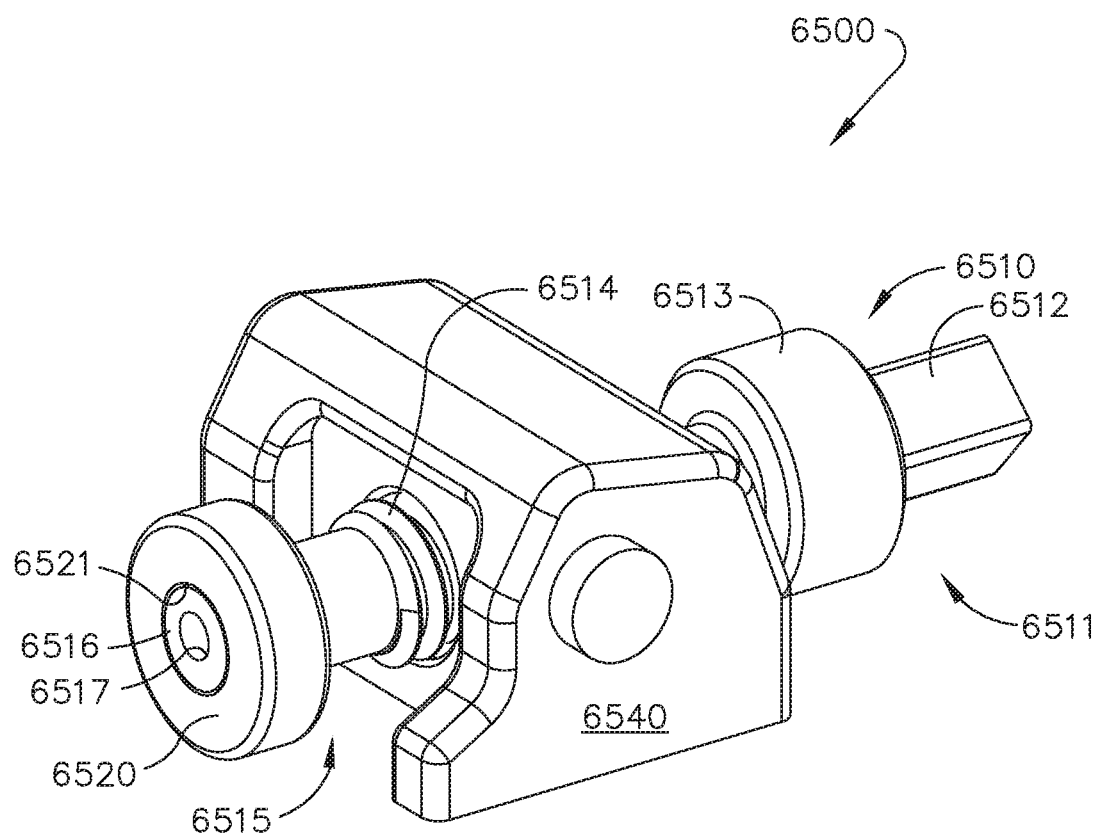
FIG. 114 is a perspective view of a closure drive comprising a drive screw shaft and a closure drive nut, in accordance with at least one aspect of the present disclosure.
Figure 115:
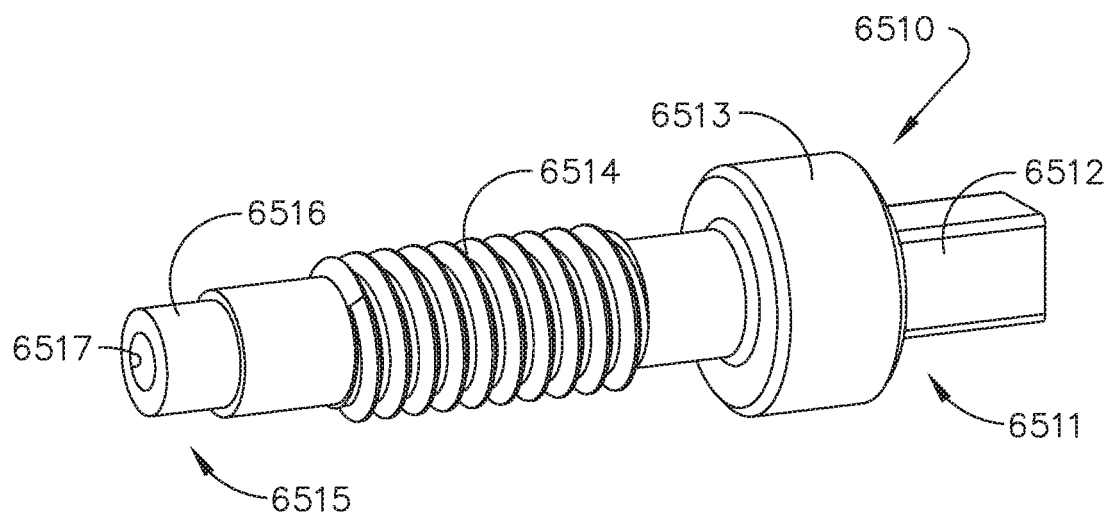
FIG. 115 is a perspective view of the drive screw shaft of FIG. 114, in accordance with at least one aspect of the present disclosure.

Referring now to FIGS. 113 and 114, upon completion of the firing stroke, the lockout key 20828 can be pushed to a distal position in the cartridge body 20802. In the distal position, the lockout key 20828 is visible through the window 20806 in the cartridge body 20802. For example, the distal nose of the cartridge body 20802 can include the window 20806 and the lockout key 20828 can be parked near the window 20806 such that the lockout key 20828 is visible. The foot 20827 of the lockout key 20828 prevents the lockout key 20828 from falling out of the cartridge body 20802 through the window 20808.

Reversing rotary motion of the rotary drive screw 20842 is configured to retract the firing member 20841. As further described herein, the knife 20830 can be retracted along with the firing member 20841 in various instances. However, the lockout key 21828 can be released from the knife 20830 and can remain at the distal position in the cartridge body 20802. Referring primarily to FIG. 231, when the firing member 20841 is retracted back to a proximal position in the cartridge body 20802, the lockout nut 21870 is also retracted proximally along the rotary drive screw 20842. Owing to the rotary direction of the rotary drive screw 20840 during a retraction motion, the lockout nut 21870 is not rotated into the lockout notch 21854. Stated differently, the lockout nut 21870 can remain in the unlocked position and move proximally past the lockout notch 21854 during the retraction motion. However, if another firing motion is initiated and the rotary direction of the rotary drive screw 20842 is reversed, upon moving distally in the end effector 21840, the lockout nut 21870 will again rotate out of alignment with the firing member 20841 and a flange 21874 of the lockout nut 21870 can be rotated into the lockout notch 21854.

In the locked position, the lockout nut 21870 cannot rotate relative to the rotary drive screw 20842 and cannot translate longitudinally through the end effector 21840. As a result, rotary motion of the rotary drive screw 20842 is resisted and the firing stroke is prevented until the lockout nut 21870 assumes the unlocked position.

The lockout arrangement 21868 described herein with respect to FIGS. 108-115 includes a threaded lockout nut 21870, which is coupled to the rotary drive screw 20842. Displacement of the threaded lockout nut 21870 is a function of the rotation of the rotary drive screw 20840. In other instances, a lockout arrangement can includes a non-threaded lock positioned around the rotary drive screw 20842. Referring now to FIGS. 116 and 117, a lockout arrangement 22868 and various components thereof are shown. The lockout arrangement 22868 is incorporated into a surgical end effector 22840, which is similar to the surgical end effector 20840 (see FIG. 215) in many aspects. The end effector 22840 is adapted to receive the staple cartridge 20800 (see FIG. 219). The end effector 22840 includes a cartridge jaw 22850, which is similar to the cartridge jaw 20850 (see FIG. 215); however, the cartridge jaw 22850 further includes a lockout notch 22854 defined in a bottom side 21856. Moreover, the end effector 22840 includes a firing member 22841, which is similar to the firing member 20841 in many aspects; however, the integral sled 20860 of the firing member 22841 includes sled rails 22868 having holes 22868 therein, as further described here.

The lockout arrangement 22868 includes a lock 22870, which is similar in many aspects to the lockout nut 21870; however, the lock 22870 is not threadably coupled to the rotary drive screw 20842. The lock 22870 includes central non-threaded aperture through a body portion, opposing flanges 22874, and a lug 22872. The flanges 22874 and the lug 22872 extend radially outward from the body portion.

In an unlocked position, the flanges 22874 extend laterally outward to an inside surface of the bottom side 22856 of the cartridge channel 22850 and are positioned to ride along and/or adjacent to the inside surface. The flanges 22874 are received in the holes 22868 in the sled 22860. For example, the holes 22868 are through-holes in the sled rails 20866 that are dimensioned and positioned to receive the opposing flanges 22874 when the lock 22870 is in the unlocked position. As a result, the firing member 22841 and sled rails 22868 thereof are configured to pull the lock 22870 along the rotary drive screw 20842 during the firing stroke. Moreover, in the unlocked positioned, the lug 22872 is aligned with the upright body portion of the firing member 22841.

In the locked position (FIGS. 116 and 117), the flanges 22874 are rotated out of alignment with the inside surface of the bottom side 22856 such that one of the flanges 22874 rotates into the lockout notch 22854. Moreover, in the locked position, the lug 22872 is rotated out of firing alignment with the upright body portion of the firing member 22841.

The lockout arrangement 22868 also includes a spring 22870, which is configured to bias the lock 22870 into the lockout notch 22854. The lockout arrangement 22868 can function like the lockout arrangement 21868; however, the spring 22870 can bias the lock 22870 into the lockout notch 22854 such that the lockout arrangement 22868 is always locked unless an unfired staple cartridge 20800 is loaded into the end effector 22840 and the lockout key 21828 thereof temporarily overcomes the lockout arrangement 22868 until the completion of the firing stroke. As described above with respect to the lockout arrangement 21868, the lockout key 21828 is configured to move through the window 20806 in the cartridge body 20802 at the completion of the firing stroke to communicate the completion of a firing stroke and that the staple cartridge has been fired/spent.

The formed staple height is a function of the space between the staple-supporting surface and the staple-forming surface. More specifically, a vertical space between (A) a staple-supporting cradle on a driver in a fired position and (B) a staple-forming pocket surface in an anvil in the clamped position controls the formed height of the staples. Different formed staple heights are selected for different surgical procedures and/or different tissue types, for example. When a staple cartridge includes a rotary firing screw therethrough, the arrangement of staples and corresponding staple cavities and drivers can be altered to accommodate the rotary firing screw. For example, the drivers can include at least one asymmetry, as further described herein. Additionally or alternatively, the drivers can be narrower and, thus, need additional support and/or strength. Moreover, in various instances, it is desirable to optimize a tissue gap while maintaining a desired formed staple height. For example, the tissue gap between the tissue-supporting deck surface and the anvil can be maximized when the end effector is in a closed configuration while the desired formed staple height is maintained.

In various instances, an underside of the tissue-supporting deck can include a contoured and/or rutted surface, which is configured to receive one or more portions of the drivers when the drivers are in their fully fired and/or overdriven positions. The interlocking and/or nesting between the underside of the tissue-supporting deck and the tissue-facing side of the drivers can maximize the tissue gap while still maintaining a desired formed staple height. Moreover, the interlocking features can improve the strength of the drivers in various instances.

In one example, a staple cartridge can include a body comprising a tissue-supporting deck, wherein staple cavities are defined through the tissue-supporting deck in the body, and wherein the tissue-supporting deck includes a tissue-facing side comprising a bumpy or ridged surface. The tissue-support deck further includes an underside opposite the tissue-facing side, wherein the underside comprises a rutted surface. Staples can be removably positioned in the staple cavities. Drivers can movably support the staples and be configured to move through a portion of the staple cavities to fired positions to eject the staples from the staple cavities. Each driver can include a base housed in the staple cartridge and comprising surface contours configured to mate with the rutted surface on the underside of the tissue-supporting deck when moved to the fired position.

Referring now to FIGS. 38-40, a staple cartridge 22100 is shown. The staple cartridge 22100 is similar in many aspects to the staple cartridge 20100 (FIG. 140). For example, the staple cartridge 22100 includes a body 22102 extending along a longitudinal axis A. Staples are removably positioned in the body 22102. The staples can be ejected from the body 22102 and fired into tissue, for example, during a firing stroke. The staples are arranged in longitudinal rows on either side of the longitudinal axis A, which is aligned with a rotary drive shaft 22242 (FIG. 155) extending therethrough. The cartridge body 22102 also includes a deck 22104, which can be referred to as a tissue-supporting deck, for example. The deck 22104 is a laterally-curved tissue supporting deck and defines a curved tissue-facing surface from a first lateral side 22101 of the body 22102 to a second lateral side 22103 of the body 22102. A peak 22105 in the laterally-curved tissue supporting deck 22104 is defined at an intermediate portion of the body 22102. The peak 22105 can be positioned between the longitudinal rows of staples and overlie the longitudinal axis A, for example. In various instances, the rotary firing screw 22242 (FIG. 155) extends through a portion of the staple cartridge 22100.

The cartridge body 22102 also includes an array of pocket extenders or ridges 22114 extending from the tissue supporting deck 22104. The ridges 22114 extend around a perimeter or opening formed in the tissue supporting deck 22104 for a staple cavity. The ridges 22114 can be configured to grip and engage tissue positioned between the staple cartridge 22100 and an opposing anvil. In various instances, the ridges 22114 can limit and/or constrain tissue flow, for example. Additionally or alternatively, the ridges 22114 can be configured to guide the legs of the staples as they enter tissue and are directed into engagement with respective forming pockets on the staple-forming surface of the anvil. The ridges 22114 can extend around the proximal and distal ends of the staple cavities, for example. Proximally- and distally-positioned projections or pocket extensions can prevent outwardly-biased staple legs (of V-shaped staples, for example) from flaring outwardly and missing the target location in the forming pocket aligned therewith.

In certain aspects, adjacent ridges 22114 can be connected. For example, the ridges 22114 can be interconnected with respect to longitudinally-offset staple cavities and/or laterally-offset staple cavities.

In various instances, an array of laterally-offset ridges 22114 can define different heights. In various instances, the ridges 22114 can define different heights laterally along the width of the cartridge body 22102. Different heights can correspond to the lateral curve of the tissue supporting deck 22104 and/or different lengths for guiding the staples beyond the tissue-supporting deck 22104 and/or different tissue gaps when the end effector is clamped, for example. With respect to the cartridge body 22102, the ridges 22114 span three laterally-spaced rows of staple cavities 22112a, 22112b, 22112c and the ridges 22114 aligned with outer row 22112c are taller than the inner rows 22112a, 22112b and, thus, would guide the staple legs over a greater distance. However, the tissue gap is also larger over the outer rows 22112c than the inner rows 22112a, 22112b owing to the lateral curve of the tissue-supporting deck 22104 and the non-stepped/non-contoured tissue-clamping surface of the anvil.

The staples are positioned in cavities defined in the cartridge body 22102, similar to the cavities 20110 (FIG. 140). For example, the staples are arranged in longitudinal rows 22112 on either side of the longitudinal axis A. The cavity rows 22112 include an inner row 22112a, an intermediate row 22112b, and an outer row 22112c on each side of the longitudinal axis A. The intermediate row 22112b can be equilaterally-spaced between the inner row 22112a and the outer row 22112c. The rotary drive screw 22242 can be aligned with the longitudinal axis A, and can extend through the cartridge body 22102 adjacent to the inner cavity rows 22112a. The rotary drive screw 22242 can be between and parallel to the inner cavity rows 22112a, for example.

The inner rows 22112a hold inner staples, the intermediate rows 22112b hold intermediate staples, and the outer rows 22112c hold outer staples. In various instances, the inner staples, the intermediate staples, and the outer staples can be identical. In other instances, the inner staples, the intermediate staples, and/or the outer staples can each be different with respect to staple type (e.g. wire or stamped), material, and/or size (e.g. different heights), for example.

In other instances, the staple cartridge 22100 may have a different arrangement of staples. For example, the staple cartridge 22100 may have less than three rows of staples on each side of the longitudinal axis A. In one aspect of the present disclosure, the staple cartridge 22100 may only have two rows of staples on each side of the longitudinal axis A. In still other instances, the staple cartridge 22100 can include four or more rows of staples on one or more sides of the longitudinal axis A. In various instances, the rows of staples may be asymmetrical relative to the longitudinal axis A. For example, the first side of the staple cartridge 22100 can have a different number of rows of staples than the second side of the staple cartridge 22100.

The staple cavities in the cartridge body 22102 can each include a proximal end, a distal end, and lateral guide surfaces intermediate the proximal end and the distal end. The staple cavities are structured and dimensioned to guide drivers 22120 through the staple cavities toward the deck 22104. Referring primarily to FIG. 157, a driver 22120 is shown. Moreover, one driver 22120 is shown in the staple cartridge 22100 in FIGS. 41 and 42. Though one driver 22120 is depicted in these figures, the reader will appreciate that additional drivers like the driver 22120 would be incorporated into the staple cartridge 22100 to fire staples from additional staple cavities during a firing stroke.

The geometry of the staple cavities can complement the geometry of the drivers 22120. For example, lateral guide surfaces in each staple cavity are configured to guide sidewalls 22134 of the driver 22120 as the driver 22120 moves through the staple cavity. Additionally or alternatively, the proximal end and/or the distal end of each staple cavity can include an upright groove configured to slidably receive an end and/or tongue thereof of the driver 22120. Alternative tongue and groove arrangements are also contemplated, which can be configured to guide the drivers 22120 through the staple cavities during firing of the staples from the staple cartridge 22100.

The drivers 22120 are configured to support and drive multiple staples from the cartridge body 22102 during a firing stroke. The drivers 22120 can movably support staples spanning two or more longitudinal rows 22112. For example, the drivers 22120 can movably support an inner staple, an intermediate staple, and an outer staple on the same side of the staple cartridge 22100.

The driver 22120 is a triple driver, which is configured to drive three staples simultaneously. The driver 22120 includes three support columns—an inner support column 22122*a* configured to support an inner staple in an inner row of staples, an intermediate support column 22122*b* laterally outboard of the inner support column 22122*a* configured to support an intermediate staple in an intermediate row of staples, and an outer support column 22122*c* laterally outboard of the intermediate support column 22122*b* and configured to support an outer staple in an outer row of staples.

The driver 22120 also includes bridges 22126 extending between adjacent support columns 22122. For example, a first bridge 22126*a* extends between the inner support column 22122*a* and the intermediate support column 22122*b*, and a second bridge 22126*b* extends between the intermediate support column 22122*b* and the outer support column 22122*c*. The bridges 22126*a*, 22126*b* each include a ramped underside 22128 configured to be drivingly engaged by a sled during a firing stroke. For example, a sled 22150 (FIG. 155) can be configured to move along a firing path during a firing stroke. The sled 22150 can comprise a central portion aligned with the longitudinal axis A, a first rail configured to drivingly engage the ramped underside 22128 of the first bridge 22126*a*, and a second rail configured to drivingly engage the ramped underside 22128 of the second bridge 22126*b*. Sleds and firing motions thereof are further described herein.

Referring primarily to FIGS. 38 and 39, the tissue-supporting deck 22104 includes a tissue-facing side 22115 having the array of ridges 22114, which form a bumpy tissue-gripping surface. The tissue-supporting surface 22104 also includes an underside 22116 opposite the tissue-facing side 22115. The underside 22116 comprises a rutted surface having an array of ruts 22118 therein. The ruts 22118 can define a pattern of recesses and/or divots in the underside 22116. The tissue-supporting deck 22104 defines a deck height between the bumpy tissue-facing side 22115 and the rutted underside 22116. The deck height varies; however, a certain minimum height around the openings in the deck 22104 provides a minimum amount of guide length for the staples during the firing stroke. For example, if the deck were too thin around the staple cavities, the staples may not be adequately supported during deployment into the tissue and toward the forming pockets.

The drivers 22120 are configured to mate or nest with the rutted underside 22116 when the drivers 22120 are move to the fired positions. Referring again primarily to FIG. 157, the bridges 22126*a*, 22126*b* of the driver 22120 includes a projection 22130. The projections 22130 are surface contours and projections on an upper tissue-facing surface of the bridges 22126*a*, 22126*b* opposite the ramped underside 22128 of the bridges 22126*a*, 22126*b*. The projections 22130 are configured to be received in the ruts 22118 on the underside 22116 of the tissue-supporting deck 22104 when the drivers 22120 are moved to their fired positions. In the fired position, referring primarily to FIG. 156, the driver 22120 is overdriven relative to the deck 22104 such that a portion of the driver 22120 extends beyond the tissue-facing side 22115 and out of the cartridge body 22102.

The top surface of the bridges 22126*a* and 22126*b* are symmetric relative to a longitudinal centerline of the respective bridge 22126*a*, 22126*b*. The centerline of each bridge 22126*a*, 22126*b* can be equidistant between the longitudinal axes defined by staple-supporting cradles 22124 of adjacent support columns 22122. The projections 22130 are symmetric relative to the longitudinal centerline of the respective bridge 22126*a*, 22126*b*.

In other instances, the drivers, the bridges thereof, and/or the top surfaces thereof, can be laterally asymmetric, as further described herein. Referring to a driver 22220 in FIG. 158, the driver 22200 is similar in many aspects to the driver 22120 (FIG. 157); however, the driver 22200 defines a lateral asymmetry with respect to the interconnecting bridges 22226*a*, 22226*b* and respective top surface 22230 thereon. The driver 22220 includes three support columns 22222*a*, 22222*b*, 22222*c* each having a staple-supporting cradle 22224. The bridges 22226*a*, 22226*b* connect laterally adjacent support columns 22222*a*, 22222*b*, 22222*c*. The bridges 22226*a*, 22226*b* includes a ramped underside 22228, which is driven by a sled during a firing stroke, as further described herein. The top surface 22230 of the bridges 22226*a*, 22226*b* includes a diagonal surface and is asymmetric relative to a centerline through the bridge 22226*a*, 22226*b* and aligned with a firing path of a sled rail during a firing stroke. The centerline of each bridge 22226*a*, 22226*b* is equidistant between the axes aligned with adjacent staple-supporting cradles 22224 and staple bases/crowns therein.

The top surface 22230 of each bridge 22226*a*, 22226*b* includes a laterally-sloped top surface, which is configured to complement a portion of the contoured underside of a tissue-supporting deck, such as the rutted underside 22116 (FIGS. 39 and 40). Such bridge configurations may provide improved column-to-column support, which can allow the overall bridges 22226*a*, 22226*b* to be thinner while sufficiently supporting the staples across multiple rows.

An anvil 22370 for a surgical end effector is shown in FIG. 159. The anvil 22370 includes a tissue compression surface 22374 and pairs of staple-forming pockets 22372 formed into the tissue compression surface 22374. Each pair of staple-forming pockets 22372 includes a proximal pocket 22372*a* and a distal pocket 22372*b*. The pockets can be aligned with the legs of a staple, e.g. the wire legs of a staple. During the firing stroke, the tips of the staple legs can be received within the staple-forming pockets 22372 and formed into B-form staples, for example. In certain aspects of the present disclosure, the length of the staple-forming pockets 22372 can be configured to match the wire diameter of the staple aligned therewith. For example, the proximal pocket 22372a and the distal pocket 22372b in a first pair of staple-forming pockets 22372 in the anvil 22370 can have a first pocket length while the proximal pocket 22372a and the distal pocket 22372b in a second pair of staple-forming pockets 22372 in the anvil 22370 can have a different pocket length. The first pocket length can correspond to a different staple wire diameter than the second pocket length. In various aspects, larger wire diameter staples can correspond to short pocket lengths.

The space d between a proximal pocket 22372a and a distal pocket 22372b in a pair of staple-forming pockets 22372 can be minimized in certain instances to maximize the longitudinal forming length of the staples. Generally, staples are over-bent during the forming process to compensate for staple spring-back. However, over-bending of staples can be reduced when the forming pockets are shorter and, thus, steeper in certain instances. Shorter and steeper staple pockets, which define a larger space or gap d between the proximal pocket 22372a and the distal pocket 22372b in a pair of staple-forming pockets 22372, can reduce spring-back. Shorter and steeper staple pockets can curve the staple legs more and deform the staples more plastically to reduce spring-back, for example. Moreover, shorter and steeper staple pockets can improve sequential staple leg bends in certain instances. Referring to the space d in FIG. 159, the proximal pocket 22372a and the distal pocket 22372b in a pair of staple-forming pockets 22372 can be shortened and the overall pair can maintain the same length L such that a larger space d is defined between the proximal pocket 22372a and the distal pocket 22372b.

For example, in an end effector, the staples and/or the drivers can vary from row-to-row. In certain instances, the staples can be shorter, comprise a different wire diameter, be lifted by a driver having a different height and/or a different amount of overdrive. In certain instances, shorter staple forming pockets, as described above, can be utilized with the one row of staples and not an adjacent row of staples in the same anvil. For example, shorter staples can utilize the shortened pockets to improve sequential staple leg bends, e.g. two sequential bends on each staple leg to assume a B-shape. In still other instances, staples along an inside row of staples, i.e. adjacent to a longitudinal knife path, can utilize the shortened pockets to bend the staples more plastically and reduce spring-back to form a tighter row. In these instances, the distance d in FIG. 159 can be different from row-to-row.

A staple cartridge, such as the staple cartridge 20100 (FIG. 140) and the staple cartridge 22100 (FIG. 155), for example, include components having minimum size limitations to ensure suitable strength, stiffness, support, and/or manufacturing requirements are met. These minimum size limitations can make it difficult to optimize and/or increase the tissue gap in view of the other constraints on the surgical end effector. As an example, the minimum height of a tissue-supporting deck is 0.01 inches in certain instances due to molding constraints. As another example, the minimum height of the bridge between support columns on a driver is 0.022 inches in certain instances due to driver strength constraints. As another example, the minimum height of the driver (e.g. support column thereof) is 0.066 inches in certain instances due to driver roll constraints. As another example, the minimum height of the staple legs is 0.166 inches in certain instances, 0.160 inches in other instances, 0.150 inches in other instances, 0.102 inches other instances, and 0.085 inches in other instances based on the type of staple cartridge and targeted tissue. As another example, the minimum thickness of the anvil is 0.134 inches and, in certain instances, 0.154 inches due to anvil stiffness and strength constraints. In view of such minimum size constraints, it can be advantageous in certain instances to reduce the minimum size limitations and/or double count certain size limitations or portions thereof in a stack-up of components.

For example, portion of the drivers can nest in recesses in the underside of the tissue-supporting deck in certain instances to reduce certain minimize size limitations. In various instances, to ensure the tissue-supporting deck maintains an appropriate height, the recesses can be aligned with localized regions along the tissue-supporting deck with an increased height, such as below pocket extenders/tissue-gripping ridges, for example. In other instances, one or more additional recesses in the underside of the tissue-supporting deck can be configured to receive a portion of the driver and/or bridge thereof. Exemplary staggering of interlocking features between the inner surfaces of the staple cartridge and the drivers is shown in FIG. 155, for example. Other driver features could similarly be received within corresponding recesses on the underside of the tissue-supporting deck.

To reduce vertical stack-up dimensions of multiple components, the tissue-supporting deck of a staple cartridge, such as the staple cartridge 20100 (FIG. 140) and the staple cartridge 22100 (FIG. 155), for example, can have predefined clearance holes therethrough, which can be separate and distinct from the staple cavities. The predefined holes along the length and/or width of the staple cartridge can receive features of the drivers (e.g. portions of the bridge) in the driver's fully fired, and in various instances overdriven, positions. Additionally or alternatively, the tissue-supporting deck can include frangible or "break locations", which are configured to be physically broken by the drivers upon moving to their fully fired positions.

Additionally, the staple cartridges such as the staple cartridge 20100 (FIG. 140) and the staple cartridge 22100 (FIG. 155), for example, can further include selectively compressible and expandable features to reduce vertical stack-up dimensions. The drivers and/or cartridge body can include such features.

For example, vertically-expandable drivers can be configured to reduce resting or unfired heights of the drivers within the staple cartridge. The drivers can be telescoping and can define a height that is approximately 50% of its final height when in the unfired position. In such instances, the staples can sit lower in the cartridge body prior to firing. In certain instances, a first part of the sled rail can activate the driver by overcoming a significant snap feature with the body of the driver and expanding it to its final height. Then, a second part of the sled rail can complete the firing of the driver to eject the staple(s) supported thereon out of the cartridge body. The first of the sled rail can be narrower than the second part of the sled rail.

Additionally or alternatively, the tissue-supporting deck can comprise a variable-height, injection molded deck, which can compress when a predefined tissue load is applied to increase the tissue gap. As the sled fires the drivers and staples, the sled and/or the drivers can locally push the deck back into the tissue to an increased height momentarily in order to temporarily decrease the tissue gap. The tissue-support deck can then relax or otherwise return to the compressed state corresponding to an increased tissue gap after the sled has passed.

For example, the cartridge body or tissue-supporting deck thereof can include selectively positioned wall segments, which can be thin and configured to buckle under the predefined tissue load while still maintaining appropriate alignment between the staples and the staple-forming pockets in the anvil. In certain instances, an electrically-actuated material (e.g. electroactive polymers) can be incorporated in the tissue-supporting deck. Components or features formed with such a material can become soft and/or more readily compressible when a current is applied thereto and rigid and/or less readily compressible when no current is applied. In certain instances, portions of the drivers can be received in the tissue-supporting deck when the material is energized and, thus, deformable to accommodate the additional structures therein.

In certain instances, 4D printed materials can facilitate selective collapse of the tissue-supporting deck of the staple cartridge, such as the staple cartridge 20100 (FIG. 140) and the staple cartridge 22100 (FIG. 155), for example. For example, the cartridge body can include a 4D printed material that is printed on a top portion or upper half thereof. The 4D printed material can be heat sensitive. In certain instances, the material can have a glass transition point between room temperature and the temperature of the human body. For example, the material can become soft and deflectable, thus, increasing the tissue gap, when the cartridge is clamped onto tissue. In such instances, the increased heat from the patient can increase the heat of the 4D printed material to effect the shape change. When the cartridge body subsequently cools (e.g. is removed from thermal transfer contact with tissue), the 4D printed material can return to its original shape and/or height. In the original and recovered state, the tissue-supporting deck can be taller than in the heated and collapsed state, for example. The increased height in the original and recovered state can ensure the staples stored in the staple cartridge remain protected and are not protruding from the cartridge body prior to being fired, for example.

Referring now to FIG. 160, a deformation and recovery process 22400 for a 4D printed matrix on a cartridge body is depicted. During a shape programming stage 22490, the 4D printed matrix 22402 is heated, deformed from an original configuration to a deformed configuration 22402', and then cooled. During a shape recovery state 22492, the 4D printed matrix 22402' is heated and returns to its original configuration 22402, and then cooled. Shape programing and recovery of 4D printed materials is further described in the article "4D Printing Reconfigurable, Deployable and Mechanically Tunable Metamaterials" from Materials Horizon, Issue 6, 2019 by Chen Yang et al.

In certain instances, 4D printed matrixes can be used in combination with foldable or collapsible drivers, for example, which are further described herein. The 4D printed matrixes on the staple cartridge, for example, can be configured to selectively fold an interfering driver feature to consolidate and/or condense the footprint and stack-up within the staple cartridge at certain temperatures. The interfering features can then unfold when withdrawn from the interference condition, such as when the cartridge body resumes the original, undeformed state. In various aspects, the driver can be fully expanded when actively lifting and firing the staples. In certain instances, the driver can encounter an interfering surface near the fully fired position thereof, and an upper portion of the driver can be configured to fold into itself. The 4D matrix can form the interference surface in certain instances.

A user may want to install a staple cartridge into a channel of an end effector or disposable loading unit quickly and easily during a surgical procedure. A robust connection can also be desired. Certain robust connections can require a clinician to overcome significant resistance and/or frictional forces between interfering components. Additionally or alternatively, a robust connection may have minimal clearances and require precise alignment of the components by the clinician. Though a robust connection between the staple cartridge and the channel may be desired, it may be helpful to make the installation of the staple cartridge quicker, easier, and/or to require less force and/or effort on the part of the clinician.

In certain instances, a stapling assembly can include leveraging features which can facilitate installation of a staple cartridge into a channel. For example, the channel and the staple cartridge can include complementary geometric alignment features. Upon placing the alignment feature of the staple cartridge against the alignment feature of the channel, the alignment feature of the channel can provide a fulcrum or abutment surface about which the staple cartridge is leveraged to properly align the staple cartridge with the channel. When the staple cartridge is properly aligned owing to the abutting relationship between the alignment features, additional alignment features (e.g. a distal lug and notch) can facilitate further connection between the staple cartridge and the channel.

In certain instances, a spring can bias the staple cartridge distally along a longitudinal axis perpendicular to an insertion axis to fully and securely seat the staple cartridge in the channel. Additionally or alternatively, a distal firing force during a firing stroke can further shift the staple cartridge distally to interconnect ramped surfaces on the alignment features (e.g. distal edges of the distal lug and notch). Alternative spring-loaded and/or resilient features are contemplated to further secure the staple cartridge to the channel upon appropriate placement of the staple cartridge relative to the channel. In certain instances, a user-activated release can be configured to release one or more resilient attachment features between the staple cartridge and the channel. In other instances, the firing stroke can result in the release and/or breakage of one or more resilient attachment features.

In one example, a stapling assembly can include a staple cartridge including a cartridge body defining a longitudinal axis, wherein the cartridge body comprises a proximal cartridge alignment feature and a distal cartridge alignment feature. The stapling assembly can further include a channel dimensioned to receive the staple cartridge, wherein the channel comprises a sidewall comprising a proximal channel alignment feature and a distal channel alignment feature positioned to receive the distal cartridge alignment feature upon positioning the proximal cartridge alignment feature in abutting engagement with the proximal channel alignment feature and moving the staple cartridge along an insertion axis to a first position in the channel. The insertion axis can be perpendicular to the longitudinal axis. A spring can be configured to bias the staple cartridge distally within the channel along the longitudinal axis from the first position to a fully seated position. The proximal alignment features can include contoured abutment surfaces. The distal alignment features can includes a notch and a lug having complementary wedge-shaped distal ends.

In various instances, the improved cartridge retention and release features can increase engagement retention forces while allowing the user to release the staple cartridge from the channel with a substantially lower force. For example, a user can slide the staple cartridge proximally by overcoming a minimal spring force to quickly and easily remove the staple cartridge from the channel. In certain instances, the force required to remove a spent or fired staple cartridge can be less than the force required to remove a new, unfired staple cartridge. For example, a firing stroke, or even a partial firing stroke, can be configured to disengage and/or release certain resilient attachment features connecting the staple cartridge to the channel.

Referring now to FIG. 161, a stapling assembly 24000 is shown. The stapling assembly 24000 includes a channel 24050 and a staple cartridge 24100 removably positioned in the channel 24050. The staple cartridge 24100 is a disposable, single-use component, which is configured to be removed from the channel 24050 after a firing stroke and surgical procedure therewith. The channel 24050 can be reusable and configured to receive replacement staple cartridge assemblies therein. In other instances, the staple cartridge 24100 can be removed from the channel 24050, loaded with additional staples, and reinstalled in the channel 24050. The channel 24050 can be a component of a disposable loading unit and/or a modular stapling assembly including an anvil and/or a shaft portion in certain instances.

The staple cartridge 24100 can be similar in certain aspects to the staple cartridge 20100 (FIG. 140). For example, the staple cartridge 24100 includes a cartridge body 24102 having a tissue-supporting deck 24104, staples 24160 removably positioned in the cartridge body 24102, and drivers 24120 movably supporting the staples 24160. The staples 24160 comprise a base from end-to-end and the base of the staples 24106 are obliquely-oriented relative to a longitudinal axis A along the length of the staple cartridge 24100. The staples 24160 can be configured to form a compliant staple line which allows a degree of twisting and/or stretching while minimizing damage to the tissue. In certain instances, the cartridge body 24102 can include staples in a plurality of longitudinal rows having longitudinally-aligned staples in longitudinal rows parallel to the longitudinal axis A, as further described herein.

The cartridge body 24102 includes at least one alignment nub 24162 having a proximal alignment surface 24164. In various instances, an alignment nub 24162 can protrude laterally from each side of the cartridge body 24102. The proximal alignment surface 24164 defines a curved proximal edge of the alignment nub 24162. In various instances, the alignment nubs 24162 on either side of the cartridge body 24102 can be symmetrical about the longitudinal axis A.

The cartridge body 24102 further includes an alignment lug 24166 having a proximal end 24168 and a distal end 24170. One alignment lug 24166 is positioned on each side of the cartridge body 24102. The proximal end 24168 defines an upright or vertical surface relative to the tissue-supporting deck 24104. The distal end 24170 of the alignment lug 24166 defines a wedge shape having a ramped distal surface. The ramped distal surface can form a narrower dimension along the deck 24104 and a wider dimension at the opposite end of the alignment lug 24166. In various instances, an alignment lug 24166 can be positioned on each side of the cartridge body 24102, and the alignment lugs 24166 can be symmetrical about the longitudinal axis A. The alignment lugs 24166 are closer to the distal end of the cartridge body 24102 than the alignment nubs 24162.

The channel 24050 includes lateral sidewalls 24052 forming a U-shaped channel. The staple cartridge 24100 can be releasably secured in the U-shaped channel between the sidewalls 24052. The sidewalls 24052 and/or other portions of the channel 24050 can include resilient snap-fit features for engaging the staple cartridge 24100. Each sidewall 24052 includes an alignment feature 24054 including a proximal alignment contour 24056. The proximal alignment contour 24056 comprises an edge, which is configured to catch the proximal alignment surface 24164 of the alignment nub 24162. The proximal alignment contour 24056 resists longitudinal displacement of the alignment nub 24162 in the proximal direction beyond the proximal alignment contour 24056. As further described herein, the alignment feature 24054 can act as a fulcrum or support about which the staple cartridge 24100 is leveraged during insertion and installation of the staple cartridge 24100 into the channel 24050.

The channel 24050 further includes an alignment notch 24058 having a proximal end 24060 and a distal end 24062. An alignment notch 24058 is positioned on each side of the channel 24050. The proximal end 24060 defines an upright or vertical surface in the sidewall 24052 and the distal end 24062 defines another upright surface in the sidewall 24052, which is not parallel with the vertical surface at the proximal end 24060. The upright surface defining the distal end 24062 of the alignment notch 24058 can define a sloped or ramped distal surface, which can form a wedge shape having a narrower dimension along an upper edge of the sidewall 24052 and a wider dimension at the opposite end of the notch 24058. In various instances, the alignment notches 24058 can be symmetrically positioned about the longitudinal axis A. The alignment notches 24058 are closer to the distal end of the cartridge body 24102 than the alignment nubs 24162. As further described herein, each alignment notch 24058 is positioned and dimensioned to receive one of the alignment lugs 24166 therein.

The alignment features between the channel 24050 and the staple cartridge 24100 are configured to interact to facilitate a quick and easy installation of the staple cartridge 24100 into the channel 24050. For example, to quickly align the alignment lugs 24166 with the alignment notches 24058, a clinician can draw the alignment nubs 24162 proximally into abutting engagement with the corresponding alignment features 24054 on the channel 24050. The proximal alignment contour 24056 on the proximal alignment feature 24054 acts as a longitudinal stop, which prevents further proximal displacement of the staple cartridge 24100 relative to the channel 24050. The contoured proximal edge 24164 of the alignment nubs 24162 can match or complement the contoured profile of the proximal alignment contour 24056. Upon mating of the complementary profiles, the alignment lugs 24166 are also each aligned with their corresponding alignment notch 24058.

A spring 24172 is positioned between an upright surface of the alignment lug 24166 and an upright surface of the alignment notch 24060. More specifically, the spring 24172 is positioned between the proximal end 24168 of the alignment lug 24166 and the proximal end 24060 of the alignment notch 24060. The spring 24172 is configured to bias the ramped distal end 24170 of the alignment lug 24166 distally into mating contact with the ramped distal end 24062 of the channel 24050 upon insertion of the staple cartridge 24100 into the channel 24050. The spring 24172 can be compressed between the upright proximal end 24060 of the alignment notch 24060 and the upright proximal end 24168 of the lug 24166 when the alignment nubs 24162 are in abutting engagement with the proximal alignment contours 24056 and the staple cartridge 24100 and alignment lugs 24166 thereof are moved in an installation direction 24101 parallel to an installation axis I into the channel 24050. The installation axis I is perpendicular to the longitudinal axis A.

In use, the cartridge body 24102 and the nubs 24162 thereof can be leveraged against the proximal alignment contour 24056 of the channel 24050 as the staple cartridge 24100 is moved along the installation axis I into the channel. The proximal leverage location of the alignment contour 24056 can improve the mechanical advantage of installing the staple cartridge 24100 and distal lugs 24166 thereof into the channel 24050. The nubs 24164 can slide downward into the channel 24050 as the staple cartridge 24100 moves in the installation direction 24101 into a first position, or an inserted position. After the staple cartridge 24100 has been moved to a first position, in which the staple cartridge 24100 is inserted, but not fully seated in the channel 24050, the spring 24172 is configured to shift the staple cartridge 24100 distally in a direction parallel to the longitudinal axis L into a second position, in which the staple cartridge 24100 is fully seated in the channel 24050.

Referring primarily to FIG. 163, the spring 24172 is a flat spring. The spring 24172 is a cantilevered spring having a first end mounted to the alignment lug 24166, a second end opposite the first end, and a curved portion intermediate the first end and the second end. The curved portion can define an S-shaped curve, which is compressible with minimal force and/or effort by the clinician upon alignment of the proximal alignment contours 24056, 24164 and leveraging of the staple cartridge 24100 proximally against the alignment feature 24054. Upon release of the leveraging force and compressive force to the spring 24172, the spring 24172 is configured to rebound and bias the staple cartridge 24100 distally relative to the channel 24050 into a fully seated position (FIG. 164).

In the fully seated position (FIG. 164), the distal ramped ends 24062, 24170 of the alignment lug 24166 and the alignment notch 24058, respectively, are in mating engagement. The undercut geometry of the distal ends 24062, 24170 is configured to secure the staple cartridge 24100 in the channel 24050 until the spring 24172 is compressed by a user-applied force to draw the staple cartridge 24100 proximally along the longitudinal axis A and then upward in a direction 24103 parallel to the installation axis I and opposite to the installation direction 24101 to remove the staple cartridge 24100 from the channel 24050.

In certain instances, a firing element is configured to apply a distal force to the staple cartridge 24100 during a firing stroke to further secure the staple cartridge 24100 in the channel 24050. For example, the ramped distal ends 24062, 24170 can form an interlock between the staple cartridge 24100 and the channel 24050 when the staple cartridge 24100 is pushed distally. In certain instances, the distal firing force and undercut geometry of the ramped distal ends 24062, 24170 can secure the staple cartridge 24100 to the channel 24050 even without the distal biasing force of the spring 24172. For example, the stapling assembly 24000 may not include a spring configured to bias the staple cartridge 24100 relative to the channel 24050 in the direction of the firing stroke. The reader will appreciate that in stapling assemblies utilizing a distal-to-proximal firing stroke, for example, the undercut interlock between the staple cartridge 24100 and the channel 24050 can be at a proximal end 24168, 24060 of the alignment lug 24166 and alignment notch 24058, respectively.

Referring primarily to FIGS. 47-48, the stapling assembly 24000 is shown with an anvil 24090 in the clamped configuration relative to the channel 24050 and the staple cartridge 24100 fully seated therein. The cartridge body 24102 includes a distal nose 24103 with a lock 24180. The lock 24180 include a latching arm 24182 on an underside of the cartridge body 24102. The latching arm 24182 is configured to overlap a portion of the channel 24050 when the staple cartridge 24100 is fully seated in the channel 24050. For example, the channel 24050 includes a ledge or shelf 24082 on the underside thereof facing the latching arm 24182. The lock 24180 is movable between a first position (FIG. 165), in which the latching arm 24182 secures the distal nose 24103 of the cartridge body 24102 to the distal end of the channel 24050 by overhanging the shelf 24082, and a second position, in which the latching arm 24182 releases the shelf 24082 facilitating release of the staple cartridge 24100 from the channel 24050.

The lock 24180 also includes an anvil-facing release button 24184 opposite the latching arm 24182. The anvil-facing release button 24184 can be flush, or substantially flush, with the top surface of the distal nose 24103. The anvil-facing release button 24148 can be depressed by a clinician to drive the lock 24180 downward and/or distally to release the latch 24182 from engagement with the shelf 24082. In certain instances, the lock 24180 can be comprised of a resilient and/or deformable material, which can flex upon receiving a user input on the anvil-facing release button 24184 to move the latching arm 24182 to the second position. In other instances, the lock 24180 can pivot relative to the cartridge body 24102 to move the latching arm 24812 to the second position.

In other instances, the distal nose of a cartridge body can be deflectable to releasably engage retention features along the distal edge of the elongate channel. For example, referring now to FIG. 166, a stapling assembly 24200 is shown with the anvil 24190 in the clamped configuration relative to the channel 24050 and a staple cartridge 24300 fully seated therein. The staple cartridge 24300 is identical to the staple cartridge 24100; however, the distal nose 24301 is comprised of a flexible material, or a flexible portion forming a lock 24380 having a latching arm, which is configured to flex in and out of engagement with the shelf 24082 on the underside of the channel 24050. In certain instances, the entire distal nose 24301 can be flexible to facilitate flexure of the latching arm 24382 out of engagement with the ledge 24082. In other instances, only the lock 24380 and/or latching arm 24382 thereof is flexible enough to disengage the ledge 24082.

In various instances, the cartridge body 24302 can be a composite cartridge body comprised of different materials in different regions such that the flexibility of the unitary composite cartridge body can vary from region to region. For example, the cartridge body 24302 can be 3D-printed and include flexible and/or resilient materials for the lock 24380 and/or latching arm 24382 and less flexible and/or less resilient materials for adjacent regions in the cartridge body. Additionally or alternatively, in certain instances, adjacent portions can be printed with materials having the same or similar relatively low durometers as the lock 24380 and/or latching arm 24382; however, embedded metallic within the cartridge body, such as a metal frame and/or longitudinal support, for example, can increase the overall strength and stiffness of the cartridge body.

Additional alignment and retention features between the staple cartridge and the channel are contemplated, which can improve retention and release of the staple cartridge relative to the channel. Various features can improve the ease of aligning the components and the force required to remove the staple cartridge from the channel while maintaining sufficient retention forces between the staple cartridge and the channel. These additional alignment and retention features can be combined with the proximal alignment features between the staple cartridge and the channel further described herein.

A stapling assembly 25000 is shown in FIG. 167. The stapling assembly 25000 is similar in many aspects to the stapling assembly 24000 and includes a staple cartridge 25100 and a channel 25050; however, the stapling assembly includes alternative proximal alignment and retention features between the staple cartridge 25100 and the channel 25050. Additionally, the staple cartridge 25100 includes longitudinal rows of staple cavities in a cartridge body 25102 thereof and longitudinally-aligned staples positioned in the staple cavities. The staple cavities are oriented parallel to a longitudinal axis A extending along a longitudinal slot and centerline of the cartridge body 25102.

The cartridge body 25102 includes an alignment lug 25166, which comprises a proximal end 25168 and a distal end 25170. An alignment lug 25166 can be positioned on each side of the cartridge body 25102. The proximal end 25168 can define an upright or vertical surface, and the distal end 24170 can also comprise an upright or vertical surface. The upright surfaces defining the proximal and distal ends 25168, 25170, respectively, can be parallel or substantially parallel. In various instances, an alignment lug 25166 can be positioned on each side of the cartridge body 25102 and the alignment lugs 25166 can be symmetrical about a centerline through the cartridge body 25102.

The staple cartridge 25100 also includes a lateral pin 25180 protruding outwardly from the cartridge body 25102. Another symmetrically-positioned lateral pin 25180 can protrude laterally outward on the other side of the cartridge body 25102.

The channel 25050 includes lateral sidewalls 25052 forming a U-shaped channel. The staple cartridge 25100 can be releasably secured in the U-shaped channel between the sidewalls 25052. The channel 25050 further includes an alignment notch 25058, which comprises a proximal end 25060 and a distal end 25062. An alignment notch 25058 can be positioned on each side of the channel 24050 to receive a corresponding alignment lug 25166. The proximal end 24060 defines an upright or vertical surface in the sidewall 24052 and the distal end 24062 defines another upright surface in the sidewall 24052. The upright surfaces can be parallel or substantially parallel.

In other instances, the distal ends 25062, 25170 of the alignment notch 25058, 25166, respectively, can be undercut, as further described herein, to further secure the staple cartridge 25100 to the channel 25050 when the staple cartridge 25100 is fully seated in the channel 25050.

The channel 25050 further includes a slot 25084 defining an internal track for the lateral pin 25180. The slot 25080 includes a V-shaped or tapered entry portion 25082 extending parallel to an insertion direction of the staple cartridge 25100 and a terminal portion 25084 extending parallel to a longitudinal axis of the cartridge body. The V-shaped entry portion 25082 provides a wider entry region 25083 for the lateral pin 25180 into the slot 25084, which ensures the clinician does not need to align the staple cartridge 25100 to the channel 25050 with exacting accuracy. Moreover, the wider entry region 25083 to the slot 25084 can define a larger range of longitudinal positions for the staple cartridge 25100 relative to the channel 25050 than the allowable range of longitudinal positions to align the alignment lug 25166 with an entry region 25063 of the alignment notch 25058.

The alignment features between the channel 25050 and the staple cartridge 25100 are configured to interact to facilitate a quick and easy installation of the staple cartridge 25100 into the channel 25050. For example, to quickly align the alignment lugs 25166 with the alignment notches 25058, a clinician can position the staple cartridge 25100 anywhere in the larger range of longitudinal positions for positioning the lateral pin 25180 in the entry portion 25083 of the slot 25080. As the lateral pin(s) 25180 move along the narrowing track of the V-shaped portion 25082 of the slot 25080, the lug(s) 25166 can be funneled into alignment with the alignment notches 25058.

In various instances, the staple cartridge 25100 can drop into the channel 25050 with minimal interference or frictional resistance. For example, the staple cartridge 25100 may not be secured to the channel 25050 with robust friction-fit features between the staple cartridge 25100 and the channel 25050. Instead of such friction-fit features or in addition thereto, the geometry of the slot 25080 can secure the staple cartridge 25100 in the channel 25050. For example, frictional forces exerted on the staple cartridge 25100 during a proximal-to-distal firing stroke can move the lateral pin 25180 distally along the terminal portion 25084 of the slot 25080 and shift the staple cartridge 25100 distally in the channel 25050. In such instances, the firing forces can move the lug(s) 25166 into their distal-most positions flush with the distal ends 25062 of the alignment notches 25058.

In various instances, to remove a spent staple cartridge 25100 from the channel 25050, a clinician can draw the staple cartridge 25100 proximally to remove the lateral pin 25180 from the terminal portion 25084 of the slot 25080. When the staple cartridge 25100 is shifted proximally by a clinician, which requires minimal force and exertion, the clinician can quickly and easily lift the staple cartridge 25100 out of the channel 25050.

An alternative latching mechanism between a staple cartridge 26100 and a channel 26050 for a stapling assembly 26000 is shown in FIGS. 52 and 53. The staple cartridge 26100 is similar in many aspects to the various staple cartridges described herein and can include a cartridge body 26102 having staples and staple-supporting drivers movably positioned within the cartridge body 26102. The channel 26050 includes opposing sidewalls 26052 forming a U-shaped channel profile, which are configured to receive the staple cartridge 26100 therebetween or at least mostly therebetween. For example, the staple cartridge 26100 includes lateral latching arms 26180 that are configured to releasably engage lateral recesses 26080 along an outside surface of the sidewalls 26052.

The latching arms 26180 extend along lateral sides of the staple cartridge 26000 and can be integrally formed with (e.g. molded with) the cartridge body 26102. For example, the cartridge body 26102 and the latching arms 26180 can be a unitary, single-piece component. In various instances, the latching arms 26180 can be deflectable. The latching arms 26180 includes a user-actuation button 26182 and a catch 26184. The catch 26184 is longitudinally offset from the user-actuation button 26182. A lever arm extends between the user-actuation button 26182 and the catch 26184 such that an actuation of the button 26182 is configured to deflect the catch 26184. For example, an inwardly-exerted actuation to the button 26182, is configured to deflect the catch 26184 outward out of engagement with the lateral recess 26080. In certain instances, deflection of the catch 26184 upon a clinician's actuation to the button 26182 is configured to remove the catch 26184 from the recess 26080. In other instances, the catch 26184 can move to a less engaged and, thus, more easily overcome position relative to the recess 26080. A clinician can apply a pinching motion to the buttons 26182 to simultaneously actuate both buttons 26182 and deflect both catches 26184 out of engagement with the recesses 26080.

In various instances, to install the staple cartridge 26100 in the channel 26050, the staple cartridge 26100 can be moved vertically in an insertion direction until a portion of the cartridge body 26102 rests in the channel 26050. In this position, the latching arms 26180 can be aligned with longitudinal guides along the outer surface of the sidewalls 26052. As the cartridge body 26102 is slid proximally toward a fully seated position in the channel 26050, the latching arms 26180 move along the longitudinal guides and the catches 26184 snap into the recesses 26080 to secure the staple cartridge 26100 in the fully seated position. When the staple cartridge 26100 is fully seated in the channel 26050 and the catches 26184 are engaged or locked in the recesses 26080, the width of the stapling assembly can still be within the traditional sized trocar (e.g. a 12-mm profile). To release the staple cartridge 26100 from the channel 26050, a clinician pinches the buttons 26182 to bias the catches 26184 outward from the recesses 26080 such that the clinician can remove the staple cartridge 26100 by drawing it distally along the longitudinal axis A and/or vertically away from the channel 26050.

In certain instances, the cartridge body 26102 is plastic and the latching arms 26180 are also plastic. For example, the cartridge body 26102 and the latching arms 26180 can be a molded composite plastic component.

In other instances, the cartridge body can be a composite assembly of plastic and metal. For example, the latching arms can be metallic springs, which are formed with the cartridge body. The latching arms can be insert molded metallic arms. Metal latching arms can provide a greater spring constant and a snappier latching feature than plastic arms in certain instances.

In certain instances, a stapling assembly can include a frangible cartridge retention feature, which is configured to secure a staple cartridge in the channel until the frangible cartridge retention feature is intentionally broken by a user. For example, a clinician can intentionally break the cartridge retention feature and/or the feature can be broken during the firing stroke, such as at or near the completion of the firing stroke. Breaking of the frangible cartridge retention feature, can reduce the retention force between the staple cartridge and the channel such that a clinician can remove the staple cartridge with a lower amount of force. In various instances, when the frangible feature is broken, it can remain connected to the staple cartridge body. For example, referring again to the lock 24380 in FIG. 166, the lock can include a frangible portion, which is configured to crack, but not fall off, when the user applies an intentional action to the staple cartridge to remove it from the channel.

In certain instances, a staple cartridge can include a detent that is engaged with the channel and is released from the channel upon completion of the firing stroke. Referring now to FIGS. 54-59, a staple cartridge 26200 is shown, which is similar in many aspects to the staple cartridge 20100 (FIG. 140). For example, the staple cartridge 26200 includes a cartridge body 26202 including a tissue-supporting deck 26204 having staple cavities defined therein; the staple cavities are arranged in three longitudinal rows 26212a, 26212b, 26212c on each side of a rotary drive screw 26242, which is similar to the firing screw 261 (see FIGS. 4 and 5) in many aspects. Staples in the staple cartridge 26200 are supported by drivers 26220, which are similar in many aspects to the triple driver 20120 (FIG. 142). For example, the driver 26220 include three parallel staple-supporting cradles configured to support staples such that the driver 26220 is configured to fire staples from the inner row 26212a, the intermediate row 26212b, and the outer row 26212c simultaneously.

The staple cartridge 26200 includes a detent 26280 that releasably engages the channel. The detent 26280 is movable between a locked configuration (FIGS. 54-57) and an unlocked configuration (FIGS. 58 and 59). In certain instances, an interior-facing side of a channel sidewall, which is positioned adjacent to the cartridge body 26202, can include a recess dimensioned and structured to receive the detent 26280 in the locked configuration. For example, the channel 20852 (FIG. 215) includes distal recesses 20853. The recess is configured to hold the detent 26280 and, thus, the staple cartridge 26200 relative to the channel until the detent 26280 is moved to the unlocked configuration. In other instances, the outward bias of the detent 26280 against the channel sidewall is configured to frictionally engage the channel without placement of the detent 26280 in a recess. Opposing detents 26280 on opposite sides of the staple cartridge 26000 are configured to frictionally-engage the channel to hold the staple cartridge 26000 therein.

The detent 26280 is housed in the distal-most staple cavity 26210 in the outer row 26212c. A through-hole 26205 is defined in an outer wall 26203 of the cartridge body 26202 into the distal staple cavity 26210 in the outer row 26212c. The detent 26280 is aligned with the through-hole 26205 and protrudes from the cartridge body 26202 at the through-hole 26205 when the detent 26280 is in the locked configuration (FIGS. 54-57). A bar 26282 extends from the detent 26280 and is operably engaged with the driver 26220 in the distal-most staple cavity 26210.

When the distal-most driver 26220 is in the unfired position (FIGS. 54-57), the distal-most driver 26200 can bias the detent 26280 into the locked position. Referring now to FIGS. 58 and 59, at the completion of the firing stroke when the distal-most driver 26200 is lifted by the sled through the staple cavity and toward the tissue-supporting deck 26204, the distal-most driver 26220 can move away from the detent 26280 and engage the bar 26282. As the distal-most driver 26220 moves along the bar 26282, the driver 26220 is configured to bias the bar laterally outward, which pivots the detent 26280 inward into and/or through the through-hole 26205 and out of engagement with the channel. In such instances, the distal-most driver 26220 releases the snap feature, i.e. the detent 26280, when the firing stroke is completed.

In certain instances, multiple driver-releasable detents can be positioned along the length of the cartridge body 26202. In certain instances, longitudinally-staggered and/or longitudinally-symmetrically detents can be positioned along both sides of the cartridge body 26202. In addition to the drive-releasable detent 26280, the sled can be configured to release snap-fit or detent features in certain aspects of the present disclosure. Moreover, in certain instances, the driver (s) can be configured to snap or break the detent 26280 and/or the bar 26282 thereof during the firing stroke to release the attachment features.

In various instances, the staple cartridge assemblies herein can include driver retention features configured to prevent the release of the drivers from the cartridge bodies. For example, certain staple cartridges include a metal pan, which is heat-staked or thermoformed to the cartridge body after the drivers are installed in the fastener cavities. The metal pan(s) can wrap around an underside of the cartridge body and hold the drivers therein. In certain instances, the drivers can be retained without a separate metal pan to create additional space in the small form factor of the cartridge assembly. For example, as further described herein, heat stakes between the cartridge body and the drivers can retain the drivers. Additionally or alternatively, the cartridge body can be over-molded with a metal pans. For example, driver retention features can include thermoformed interference features between the drivers and the cartridge body and/or insert molded components within the cartridge body.

Figure 61:
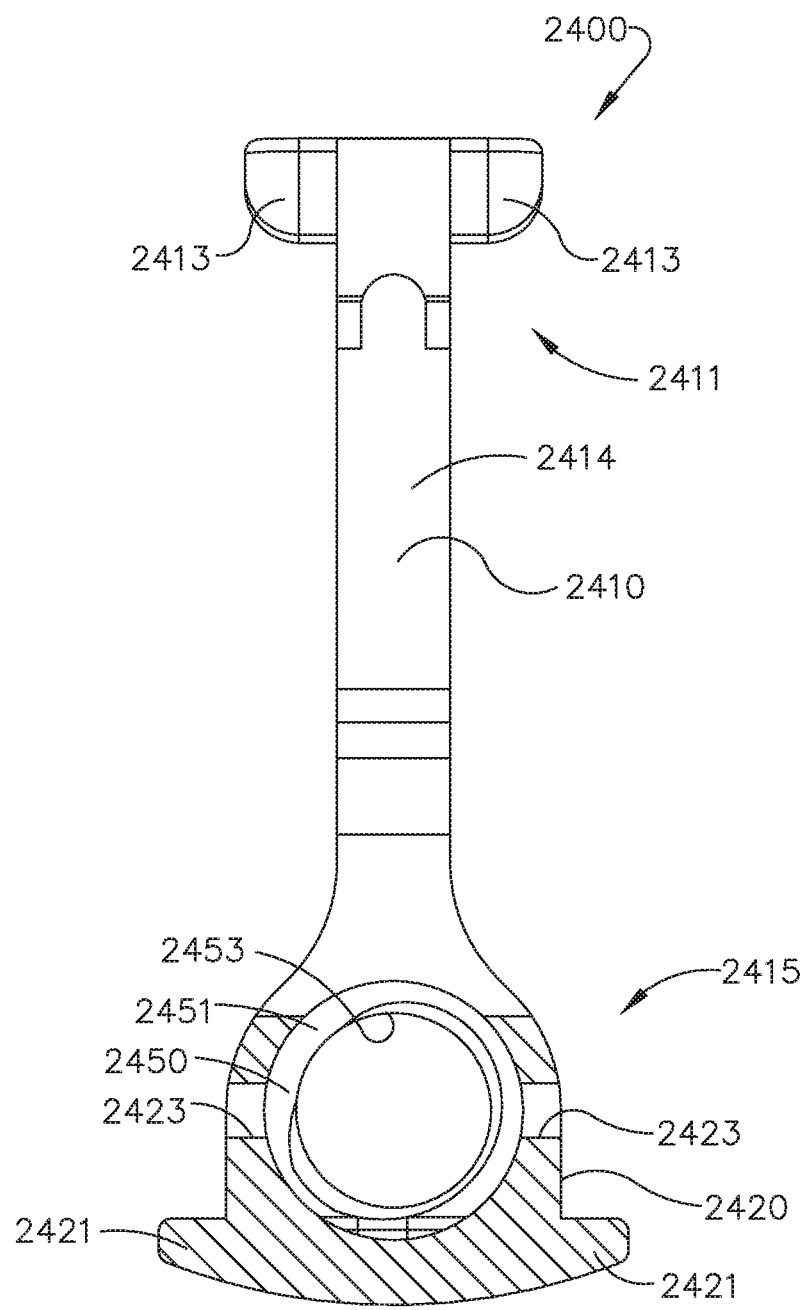
FIG. 61 is another cross-sectional elevation view of the firing member assembly of FIG. 57 taken through distal apertures of the primary body portion, in accordance with at least one aspect of the present disclosure.
Figure 66:
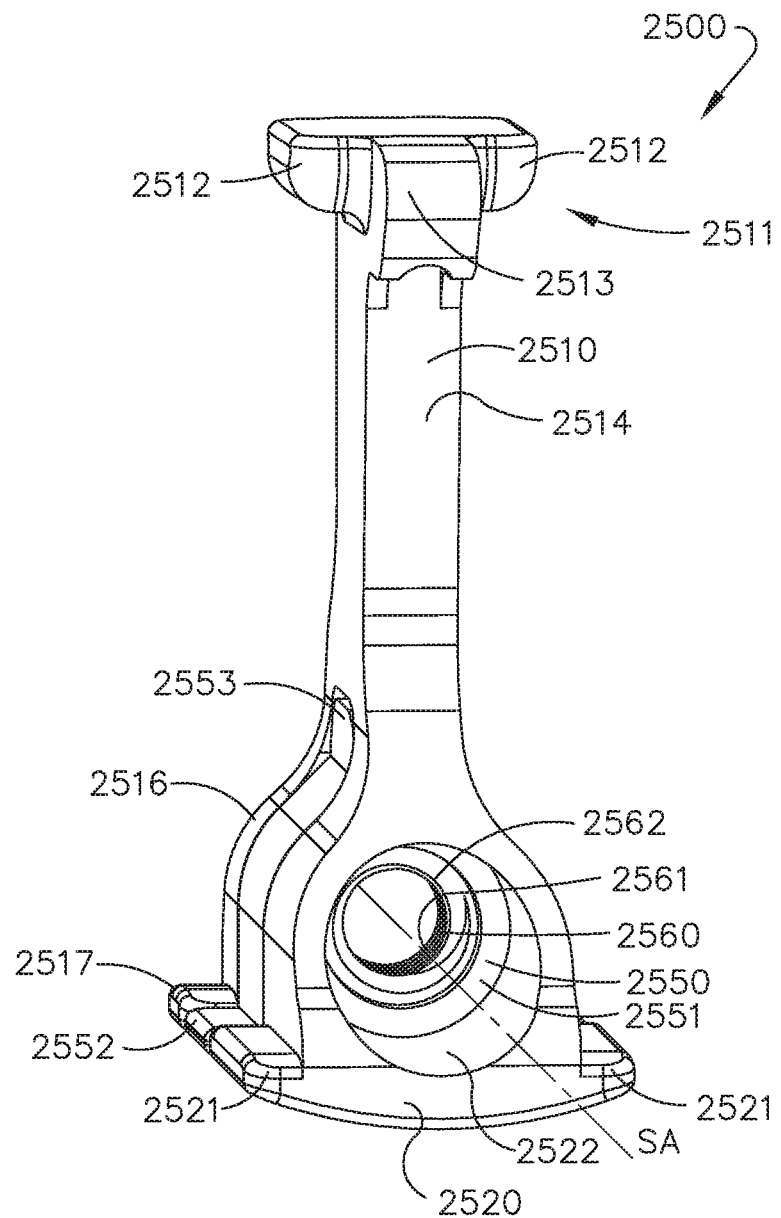
FIG. 66 is a perspective view of the firing member assembly of FIG. 62, in accordance with at least one aspect of the present disclosure.

A staple cartridge 26300 is shown in FIGS. 60 and 61. The staple cartridge 26300 is similar in many aspects to the staple cartridge 20100 (FIG. 140). For example, the staple cartridge 26300 includes a cartridge body 26302 including a tissue-supporting deck 26304 having staple cavities defined therein; the staple cavities are arranged in three longitudinal rows 26312a, 26312b, 26312c on each side of the cartridge body 26302. Staples in the staple cartridge 26300 are supported by drivers 26320 (FIG. 177), which are similar in many aspects to the triple driver 20120 (FIG. 142). For example, the driver 26320 includes three parallel staple-supporting cradles configured to support staples such that the driver 26320 is configured to fire staples from the inner row 26312a, the intermediate row 26312b, and the outer row 26312c.

The cartridge body 26302 includes a row of indentations 26330, or dimples, along a lower portion of the cartridge body 26302. The row of indentations 26330 can be positioned to engage and retain the drivers 26320 when the drivers 26320 are in their unfired positions. In FIG. 176, each indentation 26330 is configured to engage a driver 26320. For example, each driver 26320 can be held is position by an indentation 26330 adjacent to the outer surface of the adjacent staple-supporting column thereof. The indentations 26330 in the cartridge body 26302 can prevent the drivers from falling out of the cartridge body 26302 when the drivers 26320 are in their unfired and down-most positions.

The indentations 26330 in the cartridge body 26302 are configured to engage a recess 26321 in the outer surface of the driver 26320. The recess 26321 can include an upper lip or boundary, which prevents vertical displacement of the driver 26320 relative to the cartridge body 26302. In various instances, the indentations 26330 and the corresponding recesses 26320 can be thermoformed, melted, or otherwise coupled with a heat staking process. Heat staking is further described herein.

Because the drivers 26320 are triple drivers, a heat stake connection between the outer wall of the driver 26320 and the cartridge body 26302 can hold the entire driver 26320, including the intermediate support column and the inner support column, in position in the cartridge body 26302. The interference connection between the indentations 26330 and the recesses 26321 can be overcome by the sled during a firing stroke to sequentially release and lift the drivers 26320 as the sled moves along the row of indentations 26330. In certain instances, a series of heat-stakes along an inside surface in the cartridge body 26302 can engage each driver 26320 during a firing motion. In such instances, the driver 26320 can catch multiple vertical catches or dimples during the firing motion.

In certain instances, the drivers and the cartridge body can include interference features molded into the drivers and/or the cartridge body. Referring to FIG. 178, a staple cartridge 26400 is similar in many aspects to the staple cartridge 20100 (FIG. 140). For example, the staple cartridge 26400 includes a cartridge body 26402 including a tissue-supporting deck 26404 having staple cavities 26410 defined therein; the staple cavities 26410 are arranged in three longitudinal rows on each side of the cartridge body 26402. Staples in the staple cartridge 26400 are supported by drivers 26420 (FIG. 178), which are similar in many aspects to the triple driver 20120 (FIG. 142); however, the driver 26420 is a double driver. The retention features described herein with respect to the driver 26420 can be incorporated into a single driver and/or a triple driver in other instances.

The drivers 26420 include an integrally-formed wedge 26421, which is narrower along a top edge 26423 of the wedge 26421 and thicker along a bottom edge 26425 of the wedge 26421. The wedge 26421 is positioned on a sidewall of a staple support column and is configured to abut a sidewall of the staple cavity 26410. For example, the staple cavity 26410 includes a vertical groove 26405, which is aligned with the wedge 26421. The wedge 26421 is configured to move along the vertical groove 26405 as the driver 26420 is lifted upward by a sled during a firing stroke. To accommodate the wedge 26421, the cartridge walls are configured to flex outward when the driver 26420 is inserted into the cartridge body 26402. In use, the firing force by the sled is sufficient to overcome the interference fit and lift the driver 26420. Stated differently, in the depicted embodiment, the wedge 26421 is configured to travel through the vertical groove 26405; however, the depth of the groove 26405 is not sufficient to allow free and clear passage of the wedge 26421 therethrough. The narrow top edge 26423 can fit in the groove without interference; however, between the narrow top edge 26423 and the thicker bottom edge 26425, the wedge 26421 can interfere with the cartridge body 26402 despite the vertical groove 26405. The interference connection between the wedge 26421 and the vertical groove 26405 is configured to hold the driver 26420 in position within the staple cavity 26410 during the firing motion and resist downward motion; the interference can be overcome by the sled during a firing stroke to sequentially release and lift the drivers 26420 as the wedge 26421 traverses the cartridge body 26402 along the row of indentations 26330. The cartridge body 26402 can continue to flex as the driver 26420 and wedge 26421 thereof move through the cavity 26410.

Referring now to FIG. 179, a staple cartridge 26500 is shown. The staple cartridge 26500 includes a cartridge body 26502 having staple cavities defined therein; the staple cavities are arranged in three longitudinal rows on each side of the cartridge body 26502. Staples 26580 in the staple cartridge 26500 are supported by drivers 26520, which are similar in many aspects to the triple driver 20120 (FIG. 142). The staple cartridge 26500 is similar in many aspects to the staple cartridge 20100 (FIG. 140); however, the staple cartridge 26500 also includes an insert molded metal frame 26503 within the cartridge body 26502. The insert molded metal frame 26503 is a two-part assembly including a first pan 26503a and a second pan 26503b, which extends along the sides of the cartridge body 26502. The pans 26503a, 26503b can be insert molded with the cartridge body 26502, snap-fit to the cartridge body 26502 with a friction fit between bosses 26505 along the length of the cartridge body 26502 and openings 26507 in the pans 26503a, 26503b, and/or can be heat staked to the cartridge body 26502 by deforming bosses 26505 along the length of the cartridge body 26502 within the openings 26507 in the pans 26503a, 26503b.

In one aspect, flat, non-bent pans can be insert molded with the cartridge body 26502 (e.g. the pans 26503*a*, 26503*b* can initially define a linear profile instead of an L-shaped profile). The cartridge body 26502 can be formed with an over-molded metal sheet along the lateral side(s) thereof, for example. Then, the exposed length of the over-molded metal sheets can be bent around a portion of the underside of the cartridge body 26502 to at least partially overlap some of the staple cavities to retain the drivers 26520 in the cartridge body 26502 from the underside thereof. In certain instances, the drivers can be triple drivers spanning outer staple cavities, intermediate staple cavities, and inner staple cavities. The bent portion of the metal sheet can overlap, or substantially overlap, the lower portion of the outer staple cavities to maintain the drivers in the cartridge body.

Alternatively, an L-shaped pan like the pans 26503*a*, 26503*b* can be snap-fit to the lateral sides of the cartridge body 26502 to retain the drivers in the cartridge body 26502 from the underside thereof without insert molding the pans 26503*a*, 26503*b* to the cartridge body 26502.

In one aspect, the pans 26503*a*, 26503*b* can be insert molded with the cartridge body 26502 and can include exposed bendable metallic flanges or arms, that are bent around the cartridge body 26502 after the drivers 26520 have been installed in the staple cavities. For example, referring now to FIGS. 64 and 65, a portion of a metal frame or pan 26603 for a cartridge body, such as the cartridge body 26502 (FIG. 179) or the cartridge body 20102 (FIG. 140) is shown. The pan 26603 can be insert molded with the cartridge body. For example, the pan 26603 includes a frame portion 26605 over which the cartridge body has been molded. The pan 26603 also includes an arm 26609. The arm 26609 can be deformed from an initial configuration (FIG. 180) to a bent arm 26609' configuration (FIG. 181) with a deformation force in the direction F (FIG. 181), to wrap the arm 26609 around a lower portion of the staple cavities and retain the drivers therein.

In various aspects of the present disclosure, the various techniques for forming a piece of metal over the outer staple cavities to retain the drivers therein can be applied to the inner staple cavities in certain instances. For example, in various aspects of the present disclosure, the staple cartridge can include a support brace, such as the support brace 650 fitted within the staple cartridge 640 (see FIGS. 19 and 20). As further described herein, the staple cartridge 640 and the support brace 650 can be assembled together prior to installing the staple cartridge 640 into the channel 630. In certain instances, such a support brace 650 or other insert molded longitudinal frame member within the cartridge body can include a metal sheet, pan, or arm, which can be bent around an underside of the cartridge body to retain the drivers in the inner rows of staple cavities.

As described herein, driver retention and/or interlocking features with the cartridge body can be heat staked to retain the drivers in the cartridge body. In at least one aspect of the present disclosure, each driver can include a corresponding heat stake feature with the cartridge body. It can be important to ensure the heat stake depth is sufficient to keep the drivers from disengaging but does not cause interference with the drivers in their unfired or down positions. The heat stake and orbital forming techniques can be controlled to ensure sufficient engagement.

Referring now to FIG. 183, portions of a staple cartridge 26700 are shown, including a cartridge body 26702 having a driver 26720 therein. The staple cartridge 26700 is similar in many aspects to the staple cartridge 20100 (FIG. 140) but also includes a longitudinal support frame 26703 and heat staked retention features 26705 between the cartridge body 26702 and the longitudinal support frame 26703. In various instances, the heat staking can be done against a solid sheet of metal to secure the cartridge body 26702 to the longitudinal support frame 26703. Then, the drivers 26720 can be installed in the staple cavities. For example, the driver 26720 and a staple can be installed in a staple cavity 26710. After the drivers 26720 have been installed, the longitudinal support frame 26703 can be bent over the underside of the cartridge body 26702 to retain the drivers 26720 therein. For example, a portion 26709 of the longitudinal support frame 26703 can overlay openings in the underside of the staple cartridge body 26702 associated with the outer staple-supporting column on the driver 26720 and outer staple cavity 26710.

An insert support can be utilized in certain heat staking operations, which can reduce the amount of pressure and improve consistency. For example, a removable insert support or backer can be positioned behind each heat stake. Moreover, the insert supports can push the drivers into an upward position while staking to protect the drivers from deformation or other effects of the heat staking operation.

Referring to FIG. 183, a heat staking operation for a staple cartridge 26800 is shown in which a cartridge body 26802 is being secured to a longitudinal support frame 26803 with a heat stake 26805. The staple cartridge 26800 is similar in many aspects to the staple cartridge 20100 (FIG. 140) but also includes the longitudinal support frame 26803 and the heat stake 26805. The longitudinal support frame 26803 includes an upright sheet 26808 and an orthogonal flange 26809 extending therefrom to form an L-shaped profile. The upright sheet 26808 includes openings 26807 therethrough, which are aligned with the heat stakes 26805. The orthogonal flange 26809 also includes openings 26806 therethrough, which are configured to receive fingers 26892 of an insert support 26890 therein.

During a heat staking operation, the L-shaped support frame 26803 is positioned alongside a length of the cartridge body 26802 and the insert support 26890 is positioned relative to the support frame 26803 and the cartridge body 26802 such that the fingers 26892 extend through the openings 26806 in the orthogonal flange 26809 and into staple cavities 26810. The fingers 26892 are configured to push drivers 26820 upwards toward a tissue-supporting deck 26804 of the cartridge body 26802. After the heat stakes 26805 have been formed between the cartridge body 26802 and the L-shaped support frame 26803, the insert support 26890 can be removed from the staple cartridge 26800 allowing the drivers 26820 to move downward and assume their unfired positions in the staple cavities 26810. The orthogonal flange 26809 is configured to overlay a portion of the underside of the cartridge body 26802 and may overlap multiple staple-supporting columns (e.g. an outer column and an intermediate column) and/or a bridge between two adjacent staple-supporting columns to hold the drivers 26820, which span multiple rows of staple cavities 26810, in the cartridge body 26802.

As further described herein, certain end effector components may be constructed using 3D printing technology to improve component capabilities. In certain instances, 3D printing can allow the printed component to exhibit metamaterial properties, for example. A metamaterial is a synthetic composite material with a structure such that it exhibits properties not usually found in natural materials. 3D printing is one technique used to create a metamaterial by forming components with two or more materials and/or structures therein. In other instances, insert molding and over-molding can generate composite components that may have metamaterial properties in certain instances.

Composite end effector components may exhibit greater structural strength and stiffness while allowing precision in the forming of small detailed features and can provide improved frictional properties in certain instances. For example, a metal-plastic composite cartridge body can exhibit certain metamaterial properties in that it may be stronger and stiffer than a similar injection-molded, entirely plastic, or composite, cartridge body, for example, while still allowing precision with respect to small detailed features. In certain instances, a metal-plastic composite cartridge body can demonstrate improved frictional properties with respect to the drivers movably positioned within each staple cavity. Certain composite metal-plastic components can be formed with insert molding or over-molding. In other instances, 3D printing can allow for the creation of complex geometries and/or material combinations that may otherwise be too costly and time consuming to manufacture with conventional molding techniques or, in certain instances, may even be impossible to manufacture absent 3D printing technology.

Referring to FIG. 185, for example, a composite metal-plastic cartridge body 30002 is shown. The composite metal-plastic cartridge body 30002 can provide metamaterial properties in certain instances. Additionally or alternatively, the composite metal-plastic body can allow improved integration of electronic components, such as electronic sensors and flexible circuits.

In one aspect, the cartridge body 30002 is formed with a stamped metal frame 30001 or two or more pans that are stamped and otherwise formed into a skeleton shape for the cartridge body 30002. A plastic material 30003 is then molded over the metal frame 30001. In such instances, the metal frame 30001 can be insert molded to the plastic material 30003. The metal-plastic composite cartridge body 30002 can exhibit increased strength and collapse stiffness in comparison to entirely plastic cartridge bodies, i.e. injection molded cartridge body without a metal frame therein. Plastic material 30003 over a metal or composite frame can provide a structural functioning frame with intricate driver guidance features molded into the plastic material 30003.

The metal frame 30001 can comprise a thin metallic framework and the plastic material can be injection molded with structural members, in certain instances. In one aspect, the metal frame can constitute an integrated pan or pans, as further described herein, which can save space in the cartridge body and/or increase the tissue gap. Additionally, metal can be utilized for certain components related to lockouts, cartridge identification, and resetting. The metal can be less prone to breaking or cracking in certain instances and can withstand significant forces, which may be helpful for lockout components and/or mechanical keys (e.g. an extending tab or post) to prevent insertion of the staple cartridge into an incompatible channel and/or device Certain metallic components can be resilient during a firing stroke reset, i.e. when retracting the sled during manufacturing to test cartridge and ensure all components have been installed. Moreover, a composite metal-plastic cartridge body can facilitate smart cartridge technology, integrated wiring, and/or flexible circuits.

In certain instances, the metal frame 30001 could have flanges that interconnect or span multiple walls and/or columns in the cartridge body. For example, certain walls in the cartridge body can be thinner than other walls and the flanges can connect a thinner wall with a thicker wall to better distribute a torque load, rather than twisting the support. In certain instances, the main standing support walls in the cartridge body can be connected to an adjacent thicker support walls by the metal frame. For example, a thinner interior cartridge wall can be coupled to a thicker exterior cartridge wall to improve force distributions during clamping and/or firing.

In other instances, a composite plastic-metal cartridge body can be 3D-printed. The orientation of the 3D build forming the composite plastic-metal cartridge body can be optimized to ensure smooth driver motions during the firing stroke. For example, referring again to FIG. 185, the cartridge body 30002 includes staple cavities 30010 arranged in a plurality of longitudinal rows 30012. The staple cavities 30010 are defined though a tissue-supporting deck 30004 and into the cartridge body 30002. Drivers, such as the drivers 20120 (FIG. 142), further described herein, can support staples in the cartridge body 30002.

The composite plastic-metal cartridge body 30002 can be printed layer-upon-layer along the longitudinal axis A of the cartridge body 30002. Stated differently, the orientation of the 3D build can be orthogonal to the longitudinal axis A and/or orthogonal to the tissue-supporting deck 30004. When the directional 3D printing of the cartridge body 30002 is perpendicular to the longitudinal axis A (e.g. proximal-to-distal), the build layers can be aligned with the direction of driver motion during the firing stroke. Referring again to FIG. 185, each staple cavity 30010 extends along an axis D, which is perpendicular to the longitudinal axis A. As a sled moves through the cartridge body 30002 along the longitudinal axis A, each drivers is lifted upwards along its respective D axis toward the tissue-supporting deck 30004. The build direction is parallel to the staple cavities' D axes along which the drivers move during a firing stroke. Aligning the 3D build layers with the direction of driver motion can prevent driver binding and hang-ups as the drivers are lifted by the sled during the firing stroke, in certain instances.

The 3D build for a composite plastic-metal cartridge body is proximal-to-distal in certain instances. In other instances, the 3D build can be distal-to-proximal, for example. Support structures for certain 3D builds can be minimized when building the narrower body portion on top of a wider distal nose of the cartridge body, in certain instances.

In various instances, a 3D-printed composite cartridge body can include different infill percentages and/or different materials to obtain metamaterial properties related to improving the strength of the cartridge body while minimizing frictional forces during the firing stroke. Moreover, the support walls of such a cartridge body can define open spaces, voids, and/or cells therebetween. In various instances, the spaces between the support walls, such as the thin walls between the staple cavities, for example, can be configured to allow for improved bending resistance during a clamping load. For example, the spaces between the support walls of the cartridge body can include 3D-printed internal fillets, chamfers, and/or struts, which are configured to improve the open cell strength of the support walls.

Certain cartridge bodies described herein may include a smaller cross-sectional geometry, less material, and/or thinner support walls owing to the footprint of a central firing screw (e.g. the firing screw 261 in FIGS. 4 and 5) therethrough, which takes up real estate in the compact form factor of the cartridge body. High loads on the cartridge body during the firing stroke can exert deformation forces on the cartridge body, which may result in deformation of the cartridge body or portions thereof. For example, the thin walls separating the staple cavities can tend to bend or buckle in certain instances, which can direct the drivers and staples supported thereon out of alignment with the forming pockets in the anvil. In any event, connecting the lateral sides of the cartridge body with a bridge can strengthen the cartridge body and help to maintain alignment between the staples in the staple cavities and their associated forming pockets in the anvil even when subject to high loads.

Referring now to FIGS. 71 and 72, portions of a surgical end effector 30140 are shown. The surgical end effector 30140 is similar in many aspects to the surgical end effector 20240 (FIG. 145). For example, the end effector 30140 includes a staple cartridge 30100, which is similar in many aspects to the staple cartridge 20100 (FIG. 140) and includes a cartridge body 30102 and three rows of staple cavities on each side of a rotary drive screw 30142 (FIG. 188), which is similar in many aspects to the drive screw 261 (see FIGS. 4 and 5) and the rotary drive screw 20242 (FIG. 145), for example. The staple cartridge 30100 is installed in a channel 30150. A firing member 30144 having an upright cutting edge 30146 is configured to move along the rotary drive screw 30142 through the staple cartridge 30100 during a firing stroke to advance the sled and lift the drivers and staples thereon into forming contact with forming pockets in the anvil.

The cartridge body 30102 is similar in many aspects to the cartridge body 20102 (FIG. 140), for example; however, the cartridge body 30102 further includes a bridge 30106 extending between two lateral sides 30102*a*, 30102*b* of the cartridge body 30102. The bridge 30106 covers a longitudinal knife-receiving slot 30108 defined in the cartridge body 30102, along which a portion of the firing member 30144 moves during a firing stroke. The bridge 30106 forms a contiguous tissue-supporting deck 30104 between the two lateral sides 30102*a*, 30102*b* of the cartridge body 30102. In various instances, the bridge 30106 can improve the strength of the cartridge body 30102, for example, and may help to maintain alignment of the staples with the forming pockets on the anvil especially when firing under high loads, for example. In such instances, the bridge 30106 can mitigate lateral staple misalignment resulting from high clamping loads, for example.

The bridge 30106 is a frangible portion, which is configured to be cut or transected by the upright cutting edge 30146 of the firing member 30144 during a firing stroke. In various instances, the geometry of the bridge 30106 is configured to mitigate the risk of splintering. For example, the geometry can allow for a predictable geometry and orientation of destruction of the bridge 30106. In instances in which the cartridge body 30102 is 3D-printed, for example, the cartridge body 30102 can include a different material, different infill percentage, and/or different infill geometry along the bridge 30106 or portions of the bridge 30106 compared to adjacent portions of the cartridge body 30102, which can further facilitate transection of the bridge 30106 during the firing stroke without damaging the firing member 30144 and/or splintering the cartridge body 30102 from the firing load.

In certain instances, as further described herein, the staple cartridge 30100 can include a single-use knife, for example, which can transect the bridge 30106 during the firing stroke. Where a single-use knife is utilized, the knife does not risk becoming dull for a subsequent firing stroke upon transecting the frangible portion of the bridge 30106. The bridge 30106 can comprise a plastic molded and/or 3D-printed component, for example, which can be easily transected by the upright cutting edge 30146 without significant resistance thereof. In other instances, a reusable knife can be used to cut the bridge 30106.

In certain instances, the bridge 30106 can include rows of perforations and/or break/tear lines along which the bridge 30106 is configured to separate from the cartridge body 30202. Referring to FIG. 189, for example, a tamper-evident lid 30200 includes a frangible portion 30206 having a tear tab 30202 and defined by break lines 30204 between the frangible portion and the rest of the lid 30200. The frangible portion 30206 can be removed or separated from the tamper-evident lid 30200 along the break lines 30204. Similarly, the bridge 30106 can be removed from the cartridge body 30102 along break lines, which facilitate separation of the bridge 30106 from the cartridge body 30102. In certain instances, the bridge 30106 can be interrupted with pockets along the sidewall of the knife-receiving slot 30108. Deflected and/or separated portions of the bridge 30106 can be configured to move into the pockets during the firing stroke, rather than being pushed out of the cartridge body 30102 and into tissue clamped therebetween.

In certain instances, as further described herein, a replaceable staple cartridge can include a single-use knife, which may provide a fresh cutting edge for each firing stroke. However, to cut tissue clamped between the jaws of an end effector, the knife should extend beyond the tissue-supporting deck of a staple cartridge, in various instances. Such a protruding knife and cutting edge risks unintentional and/or inadvertent contacts outside of the firing stroke, which may damage tissue and/or dull the cutting edge. For example, the cutting edge may inadvertently contact and/or cut the tissue of a patient and/or clinician before the firing stroke, such as when the staple cartridge is being loaded into the end effector. In other instances, upon completion of the firing stroke, the cutting edge may remain in a distal protruding position and may inadvertently contact and/or cutting the tissue of a patient and/or clinician when the end effector unclamps the tissue and is being withdrawn from the surgical site. Additional unintentional tissue contact scenarios are contemplated.

In various instances, a tissue-transecting knife can be mounted to a sled in the staple cartridge. As the sled moves through the firing stroke, the knife can also move through the cartridge body. Moreover, the sled can interact with the firing member (e.g. the I-beam or E-beam) in the end effector. For example, the sled and knife thereon can be releasably coupled to the firing member, such that the sled and knife are advanced distally during a firing stroke. In certain instances, the sled and the knife can be retracted proximally along with the firing member upon completion or termination of the firing stroke. In such instances, the knife can be reset and/or returned to a proximal position in the cartridge body before the firing member permits the opening of the jaws. In such instances, the protruding knife and cutting edge thereof can returned to a predictable and/or at least partially-shielded position at the proximal end of the cartridge body. In other instances, a sled can include multiple separable components (e.g. a two-part sled), and a portion of the sled can be retracted proximally, while another portion of the sled remains in a distal position. In certain aspects, the retractable portion of the sled can include the knife. In still other instances, the non-retractable portion of the sled can include the knife, which can be directed downward into the cartridge body as the retractable portion of the sled moves past it. In certain instances, a portion of the sled can interact with a lockout feature to prevent a firing stroke when the cartridge is missing and/or spent.

In one aspect of the present disclosure, a firing member can include a distally-extending hook and the sled can include a proximal cavity dimensioned to receive the distally-extending hook. Moreover, the knife can be pivotably coupled to the sled and positioned to selectively engage and retain the distally-extending hook in the sled. For example, the distally-extending hook can hook around a portion of the knife. In various instances, interconnection of the distally-extending hook and the knife is configured to hold the knife in a protruding position relative to the cartridge body.

In such instances, the knife can be moved to the protruding position, in which the cutting edge is positioned to transect tissue clamped between the jaws, when the firing member is advanced into engagement with the sled. Prior to the firing stroke, the knife can be pivoted into a shielded position, in which at least a portion of the cutting edge is shielded by the sled and/or cartridge body. Moreover, upon completion of the firing stroke, the firing member can return with the sled to a proximal position in the cartridge body and return to its shielded position. In various instances, the foregoing arrangement may avoid certain inadvertent tissue contacts outside of the firing stroke.

Referring now to FIGS. 74-77, a sled assembly 30320 for an end effector 30340 (FIG. 193) is shown. The end effector 30340 is similar in many aspects to the end effector 200 (see FIGS. 4 and 5) and is configured to cut and staple the tissue of a patient. The end effector 30340 can include a cartridge jaw and an anvil jaw, for example, and the cartridge jaw can be configured to receive a staple cartridge 30300 having a tissue-supporting deck 30304, which is similar in many aspects to the staple cartridge 220 (see FIGS. 4 and 5), for example. The end effector 30340 also includes a rotary drive screw and a firing member 30342, which are similar to the firing screw 261 (see FIGS. 4 and 5) and the firing member 270 (see FIGS. 4 and 5), respectively. The cartridge jaw is configured to receive the staple cartridge 30300, including staples that can be ejected when the firing member 30342 is advanced within the staple cartridge 30300. For example, the firing member 30342 is driven through the end effector 30340 upon a rotation of the firing screw during a firing stroke to advance the sled assembly 30320.

The firing member 30342 includes a body portion 30343, upper cam members 30344 extending laterally from both sides of the body portion 30343, and lower cam members 30345 extending laterally from both sides of the body portion 30343. The upper cam members 30344 are configured to cammingly engage an upper jaw, or anvil, of the end effector 30340 during a firing stroke, and the lower cam members 30345 are configured to cammingly engage a lower jaw, or elongate channel of the end effector 30340 during the firing stroke.

Further to the above, a longitudinal opening extends through the body portion 30343. The longitudinal opening is configured to receive the rotary drive screw described above. The body portion 30343 further includes a cutout region 30349 configured to receive a firing drive nut 30350. The firing drive nut 30350 is configured to threadably engage the rotary drive screw to convert rotary motion of the rotary drive screw into translation of the firing member 30342. The firing drive nut 30350 also includes laterally-extending members 30351 that extend from both sides of the firing drive nut 30350. The laterally-extending members 30351 are aligned with the lower cam members 30345. As such, the cam members 30345, 30351 cooperate to cammingly engage the lower jaw of the end effector 30340 during the firing stroke.

The body portion 30343 of the firing member 30342 also includes a distal nose portion 30346, that extends distally and forms a distal sled-abutment surface 30352. A distal extension 30347 extends from the distal sled-abutment surface 30352 in a substantially distal direction and is configured to selectively interlock with the sled assembly 30320. More specifically, the distal extension 30347 includes a transverse portion or catch 30348 extending in a direction transverse to the distal direction. The distal extension 30347 and the catch 30347 form a hooked geometry, which selectively engages a portion of the sled assembly 30320, as further described herein.

The sled assembly 30320 includes a sled body 30321 and a knife 30338 having rails 30322 positioned to engage drivers, such as the drivers 20120 (FIG. 142), for example. The rails 30322 are configured to lift the drivers toward the tissue-supporting deck 30304 of the staple cartridge 30300. A central portion 30333 of the sled body 30321 moves along a central longitudinal path in the staple cartridge 30300 during a firing stroke. In various aspects, the central portion 30333 includes an upright hub 30334 having sidewalls 30335, which are dimensioned and structured to move along a longitudinal slot in the staple cartridge 30300. The central portion 30333 also includes an arced underside profile 30334 dimensioned and positioned to accommodate the rotary drive screw without interference.

The upright hub 30334 includes a recess or space 30328 between the sidewalls 30335 and a shaft or pin 30336 extending between the sidewalls 30335. A stop 30337 also extends between the sidewalls 30334, and is further described herein. The knife 30338 of the sled assembly 30320 is pivotably mounted to the pin 30336 at a hub 30339. In various aspects, the hub 30339 can define a hub diameter that permits rotation of the knife 30338 about the pin 30336. Moreover, the knife 30338 includes a mounting slot 30329 having a narrower width than the hub diameter and into which the pin 30336 passes to secure the hub 30339 to the pin 30336. In various instances, the knife 30338 can be snap-fit or press-fit onto the pin 30336, for example. Referring to an exploded view of the sled assembly 30320 in FIG. 191, the knife 30338 can be moved along the assembly axis A to rotatably mount the knife 30338 to the sled body 30321.

In various instances, the knife 30338 can pivot into a downward or recessed position relative to the sled body 30321. For example, the knife 30338 and cutting edge thereof can face generally downward, for example, and/or be shielded by the sidewalls 30335 when the knife 30338 is in the recessed position. In certain instances, a biasing element is configured to bias the knife 30338 toward the recessed position.

Referring primarily now to FIG. 193, during a firing stroke, the firing member 30340 is advanced distally into the staple cartridge 30300, which drives the distal extension 30347 and catch 30348 into the space 30328 between the sidewalls 30335 of the upright hub 30334. Upon insertion into the space 30348, the catch 30348 can hook around an end portion 30328 of the knife 30338. The end portion 30328 of the knife 30338 defines a planar abutment surface 30327 and bulbous end 30327 about with the catch 30348 extends to securely hold the catch 30348 against the planar abutment surface 30327. In such instances, the catch 30348 is held in the space 30328 at a location distal to the end portion 30328 of the knife 30338. Moreover, the knife 30338 is rotated into a protruding position, in which the cutting edge protrudes out of the cartridge body 30302 and into a tissue gap defined between the tissue-supporting surface 30304 and the anvil. In various instances, the distal extension 30347 and/or the end portion 30328 are configured to flex under a defined load during a distal firing motion to resiliently couple the distal extension 30347 in the space 30328 of the sled assembly 30320.

Thereafter, the firing member 30340 can advance the sled assembly 30320 distally. As the sled assembly 30320 moves distally, the knife 30338 is pushed in a clockwise direction from the orientation shown in FIG. 193. Resistance to the firing motion (e.g. tissue) can be configured to rotate the knife 30338 in the clockwise direction. The knife 30338 can be rotated in a clockwise direction from the orientation in FIG. 193 into abutting engagement with the stop 30337, which is configured to prevent further clockwise rotation of the knife 30038. In such instances, the knife 30338 is maintained in an upright or protruding position relative to the tissue-supporting deck 30304 during a distal motion of the firing stroke. For example, the abutment surface 30327 can be flush, or substantially flush, against an inside surface of the catch 30348.

A proximal retraction motion of the firing member 30320 is shown in FIG. 193 in which the firing member 30320 is withdrawn in the proximal direction P. Retraction of the firing member 30320 in the proximal direction B is configured to draw the distal extension 30347 and the catch 30348 proximally, which exerts a force on the end portion 30328 also in the proximal direction. In turn, this force on the end portion 30328 is configured to rotate the knife 30338 in the counterclockwise direction while retracting the sled assembly 30320 along with the firing member 30320. In various instances, a slight clockwise rotation of the knife 30338 is configured to pivot a cutting edge of the knife 30338 downward into an orientation less likely to contact and/or cut tissue, for example.

In various instances, the interconnection between the firing member 30340 and the sled assembly 30320 is configured to ensure that the sled assembly 30320 and the knife 30338 thereof are reset in a proximal position in the staple cartridge 30300 before the jaws are released from engagement by the cam members 30344, 30345, 30351 of the firing member 30340 and permitted to open. When firing member 30340 is further retracted and withdrawn from the staple cartridge 30300, the distal extension 30347, catch 30348, and/or the end portion 30328 can be configured to deflect to release the distal extension 30347 from the sled body 30321 and pivot the knife 30338 further counterclockwise from the orientation in FIG. 193 to a shielded orientation.

In certain aspects of the present disclosure, a sled can be stamped from a sheet of metal. In certain instances, the sled can be a two-part sled formed from two stamped sheets. The stamped sleds can having substantially W-shaped profiles in certain instances. The knife can be integral with one of the stamped sheets, for example. In certain instances, the two-part sled can include a first stamped component, which is retractable with the firing member, and a second stamped component, which is not retracted with the firing member. In a proximal, unfired position, the second stamped component is configured to interact with and overcome a missing and spent cartridge lockout. In a distal, fired position from which the second stamped component is not retracted by the firing member, the missing and spent cartridge lockout is configured to engage the firing member and prevent a firing stroke.

The two-part sled and lockout arrangement can prevent a firing stroke when the staple cartridge is missing from the end effector and/or when a spent or empty staple cartridge is installed in the end effector. Moreover, the sled being formed from two stamped metal sheets can provide a lower cost sled, in certain instances, with an integrated knife and cutting edge(s), coupling feature(s) for the firing member, and lockout engagement feature(s). Such a stamped metal sled can prevent bending or mushrooming of the sled rails under high staple-forming loads and may prevent breaking or cracking of the sled in certain instances. Moreover, the stamped metal sled can define thin rails allowing for more plastic (or other material(s)) in the cartridge body, which can improve the strength of the cartridge body including the strength of the support walls between the staple cavities. In certain instances, the thin profile of a stamped metal sled can allow the drivers to be positioned closer together and can better accommodate a rotary drive screw in certain instances.

Referring now to FIGS. 74-89, a sled assembly 30420 for an end effector 30440 (see FIG. 198) is shown. The end effector 30440 is similar in many aspects to the end effector 200 (see FIGS. 4 and 5) and is configured to cut and staple the tissue of a patient. The end effector 30440 includes a cartridge jaw 30450 and an anvil jaw 30454, for example, and the cartridge jaw 30450 is configured to receive a staple cartridge 30400 having a cartridge body 30402 and a tissue-supporting deck 30404, which is similar in many aspects to the staple cartridge 220 (see FIGS. 4 and 5), for example. The end effector 30440 also includes a firing drive system 30339 that includes a rotary drive screw 30442 and a firing member 30441, which are similar to the firing screw 261 (see FIGS. 4 and 5) and the firing member 270 (see FIGS. 4 and 5), respectively. The cartridge jaw 30450 defines a channel having opposing sidewalls 30452, which are configured to receive the staple cartridge 30400, including staples that can be ejected when the firing member 30441 is advanced through the staple cartridge 30400. For example, the firing member 30341 is driven through the end effector 30340 upon a rotation of the rotary drive screw 30442 during a firing stroke to advance the sled assembly 30420.

Referring primarily to FIG. 197, the firing member 30441 includes a body portion 30443, upper cam members 30444 extending laterally from both sides of the body portion 30443, and lower cam members 30445 extending laterally from both sides of the body portion 30443. The upper cam members 30444 are configured to cammingly engage the anvil jaw 30454 of the end effector 30440 during a firing stroke, and the lower cam members 30445 are configured to cammingly engage the cartridge jaw 30450 of the end effector 30400 during the firing stroke.

Further to the above, a longitudinal opening extends through the body portion 30343. The longitudinal opening is configured to receive the rotary drive screw 30442 described above. In certain instances, the rotary drive screw 30442 can be threadably coupled to the body portion 30343 and, in other instances, can be threadably coupled to a firing drive nut housed therein, as further described herein.

Referring primarily to FIGS. 78-81, the sled assembly 30420 includes two discrete sleds—a proximal sled 30422 and a distal sled 30424. Each sled 30422, 30424 is a separate and discrete stamped component. For example, each sled 30422, 30424 can be formed with a separate stamping. The sleds 30422, 30424 are formed from a stamped sheet of material, such as a metal sheet. In at least one aspect, the sleds 30422, 30424 are formed from steel sheets; however, other materials are also contemplated. The proximal sled 30422 and the distal sled 30422 cooperate to engage drivers 30416 housed in the cartridge body 30402. The drivers 30416 can be triple drivers in various instances, and can be similar in many aspects to the drivers 20120 (FIG. 142), for example.

The proximal sled 30422 and the distal sled 30424 can be connected with a push-connection. Stated differently, while the proximal sled 30422 is applying a pushing force to the distal sled 30424, the sleds 30422, 30424 can remain connected. Absent the pushing force, the sleds 30422, 30424 are separable components which can be selectively moved and relocated in certain instances.

Each sled 30422, 30424 includes a pair of stamped wedges, which form the rails. The proximal sled 30422 includes outer rails 30423 for the sled assembly 30420, and the distal sled 30424 includes inner rails 30425 for the sled assembly 30420. An outer rail 30423 and an inner rail 30425 can be configured to move along each side of the staple cartridge during a firing stroke and can be aligned with a row of drivers 30416. Between the rails 30423, 30425, the proximal and distal sleds 30422, 30424 includes a central upright portion 30426, 30428, respectively, defining a lower arced profile 30426a, 30428a to accommodate the rotary drive screw 30442 (FIG. 197) therethrough. The central upright portions 30426, 30428 also include a key 30426b, 30428b, respectively, which are configured to align and guide the sleds 30422, 30424 through the cartridge body 30402. The keys 30426b, 30428 are arcuate loops although other geometries are also contemplated. Orthogonal flanges connect the central upright portions 30426, 30428 to their respective rails 30423, 30425, for example. The orthogonal flanges have the same thickness as the associated rails 30423, 30425 owing to their stamped formation.

The sled assembly 30420 is shown in an staple cartridge in FIG. 204. The thickness of the metal sheet can correlate to the thickness of the rails 30423, 30425. In such instances, the inner rails 30423 necessarily have the same thickness, and the outer rails 30423 necessarily have the same thickness. In at least one aspect, the inner rails 30423 and the outer rails 30423 can have the same thickness though stamped separately. In any event, being formed from thin metal sheets, the sled assembly 30420 can have a reduced thickness while still withstanding high loads without bending and/or breaking. For example, the rails 30423, 30425 can be narrower than the cartridge walls between staple cavities in adjacent longitudinal rows. Comparatively, referring to a staple cartridge 30500 in FIG. 205 having the same overall width and staple line geometry, inner and outer rails 30523, 30525 of a sled 30530 (e.g. a molded plastic sled) in a cartridge body 30502 can be wider than the rails 30423, 30425. In such instances, the cartridge body 30502 may have less space and, thus, less material and associated strength to support the inner row of drivers, for example.

The proximal sled 30422 and the distal sled 30424 can be aligned and assembled along an assembly axis A (FIG. 195). When assembled, the central upright portions 30426, 30428 can be longitudinally staggered and a proximal portion of the inner rails 30425 can rest on the orthogonal flanges of the proximal sled 30422 (see FIG. 196). Moreover, the orthogonal flanges of both sleds 30422, 30424 are configured to slide or otherwise move along a lower support surface, such as an inner surface of the cartridge jaw 30450 (see FIG. 198).

Referring still to FIGS. 78-81, the proximal sled 30422 also includes an integral knife 30430 having a distal-facing cutting edge 30432. The knife 30430 can be cut into the sheet of material, for example, when the proximal sled 30422 is stamped. The proximal sled 30422 also includes a proximal tail or extension 30434, which is configured to releasably couple with the firing member 30441 (FIG. 197) when the staple cartridge 30400 and the driver assembly 30420 thereof are installed in the cartridge jaw 30450 (FIG. 198). The proximal extension 30434 is T-shaped and includes a lateral bias, which is configured to facilitate coupling with a T-shaped recess 30448 (FIG. 197) in the firing member 30441. For example, referring to FIG. 203, the proximal extension 30434 can initially reside in a notch in the cartridge body 30402, which can hold the proximal sled 30422 in position relative to the cartridge body 30402. Then, when the firing member 30442 moves distally, the proximal extension 30434 bends into the T-shaped recess 30448 to lock the proximal sled 30422 to the firing member 30442. Alternative complementary profiles are also contemplated for coupling the proximal extension 30434 and the firing member 30441.

In various instances, when the staple cartridge 30400 is installed in the cartridge jaw 30450, the firing member 30441 can be aligned with the driver assembly 30420, and can be configured to move into driving engagement with the driver assembly 30420, as shown in FIG. 197, when the firing member 30441 moves an initial distance distally during a firing stroke. Referring to FIG. 203, deflection of the proximal extension 30434 into the recess 30448 is permitted when the firing member 30441 starts to move proximally, for example.

The proximal extension 30434 can be biased into holding engagement with the recess 30448 in the body 30443 of the firing member 30441 and can remain in engagement with the recess 30448 during proximal and distal displacement(s) of the firing member 30441 until the firing member 30441 is finally withdrawn proximally out of the staple cartridge 30400, or nearly out of the staple cartridge 30400, at the completion of the firing stroke. When the firing member 30441 is releasably attached to the proximal sled 30422, the upright body portion 30443 of the firing member 30441 is aligned with the knife 30430. As shown in FIG. 197, the body portion 30443 can support the knife 30430 as the knife 30430 is advanced through tissue. In various instances, the additional support from the body portion is configured to prevent deflection of the knife 30430 away from the firing path and longitudinal axis of the end effector 30440.

The distal sled 30424 is pushed distally by the proximal sled 30422 during the firing stroke. The distal sled 30424 further includes a foot 30429 (FIG. 202), which extends downward from the rails 30245 and/or orthogonal flange. The foot 30429 can be configured to move through a slot in the cartridge jaw 30450 during the firing stroke as the firing member 30441 pushes the proximal sled 30422, which pushes the distal sled 30424 distally during the firing stroke. In various instances, the foot 30429 is configured to engage a lockout in the end effector 30440 when the distal sled 30424 is parked in a proximal, unfired position. The distal sled 30424 and lockout features thereof are further described herein.

Referring primarily to FIGS. 82-84, the end effector 30440 includes a lockout arm 30460, which is selectively engaged by the distal sled 30424. The lockout arm 30460 is movable between an locked position (FIGS. 82-84), in which a firing stroke is prevented, and an unlocked position (FIG. 201), in which a firing stroke is permitted. The lockout arm 30460 is flexibly positioned in a longitudinal recess 30453 in the channel portion of the cartridge jaw 30450 and is configured to pivot about a central pivot portion 40646 in certain instances.

The lockout arm 30460 includes a proximal end 30466 that is biased into a lockout notch 30449 in the firing member 30341. For example, a spring 30470 positioned in the cartridge jaw 30450 is configured to push the proximal end 30466 into the lockout notch 30449 of the firing member 30341 when the firing member 30341 is in a proximal, pre-firing stroke position. When the proximal end 30466 of the lockout arm 30460 is received in the lockout notch 30449, the lockout arm 30460 is configured to resist translation of the firing member 30441 and, thus, prevent the firing stroke The sled assembly 30420 is configured to overcome the lockout arm 30460 by removing the proximal end 30466 thereof from the lockout notch 30449. More specifically, when the distal sled 30424 is positioned in a proximal, unfired position in the staple cartridge 30400, the foot 30429 of the distal sled 30424 is positioned to engage a distal end 30462 of the lockout arm 30460 (see FIG. 201). The pivot portion 30464 of the lockout arm 30400, which is between the proximal end 30466 and the distal end 30462, is held in an arcuate support 30451 in the cartridge jaw 30450. The pivot portion 30464, and thus the entire lockout arm 20468, is configured to pivot about the arcuate support 30451 in certain instances.

For example, the lockout arm 30460 pivots from the locked position to the unlocked position when the staple cartridge 30400 is installed in the end effector 30440 and the distal sled 30424 is in the proximal unfired position, which indicates that the staple cartridge is not spent or empty. The lockout arm 30460 pivots from the unlocked position to the locked position when the firing member 30441 pushes the proximal sled 30422 distally, which pushes the distal sled 30422 distally. When the foot 30429 on the bottom of the distal sled 30422 moves out of engagement with the distal end 30462 of the lockout arm 30460, the lockout arm 30460 pivots due to the biasing force of the spring 30470. When the firing member later returns to a proximal position after a firing stroke and attempts to move the lockout notch 30449 past the lockout arm 30460, the spring 30470 pushes the proximal end 30466 of the lockout arm 30460 into the lockout notch 30449 to prevent the firing stroke. The foot 30429 moves along the longitudinal recess 30453 in the channel 30450 during the firing stroke.

As described herein, the two-part sled assembly 30420 is configured to selectively overcome the lockout arm 30460 to permit a firing stroke. Moreover, the sled assembly 30420 includes an integral knife 30430, which is a single-use knife 30420 have a suitably sharp cutting edge 30432 for transecting tissue clamped by the end effector 30440. The single-use knife 30420 is retracted proximally upon completion of the firing stroke and along with the firing member 30441. Moreover, because the firing beam 30441 includes opposing cams 30445, 30446, the firing member 30441 can ensure that the jaws 30450, 30542 remain closed until the knife 30420 is returned to a proximal position in the staple cartridge 30400.

As described herein, certain surgical devices can include a reusable knife, which is incorporated into the surgical device, such as a distal-facing knife edge on a firing member, for example. Upon completion of a firing stroke, the reusable knife can be retracted out of the staple cartridge and subsequently re-fired with another staple cartridge. In such applications, the surgical device, including the reusable knife thereof, can be cleaned and sterilized between surgical procedures.

In other instances, a single-use knife can be utilized with a surgical device. For example, a staple cartridge can include a single-use knife which is only used with that particular staple cartridge. When the staple cartridge is removed from the surgical device, the single-use knife is removed, as well. When a replacement staple cartridge is installed in the surgical device, a new single-use knife is provided therewith. In certain instances, the single-use knife can remain in the staple cartridge for the duration of the firing stroke and even after the firing stroke when the staple cartridge is removed from the surgical device. In certain instances, the cutting edge of the single-use knife can be at least partially shielded by a feature of the staple cartridge after the firing stroke and/or when the staple cartridge is removed from the surgical device. In certain instances, the knife or a portion thereof can be folded or otherwise deformed and/or pushed from a protruding orientation downward into the staple cartridge.

For example, a staple cartridge can include a two-part sled assembly including a proximal sled and a distal sled. The proximal sled can connect to a firing member upon insertion of the two-part sled assembly into a surgical device. The distal sled can include an upright cutting edge. During a firing stroke, the firing member is configured to push the proximal sled distally, which, in turn, pushes the distal sled distally to transect tissue. Upon completion of the firing stroke, the proximal sled can be retracted proximally by the firing member and can separate from the distal sled. As the proximal sled is retracted proximally, a central ledge of the proximal sled is configured to move over the upright cutting edge to fold the cutting edge downward into the cartridge body. In various instances, the proximal sled can also include support features for supporting the upright cutting edge during the firing stroke.

In certain instances, the two-part sled assembly can be manufactured from stamped metal sheets, which can be a low cost alternative to other manufacturing techniques. A stamped metal sled assembly can have thinner rails yet be stronger than a plastic sled for the same size staple cartridge, in certain instances. Moreover, a stamped metal sled assembly can form staples with less spring back and/or allow the staples to be positioned closer together in a staple line, in certain instances. In certain instance, the knife can be configured to dive and/or be deformed into the cartridge body anywhere along the length of the firing stroke and only the proximal stamped sled component can return with the firing member. The folding and/or deformation of the knife during the proximal retraction of the firing member and proximal stamped sled component can ensure the knife is not reused during a subsequent surgical operation. The proximal stamped sled component and the firing member can be positioned to support the distal stamped sled component and the knife thereof during the distal firing stroke in certain instances.

Referring now to FIGS. 90-98, a two-part sled assembly 30620 is shown. The sled assembly 30620 includes two discrete sleds—a proximal sled 30622 and a distal sled 30624. Each sled 30622, 30624 is a separate and discrete stamped component. For example, each sled 30622, 30624 can be formed with a separate stamping. The sleds 30622, 30624 are formed from a stamped sheet of material, such as a metal sheet. In at least one aspect, the sleds 30622, 30624 are formed from steel sheets; however, other materials are also contemplated. The proximal sled 30622 and the distal sled 30622 cooperate to engage drivers 30616 (FIG. 208) housed in a cartridge body 30602. The drivers 30616 can be triple drivers in various instances, and can be similar in many aspects to the drivers 20120 (FIG. 142), for example.

The proximal sled 30622 and the distal sled 30624 can be connected with a push-connection. Stated differently, while the proximal sled 30622 is applying a pushing force to the distal sled 30624, the sleds 30622, 30624 can remain connected. Absent the pushing force, the sleds 30622, 30624 are separable components that can be selectively moved and relocated in certain instances.

Each sled 30622, 30624 includes a pair of stamped wedges, which form the rails. The proximal sled 30622 includes outer rails 30623 for the sled assembly 30620, and the distal sled 30624 includes inner rails 30625 for the sled assembly 30620. An outer rail 30623 and an inner rail 30625 can be configured to move along each side of the staple cartridge during a firing stroke and can be aligned with a row of drivers 30616. The proximal sled 30622 includes a central upright portion 30626 and orthogonal flanges 30621 connecting the central upright portion 30426 to each outer rail 30623. The orthogonal flanges 30621 are configured to ride along a lower support surface during a firing stroke (e.g. along an inside surface of a cartridge jaw) and have the same thickness as the outer rails 30423 owing to the stamped formation of the proximal sled 30622. The central upright portion 20426 is dimensioned to fit around a portion of the distal sled 20624 and defines a ledge 30627.

The distal sled 30624 includes a central upright portion 30628 and orthogonal flanges 30619 connecting the central upright portion 30626 to each inner rail 30625. The orthogonal flanges 30619 are configured to ride along a lower support surface during a firing stroke (e.g. along an inside surface of a cartridge jaw) and have the same thickness as the inner rails 30625 owing to the stamped formation of the distal sled 30624. The central upright portion 30628 defines a lower arced profile 30626a dimensioned to accommodate a rotary drive screw 30642 (FIG. 208) therethrough. The rotary drive screw 30642 is similar to the firing screw 261 (see FIGS. 4 and 5) in many aspects. The central upright portion 30628 further includes an extending knife 30629 having a distally-facing cutting edge 30630. The central upright portion 30626 of the proximal sled 30622 is configured to fit around the central upright portion 30628 of the distal sled 30622 except the extending knife 30629 which extends beyond the ledge 30627 and upper edge of the central upright portion 30626. The distal sled 30624 also includes an anti-retraction arm 30632, which can be biased laterally into engagement with the cartridge body 30602 to prevent proximal retraction of the distal sled 30624 after the firing stroke. In certain instances, an anti-retraction arm 30632 can be positioned on each lateral side of the distal sled 30624.

Referring primarily to FIG. 208, the sled assembly 30620 is a component of a staple cartridge 30600, which also includes the cartridge body 30602, drivers 30616, and staples removably positioned in the cartridge body 30602. In various instances, the staple cartridge 30600, including the sled assembly 30620 thereof, can be releasably installed in a surgical device or an end effector thereof having an cartridge jaw, an anvil jaw, and a firing member, as further described herein. Upon completion of the stapling motion, the staple cartridge 30600, including the sled 30620 thereof, can be removed from the end effector. When installing the staple cartridge 30600 in the surgical end effector, the sled assembly 30620 can be aligned with the firing member in the surgical end effector and the distal sled 30622 can be releasably coupled to the firing member when the staple cartridge 30600 is installed in the surgical end effector.

Referring now to FIG. 206, a firing member 30641 for use with the sled assembly 30620 is shown. When assembled together, the firing member 30641 and the sled assembly 30620 form a firing assembly 30639, which is configured to be advanced along the rotary drive screw 30642 during a firing stroke. The firing member 30641 includes an upright body portion 30643, upper cam members 30644 extending laterally from both sides of the body portion 30643, and lower cam members 30645 extending laterally from both sides of the body portion 30643. The upper cam members 30644 are configured to cammingly engage an upper jaw, or anvil, of the end effector during a firing stroke, and the lower cam members 30645 are configured to cammingly engage a lower jaw, or elongate channel of the end effector during the firing stroke. The cam members 30644, 30645 are configured to clamp the jaws of the end effector 30640 and define a tissue gap during a firing stroke, as further described herein with respect to various firing member (e.g. I-beams and E-beams).

As shown in FIG. 206, when the staple cartridge 30600 including the sled assembly 30620 is installed in a surgical end effector, the sled assembly 30620 is brought into releasable engagement with the firing member 30641. More specifically, the proximal sled 30622 includes proximal fingers 30638, which extend laterally inward into longitudinal tracks 30637 along each inside edge of the orthogonal portions 30621. Moreover, the firing member 30641 includes ridges 30648 positioned within respective slots 30646 into the body portion 30645. Owing to the angle of insertion of the staple cartridge 30600 relative to the firing member 30641, the proximal fingers 30641 are lifted over the ridges 30648 and positioned in the slots 30646 in the firing members 30641 to releasably retain the proximal sled 30622 to the firing member 30641. Referring primarily to FIG. 211, the engagement features between the proximal sled 30622 and the firing member 30641 are symmetrical about a longitudinal axis A through the staple cartridge 30600 and aligned with the firing drive screw 30641 (FIG. 208). In other instances, the engagement features may only be positioned on one side of the firing assembly 30639.

When the staple cartridge 30600 is properly seated in the surgical end effector and the proximal sled 30622 is releasably held to the firing member 30641, a firing stroke can be initiated. At the outset of the firing stroke, the firing member 30641 is advanced distally and the firing assembly 30639 assumes the first advanced configuration of FIGS. 92-95. In this initial portion of the firing stroke, the firing member 30641 moves distally relative to the proximal sled 30622. For example, the proximal fingers 30638 move through the slots 30646 in the firing member 30641 as the ridges 30648 move along the tracks 60637. The firing member 30641 is advanced distally until the ridges 30648 on the firing member 30641 abut the ends of the tracks 30637, as shown in FIG. 211. Stated differently, the proximal sled 30622 includes hard stops 30636 in the orthogonal portions 30621 at the distal ends of the tracks 30637 (FIG. 211). The ridges 30648 cannot move distally past the hard stops 30636. In short, the firing member 30641 moves relative to the proximal sled 30622 until the ridges 30648 abut the hard stops 30636 at which point the firing assembly 30639 is in the first advanced configuration.

In the first advanced configuration, the firing member 30641 is positioned to push the proximal sled 30622 and the proximal sled 30622 is positioned to push the distal sled 30624. In effect, the firing member 30341 is in pushing engagement with the sled assembly 30620 and can push the collective sled assembly 30620 distally to fire the staples and cut tissue. In the first advanced configuration, the upright body portion 30643 of the firing member 30641 is pushed distally into abutting engagement with the knife 30629. In this configuration, the firing member 30641 is configured to support the knife 30629 during the firing stroke.

Upon completion of the firing stroke or a portion thereof, the firing member 30641 can be retracted proximally. Proximal retraction of the firing member 30641 is configured to unclamp the jaws in various instances, as further described herein. The proximal retraction motion is shown in FIGS. 96A-96D. In a first retracted configuration (FIG. 212A), the firing member 30641 has been retracted proximally and moved relative to the sled assembly 60620 including relative to the proximal sled 60622. For example, the firing member 30641 is permitted to move proximally relative to the proximal sled 60622 until the ridges 30648 abut the proximal ends of the tracks 30637. The proximal ends of the tracks 30637 are defined by the proximal fingers 30638 extending laterally inward into the slot 30645 in the firing member 30641. In the first retracted configuration, the ridges 30648 abut the distal ends of the proximal fingers 30638.

From the first retracted configuration, the firing member 30641 is configured to retract the proximal sled 30622 along with the firing member 30641. The anti-retraction arms 30632 on the distal sled 30624 are configured to hold the distal sled 30624 in place in the cartridge body 30602 as the proximal sled 30622 is retracted. In the second retracted configuration (FIG. 212B), the ledge 30627 on the central upright portion 30626 of the proximal sled 30622 is pulled over the upward-protruding knife 30629 to deform or fold the knife 30629 downward under the ledge 30627. The central upright portion 30628 of the distal sled 30624, which supports the knife 30629, comprises a slender beam having at least one corner or bend, which can be deflected by the ledge 30627 moving over the knife 30629. The bends can include a hollowed inside corner to facilitate bending when the downward force of the ledge 30627 is applied thereto. The central upright portion 30628 and the knife 30629 thereof continue to be pushed downward when the firing assembly moves from the second retracted configuration to the third retracted configuration (FIG. 212C). From the third retracted configuration to the fourth retracted configuration (FIG. 212C), the firing member 30641 continues to draw the proximal sled 30622 away from the distal sled 30624 and knife 30639 thereof, which has been folded and/or deformed by the ledge 30627 during the proximal retraction motion of the proximal sled 30622.

Referring primarily to FIGS. 97 and 98, the distal sled 30624 is retained in a distal portion of the cartridge body 30602 and the proximal sled 30622 and the firing member 30641 are retracted proximally. In various instances, after the cams 30644, 30645 of the firing member 30641 are retracted out of engagement with the camming surfaces in the anvil jaw and the cartridge jaw, the jaws can be opened and the spent/fired staple cartridge 30600 can be removed from the end effector. For example, owing to the removal angle of the staple cartridge 30600, the proximal fingers 30638 can be lifted over the ridges 30648 to disengage the proximal sled 30622 from the firing member 30641. In such instances, the staple cartridge 30600 including the bent/deformed knife 30629 shielded within the cartridge body 30602 can be removed and replaced with a new staple cartridge.

Certain staple cartridges described herein can include a central longitudinal support frame and/or a rotary drive screw extending along a substantial length of the staple cartridge. In various instances, the structures along the center of the staple cartridge can occupy a significant portion of the staple cartridge footprint and, notably, take up a significant width, which can impact the arrangement of staple cavities, staple drivers, and staples therein. Certain modifications to a staple line can impact hemostasis. Adjustments to the staple line configuration such as number of staples and spacing therebetween within a longitudinal row, lateral spacing between longitudinal rows, and variations in number of staples, spacing therebetween, and placement of proximal-most staples (i.e. offset) can be adjusted from row-to-row. Various staple line configurations are described herein, which are configured to optimize hemostasis and balance firing forces within the small footprint of the various staple cartridge assemblies described herein.

The sled is subjected to significant forces during a firing stroke. For example, as the sled engages the drivers and lifts the drivers and staples thereon through the tissue and into forming contact with the anvil, significant transverse loads can be applied to the sled rails. To smooth the force-to-fire during a firing stroke, the staple patterns on opposing sides of the cartridge can be longitudinally offset.

Referring now to FIG. 234, a staple cartridge 25000 has a cartridge body 25002 and staple cavities 25010 defined in the cartridge body 25002. The staple cavities 25010 are dimensioned and structured to hold drivers and staples therein, as further described herein. A longitudinal slot 25006 divides the cartridge body 25002 into a first side 25002*a* and a second side 25002*b*. The staple cavities 25010 are arranged in two patterns: a first pattern 25014 on the first side 25002*a* of the longitudinal slot 25006, and a second pattern 25016 on the second side 25002*b* of the longitudinal slot 25006. Each pattern 25014, 25016 includes an inner row 25012*a*, an intermediate row 25012*b*, and an outer row 25012*c*. However, the first pattern 25014 is different than the second pattern 25016.

More specifically, the first pattern 25014 is longitudinally offset from the second pattern 25016 by a distance, or longitudinal offset, O. Consequently, the first pattern 25014 and the second pattern 25016 are not symmetric relative to the longitudinal axis A. The first pattern 25014 includes proximal-most staples cavities, and the second pattern 25016 includes proximal-most staple cavities. The longitudinal offset O between the proximal ends of the proximal-most staple cavities on either side of the longitudinal axis L is the longitudinal offset O.

As further described herein, triple drivers include three staple-supporting columns connected by bridges. The triple drivers define a longitudinal length from the proximal end of the proximal-most support column to the distal end of the distal-most support column. The longitudinal length is length along the longitudinal axis A, e.g. the proximal-to-distal length of a driver configured to fire staples from a first cavity 25010*a*, a second cavity 25010*b*, and a third cavity 25010*c*. The proximal-to-distal length of a triple driver can be 0.1936 inches in certain instances. Other lengths are also contemplated.

The longitudinal offset is configured to smooth the force-to-fire of the sled during the firing stroke in various instances. In various instances the longitudinal offset O is approximately 25% of the longitudinal length of the triple drivers housed in the staple cavity. In other instances, the longitudinal offset O can be less than 25% or more than 25% of the longitudinal length of the triple driver. For example, a longitudinal offset O of 5% to 35% of the longitudinal length of the triple driver is contemplated. Referring to FIG. 235, a longitudinal offset of 29.5% between a first pattern 25114 and a second pattern 25116, which corresponds to approximately 0.0573 inches for a 0.1936 inch proximal-to-distal length triple driver, is utilized. In other instances, referring to FIG. 236, a longitudinal offset of 9.2% between a first pattern 25215 and a second pattern 25216, which corresponds to approximately 0.0178 inches for a 0.1936 inch proximal-to-distal length triple driver, is utilized. FIGS. 94-96 only depict a portion of each pattern 25014, 25016,

25114, 25115, 25214, 25216, and the same pattern continues until the distal end of the staple cavities in certain instances.

In certain instances, the triple drivers can be triangular, and the drivers on one side of the cartridge body are not aligned with the drivers on the opposite side of the cartridge body. An asymmetric arrangement of triple drivers in a cartridge body can allow the sled to be asymmetric about a longitudinal centerline. In such instances, one side of the cartridge body can have additional space at the proximal end where that side of the driver is longitudinally offset in a distal direction. The additional space can accommodate lockout components and/or rotary driver supports. Exemplary lockouts and rotary driver supports are further described herein. In certain instances, lockout components and rotary drive supports can be at least partially side-by-side in the proximal end of the cartridge body.

In other instances, the sled rails can be longitudinally offset to balance the force-to-fire. For example, the sled rail(s) on a first side of the sled can be longitudinally offset from the sled rail(s) on the opposite side of the sled by 25% of the longitudinal length of the triple drivers housed in the cartridge body 25002.

Referring again to FIG. 210, in certain instances, the longitudinal rows 25012*a*, 25012*b*, 25012*c* on each side 25002*a*, 25002*b* can be laterally spaced differently. For example, the inner row 25012*a* and the intermediate row 25012*b* on the second cartridge side 25002*b* are closer together than the inner row 25012*a* and the intermediate row 25012*b* on the first cartridge side 25002*a*. The distance between axis 25024 and axis 25025 is less than the distance between axis 25022 and axis 25023, for example. Moreover, the outer row 25012*c* and the intermediate row 25012*b* on the second cartridge side 25002*b* are farther apart than the outer row 25012*c* and the intermediate row 25012*b* on the first cartridge side 25002*a*. The distance between axis 25026 and axis 25025 is greater than the distance between axis 25021 and axis 25022, for example. Moreover, on both sides of the cartridge body 25002, the lateral spacing between the inner row 25012*a* and the intermediate row 25012*b* is different than the lateral spacing between the intermediate row 25012*c* and the outer row 25012*c*.

In other instances, none of the rows of staple patterns on one side of a cartridge body, e.g. one side of the longitudinal knife slot, can be a repeated pattern. A non-repeating and unique pattern in each row can permit customizations row-to-row to ensure a maximum number of staple cavities fit in the cartridge body, especially in a proximal region near the tissue stops. Moreover, in certain instances, the staple pattern can utilize the same drivers, e.g. the same triple driver, along the entire length of the staple line. In such instances, only a single type of driver is utilized in the staple cartridge, which can improve manufacturing processes. In certain instances, proximal-most and/or distal-most fastener cavities in the inner row and the outer row can be offset, for example.

Referring now to FIG. 237, a staple cartridge 25300 has a cartridge body 25302 and staple cavities 25310 defined in the cartridge body 25302. The staple cavities 25310 are dimensioned and structured to hold drivers and staples therein, as further described herein. A longitudinal slot 25306 divides the cartridge body 25302 into a first side 25302*a* and a second side 25302*b*. The staple cavities 25010 are arranged in two patterns: a first pattern 25314 on the first side 25002*a* of the longitudinal slot 25006, and a second pattern 25316 on the second side 25302*b* of the longitudinal slot 25306. Each pattern 25315 includes an inner row 25012*a*, an intermediate row 25012*b*, and an outer row 25012*c*. The first pattern 25014 is the same as the second pattern (e.g. a symmetrical, mirror image about the longitudinal axis L). FIG. 213 only depicts a portion of each pattern 25314, 25316, and the same pattern continues until the distal end of the staple cavities in certain instances.

In the first and second patterns 25314, 25316, the proximal-most staple cavity 24310*a* is longitudinally offset from the second proximal-most staple cavity 25310*b* by a first distance, or longitudinal offset, O1. Additionally, in the first and second patterns 25314, 25316, the second proximal-most staple cavity 24310*b* is longitudinally offset from the third proximal-most staple cavity 25310*c* by a second distance, or longitudinal offset, O2. The first longitudinal offset O1 is less than 50% of the staple crown lengths L1, L2, and L3, of staples in the inner row 25012*a*, intermediate row 25012*b*, and the outer row 25012*c*, respectively. The second longitudinal offset O2 is selected based on the longitudinal offset O1 to stagger the staples fired from the intermediate row 25012*c* relative to the staples fired from the inner rows 25012*a* and the outer rows 25012*c*. Stated differently, the second longitudinal offset O2 is selected to provide at least a small degree of longitudinal overlap row-to-row. The second longitudinal offset O2 is greater than the first longitudinal offset O1.

Referring still to the patterns 25314, 25316, the rows 25312*a*, 25312*b*, 25312*c* on each side 25002*a*, 25002*b* are different from the other rows on that side. More specifically, the number of cavities and spacing between the cavities in the same; however, the starting location of the rows 25312*a*, 25312*b*, 25312*c* differs.

Moreover, each row 25312*a*, 25312*b*, 25312*c* extends along an axis that is parallel to the longitudinal axis L. The lateral spacing of the rows 25312*a*, 25312*b*, 25312*c*, i.e. the spacing of the axes along which the rows extend, can be different. For example, on both sides 25302*a*, 25302*b*, the lateral spacing between the inner row 25312*a* and the intermediate row 25312*b* is less than the lateral spacing between the intermediate row 25312*b* and the outer row 25312*c*.

In certain instances, rows on the same side 25002*a*, 25002*b* can be configured to receive different staples and/or can be aligned with forming pockets configured to form the staples to different sizes and/or geometries. For example, on the same side 25002*a*, 25002*b* but in different rows, certain staples can be larger than the staples in other rows and/or can be configured to be formed to a taller formed height than the staples in other rows. Additionally or alternatively, staples from the same side 25002*a*, 25002*b* can be formed into a 2D, planar configuration while staples on that same side 25002*a*, 25002*b* are configured to be formed into a 3D, non-planar staple.

As further described herein, triple drivers include three staple-supporting columns connected by bridges. In various instances, the staple patterns 25314 and 25316 can be fired exclusively with triple drivers. Stated differently, a single type of driver an fire all of the staples from the patterns 25314, 25316.

Other staple patterns having non-identical rows are also contemplated. For example, in certain instances, the inner row and the outer row can be symmetrical about the intermediate row until the proximal-most cavity and/or cavities which are positioned closer together to accommodate the tissue stops. In such instances, the inner row and the outer row would have some longitudinally aligned staples row-to-row and other non-longitudinally aligned staples row-to-row. In other instances, one of the rows could have fewer staples than the other rows. For example, the outer row could have few staples, which are spaced longitudinally farther apart.

Referring now to FIG. 238, two staple cartridges 25400 and 25500 are shown side-by-side for comparative purposes. The staple cartridges 25400, 25500 includes cartridge bodies 25402, 25502, respectively, and three rows of staple cavities 25410, 25510, respectively, on each side of a longitudinal A. The staple cartridges 25400, 25500 are similar in many aspects to the various staple cartridges described herein.

Each staple cartridge 25400, 25500 also includes a datum 25408, 25508, respectively, corresponding to the distal end of a tissue stop. When the clinician initially locates the target tissue between the anvil and the staple cartridge, it is important that the target tissue be located so that the knife does not cut into the target tissue unless it is first stapled. Tissue stops can be provided on the proximal end of the anvil body to prevent the target tissue from moving proximally past the proximal most staple pockets in the staple cartridge.

In certain instance, a cartridge body can include at least one totaled or combined staple length on each side of the longitudinal axis A proximal to the tissue stop. A combined staple length is sum of the length of one or more staples or portions thereof positioned proximal to the tissue stop. The sum of those individual lengths is equivalent to the combined staple length. For example, referring to the staple cartridge 25400, one full staple and two half staples are proximal to the tissue stop for a combined staple length of two staples. However, because at least one combined staple length is desired proximal to the tissue stop datum 25408, there is little room to shift the tissue stop datum 25408 proximally.

Conversely, referring to the staple cartridge 25500, the tissue stop is in a relatively more proximal position relative to the proximal end of the staple cartridge 25500 and the proximal-most fastener cavities. Moreover, the combined staple length on each side of the cartridge body still meets the goal of at least one combined staple length proximal to the tissue stop datum 25508. Having two staple cavities longitudinally aligned, or closely aligned, at the proximal end of a pattern of staple cavities can allow the tissue stop to move proximally while still maintaining a suitable combined staple length proximal to the tissue stop.

Firing elements and various end effector components are subjected to high loads during the firing stroke. The loads imparted may cause deformation and/or wear of the firing elements and/or end effector components. For example, during a firing stroke, a firing element which cammingly engages an anvil and an elongate channel of an end effector may at least partially ride within an anvil slot in the anvil and along the bottom of the elongate channel. During firing, the anvil is in its closed position, however, as the firing element moves through the end effector, the anvil may attempt to move away from the elongate channel due to the forces associated with firing. For example, the force to form the staples, the force to sever the tissue, and the reactionary forces from the clamped tissue as it is cut and stapled. These forces are imparted onto the firing element during firing and can cause deformation or wear on the firing element and/or other end effector components.

In various embodiments, end effector components may be constructed using three dimensional ("3D") printing to improve component capabilities. In certain instances, 3D printing can allow components to exhibit metamaterial properties to aid in lowering the force to fire. A metamaterial is a synthetic composite material with a structure such that it exhibits properties not usually found in natural materials. 3D printing is one technique used to create a metamaterial to form structures with two or more materials. As such, 3D printing allows for the creation of complex geometries and/or material combinations that may otherwise be too costly and time consuming to manufacture or may even be impossible to manufacture absent 3D printing technology.

In various embodiments, a firing element may be 3D printed such that its main body acts as a spring to allow the upper and/or lower cam portions to flex and move to contact the anvil and elongate channel at an angle of reduced resistance.

FIGS. 239 and 240 depict a firing member 41000 for use with a surgical instrument, such as the surgical instruments disclosed herein. The firing member 41000 is deformable from a first or unloaded configuration (FIG. 239) in the absence of a firing load to a second or expanded configuration (FIG. 240) under a firing load. Additional configurations, such as intermediate configurations between the unloaded configuration and the expanded configuration, for example, are also contemplated in response to different firing loads. The firing member 41000 comprises a proximal firing bar portion 41100 and a distal head portion 41200 extending from the firing bar portion 41100. Specifically, the firing bar portion 41100 includes a distal protrusion 41110 that extends into a cutout portion 41250 defined in the proximal end of the distal head portion 41200. The distal protrusion 41110 includes arcuate portions and a blunt distal end for driving engagement with the distal head portion 41200. Such an arrangement permits assembly of the firing bar portion 41100 to the distal head portion 41200.

The distal head portion 41200 further includes an upper portion 41210 and a lower portion 41220 that are movable relative to one another. The cutout portion 41250 is defined in both the upper and lower portions 41210, 41220. As such, the distal end of the firing bar portion 41100 is in engagement with both the upper portion 41210 and the lower portion 41220 of the distal head portion 41200. Further, the distal head portion 41200 includes a protruding nose 41230 that extends distally. The protruding nose 41230 is configured to engage and drive a sled of a surgical staple cartridge distally during a firing stroke, for example. The protruding nose 41230 can be configured to defeat a firing lockout of a surgical instrument, for example. Further, the distal head portion 41200 includes a knife portion or cutting member for severing the tissue of a patient during a firing stroke of the firing member 41000 in certain aspects of the present disclosure.

Further to the above, the distal head portion 41200 comprises a flexible portion 41240 that connects the upper portion 41210 and the lower portion 41220 of the distal head portion 41200. Specifically, the flexible portion 41240 comprises a top end 41260 defined in the upper portion 41210, and a bottom end 41270 defined in the lower portion 41220. In at least one embodiment, the flexible portion 41240 is embedded into the distal head portion 41200. However, other attachment arrangements are envisioned for the upper portion 41220, the lower portion 41220, and the flexible portion 41240. For example, the entire distal head portion 41200 may be 3D printed having different materials for the different portions of the distal head 41200.

In at least one embodiment, the distal head 41200 is comprised of a first material and the flexible portion 41240 is comprised of a second material that is different from the first material. For example, the flexible portion 41240 may be comprised of aluminum and the remainder of the distal head portion 41200 may be comprised of stainless steel.

However, other embodiments are envisioned with different materials for the distal head portion 41200 and the flexible portion 41240 such as plastic, ABS, rubber, and/or various polymers. In the illustrated embodiment, the flexible portion 41240 is shaped like an "I" having an upright portion and orthogonal flanges at both ends of the upright portion, however other embodiments are envisioned with different cross-sectional shapes for the flexible portion 41240.

Further to the above, the distal head portion 41200 comprises an upper cam member defined on the upper portion 41210, and a lower cam member defined on the lower portion 41220. The upper and lower cam members are configured to cammingly engage a first jaw and a second jaw of an end effector of a surgical instrument to approximate the first jaw and the second jaw relative to one another during a firing stroke. As such, the upper portion 41210 and the lower portion 41220 may separate to accommodate a transverse load imparted on the distal head portion 41200 during the firing stroke. Specifically, as depicted in FIG. 240, a gap 41280 may form between the upper portion 41210 and the lower portion 41220 of the distal head 41200 during the firing stroke. In the illustrated embodiment, the upper portion 41210 moves away from the lower portion 41240, which is stationary. The distal end of the firing bar 41100 includes an extension 41120, which extends beyond the height of the upper portion 41210 when the distal head portion 41200 and flexible portion 41240 are undeformed or non-expanded. Further, the extension 41120 of the firing bar 41100 is tall enough to accommodate the expansion of the distal head 41200. As such, when the distal head 41200 is expanded, the extension 41120 of the firing bar 41100 can maintain driving contact with the proximal end of the distal head 41200.

In any event, other embodiments are envisioned where both the upper portion 41210 and the lower portion 41220 move during a firing stroke in response to a firing load. Further, other embodiments are envisioned where only the lower portion 41220 moves during a firing stroke.

Further to the above, when the distal head 41200 extends vertically to an expanded configuration, the flexible portion 41240 stretches vertically while maintaining the connection between the upper and lower portions 41210, 41220 of the distal head 41200. When the flexible portion 41240 is stretched, an intermediate portion 41265 of the flexible portion 41240 may neck down or narrow to accommodate a transverse load as depicted in FIG. 240.

FIG. 241 depicts a surgical instrument 42000 comprising an elongate shaft 42100, an end effector 42200 extending from the elongate shaft 42100, and a firing member 42300 configured to move relative to the elongate shaft 42100 and the end effector 42200 to perform a firing stroke. The elongate shaft 42100 may be a closure tube for opening and closing a pair of jaws 42240, 42210 of the end effector 42200, for example. The firing member 42300 comprises a proximal firing bar portion 42310 and a distal head portion 42320 extending therefrom. Specifically, the proximal firing bar portion 42310 includes a distal protrusion 42312 that extends into a cutout 42336 defined in the proximal end of the distal head portion 42320. Such an arrangement facilitates the assembly of the proximal firing bar portion 42310 to the distal head portion 42320.

Further to the above, the distal head portion 42320 is a two-part assembly formed from an upper portion 42330 and a lower portion 42340 that are movable relative to one another. The upper portion 42330 comprises a distally-protruding lower foot 42334 and the lower portion 42340 comprises a proximally-protruding upper foot 42342 positioned to interact and selectively interlock with the distally-protruding lower foot 42334. An opening 42400 is defined between the distally-protruding lower foot 42334 and the proximally-protruding upper foot 42342 when the upper portion 42330 and the lower portion 42340 are in a collapsed configuration, as depicted in FIG. 241. The opening 42400 permits the upper portion 42330 to move relative to the lower portion 42340, to an extent, during a firing stroke of the distal head portion 42320, as discussed in greater detail below.

Further to the above, the distally-protruding lower foot 42334 extends into a pocket, or cavity 42346, in the lower portion 42340. The cavity 42346 defines a flange 42348 on the proximal end of the lower portion 42340. The flange 42348 extends toward the upper portion 42330 and prevents the distally-protruding lower foot 42334 of the upper portion 42330 from becoming detached from the lower portion 42340. Specifically, the opening 42400 height is smaller than the height of the flange 42348 and, thus, the upper portion 42330 and the lower portion 42340 are prevented from detaching in the longitudinal direction.

Further to the above, the upper portion 42330 and the lower portion 42340 of the distal head portion 42320 can be connected via a flexible attachment member, such as the flexible portion 41240 of FIG. 239, for example, in certain instances. Further, in at least one aspect, the upper portion 42330 and the lower portion 42340 of the distal head portion 42320 can comprise two completely separate components that are not attached, but are held together due to the internal geometry of the elongate shaft 42100 and end effector 42200.

Further to the above, The upper portion 42330 comprises a first cam member configured to cammingly engage the first jaw 42240 of the end effector 42200 during a firing stroke, and the lower portion 42340 comprises a second cam member configured to cammingly engage the second jaw 42210 of the end effector 42200 during the firing stroke. As such, the first cam member and the second cam member are configured to approximate the first jaw 42240 and the second jaw 42210 of the end effector 42200 during the firing stroke. In the illustrated embodiment, the first jaw 42240 comprises a movable anvil, and the second jaw 42210 comprises an elongate channel configured to receive a staple cartridge 42220. The anvil 42240 is movable relative to the elongate channel 42210 between an open position and a closed position. Further, the firing member 42300 is configured to move a sled 42230 of the staple cartridge 42220 through the end effector 42200 to eject staples from the staple cartridge 42220.

In use, as the firing member 42300 distally advances from the unfired position depicted in FIG. 241, the distal head portion 42320 advances beyond the distal end of the elongate shaft 42100, which can allow for expansion of the distal head portion 42320 under certain firing loads. The distal head portion 42320 advances into the end effector 42200 such that the upper cam member engages the anvil 42240 and the lower cam member engages the elongate channel 42210. As such, the first cam member on the upper portion 42330 is in camming engagement with the movable anvil 42240 during the firing stroke, and the second cam member on the lower portion 42340 is in camming engagement with the elongate channel 42210 during the firing stroke.

The upper portion 42330 and the lower portion 42340 are capable of separating or moving farther apart vertically during the firing stroke. For example, when the anvil 42240 is in its closed position and the firing stroke has commenced, forces due to staple firing, cutting, and/or patient tissue may deflect or move the anvil 42240 away from the elongate channel 42210. The expansion of the distal head portion 42320 can accommodate such movement or deflection. In certain instances, the expansion of the firing member 42320 can accommodate entry of the upper cam member on the upper portion 42330 into an anvil channel of the anvil 42200 if the anvil channel is misaligned. Further, the expansion of the distal head portion 42320 is limited by the distally-protruding lower foot 42334 and the proximally-protruding upper foot 42342, which are drawn closer together to close the space 42400 therebetween and eventually engage one another to limit the extent of expansion of the distal head portion 42320.

Further to the above, after the distal head portion 42320 has been distally advanced and expanded, the distal head portion 42320 can be retracted back to the home or unfired position illustrated in FIG. 241. During retraction, a first cam surface 42338 on the upper portion 42330 engages a second cam surface 42120 on the distal end of the elongate shaft 42100. The first and second cam surfaces 42338, 42120 interact to compress the distal head 42320 into its non-expanded state (FIG. 241).

Further to the above, the lower portion 42340 of the distal head portion 42320 comprises a cutout portion 42344 defined in the distal end of the lower portion 42340. The cutout portion 42344 is configured to receive a proximal nose portion 42232 of the sled 42230 therein. As such, a distal advancement of the distal head portion 42320 will advance the sled 42230 through the staple cartridge 42220 to eject the staples. Further, the distal head portion 42320 comprises a knife portion 42332 configured to sever the tissue of a patient during the firing stroke.

FIGS. 242 and 243 depict a stapling attachment 43000 for use with a surgical instrument, such as those described herein. The stapling attachment 43000 comprises an elongate shaft 43100 attachable to a handle and/or housing, and an end effector 43200 extending from the elongate shaft 43100. The end effector 43200 comprises a first jaw, or anvil 43210, and a second jaw, or elongate channel 43220. The anvil 43210 is movable relative to the elongate channel 43220 between an open position and a closed position in response to a closure motion from a closure system. The anvil 43210 comprises landing portions 43212 on its proximal end. Further, a medium and/or low durometer material 43214 extends from the landing portion 43212. The low durometer material 43214 can comprise rubber, plastic, a polymer and/or any other suitable material, for example. The material 43214 has a lower durometer than the landing portion 43212. In one aspect, the landing portion 43212 can be metal, and the material 43214 can be rubber, for example.

Further to the above, the elongate channel 43220 is configured to receive a staple cartridge 43230 therein. The staple cartridge 43230 comprises a proximal cartridge tail 43232 with substantially flat portions on both sides of a cartridge slot 43234. Typically, the cartridge tail 43232 is configured to interact with the landing portions 43212 of the anvil 43210 when the anvil 43210 is in its closed position. In the illustrated embodiment, the low durometer material 43214 acts as a semi-compressible material between the landing portions 43212 of the anvil 43210 and the cartridge tail 43232. As such, the anvil 43210 is capable of floating relative to the staple cartridge 43230 in response to the forces exerted by the closure system and/or the firing system. Specifically, due to the compressible nature of the low durometer material 43214, the anvil 43210 can flex and/or deflect relative to the staple cartridge 43230 more than would be possible without the low durometer material 43214 present on the landing portions 43214.

Other embodiments are envisioned where the low durometer material 43214 is defined as part of the anvil 43210 and flush with the landing portions 43212 of the anvil 43210. In such an arrangement, the low durometer material 43214 may allow for over-closing of the anvil 43210 relative to the staple cartridge 43230. Specifically, a firing member engages the anvil slot 43216 and the elongate channel 43220 to close the anvil 43200 relative to the staple cartridge 43230 during an initial closing operation. During the initial closing operation of the anvil 43200, the compressible low durometer material 43214 flush with the landing portions 43212 can abut and cause interference with the rigid cartridge tail 43232 of the staple cartridge 43230. Because the low durometer material 43214 is compressible, the proximal portion of the anvil 43200 is capable of flexing to overcome the interference between the landing portions 43212 and the cartridge tail 43232. As the firing member advances through the staple cartridge 43230, the low durometer material 43214 may further compress against the rigid cartridge tail 43232. The two surfaces 43214, 43232 can move past the point of interference to allow the firing member to complete the firing stroke without binding.

Further to the above, the low durometer material 43214 may be more compressible than the anvil 43210 and/or the cartridge 43230. Further, the low durometer material 43214 may reduce the forces on a firing member which travels through the anvil 43210 and the staple cartridge slot 43234. Specifically, a firing member with an upper and lower cam member, such as those described herein, can move within the end effector 43200. For example, the upper cam of the firing member moves through anvil slot 43216. Due to the compressibility of the low durometer material 43214, the anvil slot 43216 can flex relative to the staple cartridge 43230. As such, less force will be exerted on the upper cam member of the firing member during closing and/or firing as compared to if the low durometer material 43214 were not present.

Further to the above, embodiments are envisioned which incorporate the low durometer material 43214 and the expanding firing members 41000, 42320 of FIGS. 239-241 into an end effector. The compressibility of the low durometer material 43214 of an anvil, for example, in combination with the expanding capabilities of the firing members 41000 or 42320, for example, can provide an end effector with greater variability during the firing stroke. Specifically, the low durometer material 43214 can allow the anvil to float more relative to the cartridge, and the expanding firing members 41000, 42320 can allow for greater leeway in alignment between the firing member flanges and the anvil slot.

In various embodiments, firing members, (e.g., I-beams or E-beams) can be constructed to have complex 3D printed geometries incorporated into the main body, which can act as a spring and allow the upper cam portion to flex and move with the anvil ledge to an angle of reduced or least resistance. Such geometric complex printed structures allow for metamaterial behaviors. For example, a metal I-beam could have portions that act as a solid metal structure and alternative portions having geometries that are designed to allow for greater bending and/or stretching to permit the I-beam to focus its deflection in a location and/or orientation to align the I-beam to the use and/or load. Exemplary embodiments of such I-beams are discussed in greater detail below.

FIG. 244 depicts a firing member 44000 comprising a body portion 44100, a pair of upper cam members 44140 extending laterally from both sides of the body portion 44100, and a pair of lower cam members 44150 extending laterally from both sides of the body portion 44100. The upper cam members 44140 are configured to cammingly engage an upper jaw, or anvil, of an end effector during a firing stroke, and the lower cam members 44150 are configured to cammingly engage a lower jaw, or elongate channel of the end effector during the firing stroke. The elongate channel is configured to receive a staple cartridge including staples that can be ejected when the firing member 44000 is advanced within the staple cartridge. Exemplary jaws, anvil, and staple cartridges for use with the firing member 44000 are further described herein.

Further to the above, the body portion 44100 comprises a longitudinal opening 44110 extending through the body portion 44100 and defining a longitudinal axis LA. The body portion 44100 further comprises a distal nose portion 44130 extending distally from the body portion 44100. The longitudinal opening 44110 is configured to receive a rotary firing driver, such as firing screw 261 (see, e.g. FIG. 16) described above. The body portion 44100 further comprises a cutout region 44120 configured to receive a firing drive nut 44200. The firing drive nut 44200 is configured to threadably engage the rotary firing driver to convert rotary motion of the rotary firing driver into translation of the firing member 44000. The firing drive nut 44200 comprise a pair of laterally-extending members 44210 that extend from both sides of the firing drive nut 44200. The pair of laterally-extending members 44210 are aligned with the pair of lower cam members 44150. As such, the cam members 44210, 44150 cooperate to cammingly engage the lower jaw of the end effector during the firing stroke.

Further to the above, the firing member 44000 further comprises flexible portions 44160 positioned intermediate the body portion 44100 and the pair of upper cam members 44140. In other words, the flexible portions 44160 attach at least a portion of the upper cam members 44140 to the body portion 44100. As can be seen in FIG. 246, the flexible portions 44160 comprise a three-dimensional lattice comprising an array of cavities, gaps, and/or cutouts. The array of cavities form a plurality of arcuate bars 44162 arrange in an array. The flexible portion 44160 comprises an overall cross-sectional density that is reduced compared to the adjacent upper cam member 44140 and the body portion 44100. As such, the flexible portions 44160 can flex, bend, and/or deflect a greater amount than the adjacent upper cam member 44140 and the body portion 44100. As can be seen in FIG. 246, the arcuate bars 44162 and corresponding cutout regions are symmetrical about the body portion 44100. However, other embodiments are envisioned where the arcuate bars 44162 are of varying shapes and sizes on the same side and/or or on opposite sides of the body portion 44100. In certain instances, the array of cavities can form linear bars, for example. In at least one embodiment, the flexible portion 44160 comprises a three-dimensional honeycomb lattice, for example. The three-dimensional lattice of the flexible portions 44160 can have a reduced density in comparison to adjacent portions. Moreover, the flexible portions 44160 can have a significantly reduced infill percentage in comparison to adjacent portions.

Further to the above, as can be seen in FIG. 246, the flexible portions 44160 extend longitudinally along only a portion of the upper cam members 44140 from the distal end of the upper cam members 44140 and terminate in an intermediate portion of the upper cam members 44140. As such, the distal end of the upper cam members 44140 is more flexible than the proximal end of the upper cam members 44140. Other embodiments are envisioned where the flexible members 44160 extend along the entire length of the upper cam members 44140 and/or only at the proximal end of the upper cam members 44140. Further still, other embodiments are envisioned where the flexible portions 44160 are in the middle of the upper cam members 44140 with more rigid portions at the proximal and distal ends.

Further to the above, in at least one embodiment, the firing member 44000 may be constructed using a 3D printing process. Infill and solid wall parts are traditionally used to fabricate objects that are lightweight and strong. 3D printed parts are manufactured with a specific infill percentage. The printing process uses a crosshatch or other pattern for interior surfaces to form cells within the infill portion of the 3D printed part. The density of this pattern is referred to as the infill percentage. For example, it is common to have 1-2 mm thick walls, and to have 25-35% of the part solid inside of the walls. When building parts with powder based processes, such as 3D printing, it is important to note that powder must have escape holes to ensure powder reclamation after the part is fabricated. Infill for parts can be 2D like a honeycomb, or 3D like a gyroid. Different patterns have different strength profiles. For example, patterns with larger cells can be more flexible than patterns with smaller cells. Due to the freedom of geometry, the geometry can be variably thickened and thinned to ensure that flexion can occur at a desired location and a desired amount.

Different geometries and infill percentages could be used at different locations in the firing member 44000 to achieve different degrees of deformation and/or predispositions to different directions of deformation. In certain instances, the leading end of the upper cam portion 44140 can have a different infill percentage or infill matrix/geometry than adjacent portions of the firing member 44000 to maintaining the rigidity of the proximal end of the upper cam member 44140, as depicted in FIG. 246. An increased deflection of the leading edge of the upper cam member 44140 can facilitate alignment of the upper cam member 44140 with the anvil ledge at the outset of the firing motion, which can avoid jamming or binding of the firing member in certain instances, such as when thick and/or tough tissue is clamped between the jaws. Other embodiments are envisioned where the middle of the upper cam member 44140 is flexible with both of the ends more rigid. As such, by varying the firing member geometry with 3D printing, the location and amount of flexion can be controlled based on the amount of force anticipated.

FIGS. 247 and 248 depict a firing member 45000 comprising a body portion 45100, a pair of upper cam members 45140 extending laterally from both sides of the body portion 45100, and a pair of lower cam members 45150 extending laterally from both sides of the body portion 45100. The upper cam members 45140 are configured to cammingly engage an upper jaw, or anvil, of an end effector during a firing stroke, and the lower cam members 45150 are configured to cammingly engage a lower jaw, or elongate channel of the end effector during the firing stroke. The elongate channel is configured to receive a staple cartridge including staples that can be ejected when the firing member 44000 is advanced within the staple cartridge. Exemplary jaws, anvil, and staple cartridges for use with the firing member 45000 are further described herein.

Further to the above, the body portion 45100 comprises a longitudinal opening 45110 extending through the body portion 45100, similar to the longitudinal opening 44110 (see FIG. 244). The longitudinal opening 45110 is configured to receive a rotary firing driver, such as firing screw 261

(see, e.g. FIG. 16) described above. The body portion 45100 further comprises a distal nose portion 45130 extending distally from the body portion 45100. The body portion 45100 further comprises a cutout region 45120 configured to receive a firing drive nut 45200. The firing drive nut 45200 is configured to threadably engage the rotary firing driver to convert rotary motion of the rotary firing driver into translation of the firing member 45000. The firing drive nut 45200 comprise a pair of laterally-extending cam members 45210 that extend from both sides of the firing drive nut 45200. The pair of laterally-extending cam members 45210 are aligned with the pair of lower cam members 45150. As such, the cam members 45210, 45150 cooperate to cammingly engage the lower jaw of the end effector during the firing stroke.

Further to the above, the firing member 45000 further comprises a flexible portion 45160 positioned intermediate the upper cam members 45140 and the lower cam members 45150, 45210. The flexible portion 45160 comprises a first plurality of arcuate slots 45170 extending laterally through the body portion 45100, and a second plurality of arcuate slots 45180 extending laterally through the body portion 45100. In the illustrated embodiment, the first plurality of arcuate slots 45170 are curved in a direction which resembles a backward C-shape, and the second plurality of arcuate slots are curved in the opposite direction which resembles a forward C-shape. However, other embodiments are envisioned with different curvatures or combination of curvatures for the arcuate slots 45170. Further, in the illustrated embodiment five first arcuate slots 45170 and five second arcuate slots 45180 are depicted, however, other embodiments are envisioned with more or less than five arcuate slots for each of the first plurality or arcuate slots 45170 and each of the second plurality of arcuate slots 45180.

In any event, the body portion 45100 further comprises a first cutout region 45175 on its distal end that is defined by the first plurality of arcuate slots 45170, and a second cutout region 45185 on its proximal end that is defined by the second plurality of arcuate slots 45180. The arcuate slots 45170, 45180 and the cutout regions 45175, 45185 permit the firing member 45000 to flex and/or deflect when a load is applied to the firing member 45000, as discussed in greater detail below.

Referring primarily to FIG. 248, an anvil channel or anvil ledge 45300 and an elongate channel 45400 for receiving a staple cartridge are depicted in dashed lines for the purpose of simplicity. In use, when the firing member 45000 is driven within an end effector, the upper cam members 45140 are configured to cammingly engage the anvil (i.e., ride along the anvil ledge 45300) during the firing stroke. Further, the lower cam members 45150, 45210 are configured to cammingly engage the bottom of the elongate channel 45400 during the firing stroke. During the firing stroke of the firing member 45000, the upper cam members 45140 may experience a lateral force F applied by the anvil ledge 45300 when the anvil ledge 45300 moves away from the elongate channel 45400. For example, the lateral force F may be due to clamping of patient tissue, firing of the staples, or cutting of the patient tissue. In at least one embodiment, the lateral force F may be applied to the upper cam members 45150 upon entry into the anvil channel, for example. In any event, the firing member 45000 is configured to flex and/or deflect due to the flexible portion 45160 during the firing stroke. Specifically, in FIG. 247 the firing member 45000 is in a relaxed state corresponding to an unloaded configuration, and in FIG. 248 the firing member 45000 is in an unrelaxed, or deflected state corresponding to a loaded configuration.

Further to the above, due to the lateral force F applied to the upper cam members 45140, the upper cam members 45140 rotate in a clockwise direction which causes the flexible portion 45160 and the body portion 45100 to flex and/or deflect to enable the firing member 45000 to change shape based on the load applied. Specifically, the first plurality of arcuate slots 45170 are configured to stretch and the second plurality of arcuate slots 45180 are configured to compress when the lateral force F is applied. Moreover, the first cutout region 45175 elongates and the second cutout region 45185 compresses when the lateral force F is applied. As such, the firing member body 45100 can flex and/or deflect to accommodate the lateral force F.

Further to the above, during use, the upper cam members 45140 are configured to ride along the anvil ledge 45300 within a longitudinal anvil slot. Upon initial entry of the upper cam members 45140 into the anvil slot, the upper cam members 45140 may be misaligned due to the varying amounts of tissue (i.e., thick and thin tissue) grasped between the jaws. As such, the flexible portion 45160 permits the upper cam members 45140 to flex and/or deflect to properly align the upper cam members 45140 with the anvil slot, for example. Further, the varying amounts of tissue grasped between the jaws may cause the anvil ledges 45300 to move away from the elongate channel 45400 during a firing stroke of the firing member 45000. As such, the upper cam members 45140 may become misaligned with the anvil slot during firing. However, the flexible portion 45160 permits the upper cam members 45140 to flex and/or deflect to compensate for the varying amounts of tissue to prevent the upper cam members 45140 from jamming within the anvil slot when the upper cam members 45140 are not properly aligned within the anvil slot.

Further to the above, in at least one embodiment, the firing member 45000 can comprise a longitudinal slot extending through the flexible portion 45160 to permit one lateral side of the firing member 45000 to flex at least partially independent of another lateral side of the firing member 45000. The longitudinal slot may be similar to longitudinal slot 46170 (see FIG. 249) discussed in greater detail below, for example.

FIGS. 249-251 depict a firing member 46000 comprising a body portion 46100, a pair of upper cam members 46140 extending laterally from both sides of the body portion 46100, and a pair of lower cam members 46150 extending laterally from both sides of the body portion 46100. The upper cam members 46140 are configured to cammingly engage an upper jaw, or anvil, of an end effector during a firing stroke, and the lower cam members 46150 are configured to cammingly engage a lower jaw, or elongate channel of the end effector during the firing stroke. The elongate channel is configured to receive a staple cartridge including staples that can be ejected when the firing member 46000 is advanced within the staple cartridge. Exemplary jaws, anvil, and staple cartridges for use with the firing member 46000 are further described herein.

Further to the above, the body portion 46100 comprises a longitudinal opening 46110 extending through the body portion 46100 and defining a longitudinal axis LA. The longitudinal opening 46110 is configured to receive a rotary firing driver, such as firing screw 261 (see, e.g. FIG. 16) described above. The body portion 46100 further comprises a distal nose portion 46130 extending distally from the body portion 46100. The body portion 46100 further comprises a cutout region 46120 configured to receive a firing drive nut

46200. The firing drive nut 46200 is configured to threadably engage the rotary firing driver to convert rotary motion of the rotary firing driver into translation of the firing member 46000. The firing drive nut 46200 comprise a pair of laterally-extending cam members 46210 that extend from both sides of the firing drive nut 46200. The pair of laterally-extending cam members 46210 are aligned with the pair of lower cam members 46150. As such, the cam members 46210, 46150 cooperate to cammingly engage the lower jaw of the end effector during the firing stroke.

Further to the above, the firing member 46000 further comprises a flexible portion, or lattice portion, 46160 positioned intermediate the upper cam members 46150 and the lower cam members 46150. In the illustrated embodiment, the lattice portion 46160 is bifurcated by a longitudinal slot 46170 which extends parallel to the longitudinal axis LA. The longitudinal slot 46170 extends through the body portion 46100 from the proximal end to the distal end. As such, the lattice portion 46160 is divided into a first side 46180 and a second side 46190. The first side 46180 of the lattice portion 46160 comprises a plurality of slots 46182 oriented transverse to the longitudinal axis LA in a first direction. The second side 46190 of the lattice portion 46160 comprises a plurality of slots 46192 oriented transverse to the longitudinal axis LA in a second direction that is opposite the first direction. The plurality of slots 46182, 46192 reduce the overall cross-sectional density of the firing member 46000 within the lattice portion 46160. In other words, the lattice portion 46160 is less dense (e.g. lower infill percentage) than the adjacent portions of the body portion 46100 of the firing member 46000. Further, the longitudinal slot 46170, which bifurcates the lattice portion 46160, permits the first side 46180 of the lattice 46160 to slide past the second side 46190 of the lattice 46160, and vice versa, and/or permits the first side 46180 of the lattice 46160 to stretch vertically while the second side 46190 is compressed vertically, or vice versa. Without the longitudinal slot 46170, sliding and deflection of the first and second sides 46180, 46190 relative to one another would be limited.

Further to the above, the first side 46180 comprises a notch 46185 on the proximal end of the body portion 46100, and the second side 46190 comprises a notch 46195 on the proximal end of the body portion 46100. The notches 46185, 46195 provide greater flexion and/or deflection of the proximal end of the body portion 46100 as compared to the distal end of the body portion 46100. Moreover, in the illustrated embodiment, the notches 46185, 46195 are positioned on the proximal end of the body portion 46100. However, other embodiments are envisioned where the notches 46185, 46195 are positioned on the distal end of the body portion 46100 for the opposite effect. Further still, other embodiments are envisioned with notches on the proximal and distal ends of the body portion 46100, see FIG. 253 and accompanying description below.

In use, when the firing member 46000 is advanced into an end effector, the upper cam members 46140 engage an upper jaw, or anvil of the end effector, and the lower cam members 46150, 46210 engage a lower jaw, or elongate channel of the end effector. As such, the lattice portion 46160 is configured to permit the upper cam members 46140 and the lower cam members 46150, 46210 to flex and/or deflect relative to the body portion 46100 to accommodate lateral forces during the firing stroke.

The body portion 46100 and the lattice portion 46160 can be constructed of varying geometries and materials to accommodate a desired stress profile within the firing member 46000 during the firing stroke. For example, the firing member 46000 can be constructed using 3D printing, or an equivalent process. In at least one embodiment, the body portion 46100 is 3D printed as a unitary piece with the body portion comprising a first material and the lattice portion 46160 comprising a second material that is different from the first material. Further, the first material may comprise a first density and the second material can comprise a second density that is different from the first density.

Further to the above, 3D printing generally produces structures that have some amount of open space (i.e., they are not completely solid on a micro level). As discussed above, the 3D printing process uses a crosshatch or other pattern for interior surfaces housed within more solid wall structures. The density of this pattern within the solid walls is referred to as the infill percentage. The infill percentage can be varied throughout the 3D printing process to produce a component having different infill percentages for different portions of the component. If different infill portions comprise different infill percentages, they inherently comprise different densities on a micro level. In other words, the different infill portions can be varied to produce different micro densities within a component.

Further to the above, other embodiments are envisioned where the infill percentage is uniform throughout the entire part. In such instances, flexibility can be built into the part from macro-geometry aspects, such as slots, cutouts, holes etc. upon which the 3D build is built around. For example, the firing member 46000 may comprise an entirely uniform infill percentage. In such an instance, the slots 46182, 46192 define bar structures in between the slots 46182, 46192, and the bar structures would comprise the same infill percentage as the rest of the firing member 46000, for example.

FIG. 252 depicts a graphical representation 47000 of the forces imparted on the firing member 46000 during a firing stroke. In the illustrated embodiment, the larger the force exerted on the firing member 46000 the darker the shading. The forces are shown in the legend in FIG. 252 as pounds per square inch (PSI). In the illustrated embodiment, a 150 pound load on the distal end of the firing member 46000 resulted in 1 degree of bending during the finite element analysis simulation.

FIGS. 253 and 254 depict a firing member 48000 similar in many aspects to the firing member 46000 and with the differences discussed herein. The firing member 48000 comprises a flexible portion, or lattice portion 48160. The lattice portion 48160 is bifurcated by a longitudinal slot that divides the lattice portion 48160 into a first side 48180 and second side 48190. The first side 48180 comprises a proximal notch 48182 defined in the proximal end of the firing member 48000, and a distal notch 48184 defined in the distal end of the firing member 48000. The notches 48182 and 48184 are V-shaped or triangular cutouts. The proximal notch 48182 is larger along the upper edge, while the distal notch 48184 is larger along the lower edge. The second side 48190 comprises proximal and distal notches that are opposite the proximal notch 48182 and the distal notch 48184. As such, the first side 48180 of the lattice portion 48160 is a flipped mirror image of the second side 48190 of the lattice portion 48160. Similar to the firing member 46000, the firing member 48000 comprises a plurality of slots oriented in the lattice portion 48160. Specifically, the first side 48180 comprises a plurality of slots 48186 oriented in a first direction transverse to longitudinal axis LA of the firing member 48000. Further, the second side 48190 comprises a plurality of slots 48196 oriented transverse to the longitudinal axis LA in a second direction opposite the first direction.

FIG. 255 depicts a model of a flexible portion 49000 configured for use with a firing member of a surgical instrument, such as those firing members described herein. The flexible portion 49000 is configured to flex front-to-back and side-to-side to accommodate a loading force on the firing member during a firing stroke. The flexible portions 44160, 45160, 46160, 48160 described herein can be configured to flex as shown in FIG. 255, resulting in front-to-back and side-to-side flexing of the I-beam as well. Embodiments are envisioned where the flexible portion 49000 is part of, or takes the place of, the flexible portions 44160, 45160, 46160, 48160 in the firing members described herein. The flexible portion 49000 is configured to transition from a relaxed state 49100 (shown in phantom lines) to a flexed, or deflected state 49100' (shown in solid lines) when a force is imparted onto the flexible portion 49000.

In the illustrated embodiment, the force applied is imparted onto an upper member 49100 of the flexible member 49000 while a base 49120 of the flexible member 49000 is held stationary. The upper member 49100 and the base 49120 are connected by a first vertical member 49130 and a second vertical member 49140 which crisscross to form an X-configuration. In use, when a force is applied to the upper member 49100, the upper member 49100 transitions to a deflected state 49110', the first vertical member 49130 transitions to a deflected state 49130', and the second vertical member 49140 transitions to a deflected state 49140'. The first and second vertical members 49130, 49140 can be deflected to accommodate various loads applied to the upper member 49100.

It should be appreciate that any of the discrete features of the flexible portions 44160, 45160, 46160, 48160, 49000 can be used in combination with each other. For example, the flexible portions 44160 positioned between the upper cam member 44140 and the body portion 44100 may be incorporated into the firing members 45000, 46000, and/or 48000. Moreover, the flexible portions 44160 may be incorporated into any of the lower cam members of firing members 44000, 45000, 46000, 48000, 49000 to provide for greater flexion of the lower cam members in certain instances.

3D printing may be utilized in a similar approach for various instrument components described herein, among others. For example, to accommodate a rotary drive screw in an elongate channel of a surgical instrument, the elongate channel may comprise a distal support bearing or support washer to support the distal end of the rotary drive screw. In at least one embodiment, the distal support bearing could be 3D printed to include a compressible portion that, when compressed in a first direction expands in a second direction that is transverse to the first direction to increase the bearing surface between the distal support bearing and the rotary drive screw. As a result, the coupling between the rotary drive screw and the distal support bearing is improved in certain instances due to a decrease in the bearing loads achieved by increasing the bearing surface area.

Channel retainers and various end effector components are subject to high deflection and longitudinal loads during operation of a surgical instrument. Standard materials for these components consist of aluminum and stainless steel which have limited stretch and deflection capabilities. For example, 250 to 300 pounds of force can be applied longitudinally to a channel retainer during a surgical actuation and an acceptable longitudinal flex can be less than 0.08 inches.

A composite component can include different materials for different portions to obtain complex part geometries, such as interlocking features, alignment keyways, or open sliding passages, for example, with a first material (e.g. plastic) while also maintaining appropriate strength, stiffness, and/or rigidity with a second material (e.g. metal) to support the longitudinal stress and strain loads during a surgical actuation. Metal portion(s) in a composite component can be flexible in one plane but rigid or stiff in another. For example, metal portions can permit lateral flexing but limit longitudinal stretching. Moreover, plastic material can act as a gap filler and interlocking substance between the metal substrates, while also allowing feature-rich, complex geometries. For example, a low durometer or flexible material such as plastic may be used as a body portion for an end effector component. The plastic body portion can comprise metal substrate portions defined therein to bear the loading forces during operation while the plastic body provides keying and alignment features. Such a laminate component can be constructed with 3D printed plastic and metal substrate inserts.

For example, a channel retainer for use with a surgical device can comprise a first metal substrate, a second metal substrate interlocking with the first metal substrate, and a plastic portion built around the first metal substrate and the second metal substrate. The channel retainer is positioned between a handle and an end effector of the surgical device. Further, the channel retainer can comprise alignment and connection features built into the plastic body to facilitate attachment to the surgical device.

FIGS. 256-258 depict a channel retainer 50000 for use with a surgical instrument, such as those described herein. In various embodiments, the proximal end of the channel retainer 50000 can be connected to a handle and/or housing of a surgical instrument and the distal end of the channel retainer 50000 can be connected to an articulation joint and/or end effector of a surgical instrument. The channel retainer 50000 acts as a longitudinal spine portion of the surgical instrument in such instances. Further, the channel retainer 50000 can support articulation actuators, firing actuators, and/or closure actuators of the surgical instrument. In at least one embodiment, the channel retainer 50000 bears the load of a closure tube which surrounds the channel retainer 50000. As the closure tube advances to effectuate an end effector, forces are exerted onto the channel retainer 50000. As such, the channel retainer 50000 can stretch and deflect due to the loading forces exerted by the closure tube.

Further to the above, the proximal end of the channel retainer 50000 comprises notches 50130 which facilitate attachment of the channel retainer 50000 to the handle and/or housing of a surgical instrument. The distal end of the channel retainer 50000 comprises notches 50120 which facilitate attachment of the channel retainer to an articulation joint and/or end effector of a surgical instrument. However, other embodiments are envisioned with different attachment features for connecting the channel retainer 50000 to the surgical instrument.

Further to the above, the channel retainer 50000 comprises a body portion 50100, first substrate portions 50300, and second substrate portions 50400. The channel retainer 50000 further comprises a longitudinal slot 50110 defined therein for receiving various actuators of a surgical instrument. For example, a firing member extending from a handle or housing of a surgical instrument can extend within the longitudinal slot 50110. In any event, the longitudinal slot 50110 splits the channel retainer 50000 in half with the first and second substrate portion 50300, 50400 positioned on each side of the slot 50110 (i.e., the channel retainer 50000 is symmetrical). In at least one embodiment, the body portion 50100 is 3D printed with the first and second substrate portions 50300, 50400 defined therein. In other words, the body portion 50100 is built around the first and second substrate portions 50300, 50400. In at least one embodiment, the body portion 50100 is comprised of plastic and the substrate portions 50300, 50400 are comprised of metal. The substrate portions 50300, 50400 can be comprised of stamped metal plates, for example. Other embodiments are envisioned where the substrate portions 50300, 50400 comprises materials that are more rigid and/or dense than the body portion 50100, for example.

As illustrated in FIG. 258, the first substrate portions 50300 are positioned within the body portion 50110 at the proximal end. Each first substrate portion 50300 comprises a first lateral flange 50310 at its distal end. The first lateral flanges 50310 extend toward the longitudinal slot 50110. The second substrate portions 50400 are positioned within the body portion 50100 and each comprises a first opening 50410 at their proximal end and a second opening 50420 at their distal end. The first and second substrates 50300, 50400 are positioned such that the first opening 50410 receives the first lateral flange 50310 to operably connect the first substrate portion 50200 and the second substrate portion 50400 within the body portion 50100. In other words, the first and second substrate portions 50300, 50400 are at least partially embedded and/or encapsulated within the body portion 50100.

These substrates can form a multi-interlocking load sharing assembly comprised of stamped components within the 3D-printed assembly. In certain instances, interlocking of stamped components within a 3D-printed assembly can be utilized to combine components where injection molding is not a viable alternative due to the shrinking of the composite material over elongated metal components during a molding process, which can result in a buildup of internal stresses and shear features within the assembly. For example, elongate assemblies, such as channel retainers, for example, may be better suited to 3D printing around interlocking metal components.

Further to the above, each of the first substrate portions 50300 comprise a second lateral flange 50320 positioned at their proximal end and extending away from the longitudinal slot 50110. The second lateral flanges 50320 are built and/or embedded into the body portion 50100 such that they extend behind the proximal notches 50310 defined in the body portion 50100. As such, the first substrate portions 50300 are at least partially restricted from moving longitudinally within the body portion 50100 due to their engagement with the proximal notches 50310. Further, the alignment notches 50310 may be used to attach and align the channel retainer 50000 within a handle or housing of the surgical instrument. As such, the first substrate portions 50300 within the proximal end provide additional support to the channel retainer 50000 to facilitate attachment to a surgical instrument. Other embodiments are envisioned with the first substrate portions 50300 at both the proximal and distal ends to facilitate attachment to a surgical device. In at least one embodiment, the body portion 50100 comprises a keying feature, an alignment feature, and/or an interlocking feature for use with a surgical instrument.

The first and second substrate portions 50300, 50400 can comprise more rigid metallic materials to bear the loading and stretch forces that the channel retainer 50000 experiences during operation of the surgical instrument.

Further to the above, the first substrate portion 50300 and/or the second substrate portion 50400 comprise flexible circuit boards and/or other integrated electronics supported or affixed thereto. During manufacture, the 3D printing material of the body portion 50100 can be overprinted around the substrate portions 50300, 50400 without directly affixing the build material to the electronics of the substrate portions 50300, 50400. By preventing direct application of the 3D build material onto the substrate portions 50300, 50400, the risk of damage to the substrate portions 50300, 50400 and their electronic components is reduced. For example, referring primarily to FIG. 258, there are various gaps 50500 between the substrate portions 50300, 50400 and the body portion 50100. As such, the channel retainer 50000 is constructed such that at least portions of the substrate portions 50300, 50400 are not 3D printed directly thereon. Electronic components can be positioned in locations that are not directly 3D printed on, which can inhibit heat transfer and/or inadvertent damage to the electronic components due to localized heat. However, other embodiments are envisioned where the substrate portions 50300, 50400 are completely encapsulated and surrounded by the 3D build material of the body portion 50100.

As discussed above, the channel retainer 50000 may be constructed via 3D printing. For example, before the 3D build begins, metal substrates such as substrate portions 50300, are introduced upon which the 3D plastic build will be attached. Partially through the 3D build, the build could be stopped with standing alignment features to permit the creation of a perimeter build flange. The perimeter build flange allows for the introduction of another mid-substance metallic support plate, or substrate portions 50400, for example. In at least one embodiment, the substrate portions 50300, 50400 can be aligned in such a manner as to have coupling plastic features (such as notches 50130, for example) that prevent movement of the substrates 50300, 50400 within the body portion 50100 while also preventing shear of the body portion 50100. In at least one embodiment, the channel retainer 50000 is a sandwiched laminate comprised of metal plates with 3D plastic printed coupling and assembly features. The metal plates are capable of bearing the load and stretch properties and the 3D printed elements are configured to provide all the keying, aligning, lateral support, and interlocking features with adjacent systems. 3D printing a channel retainer in this manner enables complex plastic interface features to be affixed to load bearing metallic sub-frames within and around the 3D built part.

Further to the above, a steel stamped part could have a lateral flange bend in both ends for affixing to an elongate shaft and/or an articulation joint of a surgical instrument. The flanges could be laid into the 3D printer with the flanges away from the printing head path. The 3D build is then continued to form the rest of the channel retainer. As such, the lateral flange bends extend from the 3D printed channel retainer for attachment to the surgical instrument. In other words, the lateral flange bends are not overprinted with 3D printing material, extend from the 3D printed material, and are attachable to the surgical instrument.

Further to the above, other embodiments are envisioned with a 3D printed laminate construction comprising a plastic body and metal substrates for various end effector components. For example, a staple cartridge, an elongate channel configured to receive a staple cartridge, and/or an anvil, could be constructed as a 3D printed laminate with plastic and metallic materials. As such, embodiments are envisioned where other end effector components utilize a plastic body for all of the keying and alignment features while the metal substrates bear the stretch and deflection loads during operation.

Further to the above, with traditional insert molded parts creating undercuts, interior voids, interior spaces, and/or features transverse to the parting line of the mold (e. more than 3 degrees from the parting axis of the mold) may be difficult and costly to manufacture in certain instances. The 3D-printed plastic body discussed above, can comprise undercuts, interior voids, and/or transverse alignment features for connecting components, for example.

FIGS. 259 and 260 depict a surgical instrument 51000 comprising a firing bar support 51020, a firing bar 51010, and an over-molded sleeve 51030. The firing bar support 51020 comprises two lateral plates 51022, 51024 positioned on both sides of the firing bar 51010. In the illustrated embodiment, the firing bar 51010 comprises a laminate firing bar constructed of several layers. Other embodiments are envisioned where the firing bar is a one-piece unitary structure. In any event, the firing bar support 51020 prevents bucking of the firing bar 51010 during firing of the firing bar 51010 and/or articulation of the end effector 51000. In certain instances, the firing bar support 51020 may be identical to the firing bar support disclosed in U.S. patent application Ser. No. 15/635,808 filed on Jun. 28, 2017, issued as U.S. Pat. No. 11,259,805 on Mar. 1, 2022, the entirety of which is incorporated by reference herein. Further, the firing bar support 51020 comprises a flexible portion 51040 positioned in an articulation joint of the surgical instrument 51000. Specifically, FIG. 259 illustrates the surgical instrument 51000 in an unarticulated orientation and FIG. 260 illustrates the surgical instrument 51000 in an articulated configuration.

The firing bar support 51020 is defined within the over-molded sleeve 51030 that extends along the articulation joint of the surgical instrument 51000. In other words, the over-molded sleeve 51030 encompasses and/or encapsulates the firing bar support 51020 therein. In at least one embodiment, the over-molded sleeve 51030 may be a plastic 3D printed material built around the firing bar support 51020 to embed and/or encapsulate the firing bar support 51020 therein. As such, the over-molded sleeve 51030 and the firing bar support 51020 comprise a substantially unitary piece. Further, the unitary piece formed of the over-molded sleeve 51030 and the firing bar support 51030 comprises a longitudinal slot 51032 defined therein. The longitudinal slot 51032 is configured to receiving the firing bar 51010 to permit translation of the firing member 51010 therein.

FIG. 261 depicts an anvil 52000 for use with a surgical instrument, such as those described herein. The anvil 52000 comprises a tissue contacting surface 52020 and a longitudinal slot 52030 for receiving a portion of a firing member. The anvil 52000 further comprises an anvil slot 52040 extending longitudinally along at least a portion of the anvil 52000. In the illustrated embodiment, the anvil slot 52040 is plus-shaped, however, other embodiments are envisioned where the anvil slot 52040 is T-shaped with a flat top portion. The reader will appreciate that alternative geometries and shapes for the anvil slot 52040 are contemplated. In any event, the anvil 52000 comprises a compliant portion 52050 extending longitudinally along at least a portion of the anvil slot 52040. In the illustrated embodiment, the compliant portion 52050 is positioned around the perimeter of the anvil slot 52040 on all sides. However, other embodiments are envisioned where the compliant portion 52050 resides solely on a pair of anvil slot ledges 52060 of the anvil 52000.

In at least one embodiment, the compliant portion 52050 comprises a more compressible material than the remainder of the anvil 52000. For example, the compliant portion 52050 can comprise a material that is less dense or softer (i.e., a smaller number on Mohs hardness scale) than the remainder of anvil 52000 material. In at least one embodiment, the compliant portion 52050 can be comprised of brass or bronze and the remainder of the anvil 52000 can be comprised of stainless steel. In any event, the upper pins or upper cam members of a firing member (i.e., an I-beam or E-beam) can ride along the compliant portion 52050 during firing. As such, the body of the anvil 52000 is more rigid with the anvil slot 52040 being softer and/or more compliant to facilitate more give to the firing member during firing. Further, the compliant portion 52050 may be smoother than the remainder of the anvil 52000 to further facilitate sliding of the upper pins of the firing member within the anvil slot 52040.

Further to the above, the anvil 52000 may be constructed using 3D printing to position the compliant portion 52050 within the body of the anvil 52000. For example, the 3D printer could begin by building up stainless steel from the tissue contacting surface 52020 upward. The 3D build could be stopped to insert the compliant member 52050, and then the build continued to encapsulate the compliant member 52050 within the stainless steel 3D print material of the anvil 52000. As such, the compliant member 52050 and the anvil 52000 can be 3D printed to produce a substantially unitary piece having two different materials. Other embodiments are envisioned with more than two materials 3D printed into the anvil 52000.

FIGS. 264-267 illustrate one form of a universally movable joint 60200 that may be fabricated by various additive manufacturing process commonly falling under the umbrella term of "three dimensional (3D)" printing. As will become further evident as the present disclosure proceeds, the use of such processes to produce a universally movable joint 60200 that may be employed to form various drive shaft arrangements disclosed herein may address many if not all of the size and assembly challenges discussed above.

Various forms of additive manufacturing systems are known for manufacturing components from sinterable building materials, for example. FIG. 262 illustrates in general form, an additive manufacturing system 60100 that may implement a manufacturing process 60000 for forming a universally movable joint 60200, in accordance with at least one aspect of the present disclosure. As used herein, the term "additive manufacturing" may encompass, but is not limited to, "selective laser melting (SLM)," "direct metal laser melting (DMLM)," "laser powder bed fusion (LPBF)," and various other known systems as well as those systems disclosed for example in U.S. Pat. No. 9,815,118, entitled FABRICATING MULTI-PART ASSEMBLIES, the entire disclosure of which is herein incorporated by reference.

By way of non-limiting example, the additive manufacturing system 60100 comprises a printer 60120 that may include a fused filament fabrication system, a binder jetting system, a stereolithography system, a selective laser sintering system, or any other system that can be usefully adapted or employed to form a universally movable joint 60200 described herein under computer control from or out of a build material 60130. In at least one form, the build material 60130 may comprise sinterable materials commonly employed with such printers. For example, in accordance with various aspects of the present disclosure, the build material 60130 may comprise 316 stainless steel, 17-4 stainless steel, Ti-64 titanium, etc. As will be discussed in further detail below, various other forms of build materials (metal and non-metal) may also be employed.

In one aspect, the additive manufacturing system 60100 may comprise a computer system 60125 that is configured to generate a computer aided design (CAD) three dimensional file of the universally movable joint 60200. The CAD file data may then be sliced into layers forming a two dimensional image of each layer. This file may then be loaded into a file preparation software package that assigns parameters, values, and physical supports that allow the file to be interpreted by the printer 60120. In a general form, the printer 60120 may comprise a build chamber 60122 that includes a build plate or platform 60124 and a laser 60126. In accordance with one non-limiting aspect, the build chamber 60122 may further include a material dispensing platform (not shown) and a re-coater member (not shown) that is used to move new build material 60130 over the build plate 60124. In at least one arrangement, the build material 60130 is commonly in powered form ("first state") and the laser 60126 fuses the powdered build material 60130 into a solid part ("second state") by melting it locally using the focused laser beam. For example, the component portions of the universally movable joint 60200 may be built up additively, layer by layer.

Support structures may be required in many additive manufacturing processes to dissipate heat away from the printed component and into the build plate as well as to support the component throughout the manufacturing process. Overhanging features of a printed component generally have no underlying solid layer to support them at any point. Such overhanging features may therefore be more prone to deformation during manufacturing caused by gravity, internal heat, and residual stresses. In such instances, to avoid this deformation, support structures may be employed to support those overhanging features during the additive manufacturing process. While such support structures are useful for these reasons, they must be removed from the formed component or part after the process is completed. This results in wasted material and can lead to increased manufacturing costs.

In one non-limiting example, the additive manufacturing system 60100 may include a conveyor 60140 for transporting a printed "green" universally movable joint 60200G to a post-processing station 60150. As used in this context, the term "green" may refer to a condition of the universally movable joint 60200 wherein one or more component portions thereof lacks one or more of the following attributes: (i) final desired composition, (ii) final desired strength, (iii) final desired dimension(s), (iv) final desired shape, (v) final desired density, and/or (vi) final desired finish, for example. The conveyor 60140 may be any suitable mechanism or combination of devices suitable for physically transporting the green universally movable joint 60200G. This may, for example, include a robotics and a machine vision system or the like on the printer side for detaching the green universally movable joint 60200G from the build plate 60124, as well as robotics and a machine vision system or the like on the post-processing side to accurately place the green universally movable joint 60200G within the post-processing station 60150. In another aspect, the green universally movable joint 60200G may be manually transported between the two corresponding stations.

The post-processing station 60150 may be any system or combination of systems useful for converting the green universally movable joint 60200G into the desired net final shape, net final dimension, net final density, net final strength and/or net final finish, for example. The post-processing station 60150 may also or instead, for example, include a de-binding station such as a chemical de-binding station for dissolving binder materials in a solvent or the like, or more generally, any de-binding station configured to remove at least a portion of the binder system from the various forms of build materials 60130. The post-processing station 60150 may, for example, also or instead include a thermal sintering station for applying a thermal sintering cycle at a sintering temperature for the build material 60130, or the powdered material in the build material 60130, such as a sintering furnace configured to sinter the powdered material into a densified object. The post-processing station may also or instead comprise a heat treating station. The post processing station may also or instead comprise a system for removing unformed build material and/or support material using a variety of different mediums including, but not limited to, liquids, solvents, air pressure, gravity, etc.

Further, a wide range of sintering techniques may be usefully employed by the post-processing station 60150. In one aspect, the green universally movable joint 60200G may be consolidated in a furnace to a high theoretical density using vacuum sintering, for example. In another aspect, the furnace may use a combination of flowing gas (e.g., at below atmosphere, slightly above atmosphere, or some other suitable pressure) and vacuum sintering. More generally, any sintering or other process suitable for improving object density may be used, preferably where the process yields a near-theoretical density part with little or no porosity. Hot-isostatic pressing ("HIP") may also or instead be employed, e.g., by applying elevated temperatures and pressures as a post-sintering step to increase density of the final part. In another aspect, the universally movable green joint 60200G may be processed using any of the foregoing, followed by a moderate overpressure (greater than the sintering pressure, but lower than HIP pressures). More generally, any technique or combination of techniques suitable for removing binder systems and driving a powdered material toward consolidation and densification may be used by the post-processing station 60150 to process a fabricated universally movable joint 60200 as contemplated herein.

The post-processing station 60150 may also or instead comprise machining operations configured to remove support structure(s) (if any) and/or machine the component portions of the green universally movable joint 60200G that have been printed within "near net" dimensions to provide the joint components with final desired dimensions and shapes. The post-processing station 60150 may also or instead include a Directed Energy Deposition (DED) process which in one form may comprise a three dimensional (3D) printing method that employs a focused energy source, such as a plasma arc, laser or electron beam to melt a material which is simultaneously deposited by a nozzle. Such DED process may be used for example to repair or add additional material to a green universally movable joint 60200G or finished universally movable joint 60200. The post-processing station 60150 may also or instead comprise various grit blasting and/or polishing operations for attaining a desired final surface finish of the universally movable joint 60200.

FIG. 263 illustrates one non-limiting example of a manufacturing process 60000 for forming a universally movable joint 60200. In one general aspect, the manufacturing process 60000 comprises the action 60010 of developing a computer aided designed (CAD) file of the universally movable joint 60200 in a format that is useable by the printer 60120. The manufacturing process 60000 further includes the action 60020 of implementing the computer designed file to cause the printer 60120 to form a green universally movable joint 60200G from build material 60130 that is supplied to the build chamber 60122 of the printer 60120. In at least one non-limiting form, the manufacturing process 60000 may further comprise the action 60030 of post-processing the green universally movable joint 60200G to form a final universally movable joint 60200 as described and contemplated herein. The action 60030 may include one or more actions described herein designed to provide the green universally movable joint 60200G and the components thereof with a final desired composition, strength, shape, dimensions, density, and/or finish, for example.

FIGS. 264-267 illustrate a completed or finished universally movable joint 60200 that was formed using the additive manufacturing system 60100. As shown in FIGS. 264-267, one form of the universally movable joint 60200 comprises a cross-shaped joint spine 60300, a vertical U-joint 60400 and a horizontal U-joint 60500. In at least one embodiment, for example, the joint spine 60300 defines a vertical axis VA-VA and a horizontal axis HA-HA that is transverse to the vertical axis VA-VA. In one arrangement, the horizontal axis HA-HA is orthogonal to the vertical axis VA-VA. As can be seen in FIGS. 265 and 267 for example, the joint spine 60300 comprises a bottom axle segment 60310 that is axially aligned on the vertical axis VA-VA and includes a flared bottom end 60312. The flared bottom end 60312 defines an arcuate bottom surface 60314. The joint spine 60300 further comprises a top axle segment 60320 that is axially aligned on the vertical axis VA-VA and includes a flared top end 60322 that defines an arcuate top surface 60324. The joint spine 60300 further comprises a first or right horizontal axle segment 60330 that is axially aligned on the horizontal axis HA-HA and terminates in a first conical end portion 60334. The joint spine 60300 also comprises a second or left horizontal axle segment 60340 that is axially aligned on the horizontal axis HA-HA and terminates in a second conical end portion 60344.

Still referring to FIGS. 266 and 267, the vertical U-joint 60400 in at least one form comprises a bottom "wishbone" or bottom joint ring 60410 that is journaled on the bottom axle segment 60310 for rotation therearound. The flared bottom end 60312 of the joint spine 60300 permanently retains the bottom joint ring 60410 on the bottom axle segment 60310. In one non-limiting example, the vertical U-joint 60400 further comprises a top "wishbone" or top joint ring 60420 that is journaled on the top axle segment 60320 for rotation therearound. The flared top end 60322 of the joint spine 60300 permanently retains the top joint ring 60420 on the top axle segment 60320. The vertical U-joint 60400 further comprises a U-shaped vertical bridge 60430 that protrudes from the bottom joint ring 60410 and the top joint ring 60420 and extends therebetween. The U-shaped vertical bridge 60430 comprises an arcuate outer surface 60431 that serves to facilitate pivotal travel and movement of the vertical U-joint 60400 with the tight confines of a hollow outer shaft portion of a surgical instrument and/or surgical trocar. The vertical U-joint 60400 comprises one integrally formed component of the universally movable joint 60200 that is rotatable about the vertical axis VA-VA of the joint spine 60300 and is permanently retained thereon by the flared bottom end 60312 and the flared top end 60322 as well as the U-shaped vertical bridge 60430. Stated another way, the vertical U-joint 60400 cannot be detached from the joint spine 60300 without damaging one or both of those components.

In accordance with another aspect of the present disclosure, the horizontal U-joint 60500 in at least one form comprises a first horizontal "wishbone" or joint cap 60510 that is rotatably journaled on the first horizontal axle segment 60330 and a second horizontal "wishbone" or joint cap 60520 that is rotatably journaled on the second horizontal axle segment 60340. The horizontal U-joint 60500 further comprises a U-shaped horizontal bridge 60530 (FIG. 26) that protrudes from the first horizontal joint cap 60510 and the second horizontal joint cap 60520 and extends therebetween. The U-shaped horizontal bridge 60530 comprises an arcuate (as opposed to a flat) outer surface 60531 that serves to facilitate pivotal travel and movement of the horizontal U-joint 60500 with the tight confines of a hollow outer shaft portion of a surgical instrument and or surgical trocar. The horizontal U-joint 60500 comprises one integrally formed component of the universally movable joint 60200 that is rotatable about the horizontal axis HA-HA of the joint spine 60300 and is permanently retained thereon by the U-shaped horizontal bridge 60530. See FIG. 264. Stated another way, the horizontal U-joint 60500 cannot be detached from the joint spine 60300 without damaging one or both of those components.

Turning to FIG. 267, in at least one non-limiting example, the bottom joint ring 60410 comprises a bottom ring inner surface 60412 that is spaced from an outer surface 60316 of the bottom axle segment 60310 to define a bottom joint space 60318 that extends between the bottom joint ring 60410 and the bottom axle segment 60310 and opens to the bottom of the universally movable joint 60200 around the flared bottom end 60312. Similarly, the top joint ring 60420 comprises a top ring inner surface 60422 that is spaced from an outer surface 60323 of the top axle segment 60320 to define a top joint space 60326.

Still referring to FIG. 267, in accordance with another non-limiting example, the first horizontal joint cap 60510 comprises a first hub portion 60512 that comprises a first hub inner surface 60514 and a first cap portion 60516 that defines a first tapered end surface 60518. The first hub inner surface 60514 is spaced from an outer surface 60332 of the first horizontal axle segment 60330 and the first tapered end surface 60518 is spaced from the first conical end portion 60334 to define a first horizontal joint space 60336 that extends between the first horizontal joint cap 60510 and the first horizontal axle segment 60330 and the first conical end portion 60334. The first horizontal joint space 60336 opens through a first hole 60519 in the first cap portion 60516.

Similarly, the second horizontal joint cap 60520 comprises a second hub portion 60522 that comprises a second hub inner surface 60524 and a second cap portion 60526 that defines a second tapered end surface 60528. The second hub inner surface 60524 is spaced from an outer surface 60342 of the second horizontal axle segment 60340 and the second tapered end surface 60528 is spaced from the second conical end portion 60344 to define a second horizontal joint space 60346 that extends between the second horizontal joint cap 60520 and the first horizontal axle segment 60340 and the first conical end portion 60344. The second horizontal joint space 60346 opens through a second hole 60529 in the second cap portion 60526.

As can also be seen in FIG. 265, in a non-limiting example, the bottom joint ring 60410 comprises a bottom joint ring outer surface 60414. The top joint ring 60420 comprises a top joint ring outer surface 60424. The first horizontal joint cap 60510 comprises a first cap outer surface 60517 and the second horizontal joint cap 60520 comprises a second outer cap surface 60527. In the illustrated example, the bottom joint ring outer surface 60414 is spaced from the first cap outer surface 60517 to define a first lower clearance space or "fillet" 60416 therebetween. Likewise, the bottom joint ring outer surface 60414 is spaced from the second cap outer surface 60527 to define a second lower clearance space or "fillet" 60418 therebetween. The top joint ring outer surface 60424 is spaced from the first cap outer surface 60517 to define a first upper clearance space or "fillet" 60426 therebetween. Likewise, the top joint ring outer surface 60424 is spaced from the second cap outer surface 60527 to define a second upper clearance space or "fillet" 60428 therebetween.

FIG. 268 illustrates a green universally movable joint 60200G that is still supported on the build plate 60124. In this example, one form of build material 60130 is employed. In a "first state", the build material 60130 comprises a powder material of the various types disclosed and contemplated herein. Once transformed by the laser or other component/system, for example, the build material 60130 comprises a "second" state. As shown in FIG. 268, various amounts of the build material 60130 in powder form, e.g., the "first state" (referred to in FIG. 268 as "60130U") are located in the top joint space 60326, the first upper clearance space 60426, the second upper clearance space 60428, the first horizontal joint space 60336, the second horizontal joint space 60346, the first lower clearance space 60416, the second lower clearance space 60418, and the bottom joint space 60318. Such amounts of unformed build material 60130U serve to support the vertical U-joint 60400 and the horizontal U-joint 60500 on the joint spine 60300 during the printing process and prevents those components from become fused or non-movably formed together. After the green universally movable joint 60200G has been formed, these amounts of unformed build material 60130U must be removed from between the vertical U-joint 60400 and the joint spine 60300 and the horizontal U-joint 60500 and the joint spine 60300. In various instances, the amounts of unformed build material 60130U may be removed under the influence of gravity and/or may be removed using a removal medium (air, liquid, solvent, etc.) during post processing. In one aspect, the first lower clearance or fillet 60416, the second lower clearance or fillet 60418, the first upper clearance space or fillet 60426, the second upper clearance space or fillet 60428 as well as the hole 60519 in the first horizontal joint cap 60510 and the second hole 60529 in the second horizontal joint cap 60520 serve to facilitate easy removal the amounts of build material 60130U from the green universally movable joint 60200G. See FIGS. 268A-268C.

During the printing process or formation process, the joint spine 60300 extends from the built plate 60124 and is formed vertically off the build plate 60124. The flared bottom end 60312 is formed off of the build plate 60124 and is attached thereto during formation. The flared bottom end 60312 serves to support the joint spine 60300 during the printing process. In one aspect, unformed build material 60130U around the flared bottom end 60312, the bottom joint ring 40410, the first horizontal joint cap 60510 and the second horizontal joint cap 60520, as well as the amounts of unformed build material 60130U in the spaces between the vertical U-joint 60400, the horizontal U-joint 60500, and the joint spine 60300 may further help to maintain the vertical orientation of the joint spine 60300 (and the universally movable joint 60200G) during the forming process without the use of support members between the joint components and the build plate 60124. In such arrangement, the flared bottom end 60312 facilitates thermal dissipation into the build plate 60124. The bottom joint ring 60410 is formed without being attached to the build plate 60124. In accordance with at least one aspect, universally movable joints 60200 having an overall diameter of as small as approximately 4 mm may be formed in such a manner. Joints with larger diameters, for example, of approximately 10 mm or more may require one or more support members to support the joint components in a vertical orientation during the printing process. In any event, once the amounts of unformed (i.e., still in a first state or powder form or unsolidified) build material 60130U are removed from between the joint components, the vertical U-joint 60400 is freely rotatable on the joint spine 60300 about the vertical axis VA-VA and the horizontal U-joint 60500 is freely rotatable about the joint spine 60300 about the horizontal axis HA-HA. In addition, the vertical U-joint 60400 and the horizontal U-joint 60500 cannot be removed from the joint spine 60300 without damaging the universally movable joint 60200.

FIG. 269 illustrates a non-limiting example wherein support members 60600 are formed between the flared bottom end 60312 and the build plate 60124, and/or between the bottom joint ring 60410 and the build plate 60124, and/or between the first horizontal joint cap 60510 and the build plate 60124, and/or between the second horizontal joint cap 60520 and the build plate 60124. The shapes, numbers, and compositions of such support members can vary and are configured to be removed from the universally movable joint 60200G' during post processing. In such arrangement, various amounts 60130U of unformed building material may be received in the above-described spaces between the joint components and thereafter removed during post processing.

FIG. 270 illustrates a green universally movable joint 60200G formed from a build material 60130 of the types disclosed and contemplated herein. However, during this manufacturing process, a support material SM is introduced during the process to separate components 60300, 60400, 60500 during printing. Such support material SM may comprise a powdered support material that may be removed from the spaces between the components under the influence of gravity, air pressure, liquid, etc. Other support materials SM that may be dissolved when contacted by a solvent medium are contemplated.

Other non-limiting systems and processes are contemplated wherein a universally movable joint 60200 is formed from different build materials and different support materials. For example, FIG. 271 illustrates a universally movable joint 60200' that is identical to universally movable joint 60200 except for the differences noted below relating to its composition and formation. For example, the joint spine 60300' may be formed from a first build material FBM and the vertical U-joint 60400' and/or the horizontal U-joint member 60500' may be fabricated from a second build material SBM that is different from the first build material FBM. For example, the first build material FBM may comprise a polymer and the second build material may comprise a metal build material or vice versa. The first build material FBM and the second build material SBM may be introduced in precise locations on the build plate 60124 at predetermined times and locations to facilitate printing of the components from the desired materials. In other arrangements, one of the components may be printed from the first build material FBM and thereafter the second build material SBM is introduced to form the second component(s). In one contemplated arrangement, for example, the joint spine 60300' may be printed from a material that is softer than the material used to form the vertical U-joint 60400' and/or the horizontal U-joint member 60500'. For example, in one arrangement, the joint spine 60300' is printed from a polymer material or softer material such as brass or bronze, etc. and the vertical U-joint 60400' and horizontal U-joint 60500' may be printed from a stainless steel, titanium, or other metal material, etc. Such combination of materials may result in reduced friction between these components. In still other arrangements, the joint spine 60300' may be fabricated from stainless steel, titanium, etc. and the vertical U-joint 60400' and the horizontal U-joint 60500' may be formed from softer materials such as brass, bronze, polymer, etc. Such arrangements may also employ a support material SM of the types contemplated herein to separate the component parts and thereafter be removed from between those component parts during post-processing operations.

FIGS. 272-274, illustrate another form of universally movable joint 60200" that is identical to universally movable joint 60200 except that the bottom end 60312" is not flared and the top end 60322" is not flared. The vertical U-joint 60400 is retained on the joint spine by the U-shaped vertical bridge 60430.

The various forms of universally movable joints 60200, 60200', 60200" represent vast improvements over prior joint arrangements that have been employed in various drive shafts and/or articulation joints of surgical instruments. The universally movable joints 60200, 60200', 60200" comprise a compact "integral" design that may avoid many of the challenges and increased costs associated with assembling other multiple part shaft/joint arrangements that may be employed in many surgical devices. The design of each of the universally movable joints 60200, 60200', 60200" minimize/eliminate unsupported horizontal surfaces, which could otherwise lead to increased surface roughness and component warping. The universally movable joints 60200, 60200', 60200" may be printed from metal build material and exhibit strength characteristics that are comparable to or exceed the strength characteristics of multiple part joints that are machined from similar metal material and assembled together with pins, screws, welding, etc. The present joint designs further minimize and, in many cases, eliminate the need for numerous, elaborate support members during the printing process and can also reduce post-processing operations and/or costs.

FIG. 275 illustrates a universally movable drive shaft segment 60700 that comprises multiple movable universally movable joints 60200A, 60200B, and 602000 that are printed in series in one single continuous manufacturing system of the types contemplated herein. In one non-limiting example, universally movable joint 60200A is substantially identical to universally movable joint 60200 described herein except that the U-shaped vertical bridge 60430A is formed with a U-shaped horizontal bridge 60530B of the universally movable joint 60200B. A U-shaped vertical bridge 60430B of the universally movable joint 60200B is formed with a U-shaped horizontal bridge 60530C of the universally movable joint 602000. In the illustrated non-limiting example, the universally movable joints 60200B and 6002000 may otherwise be identical in construction, fabrication, and operation to universally movable joint 60200. The universally movable drive shaft segment 60700 may comprise additional universally movable joints formed in series and is not limited to three joints formed in series. The universally movable drive shaft segment 60700 may comprise two universally movable joints, three or more than three universally movable joints serially formed together using the methods and processes contemplated herein.

FIGS. 276-278 illustrate one form of an articulation joint assembly 61000 that may be employed in the various surgical instruments disclosed and contemplated herein as well as other surgical instrument arrangements, devices, and configurations. In one non-limiting example, the articulation joint assembly 61000 comprises a proximal mounting member 61100 that is configured to interface with a shaft assembly 61010 of a surgical instrument. For example, the proximal mounting member 61100 may be welded or attached to a distal portion of the shaft assembly 61010 by any suitable means. See FIG. 277. In other arrangements, the proximal mounting member 61100 may comprise a portion of the shaft assembly 61010. Also in a non-limiting example, the articulation joint assembly 61000 further comprises a distal mounting member 61200 that is configured to interface with a surgical end effector 61020. The surgical end effector 61020 may comprise any of the surgical end effectors disclosed or contemplated herein and may comprise, but is not limited to, end effectors configured to manipulate tissue (graspers), end effectors configured to cut and staple tissue (endocutters), clip appliers, and end effectors configured to cut and fasten tissue with ultrasound, harmonic, radio frequency energy, etc. The distal mounting member 61200 may be welded or attached to a proximal portion of the surgical end effector 61020 by any suitable means. In other arrangements, the distal mounting member 61200 may comprise a portion of the surgical end effector 61020.

In the non-limiting example illustrated in FIGS. 276-278, the proximal mounting member 61100 comprises a proximal shaft hole 61110 that is axially aligned with a shaft axis SA-SA that is defined by the shaft assembly 61010. Similarly, the distal mounting member 61200 comprises a distal shaft hole 61210. The distal shaft hole 61210 may have a diameter that is the same or similar to a diameter of the proximal shaft hole 61110. The proximal shaft hole 61110 and the distal shaft hole 61210 are sized and configured to accommodate various flexible or otherwise movable drive shafts, actuator components, conductors, cables, shaft support structures, etc. that extend from the shaft assembly 61010 to the surgical end effector 61020. In various instances, such drive shafts, actuators, conductors etc. may be operably supported in one or more flexible hollow conduits or support members that span between the proximal mounting member 61100 and the distal mounting member 61200 for example. In other arrangements the drive shafts are supported in one of the shaft guides described below and contemplated herein. When the surgical end effector 61020 is aligned on the shaft axis SA-SA with the shaft assembly 61010, the distal shaft hole 61210 is aligned with the proximal shaft hole 61110.

Still referring to FIGS. 276-278, in at least one non-limiting example, the articulation joint assembly 61000 further comprises a plurality of articulation link assemblies that are attached to and extend between the proximal mounting member 61100 and the distal mounting member 61200. The illustrated non-limiting example comprises three articulation link assemblies 61300A, 61300B, and 613000. Other numbers of articulation link assemblies are contemplated. Unless otherwise noted herein, the articulation link assemblies 61300A, 61300B, 613000 are similar in construction and in at least one instance, may each be formed or printed using the manufacturing systems of the types contemplated herein. Articulation link assembly 61300A comprises a proximal movable joint 62200A and a distal movable joint 63200A that are very similar in construction and design to the universally movable joints 60200 described herein. For example, a proximal movable joint 62200A comprises a proximal joint spine 62300A, a proximal first joint member 62400A, and a proximal second joint member 62500A. Similarly, each distal movable joint 63200A comprises a distal joint spine 63300A, a distal first joint member 63400A, and a distal second joint member 63500A. In an illustrated non-limiting example, the vertical U-joint 62400A of the proximal first joint member 62400A and the vertical U-joint 63400A of the distal first joint member 63400A may be similar in design to the vertical U-joint 60400 described above, except that a link member 62600A protrudes from a proximal first bridge member 62430A of the proximal first joint member 62400A and a distal first bridge member 63430A of the distal first joint member 63400A and extends therebetween. In one instance, the link member 62600A comprises a circular cross-sectional shape. The circular cross-sectional shape better facilitates passage of operation shafts and control members in the area defined between the link members 62600A, 62600B, 626000, as will be further discussed below. The proximal first joint member 62400A is configured to pivot relative to the proximal joint spine 62300A about a first proximal axis FPA-FPA and the distal first joint member 63400A is configured to pivot relative to the distal joint spine 63300A about a first distal axis FDA-FDA.

As can be further seen in FIGS. 276-278, the proximal second joint member 62500A may be similar in design to the horizontal U-joint 60500 described above, except that a mounting feature 62700A protrudes from a proximal second bridge member 62530A of the proximal second joint member 62500A. In one non-limiting example, the mounting feature 62700A is configured to be received in a corresponding proximal axial mounting slot 61120A provided in the proximal mounting member 61100. To facilitate easy assembly, the proximal mounting feature 62700A comprises a hook portion 62702A that is configured to hook over a retaining lug 61122A formed in the proximal axial mounting slot 61120A. In one arrangement, the hook portion 62702A is spaced from the proximal second bridge member 62530A by a tapered opening 62704A and is configured to interface with the retaining lug 61122A which is wedge-shaped to non-movably wedgingly affix the proximal movable joint 62200A to the proximal mounting member 61100. In one aspect, the wedge-shaped interface may be sufficient to non-movably couple the proximal movable joint 62200A to the proximal mounting member 61100. In other arrangements, in addition to the wedge-shaped interface, the mounting feature 62700A in the alternative to or in addition to may be affixed to the proximal mounting member 61100 by welding, adhesive or other suitable mounting means. In one instance, the mounting features 62700A may simply be retained in hooking engagement with the proximal mounting member 61100 and the distal mounting member 61200 by a conduit or shaft guide that extends through the proximal shaft hole 61110 and the distal shaft hole 61210. In still other arrangements, the proximal mounting feature 62700A may comprise a stem feature (not shown) configured to be movably inserted into a corresponding axial slot (not shown) in the proximal mounting member 61100 to facilitate axial movement of the proximal movable joint 62200A relative to the proximal mounting member 61100. In at least one non-limiting example, the distal movable joint 63200A may be similarly constructed and coupled to the distal mounting member 61200 and will not be repeated in detail herein. In various instances, when a shaft guide or hollow conduit extends between the proximal mounting member 61100 and the distal mounting member 61200, the conduit or shaft guide serves to prevent the proximal mounting features 62700A from disengaging from the proximal mounting member 61100 and the distal mounting features from disengaging from the distal mounting member 61200.

Articulation link assemblies 61300B and 613000 are similar in design to the articulation link assembly 61300A described in detail above. As can be seen in FIGS. 276-278, the proximal movable joint 62200A of the articulation link assembly 61300A is attached to the proximal mounting member 61100 at a first proximal attachment location FPA defined by the axial mounting slot 61120A. Likewise, the distal movable joint 63200A of the articulation assembly 61300A is formed with a distal mounting feature (not shown) that is similar to the proximal mounting feature 62700A for attachment to the distal mounting member 61200. The distal movable joint 63200A is attached to the distal mounting member 61200 at a first distal attachment location FDA that is defined by a distal axial mounting slot 61220A in the distal mounting member 61200.

Still referring to FIGS. 276-278, the proximal movable joint 62200B of the articulation link assembly 61300B is attached to the proximal mounting member 61100 at a second proximal attachment location SPA defined by a proximal axial mounting slot 61120B and the proximal movable joint 622000 of the articulation link assembly 613000 is attached to the proximal mounting member 61100 at a third proximal attachment location TPA defined by a proximal axial mounting slot 61120C. In one non-limiting example, the first proximal attachment location FPA, the second proximal attachment location SPA, and the third proximal attachment location TPA are equally spaced about the shaft axis SA-SA. Stated another way, angles A, B, and C are each approximately 120°. Similarly, the distal movable joint 63200B of the articulation link assembly 61300B is attached to the distal mounting member 61200 at a second distal attachment location SDA defined by a distal axial mounting slot 61220B and the distal movable joint 632000 of the articulation link assembly 613000 is attached to the distal mounting member 61200 at a third distal attachment location TDA defined by a distal axial mounting slot 61220C. In one non-limiting example, the first distal attachment location FDA, the second distal attachment location SDA, and the third distal attachment location TDA are equally spaced about the shaft axis SA-SA—angles D, E, and F are each approximately 120°. In one arrangement, when the surgical end effector 61020 is in an unarticulated position or, stated another way, axially aligned with the shaft assembly 61010 on the shaft axis SA-SA, the first distal attachment location FDA is diametrically opposite to the first proximal attachment location FPA; the second distal attachment location SDA is diametrically opposite to the second proximal attachment location SPA; and the third distal attachment location TDA is diametrically opposite to the third proximal attachment location TPA. In such arrangement, each of the link members 62600A, 62600B, and 626000 may be slightly twisted around an open central tunnel area 62800 defined by the shaft holes to accommodate unencumbered passage and operation of various drive shafts and other components from the shaft assembly 61010 to the surgical end effector 61020. Stated another way, in at least one arrangement, the axis of each of the link members 62600A, 62600B, are not parallel with each other and are not parallel with the shaft axis SA-SA. In one instance, the distal mounting member 61200 is rotatable relative to the proximal mounting member 61100 during articulation to maintain the inner drive radius of the open central tunnel or open area 62800. In such arrangement, an axial distance AD between the proximal mounting member 61100 and the distal mounting member 61200 is constant throughout the articulation motions/orientations of the articulation joint assembly 61000. See FIG. 278.

To facilitate articulation of the end effector, at least two and preferably four flexible articulation actuators (not shown) are attached to the distal mounting member and movably extend through openings in the proximal mounting member to communicate with an articulation control system supported in or by the housing or robotic system. For example, the flexible articulation actuators may comprise flexible cables configured in the various manners contemplated herein and described in further detail below. Other suitable articulation drive systems may be employed.

FIG. 279 illustrates another form of an articulation joint assembly 64000 that is somewhat similar in design and use to the articulation joint assembly 61000 described above. In one non-limiting example, the articulation joint assembly 64000 comprises a proximal mounting member 64100 that is configured to interface with a shaft assembly 64010 of a surgical instrument. For example, the proximal mounting member 64100 may be welded or attached to a distal portion of the shaft assembly 64010 by any suitable means. In other arrangements, the proximal mounting member 64100 may comprise a portion of the shaft assembly 64010. Also in a non-limiting example, the articulation joint assembly 64000 further comprises a distal mounting member 64200 that is configured to interface with a surgical end effector 64020. The surgical end effector 64020 may comprise any of the surgical end effectors disclosed or contemplated herein and may comprise, but is not limited to, end effectors configured to manipulate tissue (graspers), end effectors configured to cut and staple tissue (endocutters), clip appliers, and end effectors configured to cut and fasten tissue with ultrasound, harmonic, radio frequency energy, etc. The distal mounting member 64200 may be welded or attached to a proximal portion of the surgical end effector 64020 by any suitable means. In other arrangements, the distal mounting member 64200 may comprise a portion of the surgical end effector 64020.

In the non-limiting example illustrated in FIG. 279, the proximal mounting member 64100 comprises a proximal shaft hole 64110 that is axially aligned with a shaft axis SA-SA defined by the shaft assembly 64010. Similarly, the distal mounting member 64200 comprises a distal shaft hole 64210. The distal shaft hole 64210 may have a diameter that is the same or similar to a diameter of the proximal shaft hole 64110. The proximal shaft hole 64110 and the distal shaft hole 64210 are sized and configured to accommodate various flexible or otherwise movable drive shafts, actuator components, conductors, cables, shaft support structures, etc. that extend from the shaft assembly 64010 to the surgical end effector 64020. When the surgical end effector 64020 is aligned on the shaft axis SA-SA with the shaft assembly 64010, the distal shaft hole 64210 is aligned with the proximal shaft hole 64110.

Still referring to FIG. 279, in at least one non-limiting example, the articulation joint assembly 64000 further comprises a plurality of articulation link assemblies that extend between the proximal mounting member 64100 and the distal mounting member 64200 and are attached thereto. The illustrated non-limiting example comprises three articulation link assemblies 64300A, 64300B, and 643000 that, in at least one instance, may each be formed or printed using the manufacturing systems of the types contemplated herein. Other numbers of articulation link assemblies are contemplated. For example, an articulation joint assembly that only comprises two articulation link assemblies will work, but such articulation joint assembly may only facilitate articulation through a single plane. Unless otherwise noted herein, the articulation link assemblies 64300A, 64300B, 643000 are similar in construction. Articulation link assembly 64300A comprises a proximal movable joint 65200A and a distal movable joint 66200A that are very similar in construction and design to the universally movable joints 60200 described herein. For example, a proximal movable joint 65200A comprises a proximal joint spine 65300A, a proximal first joint member 65400A, and a proximal second joint member 65500A. Similarly, each distal movable joint 66200A comprises a distal joint spine 66300A, a distal first joint member 66400A, and a distal second joint member 66500A. In an illustrated non-limiting example, the U-Joint 65400A of the proximal movable joint 65200A and the U-joint 65400B of the distal movable joint 66200A may be similar in design to the U-joint 60400 described above, except that a link member 65600A protrudes from a proximal first bridge member 65430A of the proximal first joint member 65400A and a distal first bridge member 66420A of the distal first joint member 66400A and extends therebetween. The proximal first joint member 65400A is configured to pivot relative to the proximal joint spine 65300A about a first proximal axis and the distal first joint member 66400A is configured to pivot relative to the distal joint spine 66300 about a first distal axis in the manners disclosed herein. In other embodiments, the mounting feature 65700A may comprise a hook-type feature disclosed herein.

As can be further seen in FIG. 279, the proximal second joint member 65500A may be similar in design to the horizontal U-joint 60500 described above, except that a mounting feature 65700A protrudes from a proximal second bridge member 65530A of the proximal second joint member 65500A. In one non-limiting example, the mounting feature 65700A is configured to be received in a corresponding proximal axial mounting hole 64120A provided in the proximal mounting member 64100. Such arrangement facilitates easy assembly and may, in at least one alternative arrangement, permit axial movement of the articulation link 64300A relative to the proximal mounting member 64100.

Articulation link assemblies 64300B and 643000 are similar in design to the articulation link assembly 64300A described in detail above. As can be seen in FIG. 279, the proximal movable joint 65200A of the articulation link assembly 64300A is attached to the proximal mounting member 64100 at a first proximal attachment location FPA defined by the axial mounting slot 64120A. Likewise, the distal movable joint 66200A of the articulation assembly 64300A is formed with a distal mounting feature 66700A that is similar to the proximal mounting feature 62700A for axially movable attachment to the distal mounting member 64200. The distal movable joint 65200A is attached to the distal mounting member 64200 at a first distal attachment location FDA that is defined by a distal axial mounting slot 64220A in the distal mounting member 64200. In one instance, the link assemblies 64300A, 64300B, 643000 may be compressed between the proximal mounting member 64100 and the distal mounting member 64200 during assembly. In such arrangement, an axial distance between the proximal mounting member 64100 and the distal mounting member 64200 is constant throughout the articulation motions/orientations of the articulation joint assembly 64000. In other instances, the proximal mounting member 64100 and the distal mounting member 64200 may be spaced from each other a desired distance so as to permit some limited axial movement of the link assemblies 64300A, 64300B, 643000.

Still referring to FIG. 279, the proximal movable joint 65200B of the articulation link assembly 64300B is attached to the proximal mounting member 64100 at a second proximal attachment location SPA defined by a proximal axial mounting slot 64120B and the proximal movable joint 652000 of the articulation link assembly 643000 is attached to the proximal mounting member 64100 at a third proximal attachment location TPA defined by a proximal axial mounting slot 64120C. In one non-limiting example, the first proximal attachment location FPA, the second proximal attachment location SPA, and the third proximal attachment location TPA are equally spaced about the shaft axis SA-SA. Similarly, the distal movable joint 66200B of the articulation link assembly 64300B is attached to the distal mounting member 64200 at a second distal attachment location SDA defined by a distal axial mounting slot 64220B and the distal movable joint 662000 of the articulation link assembly 643000 is attached to the distal mounting member 64200 at a third distal attachment location TDA defined by a distal axial mounting slot 64220C. In one non-limiting example, the first distal attachment location FDA, the second distal attachment location SDA, and the third distal attachment location TDA are equally spaced about the shaft axis SA-SA. In one arrangement, when the surgical end effector 64020 is in an unarticulated position or, stated another way, axially aligned with the shaft assembly 64010 on the shaft axis SA-SA, the first distal attachment location FDA is diametrically opposite to the first proximal attachment location FPA; the second distal attachment location SDA is diametrically opposite to the second proximal attachment location SPA; and the third distal attachment location TDA is diametrically opposite to the third proximal attachment location TPA. In such arrangement, each of the link members 65600A, 65600B, and 656000 are slightly twisted around an open central tunnel or open area 65800 defined by the shaft holes 64110, 64210 to accommodate unencumbered passage and operation of various drive shafts and other components from the shaft assembly 64010 to the surgical end effector 64020. Stated another way, in at least one arrangement, the axis of each of the link members 62600A, 62600B, are not parallel with each other and are not parallel with the shaft axis SA-SA. In one instance, the distal mounting 64200 is rotatable relative to the proximal mounting member 64100 during articulation to maintain the inner drive radius of the open central tunnel or open area 65800.

To facilitate articulation of the end effector, at least two and preferably four flexible articulation actuators (not shown) are attached to the distal mounting member 64200 and movably extend through openings in the proximal mounting member 64100 to communicate with an articulation control system supported in or by the housing or robotic system. For example, the flexible articulation actuators may comprise flexible cables configured in the various manners contemplated herein and described in further detail below. Other suitable articulation drive systems may also be employed.

FIGS. 280 and 281 depict another non-limiting arrangement for coupling one of the movable joint members disclosed herein to a mounting member 67100 that may be attached to a portion of a shaft assembly or a portion of a surgical end effector in the various manners disclosed herein. In the illustrated example, the mounting member 67100 comprises an axial slot 67120 that corresponds to each universally movable joint 60200" that is to be coupled thereto. Each slot 67120 has a stop 67122 formed therein to limit axial travel in one direction. The universally movable joint 60200" is substantially identical to the universally movable joints 60200, 60200' described herein except that a mounting stem or mounting feature 67700 protrudes from the U-shaped vertical bridge 60430 of the vertical U-joint 60400. A stop block 67702 is formed on the end of the mounting stem 67700 to engage the stop 67122 formed in the axial slot 67120 to limit the axial travel of the universally movable joint 60200" in the direction PD.

The mounting member 67100 includes a shaft hole 67110 configured to permit various drive shafts and/or other instrument components to pass therethrough. In one non-limiting arrangement, each slot 67120 opens into the shaft hole 67110. FIG. 281 illustrates a portion of a shaft or conduit 67200 extending through the shaft hole 67110. In such arrangement, the shaft or conduit 67200 retains the mounting member 67700 and the stop block 67702 in the corresponding axial slot 67120. Depending on the axial length of the mounting stem or feature 67700, the mounting stem 67700 and stop block 67702 may move axially in the axial slot 67120 which facilities axial movement of the universally movable joint 60200" relative to the mounting member 67100. In other arrangements, the mounting stems 67700 and stop blocks 67702 may be non-movably retained within their corresponding axial slots 67120 by welding, adhesive, or other suitable fastener means. Such arrangements facilitate easy assembly of the articulation joint components.

Returning now to the surgical stapling assembly 400 illustrated in FIGS. 12-14, as was discussed above, the surgical stapling assembly 400, in at least one form comprises an end effector 200 that is operably coupled to a shaft assembly 410 by an articulation joint 420. The end effector 200 comprises an anvil jaw 203 that is pivotally coupled to a cartridge jaw 201 and is moved between an open and closed position relative thereto by a closure drive that is configured to operably interface with the closure drive shaft segment 475. Additionally, the end effector 200 further comprises a firing member 270 that operably interfaces with the firing screw 261 such that as the firing screw 261 is rotated, the firing member 270 is advanced distally or retracted proximally along the firing screw 261. The firing screw 261 operably interfaces with the firing drive shaft segment 476 which serves to transmit rotary drive motions thereto from a firing drive. The firing drive may, for example, comprise any suitable source of rotary firing motions. For example, the firing drive may comprise a firing drive motor operably supported in a surgical instrument housing or portion of a robotic system.

In one non-limiting arrangement for example, the closure drive comprises a proximal closure drive shaft portion 68002 that extends through the outer shaft 411 of the shaft assembly 410 and operably interfaces with a source of rotary closure motions supported in or by the housing or robotic system. The closure drive may further comprise an intermediate closure drive shaft portion that bridges the articulation joint(s) and a distal closure drive shaft portion that is supported in the end effector 200. In one arrangement, the proximal portion may comprise a rigid shaft segment, a flexible shaft segment, or a combination of rigid and flexible segments, for example. In one non-limiting arrangement, the intermediate closure drive shaft portion may comprise one universally movable joint (60200) or a series of movable joints or universally movable drive shaft segment (60700) that spans the articulation joint(s). The distal closure drive shaft portion may comprise a closure drive shaft arrangement supported in the end effector to apply opening and closing motions to the anvil in the various manners disclosed herein.

Similarly, the firing drive may comprise a proximal firing shaft portion that extends through the outer shaft 411 of the shaft assembly 410 and operably interfaces with a source of rotary firing motions supported in or by the housing or robotic system. The firing drive may further comprise an intermediate firing drive shaft portion that bridges the articulation joint(s) and a distal firing drive shaft portion that is supported in the end effector 200. In one arrangement, the proximal firing drive shaft portion may comprise a rigid shaft segment, a flexible shaft segment, or a combination of rigid and flexible segments, for example. In one non-limiting arrangement, the intermediate firing drive shaft portion may comprise one universally movable joint (60200) or a series of movable joints or universally movable drive shaft segment (60700) that spans the articulation joint(s). The distal firing drive shaft portion may comprise a firing drive shaft arrangement supported in the end effector to apply drive motions to the firing member 270 in the various manners disclosed herein.

FIG. 282 illustrates a proximal closure drive shaft portion 68002, an intermediate closure drive shaft portion 68100, and a distal closure drive shaft portion 68300 employed in the surgical stapling assembly 400 described above. FIG. 282 also illustrates a proximal firing drive shaft portion 68004, an intermediate firing shaft portion 68500, and a distal firing shaft portion 68600.

FIG. 283 illustrates one example of an intermediate closure drive shaft portion 68100 in accordance with at least one aspect of the present disclosure. As can be seen in FIG. 283, a proximal closure drive shaft 68010 is attached to a closure coupler member 68110 for movement relative thereto. In at least one non-limiting arrangement, the closure coupler member 68110 is fabricated from a flexible material (polymer, rubber, etc.) that facilitates some torsional and axial flexure while remaining sufficiently rigid to effective transmit the rotary closure motions therethrough. For example, the closure coupler member 68110 comprises an elongate body 68112 that includes a proximal end 68114 and a distal end 68116 and a central portion 68118 that extends therebetween. The central portion 68118 has a central outer diameter that is less than an outer diameter of each of the proximal end 68114 and the distal end 68116 to facilitate axial flexing (arrow F).

The proximal closure drive shaft 68010 may comprise a rigid shaft segment, a flexible shaft segment (e.g., torsion cable, etc.) or a combination of rigid and flexible segments, for example. The proximal closure drive shaft 68010 may operably interface with a source of rotary closure motions (e.g., a motor, etc.) that is operably supported by or in a housing or portion of a robotic system, for example. In the illustrated arrangement, the proximal closure drive shaft 68010 comprises a bulbous distal end 68012 that is received in a proximal socket 68120 in the proximal end 68114 of the closure coupler member 68110. The bulbous distal end 68012 of the proximal closure drive shaft 68010 is pivotally coupled to the proximal end 68114 of the closure coupler member 68110 by a proximal closure pin 68130 that is received in an X-shaped passage 68014 in the bulbous distal end 68012 of the proximal closure drive shaft 68010. It will be appreciated that the X-shaped passage 68014 facilitates some pivotal travel between the proximal closure drive shaft 68010 and the closure coupler member 68110.

The closure coupler member 68110 is operably coupled to a distal closure drive shaft 68300 which comprises the closure drive shaft segment 475 depicted in FIG. 13 and includes a closure coupler shaft 68310 that operably interfaces with the closure screw 251 as will be discussed in further detail below. In at least one arrangement, the closure coupler shaft 68310 comprises a bulbous proximal end 68312 that is received in a distal socket 68122 of the closure coupler member 68110. The bulbous proximal end 68312 of the closure coupler shaft 68310 is pivotally coupled to the distal end 68116 of the closure coupler member 68110 by a distal closure pin 68132 that is received in an X-shaped passage 68314 in the bulbous proximal end 68312 of the closure coupler shaft 68310. It will be appreciated that the X-shaped passage 68314 facilitates some pivotal travel between the closure coupler shaft 68310 and the closure coupler member 68110. As can be seen in FIG. 283, the intermediate closure drive shaft portion 68100 is housed within the articulation component support structure 440. In at least one arrangement, the articulation component support structure 440 is fabricated from a flexible material such as polymer, rubber, etc. and has an accordion-like shape to facilitate axial and bending flexure.

FIG. 284 illustrates one example of an intermediate firing drive shaft portion 68500 in accordance with at least one aspect of the present disclosure. As can be seen in FIG. 284, a proximal firing drive shaft 68020 is attached to a firing coupler member 68510 for movement relative thereto. In at least one non-limiting arrangement, the firing coupler member 68510 is fabricated from a flexible material (polymer, rubber, etc.) that facilitates some torsional flexure, bending flexure, and/or axial flexure while remaining sufficiently rigid to effective transmit the rotary closure motions therethrough. For example, the firing coupler member 68510 comprises an elongate body 68512 that includes a proximal end 68514 and a distal end 68516 and a central portion 68518 that extends therebetween. The central portion 68518 has a central outer diameter that is less than an outer diameter of each of the proximal end 68514 and the distal end 68516 to facilitate axial flexing (arrow F).

The proximal firing drive shaft 68020 may comprise a rigid shaft segment, a flexible shaft segment (e.g., torsion cable, etc.) or a combination of rigid and flexible segments, for example. The proximal firing drive shaft 68020 may operably interface with a source of rotary firing motions (e.g., a motor, etc.) that is operably supported by or in a housing or portion of a robotic system, for example. In the illustrated arrangement, the proximal firing drive shaft 68020 comprises a bulbous distal end 68022 that is received in a proximal socket 68520 in the proximal end 68514 of the firing coupler member 68510. The bulbous distal end 68022 of the proximal firing drive shaft 68020 is pivotally coupled to the proximal end 68514 of the firing coupler member 68510 by a proximal firing pin 68630 that is received in an X-shaped passage 68024 in the bulbous distal end 68022 of the proximal firing drive shaft 68020. It will be appreciated that the X-shaped passage 68024 facilitates some pivotal travel between the proximal firing drive shaft 68020 and the firing coupler member 68510.

The firing coupler member 68510 is operably coupled to a distal firing drive shaft portion 68600 which comprises the firing drive shaft segment 476 depicted in FIG. 13 and includes a firing coupler shaft 68610 that operably interfaces with the firing screw 261 as will be discussed in further detail below. In at least one arrangement, the firing coupler shaft 68610 comprises a bulbous proximal end 68612 that is received in a distal socket 68522 of the firing coupler member 68510. The bulbous proximal end 68612 of the firing coupler shaft 68610 is pivotally coupled to the distal end 68516 of the firing coupler member 68510 by a distal firing pin 68532 that is received in an X-shaped passage 68614 in the bulbous proximal end 68612 of the firing coupler shaft 68610. As can be seen in FIG. 284, the intermediate firing drive shaft portion 68500 is housed within the articulation component support structure 440. It will be appreciated that the X-shaped passage 68614 facilitates some pivotal travel between the firing coupler shaft 68610 and the firing coupler member 68510.

FIG. 285 comprises a longitudinally extending cross-sectional view of a proximal end portion of the end effector 200 illustrating the distal closure drive shaft portion 68300 and the distal firing drive shaft portion 68600. In the illustrated arrangement, the distal closure drive shaft portion 68300 comprises the closure screw 251 that is rotatably supported the cartridge channel 210 by a channel mounting fixture 68700 that is mounted within a proximal end of the cartridge channel 210. The channel mounting fixture 68700 facilitates rotation of the closure screw 251 while preventing axial movement thereof. The closure screw 251 comprises a series of closure drive threads that threadably interface with a threaded passage in the closure wedge 255. Rotation of the closure screw 251 in a first rotary direction will cause the closure wedge 255 to axially move in a first axial direction and rotation of the closure screw 251 in a second rotary direction opposite to the first rotary direction will cause the closure wedge 255 to axially move in a second axial direction. For example, rotation of the closure screw 251 in a first rotary direction may cause the closure wedge 255 to axially move in a distal direction DD to apply a closure motion to the anvil 203. Rotation of the closure screw 251 in a second rotary direction may cause the closure wedge 255 to axially move in a proximal direction to apply an opening motion to the anvil 203.

Still referring to FIG. 285, the closure screw 251 defines a distal closure shaft axis DC-DC and includes a proximal mounting flange 68712 and a closure coupler stem 68710 that protrudes proximally from the proximal mounting flange 68712 and is axially aligned on the distal closure shaft axis DC-DC. The closure coupler stem 68710 has a non-circular cross-sectional shape and is adapted to be movably and non-rotationally received in a coupler socket 68316 in a distal end of the closure coupler shaft 68310. In one non-limiting arrangement, as can be seen in FIG. 286, closure coupler stem 68710 has a square cross-sectional shape. Other arrangements may, for example, have a hexagonal cross-sectional shape. Coupler socket 68316 has a similar square shape and is configured to facilitate axial movement of the closure coupler shaft 68310 relative to the closure screw 251 while transmitting rotary closure motions (torque) thereto. Such slidable coupling arrangement may also avoid binding and stackup between the coupled drive portions. The proximal mounting flange 68712, as well as the coupler socket 68316, is freely rotatable in an opening 68714 in the second shaft joint component 450. A socket flange 68318 is provided on a distal end of the coupler socket 68316 which serves to limit the proximal travel of the coupler socket 68316 when the socket flange 68318 contacts an end of the opening 68714. The closure coupler stem 68710 is sized relative to the coupler socket 68316 such that when the coupler socket 68316 has reached the limit of its proximal travel, the closure coupler stem 68710 remains in operable engagement with the coupler socket 68316 to prevent the closure screw 251 from becoming disconnected from the closure coupler shaft 68310.

In the illustrated arrangement, the distal firing drive shaft portion 68600 comprises the firing screw 261 screw that is rotatably supported the cartridge channel 210 by the channel mounting fixture 68700. The channel mounting fixture 68700 facilitates rotation of the firing screw 261 while preventing axial movement thereof. The firing screw 261 comprises a series of closure drive threads that threadably interface with a threaded passage in a threaded drive nut that is configured to operably interface with the firing member 270 or a threaded passage in the firing member 270 itself. Rotation of the firing screw 261 in a first rotary direction will cause the firing member 270 to axially move in a first axial direction and rotation of the firing screw 261 in a second rotary direction opposite to the first rotary direction will cause the firing member 270 to axially move in a second axial direction. For example, rotation of the firing screw 261 in a first rotary direction may cause the firing member 270 to axially move in a distal direction DD and rotation of the firing screw 261 in a second rotary direction may cause the firing member 270 to axially move in a proximal direction PD.

Still referring to FIG. 285, the firing screw 261 defines a distal firing shaft axis DF-DF and includes a proximal mounting flange 68722 and a firing coupler stem 68720 that protrudes proximally from the proximal mounting flange 68722 and is axially aligned on the distal firing shaft axis DF-DF. The firing coupler stem 68720 has a non-circular cross-sectional shape and is adapted to be movably and non-rotationally received in a coupler socket 68616 in a distal end of the firing coupler shaft 68610. In one non-limiting arrangement, the firing coupler stem 68720 has a square cross-sectional shape. Other arrangements may, for example, have a hexagonal cross-sectional shape. Coupler socket 68616 has a similar square shape and is configured to facilitate axial movement of the firing coupler shaft 68610 relative to the firing screw 261 while transmitting rotary (torque) firing motions thereto. Such slidable coupling arrangement may also avoid binding and stackup between the coupled drive portions.

The proximal mounting flange 68722 as well as the coupler socket 68616, are freely rotatable in an opening 68724 defined in the cartridge channel 210 and the channel mounting fixture 68700. A socket flange 68618 is provided on a distal end of the coupler socket 68616 which serves to limit the proximal travel of the coupler socket 68616 when the socket flange 68618 contacts an end of the opening 68724. The firing coupler stem 68720 is sized relative to the coupler socket 68616 such that when the coupler socket 68616 has reached the limit of its proximal travel, the firing coupler stem 68720 remains in operable engagement with the coupler socket 68616 to prevent the firing screw 261 from becoming disconnected from the firing coupler shaft 68610.

FIG. 287 illustrates intermediate closure drive shaft portion 69100 and an intermediate firing drive shaft portion 69500 employed in the surgical stapling assembly 500 described above. The intermediate closure drive shaft portion 69100 is configured to be operably attached to a distal closure drive shaft portion 68300' which may comprise the closure drive shaft segment 575 depicted in FIG. 16 and is substantially similar to the distal closure drive shaft portion 68300 described above. In this embodiment, the intermediate closure drive shaft portion 69100 includes closure coupler member 69110 that comprises a solid cylindrical body that is coupled to the proximal closure drive shaft portion 68002 and the distal closure drive shaft portion 68300' in the manners described above. In at least one non-limiting arrangement, the closure coupler member 69110 is fabricated from a flexible material (polymer, rubber, etc.) that facilitates some torsional and axial flexure while remaining sufficiently rigid to effective transmit the rotary closure motions therethrough. Similarly, the intermediate firing drive shaft portion 69500 is configured to be operably attached to a distal firing drive shaft portion 68600' which comprises the firing drive shaft 576 depicted in FIG. 16 and is substantially similar to the distal firing drive shaft portion 68600 described above. In this embodiment, the intermediate firing drive shaft portion 69500 includes firing coupler member 69510 that comprises a solid cylindrical body that is coupled to the proximal firing drive shaft portion 68004 in the manners described above. In at least one non-limiting arrangement, the firing coupler member 69510 is fabricated from a flexible material (polymer, rubber, etc.) that facilitates some torsional and axial flexure while remaining sufficiently rigid to effective transmit the rotary closure motions therethrough.

The closure and drive shaft arrangements depicted in FIGS. 282-287 comprise dual rotary drive systems wherein the first (distal) portions are prevent from moving axially and the second portions (intermediate) portion is slidably coupled thereto. Each rotary drive comprises three portions: a proximal portion located in the shaft assembly, a distal portion located in the end effector, and an intermediate portion that bridges the articulation joint(s). The intermediate portion could comprise one or more universally movable joints or a torsion cable coupling. The distal portion is fixed longitudinally to the end effector and the proximal portion is fixed to a retainer in the shaft to prevent either of those portions from moving longitudinally or axially, for example. The intermediate portion may be slidably coupled to either one or both of the proximal and distal portions. The sliding coupling could be coupled to either or both ends of the distal portion and proximal portion or it may comprise a separate sliding aspect. These arrangements allow the intermediate portion to become effectively longer or shorter as the articulation joint(s) go through the range of motion. The sliding coupling of the intermediate portion to the distal portion and/or the proximal portion could be fixed within a chamber that allows the distal end/or proximal portion to slide but limits the maximum sliding distance. This prevents the drive from becoming separated if the articulation joint becomes hyperextended. The sliding couple is a square or hexagonal geometry that facilitates torque transmission but allows for allows for longitudinal sliding of the coupled drives. The dual intermediate portions are also supported by the articulation joint support structures that bridge the articulation joint. The coupling structures of the articulation joints allow for fixed-floating, fixed-fixed (but bendable), fixed-sliding, and/or sliding-sliding coupling of components.

FIG. 288 illustrates the end effector 200 and articulation region 110 described above (FIGS. 1-6) in cross-section. As described above, the flexible drive segments 175, 176 each consist of universally movable joints arranged or formed "end-to-end". For example, the drive segments 175, 176 may each comprise a plurality of universally movable joints 60200 arranged end-to-end or the drive segments 175, 176 may comprise a universally movable drive shaft segment 60700 that was manufactured utilizing the additive manufacturing systems and processes described and contemplated herein. In one non-limiting arrangement for example, the closure drive 250 comprises a proximal closure drive shaft portion 69200 that extends through the outer shaft 411 of the shaft assembly 410 and operably interfaces with a source of rotary closure motions supported in or by the housing or robotic system (not shown). The proximal closure drive shaft portion 69200 may comprise, for example, a torsion cable 69202, a laser cut flexible shaft or other flexible rotary drive member, a rigid rotary drive member or a combination of a rigid rotary drive member(s) and a flexible rotary drive member(s). As can be seen in FIG. 288, the proximal closure drive shaft portion 69200 is coupled to an intermediate closure drive shaft portion 69300 that bridges both of the articulation joints in the articulation joint region 110 that comprises the flexible drive shaft segment 175. The flexible drive shaft segment 175 is coupled to a distal closure drive shaft portion 69400 that comprises a closure drive shaft arrangement that is supported in the end effector to apply opening and closing motions to the anvil in the various manners disclosed herein.

Still referring to FIG. 288, in one non-limiting form, the distal closure drive shaft portion 69400 comprises a closure coupler shaft 69410 that operably interfaces with the closure screw 251 in the manner described herein. In at least one arrangement, the closure coupler shaft 69410 is integrally formed with the flexible drive shaft segment such that the closure coupler shaft 69410 is printed with the flexible drive shaft segment 175 utilizing the additive manufacturing systems and processes described and contemplated herein. In other arrangements, the closure coupler shaft 69410 is otherwise attached to a distal-most universally movable joint member 60200D in the flexible drive shaft segment 175 by welding, adhesive, threads, etc. As discussed above, the closure screw 251 includes a proximal mounting flange 68712 and a closure coupler stem 68710 that protrudes proximally from the proximal mounting flange 68712. The closure coupler stem 68710 has a non-circular cross-sectional shape and is adapted to be movably and non-rotationally received in a coupler socket 69416 in a distal end of the closure coupler shaft 69410. The closure coupler stem 68710 has a square cross-sectional shape. Other arrangements may, for example, have a hexagonal cross-sectional shape. Coupler socket 68316 has a similar square shape and is configured to facilitate axial movement of the closure coupler shaft 69410 relative to the closure screw 251 while transmitting rotary closure motions (torque) thereto. Such slidable coupling arrangement may also avoid binding and stackup between the coupled drive portions. The proximal mounting flange 68712, as well as the coupler socket 69416, is freely rotatable in an opening 68714 in the second shaft joint component 450.

In one aspect, the firing drive comprises a proximal firing drive shaft portion 69500 that extends through the outer shaft 411 of the shaft assembly 410 and operably interfaces with a source of rotary firing motions that is supported in or by the housing or robotic system. The proximal firing drive shaft portion 69500 may comprise, for example, another torsion cable 69502, laser-cut flexible shaft or another flexible rotary drive member, another rigid rotary drive member or a combination of another rigid rotary drive member and another flexible rotary drive member. As can be seen in FIG. 288, the proximal firing drive shaft portion 69500 is coupled to an intermediate firing drive shaft portion 69600 that bridges both of the articulation joints in the articulation joint region 110 that comprises the flexible drive shaft segment 176. The flexible drive shaft segment 176 is coupled to a distal firing drive shaft portion 69700 that comprises a firing drive shaft arrangement supported in the end effector to apply firing drive motions to the firing member 270 in the various manners disclosed herein.

Still referring to FIG. 288, in one non-limiting form, the distal firing drive shaft portion 69700 comprises the flexible drive shaft segment 176 and includes a firing coupler shaft 69710 that operably interfaces with the firing screw 261 as was described above. In at least one arrangement, the firing coupler shaft 69710 is integrally formed with the flexible drive shaft segment 176 such that the firing coupler shaft 69710 is printed with the flexible drive shaft segment 176 utilizing the additive manufacturing systems and processes described and contemplated herein. In other arrangements, the firing coupler shaft 69710 is otherwise attached to a distal-most universally movable joint member 60200DF in the flexible drive shaft segment 176 by welding, adhesive, threads, etc.

In the illustrated arrangement, the distal firing drive shaft portion 69700 comprises the firing screw 261 that is rotatably supported the cartridge channel 210 by the channel mounting fixture 68700. The channel mounting fixture 68700 facilitates rotation of the firing screw 261 while preventing axial movement thereof. The firing screw 261 comprises a series of closure drive threads that threadably interface with a threaded passage in a threaded drive nut configured to operably interface with the firing member 270 or a threaded passage in the firing member 270 itself. Rotation of the firing screw 261 in a first rotary direction will cause the firing member 270 to axially move in a first axial direction and rotation of the firing screw 261 in a second rotary direction opposite to the first rotary direction will cause the firing member 270 to axially move in a second axial direction.

Still referring to FIG. 288, the firing screw 261 includes a firing coupler stem 68720 that protrudes proximally. The firing coupler stem 68720 has a non-circular cross-sectional shape and is adapted to be movably and non-rotationally received in a coupler socket 69716 in a distal end of the firing coupler shaft 69710. In one non-limiting arrangement, the firing coupler stem 68720 has a square cross-sectional shape. Other arrangements may, for example, have a hexagonal cross-sectional shape. Coupler socket 69716 has a similar square shape and is configured to facilitate axial movement of the firing coupler shaft 69710 relative to the firing screw 261 while transmitting rotary (torque) firing motions thereto. Such slidable coupling arrangement may also avoid binding and stackup between the coupled drive portions. Thus, rotation of the proximal closure shaft portion 69200 in a first rotary direction will drive the closure wedge 255 distally to move the anvil jaw 203 to pivot to the closed position shown in FIG. 288. Rotation of the proximal closure shaft portion 69200 in an opposite rotary direction will drive the closure wedge 255 proximally to pivot the anvil jaw 203 into an open position. After the anvil jaw 203 has been moved to the closed position to clamp target tissue between the anvil jaw 203 and the staple cartridge 220, rotation of the proximal firing shaft portion 69500 in a first direction will cause the firing member 270 to move distally within the staple cartridge 220 to drive the staples therefrom and cut through the clamped tissue in the manner described herein. Rotation of the proximal firing shaft portion 69500 in an opposite rotary direction will cause the firing member 270 to move proximally back to a starting position in which the anvil jaw 203 may be moved to the open position to release the cut and stapled tissue.

FIGS. 289-291 illustrate a portion of a surgical stapling instrument 10' that is substantially similar to the surgical stapling instrument 10 described above, except for the differences described in detail below. In particular, instead of the flexible drive shaft segments 175, 176 that are formed from universally movable joints, the surgical stapling instrument employs a closure drive 250' comprises flexible closure drive shaft 69210 that extends through the outer shaft 101 of the shaft assembly 100 and operably interfaces with a source of rotary closure motions that is supported in or by the housing or robotic system (not shown). The flexible closure drive shaft 69210 may comprise, for example, a torsion cable, a laser cut flexible shaft or other flexible rotary drive member, a rigid rotary drive member or a combination of a rigid rotary drive member(s) (portion(s) inside the outer shaft 101) and a flexible rotary drive member(s) (portion(s) that spans the articulation region 110). As can be seen in FIG. 291, the flexible closure drive shaft 69210 is coupled to the closure screw 251 to apply rotary closure motions thereto to open and close the anvil jaw 203 in the manners described herein.

As can be further seen in FIGS. 290 and 291, the firing drive 260' comprises a flexible firing drive shaft 69520 that extends through the outer shaft 101 of the shaft assembly 100 and operably interfaces with a source of rotary firing motions supported in or by the housing or robotic system (not shown). The flexible firing drive shaft 69520 may comprise, for example, a torsion cable, a laser cut flexible shaft or other flexible rotary drive member, a rigid rotary drive member or a combination of a rigid rotary drive member (portion inside the outer shaft 101) and a flexible rotary drive member (portion that spans the articulation region 110). As can be seen in FIG. 291, the flexible firing drive shaft 69520 is coupled to the firing screw 261 to apply rotary firing motions thereto to move the firing member 270 through the end effector 200 in the manners described herein. In this arrangement, the portions of the flexible closure drive shaft 69210 and the flexible firing drive shaft 69520 that span the articulation region 110 are supported in a flexible shaft guide 69000.

Figure 56:
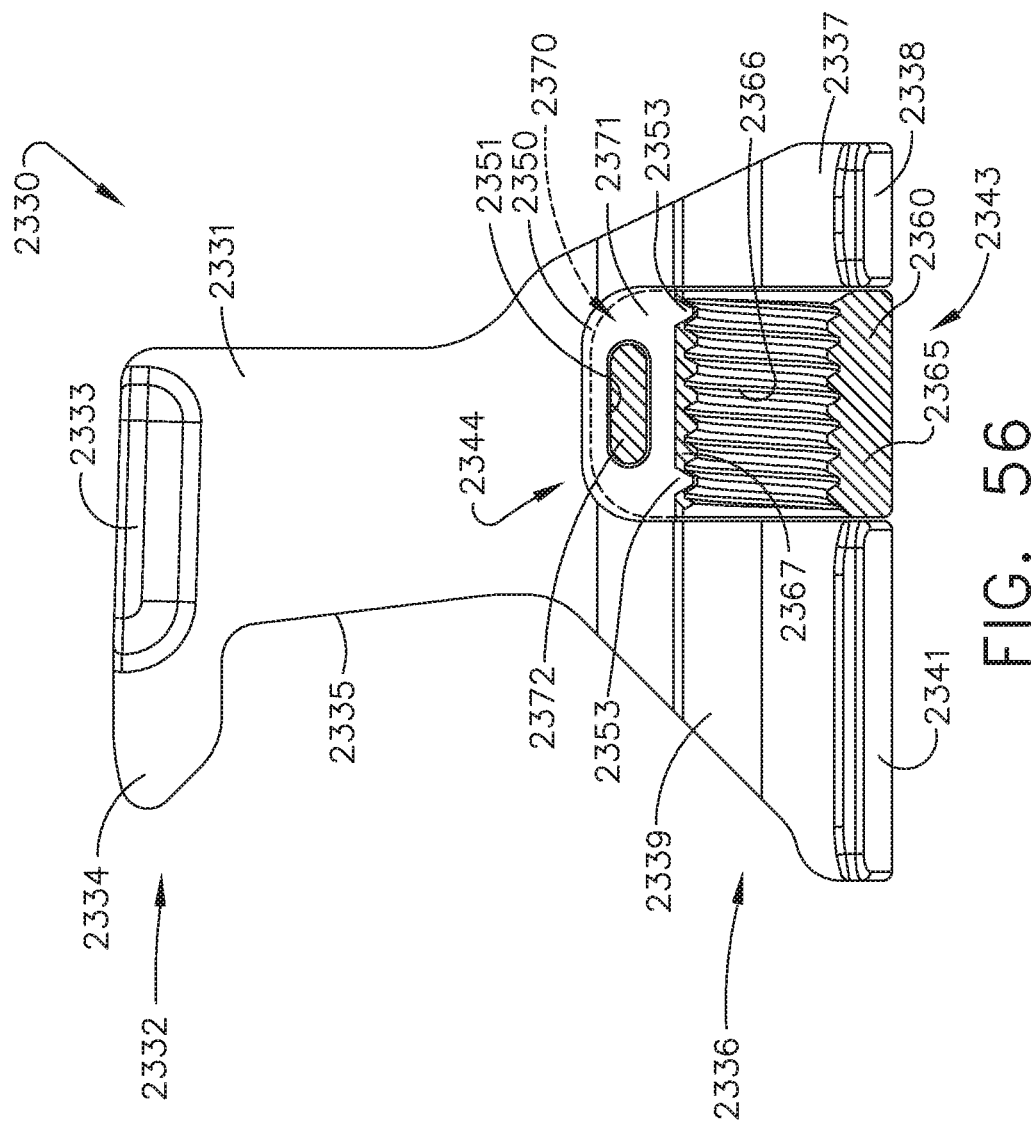
FIG. 56 is a partial cross-sectional elevation view of the firing member assembly of FIG. 53, in accordance with at least one aspect of the present disclosure.

FIGS. 292-300 illustrate one form of a shaft guide 69000 that may be employed in connection with the shaft assembly 100. In the illustrated example, the shaft guide 69000 comprises a shaft guide body 69010 that is sized to space across the articulation region 110. The shaft guide body 69010 comprises a shaft guide proximal end 69020 and a shaft guide distal end 69030 and defines a shaft guide axis SGA that extends between the shaft guide proximal end 69020 and the shaft guide distal end 69030. The shaft guide body 69010 further comprises a first passage 69022 that extends through the shaft guide body 69010 from the shaft guide proximal end 69020 to the shaft guide distal end 69030. In the illustrated example, the first passage 69022 opens through the shaft guide proximal end 69020 on a first side $FRP_1$ of a first reference plane FRP-FRP (FIG. 55) and opens through the shaft guide distal end 69030 on a first side $SRP_1$ of a second reference plane SRP (FIG. 56). In the illustrated arrangement, a central portion 69024 of the first passage 69022 at least partially passes through one or both of the first reference plane FRP and the second reference plane SRP.

Still referring to FIGS. 293 and 294, the shaft guide body 69010 further comprises a second passage that extends through the shaft guide body 69010 from the shaft guide proximal end 69020 to the shaft guide distal end 69030. The second passage 69026 opens through the shaft guide proximal end 69020 on a second side $FRP_2$ of the first reference plane FRP (FIG. 55) and opens through the shaft guide distal end 69030 on a second side $SRP_2$ of the second reference plane SRP (FIG. 56). In the illustrated arrangement, a central portion 69028 of the second passage 69026 at least partially passes through one or both of the first reference plane FRP and the second reference plane SRP. As can be seen in FIG. 293, a proximal end 69023 of the first passage 69022 is bisected by the second reference plane SRP and a proximal end 69027 of the second passage 69026 is also bisected by the second reference plane SRP. As can be seen in FIG. 294, a distal end 69025 of the first passage 69022 is bisected by the first reference plane FRP and a distal end 69029 of the second passage 69026 is bisected by eth first reference plane FRP.

In at least one arrangement, the shaft guide 69000 is fabricated from a bendable elastic or ductile material (e.g., polypropylene, low density polyethylene, liquid crystal polymer (LCP), Nylon, etc.) that facilitates twisting flexure of the shaft guide 69000 when the end effector 200 is articulated about at least one of the first articulation axis AA1-AA1 and the second articulation axis AA2-AA2. The shaft guide body 69010 comprises a central body portion 69012 that extends between the shaft guide proximal end 69020 and the shaft guide distal end 69030. In at least one non-limiting example, the central body portion 69012 comprises central bulbous portion 69014 which may further facilitate such flexure during articulation. Further, in at least one arrangement, the shaft guide body 69010 comprises a proximal necked down portion 69016 that is located between the central bulbous portion 69014 and the shaft guide proximal end 69020 and which essentially coincides with the first articulation axis AA1-AA1. The proximal necked down portion 69016 may be formed by a first pair of opposed proximal scallops 69017 that correspond to the first articulation axis AA1-AA1. See FIG. 292. The shaft guide body 69010 may further comprise a distal necked down portion 69018 that is located between the central bulbous portion 69014 and the shaft guide distal end 69030 and which essentially coincides with the second articulation axis AA2-AA2. The distal necked down portion 69018 may be formed by a second pair of opposed distal scallops 69019 that correspond to the second articulation axis AA2-AA2. Such "necked-down" or "reduced diameter" segments further facilitate flexure of the shaft guide 69000 during articulation of the end effector 200.

As can be seen in FIG. 293, in at least one arrangement, the shaft guide proximal end 69020 comprises an oval or egg shape that is aligned on a proximal long axis PLA that is aligned with the second reference plane SRP. Likewise, as can be seen in FIG. 294, the shaft guide distal end 69030 comprises an oval or egg shape that is aligned on a distal long axis DLA-DLA that is aligned with the first reference plane FRP.

As can be seen in FIG. 291, the shaft guide 69000 spans the articulation region 110 and the shaft guide distal end 69030 is supported in and/or coupled to the distal shaft feature 140 and the shaft guide proximal end 69020 is supported in and/or attached to the proximal shaft feature 120. In the illustrated arrangement, the flexible drive shaft segment 175 is received within the first passage 69022 and the flexible drive shaft segment 176 is received within the second passage 69026. The shaft guide proximal end 69020 is coupled to a portion of the proximal shaft feature 120 and the shaft guide distal end 69030 is coupled to the distal shaft feature 140. The flexible drive shaft segment 175 operably extends through the first passage 69022 and the flexible drive shaft segment 176 extends through the second passage 69026. In the illustrated example, the proximal closure drive shaft portion 69200 extends through the outer shaft 101 of the shaft assembly 100 and is located on one lateral side of the shaft guide axis SGA to be coupled to the intermediate closure drive shaft portion 69300 (flexible drive shaft segment 175) supported in the first passage 69022 in the shaft guide 69000. Likewise, the proximal firing drive shaft portion 69500 extends through the outer shaft 101 of the shaft assembly 100 and is located on another lateral side of the shaft guide axis SGA to be coupled to the intermediate firing drive shaft portion 69600 (flexible drive shaft segment 176) that is supported in the second passage 69026 in the shaft guide 69000. Thus, when the intermediate closure drive shaft portion 69300 and the intermediate firing drive shaft portion 69600 enter the shaft guide proximal end 69020, the intermediate closure drive shaft portion 69300 and the intermediate firing drive shaft portion 69600 are in a side-by-side relationship or configuration (one on each side of the shaft guide axis SGA). When the intermediate closure drive shaft portion 69300 and the intermediate firing drive shaft portion 69600 exit the shaft guide distal end in a vertically stacked relationship wherein the intermediate closure drive shaft portion 69300 is above the intermediate firing drive shaft portion 69600.

In one instance, the first passage 69022 and the second passage 69026 twist as they go from the shaft guide proximal end 69020 to the shaft guide distal end 69030. The shaft guide 69000 comprises a support for the intermediate closure drive shaft portion 69300 and the intermediate firing drive shaft portion 69600 that avoids forming a preferred bend plane. The shaft guide 69000 spans two, in-series articulation joints of a multi-axis joint arrangement without forming a preferred bending orientation. In at least one arrangement, the multi-axis joint arrangement facilitates articulation of the end effector through two articulation angles about articulation axes AA1-AA1, AA2-AA2, that are each at least approximately 75 degrees in magnitude. The exterior profile of the shaft guide 69000 as well as each of the first passage 69022 and the second passage 69026 can twist to minimize its bending resistance by aligning its minimum moment of inertia plane to that of the articulation axes. In alternative arrangements, each of the first passage 69022 and the second passage 69026 may twist multiple times between the shaft guide proximal end 69020 and the shaft guide distal end 69030. In such instances, for example, each of the first passage 69022 and the second passage 69026 may pass through each of the first reference plane FRP and the second reference plane SRP multiple times.

In accordance with at least one aspect of the present disclosure, the proximal end 69027 of the second passage 69026 opens through the shaft guide proximal end 69020 in a "first orientation" relative to the proximal end 69023 of the first passage 69022. In the example illustrated in FIG. 293, the proximal end 69027 of the second passage 69026 is horizontally spaced from or "horizontally aligned" with the proximal end 69023 of the first passage 69022. Other first orientations are contemplated. Also in accordance with at least one aspect of the present disclosure, the distal end 69029 of the second passage 69026 is oriented in a "second orientation" relative to the distal end 69025 of the first passage 69022 that differs from the first orientation. For example, as can be seen in FIG. 294, the second passage distal end 69029 is located below the first passage distal end 69025. Stated another way the first passage distal end 69025 and the second passage distal end 69029 are "vertically stacked" with each other or "vertically aligned" with each other. Other second orientations are contemplated. In still other applications, the shaft guide 69000 may be installed in a reversed orientation between the surgical end effector and the shaft assembly so that the shaft guide proximal end 69020 will actually be distal to the shaft guide distal end 69030. Thus, in such arrangement, the drive shafts entering the shaft guide 69000 will be vertically stacked relative to each other and they will exit the shaft guide 69000 in a horizontally spaced orientation, for example.

FIG. 301 illustrates a portion of another surgical stapling instrument 70010 that comprises an elongate shaft assembly 100 that may be operably coupled to a housing of a surgical instrument or portion of a robotic system of the various types and forms described and contemplated herein. The elongate shaft assembly 100 is operably coupled to an end effector 200 by an articulation joint assembly 71000. The end effector 200 may comprise a variety of different end effectors configured to perform a particular surgical function. In the illustrated arrangement, the end effector 200 is configured to clamp, staple, and cut tissue of a patient. However, other forms of end effectors may be employed. In this example, the end effector 200 comprises a cartridge jaw 201 and an anvil jaw 203. The anvil jaw 203 is pivotable relative to the cartridge jaw 203 to clamp tissue between the anvil jaw 203 and the cartridge jaw 201. Once tissue is clamped between the jaws 201, 203, the surgical stapling instrument 70010 may be actuated to advance a firing member through the jaws 201, 203 to staple and cut tissue with the end effector 200 as discussed in greater detail below.

To open and close the anvil jaw 203 relative to the cartridge jaw 201, a closure drive 250 is provided. See FIG. 302. The closure drive 250 is actuated by a flexible closure drive shaft 72000 that may comprise a flexible shaft segment (e.g., torsion cable, laser cut shaft, etc.) or a combination of rigid segment(s) and flexible segment(s), for example that operably interface with a source of rotary closure motions supported in or by the housing or robotic system. Discussed in greater detail below, the flexible closure drive shaft 72000 is driven by a closure input shaft 72010 that extends through the shaft assembly 100 and operably interfaces with a source of rotary closure motions (e.g., a motor) supported in a housing of the surgical instrument or portion of a robotic system. The flexible closure drive shaft 72000 transmits rotary actuation motions through the articulation joint assembly 71000. The closure drive 250 comprises a closure screw 251 and a closure wedge 255 that is threadably coupled to the closure screw 251. The closure wedge 255 is configured to positively cam the anvil jaw 203 open and closed in the various manners described herein. The closure screw 251 is supported by a first support body 258 and a second support body 259 secured within the channel 210. See FIG. 302.

To move the anvil jaw 203 between a clamped position and an unclamped position, the closure input shaft 72010 is actuated (rotated) to actuate (rotate) the flexible closure drive shaft 72000. The flexible closure drive shaft 72000 is coupled to the closure screw 251 by a coupler 72012 and is configured to rotate the closure screw 251, which displaces the closure wedge 255. For example, the closure wedge 255 is threadably coupled to the closure screw 251 and rotational travel of the closure wedge 255 with the staple cartridge 220 is restrained. The closure screw 251 drives the closure wedge 255 proximally or distally depending on which direction the closure screw 251 is rotated.

As discussed above, the surgical stapling instrument 70010 may be actuated to advance a firing member through the jaws 201, 203 to staple and cut tissue with the end effector 200. As was discussed above, staples that are stored in the staple cartridge 220 are deployed when a sled (not shown in FIG. 302) is driven distally through the staple cartridge 220. A knife (not shown) is operably supported on the sled and serves to cut tissue clamped between the anvil 203 and the cartridge 220 as the sled is driven distally through the staple cartridge 220 by a firing member 270. The firing member 270 is driven distally through the end effector 200 by a firing drive 260. The firing drive 260 is actuated by a flexible firing drive shaft 72100. The flexible firing drive shaft 72100 comprises a flexible shaft segment (e.g., torsion cable, laser cut flexible shaft, etc.) or a combination of rigid and flexible segments, for example, that operably interface with a source of rotary firing motions (e.g., firing drive motor) that is supported in or by the housing of the surgical instrument or robotic system. The flexible firing drive shaft 72100 is driven by a firing input shaft 72110 that extends through the shaft assembly 100. The flexible firing drive shaft 72100 transmits rotary actuation motions through the articulation joint assembly 71000 to a firing screw 261 that comprises a portion of the firing drive 260. The firing screw 261 comprises journals supported within bearings in the support member 259 and the channel 210. The firing screw 261 comprises a proximal end 262 supported within the support member 259 and the channel 210, a distal end 263 supported within the channel 210, and threads 265 extending along a portion of the length of the firing screw 261.

The firing member 270 is threadably coupled to the firing screw 261 such that as the firing screw 261 is rotated, the firing member 270 is advanced distally or retracted proximally along the firing screw 261. Specifically, the firing member 270 comprises a body portion 271 comprising a hollow passage 272 defined therein. The firing screw 261 is configured to be received within the hollow passage 272 and is configured to be threadably coupled with a threaded component 273 of the firing member 270. Thus, as the firing screw 261 is rotated, the threaded component 273 applies a linear force to the body portion 271 to advance the firing member 270 distally or retract the firing member 270 proximally. As the firing member 270 is advanced distally, the firing member 270 pushes the sled (not shown) that is movable supported in the staple cartridge 220. Distal movement of the sled causes the ejection of the staples by engaging the plurality of staple drivers, as described above. The flexible firing drive shaft 72100 is coupled to the firing screw 261 by a coupler 72112 and is configured to rotate the firing screw 251, which displaces the firing member 270.

Still referring to FIG. 302, one form of the articulation joint assembly 71000 comprises a proximal mounting member 71100 that is configured to interface with the shaft assembly 100 of the surgical stapling instrument 70010. For example, the proximal mounting member 71100 may be welded or attached to a distal portion of the shaft assembly 100 by any suitable means. In other arrangements, the proximal mounting member 71100 may comprise a portion of the shaft assembly 100. The articulation joint assembly 71000 further comprises a distal joint shaft component or distal mounting member 71300. The distal mounting member 71300 may be welded or attached to a proximal portion of the surgical end effector 200 by any suitable means. In the illustrated arrangement for example, the distal mounting member 71300 is attached to the proximal end of the cartridge jaw 201 by a retention ring 146. In other arrangements, the distal mounting member 71300 may comprise a portion of the surgical end effector 200.

In the non-limiting example illustrated in FIGS. 301 and 302, the proximal mounting member 71100 comprises a proximal shaft hole 71110 that is axially aligned on a shaft axis SA-SA that is defined by the shaft assembly 100. See FIG. 307. Similarly, the distal mounting member 71300 comprises a distal shaft hole 71310. The distal shaft hole 71310 may have a diameter that is the same or similar to a diameter of the proximal shaft hole 71110. When the surgical end effector 200 is aligned on the shaft axis SA-SA with the shaft assembly 100, the distal shaft hole 71310 is aligned with the proximal shaft hole 71110.

Referring now to FIGS. 303-307, in at least one non-limiting example, the articulation joint assembly 71000 further comprises a linkage assembly 71400 that is coupled to and extends between the proximal mounting member 71100 and the distal mounting member 71300. In at least one form, the linkage assembly 71400 comprises a plurality of articulation link members that extend between the proximal mounting member 71100 and the distal mounting member 71300 and are attached thereto. The illustrated non-limiting example comprises three articulation link members 71500A, 71500B and 715000. Other numbers of articulation link members are contemplated. For example, a linkage assembly that only comprises two link members will work, but such linkage assembly may only facilitate articulation through a single plane.

In one non-limiting arrangement, articulation link member 71500A comprises a proximal link end 71510A, a link distal link end 71520A, and a link body 71530A. The proximal link end 71510A is coupled to the proximal mounting member 71100 at a first proximal attachment location 71120A by a first proximal joint assembly 71130A. In the illustrated example, the first proximal joint assembly 71130A comprises a pair of first proximal attachment lugs 71132A that protrude from the proximal mounting member 71100. A first proximal attachment link 71134A is pivotally coupled to the first proximal attachment lugs 71132A by a first proximal joint pin 71136A that defines a first proximal joint axis $FPJA_1$. The first proximal attachment link 71134A is pivotally attached to the proximal link end 71510A by a second proximal joint pin 71138A that defines a second proximal joint axis $SPJA_2$ that is transverse to the first proximal joint axis $FPJA_1$ as well as the shaft axis SA-SA.

In the illustrated example, the distal link end 71520A is coupled to the distal mounting member 71300 at a first distal attachment location 71320A by a first distal joint assembly 71330A. In the illustrated example, the first distal joint assembly 71330A comprises a pair of first distal attachment lugs 71332A that protrude from the distal mounting member 71300. A first distal attachment link 71334A is pivotally coupled to the first distal attachment lugs 71332A by a first distal joint pin 71336A that defines a first distal joint axis $FDJA_1$. The first distal attachment link 711334A is pivotally attached to the distal link end 71520A by a second distal joint pin 71338A that defines a second distal joint axis $SDJA_2$ that is transverse to the first distal joint axis $FDJA_1$ as well as the shaft axis SA-SA.

In one non-limiting arrangement, articulation link member 71500B comprises a proximal link end 71510B, a link distal link end 71520B, and a link body 71530B. The proximal link end 71510B is coupled to the proximal mounting member 71100 at a second proximal attachment location 71120B by a second proximal joint assembly 71130B. In the illustrated example, the second proximal joint assembly 71130B comprises a pair of second proximal attachment lugs 71132B that protrude from the proximal mounting member 71100. A second proximal attachment link 71134B is pivotally coupled to the second proximal attachment lugs 71132B by a first proximal joint pin 71136B that defines a third proximal joint axis $TPJA_3$. The second proximal attachment link 71134B is pivotally attached to the proximal link end 71510B by a second proximal joint pin 71138B that defines a fourth proximal joint axis $FPJA_4$ that is transverse to the third proximal joint axis $TPJA_3$ as well as the shaft axis SA-SA.

In the illustrated example, the distal link end 71520B is coupled to the distal mounting member 71300 at a second distal attachment location 71320B by a second distal joint assembly 71330B. In the illustrated example, the second distal joint assembly 71330B comprises a pair of second distal attachment lugs 71332B that protrude from the distal mounting member 71300. A second distal attachment link 71334B is pivotally coupled to the second distal attachment lugs 71332B by a first distal joint pin 71336B that defines a third distal joint axis $TDJA_3$. The second distal attachment link 71334B is pivotally attached to the distal link end 71520B by a second distal joint pin 71338B that defines a fourth distal joint axis $FDJA_4$ that is transverse to the third distal joint axis $TDJA_3$ as well as the shaft axis SA-SA.

In one non-limiting arrangement, articulation link member 715000 comprises a proximal link end 71510C, a link distal link end 71520C, and a link body 71530C. The proximal link end 71510C is coupled to the proximal mounting member 71100 at a third proximal attachment location 71120C by a third proximal joint assembly 71130C. In the illustrated example, the third proximal joint assembly 71130C comprises a pair of third proximal attachment lugs 71132C that protrude from the proximal mounting member 71100. A third proximal attachment link 71134C is pivotally coupled to the third proximal attachment lugs 71132C by a first proximal joint pin 71136C that defines a fifth proximal joint axis $FPJA_5$. The third proximal attachment link 71134C is pivotally attached to the proximal link end 71510C by a second proximal joint pin 71138C that defines a sixth proximal joint axis $SPJA_6$ that is transverse to the fifth proximal joint axis $TPJA_5$ as well as the shaft axis SA-SA. In one non-limiting example, the first proximal attachment location 71120A, the second proximal attachment location 71120B, and the third proximal attachment location 71120C are equally spaced about the shaft axis SA-SA. Stated another way, the angles between the first proximal attachment location 71120A, the second proximal attachment location 71120B, and the third proximal attachment location 71120C are each approximately 120°.

In the illustrated example, the distal link end 71520C is coupled to the distal mounting member 71300 at a third distal attachment location 71320C by a third distal joint assembly 71330C. In the illustrated example, the third distal joint assembly 71330C comprises a pair of third distal attachment lugs 71332C that protrude from the distal mounting member 71300. A third distal attachment link 71334C is pivotally coupled to the third distal attachment lugs 71332C by a first distal joint pin 71336C that defines a fifth distal joint axis $FDJA_3$. The third distal attachment link 71334C is pivotally attached to the distal link end 71520C by a second distal joint pin 71338C that defines a sixth distal joint axis $SDJA_6$ that is transverse to the fifth distal joint axis $FDJA_5$ as well as the shaft axis SA-SA. In one non-limiting example, the first distal attachment location 71320A, the second distal attachment location 71320B, and the third distal attachment location 71320C are equally spaced about the shaft axis SA-SA. Stated another way, the angles between the first distal attachment location 71320A, the second distal attachment location 71320B, and the third distal attachment location 71320C are each approximately 120°. In one arrangement, when the surgical end effector 200 is in an unarticulated position or, stated another way, axially aligned with the shaft assembly 100 on the shaft axis SA-SA, the first distal attachment location 71320A is diametrically opposite to the first proximal attachment location 71120A; the second distal attachment location 71320B is diametrically opposite to the second proximal attachment location 71120B; and the third distal attachment location 71320C is diametrically opposite to the third proximal attachment location 71120C.

In one aspect, the proximal shaft hole 71110 in the proximal mounting member 71100 and the distal shaft hole 71310 serve to define a central open passage area 72900. FIG. 308 illustrates an end view of articulation link member 71500A. As can be seen in FIG. 308, the link body 71530A comprises a curved surface 71532A that curves around the central open passage area 79200. The link body 72530B similarly has a curve surface 71532B and the link body 71530C has a curved surface 71532C. The curved surfaces

71532A, 71532B, 7532C cooperate to maintain the central open passage area 72900 regardless of the articulated position of the articulation joint assembly 71000. See e.g., FIGS. 304-305. It will be further appreciated that the length of the articulation joint assembly 71000 remains relatively constant during such articulation motions/positions. Stated another way, the distance DA between the proximal mounting member 71100 and the distal mounting member 71300 remains the same regardless of the articulation angle. Such range of articulation is facilitated because each of the link members 71500A, 71500B, 715000 may move (rotate) through a link path LP of approximately 180 degrees, for example. See FIG. 308.

FIG. 309 illustrates one form of a shaft guide 73000 that is configured to extend between the proximal mounting member 71100 and the distal mounting member 71300 while supporting the flexible closure drive shaft 72000 and the flexible firing drive shaft 72100 therein. In one aspect, the shaft guide 73000 comprises a shaft guide proximal end 73010, a shaft guide distal end 73020, and a central body portion 73030. The shaft guide proximal end 73010 comprises a proximal mounting collar 73012 that is configured to be rotatably supported within the proximal shaft hole 71110 in the proximal mounting member 71100. Similarly, the shaft guide distal end 73020 comprises a distal mounting collar 73022 that is configured to be rotatably supported in the distal shaft hole 71310 in the distal mounting member 71300. Such arrangement facilitates rotation of the shaft guide 73000 relative to the proximal mounting member 71100 and the distal mounting member 71300 while remaining affixed thereto. In another arrangement, the proximal mounting collar 73012 may additionally be configured relative to the proximal mounting member 71100 to facilitate some axial movement relative thereto as well. In addition to or in the alternative, the distal mounting collar 73022 may be configured to facilitate some axial movement relative to the distal mounting member 71300.

In one arrangement, the entire central body portion 73030 is flexible and may be fabricated from a ductile material (e.g., polypropylene, low density polyethylene, liquid crystal polymer (LCP), Nylon, etc.) that is configured to facilitate twisting flexure when the end effector is articulated. In another arrangement, for example, the central body portion 73030 comprises a relative rigid hollow center segment that may comprise a polymer, metal, etc. and be coupled to a proximal flexible segment that is coupled to the proximal mounting collar 73012 and a distal flexible segment that is coupled to the distal mounting collar 73022. The proximal flexible segment and the distal flexible segment may be fabricated from polymer, rubber, etc. that is more flexible than the center segment. In the embodiment illustrated in FIGS. 309 and 310, the shaft guide 73000 is fabricated from a single flexible material (polymer, rubber, etc.) and additionally includes a proximal flexible ribbed segment 73032 and a distal flexible ribbed segment 73034 formed therein to facilitate additional flexibility.

In the illustrated example, the shaft guide 73000 defines a central shaft guide axis SGA that extends from the shaft guide proximal end 73010 to the shaft guide distal end 73020. The shaft guide 73000 further comprises a first passage 73040 that opens through the proximal mounting collar 73012 on a first side $RP_1$ of a reference plane RP that extends transversely through the shaft guide axis SGA. In the illustrated arrangement, the first passage 73040 is configured to operably support the portion of the flexible closure drive shaft 72000 that spans between the proximal mounting member 71100 and the distal mounting member 71300. As can be seen in FIG. 309, in at least one arrangement, the first passage 73040 passes through the reference plane RP at least two times and opens through the distal mounting collar 73022 on the first side $RP_1$ of the reference plane RP.

In the illustrated example, the shaft guide 73000 further comprises a second passage 73050 that opens through the proximal mounting collar 73012 on a second side $RP_2$ of the reference plane RP. In the illustrated arrangement, the second passage 73050 is configured to operably support the portion of the flexible firing drive shaft 72100 that spans between the proximal mounting member 71100 and the distal mounting member 71300. As can be seen in FIG. 309, in at least one arrangement, the second passage 73050 passes through the reference plane RP at least two times and opens through the distal mounting collar 73022 on the second side $RP_2$ of the reference plane RP. Such arrangement serves to operably support the flexible closure drive shaft 72000 and the flexible firing drive shaft 72100 regardless of the articulated position of the end effector 200. In addition, such "twisted" arrangement of the first passage 73040 and the second passage 73050 forms a non-preferential bending plane through the shaft guide. In other arrangements, the shaft guide 73000 may be coupled to the proximal mounting member 71100 and the distal mounting member 71300 to facilitate relative rotation therebetween.

Referring now to FIGS. 302 and 312, in at least one arrangement, the surgical instrument comprises an articulation system 74000 that comprises a horizontal articulation drive 74100 and a vertical articulation drive 74200. In one aspect, the horizontal articulation drive 74100 comprises a horizontal articulation cable 74110 that is journaled on a horizontal drive pulley 74120 that may be supported in or by the housing or robotic system. In other arrangements, the horizontal drive pulley 74120 may be supported in a portion of the shaft assembly 100. In at least one embodiment, the horizontal drive pulley 74120 comprises a horizontal drive gear 74122 that is in meshing engagement with a horizontal drive rack 74124. The horizontal drive rack 74124 is configured to be driven axially by a corresponding motor drive unit (not shown) supported in or by the housing or robotic system.

As can be seen in FIG. 302, the horizontal articulation cable 74110 comprises a first horizontal cable end portion 74112 that extends through a corresponding passage in the proximal mounting member 71100 and is attached to the distal mounting member 71300. The horizontal articulation cable 74110 further comprises a second horizontal cable end portion 74114 that extends through a corresponding passage in the proximal mounting member 71100 and is attached to the distal mounting member 71300. Rotation of the horizontal drive pulley 71420 in a first direction will cause the end effector 200 to articulate in a first horizontal direction and rotation of the horizontal drive pulley 71420 in a second direction will cause the end effector 200 to articulate in a second horizontal direction (arrows HD in FIG. 301).

Still referring to FIGS. 302 and 312, the vertical articulation drive 74200 comprises a vertical articulation cable 74210 that is journaled on a vertical drive pulley 74220 that may be supported in or by the housing or robotic system. In other arrangements, the vertical drive pulley 74220 may be supported in a portion of the shaft assembly 100. In at least one embodiment, the vertical drive pulley 74220 comprises a vertical drive gear (not shown) that is in meshing engagement with a vertical drive rack 74224. The vertical drive rack 74224 is configured to be driven axially by a corresponding motor drive unit supported in or by the housing or robotic system.

As can be seen in FIG. 302, the vertical articulation cable 74210 comprises a first vertical cable end portion 74212 that extends through a corresponding passage in the proximal mounting member 71100 and is attached to the distal mounting member 71300. The vertical articulation cable 74210 further comprises a second horizontal cable end portion 74214 that extends through a corresponding passage in the proximal mounting member 71100 and is attached to the distal mounting member 71300. Rotation of the vertical drive pulley 74220 in a first direction will cause the end effector 200 to articulate in a first vertical direction and rotation of the vertical drive pulley 74220 in a second direction will cause the end effector 200 to articulate in a second vertical direction (arrows VD in FIG. 301). When the horizontal articulation drive 74100 and a vertical articulation drive 74200 are operated in concert, they can articulate the end effector in any combination of planes creating a three dimensional cone of articulation. In various arrangements springs may be employed in connection with the cables and or the drive pulleys to reduce/minimize backlash during operation.

FIGS. 313 and 314 illustrate another articulatable surgical end effector 75000 that is configured to articulate in a single plane through an articulation angle AAG that is approximately sixty five degrees or more. Such articulatable end effectors may be particularly useful in performing a lower anterior resection (LAR) of the colon, for example. In one instance, the surgical end effector 75000 comprises a surgical stapling device that is capable of cutting and stapling tissue. Other applications may employ a surgical end effector that is configured to cut and fasten tissue with ultrasound, harmonic, radio frequency energy, etc. In the illustrated example, the surgical end effector 75000 is substantially similar to end effector 200 described above, except for the differences discussed herein.

The illustrated surgical end effector 75000, for example, comprises a first jaw 201 and an anvil jaw 203, the various details of which were provided above. The surgical end effector further comprises a distal joint component 75450 that is similar to the joint component 450 discussed above. In at least one arrangement, the distal joint component 75450 is attached to the first jaw 201 by a retention ring 358 in the various manners described herein. In accordance with one aspect, a distal articulation cam 75500 is coupled to the distal joint component 75450. The distal articulation cam 75500 is configured to cammingly interface with a proximal articulation cam 75600 that operably interfaces with a shaft assembly 75410.

In accordance with at least one aspect, the shaft assembly 75410 is substantially similar to shaft assembly 410 described herein except for the noted differences. In one example, the shaft assembly comprises an outer shaft 75411 that operably interfaces with a proximal shaft joint component 75330. In accordance with one aspect, the proximal articulation cam 75600 is supported by the proximal shaft joint component 75330 for rotation about the shaft axis SA. In one embodiment, for example, the proximal articulation cam 75600 comprises a ring gear 75610 that is configured to meshingly interface with an articulation drive gear 75710 that is attached to an articulation drive shaft 75700 that is rotatably supported in the shaft assembly 75410. The articulation drive shaft 75700 operably interfaces with a source of rotary motion (e.g., a motor, etc.) that is supported in or by the housing or robotic system. Rotation of the articulation drive shaft 75700 in a first rotary direction will cause a proximal cam face 75620 on the proximal articulation cam 75600 to cammingly interface with a distal cam face 75520 on the distal articulation cam 75500 to articulate the surgical end effector 75000 through the articulation angle AAG. Continued rotation of the articulation drive shaft 75700 in the first direction will cause the surgical end effector to articulate through a single articulation plane until the surgical end effector 75000 reaches the maximum articulated position (articulation angle AAG equals approximately 65°) illustrated in FIG. 314, for example. Rotation of the articulation drive shaft 75700 in a second rotary direction will cause the proximal articulation cam 75600 and distal articulation cam 75500 to cammingly drive the surgical end effector 75000 back to the unarticulated position illustrated in FIG. 313.

The embodiment depicted in FIGS. 313 and 314, in accordance with one aspect of the present disclosure, may employ the closure drive system and firing drive system depicted in FIGS. 282-286 that were described in detail above. It will be appreciated that the closure drive system and firing drive system serve to maintain the distal cam face 75520 in camming engagement with the proximal cam face 75620. FIGS. 313 and 314 are "plan" or "top" views which only illustrate the closure drive arrangement with it being understood that the firing drive arrangement is located directly beneath the closure drive arrangement in the manners described herein. For example, as can be seen in FIGS. 313 and 314, the closure drive arrangement comprises a proximal closure drive shaft portion 68002, an intermediate closure drive shaft portion 68100, and a distal closure drive shaft portion 68300 that operably interfaces with closure components described herein to open and close the anvil 203. As was also described above, a proximal closure drive shaft 68010 and a distal closure drive shaft 68300 are attached to a closure coupler member 68110 for movement relative thereto. The proximal closure drive shaft 68010 may operably interface with a source of rotary closure motions (e.g., a motor, etc.) that is operably supported by or in a housing or portion of a robotic system, for example. Rotation of the proximal closure drive shaft 68010 in a first direction may result in the closure of the anvil 203 and rotation of the proximal closure drive shaft 68010 in a second rotary direction, will result in the anvil 203 moving from a closed position to an open position in the manners described herein. The firing drive system that may be employed in connection with this embodiment was described in detail above and will not be repeated here for the sake of brevity.

Other embodiments may employ the shaft embodiments comprising universally movable joints 60200 in the various manners and arrangements disclosed herein. The distal articulation cam 75500 and the proximal articulation cam 75500 define an articulation region 75100 and facilitate single plane, single direction, high-degree of articulation utilizing a rotating cam twist joint.

Various aspects of the subject matter described herein are set out in the following examples.

Example 1—A method of stapling comprising obtaining a surgical stapling assembly comprising a first jaw, a second jaw, an articulation joint, a closure drive comprising a first flexible rotary drive extending through the articulation joint, and a firing drive comprising a second flexible rotary drive extending through the articulation joint and rotatable independent of the first flexible rotary drive, wherein the surgical stapling assembly further comprises a 3D-printed component; activating, by a closure trigger, the closure drive, wherein the closure drive further comprises a closure screw and a closure wedge threadably coupled to the closure screw, wherein the closure wedge is configured to engage the first jaw to move the first jaw from an open position to a closed position upon a rotation of the first flexible rotary drive; and activating, by a firing trigger, the firing drive, wherein the firing drive further comprises a firing screw and a firing member threadably coupled to the firing screw, wherein the firing member is configured to camming engage the first jaw and the second jaw and to advance a cutting member and a staple-firing sled during a firing motion upon a rotation of the second flexible rotary drive.

Example 2—The method of stapling of Example 1, further comprising actuating, by an actuation wheel on a housing of the surgical stapling assembly, an articulation motion.

Example 3—The method of stapling of Example 2, wherein the first flexible rotary drive comprises an assembly of serial 3D-printed universal joints, and wherein the method of stapling further comprises flexing of the assembly of serial 3D-printed universal joints at the articulation joint during the articulation motion.

Example 4—The method of stapling of any one of Examples 1, 2 and 3, wherein the second flexible rotary drive comprises an assembly of serial 3D-printed universal joints, and wherein the method of stapling further comprises flexing of the assembly of serial 3D-printed universal joints at the articulation joint during the articulation motion.

Example 5—The method of stapling of any one of Examples 1, 2, 3, and 4, wherein the closure screw comprises a 3D-printed screw comprising a proximal bearing flange and a distal bearing flange, and wherein the method of stapling further comprises rotating the closure screw to advance the closure wedge and move the first jaw from an open position to a closed position.

Example 6—The method of stapling of any one of Example 5, wherein the closure wedge comprises a 3D-printed wedge trapped between the proximal bearing flange and the distal bearing flange, and wherein the method of stapling further comprises moving the 3D-printed wedge along the 3D-printed screw between the proximal bearing flange and the distal bearing flange.

Example 7—The method of stapling of any one of Examples 1, 2, 3, 4, 5, and 6, wherein the firing member comprises a 3D-printed firing member comprise a flexible region and a non-flexible region adjacent to the flexible region, and wherein the method of stapling further comprises expansion of the flexible region as the firing member camming engages the first jaw and the second jaw.

Example 8—The method of stapling of Example 7, wherein the flexible region comprises a first infill geometry, wherein the non-flexible region comprises a second infill geometry, wherein the second infill geometry is different than the first infill geometry, and wherein expansion of the flexible region further comprises an expansion of the cells defined in the first infill geometry more than an expansion of cells defined in the second infill geometry.

Example 9—The method of stapling of any one of Examples 1, 2, 3, 4, 5, 6, 7, and 8, wherein the firing screw extends through the second jaw to a distal mount, and wherein the method of stapling further comprises rotating the firing screw in the distal mount during the firing motion.

Example 10—The method of stapling of Example 9, wherein the method of stapling further comprises floating of the firing screw in the distal mount within a predefined range of motion during the firing motion.

Example 11—The method of stapling of Example 1, wherein the firing member comprises a threaded nut and an overmolded body portion, wherein the threaded nut comprises a driven surface threadably engaged with the firing screw and further comprises a driving surface abutting engaged with the overmolded body portion, wherein the method of stapling further comprises the threaded nut applying a driving force to the overmolded body portion eccentrically with respect to the firing screw during the firing motion.

Example 12—The method of stapling of any one of Examples 1, 2, 3, 4, 5, 6, 7, 8, 9, 10, and 11, further comprises installing a metal-plastic composite staple cartridge comprising staples in the second jaw.

Example 13—The method of stapling of Example 12, wherein the metal-plastic composite staple cartridge comprises a 3D-printed staple cartridge comprising a first side, a second side, a slot defined between the first side and the second side, and a bridge extending over the slot from the first side to the second side, wherein the bridge comprises 3D-printed frangible features, and wherein the method of stapling further comprises breaking the 3D-printed frangible features to cut the bridge during the firing motion.

Example 14—The method of stapling of any one of Examples 12 and 13, wherein the metal-plastic composite staple cartridge comprises a 3D-printed cartridge body comprising staple cavities and build layers oriented in a first direction, wherein the metal-plastic composite staple cartridge further comprises staple drivers movably positioned in the staple cavities, and wherein the method of stapling further comprises moving the staple drivers in the staple cavities along the build layers in the first direction during the firing motion.

Example 15—The method of stapling of any one of Examples 12, 13, and 14, wherein the metal-plastic composite staple cartridge comprises a metal knife, and wherein the method of stapling further comprises cutting tissue clamped between the first jaw and the second jaw.

Example 16—The method of stapling of Example 15, wherein the metal knife comprises a pair of opposing spring arms, and wherein the method of stapling further comprises releasably mounting the pair of opposing spring arms to the firing member upon installation of the metal-plastic composite staple cartridge in the second jaw.

Example 17—The method of stapling of any one of Examples 12, 13, 14, 15, and 16 wherein the metal-plastic composite staple cartridge comprises a metal sled, and wherein the method of stapling further comprises advancing the staple-firing sled through the metal-plastic composite staple cartridge to fire staples.

Example 18—The method of stapling of Example 17, wherein the metal sled comprises a multi-part sled, and wherein the method of stapling further comprises leaving a distal part of the multi-part sled in a distal location in the metal-plastic composite staple cartridge upon retraction of the firing member after the firing motion.

Example 19—The method of stapling of Example 12, wherein the metal-plastic composite staple cartridge comprises a disposable knife comprising a cutting edge, and wherein the method of stapling further comprises pivoting the cutting edge into a shielded position during a retraction motion of the firing member.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:
- U.S. Pat. No. 5,403,312, entitled ELECTROSURGICAL HEMOSTATIC DEVICE, which issued on Apr. 4, 1995;
- U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
- U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
- U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
- U.S. Pat. No. 7,670,334, entitled SURGICAL INSTRUMENT HAVING AN ARTICULATING END EFFECTOR, which issued on Mar. 2, 2010;
- U.S. Pat. No. 7,753,245, entitled SURGICAL STAPLING INSTRUMENTS, which issued on Jul. 13, 2010;
- U.S. Pat. No. 8,393,514, entitled SELECTIVELY ORIENTABLE IMPLANTABLE FASTENER CARTRIDGE, which issued on Mar. 12, 2013;
- U.S. patent application Ser. No. 11/343,803, entitled SURGICAL INSTRUMENT HAVING RECORDING CAPABILITIES, now U.S. Pat. No. 7,845,537;
- U.S. patent application Ser. No. 12/031,573, entitled SURGICAL CUTTING AND FASTENING INSTRUMENT HAVING RF ELECTRODES, filed Feb. 14, 2008, now abandoned;
- U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
- U.S. patent application Ser. No. 12/235,782, entitled MOTOR-DRIVEN SURGICAL CUTTING INSTRUMENT, now U.S. Pat. No. 8,210,411;
- U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
- U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
- U.S. patent application Ser. No. 12/893,461, entitled STAPLE CARTRIDGE, filed Sep. 29, 2012, now U.S. Pat. No. 8,733,613;
- U.S. patent application Ser. No. 13/036,647, entitled SURGICAL STAPLING INSTRUMENT, filed Feb. 28, 2011, now U.S. Pat. No. 8,561,870;
- U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
- U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;
- U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
- U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, now abandoned;
- U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006, now abandoned; and
- U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of stapling, comprising:
   articulating a surgical stapling assembly, wherein the surgical stapling assembly comprises a first jaw, a second jaw, an articulation joint comprising a fixed pivot axis, a closure drive comprising a first flexible rotary drive extending through the articulation joint, and a firing drive comprising a second flexible rotary drive extending through the articulation joint and rotatable independent of the first flexible rotary drive, wherein the surgical stapling assembly further comprises a 3D-printed component, and wherein the articulating step comprises articulating the surgical stapling assembly about the fixed pivot axis by way of the articulation joint;
   activating, by a closure trigger, the closure drive, wherein the closure drive further comprises a closure screw and a closure wedge threadably coupled to the closure screw, wherein the closure wedge is configured to engage the first jaw to move the first jaw from an open position to a closed position upon a rotation of the first flexible rotary drive; and
   activating, by a firing trigger, the firing drive, wherein the firing drive further comprises a firing screw and a firing member threadably coupled to the firing screw, wherein the firing member comprises an upper flange and a lower flange configured to cammingly engage the first jaw and the second jaw and to advance a cutting member and a staple-firing sled during an application of a distal firing motion force to the firing member upon a rotation of the second flexible rotary drive.

2. The method of stapling of claim 1, further comprising actuating, by an actuation wheel on a housing of the surgical stapling assembly, an articulation motion.

3. The method of stapling of claim 2, wherein the first flexible rotary drive comprises an assembly of serial 3D-printed universal joints, and wherein the method of stapling further comprises flexing of the assembly of serial 3D-printed universal joints at the articulation joint during the articulation motion.

4. The method of stapling of claim 2, wherein the second flexible rotary drive comprises an assembly of serial 3D-printed universal joints, and wherein the method of stapling further comprises flexing of the assembly of serial 3D-printed universal joints at the articulation joint during the articulation motion.

5. The method of stapling of claim 1, wherein the closure screw comprises a 3D-printed screw comprising a proximal bearing flange and a distal bearing flange, and wherein the method of stapling further comprises rotating the closure screw to advance the closure wedge and move the first jaw from an open position to a closed position.

6. The method of stapling of claim 5, wherein the closure wedge comprises a 3D-printed wedge trapped between the proximal bearing flange and the distal bearing flange, and wherein the method of stapling further comprises moving the 3D-printed wedge along the 3D-printed screw between the proximal bearing flange and the distal bearing flange.

7. The method of stapling of claim 1, wherein the firing member comprises a 3D-printed firing member comprise a flexible region and a non-flexible region adjacent to the flexible region, and wherein the method of stapling further comprises expansion of the flexible region as the firing member camming engages the first jaw and the second jaw.

8. The method of stapling of claim 1, wherein the firing screw extends through the second jaw to a distal mount, and wherein the method of stapling further comprises rotating the firing screw in the distal mount during the firing motion.

9. The method of stapling of claim 8, wherein the method of stapling further comprises floating of the firing screw in the distal mount within a predefined range of motion during the firing motion.

10. The method of stapling of claim 1, wherein the firing member comprises a threaded nut and an overmolded body portion, wherein the threaded nut comprises a driven surface threadably engaged with the firing screw and further comprises a driving surface abutting engaged with the overmolded body portion, and wherein the method of stapling further comprises the threaded nut applying a driving force to the overmolded body portion eccentrically with respect to the firing screw during the firing motion.

11. The method of stapling of claim 1, further comprises installing a metal-plastic composite staple cartridge comprising staples in the second jaw.

12. The method of stapling of claim 11, wherein the metal-plastic composite staple cartridge comprises a 3D-printed cartridge body comprising a first side, a second side, a slot defined between the first side and the second side, and a bridge extending over the slot from the first side to the second side, wherein the bridge comprises 3D-printed frangible features, and wherein the method of stapling further comprises breaking the 3D-printed frangible features to cut the bridge during the firing motion.

13. The method of stapling of claim 11, wherein the metal-plastic composite staple cartridge comprises a 3D-printed cartridge body comprising staple cavities and build layers oriented in a first direction, wherein the metal-plastic composite staple cartridge further comprises staple drivers movably positioned in the staple cavities, and wherein the method of stapling further comprises moving the staple drivers in the staple cavities along the build layers in the first direction during the firing motion.

14. The method of stapling of claim 11, wherein the metal-plastic composite staple cartridge comprises a metal knife, and wherein the method of stapling further comprises cutting tissue clamped between the first jaw and the second jaw.

15. The method of stapling of claim 14, wherein the metal knife comprises a pair of opposing spring arms, and wherein the method of stapling further comprises releasably mounting the pair of opposing spring arms to the firing member upon installation of the metal-plastic composite staple cartridge in the second jaw.

16. The method of stapling of claim 11, wherein the metal-plastic composite staple cartridge comprises a metal sled, and wherein the method of stapling further comprises advancing the staple-firing sled through the metal-plastic composite staple cartridge to fire staples.

17. The method of stapling of claim 16, wherein the metal sled comprises a multi-part sled, and wherein the method of stapling further comprises leaving a distal part of the multi-part sled in a distal location in the metal-plastic composite staple cartridge upon retraction of the firing member after the firing motion.

18. The method of stapling of claim 11, wherein the metal-plastic composite staple cartridge comprises a disposable knife comprising a cutting edge, and wherein the method of stapling further comprises pivoting the cutting edge into a shielded position during a retraction motion of the firing member.

19. A method of stapling, comprising:
activating, by a closure trigger, a closure drive of a surgical stapling assembly, wherein the surgical stapling assembly comprises a first jaw, a second jaw, and an articulation joint, wherein the closure drive comprises a first flexible rotary drive extending through the articulation joint, wherein the surgical stapling assembly further comprises a firing drive comprising a second flexible rotary drive extending through the articulation joint and rotatable independent of the first flexible rotary drive, wherein the surgical stapling assembly further comprises a 3D-printed component, wherein the closure drive further comprises a closure screw and a closure wedge threadably coupled to the closure screw, and wherein the closure wedge is configured to engage the first jaw to move the first jaw from an open position to a closed position upon a rotation of the first flexible rotary drive; and
activating, by a firing trigger, the firing drive, wherein the firing drive further comprises a firing screw and a firing member threadably coupled to the firing screw, wherein the firing member is configured to camming engage the first jaw and the second jaw and to advance a cutting member and a staple-firing sled during a firing motion upon a rotation of the second flexible rotary drive,
wherein the firing member comprises a 3D-printed firing member comprise a flexible region and a non-flexible region adjacent to the flexible region, and wherein the method of stapling further comprises expansion of the flexible region as the firing member camming engages the first jaw and the second jaw,
wherein the flexible region comprises a first infill geometry, wherein the non-flexible region comprises a second infill geometry, wherein the second infill geometry is different than the first infill geometry, and wherein expansion of the flexible region further comprises an expansion of the cells defined in the first infill geometry more than an expansion of cells defined in the second infill geometry.

20. A method of stapling, comprising:
activating, by a closure trigger, a closure drive of a surgical stapling assembly, wherein the surgical stapling assembly comprises a first jaw, a second jaw, and an articulation region, wherein the closure drive comprises a first flexible rotary drive extending through the articulation region, wherein the surgical stapling assembly further comprises a firing drive comprising a second flexible rotary drive extending through the articulation region and rotatable independent of the first flexible rotary drive, wherein the surgical stapling assembly further comprises a 3D-printed component, wherein the 3D-printed component comprises a discrete 3D-printed feature for controlling a behavior of the 3D-printed component corresponding to a function of the 3D-printed component, wherein the closure drive further comprises a closure screw and a closure wedge threadably coupled to the closure screw, wherein the closure wedge is configured to engage the first jaw to move the first jaw from an open position to a closed position upon a rotation of the first flexible rotary drive; and
activating, by a firing trigger, the firing drive, wherein the firing drive further comprises a firing screw and a firing member threadably coupled to the firing screw, wherein the firing member is configured to cammingly engage the first jaw and the second jaw and to advance a cutting member and a staple-firing sled during a firing motion upon a rotation of the second flexible rotary drive.

21. The method of stapling of claim 20, wherein the discrete 3D-printed feature comprises a first infill geometry and a second infill geometry different than the first infill geometry.

22. The method of stapling of claim 21, wherein the 3D-printed component comprises a 3D-printed cartridge body comprising a longitudinal bridge portion extending between adjacent cartridge body portions of the 3D-printed cartridge body, and wherein the longitudinal bridge portion comprises the first infill geometry and the adjacent cartridge body portions comprise the second infill geometry.

23. The method of stapling of claim 21, wherein the firing member comprises a 3D-printed firing member a first portion and a second portion, wherein the first portion comprises the first infill geometry the second portion comprises the second infill geometry.

24. The method of stapling of claim 20, wherein the discrete 3D-printed feature comprises a first infill percentage and a second infill percentage different than the first infill percentage.

25. The method of stapling of claim 24, wherein the 3D-printed component comprises a 3D-printed cartridge body comprising a longitudinal bridge portion extending between adjacent cartridge body portions of the 3D-printed cartridge body, and wherein the longitudinal bridge portion comprises the first infill percentage and the adjacent cartridge body portions comprise the second infill percentage.

26. The method of stapling of claim 24, wherein the firing member comprises a 3D-printed firing member a first portion and a second portion, wherein the first portion comprises the first infill percentage the second portion comprises the second infill percentage.

27. The method of stapling of claim 20, wherein the discrete 3D-printed feature comprises a build layer orientation, and wherein the build layer orientation is oriented corresponding to the function of the 3D-printed component.

28. The method of stapling of claim 27, wherein the 3D-printed component comprises a 3D-printed cartridge body comprising a plurality of staple cavities, wherein each staple cavity defines a staple cavity axis, and wherein the build layer orientation comprises a build direction aligned with each staple cavity axis.

* * * * *